(12) United States Patent
Jagtap et al.

US008119654B2

(10) Patent No.: US 8,119,654 B2
(45) Date of Patent: Feb. 21, 2012

(54) INDENOISOQUINOLINONE ANALOGS AND METHODS OF USE THEREOF

(75) Inventors: Prakash Jagtap, N. Andover, MA (US); Duy-Phong Pham-Huu, Beverly, MA (US); Frederick Cohen, San Francisco, CA (US); Xiaojing Wang, Foster City, CA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 941 days.

(21) Appl. No.: 12/039,611

(22) Filed: Feb. 28, 2008

(65) Prior Publication Data

US 2010/0004220 A1 Jan. 7, 2010

Related U.S. Application Data

(60) Provisional application No. 60/904,393, filed on Feb. 28, 2007.

(51) Int. Cl.
*A61K 31/473* (2006.01)
*C07D 221/18* (2006.01)

(52) U.S. Cl. .......... 514/284; 546/61; 544/125; 544/361; 514/232.8; 514/253

(58) Field of Classification Search .................. 514/284, 514/232.8, 253; 546/61; 544/125, 361
See application file for complete search history.

(56) References Cited

U.S. PATENT DOCUMENTS

| | | | |
|---|---|---|---|
| 3,710,795 A | 1/1973 | Higuchi et al. |
| 4,113,731 A | 9/1978 | Winters et al. |
| 4,263,304 A | 4/1981 | Ishizumi et al. |
| 5,079,246 A | 1/1992 | Forbes et al. |
| 5,177,075 A | 1/1993 | Suto et al. |
| 5,260,316 A | 11/1993 | Van Duzer et al. |
| 5,262,564 A | 11/1993 | Kun et al. |
| 5,597,831 A | 1/1997 | Michalsky et al. |
| 5,710,162 A | 1/1998 | Okazaki et al. |
| 5,733,918 A | 3/1998 | Okazaki et al. |
| 6,028,079 A | 2/2000 | Okazaki et al. |
| 6,277,990 B1 | 8/2001 | Jagtap et al. |
| 6,346,535 B1 | 2/2002 | Cotter et al. |
| 6,346,536 B1 | 2/2002 | Li et al. |
| 6,498,194 B2 | 12/2002 | Cotter et al. |
| 6,635,642 B1 | 10/2003 | Jackson et al. |
| 6,723,733 B2 | 4/2004 | Li et al. |
| 6,828,319 B2 | 12/2004 | Jagtap et al. |
| 6,956,035 B2 | 10/2005 | Jagtap et al. |
| 7,217,709 B2 | 5/2007 | Jagtap et al. |
| 7,381,722 B2 | 6/2008 | Jagtap et al. |
| 7,652,028 B2 * | 1/2010 | Jagtap et al. .................. 514/284 |
| 2002/0099063 A1 | 7/2002 | Cotter et al. |
| 2003/0039628 A1 | 2/2003 | Hellstrand et al. |
| 2004/0039009 A1 | 2/2004 | Jagtap et al. |
| 2004/0077667 A1 | 4/2004 | Matsuoka et al. |
| 2004/0120926 A1 | 6/2004 | Hellstrand et al. |
| 2004/0229895 A1 | 11/2004 | Jagtap et al. |
| 2005/0049270 A1 | 3/2005 | Jagtap et al. |
| 2005/0228007 A1 | 10/2005 | Jagtap et al. |
| 2005/0261288 A1 | 11/2005 | Jagtap et al. |
| 2006/0019980 A1 | 1/2006 | Szabo et al. |
| 2006/0079510 A1 | 4/2006 | Hellstrand et al. |
| 2006/0287311 A1 | 12/2006 | Jagtap et al. |
| 2006/0287312 A1 | 12/2006 | Jagtap et al. |
| 2006/0287313 A1 | 12/2006 | Jagtap et al. |

FOREIGN PATENT DOCUMENTS

| | | |
|---|---|---|
| CA | 2349227 A1 | 5/2000 |
| GB | 2025932 B2 | 1/1980 |
| JP | 2003-267888 | 9/2003 |
| WO | 91/04037 A1 | 4/1991 |
| WO | 93/05023 A1 | 3/1993 |
| WO | 99/08680 A1 | 2/1999 |
| WO | 99/11311 A1 | 3/1999 |
| WO | 99/11623 A1 | 3/1999 |
| WO | 99/11628 A1 | 3/1999 |
| WO | 99/11644 A1 | 3/1999 |
| WO | 99/11645 A1 | 3/1999 |
| WO | 99/11649 A2 | 3/1999 |
| WO | 99/59973 A1 | 11/1999 |
| WO | 99/59975 A1 | 11/1999 |
| WO | 00/21537 A1 | 4/2000 |
| WO | 00/39070 A1 | 7/2000 |
| WO | 00/39104 A1 | 7/2000 |

(Continued)

OTHER PUBLICATIONS

Hiremath et al., "Synthesis of [10-substituted-6H,7H-indolo[2,3-c]iso-quinolin-5-one-6-yl]acetyl-3,5-disubstituted-pyrazoles/pryazolones and 5-[10-substituted-6H,7H-indolo[2,3-c]iso-quinolin-5-one-6-yl]methyl-1,3,4-oxadiazol-2-thiones," Journal of the Indian Chemical Society, vol. 72(10):735-738 (1995).
Hiremath et al., "Synthesis and Biological Studies of Some New Bridgehead Nitrogen Heterocycles Containing Indoloisoquinoline Nucleus," Oriental Journal of Chemistry, vol. 13(2):173-176 (1997).
Hiremath et al., "Synthesis of substituted 2-(5-oxo/thioxo-1,3,4-oxadiazol-2-yl)-indoles & 2-(5-oxo/thioxo-1,3,4-oxadiazol-2-ylamino)indoles," Indian Journal of Chemistry, Section B, vol. 22B(6):571-576 (1983).
Holl, V. et al., "Modulation of the Antiproliferative Activity of Anti-cancer Drugs in Hematopoietic Tumor Cell Lines by the Poly(ADP-Ribose) Polymerase Inhibitor 6(5H)-Phenanthridinone," Anticancer Research, vol. 20:3233-3242 (2000).
Horsman, M. et al., "Radiosensitization by Nicotinamide in Vivo: A Greater Enhancement of Tumor Damage Compared to That of Normal Tissues," Radiation Research, vol. 109:479-489 (1987).

(Continued)

*Primary Examiner* — Charanjit Aulakh
(74) *Attorney, Agent, or Firm* — Nelson Mullins Riley & Scarborough LLP; Jane E. Remillard, Esq.; Pankaj N. Desai

(57) ABSTRACT

The present invention relates to Indenoisoquinolinone Analogs, compositions comprising an effective amount of an Indenoisoquinolinone Analog and methods for treating or preventing an inflammatory disease, a reperfusion injury, diabetes mellitus, a diabetic complication, reoxygenation injury resulting from organ transplantation, an ischemic condition, a neurodegenerative disease, renal failure, a vascular disease, a cardiovascular disease, cancer, a complication of prematurity, cardiomyopathy, retinopathy, nephropathy, neuropathy, erectile dysfunction or urinary incontinence, comprising administering to a subject in need thereof an effective amount of an Indenoisoquinolinone Analog.

43 Claims, No Drawings

FOREIGN PATENT DOCUMENTS

| | | | |
|---|---|---|---|
| WO | 00/42040 | A1 | 7/2000 |
| WO | 01/12199 | A2 | 2/2001 |
| WO | 02/06284 | A1 | 1/2002 |
| WO | 2004/014862 | A1 | 2/2004 |
| WO | 2004/043959 | A1 | 5/2004 |
| WO | 2005/009398 | A2 | 2/2005 |
| WO | 2005/012524 | A1 | 2/2005 |
| WO | 2005/053662 | A1 | 6/2005 |
| WO | 2005/082079 | A2 | 9/2005 |
| WO | 2005/082368 | A1 | 9/2005 |
| WO | 2006/009718 | A2 | 1/2006 |
| WO | 2006/093666 | A2 | 9/2006 |
| WO | 2006/093667 | A1 | 9/2006 |
| WO | 2006/093677 | A1 | 9/2006 |
| WO | 2007/025009 | A2 | 3/2007 |

OTHER PUBLICATIONS

Horsman, M. et al., "Nicotinamide as a radiosensitizer in tumours and normal tissues: the importance of drug dose and timing," Radiotherapy and Oncology, vol. 45:167-174 (1997).

Hua, H. et al., "Polyadenosine Diphosphate-Ribose Polymerase Inhibition Modulates Skeletal Muscle Injury Following Ischemia Reperfusion," Arch Surg., vol. 140:344-351 (2005).

Iwashita, A. et al., "A new poly(ADP-ribose) polymerase inhibitor, 2-(4-chlorophenyl)-5-quinoxalinecarboxamide (FR261529), ameliorates methamphetamine-induced dopaminergic neurotoxicity in mice," J. Pharmacol. Exp. Ther., vol. 310:1114-1124 (2004).

Iwashita, A. et al., "A novel and potent PARP-1 inhibitor, 5-chloro-2-[3-(4-phenyl-3, 6-dihydro-1(2H)-pyridinyl)propyl]-4(3H)-quinazolinone (FR247304), attenuates neuronal damage in vitro and in vivo models of cerebral ischemia," J. Pharmacol. Exp. Ther., vol. 310:425-436 (2004).

Iwashita, A. et al., "Neuroprotective effects of a novel poly(ADP-ribose) polymerase-1 inhibitor, 2-[3-[4-(4-chlorophenyl)-1-piperazinyl] propyl]-4(3H)-quinazolinone (FR255595), in an in vitro model of cell death and in mouse 1-methyl-4-phenyl-1,2,3,6-tetrahydropyridine model of Parkinsons's disease," J. Pharmacol. Exp. Ther., vol. 309:1067-1078 (2004).

Jagtap et al., "Discovery of Potent Poly(ADP-ribose) Polymerase-1 Inhibitors from the Modification of Indeno[1,2-c] isoquinolinone," J. Med. Chem., vol. 48:5100-5103 (2005).

Jagtap et al., "Facile and Convenient Syntheses of 6,11-Dihydro-5H-Indeno[1,2-c]isoquinolin-5-ones and 6,11-Dihydro-5H-indolo[3,2-c]isoquinolin-5-one," Org. Lett., vol. 7(9):1753-1756 (2005).

Jagtap, P. et al., "Novel phenanthridinone inhibitors of poly(adenosine 5'-diphosphate-ribose) synthetase: Potent cytoprotective and antishock agents," Crit. Care Med., vol. 30:1071-1082 (2002).

Jagtap et al., "Poly(ADP-Ribose)Polymerase and the Therapeutic Effects of its Inhibitors," Nature Reviews/Drug Discovery, vol. 4:421-440 (2005).

Jagtap, P.G. et al., "The discovery and synthesis of novel adenosine substituted 2,3-dihydro-1-H-isoindol-1-ones: potent inhibitors of poly(ADP-ribose) polymerase-1 (PARP-1)," Bioorg. Med. Chem. Lett., vol. 14:81-85 (2004).

Jantzen and Robinson, Modern Pharmaceutics, 3rd Edition, Baker (Ed.), p. 596 (1995).

Jha et al., "Synthesis of Indeno[2,1-c] isocoumarins and indeno[2,1-cis]isoquinolones," Indian Journal of Chemistry, Section B, vol. 24B(4):440-444 (1985).

Jijon, H. et al., "Inhibition of poly(ADP-ribose) polymerase attenuates inflammation in a model of chronic colitis," Am. J. Physiol. Gastrointest. Liver Physiol., vol. 279:G641-G651 (2000).

Kamanaka, Y. et al., "Neuroprotective effects of ONO-1924H, an inhibitor of poly(ADP-ribose) polymerase (PARP), on cytotoxicity of PCI2 cells and ischemic cerebral damage," Life Sci., vol. 76:151-162 (2004).

Kawana et al., "Nucleoside Peptides. III. The Synthesis of N-[1-(9-Adenyl)-beta-D-ribofuranuronosyl] Derivatives of Certain Amino Acids and Peptides," J. Org. Chem., vol. 37(2):288-290 (1972).

Kelland, L. et al., "The effect of 3-aminobenzamide in the radiation response of three human cervix carcinoma xenografts," Radiotherapy and Oncology, vol. 15:363-369 (1989).

Khandoga, A. et al., "5-Aminoisoquinolinone, a novel inhibitor of poly(adenosine disphosphate-ribose) polymerase, reduces microvascular liver injury but not mortality rate after hepatic ischemia-reperfusion," Crit. Care Med., vol. 32:472-477 (2004).

Kirby et al., "Hydride hyperconjugation in 1(3)-methylazulenes," Tetrahedron Lett., vol. 27:1-4 (1960).

Kirby et al., "4,6,8-trimethylazulenium percholrate," Chemical & Industry (London, UK), pp. 1217-1218 (1960).

Koedel, U. et al., "Meningitis-Associated Central Nervous System Complications Are Mediated by the Activation of Poly(ADP-Ribose) Polymerase," Journal of Cerebral Blood Flow & Metabolism, vol. 22:39-49 (2002).

Komjati, K. et al., "Poly(ADP-ribose) polymerase inhibition protect neurons and the white matter and regulates the translocation of apoptosis-inducing factor in stroke," Int. J. Mol. Med., vol. 13:373-382 (2004).

Lal et al., "Applications of carbon-nitrogen bond cleavage reaction: A synthesis/derivisation of 11H-indeno[1,2-c] isoquinolones," Indian J. Chem., Section B, vol. 38B:33-39 (1999).

Lamping et al., "LPS-binding protein protects mice from septic shock caused by LPS or gramnegative bacteria," J. Clin. Invest., vol. 101(10):2065-2071 (1998).

Laplaca, M.C. et al., "Pharmacologic inhibition of poly(ADP-ribose) polymerase is neuroprotective following traumatic brain injury in rats," J. Neurotrauma, vol. 18(4):369-376 (2001).

Li, F. et al., "Evaluation of orally active poly(ADP-ribose) polymerase inhibitor in streptozotocin-diabetic rat model of early peripheral neuropathy," Diabetologia, vol. 47:710-717 (2004).

Liaudet, L. et al., "Activation of Poly(ADP-Ribose) Polymerase-1 is a Central Mechanism of LIpopolysaccharide-Induced Acute Lung Inflammation," Am. J. Respir. Crit. Care Med., vol. 165:372-377 (2002).

Liaudet, L. et al., "Poly(ADP-Ribose) Synthetase Mediates Intestinal Mucosal Barrier Dysfunction After Mesenteric Ischemia," Shock, vol. 142(2):134-141 (2000).

Liaudet, L. et al., "Protection against hemorrhagic shock in mice genetically deficient in poly(ADP-ribose) polymerase," PNAS, vol. 97(18):10203-10208 (2000).

Liaudet, L. et al., "Suppression of poly (ADP-ribose) polymerase activation by 3-aminobenzamide in a rat model of myocardial infarction: long-term morphological and functional consequences," British Journal of Pharmacology, vol. 133:1424-1430 (2001).

Lohinai, Z. et al., "Role of the Activation of the Nuclear Enzyme Poly(ADP-Ribose) Polymerase in the Pathogenesis of Periodontitis," J. Dent. Res., vol. 82(12):987-992 (2003).

Mabley, J.G. et al., "Anti-inflammatory effects of a novel, potent inhibitor of poly(ADP-ribose) polymerase," Inflamm. Res., vol. 50:561-569 (2001).

Mabley et al., "Inhibition of poly(ADP-ribose) synthetase by gene disruption or inhibition with 5-iodo-6-amino-1,2-benzopyrone protects mice from multiple-low-dose-streptozotocin-induced diabetes," Br. J. Pharmacol., vol. 133(6):909-919 (2001).

Mandir et al., "A novel in vivo post-translational modification of p53 by PARP-1 in MPTP-induced parkinsonism," J. Neurochem., vol. 83(1):186-192 (2002).

Mandir, et al., "Poly(ADP-ribose) polymerase activation mediates 1-methyl-4-phenyl-1,2,3,6-tetrahydropyridine (MPTP)-induced parkinsonism," Proc. Natl. Acad. Sci. USA., vol. 96(10):5774-5779 (1999).

Martin, D. et al., "Inhibition of poly (ADP-ribose) polymerase attenuates ischemic renal injury in rats," Am. J. Physiol. Regulatory Integrative Comp. Physiol., vol. 279:R1834-R1840 (2000).

Martin-Oliva, D. et al., "Crosstalk between PARP-1 and NF-KB modulates the promotion of skin neoplasia," Oncogene, vol. 23:5275-5283 (2004).

Martin-Oliva, D. et al., "Inhibition of Poly(ADP-Ribose) Polymerase Modulates Rumor-Related Gene Expression, Including Hypoxia-Inducible Factor-1 Activation, During Skin Carcinogenesis," Cancer Res., vol. 66(11):5744-5756 (2006).

Mazzon, E. et al., "Beneficial effects of GPI 6150, an inhibitor of poly(ADP-ribose) polymerase in a rat model of splanchnic artery occlusion and reperfusion," Shock, vol. 17:222-227 (2002).

Mazzon, E. et al., "GPI 6150, a PARP inhibitor, reduces the colon injury caused by dinitrobenzene sulfonic acid in the rat," Biochemical Pharmacology, vol. 64:327-337 (2002).

Mazzon, E. et al., "GPI 6150, a poly(ADP-ribose) polymerase inhibitor, exhibits an anti-inflammatory effect in rat models of inflammation," Eur. J. Pharmacol., vol. 415:85-94 (2001).

McDonald, M. et al., "Effects of inhibitors of the activity of poly (ADP-ribose) synthetase on the organ injury and dysfunction caused by haemorrhagic shock," British Journal of Pharmacology, vol. 128:1339-1345 (1999).

McDonald, M. et al., "Effects of 5-aminoisoquinolinone, a water-soluble, potent inhibitor of the activity of poly (ADP-ribose) polymerase on the organ injury and dysfunction caused by haemorrhagic shock," British Journal of Pharmacology, vol. 130:843-850 (2000).

Miknyoczki, S.J. et al., "Chemopotentiation of temozolomide, irinotecan, and cisplatin activity by CEP-6800, a novel poly(ADP-ribose) polymerase inhibitor," Mol. Cancer Ther., vol. 2:371-382 (2003).

Milam et al., "Inhibitors of poly(adenosine diphosphate-ribose) synthesis: effect on other metabolic processes," Science, 223:589-591 (1984).

Morrison and Boyd, Organic Chemistry, 5th edition, Allyn and Bacon, Inc., p. 179 (1987).

Mota, R. et al., "Inhibition of poly(ADP-ribose) polymerase attenuates the severity of acute pancreatitis and associated lung injury," Laboratory Investigation, vol. 85:1250-1262 (2005).

Nakajima, H. et al., "A newly synthesized poly(ADP-ribose) polymerase inhibitor. 2-methyl-3,5,7,8-tetrahydrothipyrano[4,3-d]pyrimidine-4-one (DR2313): pharmacological profiles, neuroprotective effects, and therapeutic time window in cerebral ischemia in rats," J. Pharmacol. Exp. Ther., vol. 312(2):472-481 (2005).

Nozaki, T et al., "Parp-1 deficiency implicated implicated in colon and liver tumorigenesis induced by azoxymethane," Cancer Sci., vol. 94:497-500 (2003).

Obrosova, I. et al., "Role of Poly(ADP-Ribose) Polymerase Activation in Diabetic Neuropathy," Diabetes, vol. 53:711-720 (2004).

Ogawa, K. et al., "Parp-1 deficiency does not enhance liver carcinogenesis induced by 2-amino-3-methylimidazo[4,5-f]quinoline in mice," Cancer Letters, vol. 236:32-38 (2006).

Ohno et al., "Modulation of adenosine receptor affinity and intrinsic efficacy in adenine nucleosides substituted at the 2 position," Biorg. Med. Chem., vol. 12:2995-3007 (2004).

Ojika et al., "Ptaquiloside, a Potent Carcinogen Isolated From Bracken Fern Pteridium Aquilinum Var. Latiusculum: Structure Elucidation Based on Chemical and Spectral Evidence, and Reactions with Amino Acids, Nucleosides, and Nucleotides," Tetrahedron, vol. 43(22):5261-5274 (1987).

Oliver, F. et al., "Resistance to endotoxic shock as a consequence of defective NF-K8 activation in poly (ADP-ribose) polymerase-1 deficient mice," The EMBO Journal, vol. 18(16):4446-4454 (1999).

Pacher, P. et al., "A New, Potent Poly(ADP-ribose) Polymerase Inhibitor Improves Cardiac and Vascular Dysfunction Associated with Advanced Aging," JPET, vol. 311(2):485-491 (2004).

Pacher, P. et al., "Beneficial effects of a novel ultrapotent poly(ADP-ribose) polymerase inhibitor in murine models of heart failure," International Journal of Molecular Medicine, vol. 17:369-375 (2006).

Pacher, P. et al., "Endothelial dysfunction in aging animals: the role of poly(ADP-ribose) polymerase activation," Br. J. Pharmacol., vol. 135:1347-1350 (2002).

Pacher, P. et al., "Pharmacologic inhibition of poly(adenosine diphosphate-ribose) polymerase may represent a novel therapeutic approach in chronic heart failure," J. Am. Coll. Cardiol., vol. 40:1006-1016 (2002).

Pacher et al., "Role of Nitrosative Stress and Peroxynitrite in the Pathogenesis of Diabetic Complications. Emerging New Therapeutical Strategies," Curr. Med. Chem., vol. 12(3):267-275 (2005).

Pacher, P. et al., "The Role of Poly(ADP-Ribose) Polymerase Activation in the Development of Myocardial and Endothelial Dysfunction in Diabetes," Diabetes, vol. 51:514-521 (2002).

Parrillo, Joseph E., "Pathogenic mechanisms of septic shock," N. Engl. J. Med., vol. 328:1471-1477 (1993).

Pellicciari, R. et al., "Towards new neuroprotective agents: design and synthesis of 4H-thieno[2,3-c]isoquinoline-5-one derivatives as potent PARP-1 inhibitors," Farmaco, vol. 58:851-858 (2003).

Petrilli, V. et al., "Noncleavable poly(ADP-ribose) polymerase-1 regulates the inflammation response in mice," Journal of Clinical Investigation, vol. 114(8):1072-1081 (2004).

Peukert, Stefan et al., "New inhibitors of poly(ADP-ribose) polymerase (PARP)," Expert Opinion on Therapeutic Patents, vol. 14(11):1531-1551 (2004).

Pieper, A. et al., "Poly (ADP-ribose) polymerase-deficient mice are protected from streptozotocin-induced diabetes," Proc. Natl. Acad. Sci. vol. 96:3059-3064 (1999).

Pieper, A. et al., "Myocardial Postischemic Injury is Reduced by PolyADPribose Polymerase-1 Gene Disruption," Molecular Medicine, vol. 6(4):271-282 (2000).

Ratnam, K. et al., "Current Development of Clinical Inhibitors of Poly(ADP-Ribose) Polymerase in Oncology," Clin. Cancer Res., vol. 13(5):1383-1388 (2007).

Scott, G. et al., "The Therapeutic Effects of PJ34 [N-(6-Oxo-5,6-dihydrophenanthridin-2-yl)-N,N-dimethylacetamide. HCl], a Selective Inhibitor of Poly(ADP-Ribose) Polymerase, in Experimental Allergic Encephaolmyelitis Are Associated with Immunomodulation," JPET, vol. 310:1053-1061 (2004).

Shinkwin et al., "Synthesis of thiophenecarboxamides, thieno[3,4-c]pyridin-4(5H)-ones and thieno[3.4-d]pyrimidin-4(3H)-ones and preliminary evaluation as inhibitors of poly(ADP-ribose)polymerase (PARP)," Bioorg. Med. Chem., vol. 7:297-308 (1999).

Skalitzky, J.D. et al., "Tricyclic benzimidazoles as potent poly(ADP-ribose) polymerase-1 inhibitors," J. Med. Chem., vol. 46:210-213 (2003).

Soriano, et al., "Diabetic endothelial dysfunction: the role of poly(ADP-ribose) polymerase activation," Nature Medicine, vol. 7(1):108-113 (2001).

Soriano, F. et al., "Rapid Reversal of the Diabetic Endothelial Dysfunction by Pharmacological Inhibition of Poly (ADP-Ribose) Polymerase," Circ. Res., vol. 89:684-691 (2001).

Southan, et al., "Poly(ADP-ribose) polymerase inhibitors," Curr. Med. Chem., vol. 10:321 (2003).

Srivastava et al., "Synthesis of Indeno[2,1-c] isocoumarins and indeno[2,1-c]isoquinolones," Journal of the Indian Chemical Society, vol. 66(4):276-281 (1989).

Steinhagen, H. et al., "Substituted uracil derivatives as potent inhibitors of poly(ADP-ribose)polymerase-1 (PARP-1)," Bioorg. Med. Chem. Lett., vol. 12:3187-3190 (2002).

Strumberg et al., "Synthesis of cytotoxic indenosoquinoline topoisomerase I poisons," J. Med. Chem., vol. 42 (3):446-457 (1999).

Suarez-Pinzon, W. et al., "Poly (ADP-Ribose) Polymerase Inhibition Prevents Spontaneous and Recurrent Autoimmune Diabetes in NOD Mice by Inducing Apoptosis of Islet-Infiltrating Leukocytes," Diabetes, vol. 52:1683-1688 (2003).

Suzuki, Y. et al., "Inhibition of Poly(ADP-Ribose) Polymerase Prevents Allergen-Induced Asthma-Like Reaction in Sensitized Guinea Pits," JPET, vol. 311:1241-1248 (2004).

Szabados, E. et al., "BGP-15, a Nicotinic Amidoxime Derivative Protecting Heart from Ischemia Reperfusion Injury through Modulation of Poly(ADP-Ribose) Polymerase," Biochem. Pharmacol., vol. 59:937-945 (2000).

Szabo, C. et al., "Angiotensin II-Mediated Endothelial Dysfunction: Role of Poly(ADP-Ribose) Polymerase Activation," Molecular Medicine, vol. 10(1-6):28-35 (2004).

Szabo, G. et al., "Contractile dysfunction in experimental cardiac allograft rejection: role of the poly (ADP-ribose) polymerase pathway," Transplant Intl., vol. 19:506-513 (2006).

Szabo, C. et al., "Poly(ADP-Ribose) Polymerase Inhibitors Ameliorate Nephropathy of Type 2 Diabetic Lepr db/db Mice," Diabetes, vol. 55:3004-3012 (2006).

Szabo, G. et al., "Poly(ADP-Ribose) Polymerase Inhibition Reduces Reperfusion Injury After Heart Transplantation," Circ. Res., vol. 90:100-106 (2002).

Szabo, C. et al., "Protection against peroxynitrite-induced fibroblast injury and arthritis development by inhibition of poly(ADP-ribose) synthase," Proc. Natl. Acad. Sci., vol. 95:3867-3872 (1998).

Szabo, C., "Role of poly(ADP-ribose) Polymerase Activation in the Pathogenesis of Diabetes mellitus and its Complications," Pharmacol. Res., vol. 52:60-71 (2005).

Szabo et al., "Role of poly(ADP-ribose) synthetase in inflammation and ischaemia-reperfusion," Trends Pharmacol. vol. 19:287-298 (1998).

Szabo et al., "The pathophysiological role of peroxynitrite in shock, inflammation, and ischemia-reperfusion injury," Shock, vol. 6:79-88 (1996).

Tentori, L. et al., "Systemic Administration of GPI 15427, Novel Poly(ADP-Ribose) Polymerase-1 Inhibitor, Increases the Antitumor Activity of Temozolomide against Intracranial Melanoma, Glioma, Lymphoma," Clinical Cancer Research, vol. 9:5370-5379 (2003).

Tentori, L. et al., "Poly(ADP-ribose) glycohydrolase inhibitor as chemosensitizer of malignant melanoma for temozolomide," European Journal of Cancer, vol. 41:2948-2957 (2005).

Thiemermann, C. et al., "Inhibition of the activity of poly(ADP-ribose) sythetase reduces ischemia-reperfusion injury in the heart and skeletal muscle," Proc. Natl. Acad. Sci., vol. 94:679-683 (1997).

Thomas, H. et al., "Preclinical Selection of a Novel Poly (ADP-Ribose) Polymerase Inhibitor for Clinical Trial," Mol. Cancer Ther., vol. 6(3):945-956 (2007).

Tikhe, J.G. et al., "Design, synthesis, and evaluation of 3,4-dihydro-2H-[1,4]diazepino[6,7,1-hi]indol-1-ones as inhibitors of poly(ADP-ribose) polymerase," J. Med. Chem., vol. 47:5467-5481 (2004).

Tong, W. et al., "Null Mutation of DNA Strand Break-Binding Molecule Poly(ADP-Ribose) Polymerase Causes Medulloblastomas in p53-/-Mice," American Journal of Pathology, vol. 162(1):343-352 (2003).

Tsujiuchi, T. et al., "Possible involvement of poly ADP-ribosylation in phenobarbital promotion of rat hepatocarcinogenesis," Carcinogenesis, vol. 11(10):1783-1787 (1990).

Tsujiuchi, T. et al., "Effects of 3-Aminobenzamide on Induction of Multiorgan Carcinogenesis by N-Nitrosobis(2-hydroxypropl)amine in Hamsters," Jpn. J. Cancer Res., vol. 82:793-799 (1991).

Tsujiuchi, T. et al., "Effects of 3-aminobenzamide on the post-initiation phase of N-nitrosobis(2-oxopropyl)amine induced pancreatic carcinogenesis in Syrian Hamsters," Cancer Letters, vol. 61:61-66 (1991).

Tsutsumi, M. et al., "Increased susceptibility of poly(ADP-ribose) polymerase-1 knockout mice to nitrosamine carcinogenicity," Carcinogenesis, vol. 22(1):1-3 (2001).

Veres, B. et al., "Regulation of Kinase Cascades and Transcription Factors by a Poly(ADP-Ribose) Polymerase-1 Inhibitor, 4-Hydroxyquinazoline, in Lipopolysaccharide-Induced Inflammation in Mice," JPET, vol. 310:247-255 (2004).

Virag et al., "Effects of poly(ADP-Ribose) Polymerase Inhibition of Inflammatory Cell Migration in a Murine Model of Asthma," Med. Sci. Monit., vol. 10:BR77-BR83 (2004).

Virag et al., "Peroxynitrite-induced thymocyte apoptosis: the role of caspases and poly(ADP-ribose) synthetase (PARP) activation," Immunol., vol. 94(3):345-355 (1998).

Virag et al., "The Therapeutic Potential of Poly(ADP-Ribose) Polymerase Inhibitors," Pharmacol. Rev., vol. 54:375-429 (2002).

Wang et al., "Apoptosis inducing factor and PARP-mediated injury in the MPTP mouse model of Parkinson's disease," Ann. N.Y. Acad. Sci., vol. 991:132-139 (2003).

Wawzonek et al., "Preparation and reactions of 4b-acetoxy-4b, 9b-dihydroindeno[2,1-a]indene-5,10-dione," Can. J. Chem., vol. 59:2833 (1981).

Wawzonek et al., "Synthesis of 6-substituted-6H-indeno[1,2-c]isoquinoline-5,11-diones," Org. Prep. Proc. Int., vol. 14:163-168 (1982).

Wawzonek et al., "The Synthesis and Reactions of 1-Carbamyl-11-ketoindeno[1,2-c]isoquinoline," J. Org. Chem., vol. 31:1004-1006 (1966).

White et al., "Resistance-modifying agents. 9. Synthesis and biological properties of benzimidazole inhibitors of the DNA repair enzyme poly(ADP-ribose) polymerase," J. Med. Chem., vol. 43:4084-4097 (2000).

Winters et al., "Synthesis and biological activities of some indolo[2. 3-c]isoquinoline derivatives," Farmaco. Ed. Sci., vol. 34(6):507-517 (1979).

Woolley, S. et al., "Role of Poly (ADP) Ribose Synthetase in Lung Ischemia-Reperfusion Injury," J. Heart Lung Transplant, vol. 23:1290-1296 (2004).

Xiao, C. et al., "Poly(ADP-Ribose) Polymerase Promotes Cardiac Remodeling, Contractile Failure, and Translocation of Apoptosis-Inducing Factor in Murine Experimental of Aortic Banding and Heart Failure," JPET, vol. 312(3):891-898 (2005).

Yamaguchi et al., "The synthesis of benzofuroquinolines. X. Some benzofuro[3,2-c]isoquinoline derivatives," J. Hetercycl. Chem., vol. 32(5):1517-1519 (1995).

Yamaguchi et al., "The Synthesis of Benzofuroquinolines. IX. A Benzofuroisoquinolinone and a Benzofuroisocoumarin," J. Hetercycl. Chem., vol. 32(2):419-423 (1995).

Zhang, J., "Beneficial effect of GPI 6150 treatment in multiple animal models of disease," PARP as a Therapeutic Agent, CRC Press, Boca Raton, FL., pp. 239-256 (2002).

Zhang et al., "GPI 6150 prevents H(2)O(2) cytotoxicity by inhibiting poly(ADP-ribose) polymerase," Biochem. Biophys. Res. Commun., vol. 278:590-598 (2000).

Zheng, J. et al., "Poly (ADP-Ribose) Polymerase-1 gene ablation protects mice from ischemic renal injury," Am. J. Physiol., vol. 288:F387-F398 (2004).

Zheng, L. et al., "Poly(ADP-Ribose) Polymerase is Involved in the Development of Diabetic Retinopathy via Regulation of Nuclear Factor-K8," Diabetes, vol. 53:2960-2967 (2004).

International Search Report for Application No. PCT/US08/55361, dated Aug. 25, 2008.

Supplementary European Search Report for Application No. EP08731015, dated Sep. 9, 2010.

Abdelkarim et al., "Protective effects of PJ34, a novel, potent inhibitor of poly(ADP-ribose) polymerase (PARP) in in vitro and in vivo models of stroke," Int. J. Mol. Med., vol. 7:255-260 (2001).

Aldrich, Aldrich Chemical Company, p. 32 (1992).

Ando et al., "Cyclization reactions of 1,2-bis(2-cyanophenyl)propionitriles. II. Synthesis of 5-amino-4,7-dimethoxy-11H-indeno[1,2-c]isoquinolin-11-one," Bull. Chem. Soc. Japan, vol. 47:1014-1017 (1974).

Andrasi, T. et al., "Poly(ADP-ribose) polymerase inhibitor PJ-34 reduces mesenteric vascular injury induced by experimental cardiopulmonary bypass with cardiac arrest," Am. J. Physiol. Heart Circ. Physiol., vol. 288:H2972-H2978 (2005).

Banasik et al., "Inhibitors and activators of ADP-ribosylation reactions," Mol. Cell. Biochem., vol. 138:185-197 (1994).

Banasik et al., "Specific inhibitors of poly(ADP-ribose) synthetase and mono(ADP-ribosyl)transferase," J. Biol. Chem., vol. 267:1569-1575 (1992).

Beller, C. et al., "Poly(ADP-ribose) Polymerase Inhibition Combined with Irradiation: A Dual Treatment Concept to Prevent Neointimal Hyperplasia After Endarterectomy," Int. J. Radiation Oncology Biol. Phys., vol. 66(3):867-875 (2006).

Besson, V. et al., "Beneficial effect of PJ34 and INO-1001, two novel water-soluble poly(ADP-ribose) polymerase inhibitors, on the consequences of traumatic brain injury in rat," Brain Research, vol. 1041:149-156 (2005).

Black, J. et al., "Poly Adenosine Diphosphate-Ribose Polymerase Inhibitor PJ34 Abolishes Systemic Proinflammatory Responses to THoracic Aortic Ischemia and Reperfusion," J. Am. Coli. Surg., vol. 203:44-53 (2006).

Bloch et al., "The role of the 5'hydroxyl group adenosine in determining substrate specificity for adenosine deaminase," J. Med. Chem., vol. 10(5):908-912 (1967).

Boulares, A. et al., "Gene Knockout of Pharmacological Inhibition of Poly(ADP-Ribose) Polymerase-1 Prevents Lung Inflammation in a Murine Model of Asthma," Am. J. Respir. Cell Mol. Biol., vol. 28:322-329 (2003).

Bryant, Helen E. et al., "Specific killing of BRCA2-deficient tumours with inhibitors of poly(ADP-ribose) polymerase," Nature, vol. 434:913-917 (2005).

Burger's Medicinal Chemistry and Drug Discovery, 5th Edition, vol. 1, Principles and Practice, John Wiley and Sons, Inc., pp. 975-977 (1994).

Burkart, V. et al., "Mice lacking the poly(AdP-ribose) polymerase gene are resistant to pancreatic beta-cell destruction and diabetes development induced by streptozocin," Nature Medicine, vol. 5(3):314-319 (1999).

Calabrese, C. et al., "Anticancer Chemosensitization and Radiosensitization by the Novel Poly(ADP-ribose) Polymerase-1 Inhibitor AG14361," J. Natl. Cancer Inst., vol. 96:56-67 (2004).

Calabrese, C.R. et al., "Identification of potent nontoxic poly(ADP-ribose) polymerase-1 inhibitors: chemopotentiation and pharmacological studies," Clin. Cancer Res., vol. 9:2711-2718 (2003).

Canan Koch, S.S. et al., "Novel tricyclic poly(ADP-ribose) polymerase-1 inhibitors with potent anticancer chemopotentiating activity: design, synthesis, and X-ray cocrystal structure," J. Med. Chem., vol. 45:4961-4974 (2002).

Chatterjea et al., "Cyclisation of alpha-benzylhomophthalic acids," Experientia, vol. 16:439-440 (1960).

Chatterjea et al., "ON 4-Keto-3:4-Dihydroisocoumarin," J. Indian Chem. Soc., vol. 44(11):911-919 (1967).

Chatterjea, J.N. et al., "The Course of Cyclisation of alpha-Benzylhomophthalic Acids. Part I. A New Route to 2:3-6:7-Dibenzotropones," Journal of Indian Chem. Soc., vol. 37(7):379-391 (1960).

Chiang, S. et al., "Post-Treatment at 12 or 18 Hours with 3-Aminobenzamide Ameliorates Retinal Ischemia-Reperfusion Damage," Invest Ophthalmol. Vis. Sci., vol. 41:3210-3214 (2000).

Chiarugi, A. et al., "Novel isoquinolinone-derived inhibitors of poly(ADP-ribose) polymerase-1: pharmacological characterization and neuroprotective effects in an in vitro model of cerebral ischemia," J. Pharmacol. Exp. Ther., vol. 305:943-949 (2003).

Conde, C. et al., "Loss of poly (ADP-ribose) polymerase-1 causes increased tumour latency in p53-deficient mice," The EMBO Journal, vol. 20(13):3535-3543 (2001).

Cosi, C. et al., "New inhibitors of poly(ADP-ribose) polymerase and their potential therapeutic targets," Expert Opin. Ther. Patents, vol. 12(7):1047-1071 (2002).

Curtin, N.J., "PARP inhibitors for cancer therapy," Expert Reviews in Molecular Medicine, vol. 7:1-20 (2005).

Curtin, N., "PARP-1: A new target for cancer treatment," Cancer Research UK Scientific Yearbook, pp. 52-54 (2002-2003).

Cushman et al., "Synthesis of new indeno[1,2-c]isoquinolines: Cytotoxic non-camptothecin topoisomerase I inhibitors," J. Med. Chem., vol. 43(20):3688-3698 (2000).

Cuzzocrea, S. et al., "Beneficial effects of 3-aminobenzamide, an inhibitor of poly (ADP-ribose) synthetase in a rat model of splanchnic artery occlusion and reperfusion," British Journal of Pharmacology, vol. 121:1065-1074 (1997).

Demiryurek, A. et al., "Protective Effects of Poly (ADP-Ribose) Synthase Inhibitors on Digoxin-Induced Cardiotoxicity in Guinea-Pig Isolated Hearts," Pharmacological Reserach, vol. 45(3):189-194 (2002).

Dorland's Illustrated Medical Dictionary, 29th Edition, p. 650 (2000).

Dusemund et al., "5-hydroxyisoindolo[2,1b]isoquinolin-7-one: Synthesis and isomerization," Arch. Pharm. (Weinheim, Ger.), vol. 317:381-382 (1984).

Eliasson, M. et al., "Poly(ADP-ribose) polymerase gene disruption renders mice resistant to cerebral ischemia," Nature Medicine, vol. 3(10):1089-1095 (1997).

Farivar, A. et al., "Poly (ADP) Ribose Polymerase Inhibition Improves Rat Cardiac Allograft Survival," Ann. Thorac. Surg., vol. 80:950-956 (2005).

Farkas, B. et al., "Reduction of acute photodamage in skin by topical application of a novel PARP inhibitor," Biochemical Pharmacology, vol. 63:921-932 (2001).

Farmer, H. et al., "Targeting the DNA repair defect in BRCA mutant cells as a therapeutic strategy," Nature, vol. 434:917-921 (2005).

Faro, R. et al., "Myocardial protection by PJ34, a novel potent poly(ADP-ribose) synthetase inhibitor," Ann. Thorac. Surg., vol. 73:575-581 (2002).

Feng, Y. et al., "Drug-induced hypothermia begun 5 minutes after injury with a poly(adenosine 5'-diphosphate-ribose) polymerase inhibitor reduces hypoxia brain injury in rat pups," Crit. Care Med., vol. 30:2420-2424 (2002).

Ferraris, D. et al., "Design and synthesis of poly ADP-ribose polymerase-1 inhibitors. Part 4. Biological evaluation of aza-5[H]-phenanthridin-6-ones as potent, aqueous-soluble compounds for the treatment of ischemic injuries," J. Med. Chem, vol. 46:3138-3151 (2003).

Ferraris, D. et al., "Design and synthesis of poly(ADP-ribose) polymerase-1 (PARP-1) inhibitors. Part 4: biological evaluation of imidazobenzodiazepines as potent PARP-1 inhibitors for treatment of ischemic injuries," Bioorg. & Med. Chem., vol. 11:3695-3707 (2003).

Goldfarb, R.D. et al., "Protective effects of a novel, potent inhibitor of poly(adenosine 5'-diphosphate-ribose) synthetase in a porcine model of severe bacterial-sepsis," Crit. Care Med., vol. 30:974-980 (2002).

Graziani et al., "Clinical perspectives of PARP inhibitors," Pharmacological Research, vol. 52:109-118 (2005).

Griffin et al., "Resistance-modifying agents. 5. Synthesis and biological properties of quinazolinone inhibitors of the DNA repair enzyme poly(ADP-ribose) polymerase (PARP)," J. Med. Chem., vol. 41:5247-5256 (1998).

Grupp et al., "Protection against hypoxia-reoxygenation in the absence of poly(ADP-ribose) synthetase in isolated working hearts," J. Mol. Cell Cardiol., vol. 31:297-303 (1999).

Hakimelahi et al., "Ring Open Analogues of Adenine Nucleoside, Aminoacyl Derivatives of Cyclo- and Acyclonucleosides," Helvetica Chemica Acta, vol. 70:219-231 (1987).

Halmosi, R. et al., "Effect of Poly(ADP-Ribose) Polymerase Inhibitors on the Ischemia-Reperfusion-Induced Oxidative Cell Damage adn Mitochondrial Metabolism in L Angendorff Heart Perfusion System," Mol. Pharmcol., vol. 59:1497-1505 (2001).

Hattori, K. et al., "Rational approaches to discovery of orally active and brain-penetrable quinazolinone inhibitors of poly(ADP-ribose)polymerase," J. Med. Chem., vol. 47:4151-4154 (2004).

Herzog, A.G. et al., "Urinary incontinence: medical and psychosocial aspects," Annu. Rev. Gerontol. Geriatr., vol. 9:74-119 (1989).

Hiremath, et al., "A New Method for the Synthesis of 6H,11H-Indol[3,2-c]-isoquinolin-5-ones/thiones and their Reactions," J. Heterocyc. Chem., vol. 30(3):603-609 (1993).

Hiremath et al., "Synthesis of Substituted 7H-Indolo[2,3-c] isoquinolines," Indian Journal of Chemistry, Section B, vol. 24B(12):1235-1238 (1985).

Hiremath et al., "Synthesis and Biological Evaluation of Some Substituted 5H, 6H, 7H-Indolo[2,3-c] Isoquinolin-5-thiones and their Derivatives," Indian Journal of Heterciclic Chemistry, vol. 3(1):37-42 (1993).

* cited by examiner

INDENOISOQUINOLINONE ANALOGS AND METHODS OF USE THEREOF

1. REFERENCE TO RELATED APPLICATIONS

This application claims priority to U.S. Provisional Application No. 60/904,393, filed on Feb. 28, 2007, the disclosure of which is incorporated by reference herein in its entirety.

2. FIELD OF THE INVENTION

The present invention relates to Indenoisoquinolinone Analogs, compositions comprising an effective amount of an Indenoisoquinolinone Analog and methods for treating or preventing an inflammatory disease, a reperfusion injury, diabetes mellitus, a diabetic complication, reoxygenation injury resulting from organ transplantation, an ischemic condition, a neurodegenerative disease, renal failure, a vascular disease, a cardiovascular disease, cancer, a complication of prematurity, cardiomyopathy, retinopathy, nephropathy, neuropathy, erectile dysfunction or urinary incontinence, comprising administering to a subject in need thereof an effective amount of an Indenoisoquinolinone Analog.

3. BACKGROUND OF THE INVENTION

Erectile dysfunction ("ED") is a significant male-health issue. While estimating its prevalence is difficult, estimates range from about 15 million to 30 million sufferers worldwide.

The etiology of erectile dysfunction can be multiple, and can include mechanical trauma to the nerves (such as during prostatectomy), or it can be due to diabetes mellitus, cardiovascular diseases, induced by radiation, certain drugs, or advanced age.

Urinary incontinence affects people of all ages and levels of physical health, both in health care settings and in the community at large. Persons suffering from urinary incontinence can be predisposed to also having urinary-tract infections, pressure ulcers, perineal rashes and urosepsis. Psychosocially, urinary incontinence can be associated with embarrassment, social stigmatization, depression and a risk of institutionalization (Herzo et al., Annu. Rev. Gerontol. Geriatr. 9:74 (1989)).

An inflammatory disease, such as arthritis, colitis, and autoimmune diabetes, typically manifests itself as a disorder distinct from that associated with a reperfusion injury, e.g., stroke and heart attack, and can clinically manifest itself as a different entity. However, there can be common underlying mechanisms between these two types of disorders. Specifically, inflammatory disease and reperfusion injury can induce proinflammatory cytokine and chemokine synthesis which can, in turn, result in production of cytotoxic free radicals such as nitric oxide and superoxide. NO and superoxide can react to form peroxynitrite (ONOO$^-$) (Szabó et al., Shock 6:79-88, 1996).

The ONOO$^-$-induced cell necrosis observed in inflammatory disease and in reperfusion injury involves the activation of the nuclear enzyme poly (ADP-ribose) polymerase (PARP). Activation of PARP is thought to be an important step in the cell-mediated death observed in inflammation and reperfusion injury (Szabó al, Trends Pharmacol. Sci. 19:287-98, 1998).

A number of PARP inhibitors have been described in the art. See, e.g., Banasik et al., J. Biol. Chem., 267:1569-75, 1992, and Banasik et al., Mol. Cell. Biochem., 138:185-97, 1994; WO 00/39104; WO 00/39070; WO 99/59975; WO 99/59973; WO 99/11649; WO 99/11645; WO 99/11644; WO 99/11628; WO 99/11623; WO 99/11311; WO 00/42040; Zhang et al., Biochem. Biophys. Res. Commun., 278:590-98, 2000; White et al, J. Med. Chem., 43:4084-4097, 2000; Griffin et al., J. Med. Chem., 41:5247-5256, 1998; Shinkwin et al., Bioorg. Med. Chem., 7:297-308, 1999; and Soriano et al., Nature Medicine, 7:108-113, 2001. Adverse effects associated with administration of PARP inhibitors have been discussed in Milan et al., Science, 223:589-591, 1984.

Indenoisoquinolinone compounds have been previously discussed in the art. For example, cytotoxic non-camptothecin topoisomerase I inhibitors are reported in Cushman et al., J. Med. Chem., 43:3688-3698, 2300 and Cushman et al., J. Med. Chem. 42:446-57, 1999; indeno[1,2-c]isoquinolines are reported as antineoplastic agents in Cushman et al., WO 00/21537; and as neoplasm inhibitors in Hrbata et al., WO 93/05023.

Syntheses of indenoisoquinolinone compounds have been reported. For example, see Wawzonek et al., Org. Prep. Proc. Int., 14:163-8, 1982; Wawzonek et al., Can. J. Chem., 59:2833, 1981; Andoi et al, Bull. Chem. Soc. Japan, 47:1014-17, 1974; Dusemund et al., Arch. Pharm (Weinheim, Ger.), 3 17:381-2, 1984; and Lal et al., Indian J. Chem., Sect. B, 38B:33-39, 1999.

There remains, however, a need in the art for compounds useful for treating or preventing an inflammatory disease, a reperfusion injury, diabetes mellitus, a diabetic complication, reoxygenation injury resulting from organ transplantation, an ischemic condition, a neurodegenerative disease, renal failure, a vascular disease, a cardiovascular disease, cancer, a complication of prematurity, cardiomyopathy, retinopathy, nephropathy, neuropathy, erectile dysfunction or urinary incontinence.

Citation of any reference in Section 3 of this application is not an admission that the reference is prior art.

4. SUMMARY OF THE INVENTION

In one aspect the invention provides a compound of Formula (Ia)

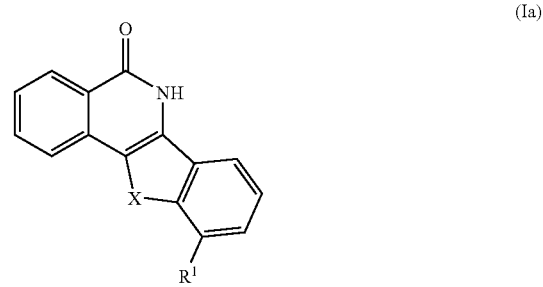

(Ia)

and pharmaceutically acceptable salts thereof,
wherein
X is —N($C_1$-$C_4$ alkyl)-, —CH(OH)—, —N(C(O)N(H)—($CH_2$)$_p$—Z)— or —N(($CH_2$)$_q$—Z)—;
$R^1$ is —($CH_2$)$_n$—N($R^2$)($R^2$) or —O—($CH_2$)$_m$—N($R^2$)($R^2$);
each $R^2$ is independently —H, —$C_1$-$C_6$ alkyl, —$C_3$-$C_8$ monocyclic cycloalkyl, —$C_1$-$C_6$ alkylene phenyl, phenyl, an N-terminal alpha amino acid residue, an N-terminal alpha amino hydroxymethyl residue, a $C_1$-$C_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —C$_1$-C$_6$ alkyl, —O—C$_1$-C$_6$ alkyl, —C$_3$-C$_8$ monocyclic cycloalkyl, a 3- to 7-membered monocyclic heterocycle, —(C$_1$-C$_6$ alkyl-substituted) 3- to 7-membered monocyclic heterocycle, or —N(Z$_3$)(Z$_4$), where Z$_3$ and Z$_4$ are independently —H, —C$_1$-C$_5$ alkyl, —(C$_1$-C$_5$ alkylene)-O—C$_1$-C$_5$ alkyl, benzyl, or —C$_3$-C$_8$ monocyclic cycloalkyl, each of which other than hydrogen is independently unsubstituted or substituted with one or more of -halo, —OH, —N(R$^a$)$_2$, —(C$_1$-C$_5$ alkylene)-O—C$_1$-C$_5$ alkyl, —NH$_2$, a nitrogen-containing 3- to 7-membered monocyclic heterocycle, or a —(C$_1$-C$_6$ alkyl-substituted) nitrogen-containing 3- to 7-membered monocyclic heterocycle, wherein each occurrence of R$^a$ is independently —H, benzyl, or —C$_1$-C$_{10}$ alkyl; or N, Z$_3$ and Z$_4$ are taken together to form a nitrogen-containing 3- to 7-membered monocyclic heterocycle which is unsubstituted or substituted with one or more of —C$_1$-C$_5$ alkyl, phenyl, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —(C$_1$-C$_5$ alkylene)-C(O)O—(C$_1$-C$_5$ alkylene)-N(R$^a$)$_2$, —COOH, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, benzyl, or —C$_1$-C$_{10}$ alkyl; or N and both R$^a$ groups are taken together to form a nitrogen-containing 3- to 7-membered monocyclic heterocycle;

or N and both R$^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —C$_1$-C$_5$ alkyl, —C$_3$-C$_8$ monocyclic cycloalkyl, phenyl, a nitrogen-containing 3- to 7-membered monocyclic heterocycle, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —C$_1$-C$_5$ alkylene-C(O)O—(C$_1$-C$_5$ alkylene)-N(R$^a$)$_2$, —COOH, —(C$_1$-C$_5$ alkylene)-O—C$_1$-C$_5$ alkyl, —(C$_1$-C$_5$ alkylene)-C$_3$-C$_8$ monocyclic cycloalkyl, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, -benzyl, —C$_1$-C$_{10}$ alkyl; or N and both R$^a$ groups are taken together to form a nitrogen-containing 3- to 7-membered monocyclic heterocycle;

Z is —CF$_3$, —F, —OH or —O—CH$_3$;

n is an integer ranging from 1 to 10;

m is an integer ranging from 2 to 10;

p is an integer ranging from 1 to 5; and q is an integer ranging from 1 to 5.

In one aspect the invention provides a compound of Formula (Ib)

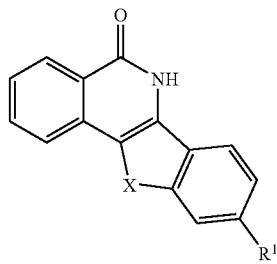

(Ib)

and pharmaceutically acceptable salts thereof, wherein

X is —N(C$_1$-C$_4$ alkyl)-, —CH(OH)—, —N(C(O)N(H)—(CH$_2$)$_p$—Z)— or —N((CH$_2$)$_q$—Z)—;

R$^1$ is —(CH$_2$)$_n$—N(R$^2$)(R$^2$) or —O—(CH$_2$)$_m$—N(R$^2$)(R$^2$);

each R$^2$ is independently —H, —C$_1$-C$_6$ alkyl, —C$_3$-C$_8$ monocyclic cycloalkyl, —C$_1$-C$_6$ alkylene phenyl, phenyl, an N-terminal alpha amino acid residue, an N-terminal alpha amino hydroxymethyl residue, a C$_1$-C$_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —C$_1$-C$_6$ alkyl, —O—C$_1$-C$_6$ alkyl, —C$_3$-C$_8$ monocyclic cycloalkyl, a 3- to 7-membered monocyclic heterocycle, —(C$_1$-C$_6$ alkyl-substituted) 3- to 7-membered monocyclic heterocycle, or —N(Z$_3$)(Z$_4$), where Z$_3$ and Z$_4$ are independently —H, —C$_1$-C$_5$ alkyl, —(C$_1$-C$_5$ alkylene)-O—C$_1$-C$_5$ alkyl, benzyl, or —C$_3$-C$_8$ monocyclic cycloalkyl, each of which other than hydrogen is independently unsubstituted or substituted with one or more of -halo, —OH, —N(R$^a$)$_2$, —(C$_1$-C$_5$ alkylene)-O—C$_1$-C$_5$ alkyl, —NH$_2$, a nitrogen-containing 3- to 7-membered monocyclic heterocycle, or a —(C$_1$-C$_6$ alkyl-substituted) nitrogen-containing 3- to 7-membered monocyclic heterocycle, wherein each occurrence of R$^a$ is independently —H, benzyl, or —C$_1$-C$_{10}$ alkyl; or N, Z$_3$ and Z$_4$ are taken together to form a nitrogen-containing 3- to 7-membered monocyclic heterocycle which is unsubstituted or substituted with one or more of —C$_1$-C$_5$ alkyl, phenyl, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —(C$_1$-C$_5$ alkylene)-C(O)O—(C$_1$-C$_5$ alkylene)-N(R$^a$)$_2$, —COOH, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, benzyl, or —C$_1$-C$_{10}$ alkyl; or N and both R$^a$ groups are taken together to form a nitrogen-containing 3- to 7-membered monocyclic heterocycle;

or N and both R$^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —C$_1$-C$_5$ alkyl, —C$_3$-C$_8$ monocyclic cycloalkyl, phenyl, a nitrogen-containing 3- to 7-membered monocyclic heterocycle, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-

$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene-C(O)O—($C_1$-$C_5$ alkylene)-N($R^a$)$_2$, —COOH, —($C_1$-$C_5$ alkylene)-O—$C_1$-$C_5$ alkyl, —($C_1$-$C_5$ alkylene)-$C_3$-$C_8$ monocyclic cycloalkyl, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, —$C_1$-$C_{10}$ alkyl; or N and both $R^a$ groups are taken together to form a nitrogen-containing 3- to 7-membered monocyclic heterocycle;

Z is —CF$_3$, —F, —OH or —O—CH$_3$;
n is an integer ranging from 1 to 10;
m is an integer ranging from 2 to 10;
p is an integer ranging from 1 to 5; and
q is an integer ranging from 1 to 5.

In one aspect the invention provides a compound of Formula (Ic)

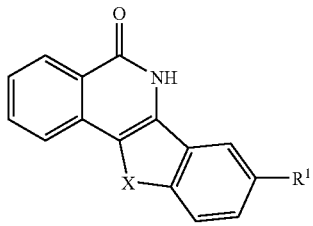

(Ic)

and pharmaceutically acceptable salts thereof,
wherein
X is —N($C_1$-$C_4$ alkyl)-, —CH(OH)—, —N(C(O)N(H)—(CH$_2$)$_p$—Z)— or —N((CH$_2$)$_q$—Z)—;
$R^1$ is —(CH$_2$)$_n$—N($R^2$)($R^2$) or —O—(CH$_2$)$_m$—N($R^2$)($R^2$);
each $R^2$ is independently —H, —$C_1$-$C_6$ alkyl, —$C_3$-$C_8$ monocyclic cycloalkyl, —$C_1$-$C_6$ alkylene phenyl, phenyl, an N-terminal alpha amino acid residue, an N-terminal alpha amino hydroxymethyl residue, a $C_1$-$C_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$), where $Z_3$ and $Z_4$ are independently —H, —$C_1$-$C_5$ alkyl, ($C_1$-$C_5$ alkylene)-O—$C_1$-$C_5$ alkyl, benzyl, or —$C_3$-$C_8$ monocyclic cycloalkyl, each of which other than hydrogen is independently unsubstituted or substituted with one or more of -halo, —OH, —N($R^a$)$_2$, —($C_1$-$C_5$ alkylene)-O—$C_1$-$C_5$ alkyl, —NH$_2$, a nitrogen-containing 3- to 7-membered monocyclic heterocycle, or a —($C_1$-$C_6$ alkyl-substituted) nitrogen-containing 3- to 7-membered monocyclic heterocycle, wherein each occurrence of $R^a$ is independently —H, benzyl, or —$C_1$-$C_{10}$ alkyl; or N, $Z_3$ and $Z_4$ are taken together to form a nitrogen-containing 3- to 7-membered monocyclic heterocycle which is unsubstituted or substituted with one or more of —$C_1$-$C_5$ alkyl, phenyl, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —($C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, benzyl, or —$C_1$-$C_{10}$ alkyl; or N and both $R^a$ groups are taken together to form a nitrogen-containing 3- to 7-membered monocyclic heterocycle;

or N and both $R^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —$C_1$-$C_5$ alkyl, —$C_3$-$C_8$ monocyclic cycloalkyl, phenyl, a nitrogen-containing 3- to 7-membered monocyclic heterocycle, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene-C(O)O—($C_1$-$C_5$ alkylene)-N($R^a$)$_2$, —COOH, —($C_1$-$C_5$ alkylene)-O—$C_1$-$C_5$ alkyl, —($C_1$-$C_5$ alkylene)-$C_3$-$C_8$ monocyclic cycloalkyl, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, —$C_1$-$C_{10}$ alkyl; or N and both $R^a$ groups are taken together to form a nitrogen-containing 3- to 7-membered monocyclic heterocycle;

Z is —CF$_3$, —F, —OH or —O—CH$_3$;
n is an integer ranging from 1 to 10;
m is an integer ranging from 2 to 10;
p is an integer ranging from 1 to 5; and
q is an integer ranging from 1 to 5.

In another aspect the invention provides a compound of Formula (IIa)

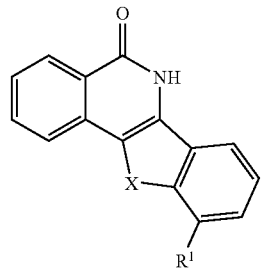

(IIa)

and pharmaceutically acceptable salts thereof;

wherein
X is —CH$_2$—, —O—, —C(O)—, —CH(OH)—, —NH—, —N(C$_1$-C$_4$ alkyl)- or —S—;
R$^1$ is —(CH$_2$)$_n$—N(R$^2$)(R$^3$) or

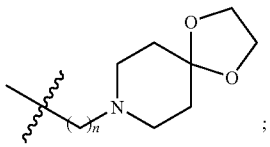

R$^2$ is —H, —C$_1$-C$_6$ alkyl, or —C$_3$-C$_8$ monocyclic cycloalkyl;
R$^3$ is —C(O)—(C$_1$-C$_6$ alkylene)-(3- to 7-membered monocyclic heterocycle), a nitrogen-containing 3- to 7-membered monocyclic heterocycle which is substituted with one or more of —C(O)O—C$_1$-C$_6$ alkyl, or —C$_3$-C$_8$ monocyclic cycloalkyl which is substituted with one or more of (hydroxy-substituted) C$_1$-C$_5$ alkyl groups;
or N, R$^2$ and R$^3$ are taken together to form a nitrogen-containing 3- to 7-membered monocyclic heterocycle, which is substituted with one or more of —C$_2$-C$_6$ alkenyl, —C(O)—C$_1$-C$_6$ alkyl, —(C$_1$-C$_4$ alkylene)-C(O)—(C$_3$-C$_8$ monocyclic cycloalkyl), —C$_7$-C$_{10}$ alkyl, —(C$_1$-C$_5$ alkylene)-C(H)(—O—C$_1$-C$_4$ alkyl)$_2$, -(cyano-substituted) C$_1$-C$_5$ alkyl, —(C$_1$-C$_5$ alkylene)-C(O)-(nitrogen-containing 3- to 7-membered monocyclic heterocycle) or —(C$_1$-C$_5$ alkylene)-(3- to 7-membered monocyclic heterocycle) groups; and
an n is an integer ranging from 1 to 10.

In another aspect the invention provides a compound of Formula (IIb)

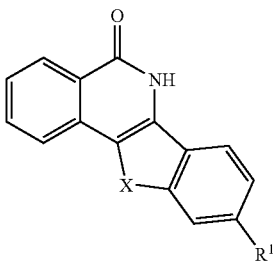

(IIb)

and pharmaceutically acceptable salts thereof,
wherein
X is —CH$_2$—, —O—, —C(O)—, —CH(OH)—, —NH—, —N(C$_1$-C$_4$ alkyl)- or —S—;
R$^1$ is —(CH$_2$)$_n$—N(R$^2$)(R$^3$) or

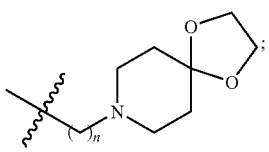

R$^2$ is —H, —C$_1$-C$_6$ alkyl, or —C$_3$-C$_8$ monocyclic cycloalkyl;
R$^3$ is —C(O)—(C$_1$-C$_6$ alkylene)-(3- to 7-membered monocyclic heterocycle), a nitrogen-containing 3- to 7-membered monocyclic heterocycle which is substituted with one or more of —C(O)O—C$_1$-C$_6$ alkyl, or —C$_3$-C$_8$ monocyclic cycloalkyl which is substituted with one or more of (hydroxy-substituted) C$_1$-C$_5$ alkyl groups;
or N, R$^2$ and R$^3$ are taken together to form a nitrogen-containing 3- to 7-membered monocyclic heterocycle, which is substituted with one or more of —C$_2$-C$_6$ alkenyl, —C(O)—C$_1$-C$_6$ alkyl, —(C$_1$-C$_4$ alkylene)-C(O)—(C$_3$-C$_8$ monocyclic cycloalkyl), —C$_7$-C$_{10}$ alkyl, —(C$_1$-C$_5$ alkylene)-C(H)(—O—C$_1$-C$_4$ alkyl)$_2$, -(cyano-substituted) C$_1$-C$_5$ alkyl, —(C$_1$-C$_5$ alkylene)-C(O)— (nitrogen-containing 3- to 7-membered monocyclic heterocycle) or —(C$_1$-C$_5$ alkylene)-(3- to 7-membered monocyclic heterocycle) groups; and
an n is an integer ranging from 1 to 10.

In another aspect the invention provides a compound of Formula (IIc)

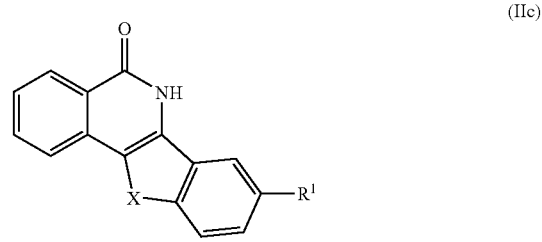

(IIc)

and pharmaceutically acceptable salts thereof,
wherein
X is —CH$_2$—, —O—, —C(O)—, —CH(OH)—, —NH—, —N(C$_1$-C$_4$ alkyl)- or —S—;
R$^1$ is —(CH$_2$)$_n$—N(R$^2$)(R$^3$) or

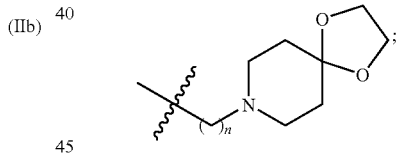

R$^2$ is —H, —C$_1$-C$_6$ alkyl, or —C$_3$-C$_8$ monocyclic cycloalkyl;
R$^3$ is —C(O)—(C$_1$-C$_6$ alkylene)-(3- to 7-membered monocyclic heterocycle), a nitrogen-containing 3- to 7-membered monocyclic heterocycle which is substituted with one or more of —C(O)O—C$_1$-C$_6$ alkyl, or —C$_3$-C$_8$ monocyclic cycloalkyl which is substituted with one or more of (hydroxy-substituted) C$_1$-C$_5$ alkyl groups;
or N, R$^2$ and R$^3$ are taken together to form a nitrogen-containing 3- to 7-membered monocyclic heterocycle, which is substituted with one or more of —C$_2$-C$_6$ alkenyl, —C(O)—C$_1$-C$_6$ alkyl, —(C$_1$-C$_4$ alkylene)-C(O)—(C$_3$-C$_8$ monocyclic cycloalkyl), —C$_7$-C$_{10}$ alkyl, —(C$_1$-C$_5$ alkylene)-C(H)(—O—C$_1$-C$_4$ alkyl)$_2$, -(cyano-substituted) C$_1$-C$_5$ alkyl, —(C$_1$-C$_5$ alkylene)-C(O)— (nitrogen-containing 3- to 7-membered monocyclic heterocycle) or —(C$_1$-C$_5$ alkylene)-(3- to 7-membered monocyclic heterocycle) groups; and
an n is an integer ranging from 1 to 10.

In one aspect, the invention provides the following Indenoisoquinolinone Analogs according to Formula (IIIa) as set forth below:

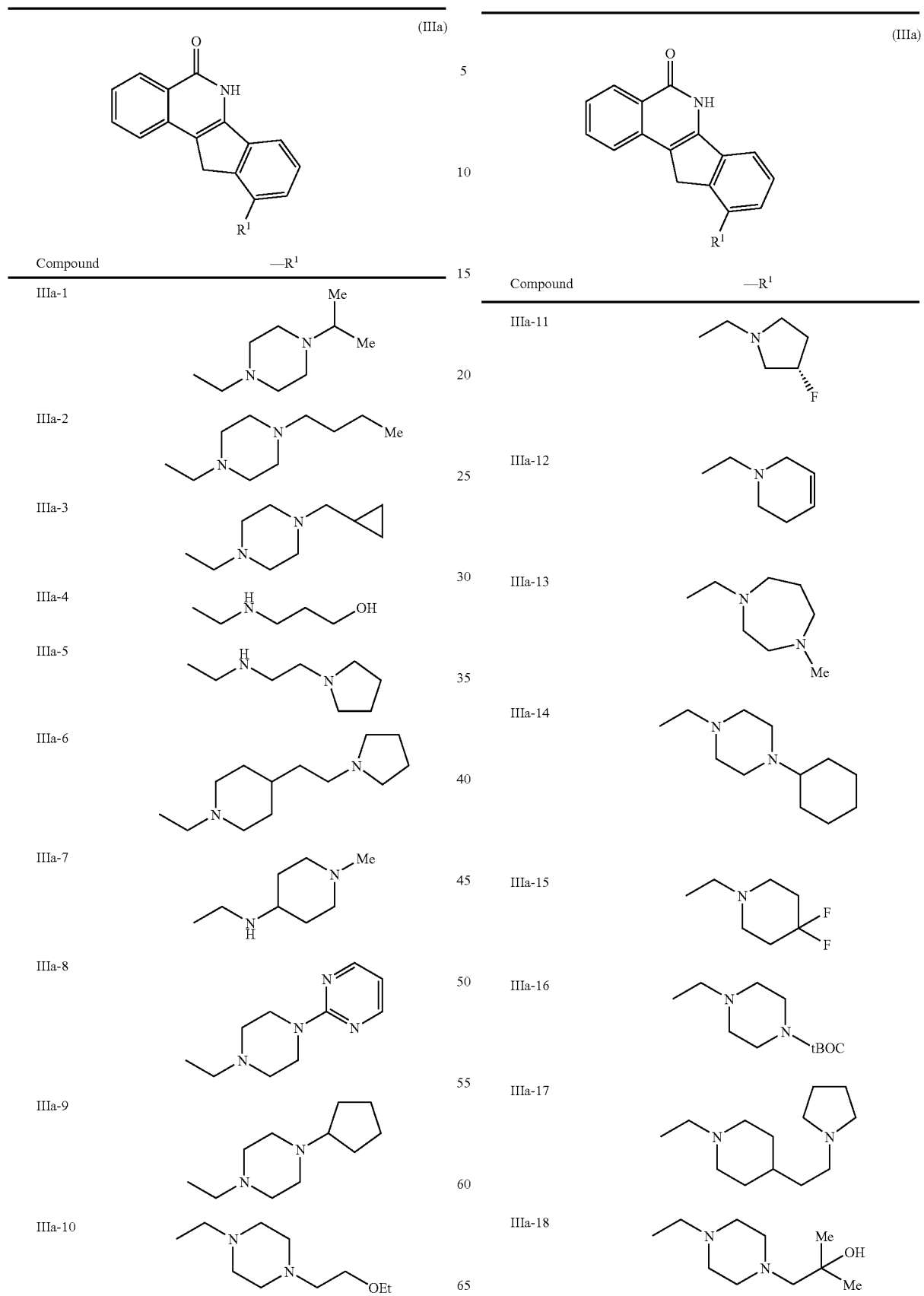

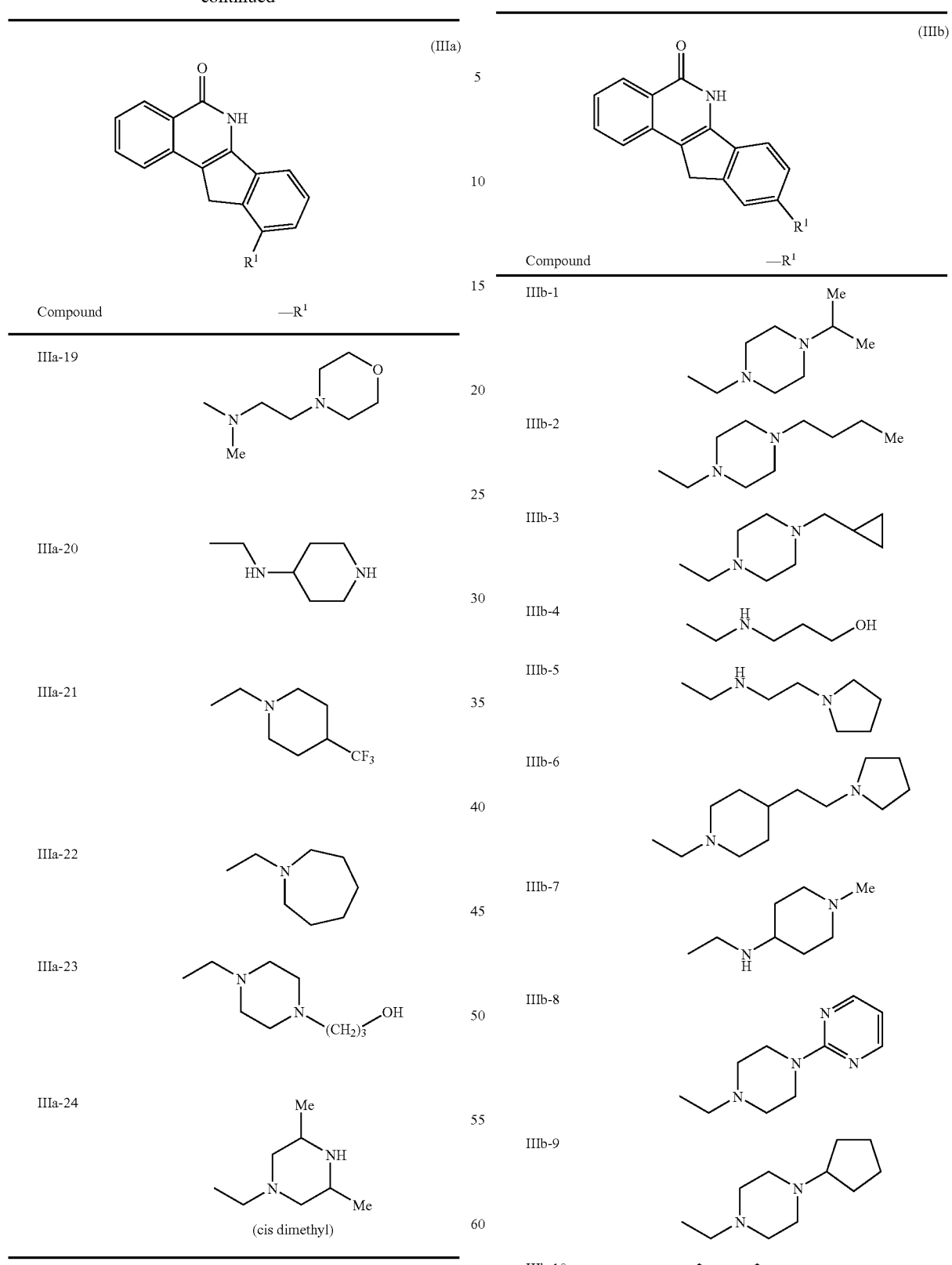
and pharmaceutically acceptable salts thereof.
In another aspect, the invention provides the following Indenoisoquinolinone Analogs according to Formula (IIIb) as set forth below:

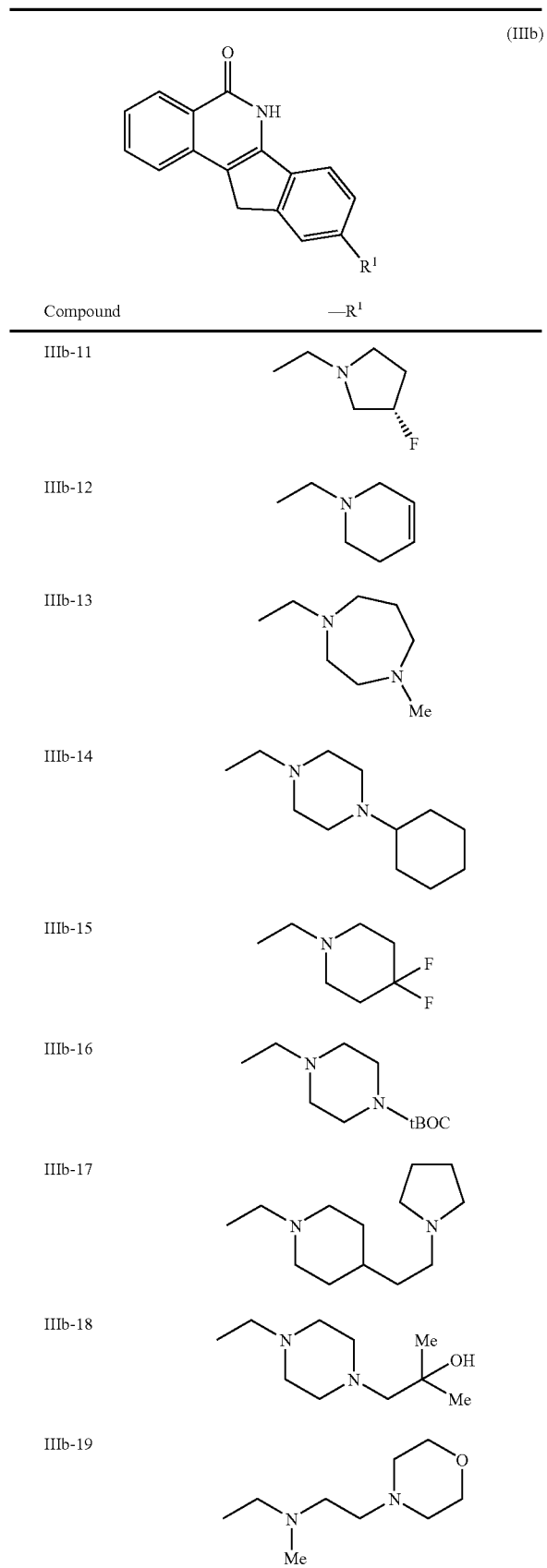

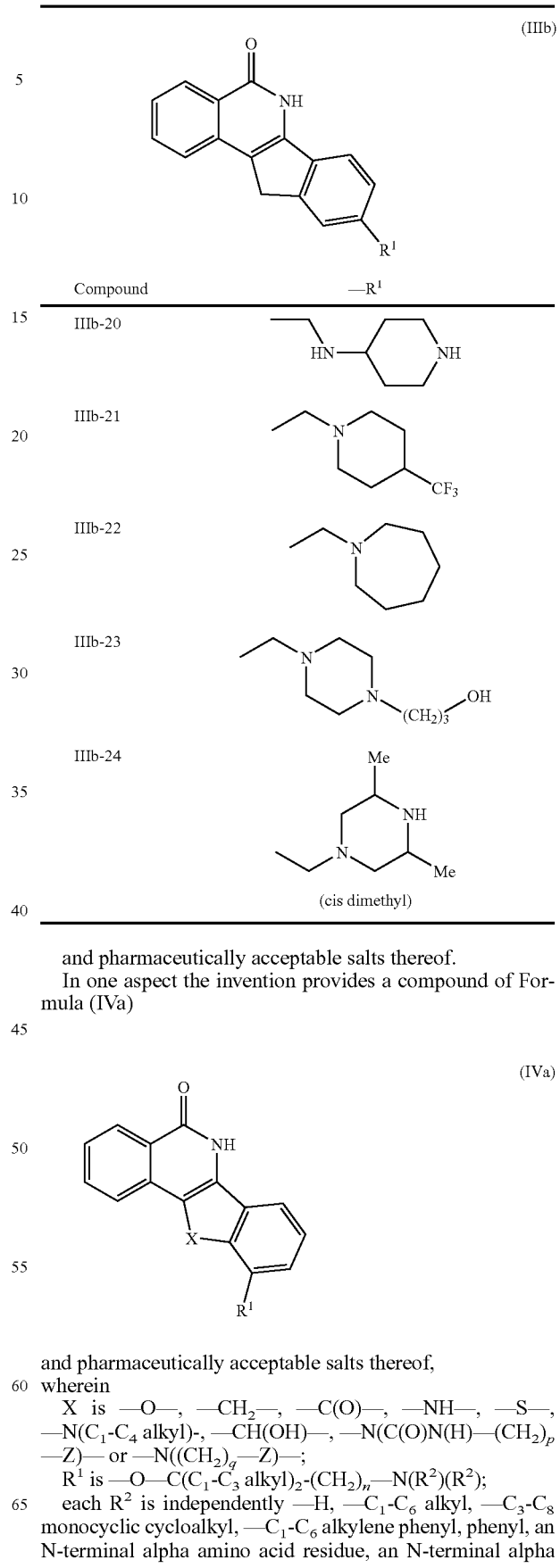

and pharmaceutically acceptable salts thereof.

In one aspect the invention provides a compound of Formula (IVa)

and pharmaceutically acceptable salts thereof, wherein

X is —O—, —CH$_2$—, —C(O)—, —NH—, —S—, —N(C$_1$-C$_4$ alkyl)-, —CH(OH)—, —N(C(O)N(H)—(CH$_2$)$_p$—Z)— or —N((CH$_2$)$_q$—Z)—;

R$^1$ is —O—C(C$_1$-C$_3$ alkyl)$_2$-(CH$_2$)$_n$—N(R$^2$)(R$^2$);

each R$^2$ is independently —H, —C$_1$-C$_6$ alkyl, —C$_3$-C$_8$ monocyclic cycloalkyl, —C$_1$-C$_6$ alkylene phenyl, phenyl, an N-terminal alpha amino acid residue, an N-terminal alpha amino hydroxymethyl residue, a $C_1$-$C_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$), where $Z_3$ and $Z_4$ are independently —H, —$C_1$-$C_5$ alkyl, —($C_1$-$C_5$ alkylene)-O—$C_1$-$C_5$ alkyl, benzyl, or —$C_3$-$C_8$ monocyclic cycloalkyl, each of which other than hydrogen is independently unsubstituted or substituted with one or more of -halo, —OH, —N($R^a$)$_2$, —($C_1$-$C_5$ alkylene)-O—$C_1$-$C_5$ alkyl, —NH$_2$, a nitrogen-containing 3- to 7-membered monocyclic heterocycle, or a —($C_1$-$C_6$ alkyl-substituted) nitrogen-containing 3- to 7-membered monocyclic heterocycle, wherein each occurrence of $R^a$ is independently —H, benzyl, or —$C_1$-$C_{10}$ alkyl; or N, $Z_3$ and $Z_4$ are taken together to form a nitrogen-containing 3- to 7-membered monocyclic heterocycle which is unsubstituted or substituted with one or more of —$C_1$-$C_5$ alkyl, phenyl, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —($C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, benzyl, or —$C_1$-$C_{10}$ alkyl; or N and both $R^a$ groups are taken together to form a nitrogen-containing 3- to 7-membered monocyclic heterocycle;

or N and both $R^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —$C_1$-$C_5$ alkyl, —$C_3$-$C_8$ monocyclic cycloalkyl, phenyl, a nitrogen-containing 3- to 7-membered monocyclic heterocycle, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, —$C_1$-$C_{10}$ alkyl; or N and both $R^a$ groups are taken together to form a nitrogen-containing 3- to 7-membered monocyclic heterocycle;

Z is —CF$_3$, —F, —OH or —O—CH$_3$;

n is an integer ranging from 1 to 10;

p is an integer ranging from 1 to 5; and q is an integer ranging from 1 to 5.

In one aspect the invention provides a compound of Formula (IVb)

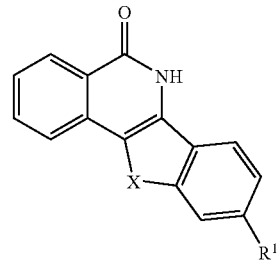

(IVb)

and pharmaceutically acceptable salts thereof, wherein

X is —O—, —CH$_2$—, —C(O)—, —NH—, —S—, —N($C_1$-$C_4$ alkyl)-, —CH(OH)—, —N(C(O)N(H)—(CH$_2$)$_p$Z)— or —N((CH$_2$)$_q$—Z)—;

$R^1$ is —O—C($C_1$-$C_3$ alkyl)$_2$-(CH$_2$)$_n$—N($R^2$)($R^2$);

each $R^2$ is independently —H, —$C_1$-$C_6$ alkyl, —$C_3$-$C_8$ monocyclic cycloalkyl, —$C_1$-$C_6$ alkylene phenyl, phenyl, an N-terminal alpha amino acid residue, an N-terminal alpha amino hydroxymethyl residue, a $C_1$-$C_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$), where $Z_3$ and $Z_4$ are independently —H, —$C_1$-$C_5$ alkyl, —($C_1$-$C_5$ alkylene)-O—$C_1$-$C_5$ alkyl, benzyl, or —$C_3$-$C_8$ monocyclic cycloalkyl, each of which other than hydrogen is independently unsubstituted or substituted with one or more of -halo, —OH, —N($R^a$)$_2$, —($C_1$-$C_5$ alkylene)-O—$C_1$-$C_5$ alkyl, —NH$_2$, a nitrogen-containing 3- to 7-membered monocyclic heterocycle, or a —($C_1$-$C_6$ alkyl-substituted) nitrogen-containing 3- to 7-membered monocyclic heterocycle, wherein each occurrence of $R^a$ is independently —H, benzyl, or —$C_1$-$C_{10}$ alkyl; or N, $Z_3$ and $Z_4$ are taken together to form a nitrogen-containing 3- to 7-membered monocyclic heterocycle which is unsubstituted or substituted with one or more of —$C_1$-$C_5$ alkyl, phenyl, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —($C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, benzyl, or —$C_1$-$C_{10}$ alkyl; or N and both $R^a$ groups are taken together to form a nitrogen-containing 3- to 7-membered monocyclic heterocycle;

or N and both $R^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —$C_1$-$C_5$ alkyl, —$C_3$-$C_8$ monocyclic cycloalkyl, phenyl, a nitrogen-containing 3- to 7-membered monocyclic heterocycle, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-

$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene-C(O)O—($C_1$-$C_5$ alkylene)-N($R^a$)$_2$, —COOH, —($C_1$-$C_5$ alkylene)-O—$C_1$-$C_5$ alkyl, —($C_1$-$C_5$ alkylene)-$C_3$-$C_8$ monocyclic cycloalkyl, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, —$C_1$-$C_{10}$ alkyl; or N and both $R^a$ groups are taken together to form a nitrogen-containing 3- to 7-membered monocyclic heterocycle;

Z is —CF$_3$, —F, —OH or —O—CH$_3$;

n is an integer ranging from 1 to 10;

p is an integer ranging from 1 to 5; and q is an integer ranging from 1 to 5.

In one aspect the invention provides a compound of Formula (IVc)

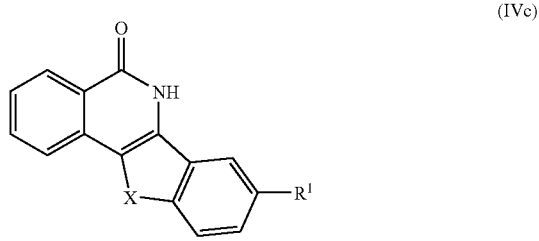

(IVc)

and pharmaceutically acceptable salts thereof,
wherein

X is —O—, —CH$_2$—, —C(O)—, —NH—, —S—, —N($C_1$-$C_4$ alkyl)-, —CH(OH)—, —N(C(O)N(H)—(CH$_2$)$_p$—Z)— or —N((CH$_2$)$_q$—Z)—;

$R^1$ is —O—C($C_1$-$C_3$ alkyl)$_2$-(CH$_2$)$_n$—N($R^2$)($R^2$);

each $R^2$ is independently —H, —$C_1$-$C_6$ alkyl, —$C_3$-$C_8$ monocyclic cycloalkyl, —$C_1$-$C_6$ alkylene phenyl, phenyl, an N-terminal alpha amino acid residue, an N-terminal alpha amino hydroxymethyl residue, a $C_1$-$C_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$), where $Z_3$ and $Z_4$ are independently —H, —$C_1$-$C_5$ alkyl, —($C_1$-$C_5$ alkylene)-O—$C_1$-$C_5$ alkyl, benzyl, or —$C_3$-$C_8$ monocyclic cycloalkyl, each of which other than hydrogen is independently unsubstituted or substituted with one or more of -halo, —OH, —N($R^a$)$_2$, —($C_1$-$C_5$ alkylene)-O—$C_1$-$C_5$ alkyl, —NH$_2$, a nitrogen-containing 3- to 7-membered monocyclic heterocycle, or a —($C_1$-$C_6$ alkyl-substituted) nitrogen-containing 3- to 7-membered monocyclic heterocycle, wherein each occurrence of $R^a$ is independently —H, benzyl, or —$C_1$-$C_{10}$ alkyl; or N, $Z_3$ and $Z_4$ are taken together to form a nitrogen-containing 3- to 7-membered monocyclic heterocycle which is unsubstituted or substituted with one or more of —$C_1$-$C_5$ alkyl, phenyl, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, benzyl, or —$C_1$-$C_{10}$ alkyl; or N and both $R^a$ groups are taken together to form a nitrogen-containing 3- to 7-membered monocyclic heterocycle;

or N and both $R^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —$C_1$-$C_5$ alkyl, —$C_3$-$C_8$ monocyclic cycloalkyl, phenyl, a nitrogen-containing 3- to 7-membered monocyclic heterocycle, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene-C(O)O—($C_1$-$C_5$ alkylene)-N($R^a$)$_2$, —COOH, —($C_1$-$C_5$ alkylene)-O—$C_1$-$C_5$ alkyl, —($C_1$-$C_5$ alkylene)-$C_3$-$C_8$ monocyclic cycloalkyl, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, —$C_1$-$C_{10}$ alkyl; or N and both $R^a$ groups are taken together to form a nitrogen-containing 3- to 7-membered monocyclic heterocycle;

Z is —CF$_3$, —F, —OH or —O—CH$_3$;

n is an integer ranging from 1 to 10;

p is an integer ranging from 1 to 5; and q is an integer ranging from 1 to 5.

In one aspect, the invention provides a compound of Formula (Va)

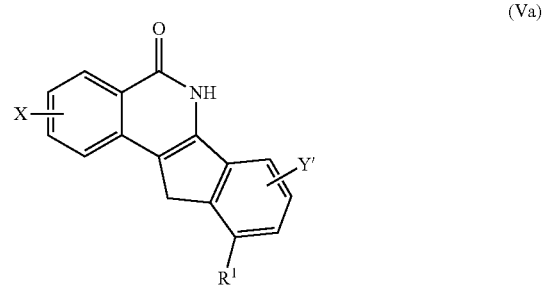

(Va)

and pharmaceutically acceptable salts thereof,
wherein $R^1$ is —CH$_2$NH—$R^2$;

$R^2$ is a —$C_3$-$C_8$ monocyclic cycloalkyl which is unsubstituted or substituted with one or more of -(hydroxy-substituted) $C_1$-$C_5$ alkyl; or a 3- to 7-membered monocyclic heterocycle;

X is halo or —H; and

Y' is halo or —H, wherein at least one of X and Y' is halo.

The invention provides compositions comprising an effective amount of a compound of Formula (Ia), (Ib), (Ic), (IIa), (IIb), (IIc), (IIIa), (IIIb), (IVa), (IVb), (IVc), (Va), or a pharmaceutically acceptable salt thereof and a physiologically acceptable carrier or vehicle.

The invention further provides methods for treating or preventing an inflammatory disease, a reperfusion injury, diabetes mellitus, a diabetic complication, reoxygenation injury resulting from organ transplantation, an ischemic condition, a neurodegenerative disease, renal failure, a vascular disease, a cardiovascular disease, cancer, a complication of prematurity, cardiomyopathy, retinopathy, nephropathy, neuropathy, erectile dysfunction or urinary incontinence (each being a "Condition"), comprising administering to a subject in need thereof an effective amount of an Indenoisoquinolinone Analog of Formula (Ia), (Ib), (Ic), (IIa), (IIb), (IIc), (IIIa), (IIIb), (IVa), (IVb), (IVc), (Va), or a pharmaceutically acceptable salt thereof.

A compound of Formula (Ia), Formula (Ib), Formula (Ic), Formula (Ia), Formula (IIb), Formula (IIc), Formula (IIIa), Formula (IIIb), Formula (IVa), Formula (IVb), Formula (IVc), Formula (Va), or a pharmaceutically acceptable salt thereof (an "Indenoisoquinolinone Analog") is useful for treating or preventing a Condition.

A composition comprising an effective amount of an Indenoisoquinolinone Analog and a physiologically acceptable carrier or vehicle is useful for treating or preventing a Condition.

The details of the invention are set forth in the accompanying description below.

All patents and publications cited in this specification are incorporated by reference in their entirety.

5. DETAILED DESCRIPTION OF THE INVENTION

5.1 Definitions and Abbreviations

The following definitions are used in connection with the Indenoisoquinolinone Analogs:

The term "—$C_1$-$C_3$ alkyl" as used herein, refers to a straight chain or branched non-cyclic hydrocarbon having from 1 to 3 carbon atoms, wherein one of the hydrocarbon's hydrogen atoms has been replaced by a single bond. Representative straight chain —$C_1$-$C_3$ alkyls include -methyl, -ethyl, and -n-propyl. Representative branched —$C_1$-$C_3$ alkyls include -isopropyl.

The term "—$C_1$-$C_4$ alkyl" as used herein, refers to a straight chain or branched non-cyclic hydrocarbon having from 1 to 4 carbon atoms, wherein one of the hydrocarbon's hydrogen atoms has been replaced by a single bond. Representative straight chain —$C_1$-$C_4$ alkyls include -methyl, -ethyl, -n-propyl, and -n-butyl. Representative branched —$C_1$-$C_4$ alkyls include -isopropyl, -sec-butyl, -isobutyl and -tert-butyl. In one embodiment, the —$C_1$-$C_4$ alkyl is substituted with one or more of -halo, —OH, —N($R^3$)$_2$, —($C_1$-$C_5$ alkylene)-O—$C_1$-$C_5$ alkyl, —NH$_2$, a nitrogen-containing 3- to 7-membered monocyclic heterocycle, or an —($C_1$-$C_6$ alkyl-substituted) nitrogen-containing 3- to 7-membered monocyclic heterocycle. Unless otherwise indicated, the —$C_1$-$C_4$ alkyl is unsubstituted.

A "$C_1$-$C_4$ alkylene" refers to a $C_1$-$C_4$ alkyl group, as defined above, wherein one of the $C_1$-$C_4$ alkyl group's hydrogen atoms has been replaced with a bond.

A "$C_2$-$C_4$ alkylene" refers to a straight or branched chain saturated hydrocarbon containing 2-4 carbon atoms, wherein two of the hydrocarbon's hydrogen atoms have been replaced by a single a bond. Representative $C_2$-$C_4$ alkylene groups include, ethylene, n-propylene, isopropylene, n-butylene and isobutylene.

The term "—$C_1$-$C_5$ alkyl" as used herein, refers to a straight chain or branched non-cyclic hydrocarbon having from 1 to 5 carbon atoms, wherein one of the hydrocarbon's hydrogen atoms has been replaced by a single bond. Representative straight chain —$C_1$-$C_5$ alkyls include -methyl, -ethyl, -n-propyl, -n-butyl and -n-pentyl. Representative branched —$C_1$-$C_5$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl. In one embodiment, the —$C_1$-$C_5$ alkyl is substituted with one or more of -halo, —OH, —N($R^3$)$_2$, —$C_1$-$C_5$ alkylene-O—$C_1$-$C_5$ alkyl, —NH$_2$, a nitrogen-containing 3- to 7-membered monocyclic heterocycle, or an —$C_1$-$C_6$ alkyl-substituted nitrogen-containing 3- to 7-membered monocyclic heterocycle. Unless otherwise indicated, the —$C_1$-$C_5$ alkyl is unsubstituted.

A "$C_1$-$C_5$ alkylene" refers to a $C_1$-$C_5$ alkyl group, as defined above, wherein one of the $C_1$-$C_5$ alkyl group's hydrogen atoms has been replaced with a bond.

The term "-phenyl-substituted $C_1$-$C_5$ alkyl" as used herein, refers to a "—$C_1$-$C_5$ alkyl" wherein one of the its hydrogen atoms has been replaced by a phenyl group.

The term "—$C_1$-$C_6$ alkyl" as used herein, refers to a straight chain or branched non-cyclic hydrocarbon having from 1 to 6 carbon atoms, wherein one of the hydrocarbon's hydrogen atoms has been replaced by a single bond. Representative straight chain —$C_1$-$C_6$ alkyls include -methyl, -ethyl, -n-propyl, -n-butyl, -n-pentyl and -n-hexyl. Representative branched —$C_1$-$C_6$ alkyls include -isopropyl, -sec-butyl, -isobutyl, -tert-butyl, -isopentyl, -neopentyl, -1-methylbutyl, -isohexyl, -neohexyl, -2-methylbutyl, -3-methylbutyl, -1,1-dimethylpropyl and -1,2-dimethylpropyl. In one embodiment, the —$C_1$-$C_6$ alkyl is substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$). Unless otherwise indicated, the —$C_1$-$C_6$ alkyl is unsubstituted.

A "$C_1$-$C_6$ alkylene" refers to a $C_1$-$C_6$ alkyl group, as defined above, wherein one of the $C_1$-$C_6$ alkyl group's hydrogen atoms has been replaced with a bond.

The term "—$C_2$-$C_6$ alkenyl" refers to a straight or branched chain hydrocarbon containing 2-6 carbon atoms and at least one double bond. Representative $C_2$-$C_6$ alkenyl groups include, but are not limited to, ethylene, propylene, 1-butylene, 2-butylene, isobutylene, sec-butylene, 1-pentene, 2-pentene, isopentene, 1-hexene, 2-hexene, 3-hexene and isohexene.

The term "—$C_1$-$C_8$ alkyl" as used herein, refers to a straight chain or branched non-cyclic hydrocarbon having from 1 to 9 carbon atoms, wherein one of the hydrocarbon's hydrogen atoms has been replaced by a single bond. Representative —$C_1$-$C_9$ alkyls include, methyl, ethyl, propyl, butyl, pentyl, hexyl, heptyl, octyl, -nonyl, isopropyl, isobutyl, sec-butyl and tert-butyl, isopentyl, neopentyl, isohexyl, isoheptyl, isooctyl and isononyl.

The term "—$C_7$-$C_{10}$ alkyl" as used herein, refers to a straight chain or branched non-cyclic hydrocarbon having from 7 to 10 carbon atoms, wherein one of the hydrocarbon's hydrogen atoms has been replaced by a single bond. Representative —$C_7$-$C_{10}$ alkyls include, but are not limited to, heptyl, octyl, nonyl, isohexyl, isoheptyl, isooctyl and isononyl, decyl, and isodecyl.

The term "—$C_1$-$C_{10}$ alkyl" as used herein, refers to a straight chain or branched non-cyclic hydrocarbon having from 1 to 10 carbon atoms, wherein one of the hydrocarbon's hydrogen atoms has been replaced by a single bond. Representative —$C_1$-$C_{10}$ alkyls include, methyl, ethyl, propyl, butyl, pentyl, hexyl, heptyl, octyl, -nonyl, decyl, isopropyl, isobutyl, sec-butyl and tert-butyl, isopentyl, neopentyl, isohexyl, isoheptyl, isooctyl, isononyl and isodecyl.

The term "—$C_3$-$C_8$ monocyclic cycloalkyl" as used herein, refers to a saturated cyclic hydrocarbon having from 3 to 8 carbon atoms. Representative —$C_3$-$C_8$ monocyclic cycloalkyls include -cyclopropyl, -cyclobutyl, -cyclopentyl, -cyclohexyl, -cycloheptyl and -cyclooctyl. In one embodiment, the —$C_3$-$C_8$ monocyclic cycloalkyl is substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —$C_1$-$C_6$ alkyl-substituted 3- to 7-membered monocyclic heterocycle. In another embodiment, the —$C_3$-$C_8$ monocyclic cycloalkyl is substituted with one or more of —N($R^3$)$_2$, —$C_1$-$C_5$ alkylene-O—$C_1$-$C_5$ alkyl, or —NH$_2$. Unless otherwise indicated, the —$C_3$-$C_8$ monocyclic cycloalkyl is unsubstituted.

A "nitrogen containing 3- to 7-membered monocyclic heterocycle" refers to a monocyclic 3- to 7-membered aromatic or non-aromatic monocyclic cycloalkyl group in which one of the cycloalkyl group's ring carbon atoms has been replaced with a nitrogen atom and 0-4 of the cycloalkyl group's remaining ring carbon atoms are independently replaced with a N, O or S atom. The nitrogen containing 3- to 7-membered monocyclic heterocycles can be attached via a nitrogen, sulfur, or carbon atom. Representative examples of nitrogen-containing -3- to 7-membered monocyclic heterocycles include, but are not limited to, piperidinyl, piperazinyl, pyrrolyl, piperidonyl, oxazinyl, thiazinyl, diazinyl, triazinyl, tetrazinyl, imidazolyl, tetrazolyl, pyrrolidinyl, isoxazolyl, pyridinyl, oxazolyl, thiazolyl, pyrazolyl, triazolyl, pyrimidinyl, morpholinyl, furuzanyl, pyrrolinyl, imidazolinyl, imidazolidinyl, pyrazolinyl, isothiazolyl, oxadiazolyl, thiadiazolyl, pyridazinyl, pyrazinyl, pyrazolidinyl, and thiomorpholinyl.

In one embodiment, the nitrogen-containing 3- to 7-membered monocyclic heterocycle is fully saturated or partially saturated.

In another embodiment, the nitrogen-containing 3- to 7-membered monocyclic heterocycle is substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$). Unless otherwise indicated, the nitrogen-containing 3- to 7-membered monocyclic heterocycle is unsubstituted.

A "nitrogen-containing 7- to 10-membered bicyclic heterocycle" refers to a 7- to 10-membered bicyclic ring system that contains at least one ring nitrogen atom. The nitrogen-containing 7- to 10-membered bicyclic heterocycles can be attached via a nitrogen, sulfur, or carbon atom. Representative nitrogen-containing 7- to 10-membered bicyclic heterocycles include -quinolinyl, -isoquinolinyl, -chromonyl, -indolyl, -isoindolyl, -indolinyl, indolizinyl, -indazolyl, -purinyl, -4H-quinolizinyl, -isoquinolyl, -quinolyl, -phthalazinyl, -naphthyridinyl, benzimidazolyl, benzthiazolyl, dihydroquinolyl, dihydroisoquinolyl, cinnolyl, phthalazyl, quinazolyl, quinoxalyl, and pteridyl.

In one embodiment, the nitrogen-containing 7- to 10-membered bicyclic heterocycle is saturated or partially saturated.

A "3- to 7-membered monocyclic heterocycle" refers to a monocyclic 3- to 7-membered aromatic or non-aromatic monocyclic cycloalkyl in which 1-4 of the ring carbon atoms have been independently replaced with a N, O or S atom. The 3- to 7-membered monocyclic heterocycles can be attached via a nitrogen, sulfur, or carbon atom. Representative examples of a 3- to 7-membered monocyclic heterocycle group include, but are not limited to, nitrogen-containing 3- to 7-membered monocyclic heterocycles discussed above, tetrahydrofuranyl, dihydrofuranyl, pyranyl, dihydropyranyl, tetrahydropyranyl, thiopyranyl, dihydrothiopyranyl, tetrahydrothiopyranyl, dioxanyl, dithianyl, trithianyl, dioxolanyl, furanyl, and thiophenyl. In one embodiment, the 3- to 7-membered monocyclic heterocycle is a nitrogen-containing 3- to 7-membered monocyclic heterocycle. In another embodiment, the 3- to 7-membered monocyclic heterocycle is saturated or partially saturated.

A "$C_1$-$C_6$ alkyl-substituted 3- to 7-membered monocyclic heterocycle" refers to a "3- to 7-membered monocyclic heterocycle," as defined above, wherein one or more of the heterocycle's hydrogen atoms has been replaced by a $C_1$-$C_6$ alkyl, as defined above.

"Halo" is —F, —Cl, —Br or —I.

"Halo-substituted $C_1$-$C_5$ alkyl" refers to a $C_1$-$C_5$ alkyl group, as defined above, wherein one or more of the $C_1$-$C_5$ alkyl group's hydrogen atoms has been replaced with —F, —Cl, —Br or —I. Representative examples of a halo-substituted $C_1$-$C_5$ alkyl include, but are not limited to, —CH$_2$F, —CCl$_3$, —CF$_3$, —CH$_2$Cl, —CH$_2$CH$_2$Br, —CH$_2$CH$_2$I, —CH$_2$CH$_2$CH$_2$F, —CH$_2$CH$_2$CH$_2$Cl, —CH$_2$CH$_2$CH$_2$CH$_2$Br, —CH$_2$CH$_2$CH$_2$CH$_2$I, —CH$_2$CH$_2$CH$_2$CH$_2$CH$_2$Br, —CH$_2$CH$_2$CH$_2$CH$_2$CH$_2$I, —CH$_2$CH(Br)CH$_3$, —CH$_2$CH(Cl)CH$_2$CH$_3$, —CH(F)CH$_2$CH$_3$ and —C(CH$_3$)$_2$(CH$_2$Cl).

"Halo-substituted phenyl" refers to a phenyl group, wherein one or more of the phenyl group's hydrogen atoms has been replaced with —F, Cl, —Br or —I.

"Cyano-substituted phenyl" refers to a phenyl group, wherein one or more of the phenyl group's hydrogen atoms has been replaced with —CN.

"Cyano-substituted $C_1$-$C_5$ alkyl" refers to a $C_1$-$C_5$ alkyl group, as defined above, wherein one or more of the $C_1$-$C_5$ alkyl group's hydrogen atoms has been replaced with —CN. Representative examples of a cyano-substituted $C_1$-$C_5$ alkyl include, but are not limited to, —CH$_2$CN, —CH$_2$CH$_2$CN, —CH$_2$CH$_2$CH$_2$CN, —CH$_2$CH$_2$CH$_2$CH$_2$CN, —CH$_2$CH$_2$CH$_2$CH$_2$CH$_2$CN, —CH$_2$CH(CN)CH$_3$, —CH$_2$CH(CN)CH$_2$CH$_3$, —CH(CN)CH$_2$CH$_3$ and —C(CH$_3$)$_2$(CH$_2$CN).

A "$C_1$-$C_6$ alkylene phenyl" refers to a $C_1$-$C_6$ alkyl group, as defined above, wherein one of the $C_1$-$C_6$ alkyl group's hydrogen atoms has been replaced with phenyl.

"Hydroxy-substituted $C_1$-$C_5$ alkyl" refers to a $C_1$-$C_5$ alkyl group, as defined above, wherein one or more of the $C_1$-$C_5$ alkyl group's hydrogen atoms has been replaced with —OH. Representative examples of a hydroxy-substituted $C_1$-$C_5$ alkyl include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_2$CH$_3$ and —C(CH$_3$)$_2$(CH$_2$OH).

A "C-terminal alpha amino acid residue" refers to an L-, D- or racemic natural or unnatural alpha amino acid, less the hydroxyl group of the alpha amino acid's carboxyl group. Representative examples of a C-terminal alpha amino acid residue include, but are not limited to, CH$_3$—CH(NH$_2$)—C(O)—, HN=C(NH$_2$)—NH—(CH$_2$)$_3$—CH(NH$_2$)—C(O)—, H$_2$N—C(O)—CH$_2$—CH(NH$_2$)—C(O)—, HOOC—CH$_2$—CH(NH$_2$)—C(O)—, HS—CH$_2$—CH(NH$_2$)—C(O)—, H$_2$N—C(O)—(CH$_2$)$_2$—CH(NH$_2$)—C(O)—, HOOC—(CH$_2$)$_2$—CH(NH$_2$)—C(O)—, H$_2$N—CH$_2$—C(O)—, CH$_3$—CH$_2$—CH(CH$_3$)—CH(NH$_2$)—C(O)—, (CH$_3$)$_2$—CH—CH$_2$—CH(NH$_2$)—C(O)—, H$_2$N—(CH$_2$)$_4$—CH(NH$_2$)—C(O)—, CH$_3$—S—(CH$_2$)$_2$—CH(NH$_2$)—C(O)—, HO—CH$_2$—CH(NH$_2$)—C(O)—, CH$_3$—CH(OH)—CH(NH$_2$)—C(O)—, (CH$_3$)$_2$—CH—CH(NH$_2$)—C(O)—,

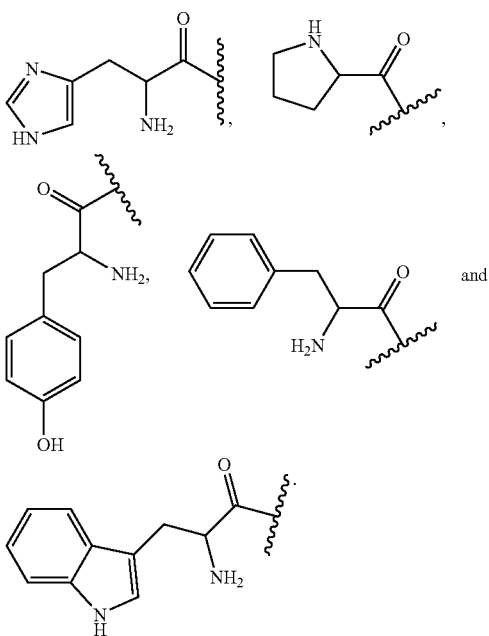

In one embodiment, the C-terminal alpha amino acid is a natural amino acid.

In another embodiment, the C-terminal alpha amino acid is an unnatural amino acid.

In one embodiment, the C-terminal alpha amino acid is an L amino acid.

An "N-terminal alpha amino acid residue" refers to an L-, D- or racemic natural or unnatural alpha amino acid, less the alpha amino acid's N-terminal amino group. Representative examples of an N-terminal alpha amino acid residue include, but are not limited to, —CH$_2$—COOH, —CH(CH$_3$)COOH, —CH(CH(CH$_3$)$_2$)COOH, —CH(CH$_2$CH(CH$_3$)$_2$)COOH, —CH(CH(CH$_3$)(CH$_2$CH$_3$))COOH, —CH((CH$_2$)$_4$—NH$_2$)COOH, —CH((CH$_2$)$_3$NH(C=NH$_2$)—NH$_2$)COOH, —CH(CH$_2$—OH)COOH, —CH(CH((CH$_3$)(OH)))COOH, —CH(CH$_2$—COOH)COOH, —CH((CH$_2$)$_2$COOH)COOH, —CH((CH$_2$)(CONH$_2$))COOH, —CH((CH$_2$)$_2$(CONH$_2$))COOH, —CH(CH$_2$—SH)COOH, —CH((CH$_2$)$_2$—S—CH$_3$)COOH,

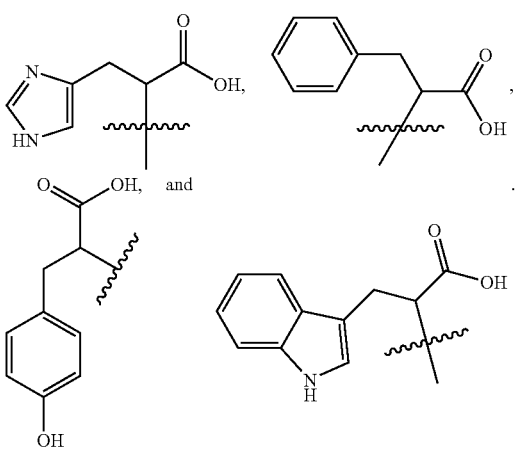

In one embodiment, the N-terminal alpha amino acid residue is substituted with one or more of -halo, —OH, —OP(O)(OH)$_2$, —OS(O)$_2$OH, —C$_1$-C$_6$ alkyl, —O—C$_1$-C$_6$ alkyl, —C$_3$-C$_8$ monocyclic cycloalkyl, a 3- to 7-membered monocyclic heterocycle, —C$_1$-C$_6$ alkyl-substituted 3- to 7-membered monocyclic heterocycle, or —N(Z$_3$)(Z$_4$). Unless otherwise indicated, the N-terminal alpha amino acid residue is unsubstituted.

An "N-terminal alpha amino hydroxymethyl residue" refers to an "N-terminal alpha amino acid residue," wherein its C-terminal carboxyl group, a side chain's carboxyl group, or both have been replaced with a hydroxymethyl group. In one embodiment, the N-terminal alpha amino hydroxymethyl residue is substituted with one or more of -halo, —OH, —OP(O)(OH)$_2$, —OS(O)$_2$OH, —C$_1$-C$_6$ alkyl, —O—C$_1$-C$_6$ alkyl, —C$_3$-C$_8$ monocyclic cycloalkyl, a 3- to 7-membered monocyclic heterocycle, —C$_1$-C$_6$ alkyl-substituted 3- to 7-membered monocyclic heterocycle, or —N(Z$_3$)(Z$_4$). In another embodiment, the hydroxyl group of the hydroxymethyl residue is substituted with —PO$_3$H$_2$, —P$_2$O$_6$H$_3$, —P$_3$O$_9$H$_4$, —SO$_3$H, —C(O)—C$_1$-C$_9$ alkyl, β-D-glucuronyl, or a C-terminal alpha amino acid residue. Unless otherwise indicated, the N-terminal alpha amino hydroxymethyl residue is unsubstituted.

A "C$_1$-C$_6$ alkyl ester of an N-terminal alpha amino acid residue" refers to an "N-terminal alpha amino acid residue," wherein the hydrogen atom of the amino acid's C-terminal carboxyl group, a side chain's carboxyl group, or both have been replaced by a —C$_1$-C$_6$ alkyl group. In one embodiment, the C$_1$-C$_6$ alkyl ester of an N-terminal alpha amino acid residue is a methyl, an ethyl, an n-propyl or an iso-propyl ester of an N-terminal alpha amino acid residue. In another embodiment, the C$_1$-C$_6$ alkyl ester of an N-terminal alpha amino acid residue is substituted with one or more of -halo, —OH, —OP(O)(OH)$_2$, —OS(O)$_2$OH, —C$_1$-C$_6$ alkyl, —O—C$_1$-C$_6$ alkyl, —C$_3$-C$_8$ monocyclic cycloalkyl, a 3- to 7-membered monocyclic heterocycle, —C$_1$-C$_6$ alkyl-substituted 3- to 7-membered monocyclic heterocycle, or —N(Z$_3$)(Z$_4$). Unless otherwise indicated, the C$_1$-C$_6$ alkyl ester of an N-terminal alpha amino acid residue is unsubstituted.

In one embodiment, the N-terminal alpha amino acid is a natural amino acid.

In another embodiment, the N-terminal alpha amino acid is an unnatural amino acid.

In one embodiment, the N-terminal alpha amino acid is an L amino acid.

A "β-D-glucuronyl" refers to a group having the formula:

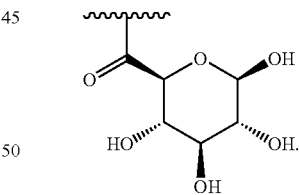

A "subject" is a mammal, e.g., a human, mouse, rat, guinea pig, dog, cat, horse, cow, pig, or non-human primate, such as a monkey, chimpanzee, baboon or rhesus. In one embodiment, the subject is a human.

The phrase "pharmaceutically acceptable salt," as used herein, is a salt of an acid and a basic nitrogen atom of an Indenoisoquinolinone Analog. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, and pamoate (i.e., 1,1'-methylene-bis-(2-hydroxy-3-naphthoate)) salts. The term "pharmaceutically acceptable salt" also refers to a salt of an Indenoisoquinolinone Analog having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a compound of the invention.

In one embodiment, the pharmaceutically acceptable salt is a mesylate salt.

In another embodiment, the pharmaceutically acceptable salt is a camphorsulfonate salt.

An "effective amount" when used in connection with an Indenoisoquinolinone Analog is an amount that is effective for treating or preventing a Condition.

An "effective amount" when used in connection with another anticancer agent is an amount that is effective for treating or preventing cancer alone or in combination with an Indenoisoquinolinone Analog. "In combination with" includes administration within the same composition and via separate compositions. In the latter instance, the other anticancer agent is administered during a time when the Indenoisoquinolinone Analog exerts its prophylactic or therapeutic effect, or vice versa.

The following abbreviations are used herein and have the indicated definitions: DMF is N,N-dimethylformamide, THF is tetrahydrofuran, DMAC is dimethylacetamide, DMSO is dimethylsulfoxide, Et is ethyl, Pr is n-propyl, i-Pr is isopropyl, EtOAc is ethyl acetate, EtOH is ethanol, Me is methyl, MS is mass spectrometry, Ts is tosylate, Tf is triflate, Ph is phenyl, NMR is Nuclear Magnetic Resonance, Ms is mesylate, LAH is lithium aluminum hydride and tBoc is t-butyloxycarbonyl.

5.2 The Indenoisoquinolinone Analogs of Formula (Ia)

The present invention provides Indenoisoquinolinone Analogs according to Formula (Ia), below:

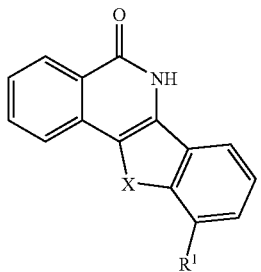

(Ia)

and pharmaceutically acceptable salts thereof, wherein X and $R^1$ are as defined above for the Indenoisoquinolinone Analogs of Formula (Ia).

In one embodiment, X is —N(CH$_3$)—. In another embodiment, X is —N(CH$_2$CH$_3$)—. In another embodiment, X is —N(CH$_2$CH$_2$CH$_3$)—. In another embodiment, X is —N(CH$_2$ CH$_2$CH$_2$CH$_3$)—. In another embodiment, X is —N(C(H)(CH$_3$)(CH$_2$CH$_3$))—. In another embodiment, X is —N(C(H)(CH$_3$)$_2$)—. In another embodiment, X is —N(CH$_2$C(H)(CH$_3$)$_2$)—. In another embodiment, X is —N(C(CH$_3$)$_3$)—.

In one embodiment, $R^1$ is —(CH$_2$)$_n$—N(R$^2$)(R$^2$) and X is —N(CH$_3$)—.

In another embodiment, $R^1$ is —(CH$_2$)$_n$—N(R$^2$)(R$^2$) and X is —N(CH$_2$CH$_3$)—.

In another embodiment, $R^1$ is —(CH$_2$)$_n$—N(R$^2$)(R$^2$) and X is —N(CH$_2$CH$_2$CH$_3$)—.

In another embodiment, $R^1$ is —(CH$_2$)$_n$—N(R$^2$)(R$^2$) and X is —N(CH$_2$CH$_2$CH$_2$CH$_3$)—.

In another embodiment, $R^1$ is —(CH$_2$)$_n$—N(R$^2$)(R$^2$) and X is —N(C(H)(CH$_3$)(CH$_2$CH$_3$))—.

In another embodiment, $R^1$ is —(CH$_2$)$_n$—N(R$^2$)(R$^2$) and X is —N(C(H)(CH$_3$)$_2$)—.

In another embodiment, $R^1$ is —(CH$_2$)$_n$—N(R$^2$)(R$^2$) and X is —N(CH$_2$C(H)(CH$_3$)$_2$)—.

In another embodiment, $R^1$ is —(CH$_2$)$_n$—N(R$^2$)(R$^2$) and X is —N(C(CH$_3$)$_3$)—.

In one embodiment, $R^1$ is —O—(CH$_2$)$_m$—N(R$^2$)(R$^2$) and X is —N(CH$_3$)—.

In another embodiment, $R^1$ is —O—(CH$_2$)$_m$—N(R$^2$)(R$^2$) and X is —N(CH$_2$CH$_3$)—.

In another embodiment, $R^1$ is —O—(CH$_2$)$_m$—N(R$^2$)(R$^2$) and X is —N(CH$_2$CH$_2$CH$_3$)—.

In another embodiment, $R^1$ is —O—(CH$_2$)$_m$—N(R$^2$)(R$^2$) and X is —N(CH$_2$CH$_2$CH$_2$CH$_3$)—.

In another embodiment, $R^1$ is —O—(CH$_2$)$_m$—N(R$^2$)(R$^2$) and X is —N(C(H)(CH$_3$)(CH$_2$CH$_3$))—.

In another embodiment, $R^1$ is —O—(CH$_2$)$_m$—N(R$^2$)(R$^2$) and X is —N(C(H)(CH$_3$)$_2$)—.

In another embodiment, $R^1$ is —O—(CH$_2$)$_m$—N(R$^2$)(R$^2$) and X is —N(CH$_2$C(H)(CH$_3$)$_2$)—.

In another embodiment, $R^1$ is —O—(CH$_2$)$_m$—N(R$^2$)(R$^2$) and X is —N(C(CH$_3$)$_3$)—.

In one embodiment, one $R^2$ is —H, and the other $R^2$ is —C$_1$-C$_6$ alkyl.

In another embodiment, each $R^2$ is —C$_1$-C$_6$ alkyl.

In another embodiment, each $R^2$ is -methyl.

In one embodiment, X is —CH(OH)—.

In another embodiment, X is —CH(OH)— and $R^1$ is —(CH$_2$)$_n$—N(R$^2$)(R$^2$).

In yet another embodiment, X is —CH(OH)— and $R^1$ is —(CH$_2$)—N(R$^2$)(R$^2$).

In another embodiment, X is —N(C(O)N(H)—(CH$_2$)$_p$—Z)—.

In another embodiment, X is —N(C(O)N(H)—(CH$_2$)—Z)—.

In another embodiment, X is —N(C(O)N(H)—(CH$_2$)$_2$—Z)—.

In another embodiment, X is —N(C(O)N(H)—(CH$_2$)$_p$—Z)— and $R^1$ is —(CH$_2$)$_n$—N(R$^2$)(R$^2$).

In yet another embodiment, X is —N(C(O)N(H)—(CH$_2$)$_p$—Z)— and $R^1$ is —(CH$_2$)—N(R$^2$)(R$^2$).

In still another embodiment, X is —N(C(O)N(H)—(CH$_2$)—Z)— and $R^1$ is —(CH$_2$)—N(R$^2$)(R$^2$).

In one embodiment, X is —N((CH$_2$)$_q$—Z)—.

In another embodiment, X is —N((CH$_2$)—Z)—.

In another embodiment, X is —N((CH$_2$)$_2$—Z)—.

In another embodiment, X is —N((CH$_2$)$_q$—Z)— and R$^1$ is —(CH$_2$)$_n$—N(R$^2$)(R$^2$).

In yet another embodiment, X is —N((CH$_2$)$_q$—Z)— and R$^1$ is —(CH$_2$)—N(R$^2$)(R$^2$).

In still another embodiment, X is —N((CH$_2$)—Z)— and R$^1$ is —(CH$_2$)—N(R$^2$)(R$^2$).

In one embodiment, Z is —CF$_3$.

In another embodiment, Z is —F.

In yet another embodiment, Z is —OH.

In still another embodiment, Z is —O—CH$_3$.

In another embodiment, X is —N(C(O)N(H)—(CH$_2$)$_p$OH)—.

In another embodiment, X is —N(C(O)N(H)—(CH$_2$)$_2$—OH)—.

In another embodiment, X is —N(C(O)N(H)—(CH$_2$)$_p$OH)— and R$^1$ is —(CH$_2$)$_n$—N(R$^2$)(R$^2$).

In yet another embodiment, X is —N(C(O)N(H)—(CH$_2$)$_p$—OH)— and R$^1$ is —(CH$_2$)—N(R$^2$)(R$^2$).

In still another embodiment, X is —N(C(O)N(H)—(CH$_2$)$_2$—OH)— and R$^1$ is —(CH$_2$)—N(R$^2$)(R$^2$).

In one embodiment, X is —N((CH$_2$)$_q$—OH)—.

In another embodiment, X is —N((CH$_2$)$_2$—OH)—.

In another embodiment, X is —N((CH$_2$)$_q$—OH)— and R$^1$ is —(CH$_2$)$_n$—N(R$^2$)(R$^2$).

In yet another embodiment, X is —N((CH$_2$)$_q$—OH)— and R$^1$ is —(CH$_2$)—N(R$^2$)(R$^2$).

In still another embodiment, X is —N((CH$_2$)$_2$—OH)— and R$^1$ is —(CH$_2$)—N(R$^2$)(R$^2$).

In another embodiment, X is —N(C(O)N(H)—(CH$_2$)$_p$F)—.

In another embodiment, X is —N(C(O)N(H)—(CH$_2$)—F)—.

In another embodiment, X is —N(C(O)N(H)—(CH$_2$)$_p$F)— and R$^1$ is —(CH$_2$)$_n$—N(R$^2$)(R$^2$).

In yet another embodiment, X is —N(C(O)N(H)—(CH$_2$)$_p$—F)— and R$^1$ is —(CH$_2$)—N(R$^2$)(R$^2$).

In still another embodiment, X is —N(C(O)N(H)—(CH$_2$)—F)— and R$^1$ is —(CH$_2$)—N(R$^2$)(R$^2$).

In one embodiment, X is —N((CH$_2$)$_q$—F)—.

In another embodiment, X is —N((CH$_2$)—F)—.

In another embodiment, X is —N((CH$_2$)$_q$—F)— and R$^1$ is —(CH$_2$)$_n$—N(R$^2$)(R$^2$).

In yet another embodiment, X is —N((CH$_2$)$_q$—F)— and R$^1$ is —(CH$_2$)—N(R$^2$)(R$^2$).

In still another embodiment, X is —N((CH$_2$)—F)— and R$^1$ is —(CH$_2$)—N(R$^2$)(R$^2$).

In another embodiment, X is —N(C(O)N(H)—(CH$_2$)$_p$—OMe)-.

In another embodiment, X is —N(C(O)N(H)—(CH$_2$)$_2$—OMe)-.

In another embodiment, X is —N(C(O)N(H)—(CH$_2$)$_p$—OMe)- and R$^1$ is —(CH$_2$)$_n$—N(R$^2$)(R$^2$).

In yet another embodiment, X is —N(C(O)N(H)—(CH$_2$)$_p$—OMe)- and R$^1$ is —(CH$_2$)—N(R$^2$)(R$^2$).

In still another embodiment, X is —N(C(O)N(H)—(CH$_2$)$_2$—OMe)- and R$^1$ is —(CH$_2$)—N(R$^2$)(R$^2$).

In one embodiment, X is —N((CH$_2$)$_q$—OMe)-.

In another embodiment, X is —N((CH$_2$)$_2$—OMe)-.

In another embodiment, X is —N((CH$_2$)$_q$—OMe)- and R$^1$ is —(CH$_2$)$_n$—N(R$^2$)(R$^2$).

In yet another embodiment, X is —N((CH$_2$)$_q$—OMe)- and R$^1$ is —(CH$_2$)—N(R$^2$)(R$^2$).

In still another embodiment, X is —N((CH$_2$)$_2$—OMe)- and R$^1$ is —(CH$_2$)—N(R$^2$)(R$^2$).

In another embodiment, X is —N(C(O)N(H)—(CH$_2$)$_p$CF$_3$)—.

In another embodiment, X is —N(C(O)N(H)—(CH$_2$)—CF$_3$)—.

In another embodiment, X is —N(C(O)N(H)—(CH$_2$)$_p$CF$_3$)— and R$^1$ is —(CH$_2$)$_n$—N(R$^2$)(R$^2$).

In yet another embodiment, X is —N(C(O)N(H)—(CH$_2$)$_p$—CF$_3$)— and R$^1$ is —(CH$_2$)—N(R$^2$)(R$^2$).

In still another embodiment, X is —N(C(O)N(H)—(CH$_2$)—CF$_3$)— and R$^1$ is —(CH$_2$)—N(R$^2$)(R$^2$).

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and R$^1$ is —(CH$_2$)$_n$—N(R$^2$)(R$^2$).

In yet another embodiment, X is —N((CH$_2$)$_q$—CF$_3$)— and R$^1$ is —(CH$_2$)—N(R$^2$)(R$^2$).

In still another embodiment, X is —N((CH$_2$)—CF$_3$)— and R$^1$ is —(CH$_2$)—N(R$^2$)(R$^2$).

In another embodiment, X is —N(C(O)N(H)—(CH$_2$)$_p$—CF$_3$)—.

In another embodiment, X is —N(C(O)N(H)—(CH$_2$)—CF$_3$)—.

In another embodiment, X is —N(C(O)N(H)—(CH$_2$)$_p$—CF$_3$)— and R$^1$ is —(CH$_2$)$_n$—N(R$^1$)(R$^2$).

In yet another embodiment, X is —N(C(O)N(H)—(CH$_2$)$_p$—CF$_3$)— and R$^1$ is —(CH$_2$)—N(R$^2$)(R$^2$).

In still another embodiment, X is —N(C(O)N(H)—(CH$_2$)—CF$_3$)— and R$^1$ is —(CH$_2$)—N(R$^2$)(R$^2$).

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and R$^1$ is —(CH$_2$)$_n$—N(R$^2$)(R$^2$).

In yet another embodiment, X is —N((CH$_2$)$_q$—CF$_3$)— and R$^1$ is —(CH$_2$)—N(R$^2$)(R$^2$).

In still another embodiment, X is —N((CH$_2$)—CF$_3$)— and R$^1$ is —(CH$_2$)—N(R$^2$)(R$^2$).

In one embodiment, n is 1.

In another embodiment, n is 2.

In yet another embodiment, n is 3.

In a further embodiment, n is 4, 5, or 6.

In yet a further embodiment, n is 7, 8, or 9.

In still a further embodiment, n is 10.

In one embodiment, m is 2.

In another embodiment, m is 3.

In yet another embodiment, m is 4, 5, or 6.

In a further embodiment, m is 7, 8, or 9.

In yet a further embodiment, m is 10.

In one embodiment, p is 1.

In another embodiment, p is 2.

In yet another embodiment, p is an integer ranging from 2 to 5.

In one embodiment, q is 1.

In another embodiment, q is 2.

In yet another embodiment, q is an integer ranging from 2 to 5.

In various embodiments, —N(R$^2$)(R$^2$) is:

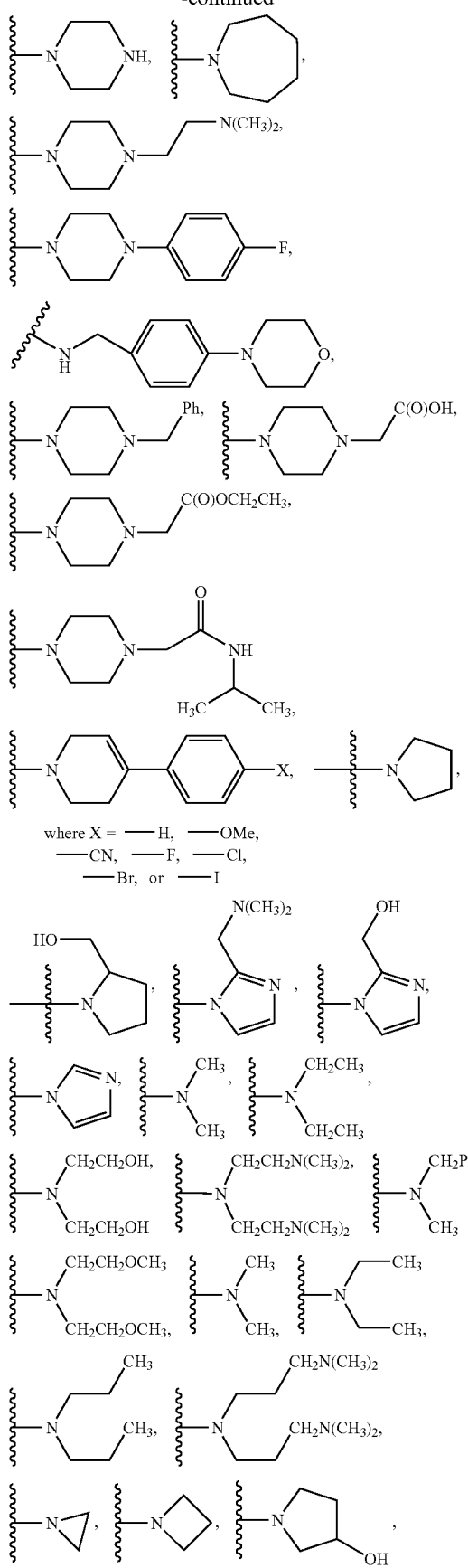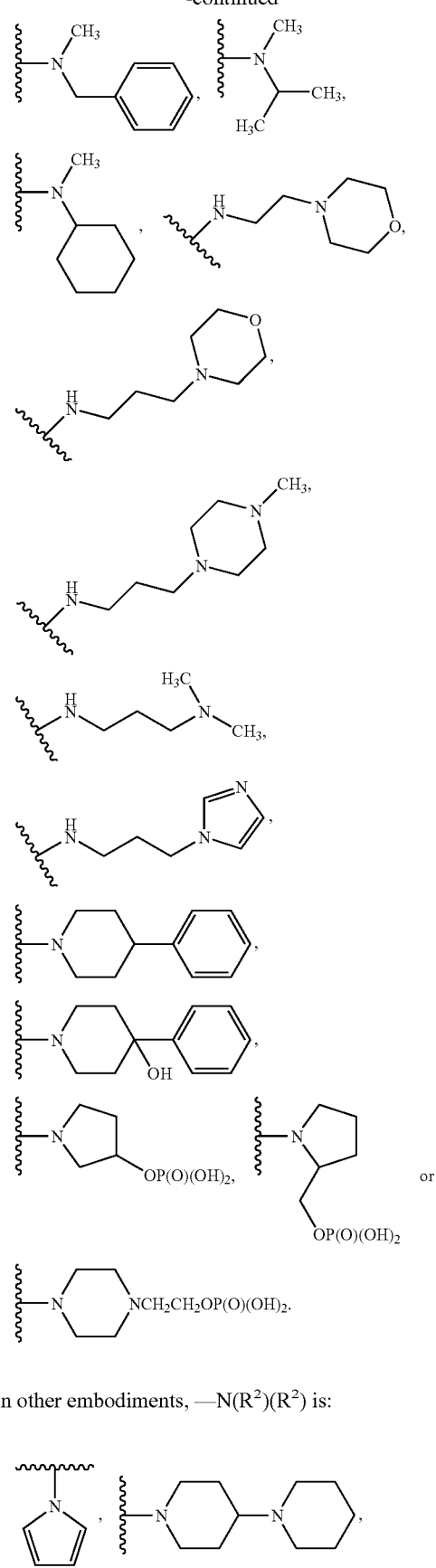
In other embodiments, —N(R²)(R²) is:

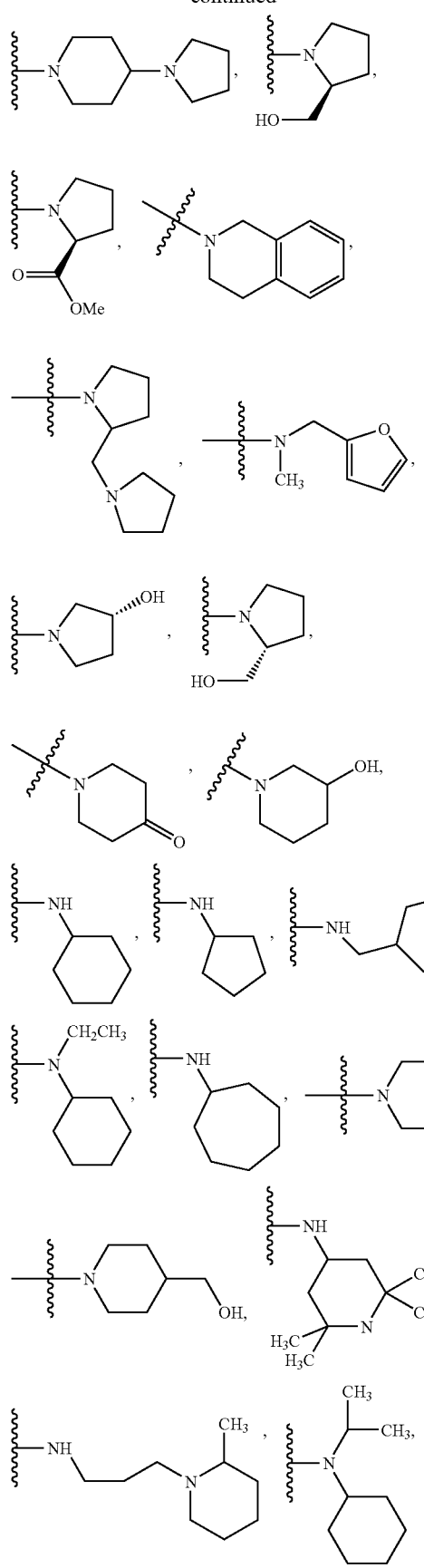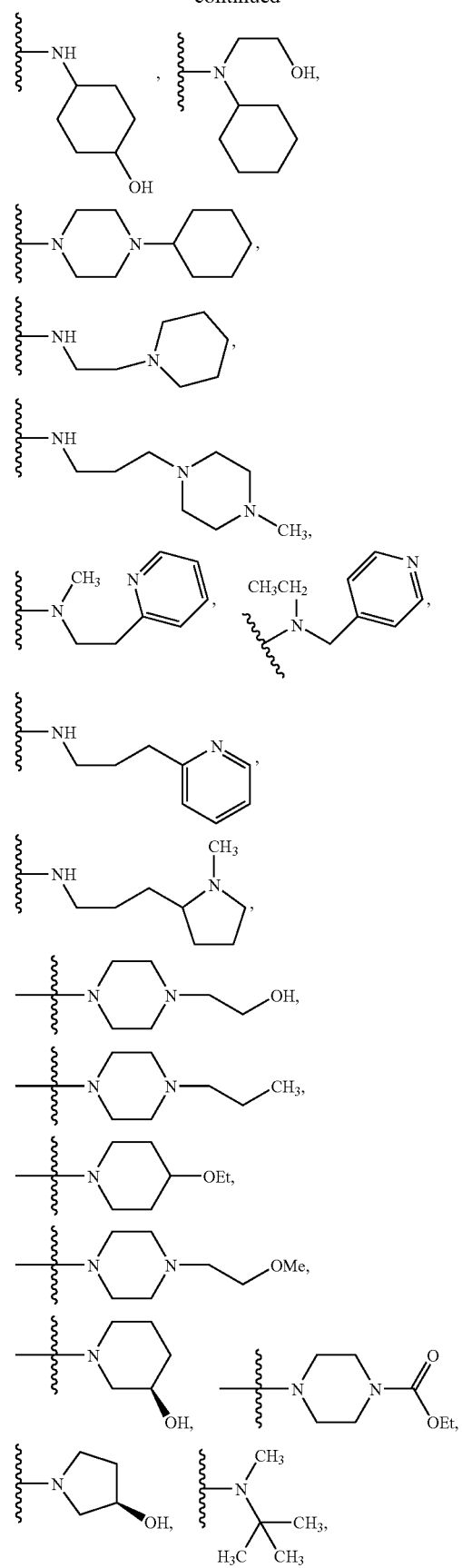

-continued
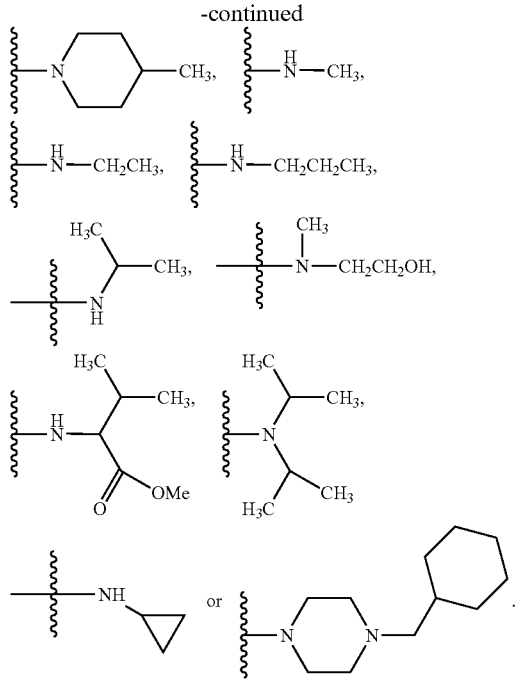
In some embodiments, —N(R²)(R²) is
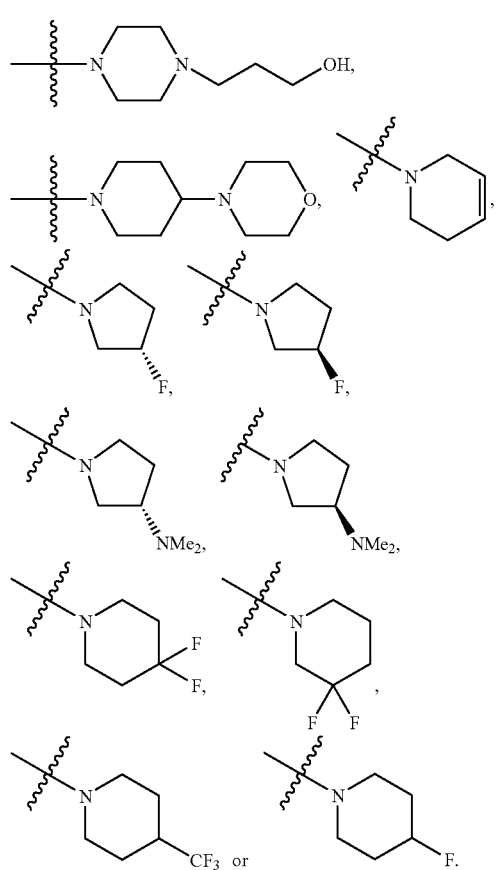
In still other embodiments, —N(R²)(R²) is
—N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.
In some embodiments, —N(R²)(R²) is
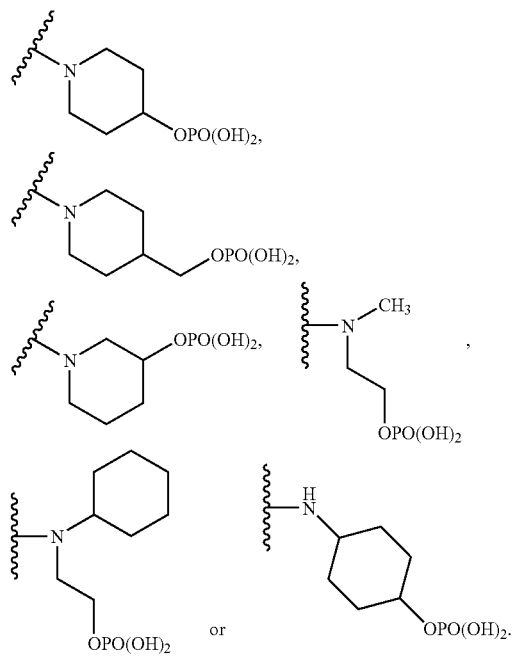
In various embodiments, —N(Z₃)(Z₄) is:
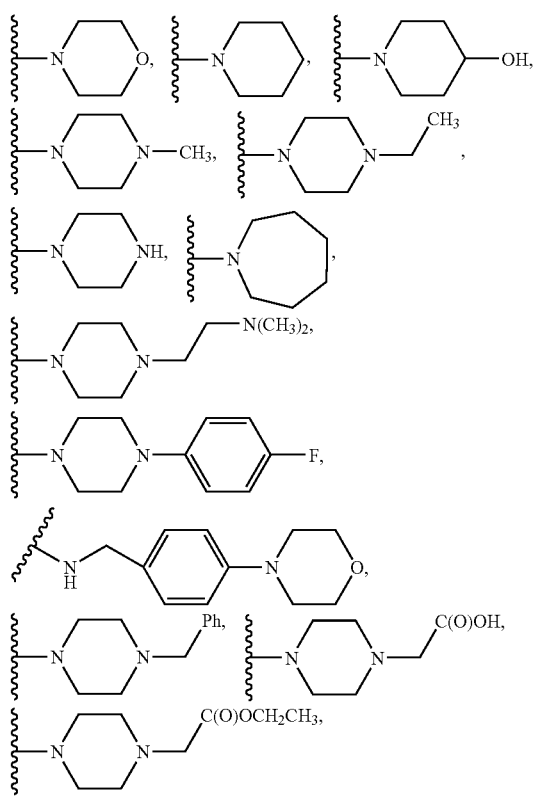

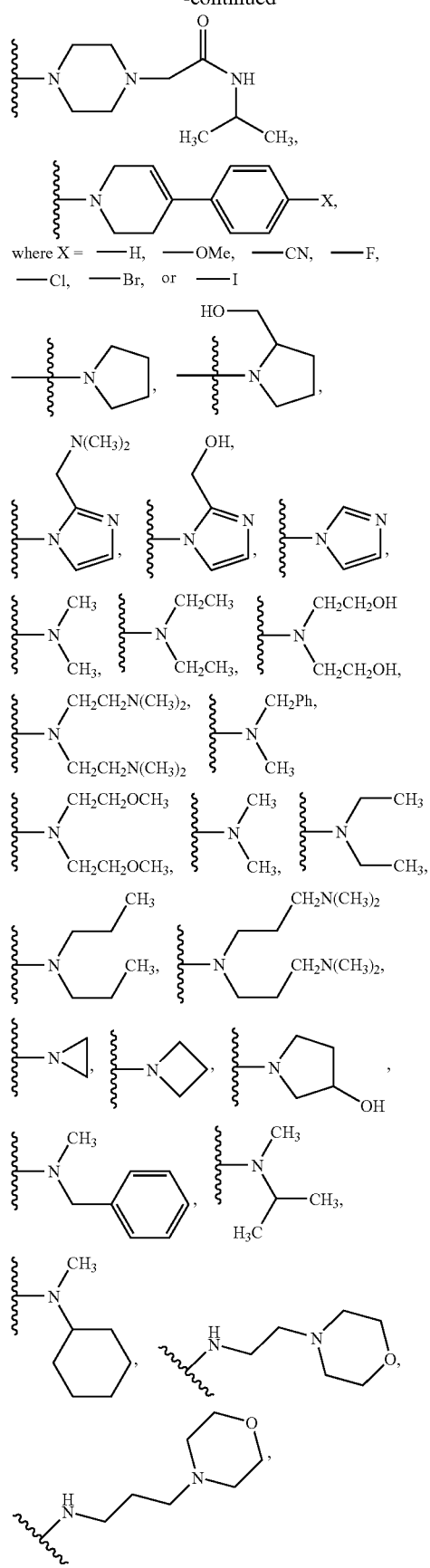
In other embodiments, —N(Z₃)(Z₄) is:

-continued
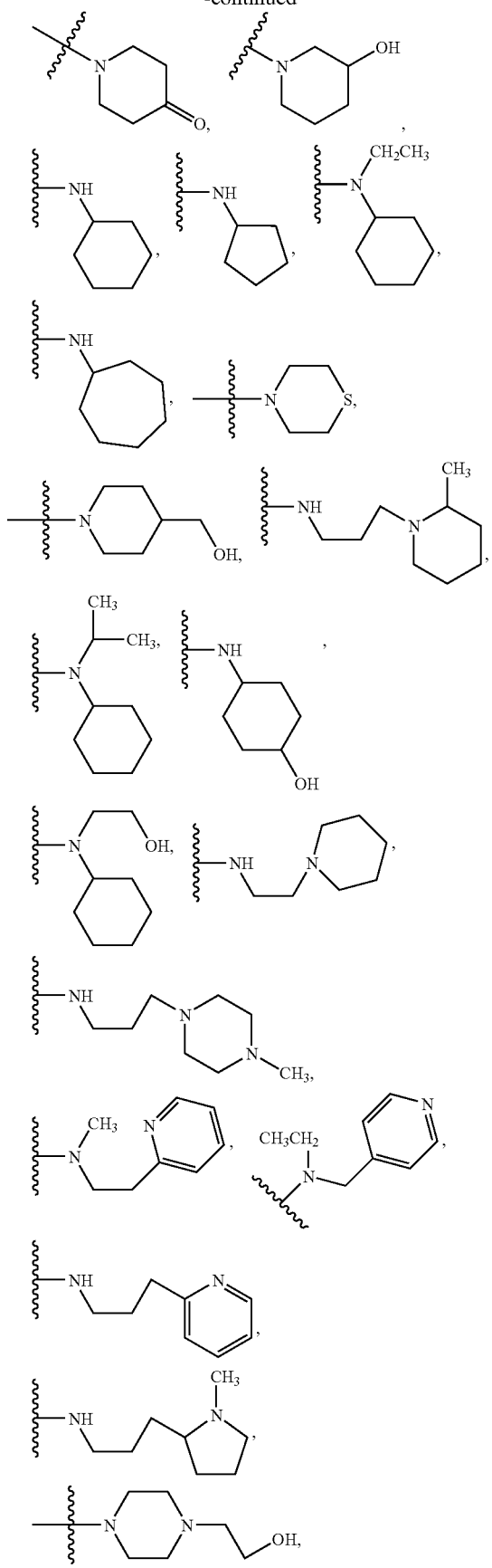
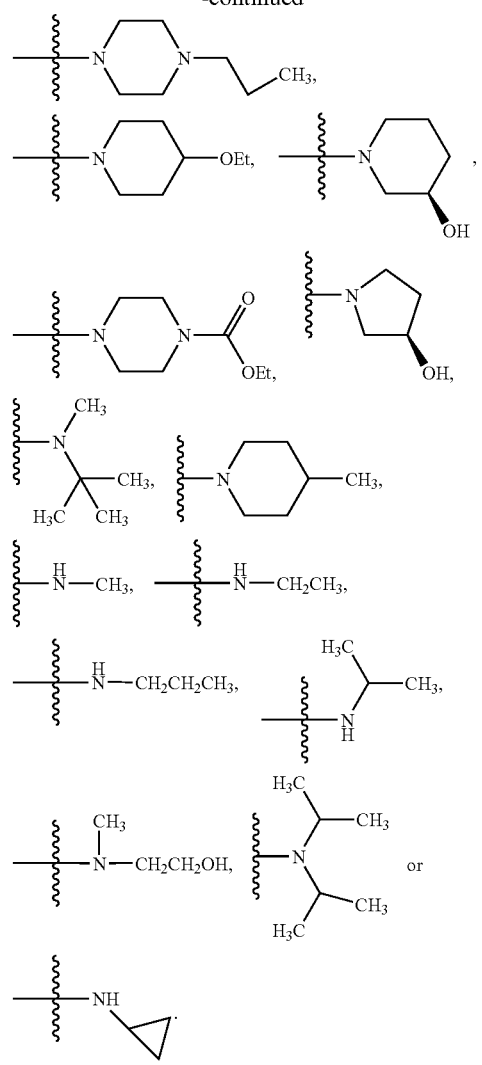
In some embodiments, —N(Z₃)(Z₄) is
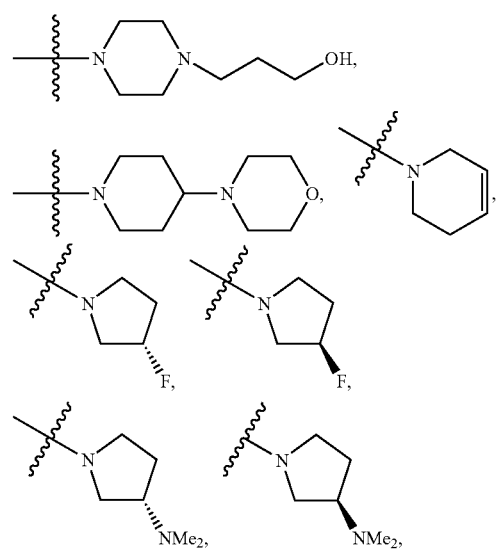

-continued

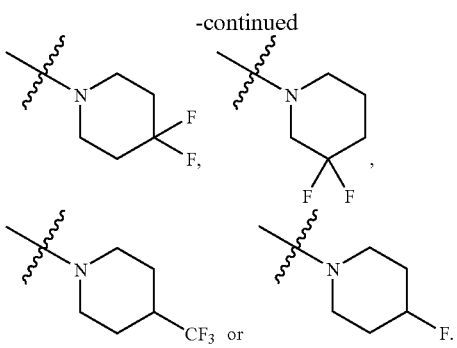

In still other embodiments, —N(Z₃)(Z₄) is
—N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.

In some embodiments, —N(Z₃)(Z₄) is

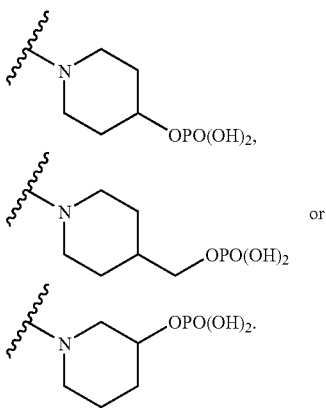

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂)— or —N(C(CH₃)₃)—;

R¹ is —(CH₂)ₙ—N(R²)(R²) or —O—(CH₂)ₘ—N(R²)(R²);

each R² is independently —H, —C₁-C₆ alkyl, cyclopropyl, cyclobutyl, cyclopentyl, cyclohexyl, —(C₁-C₆ alkylene)-phenyl or -phenyl, each of which other than hydrogen is unsubstituted or substituted with one or more of -halo, —OH, —OP(O)(OH)₂, —OS(O)₂OH or —N(Z₃)(Z₄), where Z₃ and Z₄ are independently —H, —C₁-C₅ alkyl, or —(C₁-C₅ alkylene)-O—C₁-C₅ alkyl, each of which other than hydrogen is unsubstituted or substituted with one or more of -halo, —OH or —NH₂;

or N, Z₃ and Z₄ are taken together to form a nitrogen-containing 3- to 7-membered monocyclic heterocycle which is unsubstituted or substituted with one to three of —C₁-C₅ alkyl, -phenyl, —(C₁-C₅ alkylene)-phenyl, -(hydroxy-substituted) C₁-C₅ alkyl, -halo, -(halo-substituted) C₁-C₅ alkyl, -(halo-substituted) phenyl, -phenylene-O—C₁-C₅ alkyl, -(cyano-substituted) phenyl, —OH, —O—C₁-C₅ alkyl, —N(Rᵃ)₂, —(C₁-C₅ alkylene)-N(Rᵃ)₂, —C₁-C₅ alkylene-C(O)O—(C₁-C₅ alkylene)-N(Rᵃ)₂, —COOH, —(C₁-C₅ alkylene)-COOH, —OP(O)(OH)₂, —OS(O)₂OH, —(C₁-C₅ alkylene)-OP(O)(OH)₂, —(C₁-C₅ alkylene)-OS(O)₂OH, —C(O)O—C₁-C₅ alkyl, —OC(O)—C₁-C₅ alkyl, —(C₁-C₅ alkylene)-C(O)O—C₁-C₅ alkyl, —(C₁-C₅ alkylene)-C(O)NH—C₁-C₅ alkyl, —C(O)NH₂, or —NO₂, wherein each occurrence of Rᵃ is independently —H, -benzyl, or —C₁-C₁₀ alkyl;

or N and both R² groups are taken together to form a nitrogen-containing 3- to 7-membered monocyclic heterocycle which is unsubstituted or substituted with one to three of —C₁-C₅ alkyl, -phenyl, —(C₁-C₅ alkylene)-phenyl, -(hydroxy-substituted) C₁-C₅ alkyl, -halo, -(halo-substituted) C₁-C₅ alkyl, -(halo-substituted) phenyl, -phenylene-O—C₁-C₅ alkyl, -(cyano-substituted) phenyl, —OH, —O—C₁-C₅ alkyl, —N(Rᵃ)₂, —(C₁-C₅ alkylene)-N(Rᵃ)₂, —(C₁-C₅ alkylene)-C(O)O—(C₁-C₅ alkylene)-N(Rᵃ)₂, —COOH, —(C₁-C₅ alkylene)-COOH, —OP(O)(OH)₂, —OS(O)₂OH, —(C₁-C₅ alkylene)-OP(O)(OH)₂, —(C₁-C₅ alkylene)-OS(O)₂OH, —C(O)O—C₁-C₅ alkyl, —OC(O)—C₁-C₅ alkyl, —(C₁-C₅ alkylene)-C(O)O—C₁-C₅ alkyl, —(C₁-C₅ alkylene)-C(O)NH—C₁-C₅ alkyl, —C(O)NH₂, or —NO₂, wherein each occurrence of Rᵃ is independently —H, -benzyl, or —C₁-C₁₀ alkyl;

n is an integer ranging from 1 to 10; and
m is an integer ranging from 2 to 10.

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂)— or —N(C(CH₃)₃)—; R¹ is —CH₂—N(R²)(R²); and at least one R² is methyl.

In another embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂)— or —N(C(CH₃)₃)—; R¹ is —CH₂—N(R²)(R²); and at least one R² is ethyl.

In yet another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂)— or —N(C(CH₃)₃)—; R¹ is —CH₂—N(R²)(R²); and at least one R² is propyl.

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂)— or —N(C(CH₃)₃)—; R¹ is —CH₂—N(R²)(R²); and at least one R² is —C₃-C₈ monocyclic cycloalkyl.

In another embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂)— or —N(C(CH₃)₃)—; R¹ is —CH₂—N(R²)(R²); and at least one R² is cyclohexyl.

In yet another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂)— or —N(C(CH₃)₃)—; and R¹ is —CH₂—N(R²)(R²), wherein N and both R² groups are taken together to form a nitrogen-containing 3- to 7-membered monocyclic heterocycle.

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂)— or —N(C(CH₃)₃)—; and R¹ is —CH₂—N(R²)(R²), wherein N and both R² groups are taken together to form a nitrogen-containing 3- to 7-membered monocyclic heterocycle, which is substituted with a hydroxyl.

In another embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)

$(CH_3)_2)$—, —$N(CH_2C(H)(CH_3)_2)$— or —$N(C(CH_3)_3)$—; and $R^1$ is —$CH_2$—$N(R^2)(R^2)$, wherein N and both $R^2$ groups are taken together to form a nitrogen-containing 3- to 7-membered monocyclic heterocycle, which is substituted with a nitrogen-containing 3- to 7-membered monocyclic heterocycle.

Illustrative examples of the Indenoisoquinolinone Analogs include the compounds of Formula (Ia) as set forth below:

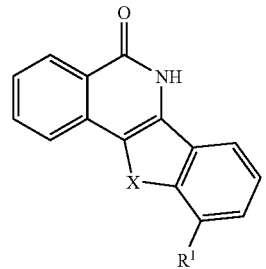

(Ia)

| Compound | n | —$R^1$ | X |
|---|---|---|---|
| Ia-1 | 1 | —$(CH_2)_n$—$N(CH_3)_2$ | —$N(CH_3)$— |
| Ia-2 | 2 | —$(CH_2)_n$—$N(CH_3)_2$ | —$N(CH_3)$— |
| Ia-3 | 3 | —$(CH_2)_n$—$N(CH_3)_2$ | —$N(CH_3)$— |
| Ia-4 | 4 | —$(CH_2)_n$—$N(CH_3)_2$ | —$N(CH_3)$— |
| Ia-5 | 5 | —$(CH_2)_n$—$N(CH_3)_2$ | —$N(CH_3)$— |
| Ia-6 | 6 | —$(CH_2)_n$—$N(CH_3)_2$ | —$N(CH_3)$— |
| Ia-7 | 1 | —$(CH_2)_n$—$N(CH_3)_2$ | —$N(CH_2CH_3)$— |
| Ia-8 | 2 | —$(CH_2)_n$—$N(CH_3)_2$ | —$N(CH_2CH_3)$— |
| Ia-9 | 3 | —$(CH_2)_n$—$N(CH_3)_2$ | —$N(CH_2CH_3)$— |
| Ia-10 | 4 | —$(CH_2)_n$—$N(CH_3)_2$ | —$N(CH_2CH_3)$— |
| Ia-11 | 5 | —$(CH_2)_n$—$N(CH_3)_2$ | —$N(CH_2CH_3)$— |
| Ia-12 | 6 | —$(CH_2)_n$—$N(CH_3)_2$ | —$N(CH_2CH_3)$— |
| Ia-13 | 1 | —$(CH_2)_n$—$N(CH_3)_2$ | —$N(CH_2CH_2CH_3)$— |
| Ia-14 | 2 | —$(CH_2)_n$—$N(CH_3)_2$ | —$N(CH_2CH_2CH_3)$— |
| Ia-15 | 3 | —$(CH_2)_n$—$N(CH_3)_2$ | —$N(CH_2CH_2CH_3)$— |
| Ia-16 | 4 | —$(CH_2)_n$—$N(CH_3)_2$ | —$N(CH_2CH_2CH_3)$— |
| Ia-17 | 5 | —$(CH_2)_n$—$N(CH_3)_2$ | —$N(CH_2CH_2CH_3)$— |
| Ia-18 | 6 | —$(CH_2)_n$—$N(CH_3)_2$ | —$N(CH_2CH_2CH_3)$— |
| Ia-19 | 1 | —$(CH_2)_n$—$N(CH_3)_2$ | —$N(CH_2CH_2CH_2CH_3)$— |
| Ia-20 | 2 | —$(CH_2)_n$—$N(CH_3)_2$ | —$N(CH_2CH_2CH_2CH_3)$— |
| Ia-21 | 3 | —$(CH_2)_n$—$N(CH_3)_2$ | —$N(CH_2CH_2CH_2CH_3)$— |
| Ia-22 | 4 | —$(CH_2)_n$—$N(CH_3)_2$ | —$N(CH_2CH_2CH_2CH_3)$— |
| Ia-23 | 5 | —$(CH_2)_n$—$N(CH_3)_2$ | —$N(CH_2CH_2CH_2CH_3)$— |
| Ia-24 | 6 | —$(CH_2)_n$—$N(CH_3)_2$ | —$N(CH_2CH_2CH_2CH_3)$— |
| Ia-25 | 1 | —$(CH_2)_n$—$N(CH_3)_2$ | —$N(C(H)(CH_3)(CH_2CH_3))$— |
| Ia-26 | 2 | —$(CH_2)_n$—$N(CH_3)_2$ | —$N(C(H)(CH_3)(CH_2CH_3))$— |
| Ia-27 | 3 | —$(CH_2)_n$—$N(CH_3)_2$ | —$N(C(H)(CH_3)(CH_2CH_3))$— |
| Ia-28 | 4 | —$(CH_2)_n$—$N(CH_3)_2$ | —$N(C(H)(CH_3)(CH_2CH_3))$— |
| Ia-29 | 5 | —$(CH_2)_n$—$N(CH_3)_2$ | —$N(C(H)(CH_3)(CH_2CH_3))$— |
| Ia-30 | 6 | —$(CH_2)_n$—$N(CH_3)_2$ | —$N(C(H)(CH_3)(CH_2CH_3))$— |
| Ia-31 | 1 | —$(CH_2)_n$—$N(CH_3)_2$ | —$N(C(H)(CH_3)_2)$— |
| Ia-32 | 2 | —$(CH_2)_n$—$N(CH_3)_2$ | —$N(C(H)(CH_3)_2)$— |
| Ia-33 | 3 | —$(CH_2)_n$—$N(CH_3)_2$ | —$N(C(H)(CH_3)_2)$— |
| Ia-34 | 4 | —$(CH_2)_n$—$N(CH_3)_2$ | —$N(C(H)(CH_3)_2)$— |
| Ia-35 | 5 | —$(CH_2)_n$—$N(CH_3)_2$ | —$N(C(H)(CH_3)_2)$— |
| Ia-36 | 6 | —$(CH_2)_n$—$N(CH_3)_2$ | —$N(C(H)(CH_3)_2)$— |
| Ia-37 | 1 | —$(CH_2)_n$—$N(CH_3)_2$ | —$N(CH_2C(H)(CH_3)_2)$— |
| Ia-38 | 2 | —$(CH_2)_n$—$N(CH_3)_2$ | —$N(CH_2C(H)(CH_3)_2)$— |
| Ia-39 | 3 | —$(CH_2)_n$—$N(CH_3)_2$ | —$N(CH_2C(H)(CH_3)_2)$— |
| Ia-40 | 4 | —$(CH_2)_n$—$N(CH_3)_2$ | —$N(CH_2C(H)(CH_3)_2)$— |
| Ia-41 | 5 | —$(CH_2)_n$—$N(CH_3)_2$ | —$N(CH_2C(H)(CH_3)_2)$— |
| Ia-42 | 6 | —$(CH_2)_n$—$N(CH_3)_2$ | —$N(CH_2C(H)(CH_3)_2)$— |
| Ia-43 | 1 | —$(CH_2)_n$—$N(CH_3)_2$ | —$N(C(CH_3)_3)$— |
| Ia-44 | 2 | —$(CH_2)_n$—$N(CH_3)_2$ | —$N(C(CH_3)_3)$— |
| Ia-45 | 3 | —$(CH_2)_n$—$N(CH_3)_2$ | —$N(C(CH_3)_3)$— |
| Ia-46 | 4 | —$(CH_2)_n$—$N(CH_3)_2$ | —$N(C(CH_3)_3)$— |
| Ia-47 | 5 | —$(CH_2)_n$—$N(CH_3)_2$ | —$N(C(CH_3)_3)$— |
| Ia-48 | 6 | —$(CH_2)_n$—$N(CH_3)_2$ | —$N(C(CH_3)_3)$— |
| Ia-49 | 1 | —$(CH_2)_n$—N(morpholine) | —$N(CH_3)$— |
| Ia-50 | 2 | —$(CH_2)_n$—N(morpholine) | —$N(CH_3)$— |

-continued

| | | | |
|---|---|---|---|
| Ia-51 | 3 | 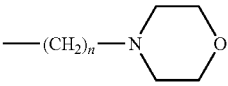 —(CH$_2$)$_n$—N(morpholine) | —N(CH$_3$)— |
| Ia-52 | 4 | 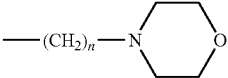 —(CH$_2$)$_n$—N(morpholine) | —N(CH$_3$)— |
| Ia-53 | 5 | 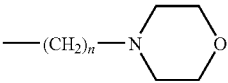 —(CH$_2$)$_n$—N(morpholine) | —N(CH$_3$)— |
| Ia-54 | 6 | 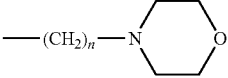 —(CH$_2$)$_n$—N(morpholine) | —N(CH$_3$)— |
| Ia-55 | 1 | 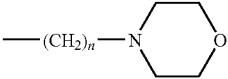 —(CH$_2$)$_n$—N(morpholine) | —N(CH$_2$CH$_3$)— |
| Ia-56 | 2 | 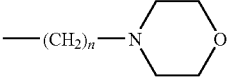 —(CH$_2$)$_n$—N(morpholine) | —N(CH$_2$CH$_3$)— |
| Ia-57 | 3 | 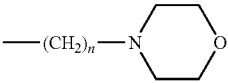 —(CH$_2$)$_n$—N(morpholine) | —N(CH$_2$CH$_3$)— |
| Ia-58 | 4 | 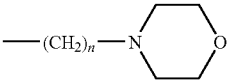 —(CH$_2$)$_n$—N(morpholine) | —N(CH$_2$CH$_3$)— |
| Ia-59 | 5 | 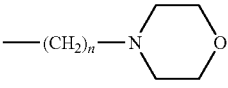 —(CH$_2$)$_n$—N(morpholine) | —N(CH$_2$CH$_3$)— |
| Ia-60 | 6 | 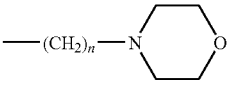 —(CH$_2$)$_n$—N(morpholine) | —N(CH$_2$CH$_3$)— |
| Ia-61 | 1 | 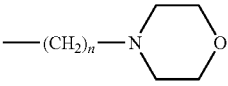 —(CH$_2$)$_n$—N(morpholine) | —N(CH$_2$CH$_2$CH$_3$)— |
| Ia-62 | 2 | 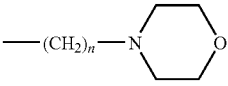 —(CH$_2$)$_n$—N(morpholine) | —N(CH$_2$CH$_2$CH$_3$)— |
| Ia-63 | 3 | 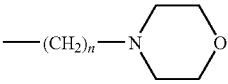 —(CH$_2$)$_n$—N(morpholine) | —N(CH$_2$CH$_2$CH$_3$)— |
| Ia-64 | 4 | 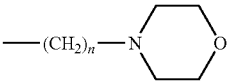 —(CH$_2$)$_n$—N(morpholine) | —N(CH$_2$CH$_2$CH$_3$)— |
| Ia-65 | 5 | 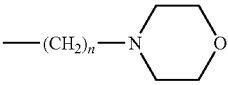 —(CH$_2$)$_n$—N(morpholine) | —N(CH$_2$CH$_2$CH$_3$)— |
| Ia-66 | 6 | 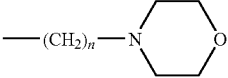 —(CH$_2$)$_n$—N(morpholine) | —N(CH$_2$CH$_2$CH$_3$)— |

-continued

| | | | |
|---|---|---|---|
| Ia-67 | 1 | 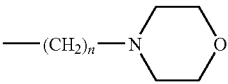—(CH$_2$)$_n$—N(morpholine) | —N(CH$_2$CH$_2$CH$_2$CH$_3$)— |
| Ia-68 | 2 | 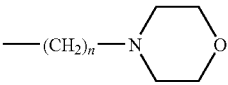—(CH$_2$)$_n$—N(morpholine) | —N(CH$_2$CH$_2$CH$_2$CH$_3$)— |
| Ia-69 | 3 | 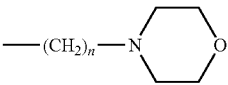—(CH$_2$)$_n$—N(morpholine) | —N(CH$_2$CH$_2$CH$_2$CH$_3$)— |
| Ia-70 | 4 | 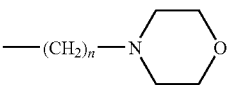—(CH$_2$)$_n$—N(morpholine) | —N(CH$_2$CH$_2$CH$_2$CH$_3$)— |
| Ia-71 | 5 | 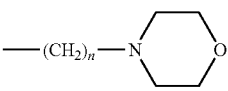—(CH$_2$)$_n$—N(morpholine) | —N(CH$_2$CH$_2$CH$_2$CH$_3$)— |
| Ia-72 | 6 | 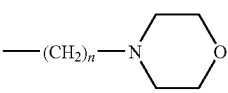—(CH$_2$)$_n$—N(morpholine) | —N(CH$_2$CH$_2$CH$_2$CH$_3$)— |
| Ia-73 | 1 | 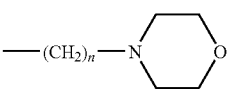—(CH$_2$)$_n$—N(morpholine) | —N(C(H)(CH$_3$)(CH$_2$CH$_3$))— |
| Ia-74 | 2 | 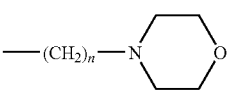—(CH$_2$)$_n$—N(morpholine) | —N(C(H)(CH$_3$)(CH$_2$CH$_3$))— |
| Ia-75 | 3 | 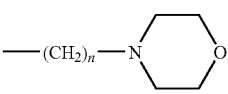—(CH$_2$)$_n$—N(morpholine) | —N(C(H)(CH$_3$)(CH$_2$CH$_3$))— |
| Ia-76 | 4 | 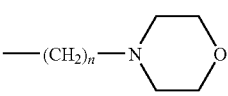—(CH$_2$)$_n$—N(morpholine) | —N(C(H)(CH$_3$)(CH$_2$CH$_3$))— |
| Ia-77 | 5 | 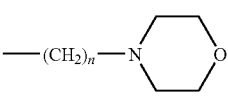—(CH$_2$)$_n$—N(morpholine) | —N(C(H)(CH$_3$)(CH$_2$CH$_3$))— |
| Ia-78 | 6 | 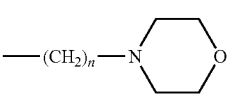—(CH$_2$)$_n$—N(morpholine) | —N(C(H)(CH$_3$)(CH$_2$CH$_3$))— |
| Ia-79 | 1 | 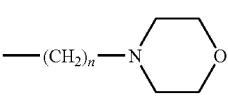—(CH$_2$)$_n$—N(morpholine) | —N(C(H)(CH$_3$)$_2$)— |
| Ia-80 | 2 | 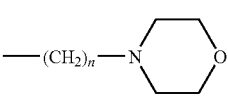—(CH$_2$)$_n$—N(morpholine) | —N(C(H)(CH$_3$)$_2$)— |
| Ia-81 | 3 | 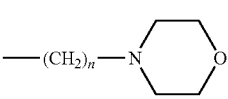—(CH$_2$)$_n$—N(morpholine) | —N(C(H)(CH$_3$)$_2$)— |
| Ia-82 | 4 | 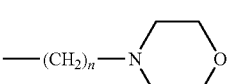—(CH$_2$)$_n$—N(morpholine) | —N(C(H)(CH$_3$)$_2$)— |

-continued

| | | | |
|---|---|---|---|
| Ia-83 | 5 | —(CH₂)ₙ—N(morpholine) | —N(C(H)(CH₃)₂)— |
| Ia-84 | 6 | —(CH₂)ₙ—N(morpholine) | —N(C(H)(CH₃)₂)— |
| Ia-85 | 1 | —(CH₂)ₙ—N(morpholine) | —N(CH₂C(H)(CH₃)₂)— |
| Ia-86 | 2 | —(CH₂)ₙ—N(morpholine) | —N(CH₂C(H)(CH₃)₂)— |
| Ia-87 | 3 | —(CH₂)ₙ—N(morpholine) | —N(CH₂C(H)(CH₃)₂)— |
| Ia-88 | 4 | —(CH₂)ₙ—N(morpholine) | —N(CH₂C(H)(CH₃)₂)— |
| Ia-89 | 5 | —(CH₂)ₙ—N(morpholine) | —N(CH₂C(H)(CH₃)₂)— |
| Ia-90 | 6 | —(CH₂)ₙ—N(morpholine) | —N(CH₂C(H)(CH₃)₂)— |
| Ia-91 | 1 | —(CH₂)ₙ—N(morpholine) | —N(C(CH₃)₃)— |
| Ia-92 | 2 | —(CH₂)ₙ—N(morpholine) | —N(C(CH₃)₃)— |
| Ia-93 | 3 | —(CH₂)ₙ—N(morpholine) | —N(C(CH₃)₃)— |
| Ia-94 | 4 | —(CH₂)ₙ—N(morpholine) | —N(C(CH₃)₃)— |
| Ia-95 | 5 | —(CH₂)ₙ—N(morpholine) | —N(C(CH₃)₃)— |
| Ia-96 | 6 | —(CH₂)ₙ—N(morpholine) | —N(C(CH₃)₃)— |

| Compound | m | —R¹ | X |
|---|---|---|---|
| Ia-146 | 2 | —O—(CH₂)ₘ—N(CH₃)₂ | —N(CH₃)— |
| Ia-147 | 3 | —O—(CH₂)ₘ—N(CH₃)₂ | —N(CH₃)— |
| Ia-148 | 4 | —O—(CH₂)ₘ—N(CH₃)₂ | —N(CH₃)— |
| Ia-149 | 5 | —O—(CH₂)ₘ—N(CH₃)₂ | —N(CH₃)— |
| Ia-150 | 6 | —O—(CH₂)ₘ—N(CH₃)₂ | —N(CH₃)— |
| Ia-151 | 2 | —O—(CH₂)ₘ—N(CH₃)₂ | —N(CH₃)— |
| Ia-152 | 3 | —O—(CH₂)ₘ—N(CH₃)₂ | —N(CH₂CH₃)— |
| Ia-153 | 4 | —O—(CH₂)ₘ—N(CH₃)₂ | —N(CH₂CH₃)— |
| Ia-154 | 5 | —O—(CH₂)ₘ—N(CH₃)₂ | —N(CH₂CH₃)— |

| | | -continued | |
|---|---|---|---|
| Ia-155 | 6 | —O—(CH$_2$)$_m$—N(CH$_3$)$_2$ | —N(CH$_2$CH$_3$)— |
| Ia-156 | 2 | —O—(CH$_2$)$_m$—N(CH$_3$)$_2$ | —N(CH$_2$CH$_3$)— |
| Ia-157 | 3 | —O—(CH$_2$)$_m$—N(CH$_3$)$_2$ | —N(CH$_2$CH$_3$)— |
| Ia-158 | 4 | —O—(CH$_2$)$_m$—N(CH$_3$)$_2$ | —N(CH$_2$CH$_2$CH$_3$)— |
| Ia-159 | 5 | —O—(CH$_2$)$_m$—N(CH$_3$)$_2$ | —N(CH$_2$CH$_2$CH$_3$)— |
| Ia-160 | 6 | —O—(CH$_2$)$_m$—N(CH$_3$)$_2$ | —N(CH$_2$CH$_2$CH$_3$)— |
| Ia-161 | 2 | —O—(CH$_2$)$_m$—N(CH$_3$)$_2$ | —N(CH$_2$CH$_2$CH$_3$)— |
| Ia-162 | 3 | —O—(CH$_2$)$_m$—N(CH$_3$)$_2$ | —N(CH$_2$CH$_2$CH$_3$)— |
| Ia-163 | 4 | —O—(CH$_2$)$_m$—N(CH$_3$)$_2$ | —N(CH$_2$CH$_2$CH$_3$)— |
| Ia-164 | 5 | —O—(CH$_2$)$_m$—N(CH$_3$)$_2$ | —N(CH$_2$CH$_2$CH$_2$CH$_3$)— |
| Ia-165 | 6 | —O—(CH$_2$)$_m$—N(CH$_3$)$_2$ | —N(CH$_2$CH$_2$CH$_2$CH$_3$)— |
| Ia-166 | 2 | —O—(CH$_2$)$_m$—N(CH$_3$)$_2$ | —N(CH$_2$CH$_2$CH$_2$CH$_3$)— |
| Ia-167 | 3 | —O—(CH$_2$)$_m$—N(CH$_3$)$_2$ | —N(CH$_2$CH$_2$CH$_2$CH$_3$)— |
| Ia-168 | 4 | —O—(CH$_2$)$_m$—N(CH$_3$)$_2$ | —N(CH$_2$CH$_2$CH$_2$CH$_3$)— |
| Ia-169 | 5 | —O—(CH$_2$)$_m$—N(CH$_3$)$_2$ | —N(CH$_2$CH$_2$CH$_2$CH$_3$)— |
| Ia-170 | 6 | —O—(CH$_2$)$_m$—N(CH$_3$)$_2$ | —N(C(H)(CH$_3$)(CH$_2$CH$_3$))— |
| Ia-171 | 2 | —O—(CH$_2$)$_m$—N(CH$_3$)$_2$ | —N(C(H)(CH$_3$)(CH$_2$CH$_3$))— |
| Ia-172 | 3 | —O—(CH$_2$)$_m$—N(CH$_3$)$_2$ | —N(C(H)(CH$_3$)(CH$_2$CH$_3$))— |
| Ia-173 | 4 | —O—(CH$_2$)$_m$—N(CH$_3$)$_2$ | —N(C(H)(CH$_3$)(CH$_2$CH$_3$))— |
| Ia-174 | 5 | —O—(CH$_2$)$_m$—N(CH$_3$)$_2$ | —N(C(H)(CH$_3$)(CH$_2$CH$_3$))— |
| Ia-175 | 6 | —O—(CH$_2$)$_m$—N(CH$_3$)$_2$ | —N(C(H)(CH$_3$)(CH$_2$CH$_3$))— |
| Ia-176 | 2 | —O—(CH$_2$)$_m$—N(CH$_3$)$_2$ | —N(C(H)(CH$_3$)$_2$)— |
| Ia-178 | 3 | —O—(CH$_2$)$_m$—N(CH$_3$)$_2$ | —N(C(H)(CH$_3$)$_2$)— |
| Ia-179 | 4 | —O—(CH$_2$)$_m$—N(CH$_3$)$_2$ | —N(C(H)(CH$_3$)$_2$)— |
| Ia-180 | 5 | —O—(CH$_2$)$_m$—N(CH$_3$)$_2$ | —N(C(H)(CH$_3$)$_2$)— |
| Ia-181 | 6 | —O—(CH$_2$)$_m$—N(CH$_3$)$_2$ | —N(C(H)(CH$_3$)$_2$)— |
| Ia-182 | 2 | —O—(CH$_2$)$_m$—N(CH$_3$)$_2$ | —N(C(H)(CH$_3$)$_2$)— |
| Ia-183 | 3 | —O—(CH$_2$)$_m$—N(CH$_3$)$_2$ | —N(CH$_2$C(H)(CH$_3$)$_2$)— |
| Ia-184 | 4 | —O—(CH$_2$)$_m$—N(CH$_3$)$_2$ | —N(CH$_2$C(H)(CH$_3$)$_2$)— |
| Ia-185 | 5 | —O—(CH$_2$)$_m$—N(CH$_3$)$_2$ | —N(CH$_2$C(H)(CH$_3$)$_2$)— |
| Ia-186 | 6 | —O—(CH$_2$)$_m$—N(CH$_3$)$_2$ | —N(CH$_2$C(H)(CH$_3$)$_2$)— |
| Ia-187 | 2 | —O—(CH$_2$)$_m$—N(morpholine) | —N(CH$_3$)— |
| Ia-188 | 3 | —O—(CH$_2$)$_m$—N(morpholine) | —N(CH$_3$)— |
| Ia-189 | 4 | —O—(CH$_2$)$_m$—N(morpholine) | —N(CH$_3$)— |
| Ia-190 | 5 | —O—(CH$_2$)$_m$—N(morpholine) | —N(CH$_3$)— |
| Ia-191 | 6 | —O—(CH$_2$)$_m$—N(morpholine) | —N(CH$_3$)— |
| Ia-192 | 2 | —O—(CH$_2$)$_m$—N(morpholine) | —N(CH$_3$)— |
| Ia-193 | 3 | —O—(CH$_2$)$_m$—N(morpholine) | —N(CH$_2$CH$_3$)— |
| Ia-194 | 4 | —O—(CH$_2$)$_m$—N(morpholine) | —N(CH$_2$CH$_3$)— |
| Ia-195 | 5 | —O—(CH$_2$)$_m$—N(morpholine) | —N(CH$_2$CH$_3$)— |
| Ia-196 | 6 | —O—(CH$_2$)$_m$—N(morpholine) | —N(CH$_2$CH$_3$)— |

-continued

| | | | |
|---|---|---|---|
| Ia-197 | 2 | —O—(CH$_2$)$_m$—N(morpholine) | —N(CH$_2$CH$_3$)— |
| Ia-198 | 3 | —O—(CH$_2$)$_m$—N(morpholine) | —N(CH$_2$CH$_3$)— |
| Ia-199 | 4 | —O—(CH$_2$)$_m$—N(morpholine) | —N(CH$_2$CH$_3$)— |
| Ia-200 | 5 | —O—(CH$_2$)$_m$—N(morpholine) | —N(CH$_2$CH$_3$)— |
| Ia-201 | 6 | —O—(CH$_2$)$_m$—N(morpholine) | —N(CH$_2$CH$_3$)— |
| Ia-202 | 2 | —O—(CH$_2$)$_m$—N(morpholine) | —N(CH$_2$CH$_2$CH$_3$)— |
| Ia-203 | 3 | —O—(CH$_2$)$_m$—N(morpholine) | —N(CH$_2$CH$_2$CH$_3$)— |
| Ia-204 | 4 | —O—(CH$_2$)$_m$—N(morpholine) | —N(CH$_2$CH$_2$CH$_3$)— |
| Ia-205 | 5 | —O—(CH$_2$)$_m$—N(morpholine) | —N(CH$_2$CH$_2$CH$_3$)— |
| Ia-206 | 6 | —O—(CH$_2$)$_m$—N(morpholine) | —N(CH$_2$CH$_2$CH$_3$)— |
| Ia-207 | 2 | —O—(CH$_2$)$_m$—N(morpholine) | —N(CH$_2$CH$_2$CH$_2$CH$_3$)— |
| Ia-208 | 3 | —O—(CH$_2$)$_m$—N(morpholine) | —N(CH$_2$CH$_2$CH$_2$CH$_3$)— |
| Ia-209 | 4 | —O—(CH$_2$)$_m$—N(morpholine) | —N(CH$_2$CH$_2$CH$_2$CH$_3$)— |
| Ia-210 | 5 | —O—(CH$_2$)$_m$—N(morpholine) | —N(CH$_2$CH$_2$CH$_2$CH$_3$)— |
| Ia-211 | 6 | —O—(CH$_2$)$_m$—N(morpholine) | —N(C(H)(CH$_3$)(CH$_2$CH$_3$))— |
| Ia-212 | 2 | —O—(CH$_2$)$_m$—N(morpholine) | —N(C(H)(CH$_3$)(CH$_2$CH$_3$))— |

-continued

| Compound | m | -R¹ | X |
|---|---|---|---|
| Ia-213 | 3 | —O—(CH₂)ₘ—N(morpholine) | —N(C(H)(CH₃)(CH₂CH₃))— |
| Ia-214 | 4 | —O—(CH₂)ₘ—N(morpholine) | —N(C(H)(CH₃)(CH₂CH₃))— |
| Ia-215 | 5 | —O—(CH₂)ₘ—N(morpholine) | —N(C(H)(CH₃)(CH₂CH₃))— |
| Ia-216 | 6 | —O—(CH₂)ₘ—N(morpholine) | —N(C(H)(CH₃)(CH₂CH₃))— |
| Ia-217 | 2 | —O—(CH₂)ₘ—N(morpholine) | —N(C(H)(CH₃)₂)— |
| Ia-218 | 3 | —O—(CH₂)ₘ—N(morpholine) | —N(C(H)(CH₃)₂)— |
| Ia-219 | 4 | —O—(CH₂)ₘ—N(morpholine) | —N(C(H)(CH₃)₂)— |
| Ia-220 | 5 | —O—(CH₂)ₘ—N(morpholine) | —N(C(H)(CH₃)₂)— |
| Ia-221 | 6 | —O—(CH₂)ₘ—N(morpholine) | —N(C(H)(CH₃)₂)— |
| Ia-222 | 2 | —O—(CH₂)ₘ—N(morpholine) | —N(C(H)(CH₃)₂)— |
| Ia-223 | 3 | —O—(CH₂)ₘ—N(morpholine) | —N(CH₂C(H)(CH₃)₂)— |
| Ia-224 | 4 | —O—(CH₂)ₘ—N(morpholine) | —N(CH₂C(H)(CH₃)₂)— |
| Ia-225 | 5 | —O—(CH₂)ₘ—N(morpholine) | —N(CH₂C(H)(CH₃)₂)— |
| Ia-226 | 6 | —O—(CH₂)ₘ—N(morpholine) | —N(CH₂C(H)(CH₃)₂)— |

| Compound | —R¹ | X |
|---|---|---|
| Ia-267 | —CH₂—N(CH₂—CH₃)₂ | —N(CH₃)— |
| Ia-268 | —CH₂—N(CH₂—CH₃)₂ | —N(CH₂CH₃)— |
| Ia-269 | —CH₂—N(CH₂—CH₃)₂ | —N(CH₂CH₂CH₃)— |
| Ia-270 | —CH₂—N(CH₂—CH₃)₂ | —N(CH₂CH₂CH₃)— |
| Ia-271 | —CH₂—N(CH₂—CH₃)₂ | —N(C(H)(CH₃)(CH₂CH₃))— |
| Ia-272 | —CH₂—N(CH₂—CH₃)₂ | —N(C(H)(CH₃)₂)— |
| Ia-273 | —CH₂—N(CH₂—CH₃)₂ | —N(CH₂C(H)(CH₃)₂)— |
| Ia-274 | —CH₂—N(CH₂—CH₃)₂ | —N(C(CH₃)₃)— |
| Ia-275 | —CH₂—N(CH₂—CH₂—CH₃)₂ | —N(CH₃)— |

| | | |
|---|---|---|
| Ia-276 | —CH₂—N(CH₂—CH₂—CH₃)₂ | —N(CH₂CH₃)— |
| Ia-277 | —CH₂—N(CH₂—CH₂—CH₃)₂ | —N(CH₂CH₂CH₃)— |
| Ia-278 | —CH₂—N(CH₂—CH₂—CH₃)₂ | —N(CH₂CH₂CH₂CH₃)— |
| Ia-279 | —CH₂—N(CH₂—CH₂—CH₃)₂ | —N(C(H)(CH₃)(CH₂CH₃))— |
| Ia-280 | —CH₂—N(CH₂—CH₂—CH₃)₂ | —N(C(H)(CH₃)₂)— |
| Ia-281 | —CH₂—N(CH₂—CH₂—CH₃)₂ | —N(CH₂C(H)(CH₃)₂)— |
| Ia-282 | —CH₂—N(CH₂—CH₂—CH₃)₂ | —N(C(CH₃)₃)— |
| Ia-283 | —CH₂—N(CH₂—CH₂OH)₂ | —N(CH₃)— |
| Ia-284 | —CH₂—N(CH₂—CH₂OH)₂ | —N(CH₂CH₃)— |
| Ia-285 | —CH₂—N(CH₂—CH₂OH)₂ | —N(CH₂CH₂CH₃)— |
| Ia-286 | —CH₂—N(CH₂—CH₂OH)₂ | —N(CH₂CH₂CH₂CH₃)— |
| Ia-287 | —CH₂—N(CH₂—CH₂OH)₂ | —N(C(H)(CH₃)(CH₂CH₃))— |
| Ia-288 | —CH₂—N(CH₂—CH₂OH)₂ | —N(C(H)(CH₃)₂)— |
| Ia-289 | —CH₂—N(CH₂—CH₂OH)₂ | —N(CH₂C(H)(CH₃)₂)— |
| Ia-290 | —CH₂—N(CH₂—CH₂OH)₂ | —N(C(CH₃)₃)— |
| Ia-291 | —CH₂—N(CH₂—CH₂—N(CH₃)₂)₂ | —N(CH₃)— |
| Ia-292 | —CH₂—N(CH₂—CH₂—N(CH₃)₂)₂ | —N(CH₂CH₃)— |
| Ia-293 | —CH₂—N(CH₂—CH₂—N(CH₃)₂)₂ | —N(CH₂CH₂CH₃)— |
| Ia-294 | —CH₂—N(CH₂—CH₂—N(CH₃)₂)₂ | —N(CH₂CH₂CH₂CH₃)— |
| Ia-295 | —CH₂—N(CH₂—CH₂—N(CH₃)₂)₂ | —N(C(H)(CH₃)(CH₂CH₃))— |
| Ia-296 | —CH₂—N(CH₂—CH₂—N(CH₃)₂)₂ | —N(C(H)(CH₃)₂)— |
| Ia-297 | —CH₂—N(CH₂—CH₂—N(CH₃)₂)₂ | —N(CH₂C(H)(CH₃)₂)— |
| Ia-298 | —CH₂—N(CH₂—CH₂—N(CH₃)₂)₂ | —N(C(CH₃)₃)— |
| Ia-299 | —CH₂—N(CH₂—CH₂—CH₂—N(CH₃)₂)₂ | —N(CH₃)— |
| Ia-300 | —CH₂—N(CH₂—CH₂—CH₂—N(CH₃)₂)₂ | —N(CH₂CH₃)— |
| Ia-301 | —CH₂—N(CH₂—CH₂—CH₂—N(CH₃)₂)₂ | —N(CH₂CH₂CH₃)— |
| Ia-302 | —CH₂—N(CH₂—CH₂—CH₂—N(CH₃)₂)₂ | —N(CH₂CH₂CH₂CH₃)— |
| Ia-303 | —CH₂—N(CH₂—CH₂—CH₂—N(CH₃)₂)₂ | —N(C(H)(CH₃)(CH₂CH₃))— |
| Ia-304 | —CH₂—N(CH₂—CH₂—CH₂—N(CH₃)₂)₂ | —N(C(H)(CH₃)₂)— |
| Ia-305 | —CH₂—N(CH₂—CH₂—CH₂—N(CH₃)₂)₂ | —N(CH₂C(H)(CH₃)₂)— |
| Ia-306 | —CH₂—N(CH₂—CH₂—CH₂—N(CH₃)₂)₂ | —N(C(CH₃)₃)— |
| Ia-307 | —CH₂—N(aziridinyl) | —N(CH₃)— |
| Ia-308 | —CH₂—N(aziridinyl) | —N(CH₂CH₃)— |
| Ia-309 | —CH₂—N(aziridinyl) | —N(CH₂CH₂CH₃)— |
| Ia-310 | —CH₂—N(aziridinyl) | —N(CH₂CH₂CH₂CH₃)— |
| Ia-311 | —CH₂—N(aziridinyl) | —N(C(H)(CH₃)(CH₂CH₃))— |
| Ia-312 | —CH₂—N(aziridinyl) | —N(C(H)(CH₃)₂)— |
| Ia-313 | —CH₂—N(aziridinyl) | —N(CH₂C(H)(CH₃)₂)— |
| Ia-314 | —CH₂—N(aziridinyl) | —N(C(CH₃)₃)— |
| Ia-315 | —CH₂—N(azetidinyl) | —N(CH₃)— |
| Ia-316 | —CH₂—N(azetidinyl) | —N(CH₂CH₃)— |
| Ia-317 | —CH₂—N(azetidinyl) | —N(CH₂CH₂CH₃)— |
| Ia-318 | —CH₂—N(azetidinyl) | —N(CH₂CH₂CH₂CH₃)— |
| Ia-319 | —CH₂—N(azetidinyl) | —N(C(H)(CH₃)(CH₂CH₃))— |

| | | -continued |
|---|---|---|
| Ia-320 | 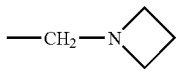 | —N(C(H)(CH₃)₂)— |
| Ia-321 | 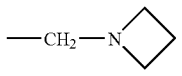 | —N(CH₂C(H)(CH₃)₂)— |
| Ia-322 | 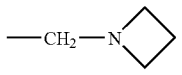 | —N(C(CH₃)₃)— |
| Ia-323 | 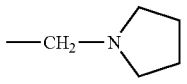 | —N(CH₃)— |
| Ia-324 | 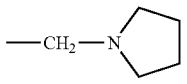 | —N(CH₂CH₃)— |
| Ia-325 | 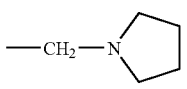 | —N(CH₂CH₂CH₃)— |
| Ia-326 | 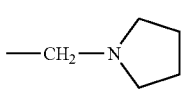 | —N(CH₂CH₂CH₃)— |
| Ia-327 | 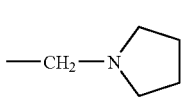 | —N(C(H)(CH₃)(CH₂CH₃))— |
| Ia-328 |  | —N(C(H)(CH₃)₂)— |
| Ia-329 |  | —N(CH₂C(H)(CH₃)₂)— |
| Ia-330 |  | —N(C(CH₃)₃)— |
| Ia-331 | 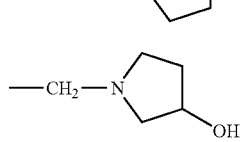 | —N(CH₃)— |
| Ia-332 | 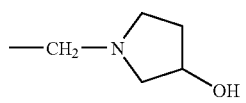 | —N(CH₂CH₃)— |
| Ia-333 | 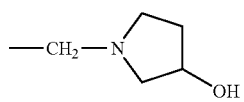 | —N(CH₂CH₃)— |
| Ia-334 | 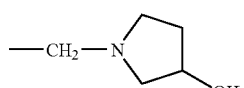 | —N(CH₂CH₂CH₃)— |
| Ia-335 | 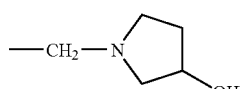 | —N(C(H)(CH₃)(CH₂CH₃))— |

-continued
| | | |
|---|---|---|
| Ia-336 | 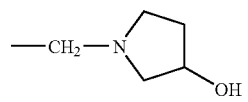 | —N(C(H)(CH$_3$)$_2$)— |
| Ia-337 | 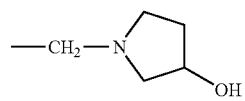 | —N(CH$_2$C(H)(CH$_3$)$_2$)— |
| Ia-338 | 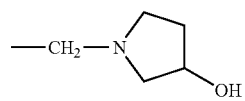 | —N(C(CH$_3$)$_3$)— |
| Ia-339 | 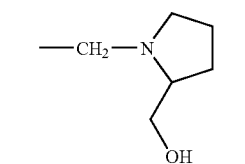 | —N(CH$_3$)— |
| Ia-340 | 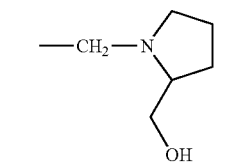 | —N(CH$_2$CH$_3$)— |
| Ia-341 | 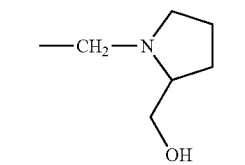 | —N(CH$_2$CH$_2$CH$_3$)— |
| Ia-342 | 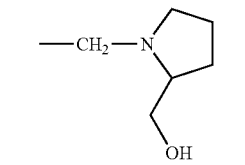 | —N(CH$_2$CH$_2$CH$_2$CH$_3$)— |
| Ia-343 | 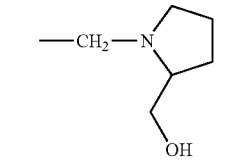 | —N(C(H)(CH$_3$)(CH$_2$CH$_3$))— |
| Ia-344 | 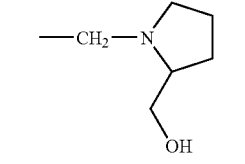 | —N(C(H)(CH$_3$)$_2$)— |
| Ia-345 | 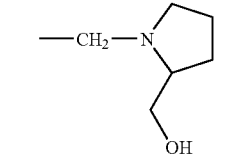 | —N(CH$_2$C(H)(CH$_3$)$_2$)— |

| | | -continued |
|---|---|---|
| Ia-346 | 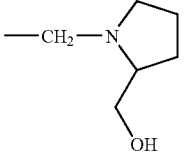 | —N(C(CH₃)₃)— |
| Ia-347 | 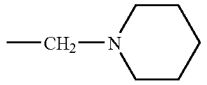 | —N(CH₃)— |
| Ia-348 | 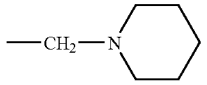 | —N(CH₂CH₃)— |
| Ia-349 | 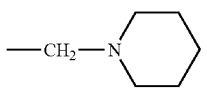 | —N(CH₂CH₂CH₃)— |
| Ia-350 | 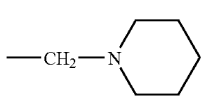 | —N(CH₂CH₂CH₂CH₃)— |
| Ia-351 | 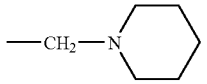 | —N(C(H)(CH₃)(CH₂CH₃))— |
| Ia-352 | 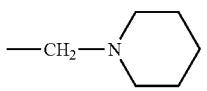 | —N(C(H)(CH₃)₂)— |
| Ia-353 | 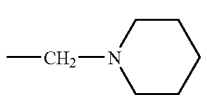 | —N(CH₂C(H)(CH₃)₂)— |
| Ia-354 | 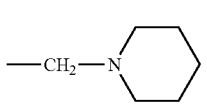 | —N(C(CH₃)₃)— |
| Ia-355 | 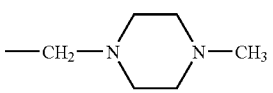 | —N(CH₃)— |
| Ia-356 | 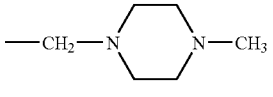 | —N(CH₂CH₃)— |
| Ia-357 | 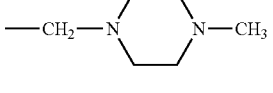 | —N(CH₂CH₂CH₃)— |
| Ia-358 | 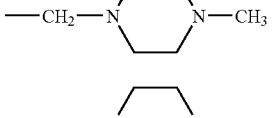 | —N(CH₂CH₂CH₂CH₃)— |
| Ia-359 | 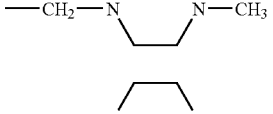 | —N(C(H)(CH₃)(CH₂CH₃))— |
| Ia-360 | 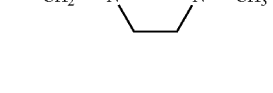 | —N(C(H)(CH₃)₂)— |

-continued

| | | |
|---|---|---|
| Ia-361 | —CH₂—N(piperazine)N—CH₃ | —N(CH₂C(H)(CH₃)₂)— |
| Ia-362 | —CH₂—N(piperazine)N—CH₃ | —N(C(CH₃)₃)— |
| Ia-363 | —CH₂—N(CH₃)(CH₂-C₆H₅) | —N(CH₃)— |
| Ia-364 | —CH₂—N(CH₃)(CH₂-C₆H₅) | —N(CH₂CH₃)— |
| Ia-365 | —CH₂—N(CH₃)(CH₂-C₆H₅) | —N(CH₂CH₂CH₃)— |
| Ia-366 | —CH₂—N(CH₃)(CH₂-C₆H₅) | —N(CH₂CH₂CH₂CH₃)— |
| Ia-367 | —CH₂—N(CH₃)(CH₂-C₆H₅) | —N(C(H)(CH₃)(CH₂CH₃))— |
| Ia-368 | —CH₂—N(CH₃)(CH₂-C₆H₅) | —N(C(H)(CH₃)₂)— |
| Ia-369 | —CH₂—N(CH₃)(CH₂-C₆H₅) | —N(CH₂C(H)(CH₃)₂)— |
| Ia-370 | —CH₂—N(CH₃)(CH₂-C₆H₅) | —N(C(CH₃)₃)— |
| Ia-371 | —CH₂—N(CH₃)(CH(CH₃)₂) | —N(CH₃)— |
| Ia-372 | —CH₂—N(CH₃)(CH(CH₃)₂) | —N(CH₂CH₃)— |

-continued
| | | |
|---|---|---|
| Ia-373 | 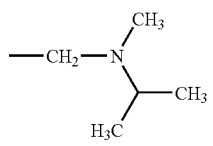 | —N(CH₂CH₂CH₃)— |
| Ia-374 | 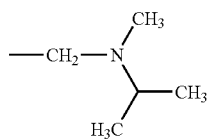 | —N(CH₂CH₂CH₂CH₃)— |
| Ia-375 | 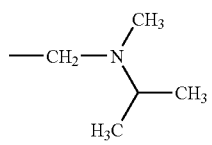 | —N(C(H)(CH₃)(CH₂CH₃))— |
| Ia-376 | 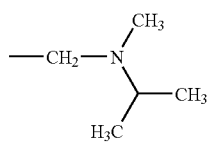 | —N(C(H)(CH₃)₂)— |
| Ia-377 | 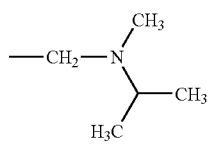 | —N(CH₂C(H)(CH₃)₂)— |
| Ia-378 | 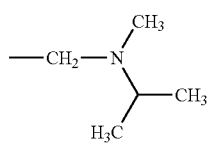 | —N(C(CH₃)₃)— |
| Ia-379 | 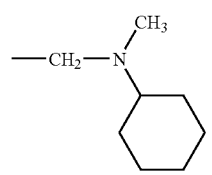 | —N(CH₃)— |
| Ia-380 | 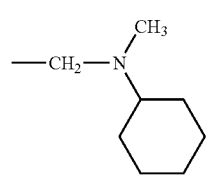 | —N(CH₂CH₃)— |
| Ia-381 | 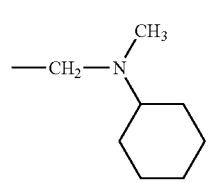 | —N(CH₂CH₂CH₃)— |
| Ia-382 | 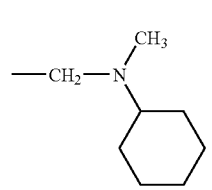 | —N(CH₂CH₂CH₂CH₃)— |

-continued
| | | |
|---|---|---|
| Ia-383 | 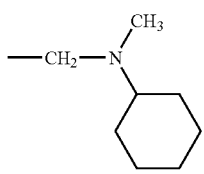 | —N(C(H)(CH₃)(CH₂CH₃))— |
| Ia-384 | 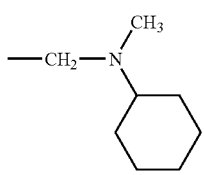 | —N(C(H)(CH₃)₂)— |
| Ia-385 | 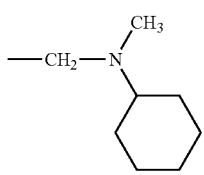 | —N(CH₂C(H)(CH₃)₂)— |
| Ia-386 | 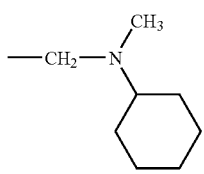 | —N(C(CH₃)₃)— |
| Ia-387 | 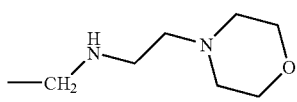 | —N(CH₃)— |
| Ia-388 | 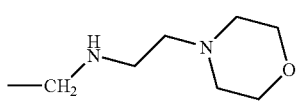 | —N(CH₂CH₃)— |
| Ia-389 | 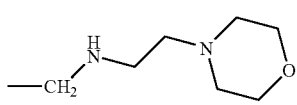 | —N(CH₂CH₂CH₃)— |
| Ia-390 | 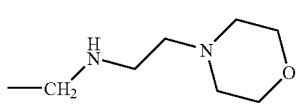 | —N(CH₂CH₂CH₂CH₃)— |
| Ia-391 | 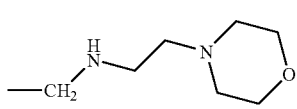 | —N(C(H)(CH₃)(CH₂CH₃))— |
| Ia-392 | 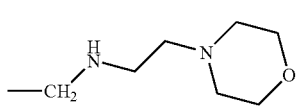 | —N(C(H)(CH₃)₂)— |
| Ia-393 | 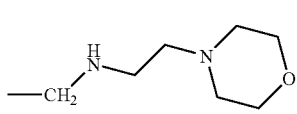 | —N(CH₂C(H)(CH₃)₂)— |
| Ia-394 | 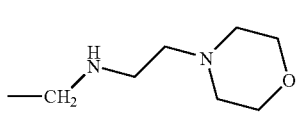 | —N(C(CH₃)₃)— |

-continued
| | | |
|---|---|---|
| Ia-395 | 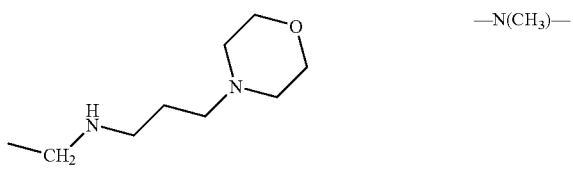 | —N(CH₃)— |
| Ia-396 | 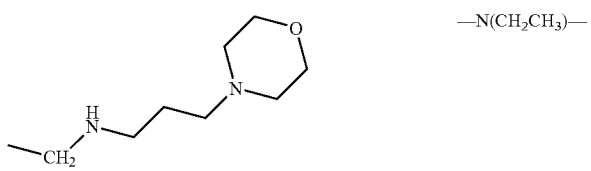 | —N(CH₂CH₃)— |
| Ia-397 | 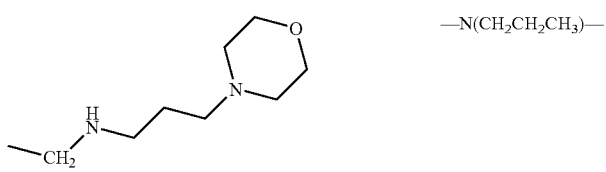 | —N(CH₂CH₂CH₃)— |
| Ia-398 | 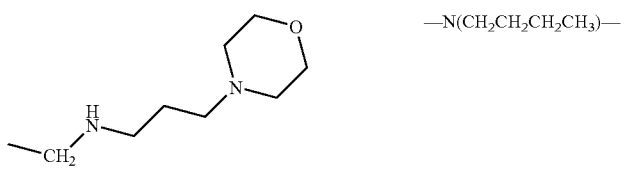 | —N(CH₂CH₂CH₂CH₃)— |
| Ia-399 | 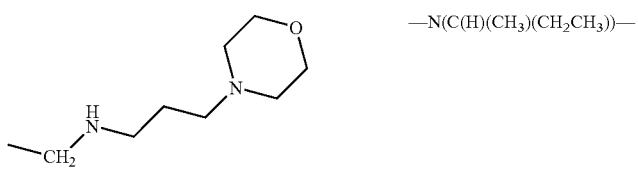 | —N(C(H)(CH₃)(CH₂CH₃))— |
| Ia-400 | 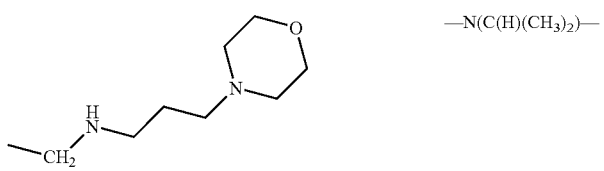 | —N(C(H)(CH₃)₂)— |
| Ia-401 | 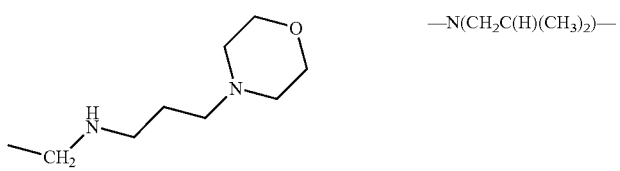 | —N(CH₂C(H)(CH₃)₂)— |
| Ia-402 | 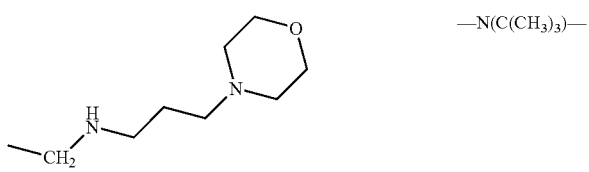 | —N(C(CH₃)₃)— |
| Ia-403 | 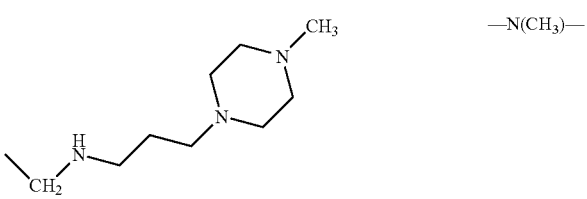 | —N(CH₃)— |

| | | |
|---|---|---|
| Ia-404 | 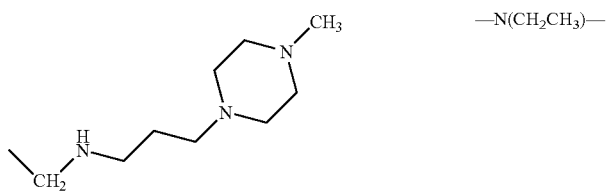 | —N(CH$_2$CH$_3$)— |
| Ia-405 | 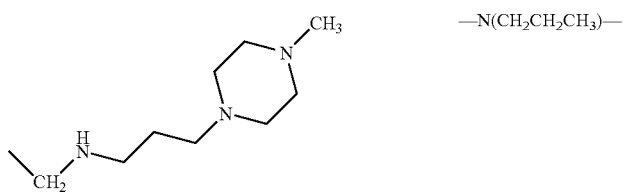 | —N(CH$_2$CH$_3$)— |
| Ia-406 | 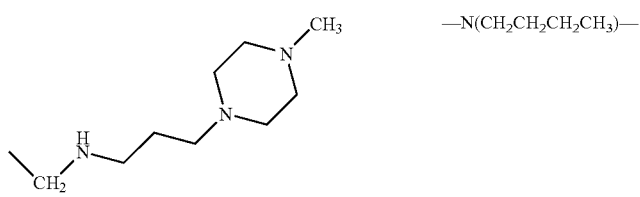 | —N(CH$_2$CH$_2$CH$_3$)— |
| Ia-407 | 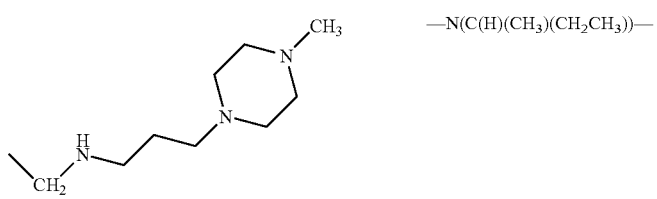 | —N(C(H)(CH$_3$)(CH$_2$CH$_3$))— |
| Ia-408 | 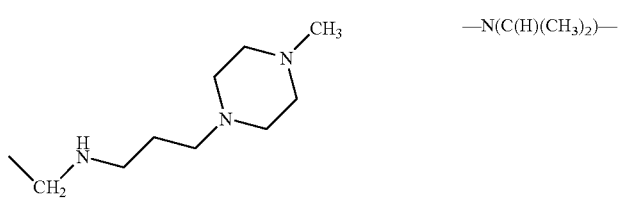 | —N(C(H)(CH$_3$)$_2$)— |
| Ia-409 | 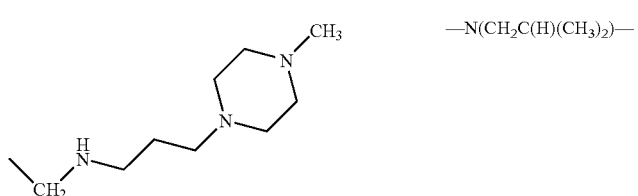 | —N(CH$_2$C(H)(CH$_3$)$_2$)— |
| Ia-410 | 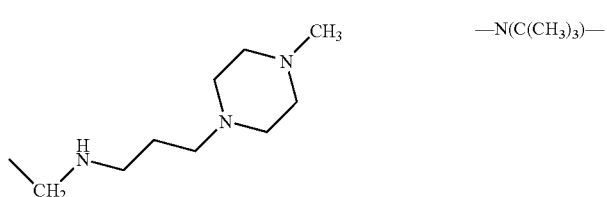 | —N(C(CH$_3$)$_3$)— |
| Ia-411 | 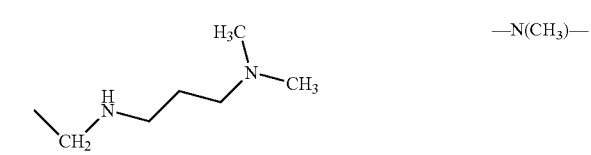 | —N(CH$_3$)— |

-continued
| | | |
|---|---|---|
| Ia-412 | 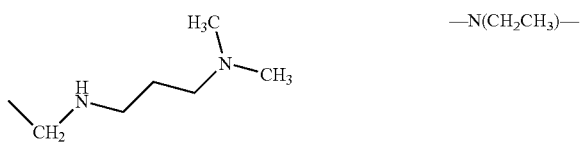 | —N(CH$_2$CH$_3$)— |
| Ia-413 | 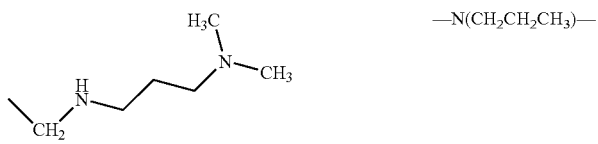 | —N(CH$_2$CH$_3$)— |
| Ia-414 | 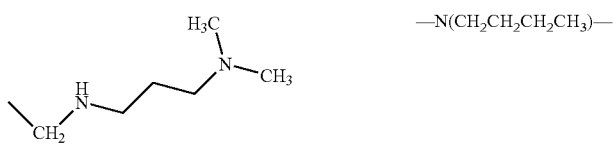 | —N(CH$_2$CH$_2$CH$_3$)— |
| Ia-415 | 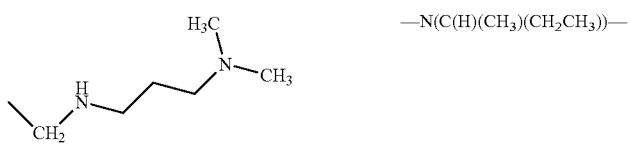 | —N(C(H)(CH$_3$)(CH$_2$CH$_3$))— |
| Ia-416 | 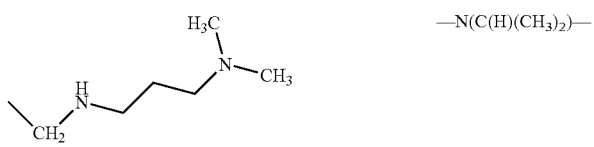 | —N(C(H)(CH$_3$)$_2$)— |
| Ia-417 | 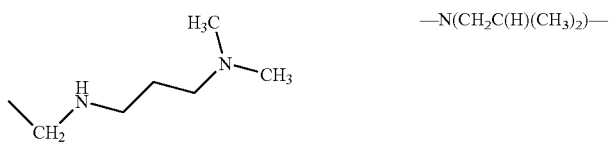 | —N(CH$_2$C(H)(CH$_3$)$_2$)— |
| Ia-418 | 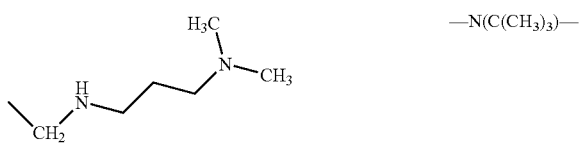 | —N(C(CH$_3$)$_3$)— |
| Ia-419 | 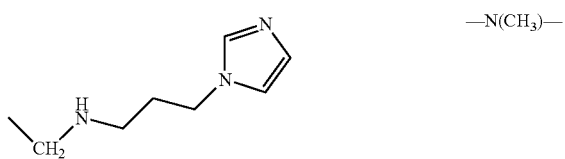 | —N(CH$_3$)— |
| Ia-420 | 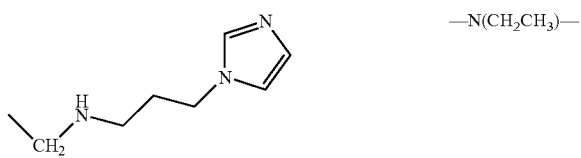 | —N(CH$_2$CH$_3$)— |
| Ia-421 | 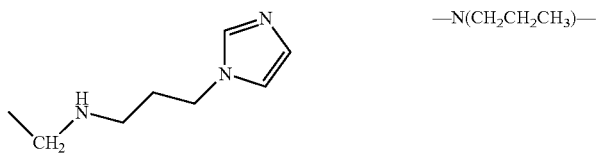 | —N(CH$_2$CH$_2$CH$_3$)— |

-continued
| | | |
|---|---|---|
| Ia-422 | 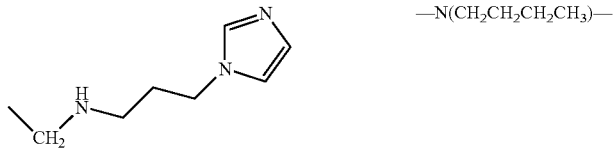 | —N(CH₂CH₂CH₂CH₃)— |
| Ia-423 | 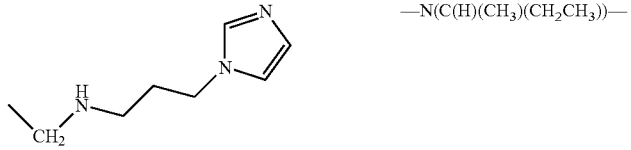 | —N(C(H)(CH₃)(CH₂CH₃))— |
| Ia-424 | 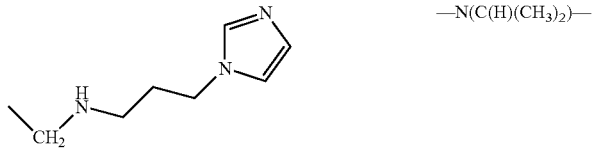 | —N(C(H)(CH₃)₂)— |
| Ia-425 | 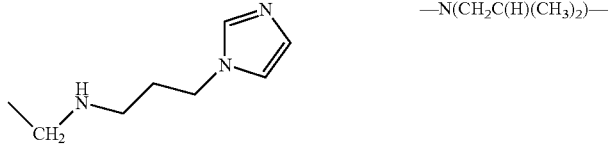 | —N(CH₂C(H)(CH₃)₂)— |
| Ia-426 | 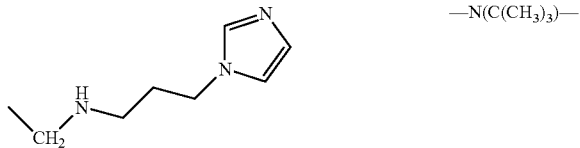 | —N(C(CH₃)₃)— |
| Ia-427 | 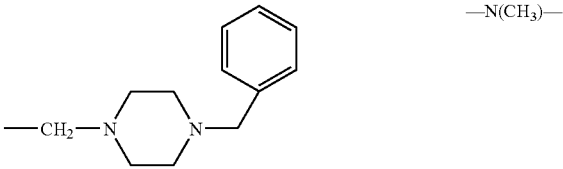 | —N(CH₃)— |
| Ia-428 | 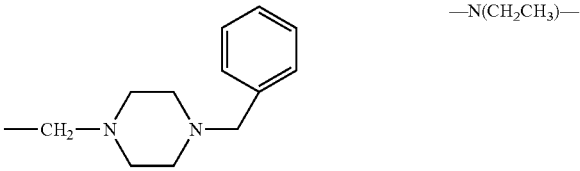 | —N(CH₂CH₃)— |
| Ia-429 |  | —N(CH₂CH₂CH₃)— |
| Ia-430 | 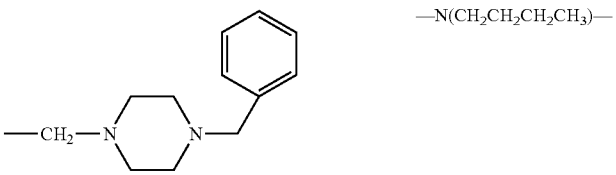 | —N(CH₂CH₂CH₂CH₃)— |

-continued
| | | |
|---|---|---|
| Ia-431 | 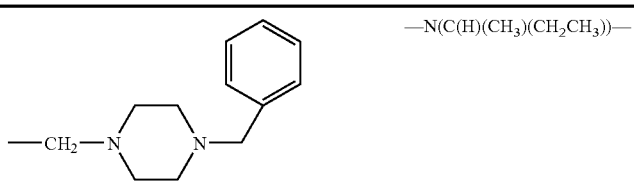 | —N(C(H)(CH₃)(CH₂CH₃))— |
| Ia-432 | 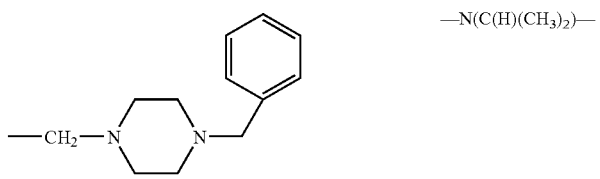 | —N(C(H)(CH₃)₂)— |
| Ia-433 | 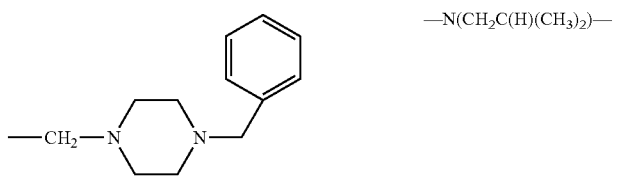 | —N(CH₂C(H)(CH₃)₂)— |
| Ia-434 | 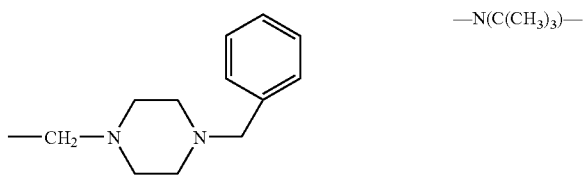 | —N(C(CH₃)₃)— |
| Ia-435 | 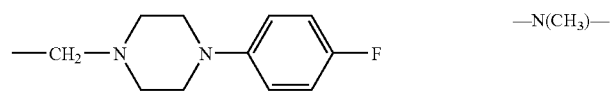 | —N(CH₃)— |
| Ia-436 | 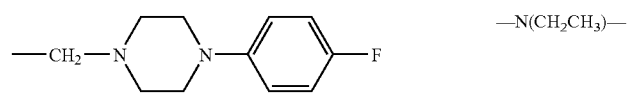 | —N(CH₂CH₃)— |
| Ia-437 | 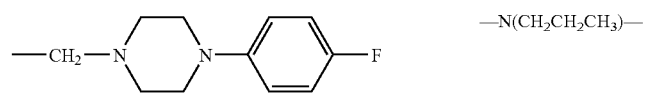 | —N(CH₂CH₂CH₃)— |
| Ia-438 | 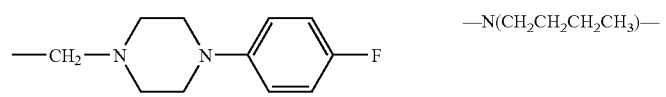 | —N(CH₂CH₂CH₂CH₃)— |
| Ia-439 | 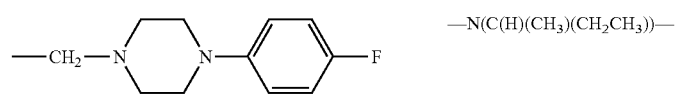 | —N(C(H)(CH₃)(CH₂CH₃))— |
| Ia-440 | 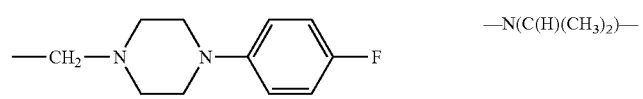 | —N(C(H)(CH₃)₂)— |
| Ia-441 | 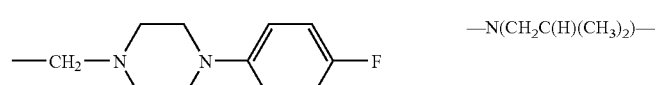 | —N(CH₂C(H)(CH₃)₂)— |
| Ia-442 | 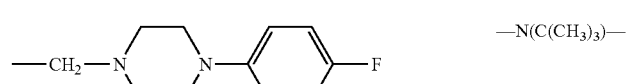 | —N(C(CH₃)₃)— |
| Ia-443 | 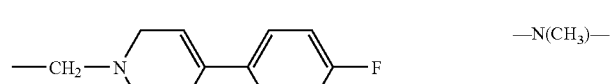 | —N(CH₃)— |

| | | |
|---|---|---|
| Ia-444 | 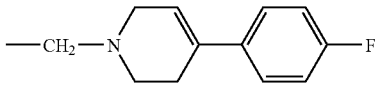 | —N(CH$_2$CH$_3$)— |
| Ia-445 | 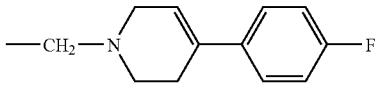 | —N(CH$_2$CH$_2$CH$_3$)— |
| Ia-446 | 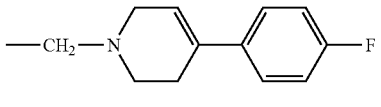 | —N(CH$_2$CH$_2$CH$_2$CH$_3$)— |
| Ia-447 | 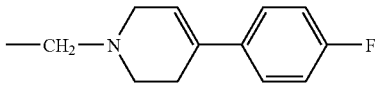 | —N(C(H)(CH$_3$)(CH$_2$CH$_3$))— |
| Ia-448 | 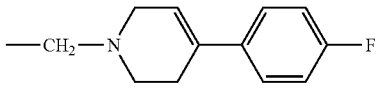 | —N(C(H)(CH$_3$)$_2$)— |
| Ia-449 |  | —N(CH$_2$C(H)(CH$_3$)$_2$)— |
| Ia-450 |  | —N(C(CH$_3$)$_3$)— |
| Ia-451 | 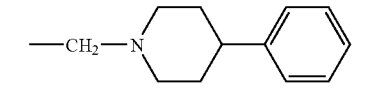 | —N(CH$_3$)— |
| Ia-452 |  | —N(CH$_2$CH$_3$)— |
| Ia-453 | 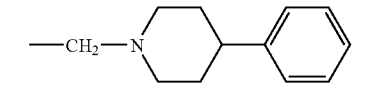 | —N(CH$_2$CH$_2$CH$_3$)— |
| Ia-454 |  | —N(CH$_2$CH$_2$CH$_2$CH$_3$)— |
| Ia-455 | 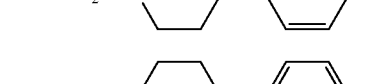 | —N(C(H)(CH$_3$)(CH$_2$CH$_3$))— |
| Ia-456 | 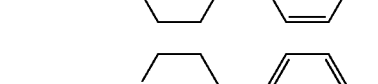 | —N(C(H)(CH$_3$)$_2$)— |
| Ia-457 | 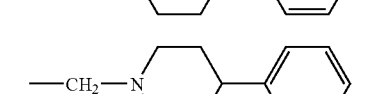 | —N(CH$_2$C(H)(CH$_3$)$_2$)— |
| Ia-458 | 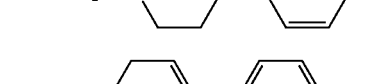 | —N(C(CH$_3$)$_3$)— |
| Ia-459 | 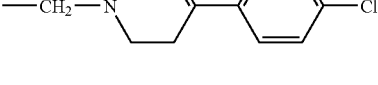 | —N(CH$_3$)— |

-continued
| | | |
|---|---|---|
| Ia-460 | 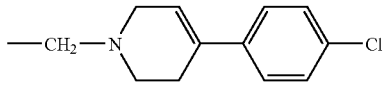 | —N(CH$_2$CH$_3$)— |
| Ia-461 | 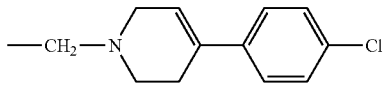 | —N(CH$_2$CH$_2$CH$_3$)— |
| Ia-462 | 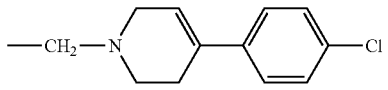 | —N(CH$_2$CH$_2$CH$_3$)— |
| Ia-463 | 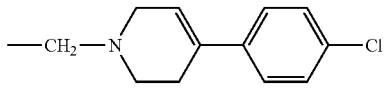 | —N(C(H)(CH$_3$)(CH$_2$CH$_3$))— |
| Ia-464 | 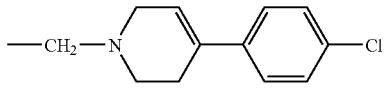 | —N(C(H)(CH$_3$)$_2$)— |
| Ia-465 | 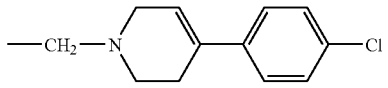 | —N(CH$_2$C(H)(CH$_3$)$_2$)— |
| Ia-466 | 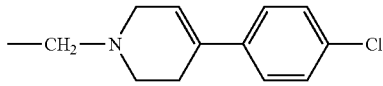 | —N(C(CH$_3$)$_3$)— |
| Ia-467 | 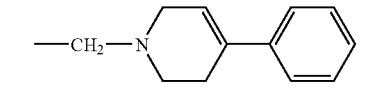 | —N(CH$_3$)— |
| Ia-468 | 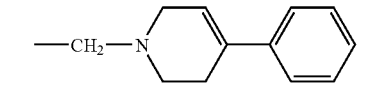 | —N(CH$_2$CH$_3$)— |
| Ia-469 | 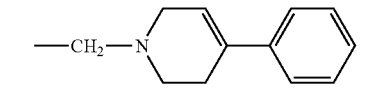 | —N(CH$_2$CH$_2$CH$_3$)— |
| Ia-470 | 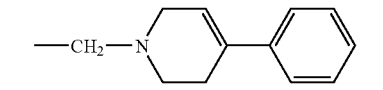 | —N(CH$_2$CH$_2$CH$_3$)— |
| Ia-471 | 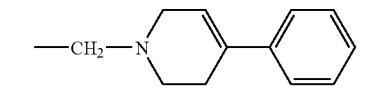 | —N(C(H)(CH$_3$)(CH$_2$CH$_3$))— |
| Ia-472 | 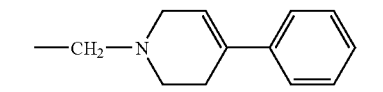 | —N(C(H)(CH$_3$)$_2$)— |
| Ia-473 | 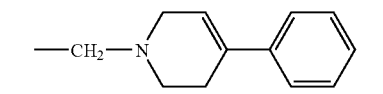 | —N(CH$_2$C(H)(CH$_3$)$_2$)— |
| Ia-474 | 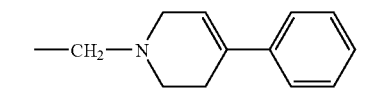 | —N(C(CH$_3$)$_3$)— |
| Ia-475 | 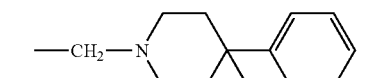 | —N(CH$_3$)— |

-continued

| | | |
|---|---|---|
| Ia-476 | —CH₂—N(piperidine-4-ol-4-phenyl) | —N(CH₂CH₃)— |
| Ia-477 | —CH₂—N(piperidine-4-ol-4-phenyl) | —N(CH₂CH₂CH₃)— |
| Ia-478 | —CH₂—N(piperidine-4-ol-4-phenyl) | —N(CH₂CH₂CH₂CH₃)— |
| Ia-479 | —CH₂—N(piperidine-4-ol-4-phenyl) | —N(C(H)(CH₃)(CH₂CH₃))— |
| Ia-480 | —CH₂—N(piperidine-4-ol-4-phenyl) | —N(C(H)(CH₃)₂)— |
| Ia-481 | —CH₂—N(piperidine-4-ol-4-phenyl) | —N(CH₂C(H)(CH₃)₂)— |
| Ia-482 | —CH₂—N(piperidine-4-ol-4-phenyl) | —N(C(CH₃)₃)— |
| Ia-483 | —CH₂—N(piperazine)NCH₂CH₂OP(O)(OH)₂ | —N(CH₃)— |
| Ia-484 | —CH₂—N(piperazine)NCH₂CH₂OP(O)(OH)₂ | —N(CH₂CH₃)— |
| Ia-485 | —CH₂—N(piperazine)NCH₂CH₂OP(O)(OH)₂ | —N(CH₂CH₂CH₃)— |
| Ia-486 | —CH₂—N(piperazine)NCH₂CH₂OP(O)(OH)₂ | —N(CH₂CH₂CH₂CH₃)— |
| Ia-487 | —CH₂—N(piperazine)NCH₂CH₂OP(O)(OH)₂ | —N(C(H)(CH₃)(CH₂CH₃))— |
| Ia-488 | —CH₂—N(piperazine)NCH₂CH₂OP(O)(OH)₂ | —N(C(H)(CH₃)₂)— |
| Ia-489 | —CH₂—N(piperazine)NCH₂CH₂OP(O)(OH)₂ | —N(CH₂C(H)(CH₃)₂)— |
| Ia-490 | —CH₂—N(piperazine)NCH₂CH₂OP(O)(OH)₂ | —N(C(CH₃)₃)— |
| Ia-491 | —CH₂—CH₂—CH₂—OP(O)(OH)₂ | —N(CH₃)— |
| Ia-492 | —CH₂—CH₂—CH₂—OP(O)(OH)₂ | —N(CH₂CH₃)— |
| Ia-493 | —CH₂—CH₂—CH₂—OP(O)(OH)₂ | —N(CH₂CH₂CH₃)— |
| Ia-494 | —CH₂—CH₂—CH₂—OP(O)(OH)₂ | —N(CH₂CH₂CH₂CH₃)— |

| | | |
|---|---|---|
| Ia-495 | —CH₂—CH₂—CH₂—OP(O)(OH)₂ | —N(C(H)(CH₃)(CH₂CH₃))— |
| Ia-496 | —CH₂—CH₂—CH₂—OP(O)(OH)₂ | —N(C(H)(CH₃)₂)— |
| Ia-497 | —CH₂—CH₂—CH₂—OP(O)(OH)₂ | —N(CH₂C(H)(CH₃)₂)— |
| Ia-498 | —CH₂—CH₂—CH₂—OP(O)(OH)₂ | —N(C(CH₃)₃)— |
| Ia-499 | —CH₂—CH₂—CH₂—OS(O)₂OH | —N(CH₃)— |
| Ia-500 | —CH₂—CH₂—CH₂—OS(O)₂OH | —N(CH₂CH₃)— |
| Ia-501 | —CH₂—CH₂—CH₂—OS(O)₂OH | —N(CH₂CH₂CH₃)— |
| Ia-502 | —CH₂—CH₂—CH₂—OS(O)₂OH | —N(CH₂CH₂CH₂CH₃)— |
| Ia-503 | —CH₂—CH₂—CH₂—OS(O)₂OH | —N(C(H)(CH₃)(CH₂CH₃))— |
| Ia-504 | —CH₂—CH₂—CH₂—OS(O)₂OH | —N(C(H)(CH₃)₂)— |
| Ia-505 | —CH₂—CH₂—CH₂—OS(O)₂OH | —N(CH₂C(H)(CH₃)₂)— |
| Ia-506 | —CH₂—CH₂—CH₂—OS(O)₂OH | —N(C(CH₃)₃)— |
| Ia-507 | 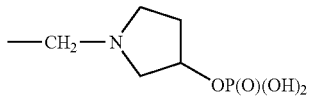 | —N(CH₃)— |
| Ia-508 | 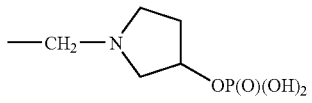 | —N(CH₂CH₃)— |
| Ia-509 | 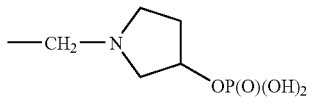 | —N(CH₂CH₂CH₃)— |
| Ia-510 | 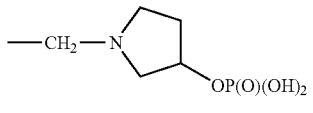 | —N(CH₂CH₂CH₂CH₃)— |
| Ia-511 | 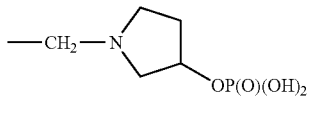 | —N(C(H)(CH₃)(CH₂CH₃))— |
| Ia-512 | 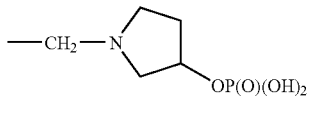 | —N(C(H)(CH₃)₂)— |
| Ia-513 | 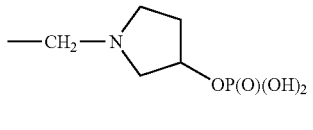 | —N(CH₂C(H)(CH₃)₂)— |
| Ia-514 | 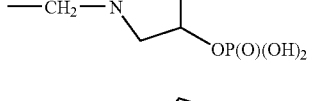 | —N(C(CH₃)₃)— |
| Ia-515 | 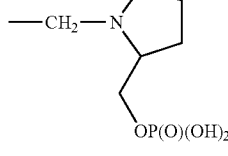 | —N(CH₃)— |
| Ia-516 | 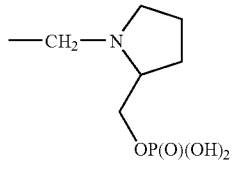 | —N(CH₂CH₃)— |

-continued

| | | |
|---|---|---|
| Ia-517 | 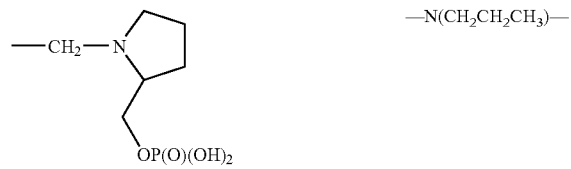 | —N(CH₂CH₂CH₃)— |
| Ia-518 | 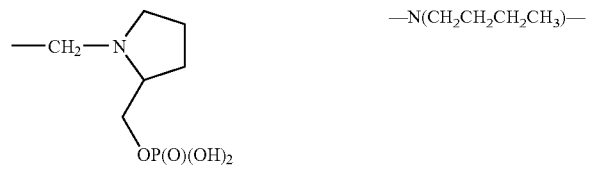 | —N(CH₂CH₂CH₃)— |
| Ia-519 | 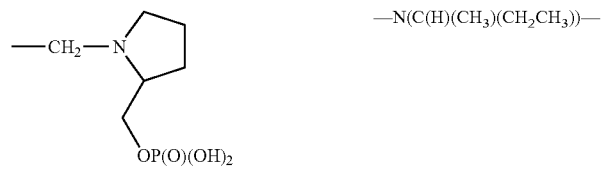 | —N(C(H)(CH₃)(CH₂CH₃))— |
| Ia-520 | 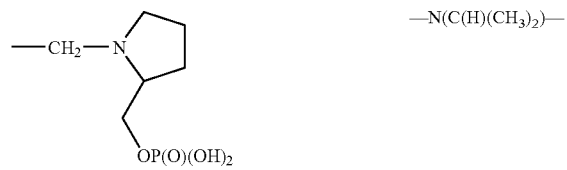 | —N(C(H)(CH₃)₂)— |
| Ia-521 | 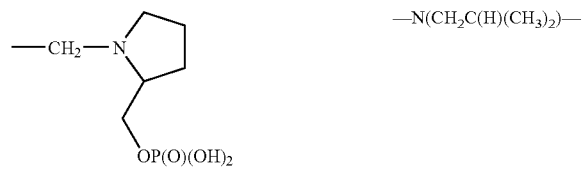 | —N(CH₂C(H)(CH₃)₂)— |
| Ia-522 | 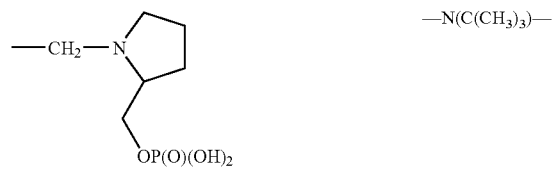 | —N(C(CH₃)₃)— |
| Ia-523 | —(CH₂)₁₀—N(CH₂—CH₂—O—CH₃)₂ | —N(CH₃)— |
| Ia-524 | —(CH₂)₁₀—N(CH₂—CH₂—O—CH₃)₂ | —N(CH₂CH₃)— |
| Ia-525 | —(CH₂)₁₀—N(CH₂—CH₂—O—CH₃)₂ | —N(CH₂CH₂CH₃)— |
| Ia-526 | —(CH₂)₁₀—N(CH₂—CH₂—O—CH₃)₂ | —N(CH₂CH₂CH₂CH₃)— |
| Ia-527 | —(CH₂)₁₀—N(CH₂—CH₂—O—CH₃)₂ | —N(C(H)(CH₃)(CH₂CH₃))— |
| Ia-528 | —(CH₂)₁₀—N(CH₂—CH₂—O—CH₃)₂ | —N(C(H)(CH₃)₂)— |
| Ia-529 | —(CH₂)₁₀—N(CH₂—CH₂—O—CH₃)₂ | —N(CH₂C(H)(CH₃)₂)— |
| Ia-530 | —(CH₂)₁₀—N(CH₂—CH₂—O—CH₃)₂ | —N(C(CH₃)₃)— |
| Ia-531 | —CH₂—N(CH₂—CH₂—O—CH₃)₂ | —N(CH₃)— |
| Ia-532 | —CH₂—N(CH₂—CH₂—O—CH₃)₂ | —N(CH₂CH₃)— |
| Ia-533 | —CH₂—N(CH₂—CH₂—O—CH₃)₂ | —N(CH₂CH₂CH₃)— |
| Ia-534 | —CH₂—N(CH₂—CH₂—O—CH₃)₂ | —N(CH₂CH₂CH₂CH₃)— |
| Ia-535 | —CH₂—N(CH₂—CH₂—O—CH₃)₂ | —N(C(H)(CH₃)(CH₂CH₃))— |
| Ia-536 | —CH₂—N(CH₂—CH₂—O—CH₃)₂ | —N(C(H)(CH₃)₂)— |
| Ia-537 | —CH₂—N(CH₂—CH₂—O—CH₃)₂ | —N(CH₂C(H)(CH₃)₂)— |
| Ia-538 | —CH₂—N(CH₂—CH₂—O—CH₃)₂ | —N(C(CH₃)₃)— |
| Ia-539 | 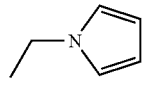 | —N(CH₃)— |
| Ia-540 | 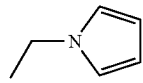 | —N(CH₂CH₃)— |

-continued
| | | |
|---|---|---|
| Ia-541 | 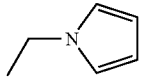 | —N(CH₂CH₂CH₃)— |
| Ia-542 | 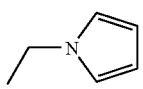 | —N(CH₂CH₂CH₃)— |
| Ia-543 | 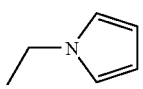 | —N(C(H)(CH₃)(CH₂CH₃))— |
| Ia-544 | 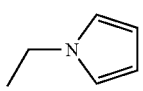 | —N(C(H)(CH₃)₂)— |
| Ia-545 | 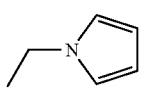 | —N(CH₂C(H)(CH₃)₂)— |
| Ia-546 | 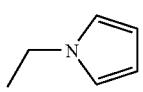 | —N(C(CH₃)₃)— |
| Ia-547 | 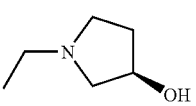 | —N(CH₃)— |
| Ia-548 | 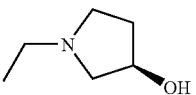 | —N(CH₂CH₃)— |
| Ia-549 | 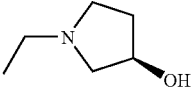 | —N(CH₂CH₂CH₃)— |
| Ia-550 | 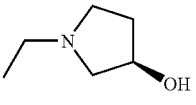 | —N(CH₂CH₂CH₃)— |
| Ia-551 | 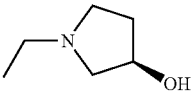 | —N(C(H)(CH₃)(CH₂CH₃))— |
| Ia-552 | 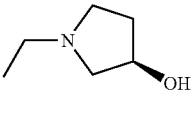 | —N(C(H)(CH₃)₂)— |
| Ia-553 | 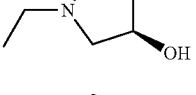 | —N(CH₂C(H)(CH₃)₂)— |
| Ia-554 | 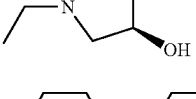 | —N(C(CH₃)₃)— |
| Ia-555 | 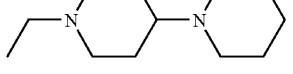 | —N(CH₃)— |

| | | |
|---|---|---|
| Ia-556 | 1-ethylpiperidin-4-yl-piperidine | —N(CH₂CH₃)— |
| Ia-557 | 1-ethylpiperidin-4-yl-piperidine | —N(CH₂CH₂CH₃)— |
| Ia-558 | 1-ethylpiperidin-4-yl-piperidine | —N(CH₂CH₂CH₂CH₃)— |
| Ia-559 | 1-ethylpiperidin-4-yl-piperidine | —N(C(H)(CH₃)(CH₂CH₃))— |
| Ia-560 | 1-ethylpiperidin-4-yl-piperidine | —N(C(H)(CH₃)₂)— |
| Ia-561 | 1-ethylpiperidin-4-yl-piperidine | —N(CH₂C(H)(CH₃)₂)— |
| Ia-562 | 1-ethylpiperidin-4-yl-piperidine | —N(C(CH₃)₃)— |
| Ia-563 | 1-ethylpiperidin-4-yl-pyrrolidine | —N(CH₃)— |
| Ia-564 | 1-ethylpiperidin-4-yl-pyrrolidine | —N(CH₂CH₃)— |
| Ia-565 | 1-ethylpiperidin-4-yl-pyrrolidine | —N(CH₂CH₂CH₃)— |
| Ia-566 | 1-ethylpiperidin-4-yl-pyrrolidine | —N(CH₂CH₂CH₂CH₃)— |
| Ia-567 | 1-ethylpiperidin-4-yl-pyrrolidine | —N(C(H)(CH₃)(CH₂CH₃))— |
| Ia-568 | 1-ethylpiperidin-4-yl-pyrrolidine | —N(C(H)(CH₃)₂)— |
| Ia-569 | 1-ethylpiperidin-4-yl-pyrrolidine | —N(CH₂C(H)(CH₃)₂)— |
| Ia-570 | 1-ethylpiperidin-4-yl-pyrrolidine | —N(C(CH₃)₃)— |
| Ia-571 | (1-ethylpyrrolidin-2-yl)methanol | —N(CH₃)— |

| | | |
|---|---|---|
| Ia-572 | 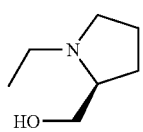 | —N(CH₂CH₃)— |
| Ia-573 | 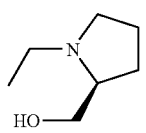 | —N(CH₂CH₂CH₃)— |
| Ia-574 | 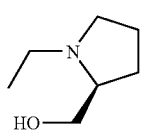 | —N(CH₂CH₂CH₂CH₃)— |
| Ia-575 | 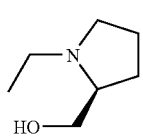 | —N(C(H)(CH₃)(CH₂CH₃))— |
| Ia-576 | 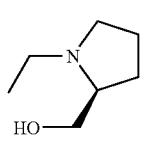 | —N(C(H)(CH₃)₂)— |
| Ia-577 | 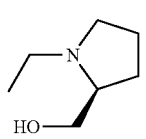 | —N(CH₂C(H)(CH₃)₂)— |
| Ia-578 | 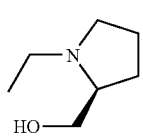 | —N(C(CH₃)₃)— |
| Ia-579 | 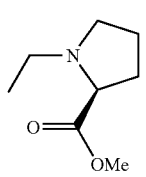 | —N(CH₃)— |
| Ia-580 | 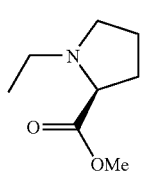 | —N(CH₂CH₃)— |
| Ia-581 | 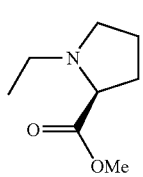 | —N(CH₂CH₂CH₃)— |

-continued
| | | |
|---|---|---|
| Ia-582 | 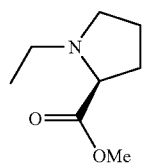 | —N(CH₂CH₂CH₂CH₃)— |
| Ia-583 | 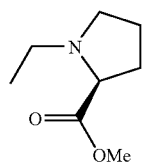 | —N(C(H)(CH₃)(CH₂CH₃))— |
| Ia-584 | 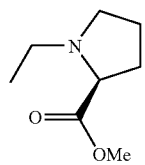 | —N(C(H)(CH₃)₂)— |
| Ia-585 | 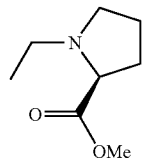 | —N(CH₂C(H)(CH₃)₂)— |
| Ia-586 | 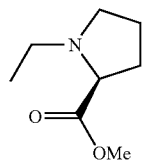 | —N(C(CH₃)₃)— |
| Ia-587 | 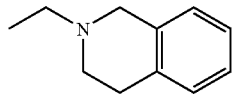 | —N(CH₃)— |
| Ia-588 | 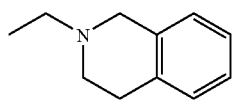 | —N(CH₂CH₃)— |
| Ia-589 | 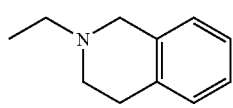 | —N(CH₂CH₂CH₃)— |
| Ia-590 | 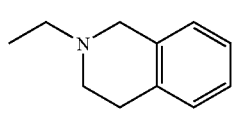 | —N(CH₂CH₂CH₂CH₃)— |
| Ia-591 | 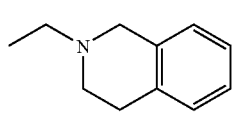 | —N(C(H)(CH₃)(CH₂CH₃))— |
| Ia-592 | 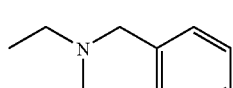 | —N(C(H)(CH₃)₂)— |
| Ia-593 | 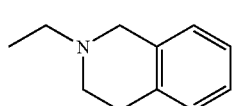 | —N(CH₂C(H)(CH₃)₂)— |

-continued
| | | |
|---|---|---|
| Ia-594 | 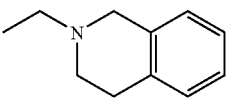 | —N(C(CH$_3$)$_3$)— |
| Ia-595 | 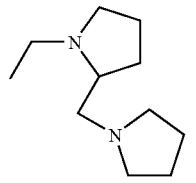 | —N(CH$_3$)— |
| Ia-596 | 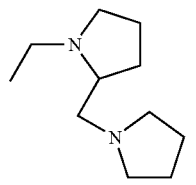 | —N(CH$_2$CH$_3$)— |
| Ia-597 | 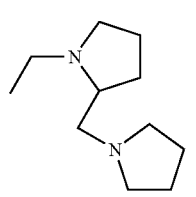 | —N(CH$_2$CH$_2$CH$_3$)— |
| Ia-598 | 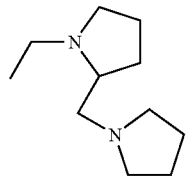 | —N(CH$_2$CH$_2$CH$_3$)— |
| Ia-599 | 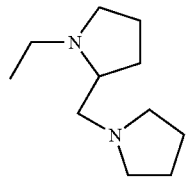 | —N(C(H)(CH$_3$)(CH$_2$CH$_3$))— |
| Ia-600 | 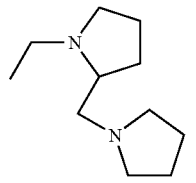 | —N(C(H)(CH$_3$)$_2$)— |
| Ia-601 | 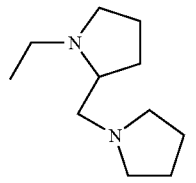 | —N(CH$_2$C(H)(CH$_3$)$_2$)— |
| Ia-602 |  | —N(C(CH$_3$)$_3$)— |

| | | |
|---|---|---|
| Ia-603 | 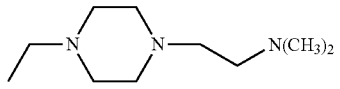 | —N(CH$_3$)— |
| Ia-604 | 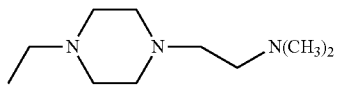 | —N(CH$_2$CH$_3$)— |
| Ia-605 | 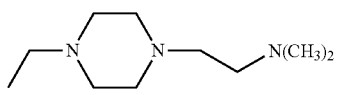 | —N(CH$_2$CH$_2$CH$_3$)— |
| Ia-606 | 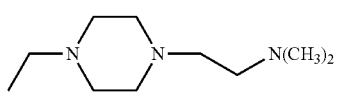 | —N(CH$_2$CH$_2$CH$_2$CH$_3$)— |
| Ia-607 | 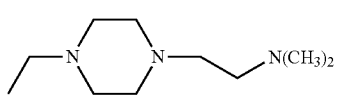 | —N(C(H)(CH$_3$)(CH$_2$CH$_3$))— |
| Ia-608 | 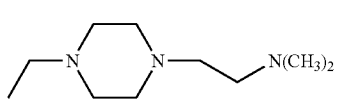 | —N(C(H)(CH$_3$)$_2$)— |
| Ia-609 | 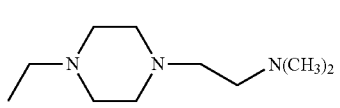 | —N(CH$_2$C(H)(CH$_3$)$_2$)— |
| Ia-610 | 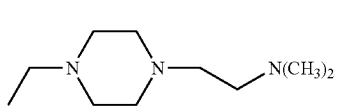 | —N(C(CH$_3$)$_3$)— |
| Ia-611 | —CH$_2$—NH—CH$_2$—CH$_2$—CH$_2$—N(CH$_3$)$_2$ | —N(CH$_3$)— |
| Ia-612 | —CH$_2$—NH—CH$_2$—CH$_2$—CH$_2$—N(CH$_3$)$_2$ | —N(CH$_2$CH$_3$)— |
| Ia-613 | —CH$_2$—NH—CH$_2$—CH$_2$—CH$_2$—N(CH$_3$)$_2$ | —N(CH$_2$CH$_2$CH$_3$)— |
| Ia-614 | —CH$_2$—NH—CH$_2$—CH$_2$—CH$_2$—N(CH$_3$)$_2$ | —N(CH$_2$CH$_2$CH$_2$CH$_3$)— |
| Ia-615 | —CH$_2$—NH—CH$_2$—CH$_2$—CH$_2$—N(CH$_3$)$_2$ | —N(C(H)(CH$_3$)(CH$_2$CH$_3$))— |
| Ia-616 | —CH$_2$—NH—CH$_2$—CH$_2$—CH$_2$—N(CH$_3$)$_2$ | —N(C(H)(CH$_3$)$_2$)— |
| Ia-617 | —CH$_2$—NH—CH$_2$—CH$_2$—CH$_2$—N(CH$_3$)$_2$ | —N(CH$_2$C(H)(CH$_3$)$_2$)— |
| Ia-618 | —CH$_2$—NH—CH$_2$—CH$_2$—CH$_2$—N(CH$_3$)$_2$ | —N(C(CH$_3$)$_3$)— |
| Ia-619 | 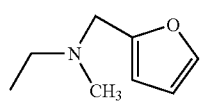 | —N(CH$_3$)— |
| Ia-620 | 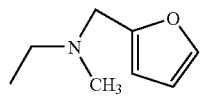 | —N(CH$_2$CH$_3$)— |
| Ia-621 |  | —N(CH$_2$CH$_2$CH$_3$)— |
| Ia-622 | 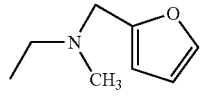 | —N(CH$_2$CH$_2$CH$_2$CH$_3$)— |
| Ia-623 | 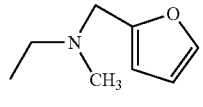 | —N(C(H)(CH$_3$)(CH$_2$CH$_3$))— |

-continued

| ID | Structure | Group |
|---|---|---|
| Ia-624 | [N-ethyl-N-methyl-aminomethyl furan] | —N(C(H)(CH₃)₂)— |
| Ia-625 | [N-ethyl-N-methyl-aminomethyl furan] | —N(CH₂C(H)(CH₃)₂)— |
| Ia-626 | [N-ethyl-N-methyl-aminomethyl furan] | —N(C(CH₃)₃)— |
| Ia-627 | [1-ethyl-3-hydroxypyrrolidine] | —N(CH₃)— |
| Ia-628 | [1-ethyl-3-hydroxypyrrolidine] | —N(CH₂CH₃)— |
| Ia-629 | [1-ethyl-3-hydroxypyrrolidine] | —N(CH₂CH₃)— |
| Ia-630 | [1-ethyl-3-hydroxypyrrolidine] | —N(CH₂CH₂CH₃)— |
| Ia-631 | [1-ethyl-3-hydroxypyrrolidine] | —N(C(H)(CH₃)(CH₂CH₃))— |
| Ia-632 | [1-ethyl-3-hydroxypyrrolidine] | —N(C(H)(CH₃)₂)— |
| Ia-633 | [1-ethyl-3-hydroxypyrrolidine] | —N(CH₂C(H)(CH₃)₂)— |
| Ia-634 | [1-ethyl-3-hydroxypyrrolidine] | —N(C(CH₃)₃)— |
| Ia-635 | [1-ethyl-2-(hydroxymethyl)pyrrolidine] | —N(CH₃)— |
| Ia-636 | [1-ethyl-2-(hydroxymethyl)pyrrolidine] | —N(CH₂CH₃)— |
| Ia-637 | [1-ethyl-2-(hydroxymethyl)pyrrolidine] | —N(CH₂CH₂CH₃)— |

-continued
| | | |
|---|---|---|
| Ia-638 | 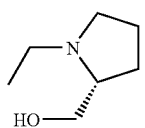 | —N(CH$_2$CH$_2$CH$_2$CH$_3$)— |
| Ia-639 | 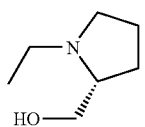 | —N(C(H)(CH$_3$)(CH$_2$CH$_3$))— |
| Ia-640 | 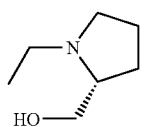 | —N(C(H)(CH$_3$)$_2$)— |
| Ia-641 | 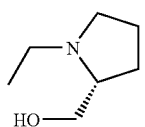 | —N(CH$_2$C(H)(CH$_3$)$_2$)— |
| Ia-642 | 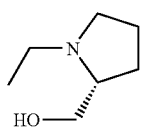 | —N(C(CH$_3$)$_3$)— |
| Ia-643 | 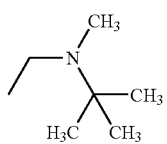 | —N(CH$_3$)— |
| Ia-644 | 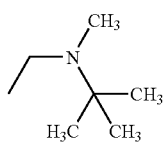 | —N(CH$_2$CH$_3$)— |
| Ia-645 | 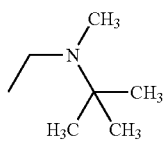 | —N(CH$_2$CH$_2$CH$_3$)— |
| Ia-646 | 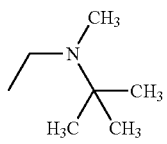 | —N(CH$_2$CH$_2$CH$_2$CH$_3$)— |
| Ia-647 | 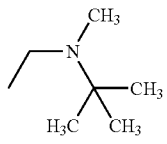 | —N(C(H)(CH$_3$)(CH$_2$CH$_3$))— |
| Ia-648 | 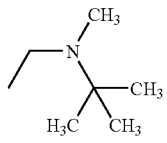 | —N(C(H)(CH$_3$)$_2$)— |

| | | |
|---|---|---|
| Ia-649 | 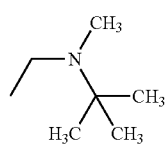 | —N(CH$_2$C(H)(CH$_3$)$_2$)— |
| Ia-650 | 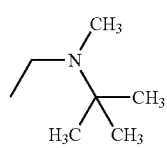 | —N(C(CH$_3$)$_3$)— |
| Ia-651 | 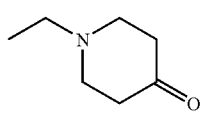 | —N(CH$_3$)— |
| Ia-652 | 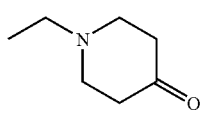 | —N(CH$_2$CH$_3$)— |
| Ia-653 | 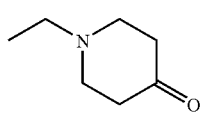 | —N(CH$_2$CH$_3$)— |
| Ia-654 | 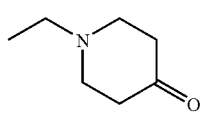 | —N(CH$_2$CH$_2$CH$_3$)— |
| Ia-655 | 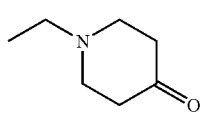 | —N(C(H)(CH$_3$)(CH$_2$CH$_3$))— |
| Ia-656 | 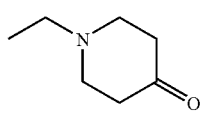 | —N(C(H)(CH$_3$)$_2$)— |
| Ia-657 | 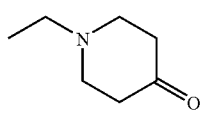 | —N(CH$_2$C(H)(CH$_3$)$_2$)— |
| Ia-658 | 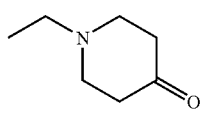 | —N(C(CH$_3$)$_3$)— |
| Ia-659 | 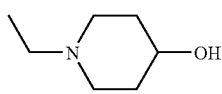 | —N(CH$_3$)— |
| Ia-660 | 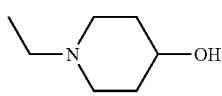 | —N(CH$_2$CH$_3$)— |
| Ia-661 | 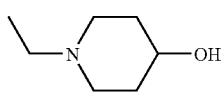 | —N(CH$_2$CH$_2$CH$_3$)— |

-continued
| | | |
|---|---|---|
| Ia-662 | 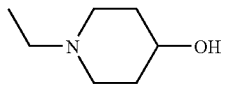 | —N(CH$_2$CH$_2$CH$_2$CH$_3$)— |
| Ia-663 | 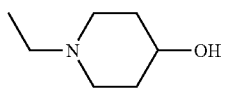 | —N(C(H)(CH$_3$)(CH$_2$CH$_3$))— |
| Ia-664 | 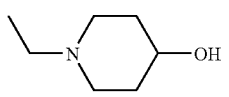 | —N(C(H)(CH$_3$)$_2$)— |
| Ia-665 | 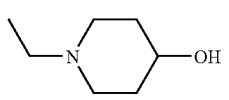 | —N(CH$_2$C(H)(CH$_3$)$_2$)— |
| Ia-666 | 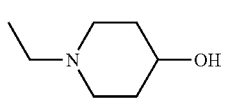 | —N(C(CH$_3$)$_3$)— |
| Ia-667 |  | —N(CH$_3$)— |
| Ia-668 | 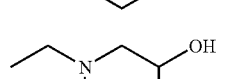 | —N(CH$_2$CH$_3$)— |
| Ia-669 |  | —N(CH$_2$CH$_2$CH$_3$)— |
| Ia-670 |  | —N(CH$_2$CH$_2$CH$_2$CH$_3$)— |
| Ia-671 | 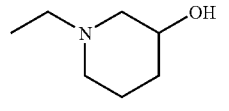 | —N(C(H)(CH$_3$)(CH$_2$CH$_3$))— |
| Ia-672 | 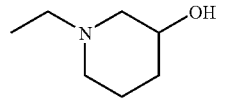 | —N(C(H)(CH$_3$)$_2$)— |
| Ia-673 | 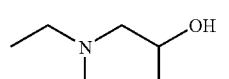 | —N(CH$_2$C(H)(CH$_3$)$_2$)— |
| Ia-674 |  | —N(C(CH$_3$)$_3$)— |
| Ia-675 | 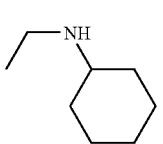 | —N(CH$_3$)— |

-continued

| | | |
|---|---|---|
| Ia-676 | ethyl-NH-cyclohexyl | —N(CH₂CH₃)— |
| Ia-677 | ethyl-NH-cyclohexyl | —N(CH₂CH₂CH₃)— |
| Ia-678 | ethyl-NH-cyclohexyl | —N(CH₂CH₂CH₂CH₃)— |
| Ia-679 | ethyl-NH-cyclohexyl | —N(C(H)(CH₃)(CH₂CH₃))— |
| Ia-680 | ethyl-NH-cyclohexyl | —N(C(H)(CH₃)₂)— |
| Ia-681 | ethyl-NH-cyclohexyl | —N(CH₂C(H)(CH₃)₂)— |
| Ia-682 | ethyl-NH-cyclohexyl | —N(C(CH₃)₃)— |
| Ia-683 | ethyl-NH-cyclopentyl | —N(CH₃)— |
| Ia-684 | ethyl-NH-cyclopentyl | —N(CH₂CH₃)— |
| Ia-685 | ethyl-NH-cyclopentyl | —N(CH₂CH₂CH₃)— |
| Ia-686 | ethyl-NH-cyclopentyl | —N(CH₂CH₂CH₂CH₃)— |
| Ia-687 | ethyl-NH-cyclopentyl | —N(C(H)(CH₃)(CH₂CH₃))— |

-continued
| | | |
|---|---|---|
| Ia-688 | 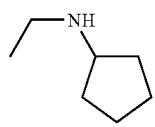 | —N(C(H)(CH$_3$)$_2$)— |
| Ia-689 | 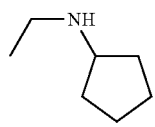 | —N(CH$_2$C(H)(CH$_3$)$_2$)— |
| Ia-690 | 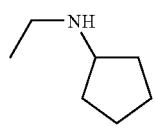 | —N(C(CH$_3$)$_3$)— |
| Ia-691 | 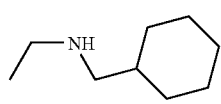 | —N(CH$_3$)— |
| Ia-692 | 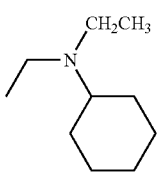 | —N(CH$_2$CH$_3$)— |
| Ia-693 | 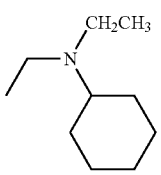 | —N(CH$_2$CH$_2$CH$_3$)— |
| Ia-694 | 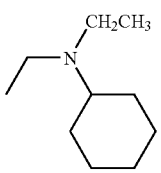 | —N(CH$_2$CH$_2$CH$_2$CH$_3$)— |
| Ia-695 | 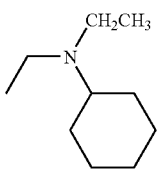 | —N(C(H)(CH$_3$)(CH$_2$CH$_3$))— |
| Ia-696 | 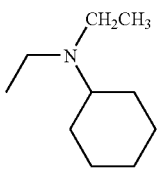 | —N(C(H)(CH$_3$)$_2$)— |
| Ia-697 | 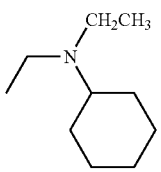 | —N(CH$_2$C(H)(CH$_3$)$_2$)— |

-continued
| | | |
|---|---|---|
| Ia-698 | 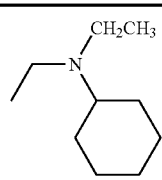 | —N(C(CH₃)₃)— |
| Ia-699 | 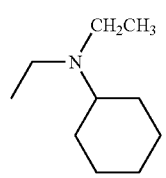 | —N(CH₃)— |
| Ia-700 | 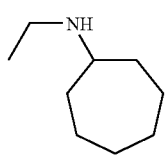 | —N(CH₂CH₃)— |
| Ia-701 | 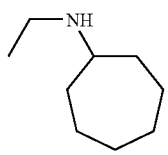 | —N(CH₂CH₃)— |
| Ia-702 | 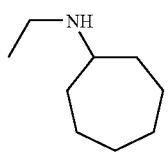 | —N(CH₂CH₂CH₃)— |
| Ia-703 | 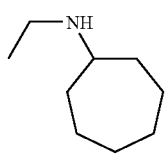 | —N(C(H)(CH₃)(CH₂CH₃))— |
| Ia-704 | 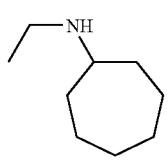 | —N(C(H)(CH₃)₂)— |
| Ia-705 | 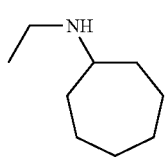 | —N(CH₂C(H)(CH₃)₂)— |
| Ia-706 | 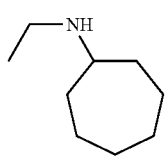 | —N(C(CH₃)₃)— |
| Ia-707 | 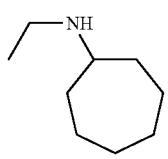 | —N(CH₃)— |

-continued

| | | |
|---|---|---|
| Ia-708 | ethyl-NH-cycloheptyl | —N(CH₂CH₃)— |
| Ia-709 | ethyl-NH-cycloheptyl | —N(CH₂CH₂CH₃)— |
| Ia-710 | ethyl-NH-cycloheptyl | —N(CH₂CH₂CH₂CH₃)— |
| Ia-711 | ethyl-NH-cycloheptyl | —N(C(H)(CH₃)(CH₂CH₃))— |
| Ia-712 | ethyl-NH-cycloheptyl | —N(C(H)(CH₃)₂)— |
| Ia-713 | ethyl-NH-cycloheptyl | —N(CH₂C(H)(CH₃)₂)— |
| Ia-714 | ethyl-NH-cycloheptyl | —N(C(CH₃)₃)— |
| Ia-715 | ethyl-thiomorpholino | —N(CH₃)— |
| Ia-716 | ethyl-thiomorpholino | —N(CH₂CH₃)— |
| Ia-717 | ethyl-thiomorpholino | —N(CH₂CH₂CH₃)— |
| Ia-718 | ethyl-thiomorpholino | —N(CH₂CH₂CH₂CH₃)— |
| Ia-719 | ethyl-thiomorpholino | —N(C(H)(CH₃)(CH₂CH₃))— |

-continued

| | | |
|---|---|---|
| Ia-720 | ethyl-thiomorpholine | —N(C(H)(CH₃)₂)— |
| Ia-721 | ethyl-thiomorpholine | —N(CH₂C(H)(CH₃)₂)— |
| Ia-722 | ethyl-thiomorpholine | —N(C(CH₃)₃)— |
| Ia-723 | ethyl-(4-hydroxymethyl)piperidine | —N(CH₃)— |
| Ia-724 | ethyl-(4-hydroxymethyl)piperidine | —N(CH₂CH₃)— |
| Ia-725 | ethyl-(4-hydroxymethyl)piperidine | —N(CH₂CH₂CH₃)— |
| Ia-726 | ethyl-(4-hydroxymethyl)piperidine | —N(CH₂CH₂CH₃)— |
| Ia-727 | ethyl-(4-hydroxymethyl)piperidine | —N(C(H)(CH₃)(CH₂CH₃))— |
| Ia-728 | ethyl-(4-hydroxymethyl)piperidine | —N(C(H)(CH₃)₂)— |
| Ia-729 | ethyl-(4-hydroxymethyl)piperidine | —N(CH₂C(H)(CH₃)₂)— |
| Ia-730 | ethyl-(4-hydroxymethyl)piperidine | —N(C(CH₃)₃)— |
| Ia-731 | ethyl-NH-(2,2,6,6-tetramethylpiperidine) | —N(CH₃)— |
| Ia-732 | ethyl-NH-(2,2,6,6-tetramethylpiperidine) | —N(CH₂CH₃)— |

-continued
| | | |
|---|---|---|
| Ia-733 | 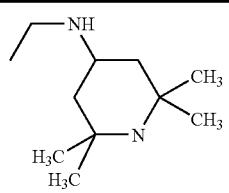 | —N(CH₂CH₂CH₃)— |
| Ia-734 | 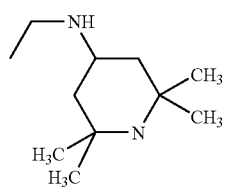 | —N(CH₂CH₂CH₂CH₃)— |
| Ia-735 | 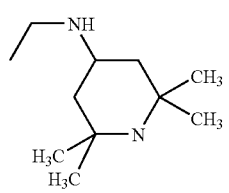 | —N(C(H)(CH₃)(CH₂CH₃))— |
| Ia-736 | 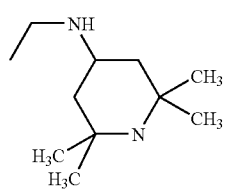 | —N(C(H)(CH₃)₂)— |
| Ia-737 | 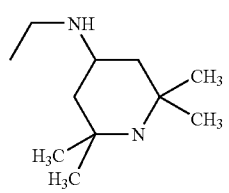 | —N(CH₂C(H)(CH₃)₂)— |
| Ia-738 | 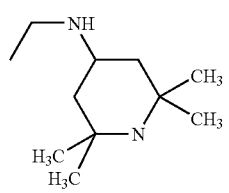 | —N(C(CH₃)₃)— |
| Ia-739 | 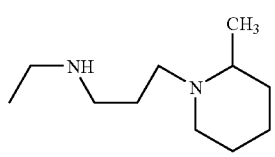 | —N(CH₃)— |
| Ia-740 | 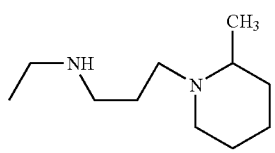 | —N(CH₂CH₃)— |
| Ia-741 | 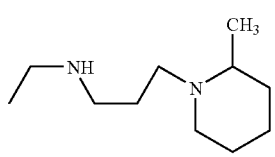 | —N(CH₂CH₂CH₃)— |

-continued
| | | |
|---|---|---|
| Ia-742 | 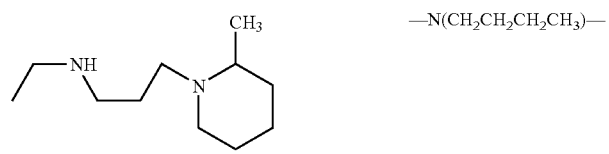 | —N(CH₂CH₂CH₂CH₃)— |
| Ia-743 | 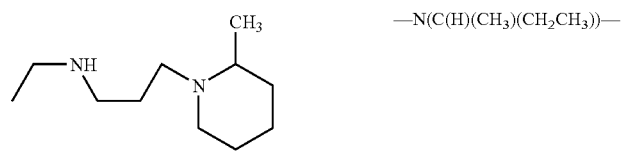 | —N(C(H)(CH₃)(CH₂CH₃))— |
| Ia-744 | 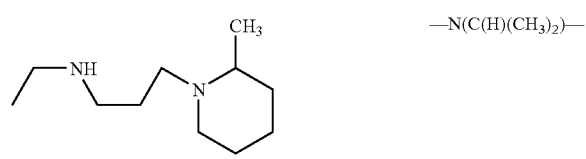 | —N(C(H)(CH₃)₂)— |
| Ia-745 | 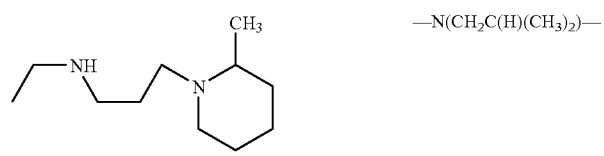 | —N(CH₂C(H)(CH₃)₂)— |
| Ia-746 | 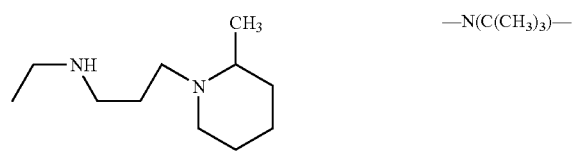 | —N(C(CH₃)₃)— |
| Ia-747 | 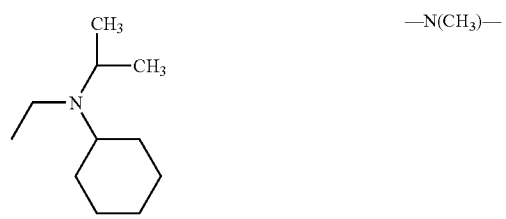 | —N(CH₃)— |
| Ia-748 | 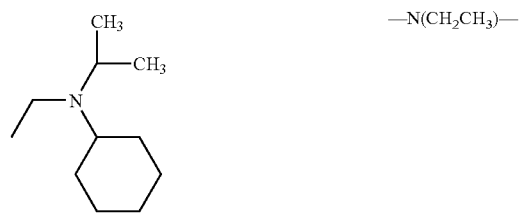 | —N(CH₂CH₃)— |
| Ia-749 |  | —N(CH₂CH₂CH₃)— |

-continued
| | | |
|---|---|---|
| Ia-750 | 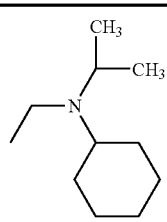 | —N(CH₂CH₂CH₂CH₃)— |
| Ia-751 | 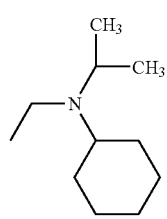 | —N(C(H)(CH₃)(CH₂CH₃))— |
| Ia-752 | 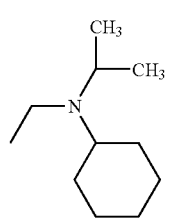 | —N(C(H)(CH₃)₂)— |
| Ia-753 | 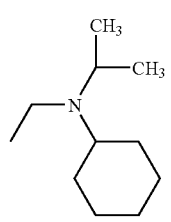 | —N(CH₂C(H)(CH₃)₂)— |
| Ia-754 | 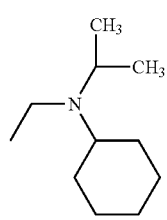 | —N(C(CH₃)₃)— |
| Ia-755 | 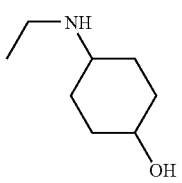 | —N(CH₃)— |
| Ia-756 | 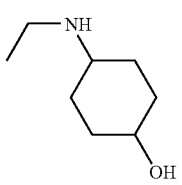 | —N(CH₂CH₃)— |
| Ia-757 | 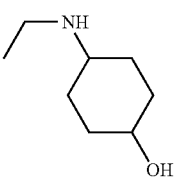 | —N(CH₂CH₂CH₃)— |

-continued
| | | |
|---|---|---|
| Ia-758 | 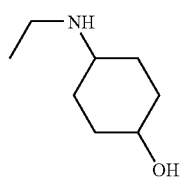 | —N(CH₂CH₂CH₂CH₃)— |
| Ia-759 | 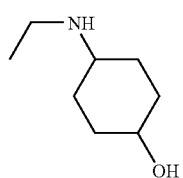 | —N(C(H)(CH₃)(CH₂CH₃))— |
| Ia-760 | 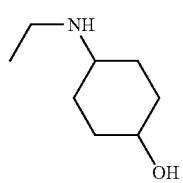 | —N(C(H)(CH₃)₂)— |
| Ia-761 | 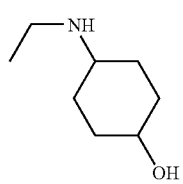 | —N(CH₂C(H)(CH₃)₂)— |
| Ia-762 | 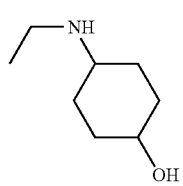 | —N(C(CH₃)₃)— |
| Ia-763 | 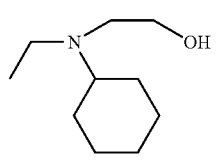 | —N(CH₃)— |
| Ia-764 |  | —N(CH₂CH₃)— |
| Ia-765 | 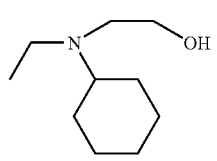 | —N(CH₂CH₂CH₃)— |
| Ia-766 | 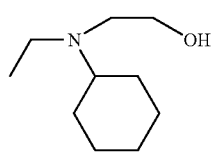 | —N(CH₂CH₂CH₂CH₃)— |

-continued

| | | |
|---|---|---|
| Ia-767 | 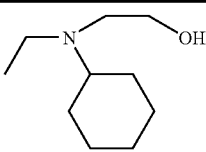 | —N(C(H)(CH$_3$)(CH$_2$CH$_3$))— |
| Ia-768 | 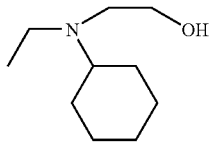 | —N(C(H)(CH$_3$)$_2$)— |
| Ia-769 | 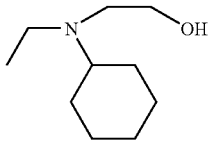 | —N(CH$_2$C(H)(CH$_3$)$_2$)— |
| Ia-770 | 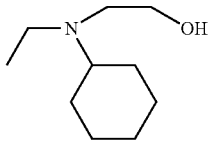 | —N(C(CH$_3$)$_3$)— |
| Ia-771 | 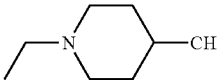 | —N(CH$_3$)— |
| Ia-772 | 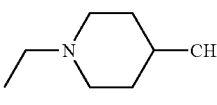 | —N(CH$_2$CH$_3$)— |
| Ia-773 | 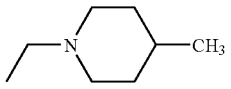 | —N(CH$_2$CH$_2$CH$_3$)— |
| Ia-774 | 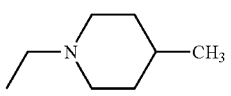 | —N(CH$_2$CH$_2$CH$_2$CH$_3$)— |
| Ia-775 | 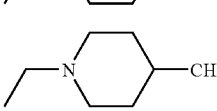 | —N(C(H)(CH$_3$)(CH$_2$CH$_3$))— |
| Ia-776 | 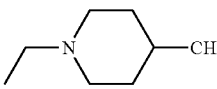 | —N(C(H)(CH$_3$)$_2$)— |
| Ia-777 | 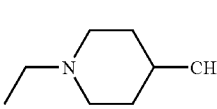 | —N(CH$_2$C(H)(CH$_3$)$_2$)— |
| Ia-778 | 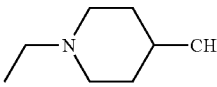 | —N(C(CH$_3$)$_3$)— |
| Ia-779 | —CH$_2$—NH—CH$_3$ | —N(CH$_3$)— |
| Ia-780 | —CH$_2$—NH—CH$_3$ | —N(CH$_2$CH$_3$)— |
| Ia-781 | —CH$_2$—NH—CH$_3$ | —N(CH$_2$CH$_2$CH$_3$)— |
| Ia-782 | —CH$_2$—NH—CH$_3$ | —N(CH$_2$CH$_2$CH$_2$CH$_3$)— |
| Ia-783 | —CH$_2$—NH—CH$_3$ | —N(C(H)(CH$_3$)(CH$_2$CH$_3$))— |
| Ia-784 | —CH$_2$—NH—CH$_3$ | —N(C(H)(CH$_3$)$_2$)— |
| Ia-785 | —CH$_2$—NH—CH$_3$ | —N(CH$_2$C(H)(CH$_3$)$_2$)— |
| Ia-786 | —CH$_2$—NH—CH$_3$ | —N(C(CH$_3$)$_3$)— |
| Ia-787 | —CH$_2$—NH—CH$_2$—CH$_3$ | —N(CH$_3$)— |
| Ia-788 | —CH$_2$—NH—CH$_2$—CH$_3$ | —N(CH$_2$CH$_3$)— |

-continued

| | | |
|---|---|---|
| Ia-789 | —CH₂—NH—CH₂—CH₃ | —N(CH₂CH₂CH₃)— |
| Ia-790 | —CH₂—NH—CH₂—CH₃ | —N(CH₂CH₂CH₂CH₃)— |
| Ia-791 | —CH₂—NH—CH₂—CH₃ | —N(C(H)(CH₃)(CH₂CH₃))— |
| Ia-792 | —CH₂—NH—CH₂—CH₃ | —N(C(H)(CH₃)₂)— |
| Ia-793 | —CH₂—NH—CH₂—CH₃ | —N(CH₂C(H)(CH₃)₂)— |
| Ia-794 | —CH₂—NH—CH₂—CH₃ | —N(C(CH₃)₃)— |
| Ia-795 | —CH₂—NH—CH₂—CH₂—CH₃ | —N(CH₃)— |
| Ia-796 | —CH₂—NH—CH₂—CH₂—CH₃ | —N(CH₂CH₃)— |
| Ia-797 | —CH₂—NH—CH₂—CH₂—CH₃ | —N(CH₂CH₂CH₃)— |
| Ia-798 | —CH₂—NH—CH₂—CH₂—CH₃ | —N(CH₂CH₂CH₂CH₃)— |
| Ia-799 | —CH₂—NH—CH₂—CH₂—CH₃ | —N(C(H)(CH₃)(CH₂CH₃))— |
| Ia-800 | —CH₂—NH—CH₂—CH₂—CH₃ | —N(C(H)(CH₃)₂)— |
| Ia-801 | —CH₂—NH—CH₂—CH₂—CH₃ | —N(CH₂C(H)(CH₃)₂)— |
| Ia-802 | —CH₂—NH—CH₂—CH₂—CH₃ | —N(C(CH₃)₃)— |
| Ia-803 | 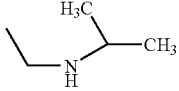 | —N(CH₃)— |
| Ia-804 | 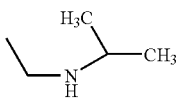 | —N(CH₂CH₃)— |
| Ia-805 | 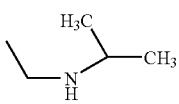 | —N(CH₂CH₂CH₃)— |
| Ia-806 | 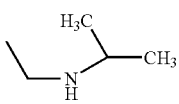 | —N(CH₂CH₂CH₂CH₃)— |
| Ia-807 | 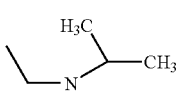 | —N(C(H)(CH₃)(CH₂CH₃))— |
| Ia-808 | 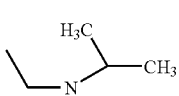 | —N(C(H)(CH₃)₂)— |
| Ia-809 | 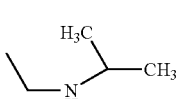 | —N(CH₂C(H)(CH₃)₂)— |
| Ia-810 | 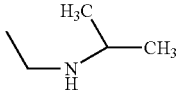 | —N(C(CH₃)₃)— |
| Ia-811 | 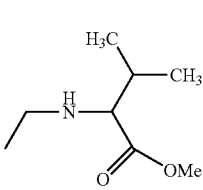 | —N(CH₃)— |
| Ia-812 | 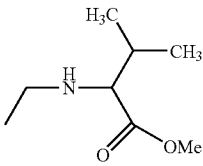 | —N(CH₂CH₃)— |

-continued
| | | |
|---|---|---|
| Ia-813 | 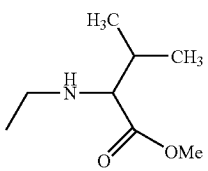 | —N(CH₂CH₂CH₃)— |
| Ia-814 | 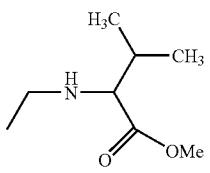 | —N(CH₂CH₂CH₃)— |
| Ia-815 | 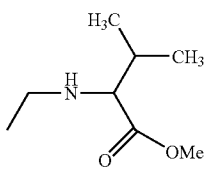 | —N(C(H)(CH₃)(CH₂CH₃))— |
| Ia-816 | 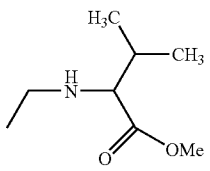 | —N(C(H)(CH₃)₂)— |
| Ia-817 | 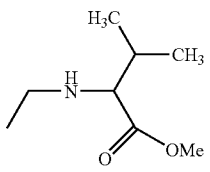 | —N(CH₂C(H)(CH₃)₂)— |
| Ia-818 | 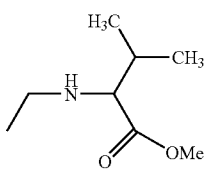 | —N(C(CH₃)₃)— |
| Ia-819 | 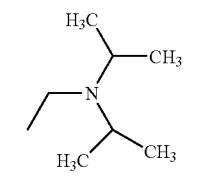 | —N(CH₃)— |
| Ia-820 | 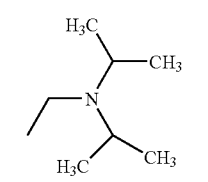 | —N(CH₂CH₃)— |
| Ia-821 | 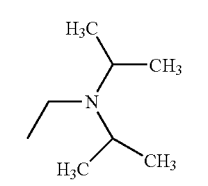 | —N(CH₂CH₂CH₃)— |

-continued

| | | |
|---|---|---|
| Ia-822 | (H3C)(CH3)CH-N(Et)-CH(CH3)(CH3) | —N(CH2CH2CH3)— |
| Ia-823 | (H3C)(CH3)CH-N(Et)-CH(CH3)(CH3) | —N(C(H)(CH3)(CH2CH3))— |
| Ia-824 | (H3C)(CH3)CH-N(Et)-CH(CH3)(CH3) | —N(C(H)(CH3)2)— |
| Ia-825 | (H3C)(CH3)CH-N(Et)-CH(CH3)(CH3) | —N(CH2C(H)(CH3)2)— |
| Ia-826 | (H3C)(CH3)CH-N(Et)-CH(CH3)(CH3) | —N(C(CH3)3)— |
| Ia-827 | Et-N(CH3)-CH2CH2-(2-pyridyl) | —N(CH3)— |
| Ia-828 | Et-N(CH3)-CH2CH2-(2-pyridyl) | —N(CH2CH3)— |
| Ia-829 | Et-N(CH3)-CH2CH2-(2-pyridyl) | —N(CH2CH2CH3)— |
| Ia-830 | Et-N(CH3)-CH2CH2-(2-pyridyl) | —N(CH2CH2CH2CH3)— |
| Ia-831 | Et-N(CH3)-CH2CH2-(2-pyridyl) | —N(C(H)(CH3)(CH2CH3))— |
| Ia-832 | Et-N(CH3)-CH2CH2-(2-pyridyl) | —N(C(H)(CH3)2)— |

| | | |
|---|---|---|
| Ia-833 | [Et(CH3)N-CH2CH2-(2-pyridyl)] | —N(CH2C(H)(CH3)2)— |
| Ia-834 | [Et(CH3)N-CH2CH2-(2-pyridyl)] | —N(C(CH3)3)— |
| Ia-835 | [Et(CH3CH2)N-CH2-(4-pyridyl)] | —N(CH3)— |
| Ia-836 | [Et(CH3CH2)N-CH2-(4-pyridyl)] | —N(CH2CH3)— |
| Ia-837 | [Et(CH3CH2)N-CH2-(3-pyridyl)] | —N(CH2CH2CH3)— |
| Ia-838 | [Et(CH3CH2)N-CH2-(3-pyridyl)] | —N(CH2CH2CH3)— |
| Ia-839 | [Et(CH3CH2)N-CH2-(3-pyridyl)] | —N(C(H)(CH3)(CH2CH3))— |
| Ia-840 | [Et(CH3CH2)N-CH2-(3-pyridyl)] | —N(C(H)(CH3)2)— |
| Ia-841 | [Et(CH3CH2)N-CH2-(3-pyridyl)] | —N(CH2C(H)(CH3)2)— |
| Ia-842 | [Et(CH3CH2)N-CH2-(3-pyridyl)] | —N(C(CH3)3)— |
| Ia-843 | [Et(CH3)N-CH2CH2OH] | —N(CH3)— |
| Ia-844 | [Et(CH3)N-CH2CH2OH] | —N(CH2CH3)— |
| Ia-845 | [Et(CH3)N-CH2CH2OH] | —N(CH2CH2CH3)— |
| Ia-846 | [Et(CH3)N-CH2CH2OH] | —N(CH2CH2CH3)— |

-continued

| | | |
|---|---|---|
| Ia-847 | CH₃–N(–CH₂CH₃)(–CH₂CH₂OH) (ethyl, methyl, hydroxyethyl amine) | —N(C(H)(CH₃)(CH₂CH₃))— |
| Ia-848 | CH₃–N(–CH₂CH₃)(–CH₂CH₂OH) | —N(C(H)(CH₃)₂)— |
| Ia-849 | CH₃–N(–CH₂CH₃)(–CH₂CH₂OH) | —N(CH₂C(H)(CH₃)₂)— |
| Ia-850 | CH₃–N(–CH₂CH₃)(–CH₂CH₂OH) | —N(C(CH₃)₃)— |
| Ia-851 | 1-ethyl-4-(piperidin-1-yl)piperidine | —N(CH₃)— |
| Ia-852 | 1-ethyl-4-(piperidin-1-yl)piperidine | —N(CH₂CH₃)— |
| Ia-853 | 1-ethyl-4-(piperidin-1-yl)piperidine | —N(CH₂CH₂CH₃)— |
| Ia-854 | 1-ethyl-4-(piperidin-1-yl)piperidine | —N(CH₂CH₂CH₃)— |
| Ia-855 | 1-ethyl-4-(piperidin-1-yl)piperidine | —N(C(H)(CH₃)(CH₂CH₃))— |
| Ia-856 | 1-ethyl-4-(piperidin-1-yl)piperidine | —N(C(H)(CH₃)₂)— |
| Ia-857 | 1-ethyl-4-(piperidin-1-yl)piperidine | —N(CH₂C(H)(CH₃)₂)— |
| Ia-858 | 1-ethyl-4-(piperidin-1-yl)piperidine | —N(C(CH₃)₃)— |
| Ia-859 | ethyl-NH-CH₂CH₂-(piperidin-1-yl) | —N(CH₃)— |
| Ia-860 | ethyl-NH-CH₂CH₂-(piperidin-1-yl) | —N(CH₂CH₃)— |
| Ia-861 | ethyl-NH-CH₂CH₂-(piperidin-1-yl) | —N(CH₂CH₂CH₃)— |
| Ia-862 | ethyl-NH-CH₂CH₂-(piperidin-1-yl) | —N(CH₂CH₂CH₃)— |

| | | -continued |
|---|---|---|
| Ia-863 | 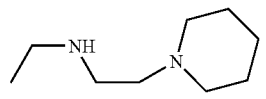 | —N(C(H)(CH₃)(CH₂CH₃))— |
| Ia-864 | 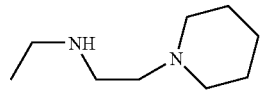 | —N(C(H)(CH₃)₂)— |
| Ia-865 | 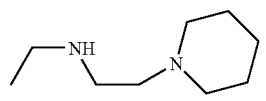 | —N(CH₂C(H)(CH₃)₂)— |
| Ia-866 | 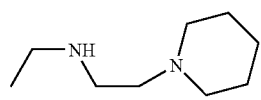 | —N(C(CH₃)₃)— |
| Ia-867 | 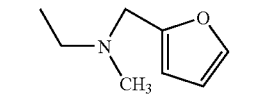 | —N(CH₃)— |
| Ia-868 | 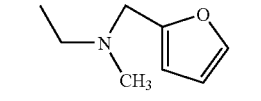 | —N(CH₂CH₃)— |
| Ia-869 | 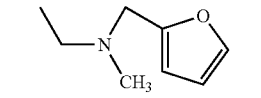 | —N(CH₂CH₂CH₃)— |
| Ia-870 | 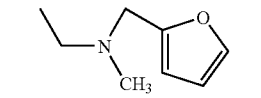 | —N(CH₂CH₂CH₂CH₃)— |
| Ia-871 | 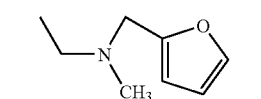 | —N(C(H)(CH₃)(CH₂CH₃))— |
| Ia-872 | 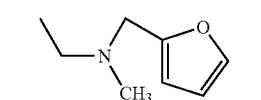 | —N(C(H)(CH₃)₂)— |
| Ia-873 | 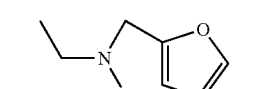 | —N(CH₂C(H)(CH₃)₂)— |
| Ia-874 | 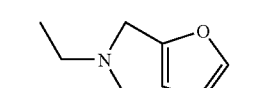 | —N(C(CH₃)₃)— |
| Ia-875 | 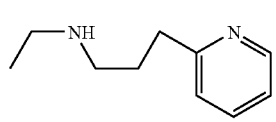 | —N(CH₃)— |
| Ia-876 | 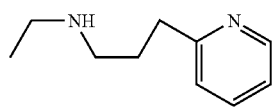 | —N(CH₂CH₃)— |

| | | -continued |
|---|---|---|
| Ia-877 | ![structure: ethylNH-CH2CH2CH2-(2-pyridyl)] | —N(CH₂CH₂CH₃)— |
| Ia-878 | ![structure: ethylNH-CH2CH2CH2-(2-pyridyl)] | —N(CH₂CH₂CH₂CH₃)— |
| Ia-879 | ![structure: ethylNH-CH2CH2CH2-(2-pyridyl)] | —N(C(H)(CH₃)(CH₂CH₃))— |
| Ia-880 | ![structure: ethylNH-CH2CH2CH2-(2-pyridyl)] | —N(C(H)(CH₃)₂)— |
| Ia-881 | ![structure: ethylNH-CH2CH2CH2-(2-pyridyl)] | —N(CH₂C(H)(CH₃)₂)— |
| Ia-882 | ![structure: ethylNH-CH2CH2CH2-(2-pyridyl)] | —N(C(CH₃)₃)— |
| Ia-883 | ![structure: ethylNH-CH2CH2CH2-(N-methylpyrrolidin-2-yl)] | —N(CH₃)— |
| Ia-884 | ![structure: ethylNH-CH2CH2CH2-(N-methylpyrrolidin-2-yl)] | —N(CH₂CH₃)— |
| Ia-885 | ![structure: ethylNH-CH2CH2CH2-(N-methylpyrrolidin-2-yl)] | —N(CH₂CH₂CH₃)— |
| Ia-886 | ![structure: ethylNH-CH2CH2CH2-(N-methylpyrrolidin-2-yl)] | —N(CH₂CH₂CH₂CH₃)— |
| Ia-887 | ![structure: ethylNH-CH2CH2CH2-(N-methylpyrrolidin-2-yl)] | —N(C(H)(CH₃)(CH₂CH₃))— |
| Ia-888 | ![structure: ethylNH-CH2CH2CH2-(N-methylpyrrolidin-2-yl)] | —N(C(H)(CH₃)₂)— |

-continued

| | | |
|---|---|---|
| Ia-889 | EtNH-CH2CH2CH2-(1-methylpyrrolidin-2-yl) | —N(CH₂C(H)(CH₃)₂)— |
| Ia-890 | EtNH-CH2CH2CH2-(1-methylpyrrolidin-2-yl) | —N(C(CH₃)₃)— |
| Ia-891 | 1-ethylpiperazine (NH) | —N(CH₃)— |
| Ia-892 | 1-ethylpiperazine (NH) | —N(CH₂CH₃)— |
| Ia-893 | 1-ethylpiperazine (NH) | —N(CH₂CH₂CH₃)— |
| Ia-894 | 1-ethylpiperazine (NH) | —N(CH₂CH₂CH₂CH₃)— |
| Ia-895 | 1-ethylpiperazine (NH) | —N(C(H)(CH₃)(CH₂CH₃))— |
| Ia-896 | 1-ethylpiperazine (NH) | —N(C(H)(CH₃)₂)— |
| Ia-897 | 1-ethylpiperazine (NH) | —N(CH₂C(H)(CH₃)₂)— |
| Ia-898 | 1-ethylpiperazine (NH) | —N(C(CH₃)₃)— |
| Ia-899 | 1-ethyl-4-methylpiperazine | —N(CH₃)— |
| Ia-900 | 1-ethyl-4-methylpiperazine | —N(CH₂CH₃)— |
| Ia-901 | 1-ethyl-4-methylpiperazine | —N(CH₂CH₂CH₃)— |
| Ia-902 | 1-ethyl-4-methylpiperazine | —N(CH₂CH₂CH₂CH₃)— |
| Ia-903 | 1-ethyl-4-methylpiperazine | —N(C(H)(CH₃)(CH₂CH₃))— |

| | | |
|---|---|---|
| Ia-904 | 1,4-diethylpiperazine, N-methyl | —N(C(H)(CH₃)₂)— |
| Ia-905 | 1,4-diethylpiperazine, N-methyl | —N(CH₂C(H)(CH₃)₂)— |
| Ia-906 | 1,4-diethylpiperazine, N-methyl | —N(C(CH₃)₃)— |
| Ia-907 | N-ethyl cyclopropylamine | —N(CH₃)— |
| Ia-908 | N-ethyl cyclopropylamine | —N(CH₂CH₃)— |
| Ia-909 | N-ethyl cyclopropylamine | —N(CH₂CH₂CH₃)— |
| Ia-910 | N-ethyl cyclopropylamine | —N(CH₂CH₂CH₃)— |
| Ia-911 | N-ethyl cyclopropylamine | —N(C(H)(CH₃)(CH₂CH₃))— |
| Ia-912 | N-ethyl cyclopropylamine | —N(C(H)(CH₃)₂)— |
| Ia-913 | N-ethyl cyclopropylamine | —N(CH₂C(H)(CH₃)₂)— |
| Ia-914 | N-ethyl cyclopropylamine | —N(C(CH₃)₃)— |
| Ia-915 | 1-ethyl-4-(2-hydroxyethyl)piperazine | —N(CH₃)— |
| Ia-916 | 1-ethyl-4-(2-hydroxyethyl)piperazine | —N(CH₂CH₃)— |
| Ia-917 | 1-ethyl-4-(2-hydroxyethyl)piperazine | —N(CH₂CH₂CH₃)— |
| Ia-918 | 1-ethyl-4-(2-hydroxyethyl)piperazine | —N(CH₂CH₂CH₃)— |

-continued
| | | |
|---|---|---|
| Ia-919 | 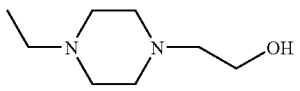 | —N(C(H)(CH₃)(CH₂CH₃))— |
| Ia-920 | 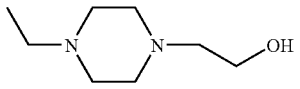 | —N(C(H)(CH₃)₂)— |
| Ia-921 | 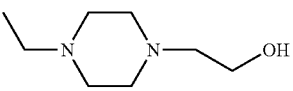 | —N(CH₂C(H)(CH₃)₂)— |
| Ia-922 | 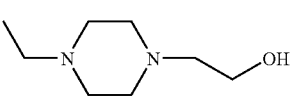 | —N(C(CH₃)₃)— |
| Ia-923 | 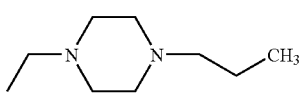 | —N(CH₃)— |
| Ia-924 | 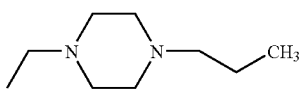 | —N(CH₂CH₃)— |
| Ia-925 | 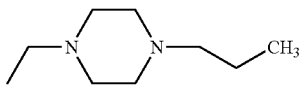 | —N(CH₂CH₃)— |
| Ia-926 | 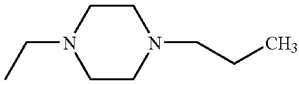 | —N(CH₂CH₂CH₃)— |
| Ia-927 | 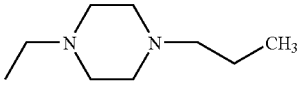 | —N(C(H)(CH₃)(CH₂CH₃))— |
| Ia-928 | 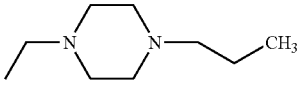 | —N(C(H)(CH₃)₂)— |
| Ia-929 | 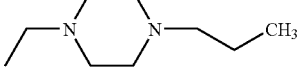 | —N(CH₂C(H)(CH₃)₂)— |
| Ia-930 | 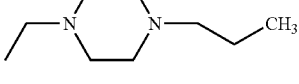 | —N(C(CH₃)₃)— |
| Ia-931 | 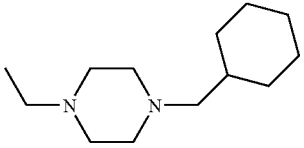 | —N(CH₃)— |
| Ia-932 | 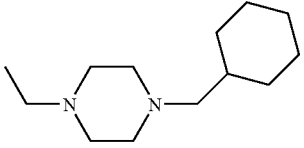 | —N(CH₂CH₃)— |

-continued
| | | |
|---|---|---|
| Ia-933 | 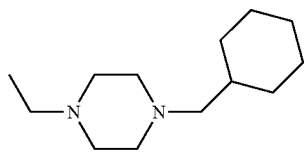 | —N(CH₂CH₂CH₃)— |
| Ia-934 | 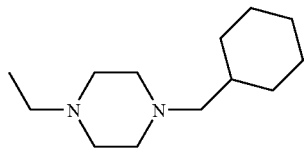 | —N(CH₂CH₂CH₂CH₃)— |
| Ia-935 | 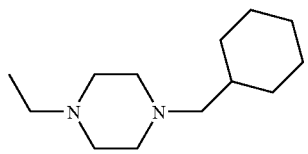 | —N(C(H)(CH₃)(CH₂CH₃))— |
| Ia-936 | 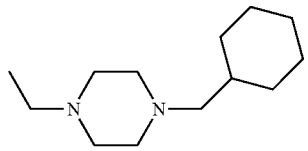 | —N(C(H)(CH₃)₂)— |
| Ia-937 | 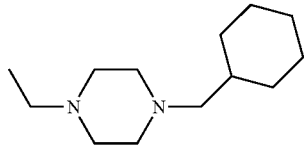 | —N(CH₂C(H)(CH₃)₂)— |
| Ia-938 | 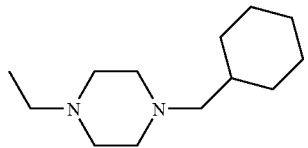 | —N(C(CH₃)₃)— |
| Ia-939 | 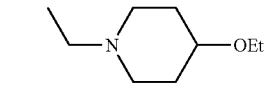 | —N(CH₃)— |
| Ia-940 | 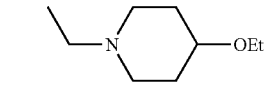 | —N(CH₂CH₃)— |
| Ia-941 | 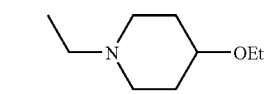 | —N(CH₂CH₂CH₃)— |
| Ia-942 | 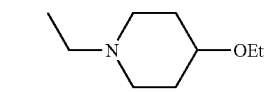 | —N(CH₂CH₂CH₂CH₃)— |
| Ia-943 | 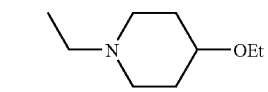 | —N(C(H)(CH₃)(CH₂CH₃))— |
| Ia-944 | 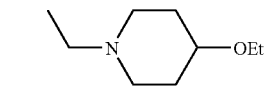 | —N(C(H)(CH₃)₂)— |

-continued

| | | |
|---|---|---|
| Ia-945 | N-ethyl-4-ethoxypiperidine | —N(CH₂C(H)(CH₃)₂)— |
| Ia-946 | N-ethyl-4-ethoxypiperidine | —N(C(CH₃)₃)— |
| Ia-947 | N-ethyl-3-hydroxypiperidine | —N(CH₃)— |
| Ia-948 | N-ethyl-3-hydroxypiperidine | —N(CH₂CH₃)— |
| Ia-949 | N-ethyl-3-hydroxypiperidine | —N(CH₂CH₂CH₃)— |
| Ia-950 | N-ethyl-3-hydroxypiperidine | —N(CH₂CH₂CH₃)— |
| Ia-951 | N-ethyl-3-hydroxypiperidine | —N(C(H)(CH₃)(CH₂CH₃))— |
| Ia-952 | N-ethyl-3-hydroxypiperidine | —N(C(H)(CH₃)₂)— |
| Ia-953 | N-ethyl-3-hydroxypiperidine | —N(CH₂C(H)(CH₃)₂)— |
| Ia-954 | N-ethyl-3-hydroxypiperidine | —N(C(CH₃)₃)— |
| Ia-955 | ethyl 2-(4-ethylpiperazin-1-yl)acetate | —N(CH₃)— |
| Ia-956 | ethyl 2-(4-ethylpiperazin-1-yl)acetate | —N(CH₂CH₃)— |
| Ia-957 | ethyl 2-(4-ethylpiperazin-1-yl)acetate | —N(CH₂CH₂CH₃)— |

-continued

| | | |
|---|---|---|
| Ia-958 | 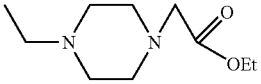 | —N(CH₂CH₂CH₂CH₃)— |
| Ia-959 | 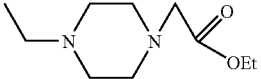 | —N(C(H)(CH₃)(CH₂CH₃))— |
| Ia-960 | 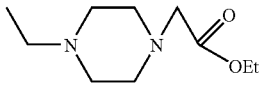 | —N(C(H)(CH₃)₂)— |
| Ia-961 | 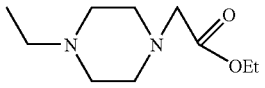 | —N(CH₂C(H)(CH₃)₂)— |
| Ia-962 | 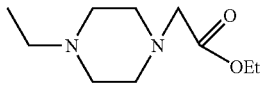 | —N(C(CH₃)₃)— |
| Ia-963 | —CH₂—N(CH₂CH₃)(CH₃) | —N(CH₃)— |
| Ia-964 | —CH₂—N(CH₂CH₃)(CH₃) | —N(CH₂CH₃)— |
| Ia-965 | —CH₂—N(CH₂CH₃)(CH₃) | —N(CH₂CH₂CH₃)— |
| Ia-966 | —CH₂—N(CH₂CH₃)(CH₃) | —N(CH₂CH₂CH₂CH₃)— |
| Ia-967 | —CH₂—N(CH₂CH₃)(CH₃) | —N(C(H)(CH₃)(CH₂CH₃))— |
| Ia-968 | —CH₂—N(CH₂CH₃)(CH₃) | —N(C(H)(CH₃)₂)— |
| Ia-969 | —CH₂—N(CH₂CH₃)(CH₃) | —N(CH₂C(H)(CH₃)₂)— |
| Ia-970 | —CH₂—N(CH₂CH₃)(CH₃) | —N(C(CH₃)₃)— |
| Ia-971 | —CH₂—N(CH₂CH₂CH₃)(CH₃) | —N(CH₃)— |
| Ia-972 | —CH₂—N(CH₂CH₂CH₃)(CH₃) | —N(CH₂CH₃)— |
| Ia-973 | —CH₂—N(CH₂CH₂CH₃)(CH₃) | —N(CH₂CH₂CH₃)— |
| Ia-974 | —CH₂—N(CH₂CH₂CH₃)(CH₃) | —N(CH₂CH₂CH₂CH₃)— |
| Ia-975 | —CH₂—N(CH₂CH₂CH₃)(CH₃) | —N(C(H)(CH₃)(CH₂CH₃))— |
| Ia-976 | —CH₂—N(CH₂CH₂CH₃)(CH₃) | —N(C(H)(CH₃)₂)— |
| Ia-977 | —CH₂—N(CH₂CH₂CH₃)(CH₃) | —N(CH₂C(H)(CH₃)₂)— |
| Ia-978 | —CH₂—N(CH₂CH₂CH₃)(CH₃) | —N(C(CH₃)₃)— |
| Ia-979 | —CH₂—N(CH₂CH₂CH₂CH₃)(CH₃) | —N(CH₃)— |
| Ia-980 | —CH₂—N(CH₂CH₂CH₂CH₃)(CH₃) | —N(CH₂CH₃)— |
| Ia-981 | —CH₂—N(CH₂CH₂CH₂CH₃)(CH₃) | —N(CH₂CH₂CH₃)— |
| Ia-982 | —CH₂—N(CH₂CH₂CH₂CH₃)(CH₃) | —N(CH₂CH₂CH₂CH₃)— |
| Ia-983 | —CH₂—N(CH₂CH₂CH₂CH₃)(CH₃) | —N(C(H)(CH₃)(CH₂CH₃))— |
| Ia-984 | —CH₂—N(CH₂CH₂CH₂CH₃)(CH₃) | —N(C(H)(CH₃)₂)— |
| Ia-985 | —CH₂—N(CH₂CH₂CH₂CH₃)(CH₃) | —N(CH₂C(H)(CH₃)₂)— |
| Ia-986 | —CH₂—N(CH₂CH₂CH₂CH₃)(CH₃) | —N(C(CH₃)₃)— |
| Ia-987 | —CH₂—NH—CH₂CH₂CH₂CH₃ | —N(CH₃)— |
| Ia-988 | —CH₂—NH—CH₂CH₂CH₂CH₃ | —N(CH₂CH₃)— |
| Ia-989 | —CH₂—NH—CH₂CH₂CH₂CH₃ | —N(CH₂CH₂CH₃)— |
| Ia-990 | —CH₂—NH—CH₂CH₂CH₂CH₃ | —N(CH₂CH₂CH₂CH₃)— |
| Ia-991 | —CH₂—NH—CH₂CH₂CH₂CH₃ | —N(C(H)(CH₃)(CH₂CH₃))— |
| Ia-992 | —CH₂—NH—CH₂CH₂CH₂CH₃ | —N(C(H)(CH₃)₂)— |
| Ia-993 | —CH₂—NH—CH₂CH₂CH₂CH₃ | —N(CH₂C(H)(CH₃)₂)— |
| Ia-994 | —CH₂—NH—CH₂CH₂CH₂CH₃ | —N(C(CH₃)₃)— |
| Ia-995 | —CH₂—NH—CH₂CH₂—O—CH₃ | —N(CH₃)— |
| Ia-996 | —CH₂—NH—CH₂CH₂—O—CH₃ | —N(CH₂CH₃)— |
| Ia-997 | —CH₂—NH—CH₂CH₂—O—CH₃ | —N(CH₂CH₂CH₃)— |
| Ia-998 | —CH₂—NH—CH₂CH₂—O—CH₃ | —N(CH₂CH₂CH₂CH₃)— |
| Ia-999 | —CH₂—NH—CH₂CH₂—O—CH₃ | —N(C(H)(CH₃)(CH₂CH₃))— |
| Ia-1000 | —CH₂—NH—CH₂CH₂—O—CH₃ | —N(C(H)(CH₃)₂)— |
| Ia-1001 | —CH₂—NH—CH₂CH₂—O—CH₃ | —N(CH₂C(H)(CH₃)₂)— |
| Ia-1002 | —CH₂—NH—CH₂CH₂—O—CH₃ | —N(C(CH₃)₃)— |
| Ia-1003 | 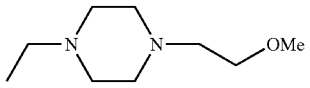 | —N(CH₃)— |
| Ia-1004 | 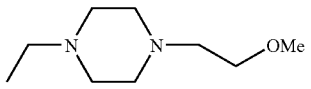 | —N(CH₂CH₃)— |
| Ia-1005 | 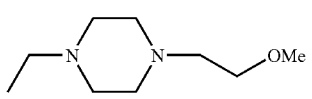 | —N(CH₂CH₂CH₃)— |

-continued
| | | |
|---|---|---|
| Ia-1006 | 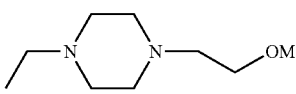 | —N(CH₂CH₂CH₂CH₃)— |
| Ia-1007 | 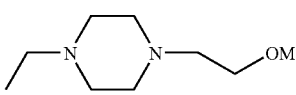 | —N(C(H)(CH₃)(CH₂CH₃))— |
| Ia-1008 | 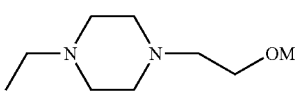 | —N(C(H)(CH₃)₂)— |
| Ia-1009 | 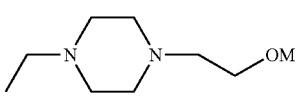 | —N(CH₂C(H)(CH₃)₂)— |
| Ia-1010 | 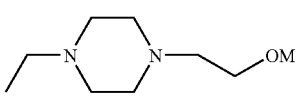 | —N(C(CH₃)₃)— |
| Ia-1011 | 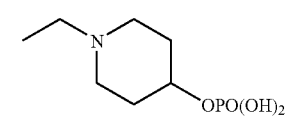 | —N(CH₃)— |
| Ia-1012 | 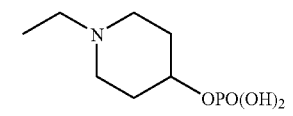 | —N(CH₂CH₃)— |
| Ia-1013 | 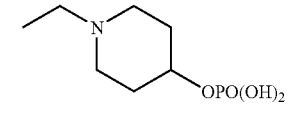 | —N(CH₂CH₂CH₃)— |
| Ia-1014 | 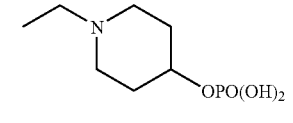 | —N(CH₂CH₂CH₂CH₃)— |
| Ia-1015 | 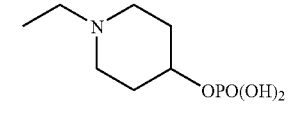 | —N(C(H)(CH₃)(CH₂CH₃))— |
| Ia-1016 | 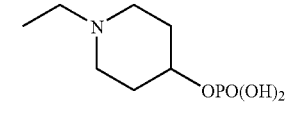 | —N(C(H)(CH₃)₂)— |
| Ia-1017 | 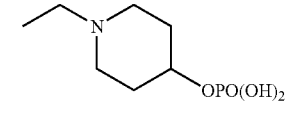 | —N(CH₂C(H)(CH₃)₂)— |
| Ia-1018 | 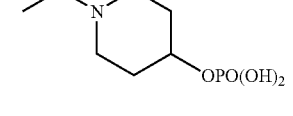 | —N(C(CH₃)₃)— |
| Ia-1019 | 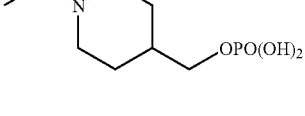 | —N(CH₃)— |

-continued
| | | |
|---|---|---|
| Ia-1020 | 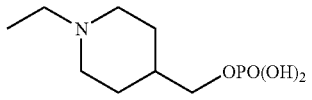 | —N(CH$_2$CH$_3$)— |
| Ia-1021 | 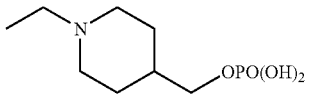 | —N(CH$_2$CH$_2$CH$_3$)— |
| Ia-1022 | 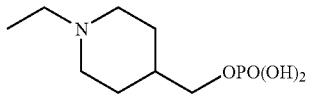 | —N(CH$_2$CH$_2$CH$_2$CH$_3$)— |
| Ia-1023 | 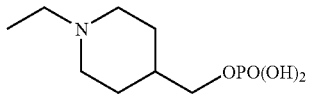 | —N(C(H)(CH$_3$)(CH$_2$CH$_3$))— |
| Ia-1024 | 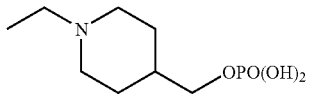 | —N(C(H)(CH$_3$)$_2$)— |
| Ia-1025 | 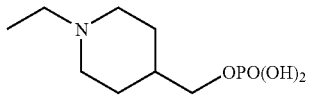 | —N(CH$_2$C(H)(CH$_3$)$_2$)— |
| Ia-1026 | 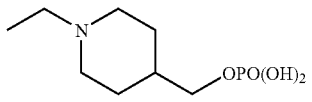 | —N(C(CH$_3$)$_3$)— |
| Ia-1027 | 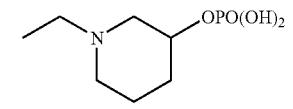 | —N(CH$_3$)— |
| Ia-1028 | 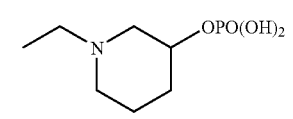 | —N(CH$_2$CH$_3$)— |
| Ia-1029 | 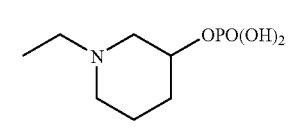 | —N(CH$_2$CH$_2$CH$_3$)— |
| Ia-1030 | 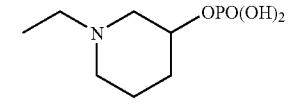 | —N(CH$_2$CH$_2$CH$_2$CH$_3$)— |
| Ia-1031 |  | —N(C(H)(CH$_3$)(CH$_2$CH$_3$))— |
| Ia-1032 | 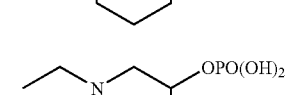 | —N(C(H)(CH$_3$)$_2$)— |
| Ia-1033 | 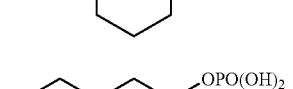 | —N(CH$_2$C(H)(CH$_3$)$_2$)— |

| | | |
|---|---|---|
| Ia-1034 | 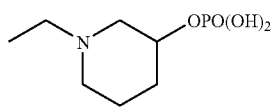 | —N(C(CH₃)₃)— |
| Ia-1035 | 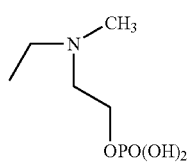 | —N(CH₃)— |
| Ia-1036 | 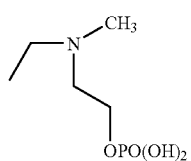 | —N(CH₂CH₃)— |
| Ia-1037 | 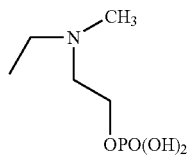 | —N(CH₂CH₂CH₃)— |
| Ia-1038 | 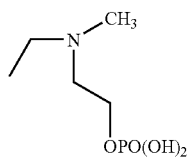 | —N(CH₂CH₂CH₂CH₃)— |
| Ia-1039 | 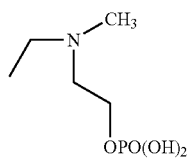 | —N(C(H)(CH₃)(CH₂CH₃))— |
| Ia-1040 | 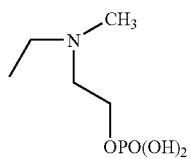 | —N(C(H)(CH₃)₂)— |
| Ia-1041 | 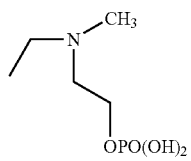 | —N(CH₂C(H)(CH₃)₂)— |
| Ia-1042 | 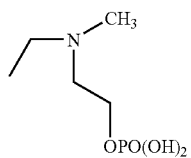 | —N(C(CH₃)₃)— |

-continued
| | | |
|---|---|---|
| Ia-1043 | 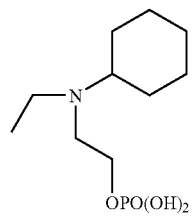 | —N(CH₃)— |
| Ia-1044 | 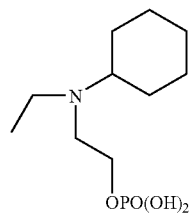 | —N(CH₂CH₃)— |
| Ia-1045 | 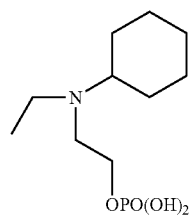 | —N(CH₂CH₂CH₃)— |
| Ia-1046 | 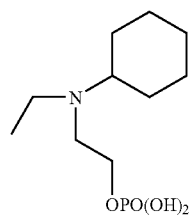 | —N(CH₂CH₂CH₂CH₃)— |
| Ia-1047 | 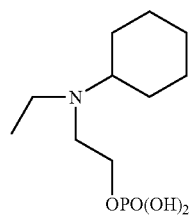 | —N(C(H)(CH₃)(CH₂CH₃))— |
| Ia-1048 | 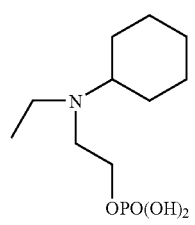 | —N(C(H)(CH₃)₂)— |
| Ia-1049 | 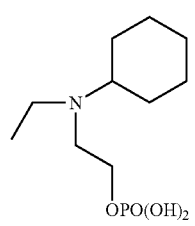 | —N(CH₂C(H)(CH₃)₂)— |

-continued
| | | |
|---|---|---|
| Ia-1050 | 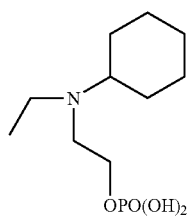 | —N(C(CH$_3$)$_3$)— |
| Ia-1051 |  | —N(CH$_3$)— |
| Ia-1052 | 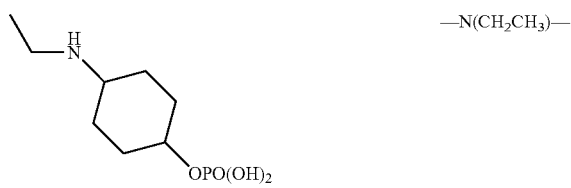 | —N(CH$_2$CH$_3$)— |
| Ia-1053 |  | —N(CH$_2$CH$_2$CH$_3$)— |
| Ia-1054 |  | —N(CH$_2$CH$_2$CH$_2$CH$_3$)— |
| Ia-1055 |  | —N(C(H)(CH$_3$)(CH$_2$CH$_3$))— |
| Ia-1056 | 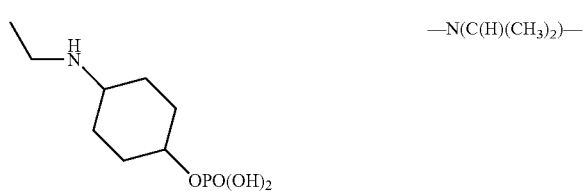 | —N(C(H)(CH$_3$)$_2$)— |
| Ia-1057 |  | —N(CH$_2$C(H)(CH$_3$)$_2$)— |

|Ia-1058|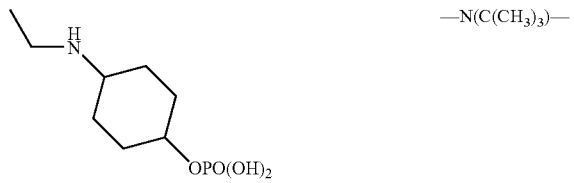| |—N(C(CH$_3$)$_3$)—|

| Compound | n | —R$^1$ | X |
|---|---|---|---|
| Ia-a1 | 1 | —(CH$_2$)$_n$—N(CH$_3$)$_2$ | —CH(OH)— |
| Ia-a2 | 2 | —(CH$_2$)$_n$—N(CH$_3$)$_2$ | —CH(OH)— |
| Ia-a3 | 3 | —(CH$_2$)$_n$—N(CH$_3$)$_2$ | —CH(OH)— |
| Ia-a4 | 4 | —(CH$_2$)$_n$—N(CH$_3$)$_2$ | —CH(OH)— |
| Ia-a5 | 5 | —(CH$_2$)$_n$—N(CH$_3$)$_2$ | —CH(OH)— |
| Ia-a6 | 6 | —(CH$_2$)$_n$—N(CH$_3$)$_2$ | —CH(OH)— |
| Ia-a7 | 1 | —(CH$_2$)$_n$—N(CH$_3$)$_2$ | —N(C(O)N(H)—CH$_2$—CH$_2$—OH)— |
| Ia-a8 | 2 | —(CH$_2$)$_n$—N(CH$_3$)$_2$ | —N(C(O)N(H)—CH$_2$—CH$_2$—OH)— |
| Ia-a9 | 3 | —(CH$_2$)$_n$—N(CH$_3$)$_2$ | —N(C(O)N(H)—CH$_2$—CH$_2$—OH)— |
| Ia-a10 | 4 | —(CH$_2$)$_n$—N(CH$_3$)$_2$ | —N(C(O)N(H)—CH$_2$—CH$_2$—OH)— |
| Ia-a11 | 5 | —(CH$_2$)$_n$—N(CH$_3$)$_2$ | —N(C(O)N(H)—CH$_2$—CH$_2$—OH)— |
| Ia-a12 | 6 | —(CH$_2$)$_n$—N(CH$_3$)$_2$ | —N(C(O)N(H)—CH$_2$—CH$_2$—OH)— |
| Ia-a13 | 1 | —(CH$_2$)$_n$—N(CH$_3$)$_2$ | —N(C(O)N(H)—CH$_2$—CH$_2$—F)— |
| Ia-a14 | 2 | —(CH$_2$)$_n$—N(CH$_3$)$_2$ | —N(C(O)N(H)—CH$_2$—CH$_2$—F)— |
| Ia-a15 | 3 | —(CH$_2$)$_n$—N(CH$_3$)$_2$ | —N(C(O)N(H)—CH$_2$—CH$_2$—F)— |
| Ia-a16 | 4 | —(CH$_2$)$_n$—N(CH$_3$)$_2$ | —N(C(O)N(H)—CH$_2$—CH$_2$—F)— |
| Ia-a17 | 5 | —(CH$_2$)$_n$—N(CH$_3$)$_2$ | —N(C(O)N(H)—CH$_2$—CH$_2$—F)— |
| Ia-a18 | 6 | —(CH$_2$)$_n$—N(CH$_3$)$_2$ | —N(C(O)N(H)—CH$_2$—CH$_2$—F)— |
| Ia-a19 | 1 | —(CH$_2$)$_n$—N(CH$_3$)$_2$ | —N(C(O)N(H)—CH$_2$—CH$_2$—OCH$_3$)— |
| Ia-a20 | 2 | —(CH$_2$)$_n$—N(CH$_3$)$_2$ | —N(C(O)N(H)—CH$_2$—CH$_2$—OCH$_3$)— |
| Ia-a21 | 3 | —(CH$_2$)$_n$—N(CH$_3$)$_2$ | —N(C(O)N(H)—CH$_2$—CH$_2$—OCH$_3$)— |
| Ia-a22 | 4 | —(CH$_2$)$_n$—N(CH$_3$)$_2$ | —N(C(O)N(H)—CH$_2$—CH$_2$—OCH$_3$)— |
| Ia-a23 | 5 | —(CH$_2$)$_n$—N(CH$_3$)$_2$ | —N(C(O)N(H)—CH$_2$—CH$_2$—OCH$_3$)— |
| Ia-a24 | 6 | —(CH$_2$)$_n$—N(CH$_3$)$_2$ | —N(C(O)N(H)—CH$_2$—CH$_2$—OCH$_3$)— |
| Ia-a25 | 1 | —(CH$_2$)$_n$—N(CH$_3$)$_2$ | —N(C(O)N(H)—CH$_2$—CH$_2$—CF$_3$)— |
| Ia-a26 | 2 | —(CH$_2$)$_n$—N(CH$_3$)$_2$ | —N(C(O)N(H)—CH$_2$—CH$_2$—CF$_3$)— |
| Ia-a27 | 3 | —(CH$_2$)$_n$—N(CH$_3$)$_2$ | —N(C(O)N(H)—CH$_2$—CH$_2$—CF$_3$)— |
| Ia-a28 | 4 | —(CH$_2$)$_n$—N(CH$_3$)$_2$ | —N(C(O)N(H)—CH$_2$—CH$_2$—CF$_3$)— |
| Ia-a29 | 5 | —(CH$_2$)$_n$—N(CH$_3$)$_2$ | —N(C(O)N(H)—CH$_2$—CH$_2$—CF$_3$)— |
| Ia-a30 | 6 | —(CH$_2$)$_n$—N(CH$_3$)$_2$ | —N(C(O)N(H)—CH$_2$—CH$_2$—CF$_3$)— |
| Ia-a31 | 1 | —(CH$_2$)$_n$—N(CH$_3$)$_2$ | —N(CH$_2$—CH$_2$—OH)— |
| Ia-a32 | 2 | —(CH$_2$)$_n$—N(CH$_3$)$_2$ | —N(CH$_2$—CH$_2$—OH)— |
| Ia-a33 | 3 | —(CH$_2$)$_n$—N(CH$_3$)$_2$ | —N(CH$_2$—CH$_2$—OH)— |
| Ia-a34 | 4 | —(CH$_2$)$_n$—N(CH$_3$)$_2$ | —N(CH$_2$—CH$_2$—OH)— |
| Ia-a35 | 5 | —(CH$_2$)$_n$—N(CH$_3$)$_2$ | —N(CH$_2$—CH$_2$—OH)— |
| Ia-a36 | 6 | —(CH$_2$)$_n$—N(CH$_3$)$_2$ | —N(CH$_2$—CH$_2$—OH)— |
| Ia-a37 | 1 | —(CH$_2$)$_n$—N(CH$_3$)$_2$ | —N(CH$_2$—CH$_2$—F)— |
| Ia-a38 | 2 | —(CH$_2$)$_n$—N(CH$_3$)$_2$ | —N(CH$_2$—CH$_2$—F)— |
| Ia-a39 | 3 | —(CH$_2$)$_n$—N(CH$_3$)$_2$ | —N(CH$_2$—CH$_2$—F)— |
| Ia-a40 | 4 | —(CH$_2$)$_n$—N(CH$_3$)$_2$ | —N(CH$_2$—CH$_2$—F)— |
| Ia-a41 | 5 | —(CH$_2$)$_n$—N(CH$_3$)$_2$ | —N(CH$_2$—CH$_2$—F)— |
| Ia-a42 | 6 | —(CH$_2$)$_n$—N(CH$_3$)$_2$ | —N(CH$_2$—CH$_2$—F)— |
| Ia-a43 | 1 | —(CH$_2$)$_n$—N(CH$_3$)$_2$ | —N(CH$_2$—CH$_2$—OCH$_3$)— |
| Ia-a44 | 2 | —(CH$_2$)$_n$—N(CH$_3$)$_2$ | —N(CH$_2$—CH$_2$—OCH$_3$)— |
| Ia-a45 | 3 | —(CH$_2$)$_n$—N(CH$_3$)$_2$ | —N(CH$_2$—CH$_2$—OCH$_3$)— |
| Ia-a46 | 4 | —(CH$_2$)$_n$—N(CH$_3$)$_2$ | —N(CH$_2$—CH$_2$—OCH$_3$)— |
| Ia-a47 | 5 | —(CH$_2$)$_n$—N(CH$_3$)$_2$ | —N(CH$_2$—CH$_2$—OCH$_3$)— |
| Ia-a48 | 6 | —(CH$_2$)$_n$—N(CH$_3$)$_2$ | —N(CH$_2$—CH$_2$—OCH$_3$)— |
| Ia-a49 | 1 | 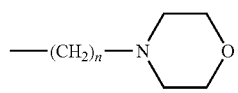 | —CH(OH)— |
| Ia-a50 | 2 | 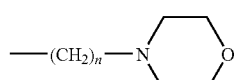 | —CH(OH)— |
| Ia-a51 | 3 | 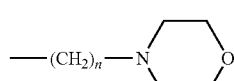 | —CH(OH)— |
| Ia-a52 | 4 | 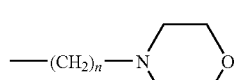 | —CH(OH)— |

| | | | |
|---|---|---|---|
| Ia-a53 | 5 | —(CH$_2$)$_n$—N(morpholine) | —CH(OH)— |
| Ia-a54 | 6 | —(CH$_2$)$_n$—N(morpholine) | —CH(OH)— |
| Ia-a55 | 1 | —(CH$_2$)$_n$—N(morpholine) | —N(C(O)N(H)—CH$_2$—CH$_2$—OH)— |
| Ia-a56 | 2 | —(CH$_2$)$_n$—N(morpholine) | —N(C(O)N(H)—CH$_2$—CH$_2$—OH)— |
| Ia-a57 | 3 | —(CH$_2$)$_n$—N(morpholine) | —N(C(O)N(H)—CH$_2$—CH$_2$—OH)— |
| Ia-a58 | 4 | —(CH$_2$)$_n$—N(morpholine) | —N(C(O)N(H)—CH$_2$—CH$_2$—OH)— |
| Ia-a59 | 5 | —(CH$_2$)$_n$—N(morpholine) | —N(C(O)N(H)—CH$_2$—CH$_2$—OH)— |
| Ia-a60 | 6 | —(CH$_2$)$_n$—N(morpholine) | —N(C(O)N(H)—CH$_2$—CH$_2$—OH)— |
| Ia-a61 | 1 | —(CH$_2$)$_n$—N(morpholine) | —N(C(O)N(H)—CH$_2$—CH$_2$—F)— |
| Ia-a62 | 2 | —(CH$_2$)$_n$—N(morpholine) | —N(C(O)N(H)—CH$_2$—CH$_2$—F)— |
| Ia-a63 | 3 | —(CH$_2$)$_n$—N(morpholine) | —N(C(O)N(H)—CH$_2$—CH$_2$—F)— |
| Ia-a64 | 4 | —(CH$_2$)$_n$—N(morpholine) | —N(C(O)N(H)—CH$_2$—CH$_2$—F)— |
| Ia-a65 | 5 | —(CH$_2$)$_n$—N(morpholine) | —N(C(O)N(H)—CH$_2$—CH$_2$—F)— |
| Ia-a66 | 6 | —(CH$_2$)$_n$—N(morpholine) | —N(C(O)N(H)—CH$_2$—CH$_2$—F)— |
| Ia-a67 | 1 | —(CH$_2$)$_n$—N(morpholine) | —N(C(O)N(H)—CH$_2$—CH$_2$—OCH$_3$)— |
| Ia-a68 | 2 | —(CH$_2$)$_n$—N(morpholine) | —N(C(O)N(H)—CH$_2$—CH$_2$—OCH$_3$)— |

-continued

| | | | |
|---|---|---|---|
| Ia-a69 | 3 | —(CH$_2$)$_n$—N(morpholine) | —N(C(O)N(H)—CH$_2$—CH$_2$—OCH$_3$)— |
| Ia-a70 | 4 | —(CH$_2$)$_n$—N(morpholine) | —N(C(O)N(H)—CH$_2$—CH$_2$—OCH$_3$)— |
| Ia-a71 | 5 | —(CH$_2$)$_n$—N(morpholine) | —N(C(O)N(H)—CH$_2$—CH$_2$—OCH$_3$)— |
| Ia-a72 | 6 | —(CH$_2$)$_n$—N(morpholine) | —N(C(O)N(H)—CH$_2$—CH$_2$—OCH$_3$)— |
| Ia-a73 | 1 | —(CH$_2$)$_n$—N(morpholine) | —N(C(O)N(H)—CH$_2$—CH$_2$—CF$_3$)— |
| Ia-a74 | 2 | —(CH$_2$)$_n$—N(morpholine) | —N(C(O)N(H)—CH$_2$—CH$_2$—CF$_3$)— |
| Ia-a75 | 3 | —(CH$_2$)$_n$—N(morpholine) | —N(C(O)N(H)—CH$_2$—CH$_2$—CF$_3$)— |
| Ia-a76 | 4 | —(CH$_2$)$_n$—N(morpholine) | —N(C(O)N(H)—CH$_2$—CH$_2$—CF$_3$)— |
| Ia-a77 | 5 | —(CH$_2$)$_n$—N(morpholine) | —N(C(O)N(H)—CH$_2$—CH$_2$—CF$_3$)— |
| Ia-a78 | 6 | —(CH$_2$)$_n$—N(morpholine) | —N(C(O)N(H)—CH$_2$—CH$_2$—CF$_3$)— |
| Ia-a79 | 1 | —(CH$_2$)$_n$—N(morpholine) | —N(CH$_2$—CH$_2$—OH)— |
| Ia-a80 | 2 | —(CH$_2$)$_n$—N(morpholine) | —N(CH$_2$—CH$_2$—OH)— |
| Ia-a81 | 3 | —(CH$_2$)$_n$—N(morpholine) | —N(CH$_2$—CH$_2$—OH)— |
| Ia-a82 | 4 | —(CH$_2$)$_n$—N(morpholine) | —N(CH$_2$—CH$_2$—OH)— |
| Ia-a83 | 5 | —(CH$_2$)$_n$—N(morpholine) | —N(CH$_2$—CH$_2$—OH)— |
| Ia-a84 | 6 | —(CH$_2$)$_n$—N(morpholine) | —N(CH$_2$—CH$_2$—OH)— |

| Compound | n | | X |
|---|---|---|---|
| Ia-a85 | 1 |  | —N(CH₂—CH₂—F)— |
| Ia-a86 | 2 |  | —N(CH₂—CH₂—F)— |
| Ia-a87 | 3 |  | —N(CH₂—CH₂—F)— |
| Ia-a88 | 4 |  | —N(CH₂—CH₂—F)— |
| Ia-a89 | 5 |  | —N(CH₂—CH₂—F)— |
| Ia-a90 | 6 |  | —N(CH₂—CH₂—F)— |
| Ia-a91 | 1 |  | —N(CH₂—CH₂—OCH₃)— |
| Ia-a92 | 2 |  | —N(CH₂—CH₂—OCH₃)— |
| Ia-a93 | 3 |  | —N(CH₂—CH₂—OCH₃)— |
| Ia-a94 | 4 |  | —N(CH₂—CH₂—OCH₃)— |
| Ia-a95 | 5 |  | —N(CH₂—CH₂—OCH₃)— |
| Ia-a96 | 6 |  | —N(CH₂—CH₂—OCH₃)— |

| Compound | m | —R¹ | X |
|---|---|---|---|
| Ia-a146 | 2 | —O—(CH₂)ₘ—N(CH₃)₂ | —CH(OH)— |
| Ia-a147 | 3 | —O—(CH₂)ₘ—N(CH₃)₂ | —CH(OH)— |
| Ia-a148 | 4 | —O—(CH₂)ₘ—N(CH₃)₂ | —CH(OH)— |
| Ia-a149 | 5 | —O—(CH₂)ₘ—N(CH₃)₂ | —CH(OH)— |
| Ia-a150 | 6 | —O—(CH₂)ₘ—N(CH₃)₂ | —CH(OH)— |
| Ia-a151 | 2 | —O—(CH₂)ₘ—N(CH₃)₂ | —N(C(O)N(H)—CH₂—CH₂—OH)— |
| Ia-a152 | 3 | —O—(CH₂)ₘ—N(CH₃)₂ | —N(C(O)N(H)—CH₂—CH₂—OH)— |
| Ia-a153 | 4 | —O—(CH₂)ₘ—N(CH₃)₂ | —N(C(O)N(H)—CH₂—CH₂—OH)— |
| Ia-a154 | 5 | —O—(CH₂)ₘ—N(CH₃)₂ | —N(C(O)N(H)—CH₂—CH₂—OH)— |
| Ia-a155 | 6 | —O—(CH₂)ₘ—N(CH₃)₂ | —N(C(O)N(H)—CH₂—CH₂—OH)— |
| Ia-a156 | 2 | —O—(CH₂)ₘ—N(CH₃)₂ | —N(C(O)N(H)—CH₂—CH₂—F)— |
| Ia-a157 | 3 | —O—(CH₂)ₘ—N(CH₃)₂ | —N(C(O)N(H)—CH₂—CH₂—F)— |
| Ia-a158 | 4 | —O—(CH₂)ₘ—N(CH₃)₂ | —N(C(O)N(H)—CH₂—CH₂—F)— |
| Ia-a159 | 5 | —O—(CH₂)ₘ—N(CH₃)₂ | —N(C(O)N(H)—CH₂—CH₂—F)— |
| Ia-a160 | 6 | —O—(CH₂)ₘ—N(CH₃)₂ | —N(C(O)N(H)—CH₂—CH₂—F)— |
| Ia-a161 | 2 | —O—(CH₂)ₘ—N(CH₃)₂ | —N(C(O)N(H)—CH₂—CH₂—OCH₃)— |
| Ia-a162 | 3 | —O—(CH₂)ₘ—N(CH₃)₂ | —N(C(O)N(H)—CH₂—CH₂—OCH₃)— |
| Ia-a163 | 4 | —O—(CH₂)ₘ—N(CH₃)₂ | —N(C(O)N(H)—CH₂—CH₂—OCH₃)— |

-continued

| | | | |
|---|---|---|---|
| Ia-a164 | 5 | —O—(CH$_2$)$_m$—N(CH$_3$)$_2$ | —N(C(O)N(H)—CH$_2$—CH$_2$—OCH$_3$)— |
| Ia-a165 | 6 | —O—(CH$_2$)$_m$—N(CH$_3$)$_2$ | —N(C(O)N(H)—CH$_2$—CH$_2$—OCH$_3$)— |
| Ia-a166 | 2 | —O—(CH$_2$)$_m$—N(CH$_3$)$_2$ | —N(C(O)N(H)—CH$_2$—CH$_2$—CF$_3$)— |
| Ia-a167 | 3 | —O—(CH$_2$)$_m$—N(CH$_3$)$_2$ | —N(C(O)N(H)—CH$_2$—CH$_2$—CF$_3$)— |
| Ia-a168 | 4 | —O—(CH$_2$)$_m$—N(CH$_3$)$_2$ | —N(C(O)N(H)—CH$_2$—CH$_2$—CF$_3$)— |
| Ia-a169 | 5 | —O—(CH$_2$)$_m$—N(CH$_3$)$_2$ | —N(C(O)N(H)—CH$_2$—CH$_2$—CF$_3$)— |
| Ia-a170 | 6 | —O—(CH$_2$)$_m$—N(CH$_3$)$_2$ | —N(C(O)N(H)—CH$_2$—CH$_2$—CF$_3$)— |
| Ia-a171 | 2 | —O—(CH$_2$)$_m$—N(CH$_3$)$_2$ | —N(CH$_2$—CH$_2$—OH)— |
| Ia-a172 | 3 | —O—(CH$_2$)$_m$—N(CH$_3$)$_2$ | —N(CH$_2$—CH$_2$—OH)— |
| Ia-a173 | 4 | —O—(CH$_2$)$_m$—N(CH$_3$)$_2$ | —N(CH$_2$—CH$_2$—OH)— |
| Ia-a174 | 5 | —O—(CH$_2$)$_m$—N(CH$_3$)$_2$ | —N(CH$_2$—CH$_2$—OH)— |
| Ia-a175 | 6 | —O—(CH$_2$)$_m$—N(CH$_3$)$_2$ | —N(CH$_2$—CH$_2$—OH)— |
| Ia-a176 | 2 | —O—(CH$_2$)$_m$—N(CH$_3$)$_2$ | —N(CH$_2$—CH$_2$—F)— |
| Ia-a178 | 3 | —O—(CH$_2$)$_m$—N(CH$_3$)$_2$ | —N(CH$_2$—CH$_2$—F)— |
| Ia-a179 | 4 | —O—(CH$_2$)$_m$—N(CH$_3$)$_2$ | —N(CH$_2$—CH$_2$—F)— |
| Ia-a180 | 5 | —O—(CH$_2$)$_m$—N(CH$_3$)$_2$ | —N(CH$_2$—CH$_2$—F)— |
| Ia-a181 | 6 | —O—(CH$_2$)$_m$—N(CH$_3$)$_2$ | —N(CH$_2$—CH$_2$—F)— |
| Ia-a182 | 2 | —O—(CH$_2$)$_m$—N(CH$_3$)$_2$ | —N(CH$_2$—CH$_2$—OCH$_3$)— |
| Ia-a183 | 3 | —O—(CH$_2$)$_m$—N(CH$_3$)$_2$ | —N(CH$_2$—CH$_2$—OCH$_3$)— |
| Ia-a184 | 4 | —O—(CH$_2$)$_m$—N(CH$_3$)$_2$ | —N(CH$_2$—CH$_2$—OCH$_3$)— |
| Ia-a185 | 5 | —O—(CH$_2$)$_m$—N(CH$_3$)$_2$ | —N(CH$_2$—CH$_2$—OCH$_3$)— |
| Ia-a186 | 6 | —O—(CH$_2$)$_m$—N(CH$_3$)$_2$ | —N(CH$_2$—CH$_2$—OCH$_3$)— |
| Ia-a187 | 2 | —O—(CH$_2$)$_m$—N(morpholino) | —CH(OH)— |
| Ia-a188 | 3 | —O—(CH$_2$)$_m$—N(morpholino) | —CH(OH)— |
| Ia-a189 | 4 | —O—(CH$_2$)$_m$—N(morpholino) | —CH(OH)— |
| Ia-a190 | 5 | —O—(CH$_2$)$_m$—N(morpholino) | —CH(OH)— |
| Ia-a191 | 6 | —O—(CH$_2$)$_m$—N(morpholino) | —CH(OH)— |
| Ia-a192 | 2 | —O—(CH$_2$)$_m$—N(morpholino) | —N(C(O)N(H)—CH$_2$—CH$_2$—OH)— |
| Ia-a193 | 3 | —O—(CH$_2$)$_m$—N(morpholino) | —N(C(O)N(H)—CH$_2$—CH$_2$—OH)— |
| Ia-a194 | 4 | —O—(CH$_2$)$_m$—N(morpholino) | —N(C(O)N(H)—CH$_2$—CH$_2$—OH)— |
| Ia-a195 | 5 | —O—(CH$_2$)$_m$—N(morpholino) | —N(C(O)N(H)—CH$_2$—CH$_2$—OH)— |
| Ia-a196 | 6 | —O—(CH$_2$)$_m$—N(morpholino) | —N(C(O)N(H)—CH$_2$—CH$_2$—OH)— |
| Ia-a197 | 2 | —O—(CH$_2$)$_m$—N(morpholino) | —N(C(O)N(H)—CH$_2$—CH$_2$—F)— |

-continued

| | | | |
|---|---|---|---|
| Ia-a198 | 3 | —O—(CH$_2$)$_m$—N(morpholine) | —N(C(O)N(H)—CH$_2$—CH$_2$—F)— |
| Ia-a199 | 4 | —O—(CH$_2$)$_m$—N(morpholine) | —N(C(O)N(H)—CH$_2$—CH$_2$—F)— |
| Ia-a200 | 5 | —O—(CH$_2$)$_m$—N(morpholine) | —N(C(O)N(H)—CH$_2$—CH$_2$—F)— |
| Ia-a201 | 6 | —O—(CH$_2$)$_m$—N(morpholine) | —N(C(O)N(H)—CH$_2$—CH$_2$—F)— |
| Ia-a202 | 2 | —O—(CH$_2$)$_m$—N(morpholine) | —N(C(O)N(H)—CH$_2$—CH$_2$—OCH$_3$)— |
| Ia-a203 | 3 | —O—(CH$_2$)$_m$—N(morpholine) | —N(C(O)N(H)—CH$_2$—CH$_2$—OCH$_3$)— |
| Ia-a204 | 4 | —O—(CH$_2$)$_m$—N(morpholine) | —N(C(O)N(H)—CH$_2$—CH$_2$—OCH$_3$)— |
| Ia-a205 | 5 | —O—(CH$_2$)$_m$—N(morpholine) | —N(C(O)N(H)—CH$_2$—CH$_2$—OCH$_3$)— |
| Ia-a206 | 6 | —O—(CH$_2$)$_m$—N(morpholine) | —N(C(O)N(H)—CH$_2$—CH$_2$—OCH$_3$)— |
| Ia-a207 | 2 | —O—(CH$_2$)$_m$—N(morpholine) | —N(C(O)N(H)—CH$_2$—CH$_2$—CF$_3$)— |
| Ia-a208 | 3 | —O—(CH$_2$)$_m$—N(morpholine) | —N(C(O)N(H)—CH$_2$—CH$_2$—CF$_3$)— |
| Ia-a209 | 4 | —O—(CH$_2$)$_m$—N(morpholine) | —N(C(O)N(H)—CH$_2$—CH$_2$—CF$_3$)— |
| Ia-a210 | 5 | —O—(CH$_2$)$_m$—N(morpholine) | —N(C(O)N(H)—CH$_2$—CH$_2$—CF$_3$)— |
| Ia-a211 | 6 | —O—(CH$_2$)$_m$—N(morpholine) | —N(C(O)N(H)—CH$_2$—CH$_2$—CF$_3$)— |
| Ia-a212 | 2 | —O—(CH$_2$)$_m$—N(morpholine) | —N(CH$_2$—CH$_2$—OH)— |
| Ia-a213 | 3 | —O—(CH$_2$)$_m$—N(morpholine) | —N(CH$_2$—CH$_2$—OH)— |

-continued

| Compound | | | X |
|---|---|---|---|
| Ia-a214 | 4 | —O—(CH₂)ₘ—N(morpholine) | —N(CH₂—CH₂—OH)— |
| Ia-a215 | 5 | —O—(CH₂)ₘ—N(morpholine) | —N(CH₂—CH₂—OH)— |
| Ia-a216 | 6 | —O—(CH₂)ₘ—N(morpholine) | —N(CH₂—CH₂—OH)— |
| Ia-a217 | 2 | —O—(CH₂)ₘ—N(morpholine) | —N(CH₂—CH₂—F)— |
| Ia-a218 | 3 | —O—(CH₂)ₘ—N(morpholine) | —N(CH₂—CH₂—F)— |
| Ia-a219 | 4 | —O—(CH₂)ₘ—N(morpholine) | —N(CH₂—CH₂—F)— |
| Ia-a220 | 5 | —O—(CH₂)ₘ—N(morpholine) | —N(CH₂—CH₂—F)— |
| Ia-a221 | 6 | —O—(CH₂)ₘ—N(morpholine) | —N(CH₂—CH₂—F)— |
| Ia-a222 | 2 | —O—(CH₂)ₘ—N(morpholine) | —N(CH₂—CH₂—OCH₃)— |
| Ia-a223 | 3 | —O—(CH₂)ₘ—N(morpholine) | —N(CH₂—CH₂—OCH₃)— |
| Ia-a224 | 4 | —O—(CH₂)ₘ—N(morpholine) | —N(CH₂—CH₂—OCH₃)— |
| Ia-a225 | 5 | —O—(CH₂)ₘ—N(morpholine) | —N(CH₂—CH₂—OCH₃)— |
| Ia-a226 | 6 | —O—(CH₂)ₘ—N(morpholine) | —N(CH₂—CH₂—OCH₃)— |

| Compound | —R¹ | X |
|---|---|---|
| Ia-a267 | —CH₂—N(CH₂—CH₃)₂ | —CH(OH)— |
| Ia-a268 | —CH₂—N(CH₂—CH₃)₂ | —N(C(O)N(H)—CH₂—CH₂—OH)— |
| Ia-a269 | —CH₂—N(CH₂—CH₃)₂ | —N(C(O)N(H)—CH₂—CH₂—F)— |
| Ia-a270 | —CH₂—N(CH₂—CH₃)₂ | —N(C(O)N(H)—CH₂—CH₂—OCH₃)— |
| Ia-a271 | —CH₂—N(CH₂—CH₃)₂ | —N(C(O)N(H)—CH₂—CH₂—CF₃)— |
| Ia-a275 | —CH₂—N(CH₂—CH₂—CH₃)₂ | —CH(OH)— |
| Ia-a276 | —CH₂—N(CH₂—CH₂—CH₃)₂ | —N(C(O)N(H)—CH₂—CH₂—OH)— |
| Ia-a277 | —CH₂—N(CH₂—CH₂—CH₃)₂ | —N(C(O)N(H)—CH₂—CH₂—F)— |
| Ia-a278 | —CH₂—N(CH₂—CH₂—CH₃)₂ | —N(C(O)N(H)—CH₂—CH₂—OCH₃)— |
| Ia-a279 | —CH₂—N(CH₂—CH₂—CH₃)₂ | —N(C(O)N(H)—CH₂—CH₂—CF₃)— |
| Ia-a283 | —CH₂—N(CH₂—CH₂OH)₂ | —CH(OH)— |
| Ia-a284 | —CH₂—N(CH₂—CH₂OH)₂ | —N(C(O)N(H)—CH₂—CH₂—OH)— |
| Ia-a285 | —CH₂—N(CH₂—CH₂OH)₂ | —N(C(O)N(H)—CH₂—CH₂—F)— |
| Ia-a286 | —CH₂—N(CH₂—CH₂OH)₂ | —N(C(O)N(H)—CH₂—CH₂—OCH₃)— |

-continued

| | | |
|---|---|---|
| Ia-a291 | —CH$_2$—N(CH$_2$—CH$_2$—N(CH$_3$)$_2$)$_2$ | —CH(OH)— |
| Ia-a292 | —CH$_2$—N(CH$_2$—CH$_2$—N(CH$_3$)$_2$)$_2$ | —N(C(O)N(H)—CH$_2$—CH$_2$—OH)— |
| Ia-a293 | —CH$_2$—N(CH$_2$—CH$_2$—N(CH$_3$)$_2$)$_2$ | —N(C(O)N(H)—CH$_2$—CH$_2$—F)— |
| Ia-a294 | —CH$_2$—N(CH$_2$—CH$_2$—N(CH$_3$)$_2$)$_2$ | —N(C(O)N(H)—CH$_2$—CH$_2$—OCH$_3$)— |
| Ia-a295 | —CH$_2$—N(CH$_2$—CH$_2$—N(CH$_3$)$_2$)$_2$ | —N(C(O)N(H)—CH$_2$—CH$_2$—CF$_3$)— |
| Ia-a296 | —CH$_2$—N(CH$_2$—CH$_2$—N(CH$_3$)$_2$)$_2$ | —N(C(O)N(H)—CH$_2$—CH$_2$—CF$_3$)— |
| Ia-a297 | —CH$_2$—N(CH$_2$—CH$_2$—N(CH$_3$)$_2$)$_2$ | —N(C(O)N(H)—CH$_2$—CF$_3$)— |
| Ia-a298 | —CH$_2$—N(CH$_2$—CH$_2$—N(CH$_3$)$_2$)$_2$ | —N(C(O)N(H)—(CH$_2$)$_3$—OH)— |
| Ia-a299 | —CH$_2$—N(CH$_2$—CH$_2$—CH$_2$—N(CH$_3$)$_2$)$_2$ | —CH(OH)— |
| Ia-a300 | —CH$_2$—N(CH$_2$—CH$_2$—CH$_2$—N(CH$_3$)$_2$)$_2$ | —N(C(O)N(H)—CH$_2$—CH$_2$—OH)— |
| Ia-a301 | —CH$_2$—N(CH$_2$—CH$_2$—CH$_2$—N(CH$_3$)$_2$)$_2$ | —N(C(O)N(H)—CH$_2$—CH$_2$—F)— |
| Ia-a302 | —CH$_2$—N(CH$_2$—CH$_2$—CH$_2$—N(CH$_3$)$_2$)$_2$ | —N(C(O)N(H)—CH$_2$—CH$_2$—OCH$_3$)— |
| Ia-a303 | —CH$_2$—N(CH$_2$—CH$_2$—CH$_2$—N(CH$_3$)$_2$)$_2$ | —N(C(O)N(H)—CH$_2$—CH$_2$—CF$_3$)— |
| Ia-a304 | —CH$_2$—N(CH$_2$—CH$_2$—CH$_2$—N(CH$_3$)$_2$)$_2$ | —N(C(O)N(H)—CH$_2$—CH$_2$—CF$_3$)— |
| Ia-a305 | —CH$_2$—N(CH$_2$—CH$_2$—CH$_2$—N(CH$_3$)$_2$)$_2$ | —N(C(O)N(H)—CH$_2$—CF$_3$)— |
| Ia-a306 | —CH$_2$—N(CH$_2$—CH$_2$—CH$_2$—N(CH$_3$)$_2$)$_2$ | —N(C(O)N(H)—(CH$_2$)$_3$—OH)— |
| Ia-a307 | —CH$_2$—N(aziridinyl) | —CH(OH)— |
| Ia-a308 | —CH$_2$—N(aziridinyl) | —N(C(O)N(H)—CH$_2$—CH$_2$—OH)— |
| Ia-a309 | —CH$_2$—N(aziridinyl) | —N(C(O)N(H)—CH$_2$—CH$_2$—F)— |
| Ia-a310 | —CH$_2$—N(aziridinyl) | —N(C(O)N(H)—CH$_2$—CH$_2$—OCH$_3$)— |
| Ia-a311 | —CH$_2$—N(aziridinyl) | —N(C(O)N(H)—CH$_2$—CH$_2$—CF$_3$)— |
| Ia-a312 | —CH$_2$—N(aziridinyl) | —N(C(O)N(H)—CH$_2$—CH$_2$—CF$_3$)— |
| Ia-a313 | —CH$_2$—N(aziridinyl) | —N(C(O)N(H)—CH$_2$—CF$_3$)— |
| Ia-a314 | —CH$_2$—N(aziridinyl) | —N(C(O)N(H)—(CH$_2$)$_3$—OH)— |
| Ia-a315 | —CH$_2$—N(azetidinyl) | —CH(OH)— |
| Ia-a316 | —CH$_2$—N(azetidinyl) | —N(C(O)N(H)—CH$_2$—CH$_2$—OH)— |
| Ia-a317 | —CH$_2$—N(azetidinyl) | —N(C(O)N(H)—CH$_2$—CH$_2$—F)— |
| Ia-a318 | —CH$_2$—N(azetidinyl) | —N(C(O)N(H)—CH$_2$—CH$_2$—OCH$_3$)— |
| Ia-a319 | —CH$_2$—N(azetidinyl) | —N(C(O)N(H)—CH$_2$—CH$_2$—CF$_3$)— |
| Ia-a320 | —CH$_2$—N(azetidinyl) | —N(C(O)N(H)—CH$_2$—CH$_2$—CF$_3$)— |
| Ia-a321 | —CH$_2$—N(azetidinyl) | —N(C(O)N(H)—CH$_2$—CF$_3$)— |
| Ia-a322 | —CH$_2$—N(azetidinyl) | —N(C(O)N(H)—(CH$_2$)$_3$—OH)— |

|         |                  |                           |
|---------|------------------|---------------------------|
| Ia-a323 | 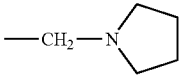 | —CH(OH)— |
| Ia-a324 | 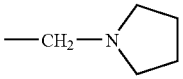 | —N(C(O)N(H)—CH$_2$—CH$_2$—OH)— |
| Ia-a325 | 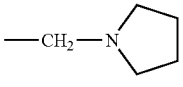 | —N(C(O)N(H)—CH$_2$—CH$_2$—F)— |
| Ia-a326 | 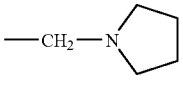 | —N(C(O)N(H)—CH$_2$—CH$_2$—OCH$_3$)— |
| Ia-a327 | 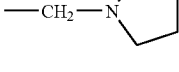 | —N(C(O)N(H)—CH$_2$—CH$_2$—CF$_3$)— |
| Ia-a328 | 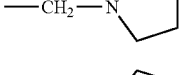 | —N(C(O)N(H)—CH$_2$—CH$_2$—CF$_3$)— |
| Ia-a329 | 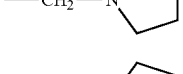 | —N(C(O)N(H)—CH$_2$—CF$_3$)— |
| Ia-a330 | 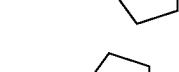 | —N(C(O)N(H)—(CH$_2$)$_3$—OH)— |
| Ia-a331 | 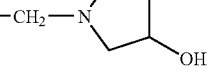 | —CH(OH)— |
| Ia-a332 | 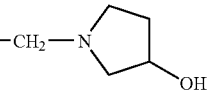 | —N(C(O)N(H)—CH$_2$—CH$_2$—OH)— |
| Ia-a333 | 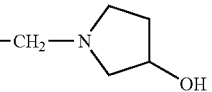 | —N(C(O)N(H)—CH$_2$—CH$_2$—F)— |
| Ia-a334 | 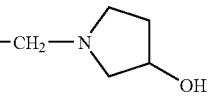 | —N(C(O)N(H)—CH$_2$—CH$_2$—OCH$_3$)— |
| Ia-a335 | 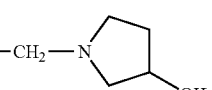 | —N(C(O)N(H)—CH$_2$—CH$_2$—CF$_3$)— |
| Ia-a336 | 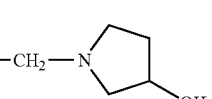 | —N(C(O)N(H)—CH$_2$—CH$_2$—CF$_3$)— |
| Ia-a337 | 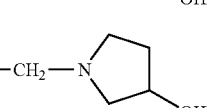 | —N(C(O)N(H)—CH$_2$—CF$_3$)— |
| Ia-a338 | 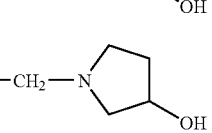 | —N(C(O)N(H)—(CH$_2$)$_3$—OH)— |

-continued
| | | |
|---|---|---|
| Ia-a339 | 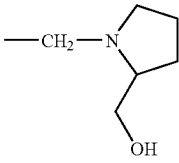 | —CH(OH)— |
| Ia-a340 | 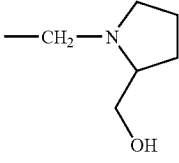 | —N(C(O)N(H)—CH$_2$—CH$_2$—OH)— |
| Ia-a341 | 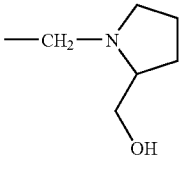 | —N(C(O)N(H)—CH$_2$—CH$_2$—F)— |
| Ia-a342 | 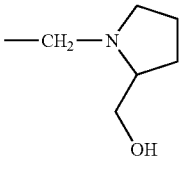 | —N(C(O)N(H)—CH$_2$—CH$_2$—OCH$_3$)— |
| Ia-a343 | 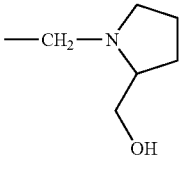 | —N(C(O)N(H)—CH$_2$—CH$_2$—CF$_3$)— |
| Ia-a344 | 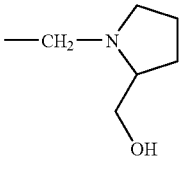 | —N(C(O)N(H)—CH$_2$—CH$_2$—CF$_3$)— |
| Ia-a345 | 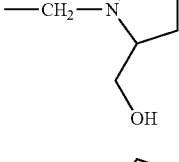 | —N(C(O)N(H)—CH$_2$—CF$_3$)— |
| Ia-a346 | 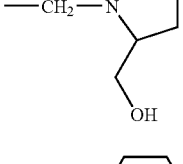 | —N(C(O)N(H)—(CH$_2$)$_3$—OH)— |
| Ia-a347 | 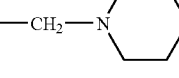 | —CH(OH)— |
| Ia-a348 | 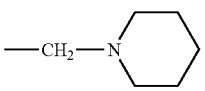 | —N(C(O)N(H)—CH$_2$—CH$_2$—OH)— |

-continued

| | | |
|---|---|---|
| Ia-a349 | 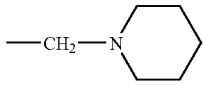 —CH₂—N(piperidine) | —N(C(O)N(H)—CH₂—CH₂—F)— |
| Ia-a350 | —CH₂—N(piperidine) | —N(C(O)N(H)—CH₂—CH₂—OCH₃)— |
| Ia-a351 | —CH₂—N(piperidine) | —N(C(O)N(H)—CH₂—CH₂—CF₃)— |
| Ia-a352 | —CH₂—N(piperidine) | —N(C(O)N(H)—CH₂—CH₂—CF₃)— |
| Ia-a353 | —CH₂—N(piperidine) | —N(C(O)N(H)—CH₂—CF₃)— |
| Ia-a354 | —CH₂—N(piperidine) | —N(C(O)N(H)—(CH₂)₃—OH)— |
| Ia-a355 | —CH₂—N(N-methylpiperazine)—CH₃ | —CH(OH)— |
| Ia-a356 | —CH₂—N(N-methylpiperazine)—CH₃ | —N(C(O)N(H)—CH₂—CH₂—OH)— |
| Ia-a357 | —CH₂—N(N-methylpiperazine)—CH₃ | —N(C(O)N(H)—CH₂—CH₂—F)— |
| Ia-a358 | —CH₂—N(N-methylpiperazine)—CH₃ | —N(C(O)N(H)—CH₂—CH₂—OCH₃)— |
| Ia-a359 | —CH₂—N(N-methylpiperazine)—CH₃ | —N(C(O)N(H)—CH₂—CH₂—CF₃)— |
| Ia-a360 | —CH₂—N(N-methylpiperazine)—CH₃ | —N(C(O)N(H)—CH₂—CH₂—CF₃)— |
| Ia-a361 | —CH₂—N(N-methylpiperazine)—CH₃ | —N(C(O)N(H)—CH₂—CF₃)— |
| Ia-a362 | —CH₂—N(N-methylpiperazine)—CH₃ | —N(C(O)N(H)—(CH₂)₃—OH)— |
| Ia-a363 | —CH₂—N(CH₃)(CH₂-phenyl) | —CH(OH)— |

-continued

| | | |
|---|---|---|
| Ia-a364 | —CH₂—N(CH₃)—CH₂—C₆H₅ | —N(C(O)N(H)—CH₂—CH₂—OH)— |
| Ia-a365 | —CH₂—N(CH₃)—CH₂—C₆H₅ | —N(C(O)N(H)—CH₂—CH₂—F)— |
| Ia-a366 | —CH₂—N(CH₃)—CH₂—C₆H₅ | —N(C(O)N(H)—CH₂—CH₂—OCH₃)— |
| Ia-a367 | —CH₂—N(CH₃)—CH₂—C₆H₅ | —N(C(O)N(H)—CH₂—CH₂—CF₃)— |
| Ia-a368 | —CH₂—N(CH₃)—CH₂—C₆H₅ | —N(C(O)N(H)—CH₂—CH₂—CF₃)— |
| Ia-a369 | —CH₂—N(CH₃)—CH₂—C₆H₅ | —N(C(O)N(H)—CH₂—CF₃)— |
| Ia-a370 | —CH₂—N(CH₃)—CH₂—C₆H₅ | —N(C(O)N(H)—(CH₂)₃—OH)— |
| Ia-a371 | —CH₂—N(CH₃)—CH(CH₃)₂ | —CH(OH)— |
| Ia-a372 | —CH₂—N(CH₃)—CH(CH₃)₂ | —N(C(O)N(H)—CH₂—CH₂—OH)— |
| Ia-a373 | —CH₂—N(CH₃)—CH(CH₃)₂ | —N(C(O)N(H)—CH₂—CH₂—F)— |
| Ia-a374 | —CH₂—N(CH₃)—CH(CH₃)₂ | —N(C(O)N(H)—CH₂—CH₂—OCH₃)— |

-continued
| | | |
|---|---|---|
| Ia-a375 | 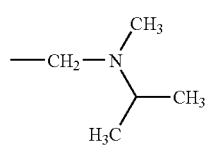 | —N(C(O)N(H)—CH$_2$—CH$_2$—CF$_3$)— |
| Ia-a376 | 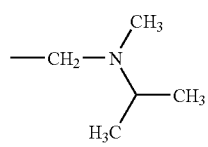 | —N(C(O)N(H)—CH$_2$—CH$_2$—CF$_3$)— |
| Ia-a377 | 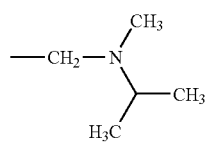 | —N(C(O)N(H)—CH$_2$—CF$_3$)— |
| Ia-a378 | 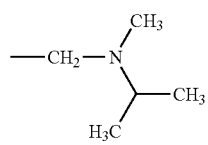 | —N(C(O)N(H)—(CH$_2$)$_3$—OH)— |
| Ia-a379 | 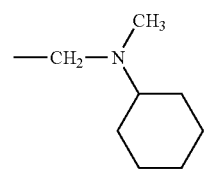 | —CH(OH)— |
| Ia-a380 | 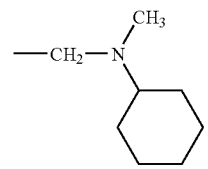 | —N(C(O)N(H)—CH$_2$—CH$_2$—OH)— |
| Ia-a381 | 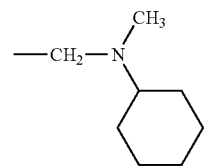 | —N(C(O)N(H)—CH$_2$—CH$_2$—F)— |
| Ia-a382 | 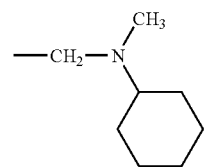 | —N(C(O)N(H)—CH$_2$—CH$_2$—OCH$_3$)— |
| Ia-a383 | 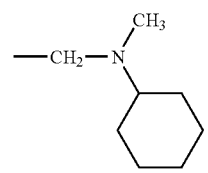 | —N(C(O)N(H)—CH$_2$—CH$_2$—CF$_3$)— |

| | | -continued |
|---|---|---|
| Ia-a384 |  —CH₂—N(CH₃)—cyclohexyl | —N(C(O)N(H)—CH₂—CH₂—CF₃)— |
| Ia-a385 |  —CH₂—N(CH₃)—cyclohexyl | —N(C(O)N(H)—CH₂—CF₃)— |
| Ia-a386 |  —CH₂—N(CH₃)—cyclohexyl | —N(C(O)N(H)—(CH₂)₃—OH)— |
| Ia-a387 |  —CH₂—NH—CH₂CH₂-morpholine | —CH(OH)— |
| Ia-a388 |  —CH₂—NH—CH₂CH₂-morpholine | —N(C(O)N(H)—CH₂—CH₂—OH)— |
| Ia-a389 |  —CH₂—NH—CH₂CH₂-morpholine | —N(C(O)N(H)—CH₂—CH₂—F)— |
| Ia-a390 |  —CH₂—NH—CH₂CH₂-morpholine | —N(C(O)N(H)—CH₂—CH₂—OCH₃)— |
| Ia-a391 |  —CH₂—NH—CH₂CH₂-morpholine | —N(C(O)N(H)—CH₂—CH₂—CF₃)— |
| Ia-a392 |  —CH₂—NH—CH₂CH₂-morpholine | —N(C(O)N(H)—CH₂—CH₂—CF₃)— |
| Ia-a393 |  —CH₂—NH—CH₂CH₂-morpholine | —N(C(O)N(H)—CH₂—CF₃)— |
| Ia-a394 |  —CH₂—NH—CH₂CH₂-morpholine | —N(C(O)N(H)—(CH₂)₃—OH)— |
| Ia-a395 |  —CH₂—NH—CH₂CH₂CH₂-morpholine | —CH(OH)— |

-continued
| | | |
|---|---|---|
| Ia-a396 |  | —N(C(O)N(H)—CH₂—CH₂—OH)— |
| Ia-a397 | 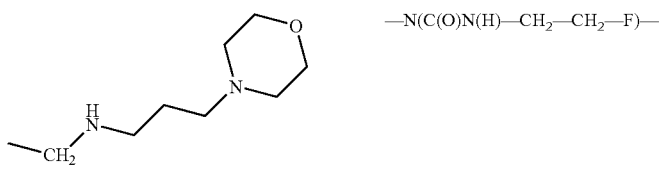 | —N(C(O)N(H)—CH₂—CH₂—F)— |
| Ia-a398 | 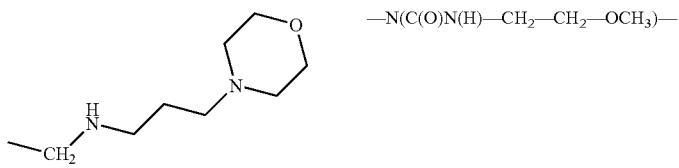 | —N(C(O)N(H)—CH₂—CH₂—OCH₃)— |
| Ia-a399 |  | —N(C(O)N(H)—CH₂—CH₂—CF₃)— |
| Ia-a400 | 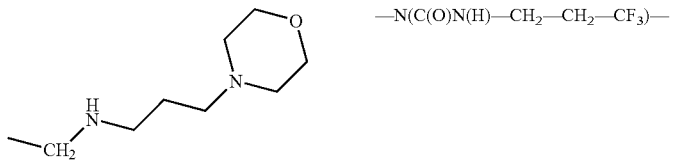 | —N(C(O)N(H)—CH₂—CH₂—CF₃)— |
| Ia-a401 | 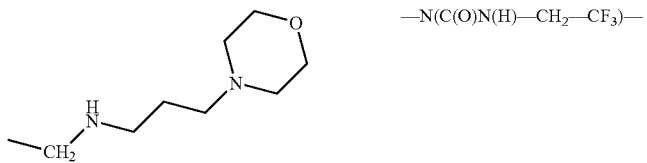 | —N(C(O)N(H)—CH₂—CF₃)— |
| Ia-a402 | 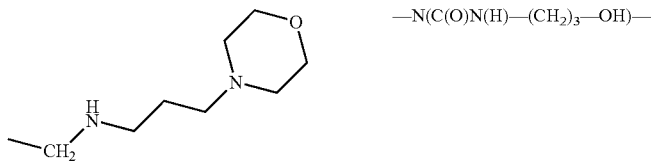 | —N(C(O)N(H)—(CH₂)₃—OH)— |
| Ia-a403 | 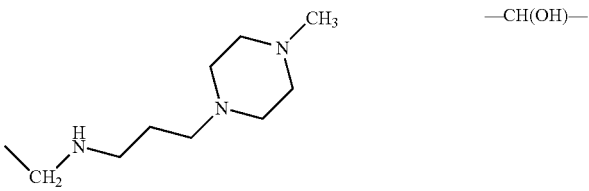 | —CH(OH)— |
| Ia-a404 | 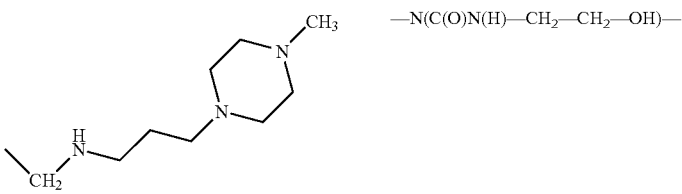 | —N(C(O)N(H)—CH₂—CH₂—OH)— |

-continued
| | | |
|---|---|---|
| Ia-a405 | 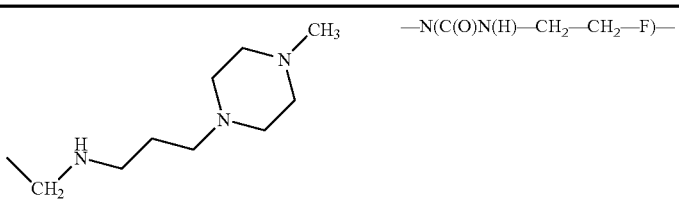 | —N(C(O)N(H)—CH$_2$—CH$_2$—F)— |
| Ia-a406 | 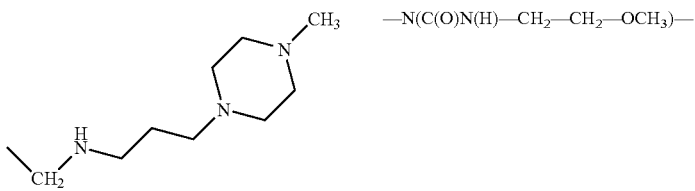 | —N(C(O)N(H)—CH$_2$—CH$_2$—OCH$_3$)— |
| Ia-a407 | 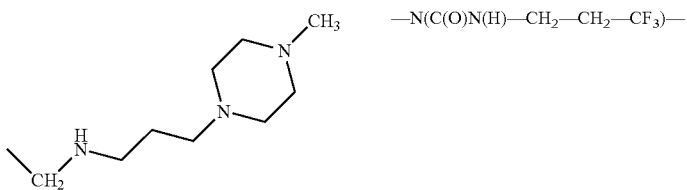 | —N(C(O)N(H)—CH$_2$—CH$_2$—CF$_3$)— |
| Ia-a408 |  | —N(C(O)N(H)—CH$_2$—CH$_2$—CF$_3$)— |
| Ia-a409 | 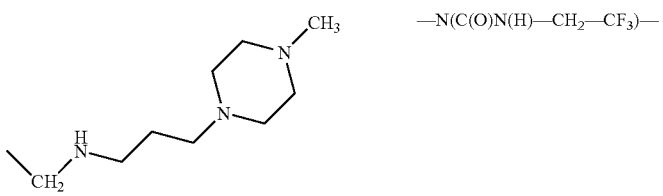 | —N(C(O)N(H)—CH$_2$—CF$_3$)— |
| Ia-a410 | 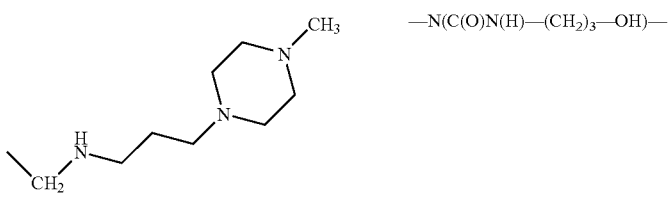 | —N(C(O)N(H)—(CH$_2$)$_3$—OH)— |
| Ia-a411 | 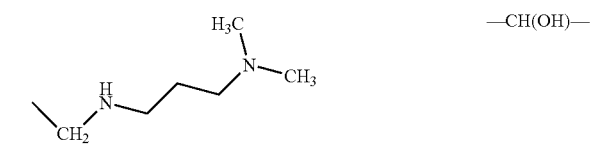 | —CH(OH)— |
| Ia-a412 | 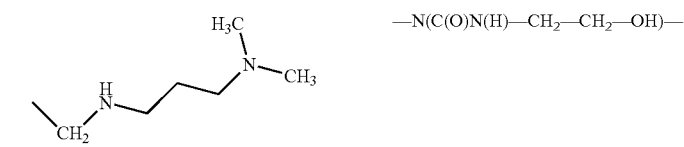 | —N(C(O)N(H)—CH$_2$—CH$_2$—OH)— |
| Ia-a413 | 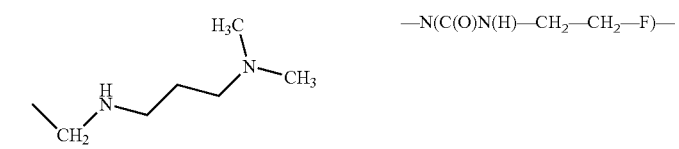 | —N(C(O)N(H)—CH$_2$—CH$_2$—F)— |

-continued
Ia-a414 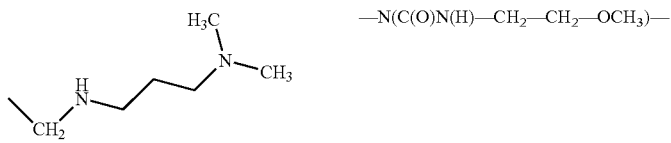 —N(C(O)N(H)—CH₂—CH₂—OCH₃)—
Ia-a415 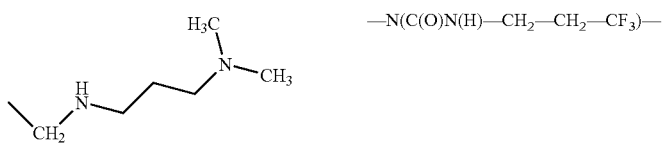 —N(C(O)N(H)—CH₂—CH₂—CF₃)—
Ia-a416 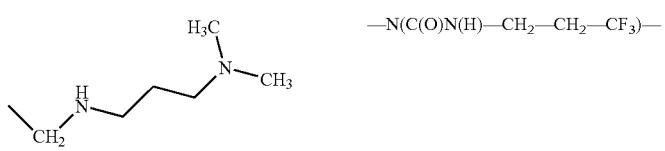 —N(C(O)N(H)—CH₂—CH₂—CF₃)—
Ia-a417 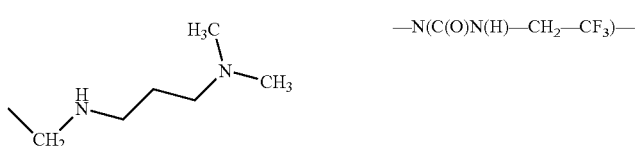 —N(C(O)N(H)—CH₂—CF₃)—
Ia-a418 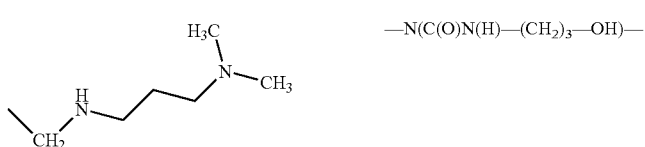 —N(C(O)N(H)—(CH₂)₃—OH)—
Ia-a419 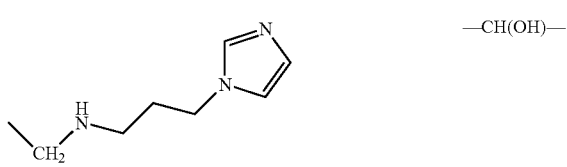 —CH(OH)—
Ia-a420 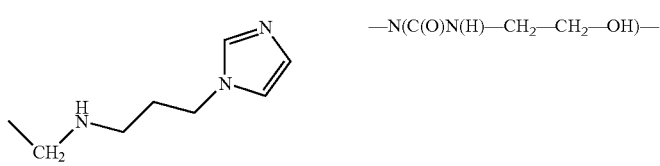 —N(C(O)N(H)—CH₂—CH₂—OH)—
Ia-a421 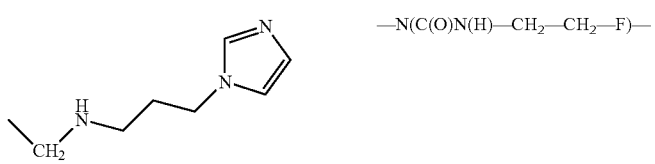 —N(C(O)N(H)—CH₂—CH₂—F)—
Ia-a422 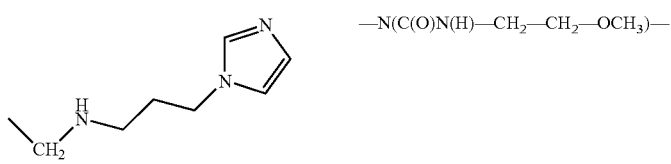 —N(C(O)N(H)—CH₂—CH₂—OCH₃)—
Ia-a423 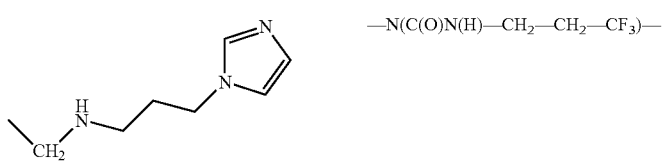 —N(C(O)N(H)—CH₂—CH₂—CF₃)—

-continued
| | | |
|---|---|---|
| Ia-a424 | | —N(C(O)N(H)—CH₂—CH₂—CF₃)— |
| Ia-a425 | | —N(C(O)N(H)—CH₂—CF₃)— |
| Ia-a426 | | —N(C(O)N(H)—(CH₂)₃—OH)— |
| Ia-a427 | | —CH(OH)— |
| Ia-a428 | | —N(C(O)N(H)—CH₂—CH₂—OH)— |
| Ia-a429 | | —N(C(O)N(H)—CH₂—CH₂—F)— |
| Ia-a430 | | —N(C(O)N(H)—CH₂—CH₂—OCH₃)— |
| Ia-a431 | | —N(C(O)N(H)—CH₂—CH₂—CF₃)— |
| Ia-a432 | | —N(C(O)N(H)—CH₂—CH₂—CF₃)— |
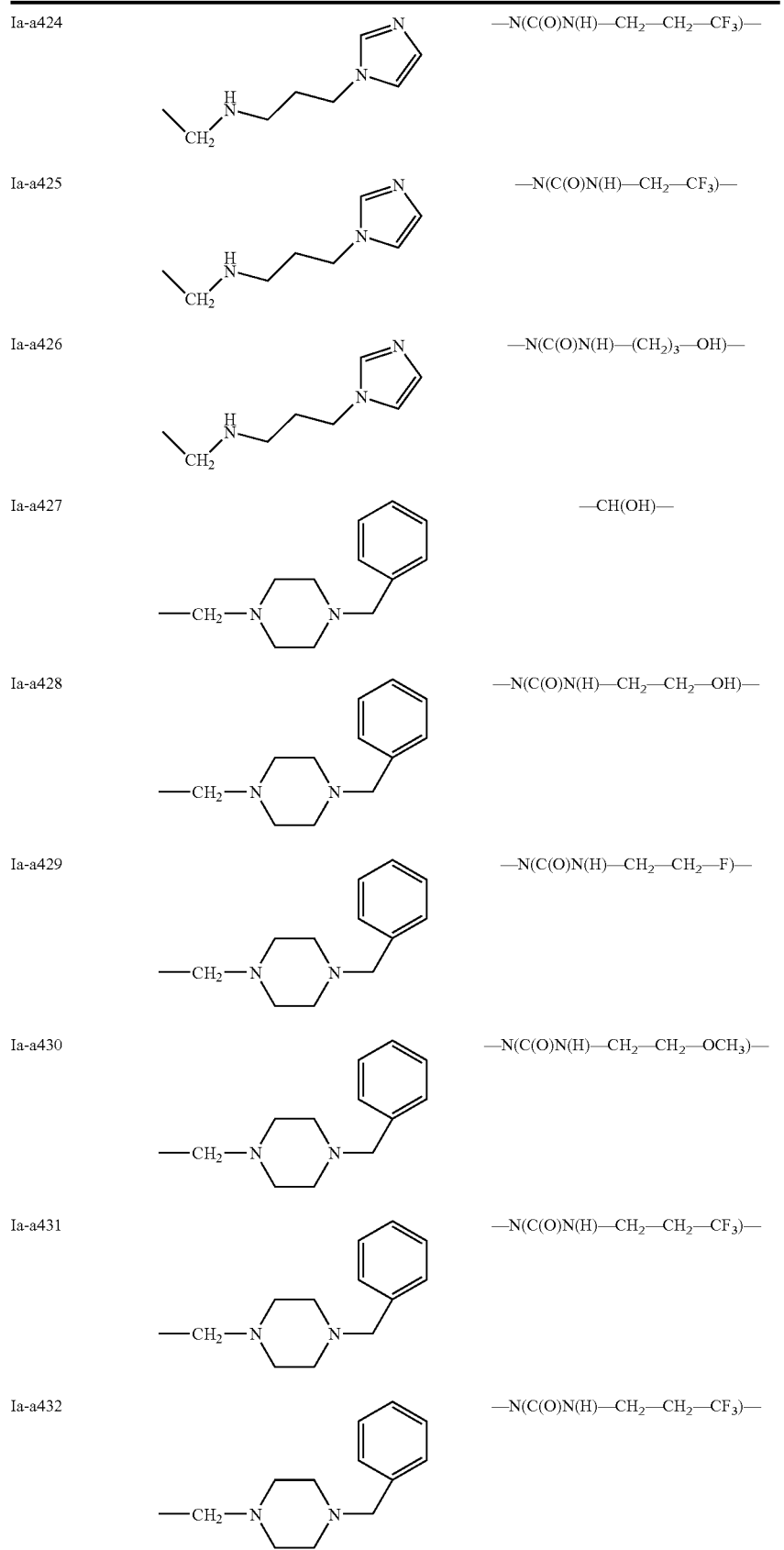

-continued

| | | |
|---|---|---|
| Ia-a433 | —CH₂—N(piperazine)N—CH₂—C₆H₅ (benzyl) | —N(C(O)N(H)—CH₂—CF₃)— |
| Ia-a434 | —CH₂—N(piperazine)N—CH₂—C₆H₅ (benzyl) | —N(C(O)N(H)—(CH₂)₃—OH)— |
| Ia-a435 | —CH₂—N(piperazine)N—C₆H₄—F (4-F) | —CH(OH)— |
| Ia-a436 | —CH₂—N(piperazine)N—C₆H₄—F (4-F) | —N(C(O)N(H)—CH₂—CH₂—OH)— |
| Ia-a437 | —CH₂—N(piperazine)N—C₆H₄—F (4-F) | —N(C(O)N(H)—CH₂—CH₂—F)— |
| Ia-a438 | —CH₂—N(piperazine)N—C₆H₄—F (4-F) | —N(C(O)N(H)—CH₂—CH₂—OCH₃)— |
| Ia-a439 | —CH₂—N(piperazine)N—C₆H₄—F (4-F) | —N(C(O)N(H)—CH₂—CH₂—CF₃)— |
| Ia-a440 | —CH₂—N(piperazine)N—C₆H₄—F (4-F) | —N(C(O)N(H)—CH₂—CH₂—CF₃)— |
| Ia-a441 | —CH₂—N(piperazine)N—C₆H₄—F (4-F) | —N(C(O)N(H)—CH₂—CF₃)— |
| Ia-a442 | —CH₂—N(piperazine)N—C₆H₄—F (4-F) | —N(C(O)N(H)—(CH₂)₃—OH)— |
| Ia-a443 | —CH₂—N(tetrahydropyridine)—C₆H₄—F (4-F) | —CH(OH)— |
| Ia-a444 | —CH₂—N(tetrahydropyridine)—C₆H₄—F (4-F) | —N(C(O)N(H)—CH₂—CH₂—OH)— |
| Ia-a445 | —CH₂—N(tetrahydropyridine)—C₆H₄—F (4-F) | —N(C(O)N(H)—CH₂—CH₂—F)— |
| Ia-a446 | —CH₂—N(tetrahydropyridine)—C₆H₄—F (4-F) | —N(C(O)N(H)—CH₂—CH₂—OCH₃)— |

-continued
| | | |
|---|---|---|
| Ia-a447 | 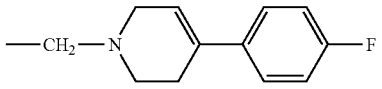 | —N(C(O)N(H)—CH₂—CH₂—CF₃)— |
| Ia-a448 | 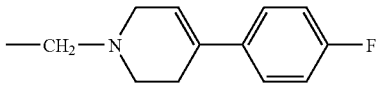 | —N(C(O)N(H)—CH₂—CH₂—CF₃)— |
| Ia-a449 | 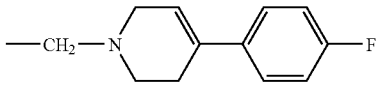 | —N(C(O)N(H)—CH₂—CF₃)— |
| Ia-a450 | 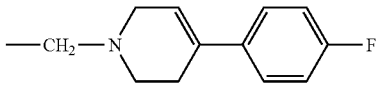 | —N(C(O)N(H)—(CH₂)₃—OH)— |
| Ia-a451 | 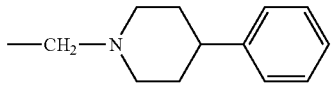 | —CH(OH)— |
| Ia-a452 | 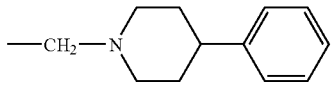 | —N(C(O)N(H)—CH₂—CH₂—OH)— |
| Ia-a453 | 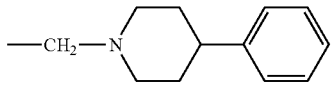 | —N(C(O)N(H)—CH₂—CH₂—F)— |
| Ia-a454 | 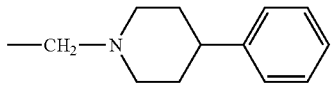 | —N(C(O)N(H)—CH₂—CH₂—OCH₃)— |
| Ia-a455 | 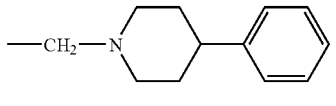 | —N(C(O)N(H)—CH₂—CH₂—CF₃)— |
| Ia-a456 | 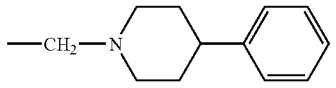 | —N(C(O)N(H)—CH₂—CH₂—CF₃)— |
| Ia-a457 | 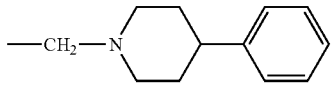 | —N(C(O)N(H)—CH₂—CF₃)— |
| Ia-a458 | 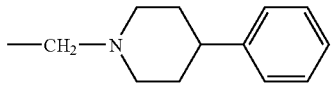 | —N(C(O)N(H)—(CH₂)₃—OH)— |
| Ia-a459 | 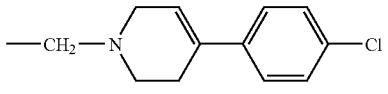 | —CH(OH)— |
| Ia-a460 | 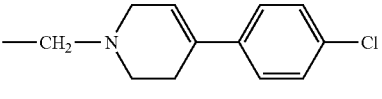 | —N(C(O)N(H)—CH₂—CH₂—OH)— |
| Ia-a461 | 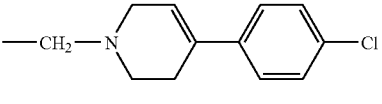 | —N(C(O)N(H)—CH₂—CH₂—F)— |
| Ia-a462 | 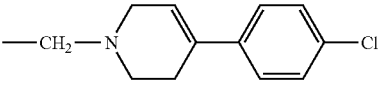 | —N(C(O)N(H)—CH₂—CH₂—OCH₃)— |

-continued
| | | |
|---|---|---|
| Ia-a463 | 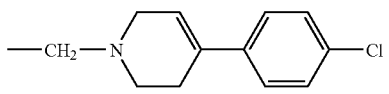 | —N(C(O)N(H)—CH$_2$—CH$_2$—CF$_3$)— |
| Ia-a464 | 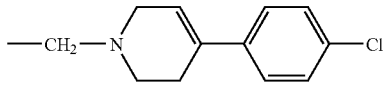 | —N(C(O)N(H)—CH$_2$—CH$_2$—CF$_3$)— |
| Ia-a465 | 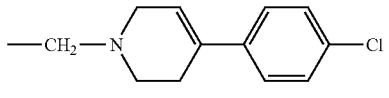 | —N(C(O)N(H)—CH$_2$—CF$_3$)— |
| Ia-a466 | 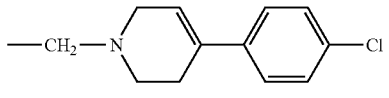 | —N(C(O)N(H)—(CH$_2$)$_3$—OH)— |
| Ia-a467 | 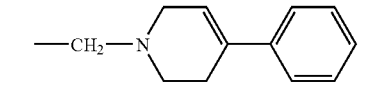 | —CH(OH)— |
| Ia-a468 | 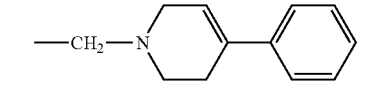 | —N(C(O)N(H)—CH$_2$—CH$_2$—OH)— |
| Ia-a469 | 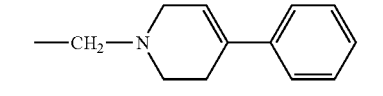 | —N(C(O)N(H)—CH$_2$—CH$_2$—F)— |
| Ia-a470 | 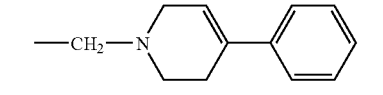 | —N(C(O)N(H)—CH$_2$—CH$_2$—OCH$_3$)— |
| Ia-a471 | 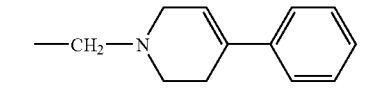 | —N(C(O)N(H)—CH$_2$—CH$_2$—CF$_3$)— |
| Ia-a472 | 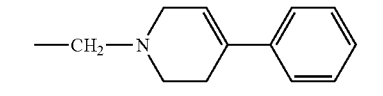 | —N(C(O)N(H)—CH$_2$—CH$_2$—CF$_3$)— |
| Ia-a473 | 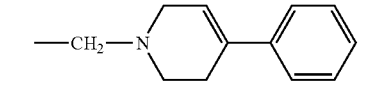 | —N(C(O)N(H)—CH$_2$—CF$_3$)— |
| Ia-a474 | 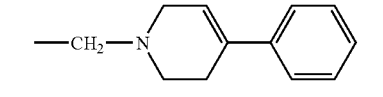 | —N(C(O)N(H)—(CH$_2$)$_3$—OH)— |
| Ia-a475 | 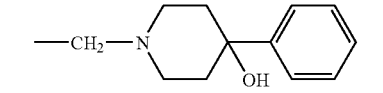 | —CH(OH)— |
| Ia-a476 | 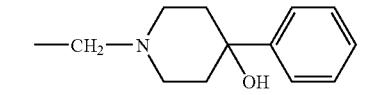 | —N(C(O)N(H)—CH$_2$—CH$_2$—OH)— |
| Ia-a477 | 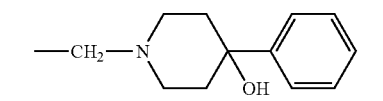 | —N(C(O)N(H)—CH$_2$—CH$_2$—F)— |
| Ia-a478 | 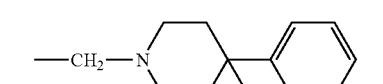 | —N(C(O)N(H)—CH$_2$—CH$_2$—OCH$_3$)— |

-continued

| | | |
|---|---|---|
| Ia-a479 | —CH₂—N(piperidine-4-OH,4-phenyl) | —N(C(O)N(H)—CH₂—CH₂—CF₃)— |
| Ia-a480 | —CH₂—N(piperidine-4-OH,4-phenyl) | —N(C(O)N(H)—CH₂—CH₂—CF₃)— |
| Ia-a481 | —CH₂—N(piperidine-4-OH,4-phenyl) | —N(C(O)N(H)—CH₂—CF₃)— |
| Ia-a482 | —CH₂—N(piperidine-4-OH,4-phenyl) | —N(C(O)N(H)—(CH₂)₃—OH)— |
| Ia-a483 | —CH₂—N(piperazine-NCH₂CH₂OP(O)(OH)₂) | —CH(OH)— |
| Ia-a484 | —CH₂—N(piperazine-NCH₂CH₂OP(O)(OH)₂) | —N(C(O)N(H)—CH₂—CH₂—OH)— |
| Ia-a485 | —CH₂—N(piperazine-NCH₂CH₂OP(O)(OH)₂) | —N(C(O)N(H)—CH₂—CH₂—F)— |
| Ia-a486 | —CH₂—N(piperazine-NCH₂CH₂OP(O)(OH)₂) | —N(C(O)N(H)—CH₂—CH₂—OCH₃)— |
| Ia-a487 | —CH₂—N(piperazine-NCH₂CH₂OP(O)(OH)₂) | —N(C(O)N(H)—CH₂—CH₂—CF₃)— |
| Ia-a488 | —CH₂—N(piperazine-NCH₂CH₂OP(O)(OH)₂) | —N(C(O)N(H)—CH₂—CH₂—CF₃)— |
| Ia-a489 | —CH₂—N(piperazine-NCH₂CH₂OP(O)(OH)₂) | —N(C(O)N(H)—CH₂—CF₃)— |
| Ia-a490 | —CH₂—N(piperazine-NCH₂CH₂OP(O)(OH)₂) | —N(C(O)N(H)—(CH₂)₃—OH)— |
| Ia-a491 | —CH₂—CH₂—CH₂—OP(O)(OH)₂ | —CH(OH)— |
| Ia-a492 | —CH₂—CH₂—CH₂—OP(O)(OH)₂ | —N(C(O)N(H)—CH₂—CH₂—OH)— |
| Ia-a493 | —CH₂—CH₂—CH₂—OP(O)(OH)₂ | —N(C(O)N(H)—CH₂—CH₂—F)— |
| Ia-a494 | —CH₂—CH₂—CH₂—OP(O)(OH)₂ | —N(C(O)N(H)—CH₂—CH₂—OCH₃)— |
| Ia-a495 | —CH₂—CH₂—CH₂—OP(O)(OH)₂ | —N(C(O)N(H)—CH₂—CH₂—CF₃)— |
| Ia-a496 | —CH₂—CH₂—CH₂—OP(O)(OH)₂ | —N(C(O)N(H)—CH₂—CH₂—CF₃)— |
| Ia-a497 | —CH₂—CH₂—CH₂—OP(O)(OH)₂ | —N(C(O)N(H)—CH₂—CF₃)— |
| Ia-a498 | —CH₂—CH₂—CH₂—OP(O)(OH)₂ | —N(C(O)N(H)—(CH₂)₃—OH)— |
| Ia-a499 | —CH₂—CH₂—CH₂—OS(O)₂OH | —CH(OH)— |
| Ia-a500 | —CH₂—CH₂—CH₂—OS(O)₂OH | —N(C(O)N(H)—CH₂—CH₂—OH)— |
| Ia-a501 | —CH₂—CH₂—CH₂—OS(O)₂OH | —N(C(O)N(H)—CH₂—CH₂—F)— |
| Ia-a502 | —CH₂—CH₂—CH₂—OS(O)₂OH | —N(C(O)N(H)—CH₂—CH₂—OCH₃)— |
| Ia-a503 | —CH₂—CH₂—CH₂—OS(O)₂OH | —N(C(O)N(H)—CH₂—CH₂—CF₃)— |
| Ia-a504 | —CH₂—CH₂—CH₂—OS(O)₂OH | —N(C(O)N(H)—CH₂—CH₂—CF₃)— |
| Ia-a505 | —CH₂—CH₂—CH₂—OS(O)₂OH | —N(C(O)N(H)—CH₂—CF₃)— |
| Ia-a506 | —CH₂—CH₂—CH₂—OS(O)₂OH | —N(C(O)N(H)—(CH₂)₃—OH)— |

| | | -continued |
|---|---|---|
| Ia-a507 | —CH₂—N⟨pyrrolidine-3-OP(O)(OH)₂⟩ | —CH(OH)— |
| Ia-a508 | —CH₂—N⟨pyrrolidine-3-OP(O)(OH)₂⟩ | —N(C(O)N(H)—CH₂—CH₂—OH)— |
| Ia-a509 | —CH₂—N⟨pyrrolidine-3-OP(O)(OH)₂⟩ | —N(C(O)N(H)—CH₂—CH₂—F)— |
| Ia-a510 | —CH₂—N⟨pyrrolidine-3-OP(O)(OH)₂⟩ | —N(C(O)N(H)—CH₂—CH₂—OCH₃)— |
| Ia-a511 | —CH₂—N⟨pyrrolidine-3-OP(O)(OH)₂⟩ | —N(C(O)N(H)—CH₂—CH₂—CF₃)— |
| Ia-a512 | —CH₂—N⟨pyrrolidine-3-OP(O)(OH)₂⟩ | —N(C(O)N(H)—CH₂—CH₂—CF₃)— |
| Ia-a513 | —CH₂—N⟨pyrrolidine-3-OP(O)(OH)₂⟩ | —N(C(O)N(H)—CH₂—CF₃)— |
| Ia-a514 | —CH₂—N⟨pyrrolidine-3-OP(O)(OH)₂⟩ | —N(C(O)N(H)—(CH₂)₃—OH)— |
| Ia-a515 | —CH₂—N⟨pyrrolidine-2-CH₂-OP(O)(OH)₂⟩ | —CH(OH)— |
| Ia-a516 | —CH₂—N⟨pyrrolidine-2-CH₂-OP(O)(OH)₂⟩ | —N(C(O)N(H)—CH₂—CH₂—OH)— |
| Ia-a517 | —CH₂—N⟨pyrrolidine-2-CH₂-OP(O)(OH)₂⟩ | —N(C(O)N(H)—CH₂—CH₂—F)— |
| Ia-a518 | —CH₂—N⟨pyrrolidine-2-CH₂-OP(O)(OH)₂⟩ | —N(C(O)N(H)—CH₂—CH₂—OCH₃)— |

-continued

| ID | R group 1 | R group 2 |
|---|---|---|
| Ia-a519 | —CH$_2$—(N-pyrrolidinyl-2-yl with CH$_2$OP(O)(OH)$_2$) | —N(C(O)N(H)—CH$_2$—CH$_2$—CF$_3$)— |
| Ia-a520 | —CH$_2$—(N-pyrrolidinyl-2-yl with CH$_2$OP(O)(OH)$_2$) | —N(C(O)N(H)—CH$_2$—CH$_2$—CF$_3$)— |
| Ia-a521 | —CH$_2$—(N-pyrrolidinyl-2-yl with CH$_2$OP(O)(OH)$_2$) | —N(C(O)N(H)—CH$_2$—CF$_3$)— |
| Ia-a522 | —CH$_2$—(N-pyrrolidinyl-2-yl with CH$_2$OP(O)(OH)$_2$) | —N(C(O)N(H)—(CH$_2$)$_3$—OH)— |
| Ia-a523 | —(CH$_2$)$_{10}$—N(CH$_2$—CH$_2$—O—CH$_3$)$_2$ | —CH(OH)— |
| Ia-a524 | —(CH$_2$)$_{10}$—N(CH$_2$—CH$_2$—O—CH$_3$)$_2$ | —N(C(O)N(H)—CH$_2$—CH$_2$—OH)— |
| Ia-a525 | —(CH$_2$)$_{10}$—N(CH$_2$—CH$_2$—O—CH$_3$)$_2$ | —N(C(O)N(H)—CH$_2$—CH$_2$—F)— |
| Ia-a526 | —(CH$_2$)$_{10}$—N(CH$_2$—CH$_2$—O—CH$_3$)$_2$ | —N(C(O)N(H)—CH$_2$—CH$_2$—OCH$_3$)— |
| Ia-a527 | —(CH$_2$)$_{10}$—N(CH$_2$—CH$_2$—O—CH$_3$)$_2$ | —N(C(O)N(H)—CH$_2$—CH$_2$—CF$_3$)— |
| Ia-a528 | —(CH$_2$)$_{10}$—N(CH$_2$—CH$_2$—O—CH$_3$)$_2$ | —N(C(O)N(H)—CH$_2$—CH$_2$—CF$_3$)— |
| Ia-a529 | —(CH$_2$)$_{10}$—N(CH$_2$—CH$_2$—O—CH$_3$)$_2$ | —N(C(O)N(H)—CH$_2$—CF$_3$)— |
| Ia-a530 | —(CH$_2$)$_{10}$—N(CH$_2$—CH$_2$—O—CH$_3$)$_2$ | —N(C(O)N(H)—(CH$_2$)$_3$—OH)— |
| Ia-a531 | —CH$_2$—N(CH$_2$—CH$_2$—O—CH$_3$)$_2$ | —CH(OH)— |
| Ia-a532 | —CH$_2$—N(CH$_2$—CH$_2$—O—CH$_3$)$_2$ | —N(C(O)N(H)—CH$_2$—CH$_2$—OH)— |
| Ia-a533 | —CH$_2$—N(CH$_2$—CH$_2$—O—CH$_3$)$_2$ | —N(C(O)N(H)—CH$_2$—CH$_2$—F)— |
| Ia-a534 | —CH$_2$—N(CH$_2$—CH$_2$—O—CH$_3$)$_2$ | —N(C(O)N(H)—CH$_2$—CH$_2$—OCH$_3$)— |
| Ia-a535 | —CH$_2$—N(CH$_2$—CH$_2$—O—CH$_3$)$_2$ | —N(C(O)N(H)—CH$_2$—CH$_2$—CF$_3$)— |
| Ia-a536 | —CH$_2$—N(CH$_2$—CH$_2$—O—CH$_3$)$_2$ | —N(C(O)N(H)—CH$_2$—CH$_2$—CF$_3$)— |
| Ia-a537 | —CH$_2$—N(CH$_2$—CH$_2$—O—CH$_3$)$_2$ | —N(C(O)N(H)—CH$_2$—CF$_3$)— |
| Ia-a538 | —CH$_2$—N(CH$_2$—CH$_2$—O—CH$_3$)$_2$ | —N(C(O)N(H)—(CH$_2$)$_3$—OH)— |
| Ia-a539 | N-ethylpyrrolyl | —CH(OH)— |
| Ia-a540 | N-ethylpyrrolyl | —N(C(O)N(H)—CH$_2$—CH$_2$—OH)— |
| Ia-a541 | N-ethylpyrrolyl | —N(C(O)N(H)—CH$_2$—CH$_2$—F)— |
| Ia-a542 | N-ethylpyrrolyl | —N(C(O)N(H)—CH$_2$—CH$_2$—OCH$_3$)— |
| Ia-a543 | N-ethylpyrrolyl | —N(C(O)N(H)—CH$_2$—CH$_2$—CF$_3$)— |
| Ia-a544 | N-ethylpyrrolyl | —N(C(O)N(H)—CH$_2$—CH$_2$—CF$_3$)— |

-continued
| | | |
|---|---|---|
| Ia-a545 | 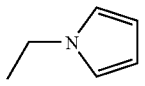 | —N(C(O)N(H)—CH₂—CF₃)— |
| Ia-a546 | 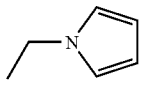 | —N(C(O)N(H)—(CH₂)₃—OH)— |
| Ia-a547 | 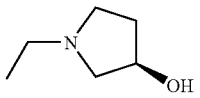 | —CH(OH)— |
| Ia-a548 | 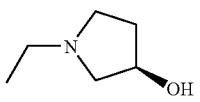 | —N(C(O)N(H)—CH₂—CH₂—OH)— |
| Ia-a549 | 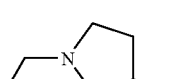 | —N(C(O)N(H)—CH₂—CH₂—F)— |
| Ia-a550 |  | —N(C(O)N(H)—CH₂—CH₂—OCH₃)— |
| Ia-a551 |  | —N(C(O)N(H)—CH₂—CH₂—CF₃)— |
| Ia-a552 |  | —N(C(O)N(H)—CH₂—CH₂—CF₃)— |
| Ia-a553 | 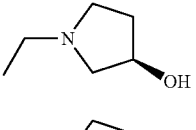 | —N(C(O)N(H)—CH₂—CF₃)— |
| Ia-a554 | 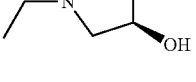 | —N(C(O)N(H)—(CH₂)₃—OH)— |
| Ia-a555 | 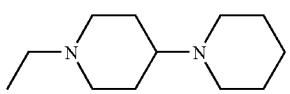 | —CH(OH)— |
| Ia-a556 | 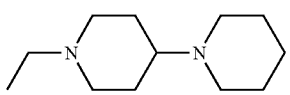 | —N(C(O)N(H)—CH₂—CH₂—OH)— |
| Ia-a557 | 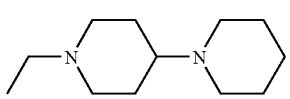 | —N(C(O)N(H)—CH₂—CH₂—F)— |
| Ia-a558 | 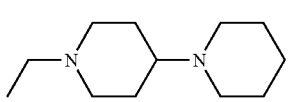 | —N(C(O)N(H)—CH₂—CH₂—OCH₃)— |
| Ia-a559 | 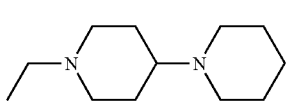 | —N(C(O)N(H)—CH₂—CH₂—CF₃)— |

| | | |
|---|---|---|
| Ia-a560 | [1-ethylpiperidin-4-yl-piperidine] | —N(C(O)N(H)—CH₂—CH₂—CF₃)— |
| Ia-a561 | [1-ethylpiperidin-4-yl-piperidine] | —N(C(O)N(H)—CH₂—CF₃)— |
| Ia-a562 | [1-ethylpiperidin-4-yl-piperidine] | —N(C(O)N(H)—(CH₂)₃—OH)— |
| Ia-a563 | [1-ethylpiperidin-4-yl-pyrrolidine] | —CH(OH)— |
| Ia-a564 | [1-ethylpiperidin-4-yl-pyrrolidine] | —N(C(O)N(H)—CH₂—CH₂—OH)— |
| Ia-a565 | [1-ethylpiperidin-4-yl-pyrrolidine] | —N(C(O)N(H)—CH₂—CH₂—F)— |
| Ia-a566 | [1-ethylpiperidin-4-yl-pyrrolidine] | —N(C(O)N(H)—CH₂—CH₂—OCH₃)— |
| Ia-a567 | [1-ethylpiperidin-4-yl-pyrrolidine] | —N(C(O)N(H)—CH₂—CH₂—CF₃)— |
| Ia-a568 | [1-ethylpiperidin-4-yl-pyrrolidine] | —N(C(O)N(H)—CH₂—CH₂—CF₃)— |
| Ia-a569 | [1-ethylpiperidin-4-yl-pyrrolidine] | —N(C(O)N(H)—CH₂—CF₃)— |
| Ia-a570 | [1-ethylpiperidin-4-yl-pyrrolidine] | —N(C(O)N(H)—(CH₂)₃—OH)— |
| Ia-a571 | [1-ethyl-2-(hydroxymethyl)pyrrolidine] | —CH(OH)— |
| Ia-a572 | [1-ethyl-2-(hydroxymethyl)pyrrolidine] | —N(C(O)N(H)—CH₂—CH₂—OH)— |
| Ia-a573 | [1-ethyl-2-(hydroxymethyl)pyrrolidine] | —N(C(O)N(H)—CH₂—CH₂—F)— |
| Ia-a574 | [1-ethyl-2-(hydroxymethyl)pyrrolidine] | —N(C(O)N(H)—CH₂—CH₂—OCH₃)— |

-continued
| | | |
|---|---|---|
| Ia-a575 |  | —N(C(O)N(H)—CH₂—CH₂—CF₃)— |
| Ia-a576 | 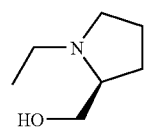 | —N(C(O)N(H)—CH₂—CH₂—CF₃)— |
| Ia-a577 |  | —N(C(O)N(H)—CH₂—CF₃)— |
| Ia-a578 | 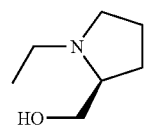 | —N(C(O)N(H)—(CH₂)₃—OH)— |
| Ia-a579 | 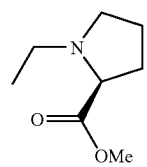 | —CH(OH)— |
| Ia-a580 | 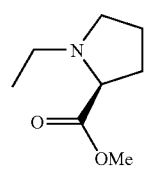 | —N(C(O)N(H)—CH₂—CH₂—OH)— |
| Ia-a581 | 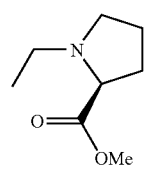 | —N(C(O)N(H)—CH₂—CH₂—F)— |
| Ia-a582 | 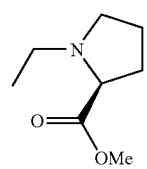 | —N(C(O)N(H)—CH₂—CH₂—OCH₃)— |
| Ia-a583 | 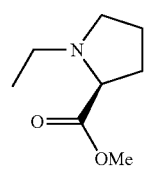 | —N(C(O)N(H)—CH₂—CH₂—CF₃)— |
| Ia-a584 | 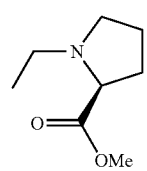 | —N(C(O)N(H)—CH₂—CH₂—CF₃)— |

-continued

| | | |
|---|---|---|
| Ia-a585 | 1-ethylpyrrolidine-2-carboxylic acid methyl ester | —N(C(O)N(H)—CH$_2$—CF$_3$)— |
| Ia-a586 | 1-ethylpyrrolidine-2-carboxylic acid methyl ester | —N(C(O)N(H)—(CH$_2$)$_3$—OH)— |
| Ia-a587 | 2-ethyl-1,2,3,4-tetrahydroisoquinoline | —CH(OH)— |
| Ia-a588 | 2-ethyl-1,2,3,4-tetrahydroisoquinoline | —N(C(O)N(H)—CH$_2$—CH$_2$—OH)— |
| Ia-a589 | 2-ethyl-1,2,3,4-tetrahydroisoquinoline | —N(C(O)N(H)—CH$_2$—CH$_2$—F)— |
| Ia-a590 | 2-ethyl-1,2,3,4-tetrahydroisoquinoline | —N(C(O)N(H)—CH$_2$—CH$_2$—OCH$_3$)— |
| Ia-a591 | 2-ethyl-1,2,3,4-tetrahydroisoquinoline | —N(C(O)N(H)—CH$_2$—CH$_2$—CF$_3$)— |
| Ia-a592 | 2-ethyl-1,2,3,4-tetrahydroisoquinoline | —N(C(O)N(H)—CH$_2$—CH$_2$—CF$_3$)— |
| Ia-a593 | 2-ethyl-1,2,3,4-tetrahydroisoquinoline | —N(C(O)N(H)—CH$_2$—CF$_3$)— |
| Ia-a594 | 2-ethyl-1,2,3,4-tetrahydroisoquinoline | —N(C(O)N(H)—(CH$_2$)$_3$—OH)— |
| Ia-a595 | 1-ethyl-2-(pyrrolidin-1-ylmethyl)pyrrolidine | —CH(OH)— |
| Ia-a596 | 1-ethyl-2-(pyrrolidin-1-ylmethyl)pyrrolidine | —N(C(O)N(H)—CH$_2$—CH$_2$—OH)— |

| | | |
|---|---|---|
| Ia-a597 | 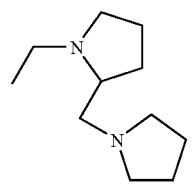 | —N(C(O)N(H)—CH₂—CH₂—F)— |
| Ia-a598 | 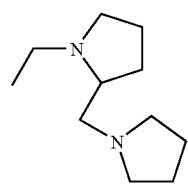 | —N(C(O)N(H)—CH₂—CH₂—OCH₃)— |
| Ia-a599 | 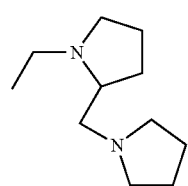 | —N(C(O)N(H)—CH₂—CH₂—CF₃)— |
| Ia-a600 | 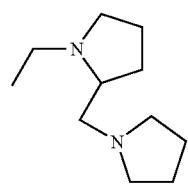 | —N(C(O)N(H)—CH₂—CH₂—CF₃)— |
| Ia-a601 | 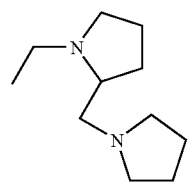 | —N(C(O)N(H)—CH₂—CF₃)— |
| Ia-a602 | 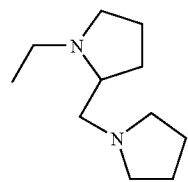 | —N(C(O)N(H)—(CH₂)₃—OH)— |
| Ia-a603 | 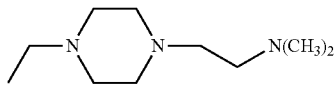 | —CH(OH)— |
| Ia-a604 | 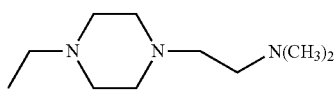 | —N(C(O)N(H)—CH₂—CH₂—OH)— |
| Ia-a605 | 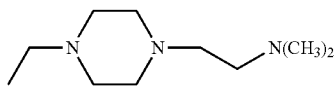 | —N(C(O)N(H)—CH₂—CH₂—F)— |
| Ia-a606 | 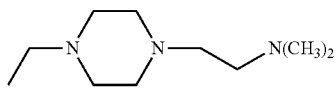 | —N(C(O)N(H)—CH₂—CH₂—OCH₃)— |
| Ia-a607 | 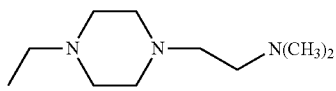 | —N(C(O)N(H)—CH₂—CH₂—CF₃)— |

| | | |
|---|---|---|
| Ia-a608 | 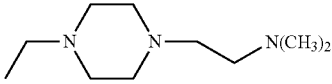 | —N(C(O)N(H)—CH$_2$—CH$_2$—CF$_3$)— |
| Ia-a609 | 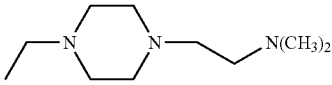 | —N(C(O)N(H)—CH$_2$—CF$_3$)— |
| Ia-a610 | 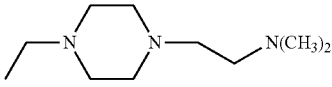 | —N(C(O)N(H)—(CH$_2$)$_3$—OH)— |
| Ia-a611 | —CH$_2$—NH—CH$_2$—CH$_2$—CH$_2$—N(CH$_3$)$_2$ | —CH(OH)— |
| Ia-a612 | —CH$_2$—NH—CH$_2$—CH$_2$—CH$_2$—N(CH$_3$)$_2$ | —N(C(O)N(H)—CH$_2$—CH$_2$—OH)— |
| Ia-a613 | —CH$_2$—NH—CH$_2$—CH$_2$—CH$_2$—N(CH$_3$)$_2$ | —N(C(O)N(H)—CH$_2$—CH$_2$—F)— |
| Ia-a614 | —CH$_2$—NH—CH$_2$—CH$_2$—CH$_2$—N(CH$_3$)$_2$ | —N(C(O)N(H)—CH$_2$—CH$_2$—OCH$_3$)— |
| Ia-a615 | —CH$_2$—NH—CH$_2$—CH$_2$—CH$_2$—N(CH$_3$)$_2$ | —N(C(O)N(H)—CH$_2$—CH$_2$—CF$_3$)— |
| Ia-a616 | —CH$_2$—NH—CH$_2$—CH$_2$—CH$_2$—N(CH$_3$)$_2$ | —N(C(O)N(H)—CH$_2$—CH$_2$—CF$_3$)— |
| Ia-a617 | —CH$_2$—NH—CH$_2$—CH$_2$—CH$_2$—N(CH$_3$)$_2$ | —N(C(O)N(H)—CH$_2$—CF$_3$)— |
| Ia-a618 | —CH$_2$—NH—CH$_2$—CH$_2$—CH$_2$—N(CH$_3$)$_2$ | —N(C(O)N(H)—(CH$_2$)$_3$—OH)— |
| Ia-a619 | 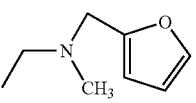 | —CH(OH)— |
| Ia-a620 | 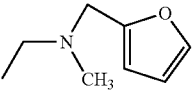 | —N(C(O)N(H)—CH$_2$—CH$_2$—OH)— |
| Ia-a621 | 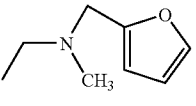 | —N(C(O)N(H)—CH$_2$—CH$_2$—F)— |
| Ia-a622 | 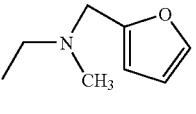 | —N(C(O)N(H)—CH$_2$—CH$_2$—OCH$_3$)— |
| Ia-a623 | 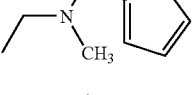 | —N(C(O)N(H)—CH$_2$—CH$_2$—CF$_3$)— |
| Ia-a624 | 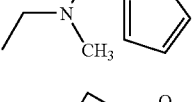 | —N(C(O)N(H)—CH$_2$—CH$_2$—CF$_3$)— |
| Ia-a625 | 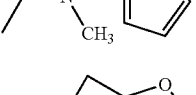 | —N(C(O)N(H)—CH$_2$—CF$_3$)— |
| Ia-a626 | 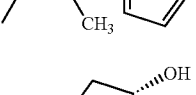 | —N(C(O)N(H)—(CH$_2$)$_3$—OH)— |
| Ia-a627 | 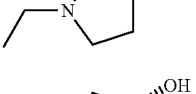 | —CH(OH)— |
| Ia-a628 | 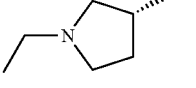 | —N(C(O)N(H)—CH$_2$—CH$_2$—OH)— |

-continued

| | | |
|---|---|---|
| Ia-a629 | 1-ethyl-3-hydroxypyrrolidine | —N(C(O)N(H)—CH$_2$—CH$_2$—F)— |
| Ia-a630 | 1-ethyl-3-hydroxypyrrolidine | —N(C(O)N(H)—CH$_2$—CH$_2$—OCH$_3$)— |
| Ia-a631 | 1-ethyl-3-hydroxypyrrolidine | —N(C(O)N(H)—CH$_2$—CH$_2$—CF$_3$)— |
| Ia-a632 | 1-ethyl-3-hydroxypyrrolidine | —N(C(O)N(H)—CH$_2$—CH$_2$—CF$_3$)— |
| Ia-a633 | 1-ethyl-3-hydroxypyrrolidine | —N(C(O)N(H)—CH$_2$—CF$_3$)— |
| Ia-a634 | 1-ethyl-3-hydroxypyrrolidine | —N(C(O)N(H)—(CH$_2$)$_3$—OH)— |
| Ia-a635 | 1-ethyl-2-(hydroxymethyl)pyrrolidine | —CH(OH)— |
| Ia-a636 | 1-ethyl-2-(hydroxymethyl)pyrrolidine | —N(C(O)N(H)—CH$_2$—CH$_2$—OH)— |
| Ia-a637 | 1-ethyl-2-(hydroxymethyl)pyrrolidine | —N(C(O)N(H)—CH$_2$—CH$_2$—F)— |
| Ia-a638 | 1-ethyl-2-(hydroxymethyl)pyrrolidine | —N(C(O)N(H)—CH$_2$—CH$_2$—OCH$_3$)— |
| Ia-a639 | 1-ethyl-2-(hydroxymethyl)pyrrolidine | —N(C(O)N(H)—CH$_2$—CH$_2$—CF$_3$)— |
| Ia-a640 | 1-ethyl-2-(hydroxymethyl)pyrrolidine | —N(C(O)N(H)—CH$_2$—CH$_2$—CF$_3$)— |
| Ia-a641 | 1-ethyl-2-(hydroxymethyl)pyrrolidine | —N(C(O)N(H)—CH$_2$—CF$_3$)— |

| | | -continued |
|---|---|---|
| Ia-a642 | 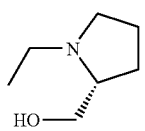 | —N(C(O)N(H)—(CH$_2$)$_3$—OH)— |
| Ia-a643 | 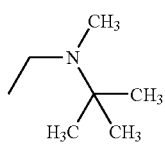 | —CH(OH)— |
| Ia-a644 | 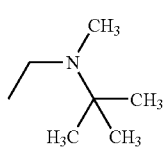 | —N(C(O)N(H)—CH$_2$—CH$_2$—OH)— |
| Ia-a645 | 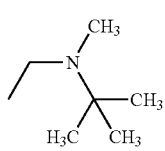 | —N(C(O)N(H)—CH$_2$—CH$_2$—F)— |
| Ia-a646 | 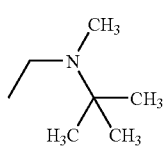 | —N(C(O)N(H)—CH$_2$—CH$_2$—OCH$_3$)— |
| Ia-a647 | 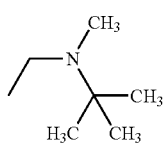 | —N(C(O)N(H)—CH$_2$—CH$_2$—CF$_3$)— |
| Ia-a648 | 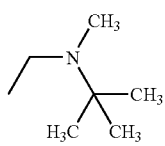 | —N(C(O)N(H)—CH$_2$—CH$_2$—CF$_3$)— |
| Ia-a649 | 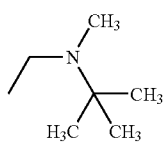 | —N(C(O)N(H)—CH$_2$—CF$_3$)— |
| Ia-a650 | 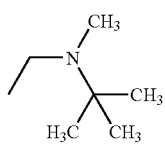 | —N(C(O)N(H)—(CH$_2$)$_3$—OH)— |
| Ia-a651 | 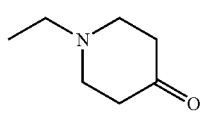 | —CH(OH)— |
| Ia-a652 | 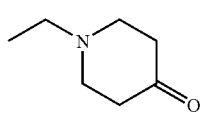 | —N(C(O)N(H)—CH$_2$—CH$_2$—OH)— |

| | | |
|---|---|---|
| Ia-a653 | 1-ethylpiperidin-4-one | —N(C(O)N(H)—CH₂—CH₂—F)— |
| Ia-a654 | 1-ethylpiperidin-4-one | —N(C(O)N(H)—CH₂—CH₂—OCH₃)— |
| Ia-a655 | 1-ethylpiperidin-4-one | —N(C(O)N(H)—CH₂—CH₂—CF₃)— |
| Ia-a656 | 1-ethylpiperidin-4-one | —N(C(O)N(H)—CH₂—CH₂—CF₃)— |
| Ia-a657 | 1-ethylpiperidin-4-one | —N(C(O)N(H)—CH₂—CF₃)— |
| Ia-a658 | 1-ethylpiperidin-4-one | —N(C(O)N(H)—(CH₂)₃—OH)— |
| Ia-a659 | 1-ethyl-4-hydroxypiperidine | —CH(OH)— |
| Ia-a660 | 1-ethyl-4-hydroxypiperidine | —N(C(O)N(H)—CH₂—CH₂—OH)— |
| Ia-a661 | 1-ethyl-4-hydroxypiperidine | —N(C(O)N(H)—CH₂—CH₂—F)— |
| Ia-a662 | 1-ethyl-4-hydroxypiperidine | —N(C(O)N(H)—CH₂—CH₂—OCH₃)— |
| Ia-a663 | 1-ethyl-4-hydroxypiperidine | —N(C(O)N(H)—CH₂—CH₂—CF₃)— |
| Ia-a664 | 1-ethyl-4-hydroxypiperidine | —N(C(O)N(H)—CH₂—CH₂—CF₃)— |
| Ia-a665 | 1-ethyl-4-hydroxypiperidine | —N(C(O)N(H)—CH₂—CF₃)— |
| Ia-a666 | 1-ethyl-4-hydroxypiperidine | —N(C(O)N(H)—(CH₂)₃—OH)— |
| Ia-a667 | 1-ethyl-3-hydroxypiperidine | —CH(OH)— |

-continued
| | | |
|---|---|---|
| Ia-a668 | 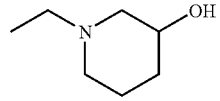 | —N(C(O)N(H)—CH₂—CH₂—OH)— |
| Ia-a669 | 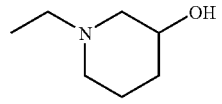 | —N(C(O)N(H)—CH₂—CH₂—F)— |
| Ia-a670 | 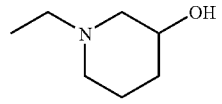 | —N(C(O)N(H)—CH₂—CH₂—OCH₃)— |
| Ia-a671 | 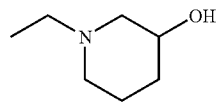 | —N(C(O)N(H)—CH₂—CH₂—CF₃)— |
| Ia-a672 | 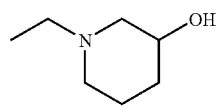 | —N(C(O)N(H)—CH₂—CH₂—CF₃)— |
| Ia-a673 | 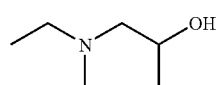 | —N(C(O)N(H)—CH₂—CF₃)— |
| Ia-a674 | 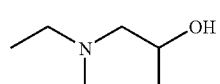 | —N(C(O)N(H)—(CH₂)₃—OH)— |
| Ia-a675 | 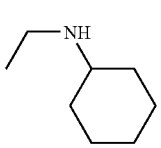 | —CH(OH)— |
| Ia-a676 | 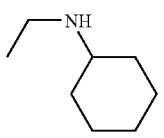 | —N(C(O)N(H)—CH₂—CH₂—OH)— |
| Ia-a677 | 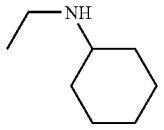 | —N(C(O)N(H)—CH₂—CH₂—F)— |
| Ia-a678 | 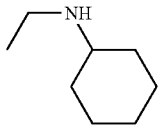 | —N(C(O)N(H)—CH₂—CH₂—OCH₃)— |
| Ia-a679 | 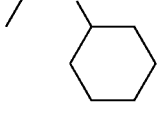 | —N(C(O)N(H)—CH₂—CH₂—CF₃)— |

-continued

| | | |
|---|---|---|
| Ia-a680 | ethyl-NH-cyclohexyl | —N(C(O)N(H)—CH₂—CH₂—CF₃)— |
| Ia-a681 | ethyl-NH-cyclohexyl | —N(C(O)N(H)—CH₂—CF₃)— |
| Ia-a682 | ethyl-NH-cyclohexyl | —N(C(O)N(H)—(CH₂)₃—OH)— |
| Ia-a683 | ethyl-NH-cyclopentyl | —CH(OH)— |
| Ia-a684 | ethyl-NH-cyclopentyl | —N(C(O)N(H)—CH₂—CH₂—OH)— |
| Ia-a685 | ethyl-NH-cyclopentyl | —N(C(O)N(H)—CH₂—CH₂—F)— |
| Ia-a686 | ethyl-NH-cyclopentyl | —N(C(O)N(H)—CH₂—CH₂—OCH₃)— |
| Ia-a687 | ethyl-NH-cyclopentyl | —N(C(O)N(H)—CH₂—CH₂—CF₃)— |
| Ia-a688 | ethyl-NH-cyclopentyl | —N(C(O)N(H)—CH₂—CH₂—CF₃)— |
| Ia-a689 | ethyl-NH-cyclopentyl | —N(C(O)N(H)—CH₂—CF₃)— |
| Ia-a690 | ethyl-NH-cyclopentyl | —N(C(O)N(H)—(CH₂)₃—OH)— |
| Ia-a691 | ethyl-NH-CH₂-cyclohexyl | —CH(OH)— |

-continued
| | | |
|---|---|---|
| Ia-a692 | 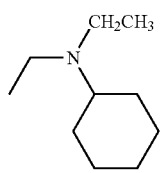 | —N(C(O)N(H)—CH₂—CH₂—OH)— |
| Ia-a693 | 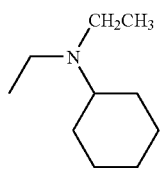 | —N(C(O)N(H)—CH₂—CH₂—F)— |
| Ia-a694 |  | —N(C(O)N(H)—CH₂—CH₂—OCH₃)— |
| Ia-a695 | 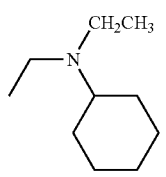 | —N(C(O)N(H)—CH₂—CH₂—CF₃)— |
| Ia-a696 | 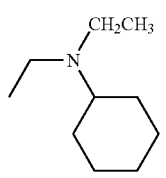 | —N(C(O)N(H)—CH₂—CH₂—CF₃)— |
| Ia-a697 | 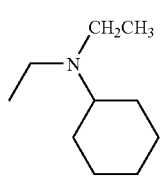 | —N(C(O)N(H)—CH₂—CF₃)— |
| Ia-a698 | 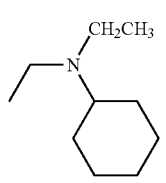 | —N(C(O)N(H)—(CH₂)₃—OH)— |
| Ia-a699 | 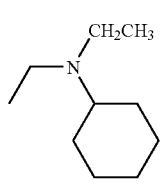 | —CH(OH)— |
| Ia-a700 | 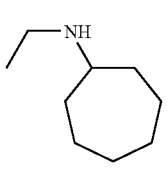 | —N(C(O)N(H)—CH₂—CH₂—OH)— |

-continued
| | | |
|---|---|---|
| Ia-a701 | 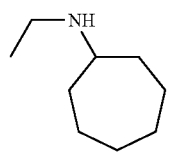 | —N(C(O)N(H)—CH$_2$—CH$_2$—F)— |
| Ia-a702 | 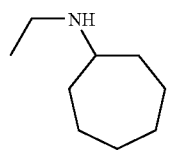 | —N(C(O)N(H)—CH$_2$—CH$_2$—OCH$_3$)— |
| Ia-a703 | 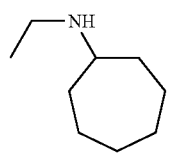 | —N(C(O)N(H)—CH$_2$—CH$_2$—CF$_3$)— |
| Ia-a704 | 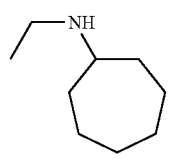 | —N(C(O)N(H)—CH$_2$—CH$_2$—CF$_3$)— |
| Ia-a705 | 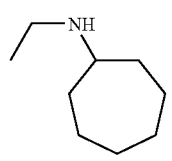 | —N(C(O)N(H)—CH$_2$—CF$_3$)— |
| Ia-a706 | 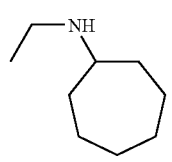 | —N(C(O)N(H)—(CH$_2$)$_3$—OH)— |
| Ia-a707 | 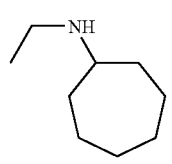 | —CH(OH)— |
| Ia-a708 | 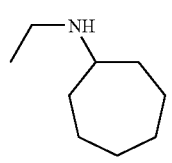 | —N(C(O)N(H)—CH$_2$—CH$_2$—OH)— |
| Ia-a709 | 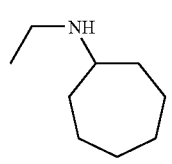 | —N(C(O)N(H)—CH$_2$—CH$_2$—F)— |
| Ia-a710 | 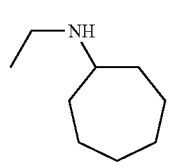 | —N(C(O)N(H)—CH$_2$—CH$_2$—OCH$_3$)— |

-continued

| | | |
|---|---|---|
| Ia-a711 | ethyl-NH-cycloheptyl | —N(C(O)N(H)—CH$_2$—CH$_2$—CF$_3$)— |
| Ia-a712 | ethyl-NH-cycloheptyl | —N(C(O)N(H)—CH$_2$—CH$_2$—CF$_3$)— |
| Ia-a713 | ethyl-NH-cycloheptyl | —N(C(O)N(H)—CH$_2$—CF$_3$)— |
| Ia-a714 | ethyl-NH-cycloheptyl | —N(C(O)N(H)—(CH$_2$)$_3$—OH)— |
| Ia-a715 | ethyl-thiomorpholine | —CH(OH)— |
| Ia-a716 | ethyl-thiomorpholine | —N(C(O)N(H)—CH$_2$—CH$_2$—OH)— |
| Ia-a717 | ethyl-thiomorpholine | —N(C(O)N(H)—CH$_2$—CH$_2$—F)— |
| Ia-a718 | ethyl-thiomorpholine | —N(C(O)N(H)—CH$_2$—CH$_2$—OCH$_3$)— |
| Ia-a719 | ethyl-thiomorpholine | —N(C(O)N(H)—CH$_2$—CH$_2$—CF$_3$)— |
| Ia-a720 | ethyl-thiomorpholine | —N(C(O)N(H)—CH$_2$—CH$_2$—CF$_3$)— |
| Ia-a721 | ethyl-thiomorpholine | —N(C(O)N(H)—CH$_2$—CF$_3$)— |
| Ia-a722 | ethyl-thiomorpholine | —N(C(O)N(H)—(CH$_2$)$_3$—OH)— |
| Ia-a723 | ethyl-(4-hydroxymethyl)piperidine | —CH(OH)— |
| Ia-a724 | ethyl-(4-hydroxymethyl)piperidine | —N(C(O)N(H)—CH$_2$—CH$_2$—OH)— |

-continued
| | | |
|---|---|---|
| Ia-a725 | 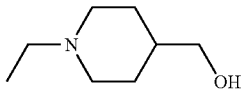 | —N(C(O)N(H)—CH₂—CH₂—F)— |
| Ia-a726 | 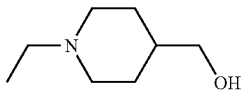 | —N(C(O)N(H)—CH₂—CH₂—OCH₃)— |
| Ia-a727 | 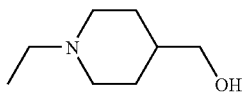 | —N(C(O)N(H)—CH₂—CH₂—CF₃)— |
| Ia-a728 | 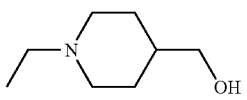 | —N(C(O)N(H)—CH₂—CH₂—CF₃)— |
| Ia-a729 | 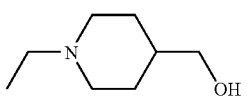 | —N(C(O)N(H)—CH₂—CF₃)— |
| Ia-a730 | 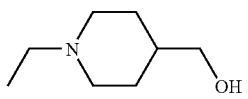 | —N(C(O)N(H)—(CH₂)₃—OH)— |
| Ia-a731 | 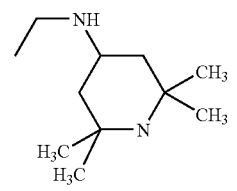 | —CH(OH)— |
| Ia-a732 | 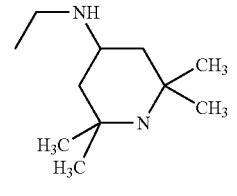 | —N(C(O)N(H)—CH₂—CH₂—OH)— |
| Ia-a733 | 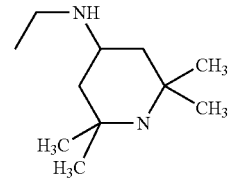 | —N(C(O)N(H)—CH₂—CH₂—F)— |
| Ia-a734 | 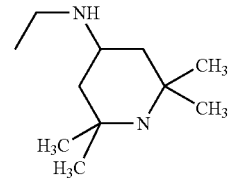 | —N(C(O)N(H)—CH₂—CH₂—OCH₃)— |
| Ia-a735 | 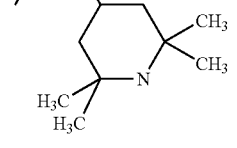 | —N(C(O)N(H)—CH₂—CH₂—CF₃)— |

-continued
| | | |
|---|---|---|
| Ia-a736 | 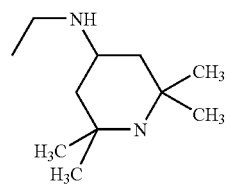 | —N(C(O)N(H)—CH₂—CH₂—CF₃)— |
| Ia-a737 | 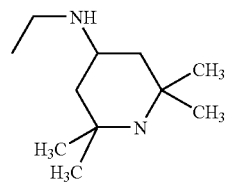 | —N(C(O)N(H)—CH₂—CF₃)— |
| Ia-a738 | 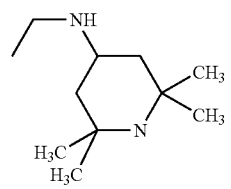 | —N(C(O)N(H)—(CH₂)₃—OH)— |
| Ia-a739 | 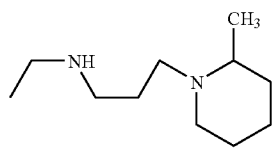 | —CH(OH)— |
| Ia-a740 | 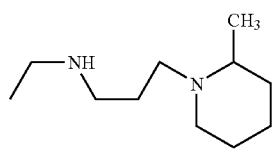 | —N(C(O)N(H)—CH₂—CH₂—OH)— |
| Ia-a741 | 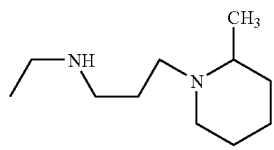 | —N(C(O)N(H)—CH₂—CH₂—F)— |
| Ia-a742 | 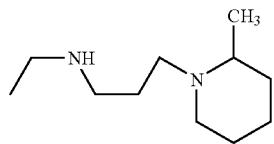 | —N(C(O)N(H)—CH₂—CH₂—OCH₃)— |
| Ia-a743 | 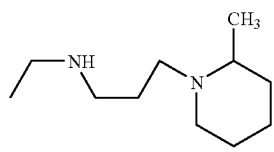 | —N(C(O)N(H)—CH₂—CH₂—CF₃)— |
| Ia-a744 | 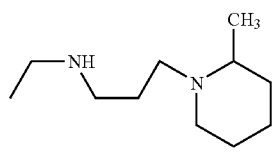 | —N(C(O)N(H)—CH₂—CH₂—CF₃)— |

-continued
| | | |
|---|---|---|
| Ia-a745 | 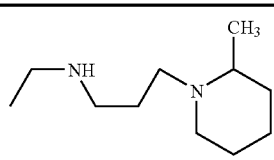 | —N(C(O)N(H)—CH$_2$—CF$_3$)— |
| Ia-a746 |  | —N(C(O)N(H)—(CH$_2$)$_3$—OH)— |
| Ia-a747 | 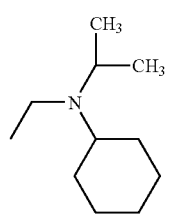 | —CH(OH)— |
| Ia-a748 | 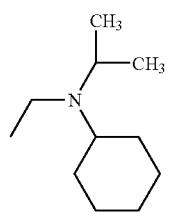 | —N(C(O)N(H)—CH$_2$—CH$_2$—OH)— |
| Ia-a749 |  | —N(C(O)N(H)—CH$_2$—CH$_2$—F)— |
| Ia-a750 | 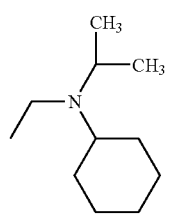 | —N(C(O)N(H)—CH$_2$—CH$_2$—OCH$_3$)— |
| Ia-a751 | 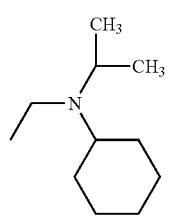 | —N(C(O)N(H)—CH$_2$—CH$_2$—CF$_3$)— |
| Ia-a752 | 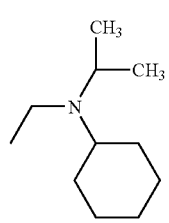 | —N(C(O)N(H)—CH$_2$—CH$_2$—CF$_3$)— |

-continued
| | | |
|---|---|---|
| Ia-a753 | 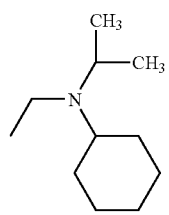 | —N(C(O)N(H)—CH₂—CF₃)— |
| Ia-a754 | 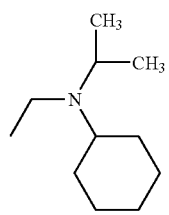 | —N(C(O)N(H)—(CH₂)₃—OH)— |
| Ia-a755 | 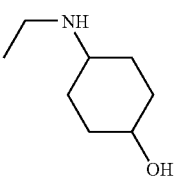 | —CH(OH)— |
| Ia-a756 | 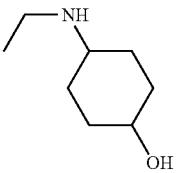 | —N(C(O)N(H)—CH₂—CH₂—OH)— |
| Ia-a757 | 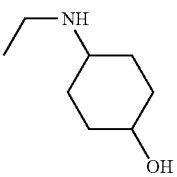 | —N(C(O)N(H)—CH₂—CH₂—F)— |
| Ia-a758 | 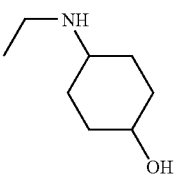 | —N(C(O)N(H)—CH₂—CH₂—OCH₃)— |
| Ia-a759 | 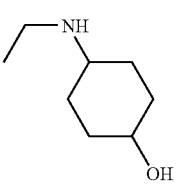 | —N(C(O)N(H)—CH₂—CH₂—CF₃)— |
| Ia-a760 | 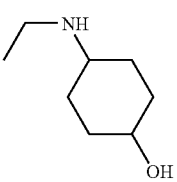 | —N(C(O)N(H)—CH₂—CH₂—CF₃)— |

-continued

| | | |
|---|---|---|
| Ia-a761 | ethyl-NH-cyclohexyl-OH | —N(C(O)N(H)—CH₂—CF₃)— |
| Ia-a762 | ethyl-NH-cyclohexyl-OH | —N(C(O)N(H)—(CH₂)₃—OH)— |
| Ia-a763 | N(ethyl)(CH₂CH₂OH)-cyclohexyl | —CH(OH)— |
| Ia-a764 | N(ethyl)(CH₂CH₂OH)-cyclohexyl | —N(C(O)N(H)—CH₂—CH₂—OH)— |
| Ia-a765 | N(ethyl)(CH₂CH₂OH)-cyclohexyl | —N(C(O)N(H)—CH₂—CH₂—F)— |
| Ia-a766 | N(ethyl)(CH₂CH₂OH)-cyclohexyl | —N(C(O)N(H)—CH₂—CH₂—OCH₃)— |
| Ia-a767 | N(ethyl)(CH₂CH₂OH)-cyclohexyl | —N(C(O)N(H)—CH₂—CH₂—CF₃)— |
| Ia-a768 | N(ethyl)(CH₂CH₂OH)-cyclohexyl | —N(C(O)N(H)—CH₂—CH₂—CF₃)— |
| Ia-a769 | N(ethyl)(CH₂CH₂OH)-cyclohexyl | —N(C(O)N(H)—CH₂—CF₃)— |
| Ia-a770 | N(ethyl)(CH₂CH₂OH)-cyclohexyl | —N(C(O)N(H)—(CH₂)₃—OH)— |

-continued

| | | |
|---|---|---|
| Ia-a771 |  | —CH(OH)— |
| Ia-a772 |  | —N(C(O)N(H)—CH$_2$—CH$_2$—OH)— |
| Ia-a773 |  | —N(C(O)N(H)—CH$_2$—CH$_2$—F)— |
| Ia-a774 |  | —N(C(O)N(H)—CH$_2$—CH$_2$—OCH$_3$)— |
| Ia-a775 | 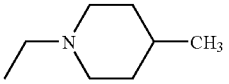 | —N(C(O)N(H)—CH$_2$—CH$_2$—CF$_3$)— |
| Ia-a776 | 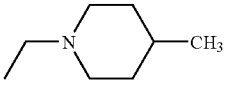 | —N(C(O)N(H)—CH$_2$—CH$_2$—CF$_3$)— |
| Ia-a777 | 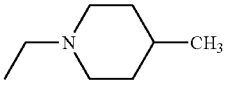 | —N(C(O)N(H)—CH$_2$—CF$_3$)— |
| Ia-a778 |  | —N(C(O)N(H)—(CH$_2$)$_3$—OH)— |
| Ia-a779 | —CH$_2$—NH—CH$_3$ | —CH(OH)— |
| Ia-a780 | —CH$_2$—NH—CH$_3$ | —N(C(O)N(H)—CH$_2$—CH$_2$—OH)— |
| Ia-a781 | —CH$_2$—NH—CH$_3$ | —N(C(O)N(H)—CH$_2$—CH$_2$—F)— |
| Ia-a782 | —CH$_2$—NH—CH$_3$ | —N(C(O)N(H)—CH$_2$—CH$_2$—OCH$_3$)— |
| Ia-a783 | —CH$_2$—NH—CH$_3$ | —N(C(O)N(H)—CH$_2$—CH$_2$—CF$_3$)— |
| Ia-a784 | —CH$_2$—NH—CH$_3$ | —N(C(O)N(H)—CH$_2$—CH$_2$—CF$_3$)— |
| Ia-a785 | —CH$_2$—NH—CH$_3$ | —N(C(O)N(H)—CH$_2$—CF$_3$)— |
| Ia-a786 | —CH$_2$—NH—CH$_3$ | —N(C(O)N(H)—(CH$_2$)$_3$—OH)— |
| Ia-a787 | —CH$_2$—NH—CH$_2$—CH$_3$ | —CH(OH)— |
| Ia-a788 | —CH$_2$—NH—CH$_2$—CH$_3$ | —N(C(O)N(H)—CH$_2$—CH$_2$—OH)— |
| Ia-a789 | —CH$_2$—NH—CH$_2$—CH$_3$ | —N(C(O)N(H)—CH$_2$—CH$_2$—F)— |
| Ia-a790 | —CH$_2$—NH—CH$_2$—CH$_3$ | —N(C(O)N(H)—CH$_2$—CH$_2$—OCH$_3$)— |
| Ia-a791 | —CH$_2$—NH—CH$_2$—CH$_3$ | —N(C(O)N(H)—CH$_2$—CH$_2$—CF$_3$)— |
| Ia-a792 | —CH$_2$—NH—CH$_2$—CH$_3$ | —N(C(O)N(H)—CH$_2$—CH$_2$—CF$_3$)— |
| Ia-a793 | —CH$_2$—NH—CH$_2$—CH$_3$ | —N(C(O)N(H)—CH$_2$—CF$_3$)— |
| Ia-a794 | —CH$_2$—NH—CH$_2$—CH$_3$ | —N(C(O)N(H)—(CH$_2$)$_3$—OH)— |
| Ia-a795 | —CH$_2$—NH—CH$_2$—CH$_2$—CH$_3$ | —CH(OH)— |
| Ia-a796 | —CH$_2$—NH—CH$_2$—CH$_2$—CH$_3$ | —N(C(O)N(H)—CH$_2$—CH$_2$—OH)— |
| Ia-a797 | —CH$_2$—NH—CH$_2$—CH$_2$—CH$_3$ | —N(C(O)N(H)—CH$_2$—CH$_2$—F)— |
| Ia-a798 | —CH$_2$—NH—CH$_2$—CH$_2$—CH$_3$ | —N(C(O)N(H)—CH$_2$—CH$_2$—OCH$_3$)— |
| Ia-a799 | —CH$_2$—NH—CH$_2$—CH$_2$—CH$_3$ | —N(C(O)N(H)—CH$_2$—CH$_2$—CF$_3$)— |
| Ia-a800 | —CH$_2$—NH—CH$_2$—CH$_2$—CH$_3$ | —N(C(O)N(H)—CH$_2$—CH$_2$—CF$_3$)— |
| Ia-a801 | —CH$_2$—NH—CH$_2$—CH$_2$—CH$_3$ | —N(C(O)N(H)—CH$_2$—CF$_3$)— |
| Ia-a802 | —CH$_2$—NH—CH$_2$—CH$_2$—CH$_3$ | —N(C(O)N(H)—(CH$_2$)$_3$—OH)— |
| Ia-a803 | 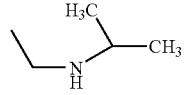 | —CH(OH)— |
| Ia-a804 | 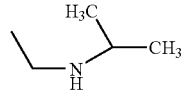 | —N(C(O)N(H)—CH$_2$—CH$_2$—OH)— |
| Ia-a805 | 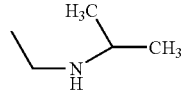 | —N(C(O)N(H)—CH$_2$—CH$_2$—F)— |

-continued

| | | |
|---|---|---|
| Ia-a806 | H₃C–CH(CH₃)–NH–CH₂CH₃ (N-ethyl isopropylamine) | —N(C(O)N(H)—CH₂—CH₂—OCH₃)— |
| Ia-a807 | H₃C–CH(CH₃)–NH–CH₂CH₃ | —N(C(O)N(H)—CH₂—CH₂—CF₃)— |
| Ia-a808 | H₃C–CH(CH₃)–NH–CH₂CH₃ | —N(C(O)N(H)—CH₂—CH₂—CF₃)— |
| Ia-a809 | H₃C–CH(CH₃)–NH–CH₂CH₃ | —N(C(O)N(H)—CH₂—CF₃)— |
| Ia-a810 | H₃C–CH(CH₃)–NH–CH₂CH₃ | —N(C(O)N(H)—(CH₂)₃—OH)— |
| Ia-a811 | N-ethyl valine methyl ester | —CH(OH)— |
| Ia-a812 | N-ethyl valine methyl ester | —N(C(O)N(H)—CH₂—CH₂—OH)— |
| Ia-a813 | N-ethyl valine methyl ester | —N(C(O)N(H)—CH₂—CH₂—F)— |
| Ia-a814 | N-ethyl valine methyl ester | —N(C(O)N(H)—CH₂—CH₂—OCH₃)— |
| Ia-a815 | N-ethyl valine methyl ester | —N(C(O)N(H)—CH₂—CH₂—CF₃)— |
| Ia-a816 | N-ethyl valine methyl ester | —N(C(O)N(H)—CH₂—CH₂—CF₃)— |

-continued
| | | |
|---|---|---|
| Ia-a817 | 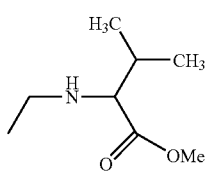 | —N(C(O)N(H)—CH₂—CF₃)— |
| Ia-a818 | 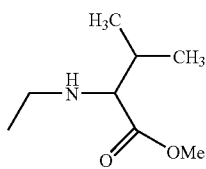 | —N(C(O)N(H)—(CH₂)₃—OH)— |
| Ia-a819 | 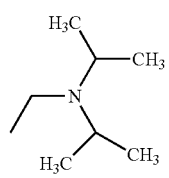 | —CH(OH)— |
| Ia-a820 | 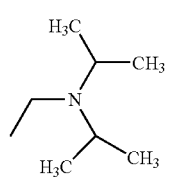 | —N(C(O)N(H)—CH₂—CH₂—OH)— |
| Ia-a821 | 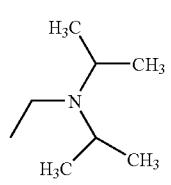 | —N(C(O)N(H)—CH₂—CH₂—F)— |
| Ia-a822 | 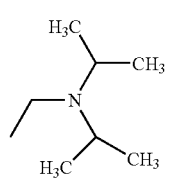 | —N(C(O)N(H)—CH₂—CH₂—OCH₃)— |
| Ia-a823 | 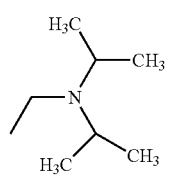 | —N(C(O)N(H)—CH₂—CH₂—CF₃)— |
| Ia-a824 | 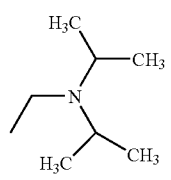 | —N(C(O)N(H)—CH₂—CH₂—CF₃)— |
| Ia-a825 | 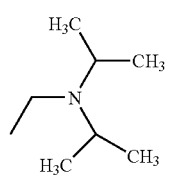 | —N(C(O)N(H)—CH₂—CF₃)— |

-continued
| | | |
|---|---|---|
| Ia-a826 | 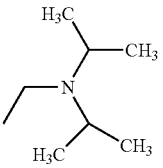 | —N(C(O)N(H)—(CH$_2$)$_3$—OH)— |
| Ia-a827 | 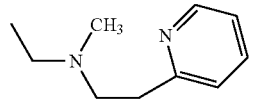 | —CH(OH)— |
| Ia-a828 | 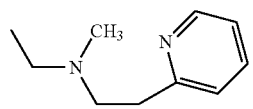 | —N(C(O)N(H)—CH$_2$—CH$_2$—OH)— |
| Ia-a829 | 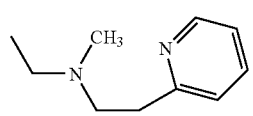 | —N(C(O)N(H)—CH$_2$—CH$_2$—F)— |
| Ia-a830 | 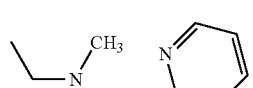 | —N(C(O)N(H)—CH$_2$—CH$_2$—OCH$_3$)— |
| Ia-a831 | 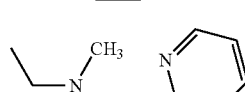 | —N(C(O)N(H)—CH$_2$—CH$_2$—CF$_3$)— |
| Ia-a832 | 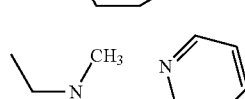 | —N(C(O)N(H)—CH$_2$—CH$_2$—CF$_3$)— |
| Ia-a833 | 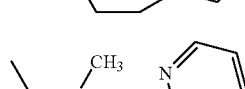 | —N(C(O)N(H)—CH$_2$—CF$_3$)— |
| Ia-a834 | 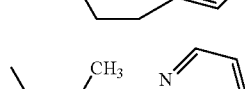 | —N(C(O)N(H)—(CH$_2$)$_3$—OH)— |
| Ia-a835 | 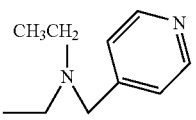 | —CH(OH)— |
| Ia-a836 | 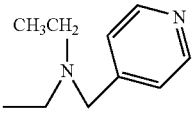 | —N(C(O)N(H)—CH$_2$—CH$_2$—OH)— |
| Ia-a837 | 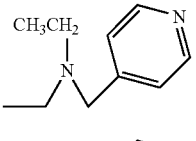 | —N(C(O)N(H)—CH$_2$—CH$_2$—F)— |
| Ia-a838 | 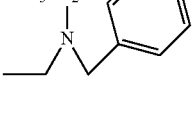 | —N(C(O)N(H)—CH$_2$—CH$_2$—OCH$_3$)— |

-continued

| | | |
|---|---|---|
| Ia-a839 | CH₃CH₂–N(CH₂CH₃)–CH₂–(pyridin-4-yl) | —N(C(O)N(H)—CH₂—CH₂—CF₃)— |
| Ia-a840 | CH₃CH₂–N(CH₂CH₃)–CH₂–(pyridin-3-yl) | —N(C(O)N(H)—CH₂—CH₂—CF₃)— |
| Ia-a841 | CH₃CH₂–N(CH₂CH₃)–CH₂–(pyridin-4-yl) | —N(C(O)N(H)—CH₂—CF₃)— |
| Ia-a842 | CH₃CH₂–N(CH₂CH₃)–CH₂–(pyridin-3-yl) | —N(C(O)N(H)—(CH₂)₃—OH)— |
| Ia-a843 | Et–N(CH₃)—CH₂CH₂OH | —CH(OH)— |
| Ia-a844 | Et–N(CH₃)—CH₂CH₂OH | —N(C(O)N(H)—CH₂—CH₂—OH)— |
| Ia-a845 | Et–N(CH₃)—CH₂CH₂OH | —N(C(O)N(H)—CH₂—CH₂—F)— |
| Ia-a846 | Et–N(CH₃)—CH₂CH₂OH | —N(C(O)N(H)—CH₂—CH₂—OCH₃)— |
| Ia-a847 | Et–N(CH₃)—CH₂CH₂OH | —N(C(O)N(H)—CH₂—CH₂—CF₃)— |
| Ia-a848 | Et–N(CH₃)—CH₂CH₂OH | —N(C(O)N(H)—CH₂—CH₂—CF₃)— |
| Ia-a849 | Et–N(CH₃)—CH₂CH₂OH | —N(C(O)N(H)—CH₂—CF₃)— |
| Ia-a850 | Et–N(CH₃)—CH₂CH₂OH | —N(C(O)N(H)—(CH₂)₃—OH)— |
| Ia-a851 | 1-ethyl-4-(piperidin-1-yl)piperidine | —CH(OH)— |
| Ia-a852 | 1-ethyl-4-(piperidin-1-yl)piperidine | —N(C(O)N(H)—CH₂—CH₂—OH)— |
| Ia-a853 | 1-ethyl-4-(piperidin-1-yl)piperidine | —N(C(O)N(H)—CH₂—CH₂—F)— |
| Ia-a854 | 1-ethyl-4-(piperidin-1-yl)piperidine | —N(C(O)N(H)—CH₂—CH₂—OCH₃)— |

| | | |
|---|---|---|
| Ia-a855 | [1-ethylpiperidin-4-yl-piperidine] | —N(C(O)N(H)—CH₂—CH₂—CF₃)— |
| Ia-a856 | [1-ethylpiperidin-4-yl-piperidine] | —N(C(O)N(H)—CH₂—CH₂—CF₃)— |
| Ia-a857 | [1-ethylpiperidin-4-yl-piperidine] | —N(C(O)N(H)—CH₂—CF₃)— |
| Ia-a858 | [1-ethylpiperidin-4-yl-piperidine] | —N(C(O)N(H)—(CH₂)₃—OH)— |
| Ia-a859 | [ethyl-NH-CH₂-piperidine] | —CH(OH)— |
| Ia-a860 | [ethyl-NH-CH₂-piperidine] | —N(C(O)N(H)—CH₂—CH₂—OH)— |
| Ia-a861 | [ethyl-NH-CH₂-piperidine] | —N(C(O)N(H)—CH₂—CH₂—F)— |
| Ia-a862 | [ethyl-NH-CH₂-piperidine] | —N(C(O)N(H)—CH₂—CH₂—OCH₃)— |
| Ia-a863 | [ethyl-NH-CH₂-piperidine] | —N(C(O)N(H)—CH₂—CH₂—CF₃)— |
| Ia-a864 | [ethyl-NH-CH₂-piperidine] | —N(C(O)N(H)—CH₂—CH₂—CF₃)— |
| Ia-a865 | [ethyl-NH-CH₂-piperidine] | —N(C(O)N(H)—CH₂—CF₃)— |
| Ia-a866 | [ethyl-NH-CH₂-piperidine] | —N(C(O)N(H)—(CH₂)₃—OH)— |
| Ia-a867 | [N-methyl-N-ethyl-furfurylamine] | —CH(OH)— |
| Ia-a868 | [N-methyl-N-ethyl-furfurylamine] | —N(C(O)N(H)—CH₂—CH₂—OH)— |
| Ia-a869 | [N-methyl-N-ethyl-furfurylamine] | —N(C(O)N(H)—CH₂—CH₂—F)— |

| | | |
|---|---|---|
| Ia-a870 | Ethyl(methyl)aminomethyl-furan | —N(C(O)N(H)—CH₂—CH₂—OCH₃)— |
| Ia-a871 | Ethyl(methyl)aminomethyl-furan | —N(C(O)N(H)—CH₂—CH₂—CF₃)— |
| Ia-a872 | Ethyl(methyl)aminomethyl-furan | —N(C(O)N(H)—CH₂—CH₂—CF₃)— |
| Ia-a873 | Ethyl(methyl)aminomethyl-furan | —N(C(O)N(H)—CH₂—CF₃)— |
| Ia-a874 | Ethyl(methyl)aminomethyl-furan | —N(C(O)N(H)—(CH₂)₃—OH)— |
| Ia-a875 | Ethylamino-propyl-pyridine | —CH(OH)— |
| Ia-a876 | Ethylamino-propyl-pyridine | —N(C(O)N(H)—CH₂—CH₂—OH)— |
| Ia-a877 | Ethylamino-propyl-pyridine | —N(C(O)N(H)—CH₂—CH₂—F)— |
| Ia-a878 | Ethylamino-propyl-pyridine | —N(C(O)N(H)—CH₂—CH₂—OCH₃)— |
| Ia-a879 | Ethylamino-propyl-pyridine | —N(C(O)N(H)—CH₂—CH₂—CF₃)— |
| Ia-a880 | Ethylamino-propyl-pyridine | —N(C(O)N(H)—CH₂—CH₂—CF₃)— |
| Ia-a881 | Ethylamino-propyl-pyridine | —N(C(O)N(H)—CH₂—CF₃)— |
| Ia-a882 | Ethylamino-propyl-pyridine | —N(C(O)N(H)—(CH₂)₃—OH)— |
| Ia-a883 | Ethylamino-propyl-(N-methyl-pyrrolidine) | —CH(OH)— |

-continued

| ID | Structure | Linker |
|---|---|---|
| Ia-a884 | ethyl-NH-CH2-CH2-(1-methylpyrrolidin-2-yl) | —N(C(O)N(H)—CH₂—CH₂—OH)— |
| Ia-a885 | ethyl-NH-CH2-CH2-(1-methylpyrrolidin-2-yl) | —N(C(O)N(H)—CH₂—CH₂—F)— |
| Ia-a886 | ethyl-NH-CH2-CH2-(1-methylpyrrolidin-2-yl) | —N(C(O)N(H)—CH₂—CH₂—OCH₃)— |
| Ia-a887 | ethyl-NH-CH2-CH2-(1-methylpyrrolidin-2-yl) | —N(C(O)N(H)—CH₂—CH₂—CF₃)— |
| Ia-a888 | ethyl-NH-CH2-CH2-(1-methylpyrrolidin-2-yl) | —N(C(O)N(H)—CH₂—CH₂—CF₃)— |
| Ia-a889 | ethyl-NH-CH2-CH2-(1-methylpyrrolidin-2-yl) | —N(C(O)N(H)—CH₂—CF₃)— |
| Ia-a890 | ethyl-NH-CH2-CH2-(1-methylpyrrolidin-2-yl) | —N(C(O)N(H)—(CH₂)₃—OH)— |
| Ia-a891 | 1-ethylpiperazine | —CH(OH)— |
| Ia-a892 | 1-ethylpiperazine | —N(C(O)N(H)—CH₂—CH₂—OH)— |
| Ia-a893 | 1-ethylpiperazine | —N(C(O)N(H)—CH₂—CH₂—F)— |
| Ia-a894 | 1-ethylpiperazine | —N(C(O)N(H)—CH₂—CH₂—OCH₃)— |
| Ia-a895 | 1-ethylpiperazine | —N(C(O)N(H)—CH₂—CH₂—CF₃)— |
| Ia-a896 | 1-ethylpiperazine | —N(C(O)N(H)—CH₂—CH₂—CF₃)— |

-continued

| ID | Amine | Linker |
|---|---|---|
| Ia-a897 | 4-ethylpiperazine (NH) | —N(C(O)N(H)—CH$_2$—CF$_3$)— |
| Ia-a898 | 4-ethylpiperazine (NH) | —N(C(O)N(H)—(CH$_2$)$_3$—OH)— |
| Ia-a899 | 1-ethyl-4-methylpiperazine-ethyl | —CH(OH)— |
| Ia-a900 | 1-ethyl-4-methylpiperazine-ethyl | —N(C(O)N(H)—CH$_2$—CH$_2$—OH)— |
| Ia-a901 | 1-ethyl-4-methylpiperazine-ethyl | —N(C(O)N(H)—CH$_2$—CH$_2$—F)— |
| Ia-a902 | 1-ethyl-4-methylpiperazine-ethyl | —N(C(O)N(H)—CH$_2$—CH$_2$—OCH$_3$)— |
| Ia-a903 | 1-ethyl-4-methylpiperazine-ethyl | —N(C(O)N(H)—CH$_2$—CH$_2$—CF$_3$)— |
| Ia-a904 | 1-ethyl-4-methylpiperazine-ethyl | —N(C(O)N(H)—CH$_2$—CH$_2$—CF$_3$)— |
| Ia-a905 | 1-ethyl-4-methylpiperazine-ethyl | —N(C(O)N(H)—CH$_2$—CF$_3$)— |
| Ia-a906 | 1-ethyl-4-methylpiperazine-ethyl | —N(C(O)N(H)—(CH$_2$)$_3$—OH)— |
| Ia-a907 | cyclopropylmethylamine-ethyl (NH) | —CH(OH)— |
| Ia-a908 | cyclopropylmethylamine-ethyl (NH) | —N(C(O)N(H)—CH$_2$—CH$_2$—OH)— |
| Ia-a909 | cyclopropylmethylamine-ethyl (NH) | —N(C(O)N(H)—CH$_2$—CH$_2$—F)— |
| Ia-a910 | cyclopropylmethylamine-ethyl (NH) | —N(C(O)N(H)—CH$_2$—CH$_2$—OCH$_3$)— |
| Ia-a911 | cyclopropylmethylamine-ethyl (NH) | —N(C(O)N(H)—CH$_2$—CH$_2$—CF$_3$)— |

| | | |
|---|---|---|
| Ia-a912 | Ethyl(cyclopropyl)amine -NH | —N(C(O)N(H)—CH₂—CH₂—CF₃)— |
| Ia-a913 | Ethyl(cyclopropyl)amine -NH | —N(C(O)N(H)—CH₂—CF₃)— |
| Ia-a914 | Ethyl(cyclopropyl)amine -NH | —N(C(O)N(H)—(CH₂)₃—OH)— |
| Ia-a915 | 1-ethyl-4-(2-hydroxyethyl)piperazine | —CH(OH)— |
| Ia-a916 | 1-ethyl-4-(2-hydroxyethyl)piperazine | —N(C(O)N(H)—CH₂—CH₂—OH)— |
| Ia-a917 | 1-ethyl-4-(2-hydroxyethyl)piperazine | —N(C(O)N(H)—CH₂—CH₂—F)— |
| Ia-a918 | 1-ethyl-4-(2-hydroxyethyl)piperazine | —N(C(O)N(H)—CH₂—CH₂—OCH₃)— |
| Ia-a919 | 1-ethyl-4-(2-hydroxyethyl)piperazine | —N(C(O)N(H)—CH₂—CH₂—CF₃)— |
| Ia-a920 | 1-ethyl-4-(2-hydroxyethyl)piperazine | —N(C(O)N(H)—CH₂—CH₂—CF₃)— |
| Ia-a921 | 1-ethyl-4-(2-hydroxyethyl)piperazine | —N(C(O)N(H)—CH₂—CF₃)— |
| Ia-a922 | 1-ethyl-4-(2-hydroxyethyl)piperazine | —N(C(O)N(H)—(CH₂)₃—OH)— |
| Ia-a923 | 1-ethyl-4-propylpiperazine | —CH(OH)— |
| Ia-a924 | 1-ethyl-4-propylpiperazine | —N(C(O)N(H)—CH₂—CH₂—OH)— |
| Ia-a925 | 1-ethyl-4-propylpiperazine | —N(C(O)N(H)—CH₂—CH₂—F)— |
| Ia-a926 | 1-ethyl-4-propylpiperazine | —N(C(O)N(H)—CH₂—CH₂—OCH₃)— |
| Ia-a927 | 1-ethyl-4-propylpiperazine | —N(C(O)N(H)—CH₂—CH₂—CF₃)— |

-continued

| | | |
|---|---|---|
| Ia-a928 | 4-ethyl-1-propyl-piperazine | —N(C(O)N(H)—CH₂—CH₂—CF₃)— |
| Ia-a929 | 4-ethyl-1-propyl-piperazine | —N(C(O)N(H)—CH₂—CF₃)— |
| Ia-a930 | 4-ethyl-1-propyl-piperazine | —N(C(O)N(H)—(CH₂)₃—OH)— |
| Ia-a931 | 1-ethyl-4-(cyclohexylmethyl)-piperazine | —CH(OH)— |
| Ia-a932 | 1-ethyl-4-(cyclohexylmethyl)-piperazine | —N(C(O)N(H)—CH₂—CH₂—OH)— |
| Ia-a933 | 1-ethyl-4-(cyclohexylmethyl)-piperazine | —N(C(O)N(H)—CH₂—CH₂—F)— |
| Ia-a934 | 1-ethyl-4-(cyclohexylmethyl)-piperazine | —N(C(O)N(H)—CH₂—CH₂—OCH₃)— |
| Ia-a935 | 1-ethyl-4-(cyclohexylmethyl)-piperazine | —N(C(O)N(H)—CH₂—CH₂—CF₃)— |
| Ia-a936 | 1-ethyl-4-(cyclohexylmethyl)-piperazine | —N(C(O)N(H)—CH₂—CH₂—CF₃)— |
| Ia-a937 | 1-ethyl-4-(cyclohexylmethyl)-piperazine | —N(C(O)N(H)—CH₂—CF₃)— |
| Ia-a938 | 1-ethyl-4-(cyclohexylmethyl)-piperazine | —N(C(O)N(H)—(CH₂)₃—OH)— |

-continued

| | | |
|---|---|---|
| Ia-a939 | N-ethyl-4-OEt piperidine | —CH(OH)— |
| Ia-a940 | N-ethyl-4-OEt piperidine | —N(C(O)N(H)—CH$_2$—CH$_2$—OH)— |
| Ia-a941 | N-ethyl-4-OEt piperidine | —N(C(O)N(H)—CH$_2$—CH$_2$—F)— |
| Ia-a942 | N-ethyl-4-OEt piperidine | —N(C(O)N(H)—CH$_2$—CH$_2$—OCH$_3$)— |
| Ia-a943 | N-ethyl-4-OEt piperidine | —N(C(O)N(H)—CH$_2$—CH$_2$—CF$_3$)— |
| Ia-a944 | N-ethyl-4-OEt piperidine | —N(C(O)N(H)—CH$_2$—CH$_2$—CF$_3$)— |
| Ia-a945 | N-ethyl-4-OEt piperidine | —N(C(O)N(H)—CH$_2$—CF$_3$)— |
| Ia-a946 | N-ethyl-4-OEt piperidine | —N(C(O)N(H)—(CH$_2$)$_3$—OH)— |
| Ia-a947 | N-ethyl-3-OH piperidine | —CH(OH)— |
| Ia-a948 | N-ethyl-3-OH piperidine | —N(C(O)N(H)—CH$_2$—CH$_2$—OH)— |
| Ia-a949 | N-ethyl-3-OH piperidine | —N(C(O)N(H)—CH$_2$—CH$_2$—F)— |
| Ia-a950 | N-ethyl-3-OH piperidine | —N(C(O)N(H)—CH$_2$—CH$_2$—OCH$_3$)— |
| Ia-a951 | N-ethyl-3-OH piperidine | —N(C(O)N(H)—CH$_2$—CH$_2$—CF$_3$)— |
| Ia-a952 | N-ethyl-3-OH piperidine | —N(C(O)N(H)—CH$_2$—CH$_2$—CF$_3$)— |

-continued

| | | |
|---|---|---|
| Ia-a953 | 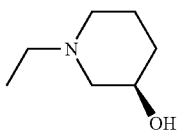 | —N(C(O)N(H)—CH₂—CF₃)— |
| Ia-a954 | 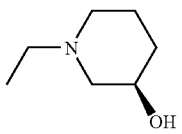 | —N(C(O)N(H)—(CH₂)₃—OH)— |
| Ia-a955 | 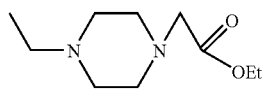 | —CH(OH)— |
| Ia-a956 | 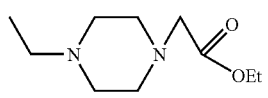 | —N(C(O)N(H)—CH₂—CH₂—OH)— |
| Ia-a957 | 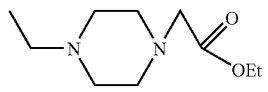 | —N(C(O)N(H)—CH₂—CH₂—F)— |
| Ia-a958 | 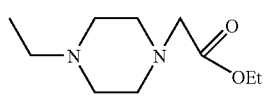 | —N(C(O)N(H)—CH₂—CH₂—OCH₃)— |
| Ia-a959 | 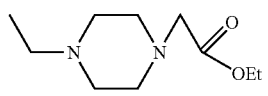 | —N(C(O)N(H)—CH₂—CH₂—CF₃)— |
| Ia-a960 |  | —N(C(O)N(H)—CH₂—CH₂—CF₃)— |
| Ia-a961 | 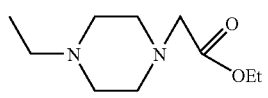 | —N(C(O)N(H)—CH₂—CF₃)— |
| Ia-a962 | 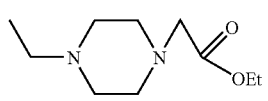 | —N(C(O)N(H)—(CH₂)₃—OH)— |
| Ia-a963 | —CH₂—N(CH₂CH₃)(CH₃) | —CH(OH)— |
| Ia-a964 | —CH₂—N(CH₂CH₃)(CH₃) | —N(C(O)N(H)—CH₂—CH₂—OH)— |
| Ia-a965 | —CH₂—N(CH₂CH₃)(CH₃) | —N(C(O)N(H)—CH₂—CH₂—F)— |
| Ia-a966 | —CH₂—N(CH₂CH₃)(CH₃) | —N(C(O)N(H)—CH₂—CH₂—OCH₃)— |
| Ia-a967 | —CH₂—N(CH₂CH₃)(CH₃) | —N(C(O)N(H)—CH₂—CH₂—CF₃)— |
| Ia-a968 | —CH₂—N(CH₂CH₃)(CH₃) | —N(C(O)N(H)—CH₂—CH₂—CF₃)— |
| Ia-a969 | —CH₂—N(CH₂CH₃)(CH₃) | —N(C(O)N(H)—CH₂—CF₃)— |
| Ia-a970 | —CH₂—N(CH₂CH₃)(CH₃) | —N(C(O)N(H)—(CH₂)₃—OH)— |
| Ia-a971 | —CH₂—N(CH₂CH₂CH₃)(CH₃) | —CH(OH)— |
| Ia-a972 | —CH₂—N(CH₂CH₂CH₃)(CH₃) | —N(C(O)N(H)—CH₂—CH₂—OH)— |
| Ia-a973 | —CH₂—N(CH₂CH₂CH₃)(CH₃) | —N(C(O)N(H)—CH₂—CH₂—F)— |
| Ia-a974 | —CH₂—N(CH₂CH₂CH₃)(CH₃) | —N(C(O)N(H)—CH₂—CH₂—OCH₃)— |
| Ia-a975 | —CH₂—N(CH₂CH₂CH₃)(CH₃) | —N(C(O)N(H)—CH₂—CH₂—CF₃)— |
| Ia-a976 | —CH₂—N(CH₂CH₂CH₃)(CH₃) | —N(C(O)N(H)—CH₂—CH₂—CF₃)— |
| Ia-a977 | —CH₂—N(CH₂CH₂CH₃)(CH₃) | —N(C(O)N(H)—CH₂—CF₃)— |
| Ia-a978 | —CH₂—N(CH₂CH₂CH₃)(CH₃) | —N(C(O)N(H)—(CH₂)₃—OH)— |
| Ia-a979 | —CH₂—N(CH₂CH₂CH₂CH₃)(CH₃) | —CH(OH)— |
| Ia-a980 | —CH₂—N(CH₂CH₂CH₂CH₃)(CH₃) | —N(C(O)N(H)—CH₂—CH₂—OH)— |
| Ia-a981 | —CH₂—N(CH₂CH₂CH₂CH₃)(CH₃) | —N(C(O)N(H)—CH₂—CH₂—F)— |
| Ia-a982 | —CH₂—N(CH₂CH₂CH₂CH₃)(CH₃) | —N(C(O)N(H)—CH₂—CH₂—OCH₃)— |
| Ia-a983 | —CH₂—N(CH₂CH₂CH₂CH₃)(CH₃) | —N(C(O)N(H)—CH₂—CH₂—CF₃)— |
| Ia-a984 | —CH₂—N(CH₂CH₂CH₂CH₃)(CH₃) | —N(C(O)N(H)—CH₂—CH₂—CF₃)— |
| Ia-a985 | —CH₂—N(CH₂CH₂CH₂CH₃)(CH₃) | —N(C(O)N(H)—CH₂—CF₃)— |
| Ia-a986 | —CH₂—N(CH₂CH₂CH₂CH₃)(CH₃) | —N(C(O)N(H)—(CH₂)₃—OH)— |
| Ia-a987 | —CH₂—NH—CH₂CH₂CH₂CH₃ | —CH(OH)— |

-continued

| | | |
|---|---|---|
| Ia-a988 | —CH$_2$—NH—CH$_2$CH$_2$CH$_3$ | —N(C(O)N(H)—CH$_2$—CH$_2$—OH)— |
| Ia-a989 | —CH$_2$—NH—CH$_2$CH$_2$CH$_3$ | —N(C(O)N(H)—CH$_2$—CH$_2$—F)— |
| Ia-a990 | —CH$_2$—NH—CH$_2$CH$_2$CH$_3$ | —N(C(O)N(H)—CH$_2$—CH$_2$—OCH$_3$)— |
| Ia-a991 | —CH$_2$—NH—CH$_2$CH$_2$CH$_3$ | —N(C(O)N(H)—CH$_2$—CH$_2$—CF$_3$)— |
| Ia-a992 | —CH$_2$—NH—CH$_2$CH$_2$CH$_3$ | —N(C(O)N(H)—CH$_2$—CH$_2$—CF$_3$)— |
| Ia-a993 | —CH$_2$—NH—CH$_2$CH$_2$CH$_3$ | —N(C(O)N(H)—CH$_2$—CF$_3$)— |
| Ia-a994 | —CH$_2$—NH—CH$_2$CH$_2$CH$_3$ | —N(C(O)N(H)—(CH$_2$)$_3$—OH)— |
| Ia-a995 | —CH$_2$—NH—CH$_2$CH$_2$—O—CH$_3$ | —CH(OH)— |
| Ia-a996 | —CH$_2$—NH—CH$_2$CH$_2$—O—CH$_3$ | —N(C(O)N(H)—CH$_2$—CH$_2$—OH)— |
| Ia-a997 | —CH$_2$—NH—CH$_2$CH$_2$—O—CH$_3$ | —N(C(O)N(H)—CH$_2$—CH$_2$—F)— |
| Ia-a998 | —CH$_2$—NH—CH$_2$CH$_2$—O—CH$_3$ | —N(C(O)N(H)—CH$_2$—CH$_2$—OCH$_3$)— |
| Ia-a999 | —CH$_2$—NH—CH$_2$CH$_2$—O—CH$_3$ | —N(C(O)N(H)—CH$_2$—CH$_2$—CF$_3$)— |
| Ia-a1000 | —CH$_2$—NH—CH$_2$CH$_2$—O—CH$_3$ | —N(C(O)N(H)—CH$_2$—CH$_2$—CF$_3$)— |
| Ia-a1001 | —CH$_2$—NH—CH$_2$CH$_2$—O—CH$_3$ | —N(C(O)N(H)—CH$_2$—CF$_3$)— |
| Ia-a1002 | —CH$_2$—NH—CH$_2$CH$_2$—O—CH$_3$ | —N(C(O)N(H)—(CH$_2$)$_3$—OH)— |
| Ia-a1003 | ethyl-piperazine-CH$_2$CH$_2$-OMe | —CH(OH)— |
| Ia-a1004 | ethyl-piperazine-CH$_2$CH$_2$-OMe | —N(C(O)N(H)—CH$_2$—CH$_2$—OH)— |
| Ia-a1005 | ethyl-piperazine-CH$_2$CH$_2$-OMe | —N(C(O)N(H)—CH$_2$—CH$_2$—F)— |
| Ia-a1006 | ethyl-piperazine-CH$_2$CH$_2$-OMe | —N(C(O)N(H)—CH$_2$—CH$_2$—OCH$_3$)— |
| Ia-a1007 | ethyl-piperazine-CH$_2$CH$_2$-OMe | —N(C(O)N(H)—CH$_2$—CH$_2$—CF$_3$)— |
| Ia-a1008 | ethyl-piperazine-CH$_2$CH$_2$-OMe | —N(C(O)N(H)—CH$_2$—CH$_2$—CF$_3$)— |
| Ia-a1009 | ethyl-piperazine-CH$_2$CH$_2$-OMe | —N(C(O)N(H)—CH$_2$—CF$_3$)— |
| Ia-a1010 | ethyl-piperazine-CH$_2$CH$_2$-OMe | —N(C(O)N(H)—(CH$_2$)$_3$—OH)— |
| Ia-a1011 | 1-ethyl-piperidin-4-yl-OPO(OH)$_2$ | —CH(OH)— |
| Ia-a1012 | 1-ethyl-piperidin-4-yl-OPO(OH)$_2$ | —N(C(O)N(H)—CH$_2$—CH$_2$—OH)— |
| Ia-a1013 | 1-ethyl-piperidin-4-yl-OPO(OH)$_2$ | —N(C(O)N(H)—CH$_2$—CH$_2$—F)— |
| Ia-a1014 | 1-ethyl-piperidin-4-yl-OPO(OH)$_2$ | —N(C(O)N(H)—CH$_2$—CH$_2$—OCH$_3$)— |

-continued
| | | |
|---|---|---|
| Ia-a1015 |  | —N(C(O)N(H)—CH$_2$—CH$_2$—CF$_3$)— |
| Ia-a1016 |  | —N(C(O)N(H)—CH$_2$—CH$_2$—CF$_3$)— |
| Ia-a1017 |  | —N(C(O)N(H)—CH$_2$—CF$_3$)— |
| Ia-a1018 |  | —N(C(O)N(H)—(CH$_2$)$_3$—OH)— |
| Ia-a1019 |  | —CH(OH)— |
| Ia-a1020 |  | —N(C(O)N(H)—CH$_2$—CH$_2$—OH)— |
| Ia-a1021 |  | —N(C(O)N(H)—CH$_2$—CH$_2$—F)— |
| Ia-a1022 |  | —N(C(O)N(H)—CH$_2$—CH$_2$—OCH$_3$)— |
| Ia-a1023 |  | —N(C(O)N(H)—CH$_2$—CH$_2$—CF$_3$)— |
| Ia-a1024 |  | —N(C(O)N(H)—CH$_2$—CH$_2$—CF$_3$)— |
| Ia-a1025 |  | —N(C(O)N(H)—CH$_2$—CF$_3$)— |
| Ia-a1026 |  | —N(C(O)N(H)—(CH$_2$)$_3$—OH)— |
| Ia-a1027 |  | —CH(OH)— |
| Ia-a1028 |  | N(C(O)N(H)—CH$_2$—CH$_2$—OH)— |

-continued

| | | |
|---|---|---|
| Ia-a1029 | 1-ethylpiperidin-3-yl OPO(OH)₂ | N(C(O)N(H)—CH₂—CH₂—F)— |
| Ia-a1030 | 1-ethylpiperidin-3-yl OPO(OH)₂ | N(C(O)N(H)—CH₂—CH₂—OCH₃)— |
| Ia-a1031 | 1-ethylpiperidin-3-yl OPO(OH)₂ | N(C(O)N(H)—CH₂—CH₂—CF₃)— |
| Ia-a1032 | 1-ethylpiperidin-3-yl OPO(OH)₂ | N(C(O)N(H)—CH₂—CH₂—CF₃)— |
| Ia-a1033 | 1-ethylpiperidin-3-yl OPO(OH)₂ | —N(C(O)N(H)—CH₂—CF₃)— |
| Ia-a1034 | 1-ethylpiperidin-3-yl OPO(OH)₂ | —N(C(O)N(H)—(CH₂)₃—OH)— |
| Ia-a1035 | N(CH₃)(Et)CH₂CH₂OPO(OH)₂ | —CH(OH)— |
| Ia-a1036 | N(CH₃)(Et)CH₂CH₂OPO(OH)₂ | —N(C(O)N(H)—CH₂—CH₂—OH)— |
| Ia-a1037 | N(CH₃)(Et)CH₂CH₂OPO(OH)₂ | —N(C(O)N(H)—CH₂—CH₂—F)— |
| Ia-a1038 | N(CH₃)(Et)CH₂CH₂OPO(OH)₂ | —N(C(O)N(H)—CH₂—CH₂—OCH₃)— |
| Ia-a1039 | N(CH₃)(Et)CH₂CH₂OPO(OH)₂ | —N(C(O)N(H)—CH₂—CH₂—CF₃)— |

-continued
| | | |
|---|---|---|
| Ia-a1040 | 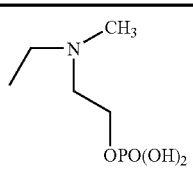 | —N(C(O)N(H)—CH₂—CH₂—CF₃)— |
| Ia-a1041 | 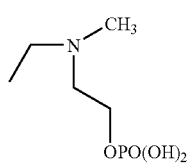 | —N(C(O)N(H)—CH₂—CF₃)— |
| Ia-a1042 | 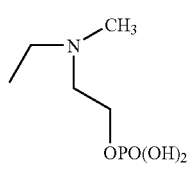 | —N(C(O)N(H)—(CH₂)₃—OH)— |
| Ia-a1043 | 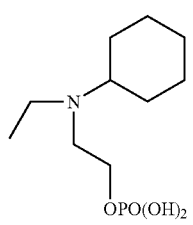 | —CH(OH)— |
| Ia-a1044 | 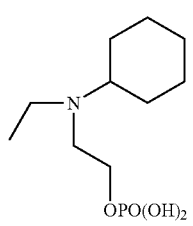 | —N(C(O)N(H)—CH₂—CH₂—OH)— |
| Ia-a1045 | 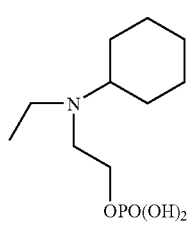 | —N(C(O)N(H)—CH₂—CH₂—F)— |
| Ia-a1046 | 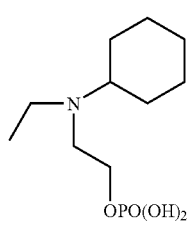 | —N(C(O)N(H)—CH₂—CH₂—OCH₃)— |
| Ia-a1047 | 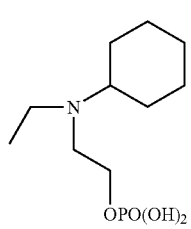 | —N(C(O)N(H)—CH₂—CH₂—CF₃)— |

-continued
| | | |
|---|---|---|
| Ia-a1048 | 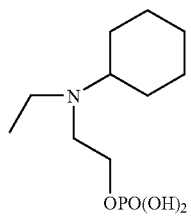 | —N(C(O)N(H)—CH$_2$—CH$_2$—CF$_3$)— |
| Ia-a1049 | 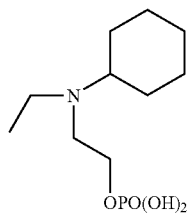 | —N(C(O)N(H)—CH$_2$—CF$_3$)— |
| Ia-a1050 | 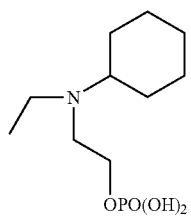 | —N(C(O)N(H)—(CH$_2$)$_3$—OH)— |
| Ia-a1051 | 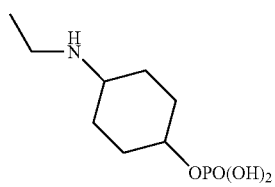 | —CH(OH)— |
| Ia-a1052 | 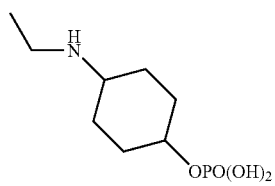 | —N(C(O)N(H)—CH$_2$—CH$_2$—OH)— |
| Ia-a1053 | 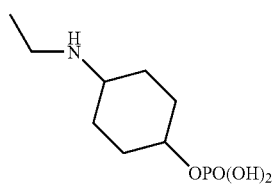 | —N(C(O)N(H)—CH$_2$—CH$_2$—F)— |
| Ia-a1054 | 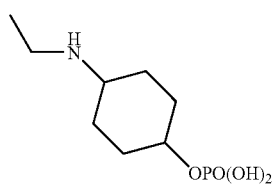 | —N(C(O)N(H)—CH$_2$—CH$_2$—OCH$_3$)— |
| Ia-a1055 | 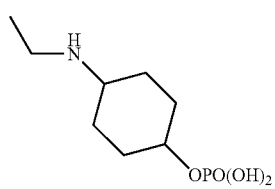 | —N(C(O)N(H)—CH$_2$—CH$_2$—CF$_3$)— |

| | | |
|---|---|---|
| Ia-a1056 | 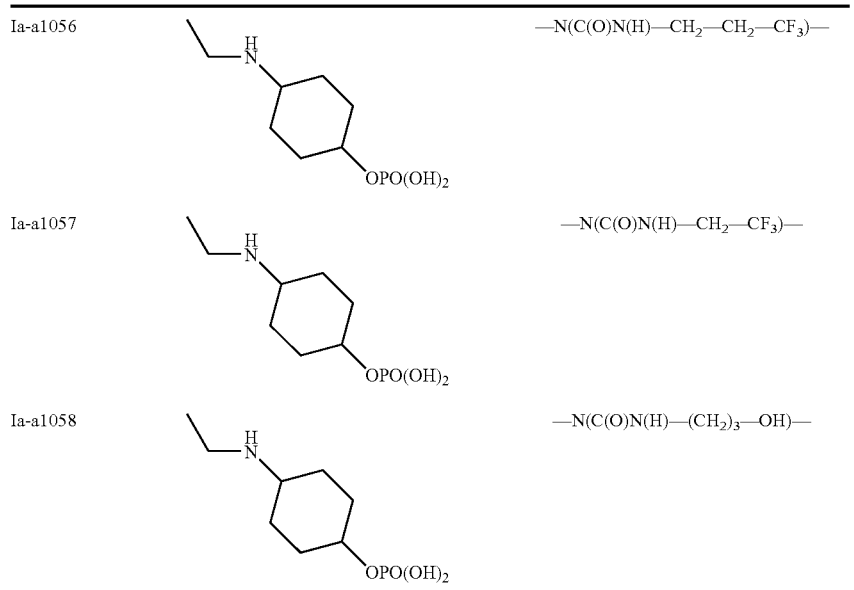 | —N(C(O)N(H)—CH₂—CH₂—CF₃)— |
| Ia-a1057 | | —N(C(O)N(H)—CH₂—CF₃)— |
| Ia-a1058 | | —N(C(O)N(H)—(CH₂)₃—OH)— |

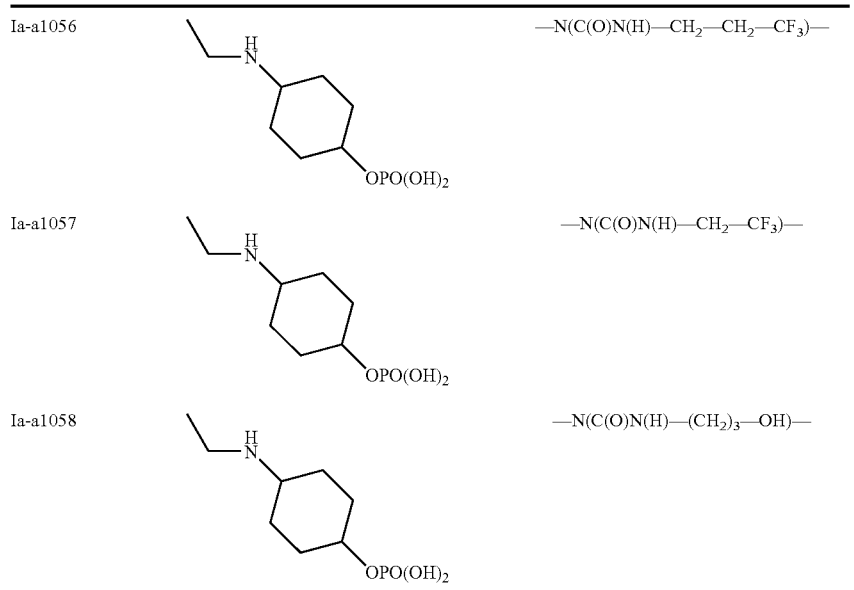

and pharmaceutically acceptable salts thereof.

5.3 The Indenoisoquinolinone Analogs of Formula (IIa)

The present invention provides Indenoisoquinolinone Analogs according to Formula (Ib), below:

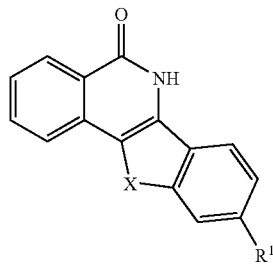

(Ib)

and pharmaceutically acceptable salts thereof,
wherein X and $R^1$ are as defined above for the Indenoisoquinolinone Analogs of Formula (Ib).

In one embodiment, X is —N(CH₃)—. In another embodiment, X is —N(CH₂CH₃)—. In another embodiment, X is —N(CH₂CH₂CH₃)—. In another embodiment, X is —N(CH₂CH₂CH₂CH₃)—. In another embodiment, X is —N(C(H)(CH₃)(CH₂CH₃))—. In another embodiment, X is —N(C(H)(CH₃)₂)—. In another embodiment, X is —N(CH₂C(H)(CH₃)₂)—. In another embodiment, X is —N(C(CH₃)₃)—.

In one embodiment, $R^1$ is —(CH₂)ₙ—N(R²)(R²) and X is —N(CH₃)—.

In another embodiment, $R^1$ is —(CH₂)ₙ—N(R²)(R²) and X is —N(CH₂CH₃)—.

In another embodiment, $R^1$ is —(CH₂)ₙ—N(R²)(R²) and X is —N(CH₂CH₂CH₃)—.

In another embodiment, $R^1$ is —(CH₂)ₙ—N(R²)(R²) and X is —N(CH₂CH₂CH₂CH₃)—.

In another embodiment, $R^1$ is —(CH₂)ₙ—N(R²)(R²) and X is —N(C(H)(CH₃)(CH₂CH₃))—.

In another embodiment, $R^1$ is —(CH₂)ₙ—N(R²)(R²) and X is —N(C(H)(CH₃)₂)—.

In another embodiment, $R^1$ is —(CH₂)ₙ—N(R²)(R²) and X is —N(CH₂C(H)(CH₃)₂)—.

In another embodiment, $R^1$ is —(CH₂)ₙ—N(R²)(R²) and X is —N(C(CH₃)₃)—.

In one embodiment, $R^1$ is —O—(CH₂)ₘ—N(R²)(R²) and X is —N(CH₃)—.

In another embodiment, $R^1$ is —O—(CH₂)ₘ—N(R²)(R²) and X is —N(CH₂CH₃)—.

In another embodiment, $R^1$ is —O—(CH₂)ₘ—N(R²)(R²) and X is —N(CH₂CH₂CH₃)—.

In another embodiment, $R^1$ is —O—(CH₂)ₘ—N(R²)(R²) and X is —N(CH₂CH₂CH₂CH₃)—.

In another embodiment, $R^1$ is —O—(CH₂)ₘ—N(R²)(R²) and X is —N(C(H)(CH₃)(CH₂CH₃))—.

In another embodiment, $R^1$ is —O—(CH₂)ₘ—N(R²)(R²) and X is —N(C(H)(CH₃)₂)—.

In another embodiment, $R^1$ is —O—(CH₂)ₘ—N(R²)(R²) and X is —N(CH₂C(H)(CH₃)₂)—.

In another embodiment, $R^1$ is —O—(CH₂)ₘ—N(R²)(R²) and X is —N(C(CH₃)₃)—.

In one embodiment, one $R^2$ is —H, and the other $R^2$ is —C₁-C₆ alkyl.

In another embodiment, each $R^2$ is —C₁-C₆ alkyl.

In another embodiment, each $R^2$ is -methyl.

In one embodiment, X is —CH(OH)—.

In another embodiment, X is —CH(OH)— and $R^1$ is —(CH₂)ₙ—N(R²)(R²).

In yet another embodiment, X is —CH(OH)— and $R^1$ is —(CH₂)—N(R²)(R²).

In another embodiment, X is —N(C(O)N(H)—(CH₂)ₚ—Z)—.

In another embodiment, X is —N(C(O)N(H)—(CH₂)—Z)—.

In another embodiment, X is —N(C(O)N(H)—(CH₂)₂—Z)—.

In another embodiment, X is —N(C(O)N(H)—(CH₂)ₚ—Z)— and $R^1$ is —(CH₂)ₙ—N(R²)(R²).

In yet another embodiment, X is —N(C(O)N(H)—(CH₂)ₚ—Z)— and $R^1$ is —(CH₂)—N(R²)(R²).

In still another embodiment, X is —N(C(O)N(H)—(CH$_2$)—Z)— and R$^1$ is —(CH$_2$)—N(R$^2$)(R$^2$).

In one embodiment, X is —N((CH$_2$)$_q$—Z)—.

In another embodiment, X is —N((CH$_2$)—Z)—.

In another embodiment, X is —N((CH$_2$)$_2$—Z)—.

In another embodiment, X is —N((CH$_2$)$_q$—Z)— and R$^1$ is —(CH$_2$)$_n$—N(R$^2$)(R$^2$).

In yet another embodiment, X is —N((CH$_2$)$_q$—Z)— and R$^1$ is —(CH$_2$)—N(R$^2$)(R$^2$).

In still another embodiment, X is —N((CH$_2$)—Z)— and R$^1$ is —(CH$_2$)—N(R$^2$)(R$^2$).

In one embodiment, Z is —CF$_3$.

In another embodiment, Z is —F.

In yet another embodiment, Z is —OH.

In still another embodiment, Z is —O—CH$_3$.

In another embodiment, X is —N(C(O)N(H)—(CH$_2$)$_p$—OH)—.

In another embodiment, X is —N(C(O)N(H)—(CH$_2$)$_2$—OH)—.

In another embodiment, X is —N(C(O)N(H)—(CH$_2$)$_p$—OH)— and R$^1$ is —(CH$_2$)$_n$—N(R$^2$)(R$^2$).

In yet another embodiment, X is —N(C(O)N(H)—(CH$_2$)$_p$—OH)— and R$^1$ is —(CH$_2$)—N(R$^2$)(R$^2$).

In still another embodiment, X is —N(C(O)N(H)—(CH$_2$)$_2$—OH)— and R$^1$ is —(CH$_2$)—N(R$^2$)(R$^2$).

In one embodiment, X is —N((CH$_2$)$_q$—OH)—.

In another embodiment, X is —N((CH$_2$)$_2$—OH)—.

In another embodiment, X is —N((CH$_2$)$_q$—OH)— and R$^1$ is —(CH$_2$)$_n$—N(R$^2$)(R$^2$).

In yet another embodiment, X is —N((CH$_2$)$_q$—OH)— and R$^1$ is —(CH$_2$)—N(R$^2$)(R$^2$).

In still another embodiment, X is —N((CH$_2$)$_2$—OH)— and R$^1$ is —(CH$_2$)—N(R$^2$)(R$^2$).

In another embodiment, X is —N(C(O)N(H)—(CH$_2$)$_p$—F)—.

In another embodiment, X is —N(C(O)N(H)—(CH$_2$)—F)—.

In another embodiment, X is —N(C(O)N(H)—(CH$_2$)$_p$—F)— and R$^1$ is —(CH$_2$)$_n$—N(R$^2$)(R$^2$).

In yet another embodiment, X is —N(C(O)N(H)—(CH$_2$)$_p$—F)— and R$^1$ is —(CH$_2$)—N(R$^2$)(R$^2$).

In still another embodiment, X is —N(C(O)N(H)—(CH$_2$)—F)— and R$^1$ is —(CH$_2$)—N(R$^2$)(R$^2$).

In one embodiment, X is —N((CH$_2$)$_q$—F)—.

In another embodiment, X is —N((CH$_2$)—F)—.

In another embodiment, X is —N((CH$_2$)$_q$—F)— and R$^1$ is —(CH$_2$)$_n$—N(R$^2$)(R$^2$).

In yet another embodiment, X is —N((CH$_2$)$_q$—F)— and R$^1$ is —(CH$_2$)—N(R$^2$)(R$^2$).

In still another embodiment, X is —N((CH$_2$)—F)— and R$^1$ is —(CH$_2$)—N(R$^2$)(R$^2$).

In another embodiment, X is —N(C(O)N(H)—(CH$_2$)$_p$—OMe)-.

In another embodiment, X is —N(C(O)N(H)—(CH$_2$)$_2$—OMe)-.

In another embodiment, X is —N(C(O)N(H)—(CH$_2$)$_p$—OMe)- and R$^1$ is —(CH$_2$)$_n$—N(R$^2$)(R$^2$).

In yet another embodiment, X is —N(C(O)N(H)—(CH$_2$)$_p$—OMe)- and R$^1$ is —(CH$_2$)—N(R$^2$)(R$^2$).

In still another embodiment, X is —N(C(O)N(H)—(CH$_2$)$_2$—OMe)- and R$^1$ is —(CH$_2$)—N(R$^2$)(R$^2$).

In one embodiment, X is —N((CH$_2$)$_q$—OMe)-.

In another embodiment, X is —N((CH$_2$)$_2$—OMe)-.

In another embodiment, X is —N((CH$_2$)$_q$—OMe)- and R$^1$ is —(CH$_2$)$_n$—N(R$^2$)(R$^2$).

In yet another embodiment, X is —N((CH$_2$)$_q$—OMe)- and R$^1$ is —(CH$_2$)—N(R$^2$)(R$^2$).

In still another embodiment, X is —N((CH$_2$)$_2$—OMe)- and R$^1$ is —(CH$_2$)—N(R$^2$)(R$^2$).

In another embodiment, X is —N(C(O)N(H)—(CH$_2$)$_p$—CF$_3$)—.

In another embodiment, X is —N(C(O)N(H)—(CH$_2$)—CF$_3$)—.

In another embodiment, X is —N(C(O)N(H)—(CH$_2$)$_p$—CF$_3$)— and R$^1$ is —(CH$_2$)$_n$—N(R$^2$)(R$^2$).

In yet another embodiment, X is —N(C(O)N(H)—(CH$_2$)$_p$—CF$_3$)— and R$^1$ is —(CH$_2$)—N(R$^2$)(R$^2$).

In still another embodiment, X is —N(C(O)N(H)—(CH$_2$)—CF$_3$)— and R$^1$ is —(CH$_2$)—N(R$^2$)(R$^2$).

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and R$^1$ is —(CH$_2$)$_n$—N(R$^2$)(R$^2$).

In yet another embodiment, X is —N((CH$_2$)$_q$—CF$_3$)— and R$^1$ is —(CH$_2$)—N(R$^2$)(R$^2$).

In still another embodiment, X is —N((CH$_2$)—CF$_3$)— and R$^1$ is —(CH$_2$)—N(R$^2$)(R$^2$).

In another embodiment, X is —N(C(O)N(H)—(CH$_2$)$_p$—CF$_3$)—.

In another embodiment, X is —N(C(O)N(H)—(CH$_2$)—CF$_3$)—.

In another embodiment, X is —N(C(O)N(H)—(CH$_2$)$_p$—CF$_3$)— and R$^1$ is —(CH$_2$)$_n$—N(R$^1$)(R$^2$).

In yet another embodiment, X is —N(C(O)N(H)—(CH$_2$)$_p$—CF$_3$)— and R$^1$ is —(CH$_2$)—N(R$^2$)(R$^2$).

In still another embodiment, X is —N(C(O)N(H)—(CH$_2$)—CF$_3$)— and R$^1$ is —(CH$_2$)—N(R$^2$)(R$^2$).

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and R$^1$ is —(CH$_2$)$_n$—N(R$^2$)(R$^2$).

In yet another embodiment, X is —N((CH$_2$)$_q$—CF$_3$)— and R$^1$ is —(CH$_2$)—N(R$^2$)(R$^2$).

In still another embodiment, X is —N((CH$_2$)—CF$_3$)— and R$^1$ is —(CH$_2$)—N(R$^2$)(R$^2$).

In one embodiment, n is 1.

In another embodiment, n is 2.

In yet another embodiment, n is 3.

In a further embodiment, n is 4, 5, or 6.

In yet a further embodiment, n is 7, 8, or 9.

In still a further embodiment, n is 10.

In one embodiment, m is 2.

In another embodiment, m is 3.

In yet another embodiment, m is 4, 5, or 6.

In a further embodiment, m is 7, 8, or 9.

In yet a further embodiment, m is 10.

In one embodiment, p is 1.

In another embodiment, p is 2.

In yet another embodiment, p is an integer ranging from 2 to 5.

In one embodiment, q is 1.

In another embodiment, q is 2.

In yet another embodiment, q is an integer ranging from 2 to 5.

In various embodiments, —N(R$^2$)(R$^2$) is:

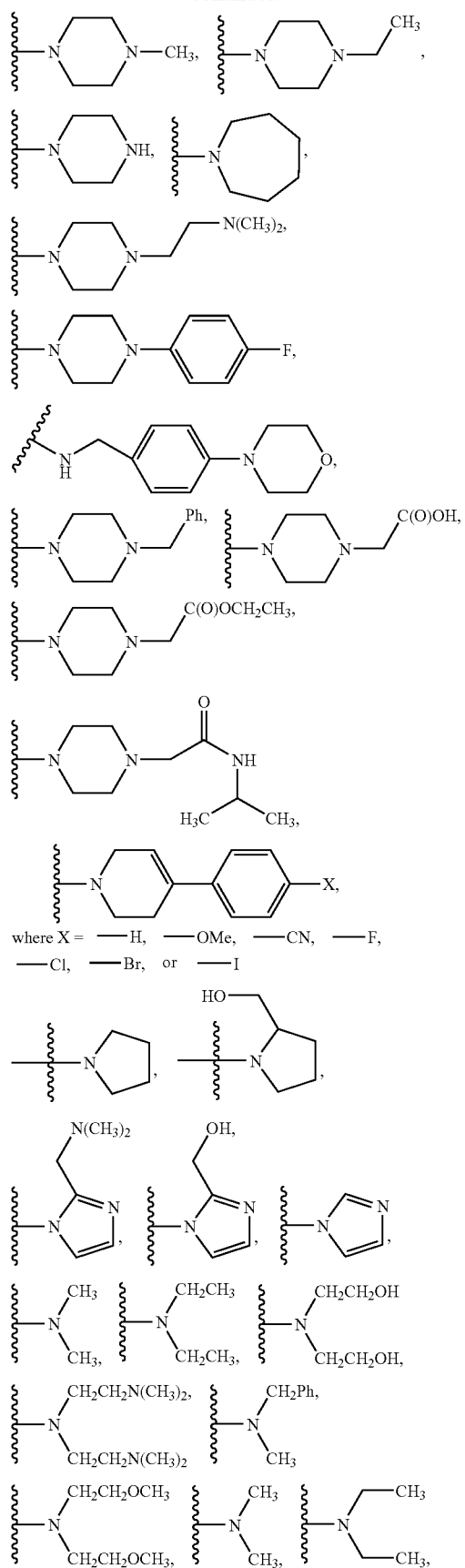
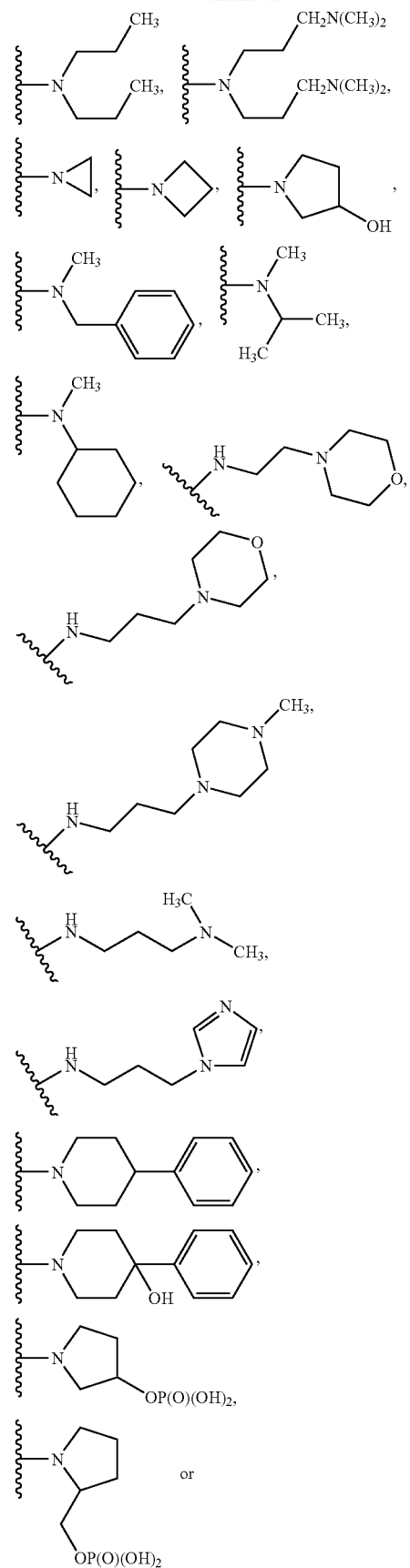

-continued
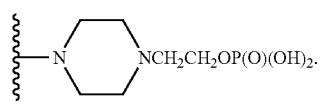
In other embodiments, —N(R²)(R²) is:
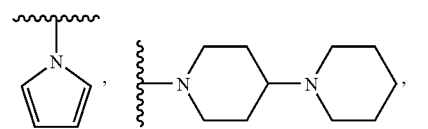
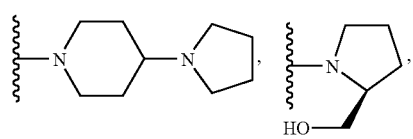
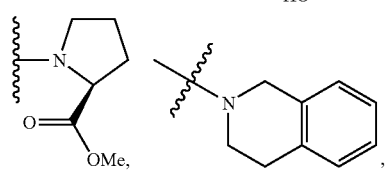
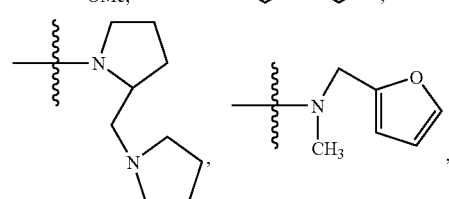
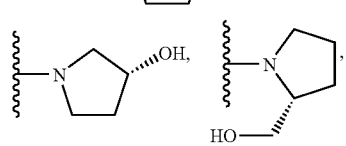
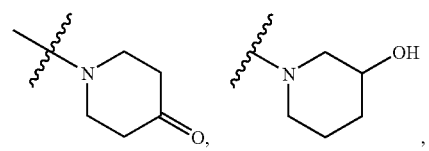
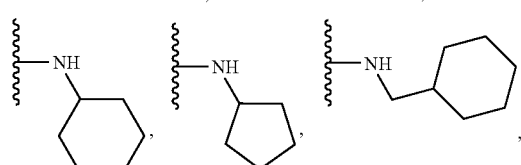
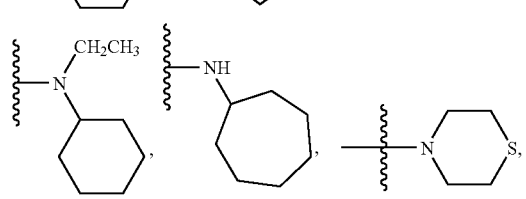
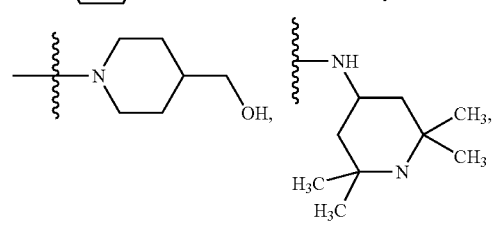
-continued
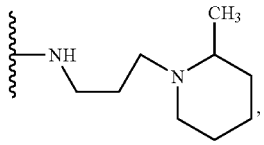
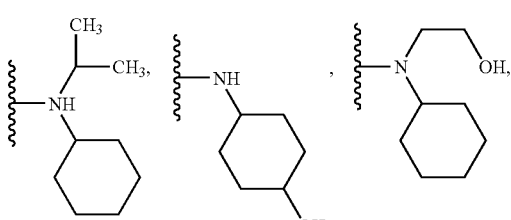
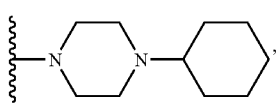
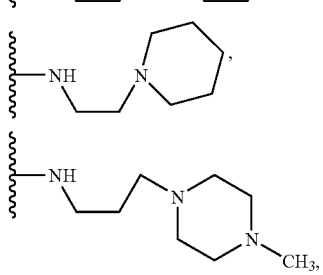
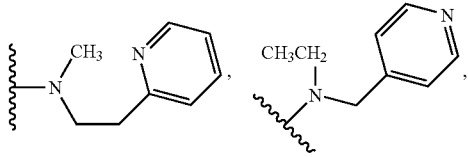
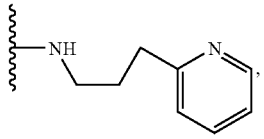
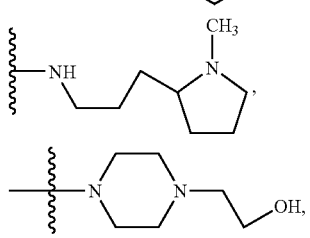
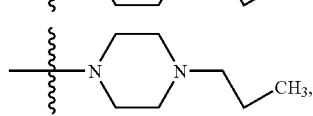
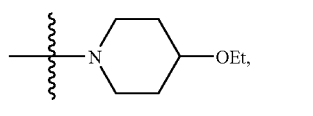
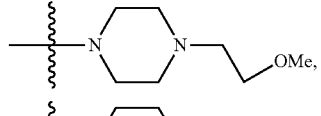
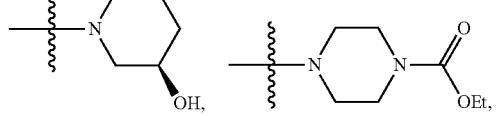

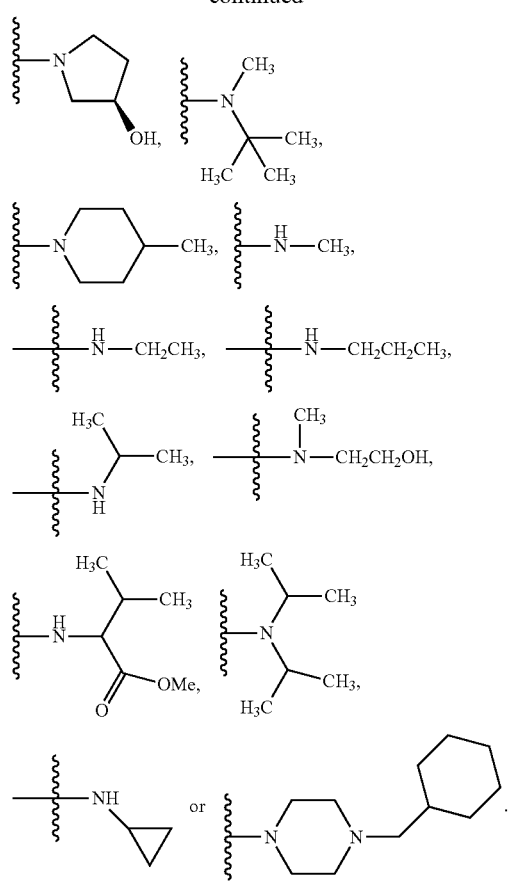
In some embodiments, —N(R²)(R²) is
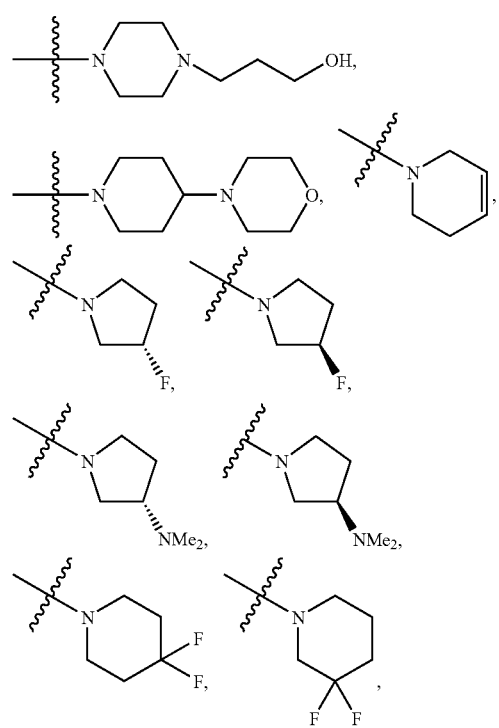
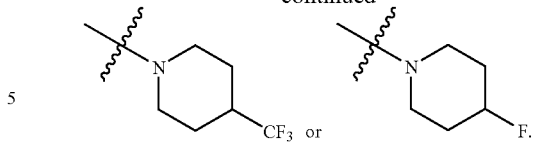
In still other embodiments, —N(R²)(R²) is —N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.
In some embodiments, —N(R²)(R²) is
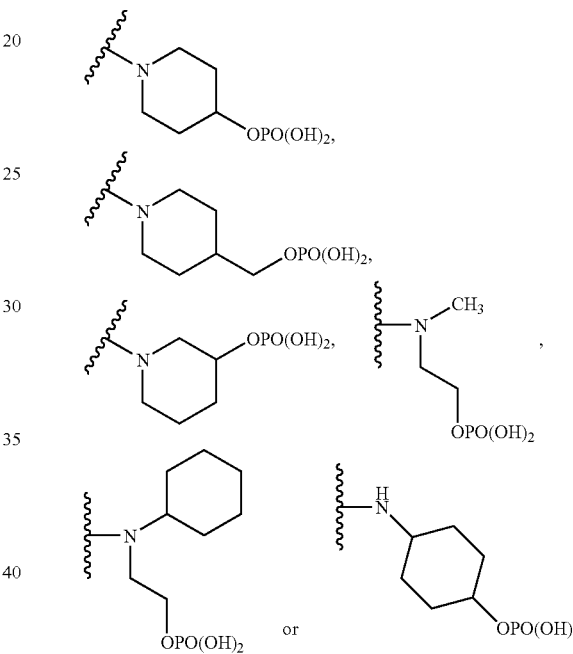
In various embodiments, —N(Z₃)(Z₄) is:
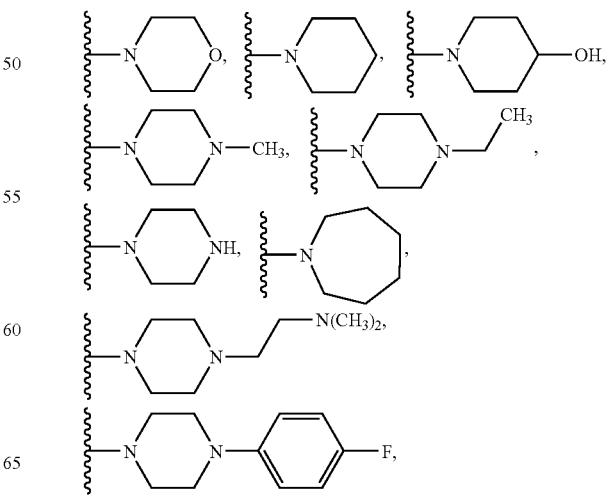

-continued
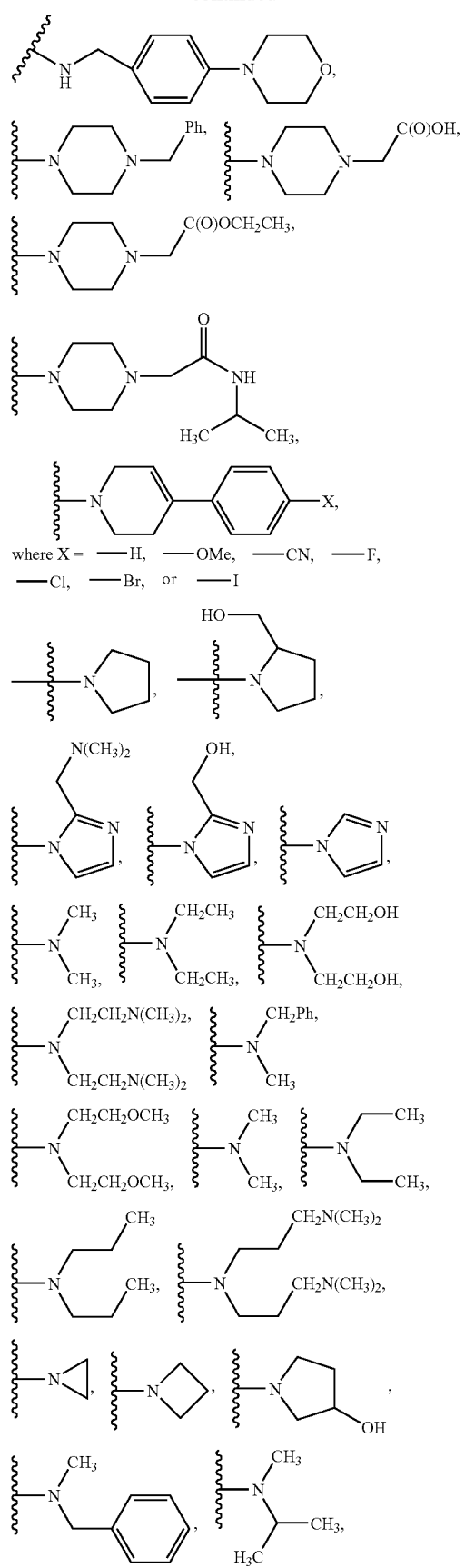
-continued
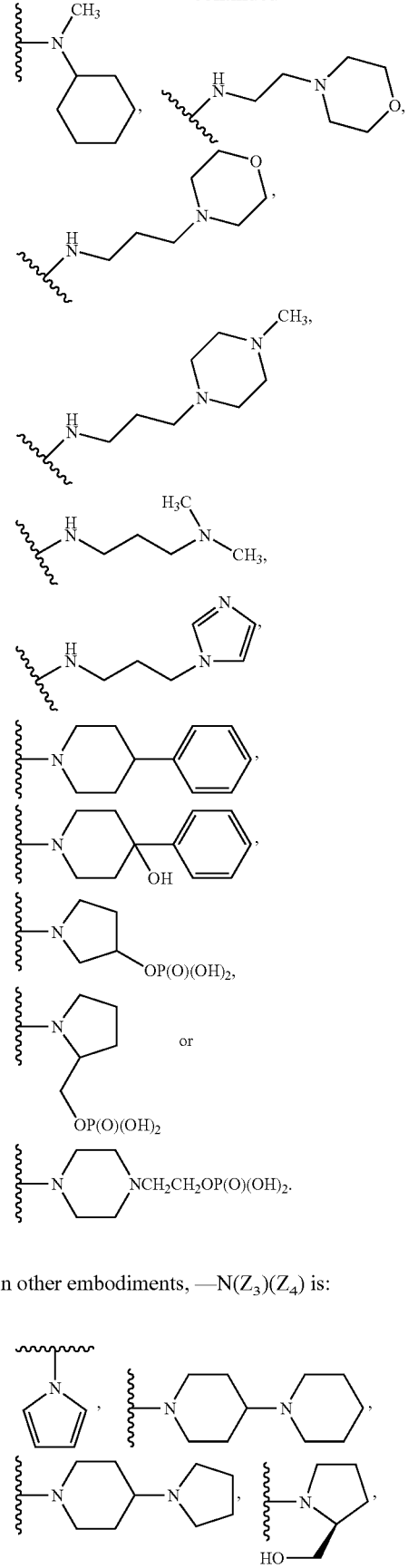
In other embodiments, —N(Z₃)(Z₄) is:

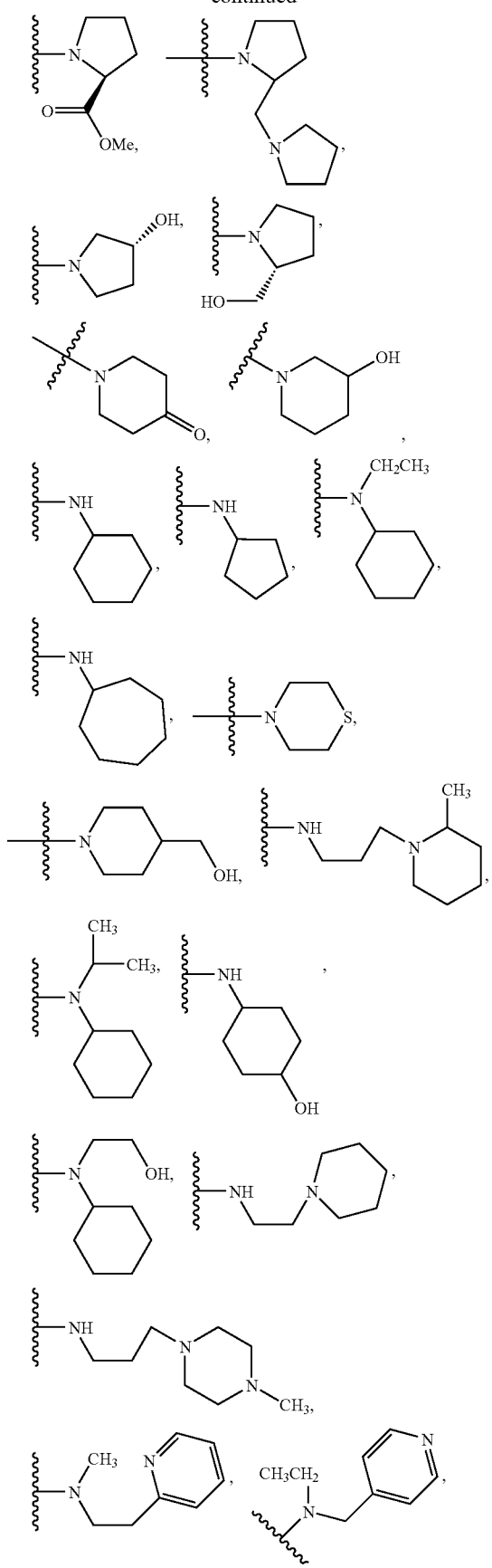
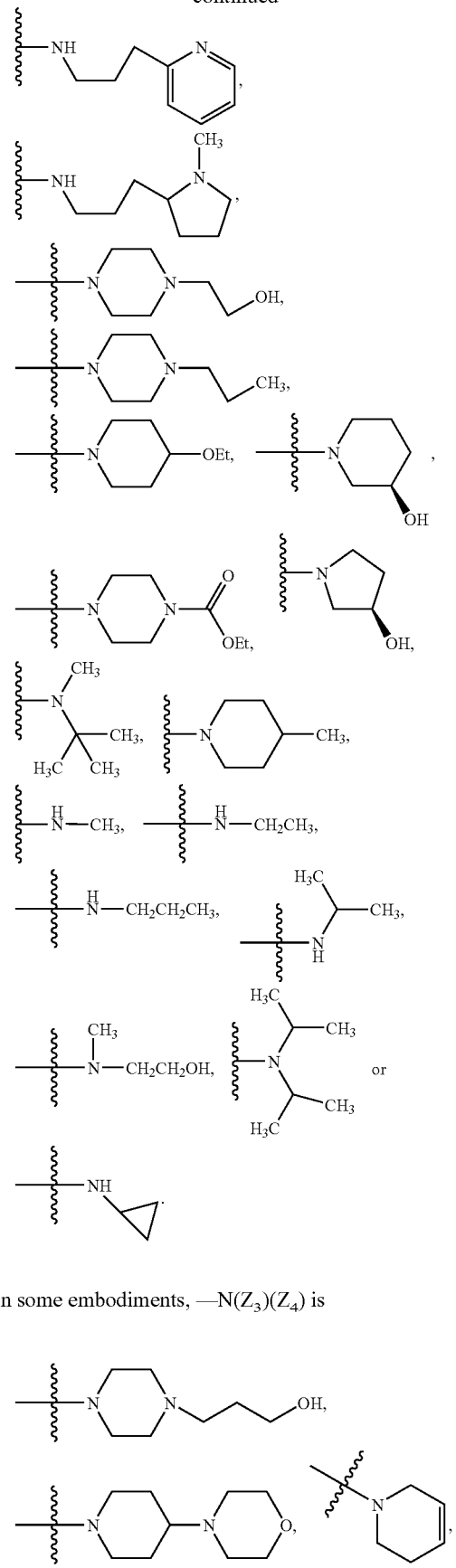
In some embodiments, —N($Z_3$)($Z_4$) is

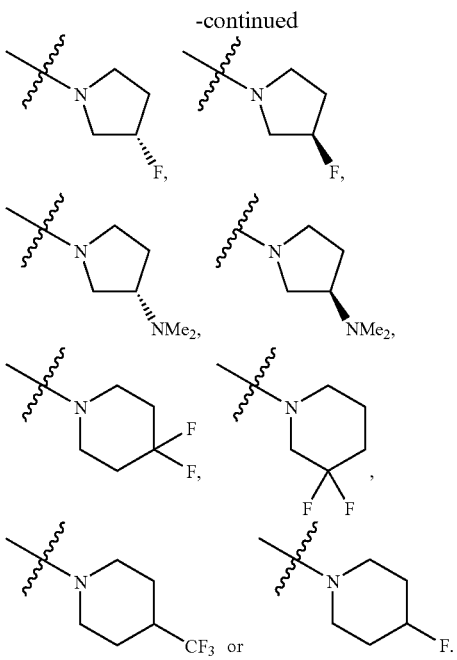

In still other embodiments, —N(Z₃)(Z₄) is —N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.

In some embodiments, —N(Z₃)(Z₄) is

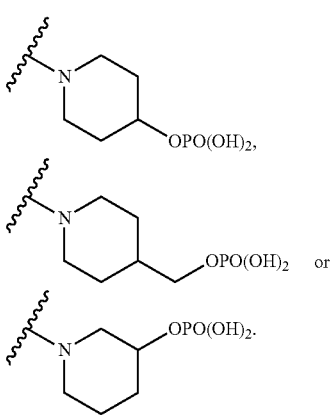

In one embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—;

R¹ is —(CH₂)ₙ—N(R²)(R²) or —O—(CH₂)ₘ—N(R²)(R²);

each R² is independently —H, —C₁-C₆ alkyl, cyclopropyl, cyclobutyl, cyclopentyl, cyclohexyl, —(C₁-C₆ alkylene)-phenyl or -phenyl, each of which other than hydrogen is unsubstituted or substituted with one or more of -halo, —OH, —OP(O)(OH)₂, —OS(O)₂OH or —N(Z₃)(Z₄), where Z₃ and Z₄ are independently —H, —C₁-C₅ alkyl, or —(C₁-C₅ alkylene)-O—C₁-C₅ alkyl, each of which other than hydrogen is unsubstituted or substituted with one or more of -halo, —OH or —NH₂;

or N, Z₃ and Z₄ are taken together to form a nitrogen-containing 3- to 7-membered monocyclic heterocycle which is unsubstituted or substituted with one to three of —C₁-C₅ alkyl, -phenyl, —(C₁-C₅ alkylene)-phenyl, -(hydroxy-substituted) C₁-C₅ alkyl, -halo, -(halo-substituted) C₁-C₅ alkyl, -(halo-substituted) phenyl, -phenylene-O—C₁-C₅ alkyl, -(cyano-substituted) phenyl, —OH, —O—C₁-C₅ alkyl, —N(Rᵃ)₂, —(C₁-C₅ alkylene)-N(Rᵃ)₂, —C₁-C₅ alkylene-C(O)O—(C₁-C₅ alkylene)-N(Rᵃ)₂, —COOH, —(C₁-C₅ alkylene)-COOH, —OP(O)(OH)₂, —OS(O)₂OH, —(C₁-C₅ alkylene)-OP(O)(OH)₂, —(C₁-C₅ alkylene)-OS(O)₂OH, —C(O)O—C₁-C₅ alkyl, —OC(O)—C₁-C₅ alkyl, —(C₁-C₅ alkylene)-C(O)O—C₁-C₅ alkyl, —(C₁-C₅ alkylene)-C(O)NH—C₁-C₅ alkyl, —C(O)NH₂, or —NO₂, wherein each occurrence of Rᵃ is independently —H, -benzyl, or —C₁-C₁₀ alkyl;

or N and both R² groups are taken together to form a nitrogen-containing 3- to 7-membered monocyclic heterocycle which is unsubstituted or substituted with one to three of —C₁-C₅ alkyl, -phenyl, —(C₁-C₅ alkylene)-phenyl, -(hydroxy-substituted) C₁-C₅ alkyl, -halo, -(halo-substituted) C₁-C₅ alkyl, -(halo-substituted) phenyl, -phenylene-O—C₁-C₅ alkyl, -(cyano-substituted) phenyl, —OH, —O—C₁-C₅ alkyl, —N(Rᵃ)₂, —(C₁-C₅ alkylene)-N(Rᵃ)₂, —(C₁-C₅ alkylene)-C(O)O—(C₁-C₅ alkylene)-N(Rᵃ)₂, —COOH, —(C₁-C₅ alkylene)-COOH, —OP(O)(OH)₂, —OS(O)₂OH, —(C₁-C₅ alkylene)-OP(O)(OH)₂, —(C₁-C₅ alkylene)-OS(O)₂OH, —C(O)O—C₁-C₅ alkyl, —OC(O)—C₁-C₅ alkyl, —(C₁-C₅ alkylene)-C(O)O—C₁-C₅ alkyl, —(C₁-C₅ alkylene)-C(O)NH—C₁-C₅ alkyl, —C(O)NH₂, or —NO₂, wherein each occurrence of Rᵃ is independently —H, -benzyl, or —C₁-C₁₀ alkyl;

n is an integer ranging from 1 to 10; and
m is an integer ranging from 2 to 10.

In one embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is methyl.

In another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is ethyl.

In yet another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is propyl.

In one embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is —C₃-C₈ monocyclic cycloalkyl.

In another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is cyclohexyl.

In yet another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; and R¹ is —CH₂—N(R²)(R²), wherein N and both R² groups are taken together to form a nitrogen-containing 3- to 7-membered monocyclic heterocycle.

In one embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; and R¹ is —CH₂—N(R²)(R²), wherein N and both R² groups are taken together to form a nitrogen-containing 3- to 7-membered monocyclic heterocycle, which is substituted with a hydroxyl.

In another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; and R¹ is —CH₂—N(R²)(R²), wherein N and both R² groups are taken together to form a nitrogen-containing 3- to 7-membered monocyclic heterocycle, which is substituted with a nitrogen-containing 3- to 7-membered monocyclic heterocycle.

Illustrative examples of the Indenoisoquinolinone Analogs include the compounds of Formula (Ib) as set forth below:

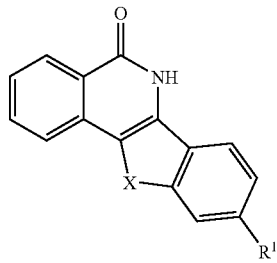

(Ib)

| Compound | n | —R¹ | X |
|---|---|---|---|
| Ib-1 | 1 | —(CH₂)ₙ—N(CH₃)₂ | —N(CH₃)— |
| Ib-2 | 2 | —(CH₂)ₙ—N(CH₃)₂ | —N(CH₃)— |
| Ib-3 | 3 | —(CH₂)ₙ—N(CH₃)₂ | —N(CH₃)— |
| Ib-4 | 4 | —(CH₂)ₙ—N(CH₃)₂ | —N(CH₃)— |
| Ib-5 | 5 | —(CH₂)ₙ—N(CH₃)₂ | —N(CH₃)— |
| Ib-6 | 6 | —(CH₂)ₙ—N(CH₃)₂ | —N(CH₃)— |
| Ib-7 | 1 | —(CH₂)ₙ—N(CH₃)₂ | —N(CH₂CH₃)— |
| Ib-8 | 2 | —(CH₂)ₙ—N(CH₃)₂ | —N(CH₂CH₃)— |
| Ib-9 | 3 | —(CH₂)ₙ—N(CH₃)₂ | —N(CH₂CH₃)— |
| Ib-10 | 4 | —(CH₂)ₙ—N(CH₃)₂ | —N(CH₂CH₃)— |
| Ib-11 | 5 | —(CH₂)ₙ—N(CH₃)₂ | —N(CH₂CH₃)— |
| Ib-12 | 6 | —(CH₂)ₙ—N(CH₃)₂ | —N(CH₂CH₃)— |
| Ib-13 | 1 | —(CH₂)ₙ—N(CH₃)₂ | —N(CH₂CH₂CH₃)— |
| Ib-14 | 2 | —(CH₂)ₙ—N(CH₃)₂ | —N(CH₂CH₂CH₃)— |
| Ib-15 | 3 | —(CH₂)ₙ—N(CH₃)₂ | —N(CH₂CH₂CH₃)— |
| Ib-16 | 4 | —(CH₂)ₙ—N(CH₃)₂ | —N(CH₂CH₂CH₃)— |
| Ib-17 | 5 | —(CH₂)ₙ—N(CH₃)₂ | —N(CH₂CH₂CH₃)— |
| Ib-18 | 6 | —(CH₂)ₙ—N(CH₃)₂ | —N(CH₂CH₂CH₃)— |
| Ib-19 | 1 | —(CH₂)ₙ—N(CH₃)₂ | —N(CH₂CH₂CH₂CH₃)— |
| Ib-20 | 2 | —(CH₂)ₙ—N(CH₃)₂ | —N(CH₂CH₂CH₂CH₃)— |
| Ib-21 | 3 | —(CH₂)ₙ—N(CH₃)₂ | —N(CH₂CH₂CH₂CH₃)— |
| Ib-22 | 4 | —(CH₂)ₙ—N(CH₃)₂ | —N(CH₂CH₂CH₂CH₃)— |
| Ib-23 | 5 | —(CH₂)ₙ—N(CH₃)₂ | —N(CH₂CH₂CH₂CH₃)— |
| Ib-24 | 6 | —(CH₂)ₙ—N(CH₃)₂ | —N(CH₂CH₂CH₂CH₃)— |
| Ib-25 | 1 | —(CH₂)ₙ—N(CH₃)₂ | —N(C(H)(CH₃)(CH₂CH₃))— |
| Ib-26 | 2 | —(CH₂)ₙ—N(CH₃)₂ | —N(C(H)(CH₃)(CH₂CH₃))— |
| Ib-27 | 3 | —(CH₂)ₙ—N(CH₃)₂ | —N(C(H)(CH₃)(CH₂CH₃))— |
| Ib-28 | 4 | —(CH₂)ₙ—N(CH₃)₂ | —N(C(H)(CH₃)(CH₂CH₃))— |
| Ib-29 | 5 | —(CH₂)ₙ—N(CH₃)₂ | —N(C(H)(CH₃)(CH₂CH₃))— |
| Ib-30 | 6 | —(CH₂)ₙ—N(CH₃)₂ | —N(C(H)(CH₃)(CH₂CH₃))— |
| Ib-31 | 1 | —(CH₂)ₙ—N(CH₃)₂ | —N(C(H)(CH₃)₂)— |
| Ib-32 | 2 | —(CH₂)ₙ—N(CH₃)₂ | —N(C(H)(CH₃)₂)— |
| Ib-33 | 3 | —(CH₂)ₙ—N(CH₃)₂ | —N(C(H)(CH₃)₂)— |
| Ib-34 | 4 | —(CH₂)ₙ—N(CH₃)₂ | —N(C(H)(CH₃)₂)— |
| Ib-35 | 5 | —(CH₂)ₙ—N(CH₃)₂ | —N(C(H)(CH₃)₂)— |
| Ib-36 | 6 | —(CH₂)ₙ—N(CH₃)₂ | —N(C(H)(CH₃)₂)— |
| Ib-37 | 1 | —(CH₂)ₙ—N(CH₃)₂ | —N(CH₂C(H)(CH₃)₂)— |
| Ib-38 | 2 | —(CH₂)ₙ—N(CH₃)₂ | —N(CH₂C(H)(CH₃)₂)— |
| Ib-39 | 3 | —(CH₂)ₙ—N(CH₃)₂ | —N(CH₂C(H)(CH₃)₂)— |
| Ib-40 | 4 | —(CH₂)ₙ—N(CH₃)₂ | —N(CH₂C(H)(CH₃)₂)— |
| Ib-41 | 5 | —(CH₂)ₙ—N(CH₃)₂ | —N(CH₂C(H)(CH₃)₂)— |
| Ib-42 | 6 | —(CH₂)ₙ—N(CH₃)₂ | —N(CH₂C(H)(CH₃)₂)— |
| Ib-43 | 1 | —(CH₂)ₙ—N(CH₃)₂ | —N(C(CH₃)₃)— |
| Ib-44 | 2 | —(CH₂)ₙ—N(CH₃)₂ | —N(C(CH₃)₃)— |
| Ib-45 | 3 | —(CH₂)ₙ—N(CH₃)₂ | —N(C(CH₃)₃)— |
| Ib-46 | 4 | —(CH₂)ₙ—N(CH₃)₂ | —N(C(CH₃)₃)— |
| Ib-47 | 5 | —(CH₂)ₙ—N(CH₃)₂ | —N(C(CH₃)₃)— |
| Ib-48 | 6 | —(CH₂)ₙ—N(CH₃)₂ | —N(C(CH₃)₃)— |

-continued

| | | | |
|---|---|---|---|
| Ib-49 | 1 | 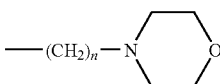—(CH$_2$)$_n$—N(morpholine) | —N(CH$_3$)— |
| Ib-50 | 2 | 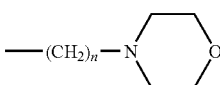—(CH$_2$)$_n$—N(morpholine) | —N(CH$_3$)— |
| Ib-51 | 3 | 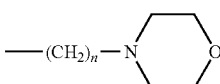—(CH$_2$)$_n$—N(morpholine) | —N(CH$_3$)— |
| Ib-52 | 4 | 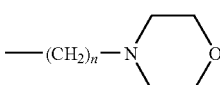—(CH$_2$)$_n$—N(morpholine) | —N(CH$_3$)— |
| Ib-53 | 5 | 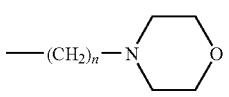—(CH$_2$)$_n$—N(morpholine) | —N(CH$_3$)— |
| Ib-54 | 6 | 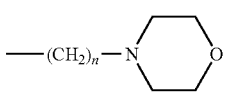—(CH$_2$)$_n$—N(morpholine) | —N(CH$_3$)— |
| Ib-55 | 1 | 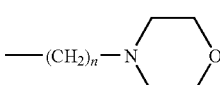—(CH$_2$)$_n$—N(morpholine) | —N(CH$_2$CH$_3$)— |
| Ib-56 | 2 | 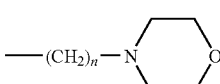—(CH$_2$)$_n$—N(morpholine) | —N(CH$_2$CH$_3$)— |
| Ib-57 | 3 | 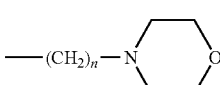—(CH$_2$)$_n$—N(morpholine) | —N(CH$_2$CH$_3$)— |
| Ib-58 | 4 | 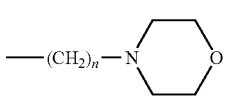—(CH$_2$)$_n$—N(morpholine) | —N(CH$_2$CH$_3$)— |
| Ib-59 | 5 | 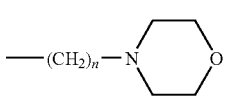—(CH$_2$)$_n$—N(morpholine) | —N(CH$_2$CH$_3$)— |
| Ib-60 | 6 | 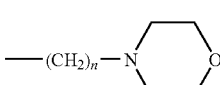—(CH$_2$)$_n$—N(morpholine) | —N(CH$_2$CH$_3$)— |
| Ib-61 | 1 | 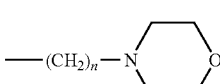—(CH$_2$)$_n$—N(morpholine) | —N(CH$_2$CH$_2$CH$_3$)— |
| Ib-62 | 2 | 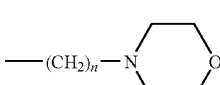—(CH$_2$)$_n$—N(morpholine) | —N(CH$_2$CH$_2$CH$_3$)— |
| Ib-63 | 3 | 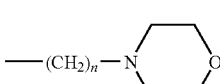—(CH$_2$)$_n$—N(morpholine) | —N(CH$_2$CH$_2$CH$_3$)— |
| Ib-64 | 4 | 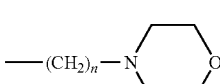—(CH$_2$)$_n$—N(morpholine) | —N(CH$_2$CH$_2$CH$_3$)— |

| | | | |
|---|---|---|---|
| Ib-65 | 5 | 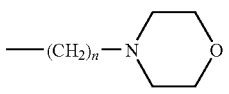 —(CH$_2$)$_n$—N(morpholine) | —N(CH$_2$CH$_3$)— |
| Ib-66 | 6 | 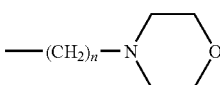 —(CH$_2$)$_n$—N(morpholine) | —N(CH$_2$CH$_3$)— |
| Ib-67 | 1 | 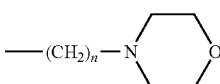 —(CH$_2$)$_n$—N(morpholine) | —N(CH$_2$CH$_2$CH$_3$)— |
| Ib-68 | 2 | 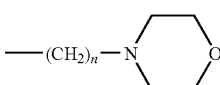 —(CH$_2$)$_n$—N(morpholine) | —N(CH$_2$CH$_2$CH$_3$)— |
| Ib-69 | 3 | 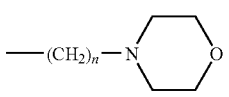 —(CH$_2$)$_n$—N(morpholine) | —N(CH$_2$CH$_2$CH$_3$)— |
| Ib-70 | 4 | 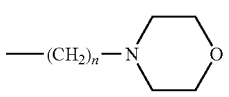 —(CH$_2$)$_n$—N(morpholine) | —N(CH$_2$CH$_2$CH$_3$)— |
| Ib-71 | 5 | 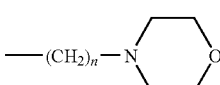 —(CH$_2$)$_n$—N(morpholine) | —N(CH$_2$CH$_2$CH$_3$)— |
| Ib-72 | 6 | 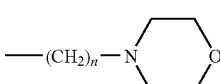 —(CH$_2$)$_n$—N(morpholine) | —N(CH$_2$CH$_2$CH$_3$)— |
| Ib-73 | 1 | 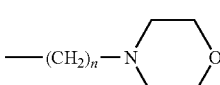 —(CH$_2$)$_n$—N(morpholine) | —N(C(H)(CH$_3$)(CH$_2$CH$_3$))— |
| Ib-74 | 2 | 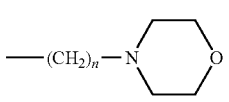 —(CH$_2$)$_n$—N(morpholine) | —N(C(H)(CH$_3$)(CH$_2$CH$_3$))— |
| Ib-75 | 3 | 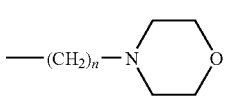 —(CH$_2$)$_n$—N(morpholine) | —N(C(H)(CH$_3$)(CH$_2$CH$_3$))— |
| Ib-76 | 4 | 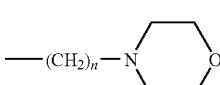 —(CH$_2$)$_n$—N(morpholine) | —N(C(H)(CH$_3$)(CH$_2$CH$_3$))— |
| Ib-77 | 5 |  —(CH$_2$)$_n$—N(morpholine) | —N(C(H)(CH$_3$)(CH$_2$CH$_3$))— |
| Ib-78 | 6 | 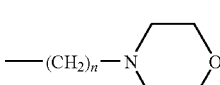 —(CH$_2$)$_n$—N(morpholine) | —N(C(H)(CH$_3$)(CH$_2$CH$_3$))— |
| Ib-79 | 1 | 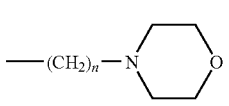 —(CH$_2$)$_n$—N(morpholine) | —N(C(H)(CH$_3$)$_2$)— |
| Ib-80 | 2 |  —(CH$_2$)$_n$—N(morpholine) | —N(C(H)(CH$_3$)$_2$)— |

-continued

| | | | |
|---|---|---|---|
| Ib-81 | 3 | 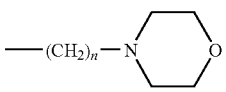 —(CH$_2$)$_n$—N⟨O⟩ | —N(C(H)(CH$_3$)$_2$)— |
| Ib-82 | 4 | 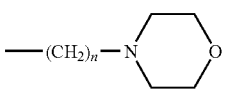 —(CH$_2$)$_n$—N⟨O⟩ | —N(C(H)(CH$_3$)$_2$)— |
| Ib-83 | 5 | 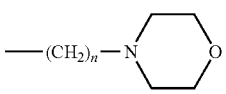 —(CH$_2$)$_n$—N⟨O⟩ | —N(C(H)(CH$_3$)$_2$)— |
| Ib-84 | 6 | 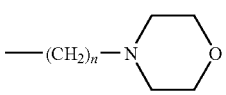 —(CH$_2$)$_n$—N⟨O⟩ | —N(C(H)(CH$_3$)$_2$)— |
| Ib-85 | 1 | 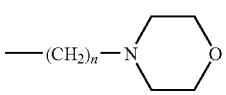 —(CH$_2$)$_n$—N⟨O⟩ | —N(CH$_2$C(H)(CH$_3$)$_2$)— |
| Ib-86 | 2 | 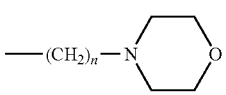 —(CH$_2$)$_n$—N⟨O⟩ | —N(CH$_2$C(H)(CH$_3$)$_2$)— |
| Ib-87 | 3 | 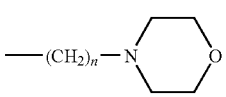 —(CH$_2$)$_n$—N⟨O⟩ | —N(CH$_2$C(H)(CH$_3$)$_2$)— |
| Ib-88 | 4 | 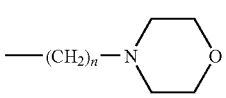 —(CH$_2$)$_n$—N⟨O⟩ | —N(CH$_2$C(H)(CH$_3$)$_2$)— |
| Ib-89 | 5 | 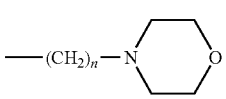 —(CH$_2$)$_n$—N⟨O⟩ | —N(CH$_2$C(H)(CH$_3$)$_2$)— |
| Ib-90 | 6 | 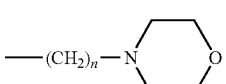 —(CH$_2$)$_n$—N⟨O⟩ | —N(CH$_2$C(H)(CH$_3$)$_2$)— |
| Ib-91 | 1 | 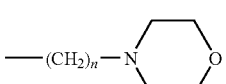 —(CH$_2$)$_n$—N⟨O⟩ | —N(C(CH$_3$)$_3$)— |
| Ib-92 | 2 | 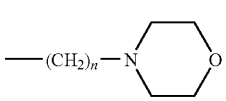 —(CH$_2$)$_n$—N⟨O⟩ | —N(C(CH$_3$)$_3$)— |
| Ib-93 | 3 | 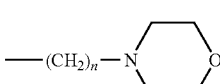 —(CH$_2$)$_n$—N⟨O⟩ | —N(C(CH$_3$)$_3$)— |
| Ib-94 | 4 | 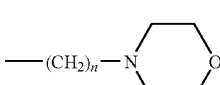 —(CH$_2$)$_n$—N⟨O⟩ | —N(C(CH$_3$)$_3$)— |
| Ib-95 | 5 | 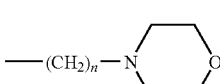 —(CH$_2$)$_n$—N⟨O⟩ | —N(C(CH$_3$)$_3$)— |
| Ib-96 | 6 | 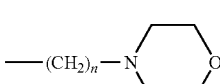 —(CH$_2$)$_n$—N⟨O⟩ | —N(C(CH$_3$)$_3$)— |

-continued

| Compound | m | —R$^1$ | X |
|---|---|---|---|
| Ib-146 | 2 | —O—(CH$_2$)$_m$—N(CH$_3$)$_2$ | —N(CH$_3$)— |
| Ib-147 | 3 | —O—(CH$_2$)$_m$—N(CH$_3$)$_2$ | —N(CH$_3$)— |
| Ib-148 | 4 | —O—(CH$_2$)$_m$—N(CH$_3$)$_2$ | —N(CH$_3$)— |
| Ib-149 | 5 | —O—(CH$_2$)$_m$—N(CH$_3$)$_2$ | —N(CH$_3$)— |
| Ib-150 | 6 | —O—(CH$_2$)$_m$—N(CH$_3$)$_2$ | —N(CH$_3$)— |
| Ib-151 | 2 | —O—(CH$_2$)$_m$—N(CH$_3$)$_2$ | —N(CH$_3$)— |
| Ib-152 | 3 | —O—(CH$_2$)$_m$—N(CH$_3$)$_2$ | —N(CH$_2$CH$_3$)— |
| Ib-153 | 4 | —O—(CH$_2$)$_m$—N(CH$_3$)$_2$ | —N(CH$_2$CH$_3$)— |
| Ib-154 | 5 | —O—(CH$_2$)$_m$—N(CH$_3$)$_2$ | —N(CH$_2$CH$_3$)— |
| Ib-155 | 6 | —O—(CH$_2$)$_m$—N(CH$_3$)$_2$ | —N(CH$_2$CH$_3$)— |
| Ib-156 | 2 | —O—(CH$_2$)$_m$—N(CH$_3$)$_2$ | —N(CH$_2$CH$_3$)— |
| Ib-157 | 3 | —O—(CH$_2$)$_m$—N(CH$_3$)$_2$ | —N(CH$_2$CH$_3$)— |
| Ib-158 | 4 | —O—(CH$_2$)$_m$—N(CH$_3$)$_2$ | —N(CH$_2$CH$_2$CH$_3$)— |
| Ib-159 | 5 | —O—(CH$_2$)$_m$—N(CH$_3$)$_2$ | —N(CH$_2$CH$_2$CH$_3$)— |
| Ib-160 | 6 | —O—(CH$_2$)$_m$—N(CH$_3$)$_2$ | —N(CH$_2$CH$_2$CH$_3$)— |
| Ib-161 | 2 | —O—(CH$_2$)$_m$—N(CH$_3$)$_2$ | —N(CH$_2$CH$_2$CH$_3$)— |
| Ib-162 | 3 | —O—(CH$_2$)$_m$—N(CH$_3$)$_2$ | —N(CH$_2$CH$_2$CH$_3$)— |
| Ib-163 | 4 | —O—(CH$_2$)$_m$—N(CH$_3$)$_2$ | —N(CH$_2$CH$_2$CH$_3$)— |
| Ib-164 | 5 | —O—(CH$_2$)$_m$—N(CH$_3$)$_2$ | —N(CH$_2$CH$_2$CH$_2$CH$_3$)— |
| Ib-165 | 6 | —O—(CH$_2$)$_m$—N(CH$_3$)$_2$ | —N(CH$_2$CH$_2$CH$_2$CH$_3$)— |
| Ib-166 | 2 | —O—(CH$_2$)$_m$—N(CH$_3$)$_2$ | —N(CH$_2$CH$_2$CH$_2$CH$_3$)— |
| Ib-167 | 3 | —O—(CH$_2$)$_m$—N(CH$_3$)$_2$ | —N(CH$_2$CH$_2$CH$_2$CH$_3$)— |
| Ib-168 | 4 | —O—(CH$_2$)$_m$—N(CH$_3$)$_2$ | —N(CH$_2$CH$_2$CH$_2$CH$_3$)— |
| Ib-169 | 5 | —O—(CH$_2$)$_m$—N(CH$_3$)$_2$ | —N(CH$_2$CH$_2$CH$_2$CH$_3$)— |
| Ib-170 | 6 | —O—(CH$_2$)$_m$—N(CH$_3$)$_2$ | —N(C(H)(CH$_3$)(CH$_2$CH$_3$))— |
| Ib-171 | 2 | —O—(CH$_2$)$_m$—N(CH$_3$)$_2$ | —N(C(H)(CH$_3$)(CH$_2$CH$_3$))— |
| Ib-172 | 3 | —O—(CH$_2$)$_m$—N(CH$_3$)$_2$ | —N(C(H)(CH$_3$)(CH$_2$CH$_3$))— |
| Ib-173 | 4 | —O—(CH$_2$)$_m$—N(CH$_3$)$_2$ | —N(C(H)(CH$_3$)(CH$_2$CH$_3$))— |
| Ib-174 | 5 | —O—(CH$_2$)$_m$—N(CH$_3$)$_2$ | —N(C(H)(CH$_3$)(CH$_2$CH$_3$))— |
| Ib-175 | 6 | —O—(CH$_2$)$_m$—N(CH$_3$)$_2$ | —N(C(H)(CH$_3$)(CH$_2$CH$_3$))— |
| Ib-176 | 2 | —O—(CH$_2$)$_m$—N(CH$_3$)$_2$ | —N(C(H)(CH$_3$)$_2$)— |
| Ib-178 | 3 | —O—(CH$_2$)$_m$—N(CH$_3$)$_2$ | —N(C(H)(CH$_3$)$_2$)— |
| Ib-179 | 4 | —O—(CH$_2$)$_m$—N(CH$_3$)$_2$ | —N(C(H)(CH$_3$)$_2$)— |
| Ib-180 | 5 | —O—(CH$_2$)$_m$—N(CH$_3$)$_2$ | —N(C(H)(CH$_3$)$_2$)— |
| Ib-181 | 6 | —O—(CH$_2$)$_m$—N(CH$_3$)$_2$ | —N(C(H)(CH$_3$)$_2$)— |
| Ib-182 | 2 | —O—(CH$_2$)$_m$—N(CH$_3$)$_2$ | —N(C(H)(CH$_3$)$_2$)— |
| Ib-183 | 3 | —O—(CH$_2$)$_m$—N(CH$_3$)$_2$ | —N(CH$_2$C(H)(CH$_3$)$_2$)— |
| Ib-184 | 4 | —O—(CH$_2$)$_m$—N(CH$_3$)$_2$ | —N(CH$_2$C(H)(CH$_3$)$_2$)— |
| Ib-185 | 5 | —O—(CH$_2$)$_m$—N(CH$_3$)$_2$ | —N(CH$_2$C(H)(CH$_3$)$_2$)— |
| Ib-186 | 6 | —O—(CH$_2$)$_m$—N(CH$_3$)$_2$ | —N(CH$_2$C(H)(CH$_3$)$_2$)— |
| Ib-187 | 2 | 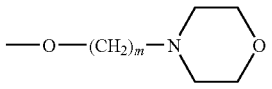 | —N(CH$_3$)— |
| Ib-188 | 3 | 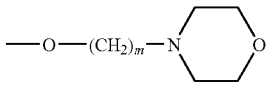 | —N(CH$_3$)— |
| Ib-189 | 4 | 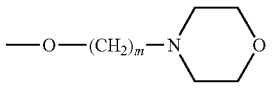 | —N(CH$_3$)— |
| Ib-190 | 5 | 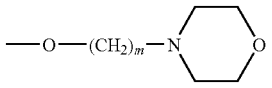 | —N(CH$_3$)— |
| Ib-191 | 6 | 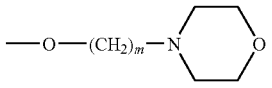 | —N(CH$_3$)— |
| Ib-192 | 2 | 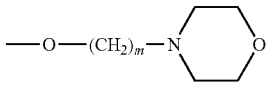 | —N(CH$_3$)— |
| Ib-193 | 3 | 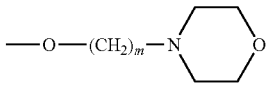 | —N(CH$_2$CH$_3$)— |

-continued

| | | | |
|---|---|---|---|
| Ib-194 | 4 | 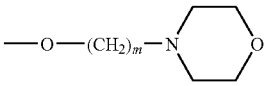 —O—(CH$_2$)$_m$—N(morpholine) | —N(CH$_2$CH$_3$)— |
| Ib-195 | 5 | 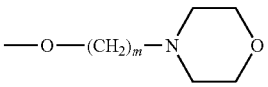 —O—(CH$_2$)$_m$—N(morpholine) | —N(CH$_2$CH$_3$)— |
| Ib-196 | 6 | 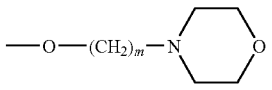 —O—(CH$_2$)$_m$—N(morpholine) | —N(CH$_2$CH$_3$)— |
| Ib-197 | 2 | 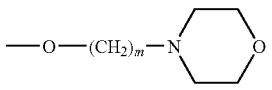 —O—(CH$_2$)$_m$—N(morpholine) | —N(CH$_2$CH$_3$)— |
| Ib-198 | 3 | 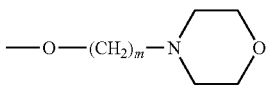 —O—(CH$_2$)$_m$—N(morpholine) | —N(CH$_2$CH$_3$)— |
| Ib-199 | 4 | 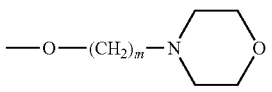 —O—(CH$_2$)$_m$—N(morpholine) | —N(CH$_2$CH$_2$CH$_3$)— |
| Ib-200 | 5 | 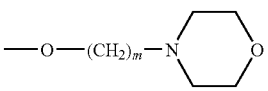 —O—(CH$_2$)$_m$—N(morpholine) | —N(CH$_2$CH$_2$CH$_3$)— |
| Ib-201 | 6 | 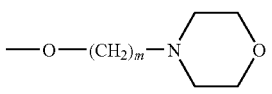 —O—(CH$_2$)$_m$—N(morpholine) | —N(CH$_2$CH$_2$CH$_3$)— |
| Ib-202 | 2 | 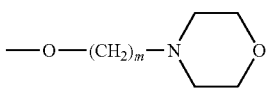 —O—(CH$_2$)$_m$—N(morpholine) | —N(CH$_2$CH$_2$CH$_3$)— |
| Ib-203 | 3 | 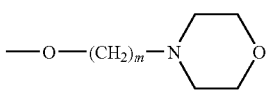 —O—(CH$_2$)$_m$—N(morpholine) | —N(CH$_2$CH$_2$CH$_3$)— |
| Ib-204 | 4 | 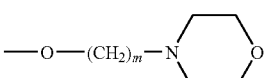 —O—(CH$_2$)$_m$—N(morpholine) | —N(CH$_2$CH$_2$CH$_3$)— |
| Ib-205 | 5 | 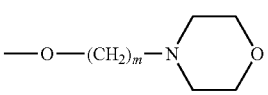 —O—(CH$_2$)$_m$—N(morpholine) | —N(CH$_2$CH$_2$CH$_2$CH$_3$)— |
| Ib-206 | 6 | 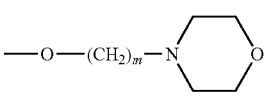 —O—(CH$_2$)$_m$—N(morpholine) | —N(CH$_2$CH$_2$CH$_2$CH$_3$)— |
| Ib-207 | 2 | 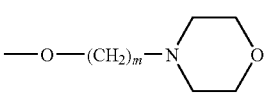 —O—(CH$_2$)$_m$—N(morpholine) | —N(CH$_2$CH$_2$CH$_2$CH$_3$)— |
| Ib-208 | 3 | 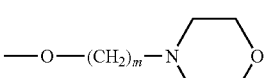 —O—(CH$_2$)$_m$—N(morpholine) | —N(CH$_2$CH$_2$CH$_2$CH$_3$)— |
| Ib-209 | 4 | 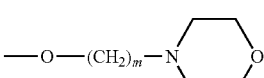 —O—(CH$_2$)$_m$—N(morpholine) | —N(CH$_2$CH$_2$CH$_2$CH$_3$)— |

-continued

| | | | |
|---|---|---|---|
| Ib-210 | 5 | —O—(CH₂)ₘ—N(morpholine) | —N(CH₂CH₂CH₂CH₃)— |
| Ib-211 | 6 | —O—(CH₂)ₘ—N(morpholine) | —N(C(H)(CH₃)(CH₂CH₃))— |
| Ib-212 | 2 | —O—(CH₂)ₘ—N(morpholine) | —N(C(H)(CH₃)(CH₂CH₃))— |
| Ib-213 | 3 | —O—(CH₂)ₘ—N(morpholine) | —N(C(H)(CH₃)(CH₂CH₃))— |
| Ib-214 | 4 | —O—(CH₂)ₘ—N(morpholine) | —N(C(H)(CH₃)(CH₂CH₃))— |
| Ib-215 | 5 | —O—(CH₂)ₘ—N(morpholine) | —N(C(H)(CH₃)(CH₂CH₃))— |
| Ib-216 | 6 | —O—(CH₂)ₘ—N(morpholine) | —N(C(H)(CH₃)(CH₂CH₃))— |
| Ib-217 | 2 | —O—(CH₂)ₘ—N(morpholine) | —N(C(H)(CH₃)₂)— |
| Ib-218 | 3 | —O—(CH₂)ₘ—N(morpholine) | —N(C(H)(CH₃)₂)— |
| Ib-219 | 4 | —O—(CH₂)ₘ—N(morpholine) | —N(C(H)(CH₃)₂)— |
| Ib-220 | 5 | —O—(CH₂)ₘ—N(morpholine) | —N(C(H)(CH₃)₂)— |
| Ib-221 | 6 | —O—(CH₂)ₘ—N(morpholine) | —N(C(H)(CH₃)₂)— |
| Ib-222 | 2 | —O—(CH₂)ₘ—N(morpholine) | —N(C(H)(CH₃)₂)— |
| Ib-223 | 3 | —O—(CH₂)ₘ—N(morpholine) | —N(CH₂C(H)(CH₃)₂)— |
| Ib-224 | 4 | —O—(CH₂)ₘ—N(morpholine) | —N(CH₂C(H)(CH₃)₂)— |
| Ib-225 | 5 | —O—(CH₂)ₘ—N(morpholine) | —N(CH₂C(H)(CH₃)₂)— |

-continued

| | | | |
|---|---|---|---|
| Ib-226 | 6 | —O—(CH₂)ₘ—N(morpholine)O | —N(CH₂C(H)(CH₃)₂)— |

| Compound | —R¹ | X |
|---|---|---|
| Ib-267 | —CH₂—N(CH₂—CH₃)₂ | —N(CH₃)— |
| Ib-268 | —CH₂—N(CH₂—CH₃)₂ | —N(CH₂CH₃)— |
| Ib-269 | —CH₂—N(CH₂—CH₃)₂ | —N(CH₂CH₂CH₃)— |
| Ib-270 | —CH₂—N(CH₂—CH₃)₂ | —N(CH₂CH₂CH₂CH₃)— |
| Ib-271 | —CH₂—N(CH₂—CH₃)₂ | —N(C(H)(CH₃)(CH₂CH₃))— |
| Ib-272 | —CH₂—N(CH₂—CH₃)₂ | —N(C(H)(CH₃)₂)— |
| Ib-273 | —CH₂—N(CH₂—CH₃)₂ | —N(CH₂C(H)(CH₃)₂)— |
| Ib-274 | —CH₂—N(CH₂—CH₃)₂ | —N(C(CH₃)₃)— |
| Ib-275 | —CH₂—N(CH₂—CH₂—CH₃)₂ | —N(CH₃)— |
| Ib-276 | —CH₂—N(CH₂—CH₂—CH₃)₂ | —N(CH₂CH₃)— |
| Ib-277 | —CH₂—N(CH₂—CH₂—CH₃)₂ | —N(CH₂CH₂CH₃)— |
| Ib-278 | —CH₂—N(CH₂—CH₂—CH₃)₂ | —N(CH₂CH₂CH₂CH₃)— |
| Ib-279 | —CH₂—N(CH₂—CH₂—CH₃)₂ | —N(C(H)(CH₃)(CH₂CH₃))— |
| Ib-280 | —CH₂—N(CH₂—CH₂—CH₃)₂ | —N(C(H)(CH₃)₂)— |
| Ib-281 | —CH₂—N(CH₂—CH₂—CH₃)₂ | —N(CH₂C(H)(CH₃)₂)— |
| Ib-282 | —CH₂—N(CH₂—CH₂—CH₃)₂ | —N(C(CH₃)₃)— |
| Ib-283 | —CH₂—N(CH₂—CH₂OH)₂ | —N(CH₃)— |
| Ib-284 | —CH₂—N(CH₂—CH₂OH)₂ | —N(CH₂CH₃)— |
| Ib-285 | —CH₂—N(CH₂—CH₂OH)₂ | —N(CH₂CH₂CH₃)— |
| Ib-286 | —CH₂—N(CH₂—CH₂OH)₂ | —N(CH₂CH₂CH₂CH₃)— |
| Ib-287 | —CH₂—N(CH₂—CH₂OH)₂ | —N(C(H)(CH₃)(CH₂CH₃))— |
| Ib-288 | —CH₂—N(CH₂—CH₂OH)₂ | —N(C(H)(CH₃)₂)— |
| Ib-289 | —CH₂—N(CH₂—CH₂OH)₂ | —N(CH₂C(H)(CH₃)₂)— |
| Ib-290 | —CH₂—N(CH₂—CH₂OH)₂ | —N(C(CH₃)₃)— |
| Ib-291 | —CH₂—N(CH₂—CH₂—N(CH₃)₂)₂ | —N(CH₃)— |
| Ib-292 | —CH₂—N(CH₂—CH₂—N(CH₃)₂)₂ | —N(CH₂CH₃)— |
| Ib-293 | —CH₂—N(CH₂—CH₂—N(CH₃)₂)₂ | —N(CH₂CH₂CH₃)— |
| Ib-294 | —CH₂—N(CH₂—CH₂—N(CH₃)₂)₂ | —N(CH₂CH₂CH₂CH₃)— |
| Ib-295 | —CH₂—N(CH₂—CH₂—N(CH₃)₂)₂ | —N(C(H)(CH₃)(CH₂CH₃))— |
| Ib-296 | —CH₂—N(CH₂—CH₂—N(CH₃)₂)₂ | —N(C(H)(CH₃)₂)— |
| Ib-297 | —CH₂—N(CH₂—CH₂—N(CH₃)₂)₂ | —N(CH₂C(H)(CH₃)₂)— |
| Ib-298 | —CH₂—N(CH₂—CH₂—N(CH₃)₂)₂ | —N(C(CH₃)₃)— |
| Ib-299 | —CH₂—N(CH₂—CH₂—CH₂N(CH₃)₂)₂ | —N(CH₃)— |
| Ib-300 | —CH₂—N(CH₂—CH₂—CH₂N(CH₃)₂)₂ | —N(CH₂CH₃)— |
| Ib-301 | —CH₂—N(CH₂—CH₂—CH₂N(CH₃)₂)₂ | —N(CH₂CH₂CH₃)— |
| Ib-302 | —CH₂—N(CH₂—CH₂—CH₂N(CH₃)₂)₂ | —N(CH₂CH₂CH₂CH₃)— |
| Ib-303 | —CH₂—N(CH₂—CH₂—CH₂N(CH₃)₂)₂ | —N(C(H)(CH₃)(CH₂CH₃))— |
| Ib-304 | —CH₂—N(CH₂—CH₂—CH₂N(CH₃)₂)₂ | —N(C(H)(CH₃)₂)— |
| Ib-305 | —CH₂—N(CH₂—CH₂—CH₂N(CH₃)₂)₂ | —N(CH₂C(H)(CH₃)₂)— |
| Ib-306 | —CH₂—N(CH₂—CH₂—CH₂N(CH₃)₂)₂ | —N(C(CH₃)₃)— |
| Ib-307 | —CH₂—N(aziridine) | —N(CH₃)— |
| Ib-308 | —CH₂—N(aziridine) | —N(CH₂CH₃)— |
| Ib-309 | —CH₂—N(aziridine) | —N(CH₂CH₂CH₃)— |
| Ib-310 | —CH₂—N(aziridine) | —N(CH₂CH₂CH₂CH₃)— |
| Ib-311 | —CH₂—N(aziridine) | —N(C(H)(CH₃)(CH₂CH₃))— |
| Ib-312 | —CH₂—N(aziridine) | —N(C(H)(CH₃)₂)— |
| Ib-313 | —CH₂—N(aziridine) | —N(CH₂C(H)(CH₃)₂)— |
| Ib-314 | —CH₂—N(aziridine) | —N(C(CH₃)₃)— |
| Ib-315 | —CH₂—N(azetidine) | —N(CH₃)— |

-continued

| | | |
|---|---|---|
| Ib-316 | —CH₂—N⃞ | —N(CH₂CH₃)— |
| Ib-317 | —CH₂—N⃞ | —N(CH₂CH₂CH₃)— |
| Ib-318 | —CH₂—N⃞ | —N(CH₂CH₂CH₂CH₃)— |
| Ib-319 | —CH₂—N⃞ | —N(C(H)(CH₃)(CH₂CH₃))— |
| Ib-320 | —CH₂—N⃞ | —N(C(H)(CH₃)₂)— |
| Ib-321 | —CH₂—N⃞ | —N(CH₂C(H)(CH₃)₂)— |
| Ib-322 | —CH₂—N⃞ | —N(C(CH₃)₃)— |
| Ib-323 | —CH₂—N(pyrrolidine) | —N(CH₃)— |
| Ib-324 | —CH₂—N(pyrrolidine) | —N(CH₂CH₃)— |
| Ib-325 | —CH₂—N(pyrrolidine) | —N(CH₂CH₂CH₃)— |
| Ib-326 | —CH₂—N(pyrrolidine) | —N(CH₂CH₂CH₂CH₃)— |
| Ib-327 | —CH₂—N(pyrrolidine) | —N(C(H)(CH₃)(CH₂CH₃))— |
| Ib-328 | —CH₂—N(pyrrolidine) | —N(C(H)(CH₃)₂)— |
| Ib-329 | —CH₂—N(pyrrolidine) | —N(CH₂C(H)(CH₃)₂)— |
| Ib-330 | —CH₂—N(pyrrolidine) | —N(C(CH₃)₃)— |
| Ib-331 | —CH₂—N(3-hydroxypyrrolidine) | —N(CH₃)— |
| Ib-332 | —CH₂—N(3-hydroxypyrrolidine) | —N(CH₂CH₃)— |

-continued

| | | |
|---|---|---|
| Ib-333 | —CH₂—[1-(3-hydroxypyrrolidinyl)] | —N(CH₂CH₃)— |
| Ib-334 | —CH₂—[1-(3-hydroxypyrrolidinyl)] | —N(CH₂CH₂CH₃)— |
| Ib-335 | —CH₂—[1-(3-hydroxypyrrolidinyl)] | —N(C(H)(CH₃)(CH₂CH₃))— |
| Ib-336 | —CH₂—[1-(3-hydroxypyrrolidinyl)] | —N(C(H)(CH₃)₂)— |
| Ib-337 | —CH₂—[1-(3-hydroxypyrrolidinyl)] | —N(CH₂C(H)(CH₃)₂)— |
| Ib-338 | —CH₂—[1-(3-hydroxypyrrolidinyl)] | —N(C(CH₃)₃)— |
| Ib-339 | —CH₂—[1-(2-(hydroxymethyl)pyrrolidinyl)] | —N(CH₃)— |
| Ib-340 | —CH₂—[1-(2-(hydroxymethyl)pyrrolidinyl)] | —N(CH₂CH₃)— |
| Ib-341 | —CH₂—[1-(2-(hydroxymethyl)pyrrolidinyl)] | —N(CH₂CH₂CH₃)— |
| Ib-342 | —CH₂—[1-(2-(hydroxymethyl)pyrrolidinyl)] | —N(CH₂CH₂CH₂CH₃)— |
| Ib-343 | —CH₂—[1-(2-(hydroxymethyl)pyrrolidinyl)] | —N(C(H)(CH₃)(CH₂CH₃))— |

-continued
| | | |
|---|---|---|
| Ib-344 | 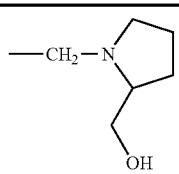 | —N(C(H)(CH$_3$)$_2$)— |
| Ib-345 | 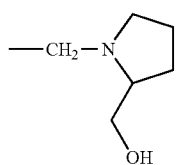 | —N(CH$_2$C(H)(CH$_3$)$_2$)— |
| Ib-346 | 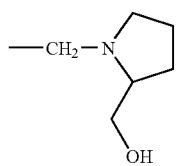 | —N(C(CH$_3$)$_3$)— |
| Ib-347 | 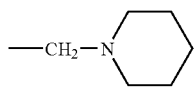 | —N(CH$_3$)— |
| Ib-348 | 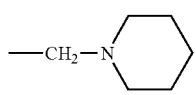 | —N(CH$_2$CH$_3$)— |
| Ib-349 | 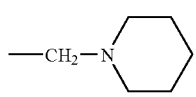 | —N(CH$_2$CH$_2$CH$_3$)— |
| Ib-350 | 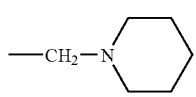 | —N(CH$_2$CH$_2$CH$_2$CH$_3$)— |
| Ib-351 | 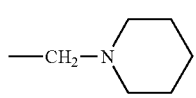 | —N(C(H)(CH$_3$)(CH$_2$CH$_3$))— |
| Ib-352 | 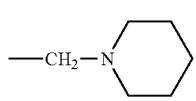 | —N(C(H)(CH$_3$)$_2$)— |
| Ib-353 | 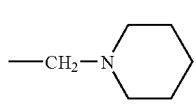 | —N(CH$_2$C(H)(CH$_3$)$_2$)— |
| Ib-354 | 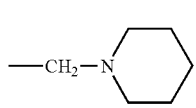 | —N(C(CH$_3$)$_3$)— |
| Ib-355 | 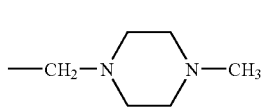 | —N(CH$_3$)— |
| Ib-356 | 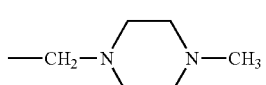 | —N(CH$_2$CH$_3$)— |
| Ib-357 | 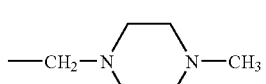 | —N(CH$_2$CH$_2$CH$_3$)— |

-continued

| | | |
|---|---|---|
| Ib-358 | —CH₂—N(piperazine)N—CH₃ | —N(CH₂CH₂CH₂CH₃)— |
| Ib-359 | —CH₂—N(piperazine)N—CH₃ | —N(C(H)(CH₃)(CH₂CH₃))— |
| Ib-360 | —CH₂—N(piperazine)N—CH₃ | —N(C(H)(CH₃)₂)— |
| Ib-361 | —CH₂—N(piperazine)N—CH₃ | —N(CH₂C(H)(CH₃)₂)— |
| Ib-362 | —CH₂—N(piperazine)N—CH₃ | —N(C(CH₃)₃)— |
| Ib-363 | —CH₂—N(CH₃)(CH₂-phenyl) | —N(CH₃)— |
| Ib-364 | —CH₂—N(CH₃)(CH₂-phenyl) | —N(CH₂CH₃)— |
| Ib-365 | —CH₂—N(CH₃)(CH₂-phenyl) | —N(CH₂CH₂CH₃)— |
| Ib-366 | —CH₂—N(CH₃)(CH₂-phenyl) | —N(CH₂CH₂CH₂CH₃)— |
| Ib-367 | —CH₂—N(CH₃)(CH₂-phenyl) | —N(C(H)(CH₃)(CH₂CH₃))— |
| Ib-368 | —CH₂—N(CH₃)(CH₂-phenyl) | —N(C(H)(CH₃)₂)— |
| Ib-369 | —CH₂—N(CH₃)(CH₂-phenyl) | —N(CH₂C(H)(CH₃)₂)— |
| Ib-370 | —CH₂—N(CH₃)(CH₂-phenyl) | —N(C(CH₃)₃)— |

-continued
| | | |
|---|---|---|
| Ib-371 | 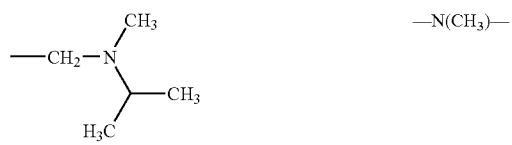 | —N(CH₃)— |
| Ib-372 |  | —N(CH₂CH₃)— |
| Ib-373 |  | —N(CH₂CH₂CH₃)— |
| Ib-374 |  | —N(CH₂CH₂CH₂CH₃)— |
| Ib-375 |  | —N(C(H)(CH₃)(CH₂CH₃))— |
| Ib-376 |  | —N(C(H)(CH₃)₂)— |
| Ib-377 |  | —N(CH₂C(H)(CH₃)₂)— |
| Ib-378 | 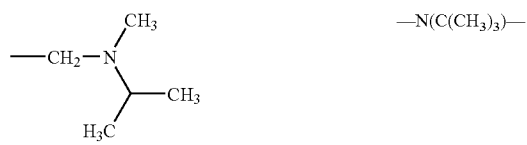 | —N(C(CH₃)₃)— |
| Ib-379 | 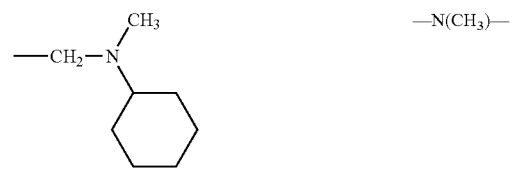 | —N(CH₃)— |
| Ib-380 | 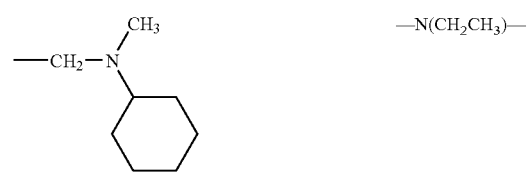 | —N(CH₂CH₃)— |

-continued

| | | |
|---|---|---|
| Ib-381 | —CH₂—N(CH₃)—cyclohexyl | —N(CH₂CH₂CH₃)— |
| Ib-382 | —CH₂—N(CH₃)—cyclohexyl | —N(CH₂CH₂CH₃)— |
| Ib-383 | —CH₂—N(CH₃)—cyclohexyl | —N(C(H)(CH₃)(CH₂CH₃))— |
| Ib-384 | —CH₂—N(CH₃)—cyclohexyl | —N(C(H)(CH₃)₂)— |
| Ib-385 | —CH₂—N(CH₃)—cyclohexyl | —N(CH₂C(H)(CH₃)₂)— |
| Ib-386 | —CH₂—N(CH₃)—cyclohexyl | —N(C(CH₃)₃)— |
| Ib-387 | —CH₂—NH—CH₂CH₂—morpholinyl | —N(CH₃)— |
| Ib-388 | —CH₂—NH—CH₂CH₂—morpholinyl | —N(CH₂CH₃)— |
| Ib-389 | —CH₂—NH—CH₂CH₂—morpholinyl | —N(CH₂CH₂CH₃)— |
| Ib-390 | —CH₂—NH—CH₂CH₂—morpholinyl | —N(CH₂CH₂CH₃)— |
| Ib-391 | —CH₂—NH—CH₂CH₂—morpholinyl | —N(C(H)(CH₃)(CH₂CH₃))— |

-continued
| | | |
|---|---|---|
| Ib-392 | 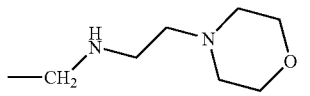 | —N(C(H)(CH$_3$)$_2$)— |
| Ib-393 | 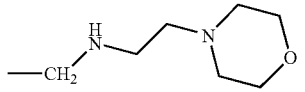 | —N(CH$_2$C(H)(CH$_3$)$_2$)— |
| Ib-394 | 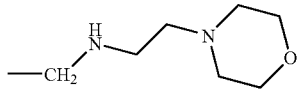 | —N(C(CH$_3$)$_3$)— |
| Ib-395 | 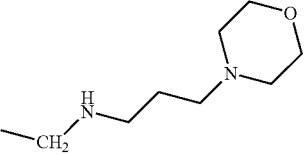 | —N(CH$_3$)— |
| Ib-396 | 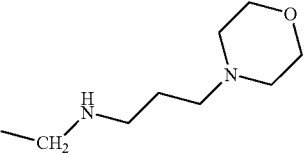 | —N(CH$_2$CH$_3$)— |
| Ib-397 | 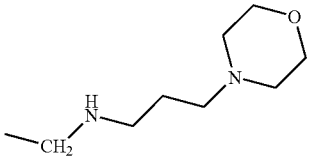 | —N(CH$_2$CH$_2$CH$_3$)— |
| Ib-398 | 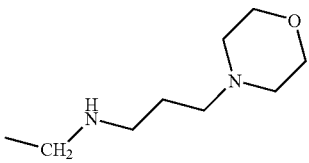 | —N(CH$_2$CH$_2$CH$_2$CH$_3$)— |
| Ib-399 | 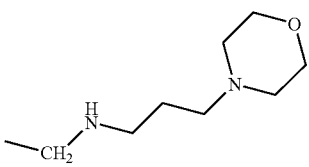 | —N(C(H)(CH$_3$)(CH$_2$CH$_3$))— |
| Ib-400 | 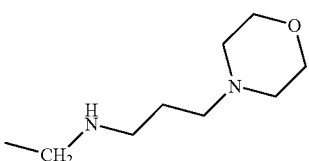 | —N(C(H)(CH$_3$)$_2$)— |
| Ib-401 | 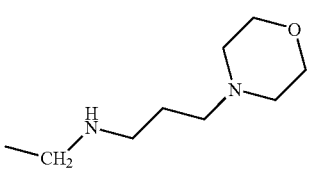 | —N(CH$_2$C(H)(CH$_3$)$_2$)— |

-continued
| | | |
|---|---|---|
| Ib-402 | 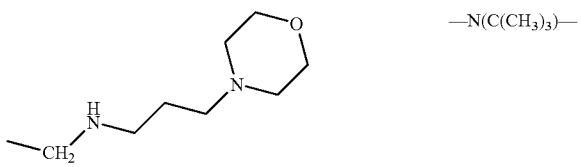 | —N(C(CH$_3$)$_3$)— |
| Ib-403 | 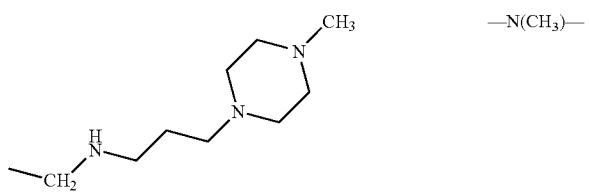 | —N(CH$_3$)— |
| Ib-404 | 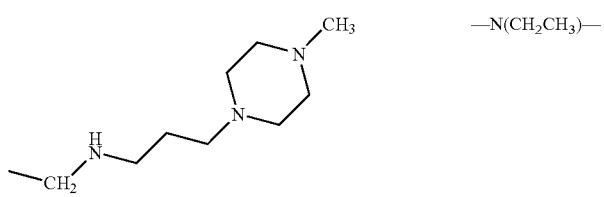 | —N(CH$_2$CH$_3$)— |
| Ib-405 | 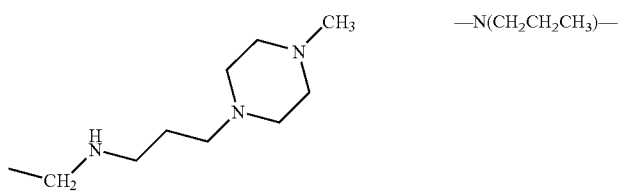 | —N(CH$_2$CH$_2$CH$_3$)— |
| Ib-406 | 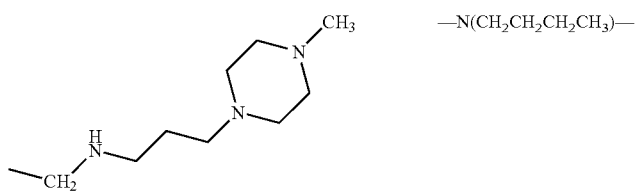 | —N(CH$_2$CH$_2$CH$_2$CH$_3$)— |
| Ib-407 | 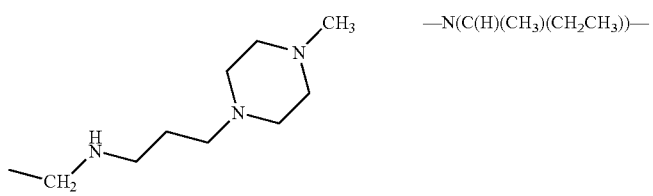 | —N(C(H)(CH$_3$)(CH$_2$CH$_3$))— |
| Ib-408 | 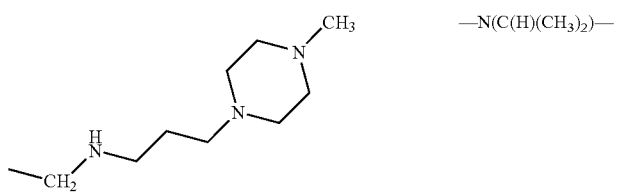 | —N(C(H)(CH$_3$)$_2$)— |
| Ib-409 | 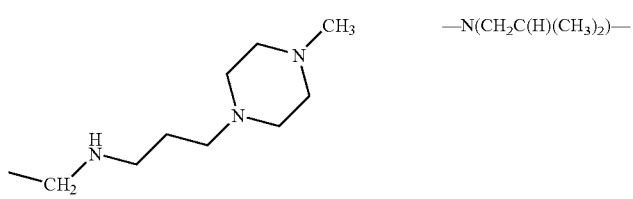 | —N(CH$_2$C(H)(CH$_3$)$_2$)— |

-continued
| | | |
|---|---|---|
| Ib-410 | 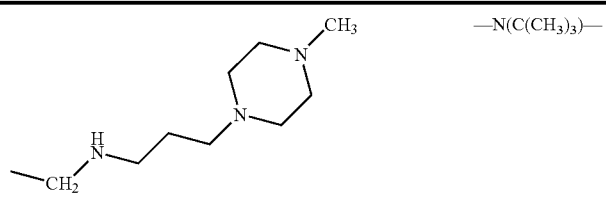 | —N(C(CH$_3$)$_3$)— |
| Ib-411 | 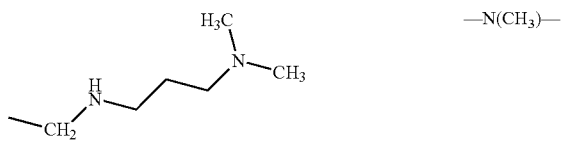 | —N(CH$_3$)— |
| Ib-412 | 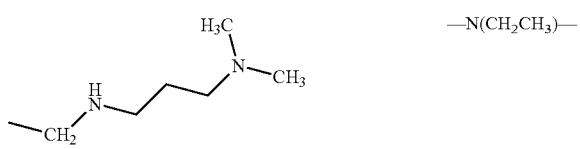 | —N(CH$_2$CH$_3$)— |
| Ib-413 | 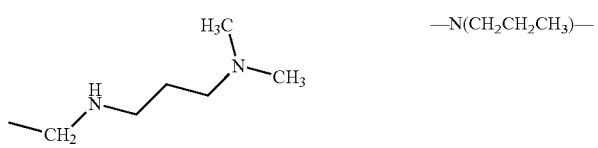 | —N(CH$_2$CH$_2$CH$_3$)— |
| Ib-414 | 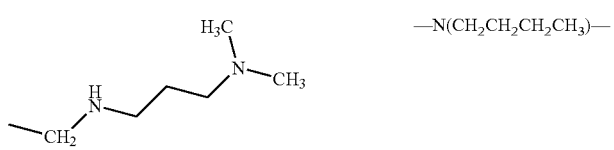 | —N(CH$_2$CH$_2$CH$_2$CH$_3$)— |
| Ib-415 | 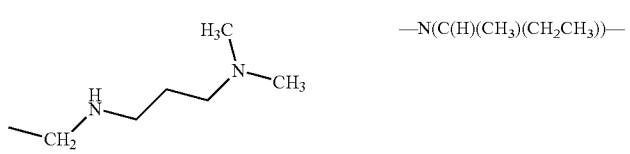 | —N(C(H)(CH$_3$)(CH$_2$CH$_3$))— |
| Ib-416 | 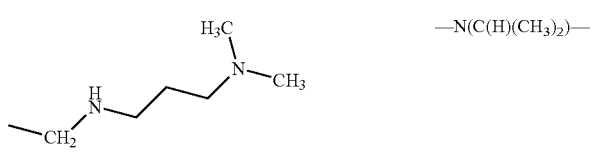 | —N(C(H)(CH$_3$)$_2$)— |
| Ib-417 | 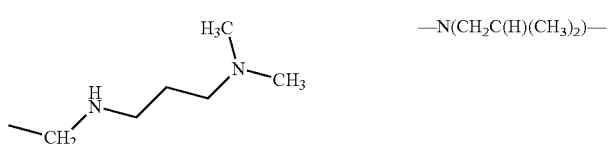 | —N(CH$_2$C(H)(CH$_3$)$_2$)— |
| Ib-418 | 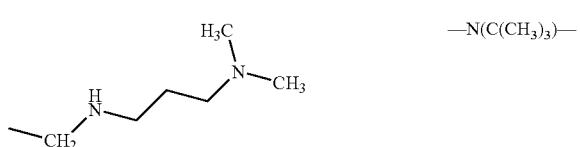 | —N(C(CH$_3$)$_3$)— |
| Ib-419 | 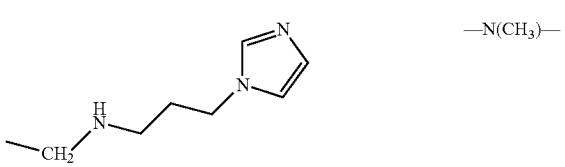 | —N(CH$_3$)— |

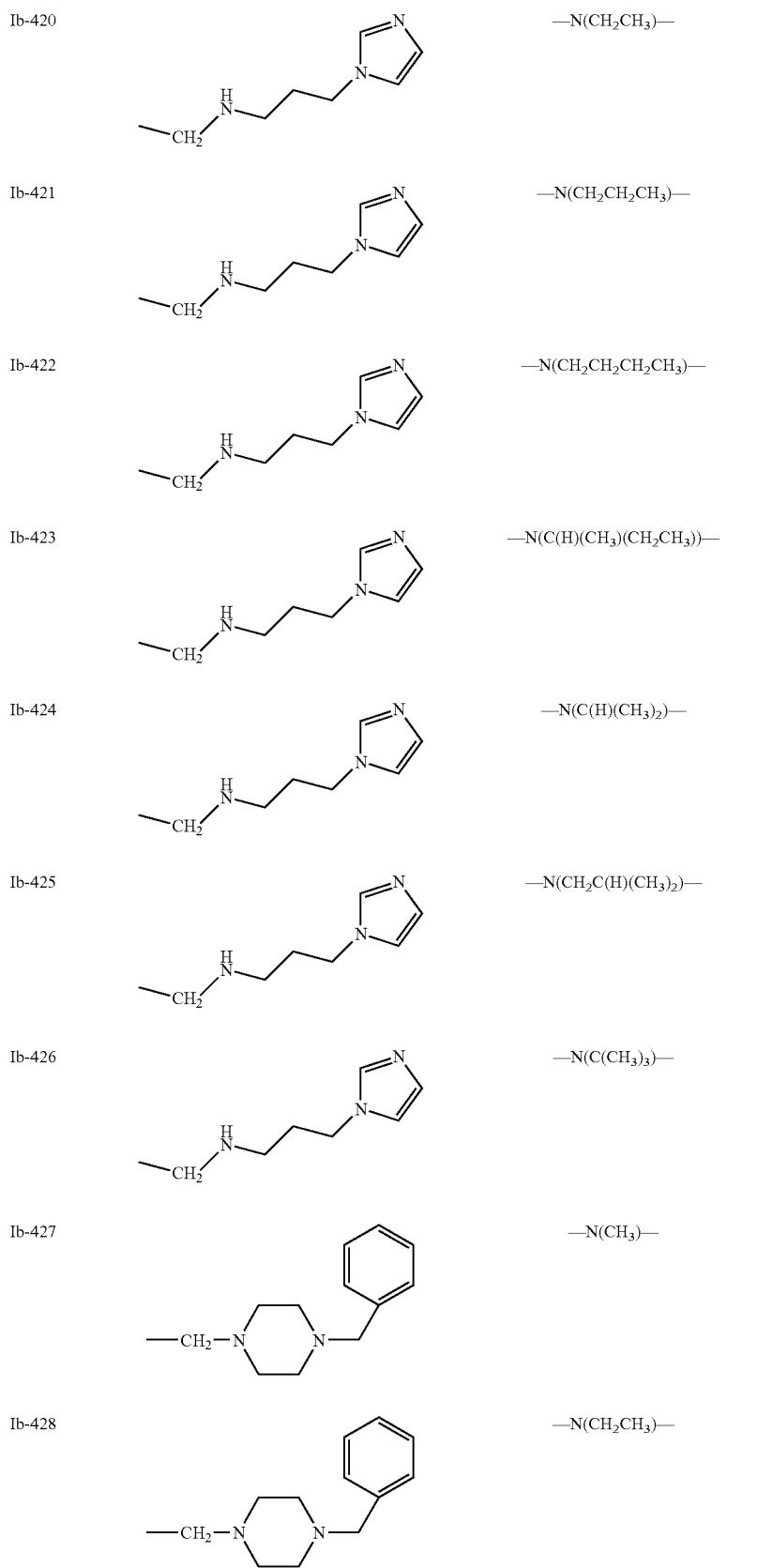
| | | |
|---|---|---|
| Ib-420 | | —N(CH$_2$CH$_3$)— |
| Ib-421 | | —N(CH$_2$CH$_2$CH$_3$)— |
| Ib-422 | | —N(CH$_2$CH$_2$CH$_2$CH$_3$)— |
| Ib-423 | | —N(C(H)(CH$_3$)(CH$_2$CH$_3$))— |
| Ib-424 | | —N(C(H)(CH$_3$)$_2$)— |
| Ib-425 | | —N(CH$_2$C(H)(CH$_3$)$_2$)— |
| Ib-426 | | —N(C(CH$_3$)$_3$)— |
| Ib-427 | | —N(CH$_3$)— |
| Ib-428 | | —N(CH$_2$CH$_3$)— |

-continued
| | | |
|---|---|---|
| Ib-429 | 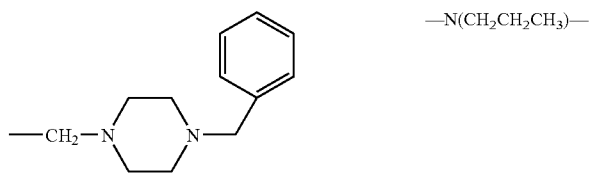 | —N(CH₂CH₂CH₃)— |
| Ib-430 | 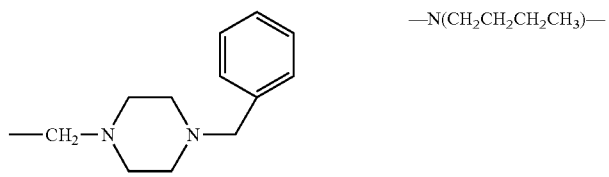 | —N(CH₂CH₂CH₂CH₃)— |
| Ib-431 | 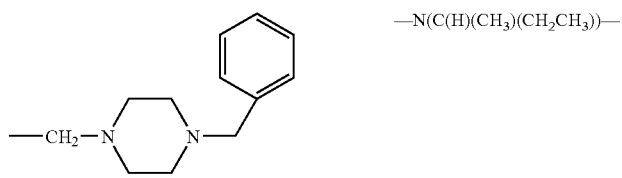 | —N(C(H)(CH₃)(CH₂CH₃))— |
| Ib-432 | 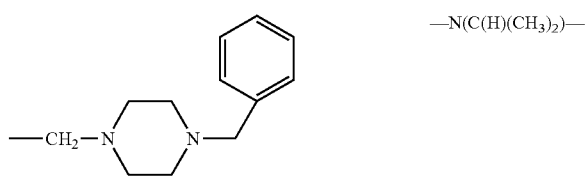 | —N(C(H)(CH₃)₂)— |
| Ib-433 | 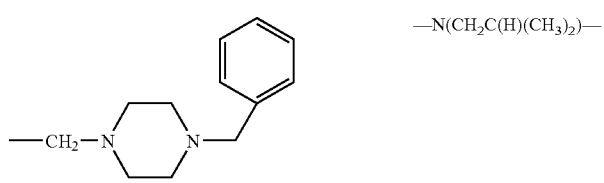 | —N(CH₂C(H)(CH₃)₂)— |
| Ib-434 | 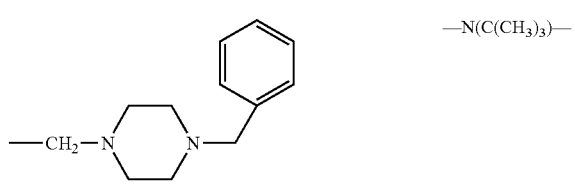 | —N(C(CH₃)₃)— |
| Ib-435 | 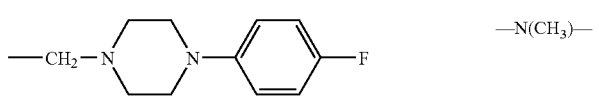 | —N(CH₃)— |
| Ib-436 | 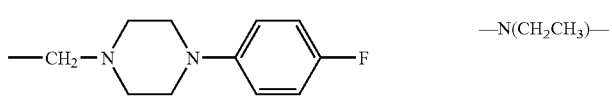 | —N(CH₂CH₃)— |
| Ib-437 | 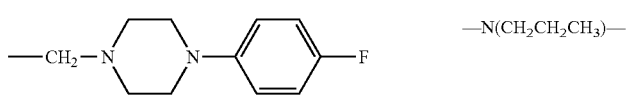 | —N(CH₂CH₂CH₃)— |
| Ib-438 | 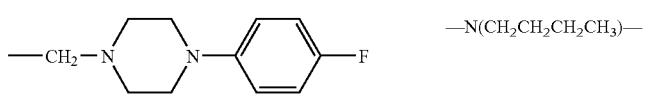 | —N(CH₂CH₂CH₂CH₃)— |
| Ib-439 | 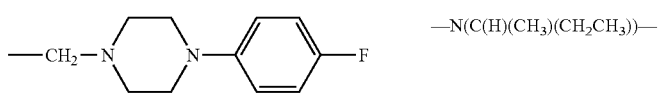 | —N(C(H)(CH₃)(CH₂CH₃))— |

-continued

| | | |
|---|---|---|
| Ib-440 | —CH₂—N(piperazine)N—(4-F-phenyl) | —N(C(H)(CH₃)₂)— |
| Ib-441 | —CH₂—N(piperazine)N—(4-F-phenyl) | —N(CH₂C(H)(CH₃)₂)— |
| Ib-442 | —CH₂—N(piperazine)N—(4-F-phenyl) | —N(C(CH₃)₃)— |
| Ib-443 | —CH₂—N(tetrahydropyridine)—(4-F-phenyl) | —N(CH₃)— |
| Ib-444 | —CH₂—N(tetrahydropyridine)—(4-F-phenyl) | —N(CH₂CH₃)— |
| Ib-445 | —CH₂—N(tetrahydropyridine)—(4-F-phenyl) | —N(CH₂CH₂CH₃)— |
| Ib-446 | —CH₂—N(tetrahydropyridine)—(4-F-phenyl) | —N(CH₂CH₂CH₃)— |
| Ib-447 | —CH₂—N(tetrahydropyridine)—(4-F-phenyl) | —N(C(H)(CH₃)(CH₂CH₃))— |
| Ib-448 | —CH₂—N(tetrahydropyridine)—(4-F-phenyl) | —N(C(H)(CH₃)₂)— |
| Ib-449 | —CH₂—N(tetrahydropyridine)—(4-F-phenyl) | —N(CH₂C(H)(CH₃)₂)— |
| Ib-450 | —CH₂—N(tetrahydropyridine)—(4-F-phenyl) | —N(C(CH₃)₃)— |
| Ib-451 | —CH₂—N(piperidine)—(phenyl) | —N(CH₃)— |
| Ib-452 | —CH₂—N(piperidine)—(phenyl) | —N(CH₂CH₃)— |
| Ib-453 | —CH₂—N(piperidine)—(phenyl) | —N(CH₂CH₂CH₃)— |
| Ib-454 | —CH₂—N(piperidine)—(phenyl) | —N(CH₂CH₂CH₂CH₃)— |
| Ib-455 | —CH₂—N(piperidine)—(phenyl) | —N(C(H)(CH₃)(CH₂CH₃))— |

-continued
| | | |
|---|---|---|
| Ib-456 | 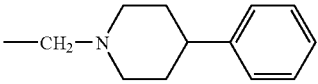 | —N(C(H)(CH₃)₂)— |
| Ib-457 | 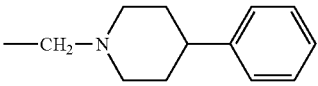 | —N(CH₂C(H)(CH₃)₂)— |
| Ib-458 | 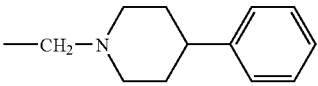 | —N(C(CH₃)₃)— |
| Ib-459 | 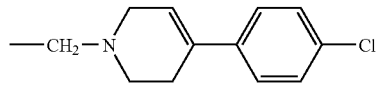 | —N(CH₃)— |
| Ib-460 | 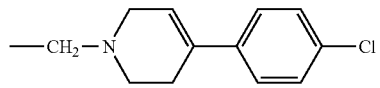 | —N(CH₂CH₃)— |
| Ib-461 | 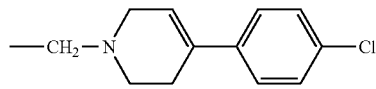 | —N(CH₂CH₂CH₃)— |
| Ib-462 | 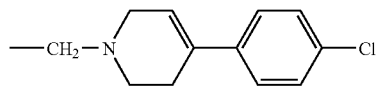 | —N(CH₂CH₂CH₂CH₃)— |
| Ib-463 | 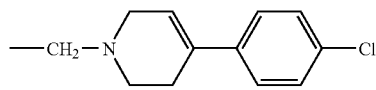 | —N(C(H)(CH₃)(CH₂CH₃))— |
| Ib-464 | 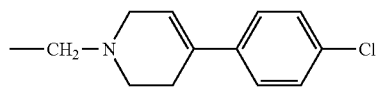 | —N(C(H)(CH₃)₂)— |
| Ib-465 | 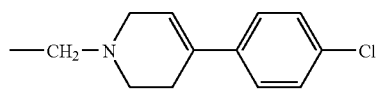 | —N(CH₂C(H)(CH₃)₂)— |
| Ib-466 | 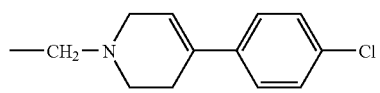 | —N(C(CH₃)₃)— |
| Ib-467 | 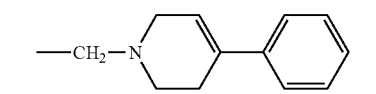 | —N(CH₃)— |
| Ib-468 | 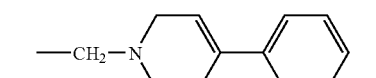 | —N(CH₂CH₃)— |
| Ib-469 | 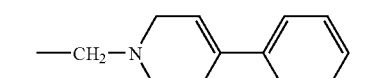 | —N(CH₂CH₃)— |
| Ib-470 | 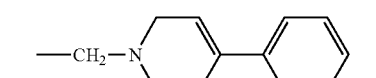 | —N(CH₂CH₂CH₂CH₃)— |
| Ib-471 | 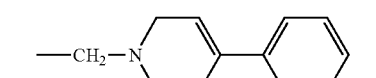 | —N(C(H)(CH₃)(CH₂CH₃))— |

-continued

| | | |
|---|---|---|
| Ib-472 | —CH₂—N⌬—C₆H₅ (tetrahydropyridine-phenyl) | —N(C(H)(CH₃)₂)— |
| Ib-473 | —CH₂—N⌬—C₆H₅ | —N(CH₂C(H)(CH₃)₂)— |
| Ib-474 | —CH₂—N⌬—C₆H₅ | —N(C(CH₃)₃)— |
| Ib-475 | —CH₂—N(piperidine-4-OH-4-phenyl) | —N(CH₃)— |
| Ib-476 | —CH₂—N(piperidine-4-OH-4-phenyl) | —N(CH₂CH₃)— |
| Ib-477 | —CH₂—N(piperidine-4-OH-4-phenyl) | —N(CH₂CH₂CH₃)— |
| Ib-478 | —CH₂—N(piperidine-4-OH-4-phenyl) | —N(CH₂CH₂CH₃)— |
| Ib-479 | —CH₂—N(piperidine-4-OH-4-phenyl) | —N(C(H)(CH₃)(CH₂CH₃))— |
| Ib-480 | —CH₂—N(piperidine-4-OH-4-phenyl) | —N(C(H)(CH₃)₂)— |
| Ib-481 | —CH₂—N(piperidine-4-OH-4-phenyl) | —N(CH₂C(H)(CH₃)₂)— |
| Ib-482 | —CH₂—N(piperidine-4-OH-4-phenyl) | —N(C(CH₃)₃)— |
| Ib-483 | —CH₂—N(piperazine)NCH₂CH₂OP(O)(OH)₂ | —N(CH₃)— |
| Ib-484 | —CH₂—N(piperazine)NCH₂CH₂OP(O)(OH)₂ | —N(CH₂CH₃)— |
| Ib-485 | —CH₂—N(piperazine)NCH₂CH₂OP(O)(OH)₂ | —N(CH₂CH₂CH₃)— |
| Ib-486 | —CH₂—N(piperazine)NCH₂CH₂OP(O)(OH)₂ | —N(CH₂CH₂CH₂CH₃)— |
| Ib-487 | —CH₂—N(piperazine)NCH₂CH₂OP(O)(OH)₂ | —N(C(H)(CH₃)(CH₂CH₃))— |

-continued

| | | |
|---|---|---|
| Ib-488 | —CH₂—N(piperazine)NCH₂CH₂OP(O)(OH)₂ | —N(C(H)(CH₃)₂)— |
| Ib-489 | —CH₂—N(piperazine)NCH₂CH₂OP(O)(OH)₂ | —N(CH₂C(H)(CH₃)₂)— |
| Ib-490 | —CH₂—N(piperazine)NCH₂CH₂OP(O)(OH)₂ | —N(C(CH₃)₃)— |
| Ib-491 | —CH₂—CH₂—CH₂—OP(O)(OH)₂ | —N(CH₃)— |
| Ib-492 | —CH₂—CH₂—CH₂—OP(O)(OH)₂ | —N(CH₂CH₃)— |
| Ib-493 | —CH₂—CH₂—CH₂—OP(O)(OH)₂ | —N(CH₂CH₂CH₃)— |
| Ib-494 | —CH₂—CH₂—CH₂—OP(O)(OH)₂ | —N(CH₂CH₂CH₂CH₃)— |
| Ib-495 | —CH₂—CH₂—CH₂—OP(O)(OH)₂ | —N(C(H)(CH₃)(CH₂CH₃))— |
| Ib-496 | —CH₂—CH₂—CH₂—OP(O)(OH)₂ | —N(C(H)(CH₃)₂)— |
| Ib-497 | —CH₂—CH₂—CH₂—OP(O)(OH)₂ | —N(CH₂C(H)(CH₃)₂)— |
| Ib-498 | —CH₂—CH₂—CH₂—OP(O)(OH)₂ | —N(C(CH₃)₃)— |
| Ib-499 | —CH₂—CH₂—CH₂—OS(O)₂OH | —N(CH₃)— |
| Ib-500 | —CH₂—CH₂—CH₂—OS(O)₂OH | —N(CH₂CH₃)— |
| Ib-501 | —CH₂—CH₂—CH₂—OS(O)₂OH | —N(CH₂CH₃)— |
| Ib-502 | —CH₂—CH₂—CH₂—OS(O)₂OH | —N(CH₂CH₂CH₂CH₃)— |
| Ib-503 | —CH₂—CH₂—CH₂—OS(O)₂OH | —N(C(H)(CH₃)(CH₂CH₃))— |
| Ib-504 | —CH₂—CH₂—CH₂—OS(O)₂OH | —N(C(H)(CH₃)₂)— |
| Ib-505 | —CH₂—CH₂—CH₂—OS(O)₂OH | —N(CH₂C(H)(CH₃)₂)— |
| Ib-506 | —CH₂—CH₂—CH₂—OS(O)₂OH | —N(C(CH₃)₃)— |
| Ib-507 | —CH₂—N(pyrrolidine)-OP(O)(OH)₂ | —N(CH₃)— |
| Ib-508 | —CH₂—N(pyrrolidine)-OP(O)(OH)₂ | —N(CH₂CH₃)— |
| Ib-509 | —CH₂—N(pyrrolidine)-OP(O)(OH)₂ | —N(CH₂CH₂CH₃)— |
| Ib-510 | —CH₂—N(pyrrolidine)-OP(O)(OH)₂ | —N(CH₂CH₂CH₂CH₃)— |
| Ib-511 | —CH₂—N(pyrrolidine)-OP(O)(OH)₂ | —N(C(H)(CH₃)(CH₂CH₃))— |
| Ib-512 | —CH₂—N(pyrrolidine)-OP(O)(OH)₂ | —N(C(H)(CH₃)₂)— |
| Ib-513 | —CH₂—N(pyrrolidine)-OP(O)(OH)₂ | —N(CH₂C(H)(CH₃)₂)— |
| Ib-514 | —CH₂—N(pyrrolidine)-OP(O)(OH)₂ | —N(C(CH₃)₃)— |

-continued

| ID | Structure 1 | Structure 2 |
|---|---|---|
| Ib-515 | —CH₂—(N-pyrrolidinyl-2-yl with CH₂OP(O)(OH)₂) | —N(CH₃)— |
| Ib-516 | —CH₂—(N-pyrrolidinyl-2-yl with CH₂OP(O)(OH)₂) | —N(CH₂CH₃)— |
| Ib-517 | —CH₂—(N-pyrrolidinyl-2-yl with CH₂OP(O)(OH)₂) | —N(CH₂CH₂CH₃)— |
| Ib-518 | —CH₂—(N-pyrrolidinyl-2-yl with CH₂OP(O)(OH)₂) | —N(CH₂CH₂CH₂CH₃)— |
| Ib-519 | —CH₂—(N-pyrrolidinyl-2-yl with CH₂OP(O)(OH)₂) | —N(C(H)(CH₃)(CH₂CH₃))— |
| Ib-520 | —CH₂—(N-pyrrolidinyl-2-yl with CH₂OP(O)(OH)₂) | —N(C(H)(CH₃)₂)— |
| Ib-521 | —CH₂—(N-pyrrolidinyl-2-yl with CH₂OP(O)(OH)₂) | —N(CH₂C(H)(CH₃)₂)— |
| Ib-522 | —CH₂—(N-pyrrolidinyl-2-yl with CH₂OP(O)(OH)₂) | —N(C(CH₃)₃)— |
| Ib-523 | —(CH₂)₁₀—N(CH₂—CH₂—O—CH₃)₂ | —N(CH₃)— |
| Ib-524 | —(CH₂)₁₀—N(CH₂—CH₂—O—CH₃)₂ | —N(CH₂CH₃)— |
| Ib-525 | —(CH₂)₁₀—N(CH₂—CH₂—O—CH₃)₂ | —N(CH₂CH₂CH₃)— |
| Ib-526 | —(CH₂)₁₀—N(CH₂—CH₂—O—CH₃)₂ | —N(CH₂CH₂CH₂CH₃)— |
| Ib-527 | —(CH₂)₁₀—N(CH₂—CH₂—O—CH₃)₂ | —N(C(H)(CH₃)(CH₂CH₃))— |
| Ib-528 | —(CH₂)₁₀—N(CH₂—CH₂—O—CH₃)₂ | —N(C(H)(CH₃)₂)— |
| Ib-529 | —(CH₂)₁₀—N(CH₂—CH₂—O—CH₃)₂ | —N(CH₂C(H)(CH₃)₂)— |
| Ib-530 | —(CH₂)₁₀—N(CH₂—CH₂—O—CH₃)₂ | —N(C(CH₃)₃)— |
| Ib-531 | —CH₂—N(CH₂—CH₂—O—CH₃)₂ | —N(CH₃)— |
| Ib-532 | —CH₂—N(CH₂—CH₂—O—CH₃)₂ | —N(CH₂CH₃)— |
| Ib-533 | —CH₂—N(CH₂—CH₂—O—CH₃)₂ | —N(CH₂CH₂CH₃)— |

-continued
| | | |
|---|---|---|
| Ib-534 | —CH₂—N(CH₂—CH₂—O—CH₃)₂ | —N(CH₂CH₂CH₂CH₃)— |
| Ib-535 | —CH₂—N(CH₂—CH₂—O—CH₃)₂ | —N(C(H)(CH₃)(CH₂CH₃))— |
| Ib-536 | —CH₂—N(CH₂—CH₂—O—CH₃)₂ | —N(C(H)(CH₃)₂)— |
| Ib-537 | —CH₂—N(CH₂—CH₂—O—CH₃)₂ | —N(CH₂C(H)(CH₃)₂)— |
| Ib-538 | —CH₂—N(CH₂—CH₂—O—CH₃)₂ | —N(C(CH₃)₃)— |
| Ib-539 | 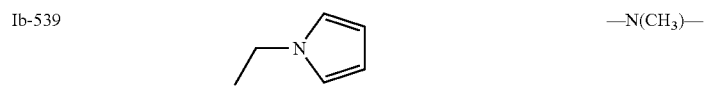 | —N(CH₃)— |
| Ib-540 | 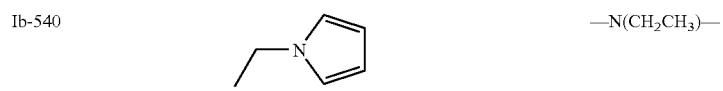 | —N(CH₂CH₃)— |
| Ib-541 | 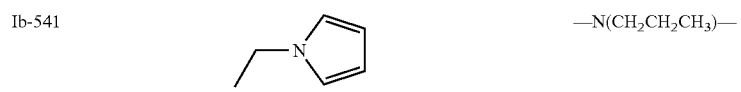 | —N(CH₂CH₂CH₃)— |
| Ib-542 | 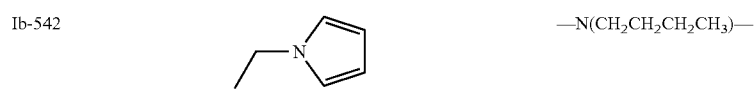 | —N(CH₂CH₂CH₂CH₃)— |
| Ib-543 | 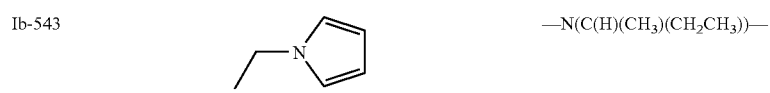 | —N(C(H)(CH₃)(CH₂CH₃))— |
| Ib-544 | 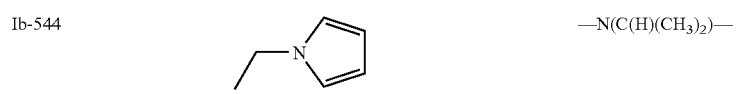 | —N(C(H)(CH₃)₂)— |
| Ib-545 | 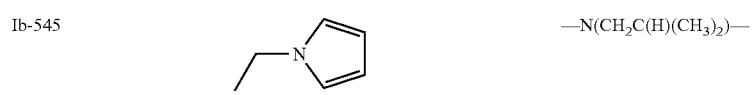 | —N(CH₂C(H)(CH₃)₂)— |
| Ib-546 |  | —N(C(CH₃)₃)— |
| Ib-547 | 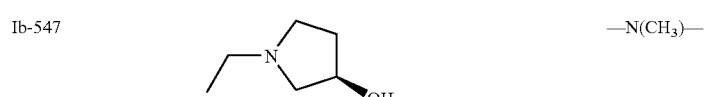 | —N(CH₃)— |
| Ib-548 | 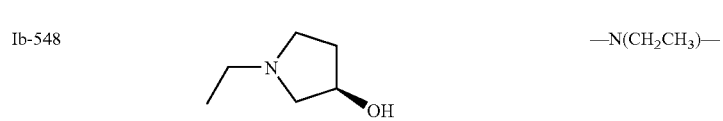 | —N(CH₂CH₃)— |
| Ib-549 | 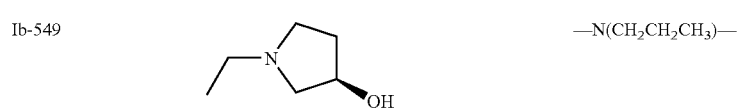 | —N(CH₂CH₂CH₃)— |
| Ib-550 | 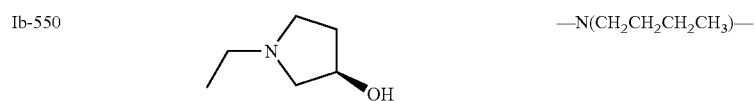 | —N(CH₂CH₂CH₂CH₃)— |
| Ib-551 |  | —N(C(H)(CH₃)(CH₂CH₃))— |
| Ib-552 | 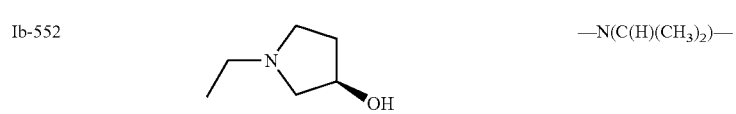 | —N(C(H)(CH₃)₂)— |

-continued
| | | |
|---|---|---|
| Ib-553 | 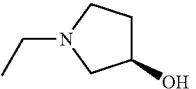 | —N(CH₂C(H)(CH₃)₂)— |
| Ib-554 | 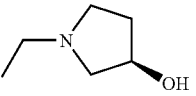 | —N(C(CH₃)₃)— |
| Ib-555 | 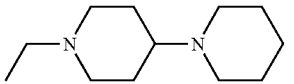 | —N(CH₃)— |
| Ib-556 | 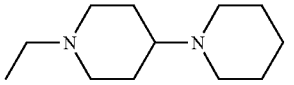 | —N(CH₂CH₃)— |
| Ib-557 | 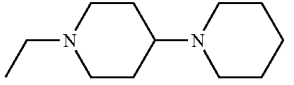 | —N(CH₂CH₂CH₃)— |
| Ib-558 | 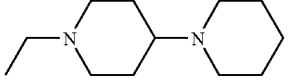 | —N(CH₂CH₂CH₂CH₃)— |
| Ib-559 | 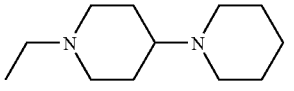 | —N(C(H)(CH₃)(CH₂CH₃))— |
| Ib-560 | 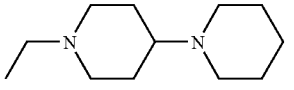 | —N(C(H)(CH₃)₂)— |
| Ib-561 | 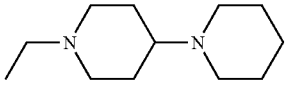 | —N(CH₂C(H)(CH₃)₂)— |
| Ib-562 | 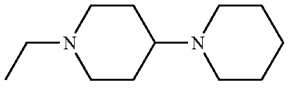 | —N(C(CH₃)₃)— |
| Ib-563 | 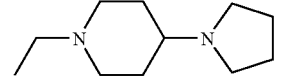 | —N(CH₃)— |
| Ib-564 | 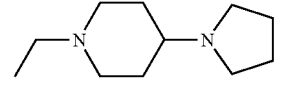 | —N(CH₂CH₃)— |
| Ib-565 | 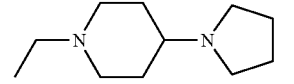 | —N(CH₂CH₂CH₃)— |
| Ib-566 | 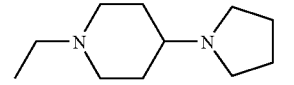 | —N(CH₂CH₂CH₂CH₃)— |
| Ib-567 | 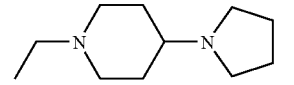 | —N(C(H)(CH₃)(CH₂CH₃))— |
| Ib-568 | 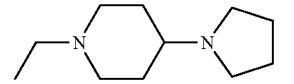 | —N(C(H)(CH₃)₂)— |

-continued
| | | |
|---|---|---|
| Ib-569 |  | —N(CH₂C(H)(CH₃)₂)— |
| Ib-570 | 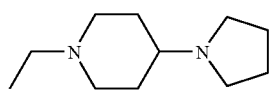 | —N(C(CH₃)₃)— |
| Ib-571 | 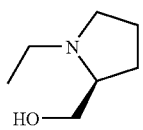 | —N(CH₃)— |
| Ib-572 | 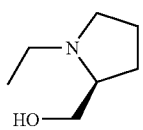 | —N(CH₂CH₃)— |
| Ib-573 | 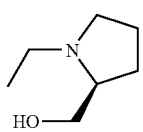 | —N(CH₂CH₃)— |
| Ib-574 | 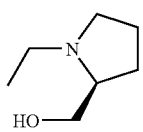 | —N(CH₂CH₂CH₃)— |
| Ib-575 | 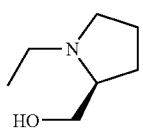 | —N(C(H)(CH₃)(CH₂CH₃))— |
| Ib-576 | 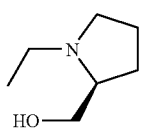 | —N(C(H)(CH₃)₂)— |
| Ib-577 | 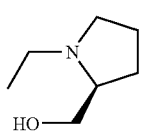 | —N(CH₂C(H)(CH₃)₂)— |
| Ib-578 | 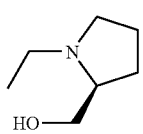 | —N(C(CH₃)₃)— |
| Ib-579 | 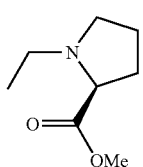 | —N(CH₃)— |
| Ib-580 | 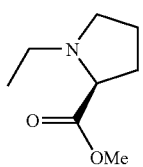 | —N(CH₂CH₃)— |

-continued
| | | |
|---|---|---|
| Ib-581 | 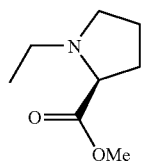 | —N(CH₂CH₂CH₃)— |
| Ib-582 | 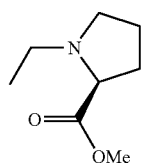 | —N(CH₂CH₂CH₂CH₃)— |
| Ib-583 | 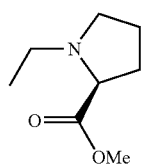 | —N(C(H)(CH₃)(CH₂CH₃))— |
| Ib-584 | 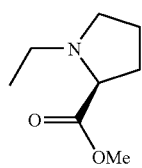 | —N(C(H)(CH₃)₂)— |
| Ib-585 | 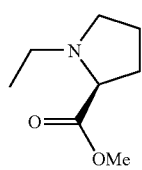 | —N(CH₂C(H)(CH₃)₂)— |
| Ib-586 | 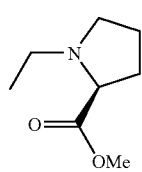 | —N(C(CH₃)₃)— |
| Ib-587 | 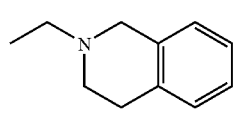 | —N(CH₃)— |
| Ib-588 | 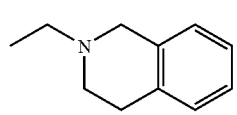 | —N(CH₂CH₃)— |
| Ib-589 | 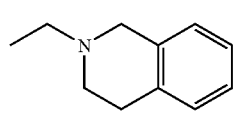 | —N(CH₂CH₂CH₃)— |
| Ib-590 | 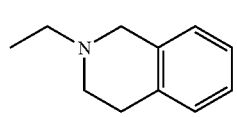 | —N(CH₂CH₂CH₂CH₃)— |
| Ib-591 | 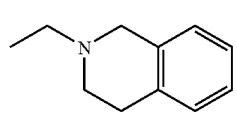 | —N(C(H)(CH₃)(CH₂CH₃))— |

-continued
| | | |
|---|---|---|
| Ib-592 | 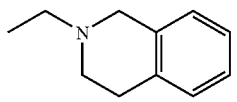 | —N(C(H)(CH₃)₂)— |
| Ib-593 | 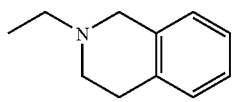 | —N(CH₂C(H)(CH₃)₂)— |
| Ib-594 | 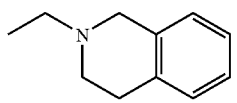 | —N(C(CH₃)₃)— |
| Ib-595 | 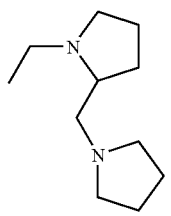 | —N(CH₃)— |
| Ib-596 | 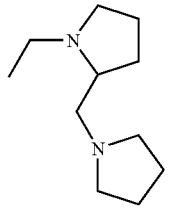 | —N(CH₂CH₃)— |
| Ib-597 | 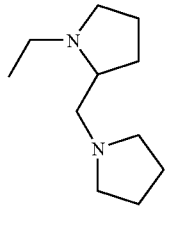 | —N(CH₂CH₂CH₃)— |
| Ib-598 | 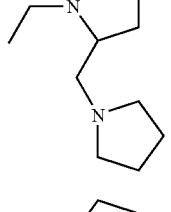 | —N(CH₂CH₂CH₂CH₃)— |
| Ib-599 | 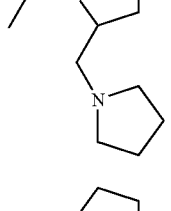 | —N(C(H)(CH₃)(CH₂CH₃))— |
| Ib-600 | 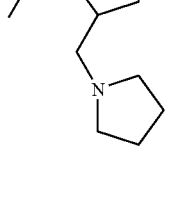 | —N(C(H)(CH₃)₂)— |

| | | |
|---|---|---|
| Ib-601 | 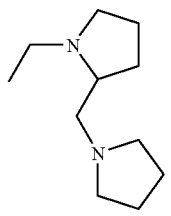 | —N(CH₂C(H)(CH₃)₂)— |
| Ib-602 | 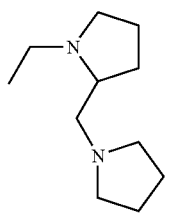 | —N(C(CH₃)₃)— |
| Ib-603 | 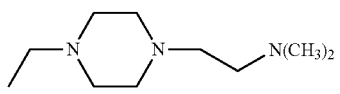 | —N(CH₃)— |
| Ib-604 | 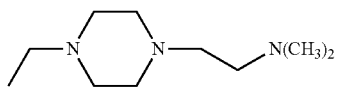 | —N(CH₂CH₃)— |
| Ib-605 | 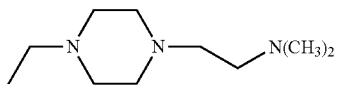 | —N(CH₂CH₂CH₃)— |
| Ib-606 | 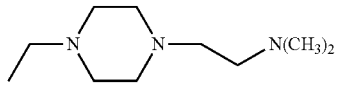 | —N(CH₂CH₂CH₂CH₃)— |
| Ib-607 | 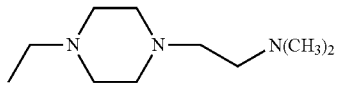 | —N(C(H)(CH₃)(CH₂CH₃))— |
| Ib-608 | 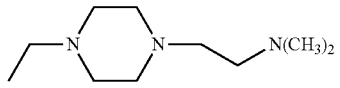 | —N(C(H)(CH₃)₂)— |
| Ib-609 | 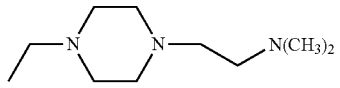 | —N(CH₂C(H)(CH₃)₂)— |
| Ib-610 | 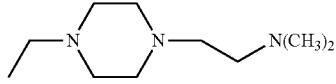 | —N(C(CH₃)₃)— |
| Ib-611 | —CH₂—NH—CH₂—CH₂—CH₂—N(CH₃)₂ | —N(CH₃)— |
| Ib-612 | —CH₂—NH—CH₂—CH₂—CH₂—N(CH₃)₂ | —N(CH₂CH₃)— |
| Ib-613 | —CH₂—NH—CH₂—CH₂—CH₂—N(CH₃)₂ | —N(CH₂CH₂CH₃)— |
| Ib-614 | —CH₂—NH—CH₂—CH₂—CH₂—N(CH₃)₂ | —N(CH₂CH₂CH₂CH₃)— |
| Ib-615 | —CH₂—NH—CH₂—CH₂—CH₂—N(CH₃)₂ | —N(C(H)(CH₃)(CH₂CH₃))— |
| Ib-616 | —CH₂—NH—CH₂—CH₂—CH₂—N(CH₃)₂ | —N(C(H)(CH₃)₂)— |
| Ib-617 | —CH₂—NH—CH₂—CH₂—CH₂—N(CH₃)₂ | —N(CH₂C(H)(CH₃)₂)— |
| Ib-618 | —CH₂—NH—CH₂—CH₂—CH₂—N(CH₃)₂ | —N(C(CH₃)₃)— |
| Ib-619 | 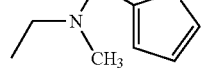 | —N(CH₃)— |

-continued

| | | |
|---|---|---|
| Ib-620 | N-CH2-furan with N-Et, N-CH3 | —N(CH2CH3)— |
| Ib-621 | N-CH2-furan with N-Et, N-CH3 | —N(CH2CH2CH3)— |
| Ib-622 | N-CH2-furan with N-Et, N-CH3 | —N(CH2CH2CH3)— |
| Ib-623 | N-CH2-furan with N-Et, N-CH3 | —N(C(H)(CH3)(CH2CH3))— |
| Ib-624 | N-CH2-furan with N-Et, N-CH3 | —N(C(H)(CH3)2)— |
| Ib-625 | N-CH2-furan with N-Et, N-CH3 | —N(CH2C(H)(CH3)2)— |
| Ib-626 | N-CH2-furan with N-Et, N-CH3 | —N(C(CH3)3)— |
| Ib-627 | N-ethyl-3-hydroxypyrrolidine | —N(CH3)— |
| Ib-628 | N-ethyl-3-hydroxypyrrolidine | —N(CH2CH3)— |
| Ib-629 | N-ethyl-3-hydroxypyrrolidine | —N(CH2CH3)— |
| Ib-630 | N-ethyl-3-hydroxypyrrolidine | —N(CH2CH2CH3)— |
| Ib-631 | N-ethyl-3-hydroxypyrrolidine | —N(C(H)(CH3)(CH2CH3))— |
| Ib-632 | N-ethyl-3-hydroxypyrrolidine | —N(C(H)(CH3)2)— |
| Ib-633 | N-ethyl-3-hydroxypyrrolidine | —N(CH2C(H)(CH3)2)— |

-continued
| | | |
|---|---|---|
| Ib-634 | 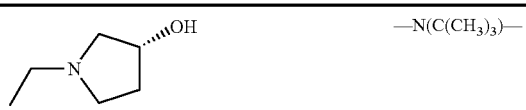 | —N(C(CH$_3$)$_3$)— |
| Ib-635 |  | —N(CH$_3$)— |
| Ib-636 |  | —N(CH$_2$CH$_3$)— |
| Ib-637 |  | —N(CH$_2$CH$_2$CH$_3$)— |
| Ib-638 |  | —N(CH$_2$CH$_2$CH$_3$)— |
| Ib-639 |  | —N(C(H)(CH$_3$)(CH$_2$CH$_3$))— |
| Ib-640 |  | —N(C(H)(CH$_3$)$_2$)— |
| Ib-641 |  | —N(CH$_2$C(H)(CH$_3$)$_2$)— |
| Ib-642 |  | —N(C(CH$_3$)$_3$)— |
| Ib-643 |  | —N(CH$_3$)— |
| Ib-644 |  | —N(CH$_2$CH$_3$)— |
| Ib-645 |  | —N(CH$_2$CH$_2$CH$_3$)— |

-continued
| | | |
|---|---|---|
| Ib-646 | 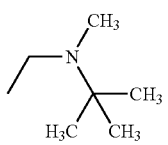 | —N(CH₂CH₂CH₂CH₃)— |
| Ib-647 | 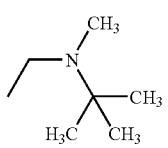 | —N(C(H)(CH₃)(CH₂CH₃))— |
| Ib-648 | 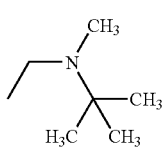 | —N(C(H)(CH₃)₂)— |
| Ib-649 | 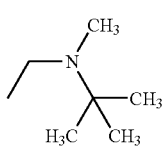 | —N(CH₂C(H)(CH₃)₂)— |
| Ib-650 | 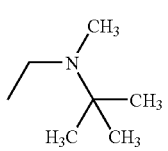 | —N(C(CH₃)₃)— |
| Ib-651 | 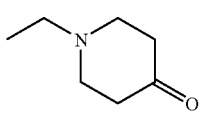 | —N(CH₃)— |
| Ib-652 | 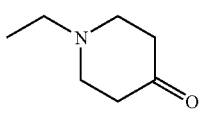 | —N(CH₂CH₃)— |
| Ib-653 | 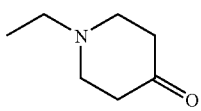 | —N(CH₂CH₂CH₃)— |
| Ib-654 | 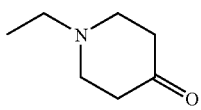 | —N(CH₂CH₂CH₂CH₃)— |
| Ib-655 | 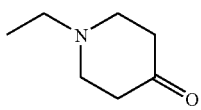 | —N(C(H)(CH₃)(CH₂CH₃))— |
| Ib-656 | 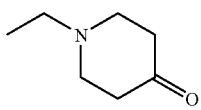 | —N(C(H)(CH₃)₂)— |
| Ib-657 | 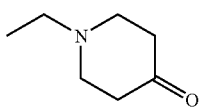 | —N(CH₂C(H)(CH₃)₂)— |

-continued

| | | |
|---|---|---|
| Ib-658 | 1-ethylpiperidin-4-one | —N(C(CH₃)₃)— |
| Ib-659 | 1-ethyl-4-hydroxypiperidine | —N(CH₃)— |
| Ib-660 | 1-ethyl-4-hydroxypiperidine | —N(CH₂CH₃)— |
| Ib-661 | 1-ethyl-4-hydroxypiperidine | —N(CH₂CH₂CH₃)— |
| Ib-662 | 1-ethyl-4-hydroxypiperidine | —N(CH₂CH₂CH₃)— |
| Ib-663 | 1-ethyl-4-hydroxypiperidine | —N(C(H)(CH₃)(CH₂CH₃))— |
| Ib-664 | 1-ethyl-4-hydroxypiperidine | —N(C(H)(CH₃)₂)— |
| Ib-665 | 1-ethyl-4-hydroxypiperidine | —N(CH₂C(H)(CH₃)₂)— |
| Ib-666 | 1-ethyl-4-hydroxypiperidine | —N(C(CH₃)₃)— |
| Ib-667 | 1-ethyl-3-hydroxypiperidine | —N(CH₃)— |
| Ib-668 | 1-ethyl-3-hydroxypiperidine | —N(CH₂CH₃)— |
| Ib-669 | 1-ethyl-3-hydroxypiperidine | —N(CH₂CH₂CH₃)— |
| Ib-670 | 1-ethyl-3-hydroxypiperidine | —N(CH₂CH₂CH₃)— |
| Ib-671 | 1-ethyl-3-hydroxypiperidine | —N(C(H)(CH₃)(CH₂CH₃))— |
| Ib-672 | 1-ethyl-3-hydroxypiperidine | —N(C(H)(CH₃)₂)— |

-continued
| | | |
|---|---|---|
| Ib-673 | 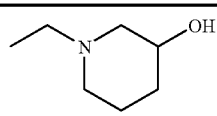 | —N(CH$_2$C(H)(CH$_3$)$_2$)— |
| Ib-674 | 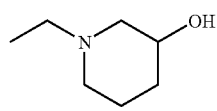 | —N(C(CH$_3$)$_3$)— |
| Ib-675 | 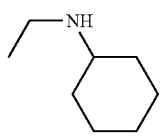 | —N(CH$_3$)— |
| Ib-676 | 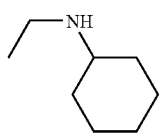 | —N(CH$_2$CH$_3$)— |
| Ib-677 |  | —N(CH$_2$CH$_2$CH$_3$)— |
| Ib-678 | 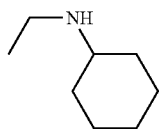 | —N(CH$_2$CH$_2$CH$_2$CH$_3$)— |
| Ib-679 | 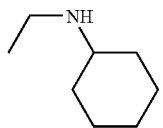 | —N(C(H)(CH$_3$)(CH$_2$CH$_3$))— |
| Ib-680 | 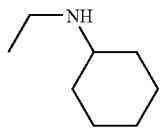 | —N(C(H)(CH$_3$)$_2$)— |
| Ib-681 | 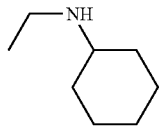 | —N(CH$_2$C(H)(CH$_3$)$_2$)— |
| Ib-682 | 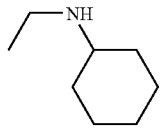 | —N(C(CH$_3$)$_3$)— |
| Ib-683 | 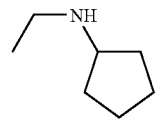 | —N(CH$_3$)— |
| Ib-684 | 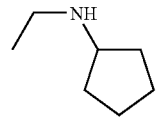 | —N(CH$_2$CH$_3$)— |

-continued
| | | |
|---|---|---|
| Ib-685 | 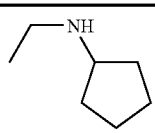 | —N(CH₂CH₂CH₃)— |
| Ib-686 | 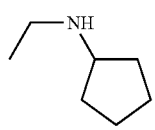 | —N(CH₂CH₂CH₂CH₃)— |
| Ib-687 | 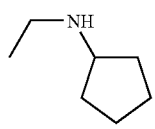 | —N(C(H)(CH₃)(CH₂CH₃))— |
| Ib-688 | 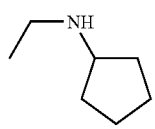 | —N(C(H)(CH₃)₂)— |
| Ib-689 | 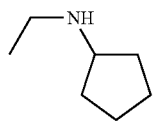 | —N(CH₂C(H)(CH₃)₂)— |
| Ib-690 | 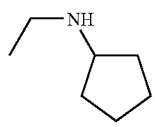 | —N(C(CH₃)₃)— |
| Ib-691 | 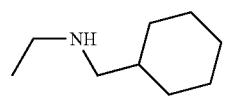 | —N(CH₃)— |
| Ib-692 | 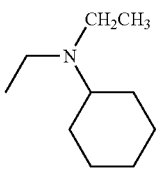 | —N(CH₂CH₃)— |
| Ib-693 | 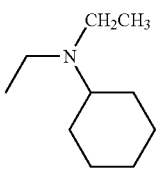 | —N(CH₂CH₂CH₃)— |
| Ib-694 | 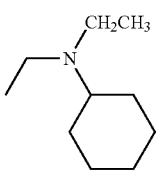 | —N(CH₂CH₂CH₂CH₃)— |
| Ib-695 | 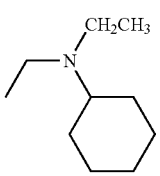 | —N(C(H)(CH₃)(CH₂CH₃))— |

-continued
| | | |
|---|---|---|
| Ib-696 | 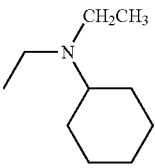 | —N(C(H)(CH$_3$)$_2$)— |
| Ib-697 | 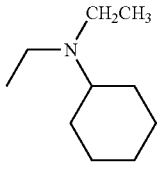 | —N(CH$_2$C(H)(CH$_3$)$_2$)— |
| Ib-698 | 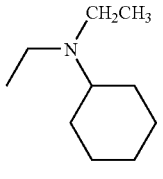 | —N(C(CH$_3$)$_3$)— |
| Ib-699 | 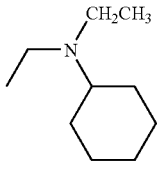 | —N(CH$_3$)— |
| Ib-700 | 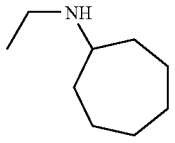 | —N(CH$_2$CH$_3$)— |
| Ib-701 |  | —N(CH$_2$CH$_2$CH$_3$)— |
| Ib-702 | 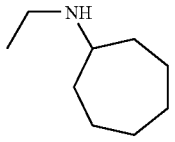 | —N(CH$_2$CH$_2$CH$_2$CH$_3$)— |
| Ib-703 | 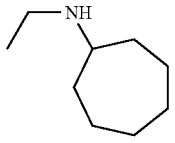 | —N(C(H)(CH$_3$)(CH$_2$CH$_3$))— |
| Ib-704 |  | —N(C(H)(CH$_3$)$_2$)— |
| Ib-705 | 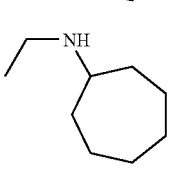 | —N(CH$_2$C(H)(CH$_3$)$_2$)— |

-continued
| | | |
|---|---|---|
| Ib-706 | 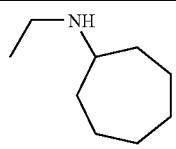 | —N(C(CH₃)₃)— |
| Ib-707 | 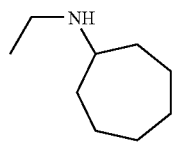 | —N(CH₃)— |
| Ib-708 | 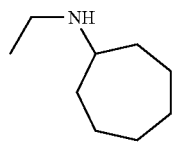 | —N(CH₂CH₃)— |
| Ib-709 | 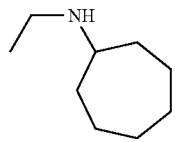 | —N(CH₂CH₂CH₃)— |
| Ib-710 | 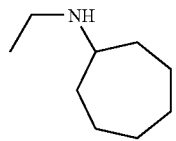 | —N(CH₂CH₂CH₃)— |
| Ib-711 | 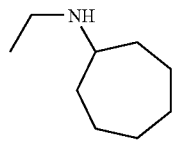 | —N(C(H)(CH₃)(CH₂CH₃))— |
| Ib-712 | 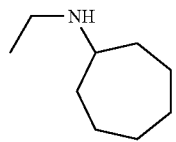 | —N(C(H)(CH₃)₂)— |
| Ib-713 | 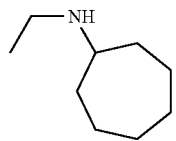 | —N(CH₂C(H)(CH₃)₂)— |
| Ib-714 | 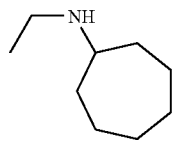 | —N(C(CH₃)₃)— |
| Ib-715 | 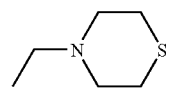 | —N(CH₃)— |
| Ib-716 | 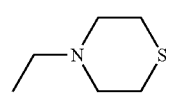 | —N(CH₂CH₃)— |

| | | -continued |
|---|---|---|
| Ib-717 | N-ethyl thiomorpholine | —N(CH₂CH₂CH₃)— |
| Ib-718 | N-ethyl thiomorpholine | —N(CH₂CH₂CH₂CH₃)— |
| Ib-719 | N-ethyl thiomorpholine | —N(C(H)(CH₃)(CH₂CH₃))— |
| Ib-720 | N-ethyl thiomorpholine | —N(C(H)(CH₃)₂)— |
| Ib-721 | N-ethyl thiomorpholine | —N(CH₂C(H)(CH₃)₂)— |
| Ib-722 | N-ethyl thiomorpholine | —N(C(CH₃)₃)— |
| Ib-723 | 1-ethyl-4-(hydroxymethyl)piperidine | —N(CH₃)— |
| Ib-724 | 1-ethyl-4-(hydroxymethyl)piperidine | —N(CH₂CH₃)— |
| Ib-725 | 1-ethyl-4-(hydroxymethyl)piperidine | —N(CH₂CH₂CH₃)— |
| Ib-726 | 1-ethyl-4-(hydroxymethyl)piperidine | —N(CH₂CH₂CH₂CH₃)— |
| Ib-727 | 1-ethyl-4-(hydroxymethyl)piperidine | —N(C(H)(CH₃)(CH₂CH₃))— |
| Ib-728 | 1-ethyl-4-(hydroxymethyl)piperidine | —N(C(H)(CH₃)₂)— |
| Ib-729 | 1-ethyl-4-(hydroxymethyl)piperidine | —N(CH₂C(H)(CH₃)₂)— |
| Ib-730 | 1-ethyl-4-(hydroxymethyl)piperidine | —N(C(CH₃)₃)— |
| Ib-731 | 4-ethylamino-2,2,6,6-tetramethylpiperidine | —N(CH₃)— |

| | | |
|---|---|---|
| Ib-732 | 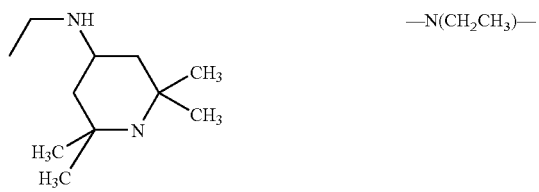 | —N(CH$_2$CH$_3$)— |
| Ib-733 | 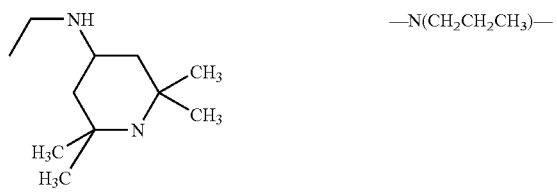 | —N(CH$_2$CH$_2$CH$_3$)— |
| Ib-734 | 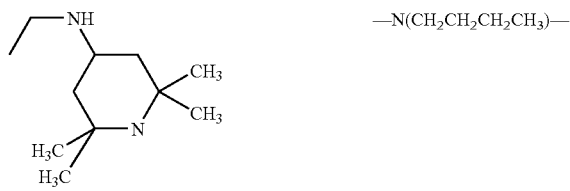 | —N(CH$_2$CH$_2$CH$_2$CH$_3$)— |
| Ib-735 | 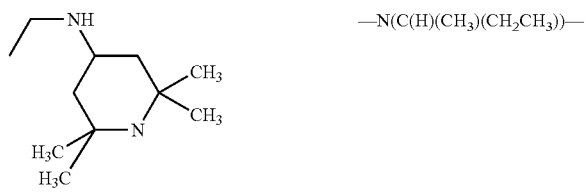 | —N(C(H)(CH$_3$)(CH$_2$CH$_3$))— |
| Ib-736 | 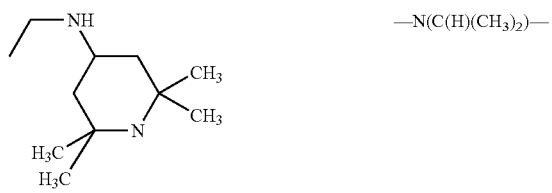 | —N(C(H)(CH$_3$)$_2$)— |
| Ib-737 | 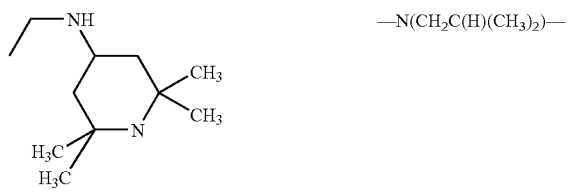 | —N(CH$_2$C(H)(CH$_3$)$_2$)— |
| Ib-738 | 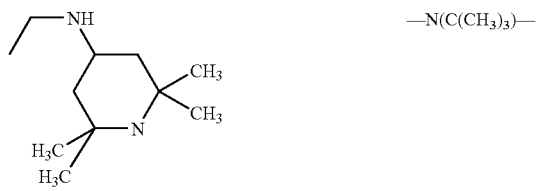 | —N(C(CH$_3$)$_3$)— |
| Ib-739 | 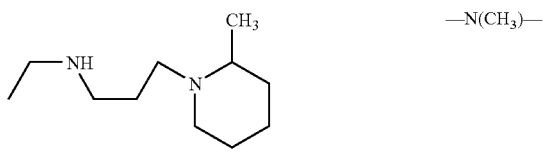 | —N(CH$_3$)— |

-continued
| | | |
|---|---|---|
| Ib-740 | 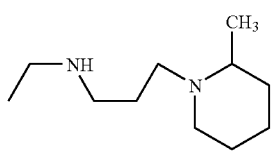 | —N(CH₂CH₃)— |
| Ib-741 | 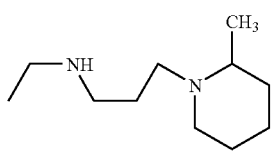 | —N(CH₂CH₃)— |
| Ib-742 | 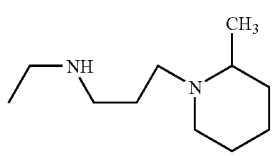 | —N(CH₂CH₂CH₃)— |
| Ib-743 | 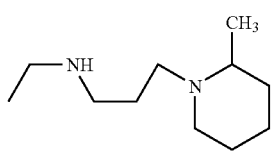 | —N(C(H)(CH₃)(CH₂CH₃))— |
| Ib-744 | 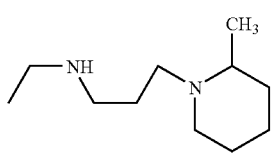 | —N(C(H)(CH₃)₂)— |
| Ib-745 | 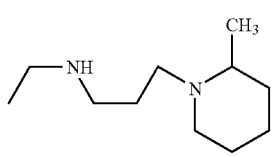 | —N(CH₂C(H)(CH₃)₂)— |
| Ib-746 | 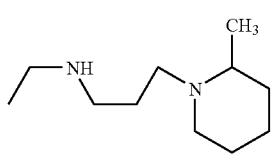 | —N(C(CH₃)₃)— |
| Ib-747 | 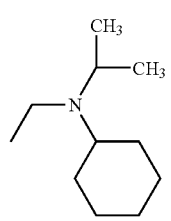 | —N(CH₃)— |
| Ib-748 | 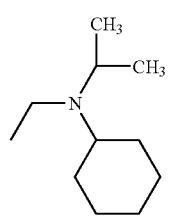 | —N(CH₂CH₃)— |

-continued
| | | |
|---|---|---|
| Ib-749 | 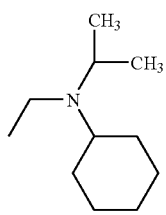 | —N(CH₂CH₂CH₃)— |
| Ib-750 | 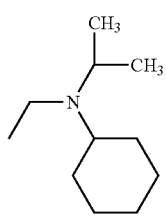 | —N(CH₂CH₂CH₂CH₃)— |
| Ib-751 | 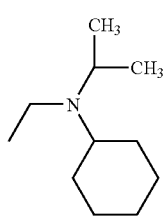 | —N(C(H)(CH₃)(CH₂CH₃))— |
| Ib-752 | 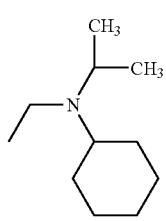 | —N(C(H)(CH₃)₂)— |
| Ib-753 | 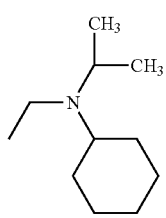 | —N(CH₂C(H)(CH₃)₂)— |
| Ib-754 | 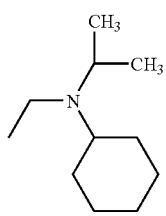 | —N(C(CH₃)₃)— |
| Ib-755 | 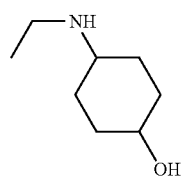 | —N(CH₃)— |

-continued

| | | |
|---|---|---|
| Ib-756 | 4-(ethylamino)cyclohexan-1-ol | —N(CH₂CH₃)— |
| Ib-757 | 4-(ethylamino)cyclohexan-1-ol | —N(CH₂CH₂CH₃)— |
| Ib-758 | 4-(ethylamino)cyclohexan-1-ol | —N(CH₂CH₂CH₃)— |
| Ib-759 | 4-(ethylamino)cyclohexan-1-ol | —N(C(H)(CH₃)(CH₂CH₃))— |
| Ib-760 | 4-(ethylamino)cyclohexan-1-ol | —N(C(H)(CH₃)₂)— |
| Ib-761 | 4-(ethylamino)cyclohexan-1-ol | —N(CH₂C(H)(CH₃)₂)— |
| Ib-762 | 4-(ethylamino)cyclohexan-1-ol | —N(C(CH₃)₃)— |
| Ib-763 | 2-(N-cyclohexyl-N-ethylamino)ethanol | —N(CH₃)— |
| Ib-764 | 2-(N-cyclohexyl-N-ethylamino)ethanol | —N(CH₂CH₃)— |

-continued

| | | |
|---|---|---|
| Ib-765 | N-ethyl-N-(2-hydroxyethyl)cyclohexylamine | —N(CH₂CH₃)— |
| Ib-766 | N-ethyl-N-(2-hydroxyethyl)cyclohexylamine | —N(CH₂CH₂CH₃)— |
| Ib-767 | N-ethyl-N-(2-hydroxyethyl)cyclohexylamine | —N(C(H)(CH₃)(CH₂CH₃))— |
| Ib-768 | N-ethyl-N-(2-hydroxyethyl)cyclohexylamine | —N(C(H)(CH₃)₂)— |
| Ib-769 | N-ethyl-N-(2-hydroxyethyl)cyclohexylamine | —N(CH₂C(H)(CH₃)₂)— |
| Ib-770 | N-ethyl-N-(2-hydroxyethyl)cyclohexylamine | —N(C(CH₃)₃)— |
| Ib-771 | 1-ethyl-4-methylpiperidine | —N(CH₃)— |
| Ib-772 | 1-ethyl-4-methylpiperidine | —N(CH₂CH₃)— |
| Ib-773 | 1-ethyl-4-methylpiperidine | —N(CH₂CH₂CH₃)— |
| Ib-774 | 1-ethyl-4-methylpiperidine | —N(CH₂CH₂CH₂CH₃)— |
| Ib-775 | 1-ethyl-4-methylpiperidine | —N(C(H)(CH₃)(CH₂CH₃))— |
| Ib-776 | 1-ethyl-4-methylpiperidine | —N(C(H)(CH₃)₂)— |

-continued

| | | |
|---|---|---|
| Ib-777 | 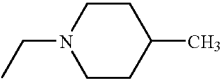 | —N(CH₂C(H)(CH₃)₂)— |
| Ib-778 | 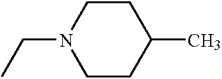 | —N(C(CH₃)₃)— |
| Ib-779 | —CH₂—NH—CH₃ | —N(CH₃)— |
| Ib-780 | —CH₂—NH—CH₃ | —N(CH₂CH₃)— |
| Ib-781 | —CH₂—NH—CH₃ | —N(CH₂CH₂CH₃)— |
| Ib-782 | —CH₂—NH—CH₃ | —N(CH₂CH₂CH₂CH₃)— |
| Ib-783 | —CH₂—NH—CH₃ | —N(C(H)(CH₃)(CH₂CH₃))— |
| Ib-784 | —CH₂—NH—CH₃ | —N(C(H)(CH₃)₂)— |
| Ib-785 | —CH₂—NH—CH₃ | —N(CH₂C(H)(CH₃)₂)— |
| Ib-786 | —CH₂—NH—CH₃ | —N(C(CH₃)₃)— |
| Ib-787 | —CH₂—NH—CH₂—CH₃ | —N(CH₃)— |
| Ib-788 | —CH₂—NH—CH₂—CH₃ | —N(CH₂CH₃)— |
| Ib-789 | —CH₂—NH—CH₂—CH₃ | —N(CH₂CH₂CH₃)— |
| Ib-790 | —CH₂—NH—CH₂—CH₃ | —N(CH₂CH₂CH₂CH₃)— |
| Ib-791 | —CH₂—NH—CH₂—CH₃ | —N(C(H)(CH₃)(CH₂CH₃))— |
| Ib-792 | —CH₂—NH—CH₂—CH₃ | —N(C(H)(CH₃)₂)— |
| Ib-793 | —CH₂—NH—CH₂—CH₃ | —N(CH₂C(H)(CH₃)₂)— |
| Ib-794 | —CH₂—NH—CH₂—CH₃ | —N(C(CH₃)₃)— |
| Ib-795 | —CH₂—NH—CH₂—CH₂—CH₃ | —N(CH₃)— |
| Ib-796 | —CH₂—NH—CH₂—CH₂—CH₃ | —N(CH₂CH₃)— |
| Ib-797 | —CH₂—NH—CH₂—CH₂—CH₃ | —N(CH₂CH₂CH₃)— |
| Ib-798 | —CH₂—NH—CH₂—CH₂—CH₃ | —N(CH₂CH₂CH₂CH₃)— |
| Ib-799 | —CH₂—NH—CH₂—CH₂—CH₃ | —N(C(H)(CH₃)(CH₂CH₃))— |
| Ib-800 | —CH₂—NH—CH₂—CH₂—CH₃ | —N(C(H)(CH₃)₂)— |
| Ib-801 | —CH₂—NH—CH₂—CH₂—CH₃ | —N(CH₂C(H)(CH₃)₂)— |
| Ib-802 | —CH₂—NH—CH₂—CH₂—CH₃ | —N(C(CH₃)₃)— |
| Ib-803 | 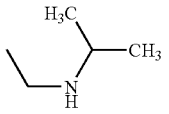 | —N(CH₃)— |
| Ib-804 | 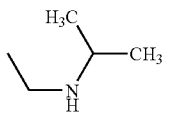 | —N(CH₂CH₃)— |
| Ib-805 | 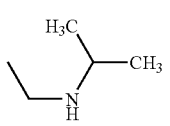 | —N(CH₂CH₂CH₃)— |
| Ib-806 | 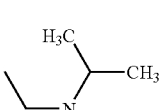 | —N(CH₂CH₂CH₂CH₃)— |
| Ib-807 | 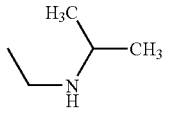 | —N(C(H)(CH₃)(CH₂CH₃))— |
| Ib-808 |  | —N(C(H)(CH₃)₂)— |
| Ib-809 | 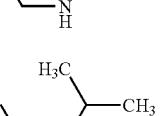 | —N(CH₂C(H)(CH₃)₂)— |

-continued
| | | |
|---|---|---|
| Ib-810 | 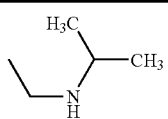 | —N(C(CH₃)₃)— |
| Ib-811 | 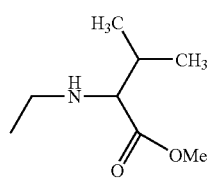 | —N(CH₃)— |
| Ib-812 | 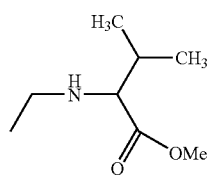 | —N(CH₂CH₃)— |
| Ib-813 | 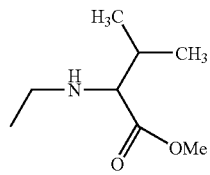 | —N(CH₂CH₂CH₃)— |
| Ib-814 | 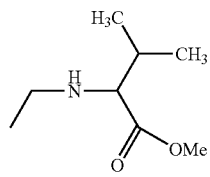 | —N(CH₂CH₂CH₂CH₃)— |
| Ib-815 | 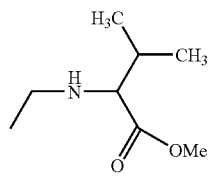 | —N(C(H)(CH₃)(CH₂CH₃))— |
| Ib-816 | 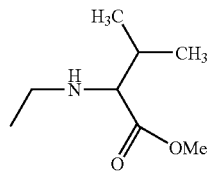 | —N(C(H)(CH₃)₂)— |
| Ib-817 | 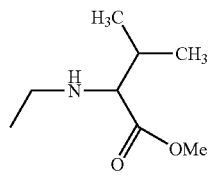 | —N(CH₂C(H)(CH₃)₂)— |
| Ib-818 | 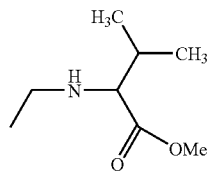 | —N(C(CH₃)₃)— |

-continued
| | | |
|---|---|---|
| Ib-819 | 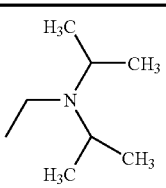 | —N(CH₃)— |
| Ib-820 | 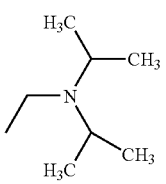 | —N(CH₂CH₃)— |
| Ib-821 | 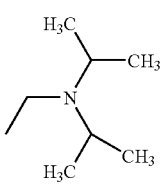 | —N(CH₂CH₂CH₃)— |
| Ib-822 | 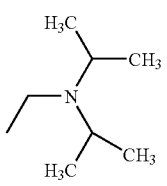 | —N(CH₂CH₂CH₂CH₃)— |
| Ib-823 | 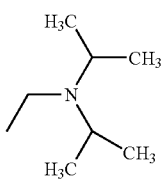 | —N(C(H)(CH₃)(CH₂CH₃))— |
| Ib-824 | 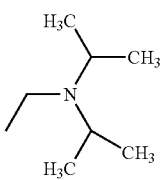 | —N(C(H)(CH₃)₂)— |
| Ib-825 | 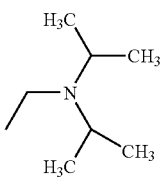 | —N(CH₂C(H)(CH₃)₂)— |
| Ib-826 | 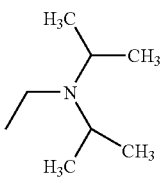 | —N(C(CH₃)₃)— |
| Ib-827 | 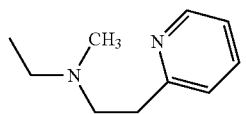 | —N(CH₃)— |

-continued
| | | |
|---|---|---|
| Ib-828 | 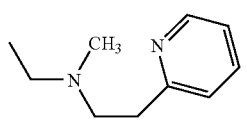 | —N(CH₂CH₃)— |
| Ib-829 | 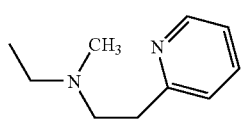 | —N(CH₂CH₂CH₃)— |
| Ib-830 | 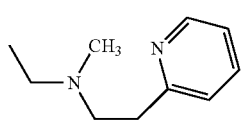 | —N(CH₂CH₂CH₂CH₃)— |
| Ib-831 | 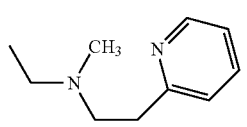 | —N(C(H)(CH₃)(CH₂CH₃))— |
| Ib-832 | 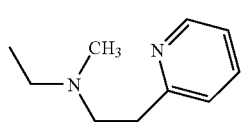 | —N(C(H)(CH₃)₂)— |
| Ib-833 | 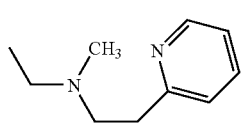 | —N(CH₂C(H)(CH₃)₂)— |
| Ib-834 | 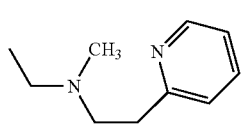 | —N(C(CH₃)₃)— |
| Ib-835 | 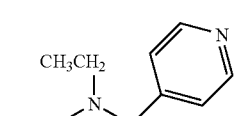 | —N(CH₃)— |
| Ib-836 | 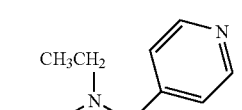 | —N(CH₂CH₃)— |
| Ib-837 | 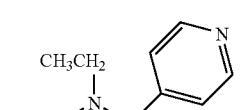 | —N(CH₂CH₂CH₃)— |
| Ib-838 | 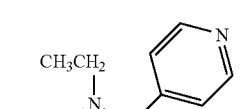 | —N(CH₂CH₂CH₂CH₃)— |
| Ib-839 | 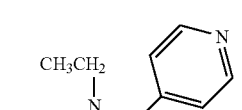 | —N(C(H)(CH₃)(CH₂CH₃))— |

-continued

| | | |
|---|---|---|
| Ib-840 | CH₃CH₂-N(ethyl)-CH₂-(4-pyridyl) | —N(C(H)(CH₃)₂)— |
| Ib-841 | CH₃CH₂-N(ethyl)-CH₂-(4-pyridyl) | —N(CH₂C(H)(CH₃)₂)— |
| Ib-842 | CH₃CH₂-N(ethyl)-CH₂-(4-pyridyl) | —N(C(CH₃)₃)— |
| Ib-843 | CH₃CH₂-N(CH₃)-CH₂CH₂OH | —N(CH₃)— |
| Ib-844 | CH₃CH₂-N(CH₃)-CH₂CH₂OH | —N(CH₂CH₃)— |
| Ib-845 | CH₃CH₂-N(CH₃)-CH₂CH₂OH | —N(CH₂CH₂CH₃)— |
| Ib-846 | CH₃CH₂-N(CH₃)-CH₂CH₂OH | —N(CH₂CH₂CH₂CH₃)— |
| Ib-847 | CH₃CH₂-N(CH₃)-CH₂CH₂OH | —N(C(H)(CH₃)(CH₂CH₃))— |
| Ib-848 | CH₃CH₂-N(CH₃)-CH₂CH₂OH | —N(C(H)(CH₃)₂)— |
| Ib-849 | CH₃CH₂-N(CH₃)-CH₂CH₂OH | —N(CH₂C(H)(CH₃)₂)— |
| Ib-850 | CH₃CH₂-N(CH₃)-CH₂CH₂OH | —N(C(CH₃)₃)— |
| Ib-851 | Et-piperidinyl-piperidinyl | —N(CH₃)— |
| Ib-852 | Et-piperidinyl-piperidinyl | —N(CH₂CH₃)— |
| Ib-853 | Et-piperidinyl-piperidinyl | —N(CH₂CH₂CH₃)— |
| Ib-854 | Et-piperidinyl-piperidinyl | —N(CH₂CH₂CH₂CH₃)— |
| Ib-855 | Et-piperidinyl-piperidinyl | —N(C(H)(CH₃)(CH₂CH₃))— |

-continued
| | | |
|---|---|---|
| Ib-856 | 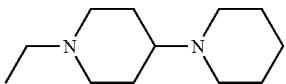 | —N(C(H)(CH$_3$)$_2$)— |
| Ib-857 | 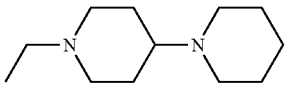 | —N(CH$_2$C(H)(CH$_3$)$_2$)— |
| Ib-858 | 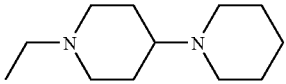 | —N(C(CH$_3$)$_3$)— |
| Ib-859 | 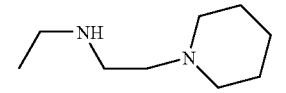 | —N(CH$_3$)— |
| Ib-860 | 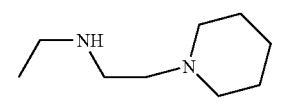 | —N(CH$_2$CH$_3$)— |
| Ib-861 | 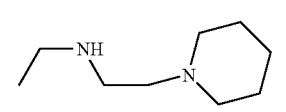 | —N(CH$_2$CH$_2$CH$_3$)— |
| Ib-862 | 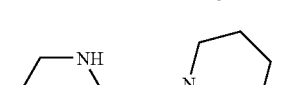 | —N(CH$_2$CH$_2$CH$_3$)— |
| Ib-863 | 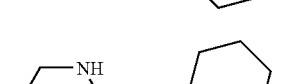 | —N(C(H)(CH$_3$)(CH$_2$CH$_3$))— |
| Ib-864 | 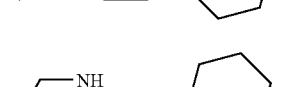 | —N(C(H)(CH$_3$)$_2$)— |
| Ib-865 |  | —N(CH$_2$C(H)(CH$_3$)$_2$)— |
| Ib-866 |  | —N(C(CH$_3$)$_3$)— |
| Ib-867 | 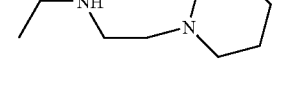 | —N(CH$_3$)— |
| Ib-868 |  | —N(CH$_2$CH$_3$)— |
| Ib-869 | 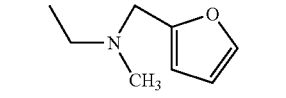 | —N(CH$_2$CH$_2$CH$_3$)— |
| Ib-870 | 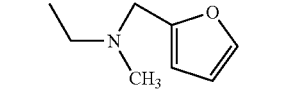 | —N(CH$_2$CH$_2$CH$_2$CH$_3$)— |

-continued
| | | |
|---|---|---|
| Ib-871 | 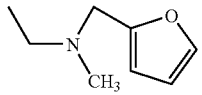 | —N(C(H)(CH₃)(CH₂CH₃))— |
| Ib-872 | 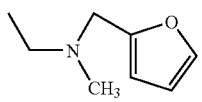 | —N(C(H)(CH₃)₂)— |
| Ib-873 | 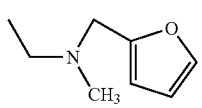 | —N(CH₂C(H)(CH₃)₂)— |
| Ib-874 | 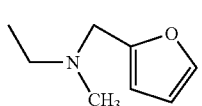 | —N(C(CH₃)₃)— |
| Ib-875 | 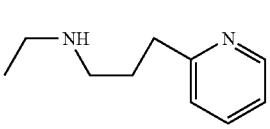 | —N(CH₃)— |
| Ib-876 | 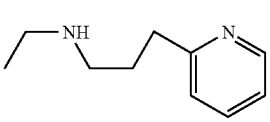 | —N(CH₂CH₃)— |
| Ib-877 | 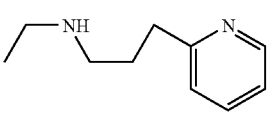 | —N(CH₂CH₂CH₃)— |
| Ib-878 | 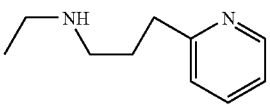 | —N(CH₂CH₂CH₂CH₃)— |
| Ib-879 | 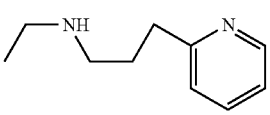 | —N(C(H)(CH₃)(CH₂CH₃))— |
| Ib-880 | 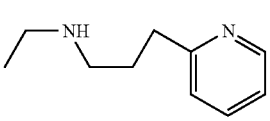 | —N(C(H)(CH₃)₂)— |
| Ib-881 | 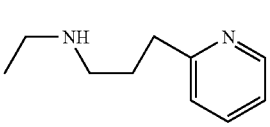 | —N(CH₂C(H)(CH₃)₂)— |
| Ib-882 | 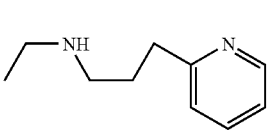 | —N(C(CH₃)₃)— |
| Ib-883 | 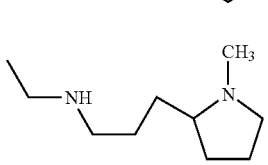 | —N(CH₃)— |

| | | |
|---|---|---|
| Ib-884 | ethyl-NH-CH2CH2CH2-(N-methylpyrrolidin-2-yl) | —N(CH₂CH₃)— |
| Ib-885 | ethyl-NH-CH2CH2CH2-(N-methylpyrrolidin-2-yl) | —N(CH₂CH₃)— |
| Ib-886 | ethyl-NH-CH2CH2CH2-(N-methylpyrrolidin-2-yl) | —N(CH₂CH₂CH₃)— |
| Ib-887 | ethyl-NH-CH2CH2CH2-(N-methylpyrrolidin-2-yl) | —N(C(H)(CH₃)(CH₂CH₃))— |
| Ib-888 | ethyl-NH-CH2CH2CH2-(N-methylpyrrolidin-2-yl) | —N(C(H)(CH₃)₂)— |
| Ib-889 | ethyl-NH-CH2CH2CH2-(N-methylpyrrolidin-2-yl) | —N(CH₂C(H)(CH₃)₂)— |
| Ib-890 | ethyl-NH-CH2CH2CH2-(N-methylpyrrolidin-2-yl) | —N(C(CH₃)₃)— |
| Ib-891 | 4-ethylpiperazine | —N(CH₃)— |
| Ib-892 | 4-ethylpiperazine | —N(CH₂CH₃)— |
| Ib-893 | 4-ethylpiperazine | —N(CH₂CH₂CH₃)— |
| Ib-894 | 4-ethylpiperazine | —N(CH₂CH₂CH₂CH₃)— |
| Ib-895 | 4-ethylpiperazine | —N(C(H)(CH₃)(CH₂CH₃))— |
| Ib-896 | 4-ethylpiperazine | —N(C(H)(CH₃)₂)— |

-continued
| | | |
|---|---|---|
| Ib-897 | 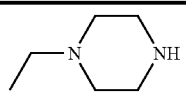 | —N(CH₂C(H)(CH₃)₂)— |
| Ib-898 | 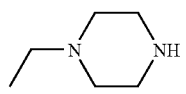 | —N(C(CH₃)₃)— |
| Ib-899 | 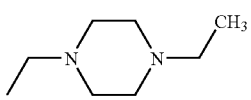 | —N(CH₃)— |
| Ib-900 | 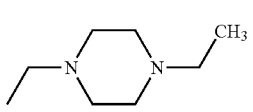 | —N(CH₂CH₃)— |
| Ib-901 | 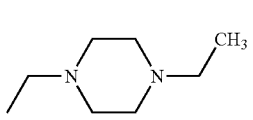 | —N(CH₂CH₂CH₃)— |
| Ib-902 | 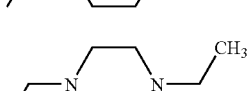 | —N(CH₂CH₂CH₂CH₃)— |
| Ib-903 | 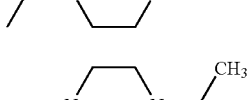 | —N(C(H)(CH₃)(CH₂CH₃))— |
| Ib-904 | 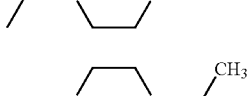 | —N(C(H)(CH₃)₂)— |
| Ib-905 |  | —N(CH₂C(H)(CH₃)₂)— |
| Ib-906 | 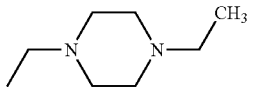 | —N(C(CH₃)₃)— |
| Ib-907 | 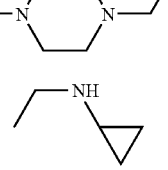 | —N(CH₃)— |
| Ib-908 | 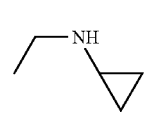 | —N(CH₂CH₃)— |
| Ib-909 | 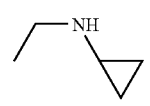 | —N(CH₂CH₂CH₃)— |
| Ib-910 | 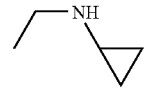 | —N(CH₂CH₂CH₂CH₃)— |
| Ib-911 | 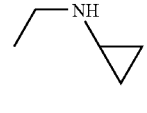 | —N(C(H)(CH₃)(CH₂CH₃))— |

-continued

| | | |
|---|---|---|
| Ib-912 | ethyl-NH-cyclopropyl | —N(C(H)(CH₃)₂)— |
| Ib-913 | ethyl-NH-cyclopropyl | —N(CH₂C(H)(CH₃)₂)— |
| Ib-914 | ethyl-NH-cyclopropyl | —N(C(CH₃)₃)— |
| Ib-915 | ethyl-piperazine-CH₂CH₂OH | —N(CH₃)— |
| Ib-916 | ethyl-piperazine-CH₂CH₂OH | —N(CH₂CH₃)— |
| Ib-917 | ethyl-piperazine-CH₂CH₂OH | —N(CH₂CH₂CH₃)— |
| Ib-918 | ethyl-piperazine-CH₂CH₂OH | —N(CH₂CH₂CH₂CH₃)— |
| Ib-919 | ethyl-piperazine-CH₂CH₂OH | —N(C(H)(CH₃)(CH₂CH₃))— |
| Ib-920 | ethyl-piperazine-CH₂CH₂OH | —N(C(H)(CH₃)₂)— |
| Ib-921 | ethyl-piperazine-CH₂CH₂OH | —N(CH₂C(H)(CH₃)₂)— |
| Ib-922 | ethyl-piperazine-CH₂CH₂OH | —N(C(CH₃)₃)— |
| Ib-923 | ethyl-piperazine-CH₂CH₃ | —N(CH₃)— |
| Ib-924 | ethyl-piperazine-CH₂CH₃ | —N(CH₂CH₃)— |
| Ib-925 | ethyl-piperazine-CH₂CH₃ | —N(CH₂CH₂CH₃)— |
| Ib-926 | ethyl-piperazine-CH₂CH₃ | —N(CH₂CH₂CH₂CH₃)— |
| Ib-927 | ethyl-piperazine-CH₂CH₃ | —N(C(H)(CH₃)(CH₂CH₃))— |

-continued

| | | |
|---|---|---|
| Ib-928 | (4-ethylpiperazin-1-yl)-CH(CH3)- (N-ethyl, N'-propyl piperazine) | —N(C(H)(CH3)2)— |
| Ib-929 | (4-ethylpiperazin-1-yl)-CH(CH3)- | —N(CH2C(H)(CH3)2)— |
| Ib-930 | (4-ethylpiperazin-1-yl)-CH(CH3)- | —N(C(CH3)3)— |
| Ib-931 | 1-ethyl-4-(cyclohexylmethyl)piperazine | —N(CH3)— |
| Ib-932 | 1-ethyl-4-(cyclohexylmethyl)piperazine | —N(CH2CH3)— |
| Ib-933 | 1-ethyl-4-(cyclohexylmethyl)piperazine | —N(CH2CH2CH3)— |
| Ib-934 | 1-ethyl-4-(cyclohexylmethyl)piperazine | —N(CH2CH2CH2CH3)— |
| Ib-935 | 1-ethyl-4-(cyclohexylmethyl)piperazine | —N(C(H)(CH3)(CH2CH3))— |
| Ib-936 | 1-ethyl-4-(cyclohexylmethyl)piperazine | —N(C(H)(CH3)2)— |
| Ib-937 | 1-ethyl-4-(cyclohexylmethyl)piperazine | —N(CH2C(H)(CH3)2)— |
| Ib-938 | 1-ethyl-4-(cyclohexylmethyl)piperazine | —N(C(CH3)3)— |

-continued

| | | |
|---|---|---|
| Ib-939 | N-ethyl-4-ethoxypiperidine | —N(CH₃)— |
| Ib-940 | N-ethyl-4-ethoxypiperidine | —N(CH₂CH₃)— |
| Ib-941 | N-ethyl-4-ethoxypiperidine | —N(CH₂CH₂CH₃)— |
| Ib-942 | N-ethyl-4-ethoxypiperidine | —N(CH₂CH₂CH₃)— |
| Ib-943 | N-ethyl-4-ethoxypiperidine | —N(C(H)(CH₃)(CH₂CH₃))— |
| Ib-944 | N-ethyl-4-ethoxypiperidine | —N(C(H)(CH₃)₂)— |
| Ib-945 | N-ethyl-4-ethoxypiperidine | —N(CH₂C(H)(CH₃)₂)— |
| Ib-946 | N-ethyl-4-ethoxypiperidine | —N(C(CH₃)₃)— |
| Ib-947 | N-ethyl-3-hydroxypiperidine | —N(CH₃)— |
| Ib-948 | N-ethyl-3-hydroxypiperidine | —N(CH₂CH₃)— |
| Ib-949 | N-ethyl-3-hydroxypiperidine | —N(CH₂CH₂CH₃)— |
| Ib-950 | N-ethyl-3-hydroxypiperidine | —N(CH₂CH₂CH₃)— |
| Ib-951 | N-ethyl-3-hydroxypiperidine | —N(C(H)(CH₃)(CH₂CH₃))— |
| Ib-952 | N-ethyl-3-hydroxypiperidine | —N(C(H)(CH₃)₂)— |

-continued

| | | |
|---|---|---|
| Ib-953 | 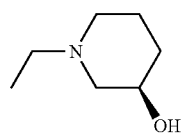 | —N(CH₂C(H)(CH₃)₂)— |
| Ib-954 | 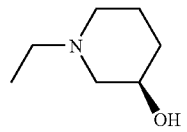 | —N(C(CH₃)₃)— |
| Ib-955 | 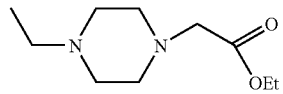 | —N(CH₃)— |
| Ib-956 | 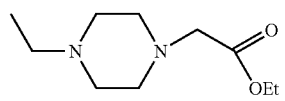 | —N(CH₂CH₃)— |
| Ib-957 | 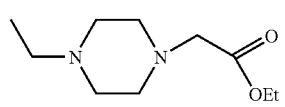 | —N(CH₂CH₂CH₃)— |
| Ib-958 | 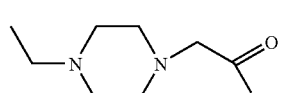 | —N(CH₂CH₂CH₂CH₃)— |
| Ib-959 | 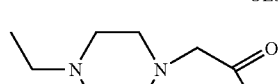 | —N(C(H)(CH₃)(CH₂CH₃))— |
| Ib-960 | 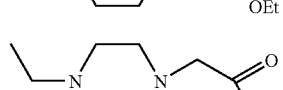 | —N(C(H)(CH₃)₂)— |
| Ib-961 | 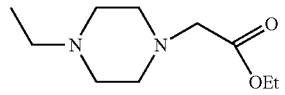 | —N(CH₂C(H)(CH₃)₂)— |
| Ib-962 |  | —N(C(CH₃)₃)— |
| Ib-963 | —CH₂—N(CH₂CH₃)(CH₃) | —N(CH₃)— |
| Ib-964 | —CH₂—N(CH₂CH₃)(CH₃) | —N(CH₂CH₃)— |
| Ib-965 | —CH₂—N(CH₂CH₃)(CH₃) | —N(CH₂CH₂CH₃)— |
| Ib-966 | —CH₂—N(CH₂CH₃)(CH₃) | —N(CH₂CH₂CH₂CH₃)— |
| Ib-967 | —CH₂—N(CH₂CH₃)(CH₃) | —N(C(H)(CH₃)(CH₂CH₃))— |
| Ib-968 | —CH₂—N(CH₂CH₃)(CH₃) | —N(C(H)(CH₃)₂)— |
| Ib-969 | —CH₂—N(CH₂CH₃)(CH₃) | —N(CH₂C(H)(CH₃)₂)— |
| Ib-970 | —CH₂—N(CH₂CH₃)(CH₃) | —N(C(CH₃)₃)— |
| Ib-971 | —CH₂—N(CH₂CH₂CH₃)(CH₃) | —N(CH₃)— |
| Ib-972 | —CH₂—N(CH₂CH₂CH₃)(CH₃) | —N(CH₂CH₃)— |
| Ib-973 | —CH₂—N(CH₂CH₂CH₃)(CH₃) | —N(CH₂CH₂CH₃)— |
| Ib-974 | —CH₂—N(CH₂CH₂CH₃)(CH₃) | —N(CH₂CH₂CH₂CH₃)— |
| Ib-975 | —CH₂—N(CH₂CH₂CH₃)(CH₃) | —N(C(H)(CH₃)(CH₂CH₃))— |
| Ib-976 | —CH₂—N(CH₂CH₂CH₃)(CH₃) | —N(C(H)(CH₃)₂)— |
| Ib-977 | —CH₂—N(CH₂CH₂CH₃)(CH₃) | —N(CH₂C(H)(CH₃)₂)— |
| Ib-978 | —CH₂—N(CH₂CH₂CH₃)(CH₃) | —N(C(CH₃)₃)— |
| Ib-979 | —CH₂—N(CH₂CH₂CH₂CH₃)(CH₃) | —N(CH₃)— |
| Ib-980 | —CH₂—N(CH₂CH₂CH₂CH₃)(CH₃) | —N(CH₂CH₃)— |
| Ib-981 | —CH₂—N(CH₂CH₂CH₂CH₃)(CH₃) | —N(CH₂CH₂CH₃)— |
| Ib-982 | —CH₂—N(CH₂CH₂CH₂CH₃)(CH₃) | —N(CH₂CH₂CH₂CH₃)— |
| Ib-983 | —CH₂—N(CH₂CH₂CH₂CH₃)(CH₃) | —N(C(H)(CH₃)(CH₂CH₃))— |
| Ib-984 | —CH₂—N(CH₂CH₂CH₂CH₃)(CH₃) | —N(C(H)(CH₃)₂)— |
| Ib-985 | —CH₂—N(CH₂CH₂CH₂CH₃)(CH₃) | —N(CH₂C(H)(CH₃)₂)— |

| | | |
|---|---|---|
| Ib-986 | —CH$_2$—N(CH$_2$CH$_2$CH$_3$)(CH$_3$) | —N(C(CH$_3$)$_3$)— |
| Ib-987 | —CH$_2$—NH—CH$_2$CH$_2$CH$_3$ | —N(CH$_3$)— |
| Ib-988 | —CH$_2$—NH—CH$_2$CH$_2$CH$_3$ | —N(CH$_2$CH$_3$)— |
| Ib-989 | —CH$_2$—NH—CH$_2$CH$_2$CH$_3$ | —N(CH$_2$CH$_2$CH$_3$)— |
| Ib-990 | —CH$_2$—NH—CH$_2$CH$_2$CH$_3$ | —N(CH$_2$CH$_2$CH$_2$CH$_3$)— |
| Ib-991 | —CH$_2$—NH—CH$_2$CH$_2$CH$_3$ | —N(C(H)(CH$_3$)(CH$_2$CH$_3$))— |
| Ib-992 | —CH$_2$—NH—CH$_2$CH$_2$CH$_3$ | —N(C(H)(CH$_3$)$_2$)— |
| Ib-993 | —CH$_2$—NH—CH$_2$CH$_2$CH$_3$ | —N(CH$_2$C(H)(CH$_3$)$_2$)— |
| Ib-994 | —CH$_2$—NH—CH$_2$CH$_2$CH$_3$ | —N(C(CH$_3$)$_3$)— |
| Ib-995 | —CH$_2$—NH—CH$_2$CH$_2$—O—CH$_3$ | —N(CH$_3$)— |
| Ib-996 | —CH$_2$—NH—CH$_2$CH$_2$—O—CH$_3$ | —N(CH$_2$CH$_3$)— |
| Ib-997 | —CH$_2$—NH—CH$_2$CH$_2$—O—CH$_3$ | —N(CH$_2$CH$_2$CH$_3$)— |
| Ib-998 | —CH$_2$—NH—CH$_2$CH$_2$—O—CH$_3$ | —N(CH$_2$CH$_2$CH$_2$CH$_3$)— |
| Ib-999 | —CH$_2$—NH—CH$_2$CH$_2$—O—CH$_3$ | —N(C(H)(CH$_3$)(CH$_2$CH$_3$))— |
| Ib-1000 | —CH$_2$—NH—CH$_2$CH$_2$—O—CH$_3$ | —N(C(H)(CH$_3$)$_2$)— |
| Ib-1001 | —CH$_2$—NH—CH$_2$CH$_2$—O—CH$_3$ | —N(CH$_2$C(H)(CH$_3$)$_2$)— |
| Ib-1002 | —CH$_2$—NH—CH$_2$CH$_2$—O—CH$_3$ | —N(C(CH$_3$)$_3$)— |
| Ib-1003 | ethyl-piperazine-CH$_2$CH$_2$OMe | —N(CH$_3$)— |
| Ib-1004 | ethyl-piperazine-CH$_2$CH$_2$OMe | —N(CH$_2$CH$_3$)— |
| Ib-1005 | ethyl-piperazine-CH$_2$CH$_2$OMe | —N(CH$_2$CH$_2$CH$_3$)— |
| Ib-1006 | ethyl-piperazine-CH$_2$CH$_2$OMe | —N(CH$_2$CH$_2$CH$_2$CH$_3$)— |
| Ib-1007 | ethyl-piperazine-CH$_2$CH$_2$OMe | —N(C(H)(CH$_3$)(CH$_2$CH$_3$))— |
| Ib-1008 | ethyl-piperazine-CH$_2$CH$_2$OMe | —N(C(H)(CH$_3$)$_2$)— |
| Ib-1009 | ethyl-piperazine-CH$_2$CH$_2$OMe | —N(CH$_2$C(H)(CH$_3$)$_2$)— |
| Ib-1010 | ethyl-piperazine-CH$_2$CH$_2$OMe | —N(C(CH$_3$)$_3$)— |
| Ib-1011 | 1-ethyl-piperidin-4-yl-OPO(OH)$_2$ | —N(CH$_3$)— |
| Ib-1012 | 1-ethyl-piperidin-4-yl-OPO(OH)$_2$ | —N(CH$_2$CH$_3$)— |
| Ib-1013 | 1-ethyl-piperidin-4-yl-OPO(OH)$_2$ | —N(CH$_2$CH$_3$)— |
| Ib-1014 | 1-ethyl-piperidin-4-yl-OPO(OH)$_2$ | —N(CH$_2$CH$_2$CH$_3$)— |

-continued

| | | |
|---|---|---|
| Ib-1015 | *N-ethylpiperidin-4-yl OPO(OH)₂* | —N(C(H)(CH₃)(CH₂CH₃))— |
| Ib-1016 | *N-ethylpiperidin-4-yl OPO(OH)₂* | —N(C(H)(CH₃)₂)— |
| Ib-1017 | *N-ethylpiperidin-4-yl OPO(OH)₂* | —N(CH₂C(H)(CH₃)₂)— |
| Ib-1018 | *N-ethylpiperidin-4-yl OPO(OH)₂* | —N(C(CH₃)₃)— |
| Ib-1019 | *N-ethylpiperidin-4-yl CH₂OPO(OH)₂* | —N(CH₃)— |
| Ib-1020 | *N-ethylpiperidin-4-yl CH₂OPO(OH)₂* | —N(CH₂CH₃)— |
| Ib-1021 | *N-ethylpiperidin-4-yl CH₂OPO(OH)₂* | —N(CH₂CH₂CH₃)— |
| Ib-1022 | *N-ethylpiperidin-4-yl CH₂OPO(OH)₂* | —N(CH₂CH₂CH₃)— |
| Ib-1023 | *N-ethylpiperidin-4-yl CH₂OPO(OH)₂* | —N(C(H)(CH₃)(CH₂CH₃))— |
| Ib-1024 | *N-ethylpiperidin-4-yl CH₂OPO(OH)₂* | —N(C(H)(CH₃)₂)— |
| Ib-1025 | *N-ethylpiperidin-4-yl CH₂OPO(OH)₂* | —N(CH₂C(H)(CH₃)₂)— |
| Ib-1026 | *N-ethylpiperidin-4-yl CH₂OPO(OH)₂* | —N(C(CH₃)₃)— |
| Ib-1027 | *N-ethylpiperidin-3-yl OPO(OH)₂* | —N(CH₃)— |
| Ib-1028 | *N-ethylpiperidin-3-yl OPO(OH)₂* | —N(CH₂CH₃)— |

-continued

| ID | Structure | Group |
|---|---|---|
| Ib-1029 | 1-ethylpiperidin-3-yl OPO(OH)$_2$ | —N(CH$_2$CH$_2$CH$_3$)— |
| Ib-1030 | 1-ethylpiperidin-3-yl OPO(OH)$_2$ | —N(CH$_2$CH$_2$CH$_2$CH$_3$)— |
| Ib-1031 | 1-ethylpiperidin-3-yl OPO(OH)$_2$ | —N(C(H)(CH$_3$)(CH$_2$CH$_3$))— |
| Ib-1032 | 1-ethylpiperidin-3-yl OPO(OH)$_2$ | —N(C(H)(CH$_3$)$_2$)— |
| Ib-1033 | 1-ethylpiperidin-3-yl OPO(OH)$_2$ | —N(CH$_2$C(H)(CH$_3$)$_2$)— |
| Ib-1034 | 1-ethylpiperidin-3-yl OPO(OH)$_2$ | —N(C(CH$_3$)$_3$)— |
| Ib-1035 | Et-N(CH$_3$)-CH$_2$CH$_2$-OPO(OH)$_2$ | —N(CH$_3$)— |
| Ib-1036 | Et-N(CH$_3$)-CH$_2$CH$_2$-OPO(OH)$_2$ | —N(CH$_2$CH$_3$)— |
| Ib-1037 | Et-N(CH$_3$)-CH$_2$CH$_2$-OPO(OH)$_2$ | —N(CH$_2$CH$_2$CH$_3$)— |
| Ib-1038 | Et-N(CH$_3$)-CH$_2$CH$_2$-OPO(OH)$_2$ | —N(CH$_2$CH$_2$CH$_2$CH$_3$)— |
| Ib-1039 | Et-N(CH$_3$)-CH$_2$CH$_2$-OPO(OH)$_2$ | —N(C(H)(CH$_3$)(CH$_2$CH$_3$))— |

-continued
| | | |
|---|---|---|
| Ib-1040 | 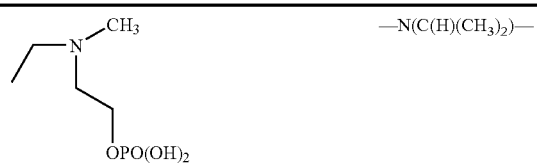 | —N(C(H)(CH₃)₂)— |
| Ib-1041 | 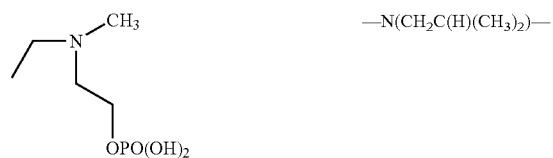 | —N(CH₂C(H)(CH₃)₂)— |
| Ib-1042 | 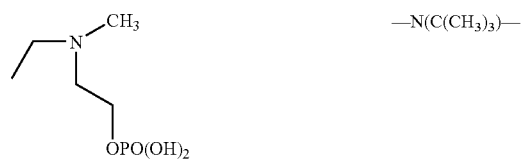 | —N(C(CH₃)₃)— |
| Ib-1043 | 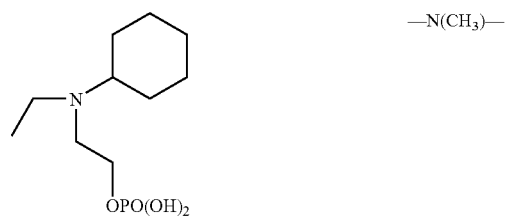 | —N(CH₃)— |
| Ib-1044 | 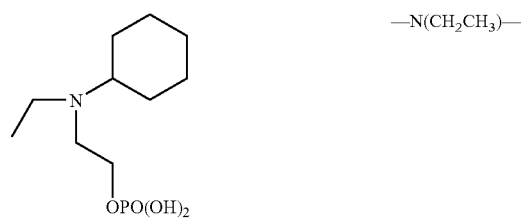 | —N(CH₂CH₃)— |
| Ib-1045 | 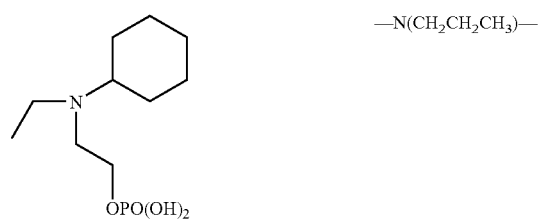 | —N(CH₂CH₂CH₃)— |
| Ib-1046 | 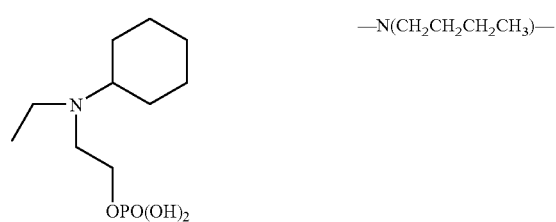 | —N(CH₂CH₂CH₂CH₃)— |
| Ib-1047 | 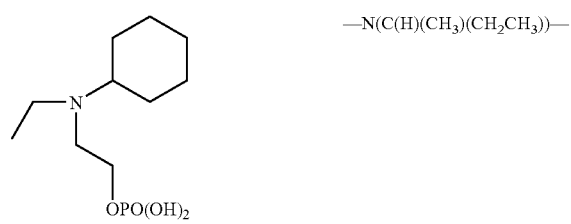 | —N(C(H)(CH₃)(CH₂CH₃))— |

-continued
| | | |
|---|---|---|
| Ib-1048 | 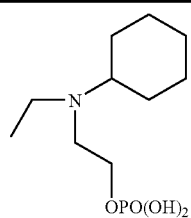 | —N(C(H)(CH$_3$)$_2$)— |
| Ib-1049 | 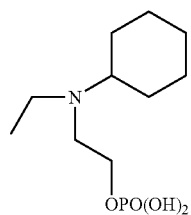 | —N(CH$_2$C(H)(CH$_3$)$_2$)— |
| Ib-1050 | 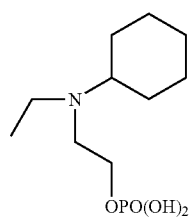 | —N(C(CH$_3$)$_3$)— |
| Ib-1051 | 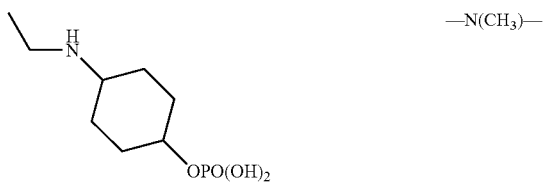 | —N(CH$_3$)— |
| Ib-1052 | 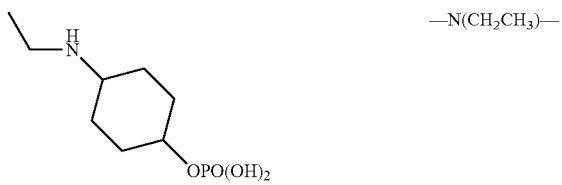 | —N(CH$_2$CH$_3$)— |
| Ib-1053 | 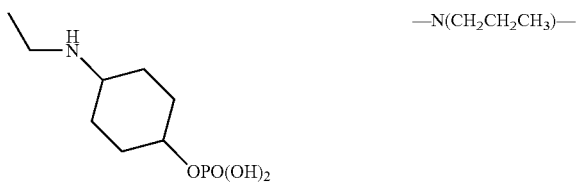 | —N(CH$_2$CH$_2$CH$_3$)— |
| Ib-1054 | 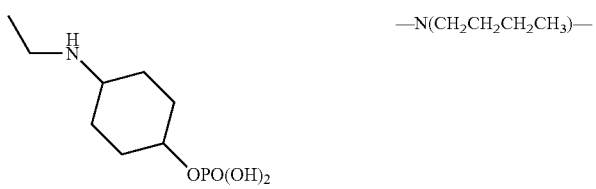 | —N(CH$_2$CH$_2$CH$_2$CH$_3$)— |
| Ib-1055 |  | —N(C(H)(CH$_3$)(CH$_2$CH$_3$))— |

-continued

| | | | |
|---|---|---|---|
| Ib-1056 | | 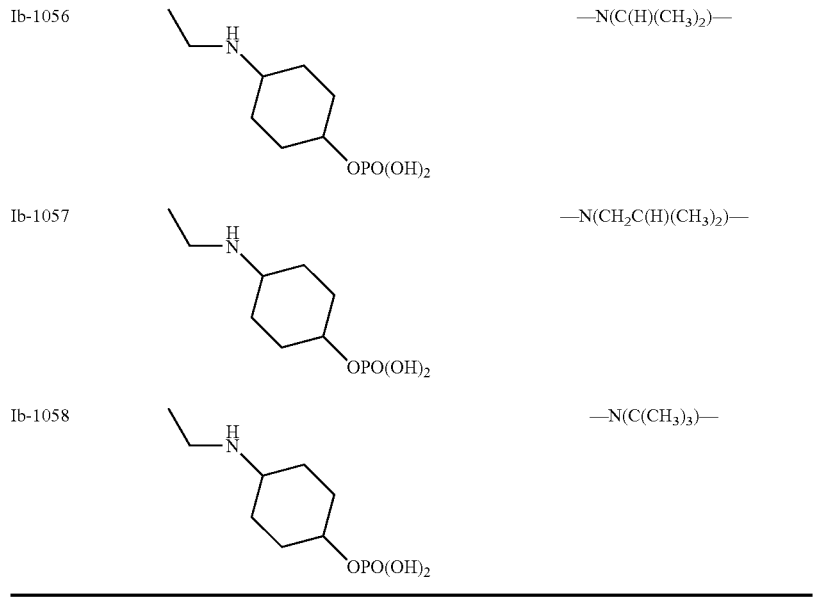 | —N(C(H)(CH₃)₂)— |
| Ib-1057 | | | —N(CH₂C(H)(CH₃)₂)— |
| Ib-1058 | | | —N(C(CH₃)₃)— |

| Compound | n | —R¹ | X |
|---|---|---|---|
| Ib-b1 | 1 | —(CH₂)$_n$—N(CH₃)₂ | —CH(OH)— |
| Ib-b2 | 2 | —(CH₂)$_n$—N(CH₃)₂ | —CH(OH)— |
| Ib-b3 | 3 | —(CH₂)$_n$—N(CH₃)₂ | —CH(OH)— |
| Ib-b4 | 4 | —(CH₂)$_n$—N(CH₃)₂ | —CH(OH)— |
| Ib-b5 | 5 | —(CH₂)$_n$—N(CH₃)₂ | —CH(OH)— |
| Ib-b6 | 6 | —(CH₂)$_n$—N(CH₃)₂ | —CH(OH)— |
| Ib-b7 | 1 | —(CH₂)$_n$—N(CH₃)₂ | —N(C(O)N(H)—CH₂—CH₂—OH)— |
| Ib-b8 | 2 | —(CH₂)$_n$—N(CH₃)₂ | —N(C(O)N(H)—CH₂—CH₂—OH)— |
| Ib-b9 | 3 | —(CH₂)$_n$—N(CH₃)₂ | —N(C(O)N(H)—CH₂—CH₂—OH)— |
| Ib-b10 | 4 | —(CH₂)$_n$—N(CH₃)₂ | —N(C(O)N(H)—CH₂—CH₂—OH)— |
| Ib-b11 | 5 | —(CH₂)$_n$—N(CH₃)₂ | —N(C(O)N(H)—CH₂—CH₂—OH)— |
| Ib-b12 | 6 | —(CH₂)$_n$—N(CH₃)₂ | —N(C(O)N(H)—CH₂—CH₂—OH)— |
| Ib-b13 | 1 | —(CH₂)$_n$—N(CH₃)₂ | —N(C(O)N(H)—CH₂—CH₂—F)— |
| Ib-b14 | 2 | —(CH₂)$_n$—N(CH₃)₂ | —N(C(O)N(H)—CH₂—CH₂—F)— |
| Ib-b15 | 3 | —(CH₂)$_n$—N(CH₃)₂ | —N(C(O)N(H)—CH₂—CH₂—F)— |
| Ib-b16 | 4 | —(CH₂)$_n$—N(CH₃)₂ | —N(C(O)N(H)—CH₂—CH₂—F)— |
| Ib-b17 | 5 | —(CH₂)$_n$—N(CH₃)₂ | —N(C(O)N(H)—CH₂—CH₂—F)— |
| Ib-b18 | 6 | —(CH₂)$_n$—N(CH₃)₂ | —N(C(O)N(H)—CH₂—CH₂—F)— |
| Ib-b19 | 1 | —(CH₂)$_n$—N(CH₃)₂ | —N(C(O)N(H)—CH₂—CH₂—OCH₃)— |
| Ib-b20 | 2 | —(CH₂)$_n$—N(CH₃)₂ | —N(C(O)N(H)—CH₂—CH₂—OCH₃)— |
| Ib-b21 | 3 | —(CH₂)$_n$—N(CH₃)₂ | —N(C(O)N(H)—CH₂—CH₂—OCH₃)— |
| Ib-b22 | 4 | —(CH₂)$_n$—N(CH₃)₂ | —N(C(O)N(H)—CH₂—CH₂—OCH₃)— |
| Ib-b23 | 5 | —(CH₂)$_n$—N(CH₃)₂ | —N(C(O)N(H)—CH₂—CH₂—OCH₃)— |
| Ib-b24 | 6 | —(CH₂)$_n$—N(CH₃)₂ | —N(C(O)N(H)—CH₂—CH₂—OCH₃)— |
| Ib-b25 | 1 | —(CH₂)$_n$—N(CH₃)₂ | —N(C(O)N(H)—CH₂—CH₂—CF₃)— |
| Ib-b26 | 2 | —(CH₂)$_n$—N(CH₃)₂ | —N(C(O)N(H)—CH₂—CH₂—CF₃)— |
| Ib-b27 | 3 | —(CH₂)$_n$—N(CH₃)₂ | —N(C(O)N(H)—CH₂—CH₂—CF₃)— |
| Ib-b28 | 4 | —(CH₂)$_n$—N(CH₃)₂ | —N(C(O)N(H)—CH₂—CH₂—CF₃)— |
| Ib-b29 | 5 | —(CH₂)$_n$—N(CH₃)₂ | —N(C(O)N(H)—CH₂—CH₂—CF₃)— |
| Ib-b30 | 6 | —(CH₂)$_n$—N(CH₃)₂ | —N(C(O)N(H)—CH₂—CH₂—CF₃)— |
| Ib-b31 | 1 | —(CH₂)$_n$—N(CH₃)₂ | —N(CH₂—CH₂—OH)— |
| Ib-b32 | 2 | —(CH₂)$_n$—N(CH₃)₂ | —N(CH₂—CH₂—OH)— |
| Ib-b33 | 3 | —(CH₂)$_n$—N(CH₃)₂ | —N(CH₂—CH₂—OH)— |
| Ib-b34 | 4 | —(CH₂)$_n$—N(CH₃)₂ | —N(CH₂—CH₂—OH)— |
| Ib-b35 | 5 | —(CH₂)$_n$—N(CH₃)₂ | —N(CH₂—CH₂—OH)— |
| Ib-b36 | 6 | —(CH₂)$_n$—N(CH₃)₂ | —N(CH₂—CH₂—OH)— |
| Ib-b37 | 1 | —(CH₂)$_n$—N(CH₃)₂ | —N(CH₂—CH₂—F)— |
| Ib-b38 | 2 | —(CH₂)$_n$—N(CH₃)₂ | —N(CH₂—CH₂—F)— |
| Ib-b39 | 3 | —(CH₂)$_n$—N(CH₃)₂ | —N(CH₂—CH₂—F)— |
| Ib-b40 | 4 | —(CH₂)$_n$—N(CH₃)₂ | —N(CH₂—CH₂—F)— |
| Ib-b41 | 5 | —(CH₂)$_n$—N(CH₃)₂ | —N(CH₂—CH₂—F)— |
| Ib-b42 | 6 | —(CH₂)$_n$—N(CH₃)₂ | —N(CH₂—CH₂—F)— |
| Ib-b43 | 1 | —(CH₂)$_n$—N(CH₃)₂ | —N(CH₂—CH₂—OCH₃)— |
| Ib-b44 | 2 | —(CH₂)$_n$—N(CH₃)₂ | —N(CH₂—CH₂—OCH₃)— |
| Ib-b45 | 3 | —(CH₂)$_n$—N(CH₃)₂ | —N(CH₂—CH₂—OCH₃)— |
| Ib-b46 | 4 | —(CH₂)$_n$—N(CH₃)₂ | —N(CH₂—CH₂—OCH₃)— |
| Ib-b47 | 5 | —(CH₂)$_n$—N(CH₃)₂ | —N(CH₂—CH₂—OCH₃)— |
| Ib-b48 | 6 | —(CH₂)$_n$—N(CH₃)₂ | —N(CH₂—CH₂—OCH₃)— |

-continued

| | | | |
|---|---|---|---|
| Ib-b49 | 1 | —(CH₂)ₙ—N(morpholine) | —CH(OH)— |
| Ib-b50 | 2 | —(CH₂)ₙ—N(morpholine) | —CH(OH)— |
| Ib-b51 | 3 | —(CH₂)ₙ—N(morpholine) | —CH(OH)— |
| Ib-b52 | 4 | —(CH₂)ₙ—N(morpholine) | —CH(OH)— |
| Ib-b53 | 5 | —(CH₂)ₙ—N(morpholine) | —CH(OH)— |
| Ib-b54 | 6 | —(CH₂)ₙ—N(morpholine) | —CH(OH)— |
| Ib-b55 | 1 | —(CH₂)ₙ—N(morpholine) | —N(C(O)N(H)—CH₂—CH₂—OH)— |
| Ib-b56 | 2 | —(CH₂)ₙ—N(morpholine) | —N(C(O)N(H)—CH₂—CH₂—OH)— |
| Ib-b57 | 3 | —(CH₂)ₙ—N(morpholine) | —N(C(O)N(H)—CH₂—CH₂—OH)— |
| Ib-b58 | 4 | —(CH₂)ₙ—N(morpholine) | —N(C(O)N(H)—CH₂—CH₂—OH)— |
| Ib-b59 | 5 | —(CH₂)ₙ—N(morpholine) | —N(C(O)N(H)—CH₂—CH₂—OH)— |
| Ib-b60 | 6 | —(CH₂)ₙ—N(morpholine) | —N(C(O)N(H)—CH₂—CH₂—OH)— |
| Ib-b61 | 1 | —(CH₂)ₙ—N(morpholine) | —N(C(O)N(H)—CH₂—CH₂—F)— |
| Ib-b62 | 2 | —(CH₂)ₙ—N(morpholine) | —N(C(O)N(H)—CH₂—CH₂—F)— |
| Ib-b63 | 3 | —(CH₂)ₙ—N(morpholine) | —N(C(O)N(H)—CH₂—CH₂—F)— |
| Ib-b64 | 4 | —(CH₂)ₙ—N(morpholine) | —N(C(O)N(H)—CH₂—CH₂—F)— |

-continued

| | | | |
|---|---|---|---|
| Ib-b65 | 5 | —(CH$_2$)$_n$—N(morpholine) | —N(C(O)N(H)—CH$_2$—CH$_2$—F)— |
| Ib-b66 | 6 | —(CH$_2$)$_n$—N(morpholine) | —N(C(O)N(H)—CH$_2$—CH$_2$—F)— |
| Ib-b67 | 1 | —(CH$_2$)$_n$—N(morpholine) | —N(C(O)N(H)—CH$_2$—CH$_2$—OCH$_3$)— |
| Ib-b68 | 2 | —(CH$_2$)$_n$—N(morpholine) | —N(C(O)N(H)—CH$_2$—CH$_2$—OCH$_3$)— |
| Ib-b69 | 3 | —(CH$_2$)$_n$—N(morpholine) | —N(C(O)N(H)—CH$_2$—CH$_2$—OCH$_3$)— |
| Ib-b70 | 4 | —(CH$_2$)$_n$—N(morpholine) | —N(C(O)N(H)—CH$_2$—CH$_2$—OCH$_3$)— |
| Ib-b71 | 5 | —(CH$_2$)$_n$—N(morpholine) | —N(C(O)N(H)—CH$_2$—CH$_2$—OCH$_3$)— |
| Ib-b72 | 6 | —(CH$_2$)$_n$—N(morpholine) | —N(C(O)N(H)—CH$_2$—CH$_2$—OCH$_3$)— |
| Ib-b73 | 1 | —(CH$_2$)$_n$—N(morpholine) | —N(C(O)N(H)—CH$_2$—CH$_2$—CF$_3$)— |
| Ib-b74 | 2 | —(CH$_2$)$_n$—N(morpholine) | —N(C(O)N(H)—CH$_2$—CH$_2$—CF$_3$)— |
| Ib-b75 | 3 | —(CH$_2$)$_n$—N(morpholine) | —N(C(O)N(H)—CH$_2$—CH$_2$—CF$_3$)— |
| Ib-b76 | 4 | —(CH$_2$)$_n$—N(morpholine) | —N(C(O)N(H)—CH$_2$—CH$_2$—CF$_3$)— |
| Ib-b77 | 5 | —(CH$_2$)$_n$—N(morpholine) | —N(C(O)N(H)—CH$_2$—CH$_2$—CF$_3$)— |
| Ib-b78 | 6 | —(CH$_2$)$_n$—N(morpholine) | —N(C(O)N(H)—CH$_2$—CH$_2$—CF$_3$)— |
| Ib-b79 | 1 | —(CH$_2$)$_n$—N(morpholine) | —N(CH$_2$—CH$_2$—OH)— |
| Ib-b80 | 2 | —(CH$_2$)$_n$—N(morpholine) | —N(CH$_2$—CH$_2$—OH)— |

-continued

| | | | |
|---|---|---|---|
| Ib-b81 | 3 | —(CH$_2$)$_n$—N(morpholine) 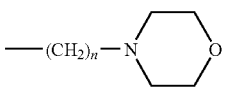 | —N(CH$_2$—CH$_2$—OH)— |
| Ib-b82 | 4 | —(CH$_2$)$_n$—N(morpholine) 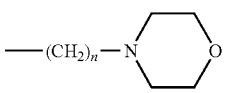 | —N(CH$_2$—CH$_2$—OH)— |
| Ib-b83 | 5 | —(CH$_2$)$_n$—N(morpholine) 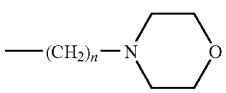 | —N(CH$_2$—CH$_2$—OH)— |
| Ib-b84 | 6 | —(CH$_2$)$_n$—N(morpholine) 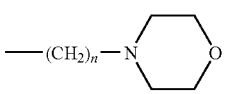 | —N(CH$_2$—CH$_2$—OH)— |
| Ib-b85 | 1 | —(CH$_2$)$_n$—N(morpholine) 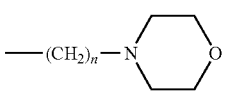 | —N(CH$_2$—CH$_2$—F)— |
| Ib-b86 | 2 | —(CH$_2$)$_n$—N(morpholine) 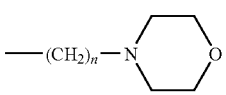 | —N(CH$_2$—CH$_2$—F)— |
| Ib-b87 | 3 | —(CH$_2$)$_n$—N(morpholine) 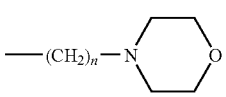 | —N(CH$_2$—CH$_2$—F)— |
| Ib-b88 | 4 | —(CH$_2$)$_n$—N(morpholine) 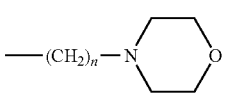 | —N(CH$_2$—CH$_2$—F)— |
| Ib-b89 | 5 | —(CH$_2$)$_n$—N(morpholine) 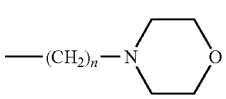 | —N(CH$_2$—CH$_2$—F)— |
| Ib-b90 | 6 | —(CH$_2$)$_n$—N(morpholine) 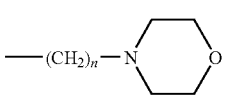 | —N(CH$_2$—CH$_2$—F)— |
| Ib-b91 | 1 | —(CH$_2$)$_n$—N(morpholine) 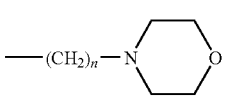 | —N(CH$_2$—CH$_2$—OCH$_3$)— |
| Ib-b92 | 2 | —(CH$_2$)$_n$—N(morpholine) 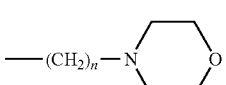 | —N(CH$_2$—CH$_2$—OCH$_3$)— |
| Ib-b93 | 3 | —(CH$_2$)$_n$—N(morpholine) 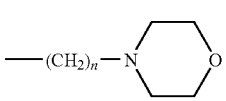 | —N(CH$_2$—CH$_2$—OCH$_3$)— |
| Ib-b94 | 4 | —(CH$_2$)$_n$—N(morpholine) 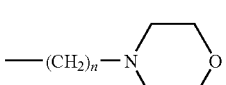 | —N(CH$_2$—CH$_2$—OCH$_3$)— |
| Ib-b95 | 5 | —(CH$_2$)$_n$—N(morpholine) 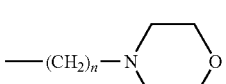 | —N(CH$_2$—CH$_2$—OCH$_3$)— |
| Ib-b96 | 6 | —(CH$_2$)$_n$—N(morpholine) 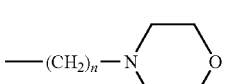 | —N(CH$_2$—CH$_2$—OCH$_3$)— |

| Compound | m | —R¹ | X |
| --- | --- | --- | --- |
| Ib-b146 | 2 | —O—(CH₂)ₘ—N(CH₃)₂ | —CH(OH)— |
| Ib-b147 | 3 | —O—(CH₂)ₘ—N(CH₃)₂ | —CH(OH)— |
| Ib-b148 | 4 | —O—(CH₂)ₘ—N(CH₃)₂ | —CH(OH)— |
| Ib-b149 | 5 | —O—(CH₂)ₘ—N(CH₃)₂ | —CH(OH)— |
| Ib-b150 | 6 | —O—(CH₂)ₘ—N(CH₃)₂ | —CH(OH)— |
| Ib-b151 | 2 | —O—(CH₂)ₘ—N(CH₃)₂ | —N(C(O)N(H)—CH₂—CH₂—OH)— |
| Ib-b152 | 3 | —O—(CH₂)ₘ—N(CH₃)₂ | —N(C(O)N(H)—CH₂—CH₂—OH)— |
| Ib-b153 | 4 | —O—(CH₂)ₘ—N(CH₃)₂ | —N(C(O)N(H)—CH₂—CH₂—OH)— |
| Ib-b154 | 5 | —O—(CH₂)ₘ—N(CH₃)₂ | —N(C(O)N(H)—CH₂—CH₂—OH)— |
| Ib-b155 | 6 | —O—(CH₂)ₘ—N(CH₃)₂ | —N(C(O)N(H)—CH₂—CH₂—OH)— |
| Ib-b156 | 2 | —O—(CH₂)ₘ—N(CH₃)₂ | —N(C(O)N(H)—CH₂—CH₂—F)— |
| Ib-b157 | 3 | —O—(CH₂)ₘ—N(CH₃)₂ | —N(C(O)N(H)—CH₂—CH₂—F)— |
| Ib-b158 | 4 | —O—(CH₂)ₘ—N(CH₃)₂ | —N(C(O)N(H)—CH₂—CH₂—F)— |
| Ib-b159 | 5 | —O—(CH₂)ₘ—N(CH₃)₂ | —N(C(O)N(H)—CH₂—CH₂—F)— |
| Ib-b160 | 6 | —O—(CH₂)ₘ—N(CH₃)₂ | —N(C(O)N(H)—CH₂—CH₂—F)— |
| Ib-b161 | 2 | —O—(CH₂)ₘ—N(CH₃)₂ | —N(C(O)N(H)—CH₂—CH₂—OCH₃)— |
| Ib-b162 | 3 | —O—(CH₂)ₘ—N(CH₃)₂ | —N(C(O)N(H)—CH₂—CH₂—OCH₃)— |
| Ib-b163 | 4 | —O—(CH₂)ₘ—N(CH₃)₂ | —N(C(O)N(H)—CH₂—CH₂—OCH₃)— |
| Ib-b164 | 5 | —O—(CH₂)ₘ—N(CH₃)₂ | —N(C(O)N(H)—CH₂—CH₂—OCH₃)— |
| Ib-b165 | 6 | —O—(CH₂)ₘ—N(CH₃)₂ | —N(C(O)N(H)—CH₂—CH₂—OCH₃)— |
| Ib-b166 | 2 | —O—(CH₂)ₘ—N(CH₃)₂ | —N(C(O)N(H)—CH₂—CH₂—CF₃)— |
| Ib-b167 | 3 | —O—(CH₂)ₘ—N(CH₃)₂ | —N(C(O)N(H)—CH₂—CH₂—CF₃)— |
| Ib-b168 | 4 | —O—(CH₂)ₘ—N(CH₃)₂ | —N(C(O)N(H)—CH₂—CH₂—CF₃)— |
| Ib-b169 | 5 | —O—(CH₂)ₘ—N(CH₃)₂ | —N(C(O)N(H)—CH₂—CH₂—CF₃)— |
| Ib-b170 | 6 | —O—(CH₂)ₘ—N(CH₃)₂ | —N(C(O)N(H)—CH₂—CH₂—CF₃)— |
| Ib-b171 | 2 | —O—(CH₂)ₘ—N(CH₃)₂ | —N(CH₂—CH₂—OH)— |
| Ib-b172 | 3 | —O—(CH₂)ₘ—N(CH₃)₂ | —N(CH₂—CH₂—OH)— |
| Ib-b173 | 4 | —O—(CH₂)ₘ—N(CH₃)₂ | —N(CH₂—CH₂—OH)— |
| Ib-b174 | 5 | —O—(CH₂)ₘ—N(CH₃)₂ | —N(CH₂—CH₂—OH)— |
| Ib-b175 | 6 | —O—(CH₂)ₘ—N(CH₃)₂ | —N(CH₂—CH₂—OH)— |
| Ib-b176 | 2 | —O—(CH₂)ₘ—N(CH₃)₂ | —N(CH₂—CH₂—F)— |
| Ib-b178 | 3 | —O—(CH₂)ₘ—N(CH₃)₂ | —N(CH₂—CH₂—F)— |
| Ib-b179 | 4 | —O—(CH₂)ₘ—N(CH₃)₂ | —N(CH₂—CH₂—F)— |
| Ib-b180 | 5 | —O—(CH₂)ₘ—N(CH₃)₂ | —N(CH₂—CH₂—F)— |
| Ib-b181 | 6 | —O—(CH₂)ₘ—N(CH₃)₂ | —N(CH₂—CH₂—F)— |
| Ib-b182 | 2 | —O—(CH₂)ₘ—N(CH₃)₂ | —N(CH₂—CH₂—OCH₃)— |
| Ib-b183 | 3 | —O—(CH₂)ₘ—N(CH₃)₂ | —N(CH₂—CH₂—OCH₃)— |
| Ib-b184 | 4 | —O—(CH₂)ₘ—N(CH₃)₂ | —N(CH₂—CH₂—OCH₃)— |
| Ib-b185 | 5 | —O—(CH₂)ₘ—N(CH₃)₂ | —N(CH₂—CH₂—OCH₃)— |
| Ib-b186 | 6 | —O—(CH₂)ₘ—N(CH₃)₂ | —N(CH₂—CH₂—OCH₃)— |
| Ib-b187 | 2 | 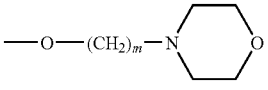 | —CH(OH)— |
| Ib-b188 | 3 | 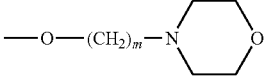 | —CH(OH)— |
| Ib-b189 | 4 | 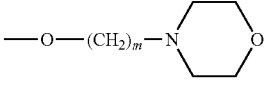 | —CH(OH)— |
| Ib-b190 | 5 | 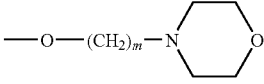 | —CH(OH)— |
| Ib-b191 | 6 | 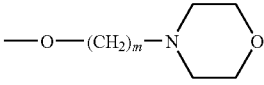 | —CH(OH)— |
| Ib-b192 | 2 | 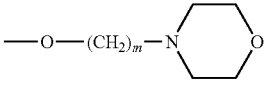 | —N(C(O)N(H)—CH₂—CH₂—OH)— |
| Ib-b193 | 3 | 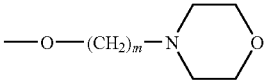 | —N(C(O)N(H)—CH₂—CH₂—OH)— |

-continued

| | | | |
|---|---|---|---|
| Ib-b194 | 4 | —O—(CH$_2$)$_m$—N(morpholine) | —N(C(O)N(H)—CH$_2$—CH$_2$—OH)— |
| Ib-b195 | 5 | —O—(CH$_2$)$_m$—N(morpholine) | —N(C(O)N(H)—CH$_2$—CH$_2$—OH)— |
| Ib-b196 | 6 | —O—(CH$_2$)$_m$—N(morpholine) | —N(C(O)N(H)—CH$_2$—CH$_2$—OH)— |
| Ib-b197 | 2 | —O—(CH$_2$)$_m$—N(morpholine) | —N(C(O)N(H)—CH$_2$—CH$_2$—F)— |
| Ib-b198 | 3 | —O—(CH$_2$)$_m$—N(morpholine) | —N(C(O)N(H)—CH$_2$—CH$_2$—F)— |
| Ib-b199 | 4 | —O—(CH$_2$)$_m$—N(morpholine) | —N(C(O)N(H)—CH$_2$—CH$_2$—F)— |
| Ib-b200 | 5 | —O—(CH$_2$)$_m$—N(morpholine) | —N(C(O)N(H)—CH$_2$—CH$_2$—F)— |
| Ib-b201 | 6 | —O—(CH$_2$)$_m$—N(morpholine) | —N(C(O)N(H)—CH$_2$—CH$_2$—F)— |
| Ib-b202 | 2 | —O—(CH$_2$)$_m$—N(morpholine) | —N(C(O)N(H)—CH$_2$—CH$_2$—OCH$_3$)— |
| Ib-b203 | 3 | —O—(CH$_2$)$_m$—N(morpholine) | —N(C(O)N(H)—CH$_2$—CH$_2$—OCH$_3$)— |
| Ib-b204 | 4 | —O—(CH$_2$)$_m$—N(morpholine) | —N(C(O)N(H)—CH$_2$—CH$_2$—OCH$_3$)— |
| Ib-b205 | 5 | —O—(CH$_2$)$_m$—N(morpholine) | —N(C(O)N(H)—CH$_2$—CH$_2$—OCH$_3$)— |
| Ib-b206 | 6 | —O—(CH$_2$)$_m$—N(morpholine) | —N(C(O)N(H)—CH$_2$—CH$_2$—OCH$_3$)— |
| Ib-b207 | 2 | —O—(CH$_2$)$_m$—N(morpholine) | —N(C(O)N(H)—CH$_2$—CH$_2$—CF$_3$)— |
| Ib-b208 | 3 | —O—(CH$_2$)$_m$—N(morpholine) | —N(C(O)N(H)—CH$_2$—CH$_2$—CF$_3$)— |
| Ib-b209 | 4 | —O—(CH$_2$)$_m$—N(morpholine) | —N(C(O)N(H)—CH$_2$—CH$_2$—CF$_3$)— |

-continued

| | | | |
|---|---|---|---|
| Ib-b210 | 5 | —O—(CH$_2$)$_m$—N(morpholine) | —N(C(O)N(H)—CH$_2$—CH$_2$—CF$_3$)— |
| Ib-b211 | 6 | —O—(CH$_2$)$_m$—N(morpholine) | —N(C(O)N(H)—CH$_2$—CH$_2$—CF$_3$)— |
| Ib-b212 | 2 | —O—(CH$_2$)$_m$—N(morpholine) | —N(CH$_2$—CH$_2$—OH)— |
| Ib-b213 | 3 | —O—(CH$_2$)$_m$—N(morpholine) | —N(CH$_2$—CH$_2$—OH)— |
| Ib-b214 | 4 | —O—(CH$_2$)$_m$—N(morpholine) | —N(CH$_2$—CH$_2$—OH)— |
| Ib-b215 | 5 | —O—(CH$_2$)$_m$—N(morpholine) | —N(CH$_2$—CH$_2$—OH)— |
| Ib-b216 | 6 | —O—(CH$_2$)$_m$—N(morpholine) | —N(CH$_2$—CH$_2$—OH)— |
| Ib-b217 | 2 | —O—(CH$_2$)$_m$—N(morpholine) | —N(CH$_2$—CH$_2$—F)— |
| Ib-b218 | 3 | —O—(CH$_2$)$_m$—N(morpholine) | —N(CH$_2$—CH$_2$—F)— |
| Ib-b219 | 4 | —O—(CH$_2$)$_m$—N(morpholine) | —N(CH$_2$—CH$_2$—F)— |
| Ib-b220 | 5 | —O—(CH$_2$)$_m$—N(morpholine) | —N(CH$_2$—CH$_2$—F)— |
| Ib-b221 | 6 | —O—(CH$_2$)$_m$—N(morpholine) | —N(CH$_2$—CH$_2$—F)— |
| Ib-b222 | 2 | —O—(CH$_2$)$_m$—N(morpholine) | —N(CH$_2$—CH$_2$—OCH$_3$)— |
| Ib-b223 | 3 | —O—(CH$_2$)$_m$—N(morpholine) | —N(CH$_2$—CH$_2$—OCH$_3$)— |
| Ib-b224 | 4 | —O—(CH$_2$)$_m$—N(morpholine) | —N(CH$_2$—CH$_2$—OCH$_3$)— |
| Ib-b225 | 5 | —O—(CH$_2$)$_m$—N(morpholine) | —N(CH$_2$—CH$_2$—OCH$_3$)— |

-continued

| | | | |
|---|---|---|---|
| Ib-b226 | 6 | —O—(CH₂)ₘ—N(morpholine) | —N(CH₂—CH₂—OCH₃)— |

| Compound | —R¹ | X |
|---|---|---|
| Ib-b267 | —CH₂—N(CH₂—CH₃)₂ | —CH(OH)— |
| Ib-b268 | —CH₂—N(CH₂—CH₃)₂ | —N(C(O)N(H)—CH₂—CH₂—OH)— |
| Ib-b269 | —CH₂—N(CH₂—CH₃)₂ | —N(C(O)N(H)—CH₂—CH₂—F)— |
| Ib-b270 | —CH₂—N(CH₂—CH₃)₂ | —N(C(O)N(H)—CH₂—CH₂—OCH₃)— |
| Ib-b271 | —CH₂—N(CH₂—CH₃)₂ | —N(C(O)N(H)—CH₂—CH₂—CF₃)— |
| Ib-b275 | —CH₂—N(CH₂—CH₂—CH₃)₂ | —CH(OH)— |
| Ib-b276 | —CH₂—N(CH₂—CH₂—CH₃)₂ | —N(C(O)N(H)—CH₂—CH₂—OH)— |
| Ib-b277 | —CH₂—N(CH₂—CH₂—CH₃)₂ | —N(C(O)N(H)—CH₂—CH₂—F)— |
| Ib-b278 | —CH₂—N(CH₂—CH₂—CH₃)₂ | —N(C(O)N(H)—CH₂—CH₂—OCH₃)— |
| Ib-b279 | —CH₂—N(CH₂—CH₂—CH₃)₂ | —N(C(O)N(H)—CH₂—CH₂—CF₃)— |
| Ib-b283 | —CH₂—N(CH₂—CH₂OH)₂ | —CH(OH)— |
| Ib-b284 | —CH₂—N(CH₂—CH₂OH)₂ | —N(C(O)N(H)—CH₂—CH₂—OH)— |
| Ib-b285 | —CH₂—N(CH₂—CH₂OH)₂ | —N(C(O)N(H)—CH₂—CH₂—F)— |
| Ib-b286 | —CH₂—N(CH₂—CH₂OH)₂ | —N(C(O)N(H)—CH₂—CH₂—OCH₃)— |
| Ib-b291 | —CH₂—N(CH₂—CH₂—N(CH₃)₂)₂ | —CH(OH)— |
| Ib-b292 | —CH₂—N(CH₂—CH₂—N(CH₃)₂)₂ | —N(C(O)N(H)—CH₂—CH₂—OH)— |
| Ib-b293 | —CH₂—N(CH₂—CH₂—N(CH₃)₂)₂ | —N(C(O)N(H)—CH₂—CH₂—F)— |
| Ib-b294 | —CH₂—N(CH₂—CH₂—N(CH₃)₂)₂ | —N(C(O)N(H)—CH₂—CH₂—OCH₃)— |
| Ib-b295 | —CH₂—N(CH₂—CH₂—N(CH₃)₂)₂ | —N(C(O)N(H)—CH₂—CH₂—CF₃)— |
| Ib-b296 | —CH₂—N(CH₂—CH₂—N(CH₃)₂)₂ | —N(C(O)N(H)—CH₂—CH₂—CF₃)— |
| Ib-b297 | —CH₂—N(CH₂—CH₂—N(CH₃)₂)₂ | —N(C(O)N(H)—CH₂—CF₃)— |
| Ib-b298 | —CH₂—N(CH₂—CH₂—N(CH₃)₂)₂ | —N(C(O)N(H)—(CH₂)₃—OH)— |
| Ib-b299 | —CH₂—N(CH₂—CH₂—CH₂—N(CH₃)₂)₂ | —CH(OH)— |
| Ib-b300 | —CH₂—N(CH₂—CH₂—CH₂—N(CH₃)₂)₂ | —N(C(O)N(H)—CH₂—CH₂—OH)— |
| Ib-b301 | —CH₂—N(CH₂—CH₂—CH₂—N(CH₃)₂)₂ | —N(C(O)N(H)—CH₂—CH₂—F)— |
| Ib-b302 | —CH₂—N(CH₂—CH₂—CH₂—N(CH₃)₂)₂ | —N(C(O)N(H)—CH₂—CH₂—OCH₃)— |
| Ib-b303 | —CH₂—N(CH₂—CH₂—CH₂—N(CH₃)₂)₂ | —N(C(O)N(H)—CH₂—CH₂—CF₃)— |
| Ib-b304 | —CH₂—N(CH₂—CH₂—CH₂—N(CH₃)₂)₂ | —N(C(O)N(H)—CH₂—CH₂—CF₃)— |
| Ib-b305 | —CH₂—N(CH₂—CH₂—CH₂—N(CH₃)₂)₂ | —N(C(O)N(H)—CH₂—CF₃)— |
| Ib-b306 | —CH₂—N(CH₂—CH₂—CH₂—N(CH₃)₂)₂ | N(C(O)N(H)—(CH₂)₃—OH)— |
| Ib-b307 | —CH₂—N(aziridinyl) | —CH(OH)— |
| Ib-b308 | —CH₂—N(aziridinyl) | —N(C(O)N(H)—CH₂—CH₂—OH)— |
| Ib-b309 | —CH₂—N(aziridinyl) | —N(C(O)N(H)—CH₂—CH₂—F)— |
| Ib-b310 | —CH₂—N(aziridinyl) | —N(C(O)N(H)—CH₂—CH₂—OCH₃)— |
| Ib-b311 | —CH₂—N(aziridinyl) | —N(C(O)N(H)—CH₂—CH₂—CF₃)— |
| Ib-b312 | —CH₂—N(aziridinyl) | —N(C(O)N(H)—CH₂—CH₂—CF₃)— |
| Ib-b313 | —CH₂—N(aziridinyl) | —N(C(O)N(H)—CH₂—CF₃)— |
| Ib-b314 | —CH₂—N(aziridinyl) | —N(C(O)N(H)—(CH₂)₃—OH)— |
| Ib-b315 | —CH₂—N(azetidinyl) | —CH(OH)— |
| Ib-b316 | —CH₂—N(azetidinyl) | —N(C(O)N(H)—CH₂—CH₂—OH)— |
| Ib-b317 | —CH₂—N(azetidinyl) | —N(C(O)N(H)—CH₂—CH₂—F)— |

-continued

| | | |
|---|---|---|
| Ib-b318 | —CH₂—N⟨azetidine⟩ | —N(C(O)N(H)—CH₂—CH₂—OCH₃)— |
| Ib-b319 | —CH₂—N⟨azetidine⟩ | —N(C(O)N(H)—CH₂—CH₂—CF₃)— |
| Ib-b320 | —CH₂—N⟨azetidine⟩ | —N(C(O)N(H)—CH₂—CH₂—CF₃)— |
| Ib-b321 | —CH₂—N⟨azetidine⟩ | —N(C(O)N(H)—CH₂—CF₃)— |
| Ib-b322 | —CH₂—N⟨azetidine⟩ | —N(C(O)N(H)—(CH₂)₃—OH)— |
| Ib-b323 | —CH₂—N⟨pyrrolidine⟩ | —CH(OH)— |
| Ib-b324 | —CH₂—N⟨pyrrolidine⟩ | —N(C(O)N(H)—CH₂—CH₂—OH)— |
| Ib-b325 | —CH₂—N⟨pyrrolidine⟩ | —N(C(O)N(H)—CH₂—CH₂—F)— |
| Ib-b326 | —CH₂—N⟨pyrrolidine⟩ | —N(C(O)N(H)—CH₂—CH₂—OCH₃)— |
| Ib-b327 | —CH₂—N⟨pyrrolidine⟩ | —N(C(O)N(H)—CH₂—CH₂—CF₃)— |
| Ib-b328 | —CH₂—N⟨pyrrolidine⟩ | —N(C(O)N(H)—CH₂—CH₂—CF₃)— |
| Ib-b329 | —CH₂—N⟨pyrrolidine⟩ | —N(C(O)N(H)—CH₂—CF₃)— |
| Ib-b330 | —CH₂—N⟨pyrrolidine⟩ | —N(C(O)N(H)—(CH₂)₃—OH)— |
| Ib-b331 | —CH₂—N⟨3-hydroxypyrrolidine⟩ | —CH(OH)— |
| Ib-b332 | —CH₂—N⟨3-hydroxypyrrolidine⟩ | —N(C(O)N(H)—CH₂—CH₂—OH)— |
| Ib-b333 | —CH₂—N⟨3-hydroxypyrrolidine⟩ | —N(C(O)N(H)—CH₂—CH₂—F)— |
| Ib-b334 | —CH₂—N⟨3-hydroxypyrrolidine⟩ | —N(C(O)N(H)—CH₂—CH₂—OCH₃)— |

-continued

| | | |
|---|---|---|
| Ib-b335 | —CH₂—N(pyrrolidine-3-OH) | —N(C(O)N(H)—CH₂—CH₂—CF₃)— |
| Ib-b336 | —CH₂—N(pyrrolidine-3-OH) | —N(C(O)N(H)—CH₂—CH₂—CF₃)— |
| Ib-b337 | —CH₂—N(pyrrolidine-3-OH) | —N(C(O)N(H)—CH₂—CF₃)— |
| Ib-b338 | —CH₂—N(pyrrolidine-3-OH) | —N(C(O)N(H)—(CH₂)₃—OH)— |
| Ib-b339 | —CH₂—N(pyrrolidine-2-CH₂OH) | —CH(OH)— |
| Ib-b340 | —CH₂—N(pyrrolidine-2-CH₂OH) | —N(C(O)N(H)—CH₂—CH₂—OH)— |
| Ib-b341 | —CH₂—N(pyrrolidine-2-CH₂OH) | —N(C(O)N(H)—CH₂—CH₂—F)— |
| Ib-b342 | —CH₂—N(pyrrolidine-2-CH₂OH) | —N(C(O)N(H)—CH₂—CH₂—OCH₃)— |
| Ib-b343 | —CH₂—N(pyrrolidine-2-CH₂OH) | —N(C(O)N(H)—CH₂—CH₂—CF₃)— |
| Ib-b344 | —CH₂—N(pyrrolidine-2-CH₂OH) | —N(C(O)N(H)—CH₂—CH₂—CF₃)— |

| | | |
|---|---|---|
| Ib-b345 | 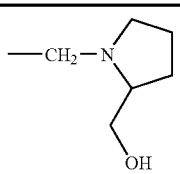 | —N(C(O)N(H)—CH₂—CF₃)— |
| Ib-b346 | 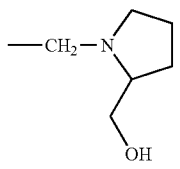 | —N(C(O)N(H)—(CH₂)₃—OH)— |
| Ib-b347 | 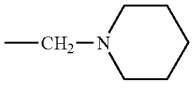 | —CH(OH)— |
| Ib-b348 | 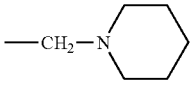 | —N(C(O)N(H)—CH₂—CH₂—OH)— |
| Ib-b349 | 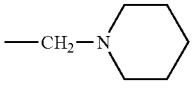 | —N(C(O)N(H)—CH₂—CH₂—F)— |
| Ib-b350 | 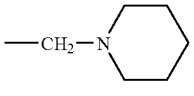 | —N(C(O)N(H)—CH₂—CH₂—OCH₃)— |
| Ib-b351 | 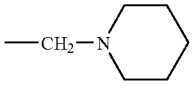 | —N(C(O)N(H)—CH₂—CH₂—CF₃)— |
| Ib-b352 | 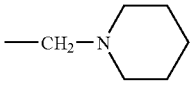 | —N(C(O)N(H)—CH₂—CH₂—CF₃)— |
| Ib-b353 | 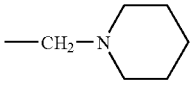 | —N(C(O)N(H)—CH₂—CF₃)— |
| Ib-b354 | 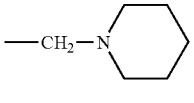 | —N(C(O)N(H)—(CH₂)₃—OH)— |
| Ib-b355 | 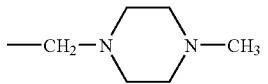 | —CH(OH)— |
| Ib-b356 | 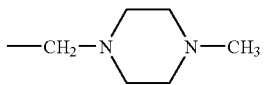 | —N(C(O)N(H)—CH₂—CH₂—OH)— |
| Ib-b357 | 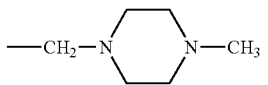 | —N(C(O)N(H)—CH₂—CH₂—F)— |
| Ib-b358 | 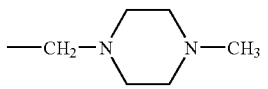 | —N(C(O)N(H)—CH₂—CH₂—OCH₃)— |
| Ib-b359 | 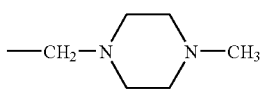 | —N(C(O)N(H)—CH₂—CH₂—CF₃)— |

-continued

| | | |
|---|---|---|
| Ib-b360 | —CH₂—N(piperazine)N—CH₃ | —N(C(O)N(H)—CH₂—CH₂—CF₃)— |
| Ib-b361 | —CH₂—N(piperazine)N—CH₃ | —N(C(O)N(H)—CH₂—CF₃)— |
| Ib-b362 | —CH₂—N(piperazine)N—CH₃ | —N(C(O)N(H)—(CH₂)₃—OH)— |
| Ib-b363 | —CH₂—N(CH₃)(CH₂-phenyl) | —CH(OH)— |
| Ib-b364 | —CH₂—N(CH₃)(CH₂-phenyl) | —N(C(O)N(H)—CH₂—CH₂—OH)— |
| Ib-b365 | —CH₂—N(CH₃)(CH₂-phenyl) | —N(C(O)N(H)—CH₂—CH₂—F)— |
| Ib-b366 | —CH₂—N(CH₃)(CH₂-phenyl) | —N(C(O)N(H)—CH₂—CH₂—OCH₃)— |
| Ib-b367 | —CH₂—N(CH₃)(CH₂-phenyl) | —N(C(O)N(H)—CH₂—CH₂—CF₃)— |
| Ib-b368 | —CH₂—N(CH₃)(CH₂-phenyl) | —N(C(O)N(H)—CH₂—CH₂—CF₃)— |
| Ib-b369 | —CH₂—N(CH₃)(CH₂-phenyl) | —N(C(O)N(H)—CH₂—CF₃)— |
| Ib-b370 | —CH₂—N(CH₃)(CH₂-phenyl) | —N(C(O)N(H)—(CH₂)₃—OH)— |
| Ib-b371 | —CH₂—N(CH₃)(CH(CH₃)₂) | —CH(OH)— |

| | | |
|---|---|---|
| Ib-b372 | —CH₂—N(CH₃)(CH(CH₃)₂) | —N(C(O)N(H)—CH₂—CH₂—OH)— |
| Ib-b373 | —CH₂—N(CH₃)(CH(CH₃)₂) | —N(C(O)N(H)—CH₂—CH₂—F)— |
| Ib-b374 | —CH₂—N(CH₃)(CH(CH₃)₂) | —N(C(O)N(H)—CH₂—CH₂—OCH₃)— |
| Ib-b375 | —CH₂—N(CH₃)(CH(CH₃)₂) | —N(C(O)N(H)—CH₂—CH₂—CF₃)— |
| Ib-b376 | —CH₂—N(CH₃)(CH(CH₃)₂) | —N(C(O)N(H)—CH₂—CH₂—CF₃)— |
| Ib-b377 | —CH₂—N(CH₃)(CH(CH₃)₂) | —N(C(O)N(H)—CH₂—CF₃)— |
| Ib-b378 | —CH₂—N(CH₃)(CH(CH₃)₂) | —N(C(O)N(H)—(CH₂)₃—OH)— |
| Ib-b379 | —CH₂—N(CH₃)(cyclohexyl) | —CH(OH)— |
| Ib-b380 | —CH₂—N(CH₃)(cyclohexyl) | —N(C(O)N(H)—CH₂—CH₂—OH)— |
| Ib-b381 | —CH₂—N(CH₃)(cyclohexyl) | —N(C(O)N(H)—CH₂—CH₂—F)— |

-continued
| | | |
|---|---|---|
| Ib-b382 | 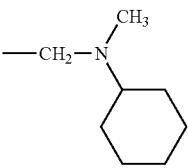 | —N(C(O)N(H)—CH₂—CH₂—OCH₃)— |
| Ib-b383 | 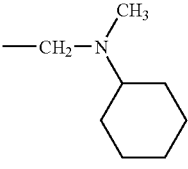 | —N(C(O)N(H)—CH₂—CH₂—CF₃)— |
| Ib-b384 | 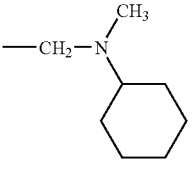 | —N(C(O)N(H)—CH₂—CH₂—CF₃)— |
| Ib-b385 | 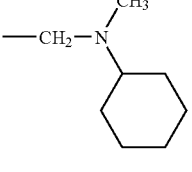 | —N(C(O)N(H)—CH₂—CF₃)— |
| Ib-b386 | 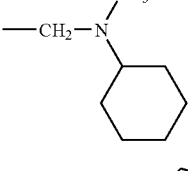 | —N(C(O)N(H)—(CH₂)₃—OH)— |
| Ib-b387 | 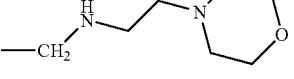 | —CH(OH)— |
| Ib-b388 | 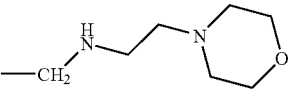 | —N(C(O)N(H)—CH₂—CH₂—OH)— |
| Ib-b389 | 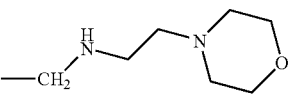 | —N(C(O)N(H)—CH₂—CH₂—F)— |
| Ib-b390 | 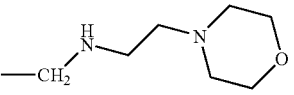 | —N(C(O)N(H)—CH₂—CH₂—OCH₃)— |
| Ib-b391 | 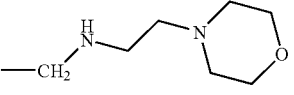 | —N(C(O)N(H)—CH₂—CH₂—CF₃)— |
| Ib-b392 | 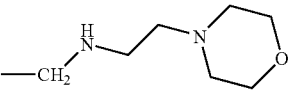 | —N(C(O)N(H)—CH₂—CH₂—CF₃)— |
| Ib-b393 | 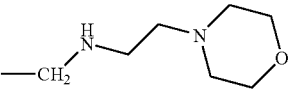 | —N(C(O)N(H)—CH₂—CF₃)— |

-continued
| | | |
|---|---|---|
| Ib-b394 | 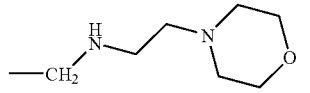 | —N(C(O)N(H)—(CH₂)₃—OH)— |
| Ib-b395 | 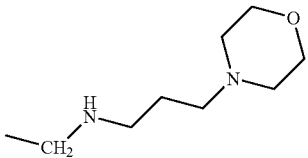 | —CH(OH)— |
| Ib-b396 | 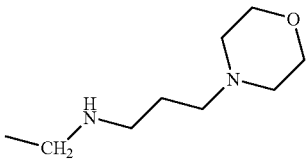 | —N(C(O)N(H)—CH₂—CH₂—OH)— |
| Ib-b397 | 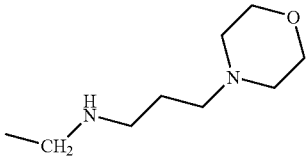 | —N(C(O)N(H)—CH₂—CH₂—F)— |
| Ib-b398 | 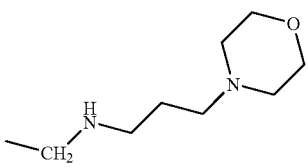 | —N(C(O)N(H)—CH₂—CH₂—OCH₃)— |
| Ib-b399 | 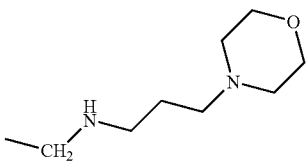 | —N(C(O)N(H)—CH₂—CH₂—CF₃)— |
| Ib-b400 | 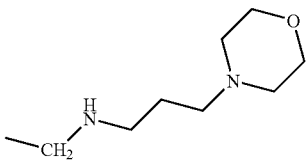 | —N(C(O)N(H)—CH₂—CH₂—CF₃)— |
| Ib-b401 | 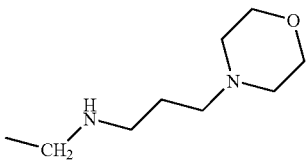 | —N(C(O)N(H)—CH₂—CF₃)— |
| Ib-b402 | 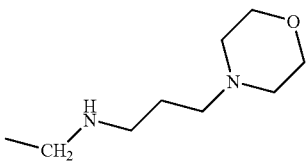 | —N(C(O)N(H)—(CH₂)₃—OH)— |

| | | -continued |
|---|---|---|
| Ib-b403 | 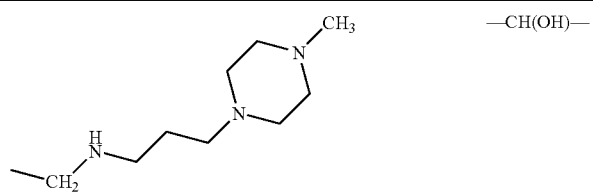 | —CH(OH)— |
| Ib-b404 | 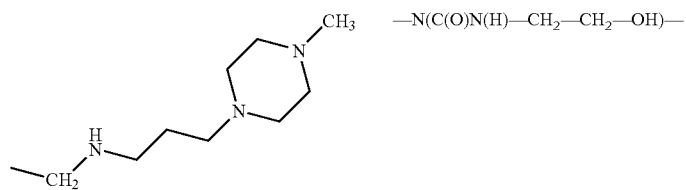 | —N(C(O)N(H)—CH$_2$—CH$_2$—OH)— |
| Ib-b405 | 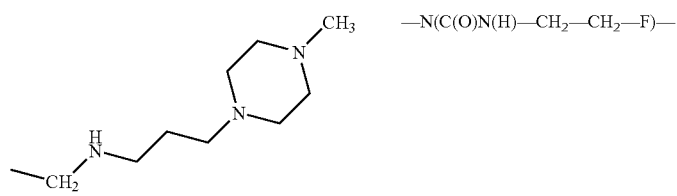 | —N(C(O)N(H)—CH$_2$—CH$_2$—F)— |
| Ib-b406 | 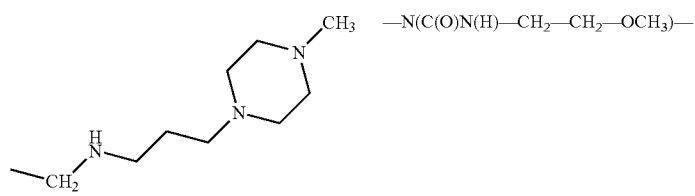 | —N(C(O)N(H)—CH$_2$—CH$_2$—OCH$_3$)— |
| Ib-b407 |  | —N(C(O)N(H)—CH$_2$—CH$_2$—CF$_3$)— |
| Ib-b408 |  | —N(C(O)N(H)—CH$_2$—CH$_2$—CF$_3$)— |
| Ib-b409 | 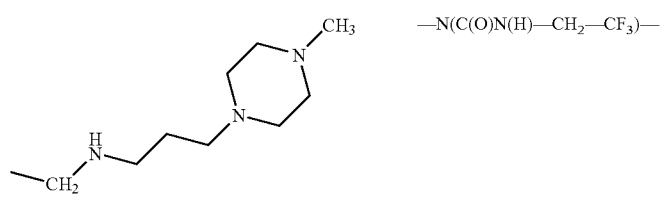 | —N(C(O)N(H)—CH$_2$—CF$_3$)— |
| Ib-b410 | 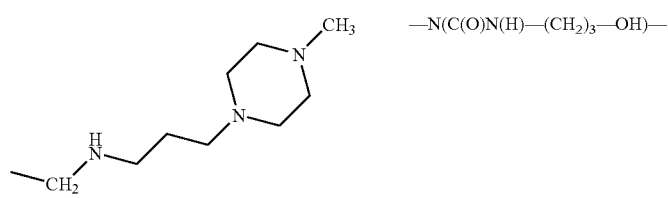 | —N(C(O)N(H)—(CH$_2$)$_3$—OH)— |

| | | -continued |
|---|---|---|
| Ib-b411 | H₃C–N(CH₃)–CH₂CH₂CH₂–N(H)–CH₂– | —CH(OH)— |
| Ib-b412 | H₃C–N(CH₃)–CH₂CH₂CH₂–N(H)–CH₂– | —N(C(O)N(H)—CH₂—CH₂—OH)— |
| Ib-b413 | H₃C–N(CH₃)–CH₂CH₂CH₂–N(H)–CH₂– | —N(C(O)N(H)—CH₂—CH₂—F)— |
| Ib-b414 | H₃C–N(CH₃)–CH₂CH₂CH₂–N(H)–CH₂– | —N(C(O)N(H)—CH₂—CH₂—OCH₃)— |
| Ib-b415 | H₃C–N(CH₃)–CH₂CH₂CH₂–N(H)–CH₂– | —N(C(O)N(H)—CH₂—CH₂—CF₃)— |
| Ib-b416 | H₃C–N(CH₃)–CH₂CH₂CH₂–N(H)–CH₂– | —N(C(O)N(H)—CH₂—CH₂—CF₃)— |
| Ib-b417 | H₃C–N(CH₃)–CH₂CH₂CH₂–N(H)–CH₂– | —N(C(O)N(H)—CH₂—CF₃)— |
| Ib-b418 | H₃C–N(CH₃)–CH₂CH₂CH₂–N(H)–CH₂– | —N(C(O)N(H)—(CH₂)₃—OH)— |
| Ib-b419 | (imidazol-1-yl)–CH₂CH₂CH₂–N(H)–CH₂– | —CH(OH)— |
| Ib-b420 | (imidazol-1-yl)–CH₂CH₂CH₂–N(H)–CH₂– | —N(C(O)N(H)—CH₂—CH₂—OH)— |

-continued
| | | |
|---|---|---|
| Ib-b421 | 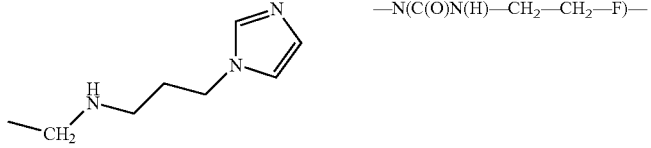 | —N(C(O)N(H)—CH₂—CH₂—F)— |
| Ib-b422 | 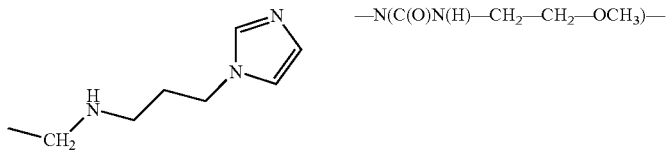 | —N(C(O)N(H)—CH₂—CH₂—OCH₃)— |
| Ib-b423 | 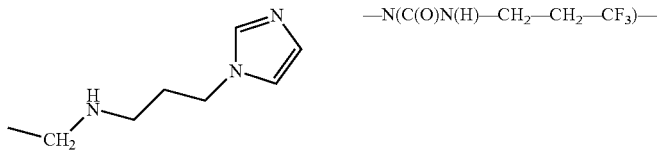 | —N(C(O)N(H)—CH₂—CH₂—CF₃)— |
| Ib-b424 | 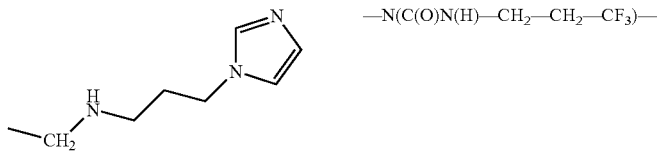 | —N(C(O)N(H)—CH₂—CH₂—CF₃)— |
| Ib-b425 | 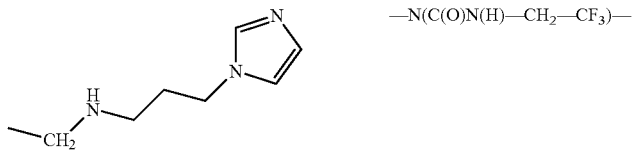 | —N(C(O)N(H)—CH₂—CF₃)— |
| Ib-b426 | 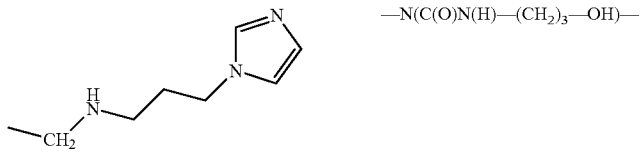 | —N(C(O)N(H)—(CH₂)₃—OH)— |
| Ib-b427 | 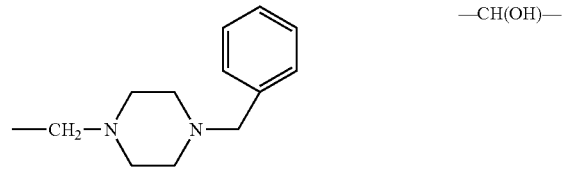 | —CH(OH)— |
| Ib-b428 | 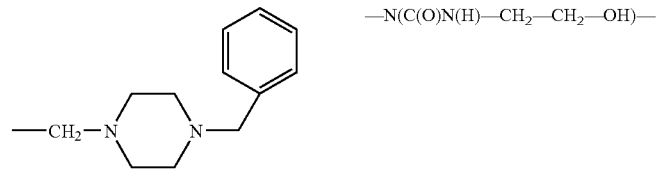 | —N(C(O)N(H)—CH₂—CH₂—OH)— |
| Ib-b429 | 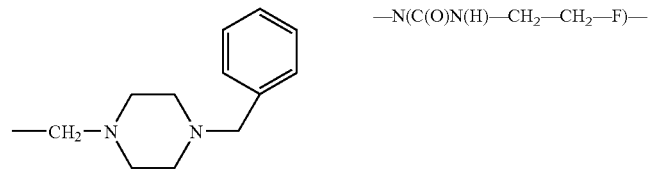 | —N(C(O)N(H)—CH₂—CH₂—F)— |

-continued

| | | |
|---|---|---|
| Ib-b430 | —CH₂—N(piperazine)N—CH₂—C₆H₅ | —N(C(O)N(H)—CH₂—CH₂—OCH₃)— |
| Ib-b431 | —CH₂—N(piperazine)N—CH₂—C₆H₅ | —N(C(O)N(H)—CH₂—CH₂—CF₃)— |
| Ib-b432 | —CH₂—N(piperazine)N—CH₂—C₆H₅ | —N(C(O)N(H)—CH₂—CH₂—CF₃)— |
| Ib-b433 | —CH₂—N(piperazine)N—CH₂—C₆H₅ | —N(C(O)N(H)—CH₂—CF₃)— |
| Ib-b434 | —CH₂—N(piperazine)N—CH₂—C₆H₅ | —N(C(O)N(H)—(CH₂)₃—OH)— |
| Ib-b435 | —CH₂—N(piperazine)N—C₆H₄—F | —CH(OH)— |
| Ib-b436 | —CH₂—N(piperazine)N—C₆H₄—F | —N(C(O)N(H)—CH₂—CH₂—OH)— |
| Ib-b437 | —CH₂—N(piperazine)N—C₆H₄—F | —N(C(O)N(H)—CH₂—CH₂—F)— |
| Ib-b438 | —CH₂—N(piperazine)N—C₆H₄—F | —N(C(O)N(H)—CH₂—CH₂—OCH₃)— |
| Ib-b439 | —CH₂—N(piperazine)N—C₆H₄—F | —N(C(O)N(H)—CH₂—CH₂—CF₃)— |
| Ib-b440 | —CH₂—N(piperazine)N—C₆H₄—F | —N(C(O)N(H)—CH₂—CH₂—CF₃)— |
| Ib-b441 | —CH₂—N(piperazine)N—C₆H₄—F | —N(C(O)N(H)—CH₂—CF₃)— |

| | | |
|---|---|---|
| Ib-b442 | 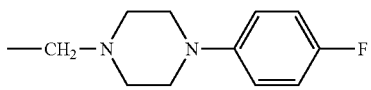 | —N(C(O)N(H)—(CH$_2$)$_3$—OH)— |
| Ib-b443 | 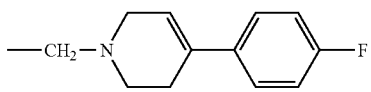 | —CH(OH)— |
| Ib-b444 | 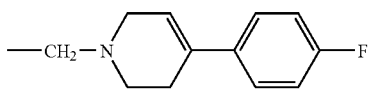 | —N(C(O)N(H)—CH$_2$—CH$_2$—OH)— |
| Ib-b445 | 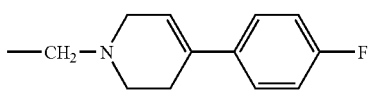 | —N(C(O)N(H)—CH$_2$—CH$_2$—F)— |
| Ib-b446 | 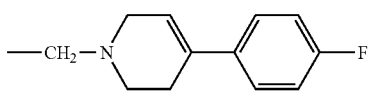 | —N(C(O)N(H)—CH$_2$—CH$_2$—OCH$_3$)— |
| Ib-b447 | 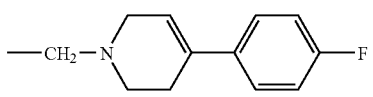 | —N(C(O)N(H)—CH$_2$—CH$_2$—CF$_3$)— |
| Ib-b448 | 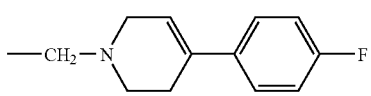 | —N(C(O)N(H)—CH$_2$—CH$_2$—CF$_3$)— |
| Ib-b449 | 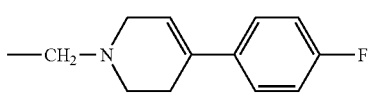 | —N(C(O)N(H)—CH$_2$—CF$_3$)— |
| Ib-b450 | 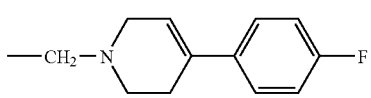 | —N(C(O)N(H)—(CH$_2$)$_3$—OH)— |
| Ib-b451 | 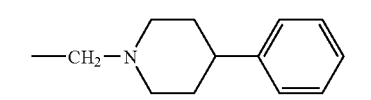 | —CH(OH)— |
| Ib-b452 | 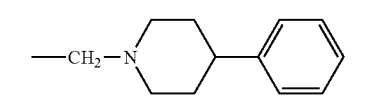 | —N(C(O)N(H)—CH$_2$—CH$_2$—OH)— |
| Ib-b453 | 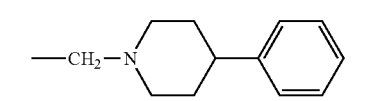 | —N(C(O)N(H)—CH$_2$—CH$_2$—F)— |
| Ib-b454 | 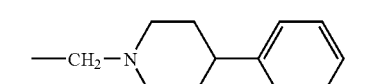 | —N(C(O)N(H)—CH$_2$—CH$_2$—OCH$_3$)— |
| Ib-b455 | 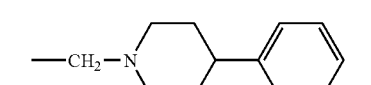 | —N(C(O)N(H)—CH$_2$—CH$_2$—CF$_3$)— |
| Ib-b456 | 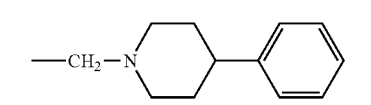 | —N(C(O)N(H)—CH$_2$—CH$_2$—CF$_3$)— |
| Ib-b457 | 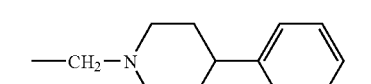 | —N(C(O)N(H)—CH$_2$—CF$_3$)— |

-continued

| ID | Group 1 | Group 2 |
|---|---|---|
| Ib-b458 | —CH₂—N(piperidine-Ph) | —N(C(O)N(H)—(CH₂)₃—OH)— |
| Ib-b459 | —CH₂—N(piperidine-Ph-4-Cl) | —CH(OH)— |
| Ib-b460 | —CH₂—N(piperidine-Ph-4-Cl) | —N(C(O)N(H)—CH₂—CH₂—OH)— |
| Ib-b461 | —CH₂—N(piperidine-Ph-4-Cl) | —N(C(O)N(H)—CH₂—CH₂—F)— |
| Ib-b462 | —CH₂—N(piperidine-Ph-4-Cl) | —N(C(O)N(H)—CH₂—CH₂—OCH₃)— |
| Ib-b463 | —CH₂—N(piperidine-Ph-4-Cl) | —N(C(O)N(H)—CH₂—CH₂—CF₃)— |
| Ib-b464 | —CH₂—N(piperidine-Ph-4-Cl) | —N(C(O)N(H)—CH₂—CH₂—CF₃)— |
| Ib-b465 | —CH₂—N(piperidine-Ph-4-Cl) | —N(C(O)N(H)—CH₂—CF₃)— |
| Ib-b466 | —CH₂—N(piperidine-Ph-4-Cl) | —N(C(O)N(H)—(CH₂)₃—OH)— |
| Ib-b467 | —CH₂—N(piperidine-Ph) | —CH(OH)— |
| Ib-b468 | —CH₂—N(piperidine-Ph) | —N(C(O)N(H)—CH₂—CH₂—OH)— |
| Ib-b469 | —CH₂—N(piperidine-Ph) | —N(C(O)N(H)—CH₂—CH₂—F)— |
| Ib-b470 | —CH₂—N(piperidine-Ph) | —N(C(O)N(H)—CH₂—CH₂—OCH₃)— |
| Ib-b471 | —CH₂—N(piperidine-Ph) | —N(C(O)N(H)—CH₂—CH₂—CF₃)— |
| Ib-b472 | —CH₂—N(piperidine-Ph) | —N(C(O)N(H)—CH₂—CH₂—CF₃)— |
| Ib-b473 | —CH₂—N(piperidine-Ph) | N(C(O)N(H)—CH₂—CF₃)— |

-continued
| | | |
|---|---|---|
| Ib-b474 | 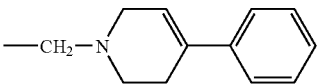 | N(C(O)N(H)—(CH₂)₃—OH)— |
| Ib-b475 | 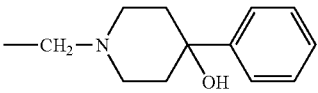 | —CH(OH)— |
| Ib-b476 |  | —N(C(O)N(H)—CH₂—CH₂—OH)— |
| Ib-b477 |  | —N(C(O)N(H)—CH₂—CH₂—F)— |
| Ib-b478 |  | —N(C(O)N(H)—CH₂—CH₂—OCH₃)— |
| Ib-b479 | 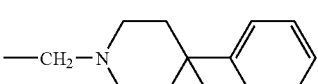 | —N(C(O)N(H)—CH₂—CH₂—CF₃)— |
| Ib-b480 |  | —N(C(O)N(H)—CH₂—CH₂—CF₃)— |
| Ib-b481 | 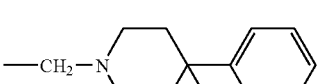 | N(C(O)N(H)—CH₂—CF₃)— |
| Ib-b482 | 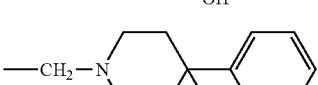 | N(C(O)N(H)—(CH₂)₃—OH)— |
| Ib-b483 | 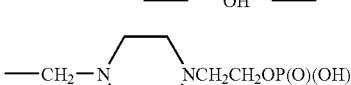 | —CH(OH)— |
| Ib-b484 | 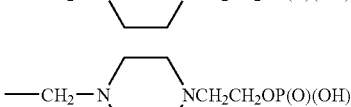 | —N(C(O)N(H)—CH₂—CH₂—OH)— |
| Ib-b485 | 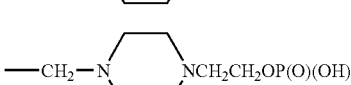 | —N(C(O)N(H)—CH₂—CH₂—F)— |
| Ib-b486 | 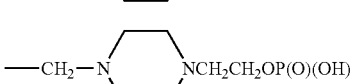 | —N(C(O)N(H)—CH₂—CH₂—OCH₃)— |
| Ib-b487 | 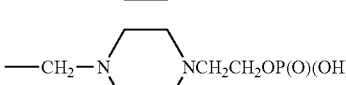 | —N(C(O)N(H)—CH₂—CH₂—CF₃)— |
| Ib-b488 | 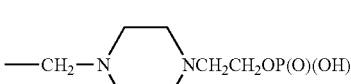 | —N(C(O)N(H)—CH₂—CH₂—CF₃)— |
| Ib-b489 | 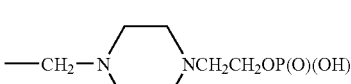 | N(C(O)N(H)—CH₂—CF₃)— |

-continued

| | | |
|---|---|---|
| Ib-b490 | —CH₂—N(piperazine)NCH₂CH₂OP(O)(OH)₂ | N(C(O)N(H)—(CH₂)₃—OH)— |
| Ib-b491 | —CH₂—CH₂—CH₂—OP(O)(OH)₂ | —CH(OH)— |
| Ib-b492 | —CH₂—CH₂—CH₂—OP(O)(OH)₂ | —N(C(O)N(H)—CH₂—CH₂—OH)— |
| Ib-b493 | —CH₂—CH₂—CH₂—OP(O)(OH)₂ | —N(C(O)N(H)—CH₂—CH₂—F)— |
| Ib-b494 | —CH₂—CH₂—CH₂—OP(O)(OH)₂ | —N(C(O)N(H)—CH₂—CH₂—OCH₃)— |
| Ib-b495 | —CH₂—CH₂—CH₂—OP(O)(OH)₂ | —N(C(O)N(H)—CH₂—CH₂—CF₃)— |
| Ib-b496 | —CH₂—CH₂—CH₂—OP(O)(OH)₂ | —N(C(O)N(H)—CH₂—CH₂—CF₃)— |
| Ib-b497 | —CH₂—CH₂—CH₂—OP(O)(OH)₂ | —N(C(O)N(H)—CH₂—CF₃)— |
| Ib-b498 | —CH₂—CH₂—CH₂—OP(O)(OH)₂ | —N(C(O)N(H)—(CH₂)₃—OH)— |
| Ib-b499 | —CH₂—CH₂—CH₂—OS(O)₂OH | —CH(OH)— |
| Ib-b500 | —CH₂—CH₂—CH₂—OS(O)₂OH | —N(C(O)N(H)—CH₂—CH₂—OH)— |
| Ib-b501 | —CH₂—CH₂—CH₂—OS(O)₂OH | —N(C(O)N(H)—CH₂—CH₂—F)— |
| Ib-b502 | —CH₂—CH₂—CH₂—OS(O)₂OH | —N(C(O)N(H)—CH₂—CH₂—OCH₃)— |
| Ib-b503 | —CH₂—CH₂—CH₂—OS(O)₂OH | —N(C(O)N(H)—CH₂—CH₂—CF₃)— |
| Ib-b504 | —CH₂—CH₂—CH₂—OS(O)₂OH | —N(C(O)N(H)—CH₂—CH₂—CF₃)— |
| Ib-b505 | —CH₂—CH₂—CH₂—OS(O)₂OH | —N(C(O)N(H)—CH₂—CF₃)— |
| Ib-b506 | —CH₂—CH₂—CH₂—OS(O)₂OH | —N(C(O)N(H)—(CH₂)₃—OH)— |
| Ib-b507 | —CH₂—N(pyrrolidin-3-yl-OP(O)(OH)₂) | —CH(OH)— |
| Ib-b508 | —CH₂—N(pyrrolidin-3-yl-OP(O)(OH)₂) | —N(C(O)N(H)—CH₂—CH₂—OH)— |
| Ib-b509 | —CH₂—N(pyrrolidin-3-yl-OP(O)(OH)₂) | —N(C(O)N(H)—CH₂—CH₂—F)— |
| Ib-b510 | —CH₂—N(pyrrolidin-3-yl-OP(O)(OH)₂) | —N(C(O)N(H)—CH₂—CH₂—OCH₃)— |
| Ib-b511 | —CH₂—N(pyrrolidin-3-yl-OP(O)(OH)₂) | —N(C(O)N(H)—CH₂—CH₂—CF₃)— |
| Ib-b512 | —CH₂—N(pyrrolidin-3-yl-OP(O)(OH)₂) | —N(C(O)N(H)—CH₂—CH₂—CF₃)— |
| Ib-b513 | —CH₂—N(pyrrolidin-3-yl-OP(O)(OH)₂) | —N(C(O)N(H)—CH₂—CF₃)— |
| Ib-b514 | —CH₂—N(pyrrolidin-3-yl-OP(O)(OH)₂) | —N(C(O)N(H)—(CH₂)₃—OH)— |
| Ib-b515 | —CH₂—N(pyrrolidin-2-yl-CH₂-OP(O)(OH)₂) | —CH(OH)— |

-continued

| ID | R1 | R2 |
|---|---|---|
| Ib-b516 | —CH₂—N(pyrrolidine with OP(O)(OH)₂ at 2-position CH₂) | —N(C(O)N(H)—CH₂—CH₂—OH)— |
| Ib-b517 | —CH₂—N(pyrrolidine with OP(O)(OH)₂ at 2-position CH₂) | —N(C(O)N(H)—CH₂—CH₂—F)— |
| Ib-b518 | —CH₂—N(pyrrolidine with OP(O)(OH)₂ at 2-position CH₂) | —N(C(O)N(H)—CH₂—CH₂—OCH₃)— |
| Ib-b519 | —CH₂—N(pyrrolidine with OP(O)(OH)₂ at 2-position CH₂) | —N(C(O)N(H)—CH₂—CH₂—CF₃)— |
| Ib-b520 | —CH₂—N(pyrrolidine with OP(O)(OH)₂ at 2-position CH₂) | —N(C(O)N(H)—CH₂—CH₂—CF₃)— |
| Ib-b521 | —CH₂—N(pyrrolidine with OP(O)(OH)₂ at 2-position CH₂) | —N(C(O)N(H)—CH₂—CF₃)— |
| Ib-b522 | —CH₂—N(pyrrolidine with OP(O)(OH)₂ at 2-position CH₂) | —N(C(O)N(H)—(CH₂)₃—OH)— |
| Ib-b523 | —(CH₂)₁₀—N(CH₂—CH₂—O—CH₃)₂ | —CH(OH)— |
| Ib-b524 | —(CH₂)₁₀—N(CH₂—CH₂—O—CH₃)₂ | —N(C(O)N(H)—CH₂—CH₂—OH)— |
| Ib-b525 | —(CH₂)₁₀—N(CH₂—CH₂—O—CH₃)₂ | —N(C(O)N(H)—CH₂—CH₂—F)— |
| Ib-b526 | —(CH₂)₁₀—N(CH₂—CH₂—O—CH₃)₂ | —N(C(O)N(H)—CH₂—CH₂—OCH₃)— |
| Ib-b527 | —(CH₂)₁₀—N(CH₂—CH₂—O—CH₃)₂ | —N(C(O)N(H)—CH₂—CH₂—CF₃)— |
| Ib-b528 | —(CH₂)₁₀—N(CH₂—CH₂—O—CH₃)₂ | —N(C(O)N(H)—CH₂—CH₂—CF₃)— |
| Ib-b529 | —(CH₂)₁₀—N(CH₂—CH₂—O—CH₃)₂ | —N(C(O)N(H)—CH₂—CF₃)— |
| Ib-b530 | —(CH₂)₁₀—N(CH₂—CH₂—O—CH₃)₂ | —N(C(O)N(H)—(CH₂)₃—OH)— |
| Ib-b531 | —CH₂—N(CH₂—CH₂—O—CH₃)₂ | —CH(OH)— |
| Ib-b532 | —CH₂—N(CH₂—CH₂—O—CH₃)₂ | —N(C(O)N(H)—CH₂—CH₂—OH)— |
| Ib-b533 | —CH₂—N(CH₂—CH₂—O—CH₃)₂ | —N(C(O)N(H)—CH₂—CH₂—F)— |
| Ib-b534 | —CH₂—N(CH₂—CH₂—O—CH₃)₂ | —N(C(O)N(H)—CH₂—CH₂—OCH₃)— |
| Ib-b535 | —CH₂—N(CH₂—CH₂—O—CH₃)₂ | —N(C(O)N(H)—CH₂—CH₂—CF₃)— |
| Ib-b536 | —CH₂—N(CH₂—CH₂—O—CH₃)₂ | —N(C(O)N(H)—CH₂—CH₂—CF₃)— |
| Ib-b537 | —CH₂—N(CH₂—CH₂—O—CH₃)₂ | —N(C(O)N(H)—CH₂—CF₃)— |
| Ib-b538 | —CH₂—N(CH₂—CH₂—O—CH₃)₂ | —N(C(O)N(H)—(CH₂)₃—OH)— |

-continued
| | | |
|---|---|---|
| Ib-b539 | 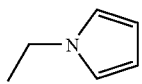 | —CH(OH)— |
| Ib-b540 | 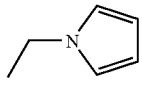 | —N(C(O)N(H)—CH$_2$—CH$_2$—OH)— |
| Ib-b541 | 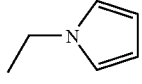 | —N(C(O)N(H)—CH$_2$—CH$_2$—F)— |
| Ib-b542 | 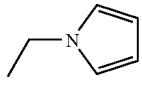 | —N(C(O)N(H)—CH$_2$—CH$_2$—OCH$_3$)— |
| Ib-b543 | 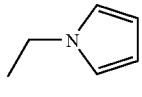 | —N(C(O)N(H)—CH$_2$—CH$_2$—CF$_3$)— |
| Ib-b544 | 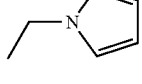 | —N(C(O)N(H)—CH$_2$—CH$_2$—CF$_3$)— |
| Ib-b545 | 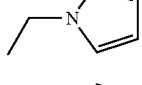 | —N(C(O)N(H)—CH$_2$—CF$_3$)— |
| Ib-b546 | 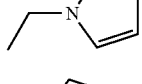 | —N(C(O)N(H)—(CH$_2$)$_3$—OH)— |
| Ib-b547 | 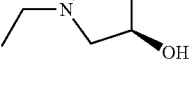 | —CH(OH)— |
| Ib-b548 | 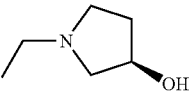 | —N(C(O)N(H)—CH$_2$—CH$_2$—OH)— |
| Ib-b549 | 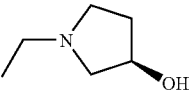 | —N(C(O)N(H)—CH$_2$—CH$_2$—F)— |
| Ib-b550 | 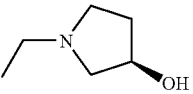 | —N(C(O)N(H)—CH$_2$—CH$_2$—OCH$_3$)— |
| Ib-b551 | 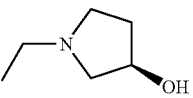 | —N(C(O)N(H)—CH$_2$—CH$_2$—CF$_3$)— |
| Ib-b552 | 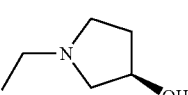 | —N(C(O)N(H)—CH$_2$—CH$_2$—CF$_3$)— |
| Ib-b553 | 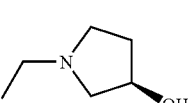 | —N(C(O)N(H)—CH$_2$—CF$_3$)— |
| Ib-b554 | 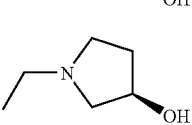 | —N(C(O)N(H)—(CH$_2$)$_3$—OH)— |

-continued

| | | |
|---|---|---|
| Ib-b555 | [ethyl-piperidine-piperidine] | —CH(OH)— |
| Ib-b556 | [ethyl-piperidine-piperidine] | —N(C(O)N(H)—CH₂—CH₂—OH)— |
| Ib-b557 | [ethyl-piperidine-piperidine] | —N(C(O)N(H)—CH₂—CH₂—F)— |
| Ib-b558 | [ethyl-piperidine-piperidine] | —N(C(O)N(H)—CH₂—CH₂—OCH₃)— |
| Ib-b559 | [ethyl-piperidine-piperidine] | —N(C(O)N(H)—CH₂—CH₂—CF₃)— |
| Ib-b560 | [ethyl-piperidine-piperidine] | —N(C(O)N(H)—CH₂—CH₂—CF₃)— |
| Ib-b561 | [ethyl-piperidine-piperidine] | —N(C(O)N(H)—CH₂—CF₃)— |
| Ib-b562 | [ethyl-piperidine-piperidine] | —N(C(O)N(H)—(CH₂)₃—OH)— |
| Ib-b563 | [ethyl-piperidine-pyrrolidine] | —CH(OH)— |
| Ib-b564 | [ethyl-piperidine-pyrrolidine] | —N(C(O)N(H)—CH₂—CH₂—OH)— |
| Ib-b565 | [ethyl-piperidine-pyrrolidine] | —N(C(O)N(H)—CH₂—CH₂—F)— |
| Ib-b566 | [ethyl-piperidine-pyrrolidine] | —N(C(O)N(H)—CH₂—CH₂—OCH₃)— |
| Ib-b567 | [ethyl-piperidine-pyrrolidine] | —N(C(O)N(H)—CH₂—CH₂—CF₃)— |
| Ib-b568 | [ethyl-piperidine-pyrrolidine] | —N(C(O)N(H)—CH₂—CH₂—CF₃)— |
| Ib-b569 | [ethyl-piperidine-pyrrolidine] | —N(C(O)N(H)—CH₂—CF₃)— |
| Ib-b570 | [ethyl-piperidine-pyrrolidine] | —N(C(O)N(H)—(CH₂)₃—OH)— |

-continued
| | | |
|---|---|---|
| Ib-b571 | 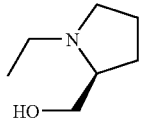 | —CH(OH)— |
| Ib-b572 | 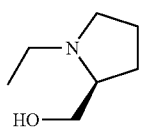 | —N(C(O)N(H)—CH$_2$—CH$_2$—OH)— |
| Ib-b573 | 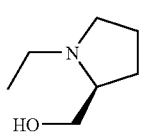 | —N(C(O)N(H)—CH$_2$—CH$_2$—F)— |
| Ib-b574 | 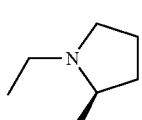 | —N(C(O)N(H)—CH$_2$—CH$_2$—OCH$_3$)— |
| Ib-b575 | 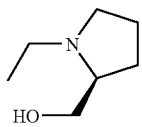 | —N(C(O)N(H)—CH$_2$—CH$_2$—CF$_3$)— |
| Ib-b576 | 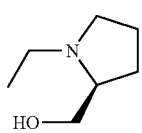 | —N(C(O)N(H)—CH$_2$—CH$_2$—CF$_3$)— |
| Ib-b577 | 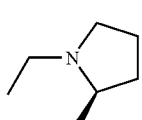 | —N(C(O)N(H)—CH$_2$—CF$_3$)— |
| Ib-b578 | 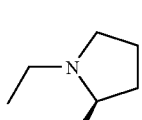 | —N(C(O)N(H)—(CH$_2$)$_3$—OH)— |
| Ib-b579 | 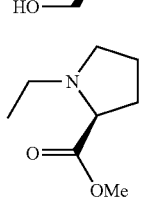 | —CH(OH)— |
| Ib-b580 | 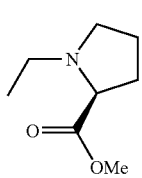 | —N(C(O)N(H)—CH$_2$—CH$_2$—OH)— |
| Ib-b581 | 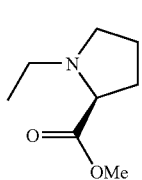 | —N(C(O)N(H)—CH$_2$—CH$_2$—F)— |

-continued

| | | |
|---|---|---|
| Ib-b582 | *N-ethylpyrrolidine-2-carboxylic acid methyl ester* | —N(C(O)N(H)—CH$_2$—CH$_2$—OCH$_3$)— |
| Ib-b583 | *N-ethylpyrrolidine-2-carboxylic acid methyl ester* | —N(C(O)N(H)—CH$_2$—CH$_2$—CF$_3$)— |
| Ib-b584 | *N-ethylpyrrolidine-2-carboxylic acid methyl ester* | —N(C(O)N(H)—CH$_2$—CH$_2$—CF$_3$)— |
| Ib-b585 | *N-ethylpyrrolidine-2-carboxylic acid methyl ester* | —N(C(O)N(H)—CH$_2$—CF$_3$)— |
| Ib-b586 | *N-ethylpyrrolidine-2-carboxylic acid methyl ester* | —N(C(O)N(H)—(CH$_2$)$_3$—OH)— |
| Ib-b587 | *2-ethyl-1,2,3,4-tetrahydroisoquinoline* | —CH(OH)— |
| Ib-b588 | *2-ethyl-1,2,3,4-tetrahydroisoquinoline* | —N(C(O)N(H)—CH$_2$—CH$_2$—OH)— |
| Ib-b589 | *2-ethyl-1,2,3,4-tetrahydroisoquinoline* | —N(C(O)N(H)—CH$_2$—CH$_2$—F)— |
| Ib-b590 | *2-ethyl-1,2,3,4-tetrahydroisoquinoline* | —N(C(O)N(H)—CH$_2$—CH$_2$—OCH$_3$)— |
| Ib-b591 | *2-ethyl-1,2,3,4-tetrahydroisoquinoline* | —N(C(O)N(H)—CH$_2$—CH$_2$—CF$_3$)— |
| Ib-b592 | *2-ethyl-1,2,3,4-tetrahydroisoquinoline* | —N(C(O)N(H)—CH$_2$—CH$_2$—CF$_3$)— |
| Ib-b593 | *2-ethyl-1,2,3,4-tetrahydroisoquinoline* | —N(C(O)N(H)—CH$_2$—CF$_3$)— |

-continued
| | | |
|---|---|---|
| Ib-b594 | 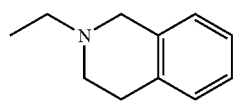 | —N(C(O)N(H)—(CH₂)₃—OH)— |
| Ib-b595 | 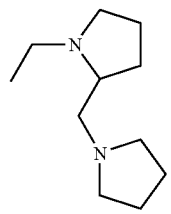 | —CH(OH)— |
| Ib-b596 | 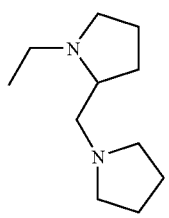 | —N(C(O)N(H)—CH₂—CH₂—OH)— |
| Ib-b597 | 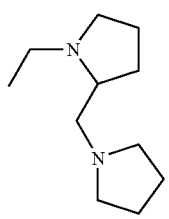 | —N(C(O)N(H)—CH₂—CH₂—F)— |
| Ib-b598 | 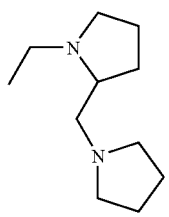 | —N(C(O)N(H)—CH₂—CH₂—OCH₃)— |
| Ib-b599 | 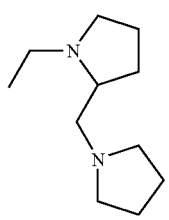 | —N(C(O)N(H)—CH₂—CH₂—CF₃)— |
| Ib-b600 | 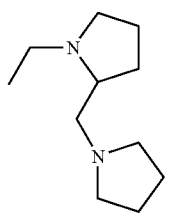 | —N(C(O)N(H)—CH₂—CH₂—CF₃)— |

-continued

| ID | Group 1 | Group 2 |
|---|---|---|
| Ib-b601 | 1-ethyl-2-(pyrrolidin-1-ylmethyl)pyrrolidine | —N(C(O)N(H)—CH₂—CF₃)— |
| Ib-b602 | 1-ethyl-2-(pyrrolidin-1-ylmethyl)pyrrolidine | —N(C(O)N(H)—(CH₂)₃—OH)— |
| Ib-b603 | 4-ethyl-1-(2-(dimethylamino)ethyl)piperazine | —CH(OH)— |
| Ib-b604 | 4-ethyl-1-(2-(dimethylamino)ethyl)piperazine | —N(C(O)N(H)—CH₂—CH₂—OH)— |
| Ib-b605 | 4-ethyl-1-(2-(dimethylamino)ethyl)piperazine | —N(C(O)N(H)—CH₂—CH₂—F)— |
| Ib-b606 | 4-ethyl-1-(2-(dimethylamino)ethyl)piperazine | —N(C(O)N(H)—CH₂—CH₂—OCH₃)— |
| Ib-b607 | 4-ethyl-1-(2-(dimethylamino)ethyl)piperazine | —N(C(O)N(H)—CH₂—CH₂—CF₃)— |
| Ib-b608 | 4-ethyl-1-(2-(dimethylamino)ethyl)piperazine | —N(C(O)N(H)—CH₂—CH₂—CF₃)— |
| Ib-b609 | 4-ethyl-1-(2-(dimethylamino)ethyl)piperazine | —N(C(O)N(H)—CH₂—CF₃)— |
| Ib-b610 | 4-ethyl-1-(2-(dimethylamino)ethyl)piperazine | —N(C(O)N(H)—(CH₂)₃—OH)— |
| Ib-b611 | —CH₂—NH—CH₂—CH₂—CH₂—N(CH₃)₂ | —CH(OH)— |
| Ib-b612 | —CH₂—NH—CH₂—CH₂—CH₂—N(CH₃)₂ | —N(C(O)N(H)—CH₂—CH₂—OH)— |
| Ib-b613 | —CH₂—NH—CH₂—CH₂—CH₂—N(CH₃)₂ | —N(C(O)N(H)—CH₂—CH₂—F)— |
| Ib-b614 | —CH₂—NH—CH₂—CH₂—CH₂—N(CH₃)₂ | —N(C(O)N(H)—CH₂—CH₂—OCH₃)— |
| Ib-b615 | —CH₂—NH—CH₂—CH₂—CH₂—N(CH₃)₂ | —N(C(O)N(H)—CH₂—CH₂—CF₃)— |
| Ib-b616 | —CH₂—NH—CH₂—CH₂—CH₂—N(CH₃)₂ | —N(C(O)N(H)—CH₂—CH₂—CF₃)— |
| Ib-b617 | —CH₂—NH—CH₂—CH₂—CH₂—N(CH₃)₂ | —N(C(O)N(H)—CH₂—CF₃)— |
| Ib-b618 | —CH₂—NH—CH₂—CH₂—CH₂—N(CH₃)₂ | —N(C(O)N(H)—(CH₂)₃—OH)— |
| Ib-b619 | N-ethyl-N-methyl-(furan-2-ylmethyl)amine | —CH(OH)— |
| Ib-b620 | N-ethyl-N-methyl-(furan-2-ylmethyl)amine | —N(C(O)N(H)—CH₂—CH₂—OH)— |

| | | |
|---|---|---|
| Ib-b621 | [N-ethyl-N-methyl-aminomethyl furan] | —N(C(O)N(H)—CH₂—CH₂—F)— |
| Ib-b622 | [N-ethyl-N-methyl-aminomethyl furan] | —N(C(O)N(H)—CH₂—CH₂—OCH₃)— |
| Ib-b623 | [N-ethyl-N-methyl-aminomethyl furan] | —N(C(O)N(H)—CH₂—CH₂—CF₃)— |
| Ib-b624 | [N-ethyl-N-methyl-aminomethyl furan] | —N(C(O)N(H)—CH₂—CH₂—CF₃)— |
| Ib-b625 | [N-ethyl-N-methyl-aminomethyl furan] | —N(C(O)N(H)—CH₂—CF₃)— |
| Ib-b626 | [N-ethyl-N-methyl-aminomethyl furan] | —N(C(O)N(H)—(CH₂)₃—OH)— |
| Ib-b627 | [1-ethyl-3-hydroxypyrrolidine] | —CH(OH)— |
| Ib-b628 | [1-ethyl-3-hydroxypyrrolidine] | —N(C(O)N(H)—CH₂—CH₂—OH)— |
| Ib-b629 | [1-ethyl-3-hydroxypyrrolidine] | —N(C(O)N(H)—CH₂—CH₂—F)— |
| Ib-b630 | [1-ethyl-3-hydroxypyrrolidine] | —N(C(O)N(H)—CH₂—CH₂—OCH₃)— |
| Ib-b631 | [1-ethyl-3-hydroxypyrrolidine] | —N(C(O)N(H)—CH₂—CH₂—CF₃)— |
| Ib-b632 | [1-ethyl-3-hydroxypyrrolidine] | —N(C(O)N(H)—CH₂—CH₂—CF₃)— |
| Ib-b633 | [1-ethyl-3-hydroxypyrrolidine] | —N(C(O)N(H)—CH₂—CF₃)— |
| Ib-b634 | [1-ethyl-3-hydroxypyrrolidine] | —N(C(O)N(H)—(CH₂)₃—OH)— |

| | | |
|---|---|---|
| Ib-b635 | 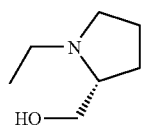 | —CH(OH)— |
| Ib-b636 | 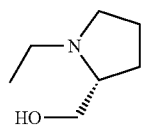 | —N(C(O)N(H)—CH$_2$—CH$_2$—OH)— |
| Ib-b637 | 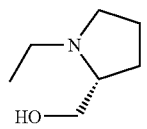 | —N(C(O)N(H)—CH$_2$—CH$_2$—F)— |
| Ib-b638 | 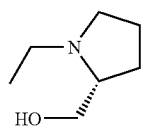 | —N(C(O)N(H)—CH$_2$—CH$_2$—OCH$_3$)— |
| Ib-b639 | 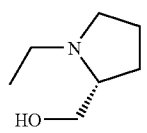 | —N(C(O)N(H)—CH$_2$—CH$_2$—CF$_3$)— |
| Ib-b640 | 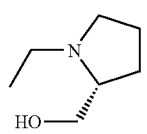 | —N(C(O)N(H)—CH$_2$—CH$_2$—CF$_3$)— |
| Ib-b641 | 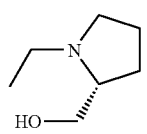 | —N(C(O)N(H)—CH$_2$—CF$_3$)— |
| Ib-b642 | 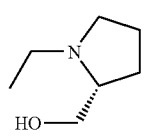 | —N(C(O)N(H)—(CH$_2$)$_3$—OH)— |
| Ib-b643 | 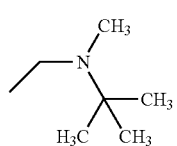 | —CH(OH)— |
| Ib-b644 | 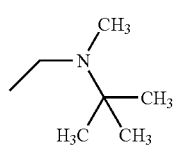 | —N(C(O)N(H)—CH$_2$—CH$_2$—OH)— |
| Ib-b645 | 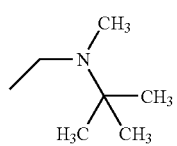 | —N(C(O)N(H)—CH$_2$—CH$_2$—F)— |

-continued
| | | |
|---|---|---|
| Ib-b646 | 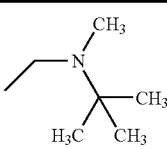 | —N(C(O)N(H)—CH₂—CH₂—OCH₃)— |
| Ib-b647 | 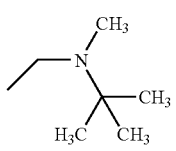 | —N(C(O)N(H)—CH₂—CH₂—CF₃)— |
| Ib-b648 | 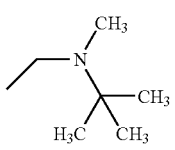 | —N(C(O)N(H)—CH₂—CH₂—CF₃)— |
| Ib-b649 | 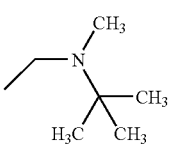 | —N(C(O)N(H)—CH₂—CF₃)— |
| Ib-b650 | 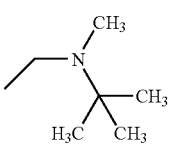 | —N(C(O)N(H)—(CH₂)₃—OH)— |
| Ib-b651 | 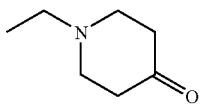 | —CH(OH)— |
| Ib-b652 | 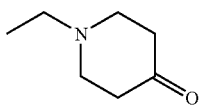 | —N(C(O)N(H)—CH₂—CH₂—OH)— |
| Ib-b653 | 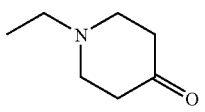 | —N(C(O)N(H)—CH₂—CH₂—F)— |
| Ib-b654 | 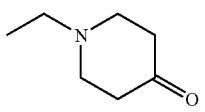 | —N(C(O)N(H)—CH₂—CH₂—OCH₃)— |
| Ib-b655 | 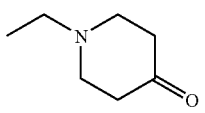 | —N(C(O)N(H)—CH₂—CH₂—CF₃)— |
| Ib-b656 | 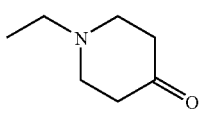 | —N(C(O)N(H)—CH₂—CH₂—CF₃)— |
| Ib-b657 | 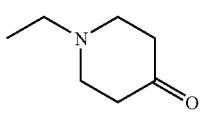 | —N(C(O)N(H)—CH₂—CF₃)— |

-continued

| | | |
|---|---|---|
| Ib-b658 | 1-ethylpiperidin-4-one | —N(C(O)N(H)—(CH$_2$)$_3$—OH)— |
| Ib-b659 | 1-ethyl-4-hydroxypiperidine | —CH(OH)— |
| Ib-b660 | 1-ethyl-4-hydroxypiperidine | —N(C(O)N(H)—CH$_2$—CH$_2$—OH)— |
| Ib-b661 | 1-ethyl-4-hydroxypiperidine | —N(C(O)N(H)—CH$_2$—CH$_2$—F)— |
| Ib-b662 | 1-ethyl-4-hydroxypiperidine | —N(C(O)N(H)—CH$_2$—CH$_2$—OCH$_3$)— |
| Ib-b663 | 1-ethyl-4-hydroxypiperidine | —N(C(O)N(H)—CH$_2$—CH$_2$—CF$_3$)— |
| Ib-b664 | 1-ethyl-4-hydroxypiperidine | —N(C(O)N(H)—CH$_2$—CH$_2$—CF$_3$)— |
| Ib-b665 | 1-ethyl-4-hydroxypiperidine | —N(C(O)N(H)—CH$_2$—CF$_3$)— |
| Ib-b666 | 1-ethyl-4-hydroxypiperidine | —N(C(O)N(H)—(CH$_2$)$_3$—OH)— |
| Ib-b667 | 1-ethyl-3-hydroxypiperidine | —CH(OH)— |
| Ib-b668 | 1-ethyl-3-hydroxypiperidine | —N(C(O)N(H)—CH$_2$—CH$_2$—OH)— |
| Ib-b669 | 1-ethyl-3-hydroxypiperidine | —N(C(O)N(H)—CH$_2$—CH$_2$—F)— |
| Ib-b670 | 1-ethyl-3-hydroxypiperidine | —N(C(O)N(H)—CH$_2$—CH$_2$—OCH$_3$)— |
| Ib-b671 | 1-ethyl-3-hydroxypiperidine | —N(C(O)N(H)—CH$_2$—CH$_2$—CF$_3$)— |
| Ib-b672 | 1-ethyl-3-hydroxypiperidine | —N(C(O)N(H)—CH$_2$—CH$_2$—CF$_3$)— |

-continued
| | | |
|---|---|---|
| Ib-b673 | 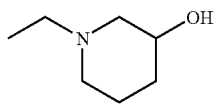 | —N(C(O)N(H)—CH₂—CF₃)— |
| Ib-b674 | 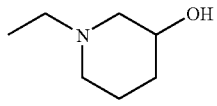 | —N(C(O)N(H)—(CH₂)₃—OH)— |
| Ib-b675 | 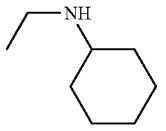 | —CH(OH)— |
| Ib-b676 | 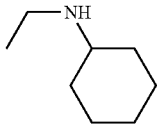 | —N(C(O)N(H)—CH₂—CH₂—OH)— |
| Ib-b677 | 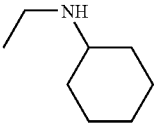 | —N(C(O)N(H)—CH₂—CH₂—F)— |
| Ib-b678 | 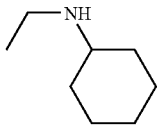 | —N(C(O)N(H)—CH₂—CH₂—OCH₃)— |
| Ib-b679 |  | —N(C(O)N(H)—CH₂—CH₂—CF₃)— |
| Ib-b680 |  | —N(C(O)N(H)—CH₂—CH₂—CF₃)— |
| Ib-b681 |  | —N(C(O)N(H)—CH₂—CF₃)— |
| Ib-b682 | 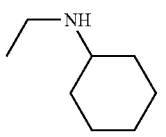 | —N(C(O)N(H)—(CH₂)₃—OH)— |
| Ib-b683 | 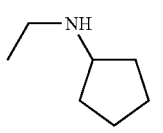 | —CH(OH)— |
| Ib-b684 | 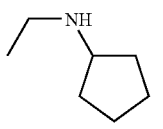 | —N(C(O)N(H)—CH₂—CH₂—OH)— |

-continued

| | | |
|---|---|---|
| Ib-b685 | Ethyl-NH-cyclopentyl | —N(C(O)N(H)—CH₂—CH₂—F)— |
| Ib-b686 | Ethyl-NH-cyclopentyl | —N(C(O)N(H)—CH₂—CH₂—OCH₃)— |
| Ib-b687 | Ethyl-NH-cyclopentyl | —N(C(O)N(H)—CH₂—CH₂—CF₃)— |
| Ib-b688 | Ethyl-NH-cyclopentyl | —N(C(O)N(H)—CH₂—CH₂—CF₃)— |
| Ib-b689 | Ethyl-NH-cyclopentyl | —N(C(O)N(H)—CH₂—CF₃)— |
| Ib-b690 | Ethyl-NH-cyclopentyl | —N(C(O)N(H)—(CH₂)₃—OH)— |
| Ib-b691 | Ethyl-NH-CH₂-cyclohexyl | —CH(OH)— |
| Ib-b692 | N(CH₂CH₃)(ethyl)-cyclohexyl | —N(C(O)N(H)—CH₂—CH₂—OH)— |
| Ib-b693 | N(CH₂CH₃)(ethyl)-cyclohexyl | —N(C(O)N(H)—CH₂—CH₂—F)— |
| Ib-b694 | N(CH₂CH₃)(ethyl)-cyclohexyl | —N(C(O)N(H)—CH₂—CH₂—OCH₃)— |
| Ib-b695 | N(CH₂CH₃)(ethyl)-cyclohexyl | —N(C(O)N(H)—CH₂—CH₂—CF₃)— |

| | | |
|---|---|---|
| Ib-b696 | 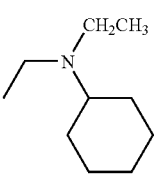 N-ethyl-N-cyclohexyl with CH₂CH₃ | —N(C(O)N(H)—CH₂—CH₂—CF₃)— |
| Ib-b697 | 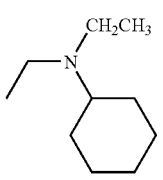 N-ethyl-N-cyclohexyl with CH₂CH₃ | —N(C(O)N(H)—CH₂—CF₃)— |
| Ib-b698 | 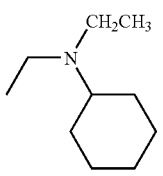 N-ethyl-N-cyclohexyl with CH₂CH₃ | —N(C(O)N(H)—(CH₂)₃—OH)— |
| Ib-b699 | 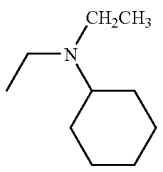 N-ethyl-N-cyclohexyl with CH₂CH₃ | —CH(OH)— |
| Ib-b700 | 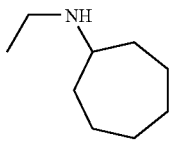 ethyl-NH-cycloheptyl | —N(C(O)N(H)—CH₂—CH₂—OH)— |
| Ib-b701 | 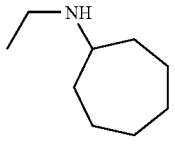 ethyl-NH-cycloheptyl | —N(C(O)N(H)—CH₂—CH₂—F)— |
| Ib-b702 | 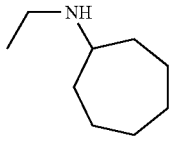 ethyl-NH-cycloheptyl | —N(C(O)N(H)—CH₂—CH₂—OCH₃)— |
| Ib-b703 | 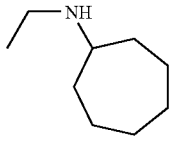 ethyl-NH-cycloheptyl | —N(C(O)N(H)—CH₂—CH₂—CF₃)— |
| Ib-b704 | 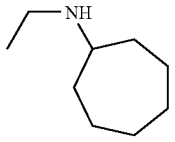 ethyl-NH-cycloheptyl | —N(C(O)N(H)—CH₂—CH₂—CF₃)— |
| Ib-b705 | 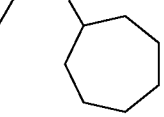 ethyl-NH-cycloheptyl | —N(C(O)N(H)—CH₂—CF₃)— |

| | | |
|---|---|---|
| Ib-b706 | 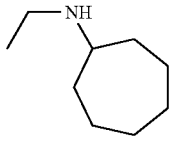 | —N(C(O)N(H)—(CH$_2$)$_3$—OH)— |
| Ib-b707 | 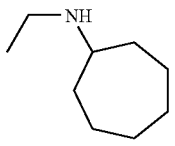 | —CH(OH)— |
| Ib-b708 | 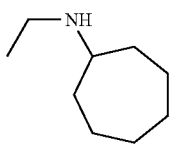 | —N(C(O)N(H)—CH$_2$—CH$_2$—OH)— |
| Ib-b709 | 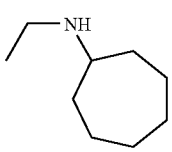 | —N(C(O)N(H)—CH$_2$—CH$_2$—F)— |
| Ib-b710 | 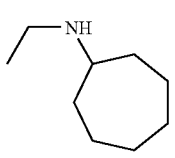 | —N(C(O)N(H)—CH$_2$—CH$_2$—OCH$_3$)— |
| Ib-b711 | 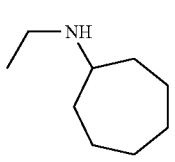 | —N(C(O)N(H)—CH$_2$—CH$_2$—CF$_3$)— |
| Ib-b712 | 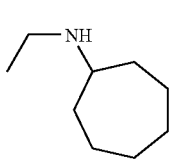 | —N(C(O)N(H)—CH$_2$—CH$_2$—CF$_3$)— |
| Ib-b713 | 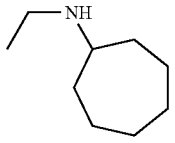 | —N(C(O)N(H)—CH$_2$—CF$_3$)— |
| Ib-b714 | 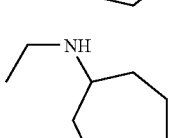 | —N(C(O)N(H)—(CH$_2$)$_3$—OH)— |
| Ib-b715 | 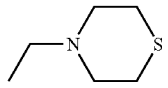 | —CH(OH)— |
| Ib-b716 | 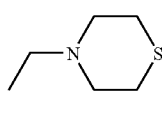 | —N(C(O)N(H)—CH$_2$—CH$_2$—OH)— |

-continued
| | | |
|---|---|---|
| Ib-b717 | 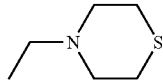 | —N(C(O)N(H)—CH$_2$—CH$_2$—F)— |
| Ib-b718 | 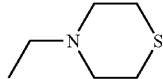 | —N(C(O)N(H)—CH$_2$—CH$_2$—OCH$_3$)— |
| Ib-b719 | 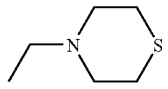 | —N(C(O)N(H)—CH$_2$—CH$_2$—CF$_3$)— |
| Ib-b720 | 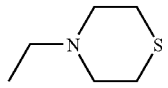 | —N(C(O)N(H)—CH$_2$—CH$_2$—CF$_3$)— |
| Ib-b721 | 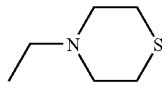 | —N(C(O)N(H)—CH$_2$—CF$_3$)— |
| Ib-b722 | 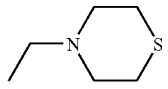 | —N(C(O)N(H)—(CH$_2$)$_3$—OH)— |
| Ib-b723 | 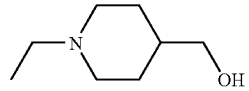 | —CH(OH)— |
| Ib-b724 | 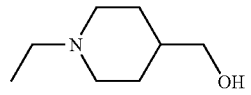 | —N(C(O)N(H)—CH$_2$—CH$_2$—OH)— |
| Ib-b725 | 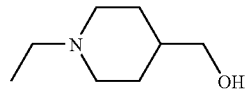 | —N(C(O)N(H)—CH$_2$—CH$_2$—F)— |
| Ib-b726 | 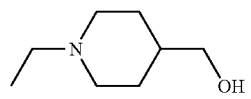 | —N(C(O)N(H)—CH$_2$—CH$_2$—OCH$_3$)— |
| Ib-b727 | 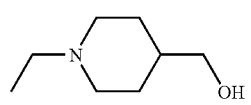 | —N(C(O)N(H)—CH$_2$—CH$_2$—CF$_3$)— |
| Ib-b728 | 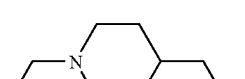 | —N(C(O)N(H)—CH$_2$—CH$_2$—CF$_3$)— |
| Ib-b729 | 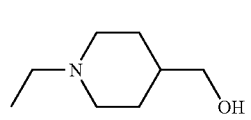 | —N(C(O)N(H)—CH$_2$—CF$_3$)— |
| Ib-b730 |  | —N(C(O)N(H)—(CH$_2$)$_3$—OH)— |
| Ib-b731 | 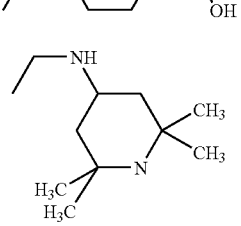 | —CH(OH)— |

-continued
| | | |
|---|---|---|
| Ib-b732 | 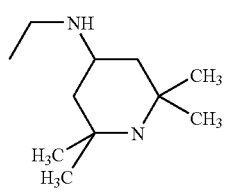 | —N(C(O)N(H)—CH$_2$—CH$_2$—OH)— |
| Ib-b733 | 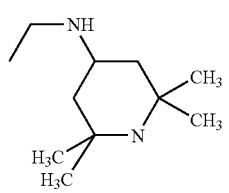 | —N(C(O)N(H)—CH$_2$—CH$_2$—F)— |
| Ib-b734 | 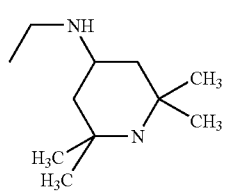 | —N(C(O)N(H)—CH$_2$—CH$_2$—OCH$_3$)— |
| Ib-b735 | 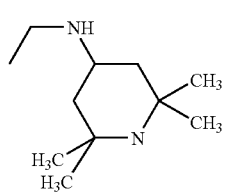 | —N(C(O)N(H)—CH$_2$—CH$_2$—CF$_3$)— |
| Ib-b736 | 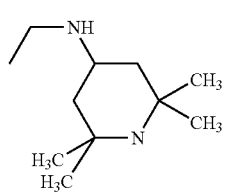 | —N(C(O)N(H)—CH$_2$—CH$_2$—CF$_3$)— |
| Ib-b737 | 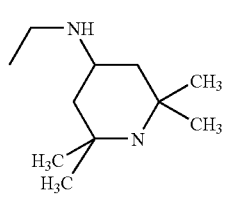 | —N(C(O)N(H)—CH$_2$—CF$_3$)— |
| Ib-b738 | 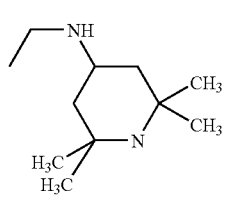 | —N(C(O)N(H)—(CH$_2$)$_3$—OH)— |
| Ib-b739 | 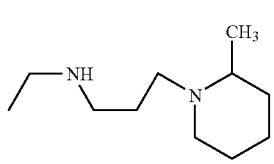 | —CH(OH)— |

| | | |
|---|---|---|
| Ib-b740 | 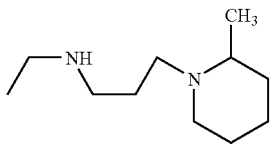 | —N(C(O)N(H)—CH₂—CH₂—OH)— |
| Ib-b741 | 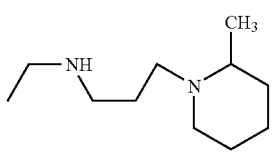 | —N(C(O)N(H)—CH₂—CH₂—F)— |
| Ib-b742 | 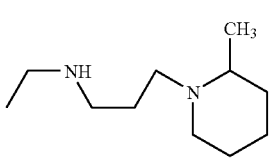 | —N(C(O)N(H)—CH₂—CH₂—OCH₃)— |
| Ib-b743 | 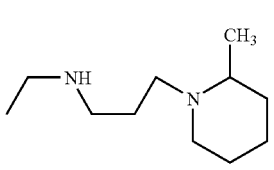 | —N(C(O)N(H)—CH₂—CH₂—CF₃)— |
| Ib-b744 | 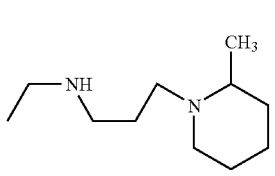 | —N(C(O)N(H)—CH₂—CH₂—CF₃)— |
| Ib-b745 | 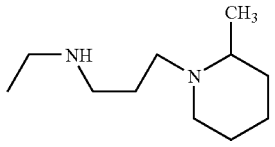 | —N(C(O)N(H)—CH₂—CF₃)— |
| Ib-b746 | 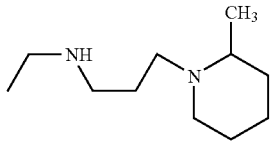 | —N(C(O)N(H)—(CH₂)₃—OH)— |
| Ib-b747 | 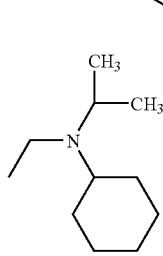 | —CH(OH)— |
| Ib-b748 | 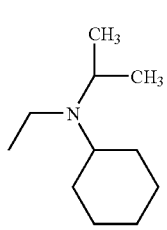 | —N(C(O)N(H)—CH₂—CH₂—OH)— |

| | | |
|---|---|---|
| Ib-b749 | 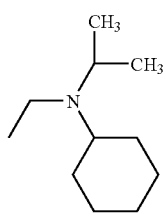 | —N(C(O)N(H)—CH₂—CH₂—F)— |
| Ib-b750 | 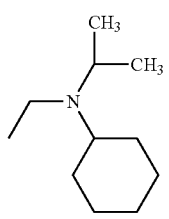 | —N(C(O)N(H)—CH₂—CH₂—OCH₃)— |
| Ib-b751 | 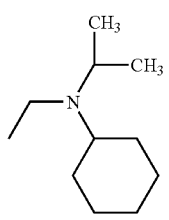 | —N(C(O)N(H)—CH₂—CH₂—CF₃)— |
| Ib-b752 | 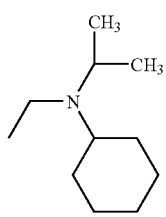 | —N(C(O)N(H)—CH₂—CH₂—CF₃)— |
| Ib-b753 | 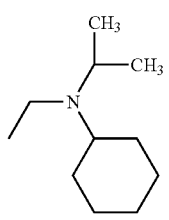 | —N(C(O)N(H)—CH₂—CF₃)— |
| Ib-b754 | 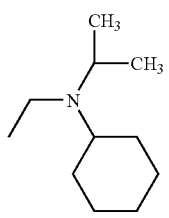 | —N(C(O)N(H)—(CH₂)₃—OH)— |
| Ib-b755 | 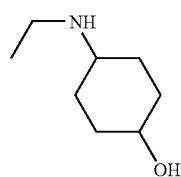 | —CH(OH)— |

-continued

| | | |
|---|---|---|
| Ib-b756 | 4-(ethylamino)cyclohexan-1-ol | —N(C(O)N(H)—CH$_2$—CH$_2$—OH)— |
| Ib-b757 | 4-(ethylamino)cyclohexan-1-ol | —N(C(O)N(H)—CH$_2$—CH$_2$—F)— |
| Ib-b758 | 4-(ethylamino)cyclohexan-1-ol | —N(C(O)N(H)—CH$_2$—CH$_2$—OCH$_3$)— |
| Ib-b759 | 4-(ethylamino)cyclohexan-1-ol | —N(C(O)N(H)—CH$_2$—CH$_2$—CF$_3$)— |
| Ib-b760 | 4-(ethylamino)cyclohexan-1-ol | —N(C(O)N(H)—CH$_2$—CH$_2$—CF$_3$)— |
| Ib-b761 | 4-(ethylamino)cyclohexan-1-ol | —N(C(O)N(H)—CH$_2$—CF$_3$)— |
| Ib-b762 | 4-(ethylamino)cyclohexan-1-ol | —N(C(O)N(H)—(CH$_2$)$_3$—OH)— |
| Ib-b763 | 2-(cyclohexyl(ethyl)amino)ethan-1-ol | —CH(OH)— |
| Ib-b764 | 2-(cyclohexyl(ethyl)amino)ethan-1-ol | —N(C(O)N(H)—CH$_2$—CH$_2$—OH)— |

-continued

| | | |
|---|---|---|
| Ib-b765 | N-ethyl-N-(cyclohexyl)-2-hydroxyethylamine | —N(C(O)N(H)—CH₂—CH₂—F)— |
| Ib-b766 | N-ethyl-N-(cyclohexyl)-2-hydroxyethylamine | —N(C(O)N(H)—CH₂—CH₂—OCH₃)— |
| Ib-b767 | N-ethyl-N-(cyclohexyl)-2-hydroxyethylamine | —N(C(O)N(H)—CH₂—CH₂—CF₃)— |
| Ib-b768 | N-ethyl-N-(cyclohexyl)-2-hydroxyethylamine | —N(C(O)N(H)—CH₂—CH₂—CF₃)— |
| Ib-b769 | N-ethyl-N-(cyclohexyl)-2-hydroxyethylamine | —N(C(O)N(H)—CH₂—CF₃)— |
| Ib-b770 | N-ethyl-N-(cyclohexyl)-2-hydroxyethylamine | —N(C(O)N(H)—(CH₂)₃—OH)— |
| Ib-b771 | 1-ethyl-4-methylpiperidine | —CH(OH)— |
| Ib-b772 | 1-ethyl-4-methylpiperidine | —N(C(O)N(H)—CH₂—CH₂—OH)— |
| Ib-b773 | 1-ethyl-4-methylpiperidine | —N(C(O)N(H)—CH₂—CH₂—F)— |
| Ib-b774 | 1-ethyl-4-methylpiperidine | —N(C(O)N(H)—CH₂—CH₂—OCH₃)— |
| Ib-b775 | 1-ethyl-4-methylpiperidine | —N(C(O)N(H)—CH₂—CH₂—CF₃)— |
| Ib-b776 | 1-ethyl-4-methylpiperidine | —N(C(O)N(H)—CH₂—CH₂—CF₃)— |

-continued

| | | |
|---|---|---|
| Ib-b777 | 1-ethyl-4-methylpiperidine | —N(C(O)N(H)—CH₂—CF₃— |
| Ib-b778 | 1-ethyl-4-methylpiperidine | —N(C(O)N(H)—(CH₂)₃—OH)— |
| Ib-b779 | —CH₂—NH—CH₃ | —CH(OH)— |
| Ib-b780 | —CH₂—NH—CH₃ | —N(C(O)N(H)—CH₂—CH₂—OH)— |
| Ib-b781 | —CH₂—NH—CH₃ | —N(C(O)N(H)—CH₂—CH₂—F)— |
| Ib-b782 | —CH₂—NH—CH₃ | —N(C(O)N(H)—CH₂—CH₂—OCH₃)— |
| Ib-b783 | —CH₂—NH—CH₃ | —N(C(O)N(H)—CH₂—CH₂—CF₃)— |
| Ib-b784 | —CH₂—NH—CH₃ | —N(C(O)N(H)—CH₂—CH₂—CF₃)— |
| Ib-b785 | —CH₂—NH—CH₃ | —N(C(O)N(H)—CH₂—CF₃)— |
| Ib-b786 | —CH₂—NH—CH₃ | —N(C(O)N(H)—(CH₂)₃—OH)— |
| Ib-b787 | —CH₂—NH—CH₂—CH₃ | —CH(OH)— |
| Ib-b788 | —CH₂—NH—CH₂—CH₃ | —N(C(O)N(H)—CH₂—CH₂—OH)— |
| Ib-b789 | —CH₂—NH—CH₂—CH₃ | —N(C(O)N(H)—CH₂—CH₂—F)— |
| Ib-b790 | —CH₂—NH—CH₂—CH₃ | —N(C(O)N(H)—CH₂—CH₂—OCH₃)— |
| Ib-b791 | —CH₂—NH—CH₂—CH₃ | —N(C(O)N(H)—CH₂—CH₂—CF₃)— |
| Ib-b792 | —CH₂—NH—CH₂—CH₃ | —N(C(O)N(H)—CH₂—CH₂—CF₃)— |
| Ib-b793 | —CH₂—NH—CH₂—CH₃ | —N(C(O)N(H)—CH₂—CF₃)— |
| Ib-b794 | —CH₂—NH—CH₂—CH₃ | —N(C(O)N(H)—(CH₂)₃—OH)— |
| Ib-b795 | —CH₂—NH—CH₂—CH₂—CH₃ | —CH(OH)— |
| Ib-b796 | —CH₂—NH—CH₂—CH₂—CH₃ | —N(C(O)N(H)—CH₂—CH₂—OH)— |
| Ib-b797 | —CH₂—NH—CH₂—CH₂—CH₃ | —N(C(O)N(H)—CH₂—CH₂—F)— |
| Ib-b798 | —CH₂—NH—CH₂—CH₂—CH₃ | —N(C(O)N(H)—CH₂—CH₂—OCH₃)— |
| Ib-b799 | —CH₂—NH—CH₂—CH₂—CH₃ | —N(C(O)N(H)—CH₂—CH₂—CF₃)— |
| Ib-b800 | —CH₂—NH—CH₂—CH₂—CH₃ | —N(C(O)N(H)—CH₂—CH₂—CF₃)— |
| Ib-b801 | —CH₂—NH—CH₂—CH₂—CH₃ | —N(C(O)N(H)—CH₂—CF₃)— |
| Ib-b802 | —CH₂—NH—CH₂—CH₂—CH₃ | —N(C(O)N(H)—(CH₂)₃—OH)— |
| Ib-b803 | N-ethyl-isopropylamine | —CH(OH)— |
| Ib-b804 | N-ethyl-isopropylamine | —N(C(O)N(H)—CH₂—CH₂—OH)— |
| Ib-b805 | N-ethyl-isopropylamine | —N(C(O)N(H)—CH₂—CH₂—F)— |
| Ib-b806 | N-ethyl-isopropylamine | —N(C(O)N(H)—CH₂—CH₂—OCH₃)— |
| Ib-b807 | N-ethyl-isopropylamine | —N(C(O)N(H)—CH₂—CH₂—CF₃)— |
| Ib-b808 | N-ethyl-isopropylamine | —N(C(O)N(H)—CH₂—CH₂—CF₃)— |
| Ib-b809 | N-ethyl-isopropylamine | —N(C(O)N(H)—CH₂—CF₃)— |

| | | |
|---|---|---|
| Ib-b810 | H3C-CH(CH3)-N(H)-Et | —N(C(O)N(H)—(CH2)3—OH)— |
| Ib-b811 | H3C-CH(CH3)-CH(NHEt)-C(O)OMe | —CH(OH)— |
| Ib-b812 | H3C-CH(CH3)-CH(NHEt)-C(O)OMe | —N(C(O)N(H)—CH2—CH2—OH)— |
| Ib-b813 | H3C-CH(CH3)-CH(NHEt)-C(O)OMe | —N(C(O)N(H)—CH2—CH2—F)— |
| Ib-b814 | H3C-CH(CH3)-CH(NHEt)-C(O)OMe | —N(C(O)N(H)—CH2—CH2—OCH3)— |
| Ib-b815 | H3C-CH(CH3)-CH(NHEt)-C(O)OMe | —N(C(O)N(H)—CH2—CH2—CF3)— |
| Ib-b816 | H3C-CH(CH3)-CH(NHEt)-C(O)OMe | —N(C(O)N(H)—CH2—CH2—CF3)— |
| Ib-b817 | H3C-CH(CH3)-CH(NHEt)-C(O)OMe | N(C(O)N(H)—CH2—CF3)— |
| Ib-b818 | H3C-CH(CH3)-CH(NHEt)-C(O)OMe | N(C(O)N(H)—(CH2)3—OH)— |

| | | |
|---|---|---|
| Ib-b819 | N(iPr)(iPr)(Et) | —CH(OH)— |
| Ib-b820 | N(iPr)(iPr)(Et) | —N(C(O)N(H)—CH$_2$—CH$_2$—OH)— |
| Ib-b821 | N(iPr)(iPr)(Et) | —N(C(O)N(H)—CH$_2$—CH$_2$—F)— |
| Ib-b822 | N(iPr)(iPr)(Et) | —N(C(O)N(H)—CH$_2$—CH$_2$—OCH$_3$)— |
| Ib-b823 | N(iPr)(iPr)(Et) | —N(C(O)N(H)—CH$_2$—CH$_2$—CF$_3$)— |
| Ib-b824 | N(iPr)(iPr)(Et) | —N(C(O)N(H)—CH$_2$—CH$_2$—CF$_3$)— |
| Ib-b825 | N(iPr)(iPr)(Et) | —N(C(O)N(H)—CH$_2$—CF$_3$)— |
| Ib-b826 | N(iPr)(iPr)(Et) | —N(C(O)N(H)—(CH$_2$)$_3$—OH)— |
| Ib-b827 | 2-(N-ethyl-N-methylaminoethyl)pyridine | —CH(OH)— |

| | | |
|---|---|---|
| Ib-b828 | Ethyl-N(CH₃)-CH₂CH₂-(2-pyridyl) | —N(C(O)N(H)—CH₂—CH₂—OH)— |
| Ib-b829 | Ethyl-N(CH₃)-CH₂CH₂-(2-pyridyl) | —N(C(O)N(H)—CH₂—CH₂—F)— |
| Ib-b830 | Ethyl-N(CH₃)-CH₂CH₂-(2-pyridyl) | —N(C(O)N(H)—CH₂—CH₂—OCH₃)— |
| Ib-b831 | Ethyl-N(CH₃)-CH₂CH₂-(2-pyridyl) | —N(C(O)N(H)—CH₂—CH₂—CF₃)— |
| Ib-b832 | Ethyl-N(CH₃)-CH₂CH₂-(2-pyridyl) | —N(C(O)N(H)—CH₂—CH₂—CF₃)— |
| Ib-b833 | Ethyl-N(CH₃)-CH₂CH₂-(2-pyridyl) | —N(C(O)N(H)—CH₂—CF₃)— |
| Ib-b834 | Ethyl-N(CH₃)-CH₂CH₂-(2-pyridyl) | —N(C(O)N(H)—(CH₂)₃—OH)— |
| Ib-b835 | (CH₃CH₂)(Ethyl)N-CH₂-(4-pyridyl) | —CH(OH)— |
| Ib-b836 | (CH₃CH₂)(Ethyl)N-CH₂-(4-pyridyl) | —N(C(O)N(H)—CH₂—CH₂—OH)— |
| Ib-b837 | (CH₃CH₂)(Ethyl)N-CH₂-(4-pyridyl) | —N(C(O)N(H)—CH₂—CH₂—F)— |
| Ib-b838 | (CH₃CH₂)(Ethyl)N-CH₂-(4-pyridyl) | —N(C(O)N(H)—CH₂—CH₂—OCH₃)— |
| Ib-b839 | (CH₃CH₂)(Ethyl)N-CH₂-(4-pyridyl) | —N(C(O)N(H)—CH₂—CH₂—CF₃)— |
| Ib-b840 | (CH₃CH₂)(Ethyl)N-CH₂-(4-pyridyl) | —N(C(O)N(H)—CH₂—CH₂—CF₃)— |

-continued

| | | |
|---|---|---|
| Ib-b841 | CH₃CH₂-N(CH₂CH₃)-CH₂-(4-pyridyl) | —N(C(O)N(H)—CH₂—CF₃)— |
| Ib-b842 | CH₃CH₂-N(CH₂CH₃)-CH₂-(4-pyridyl) | —N(C(O)N(H)—(CH₂)₃—OH)— |
| Ib-b843 | CH₃CH₂-N(CH₃)-CH₂CH₂OH | —CH(OH)— |
| Ib-b844 | CH₃CH₂-N(CH₃)-CH₂CH₂OH | —N(C(O)N(H)—CH₂—CH₂—OH)— |
| Ib-b845 | CH₃CH₂-N(CH₃)-CH₂CH₂OH | —N(C(O)N(H)—CH₂—CH₂—F)— |
| Ib-b846 | CH₃CH₂-N(CH₃)-CH₂CH₂OH | —N(C(O)N(H)—CH₂—CH₂—OCH₃)— |
| Ib-b847 | CH₃CH₂-N(CH₃)-CH₂CH₂OH | —N(C(O)N(H)—CH₂—CH₂—CF₃)— |
| Ib-b848 | CH₃CH₂-N(CH₃)-CH₂CH₂OH | —N(C(O)N(H)—CH₂—CH₂—CF₃)— |
| Ib-b849 | CH₃CH₂-N(CH₃)-CH₂CH₂OH | —N(C(O)N(H)—CH₂—CF₃)— |
| Ib-b850 | CH₃CH₂-N(CH₃)-CH₂CH₂OH | —N(C(O)N(H)—(CH₂)₃—OH)— |
| Ib-b851 | ethyl-piperidin-4-yl-piperidine | —CH(OH)— |
| Ib-b852 | ethyl-piperidin-4-yl-piperidine | —N(C(O)N(H)—CH₂—CH₂—OH)— |
| Ib-b853 | ethyl-piperidin-4-yl-piperidine | —N(C(O)N(H)—CH₂—CH₂—F)— |
| Ib-b854 | ethyl-piperidin-4-yl-piperidine | —N(C(O)N(H)—CH₂—CH₂—OCH₃)— |
| Ib-b855 | ethyl-piperidin-4-yl-piperidine | —N(C(O)N(H)—CH₂—CH₂—CF₃)— |
| Ib-b856 | ethyl-piperidin-4-yl-piperidine | —N(C(O)N(H)—CH₂—CH₂—CF₃)— |

-continued

| | | |
|---|---|---|
| Ib-b857 | [1-ethylpiperidin-4-yl-piperidine structure] | —N(C(O)N(H)—CH₂—CF₃— |
| Ib-b858 | [1-ethylpiperidin-4-yl-piperidine structure] | —N(C(O)N(H)—(CH₂)₃—OH— |
| Ib-b859 | [ethylaminoethyl-piperidine structure] | —CH(OH)— |
| Ib-b860 | [ethylaminoethyl-piperidine structure] | —N(C(O)N(H)—CH₂—CH₂—OH— |
| Ib-b861 | [ethylaminoethyl-piperidine structure] | —N(C(O)N(H)—CH₂—CH₂—F— |
| Ib-b862 | [ethylaminoethyl-piperidine structure] | —N(C(O)N(H)—CH₂—CH₂—OCH₃— |
| Ib-b863 | [ethylaminoethyl-piperidine structure] | —N(C(O)N(H)—CH₂—CH₂—CF₃— |
| Ib-b864 | [ethylaminoethyl-piperidine structure] | —N(C(O)N(H)—CH₂—CH₂—CF₃— |
| Ib-b865 | [ethylaminoethyl-piperidine structure] | —N(C(O)N(H)—CH₂—CF₃— |
| Ib-b866 | [ethylaminoethyl-piperidine structure] | —N(C(O)N(H)—(CH₂)₃—OH— |
| Ib-b867 | [N-ethyl-N-methyl-furfurylamine structure] | —CH(OH)— |
| Ib-b868 | [N-ethyl-N-methyl-furfurylamine structure] | —N(C(O)N(H)—CH₂—CH₂—OH— |
| Ib-b869 | [N-ethyl-N-methyl-furfurylamine structure] | —N(C(O)N(H)—CH₂—CH₂—F— |
| Ib-b870 | [N-ethyl-N-methyl-furfurylamine structure] | —N(C(O)N(H)—CH₂—CH₂—OCH₃— |
| Ib-b871 | [N-ethyl-N-methyl-furfurylamine structure] | —N(C(O)N(H)—CH₂—CH₂—CF₃— |

-continued

| ID | R | Linker |
|---|---|---|
| Ib-b872 | N-ethyl-N-methyl-(furan-2-ylmethyl)amine | —N(C(O)N(H)—CH₂—CH₂—CF₃)— |
| Ib-b873 | N-ethyl-N-methyl-(furan-2-ylmethyl)amine | —N(C(O)N(H)—CH₂—CF₃)— |
| Ib-b874 | N-ethyl-N-methyl-(furan-2-ylmethyl)amine | —N(C(O)N(H)—(CH₂)₃—OH)— |
| Ib-b875 | N-ethyl-2-(pyridin-2-yl)ethylamine | —CH(OH)— |
| Ib-b876 | N-ethyl-2-(pyridin-2-yl)ethylamine | —N(C(O)N(H)—CH₂—CH₂—OH)— |
| Ib-b877 | N-ethyl-2-(pyridin-2-yl)ethylamine | —N(C(O)N(H)—CH₂—CH₂—F)— |
| Ib-b878 | N-ethyl-2-(pyridin-2-yl)ethylamine | —N(C(O)N(H)—CH₂—CH₂—OCH₃)— |
| Ib-b879 | N-ethyl-2-(pyridin-2-yl)ethylamine | —N(C(O)N(H)—CH₂—CH₂—CF₃)— |
| Ib-b880 | N-ethyl-2-(pyridin-2-yl)ethylamine | —N(C(O)N(H)—CH₂—CH₂—CF₃)— |
| Ib-b881 | N-ethyl-2-(pyridin-2-yl)ethylamine | —N(C(O)N(H)—CH₂—CF₃)— |
| Ib-b882 | N-ethyl-2-(pyridin-2-yl)ethylamine | —N(C(O)N(H)—(CH₂)₃—OH)— |
| Ib-b883 | N-ethyl-3-(1-methylpyrrolidin-2-yl)propylamine | —CH(OH)— |
| Ib-b884 | N-ethyl-3-(1-methylpyrrolidin-2-yl)propylamine | —N(C(O)N(H)—CH₂—CH₂—OH)— |

| | | -continued |
|---|---|---|
| Ib-b885 | ethyl-NH-CH2CH2CH2-[2-(1-methylpyrrolidinyl)] | —N(C(O)N(H)—CH2—CH2—F)— |
| Ib-b886 | ethyl-NH-CH2CH2CH2-[2-(1-methylpyrrolidinyl)] | —N(C(O)N(H)—CH2—CH2—OCH3)— |
| Ib-b887 | ethyl-NH-CH2CH2CH2-[2-(1-methylpyrrolidinyl)] | —N(C(O)N(H)—CH2—CH2—CF3)— |
| Ib-b888 | ethyl-NH-CH2CH2CH2-[2-(1-methylpyrrolidinyl)] | —N(C(O)N(H)—CH2—CH2—CF3)— |
| Ib-b889 | ethyl-NH-CH2CH2CH2-[2-(1-methylpyrrolidinyl)] | —N(C(O)N(H)—CH2—CF3)— |
| Ib-b890 | ethyl-NH-CH2CH2CH2-[2-(1-methylpyrrolidinyl)] | —N(C(O)N(H)—(CH2)3—OH)— |
| Ib-b891 | 1-ethylpiperazine | —CH(OH)— |
| Ib-b892 | 1-ethylpiperazine | —N(C(O)N(H)—CH2—CH2—OH)— |
| Ib-b893 | 1-ethylpiperazine | —N(C(O)N(H)—CH2—CH2—F)— |
| Ib-b894 | 1-ethylpiperazine | —N(C(O)N(H)—CH2—CH2—OCH3)— |
| Ib-b895 | 1-ethylpiperazine | —N(C(O)N(H)—CH2—CH2—CF3)— |
| Ib-b896 | 1-ethylpiperazine | —N(C(O)N(H)—CH2—CH2—CF3)— |
| Ib-b897 | 1-ethylpiperazine | —N(C(O)N(H)—CH2—CF3)— |
| Ib-b898 | 1-ethylpiperazine | —N(C(O)N(H)—(CH2)3—OH)— |

-continued

| | | |
|---|---|---|
| Ib-b899 | 4-ethylpiperazin-1-yl-ethyl | —CH(OH)— |
| Ib-b900 | 4-ethylpiperazin-1-yl-ethyl | —N(C(O)N(H)—CH$_2$—CH$_2$—OH)— |
| Ib-b901 | 4-ethylpiperazin-1-yl-ethyl | —N(C(O)N(H)—CH$_2$—CH$_2$—F)— |
| Ib-b902 | 4-ethylpiperazin-1-yl-ethyl | —N(C(O)N(H)—CH$_2$—CH$_2$—OCH$_3$)— |
| Ib-b903 | 4-ethylpiperazin-1-yl-ethyl | —N(C(O)N(H)—CH$_2$—CH$_2$—CF$_3$)— |
| Ib-b904 | 4-ethylpiperazin-1-yl-ethyl | —N(C(O)N(H)—CH$_2$—CH$_2$—CF$_3$)— |
| Ib-b905 | 4-ethylpiperazin-1-yl-ethyl | —N(C(O)N(H)—CH$_2$—CF$_3$)— |
| Ib-b906 | 4-ethylpiperazin-1-yl-ethyl | —N(C(O)N(H)—(CH$_2$)$_3$—OH)— |
| Ib-b907 | cyclopropylmethylamino-ethyl | —CH(OH)— |
| Ib-b908 | cyclopropylmethylamino-ethyl | —N(C(O)N(H)—CH$_2$—CH$_2$—OH)— |
| Ib-b909 | cyclopropylmethylamino-ethyl | —N(C(O)N(H)—CH$_2$—CH$_2$—F)— |
| Ib-b910 | cyclopropylmethylamino-ethyl | —N(C(O)N(H)—CH$_2$—CH$_2$—OCH$_3$)— |
| Ib-b911 | cyclopropylmethylamino-ethyl | —N(C(O)N(H)—CH$_2$—CH$_2$—CF$_3$)— |
| Ib-b912 | cyclopropylmethylamino-ethyl | —N(C(O)N(H)—CH$_2$—CH$_2$—CF$_3$)— |
| Ib-b913 | cyclopropylmethylamino-ethyl | —N(C(O)N(H)—CH$_2$—CF$_3$)— |

-continued

| ID | R | Linker |
|---|---|---|
| Ib-b914 | ethyl-NH-cyclopropyl | —N(C(O)N(H)—(CH₂)₃—OH)— |
| Ib-b915 | 1-ethyl-4-(2-hydroxyethyl)piperazine | —CH(OH)— |
| Ib-b916 | 1-ethyl-4-(2-hydroxyethyl)piperazine | —N(C(O)N(H)—CH₂—CH₂—OH)— |
| Ib-b917 | 1-ethyl-4-(2-hydroxyethyl)piperazine | —N(C(O)N(H)—CH₂—CH₂—F)— |
| Ib-b918 | 1-ethyl-4-(2-hydroxyethyl)piperazine | —N(C(O)N(H)—CH₂—CH₂—OCH₃)— |
| Ib-b919 | 1-ethyl-4-(2-hydroxyethyl)piperazine | —N(C(O)N(H)—CH₂—CH₂—CF₃)— |
| Ib-b920 | 1-ethyl-4-(2-hydroxyethyl)piperazine | —N(C(O)N(H)—CH₂—CH₂—CF₃)— |
| Ib-b921 | 1-ethyl-4-(2-hydroxyethyl)piperazine | —N(C(O)N(H)—CH₂—CF₃)— |
| Ib-b922 | 1-ethyl-4-(2-hydroxyethyl)piperazine | —N(C(O)N(H)—(CH₂)₃—OH)— |
| Ib-b923 | 1-ethyl-4-ethylpiperazine | —CH(OH)— |
| Ib-b924 | 1-ethyl-4-ethylpiperazine | —N(C(O)N(H)—CH₂—CH₂—OH)— |
| Ib-b925 | 1-ethyl-4-ethylpiperazine | —N(C(O)N(H)—CH₂—CH₂—F)— |
| Ib-b926 | 1-ethyl-4-ethylpiperazine | —N(C(O)N(H)—CH₂—CH₂—OCH₃)— |
| Ib-b927 | 1-ethyl-4-ethylpiperazine | —N(C(O)N(H)—CH₂—CH₂—CF₃)— |
| Ib-b928 | 1-ethyl-4-ethylpiperazine | —N(C(O)N(H)—CH₂—CH₂—CF₃)— |
| Ib-b929 | 1-ethyl-4-ethylpiperazine | —N(C(O)N(H)—CH₂—CF₃)— |

-continued
| | | |
|---|---|---|
| Ib-b930 | 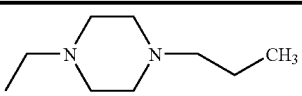 | —N(C(O)N(H)—(CH₂)₃—OH)— |
| Ib-b931 | 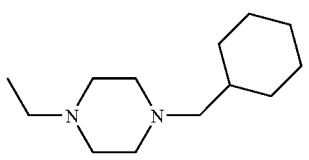 | —CH(OH)— |
| Ib-b932 | 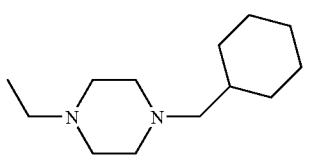 | —N(C(O)N(H)—CH₂—CH₂—OH)— |
| Ib-b933 | 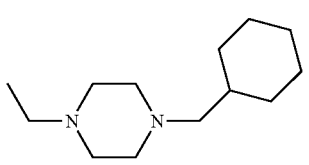 | —N(C(O)N(H)—CH₂—CH₂—F)— |
| Ib-b934 | 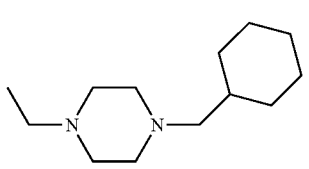 | —N(C(O)N(H)—CH₂—CH₂—OCH₃)— |
| Ib-b935 | 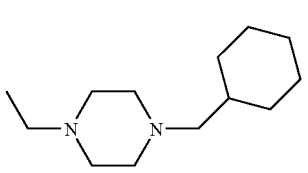 | —N(C(O)N(H)—CH₂—CH₂—CF₃)— |
| Ib-b936 | 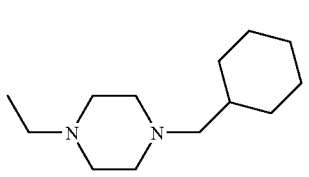 | —N(C(O)N(H)—CH₂—CH₂—CF₃)— |
| Ib-b937 | 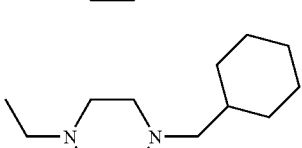 | —N(C(O)N(H)—CH₂—CF₃)— |
| Ib-b938 | 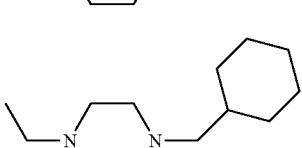 | —N(C(O)N(H)—(CH₂)₃—OH)— |
| Ib-b939 | 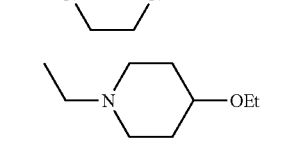 | —CH(OH)— |
| Ib-b940 | 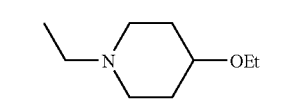 | —N(C(O)N(H)—CH₂—CH₂—OH)— |

-continued

| | | |
|---|---|---|
| Ib-b941 | 1-ethyl-4-ethoxy-piperidine | —N(C(O)N(H)—CH₂—CH₂—F)— |
| Ib-b942 | 1-ethyl-4-ethoxy-piperidine | —N(C(O)N(H)—CH₂—CH₂—OCH₃)— |
| Ib-b943 | 1-ethyl-4-ethoxy-piperidine | —N(C(O)N(H)—CH₂—CH₂—CF₃)— |
| Ib-b944 | 1-ethyl-4-ethoxy-piperidine | —N(C(O)N(H)—CH₂—CH₂—CF₃)— |
| Ib-b945 | 1-ethyl-4-ethoxy-piperidine | —N(C(O)N(H)—CH₂—CF₃)— |
| Ib-b946 | 1-ethyl-4-ethoxy-piperidine | —N(C(O)N(H)—(CH₂)₃—OH)— |
| Ib-b947 | 1-ethyl-3-hydroxy-piperidine | —CH(OH)— |
| Ib-b948 | 1-ethyl-3-hydroxy-piperidine | —N(C(O)N(H)—CH₂—CH₂—OH)— |
| Ib-b949 | 1-ethyl-3-hydroxy-piperidine | —N(C(O)N(H)—CH₂—CH₂—F)— |
| Ib-b950 | 1-ethyl-3-hydroxy-piperidine | —N(C(O)N(H)—CH₂—CH₂—OCH₃)— |
| Ib-b951 | 1-ethyl-3-hydroxy-piperidine | —N(C(O)N(H)—CH₂—CH₂—CF₃)— |
| Ib-b952 | 1-ethyl-3-hydroxy-piperidine | —N(C(O)N(H)—CH₂—CH₂—CF₃)— |
| Ib-b953 | 1-ethyl-3-hydroxy-piperidine | —N(C(O)N(H)—CH₂—CF₃)— |

-continued

| ID | Group 1 | Group 2 |
|---|---|---|
| Ib-b954 | 1-ethyl-3-hydroxypiperidine | —N(C(O)N(H)—(CH$_2$)$_3$—OH)— |
| Ib-b955 | ethyl 2-(4-ethylpiperazin-1-yl)acetate | —CH(OH)— |
| Ib-b956 | ethyl 2-(4-ethylpiperazin-1-yl)acetate | —N(C(O)N(H)—CH$_2$—CH$_2$—OH)— |
| Ib-b957 | ethyl 2-(4-ethylpiperazin-1-yl)acetate | —N(C(O)N(H)—CH$_2$—CH$_2$—F)— |
| Ib-b958 | ethyl 2-(4-ethylpiperazin-1-yl)acetate | —N(C(O)N(H)—CH$_2$—CH$_2$—OCH$_3$)— |
| Ib-b959 | ethyl 2-(4-ethylpiperazin-1-yl)acetate | —N(C(O)N(H)—CH$_2$—CH$_2$—CF$_3$)— |
| Ib-b960 | ethyl 2-(4-ethylpiperazin-1-yl)acetate | —N(C(O)N(H)—CH$_2$—CH$_2$—CF$_3$)— |
| Ib-b961 | ethyl 2-(4-ethylpiperazin-1-yl)acetate | —N(C(O)N(H)—CH$_2$—CF$_3$)— |
| Ib-b962 | ethyl 2-(4-ethylpiperazin-1-yl)acetate | —N(C(O)N(H)—(CH$_2$)$_3$—OH)— |
| Ib-b963 | —CH$_2$—N(CH$_2$CH$_3$)(CH$_3$) | —CH(OH)— |
| Ib-b964 | —CH$_2$—N(CH$_2$CH$_3$)(CH$_3$) | —N(C(O)N(H)—CH$_2$—CH$_2$—OH)— |
| Ib-b965 | —CH$_2$—N(CH$_2$CH$_3$)(CH$_3$) | —N(C(O)N(H)—CH$_2$—CH$_2$—F)— |
| Ib-b966 | —CH$_2$—N(CH$_2$CH$_3$)(CH$_3$) | —N(C(O)N(H)—CH$_2$—CH$_2$—OCH$_3$)— |
| Ib-b967 | —CH$_2$—N(CH$_2$CH$_3$)(CH$_3$) | —N(C(O)N(H)—CH$_2$—CH$_2$—CF$_3$)— |
| Ib-b968 | —CH$_2$—N(CH$_2$CH$_3$)(CH$_3$) | —N(C(O)N(H)—CH$_2$—CH$_2$—CF$_3$)— |
| Ib-b969 | —CH$_2$—N(CH$_2$CH$_3$)(CH$_3$) | —N(C(O)N(H)—CH$_2$—CF$_3$)— |
| Ib-b970 | —CH$_2$—N(CH$_2$CH$_3$)(CH$_3$) | —N(C(O)N(H)—(CH$_2$)$_3$—OH)— |
| Ib-b971 | —CH$_2$—N(CH$_2$CH$_2$CH$_3$)(CH$_3$) | —CH(OH)— |
| Ib-b972 | —CH$_2$—N(CH$_2$CH$_2$CH$_3$)(CH$_3$) | —N(C(O)N(H)—CH$_2$—CH$_2$—OH)— |
| Ib-b973 | —CH$_2$—N(CH$_2$CH$_2$CH$_3$)(CH$_3$) | —N(C(O)N(H)—CH$_2$—CH$_2$—F)— |
| Ib-b974 | —CH$_2$—N(CH$_2$CH$_2$CH$_3$)(CH$_3$) | —N(C(O)N(H)—CH$_2$—CH$_2$—OCH$_3$)— |
| Ib-b975 | —CH$_2$—N(CH$_2$CH$_2$CH$_3$)(CH$_3$) | —N(C(O)N(H)—CH$_2$—CH$_2$—CF$_3$)— |
| Ib-b976 | —CH$_2$—N(CH$_2$CH$_2$CH$_3$)(CH$_3$) | —N(C(O)N(H)—CH$_2$—CH$_2$—CF$_3$)— |
| Ib-b977 | —CH$_2$—N(CH$_2$CH$_2$CH$_3$)(CH$_3$) | —N(C(O)N(H)—CH$_2$—CF$_3$)— |
| Ib-b978 | —CH$_2$—N(CH$_2$CH$_2$CH$_3$)(CH$_3$) | —N(C(O)N(H)—(CH$_2$)$_3$—OH)— |
| Ib-b979 | —CH$_2$—N(CH$_2$CH$_2$CH$_2$CH$_3$)(CH$_3$) | —CH(OH)— |
| Ib-b980 | —CH$_2$—N(CH$_2$CH$_2$CH$_2$CH$_3$)(CH$_3$) | —N(C(O)N(H)—CH$_2$—CH$_2$—OH)— |
| Ib-b981 | —CH$_2$—N(CH$_2$CH$_2$CH$_2$CH$_3$)(CH$_3$) | —N(C(O)N(H)—CH$_2$—CH$_2$—F)— |
| Ib-b982 | —CH$_2$—N(CH$_2$CH$_2$CH$_2$CH$_3$)(CH$_3$) | —N(C(O)N(H)—CH$_2$—CH$_2$—OCH$_3$)— |
| Ib-b983 | —CH$_2$—N(CH$_2$CH$_2$CH$_2$CH$_3$)(CH$_3$) | —N(C(O)N(H)—CH$_2$—CH$_2$—CF$_3$)— |
| Ib-b984 | —CH$_2$—N(CH$_2$CH$_2$CH$_2$CH$_3$)(CH$_3$) | —N(C(O)N(H)—CH$_2$—CH$_2$—CF$_3$)— |
| Ib-b985 | —CH$_2$—N(CH$_2$CH$_2$CH$_2$CH$_3$)(CH$_3$) | —N(C(O)N(H)—CH$_2$—CF$_3$)— |
| Ib-b986 | —CH$_2$—N(CH$_2$CH$_2$CH$_2$CH$_3$)(CH$_3$) | —N(C(O)N(H)—(CH$_2$)$_3$—OH)— |
| Ib-b987 | —CH$_2$—NH—CH$_2$CH$_2$CH$_3$ | —CH(OH)— |
| Ib-b988 | —CH$_2$—NH—CH$_2$CH$_2$CH$_3$ | —N(C(O)N(H)—CH$_2$—CH$_2$—OH)— |
| Ib-b989 | —CH$_2$—NH—CH$_2$CH$_2$CH$_3$ | —N(C(O)N(H)—CH$_2$—CH$_2$—F)— |
| Ib-b990 | —CH$_2$—NH—CH$_2$CH$_2$CH$_3$ | —N(C(O)N(H)—CH$_2$—CH$_2$—OCH$_3$)— |
| Ib-b991 | —CH$_2$—NH—CH$_2$CH$_2$CH$_3$ | —N(C(O)N(H)—CH$_2$—CH$_2$—CF$_3$)— |
| Ib-b992 | —CH$_2$—NH—CH$_2$CH$_2$CH$_3$ | —N(C(O)N(H)—CH$_2$—CH$_2$—CF$_3$)— |
| Ib-b993 | —CH$_2$—NH—CH$_2$CH$_2$CH$_3$ | —N(C(O)N(H)—CH$_2$—CF$_3$)— |
| Ib-b994 | —CH$_2$—NH—CH$_2$CH$_2$CH$_3$ | —N(C(O)N(H)—(CH$_2$)$_3$—OH)— |

| | | |
|---|---|---|
| Ib-b995 | —CH₂—NH—CH₂CH₂—O—CH₃ | —CH(OH)— |
| Ib-b996 | —CH₂—NH—CH₂CH₂—O—CH₃ | —N(C(O)N(H)—CH₂—CH₂—OH)— |
| Ib-b997 | —CH₂—NH—CH₂CH₂—O—CH₃ | —N(C(O)N(H)—CH₂—CH₂—F)— |
| Ib-b998 | —CH₂—NH—CH₂CH₂—O—CH₃ | —N(C(O)N(H)—CH₂—CH₂—OCH₃)— |
| Ib-b999 | —CH₂—NH—CH₂CH₂—O—CH₃ | —N(C(O)N(H)—CH₂—CH₂—CF₃)— |
| Ib-b1000 | —CH₂—NH—CH₂CH₂—O—CH₃ | —N(C(O)N(H)—CH₂—CH₂—CF₃)— |
| Ib-b1001 | —CH₂—NH—CH₂CH₂—O—CH₃ | —N(C(O)N(H)—CH₂—CF₃)— |
| Ib-b1002 | —CH₂—NH—CH₂CH₂—O—CH₃ | —N(C(O)N(H)—(CH₂)₃—OH)— |
| Ib-b1003 | Et-piperazine-CH₂CH₂-OMe | —CH(OH)— |
| Ib-b1004 | Et-piperazine-CH₂CH₂-OMe | —N(C(O)N(H)—CH₂—CH₂—OH)— |
| Ib-b1005 | Et-piperazine-CH₂CH₂-OMe | —N(C(O)N(H)—CH₂—CH₂—F)— |
| Ib-b1006 | Et-piperazine-CH₂CH₂-OMe | —N(C(O)N(H)—CH₂—CH₂—OCH₃)— |
| Ib-b1007 | Et-piperazine-CH₂CH₂-OMe | —N(C(O)N(H)—CH₂—CH₂—CF₃)— |
| Ib-b1008 | Et-piperazine-CH₂CH₂-OMe | —N(C(O)N(H)—CH₂—CH₂—CF₃)— |
| Ib-b1009 | Et-piperazine-CH₂CH₂-OMe | —N(C(O)N(H)—CH₂—CF₃)— |
| Ib-b1010 | Et-piperazine-CH₂CH₂-OMe | —N(C(O)N(H)—(CH₂)₃—OH)— |
| Ib-b1011 | Et-piperidine-4-OPO(OH)₂ | —CH(OH)— |
| Ib-b1012 | Et-piperidine-4-OPO(OH)₂ | —N(C(O)N(H)—CH₂—CH₂—OH)— |
| Ib-b1013 | Et-piperidine-4-OPO(OH)₂ | —N(C(O)N(H)—CH₂—CH₂—F)— |
| Ib-b1014 | Et-piperidine-4-OPO(OH)₂ | —N(C(O)N(H)—CH₂—CH₂—OCH₃)— |
| Ib-b1015 | Et-piperidine-4-OPO(OH)₂ | —N(C(O)N(H)—CH₂—CH₂—CF₃)— |

| | | |
|---|---|---|
| Ib-b1016 | N-ethylpiperidin-4-yl-OPO(OH)₂ | —N(C(O)N(H)—CH₂—CH₂—CF₃)— |
| Ib-b1017 | N-ethylpiperidin-4-yl-OPO(OH)₂ | —N(C(O)N(H)—CH₂—CF₃)— |
| Ib-b1018 | N-ethylpiperidin-4-yl-OPO(OH)₂ | —N(C(O)N(H)—(CH₂)₃—OH)— |
| Ib-b1019 | N-ethylpiperidin-4-yl-CH₂-OPO(OH)₂ | —CH(OH)— |
| Ib-b1020 | N-ethylpiperidin-4-yl-CH₂-OPO(OH)₂ | —N(C(O)N(H)—CH₂—CH₂—OH)— |
| Ib-b1021 | N-ethylpiperidin-4-yl-CH₂-OPO(OH)₂ | —N(C(O)N(H)—CH₂—CH₂—F)— |
| Ib-b1022 | N-ethylpiperidin-4-yl-CH₂-OPO(OH)₂ | —N(C(O)N(H)—CH₂—CH₂—OCH₃)— |
| Ib-b1023 | N-ethylpiperidin-4-yl-CH₂-OPO(OH)₂ | —N(C(O)N(H)—CH₂—CH₂—CF₃)— |
| Ib-b1024 | N-ethylpiperidin-4-yl-CH₂-OPO(OH)₂ | —N(C(O)N(H)—CH₂—CH₂—CF₃)— |
| Ib-b1025 | N-ethylpiperidin-4-yl-CH₂-OPO(OH)₂ | —N(C(O)N(H)—CH₂—CF₃)— |
| Ib-b1026 | N-ethylpiperidin-4-yl-CH₂-OPO(OH)₂ | —N(C(O)N(H)—(CH₂)₃—OH)— |
| Ib-b1027 | N-ethylpiperidin-3-yl-OPO(OH)₂ | —CH(OH)— |
| Ib-b1028 | N-ethylpiperidin-3-yl-OPO(OH)₂ | —N(C(O)N(H)—CH₂—CH₂—OH)— |
| Ib-b1029 | N-ethylpiperidin-3-yl-OPO(OH)₂ | —N(C(O)N(H)—CH₂—CH₂—F)— |

| | | |
|---|---|---|
| Ib-b1030 | 1-ethylpiperidin-3-yl OPO(OH)₂ | —N(C(O)N(H)—CH₂—CH₂—OCH₃)— |
| Ib-b1031 | 1-ethylpiperidin-3-yl OPO(OH)₂ | —N(C(O)N(H)—CH₂—CH₂—CF₃)— |
| Ib-b1032 | 1-ethylpiperidin-3-yl OPO(OH)₂ | —N(C(O)N(H)—CH₂—CH₂—CF₃)— |
| Ib-b1033 | 1-ethylpiperidin-3-yl OPO(OH)₂ | —N(C(O)N(H)—CH₂—CF₃)— |
| Ib-b1034 | 1-ethylpiperidin-3-yl OPO(OH)₂ | —N(C(O)N(H)—(CH₂)₃—OH)— |
| Ib-b1035 | N(Et)(CH₃)CH₂CH₂OPO(OH)₂ | —CH(OH)— |
| Ib-b1036 | N(Et)(CH₃)CH₂CH₂OPO(OH)₂ | —N(C(O)N(H)—CH₂—CH₂—OH)— |
| Ib-b1037 | N(Et)(CH₃)CH₂CH₂OPO(OH)₂ | —N(C(O)N(H)—CH₂—CH₂—F)— |
| Ib-b1038 | N(Et)(CH₃)CH₂CH₂OPO(OH)₂ | —N(C(O)N(H)—CH₂—CH₂—OCH₃)— |
| Ib-b1039 | N(Et)(CH₃)CH₂CH₂OPO(OH)₂ | —N(C(O)N(H)—CH₂—CH₂—CF₃)— |
| Ib-b1040 | N(Et)(CH₃)CH₂CH₂OPO(OH)₂ | —N(C(O)N(H)—CH₂—CH₂—CF₃)— |

| | | |
|---|---|---|
| Ib-b1041 | 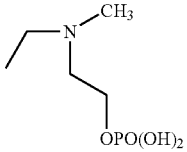 | —N(C(O)N(H)—CH$_2$—CF$_3$)— |
| Ib-b1042 | 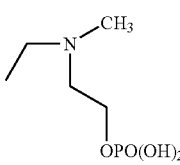 | —N(C(O)N(H)—(CH$_2$)$_3$—OH)— |
| Ib-b1043 | 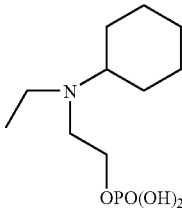 | —CH(OH)— |
| Ib-b1044 | 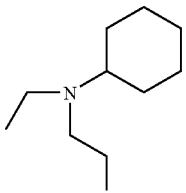 | —N(C(O)N(H)—CH$_2$—CH$_2$—OH)— |
| Ib-b1045 | 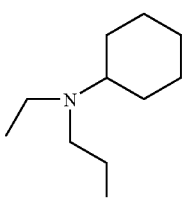 | —N(C(O)N(H)—CH$_2$—CH$_2$—F)— |
| Ib-b1046 | 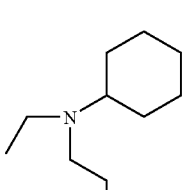 | —N(C(O)N(H)—CH$_2$—CH$_2$—OCH$_3$)— |
| Ib-b1047 | 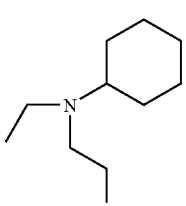 | —N(C(O)N(H)—CH$_2$—CH$_2$—CF$_3$)— |

-continued
| | | |
|---|---|---|
| Ib-b1048 | 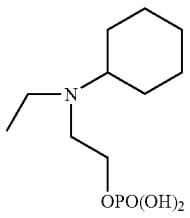 | —N(C(O)N(H)—CH₂—CH₂—CF₃)— |
| Ib-b1049 | 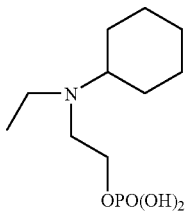 | —N(C(O)N(H)—CH₂—CF₃)— |
| Ib-b1050 | 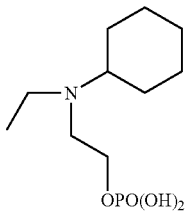 | —N(C(O)N(H)—(CH₂)₃—OH)— |
| Ib-b1051 | 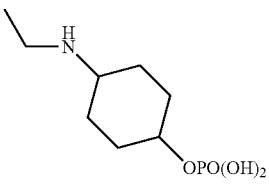 | —CH(OH)— |
| Ib-b1052 | 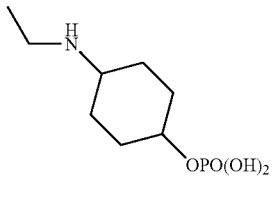 | —N(C(O)N(H)—CH₂—CH₂—OH)— |
| Ib-b1053 | 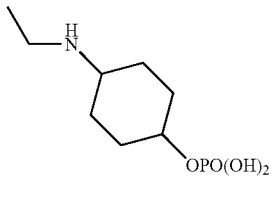 | —N(C(O)N(H)—CH₂—CH₂—F)— |
| Ib-b1054 | 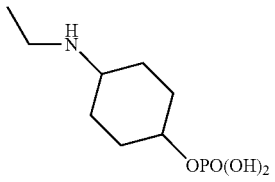 | —N(C(O)N(H)—CH₂—CH₂—OCH₃)— |
| Ib-b1055 | 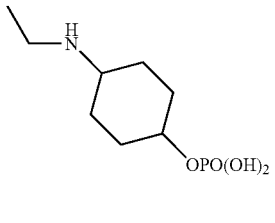 | —N(C(O)N(H)—CH₂—CH₂—CF₃)— |

-continued

| | | |
|---|---|---|
| Ib-b1056 | 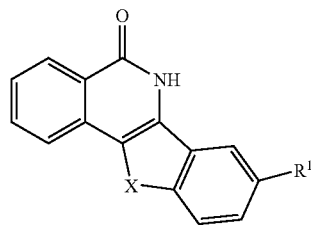 | —N(C(O)N(H)—CH$_2$—CH$_2$—CF$_3$)— |
| Ib-b1057 | | —N(C(O)N(H)—CH$_2$—CF$_3$)— |
| Ib-b1058 | | —N(C(O)N(H)—(CH$_2$)$_3$—OH)— | and pharmaceutically acceptable salts thereof.

5.4 The Indenoisoquinolinone Analogs of Formula (Ic)

The present invention provides Indenoisoquinolinone Analogs according to Formula (Ic), below:

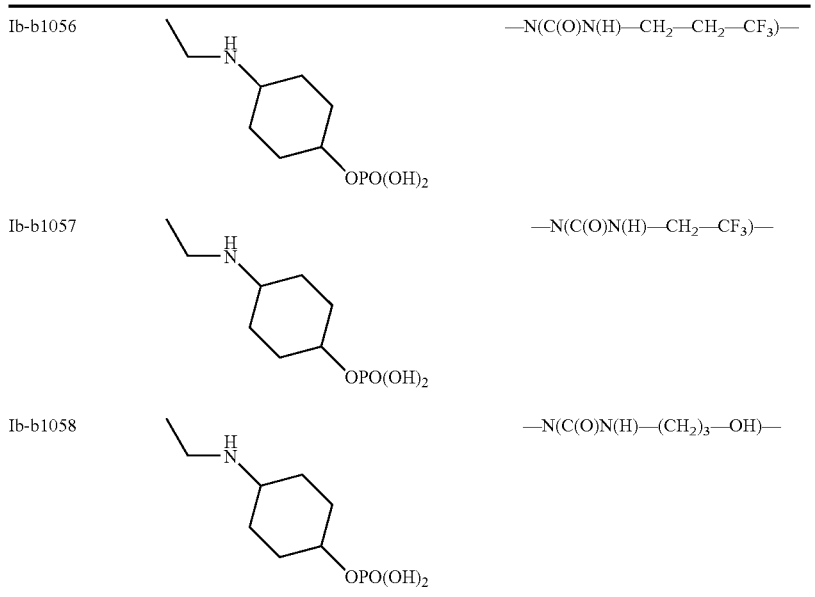

(Ic)

and pharmaceutically acceptable salts thereof,
wherein X and R$^1$ are as defined above for the Indenoisoquinolinone Analogs of Formula (Ic).

In one embodiment, X is —N(CH$_3$)—. In another embodiment, X is —N(CH$_2$CH$_3$)—. In another embodiment, X is —N(CH$_2$CH$_2$CH$_3$)—. In another embodiment, X is —N(CH$_2$ CH$_2$CH$_2$CH$_3$)—. In another embodiment, X is —N(C(H)(CH$_3$)(CH$_2$CH$_3$))—. In another embodiment, X is —N(C(H)(CH$_3$)$_2$)—. In another embodiment, X is —N(CH$_2$C(H)(CH$_3$)$_2$)—. In another embodiment, X is —N(C(CH$_3$)$_3$)—.

In one embodiment, R$^1$ is —(CH$_2$)$_n$—N(R$^2$)(R$^2$) and X is —N(CH$_3$)—.
In another embodiment, R$^1$ is —(CH$_2$)$_n$—N(R$^2$)(R$^2$) and X is —N(CH$_2$CH$_3$)—.
In another embodiment, R$^1$ is —(CH$_2$)$_n$—N(R$^2$)(R$^2$) and X is —N(CH$_2$CH$_2$CH$_3$)—.
In another embodiment, R$^1$ is —(CH$_2$)$_n$—N(R$^2$)(R$^2$) and X is —N(CH$_2$CH$_2$CH$_2$CH$_3$)—.
In another embodiment, R$^1$ is —(CH$_2$)$_n$—N(R$^2$)(R$^2$) and X is —N(C(H)(CH$_3$)(CH$_2$CH$_3$))—.
In another embodiment, R$^1$ is —(CH$_2$)$_n$—N(R$^2$)(R$^2$) and X is —N(C(H)(CH$_3$)$_2$)—.
In another embodiment, R$^1$ is —(CH$_2$)$_n$—N(R$^2$)(R$^2$) and X is —N(CH$_2$C(H)(CH$_3$)$_2$)—.
In another embodiment, R$^1$ is —(CH$_2$)$_n$—N(R$^2$)(R$^2$) and X is —N(C(CH$_3$)$_3$)—.
In one embodiment, R$^1$ is —O—(CH$_2$)$_m$—N(R$^2$)(R$^2$) and X is —N(CH$_3$)—.
In another embodiment, R$^1$ is —O—(CH$_2$)$_m$—N(R$^2$)(R$^2$) and X is —N(CH$_2$CH$_3$)—.
In another embodiment, R$^1$ is —O—(CH$_2$)$_m$—N(R$^2$)(R$^2$) and X is —N(CH$_2$CH$_2$CH$_3$)—.
In another embodiment, R$^1$ is —O—(CH$_2$)$_m$—N(R$^2$)(R$^2$) and X is —N(CH$_2$CH$_2$CH$_2$CH$_3$)—.
In another embodiment, R$^1$ is —O—(CH$_2$)$_m$—N(R$^2$)(R$^2$) and X is —N(C(H)(CH$_3$)(CH$_2$CH$_3$))—.
In another embodiment, R$^1$ is —O—(CH$_2$)$_m$—N(R$^2$)(R$^2$) and X is —N(C(H)(CH$_3$)$_2$)—.
In another embodiment, R$^1$ is —O—(CH$_2$)$_m$—N(R$^2$)(R$^2$) and X is —N(CH$_2$C(H)(CH$_3$)$_2$)—.
In another embodiment, R$^1$ is —O—(CH$_2$)$_m$—N(R$^2$)(R$^2$) and X is —N(C(CH$_3$)$_3$)—.

In one embodiment, one R$^2$ is —H, and the other R$^2$ is —C$_1$-C$_6$ alkyl.
In another embodiment, each R$^2$ is —C$_1$-C$_6$ alkyl.
In another embodiment, each R$^2$ is -methyl.
In one embodiment, X is —CH(OH)—.
In another embodiment, X is —CH(OH)— and R$^1$ is —(CH$_2$)$_n$—N(R$^2$)(R$^2$).
In yet another embodiment, X is —CH(OH)— and R$^1$ is —(CH$_2$)—N(R$^2$)(R$^2$).
In another embodiment, X is —N(C(O)N(H)—(CH$_2$)$_p$—Z)—.
In another embodiment, X is —N(C(O)N(H)—(CH$_2$)—Z)—.
In another embodiment, X is —N(C(O)N(H)—(CH$_2$)$_2$—Z)—.
In another embodiment, X is —N(C(O)N(H)—(CH$_2$)$_p$—Z)— and R$^1$ is —(CH$_2$)$_n$—N(R$^2$)(R$^2$).
In yet another embodiment, X is —N(C(O)N(H)—(CH$_2$)$_p$—Z)— and R$^1$ is —(CH$_2$)—N(R$^2$)(R$^2$).

In still another embodiment, X is —N(C(O)N(H)—(CH$_2$)—Z)— and R$^1$ is —(CH$_2$)—N(R$^2$)(R$^2$).

In one embodiment, X is —N((CH$_2$)$_q$—Z)—.

In another embodiment, X is —N((CH$_2$)—Z)—.

In another embodiment, X is —N((CH$_2$)$_2$—Z)—.

In another embodiment, X is —N((CH$_2$)$_q$—Z)— and R$^1$ is —(CH$_2$)$_n$—N(R$^2$)(R$^2$).

In yet another embodiment, X is —N((CH$_2$)$_q$—Z)— and R$^1$ is —(CH$_2$)—N(R$^2$)(R$^2$).

In still another embodiment, X is —N((CH$_2$)—Z)— and R$^1$ is —(CH$_2$)—N(R$^2$)(R$^2$).

In one embodiment, Z is —CF$_3$.

In another embodiment, Z is —F.

In yet another embodiment, Z is —OH.

In still another embodiment, Z is —O—CH$_3$.

In another embodiment, X is —N(C(O)N(H)—(CH$_2$)$_p$—OH)—.

In another embodiment, X is —N(C(O)N(H)—(CH$_2$)$_2$—OH)—.

In another embodiment, X is —N(C(O)N(H)—(CH$_2$)$_p$—OH)— and R$^1$ is —(CH$_2$)$_n$—N(R$^2$)(R$^2$).

In yet another embodiment, X is —N(C(O)N(H)—(CH$_2$)$_p$—OH)— and R$^1$ is —(CH$_2$)—N(R$^2$)(R$^2$).

In still another embodiment, X is —N(C(O)N(H)—(CH$_2$)$_2$—OH)— and R$^1$ is —(CH$_2$)—N(R$^2$)(R$^2$).

In one embodiment, X is —N((CH$_2$)$_q$—OH)—.

In another embodiment, X is —N((CH$_2$)$_2$—OH)—.

In another embodiment, X is —N((CH$_2$)$_q$—OH)— and R$^1$ is —(CH$_2$)$_n$—N(R$^2$)(R$^2$).

In yet another embodiment, X is —N((CH$_2$)$_q$—OH)— and R$^1$ is —(CH$_2$)—N(R$^2$)(R$^2$).

In still another embodiment, X is —N((CH$_2$)$_2$—OH)— and R$^1$ is —(CH$_2$)—N(R$^2$)(R$^2$).

In another embodiment, X is —N(C(O)N(H)—(CH$_2$)$_p$—F)—.

In another embodiment, X is —N(C(O)N(H)—(CH$_2$)—F)—.

In another embodiment, X is —N(C(O)N(H)—(CH$_2$)$_p$—F)— and R$^1$ is —(CH$_2$)$_n$—N(R$^2$)(R$^2$).

In yet another embodiment, X is —N(C(O)N(H)—(CH$_2$)$_p$—F)— and R$^1$ is —(CH$_2$)—N(R$^2$)(R$^2$).

In still another embodiment, X is —N(C(O)N(H)—(CH$_2$)—F)— and R$^1$ is —(CH$_2$)—N(R$^2$)(R$^2$).

In one embodiment, X is —N((CH$_2$)$_q$—F)—.

In another embodiment, X is —N((CH$_2$)—F)—.

In another embodiment, X is —N((CH$_2$)$_q$—F)— and R$^1$ is —(CH$_2$)$_n$—N(R$^2$)(R$^2$).

In yet another embodiment, X is —N((CH$_2$)$_q$—F)— and R$^1$ is —(CH$_2$)—N(R$^2$)(R$^2$).

In still another embodiment, X is —N((CH$_2$)—F)— and R$^1$ is —(CH$_2$)—N(R$^2$)(R$^2$).

In another embodiment, X is —N(C(O)N(H)—(CH$_2$)$_p$—OMe)-.

In another embodiment, X is —N(C(O)N(H)—(CH$_2$)$_2$—OMe)-.

In another embodiment, X is —N(C(O)N(H)—(CH$_2$)$_p$—OMe)- and R$^1$ is —(CH$_2$)$_n$—N(R$^2$)(R$^2$).

In yet another embodiment, X is —N(C(O)N(H)—(CH$_2$)$_p$—OMe)- and R$^1$ is —(CH$_2$)—N(R$^2$)(R$^2$).

In still another embodiment, X is —N(C(O)N(H)—(CH$_2$)$_2$—OMe)- and R$^1$ is —(CH$_2$)—N(R$^2$)(R$^2$).

In one embodiment, X is —N((CH$_2$)$_q$—OMe)-.

In another embodiment, X is —N((CH$_2$)$_2$—OMe)-.

In another embodiment, X is —N((CH$_2$)$_q$—OMe)- and R$^1$ is —(CH$_2$)$_n$—N(R$^2$)(R$^2$).

In yet another embodiment, X is —N((CH$_2$)$_q$—OMe)- and R$^1$ is —(CH$_2$)—N(R$^2$)(R$^2$).

In still another embodiment, X is —N((CH$_2$)$_2$—OMe)- and R$^1$ is —(CH$_2$)—N(R$^2$)(R$^2$).

In another embodiment, X is —N(C(O)N(H)—(CH$_2$)$_p$—CF$_3$)—.

In another embodiment, X is —N(C(O)N(H)—(CH$_2$)—CF$_3$)—.

In another embodiment, X is —N(C(O)N(H)—(CH$_2$)$_p$—CF$_3$)— and R$^1$ is —(CH$_2$)$_n$—N(R$^2$)(R$^2$).

In yet another embodiment, X is —N(C(O)N(H)—(CH$_2$)$_p$—CF$_3$)— and R$^1$ is —(CH$_2$)—N(R$^2$)(R$^2$).

In still another embodiment, X is —N(C(O)N(H)—(CH$_2$)—CF$_3$)— and R$^1$ is —(CH$_2$)—N(R$^2$)(R$^2$).

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and R$^1$ is —(CH$_2$)$_n$—N(R$^2$)(R$^2$).

In yet another embodiment, X is —N((CH$_2$)$_q$—CF$_3$)— and R$^1$ is —(CH$_2$)—N(R$^2$)(R$^2$).

In still another embodiment, X is —N((CH$_2$)—CF$_3$)— and R$^1$ is —(CH$_2$)—N(R$^2$)(R$^2$).

In another embodiment, X is —N(C(O)N(H)—(CH$_2$)$_p$—CF$_3$)—.

In another embodiment, X is —N(C(O)N(H)—(CH$_2$)—CF$_3$)—.

In another embodiment, X is —N(C(O)N(H)—(CH$_2$)$_p$—CF$_3$)— and R$^1$ is —(CH$_2$)$_n$—N(R$^2$)(R$^2$).

In yet another embodiment, X is —N(C(O)N(H)—(CH$_2$)$_p$—CF$_3$)— and R$^1$ is —(CH$_2$)—N(R$^2$)(R$^2$).

In still another embodiment, X is —N(C(O)N(H)—(CH$_2$)—CF$_3$)— and R$^1$ is —(CH$_2$)—N(R$^2$)(R$^2$).

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and R$^1$ is —(CH$_2$)$_n$—N(R$^2$)(R$^2$).

In yet another embodiment, X is —N((CH$_2$)$_q$—CF$_3$)— and R$^1$ is —(CH$_2$)—N(R$^2$)(R$^2$).

In still another embodiment, X is —N((CH$_2$)—CF$_3$)— and R$^1$ is —(CH$_2$)—N(R$^2$)(R$^2$).

In one embodiment, n is 1.

In another embodiment, n is 2.

In yet another embodiment, n is 3.

In a further embodiment, n is 4, 5, or 6.

In yet a further embodiment, n is 7, 8, or 9.

In still a further embodiment, n is 10.

In one embodiment, m is 2.

In another embodiment, m is 3.

In yet another embodiment, m is 4, 5, or 6.

In a further embodiment, m is 7, 8, or 9.

In yet a further embodiment, m is 10.

In one embodiment, p is 1.

In another embodiment, p is 2.

In yet another embodiment, p is an integer ranging from 2 to 5.

In one embodiment, q is 1.

In another embodiment, q is 2.

In yet another embodiment, q is an integer ranging from 2 to 5.

In various embodiments, —N(R$^2$)(R$^2$) is:

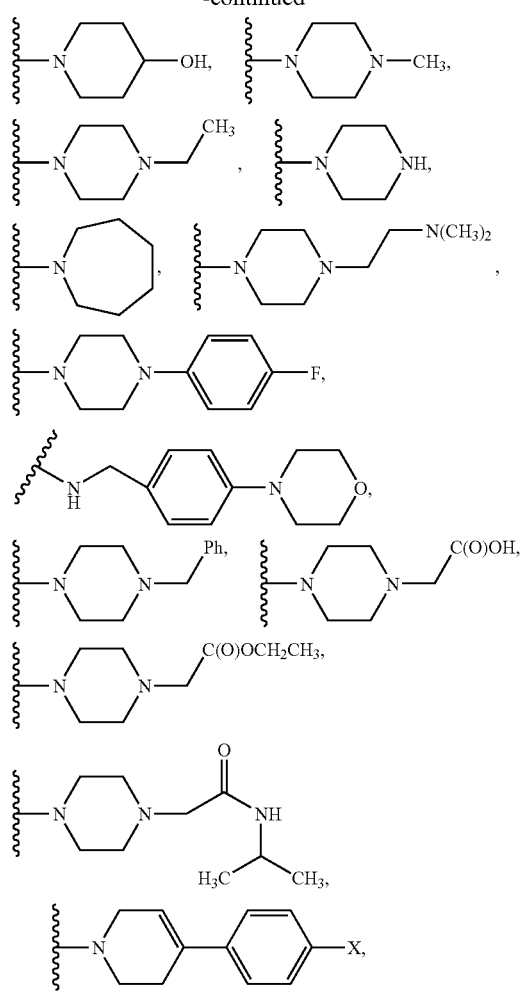
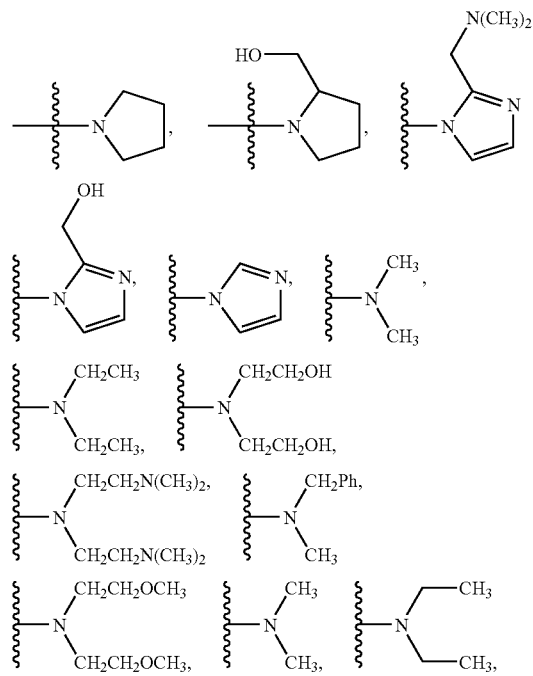
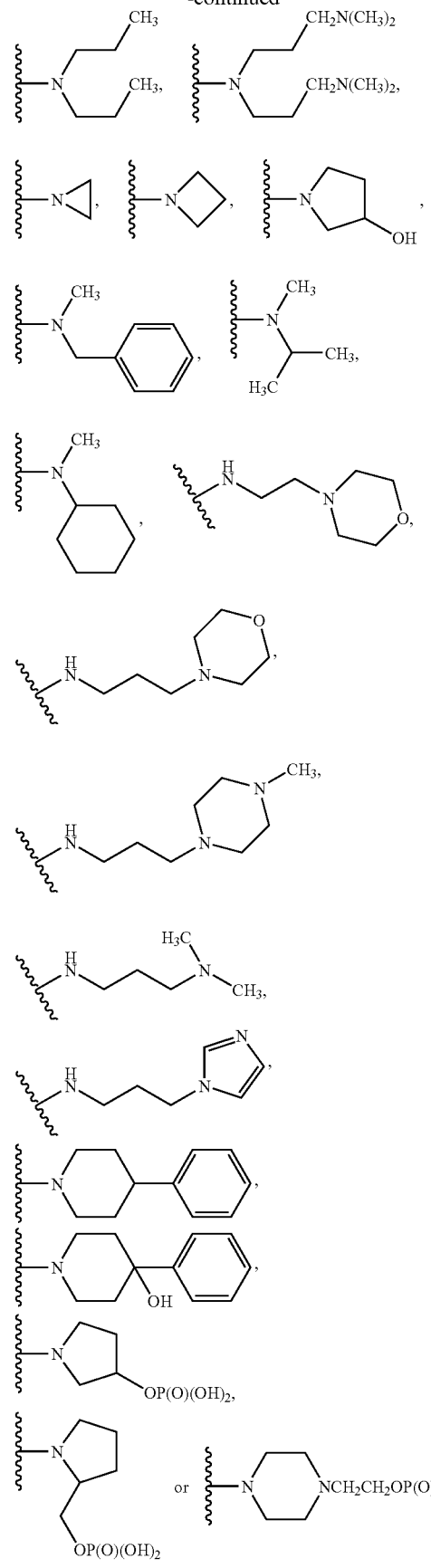

In other embodiments, —N($R^2$)($R^2$) is:
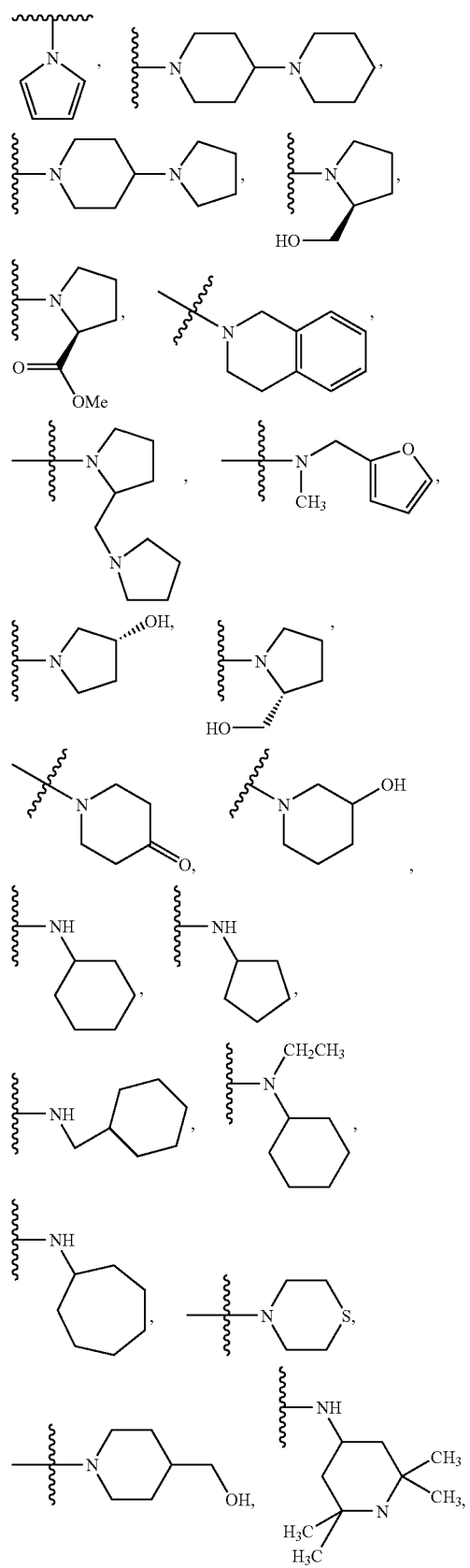
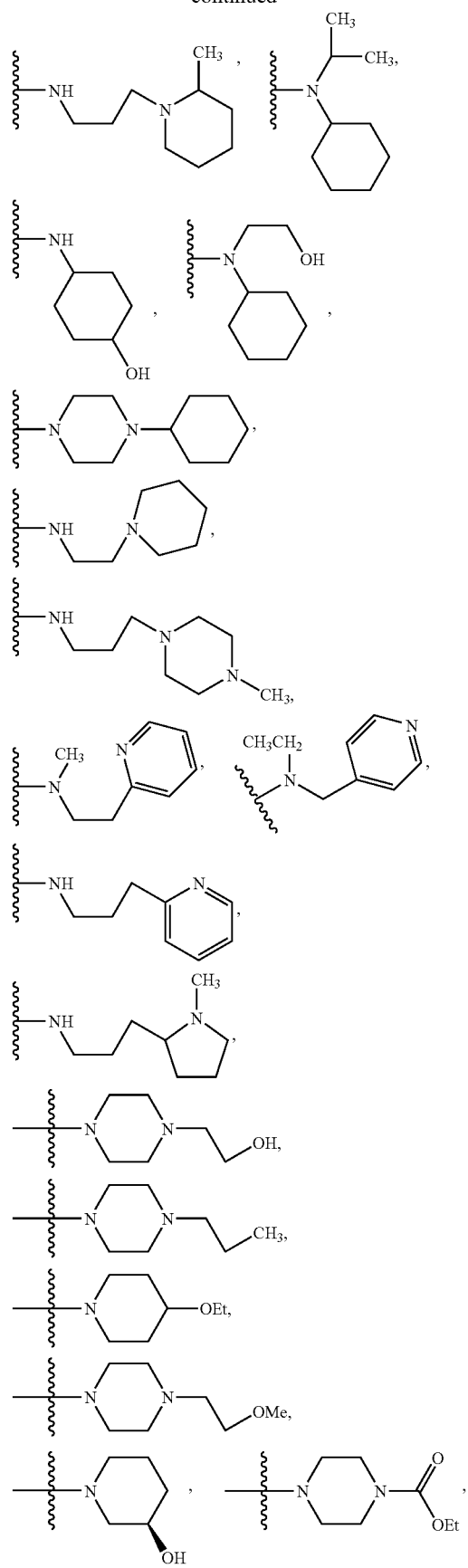

-continued
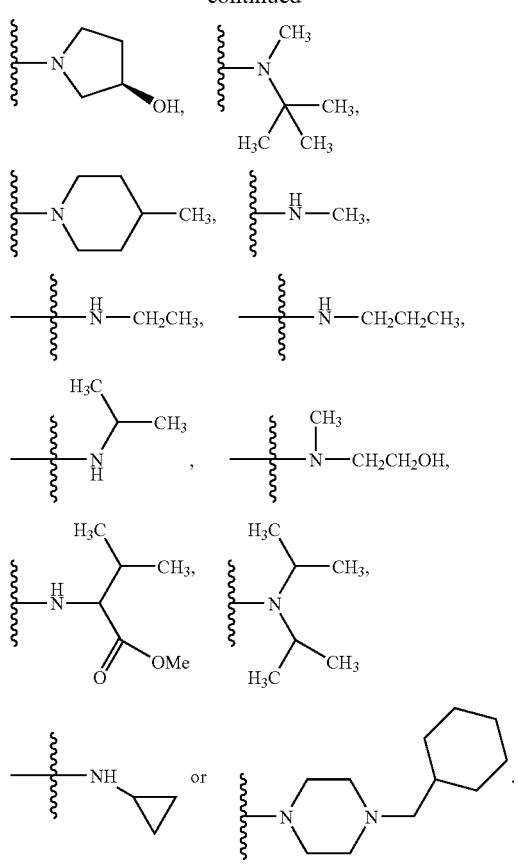
In some embodiments, —N(R²)(R²) is
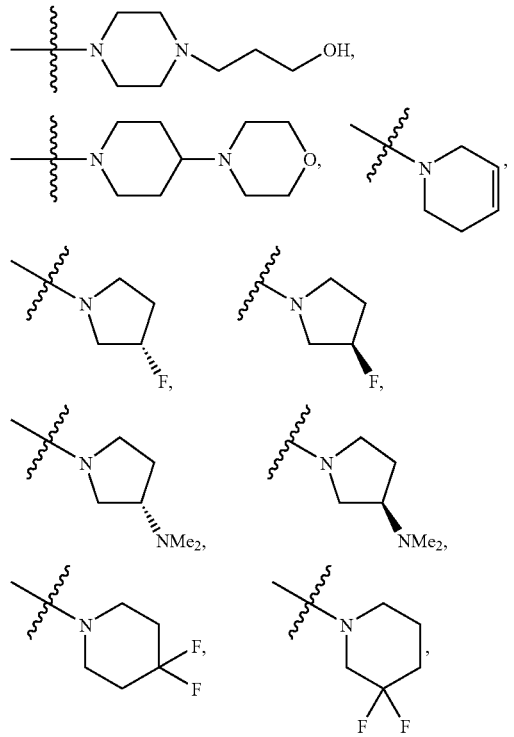
-continued
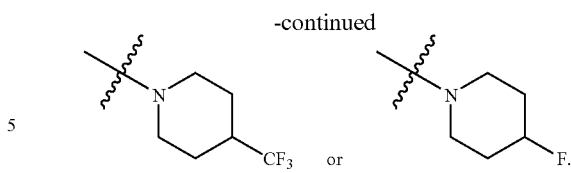
In still other embodiments, —N(R²)(R²) is —N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.
In some embodiments, —N(R²)(R²) is
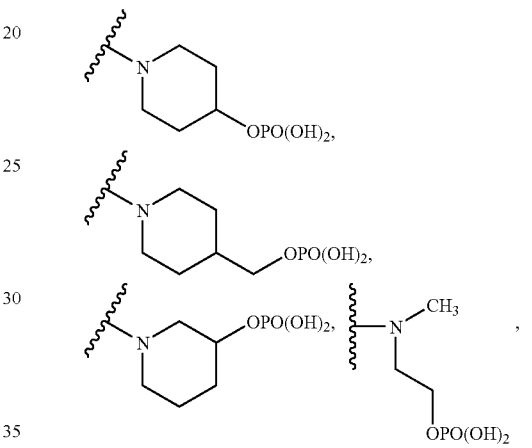
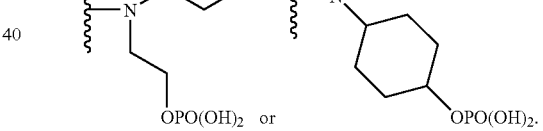
In various embodiments, —N(Z₃)(Z₄) is:
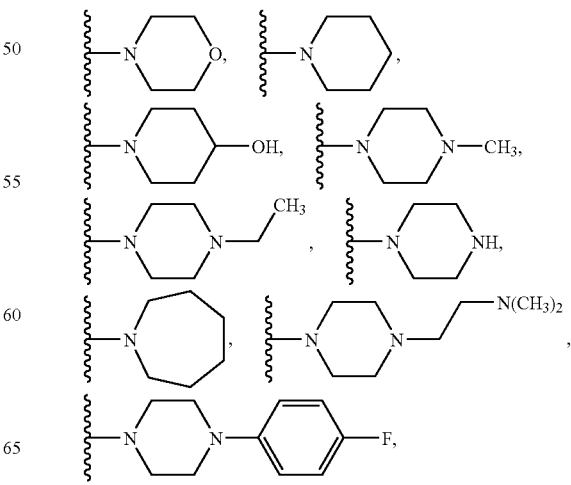

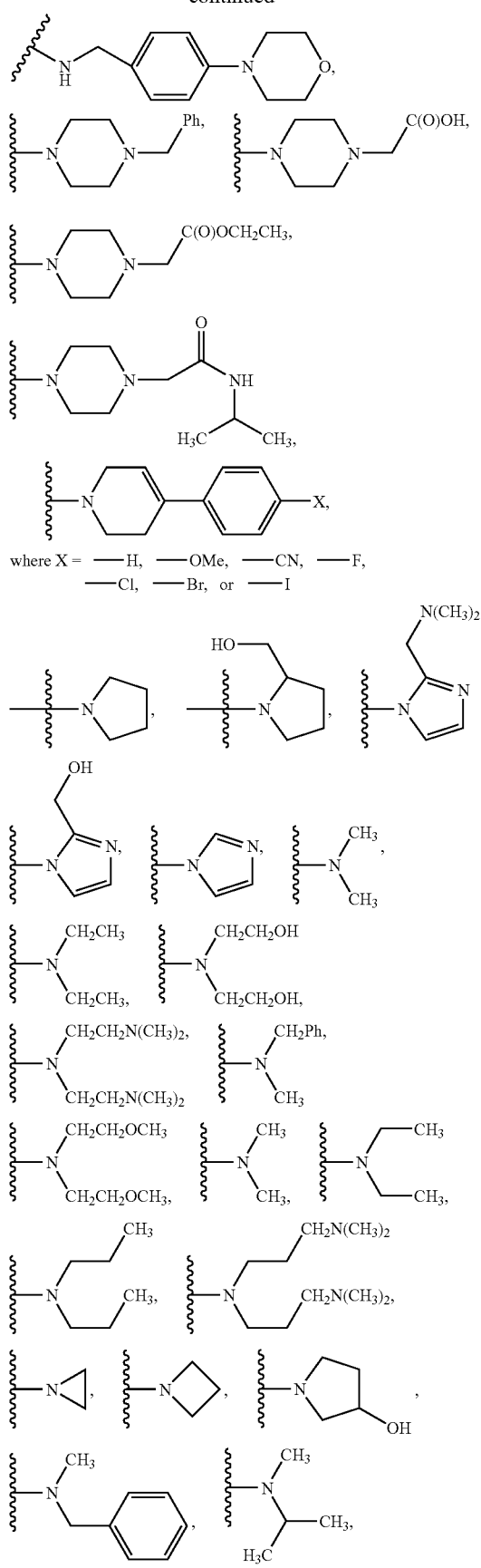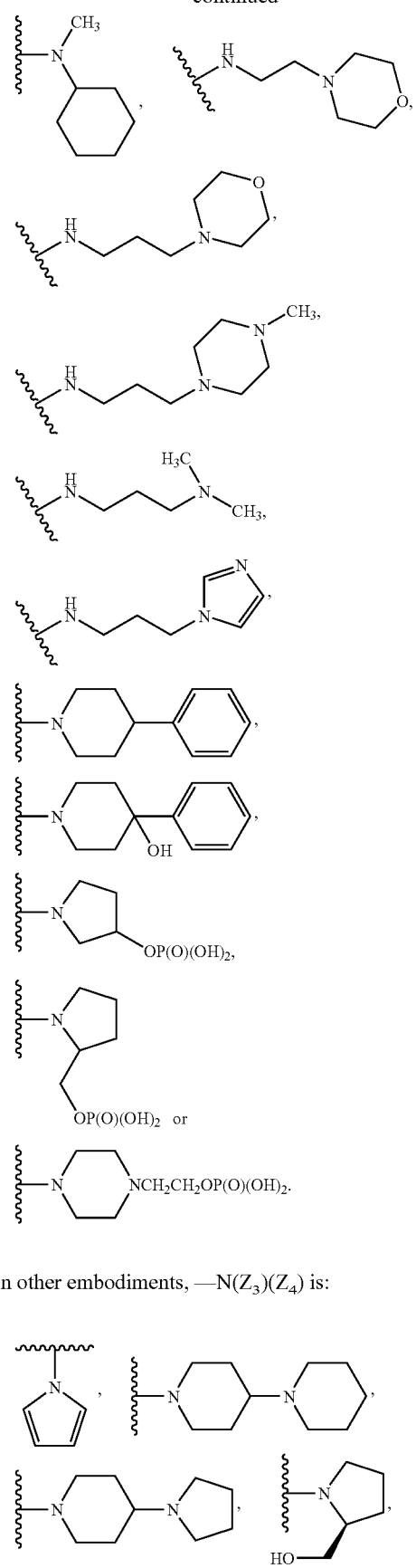
In other embodiments, —N($Z_3$)($Z_4$) is:

563
-continued
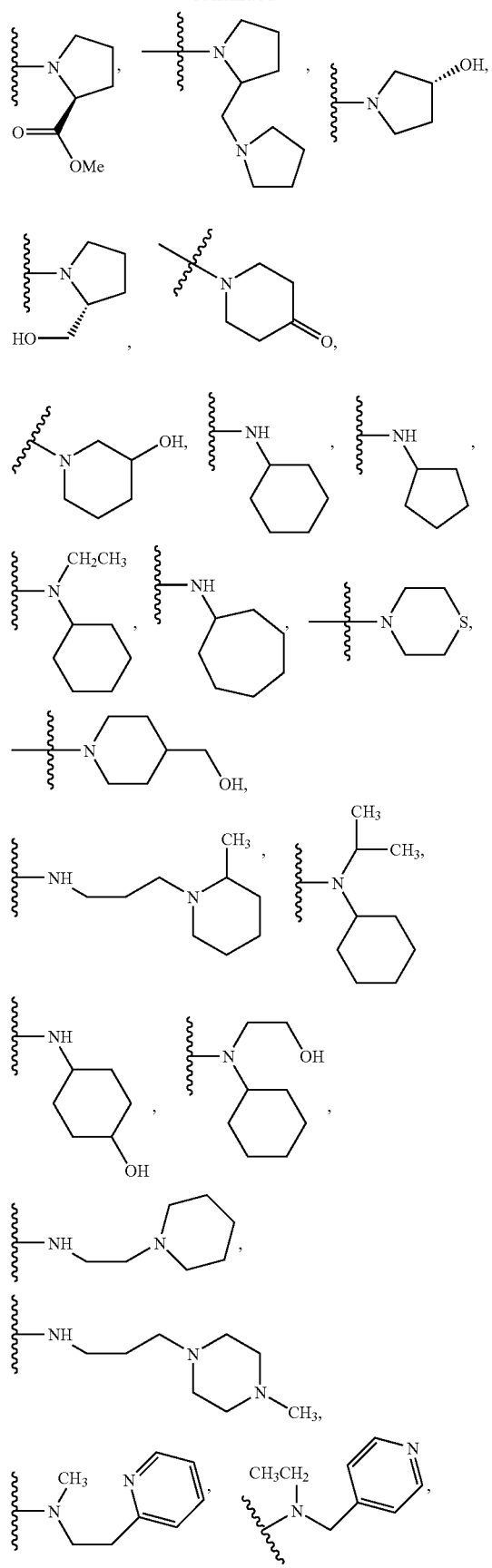
564
-continued
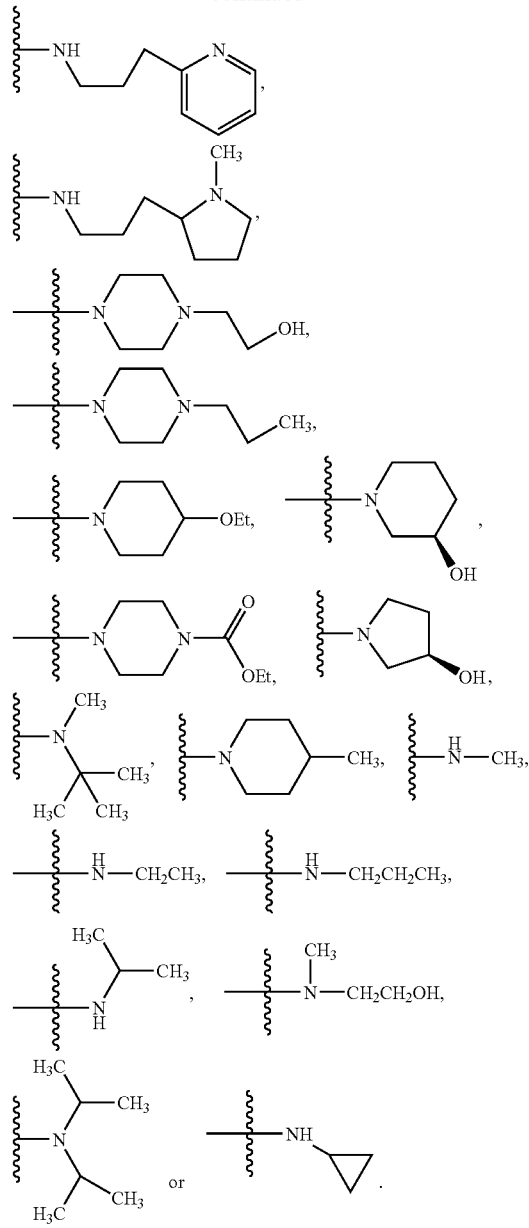
In some embodiments, —N(Z₃)(Z₄) is

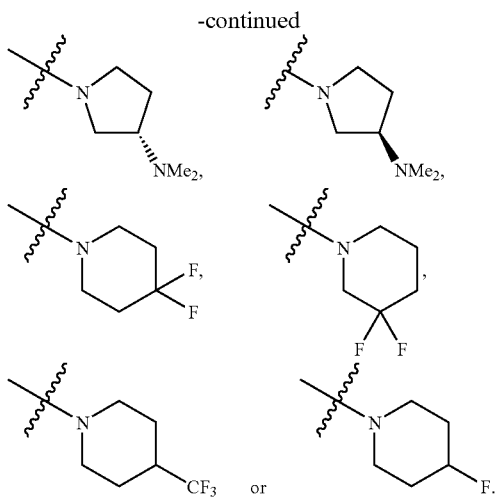

In still other embodiments, —N(Z₃)(Z₄) is
—N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.

In some embodiments, —N(Z₃)(Z₄) is

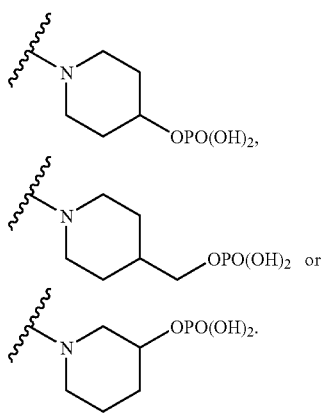

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—;

R¹ is —(CH₂)ₙ—N(R²)(R²) or —O—(CH₂)ₘ—N(R²)(R²);

each R² is independently —H, —C₁-C₆ alkyl, cyclopropyl, cyclobutyl, cyclopentyl, cyclohexyl, —(C₁-C₆ alkylene)-phenyl or -phenyl, each of which other than hydrogen is unsubstituted or substituted with one or more of -halo, —OH, —OP(O)(OH)₂, —OS(O)₂OH or —N(Z₃)(Z₄), where Z₃ and Z₄ are independently —H, —C₁-C₅ alkyl, or —(C₁-C₅ alkylene)-O—C₁-C₅ alkyl, each of which other than hydrogen is unsubstituted or substituted with one or more of -halo, —OH or —NH₂;

or N, Z₃ and Z₄ are taken together to form a nitrogen-containing 3- to 7-membered monocyclic heterocycle which is unsubstituted or substituted with one to three of —C₁-C₅ alkyl, -phenyl, —(C₁-C₅ alkylene)-phenyl, -(hydroxy-substituted) C₁-C₅ alkyl, -halo, -(halo-substituted) C₁-C₅ alkyl, -(halo-substituted) phenyl, -phenylene-O—C₁-C₅ alkyl, -(cyano-substituted) phenyl, —OH, —O—C₁-C₅ alkyl, —N(Rᵃ)₂, —(C₁-C₅ alkylene)-N(Rᵃ)₂, —C₁-C₅ alkylene-C(O)O—(C₁-C₅ alkylene)-N(Rᵃ)₂, —COOH, —(C₁-C₅ alkylene)-COOH, —OP(O)(OH)₂, —OS(O)₂OH, —(C₁-C₅ alkylene)-OP(O)(OH)₂, —(C₁-C₅ alkylene)-OS(O)₂OH, —C(O)O—C₁-C₅ alkyl, —OC(O)—C₁-C₅ alkyl, —(C₁-C₅ alkylene)-C(O)O—C₁-C₅ alkyl, —(C₁-C₅ alkylene)-C(O)NH—C₁-C₅ alkyl, —C(O)NH₂, or —NO₂, wherein each occurrence of Rᵃ is independently —H, -benzyl, or —C₁-C₁₀ alkyl;

or N and both R² groups are taken together to form a nitrogen-containing 3- to 7-membered monocyclic heterocycle which is unsubstituted or substituted with one to three of —C₁-C₅ alkyl, -phenyl, —(C₁-C₅ alkylene)-phenyl, -(hydroxy-substituted) C₁-C₅ alkyl, -halo, -(halo-substituted) C₁-C₅ alkyl, -(halo-substituted) phenyl, -phenylene-O—C₁-C₅ alkyl, -(cyano-substituted) phenyl, —OH, —O—C₁-C₅ alkyl, —N(Rᵃ)₂, —(C₁-C₅ alkylene)-N(Rᵃ)₂, —(C₁-C₅ alkylene)-C(O)O—(C₁-C₅ alkylene)-N(Rᵃ)₂, —COOH, —(C₁-C₅ alkylene)-COOH, —OP(O)(OH)₂, —OS(O)₂OH, —(C₁-C₅ alkylene)-OP(O)(OH)₂, —(C₁-C₅ alkylene)-OS(O)₂OH, —C(O)O—C₁-C₅ alkyl, —OC(O)—C₁-C₅ alkyl, —(C₁-C₅ alkylene)-C(O)O—C₁-C₅ alkyl, —(C₁-C₅ alkylene)-C(O)NH—C₁-C₅ alkyl, —C(O)NH₂, or —NO₂, wherein each occurrence of Rᵃ is independently —H, -benzyl, or —C₁-C₁₀ alkyl;

n is an integer ranging from 1 to 10; and
m is an integer ranging from 2 to 10.

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is methyl.

In another embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is ethyl.

In yet another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is propyl.

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is —C₃-C₈ monocyclic cycloalkyl.

In another embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; R¹ is —CH₂—N(R²)(R²); and at least one R² is cyclohexyl.

In yet another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; and R¹ is —CH₂—N(R²)(R²), wherein N and both R² groups are taken together to form a nitrogen-containing 3- to 7-membered monocyclic heterocycle.

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; and R¹ is —CH₂—N(R²)(R²), wherein N and both R² groups are taken together to form a nitrogen-containing 3- to 7-membered monocyclic heterocycle, which is substituted with a hydroxyl.

In another embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—; and R$^1$ is —CH$_2$—N(R$^2$)(R$^2$), wherein N and both R$^2$ groups are taken together to form a nitrogen-containing 3- to 7-membered monocyclic heterocycle, which is substituted with a nitrogen-containing 3- to 7-membered monocyclic heterocycle.

Illustrative examples of the Indenoisoquinolinone Analogs include the compounds of Formula (Ic) as set forth below:

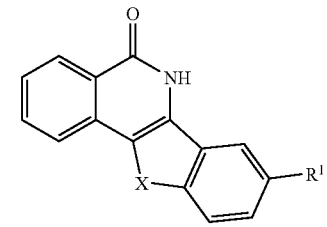

(Ic)

| Compound | n | —R$^1$ | X |
|---|---|---|---|
| Ic-1 | 1 | —(CH$_2$)$_n$—N(CH$_3$)$_2$ | —N(CH$_3$)— |
| Ic-2 | 2 | —(CH$_2$)$_n$—N(CH$_3$)$_2$ | —N(CH$_3$)— |
| Ic-3 | 3 | —(CH$_2$)$_n$—N(CH$_3$)$_2$ | —N(CH$_3$)— |
| Ic-4 | 4 | —(CH$_2$)$_n$—N(CH$_3$)$_2$ | —N(CH$_3$)— |
| Ic-5 | 5 | —(CH$_2$)$_n$—N(CH$_3$)$_2$ | —N(CH$_3$)— |
| Ic-6 | 6 | —(CH$_2$)$_n$—N(CH$_3$)$_2$ | —N(CH$_3$)— |
| Ic-7 | 1 | —(CH$_2$)$_n$—N(CH$_3$)$_2$ | —N(CH$_2$CH$_3$)— |
| Ic-8 | 2 | —(CH$_2$)$_n$—N(CH$_3$)$_2$ | —N(CH$_2$CH$_3$)— |
| Ic-9 | 3 | —(CH$_2$)$_n$—N(CH$_3$)$_2$ | —N(CH$_2$CH$_3$)— |
| Ic-10 | 4 | —(CH$_2$)$_n$—N(CH$_3$)$_2$ | —N(CH$_2$CH$_3$)— |
| Ic-11 | 5 | —(CH$_2$)$_n$—N(CH$_3$)$_2$ | —N(CH$_2$CH$_3$)— |
| Ic-12 | 6 | —(CH$_2$)$_n$—N(CH$_3$)$_2$ | —N(CH$_2$CH$_3$)— |
| Ic-13 | 1 | —(CH$_2$)$_n$—N(CH$_3$)$_2$ | —N(CH$_2$CH$_2$CH$_3$)— |
| Ic-14 | 2 | —(CH$_2$)$_n$—N(CH$_3$)$_2$ | —N(CH$_2$CH$_2$CH$_3$)— |
| Ic-15 | 3 | —(CH$_2$)$_n$—N(CH$_3$)$_2$ | —N(CH$_2$CH$_2$CH$_3$)— |
| Ic-16 | 4 | —(CH$_2$)$_n$—N(CH$_3$)$_2$ | —N(CH$_2$CH$_2$CH$_3$)— |
| Ic-17 | 5 | —(CH$_2$)$_n$—N(CH$_3$)$_2$ | —N(CH$_2$CH$_2$CH$_3$)— |
| Ic-18 | 6 | —(CH$_2$)$_n$—N(CH$_3$)$_2$ | —N(CH$_2$CH$_2$CH$_3$)— |
| Ic-19 | 1 | —(CH$_2$)$_n$—N(CH$_3$)$_2$ | —N(CH$_2$CH$_2$CH$_2$CH$_3$)— |
| Ic-20 | 2 | —(CH$_2$)$_n$—N(CH$_3$)$_2$ | —N(CH$_2$CH$_2$CH$_2$CH$_3$)— |
| Ic-21 | 3 | —(CH$_2$)$_n$—N(CH$_3$)$_2$ | —N(CH$_2$CH$_2$CH$_2$CH$_3$)— |
| Ic-22 | 4 | —(CH$_2$)$_n$—N(CH$_3$)$_2$ | —N(CH$_2$CH$_2$CH$_2$CH$_3$)— |
| Ic-23 | 5 | —(CH$_2$)$_n$—N(CH$_3$)$_2$ | —N(CH$_2$CH$_2$CH$_2$CH$_3$)— |
| Ic-24 | 6 | —(CH$_2$)$_n$—N(CH$_3$)$_2$ | —N(CH$_2$CH$_2$CH$_2$CH$_3$)— |
| Ic-25 | 1 | —(CH$_2$)$_n$—N(CH$_3$)$_2$ | —N(C(H)(CH$_3$)(CH$_2$CH$_3$))— |
| Ic-26 | 2 | —(CH$_2$)$_n$—N(CH$_3$)$_2$ | —N(C(H)(CH$_3$)(CH$_2$CH$_3$))— |
| Ic-27 | 3 | —(CH$_2$)$_n$—N(CH$_3$)$_2$ | —N(C(H)(CH$_3$)(CH$_2$CH$_3$))— |
| Ic-28 | 4 | —(CH$_2$)$_n$—N(CH$_3$)$_2$ | —N(C(H)(CH$_3$)(CH$_2$CH$_3$))— |
| Ic-29 | 5 | —(CH$_2$)$_n$—N(CH$_3$)$_2$ | —N(C(H)(CH$_3$)(CH$_2$CH$_3$))— |
| Ic-30 | 6 | —(CH$_2$)$_n$—N(CH$_3$)$_2$ | —N(C(H)(CH$_3$)(CH$_2$CH$_3$))— |
| Ic-31 | 1 | —(CH$_2$)$_n$—N(CH$_3$)$_2$ | —N(C(H)(CH$_3$)$_2$)— |
| Ic-32 | 2 | —(CH$_2$)$_n$—N(CH$_3$)$_2$ | —N(C(H)(CH$_3$)$_2$)— |
| Ic-33 | 3 | —(CH$_2$)$_n$—N(CH$_3$)$_2$ | —N(C(H)(CH$_3$)$_2$)— |
| Ic-34 | 4 | —(CH$_2$)$_n$—N(CH$_3$)$_2$ | —N(C(H)(CH$_3$)$_2$)— |
| Ic-35 | 5 | —(CH$_2$)$_n$—N(CH$_3$)$_2$ | —N(C(H)(CH$_3$)$_2$)— |
| Ic-36 | 6 | —(CH$_2$)$_n$—N(CH$_3$)$_2$ | —N(C(H)(CH$_3$)$_2$)— |
| Ic-37 | 1 | —(CH$_2$)$_n$—N(CH$_3$)$_2$ | —N(CH$_2$C(H)(CH$_3$)$_2$)— |
| Ic-38 | 2 | —(CH$_2$)$_n$—N(CH$_3$)$_2$ | —N(CH$_2$C(H)(CH$_3$)$_2$)— |
| Ic-39 | 3 | —(CH$_2$)$_n$—N(CH$_3$)$_2$ | —N(CH$_2$C(H)(CH$_3$)$_2$)— |
| Ic-40 | 4 | —(CH$_2$)$_n$—N(CH$_3$)$_2$ | —N(CH$_2$C(H)(CH$_3$)$_2$)— |
| Ic-41 | 5 | —(CH$_2$)$_n$—N(CH$_3$)$_2$ | —N(CH$_2$C(H)(CH$_3$)$_2$)— |
| Ic-42 | 6 | —(CH$_2$)$_n$—N(CH$_3$)$_2$ | —N(CH$_2$C(H)(CH$_3$)$_2$)— |
| Ic-43 | 1 | —(CH$_2$)$_n$—N(CH$_3$)$_2$ | —N(C(CH$_3$)$_3$)— |
| Ic-44 | 2 | —(CH$_2$)$_n$—N(CH$_3$)$_2$ | —N(C(CH$_3$)$_3$)— |
| Ic-45 | 3 | —(CH$_2$)$_n$—N(CH$_3$)$_2$ | —N(C(CH$_3$)$_3$)— |
| Ic-46 | 4 | —(CH$_2$)$_n$—N(CH$_3$)$_2$ | —N(C(CH$_3$)$_3$)— |
| Ic-47 | 5 | —(CH$_2$)$_n$—N(CH$_3$)$_2$ | —N(C(CH$_3$)$_3$)— |
| Ic-48 | 6 | —(CH$_2$)$_n$—N(CH$_3$)$_2$ | —N(C(CH$_3$)$_3$)— |
| Ic-49 | 1 | —(CH$_2$)$_n$—N(morpholine) | —N(CH$_3$)— |

-continued

| | | | |
|---|---|---|---|
| Ic-50 | 2 | 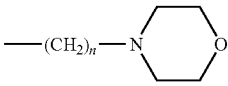—(CH$_2$)$_n$—N⏝O | —N(CH$_3$)— |
| Ic-51 | 3 | 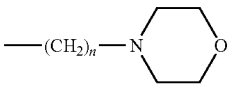—(CH$_2$)$_n$—N⏝O | —N(CH$_3$)— |
| Ic-52 | 4 | 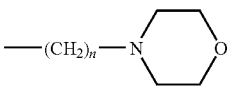—(CH$_2$)$_n$—N⏝O | —N(CH$_3$)— |
| Ic-53 | 5 | 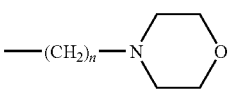—(CH$_2$)$_n$—N⏝O | —N(CH$_3$)— |
| Ic-54 | 6 | 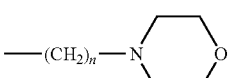—(CH$_2$)$_n$—N⏝O | —N(CH$_3$)— |
| Ic-55 | 1 | 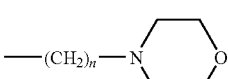—(CH$_2$)$_n$—N⏝O | —N(CH$_2$CH$_3$)— |
| Ic-56 | 2 | 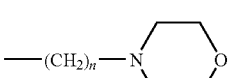—(CH$_2$)$_n$—N⏝O | —N(CH$_2$CH$_3$)— |
| Ic-57 | 3 | 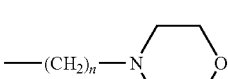—(CH$_2$)$_n$—N⏝O | —N(CH$_2$CH$_3$)— |
| Ic-58 | 4 | 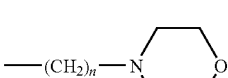—(CH$_2$)$_n$—N⏝O | —N(CH$_2$CH$_3$)— |
| Ic-59 | 5 | 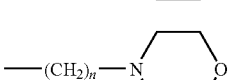—(CH$_2$)$_n$—N⏝O | —N(CH$_2$CH$_3$)— |
| Ic-60 | 6 | 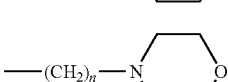—(CH$_2$)$_n$—N⏝O | —N(CH$_2$CH$_3$)— |
| Ic-61 | 1 | 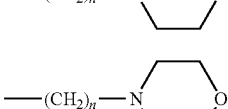—(CH$_2$)$_n$—N⏝O | —N(CH$_2$CH$_2$CH$_3$)— |
| Ic-62 | 2 | 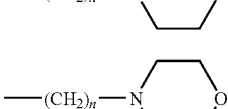—(CH$_2$)$_n$—N⏝O | —N(CH$_2$CH$_2$CH$_3$)— |
| Ic-63 | 3 | —(CH$_2$)$_n$—N⏝O | —N(CH$_2$CH$_2$CH$_3$)— |
| Ic-64 | 4 | —(CH$_2$)$_n$—N⏝O | —N(CH$_2$CH$_2$CH$_3$)— |
| Ic-65 | 5 | 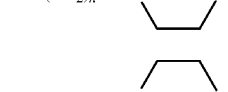—(CH$_2$)$_n$—N⏝O | —N(CH$_2$CH$_2$CH$_3$)— |

-continued

| | | | |
|---|---|---|---|
| Ic-66 | 6 | —(CH$_2$)$_n$—N⟨morpholine⟩ | —N(CH$_2$CH$_2$CH$_3$)— |
| Ic-67 | 1 | —(CH$_2$)$_n$—N⟨morpholine⟩ | —N(CH$_2$CH$_2$CH$_2$CH$_3$)— |
| Ic-68 | 2 | —(CH$_2$)$_n$—N⟨morpholine⟩ | —N(CH$_2$CH$_2$CH$_2$CH$_3$)— |
| Ic-69 | 3 | —(CH$_2$)$_n$—N⟨morpholine⟩ | —N(CH$_2$CH$_2$CH$_2$CH$_3$)— |
| Ic-70 | 4 | —(CH$_2$)$_n$—N⟨morpholine⟩ | —N(CH$_2$CH$_2$CH$_2$CH$_3$)— |
| Ic-71 | 5 | —(CH$_2$)$_n$—N⟨morpholine⟩ | —N(CH$_2$CH$_2$CH$_2$CH$_3$)— |
| Ic-72 | 6 | —(CH$_2$)$_n$—N⟨morpholine⟩ | —N(CH$_2$CH$_2$CH$_2$CH$_3$)— |
| Ic-73 | 1 | —(CH$_2$)$_n$—N⟨morpholine⟩ | —N(C(H)(CH$_3$)(CH$_2$CH$_3$))— |
| Ic-74 | 2 | —(CH$_2$)$_n$—N⟨morpholine⟩ | —N(C(H)(CH$_3$)(CH$_2$CH$_3$))— |
| Ic-75 | 3 | —(CH$_2$)$_n$—N⟨morpholine⟩ | —N(C(H)(CH$_3$)(CH$_2$CH$_3$))— |
| Ic-76 | 4 | —(CH$_2$)$_n$—N⟨morpholine⟩ | —N(C(H)(CH$_3$)(CH$_2$CH$_3$))— |
| Ic-77 | 5 | —(CH$_2$)$_n$—N⟨morpholine⟩ | —N(C(H)(CH$_3$)(CH$_2$CH$_3$))— |
| Ic-78 | 6 | —(CH$_2$)$_n$—N⟨morpholine⟩ | —N(C(H)(CH$_3$)(CH$_2$CH$_3$))— |
| Ic-79 | 1 | —(CH$_2$)$_n$—N⟨morpholine⟩ | —N(C(H)(CH$_3$)$_2$)— |
| Ic-80 | 2 | —(CH$_2$)$_n$—N⟨morpholine⟩ | —N(C(H)(CH$_3$)$_2$)— |
| Ic-81 | 3 | —(CH$_2$)$_n$—N⟨morpholine⟩ | —N(C(H)(CH$_3$)$_2$)— |

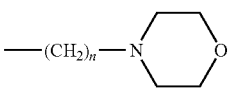
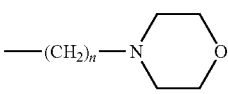
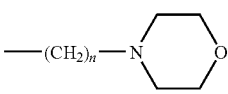
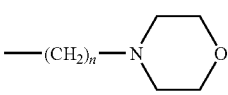
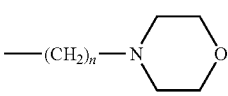
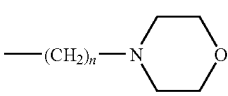
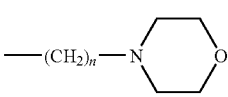
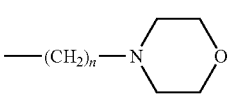
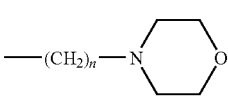
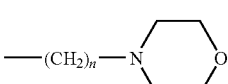
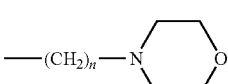
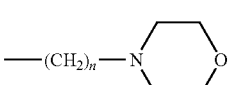
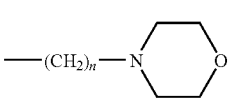
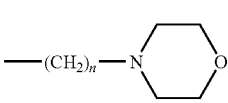
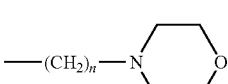
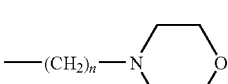

-continued

| Compound | n | | X |
|---|---|---|---|
| Ic-82 | 4 | —(CH$_2$)$_n$—N(morpholine) | —N(C(H)(CH$_3$)$_2$)— |
| Ic-83 | 5 | —(CH$_2$)$_n$—N(morpholine) | —N(C(H)(CH$_3$)$_2$)— |
| Ic-84 | 6 | —(CH$_2$)$_n$—N(morpholine) | —N(C(H)(CH$_3$)$_2$)— |
| Ic-85 | 1 | —(CH$_2$)$_n$—N(morpholine) | —N(CH$_2$C(H)(CH$_3$)$_2$)— |
| Ic-86 | 2 | —(CH$_2$)$_n$—N(morpholine) | —N(CH$_2$C(H)(CH$_3$)$_2$)— |
| Ic-87 | 3 | —(CH$_2$)$_n$—N(morpholine) | —N(CH$_2$C(H)(CH$_3$)$_2$)— |
| Ic-88 | 4 | —(CH$_2$)$_n$—N(morpholine) | —N(CH$_2$C(H)(CH$_3$)$_2$)— |
| Ic-89 | 5 | —(CH$_2$)$_n$—N(morpholine) | —N(CH$_2$C(H)(CH$_3$)$_2$)— |
| Ic-90 | 6 | —(CH$_2$)$_n$—N(morpholine) | —N(CH$_2$C(H)(CH$_3$)$_2$)— |
| Ic-91 | 1 | —(CH$_2$)$_n$—N(morpholine) | —N(C(CH$_3$)$_3$)— |
| Ic-92 | 2 | —(CH$_2$)$_n$—N(morpholine) | —N(C(CH$_3$)$_3$)— |
| Ic-93 | 3 | —(CH$_2$)$_n$—N(morpholine) | —N(C(CH$_3$)$_3$)— |
| Ic-94 | 4 | —(CH$_2$)$_n$—N(morpholine) | —N(C(CH$_3$)$_3$)— |
| Ic-95 | 5 | —(CH$_2$)$_n$—N(morpholine) | —N(C(CH$_3$)$_3$)— |
| Ic-96 | 6 | —(CH$_2$)$_n$—N(morpholine) | —N(C(CH$_3$)$_3$)— |

| Compound | m | —R$^1$ | X |
|---|---|---|---|
| Ic-146 | 2 | —O—(CH$_2$)$_m$—N(CH$_3$)$_2$ | —N(CH$_3$)— |
| Ic-147 | 3 | —O—(CH$_2$)$_m$—N(CH$_3$)$_2$ | —N(CH$_3$)— |
| Ic-148 | 4 | —O—(CH$_2$)$_m$—N(CH$_3$)$_2$ | —N(CH$_3$)— |
| Ic-149 | 5 | —O—(CH$_2$)$_m$—N(CH$_3$)$_2$ | —N(CH$_3$)— |
| Ic-150 | 6 | —O—(CH$_2$)$_m$—N(CH$_3$)$_2$ | —N(CH$_3$)— |

-continued

| | | | |
|---|---|---|---|
| Ic-151 | 2 | —O—(CH$_2$)$_m$—N(CH$_3$)$_2$ | —N(CH$_3$)— |
| Ic-152 | 3 | —O—(CH$_2$)$_m$—N(CH$_3$)$_2$ | —N(CH$_2$CH$_3$)— |
| Ic-153 | 4 | —O—(CH$_2$)$_m$—N(CH$_3$)$_2$ | —N(CH$_2$CH$_3$)— |
| Ic-154 | 5 | —O—(CH$_2$)$_m$—N(CH$_3$)$_2$ | —N(CH$_2$CH$_3$)— |
| Ic-155 | 6 | —O—(CH$_2$)$_m$—N(CH$_3$)$_2$ | —N(CH$_2$CH$_3$)— |
| Ic-156 | 2 | —O—(CH$_2$)$_m$—N(CH$_3$)$_2$ | —N(CH$_2$CH$_3$)— |
| Ic-157 | 3 | —O—(CH$_2$)$_m$—N(CH$_3$)$_2$ | —N(CH$_2$CH$_3$)— |
| Ic-158 | 4 | —O—(CH$_2$)$_m$—N(CH$_3$)$_2$ | —N(CH$_2$CH$_2$CH$_3$)— |
| Ic-159 | 5 | —O—(CH$_2$)$_m$—N(CH$_3$)$_2$ | —N(CH$_2$CH$_2$CH$_3$)— |
| Ic-160 | 6 | —O—(CH$_2$)$_m$—N(CH$_3$)$_2$ | —N(CH$_2$CH$_2$CH$_3$)— |
| Ic-161 | 2 | —O—(CH$_2$)$_m$—N(CH$_3$)$_2$ | —N(CH$_2$CH$_2$CH$_3$)— |
| Ic-162 | 3 | —O—(CH$_2$)$_m$—N(CH$_3$)$_2$ | —N(CH$_2$CH$_2$CH$_3$)— |
| Ic-163 | 4 | —O—(CH$_2$)$_m$—N(CH$_3$)$_2$ | —N(CH$_2$CH$_2$CH$_3$)— |
| Ic-164 | 5 | —O—(CH$_2$)$_m$—N(CH$_3$)$_2$ | —N(CH$_2$CH$_2$CH$_3$)— |
| Ic-165 | 6 | —O—(CH$_2$)$_m$—N(CH$_3$)$_2$ | —N(CH$_2$CH$_2$CH$_3$)— |
| Ic-166 | 2 | —O—(CH$_2$)$_m$—N(CH$_3$)$_2$ | —N(CH$_2$CH$_2$CH$_3$)— |
| Ic-167 | 3 | —O—(CH$_2$)$_m$—N(CH$_3$)$_2$ | —N(CH$_2$CH$_2$CH$_3$)— |
| Ic-168 | 4 | —O—(CH$_2$)$_m$—N(CH$_3$)$_2$ | —N(CH$_2$CH$_2$CH$_3$)— |
| Ic-169 | 5 | —O—(CH$_2$)$_m$—N(CH$_3$)$_2$ | —N(CH$_2$CH$_2$CH$_3$)— |
| Ic-170 | 6 | —O—(CH$_2$)$_m$—N(CH$_3$)$_2$ | —N(C(H)(CH$_3$)(CH$_2$CH$_3$))— |
| Ic-171 | 2 | —O—(CH$_2$)$_m$—N(CH$_3$)$_2$ | —N(C(H)(CH$_3$)(CH$_2$CH$_3$))— |
| Ic-172 | 3 | —O—(CH$_2$)$_m$—N(CH$_3$)$_2$ | —N(C(H)(CH$_3$)(CH$_2$CH$_3$))— |
| Ic-173 | 4 | —O—(CH$_2$)$_m$—N(CH$_3$)$_2$ | —N(C(H)(CH$_3$)(CH$_2$CH$_3$))— |
| Ic-174 | 5 | —O—(CH$_2$)$_m$—N(CH$_3$)$_2$ | —N(C(H)(CH$_3$)(CH$_2$CH$_3$))— |
| Ic-175 | 6 | —O—(CH$_2$)$_m$—N(CH$_3$)$_2$ | —N(C(H)(CH$_3$)(CH$_2$CH$_3$))— |
| Ic-176 | 2 | —O—(CH$_2$)$_m$—N(CH$_3$)$_2$ | —N(C(H)(CH$_3$)$_2$)— |
| Ic-178 | 3 | —O—(CH$_2$)$_m$—N(CH$_3$)$_2$ | —N(C(H)(CH$_3$)$_2$)— |
| Ic-179 | 4 | —O—(CH$_2$)$_m$—N(CH$_3$)$_2$ | —N(C(H)(CH$_3$)$_2$)— |
| Ic-180 | 5 | —O—(CH$_2$)$_m$—N(CH$_3$)$_2$ | —N(C(H)(CH$_3$)$_2$)— |
| Ic-181 | 6 | —O—(CH$_2$)$_m$—N(CH$_3$)$_2$ | —N(C(H)(CH$_3$)$_2$)— |
| Ic-182 | 2 | —O—(CH$_2$)$_m$—N(CH$_3$)$_2$ | —N(C(H)(CH$_3$)$_2$)— |
| Ic-183 | 3 | —O—(CH$_2$)$_m$—N(CH$_3$)$_2$ | —N(CH$_2$C(H)(CH$_3$)$_2$)— |
| Ic-184 | 4 | —O—(CH$_2$)$_m$—N(CH$_3$)$_2$ | —N(CH$_2$C(H)(CH$_3$)$_2$)— |
| Ic-185 | 5 | —O—(CH$_2$)$_m$—N(CH$_3$)$_2$ | —N(CH$_2$C(H)(CH$_3$)$_2$)— |
| Ic-186 | 6 | —O—(CH$_2$)$_m$—N(CH$_3$)$_2$ | —N(CH$_2$C(H)(CH$_3$)$_2$)— |
| Ic-187 | 2 | 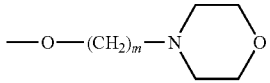 | —N(CH$_3$)— |
| Ic-188 | 3 | 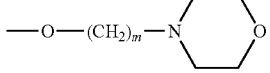 | —N(CH$_3$)— |
| Ic-189 | 4 | 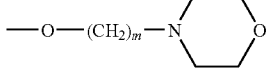 | —N(CH$_3$)— |
| Ic-190 | 5 | 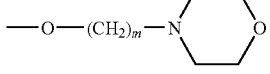 | —N(CH$_3$)— |
| Ic-191 | 6 | 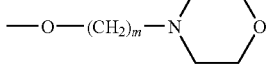 | —N(CH$_3$)— |
| Ic-192 | 2 | 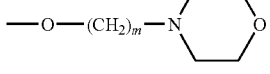 | —N(CH$_3$)— |
| Ic-193 | 3 | 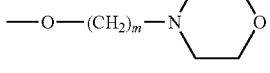 | —N(CH$_2$CH$_3$)— |
| Ic-194 | 4 | 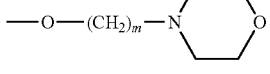 | —N(CH$_2$CH$_3$)— |
| Ic-195 | 5 | 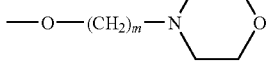 | —N(CH$_2$CH$_3$)— |

-continued

| | | | |
|---|---|---|---|
| Ic-196 | 6 | 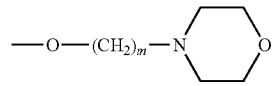 —O—(CH₂)ₘ—N(morpholine) | —N(CH₂CH₃)— |
| Ic-197 | 2 | 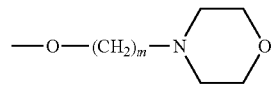 —O—(CH₂)ₘ—N(morpholine) | —N(CH₂CH₃)— |
| Ic-198 | 3 |  —O—(CH₂)ₘ—N(morpholine) | —N(CH₂CH₃)— |
| Ic-199 | 4 |  —O—(CH₂)ₘ—N(morpholine) | —N(CH₂CH₂CH₃)— |
| Ic-200 | 5 |  —O—(CH₂)ₘ—N(morpholine) | —N(CH₂CH₂CH₃)— |
| Ic-201 | 6 | 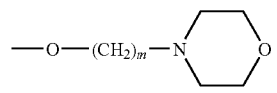 —O—(CH₂)ₘ—N(morpholine) | —N(CH₂CH₂CH₃)— |
| Ic-202 | 2 | 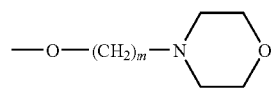 —O—(CH₂)ₘ—N(morpholine) | —N(CH₂CH₂CH₃)— |
| Ic-203 | 3 | 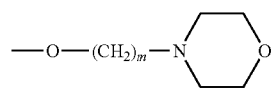 —O—(CH₂)ₘ—N(morpholine) | —N(CH₂CH₂CH₃)— |
| Ic-204 | 4 | 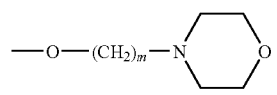 —O—(CH₂)ₘ—N(morpholine) | —N(CH₂CH₂CH₃)— |
| Ic-205 | 5 | 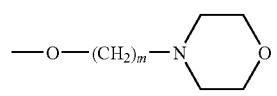 —O—(CH₂)ₘ—N(morpholine) | —N(CH₂CH₂CH₂CH₃)— |
| Ic-206 | 6 | 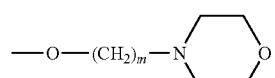 —O—(CH₂)ₘ—N(morpholine) | —N(CH₂CH₂CH₂CH₃)— |
| Ic-207 | 2 | 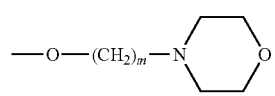 —O—(CH₂)ₘ—N(morpholine) | —N(CH₂CH₂CH₂CH₃)— |
| Ic-208 | 3 | 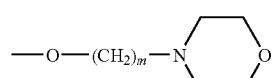 —O—(CH₂)ₘ—N(morpholine) | —N(CH₂CH₂CH₂CH₃)— |
| Ic-209 | 4 | 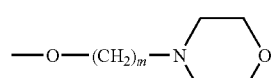 —O—(CH₂)ₘ—N(morpholine) | —N(CH₂CH₂CH₂CH₃)— |
| Ic-210 | 5 | 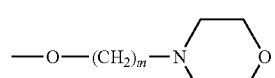 —O—(CH₂)ₘ—N(morpholine) | —N(CH₂CH₂CH₂CH₃)— |
| Ic-211 | 6 | 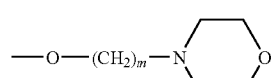 —O—(CH₂)ₘ—N(morpholine) | —N(C(H)(CH₃)(CH₂CH₃))— |

-continued

| | | | |
|---|---|---|---|
| Ic-212 | 2 | —O—(CH$_2$)$_m$—N(morpholine) | —N(C(H)(CH$_3$)(CH$_2$CH$_3$))— |
| Ic-213 | 3 | —O—(CH$_2$)$_m$—N(morpholine) | —N(C(H)(CH$_3$)(CH$_2$CH$_3$))— |
| Ic-214 | 4 | —O—(CH$_2$)$_m$—N(morpholine) | —N(C(H)(CH$_3$)(CH$_2$CH$_3$))— |
| Ic-215 | 5 | —O—(CH$_2$)$_m$—N(morpholine) | —N(C(H)(CH$_3$)(CH$_2$CH$_3$))— |
| Ic-216 | 6 | —O—(CH$_2$)$_m$—N(morpholine) | —N(C(H)(CH$_3$)(CH$_2$CH$_3$))— |
| Ic-217 | 2 | —O—(CH$_2$)$_m$—N(morpholine) | —N(C(H)(CH$_3$)$_2$)— |
| Ic-218 | 3 | —O—(CH$_2$)$_m$—N(morpholine) | —N(C(H)(CH$_3$)$_2$)— |
| Ic-219 | 4 | —O—(CH$_2$)$_m$—N(morpholine) | —N(C(H)(CH$_3$)$_2$)— |
| Ic-220 | 5 | —O—(CH$_2$)$_m$—N(morpholine) | —N(C(H)(CH$_3$)$_2$)— |
| Ic-221 | 6 | —O—(CH$_2$)$_m$—N(morpholine) | —N(C(H)(CH$_3$)$_2$)— |
| Ic-222 | 2 | —O—(CH$_2$)$_m$—N(morpholine) | —N(C(H)(CH$_3$)$_2$)— |
| Ic-223 | 3 | —O—(CH$_2$)$_m$—N(morpholine) | —N(CH$_2$C(H)(CH$_3$)$_2$)— |
| Ic-224 | 4 | —O—(CH$_2$)$_m$—N(morpholine) | —N(CH$_2$C(H)(CH$_3$)$_2$)— |
| Ic-225 | 5 | —O—(CH$_2$)$_m$—N(morpholine) | —N(CH$_2$C(H)(CH$_3$)$_2$)— |
| Ic-226 | 6 | —O—(CH$_2$)$_m$—N(morpholine) | —N(CH$_2$C(H)(CH$_3$)$_2$)— |

| Compound | —R$^1$ | X |
|---|---|---|
| Ic-267 | —CH$_2$—N(CH$_2$—CH$_3$)$_2$ | —N(CH$_3$)— |
| Ic-268 | —CH$_2$—N(CH$_2$—CH$_3$)$_2$ | —N(CH$_2$CH$_3$)— |
| Ic-269 | —CH$_2$—N(CH$_2$—CH$_3$)$_2$ | —N(CH$_2$CH$_2$CH$_3$)— |
| Ic-270 | —CH$_2$—N(CH$_2$—CH$_3$)$_2$ | —N(CH$_2$CH$_2$CH$_2$CH$_3$)— |
| Ic-271 | —CH$_2$—N(CH$_2$—CH$_3$)$_2$ | —N(C(H)(CH$_3$)(CH$_2$CH$_3$))— |

-continued

| | | |
|---|---|---|
| Ic-272 | —CH₂—N(CH₂—CH₃)₂ | —N(C(H)(CH₃)₂)— |
| Ic-273 | —CH₂—N(CH₂—CH₃)₂ | —N(CH₂C(H)(CH₃)₂)— |
| Ic-274 | —CH₂—N(CH₂—CH₃)₂ | —N(C(CH₃)₃)— |
| Ic-275 | —CH₂—N(CH₂—CH₂—CH₃)₂ | —N(CH₃)— |
| Ic-276 | —CH₂—N(CH₂—CH₂—CH₃)₂ | —N(CH₂CH₃)— |
| Ic-277 | —CH₂—N(CH₂—CH₂—CH₃)₂ | —N(CH₂CH₂CH₃)— |
| Ic-278 | —CH₂—N(CH₂—CH₂—CH₃)₂ | —N(CH₂CH₂CH₂CH₃)— |
| Ic-279 | —CH₂—N(CH₂—CH₂—CH₃)₂ | —N(C(H)(CH₃)(CH₂CH₃))— |
| Ic-280 | —CH₂—N(CH₂—CH₂—CH₃)₂ | —N(C(H)(CH₃)₂)— |
| Ic-281 | —CH₂—N(CH₂—CH₂—CH₃)₂ | —N(CH₂C(H)(CH₃)₂)— |
| Ic-282 | —CH₂—N(CH₂—CH₂—CH₃)₂ | —N(C(CH₃)₃)— |
| Ic-283 | —CH₂—N(CH₂—CH₂OH)₂ | —N(CH₃)— |
| Ic-284 | —CH₂—N(CH₂—CH₂OH)₂ | —N(CH₂CH₃)— |
| Ic-285 | —CH₂—N(CH₂—CH₂OH)₂ | —N(CH₂CH₂CH₃)— |
| Ic-286 | —CH₂—N(CH₂—CH₂OH)₂ | —N(CH₂CH₂CH₂CH₃)— |
| Ic-287 | —CH₂—N(CH₂—CH₂OH)₂ | —N(C(H)(CH₃)(CH₂CH₃))— |
| Ic-288 | —CH₂—N(CH₂—CH₂OH)₂ | —N(C(H)(CH₃)₂)— |
| Ic-289 | —CH₂—N(CH₂—CH₂OH)₂ | —N(CH₂C(H)(CH₃)₂)— |
| Ic-290 | —CH₂—N(CH₂—CH₂OH)₂ | —N(C(CH₃)₃)— |
| Ic-291 | —CH₂—N(CH₂—CH₂—N(CH₃)₂)₂ | —N(CH₃)— |
| Ic-292 | —CH₂—N(CH₂—CH₂—N(CH₃)₂)₂ | —N(CH₂CH₃)— |
| Ic-293 | —CH₂—N(CH₂—CH₂—N(CH₃)₂)₂ | —N(CH₂CH₂CH₃)— |
| Ic-294 | —CH₂—N(CH₂—CH₂—N(CH₃)₂)₂ | —N(CH₂CH₂CH₂CH₃)— |
| Ic-295 | —CH₂—N(CH₂—CH₂—N(CH₃)₂)₂ | —N(C(H)(CH₃)(CH₂CH₃))— |
| Ic-296 | —CH₂—N(CH₂—CH₂—N(CH₃)₂)₂ | —N(C(H)(CH₃)₂)— |
| Ic-297 | —CH₂—N(CH₂—CH₂—N(CH₃)₂)₂ | —N(CH₂C(H)(CH₃)₂)— |
| Ic-298 | —CH₂—N(CH₂—CH₂—N(CH₃)₂)₂ | —N(C(CH₃)₃)— |
| Ic-299 | —CH₂—N(CH₂—CH₂—CH₂—N(CH₃)₂)₂ | —N(CH₃)— |
| Ic-300 | —CH₂—N(CH₂—CH₂—CH₂—N(CH₃)₂)₂ | —N(CH₂CH₃)— |
| Ic-301 | —CH₂—N(CH₂—CH₂—CH₂—N(CH₃)₂)₂ | —N(CH₂CH₂CH₃)— |
| Ic-302 | —CH₂—N(CH₂—CH₂—CH₂—N(CH₃)₂)₂ | —N(CH₂CH₂CH₂CH₃)— |
| Ic-303 | —CH₂—N(CH₂—CH₂—CH₂—N(CH₃)₂)₂ | —N(C(H)(CH₃)(CH₂CH₃))— |
| Ic-304 | —CH₂—N(CH₂—CH₂—CH₂—N(CH₃)₂)₂ | —N(C(H)(CH₃)₂)— |
| Ic-305 | —CH₂—N(CH₂—CH₂—CH₂—N(CH₃)₂)₂ | —N(CH₂C(H)(CH₃)₂)— |
| Ic-306 | —CH₂—N(CH₂—CH₂—CH₂—N(CH₃)₂)₂ | —N(C(CH₃)₃)— |
| Ic-307 | —CH₂—N(aziridinyl) | —N(CH₃)— |
| Ic-308 | —CH₂—N(aziridinyl) | —N(CH₂CH₃)— |
| Ic-309 | —CH₂—N(aziridinyl) | —N(CH₂CH₂CH₃)— |
| Ic-310 | —CH₂—N(aziridinyl) | —N(CH₂CH₂CH₂CH₃)— |
| Ic-311 | —CH₂—N(aziridinyl) | —N(C(H)(CH₃)(CH₂CH₃))— |
| Ic-312 | —CH₂—N(aziridinyl) | —N(C(H)(CH₃)₂)— |
| Ic-313 | —CH₂—N(aziridinyl) | —N(CH₂C(H)(CH₃)₂)— |
| Ic-314 | —CH₂—N(aziridinyl) | —N(C(CH₃)₃)— |
| Ic-315 | —CH₂—N(azetidinyl) | —N(CH₃)— |
| Ic-316 | —CH₂—N(azetidinyl) | —N(CH₂CH₃)— |
| Ic-317 | —CH₂—N(azetidinyl) | —N(CH₂CH₂CH₃)— |
| Ic-318 | —CH₂—N(azetidinyl) | —N(CH₂CH₂CH₂CH₃)— |

| | | |
|---|---|---|
| Ic-319 | —CH₂—N⟨azetidine⟩ | —N(C(H)(CH₃)(CH₂CH₃))— |
| Ic-320 | —CH₂—N⟨azetidine⟩ | —N(C(H)(CH₃)₂)— |
| Ic-321 | —CH₂—N⟨azetidine⟩ | —N(CH₂C(H)(CH₃)₂)— |
| Ic-322 | —CH₂—N⟨azetidine⟩ | —N(C(CH₃)₃)— |
| Ic-323 | —CH₂—N⟨pyrrolidine⟩ | —N(CH₃)— |
| Ic-324 | —CH₂—N⟨pyrrolidine⟩ | —N(CH₂CH₃)— |
| Ic-325 | —CH₂—N⟨pyrrolidine⟩ | —N(CH₂CH₃)— |
| Ic-326 | —CH₂—N⟨pyrrolidine⟩ | —N(CH₂CH₂CH₃)— |
| Ic-327 | —CH₂—N⟨pyrrolidine⟩ | —N(C(H)(CH₃)(CH₂CH₃))— |
| Ic-328 | —CH₂—N⟨pyrrolidine⟩ | —N(C(H)(CH₃)₂)— |
| Ic-329 | —CH₂—N⟨pyrrolidine⟩ | —N(CH₂C(H)(CH₃)₂)— |
| Ic-330 | —CH₂—N⟨pyrrolidine⟩ | —N(C(CH₃)₃)— |
| Ic-331 | —CH₂—N⟨3-hydroxypyrrolidine⟩ | —N(CH₃)— |
| Ic-332 | —CH₂—N⟨3-hydroxypyrrolidine⟩ | —N(CH₂CH₃)— |
| Ic-333 | —CH₂—N⟨3-hydroxypyrrolidine⟩ | —N(CH₂CH₂CH₃)— |
| Ic-334 | —CH₂—N⟨3-hydroxypyrrolidine⟩ | —N(CH₂CH₂CH₂CH₃)— |

-continued
| | | |
|---|---|---|
| Ic-335 | 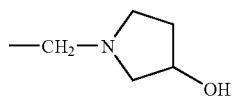 | —N(C(H)(CH$_3$)(CH$_2$CH$_3$))— |
| Ic-336 | 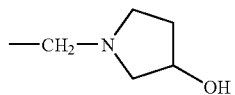 | —N(C(H)(CH$_3$)$_2$)— |
| Ic-337 | 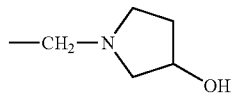 | —N(CH$_2$C(H)(CH$_3$)$_2$)— |
| Ic-338 | 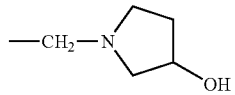 | —N(C(CH$_3$)$_3$)— |
| Ic-339 | 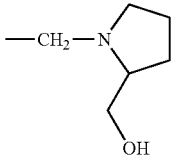 | —N(CH$_3$)— |
| Ic-340 | 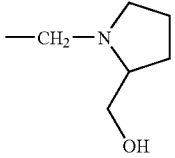 | —N(CH$_2$CH$_3$)— |
| Ic-341 | 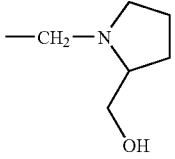 | —N(CH$_2$CH$_2$CH$_3$)— |
| Ic-342 | 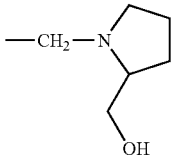 | —N(CH$_2$CH$_2$CH$_2$CH$_3$)— |
| Ic-343 | 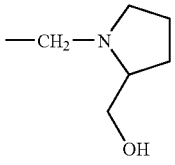 | —N(C(H)(CH$_3$)(CH$_2$CH$_3$))— |
| Ic-344 | 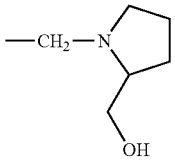 | —N(C(H)(CH$_3$)$_2$)— |
| Ic-345 | 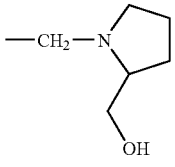 | —N(CH$_2$C(H)(CH$_3$)$_2$)— |

| | | |
|---|---|---|
| Ic-346 | —CH₂—N(pyrrolidine with CH₂OH at 2-position) | —N(C(CH₃)₃)— |
| Ic-347 | —CH₂—N(piperidine) | —N(CH₃)— |
| Ic-348 | —CH₂—N(piperidine) | —N(CH₂CH₃)— |
| Ic-349 | —CH₂—N(piperidine) | —N(CH₂CH₂CH₃)— |
| Ic-350 | —CH₂—N(piperidine) | —N(CH₂CH₂CH₃)— |
| Ic-351 | —CH₂—N(piperidine) | —N(C(H)(CH₃)(CH₂CH₃))— |
| Ic-352 | —CH₂—N(piperidine) | —N(C(H)(CH₃)₂)— |
| Ic-353 | —CH₂—N(piperidine) | —N(CH₂C(H)(CH₃)₂)— |
| Ic-354 | —CH₂—N(piperidine) | —N(C(CH₃)₃)— |
| Ic-355 | —CH₂—N(piperazine)N—CH₃ | —N(CH₃)— |
| Ic-356 | —CH₂—N(piperazine)N—CH₃ | —N(CH₂CH₃)— |
| Ic-357 | —CH₂—N(piperazine)N—CH₃ | —N(CH₂CH₃)— |
| Ic-358 | —CH₂—N(piperazine)N—CH₃ | —N(CH₂CH₂CH₃)— |
| Ic-359 | —CH₂—N(piperazine)N—CH₃ | —N(C(H)(CH₃)(CH₂CH₃))— |
| Ic-360 | —CH₂—N(piperazine)N—CH₃ | —N(C(H)(CH₃)₂)— |

-continued

| | | |
|---|---|---|
| Ic-361 | —CH₂—N(piperazine)N—CH₃ | —N(CH₂C(H)(CH₃)₂)— |
| Ic-362 | —CH₂—N(piperazine)N—CH₃ | —N(C(CH₃)₃)— |
| Ic-363 | —CH₂—N(CH₃)(CH₂-phenyl) | —N(CH₃)— |
| Ic-364 | —CH₂—N(CH₃)(CH₂-phenyl) | —N(CH₂CH₃)— |
| Ic-365 | —CH₂—N(CH₃)(CH₂-phenyl) | —N(CH₂CH₂CH₃)— |
| Ic-366 | —CH₂—N(CH₃)(CH₂-phenyl) | —N(CH₂CH₂CH₃)— |
| Ic-367 | —CH₂—N(CH₃)(CH₂-phenyl) | —N(C(H)(CH₃)(CH₂CH₃))— |
| Ic-368 | —CH₂—N(CH₃)(CH₂-phenyl) | —N(C(H)(CH₃)₂)— |
| Ic-369 | —CH₂—N(CH₃)(CH₂-phenyl) | —N(CH₂C(H)(CH₃)₂)— |
| Ic-370 | —CH₂—N(CH₃)(CH₂-phenyl) | —N(C(CH₃)₃)— |
| Ic-371 | —CH₂—N(CH₃)(CH(CH₃)₂) | —N(CH₃)— |
| Ic-372 | —CH₂—N(CH₃)(CH(CH₃)₂) | —N(CH₂CH₃)— |

-continued
| | | |
|---|---|---|
| Ic-373 | 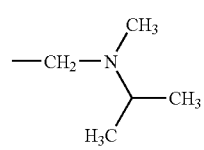 | —N(CH₂CH₂CH₃)— |
| Ic-374 | 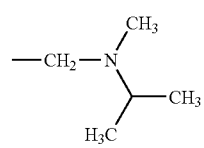 | —N(CH₂CH₂CH₂CH₃)— |
| Ic-375 | 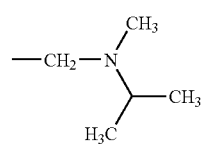 | —N(C(H)(CH₃)(CH₂CH₃))— |
| Ic-376 | 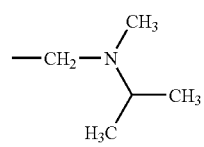 | —N(C(H)(CH₃)₂)— |
| Ic-377 | 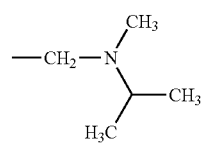 | —N(CH₂C(H)(CH₃)₂)— |
| Ic-378 | 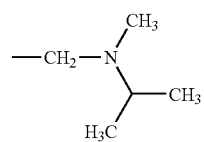 | —N(C(CH₃)₃)— |
| Ic-379 | 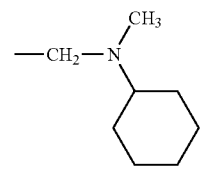 | —N(CH₃)— |
| Ic-380 | 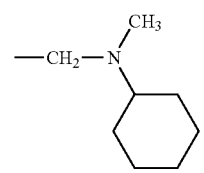 | —N(CH₂CH₃)— |
| Ic-381 | 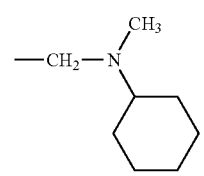 | —N(CH₂CH₃)— |
| Ic-382 | 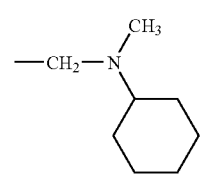 | —N(CH₂CH₂CH₃)— |

| | | |
|---|---|---|
| Ic-383 | 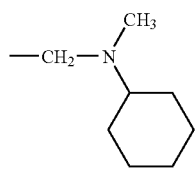 | —N(C(H)(CH₃)(CH₂CH₃))— |
| Ic-384 | 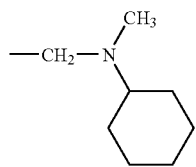 | —N(C(H)(CH₃)₂)— |
| Ic-385 | 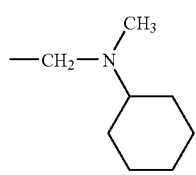 | —N(CH₂C(H)(CH₃)₂)— |
| Ic-386 | 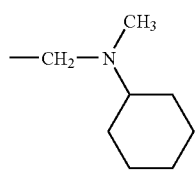 | —N(C(CH₃)₃)— |
| Ic-387 | 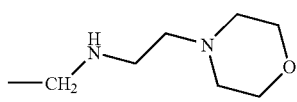 | —N(CH₃)— |
| Ic-388 | 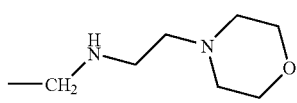 | —N(CH₂CH₃)— |
| Ic-389 | 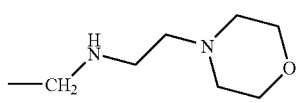 | —N(CH₂CH₂CH₃)— |
| Ic-390 | 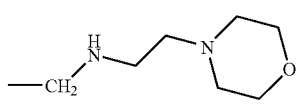 | —N(CH₂CH₂CH₂CH₃)— |
| Ic-391 | 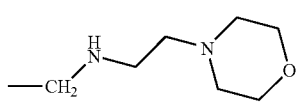 | —N(C(H)(CH₃)(CH₂CH₃))— |
| Ic-392 | 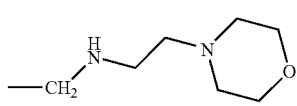 | —N(C(H)(CH₃)₂)— |
| Ic-393 | 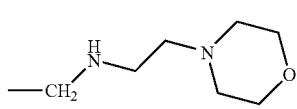 | —N(CH₂C(H)(CH₃)₂)— |
| Ic-394 | 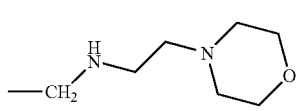 | —N(C(CH₃)₃)— |

| | | |
|---|---|---|
| Ic-395 | 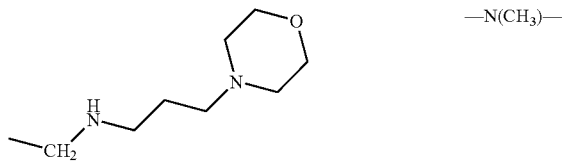 | —N(CH₃)— |
| Ic-396 | 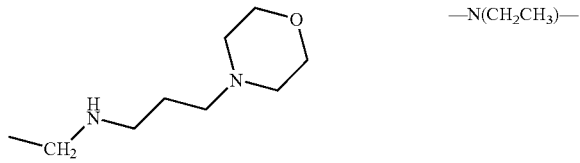 | —N(CH₂CH₃)— |
| Ic-397 | 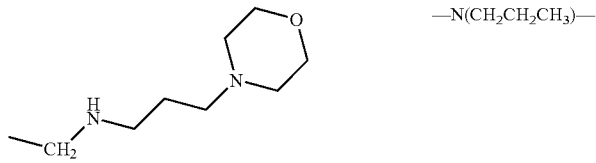 | —N(CH₂CH₂CH₃)— |
| Ic-398 | 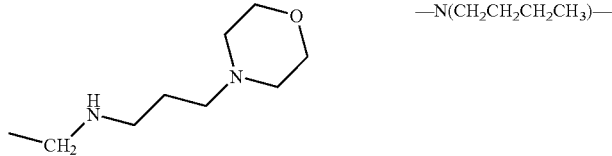 | —N(CH₂CH₂CH₂CH₃)— |
| Ic-399 | 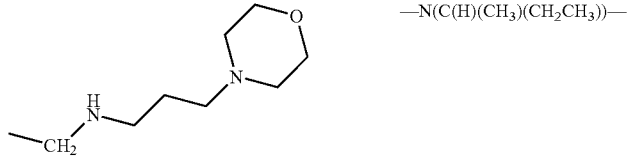 | —N(C(H)(CH₃)(CH₂CH₃))— |
| Ic-400 | 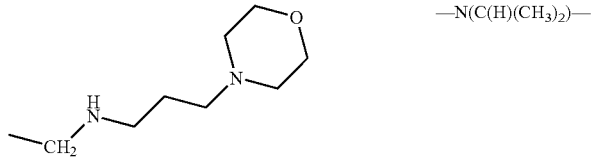 | —N(C(H)(CH₃)₂)— |
| Ic-401 | 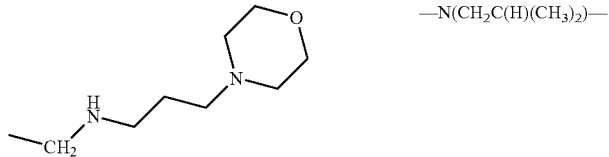 | —N(CH₂C(H)(CH₃)₂)— |
| Ic-402 | 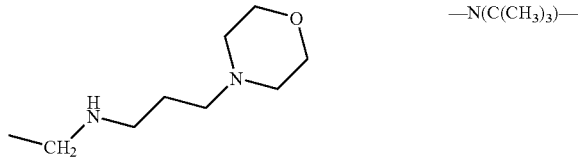 | —N(C(CH₃)₃)— |
| Ic-403 | 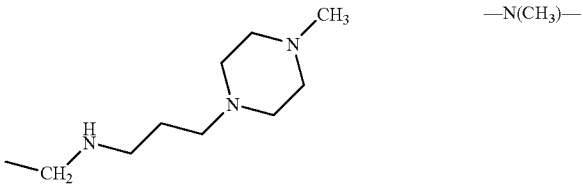 | —N(CH₃)— |

-continued
| | | |
|---|---|---|
| Ic-404 | 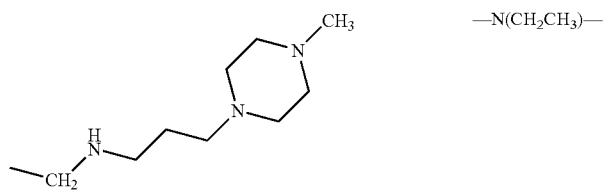 | —N(CH₂CH₃)— |
| Ic-405 | 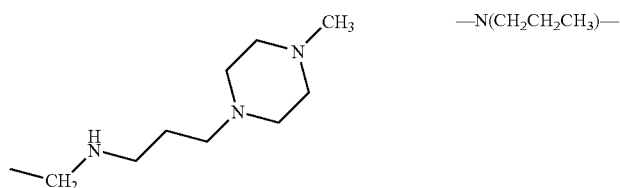 | —N(CH₂CH₂CH₃)— |
| Ic-406 | 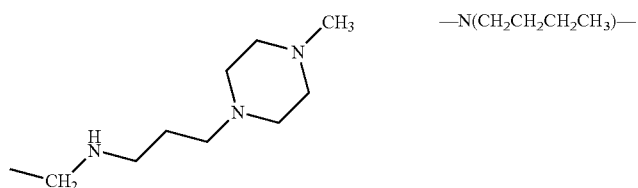 | —N(CH₂CH₂CH₂CH₃)— |
| Ic-407 | 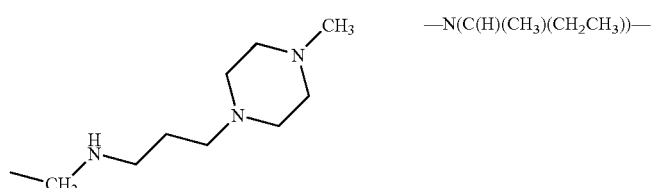 | —N(C(H)(CH₃)(CH₂CH₃))— |
| Ic-408 | 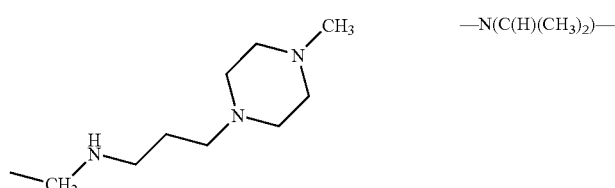 | —N(C(H)(CH₃)₂)— |
| Ic-409 | 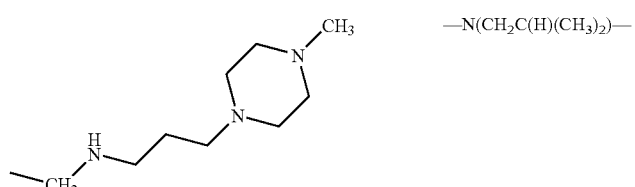 | —N(CH₂C(H)(CH₃)₂)— |
| Ic-410 | 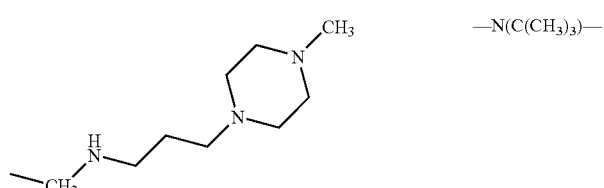 | —N(C(CH₃)₃)— |
| Ic-411 | 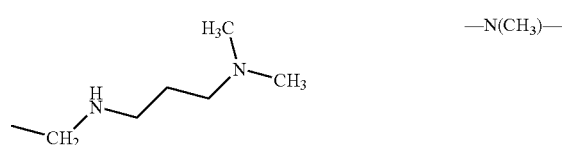 | —N(CH₃)— |
Rewriting with LaTeX:
| | | |
|---|---|---|
| Ic-404 | 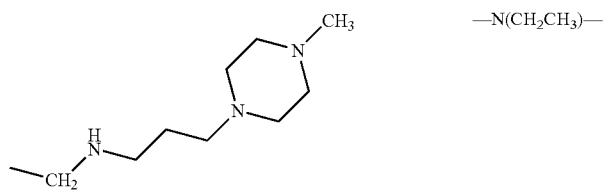 | $-N(CH_2CH_3)-$ |
| Ic-405 | 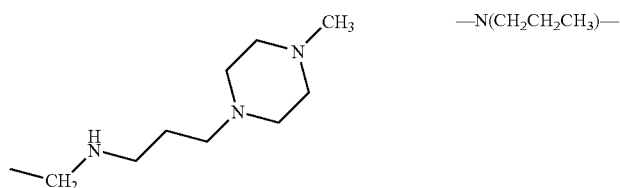 | $-N(CH_2CH_2CH_3)-$ |
| Ic-406 | 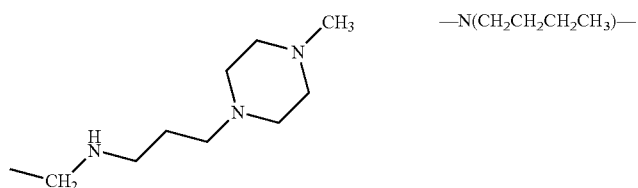 | $-N(CH_2CH_2CH_2CH_3)-$ |
| Ic-407 | 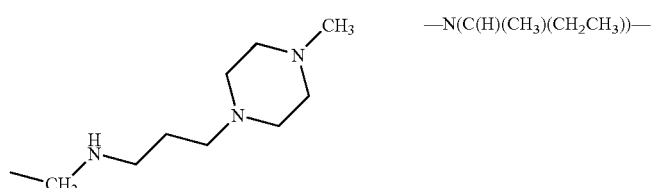 | $-N(C(H)(CH_3)(CH_2CH_3))-$ |
| Ic-408 | 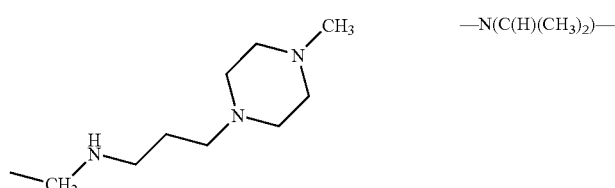 | $-N(C(H)(CH_3)_2)-$ |
| Ic-409 | 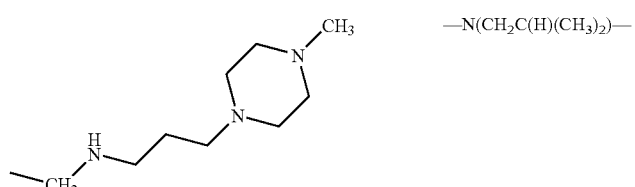 | $-N(CH_2C(H)(CH_3)_2)-$ |
| Ic-410 | 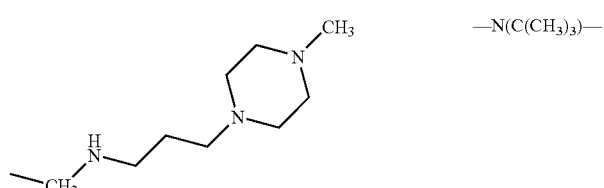 | $-N(C(CH_3)_3)-$ |
| Ic-411 | 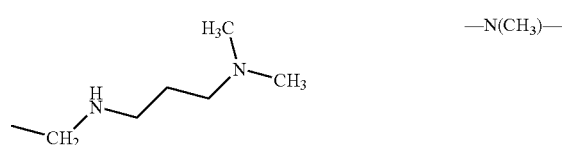 | $-N(CH_3)-$ |

-continued
| | | |
|---|---|---|
| Ic-412 | 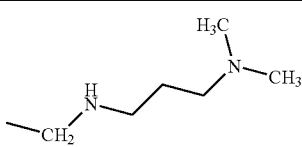 | —N(CH$_2$CH$_3$)— |
| Ic-413 | 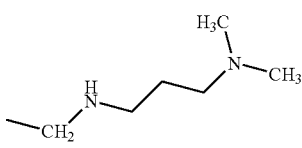 | —N(CH$_2$CH$_3$)— |
| Ic-414 | 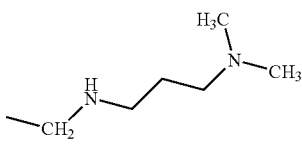 | —N(CH$_2$CH$_2$CH$_3$)— |
| Ic-415 | 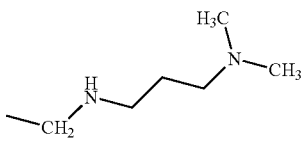 | —N(C(H)(CH$_3$)(CH$_2$CH$_3$))— |
| Ic-416 | 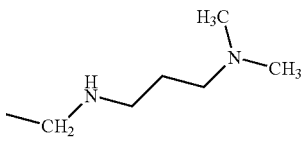 | —N(C(H)(CH$_3$)$_2$)— |
| Ic-417 | 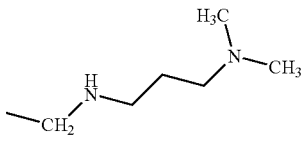 | —N(CH$_2$C(H)(CH$_3$)$_2$)— |
| Ic-418 | 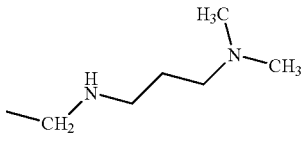 | —N(C(CH$_3$)$_3$)— |
| Ic-419 | 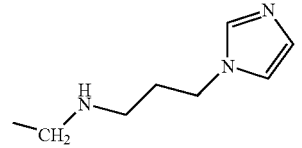 | —N(CH$_3$)— |
| Ic-420 | 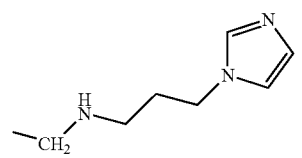 | —N(CH$_2$CH$_3$)— |
| Ic-421 | 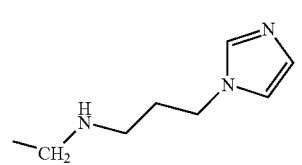 | —N(CH$_2$CH$_2$CH$_3$)— |

-continued
| | | |
|---|---|---|
| Ic-422 | 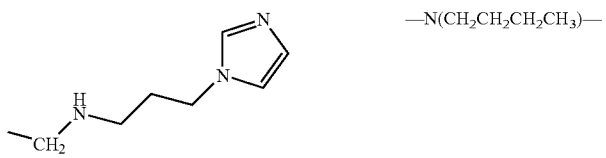 | —N(CH₂CH₂CH₃)— |
| Ic-423 | 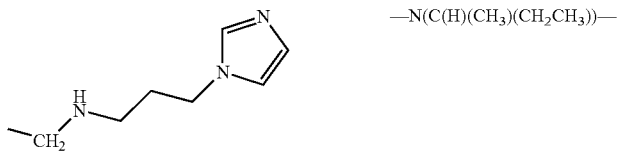 | —N(C(H)(CH₃)(CH₂CH₃))— |
| Ic-424 | 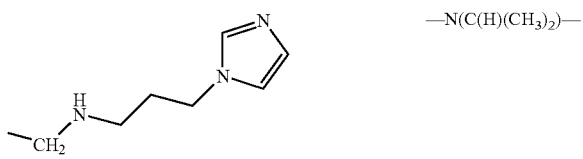 | —N(C(H)(CH₃)₂)— |
| Ic-425 | 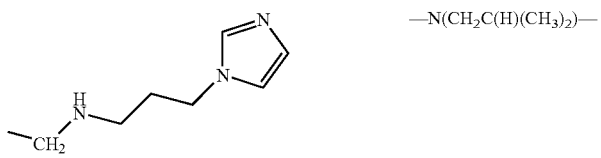 | —N(CH₂C(H)(CH₃)₂)— |
| Ic-426 | 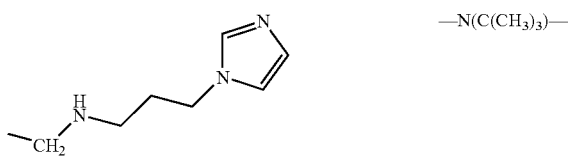 | —N(C(CH₃)₃)— |
| Ic-427 | 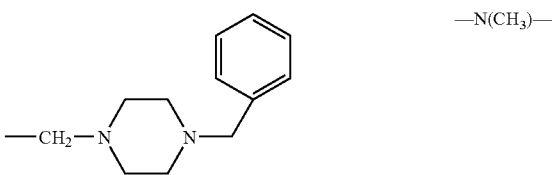 | —N(CH₃)— |
| Ic-428 | 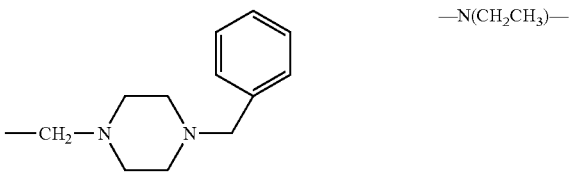 | —N(CH₂CH₃)— |
| Ic-429 | 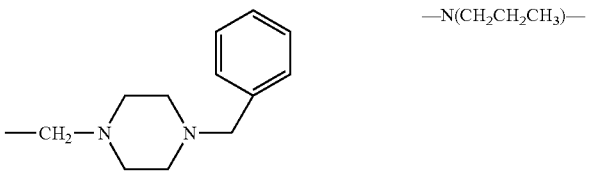 | —N(CH₂CH₂CH₃)— |
| Ic-430 | 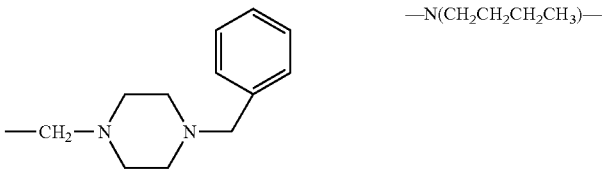 | —N(CH₂CH₂CH₃)— |

-continued
| | | |
|---|---|---|
| Ic-431 | 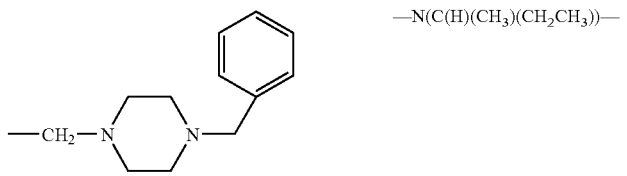 | —N(C(H)(CH₃)(CH₂CH₃))— |
| Ic-432 | 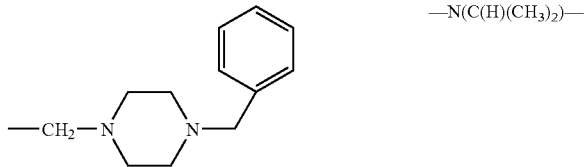 | —N(C(H)(CH₃)₂)— |
| Ic-433 | 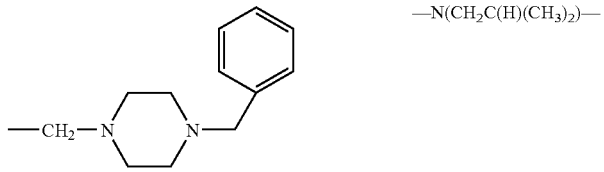 | —N(CH₂C(H)(CH₃)₂)— |
| Ic-434 | 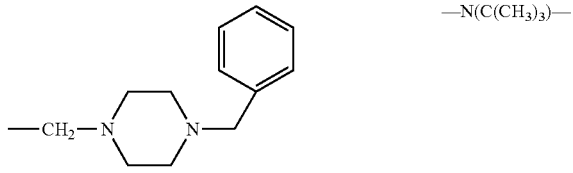 | —N(C(CH₃)₃)— |
| Ic-435 | 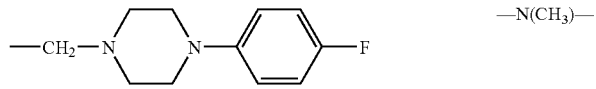 | —N(CH₃)— |
| Ic-436 | 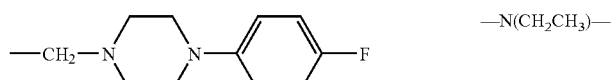 | —N(CH₂CH₃)— |
| Ic-437 | 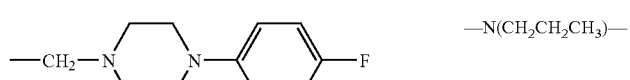 | —N(CH₂CH₂CH₃)— |
| Ic-438 | 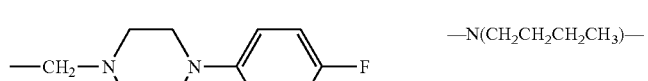 | —N(CH₂CH₂CH₂CH₃)— |
| Ic-439 | 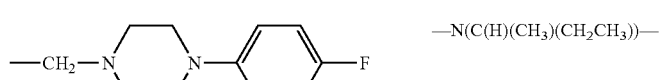 | —N(C(H)(CH₃)(CH₂CH₃))— |
| Ic-440 | 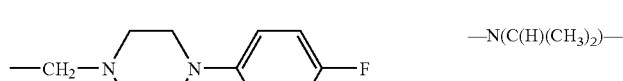 | —N(C(H)(CH₃)₂)— |
| Ic-441 | 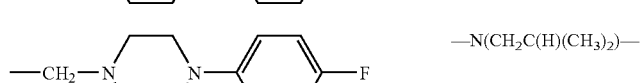 | —N(CH₂C(H)(CH₃)₂)— |
| Ic-442 | 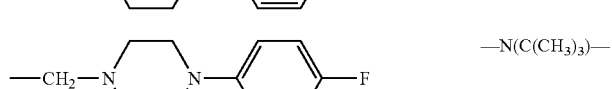 | —N(C(CH₃)₃)— |
| Ic-443 | 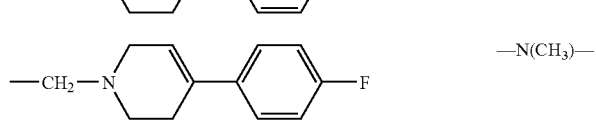 | —N(CH₃)— |

-continued
| | | |
|---|---|---|
| Ic-444 | 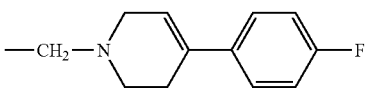 | —N(CH$_2$CH$_3$)— |
| Ic-445 | 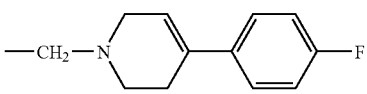 | —N(CH$_2$CH$_3$)— |
| Ic-446 | 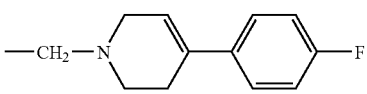 | —N(CH$_2$CH$_2$CH$_3$)— |
| Ic-447 | 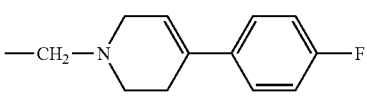 | —N(C(H)(CH$_3$)(CH$_2$CH$_3$))— |
| Ic-448 | 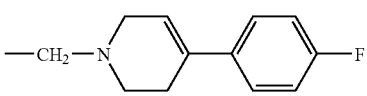 | —N(C(H)(CH$_3$)$_2$)— |
| Ic-449 | 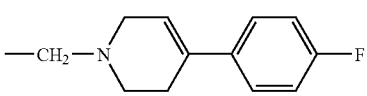 | —N(CH$_2$C(H)(CH$_3$)$_2$)— |
| Ic-450 | 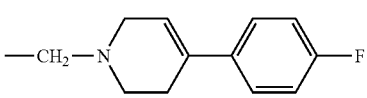 | —N(C(CH$_3$)$_3$)— |
| Ic-451 | 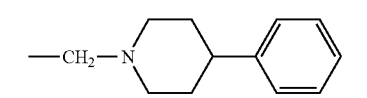 | —N(CH$_3$)— |
| Ic-452 | 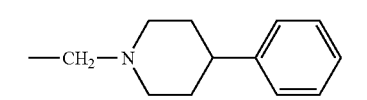 | —N(CH$_2$CH$_3$)— |
| Ic-453 | 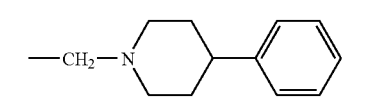 | —N(CH$_2$CH$_2$CH$_3$)— |
| Ic-454 | 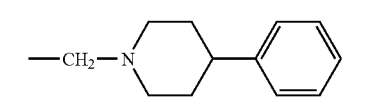 | —N(CH$_2$CH$_2$CH$_2$CH$_3$)— |
| Ic-455 | 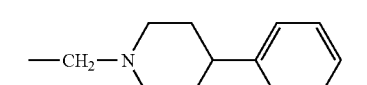 | —N(C(H)(CH$_3$)(CH$_2$CH$_3$))— |
| Ic-456 | 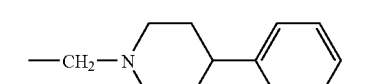 | —N(C(H)(CH$_3$)$_2$)— |
| Ic-457 | 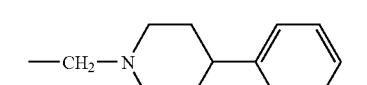 | —N(CH$_2$C(H)(CH$_3$)$_2$)— |
| Ic-458 | 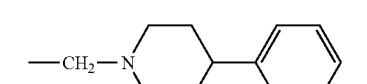 | —N(C(CH$_3$)$_3$)— |
| Ic-459 | 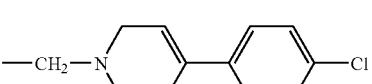 | —N(CH$_3$)— |

-continued

| | | |
|---|---|---|
| Ic-460 | —CH₂—N(tetrahydropyridine)—C₆H₄—Cl | —N(CH₂CH₃)— |
| Ic-461 | —CH₂—N(tetrahydropyridine)—C₆H₄—Cl | —N(CH₂CH₂CH₃)— |
| Ic-462 | —CH₂—N(tetrahydropyridine)—C₆H₄—Cl | —N(CH₂CH₂CH₂CH₃)— |
| Ic-463 | —CH₂—N(tetrahydropyridine)—C₆H₄—Cl | —N(C(H)(CH₃)(CH₂CH₃))— |
| Ic-464 | —CH₂—N(tetrahydropyridine)—C₆H₄—Cl | —N(C(H)(CH₃)₂)— |
| Ic-465 | —CH₂—N(tetrahydropyridine)—C₆H₄—Cl | —N(CH₂C(H)(CH₃)₂)— |
| Ic-466 | —CH₂—N(tetrahydropyridine)—C₆H₄—Cl | —N(C(CH₃)₃)— |
| Ic-467 | —CH₂—N(tetrahydropyridine)—C₆H₅ | —N(CH₃)— |
| Ic-468 | —CH₂—N(tetrahydropyridine)—C₆H₅ | —N(CH₂CH₃)— |
| Ic-469 | —CH₂—N(tetrahydropyridine)—C₆H₅ | —N(CH₂CH₂CH₃)— |
| Ic-470 | —CH₂—N(tetrahydropyridine)—C₆H₅ | —N(CH₂CH₂CH₂CH₃)— |
| Ic-471 | —CH₂—N(tetrahydropyridine)—C₆H₅ | —N(C(H)(CH₃)(CH₂CH₃))— |
| Ic-472 | —CH₂—N(tetrahydropyridine)—C₆H₅ | —N(C(H)(CH₃)₂)— |
| Ic-473 | —CH₂—N(tetrahydropyridine)—C₆H₅ | —N(CH₂C(H)(CH₃)₂)— |
| Ic-474 | —CH₂—N(tetrahydropyridine)—C₆H₅ | —N(C(CH₃)₃)— |
| Ic-475 | —CH₂—N(piperidine-4-OH)—C₆H₅ | —N(CH₃)— |

-continued

| | | |
|---|---|---|
| Ic-476 | —CH₂—N(piperidine-4-OH-4-phenyl) | —N(CH₂CH₃)— |
| Ic-477 | —CH₂—N(piperidine-4-OH-4-phenyl) | —N(CH₂CH₂CH₃)— |
| Ic-478 | —CH₂—N(piperidine-4-OH-4-phenyl) | —N(CH₂CH₂CH₃)— |
| Ic-479 | —CH₂—N(piperidine-4-OH-4-phenyl) | —N(C(H)(CH₃)(CH₂CH₃))— |
| Ic-480 | —CH₂—N(piperidine-4-OH-4-phenyl) | —N(C(H)(CH₃)₂)— |
| Ic-481 | —CH₂—N(piperidine-4-OH-4-phenyl) | —N(CH₂C(H)(CH₃)₂)— |
| Ic-482 | —CH₂—N(piperidine-4-OH-4-phenyl) | —N(C(CH₃)₃)— |
| Ic-483 | —CH₂—N(piperazine-NCH₂CH₂OP(O)(OH)₂) | —N(CH₃)— |
| Ic-484 | —CH₂—N(piperazine-NCH₂CH₂OP(O)(OH)₂) | —N(CH₂CH₃)— |
| Ic-485 | —CH₂—N(piperazine-NCH₂CH₂OP(O)(OH)₂) | —N(CH₂CH₂CH₃)— |
| Ic-486 | —CH₂—N(piperazine-NCH₂CH₂OP(O)(OH)₂) | —N(CH₂CH₂CH₂CH₃)— |
| Ic-487 | —CH₂—N(piperazine-NCH₂CH₂OP(O)(OH)₂) | —N(C(H)(CH₃)(CH₂CH₃))— |
| Ic-488 | —CH₂—N(piperazine-NCH₂CH₂OP(O)(OH)₂) | —N(C(H)(CH₃)₂)— |
| Ic-489 | —CH₂—N(piperazine-NCH₂CH₂OP(O)(OH)₂) | —N(CH₂C(H)(CH₃)₂)— |
| Ic-490 | —CH₂—N(piperazine-NCH₂CH₂OP(O)(OH)₂) | —N(C(CH₃)₃)— |
| Ic-491 | —CH₂—CH₂—CH₂—OP(O)(OH)₂ | —N(CH₃)— |
| Ic-492 | —CH₂—CH₂—CH₂—OP(O)(OH)₂ | —N(CH₂CH₃)— |
| Ic-493 | —CH₂—CH₂—CH₂—OP(O)(OH)₂ | —N(CH₂CH₂CH₃)— |
| Ic-494 | —CH₂—CH₂—CH₂—OP(O)(OH)₂ | —N(CH₂CH₂CH₂CH₃)— |

| | | |
|---|---|---|
| Ic-495 | —CH₂—CH₂—CH₂—OP(O)(OH)₂ | —N(C(H)(CH₃)(CH₂CH₃))— |
| Ic-496 | —CH₂—CH₂—CH₂—OP(O)(OH)₂ | —N(C(H)(CH₃)₂)— |
| Ic-497 | —CH₂—CH₂—CH₂—OP(O)(OH)₂ | —N(CH₂C(H)(CH₃)₂)— |
| Ic-498 | —CH₂—CH₂—CH₂—OP(O)(OH)₂ | —N(C(CH₃)₃)— |
| Ic-499 | —CH₂—CH₂—CH₂—OS(O)₂OH | —N(CH₃)— |
| Ic-500 | —CH₂—CH₂—CH₂—OS(O)₂OH | —N(CH₂CH₃)— |
| Ic-501 | —CH₂—CH₂—CH₂—OS(O)₂OH | —N(CH₂CH₂CH₃)— |
| Ic-502 | —CH₂—CH₂—CH₂—OS(O)₂OH | —N(CH₂CH₂CH₂CH₃)— |
| Ic-503 | —CH₂—CH₂—CH₂—OS(O)₂OH | —N(C(H)(CH₃)(CH₂CH₃))— |
| Ic-504 | —CH₂—CH₂—CH₂—OS(O)₂OH | —N(C(H)(CH₃)₂)— |
| Ic-505 | —CH₂—CH₂—CH₂—OS(O)₂OH | —N(CH₂C(H)(CH₃)₂)— |
| Ic-506 | —CH₂—CH₂—CH₂—OS(O)₂OH | —N(C(CH₃)₃)— |
| Ic-507 | 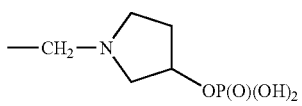 | —N(CH₃)— |
| Ic-508 | 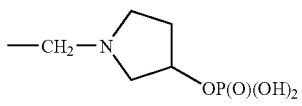 | —N(CH₂CH₃)— |
| Ic-509 | 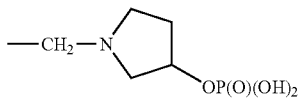 | —N(CH₂CH₂CH₃)— |
| Ic-510 | 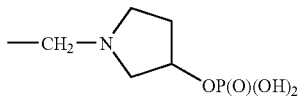 | —N(CH₂CH₂CH₂CH₃)— |
| Ic-511 | 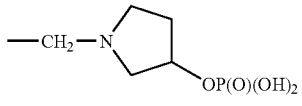 | —N(C(H)(CH₃)(CH₂CH₃))— |
| Ic-512 | 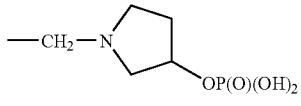 | —N(C(H)(CH₃)₂)— |
| Ic-513 | 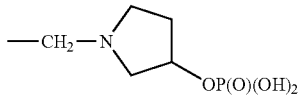 | —N(CH₂C(H)(CH₃)₂)— |
| Ic-514 | 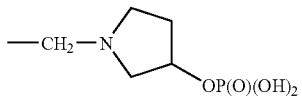 | —N(C(CH₃)₃)— |
| Ic-515 | 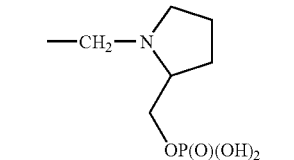 | —N(CH₃)— |
| Ic-516 | 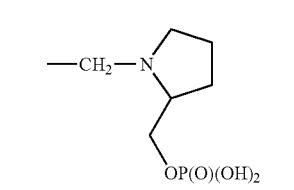 | —N(CH₂CH₃)— |

-continued

| | | |
|---|---|---|
| Ic-517 | 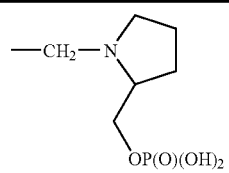 | —N(CH₂CH₂CH₃)— |
| Ic-518 | 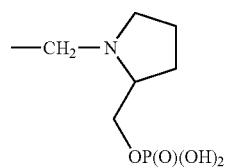 | —N(CH₂CH₂CH₃)— |
| Ic-519 | 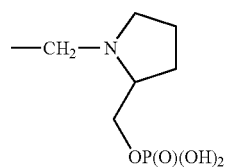 | —N(C(H)(CH₃)(CH₂CH₃))— |
| Ic-520 | 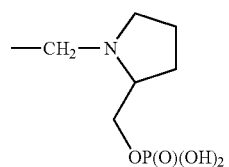 | —N(C(H)(CH₃)₂)— |
| Ic-521 | 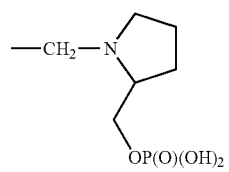 | —N(CH₂C(H)(CH₃)₂)— |
| Ic-522 | 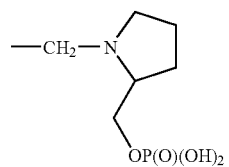 | —N(C(CH₃)₃)— |
| Ic-523 | —(CH₂)₁₀—N(CH₂—CH₂—O—CH₃)₂ | —N(CH₃)— |
| Ic-524 | —(CH₂)₁₀—N(CH₂—CH₂—O—CH₃)₂ | —N(CH₂CH₃)— |
| Ic-525 | —(CH₂)₁₀—N(CH₂—CH₂—O—CH₃)₂ | —N(CH₂CH₂CH₃)— |
| Ic-526 | —(CH₂)₁₀—N(CH₂—CH₂—O—CH₃)₂ | —N(CH₂CH₂CH₂CH₃)— |
| Ic-527 | —(CH₂)₁₀—N(CH₂—CH₂—O—CH₃)₂ | —N(C(H)(CH₃)(CH₂CH₃))— |
| Ic-528 | —(CH₂)₁₀—N(CH₂—CH₂—O—CH₃)₂ | —N(C(H)(CH₃)₂)— |
| Ic-529 | —(CH₂)₁₀—N(CH₂—CH₂—O—CH₃)₂ | —N(CH₂C(H)(CH₃)₂)— |
| Ic-530 | —(CH₂)₁₀—N(CH₂—CH₂—O—CH₃)₂ | —N(C(CH₃)₃)— |
| Ic-531 | —CH₂—N(CH₂—CH₂—O—CH₃)₂ | —N(CH₃)— |
| Ic-532 | —CH₂—N(CH₂—CH₂—O—CH₃)₂ | —N(CH₂CH₃)— |
| Ic-533 | —CH₂—N(CH₂—CH₂—O—CH₃)₂ | —N(CH₂CH₂CH₃)— |
| Ic-534 | —CH₂—N(CH₂—CH₂—O—CH₃)₂ | —N(CH₂CH₂CH₂CH₃)— |
| Ic-535 | —CH₂—N(CH₂—CH₂—O—CH₃)₂ | —N(C(H)(CH₃)(CH₂CH₃))— |
| Ic-536 | —CH₂—N(CH₂—CH₂—O—CH₃)₂ | —N(C(H)(CH₃)₂)— |
| Ic-537 | —CH₂—N(CH₂—CH₂—O—CH₃)₂ | —N(CH₂C(H)(CH₃)₂)— |
| Ic-538 | —CH₂—N(CH₂—CH₂—O—CH₃)₂ | —N(C(CH₃)₃)— |
| Ic-539 | 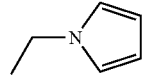 | —N(CH₃)— |
| Ic-540 | 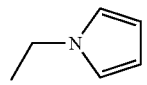 | —N(CH₂CH₃)— |

-continued
| | | |
|---|---|---|
| Ic-541 | 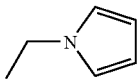 | —N(CH₂CH₂CH₃)— |
| Ic-542 | 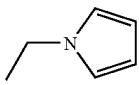 | —N(CH₂CH₂CH₂CH₃)— |
| Ic-543 | 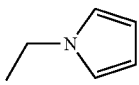 | —N(C(H)(CH₃)(CH₂CH₃))— |
| Ic-544 | 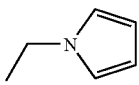 | —N(C(H)(CH₃)₂)— |
| Ic-545 | 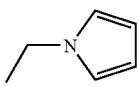 | —N(CH₂C(H)(CH₃)₂)— |
| Ic-546 | 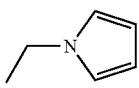 | —N(C(CH₃)₃)— |
| Ic-547 | 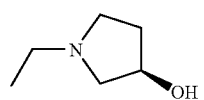 | —N(CH₃)— |
| Ic-548 | 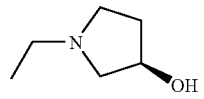 | —N(CH₂CH₃)— |
| Ic-549 | 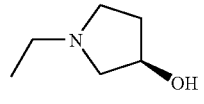 | —N(CH₂CH₃)— |
| Ic-550 | 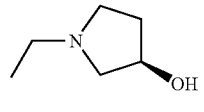 | —N(CH₂CH₂CH₂CH₃)— |
| Ic-551 | 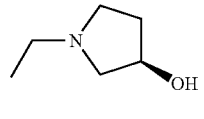 | —N(C(H)(CH₃)(CH₂CH₃))— |
| Ic-552 | 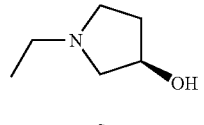 | —N(C(H)(CH₃)₂)— |
| Ic-553 | 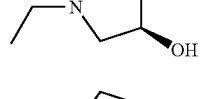 | —N(CH₂C(H)(CH₃)₂)— |
| Ic-554 | 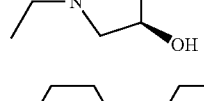 | —N(C(CH₃)₃)— |
| Ic-555 | 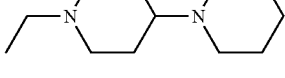 | —N(CH₃)— |

| | | -continued |
|---|---|---|
| Ic-556 | (1-ethylpiperidin-4-yl)piperidine | —N(CH₂CH₃)— |
| Ic-557 | (1-ethylpiperidin-4-yl)piperidine | —N(CH₂CH₃)— |
| Ic-558 | (1-ethylpiperidin-4-yl)piperidine | —N(CH₂CH₂CH₃)— |
| Ic-559 | (1-ethylpiperidin-4-yl)piperidine | —N(C(H)(CH₃)(CH₂CH₃))— |
| Ic-560 | (1-ethylpiperidin-4-yl)piperidine | —N(C(H)(CH₃)₂)— |
| Ic-561 | (1-ethylpiperidin-4-yl)piperidine | —N(CH₂C(H)(CH₃)₂)— |
| Ic-562 | (1-ethylpiperidin-4-yl)piperidine | —N(C(CH₃)₃)— |
| Ic-563 | (1-ethylpiperidin-4-yl)pyrrolidine | —N(CH₃)— |
| Ic-564 | (1-ethylpiperidin-4-yl)pyrrolidine | —N(CH₂CH₃)— |
| Ic-565 | (1-ethylpiperidin-4-yl)pyrrolidine | —N(CH₂CH₃)— |
| Ic-566 | (1-ethylpiperidin-4-yl)pyrrolidine | —N(CH₂CH₂CH₃)— |
| Ic-567 | (1-ethylpiperidin-4-yl)pyrrolidine | —N(C(H)(CH₃)(CH₂CH₃))— |
| Ic-568 | (1-ethylpiperidin-4-yl)pyrrolidine | —N(C(H)(CH₃)₂)— |
| Ic-569 | (1-ethylpiperidin-4-yl)pyrrolidine | —N(CH₂C(H)(CH₃)₂)— |
| Ic-570 | (1-ethylpiperidin-4-yl)pyrrolidine | —N(C(CH₃)₃)— |
| Ic-571 | (1-ethyl-2-(hydroxymethyl)pyrrolidine) | —N(CH₃)— |

-continued
| | | |
|---|---|---|
| Ic-572 | 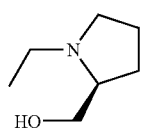 | —N(CH$_2$CH$_3$)— |
| Ic-573 | 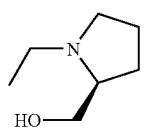 | —N(CH$_2$CH$_3$)— |
| Ic-574 | 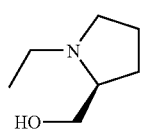 | —N(CH$_2$CH$_2$CH$_3$)— |
| Ic-575 | 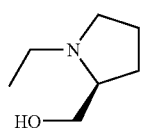 | —N(C(H)(CH$_3$)(CH$_2$CH$_3$))— |
| Ic-576 | 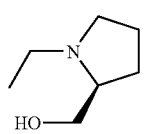 | —N(C(H)(CH$_3$)$_2$)— |
| Ic-577 | 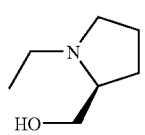 | —N(CH$_2$C(H)(CH$_3$)$_2$)— |
| Ic-578 | 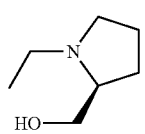 | —N(C(CH$_3$)$_3$)— |
| Ic-579 | 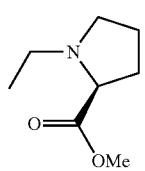 | —N(CH$_3$)— |
| Ic-580 | 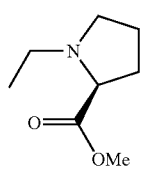 | —N(CH$_2$CH$_3$)— |
| Ic-581 | 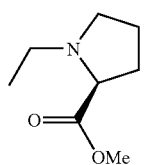 | —N(CH$_2$CH$_3$)— |

-continued

| | | |
|---|---|---|
| Ic-582 | N-ethyl pyrrolidine-2-carboxylic acid methyl ester | —N(CH₂CH₂CH₃)— |
| Ic-583 | N-ethyl pyrrolidine-2-carboxylic acid methyl ester | —N(C(H)(CH₃)(CH₂CH₃))— |
| Ic-584 | N-ethyl pyrrolidine-2-carboxylic acid methyl ester | —N(C(H)(CH₃)₂)— |
| Ic-585 | N-ethyl pyrrolidine-2-carboxylic acid methyl ester | —N(CH₂C(H)(CH₃)₂)— |
| Ic-586 | N-ethyl pyrrolidine-2-carboxylic acid methyl ester | —N(C(CH₃)₃)— |
| Ic-587 | 2-ethyl-1,2,3,4-tetrahydroisoquinoline | —N(CH₃)— |
| Ic-588 | 2-ethyl-1,2,3,4-tetrahydroisoquinoline | —N(CH₂CH₃)— |
| Ic-589 | 2-ethyl-1,2,3,4-tetrahydroisoquinoline | —N(CH₂CH₂CH₃)— |
| Ic-590 | 2-ethyl-1,2,3,4-tetrahydroisoquinoline | —N(CH₂CH₂CH₂CH₃)— |
| Ic-591 | 2-ethyl-1,2,3,4-tetrahydroisoquinoline | —N(C(H)(CH₃)(CH₂CH₃))— |
| Ic-592 | 2-ethyl-1,2,3,4-tetrahydroisoquinoline | —N(C(H)(CH₃)₂)— |
| Ic-593 | 2-ethyl-1,2,3,4-tetrahydroisoquinoline | —N(CH₂C(H)(CH₃)₂)— |

-continued
| | | |
|---|---|---|
| Ic-594 | 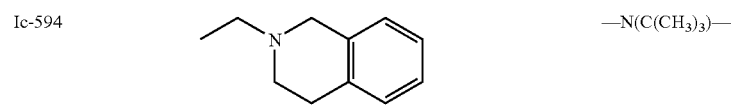 | —N(C(CH$_3$)$_3$)— |
| Ic-595 | 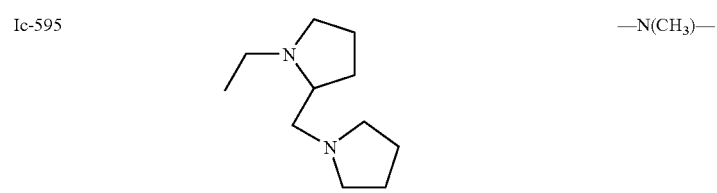 | —N(CH$_3$)— |
| Ic-596 | 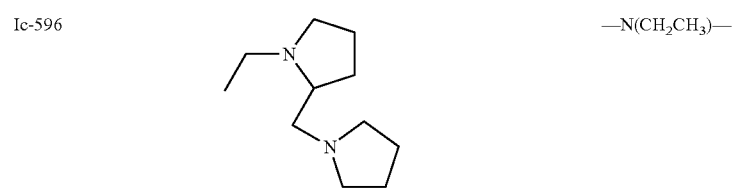 | —N(CH$_2$CH$_3$)— |
| Ic-597 | 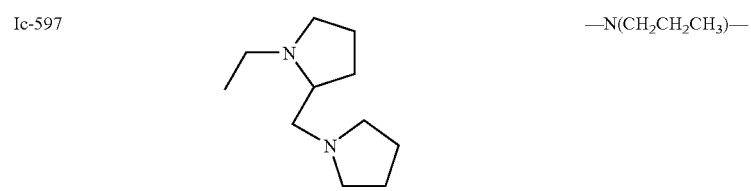 | —N(CH$_2$CH$_2$CH$_3$)— |
| Ic-598 | 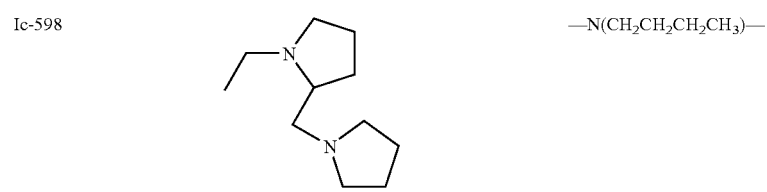 | —N(CH$_2$CH$_2$CH$_2$CH$_3$)— |
| Ic-599 | 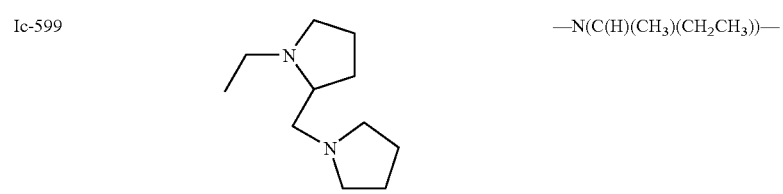 | —N(C(H)(CH$_3$)(CH$_2$CH$_3$))— |
| Ic-600 | 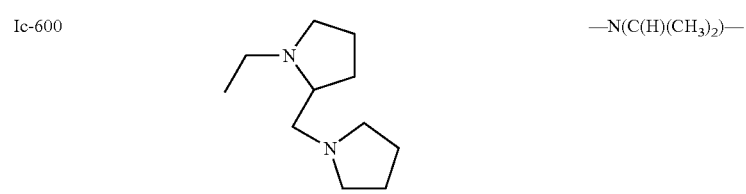 | —N(C(H)(CH$_3$)$_2$)— |
| Ic-601 | 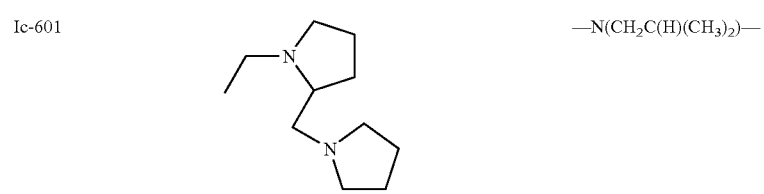 | —N(CH$_2$C(H)(CH$_3$)$_2$)— |
| Ic-602 | 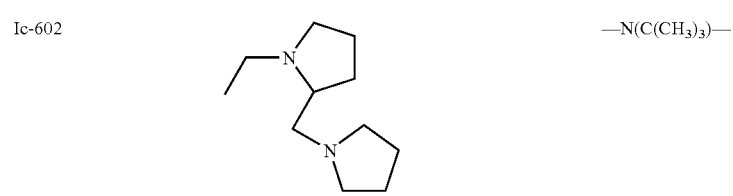 | —N(C(CH$_3$)$_3$)— |

-continued

| | | |
|---|---|---|
| Ic-603 | 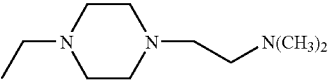 | —N(CH₃)— |
| Ic-604 | 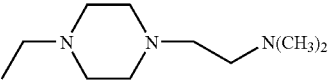 | —N(CH₂CH₃)— |
| Ic-605 | 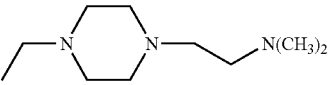 | —N(CH₂CH₂CH₃)— |
| Ic-606 | 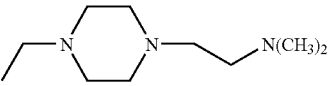 | —N(CH₂CH₂CH₂CH₃)— |
| Ic-607 | 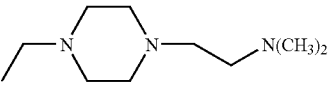 | —N(C(H)(CH₃)(CH₂CH₃))— |
| Ic-608 | 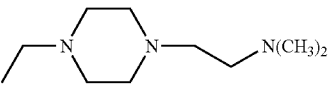 | —N(C(H)(CH₃)₂)— |
| Ic-609 | 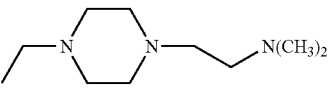 | —N(CH₂C(H)(CH₃)₂)— |
| Ic-610 | 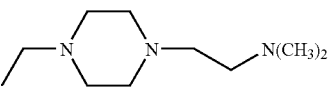 | —N(C(CH₃)₃)— |
| Ic-611 | —CH₂—NH—CH₂—CH₂—CH₂—N(CH₃)₂ | —N(CH₃)— |
| Ic-612 | —CH₂—NH—CH₂—CH₂—CH₂—N(CH₃)₂ | —N(CH₂CH₃)— |
| Ic-613 | —CH₂—NH—CH₂—CH₂—CH₂—N(CH₃)₂ | —N(CH₂CH₂CH₃)— |
| Ic-614 | —CH₂—NH—CH₂—CH₂—CH₂—N(CH₃)₂ | —N(CH₂CH₂CH₂CH₃)— |
| Ic-615 | —CH₂—NH—CH₂—CH₂—CH₂—N(CH₃)₂ | —N(C(H)(CH₃)(CH₂CH₃))— |
| Ic-616 | —CH₂—NH—CH₂—CH₂—CH₂—N(CH₃)₂ | —N(C(H)(CH₃)₂)— |
| Ic-617 | —CH₂—NH—CH₂—CH₂—CH₂—N(CH₃)₂ | —N(CH₂C(H)(CH₃)₂)— |
| Ic-618 | —CH₂—NH—CH₂—CH₂—CH₂—N(CH₃)₂ | —N(C(CH₃)₃)— |
| Ic-619 | 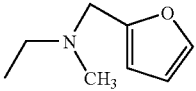 | —N(CH₃)— |
| Ic-620 | 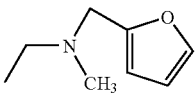 | —N(CH₂CH₃)— |
| Ic-621 | 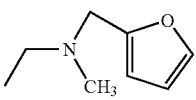 | —N(CH₂CH₂CH₃)— |
| Ic-622 | 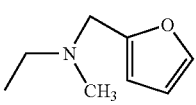 | —N(CH₂CH₂CH₂CH₃)— |
| Ic-623 | 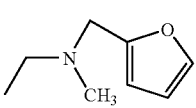 | —N(C(H)(CH₃)(CH₂CH₃))— |

-continued

| | | |
|---|---|---|
| Ic-624 | [N-ethyl-N-methyl-furfurylamine structure] | —N(C(H)(CH₃)₂)— |
| Ic-625 | [N-ethyl-N-methyl-furfurylamine structure] | —N(CH₂C(H)(CH₃)₂)— |
| Ic-626 | [N-ethyl-N-methyl-furfurylamine structure] | —N(C(CH₃)₃)— |
| Ic-627 | [1-ethyl-3-hydroxypyrrolidine structure] | —N(CH₃)— |
| Ic-628 | [1-ethyl-3-hydroxypyrrolidine structure] | —N(CH₂CH₃)— |
| Ic-629 | [1-ethyl-3-hydroxypyrrolidine structure] | —N(CH₂CH₃)— |
| Ic-630 | [1-ethyl-3-hydroxypyrrolidine structure] | —N(CH₂CH₂CH₃)— |
| Ic-631 | [1-ethyl-3-hydroxypyrrolidine structure] | —N(C(H)(CH₃)(CH₂CH₃))— |
| Ic-632 | [1-ethyl-3-hydroxypyrrolidine structure] | —N(C(H)(CH₃)₂)— |
| Ic-633 | [1-ethyl-3-hydroxypyrrolidine structure] | —N(CH₂C(H)(CH₃)₂)— |
| Ic-634 | [1-ethyl-3-hydroxypyrrolidine structure] | —N(C(CH₃)₃)— |
| Ic-635 | [1-ethyl-2-(hydroxymethyl)pyrrolidine structure] | —N(CH₃)— |
| Ic-636 | [1-ethyl-2-(hydroxymethyl)pyrrolidine structure] | —N(CH₂CH₃)— |
| Ic-637 | [1-ethyl-2-(hydroxymethyl)pyrrolidine structure] | —N(CH₂CH₂CH₃)— |

-continued
| | | |
|---|---|---|
| Ic-638 | 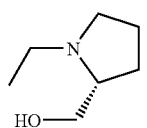 | —N(CH₂CH₂CH₃)— |
| Ic-639 | 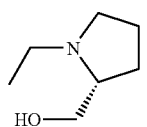 | —N(C(H)(CH₃)(CH₂CH₃))— |
| Ic-640 | 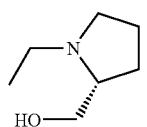 | —N(C(H)(CH₃)₂)— |
| Ic-641 | 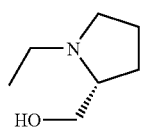 | —N(CH₂C(H)(CH₃)₂)— |
| Ic-642 | 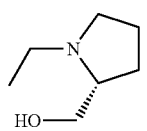 | —N(C(CH₃)₃)— |
| Ic-643 | 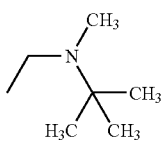 | —N(CH₃)— |
| Ic-644 | 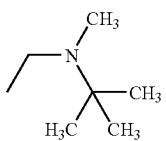 | —N(CH₂CH₃)— |
| Ic-645 | 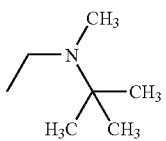 | —N(CH₂CH₂CH₃)— |
| Ic-646 | 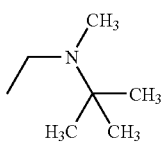 | —N(CH₂CH₂CH₂CH₃)— |
| Ic-647 | 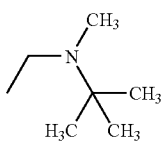 | —N(C(H)(CH₃)(CH₂CH₃))— |
| Ic-648 | 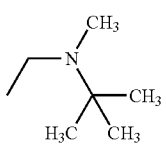 | —N(C(H)(CH₃)₂)— |

-continued
| | | |
|---|---|---|
| Ic-649 | 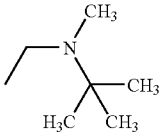 | —N(CH₂C(H)(CH₃)₂)— |
| Ic-650 | 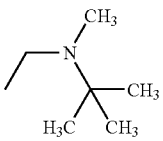 | —N(C(CH₃)₃)— |
| Ic-651 | 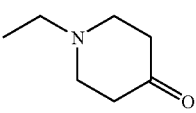 | —N(CH₃)— |
| Ic-652 | 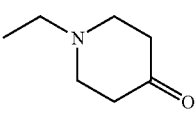 | —N(CH₂CH₃)— |
| Ic-653 | 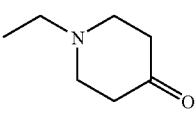 | —N(CH₂CH₃)— |
| Ic-654 | 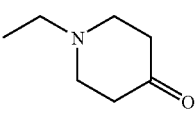 | —N(CH₂CH₂CH₃)— |
| Ic-655 | 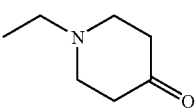 | —N(C(H)(CH₃)(CH₂CH₃))— |
| Ic-656 | 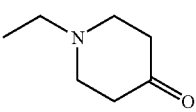 | —N(C(H)(CH₃)₂)— |
| Ic-657 | 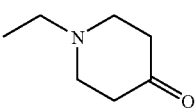 | —N(CH₂C(H)(CH₃)₂)— |
| Ic-658 | 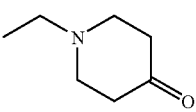 | —N(C(CH₃)₃)— |
| Ic-659 | 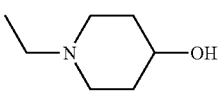 | —N(CH₃)— |
| Ic-660 | 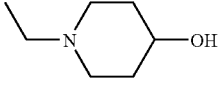 | —N(CH₂CH₃)— |
| Ic-661 | 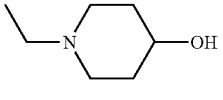 | —N(CH₂CH₃)— |
| Ic-662 | 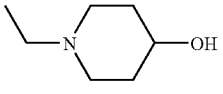 | —N(CH₂CH₂CH₃)— |

-continued
| | | |
|---|---|---|
| Ic-663 | 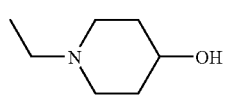 | —N(C(H)(CH$_3$)(CH$_2$CH$_3$))— |
| Ic-664 | 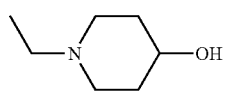 | —N(C(H)(CH$_3$)$_2$)— |
| Ic-665 | 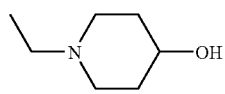 | —N(CH$_2$C(H)(CH$_3$)$_2$)— |
| Ic-666 | 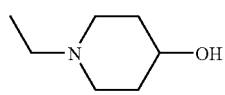 | —N(C(CH$_3$)$_3$)— |
| Ic-667 | 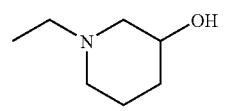 | —N(CH$_3$)— |
| Ic-668 | 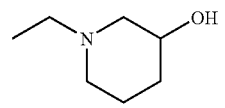 | —N(CH$_2$CH$_3$)— |
| Ic-669 | 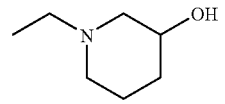 | —N(CH$_2$CH$_3$)— |
| Ic-670 | 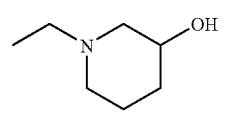 | —N(CH$_2$CH$_2$CH$_3$)— |
| Ic-671 | 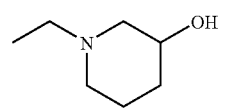 | —N(C(H)(CH$_3$)(CH$_2$CH$_3$))— |
| Ic-672 | 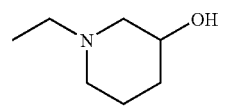 | —N(C(H)(CH$_3$)$_2$)— |
| Ic-673 | 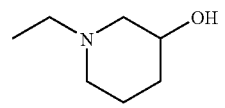 | —N(CH$_2$C(H)(CH$_3$)$_2$)— |
| Ic-674 | 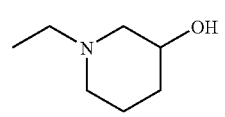 | —N(C(CH$_3$)$_3$)— |
| Ic-675 | 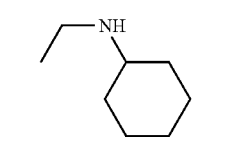 | —N(CH$_3$)— |
| Ic-676 | 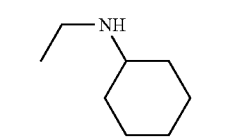 | —N(CH$_2$CH$_3$)— |

-continued
| | | |
|---|---|---|
| Ic-677 | 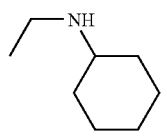 | —N(CH$_2$CH$_2$CH$_3$)— |
| Ic-678 | 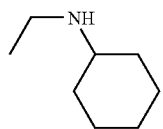 | —N(CH$_2$CH$_2$CH$_2$CH$_3$)— |
| Ic-679 | 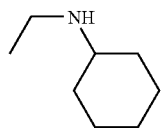 | —N(C(H)(CH$_3$)(CH$_2$CH$_3$))— |
| Ic-680 | 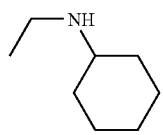 | —N(C(H)(CH$_3$)$_2$)— |
| Ic-681 | 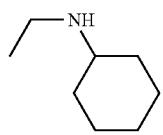 | —N(CH$_2$C(H)(CH$_3$)$_2$)— |
| Ic-682 | 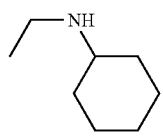 | —N(C(CH$_3$)$_3$)— |
| Ic-683 | 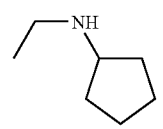 | —N(CH$_3$)— |
| Ic-684 | 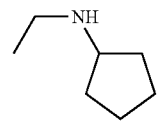 | —N(CH$_2$CH$_3$)— |
| Ic-685 | 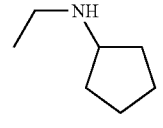 | —N(CH$_2$CH$_2$CH$_3$)— |
| Ic-686 | 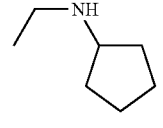 | —N(CH$_2$CH$_2$CH$_2$CH$_3$)— |
| Ic-687 | 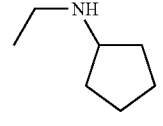 | —N(C(H)(CH$_3$)(CH$_2$CH$_3$))— |

-continued
| | | |
|---|---|---|
| Ic-688 | 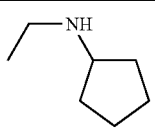 | —N(C(H)(CH$_3$)$_2$)— |
| Ic-689 | 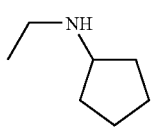 | —N(CH$_2$C(H)(CH$_3$)$_2$)— |
| Ic-690 | 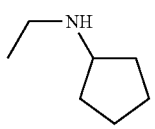 | —N(C(CH$_3$)$_3$)— |
| Ic-691 | 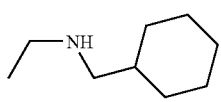 | —N(CH$_3$)— |
| Ic-692 | 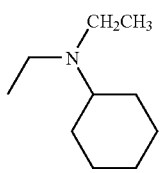 | —N(CH$_2$CH$_3$)— |
| Ic-693 | 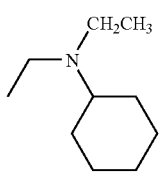 | —N(CH$_2$CH$_3$)— |
| Ic-694 | 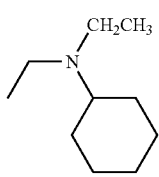 | —N(CH$_2$CH$_2$CH$_2$CH$_3$)— |
| Ic-695 | 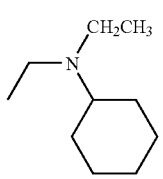 | —N(C(H)(CH$_3$)(CH$_2$CH$_3$))— |
| Ic-696 | 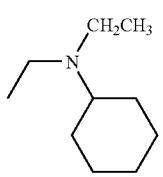 | —N(C(H)(CH$_3$)$_2$)— |
| Ic-697 | 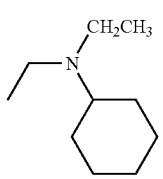 | —N(CH$_2$C(H)(CH$_3$)$_2$)— |

-continued
| | | |
|---|---|---|
| Ic-698 | 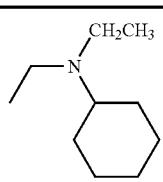 | —N(C(CH$_3$)$_3$)— |
| Ic-699 | 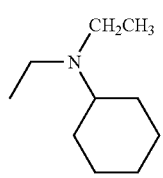 | —N(CH$_3$)— |
| Ic-700 | 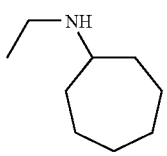 | —N(CH$_2$CH$_3$)— |
| Ic-701 | 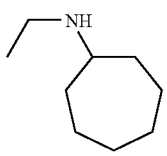 | —N(CH$_2$CH$_2$CH$_3$)— |
| Ic-702 | 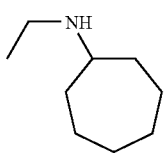 | —N(CH$_2$CH$_2$CH$_2$CH$_3$)— |
| Ic-703 | 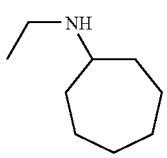 | —N(C(H)(CH$_3$)(CH$_2$CH$_3$))— |
| Ic-704 | 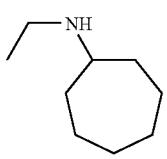 | —N(C(H)(CH$_3$)$_2$)— |
| Ic-705 | 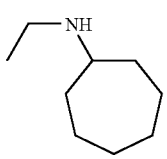 | —N(CH$_2$C(H)(CH$_3$)$_2$)— |
| Ic-706 | 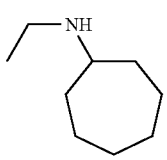 | —N(C(CH$_3$)$_3$)— |
| Ic-707 | 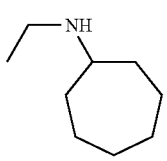 | —N(CH$_3$)— |

-continued
| | | |
|---|---|---|
| Ic-708 | 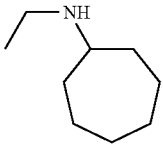 | —N(CH₂CH₃)— |
| Ic-709 | 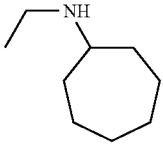 | —N(CH₂CH₃)— |
| Ic-710 | 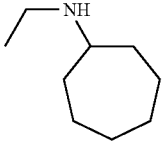 | —N(CH₂CH₂CH₃)— |
| Ic-711 | 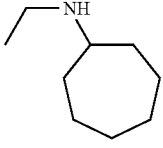 | —N(C(H)(CH₃)(CH₂CH₃))— |
| Ic-712 | 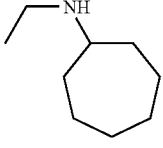 | —N(C(H)(CH₃)₂)— |
| Ic-713 | 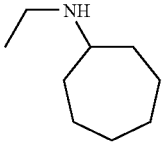 | —N(CH₂C(H)(CH₃)₂)— |
| Ic-714 | 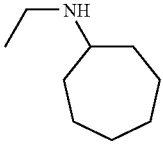 | —N(C(CH₃)₃)— |
| Ic-715 | 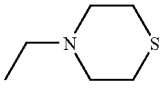 | —N(CH₃)— |
| Ic-716 | 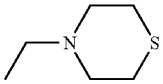 | —N(CH₂CH₃)— |
| Ic-717 | 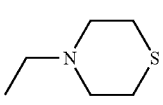 | —N(CH₂CH₃)— |
| Ic-718 | 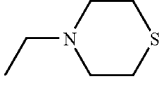 | —N(CH₂CH₂CH₃)— |
| Ic-719 | 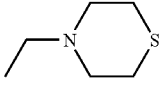 | —N(C(H)(CH₃)(CH₂CH₃))— |

-continued

| | | |
|---|---|---|
| Ic-720 | 4-ethylthiomorpholine | —N(C(H)(CH₃)₂)— |
| Ic-721 | 4-ethylthiomorpholine | —N(CH₂C(H)(CH₃)₂)— |
| Ic-722 | 4-ethylthiomorpholine | —N(C(CH₃)₃)— |
| Ic-723 | (1-ethylpiperidin-4-yl)methanol | —N(CH₃)— |
| Ic-724 | (1-ethylpiperidin-4-yl)methanol | —N(CH₂CH₃)— |
| Ic-725 | (1-ethylpiperidin-4-yl)methanol | —N(CH₂CH₃)— |
| Ic-726 | (1-ethylpiperidin-4-yl)methanol | —N(CH₂CH₂CH₃)— |
| Ic-727 | (1-ethylpiperidin-4-yl)methanol | —N(C(H)(CH₃)(CH₂CH₃))— |
| Ic-728 | (1-ethylpiperidin-4-yl)methanol | —N(C(H)(CH₃)₂)— |
| Ic-729 | (1-ethylpiperidin-4-yl)methanol | —N(CH₂C(H)(CH₃)₂)— |
| Ic-730 | (1-ethylpiperidin-4-yl)methanol | —N(C(CH₃)₃)— |
| Ic-731 | N-ethyl-2,2,6,6-tetramethylpiperidin-4-amine | —N(CH₃)— |
| Ic-732 | N-ethyl-2,2,6,6-tetramethylpiperidin-4-amine | —N(CH₂CH₃)— |

-continued
| | | |
|---|---|---|
| Ic-733 | 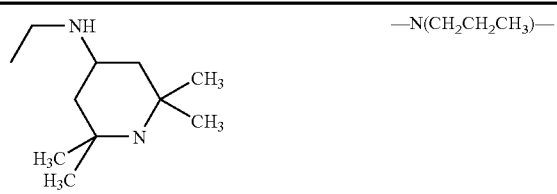 | —N(CH₂CH₂CH₃)— |
| Ic-734 |  | —N(CH₂CH₂CH₃)— |
| Ic-735 | 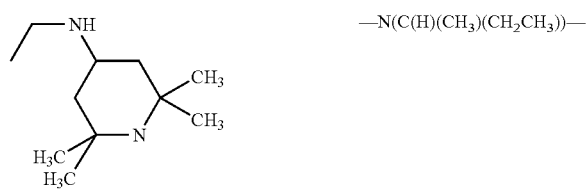 | —N(C(H)(CH₃)(CH₂CH₃))— |
| Ic-736 | 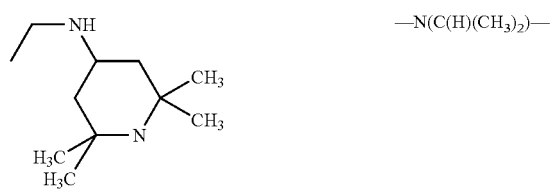 | —N(C(H)(CH₃)₂)— |
| Ic-737 |  | —N(CH₂C(H)(CH₃)₂)— |
| Ic-738 | 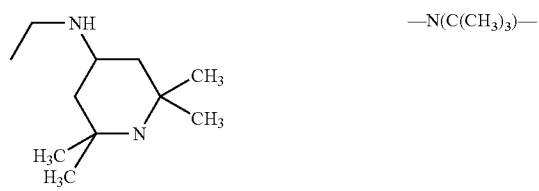 | —N(C(CH₃)₃)— |
| Ic-739 | 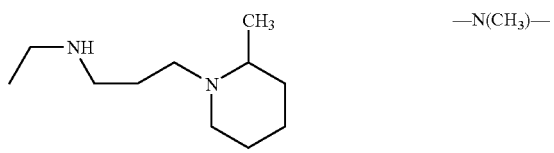 | —N(CH₃)— |
| Ic-740 | 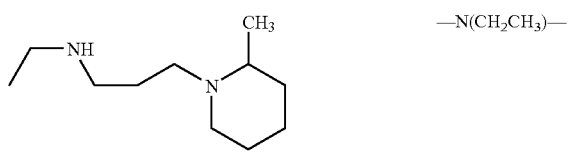 | —N(CH₂CH₃)— |
| Ic-741 | 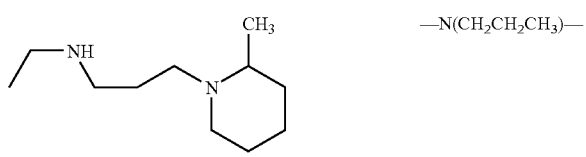 | —N(CH₂CH₂CH₃)— |

-continued

| | | |
|---|---|---|
| Ic-742 | [structure: ethyl-NH-CH2CH2CH2-N(2-methylpiperidine)] | —N(CH₂CH₂CH₃)— |
| Ic-743 | [structure: ethyl-NH-CH2CH2CH2-N(2-methylpiperidine)] | —N(C(H)(CH₃)(CH₂CH₃))— |
| Ic-744 | [structure: ethyl-NH-CH2CH2CH2-N(2-methylpiperidine)] | —N(C(H)(CH₃)₂)— |
| Ic-745 | [structure: ethyl-NH-CH2CH2CH2-N(2-methylpiperidine)] | —N(CH₂C(H)(CH₃)₂)— |
| Ic-746 | [structure: ethyl-NH-CH2CH2CH2-N(2-methylpiperidine)] | —N(C(CH₃)₃)— |
| Ic-747 | [structure: N(ethyl)(isopropyl)(cyclohexyl)] | —N(CH₃)— |
| Ic-748 | [structure: N(ethyl)(isopropyl)(cyclohexyl)] | —N(CH₂CH₃)— |
| Ic-749 | [structure: N(ethyl)(isopropyl)(cyclohexyl)] | —N(CH₂CH₂CH₃)— |
| Ic-750 | [structure: N(ethyl)(isopropyl)(cyclohexyl)] | —N(CH₂CH₂CH₂CH₃)— |

-continued
| | | |
|---|---|---|
| Ic-751 | 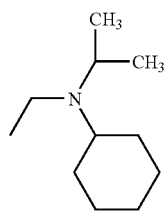 | —N(C(H)(CH₃)(CH₂CH₃))— |
| Ic-752 | 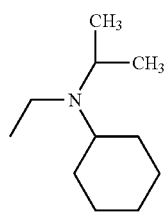 | —N(C(H)(CH₃)₂)— |
| Ic-753 | 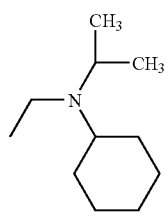 | —N(CH₂C(H)(CH₃)₂)— |
| Ic-754 | 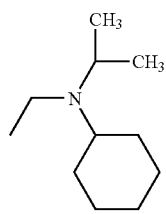 | —N(C(CH₃)₃)— |
| Ic-755 | 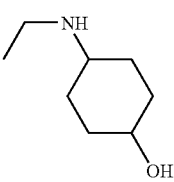 | —N(CH₃)— |
| Ic-756 | 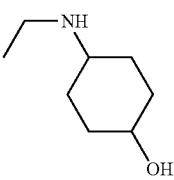 | —N(CH₂CH₃)— |
| Ic-757 | 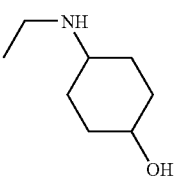 | —N(CH₂CH₂CH₃)— |
| Ic-758 | 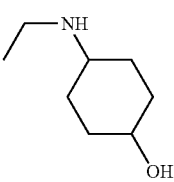 | —N(CH₂CH₂CH₂CH₃)— |

| | | |
|---|---|---|
| Ic-759 | 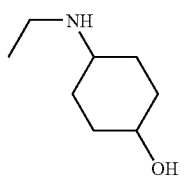 | —N(C(H)(CH₃)(CH₂CH₃))— |
| Ic-760 | 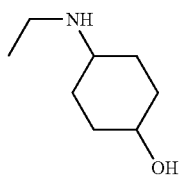 | —N(C(H)(CH₃)₂)— |
| Ic-761 | 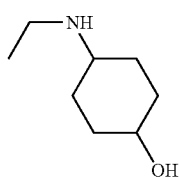 | —N(CH₂C(H)(CH₃)₂)— |
| Ic-762 | 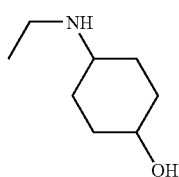 | —N(C(CH₃)₃)— |
| Ic-763 | 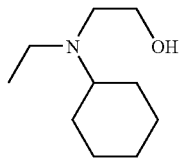 | —N(CH₃)— |
| Ic-764 | 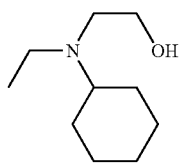 | —N(CH₂CH₃)— |
| Ic-765 | 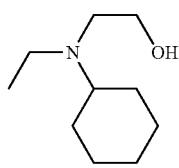 | —N(CH₂CH₃)— |
| Ic-766 | 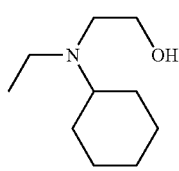 | —N(CH₂CH₂CH₃)— |
| Ic-767 | 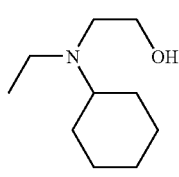 | —N(C(H)(CH₃)(CH₂CH₃))— |

-continued

| | | |
|---|---|---|
| Ic-768 | N-ethyl-N-(2-hydroxyethyl)cyclohexylamine group | —N(C(H)(CH₃)₂)— |
| Ic-769 | N-ethyl-N-(2-hydroxyethyl)cyclohexylamine group | —N(CH₂C(H)(CH₃)₂)— |
| Ic-770 | N-ethyl-N-(2-hydroxyethyl)cyclohexylamine group | —N(C(CH₃)₃)— |
| Ic-771 | 1-ethyl-4-methylpiperidine group | —N(CH₃)— |
| Ic-772 | 1-ethyl-4-methylpiperidine group | —N(CH₂CH₃)— |
| Ic-773 | 1-ethyl-4-methylpiperidine group | —N(CH₂CH₂CH₃)— |
| Ic-774 | 1-ethyl-4-methylpiperidine group | —N(CH₂CH₂CH₂CH₃)— |
| Ic-775 | 1-ethyl-4-methylpiperidine group | —N(C(H)(CH₃)(CH₂CH₃))— |
| Ic-776 | 1-ethyl-4-methylpiperidine group | —N(C(H)(CH₃)₂)— |
| Ic-777 | 1-ethyl-4-methylpiperidine group | —N(CH₂C(H)(CH₃)₂)— |
| Ic-778 | 1-ethyl-4-methylpiperidine group | —N(C(CH₃)₃)— |
| Ic-779 | —CH₂—NH—CH₃ | —N(CH₃)— |
| Ic-780 | —CH₂—NH—CH₃ | —N(CH₂CH₃)— |
| Ic-781 | —CH₂—NH—CH₃ | —N(CH₂CH₂CH₃)— |
| Ic-782 | —CH₂—NH—CH₃ | —N(CH₂CH₂CH₂CH₃)— |
| Ic-783 | —CH₂—NH—CH₃ | —N(C(H)(CH₃)(CH₂CH₃))— |
| Ic-784 | —CH₂—NH—CH₃ | —N(C(H)(CH₃)₂)— |
| Ic-785 | —CH₂—NH—CH₃ | —N(CH₂C(H)(CH₃)₂)— |
| Ic-786 | —CH₂—NH—CH₃ | —N(C(CH₃)₃)— |
| Ic-787 | —CH₂—NH—CH₂—CH₃ | —N(CH₃)— |
| Ic-788 | —CH₂—NH—CH₂—CH₃ | —N(CH₂CH₃)— |
| Ic-789 | —CH₂—NH—CH₂—CH₃ | —N(CH₂CH₂CH₃)— |
| Ic-790 | —CH₂—NH—CH₂—CH₃ | —N(CH₂CH₂CH₂CH₃)— |
| Ic-791 | —CH₂—NH—CH₂—CH₃ | —N(C(H)(CH₃)(CH₂CH₃))— |
| Ic-792 | —CH₂—NH—CH₂—CH₃ | —N(C(H)(CH₃)₂)— |
| Ic-793 | —CH₂—NH—CH₂—CH₃ | —N(CH₂C(H)(CH₃)₂)— |
| Ic-794 | —CH₂—NH—CH₂—CH₃ | —N(C(CH₃)₃)— |

-continued

| | | |
|---|---|---|
| Ic-795 | —CH₂—NH—CH₂—CH₂—CH₃ | —N(CH₃)— |
| Ic-796 | —CH₂—NH—CH₂—CH₂—CH₃ | —N(CH₂CH₃)— |
| Ic-797 | —CH₂—NH—CH₂—CH₂—CH₃ | —N(CH₂CH₂CH₃)— |
| Ic-798 | —CH₂—NH—CH₂—CH₂—CH₃ | —N(CH₂CH₂CH₂CH₃)— |
| Ic-799 | —CH₂—NH—CH₂—CH₂—CH₃ | —N(C(H)(CH₃)(CH₂CH₃))— |
| Ic-800 | —CH₂—NH—CH₂—CH₂—CH₃ | —N(C(H)(CH₃)₂)— |
| Ic-801 | —CH₂—NH—CH₂—CH₂—CH₃ | —N(CH₂C(H)(CH₃)₂)— |
| Ic-802 | —CH₂—NH—CH₂—CH₂—CH₃ | —N(C(CH₃)₃)— |
| Ic-803 | 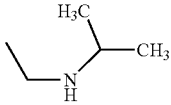 | —N(CH₃)— |
| Ic-804 | 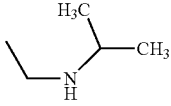 | —N(CH₂CH₃)— |
| Ic-805 | 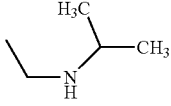 | —N(CH₂CH₂CH₃)— |
| Ic-806 | 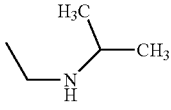 | —N(CH₂CH₂CH₂CH₃)— |
| Ic-807 | 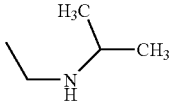 | —N(C(H)(CH₃)(CH₂CH₃))— |
| Ic-808 | 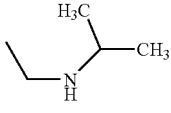 | —N(C(H)(CH₃)₂)— |
| Ic-809 | 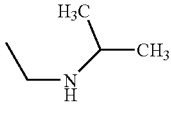 | —N(CH₂C(H)(CH₃)₂)— |
| Ic-810 | 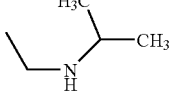 | —N(C(CH₃)₃)— |
| Ic-811 | 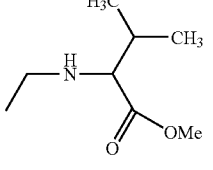 | —N(CH₃)— |
| Ic-812 | 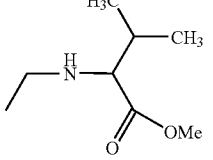 | —N(CH₂CH₃)— |

-continued
| | | |
|---|---|---|
| Ic-813 | 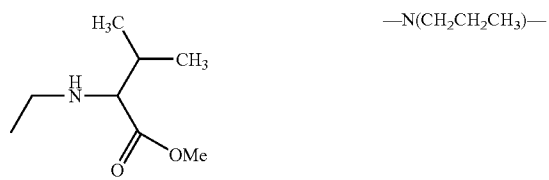 | —N(CH₂CH₂CH₃)— |
| Ic-814 | 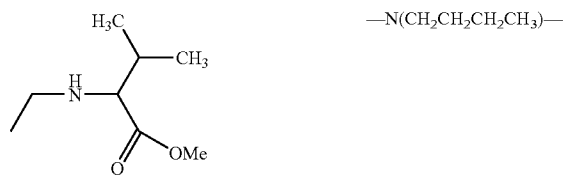 | —N(CH₂CH₂CH₂CH₃)— |
| Ic-815 | 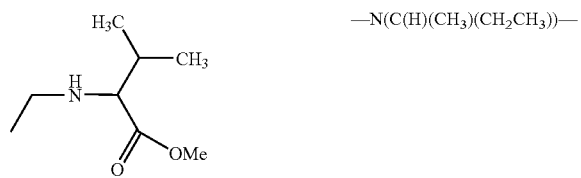 | —N(C(H)(CH₃)(CH₂CH₃))— |
| Ic-816 | 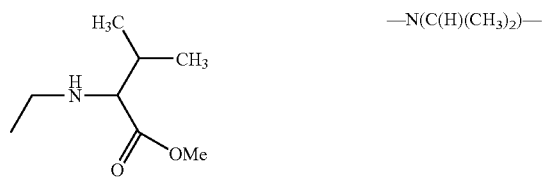 | —N(C(H)(CH₃)₂)— |
| Ic-817 | 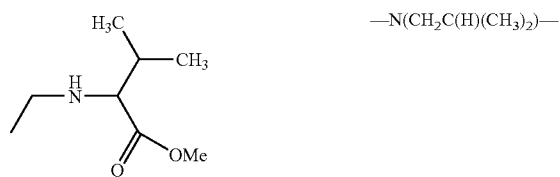 | —N(CH₂C(H)(CH₃)₂)— |
| Ic-818 | 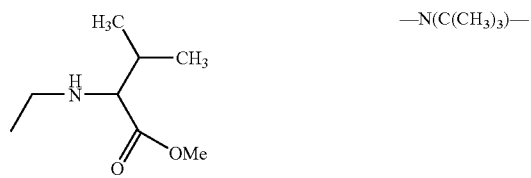 | —N(C(CH₃)₃)— |
| Ic-819 | 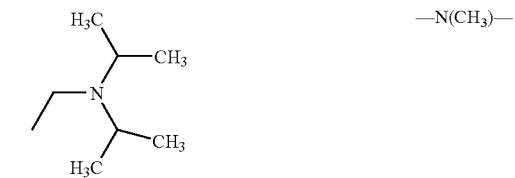 | —N(CH₃)— |
| Ic-820 | 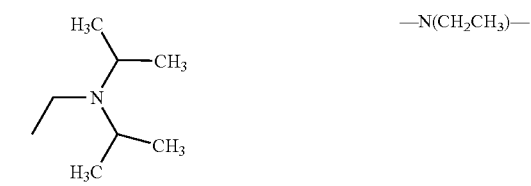 | —N(CH₂CH₃)— |

-continued

| | | |
|---|---|---|
| Ic-821 | (iPr)(Et)(iPr)N— | —N(CH₂CH₂CH₃)— |
| Ic-822 | (iPr)(Et)(iPr)N— | —N(CH₂CH₂CH₂CH₃)— |
| Ic-823 | (iPr)(Et)(iPr)N— | —N(C(H)(CH₃)(CH₂CH₃))— |
| Ic-824 | (iPr)(Et)(iPr)N— | —N(C(H)(CH₃)₂)— |
| Ic-825 | (iPr)(Et)(iPr)N— | —N(CH₂C(H)(CH₃)₂)— |
| Ic-826 | (iPr)(Et)(iPr)N— | —N(C(CH₃)₃)— |
| Ic-827 | Et-N(CH₃)-CH₂CH₂-(2-pyridyl) | —N(CH₃)— |
| Ic-828 | Et-N(CH₃)-CH₂CH₂-(2-pyridyl) | —N(CH₂CH₃)— |
| Ic-829 | Et-N(CH₃)-CH₂CH₂-(2-pyridyl) | —N(CH₂CH₃)— |
| Ic-830 | Et-N(CH₃)-CH₂CH₂-(2-pyridyl) | —N(CH₂CH₂CH₃)— |

-continued
| | | |
|---|---|---|
| Ic-831 | 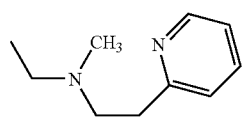 | —N(C(H)(CH₃)(CH₂CH₃))— |
| Ic-832 | 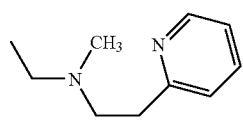 | —N(C(H)(CH₃)₂)— |
| Ic-833 | 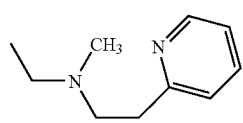 | —N(CH₂C(H)(CH₃)₂)— |
| Ic-834 | 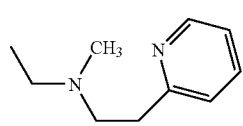 | —N(C(CH₃)₃)— |
| Ic-835 | 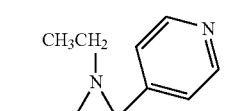 | —N(CH₃)— |
| Ic-836 | 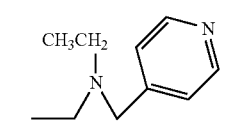 | —N(CH₂CH₃)— |
| Ic-837 | 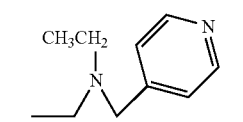 | —N(CH₂CH₃)— |
| Ic-838 | 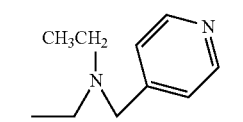 | —N(CH₂CH₂CH₃)— |
| Ic-839 | 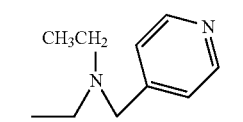 | —N(C(H)(CH₃)(CH₂CH₃))— |
| Ic-840 | 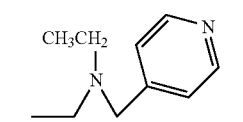 | —N(C(H)(CH₃)₂)— |
| Ic-841 | 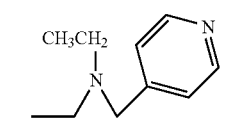 | —N(CH₂C(H)(CH₃)₂)— |
| Ic-842 | 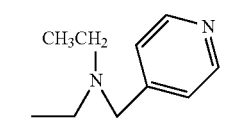 | —N(C(CH₃)₃)— |
| Ic-843 | 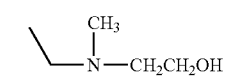 | —N(CH₃)— |

-continued

| ID | Structure 1 | Structure 2 |
|---|---|---|
| Ic-844 | CH₃–N(Et)–CH₂CH₂OH | —N(CH₂CH₃)— |
| Ic-845 | CH₃–N(Et)–CH₂CH₂OH | —N(CH₂CH₃)— |
| Ic-846 | CH₃–N(Et)–CH₂CH₂OH | —N(CH₂CH₂CH₃)— |
| Ic-847 | CH₃–N(Et)–CH₂CH₂OH | —N(C(H)(CH₃)(CH₂CH₃))— |
| Ic-848 | CH₃–N(Et)–CH₂CH₂OH | —N(C(H)(CH₃)₂)— |
| Ic-849 | CH₃–N(Et)–CH₂CH₂OH | —N(CH₂C(H)(CH₃)₂)— |
| Ic-850 | CH₃–N(Et)–CH₂CH₂OH | —N(C(CH₃)₃)— |
| Ic-851 | Et–N(piperidinyl)-piperidine | —N(CH₃)— |
| Ic-852 | Et–N(piperidinyl)-piperidine | —N(CH₂CH₃)— |
| Ic-853 | Et–N(piperidinyl)-piperidine | —N(CH₂CH₂CH₃)— |
| Ic-854 | Et–N(piperidinyl)-piperidine | —N(CH₂CH₂CH₂CH₃)— |
| Ic-855 | Et–N(piperidinyl)-piperidine | —N(C(H)(CH₃)(CH₂CH₃))— |
| Ic-856 | Et–N(piperidinyl)-piperidine | —N(C(H)(CH₃)₂)— |
| Ic-857 | Et–N(piperidinyl)-piperidine | —N(CH₂C(H)(CH₃)₂)— |
| Ic-858 | Et–N(piperidinyl)-piperidine | —N(C(CH₃)₃)— |
| Ic-859 | Et–NH–CH₂–(piperidin-1-yl) | —N(CH₃)— |
| Ic-860 | Et–NH–CH₂–(piperidin-1-yl) | —N(CH₂CH₃)— |

-continued
| | | |
|---|---|---|
| Ic-861 | 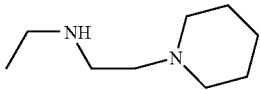 | —N(CH$_2$CH$_2$CH$_3$)— |
| Ic-862 | 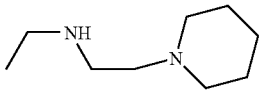 | —N(CH$_2$CH$_2$CH$_2$CH$_3$)— |
| Ic-863 | 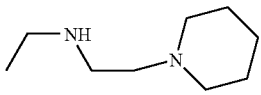 | —N(C(H)(CH$_3$)(CH$_2$CH$_3$))— |
| Ic-864 | 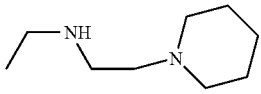 | —N(C(H)(CH$_3$)$_2$)— |
| Ic-865 | 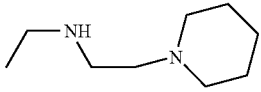 | —N(CH$_2$C(H)(CH$_3$)$_2$)— |
| Ic-866 | 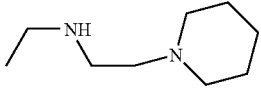 | —N(C(CH$_3$)$_3$)— |
| Ic-867 | 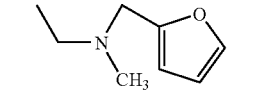 | —N(CH$_3$)— |
| Ic-868 | 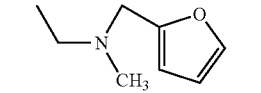 | —N(CH$_2$CH$_3$)— |
| Ic-869 | 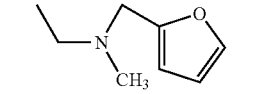 | —N(CH$_2$CH$_2$CH$_3$)— |
| Ic-870 | 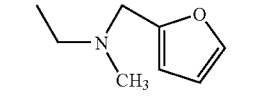 | —N(CH$_2$CH$_2$CH$_2$CH$_3$)— |
| Ic-871 | 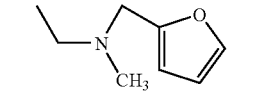 | —N(C(H)(CH$_3$)(CH$_2$CH$_3$))— |
| Ic-872 | 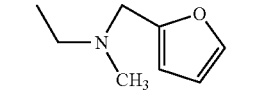 | —N(C(H)(CH$_3$)$_2$)— |
| Ic-873 | 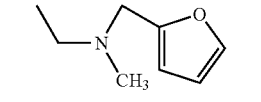 | —N(CH$_2$C(H)(CH$_3$)$_2$)— |
| Ic-874 | 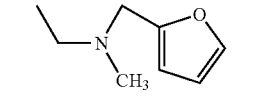 | —N(C(CH$_3$)$_3$)— |
| Ic-875 | 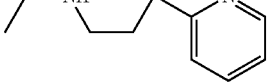 | —N(CH$_3$)— |

-continued
| | | |
|---|---|---|
| Ic-876 | 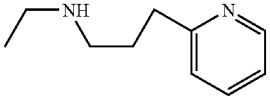 | —N(CH₂CH₃)— |
| Ic-877 | 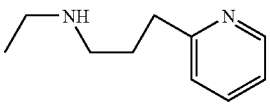 | —N(CH₂CH₃)— |
| Ic-878 | 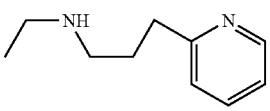 | —N(CH₂CH₂CH₃)— |
| Ic-879 | 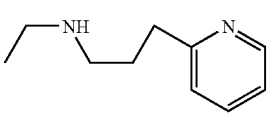 | —N(C(H)(CH₃)(CH₂CH₃))— |
| Ic-880 | 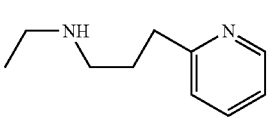 | —N(C(H)(CH₃)₂)— |
| Ic-881 | 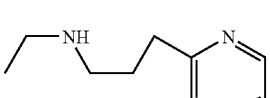 | —N(CH₂C(H)(CH₃)₂)— |
| Ic-882 | 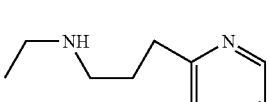 | —N(C(CH₃)₃)— |
| Ic-883 | 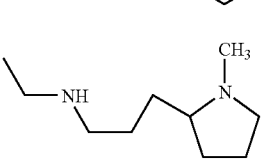 | —N(CH₃)— |
| Ic-884 | 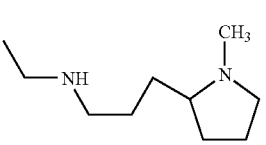 | —N(CH₂CH₃)— |
| Ic-885 | 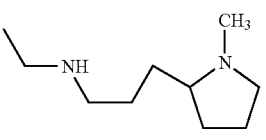 | —N(CH₂CH₂CH₃)— |
| Ic-886 | 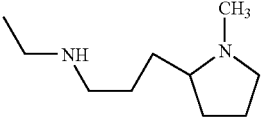 | —N(CH₂CH₂CH₃)— |
| Ic-887 | 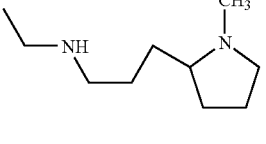 | —N(C(H)(CH₃)(CH₂CH₃))— |

-continued

| | | |
|---|---|---|
| Ic-888 | [ethyl-NH-CH2CH2-(1-methylpyrrolidin-2-yl)] | —N(C(H)(CH$_3$)$_2$)— |
| Ic-889 | [ethyl-NH-CH2CH2-(1-methylpyrrolidin-2-yl)] | —N(CH$_2$C(H)(CH$_3$)$_2$)— |
| Ic-890 | [ethyl-NH-CH2CH2-(1-methylpyrrolidin-2-yl)] | —N(C(CH$_3$)$_3$)— |
| Ic-891 | [1-ethylpiperazine, 4-NH] | —N(CH$_3$)— |
| Ic-892 | [1-ethylpiperazine, 4-NH] | —N(CH$_2$CH$_3$)— |
| Ic-893 | [1-ethylpiperazine, 4-NH] | —N(CH$_2$CH$_2$CH$_3$)— |
| Ic-894 | [1-ethylpiperazine, 4-NH] | —N(CH$_2$CH$_2$CH$_2$CH$_3$)— |
| Ic-895 | [1-ethylpiperazine, 4-NH] | —N(C(H)(CH$_3$)(CH$_2$CH$_3$))— |
| Ic-896 | [1-ethylpiperazine, 4-NH] | —N(C(H)(CH$_3$)$_2$)— |
| Ic-897 | [1-ethylpiperazine, 4-NH] | —N(CH$_2$C(H)(CH$_3$)$_2$)— |
| Ic-898 | [1-ethylpiperazine, 4-NH] | —N(C(CH$_3$)$_3$)— |
| Ic-899 | [1,4-diethylpiperazine] | —N(CH$_3$)— |
| Ic-900 | [1,4-diethylpiperazine] | —N(CH$_2$CH$_3$)— |
| Ic-901 | [1,4-diethylpiperazine] | —N(CH$_2$CH$_2$CH$_3$)— |
| Ic-902 | [1,4-diethylpiperazine] | —N(CH$_2$CH$_2$CH$_2$CH$_3$)— |

-continued

| | | |
|---|---|---|
| Ic-903 | [piperazine with two ethyl groups, one with CH3] | —N(C(H)(CH₃)(CH₂CH₃))— |
| Ic-904 | [piperazine with two ethyl groups, one with CH3] | —N(C(H)(CH₃)₂)— |
| Ic-905 | [piperazine with two ethyl groups, one with CH3] | —N(CH₂C(H)(CH₃)₂)— |
| Ic-906 | [piperazine with two ethyl groups, one with CH3] | —N(C(CH₃)₃)— |
| Ic-907 | [cyclopropyl-CH₂-NH-CH₂-] | —N(CH₃)— |
| Ic-908 | [cyclopropyl-CH₂-NH-CH₂-] | —N(CH₂CH₃)— |
| Ic-909 | [cyclopropyl-CH₂-NH-CH₂-] | —N(CH₂CH₂CH₃)— |
| Ic-910 | [cyclopropyl-CH₂-NH-CH₂-] | —N(CH₂CH₂CH₂CH₃)— |
| Ic-911 | [cyclopropyl-CH₂-NH-CH₂-] | —N(C(H)(CH₃)(CH₂CH₃))— |
| Ic-912 | [cyclopropyl-CH₂-NH-CH₂-] | —N(C(H)(CH₃)₂)— |
| Ic-913 | [cyclopropyl-CH₂-NH-CH₂-] | —N(CH₂C(H)(CH₃)₂)— |
| Ic-914 | [cyclopropyl-CH₂-NH-CH₂-] | —N(C(CH₃)₃)— |
| Ic-915 | [piperazine with ethyl and hydroxyethyl] | —N(CH₃)— |
| Ic-916 | [piperazine with ethyl and hydroxyethyl] | —N(CH₂CH₃)— |
| Ic-917 | [piperazine with ethyl and hydroxyethyl] | —N(CH₂CH₂CH₃)— |
| Ic-918 | [piperazine with ethyl and hydroxyethyl] | —N(CH₂CH₂CH₂CH₃)— |

-continued
| | | |
|---|---|---|
| Ic-919 | 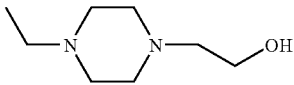 | —N(C(H)(CH₃)(CH₂CH₃))— |
| Ic-920 | 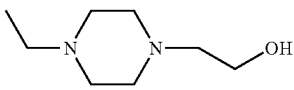 | —N(C(H)(CH₃)₂)— |
| Ic-921 | 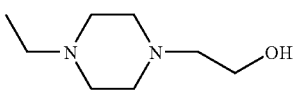 | —N(CH₂C(H)(CH₃)₂)— |
| Ic-922 | 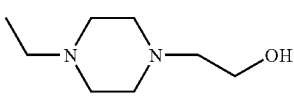 | —N(C(CH₃)₃)— |
| Ic-923 | 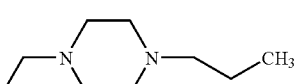 | —N(CH₃)— |
| Ic-924 | 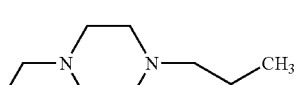 | —N(CH₂CH₃)— |
| Ic-925 | 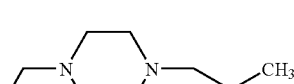 | —N(CH₂CH₃)— |
| Ic-926 | 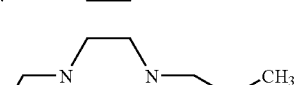 | —N(CH₂CH₂CH₃)— |
| Ic-927 | 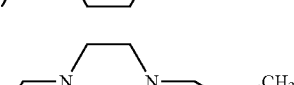 | —N(C(H)(CH₃)(CH₂CH₃))— |
| Ic-928 | 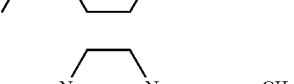 | —N(C(H)(CH₃)₂)— |
| Ic-929 | 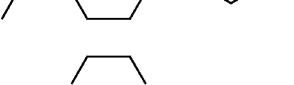 | —N(CH₂C(H)(CH₃)₂)— |
| Ic-930 | 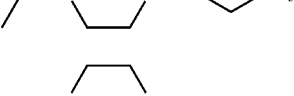 | —N(C(CH₃)₃)— |
| Ic-931 | 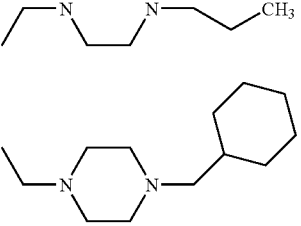 | —N(CH₃)— |
| Ic-932 | 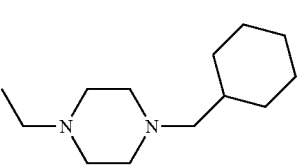 | —N(CH₂CH₃)— |

-continued
| | | |
|---|---|---|
| Ic-933 | 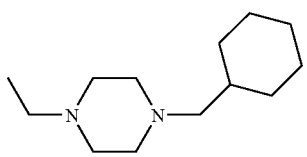 | —N(CH₂CH₂CH₃)— |
| Ic-934 | 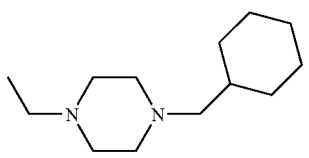 | —N(CH₂CH₂CH₃)— |
| Ic-935 | 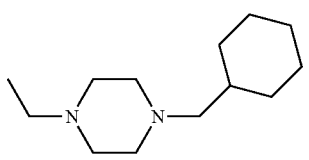 | —N(C(H)(CH₃)(CH₂CH₃))— |
| Ic-936 | 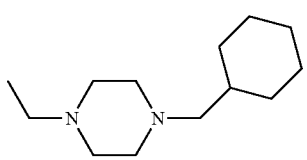 | —N(C(H)(CH₃)₂)— |
| Ic-937 | 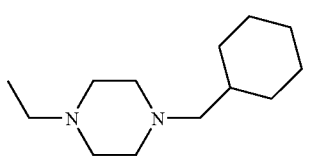 | —N(CH₂C(H)(CH₃)₂)— |
| Ic-938 | 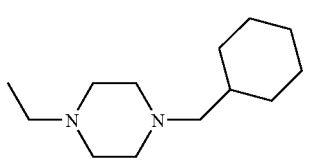 | —N(C(CH₃)₃)— |
| Ic-939 | 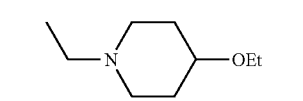 | —N(CH₃)— |
| Ic-940 |  | —N(CH₂CH₃)— |
| Ic-941 | 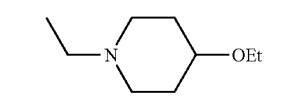 | —N(CH₂CH₂CH₃)— |
| Ic-942 | 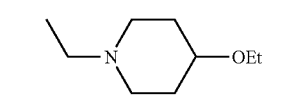 | —N(CH₂CH₂CH₃)— |
| Ic-943 | 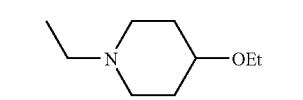 | —N(C(H)(CH₃)(CH₂CH₃))— |
| Ic-944 | 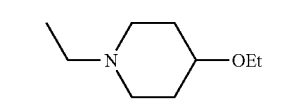 | —N(C(H)(CH₃)₂)— |

-continued
| | | |
|---|---|---|
| Ic-945 | 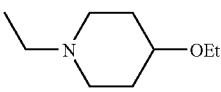 | —N(CH₂C(H)(CH₃)₂)— |
| Ic-946 | 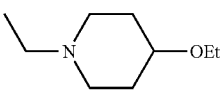 | —N(C(CH₃)₃)— |
| Ic-947 | 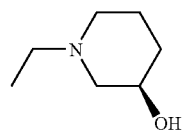 | —N(CH₃)— |
| Ic-948 | 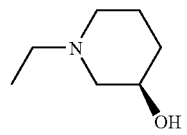 | —N(CH₂CH₃)— |
| Ic-949 | 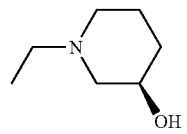 | —N(CH₂CH₂CH₃)— |
| Ic-950 | 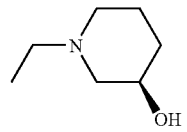 | —N(CH₂CH₂CH₃)— |
| Ic-951 | 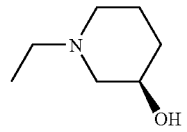 | —N(C(H)(CH₃)(CH₂CH₃))— |
| Ic-952 | 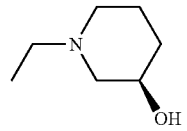 | —N(C(H)(CH₃)₂)— |
| Ic-953 | 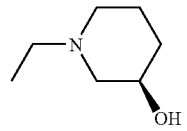 | —N(CH₂C(H)(CH₃)₂)— |
| Ic-954 | 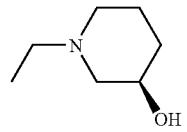 | —N(C(CH₃)₃)— |
| Ic-955 | 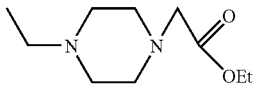 | —N(CH₃)— |
| Ic-956 | 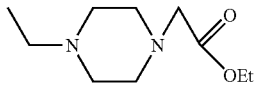 | —N(CH₂CH₃)— |
| Ic-957 | 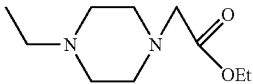 | —N(CH₂CH₂CH₃)— |

-continued

| ID | Structure | Group |
|---|---|---|
| Ic-958 | Ethyl-piperazine-CH₂-C(=O)-OEt | —N(CH₂CH₂CH₂CH₃)— |
| Ic-959 | Ethyl-piperazine-CH₂-C(=O)-OEt | —N(C(H)(CH₃)(CH₂CH₃))— |
| Ic-960 | Ethyl-piperazine-CH₂-C(=O)-OEt | —N(C(H)(CH₃)₂)— |
| Ic-961 | Ethyl-piperazine-CH₂-C(=O)-OEt | —N(CH₂C(H)(CH₃)₂)— |
| Ic-962 | Ethyl-piperazine-CH₂-C(=O)-OEt | —N(C(CH₃)₃)— |
| Ic-963 | —CH₂—N(CH₂CH₃)(CH₃) | —N(CH₃)— |
| Ic-964 | —CH₂—N(CH₂CH₃)(CH₃) | —N(CH₂CH₃)— |
| Ic-965 | —CH₂—N(CH₂CH₃)(CH₃) | —N(CH₂CH₂CH₃)— |
| Ic-966 | —CH₂—N(CH₂CH₃)(CH₃) | —N(CH₂CH₂CH₂CH₃)— |
| Ic-967 | —CH₂—N(CH₂CH₃)(CH₃) | —N(C(H)(CH₃)(CH₂CH₃))— |
| Ic-968 | —CH₂—N(CH₂CH₃)(CH₃) | —N(C(H)(CH₃)₂)— |
| Ic-969 | —CH₂—N(CH₂CH₃)(CH₃) | —N(CH₂C(H)(CH₃)₂)— |
| Ic-970 | —CH₂—N(CH₂CH₃)(CH₃) | —N(C(CH₃)₃)— |
| Ic-971 | —CH₂—N(CH₂CH₂CH₃)(CH₃) | —N(CH₃)— |
| Ic-972 | —CH₂—N(CH₂CH₂CH₃)(CH₃) | —N(CH₂CH₃)— |
| Ic-973 | —CH₂—N(CH₂CH₂CH₃)(CH₃) | —N(CH₂CH₂CH₃)— |
| Ic-974 | —CH₂—N(CH₂CH₂CH₃)(CH₃) | —N(CH₂CH₂CH₂CH₃)— |
| Ic-975 | —CH₂—N(CH₂CH₂CH₃)(CH₃) | —N(C(H)(CH₃)(CH₂CH₃))— |
| Ic-976 | —CH₂—N(CH₂CH₂CH₃)(CH₃) | —N(C(H)(CH₃)₂)— |
| Ic-977 | —CH₂—N(CH₂CH₂CH₃)(CH₃) | —N(CH₂C(H)(CH₃)₂)— |
| Ic-978 | —CH₂—N(CH₂CH₂CH₃)(CH₃) | —N(C(CH₃)₃)— |
| Ic-979 | —CH₂—N(CH₂CH₂CH₂CH₃)(CH₃) | —N(CH₃)— |
| Ic-980 | —CH₂—N(CH₂CH₂CH₂CH₃)(CH₃) | —N(CH₂CH₃)— |
| Ic-981 | —CH₂—N(CH₂CH₂CH₂CH₃)(CH₃) | —N(CH₂CH₂CH₃)— |
| Ic-982 | —CH₂—N(CH₂CH₂CH₂CH₃)(CH₃) | —N(CH₂CH₂CH₂CH₃)— |
| Ic-983 | —CH₂—N(CH₂CH₂CH₂CH₃)(CH₃) | —N(C(H)(CH₃)(CH₂CH₃))— |
| Ic-984 | —CH₂—N(CH₂CH₂CH₂CH₃)(CH₃) | —N(C(H)(CH₃)₂)— |
| Ic-985 | —CH₂—N(CH₂CH₂CH₂CH₃)(CH₃) | —N(CH₂C(H)(CH₃)₂)— |
| Ic-986 | —CH₂—N(CH₂CH₂CH₂CH₃)(CH₃) | —N(C(CH₃)₃)— |
| Ic-987 | —CH₂—NH—CH₂CH₂CH₂CH₃ | —N(CH₃)— |
| Ic-988 | —CH₂—NH—CH₂CH₂CH₂CH₃ | —N(CH₂CH₃)— |
| Ic-989 | —CH₂—NH—CH₂CH₂CH₂CH₃ | —N(CH₂CH₂CH₃)— |
| Ic-990 | —CH₂—NH—CH₂CH₂CH₂CH₃ | —N(CH₂CH₂CH₂CH₃)— |
| Ic-991 | —CH₂—NH—CH₂CH₂CH₂CH₃ | —N(C(H)(CH₃)(CH₂CH₃))— |
| Ic-992 | —CH₂—NH—CH₂CH₂CH₂CH₃ | —N(C(H)(CH₃)₂)— |
| Ic-993 | —CH₂—NH—CH₂CH₂CH₂CH₃ | —N(CH₂C(H)(CH₃)₂)— |
| Ic-994 | —CH₂—NH—CH₂CH₂CH₂CH₃ | —N(C(CH₃)₃)— |
| Ic-995 | —CH₂—NH—CH₂CH₂—O—CH₃ | —N(CH₃)— |
| Ic-996 | —CH₂—NH—CH₂CH₂—O—CH₃ | —N(CH₂CH₃)— |
| Ic-997 | —CH₂—NH—CH₂CH₂—O—CH₃ | —N(CH₂CH₂CH₃)— |
| Ic-998 | —CH₂—NH—CH₂CH₂—O—CH₃ | —N(CH₂CH₂CH₂CH₃)— |
| Ic-999 | —CH₂—NH—CH₂CH₂—O—CH₃ | —N(C(H)(CH₃)(CH₂CH₃))— |
| Ic-1000 | —CH₂—NH—CH₂CH₂—O—CH₃ | —N(C(H)(CH₃)₂)— |
| Ic-1001 | —CH₂—NH—CH₂CH₂—O—CH₃ | —N(CH₂C(H)(CH₃)₂)— |
| Ic-1002 | —CH₂—NH—CH₂CH₂—O—CH₃ | —N(C(CH₃)₃)— |
| Ic-1003 | Ethyl-piperazine-CH₂CH₂-OMe | —N(CH₃)— |
| Ic-1004 | Ethyl-piperazine-CH₂CH₂-OMe | —N(CH₂CH₃)— |
| Ic-1005 | Ethyl-piperazine-CH₂CH₂-OMe | —N(CH₂CH₂CH₃)— |

-continued
| | | |
|---|---|---|
| Ic-1006 | 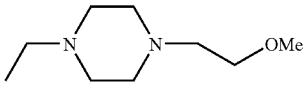 | —N(CH$_2$CH$_2$CH$_2$CH$_3$)— |
| Ic-1007 | 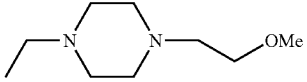 | —N(C(H)(CH$_3$)(CH$_2$CH$_3$))— |
| Ic-1008 | 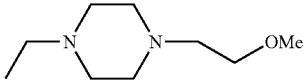 | —N(C(H)(CH$_3$)$_2$)— |
| Ic-1009 | 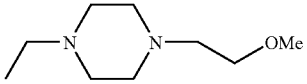 | —N(CH$_2$C(H)(CH$_3$)$_2$)— |
| Ic-1010 | 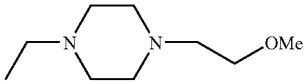 | —N(C(CH$_3$)$_3$)— |
| Ic-1011 | 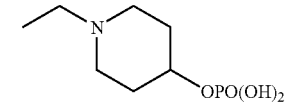 | —N(CH$_3$)— |
| Ic-1012 | 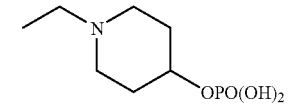 | —N(CH$_2$CH$_3$)— |
| Ic-1013 | 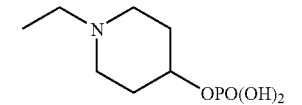 | —N(CH$_2$CH$_3$)— |
| Ic-1014 | 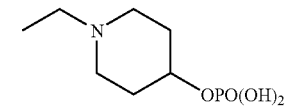 | —N(CH$_2$CH$_2$CH$_3$)— |
| Ic-1015 | 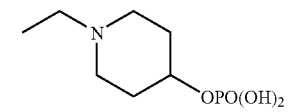 | —N(C(H)(CH$_3$)(CH$_2$CH$_3$))— |
| Ic-1016 | 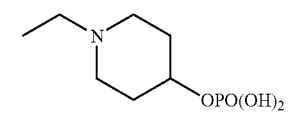 | —N(C(H)(CH$_3$)$_2$)— |
| Ic-1017 | 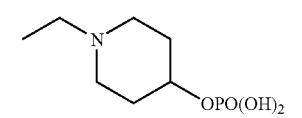 | —N(CH$_2$C(H)(CH$_3$)$_2$)— |
| Ic-1018 | 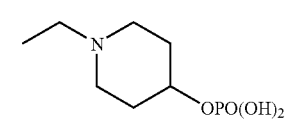 | —N(C(CH$_3$)$_3$)— |
| Ic-1019 | 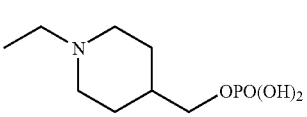 | —N(CH$_3$)— |

-continued

| | | |
|---|---|---|
| Ic-1020 | 1-ethylpiperidin-4-yl-CH2-OPO(OH)2 | —N(CH2CH3)— |
| Ic-1021 | 1-ethylpiperidin-4-yl-CH2-OPO(OH)2 | —N(CH2CH3)— |
| Ic-1022 | 1-ethylpiperidin-4-yl-CH2-OPO(OH)2 | —N(CH2CH2CH3)— |
| Ic-1023 | 1-ethylpiperidin-4-yl-CH2-OPO(OH)2 | —N(C(H)(CH3)(CH2CH3))— |
| Ic-1024 | 1-ethylpiperidin-4-yl-CH2-OPO(OH)2 | —N(C(H)(CH3)2)— |
| Ic-1025 | 1-ethylpiperidin-4-yl-CH2-OPO(OH)2 | —N(CH2C(H)(CH3)2)— |
| Ic-1026 | 1-ethylpiperidin-4-yl-CH2-OPO(OH)2 | —N(C(CH3)3)— |
| Ic-1027 | 1-ethylpiperidin-3-yl-OPO(OH)2 | —N(CH3)— |
| Ic-1028 | 1-ethylpiperidin-3-yl-OPO(OH)2 | —N(CH2CH3)— |
| Ic-1029 | 1-ethylpiperidin-3-yl-OPO(OH)2 | —N(CH2CH3)— |
| Ic-1030 | 1-ethylpiperidin-3-yl-OPO(OH)2 | —N(CH2CH2CH3)— |
| Ic-1031 | 1-ethylpiperidin-3-yl-OPO(OH)2 | —N(C(H)(CH3)(CH2CH3))— |
| Ic-1032 | 1-ethylpiperidin-3-yl-OPO(OH)2 | —N(C(H)(CH3)2)— |
| Ic-1033 | 1-ethylpiperidin-3-yl-OPO(OH)2 | —N(CH2C(H)(CH3)2)— |

-continued

| | | |
|---|---|---|
| Ic-1034 | 1-ethylpiperidin-3-yl OPO(OH)₂ | —N(C(CH₃)₃)— |
| Ic-1035 | CH₃CH₂-N(CH₃)-CH₂CH₂-OPO(OH)₂ | —N(CH₃)— |
| Ic-1036 | CH₃CH₂-N(CH₃)-CH₂CH₂-OPO(OH)₂ | —N(CH₂CH₃)— |
| Ic-1037 | CH₃CH₂-N(CH₃)-CH₂CH₂-OPO(OH)₂ | —N(CH₂CH₃)— |
| Ic-1038 | CH₃CH₂-N(CH₃)-CH₂CH₂-OPO(OH)₂ | —N(CH₂CH₂CH₃)— |
| Ic-1039 | CH₃CH₂-N(CH₃)-CH₂CH₂-OPO(OH)₂ | —N(C(H)(CH₃)(CH₂CH₃))— |
| Ic-1040 | CH₃CH₂-N(CH₃)-CH₂CH₂-OPO(OH)₂ | —N(C(H)(CH₃)₂)— |
| Ic-1041 | CH₃CH₂-N(CH₃)-CH₂CH₂-OPO(OH)₂ | —N(CH₂C(H)(CH₃)₂)— |
| Ic-1042 | CH₃CH₂-N(CH₃)-CH₂CH₂-OPO(OH)₂ | —N(C(CH₃)₃)— |

| | | |
|---|---|---|
| Ic-1043 | 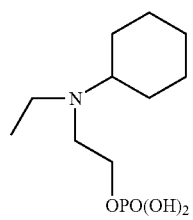 | —N(CH₃)— |
| Ic-1044 | 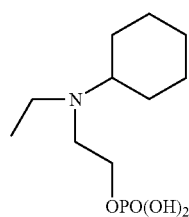 | —N(CH₂CH₃)— |
| Ic-1045 | 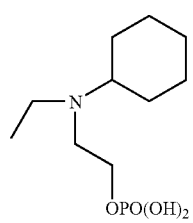 | —N(CH₂CH₂CH₃)— |
| Ic-1046 | 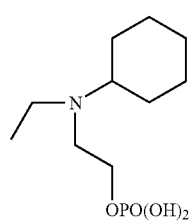 | —N(CH₂CH₂CH₂CH₃)— |
| Ic-1047 | 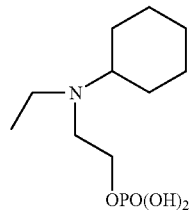 | —N(C(H)(CH₃)(CH₂CH₃))— |
| Ic-1048 | 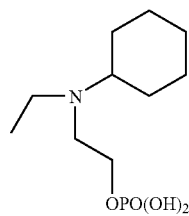 | —N(C(H)(CH₃)₂)— |
| Ic-1049 | 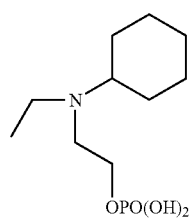 | —N(CH₂C(H)(CH₃)₂)— |

-continued
| | | |
|---|---|---|
| Ic-1050 | 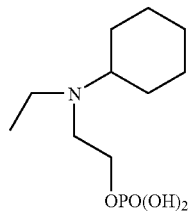 | —N(C(CH$_3$)$_3$)— |
| Ic-1051 | 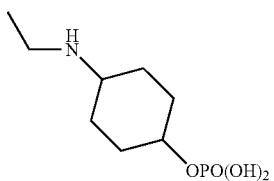 | —N(CH$_3$)— |
| Ic-1052 | 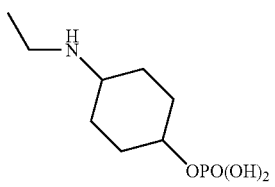 | —N(CH$_2$CH$_3$)— |
| Ic-1053 | 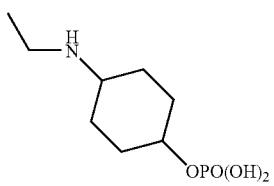 | —N(CH$_2$CH$_3$)— |
| Ic-1054 | 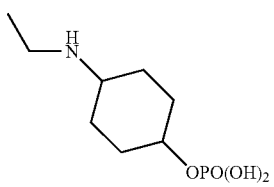 | —N(CH$_2$CH$_2$CH$_3$)— |
| Ic-1055 | 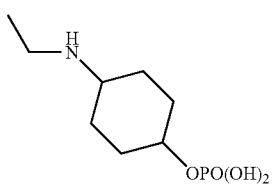 | —N(C(H)(CH$_3$)(CH$_2$CH$_3$))— |
| Ic-1056 | 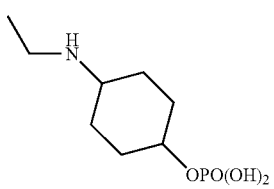 | —N(C(H)(CH$_3$)$_2$)— |
| Ic-1057 | 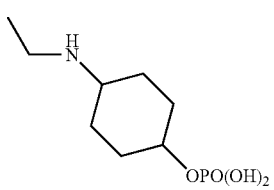 | —N(CH$_2$C(H)(CH$_3$)$_2$)— |

-continued

| | | | |
|---|---|---|---|
| Ic-1058 | 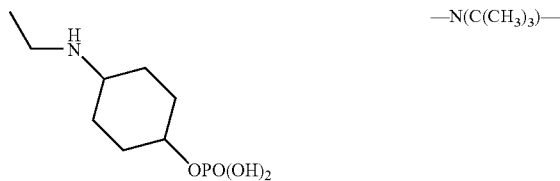 | | —N(C(CH$_3$)$_3$)— |

| Compound | n | —R$^1$ | X |
|---|---|---|---|
| Ic-c1 | 1 | —(CH$_2$)$_n$—N(CH$_3$)$_2$ | —CH(OH)— |
| Ic-c2 | 2 | —(CH$_2$)$_n$—N(CH$_3$)$_2$ | —CH(OH)— |
| Ic-c3 | 3 | —(CH$_2$)$_n$—N(CH$_3$)$_2$ | —CH(OH)— |
| Ic-c4 | 4 | —(CH$_2$)$_n$—N(CH$_3$)$_2$ | —CH(OH)— |
| Ic-c5 | 5 | —(CH$_2$)$_n$—N(CH$_3$)$_2$ | —CH(OH)— |
| Ic-c6 | 6 | —(CH$_2$)$_n$—N(CH$_3$)$_2$ | —CH(OH)— |
| Ic-c7 | 1 | —(CH$_2$)$_n$—N(CH$_3$)$_2$ | —N(C(O)N(H)—CH$_2$—CH$_2$—OH)— |
| Ic-c8 | 2 | —(CH$_2$)$_n$—N(CH$_3$)$_2$ | —N(C(O)N(H)—CH$_2$—CH$_2$—OH)— |
| Ic-c9 | 3 | —(CH$_2$)$_n$—N(CH$_3$)$_2$ | —N(C(O)N(H)—CH$_2$—CH$_2$—OH)— |
| Ic-c10 | 4 | —(CH$_2$)$_n$—N(CH$_3$)$_2$ | —N(C(O)N(H)—CH$_2$—CH$_2$—OH)— |
| Ic-c11 | 5 | —(CH$_2$)$_n$—N(CH$_3$)$_2$ | —N(C(O)N(H)—CH$_2$—CH$_2$—OH)— |
| Ic-c12 | 6 | —(CH$_2$)$_n$—N(CH$_3$)$_2$ | —N(C(O)N(H)—CH$_2$—CH$_2$—OH)— |
| Ic-c13 | 1 | —(CH$_2$)$_n$—N(CH$_3$)$_2$ | —N(C(O)N(H)—CH$_2$—CH$_2$—F)— |
| Ic-c14 | 2 | —(CH$_2$)$_n$—N(CH$_3$)$_2$ | —N(C(O)N(H)—CH$_2$—CH$_2$—F)— |
| Ic-c15 | 3 | —(CH$_2$)$_n$—N(CH$_3$)$_2$ | —N(C(O)N(H)—CH$_2$—CH$_2$—F)— |
| Ic-c16 | 4 | —(CH$_2$)$_n$—N(CH$_3$)$_2$ | —N(C(O)N(H)—CH$_2$—CH$_2$—F)— |
| Ic-c17 | 5 | —(CH$_2$)$_n$—N(CH$_3$)$_2$ | —N(C(O)N(H)—CH$_2$—CH$_2$—F)— |
| Ic-c18 | 6 | —(CH$_2$)$_n$—N(CH$_3$)$_2$ | —N(C(O)N(H)—CH$_2$—CH$_2$—F)— |
| Ic-c19 | 1 | —(CH$_2$)$_n$—N(CH$_3$)$_2$ | —N(C(O)N(H)—CH$_2$—CH$_2$—OCH$_3$)— |
| Ic-c20 | 2 | —(CH$_2$)$_n$—N(CH$_3$)$_2$ | —N(C(O)N(H)—CH$_2$—CH$_2$—OCH$_3$)— |
| Ic-c21 | 3 | —(CH$_2$)$_n$—N(CH$_3$)$_2$ | —N(C(O)N(H)—CH$_2$—CH$_2$—OCH$_3$)— |
| Ic-c22 | 4 | —(CH$_2$)$_n$—N(CH$_3$)$_2$ | —N(C(O)N(H)—CH$_2$—CH$_2$—OCH$_3$)— |
| Ic-c23 | 5 | —(CH$_2$)$_n$—N(CH$_3$)$_2$ | —N(C(O)N(H)—CH$_2$—CH$_2$—OCH$_3$)— |
| Ic-c24 | 6 | —(CH$_2$)$_n$—N(CH$_3$)$_2$ | —N(C(O)N(H)—CH$_2$—CH$_2$—OCH$_3$)— |
| Ic-c25 | 1 | —(CH$_2$)$_n$—N(CH$_3$)$_2$ | —N(C(O)N(H)—CH$_2$—CH$_2$—CF$_3$)— |
| Ic-c26 | 2 | —(CH$_2$)$_n$—N(CH$_3$)$_2$ | —N(C(O)N(H)—CH$_2$—CH$_2$—CF$_3$)— |
| Ic-c27 | 3 | —(CH$_2$)$_n$—N(CH$_3$)$_2$ | —N(C(O)N(H)—CH$_2$—CH$_2$—CF$_3$)— |
| Ic-c28 | 4 | —(CH$_2$)$_n$—N(CH$_3$)$_2$ | —N(C(O)N(H)—CH$_2$—CH$_2$—CF$_3$)— |
| Ic-c29 | 5 | —(CH$_2$)$_n$—N(CH$_3$)$_2$ | —N(C(O)N(H)—CH$_2$—CH$_2$—CF$_3$)— |
| Ic-c30 | 6 | —(CH$_2$)$_n$—N(CH$_3$)$_2$ | —N(C(O)N(H)—CH$_2$—CH$_2$—CF$_3$)— |
| Ic-c31 | 1 | —(CH$_2$)$_n$—N(CH$_3$)$_2$ | —N(CH$_2$—CH$_2$—OH)— |
| Ic-c32 | 2 | —(CH$_2$)$_n$—N(CH$_3$)$_2$ | —N(CH$_2$—CH$_2$—OH)— |
| Ic-c33 | 3 | —(CH$_2$)$_n$—N(CH$_3$)$_2$ | —N(CH$_2$—CH$_2$—OH)— |
| Ic-c34 | 4 | —(CH$_2$)$_n$—N(CH$_3$)$_2$ | —N(CH$_2$—CH$_2$—OH)— |
| Ic-c35 | 5 | —(CH$_2$)$_n$—N(CH$_3$)$_2$ | —N(CH$_2$—CH$_2$—OH)— |
| Ic-c36 | 6 | —(CH$_2$)$_n$—N(CH$_3$)$_2$ | —N(CH$_2$—CH$_2$—OH)— |
| Ic-c37 | 1 | —(CH$_2$)$_n$—N(CH$_3$)$_2$ | —N(CH$_2$—CH$_2$—F)— |
| Ic-c38 | 2 | —(CH$_2$)$_n$—N(CH$_3$)$_2$ | —N(CH$_2$—CH$_2$—F)— |
| Ic-c39 | 3 | —(CH$_2$)$_n$—N(CH$_3$)$_2$ | —N(CH$_2$—CH$_2$—F)— |
| Ic-c40 | 4 | —(CH$_2$)$_n$—N(CH$_3$)$_2$ | —N(CH$_2$—CH$_2$—F)— |
| Ic-c41 | 5 | —(CH$_2$)$_n$—N(CH$_3$)$_2$ | —N(CH$_2$—CH$_2$—F)— |
| Ic-c42 | 6 | —(CH$_2$)$_n$—N(CH$_3$)$_2$ | —N(CH$_2$—CH$_2$—F)— |
| Ic-c43 | 1 | —(CH$_2$)$_n$—N(CH$_3$)$_2$ | —N(CH$_2$—CH$_2$—OCH$_3$)— |
| Ic-c44 | 2 | —(CH$_2$)$_n$—N(CH$_3$)$_2$ | —N(CH$_2$—CH$_2$—OCH$_3$)— |
| Ic-c45 | 3 | —(CH$_2$)$_n$—N(CH$_3$)$_2$ | —N(CH$_2$—CH$_2$—OCH$_3$)— |
| Ic-c46 | 4 | —(CH$_2$)$_n$—N(CH$_3$)$_2$ | —N(CH$_2$—CH$_2$—OCH$_3$)— |
| Ic-c47 | 5 | —(CH$_2$)$_n$—N(CH$_3$)$_2$ | —N(CH$_2$—CH$_2$—OCH$_3$)— |
| Ic-c48 | 6 | —(CH$_2$)$_n$—N(CH$_3$)$_2$ | —N(CH$_2$—CH$_2$—OCH$_3$)— |
| Ic-c49 | 1 | 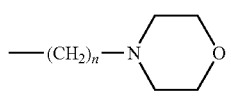 | —CH(OH)— |
| Ic-c50 | 2 | 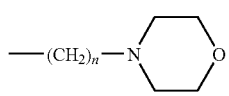 | —CH(OH)— |
| Ic-c51 | 3 | 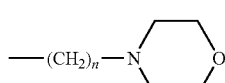 | —CH(OH)— |
| Ic-c52 | 4 | 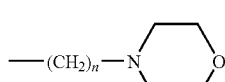 | —CH(OH)— |

| | | | |
|---|---|---|---|
| Ic-c53 | 5 | —(CH₂)ₙ—N(morpholine) | —CH(OH)— |
| Ic-c54 | 6 | —(CH₂)ₙ—N(morpholine) | —CH(OH)— |
| Ic-c55 | 1 | —(CH₂)ₙ—N(morpholine) | —N(C(O)N(H)—CH₂—CH₂—OH)— |
| Ic-c56 | 2 | —(CH₂)ₙ—N(morpholine) | —N(C(O)N(H)—CH₂—CH₂—OH)— |
| Ic-c57 | 3 | —(CH₂)ₙ—N(morpholine) | —N(C(O)N(H)—CH₂—CH₂—OH)— |
| Ic-c58 | 4 | —(CH₂)ₙ—N(morpholine) | —N(C(O)N(H)—CH₂—CH₂—OH)— |
| Ic-c59 | 5 | —(CH₂)ₙ—N(morpholine) | —N(C(O)N(H)—CH₂—CH₂—OH)— |
| Ic-c60 | 6 | —(CH₂)ₙ—N(morpholine) | —N(C(O)N(H)—CH₂—CH₂—OH)— |
| Ic-c61 | 1 | —(CH₂)ₙ—N(morpholine) | —N(C(O)N(H)—CH₂—CH₂—F)— |
| Ic-c62 | 2 | —(CH₂)ₙ—N(morpholine) | —N(C(O)N(H)—CH₂—CH₂—F)— |
| Ic-c63 | 3 | —(CH₂)ₙ—N(morpholine) | —N(C(O)N(H)—CH₂—CH₂—F)— |
| Ic-c64 | 4 | —(CH₂)ₙ—N(morpholine) | —N(C(O)N(H)—CH₂—CH₂—F)— |
| Ic-c65 | 5 | —(CH₂)ₙ—N(morpholine) | —N(C(O)N(H)—CH₂—CH₂—F)— |
| Ic-c66 | 6 | —(CH₂)ₙ—N(morpholine) | —N(C(O)N(H)—CH₂—CH₂—F)— |
| Ic-c67 | 1 | —(CH₂)ₙ—N(morpholine) | —N(C(O)N(H)—CH₂—CH₂—OCH₃)— |
| Ic-c68 | 2 | —(CH₂)ₙ—N(morpholine) | —N(C(O)N(H)—CH₂—CH₂—OCH₃)— |

| | | | |
|---|---|---|---|
| Ic-c69 | 3 | —(CH$_2$)$_n$—N(morpholine) | —N(C(O)N(H)—CH$_2$—CH$_2$—OCH$_3$)— |
| Ic-c70 | 4 | —(CH$_2$)$_n$—N(morpholine) | —N(C(O)N(H)—CH$_2$—CH$_2$—OCH$_3$)— |
| Ic-c71 | 5 | —(CH$_2$)$_n$—N(morpholine) | —N(C(O)N(H)—CH$_2$—CH$_2$—OCH$_3$)— |
| Ic-c72 | 6 | —(CH$_2$)$_n$—N(morpholine) | —N(C(O)N(H)—CH$_2$—CH$_2$—OCH$_3$)— |
| Ic-c73 | 1 | —(CH$_2$)$_n$—N(morpholine) | —N(C(O)N(H)—CH$_2$—CH$_2$—CF$_3$)— |
| Ic-c74 | 2 | —(CH$_2$)$_n$—N(morpholine) | —N(C(O)N(H)—CH$_2$—CH$_2$—CF$_3$)— |
| Ic-c75 | 3 | —(CH$_2$)$_n$—N(morpholine) | —N(C(O)N(H)—CH$_2$—CH$_2$—CF$_3$)— |
| Ic-c76 | 4 | —(CH$_2$)$_n$—N(morpholine) | —N(C(O)N(H)—CH$_2$—CH$_2$—CF$_3$)— |
| Ic-c77 | 5 | —(CH$_2$)$_n$—N(morpholine) | —N(C(O)N(H)—CH$_2$—CH$_2$—CF$_3$)— |
| Ic-c78 | 6 | —(CH$_2$)$_n$—N(morpholine) | —N(C(O)N(H)—CH$_2$—CH$_2$—CF$_3$)— |
| Ic-c79 | 1 | —(CH$_2$)$_n$—N(morpholine) | —N(CH$_2$—CH$_2$—OH)— |
| Ic-c80 | 2 | —(CH$_2$)$_n$—N(morpholine) | —N(CH$_2$—CH$_2$—OH)— |
| Ic-c81 | 3 | —(CH$_2$)$_n$—N(morpholine) | —N(CH$_2$—CH$_2$—OH)— |
| Ic-c82 | 4 | —(CH$_2$)$_n$—N(morpholine) | —N(CH$_2$—CH$_2$—OH)— |
| Ic-c83 | 5 | —(CH$_2$)$_n$—N(morpholine) | —N(CH$_2$—CH$_2$—OH)— |
| Ic-c84 | 6 | —(CH$_2$)$_n$—N(morpholine) | —N(CH$_2$—CH$_2$—OH)— |

-continued

| Compound | n | —R¹ (morpholinoalkyl) | X |
|---|---|---|---|
| Ic-c85 | 1 | —(CH₂)ₙ—N(morpholine) | —N(CH₂—CH₂—F)— |
| Ic-c86 | 2 | —(CH₂)ₙ—N(morpholine) | —N(CH₂—CH₂—F)— |
| Ic-c87 | 3 | —(CH₂)ₙ—N(morpholine) | —N(CH₂—CH₂—F)— |
| Ic-c88 | 4 | —(CH₂)ₙ—N(morpholine) | —N(CH₂—CH₂—F)— |
| Ic-c89 | 5 | —(CH₂)ₙ—N(morpholine) | —N(CH₂—CH₂—F)— |
| Ic-c90 | 6 | —(CH₂)ₙ—N(morpholine) | —N(CH₂—CH₂—F)— |
| Ic-c91 | 1 | —(CH₂)ₙ—N(morpholine) | —N(CH₂—CH₂—OCH₃)— |
| Ic-c92 | 2 | —(CH₂)ₙ—N(morpholine) | —N(CH₂—CH₂—OCH₃)— |
| Ic-c93 | 3 | —(CH₂)ₙ—N(morpholine) | —N(CH₂—CH₂—OCH₃)— |
| Ic-c94 | 4 | —(CH₂)ₙ—N(morpholine) | —N(CH₂—CH₂—OCH₃)— |
| Ic-c95 | 5 | —(CH₂)ₙ—N(morpholine) | —N(CH₂—CH₂—OCH₃)— |
| Ic-c96 | 6 | —(CH₂)ₙ—N(morpholine) | —N(CH₂—CH₂—OCH₃)— |

| Compound | m | —R¹ | X |
|---|---|---|---|
| Ic-c146 | 2 | —O—(CH₂)ₘ—N(CH₃)₂ | —CH(OH)— |
| Ic-c147 | 3 | —O—(CH₂)ₘ—N(CH₃)₂ | —CH(OH)— |
| Ic-c148 | 4 | —O—(CH₂)ₘ—N(CH₃)₂ | —CH(OH)— |
| Ic-c149 | 5 | —O—(CH₂)ₘ—N(CH₃)₂ | —CH(OH)— |
| Ic-c150 | 6 | —O—(CH₂)ₘ—N(CH₃)₂ | —CH(OH)— |
| Ic-c151 | 2 | —O—(CH₂)ₘ—N(CH₃)₂ | —N(C(O)N(H)—CH₂—CH₂—OH)— |
| Ic-c152 | 3 | —O—(CH₂)ₘ—N(CH₃)₂ | —N(C(O)N(H)—CH₂—CH₂—OH)— |
| Ic-c153 | 4 | —O—(CH₂)ₘ—N(CH₃)₂ | —N(C(O)N(H)—CH₂—CH₂—OH)— |
| Ic-c154 | 5 | —O—(CH₂)ₘ—N(CH₃)₂ | —N(C(O)N(H)—CH₂—CH₂—OH)— |
| Ic-c155 | 6 | —O—(CH₂)ₘ—N(CH₃)₂ | —N(C(O)N(H)—CH₂—CH₂—OH)— |
| Ic-c156 | 2 | —O—(CH₂)ₘ—N(CH₃)₂ | —N(C(O)N(H)—CH₂—CH₂—F)— |
| Ic-c157 | 3 | —O—(CH₂)ₘ—N(CH₃)₂ | —N(C(O)N(H)—CH₂—CH₂—F)— |
| Ic-c158 | 4 | —O—(CH₂)ₘ—N(CH₃)₂ | —N(C(O)N(H)—CH₂—CH₂—F)— |
| Ic-c159 | 5 | —O—(CH₂)ₘ—N(CH₃)₂ | —N(C(O)N(H)—CH₂—CH₂—F)— |
| Ic-c160 | 6 | —O—(CH₂)ₘ—N(CH₃)₂ | —N(C(O)N(H)—CH₂—CH₂—F)— |
| Ic-c161 | 2 | —O—(CH₂)ₘ—N(CH₃)₂ | —N(C(O)N(H)—CH₂—CH₂—OCH₃)— |
| Ic-c162 | 3 | —O—(CH₂)ₘ—N(CH₃)₂ | —N(C(O)N(H)—CH₂—CH₂—OCH₃)— |

-continued

| | | | |
|---|---|---|---|
| Ic-c163 | 4 | —O—(CH$_2$)$_m$—N(CH$_3$)$_2$ | —N(C(O)N(H)—CH$_2$—CH$_2$—OCH$_3$)— |
| Ic-c164 | 5 | —O—(CH$_2$)$_m$—N(CH$_3$)$_2$ | —N(C(O)N(H)—CH$_2$—CH$_2$—OCH$_3$)— |
| Ic-c165 | 6 | —O—(CH$_2$)$_m$—N(CH$_3$)$_2$ | —N(C(O)N(H)—CH$_2$—CH$_2$—OCH$_3$)— |
| Ic-c166 | 2 | —O—(CH$_2$)$_m$—N(CH$_3$)$_2$ | —N(C(O)N(H)—CH$_2$—CH$_2$—CF$_3$)— |
| Ic-c167 | 3 | —O—(CH$_2$)$_m$—N(CH$_3$)$_2$ | —N(C(O)N(H)—CH$_2$—CH$_2$—CF$_3$)— |
| Ic-c168 | 4 | —O—(CH$_2$)$_m$—N(CH$_3$)$_2$ | —N(C(O)N(H)—CH$_2$—CH$_2$—CF$_3$)— |
| Ic-c169 | 5 | —O—(CH$_2$)$_m$—N(CH$_3$)$_2$ | —N(C(O)N(H)—CH$_2$—CH$_2$—CF$_3$)— |
| Ic-c170 | 6 | —O—(CH$_2$)$_m$—N(CH$_3$)$_2$ | —N(C(O)N(H)—CH$_2$—CH$_2$—CF$_3$)— |
| Ic-c171 | 2 | —O—(CH$_2$)$_m$—N(CH$_3$)$_2$ | —N(CH$_2$—CH$_2$—OH)— |
| Ic-c172 | 3 | —O—(CH$_2$)$_m$—N(CH$_3$)$_2$ | —N(CH$_2$—CH$_2$—OH)— |
| Ic-c173 | 4 | —O—(CH$_2$)$_m$—N(CH$_3$)$_2$ | —N(CH$_2$—CH$_2$—OH)— |
| Ic-c174 | 5 | —O—(CH$_2$)$_m$—N(CH$_3$)$_2$ | —N(CH$_2$—CH$_2$—OH)— |
| Ic-c175 | 6 | —O—(CH$_2$)$_m$—N(CH$_3$)$_2$ | —N(CH$_2$—CH$_2$—OH)— |
| Ic-c176 | 2 | —O—(CH$_2$)$_m$—N(CH$_3$)$_2$ | —N(CH$_2$—CH$_2$—F)— |
| Ic-c178 | 3 | —O—(CH$_2$)$_m$—N(CH$_3$)$_2$ | —N(CH$_2$—CH$_2$—F)— |
| Ic-c179 | 4 | —O—(CH$_2$)$_m$—N(CH$_3$)$_2$ | —N(CH$_2$—CH$_2$—F)— |
| Ic-c180 | 5 | —O—(CH$_2$)$_m$—N(CH$_3$)$_2$ | —N(CH$_2$—CH$_2$—F)— |
| Ic-c181 | 6 | —O—(CH$_2$)$_m$—N(CH$_3$)$_2$ | —N(CH$_2$—CH$_2$—F)— |
| Ic-c182 | 2 | —O—(CH$_2$)$_m$—N(CH$_3$)$_2$ | —N(CH$_2$—CH$_2$—OCH$_3$)— |
| Ic-c183 | 3 | —O—(CH$_2$)$_m$—N(CH$_3$)$_2$ | —N(CH$_2$—CH$_2$—OCH$_3$)— |
| Ic-c184 | 4 | —O—(CH$_2$)$_m$—N(CH$_3$)$_2$ | —N(CH$_2$—CH$_2$—OCH$_3$)— |
| Ic-c185 | 5 | —O—(CH$_2$)$_m$—N(CH$_3$)$_2$ | —N(CH$_2$—CH$_2$—OCH$_3$)— |
| Ic-c186 | 6 | —O—(CH$_2$)$_m$—N(CH$_3$)$_2$ | —N(CH$_2$—CH$_2$—OCH$_3$)— |
| Ic-c187 | 2 | 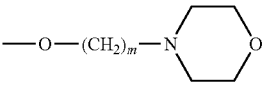 | —CH(OH)— |
| Ic-c188 | 3 | 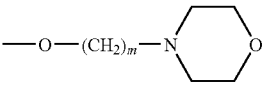 | —CH(OH)— |
| Ic-c189 | 4 | 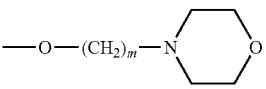 | —CH(OH)— |
| Ic-c190 | 5 | 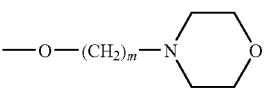 | —CH(OH)— |
| Ic-c191 | 6 | 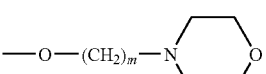 | —CH(OH)— |
| Ic-c192 | 2 | 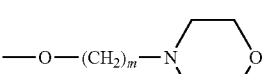 | —N(C(O)N(H)—CH$_2$—CH$_2$—OH)— |
| Ic-c193 | 3 | 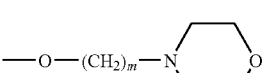 | —N(C(O)N(H)—CH$_2$—CH$_2$—OH)— |
| Ic-c194 | 4 | 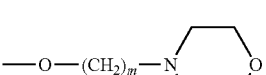 | —N(C(O)N(H)—CH$_2$—CH$_2$—OH)— |
| Ic-c195 | 5 | 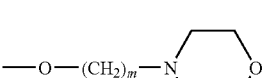 | —N(C(O)N(H)—CH$_2$—CH$_2$—OH)— |
| Ic-c196 | 6 | 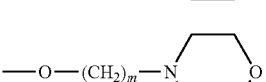 | —N(C(O)N(H)—CH$_2$—CH$_2$—OH)— |
| Ic-c197 | 2 |  | —N(C(O)N(H)—CH$_2$—CH$_2$—F)— |

| | | | |
|---|---|---|---|
| Ic-c198 | 3 | —O—(CH$_2$)$_m$—N(morpholine) | —N(C(O)N(H)—CH$_2$—CH$_2$—F)— |
| Ic-c199 | 4 | —O—(CH$_2$)$_m$—N(morpholine) | —N(C(O)N(H)—CH$_2$—CH$_2$—F)— |
| Ic-c200 | 5 | —O—(CH$_2$)$_m$—N(morpholine) | —N(C(O)N(H)—CH$_2$—CH$_2$—F)— |
| Ic-c201 | 6 | —O—(CH$_2$)$_m$—N(morpholine) | —N(C(O)N(H)—CH$_2$—CH$_2$—F)— |
| Ic-c202 | 2 | —O—(CH$_2$)$_m$—N(morpholine) | —N(C(O)N(H)—CH$_2$—CH$_2$—OCH$_3$)— |
| Ic-c203 | 3 | —O—(CH$_2$)$_m$—N(morpholine) | —N(C(O)N(H)—CH$_2$—CH$_2$—OCH$_3$)— |
| Ic-c204 | 4 | —O—(CH$_2$)$_m$—N(morpholine) | —N(C(O)N(H)—CH$_2$—CH$_2$—OCH$_3$)— |
| Ic-c205 | 5 | —O—(CH$_2$)$_m$—N(morpholine) | —N(C(O)N(H)—CH$_2$—CH$_2$—OCH$_3$)— |
| Ic-c206 | 6 | —O—(CH$_2$)$_m$—N(morpholine) | —N(C(O)N(H)—CH$_2$—CH$_2$—OCH$_3$)— |
| Ic-c207 | 2 | —O—(CH$_2$)$_m$—N(morpholine) | —N(C(O)N(H)—CH$_2$—CH$_2$—CF$_3$)— |
| Ic-c208 | 3 | —O—(CH$_2$)$_m$—N(morpholine) | —N(C(O)N(H)—CH$_2$—CH$_2$—CF$_3$)— |
| Ic-c209 | 4 | —O—(CH$_2$)$_m$—N(morpholine) | —N(C(O)N(H)—CH$_2$—CH$_2$—CF$_3$)— |
| Ic-c210 | 5 | —O—(CH$_2$)$_m$—N(morpholine) | —N(C(O)N(H)—CH$_2$—CH$_2$—CF$_3$)— |
| Ic-c211 | 6 | —O—(CH$_2$)$_m$—N(morpholine) | —N(C(O)N(H)—CH$_2$—CH$_2$—CF$_3$)— |
| Ic-c212 | 2 | —O—(CH$_2$)$_m$—N(morpholine) | —N(CH$_2$—CH$_2$—OH)— |
| Ic-c213 | 3 | —O—(CH$_2$)$_m$—N(morpholine) | —N(CH$_2$—CH$_2$—OH)— |

-continued

| | | | |
|---|---|---|---|
| Ic-c214 | 4 | —O—(CH$_2$)$_m$—N(morpholine) | —N(CH$_2$—CH$_2$—OH)— |
| Ic-c215 | 5 | —O—(CH$_2$)$_m$—N(morpholine) | —N(CH$_2$—CH$_2$—OH)— |
| Ic-c216 | 6 | —O—(CH$_2$)$_m$—N(morpholine) | —N(CH$_2$—CH$_2$—OH)— |
| Ic-c217 | 2 | —O—(CH$_2$)$_m$—N(morpholine) | —N(CH$_2$—CH$_2$—F)— |
| Ic-c218 | 3 | —O—(CH$_2$)$_m$—N(morpholine) | —N(CH$_2$—CH$_2$—F)— |
| Ic-c219 | 4 | —O—(CH$_2$)$_m$—N(morpholine) | —N(CH$_2$—CH$_2$—F)— |
| Ic-c220 | 5 | —O—(CH$_2$)$_m$—N(morpholine) | —N(CH$_2$—CH$_2$—F)— |
| Ic-c221 | 6 | —O—(CH$_2$)$_m$—N(morpholine) | —N(CH$_2$—CH$_2$—F)— |
| Ic-c222 | 2 | —O—(CH$_2$)$_m$—N(morpholine) | —N(CH$_2$—CH$_2$—OCH$_3$)— |
| Ic-c223 | 3 | —O—(CH$_2$)$_m$—N(morpholine) | —N(CH$_2$—CH$_2$—OCH$_3$)— |
| Ic-c224 | 4 | —O—(CH$_2$)$_m$—N(morpholine) | —N(CH$_2$—CH$_2$—OCH$_3$)— |
| Ic-c225 | 5 | —O—(CH$_2$)$_m$—N(morpholine) | —N(CH$_2$—CH$_2$—OCH$_3$)— |
| Ic-c226 | 6 | —O—(CH$_2$)$_m$—N(morpholine) | —N(CH$_2$—CH$_2$—OCH$_3$)— |

| Compound | —R$^1$ | X |
|---|---|---|
| Ic-c267 | —CH$_2$—N(CH$_2$—CH$_3$)$_2$ | —CH(OH)— |
| Ic-c268 | —CH$_2$—N(CH$_2$—CH$_3$)$_2$ | N(C(O)N(H)—CH$_2$—CH$_2$—OH)— |
| Ic-c269 | —CH$_2$—N(CH$_2$—CH$_3$)$_2$ | —N(C(O)N(H)—CH$_2$—CH$_2$—F)— |
| Ic-c270 | —CH$_2$—N(CH$_2$—CH$_3$)$_2$ | —N(C(O)N(H)—CH$_2$—CH$_2$—OCH$_3$)— |
| Ic-c271 | —CH$_2$—N(CH$_2$—CH$_3$)$_2$ | —N(C(O)N(H)—CH$_2$—CH$_2$—CF$_3$)— |
| Ic-c275 | —CH$_2$—N(CH$_2$—CH$_2$—CH$_3$)$_2$ | —CH(OH)— |
| Ic-c276 | —CH$_2$—N(CH$_2$—CH$_2$—CH$_3$)$_2$ | —N(C(O)N(H)—CH$_2$—CH$_2$—OH)— |
| Ic-c277 | —CH$_2$—N(CH$_2$—CH$_2$—CH$_3$)$_2$ | —N(C(O)N(H)—CH$_2$—CH$_2$—F)— |
| Ic-c278 | —CH$_2$—N(CH$_2$—CH$_2$—CH$_3$)$_2$ | —N(C(O)N(H)—CH$_2$—CH$_2$—OCH$_3$)— |
| Ic-c279 | —CH$_2$—N(CH$_2$—CH$_2$—CH$_3$)$_2$ | —N(C(O)N(H)—CH$_2$—CH$_2$—CF$_3$)— |
| Ic-c283 | —CH$_2$—N(CH$_2$—CH$_2$OH)$_2$ | —CH(OH)— |
| Ic-c284 | —CH$_2$—N(CH$_2$—CH$_2$OH)$_2$ | —N(C(O)N(H)—CH$_2$—CH$_2$—OH)— |
| Ic-c285 | —CH$_2$—N(CH$_2$—CH$_2$OH)$_2$ | —N(C(O)N(H)—CH$_2$—CH$_2$—F)— |

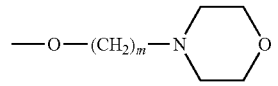
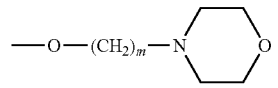

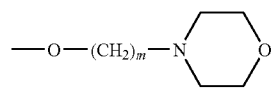

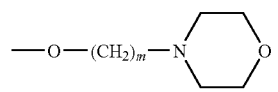
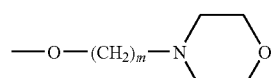
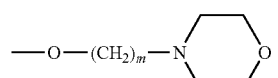
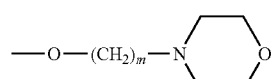
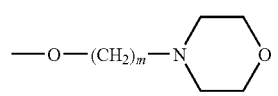

-continued

| ID | Col2 | Col3 |
|---|---|---|
| Ic-c286 | —CH₂—N(CH₂—CH₂OH)₂ | —N(C(O)N(H)—CH₂—CH₂—OCH₃)— |
| Ic-c291 | —CH₂—N(CH₂—CH₂—N(CH₃)₂)₂ | —CH(OH)— |
| Ic-c292 | —CH₂—N(CH₂—CH₂—N(CH₃)₂)₂ | —N(C(O)N(H)—CH₂—CH₂—OH)— |
| Ic-c293 | —CH₂—N(CH₂—CH₂—N(CH₃)₂)₂ | —N(C(O)N(H)—CH₂—CH₂—F)— |
| Ic-c294 | —CH₂—N(CH₂—CH₂—N(CH₃)₂)₂ | —N(C(O)N(H)—CH₂—CH₂—OCH₃)— |
| Ic-c295 | —CH₂—N(CH₂—CH₂—N(CH₃)₂)₂ | —N(C(O)N(H)—CH₂—CH₂—CF₃)— |
| Ic-c296 | —CH₂—N(CH₂—CH₂—N(CH₃)₂)₂ | —N(C(O)N(H)—CH₂—CH₂—CF₃)— |
| Ic-c297 | —CH₂—N(CH₂—CH₂—N(CH₃)₂)₂ | —N(C(O)N(H)—CH₂—CF₃)— |
| Ic-c298 | —CH₂—N(CH₂—CH₂—N(CH₃)₂)₂ | —N(C(O)N(H)—(CH₂)₃—OH)— |
| Ic-c299 | —CH₂—N(CH₂—CH₂—CH₂—N(CH₃)₂)₂ | —CH(OH)— |
| Ic-c300 | —CH₂—N(CH₂—CH₂—CH₂—N(CH₃)₂)₂ | —N(C(O)N(H)—CH₂—CH₂—OH)— |
| Ic-c301 | —CH₂—N(CH₂—CH₂—CH₂—N(CH₃)₂)₂ | —N(C(O)N(H)—CH₂—CH₂—F)— |
| Ic-c302 | —CH₂—N(CH₂—CH₂—CH₂—N(CH₃)₂)₂ | —N(C(O)N(H)—CH₂—CH₂—OCH₃)— |
| Ic-c303 | —CH₂—N(CH₂—CH₂—CH₂—N(CH₃)₂)₂ | —N(C(O)N(H)—CH₂—CH₂—CF₃)— |
| Ic-c304 | —CH₂—N(CH₂—CH₂—CH₂—N(CH₃)₂)₂ | —N(C(O)N(H)—CH₂—CH₂—CF₃)— |
| Ic-c305 | —CH₂—N(CH₂—CH₂—CH₂—N(CH₃)₂)₂ | —N(C(O)N(H)—CH₂—CF₃)— |
| Ic-c306 | —CH₂—N(CH₂—CH₂—CH₂—N(CH₃)₂)₂ | N(C(O)N(H)—(CH₂)₃—OH)— |
| Ic-c307 | —CH₂—N(aziridinyl) | —CH(OH)— |
| Ic-c308 | —CH₂—N(aziridinyl) | —N(C(O)N(H)—CH₂—CH₂—OH)— |
| Ic-c309 | —CH₂—N(aziridinyl) | —N(C(O)N(H)—CH₂—CH₂—F)— |
| Ic-c310 | —CH₂—N(aziridinyl) | —N(C(O)N(H)—CH₂—CH₂—OCH₃)— |
| Ic-c311 | —CH₂—N(aziridinyl) | —N(C(O)N(H)—CH₂—CH₂—CF₃)— |
| Ic-c312 | —CH₂—N(aziridinyl) | —N(C(O)N(H)—CH₂—CH₂—CF₃)— |
| Ic-c313 | —CH₂—N(aziridinyl) | —N(C(O)N(H)—CH₂—CF₃)— |
| Ic-c314 | —CH₂—N(aziridinyl) | —N(C(O)N(H)—(CH₂)₃—OH)— |
| Ic-c315 | —CH₂—N(azetidinyl) | —CH(OH)— |
| Ic-c316 | —CH₂—N(azetidinyl) | —N(C(O)N(H)—CH₂—CH₂—OH)— |
| Ic-c317 | —CH₂—N(azetidinyl) | —N(C(O)N(H)—CH₂—CH₂—F)— |
| Ic-c318 | —CH₂—N(azetidinyl) | —N(C(O)N(H)—CH₂—CH₂—OCH₃)— |
| Ic-c319 | —CH₂—N(azetidinyl) | —N(C(O)N(H)—CH₂—CH₂—CF₃)— |
| Ic-c320 | —CH₂—N(azetidinyl) | —N(C(O)N(H)—CH₂—CH₂—CF₃)— |
| Ic-c321 | —CH₂—N(azetidinyl) | —N(C(O)N(H)—CH₂—CF₃)— |
| Ic-c322 | —CH₂—N(azetidinyl) | —N(C(O)N(H)—(CH₂)₃—OH)— |

-continued

| | | |
|---|---|---|
| Ic-c323 | 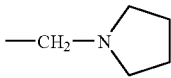 —CH₂—N(pyrrolidine) | —CH(OH)— |
| Ic-c324 | 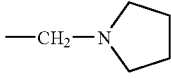 —CH₂—N(pyrrolidine) | —N(C(O)N(H)—CH₂—CH₂—OH)— |
| Ic-c325 | 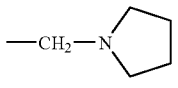 —CH₂—N(pyrrolidine) | —N(C(O)N(H)—CH₂—CH₂—F)— |
| Ic-c326 | 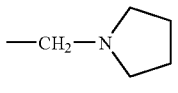 —CH₂—N(pyrrolidine) | —N(C(O)N(H)—CH₂—CH₂—OCH₃)— |
| Ic-c327 | 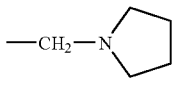 —CH₂—N(pyrrolidine) | —N(C(O)N(H)—CH₂—CH₂—CF₃)— |
| Ic-c328 | 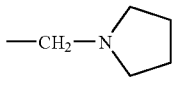 —CH₂—N(pyrrolidine) | —N(C(O)N(H)—CH₂—CH₂—CF₃)— |
| Ic-c329 | 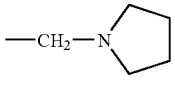 —CH₂—N(pyrrolidine) | —N(C(O)N(H)—CH₂—CF₃)— |
| Ic-c330 | 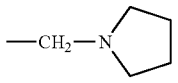 —CH₂—N(pyrrolidine) | —N(C(O)N(H)—(CH₂)₃—OH)— |
| Ic-c331 | 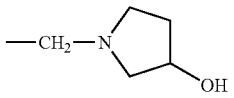 —CH₂—N(3-hydroxypyrrolidine) | —CH(OH)— |
| Ic-c332 | 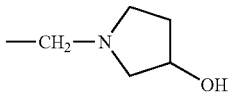 —CH₂—N(3-hydroxypyrrolidine) | —N(C(O)N(H)—CH₂—CH₂—OH)— |
| Ic-c333 | 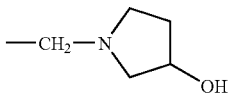 —CH₂—N(3-hydroxypyrrolidine) | —N(C(O)N(H)—CH₂—CH₂—F)— |
| Ic-c334 | 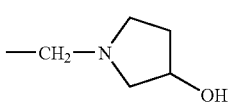 —CH₂—N(3-hydroxypyrrolidine) | —N(C(O)N(H)—CH₂—CH₂—OCH₃)— |
| Ic-c335 |  —CH₂—N(3-hydroxypyrrolidine) | —N(C(O)N(H)—CH₂—CH₂—CF₃)— |
| Ic-c336 | 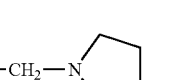 —CH₂—N(3-hydroxypyrrolidine) | —N(C(O)N(H)—CH₂—CH₂—CF₃)— |
| Ic-c337 | 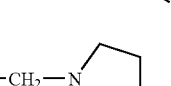 —CH₂—N(3-hydroxypyrrolidine) | —N(C(O)N(H)—CH₂—CF₃)— |
| Ic-c338 |  —CH₂—N(3-hydroxypyrrolidine) | —N(C(O)N(H)—(CH₂)₃—OH)— |

-continued
| | | |
|---|---|---|
| Ic-c339 | 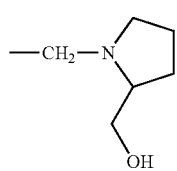 | —CH(OH)— |
| Ic-c340 | 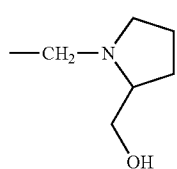 | —N(C(O)N(H)—CH$_2$—CH$_2$—OH)— |
| Ic-c341 | 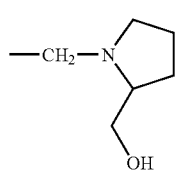 | —N(C(O)N(H)—CH$_2$—CH$_2$—F)— |
| Ic-c342 | 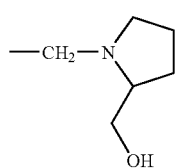 | —N(C(O)N(H)—CH$_2$—CH$_2$—OCH$_3$)— |
| Ic-c343 | 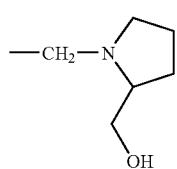 | —N(C(O)N(H)—CH$_2$—CH$_2$—CF$_3$)— |
| Ic-c344 | 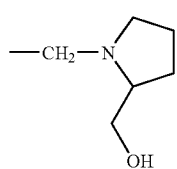 | —N(C(O)N(H)—CH$_2$—CH$_2$—CF$_3$)— |
| Ic-c345 | 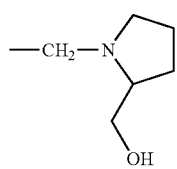 | —N(C(O)N(H)—CH$_2$—CF$_3$)— |
| Ic-c346 | 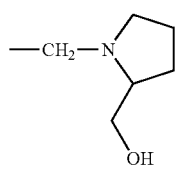 | —N(C(O)N(H)—(CH$_2$)$_3$—OH)— |
| Ic-c347 | 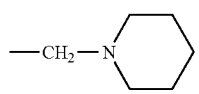 | —CH(OH)— |
| Ic-c348 | 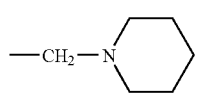 | —N(C(O)N(H)—CH$_2$—CH$_2$—OH)— |

-continued
| | | |
|---|---|---|
| Ic-c349 | 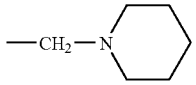 | —N(C(O)N(H)—CH₂—CH₂—F)— |
| Ic-c350 | 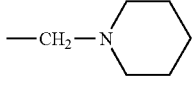 | —N(C(O)N(H)—CH₂—CH₂—OCH₃)— |
| Ic-c351 | 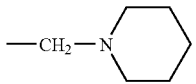 | —N(C(O)N(H)—CH₂—CH₂—CF₃)— |
| Ic-c352 | 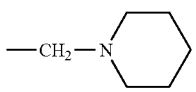 | —N(C(O)N(H)—CH₂—CH₂—CF₃)— |
| Ic-c353 | 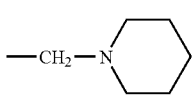 | —N(C(O)N(H)—CH₂—CF₃)— |
| Ic-c354 | 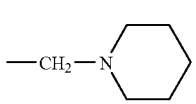 | —N(C(O)N(H)—(CH₂)₃—OH)— |
| Ic-c355 | 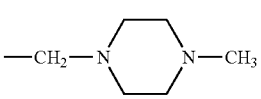 | —CH(OH)— |
| Ic-c356 | 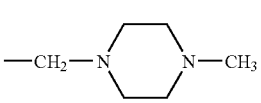 | —N(C(O)N(H)—CH₂—CH₂—OH)— |
| Ic-c357 | 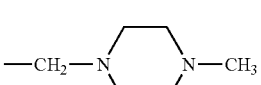 | —N(C(O)N(H)—CH₂—CH₂—F)— |
| Ic-c358 | 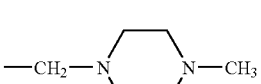 | —N(C(O)N(H)—CH₂—CH₂—OCH₃)— |
| Ic-c359 | 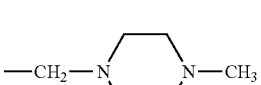 | —N(C(O)N(H)—CH₂—CH₂—CF₃)— |
| Ic-c360 | 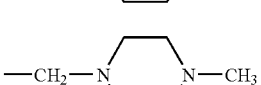 | —N(C(O)N(H)—CH₂—CH₂—CF₃)— |
| Ic-c361 | 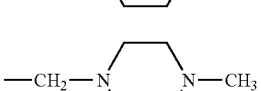 | —N(C(O)N(H)—CH₂—CF₃)— |
| Ic-c362 | 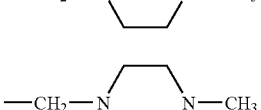 | —N(C(O)N(H)—(CH₂)₃—OH)— |
| Ic-c363 | 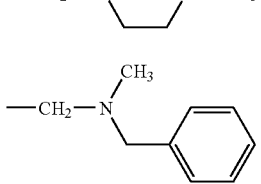 | —CH(OH)— |

-continued

| | | |
|---|---|---|
| Ic-c364 | —CH₂—N(CH₃)—CH₂—C₆H₅ | —N(C(O)N(H)—CH₂—CH₂—OH)— |
| Ic-c365 | —CH₂—N(CH₃)—CH₂—C₆H₅ | —N(C(O)N(H)—CH₂—CH₂—F)— |
| Ic-c366 | —CH₂—N(CH₃)—CH₂—C₆H₅ | —N(C(O)N(H)—CH₂—CH₂—OCH₃)— |
| Ic-c367 | —CH₂—N(CH₃)—CH₂—C₆H₅ | —N(C(O)N(H)—CH₂—CH₂—CF₃)— |
| Ic-c368 | —CH₂—N(CH₃)—CH₂—C₆H₅ | —N(C(O)N(H)—CH₂—CH₂—CF₃)— |
| Ic-c369 | —CH₂—N(CH₃)—CH₂—C₆H₅ | —N(C(O)N(H)—CH₂—CF₃)— |
| Ic-c370 | —CH₂—N(CH₃)—CH₂—C₆H₅ | —N(C(O)N(H)—(CH₂)₃—OH)— |
| Ic-c371 | —CH₂—N(CH₃)—CH(CH₃)₂ | —CH(OH)— |
| Ic-c372 | —CH₂—N(CH₃)—CH(CH₃)₂ | —N(C(O)N(H)—CH₂—CH₂—OH)— |
| Ic-c373 | —CH₂—N(CH₃)—CH(CH₃)₂ | —N(C(O)N(H)—CH₂—CH₂—F)— |
| Ic-c374 | —CH₂—N(CH₃)—CH(CH₃)₂ | —N(C(O)N(H)—CH₂—CH₂—OCH₃)— |

-continued
| | | |
|---|---|---|
| Ic-c375 | 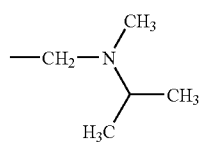 | —N(C(O)N(H)—CH₂—CH₂—CF₃)— |
| Ic-c376 | 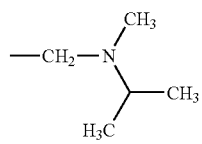 | —N(C(O)N(H)—CH₂—CH₂—CF₃)— |
| Ic-c377 | 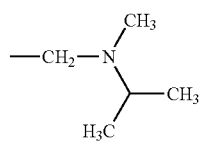 | —N(C(O)N(H)—CH₂—CF₃)— |
| Ic-c378 | 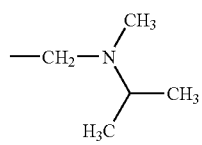 | —N(C(O)N(H)—(CH₂)₃—OH)— |
| Ic-c379 | 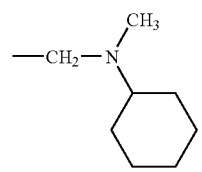 | —CH(OH)— |
| Ic-c380 | 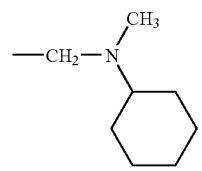 | —N(C(O)N(H)—CH₂—CH₂—OH)— |
| Ic-c381 | 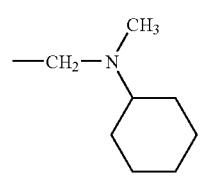 | —N(C(O)N(H)—CH₂—CH₂—F)— |
| Ic-c382 | 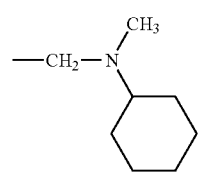 | —N(C(O)N(H)—CH₂—CH₂—OCH₃)— |
| Ic-c383 | 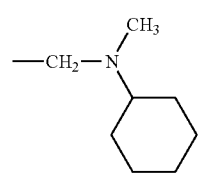 | —N(C(O)N(H)—CH₂—CH₂—CF₃)— |

| | | |
|---|---|---|
| Ic-c384 | 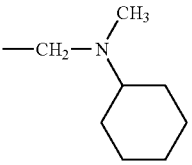 | —N(C(O)N(H)—CH₂—CH₂—CF₃)— |
| Ic-c385 | 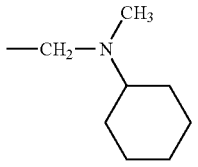 | —N(C(O)N(H)—CH₂—CF₃)— |
| Ic-c386 | 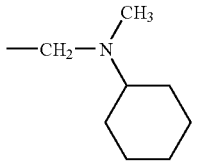 | —N(C(O)N(H)—(CH₂)₃—OH)— |
| Ic-c387 | 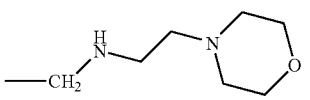 | —CH(OH)— |
| Ic-c388 | 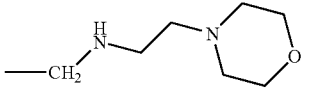 | —N(C(O)N(H)—CH₂—CH₂—OH)— |
| Ic-c389 | 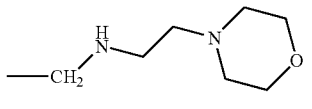 | —N(C(O)N(H)—CH₂—CH₂—F)— |
| Ic-c390 | 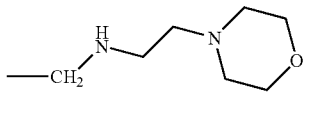 | —N(C(O)N(H)—CH₂—CH₂—OCH₃)— |
| Ic-c391 | 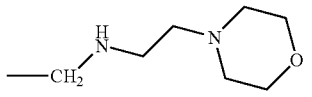 | —N(C(O)N(H)—CH₂—CH₂—CF₃)— |
| Ic-c392 | 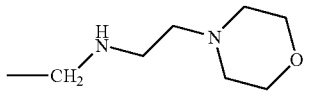 | —N(C(O)N(H)—CH₂—CH₂—CF₃)— |
| Ic-c393 | 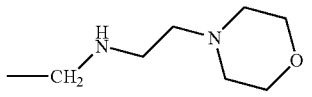 | —N(C(O)N(H)—CH₂—CF₃)— |
| Ic-c394 |  | —N(C(O)N(H)—(CH₂)₃—OH)— |
| Ic-c395 | 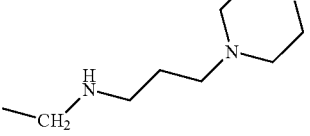 | —CH(OH)— |

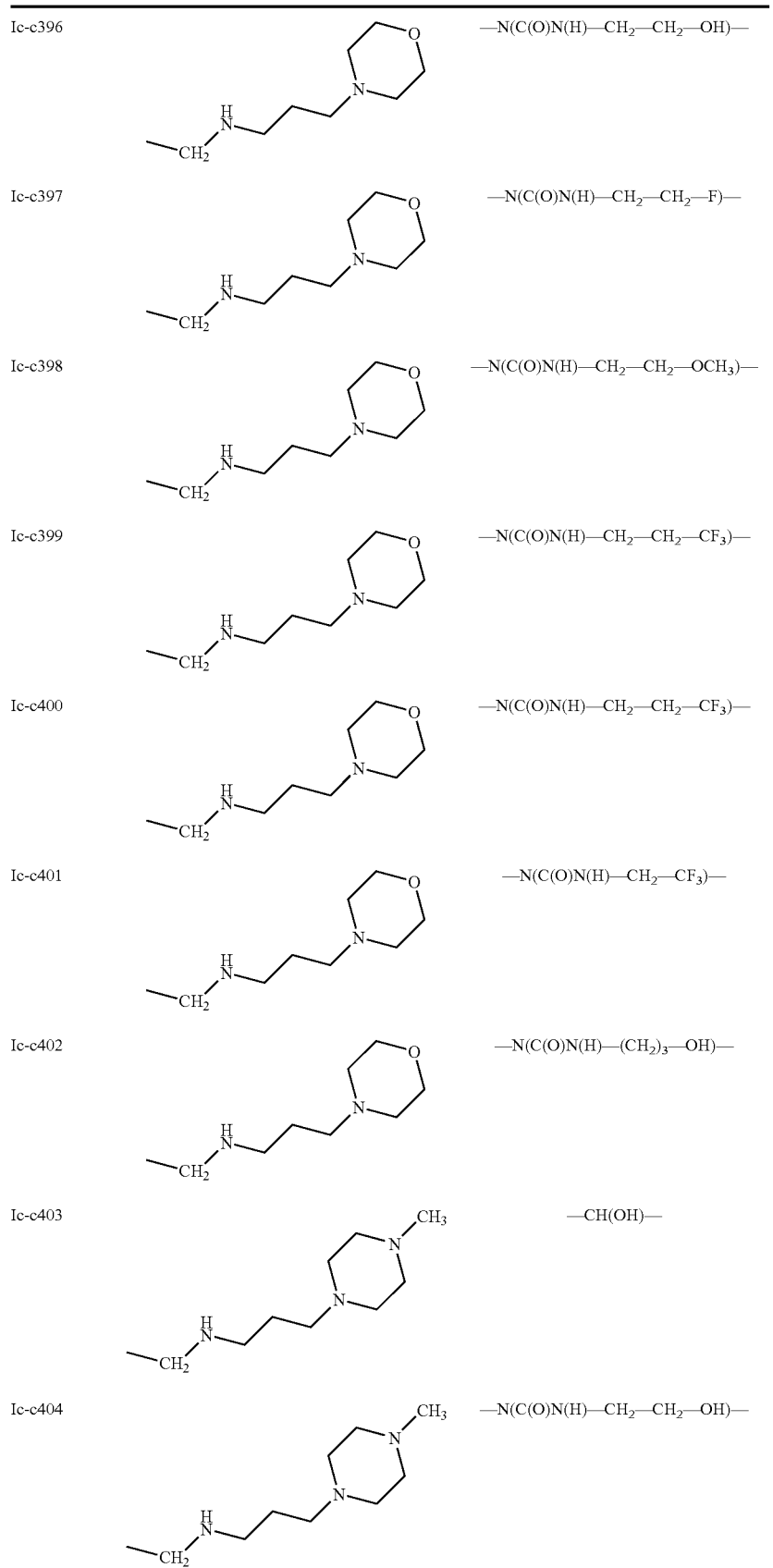
| | | |
|---|---|---|
| Ic-c396 | | —N(C(O)N(H)—CH₂—CH₂—OH)— |
| Ic-c397 | | —N(C(O)N(H)—CH₂—CH₂—F)— |
| Ic-c398 | | —N(C(O)N(H)—CH₂—CH₂—OCH₃)— |
| Ic-c399 | | —N(C(O)N(H)—CH₂—CH₂—CF₃)— |
| Ic-c400 | | —N(C(O)N(H)—CH₂—CH₂—CF₃)— |
| Ic-c401 | | —N(C(O)N(H)—CH₂—CF₃)— |
| Ic-c402 | | —N(C(O)N(H)—(CH₂)₃—OH)— |
| Ic-c403 | | —CH(OH)— |
| Ic-c404 | | —N(C(O)N(H)—CH₂—CH₂—OH)— |

-continued
| | | |
|---|---|---|
| Ic-c405 | 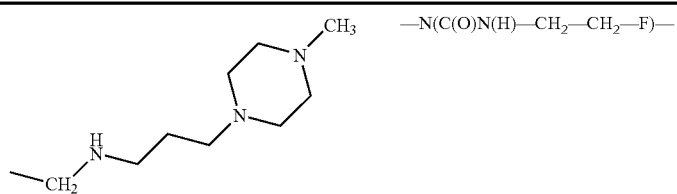 | —N(C(O)N(H)—CH₂—CH₂—F)— |
| Ic-c406 | 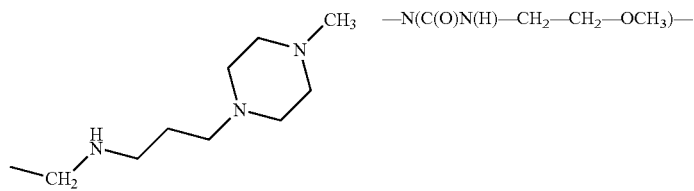 | —N(C(O)N(H)—CH₂—CH₂—OCH₃)— |
| Ic-c407 | 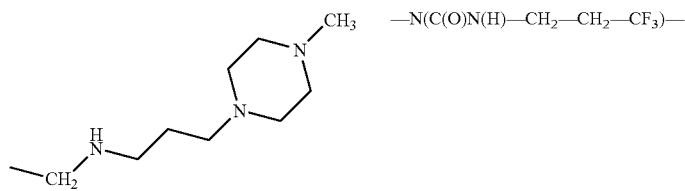 | —N(C(O)N(H)—CH₂—CH₂—CF₃)— |
| Ic-c408 | 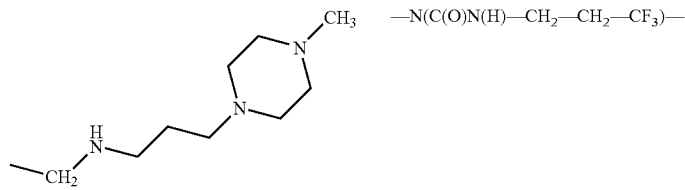 | —N(C(O)N(H)—CH₂—CH₂—CF₃)— |
| Ic-c409 | 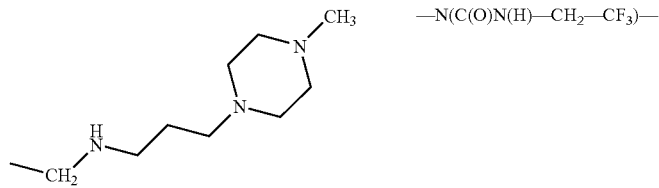 | —N(C(O)N(H)—CH₂—CF₃)— |
| Ic-c410 | 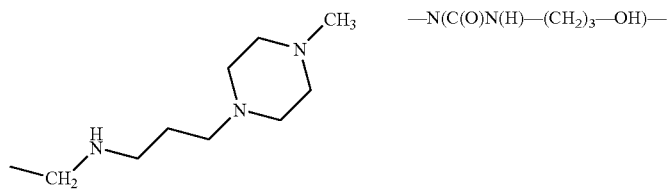 | —N(C(O)N(H)—(CH₂)₃—OH)— |
| Ic-c411 | 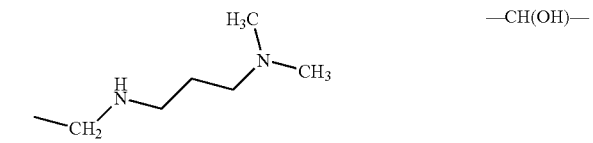 | —CH(OH)— |
| Ic-c412 | 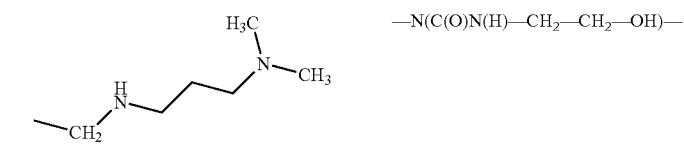 | —N(C(O)N(H)—CH₂—CH₂—OH)— |
| Ic-c413 | 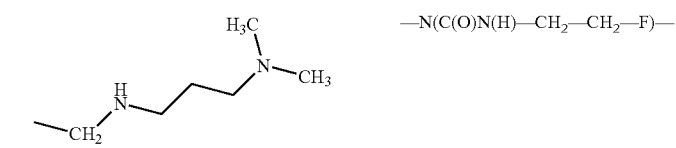 | —N(C(O)N(H)—CH₂—CH₂—F)— |

| | | |
|---|---|---|
| Ic-c414 | H₃C\N-CH₃ on propyl-NH-CH₂ | —N(C(O)N(H)—CH₂—CH₂—OCH₃)— |
| Ic-c415 | H₃C\N-CH₃ on propyl-NH-CH₂ | —N(C(O)N(H)—CH₂—CH₂—CF₃)— |
| Ic-c416 | H₃C\N-CH₃ on propyl-NH-CH₂ | —N(C(O)N(H)—CH₂—CH₂—CF₃)— |
| Ic-c417 | H₃C\N-CH₃ on propyl-NH-CH₂ | —N(C(O)N(H)—CH₂—CF₃)— |
| Ic-c418 | H₃C\N-CH₃ on propyl-NH-CH₂ | —N(C(O)N(H)—(CH₂)₃—OH)— |
| Ic-c419 | imidazolyl-propyl-NH-CH₂ | —CH(OH)— |
| Ic-c420 | imidazolyl-propyl-NH-CH₂ | —N(C(O)N(H)—CH₂—CH₂—OH)— |
| Ic-c421 | imidazolyl-propyl-NH-CH₂ | —N(C(O)N(H)—CH₂—CH₂—F)— |
| Ic-c422 | imidazolyl-propyl-NH-CH₂ | —N(C(O)N(H)—CH₂—CH₂—OCH₃)— |
| Ic-c423 | imidazolyl-propyl-NH-CH₂ | —N(C(O)N(H)—CH₂—CH₂—CF₃)— |

-continued
| | | |
|---|---|---|
| Ic-c424 | 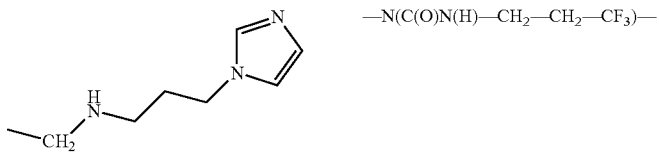 | —N(C(O)N(H)—CH₂—CH₂—CF₃)— |
| Ic-c425 | 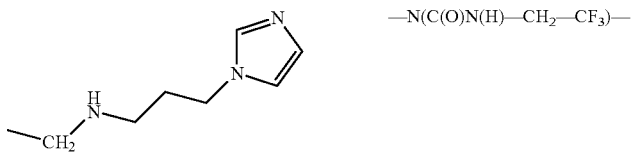 | —N(C(O)N(H)—CH₂—CF₃)— |
| Ic-c426 | 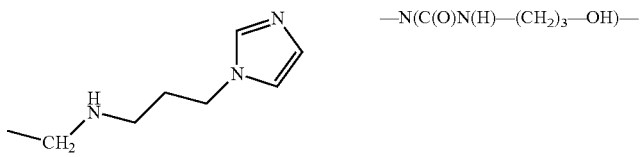 | —N(C(O)N(H)—(CH₂)₃—OH)— |
| Ic-c427 | 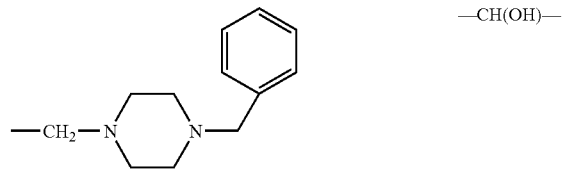 | —CH(OH)— |
| Ic-c428 | 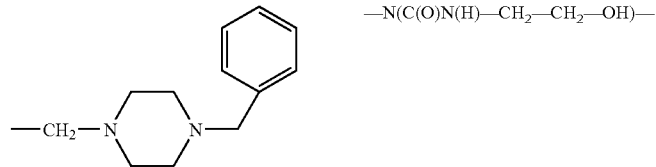 | —N(C(O)N(H)—CH₂—CH₂—OH)— |
| Ic-c429 | 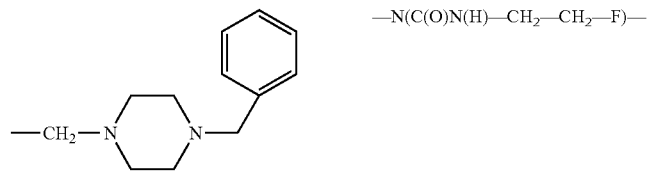 | —N(C(O)N(H)—CH₂—CH₂—F)— |
| Ic-c430 | 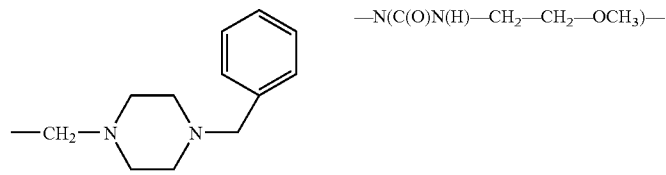 | —N(C(O)N(H)—CH₂—CH₂—OCH₃)— |
| Ic-c431 | 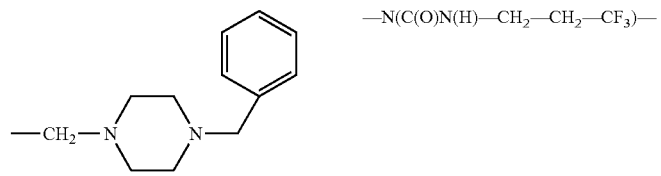 | —N(C(O)N(H)—CH₂—CH₂—CF₃)— |
| Ic-c432 | 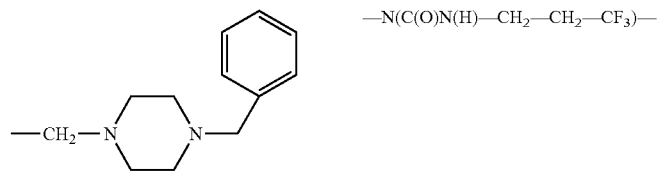 | —N(C(O)N(H)—CH₂—CH₂—CF₃)— |

-continued

| | | |
|---|---|---|
| Ic-c433 | —CH₂—N(piperazine)N—CH₂—C₆H₅ | —N(C(O)N(H)—CH₂—CF₃— |
| Ic-c434 | —CH₂—N(piperazine)N—CH₂—C₆H₅ | —N(C(O)N(H)—(CH₂)₃—OH— |
| Ic-c435 | —CH₂—N(piperazine)N—C₆H₄—F | —CH(OH)— |
| Ic-c436 | —CH₂—N(piperazine)N—C₆H₄—F | —N(C(O)N(H)—CH₂—CH₂—OH— |
| Ic-c437 | —CH₂—N(piperazine)N—C₆H₄—F | —N(C(O)N(H)—CH₂—CH₂—F)— |
| Ic-c438 | —CH₂—N(piperazine)N—C₆H₄—F | —N(C(O)N(H)—CH₂—CH₂—OCH₃)— |
| Ic-c439 | —CH₂—N(piperazine)N—C₆H₄—F | —N(C(O)N(H)—CH₂—CH₂—CF₃)— |
| Ic-c440 | —CH₂—N(piperazine)N—C₆H₄—F | —N(C(O)N(H)—CH₂—CH₂—CF₃)— |
| Ic-c441 | —CH₂—N(piperazine)N—C₆H₄—F | —N(C(O)N(H)—CH₂—CF₃)— |
| Ic-c442 | —CH₂—N(piperazine)N—C₆H₄—F | —N(C(O)N(H)—(CH₂)₃—OH)— |
| Ic-c443 | —CH₂—N(tetrahydropyridine)—C₆H₄—F | —CH(OH)— |
| Ic-c444 | —CH₂—N(tetrahydropyridine)—C₆H₄—F | —N(C(O)N(H)—CH₂—CH₂—OH)— |
| Ic-c445 | —CH₂—N(tetrahydropyridine)—C₆H₄—F | —N(C(O)N(H)—CH₂—CH₂—F)— |
| Ic-c446 | —CH₂—N(tetrahydropyridine)—C₆H₄—F | —N(C(O)N(H)—CH₂—CH₂—OCH₃)— |
| Ic-c447 | —CH₂—N(tetrahydropyridine)—C₆H₄—F | —N(C(O)N(H)—CH₂—CH₂—CF₃)— |

-continued

| | | |
|---|---|---|
| Ic-c448 | 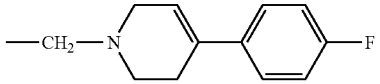 —CH₂—N(ring)—C₆H₄—F | —N(C(O)N(H)—CH₂—CH₂—CF₃)— |
| Ic-c449 | 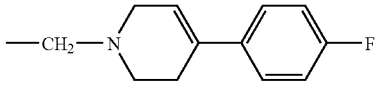 —CH₂—N(ring)—C₆H₄—F | —N(C(O)N(H)—CH₂—CF₃)— |
| Ic-c450 | 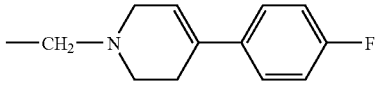 —CH₂—N(ring)—C₆H₄—F | —N(C(O)N(H)—(CH₂)₃—OH)— |
| Ic-c451 | 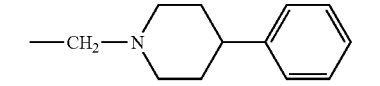 —CH₂—N(ring)—C₆H₅ | —CH(OH)— |
| Ic-c452 | 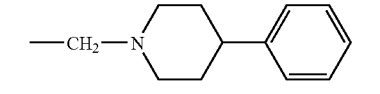 —CH₂—N(ring)—C₆H₅ | —N(C(O)N(H)—CH₂—CH₂—OH)— |
| Ic-c453 | 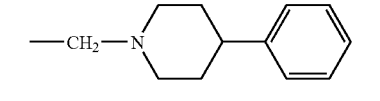 —CH₂—N(ring)—C₆H₅ | —N(C(O)N(H)—CH₂—CH₂—F)— |
| Ic-c454 | 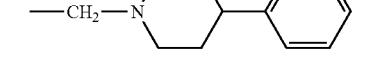 —CH₂—N(ring)—C₆H₅ | —N(C(O)N(H)—CH₂—CH₂—OCH₃)— |
| Ic-c455 | 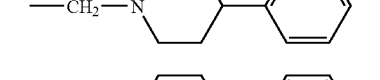 —CH₂—N(ring)—C₆H₅ | —N(C(O)N(H)—CH₂—CH₂—CF₃)— |
| Ic-c456 | 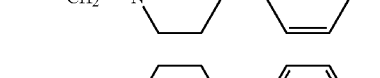 —CH₂—N(ring)—C₆H₅ | —N(C(O)N(H)—CH₂—CH₂—CF₃)— |
| Ic-c457 | 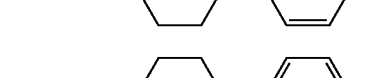 —CH₂—N(ring)—C₆H₅ | —N(C(O)N(H)—CH₂—CF₃)— |
| Ic-c458 | 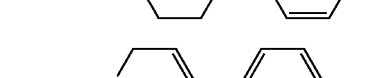 —CH₂—N(ring)—C₆H₅ | —N(C(O)N(H)—(CH₂)₃—OH)— |
| Ic-c459 | 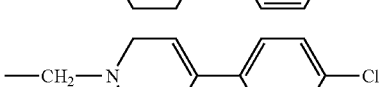 —CH₂—N(ring)—C₆H₄—Cl | —CH(OH)— |
| Ic-c460 | 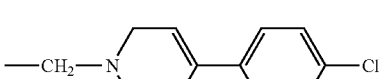 —CH₂—N(ring)—C₆H₄—Cl | —N(C(O)N(H)—CH₂—CH₂—OH)— |
| Ic-c461 | 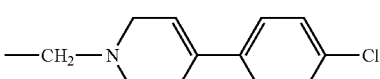 —CH₂—N(ring)—C₆H₄—Cl | —N(C(O)N(H)—CH₂—CH₂—F)— |
| Ic-c462 | 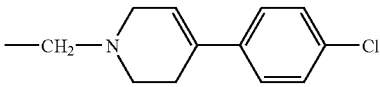 —CH₂—N(ring)—C₆H₄—Cl | —N(C(O)N(H)—CH₂—CH₂—OCH₃)— |
| Ic-c463 |  —CH₂—N(ring)—C₆H₄—Cl | —N(C(O)N(H)—CH₂—CH₂—CF₃)— |

-continued
| | | |
|---|---|---|
| Ic-c464 | 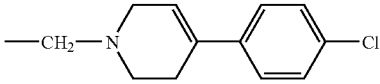 | —N(C(O)N(H)—CH₂—CH₂—CF₃)— |
| Ic-c465 | 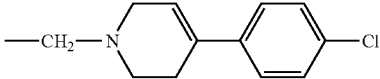 | —N(C(O)N(H)—CH₂—CF₃)— |
| Ic-c466 | 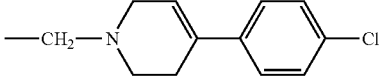 | —N(C(O)N(H)—(CH₂)₃—OH)— |
| Ic-c467 | 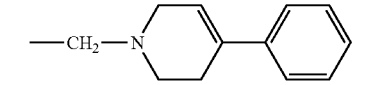 | —CH(OH)— |
| Ic-c468 | 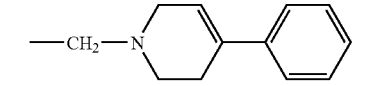 | —N(C(O)N(H)—CH₂—CH₂—OH)— |
| Ic-c469 | 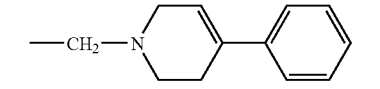 | —N(C(O)N(H)—CH₂—CH₂—F)— |
| Ic-c470 | 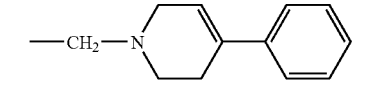 | —N(C(O)N(H)—CH₂—CH₂—OCH₃)— |
| Ic-c471 | 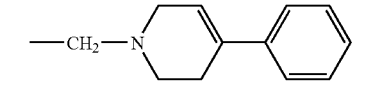 | —N(C(O)N(H)—CH₂—CH₂—CF₃)— |
| Ic-c472 | 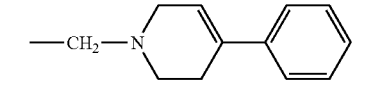 | —N(C(O)N(H)—CH₂—CH₂—CF₃)— |
| Ic-c473 | 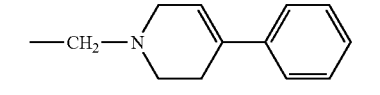 | —N(C(O)N(H)—CH₂—CF₃)— |
| Ic-c474 | 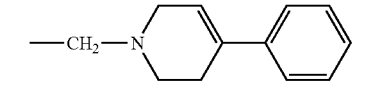 | —N(C(O)N(H)—(CH₂)₃—OH)— |
| Ic-c475 | 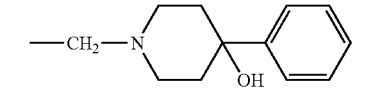 | —CH(OH)— |
| Ic-c476 | 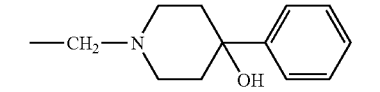 | —N(C(O)N(H)—CH₂—CH₂—OH)— |
| Ic-c477 | 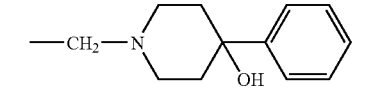 | —N(C(O)N(H)—CH₂—CH₂—F)— |
| Ic-c478 |  | —N(C(O)N(H)—CH₂—CH₂—OCH₃)— |
| Ic-c479 | 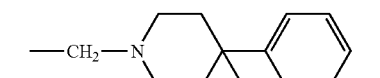 | —N(C(O)N(H)—CH₂—CH₂—CF₃)— |

-continued

| | | |
|---|---|---|
| Ic-c480 | —CH₂—N⟨piperidine-4-OH, 4-phenyl⟩ | —N(C(O)N(H)—CH₂—CH₂—CF₃)— |
| Ic-c481 | —CH₂—N⟨piperidine-4-OH, 4-phenyl⟩ | N(C(O)N(H)—CH₂—CF₃)— |
| Ic-c482 | —CH₂—N⟨piperidine-4-OH, 4-phenyl⟩ | N(C(O)N(H)—(CH₂)₃—OH)— |
| Ic-c483 | —CH₂—N⟨piperazine⟩NCH₂CH₂OP(O)(OH)₂ | —CH(OH)— |
| Ic-c484 | —CH₂—N⟨piperazine⟩NCH₂CH₂OP(O)(OH)₂ | —N(C(O)N(H)—CH₂—CH₂—OH)— |
| Ic-c485 | —CH₂—N⟨piperazine⟩NCH₂CH₂OP(O)(OH)₂ | —N(C(O)N(H)—CH₂—CH₂—F)— |
| Ic-c486 | —CH₂—N⟨piperazine⟩NCH₂CH₂OP(O)(OH)₂ | —N(C(O)N(H)—CH₂—CH₂—OCH₃)— |
| Ic-c487 | —CH₂—N⟨piperazine⟩NCH₂CH₂OP(O)(OH)₂ | —N(C(O)N(H)—CH₂—CH₂—CF₃)— |
| Ic-c488 | —CH₂—N⟨piperazine⟩NCH₂CH₂OP(O)(OH)₂ | —N(C(O)N(H)—CH₂—CH₂—CF₃)— |
| Ic-c489 | —CH₂—N⟨piperazine⟩NCH₂CH₂OP(O)(OH)₂ | N(C(O)N(H)—CH₂—CF₃)— |
| Ic-c490 | —CH₂—N⟨piperazine⟩NCH₂CH₂OP(O)(OH)₂ | N(C(O)N(H)—(CH₂)₃—OH)— |
| Ic-c491 | —CH₂—CH₂—CH₂—OP(O)(OH)₂ | —CH(OH)— |
| Ic-c492 | —CH₂—CH₂—CH₂—OP(O)(OH)₂ | —N(C(O)N(H)—CH₂—CH₂—OH)— |
| Ic-c493 | —CH₂—CH₂—CH₂—OP(O)(OH)₂ | —N(C(O)N(H)—CH₂—CH₂—F)— |
| Ic-c494 | —CH₂—CH₂—CH₂—OP(O)(OH)₂ | —N(C(O)N(H)—CH₂—CH₂—OCH₃)— |
| Ic-c495 | —CH₂—CH₂—CH₂—OP(O)(OH)₂ | —N(C(O)N(H)—CH₂—CH₂—CF₃)— |
| Ic-c496 | —CH₂—CH₂—CH₂—OP(O)(OH)₂ | —N(C(O)N(H)—CH₂—CH₂—CF₃)— |
| Ic-c497 | —CH₂—CH₂—CH₂—OP(O)(OH)₂ | —N(C(O)N(H)—CH₂—CF₃)— |
| Ic-c498 | —CH₂—CH₂—CH₂—OP(O)(OH)₂ | —N(C(O)N(H)—(CH₂)₃—OH)— |
| Ic-c499 | —CH₂—CH₂—CH₂—OS(O)₂OH | —CH(OH)— |
| Ic-c500 | —CH₂—CH₂—CH₂—OS(O)₂OH | —N(C(O)N(H)—CH₂—CH₂—OH)— |
| Ic-c501 | —CH₂—CH₂—CH₂—OS(O)₂OH | —N(C(O)N(H)—CH₂—CH₂—F)— |
| Ic-c502 | —CH₂—CH₂—CH₂—OS(O)₂OH | —N(C(O)N(H)—CH₂—CH₂—OCH₃)— |
| Ic-c503 | —CH₂—CH₂—CH₂—OS(O)₂OH | —N(C(O)N(H)—CH₂—CH₂—CF₃)— |
| Ic-c504 | —CH₂—CH₂—CH₂—OS(O)₂OH | —N(C(O)N(H)—CH₂—CH₂—CF₃)— |
| Ic-c505 | —CH₂—CH₂—CH₂—OS(O)₂OH | —N(C(O)N(H)—CH₂—CF₃)— |
| Ic-c506 | —CH₂—CH₂—CH₂—OS(O)₂OH | —N(C(O)N(H)—(CH₂)₃—OH)— |
| Ic-c507 | —CH₂—N⟨pyrrolidine-3-OP(O)(OH)₂⟩ | —CH(OH)— |

| | | |
|---|---|---|
| Ic-c508 | —CH₂—N(pyrrolidine-3-OP(O)(OH)₂) | —N(C(O)N(H)—CH₂—CH₂—OH)— |
| Ic-c509 | —CH₂—N(pyrrolidine-3-OP(O)(OH)₂) | —N(C(O)N(H)—CH₂—CH₂—F)— |
| Ic-c510 | —CH₂—N(pyrrolidine-3-OP(O)(OH)₂) | —N(C(O)N(H)—CH₂—CH₂—OCH₃)— |
| Ic-c511 | —CH₂—N(pyrrolidine-3-OP(O)(OH)₂) | —N(C(O)N(H)—CH₂—CH₂—CF₃)— |
| Ic-c512 | —CH₂—N(pyrrolidine-3-OP(O)(OH)₂) | —N(C(O)N(H)—CH₂—CH₂—CF₃)— |
| Ic-c513 | —CH₂—N(pyrrolidine-3-OP(O)(OH)₂) | —N(C(O)N(H)—CH₂—CF₃)— |
| Ic-c514 | —CH₂—N(pyrrolidine-3-OP(O)(OH)₂) | —N(C(O)N(H)—(CH₂)₃—OH)— |
| Ic-c515 | —CH₂—N(pyrrolidine-2-CH₂-OP(O)(OH)₂) | —CH(OH)— |
| Ic-c516 | —CH₂—N(pyrrolidine-2-CH₂-OP(O)(OH)₂) | —N(C(O)N(H)—CH₂—CH₂—OH)— |
| Ic-c517 | —CH₂—N(pyrrolidine-2-CH₂-OP(O)(OH)₂) | —N(C(O)N(H)—CH₂—CH₂—F)— |
| Ic-c518 | —CH₂—N(pyrrolidine-2-CH₂-OP(O)(OH)₂) | —N(C(O)N(H)—CH₂—CH₂—OCH₃)— |

-continued

| | | |
|---|---|---|
| Ic-c519 | 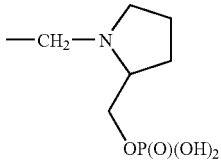 | —N(C(O)N(H)—CH₂—CH₂—CF₃)— |
| Ic-c520 | 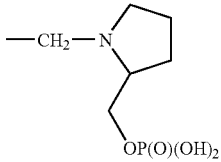 | —N(C(O)N(H)—CH₂—CH₂—CF₃)— |
| Ic-c521 | 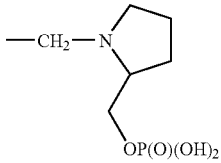 | —N(C(O)N(H)—CH₂—CF₃)— |
| Ic-c522 | 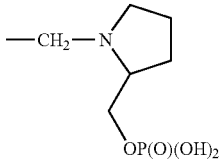 | —N(C(O)N(H)—(CH₂)₃—OH)— |
| Ic-c523 | —(CH₂)₁₀—N(CH₂—CH₂—O—CH₃)₂ | —CH(OH)— |
| Ic-c524 | —(CH₂)₁₀—N(CH₂—CH₂—O—CH₃)₂ | —N(C(O)N(H)—CH₂—CH₂—OH)— |
| Ic-c525 | —(CH₂)₁₀—N(CH₂—CH₂—O—CH₃)₂ | —N(C(O)N(H)—CH₂—CH₂—F)— |
| Ic-c526 | —(CH₂)₁₀—N(CH₂—CH₂—O—CH₃)₂ | —N(C(O)N(H)—CH₂—CH₂—OCH₃)— |
| Ic-c527 | —(CH₂)₁₀—N(CH₂—CH₂—O—CH₃)₂ | —N(C(O)N(H)—CH₂—CH₂—CF₃)— |
| Ic-c528 | —(CH₂)₁₀—N(CH₂—CH₂—O—CH₃)₂ | —N(C(O)N(H)—CH₂—CH₂—CF₃)— |
| Ic-c529 | —(CH₂)₁₀—N(CH₂—CH₂—O—CH₃)₂ | —N(C(O)N(H)—CH₂—CF₃)— |
| Ic-c530 | —(CH₂)₁₀—N(CH₂—CH₂—O—CH₃)₂ | —N(C(O)N(H)—(CH₂)₃—OH)— |
| Ic-c531 | —CH₂—N(CH₂—CH₂—O—CH₃)₂ | —CH(OH)— |
| Ic-c532 | —CH₂—N(CH₂—CH₂—O—CH₃)₂ | —N(C(O)N(H)—CH₂—CH₂—OH)— |
| Ic-c533 | —CH₂—N(CH₂—CH₂—O—CH₃)₂ | —N(C(O)N(H)—CH₂—CH₂—F)— |
| Ic-c534 | —CH₂—N(CH₂—CH₂—O—CH₃)₂ | —N(C(O)N(H)—CH₂—CH₂—OCH₃)— |
| Ic-c535 | —CH₂—N(CH₂—CH₂—O—CH₃)₂ | —N(C(O)N(H)—CH₂—CH₂—CF₃)— |
| Ic-c536 | —CH₂—N(CH₂—CH₂—O—CH₃)₂ | —N(C(O)N(H)—CH₂—CH₂—CF₃)— |
| Ic-c537 | —CH₂—N(CH₂—CH₂—O—CH₃)₂ | —N(C(O)N(H)—CH₂—CF₃)— |
| Ic-c538 | —CH₂—N(CH₂—CH₂—O—CH₃)₂ | —N(C(O)N(H)—(CH₂)₃—OH)— |
| Ic-c539 | 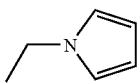 | —CH(OH)— |
| Ic-c540 | 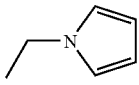 | —N(C(O)N(H)—CH₂—CH₂—OH)— |
| Ic-c541 | 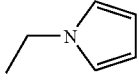 | —N(C(O)N(H)—CH₂—CH₂—F)— |
| Ic-c542 | 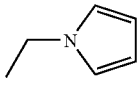 | —N(C(O)N(H)—CH₂—CH₂—OCH₃)— |
| Ic-c543 | 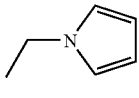 | —N(C(O)N(H)—CH₂—CH₂—CF₃)— |
| Ic-c544 | 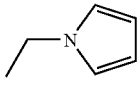 | —N(C(O)N(H)—CH₂—CH₂—CF₃)— |

-continued
| | | |
|---|---|---|
| Ic-c545 | 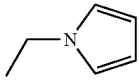 | —N(C(O)N(H)—CH$_2$—CF$_3$)— |
| Ic-c546 | 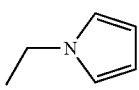 | —N(C(O)N(H)—(CH$_2$)$_3$—OH)— |
| Ic-c547 | 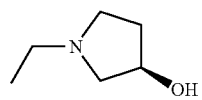 | —CH(OH)— |
| Ic-c548 | 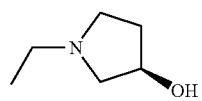 | —N(C(O)N(H)—CH$_2$—CH$_2$—OH)— |
| Ic-c549 | 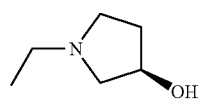 | —N(C(O)N(H)—CH$_2$—CH$_2$—F)— |
| Ic-c550 | 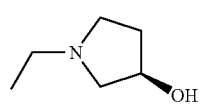 | —N(C(O)N(H)—CH$_2$—CH$_2$—OCH$_3$)— |
| Ic-c551 | 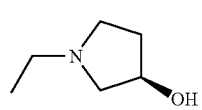 | —N(C(O)N(H)—CH$_2$—CH$_2$—CF$_3$)— |
| Ic-c552 | 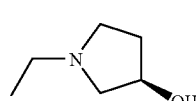 | —N(C(O)N(H)—CH$_2$—CH$_2$—CF$_3$)— |
| Ic-c553 | 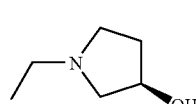 | —N(C(O)N(H)—CH$_2$—CF$_3$)— |
| Ic-c554 | 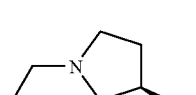 | —N(C(O)N(H)—(CH$_2$)$_3$—OH)— |
| Ic-c555 | 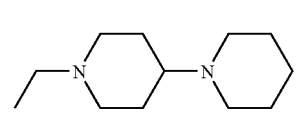 | —CH(OH)— |
| Ic-c556 | 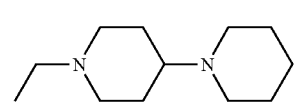 | —N(C(O)N(H)—CH$_2$—CH$_2$—OH)— |
| Ic-c557 | 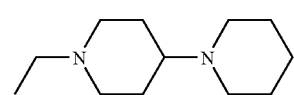 | —N(C(O)N(H)—CH$_2$—CH$_2$—F)— |
| Ic-c558 | 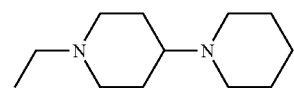 | —N(C(O)N(H)—CH$_2$—CH$_2$—OCH$_3$)— |
| Ic-c559 | 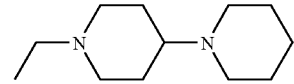 | —N(C(O)N(H)—CH$_2$—CH$_2$—CF$_3$)— |

-continued

| | | |
|---|---|---|
| Ic-c560 | [1-ethylpiperidin-4-yl-piperidine] | —N(C(O)N(H)—CH$_2$—CH$_2$—CF$_3$)— |
| Ic-c561 | [1-ethylpiperidin-4-yl-piperidine] | —N(C(O)N(H)—CH$_2$—CF$_3$)— |
| Ic-c562 | [1-ethylpiperidin-4-yl-piperidine] | —N(C(O)N(H)—(CH$_2$)$_3$—OH)— |
| Ic-c563 | [1-ethylpiperidin-4-yl-pyrrolidine] | —CH(OH)— |
| Ic-c564 | [1-ethylpiperidin-4-yl-pyrrolidine] | —N(C(O)N(H)—CH$_2$—CH$_2$—OH)— |
| Ic-c565 | [1-ethylpiperidin-4-yl-pyrrolidine] | —N(C(O)N(H)—CH$_2$—CH$_2$—F)— |
| Ic-c566 | [1-ethylpiperidin-4-yl-pyrrolidine] | —N(C(O)N(H)—CH$_2$—CH$_2$—OCH$_3$)— |
| Ic-c567 | [1-ethylpiperidin-4-yl-pyrrolidine] | —N(C(O)N(H)—CH$_2$—CH$_2$—CF$_3$)— |
| Ic-c568 | [1-ethylpiperidin-4-yl-pyrrolidine] | —N(C(O)N(H)—CH$_2$—CH$_2$—CF$_3$)— |
| Ic-c569 | [1-ethylpiperidin-4-yl-pyrrolidine] | —N(C(O)N(H)—CH$_2$—CF$_3$)— |
| Ic-c570 | [1-ethylpiperidin-4-yl-pyrrolidine] | —N(C(O)N(H)—(CH$_2$)$_3$—OH)— |
| Ic-c571 | [1-ethyl-2-(hydroxymethyl)pyrrolidine] | —CH(OH)— |
| Ic-c572 | [1-ethyl-2-(hydroxymethyl)pyrrolidine] | —N(C(O)N(H)—CH$_2$—CH$_2$—OH)— |
| Ic-c573 | [1-ethyl-2-(hydroxymethyl)pyrrolidine] | —N(C(O)N(H)—CH$_2$—CH$_2$—F)— |
| Ic-c574 | [1-ethyl-2-(hydroxymethyl)pyrrolidine] | —N(C(O)N(H)—CH$_2$—CH$_2$—OCH$_3$)— |

-continued
| | | |
|---|---|---|
| Ic-c575 | 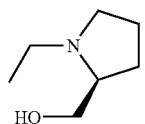 | —N(C(O)N(H)—CH₂—CH₂—CF₃)— |
| Ic-c576 | 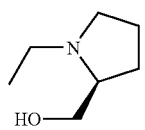 | —N(C(O)N(H)—CH₂—CH₂—CF₃)— |
| Ic-c577 | 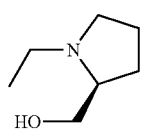 | —N(C(O)N(H)—CH₂—CF₃)— |
| Ic-c578 | 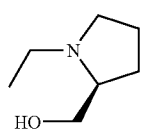 | —N(C(O)N(H)—(CH₂)₃—OH)— |
| Ic-c579 | 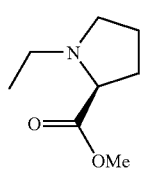 | —CH(OH)— |
| Ic-c580 | 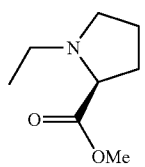 | —N(C(O)N(H)—CH₂—CH₂—OH)— |
| Ic-c581 | 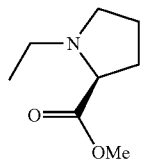 | —N(C(O)N(H)—CH₂—CH₂—F)— |
| Ic-c582 | 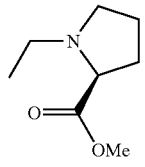 | —N(C(O)N(H)—CH₂—CH₂—OCH₃)— |
| Ic-c583 | 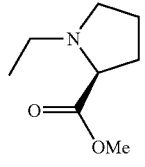 | —N(C(O)N(H)—CH₂—CH₂—CF₃)— |
| Ic-c584 | 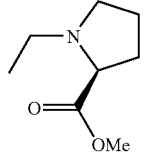 | —N(C(O)N(H)—CH₂—CH₂—CF₃)— |

-continued

| | | |
|---|---|---|
| Ic-c585 | N-ethyl pyrrolidine-2-carboxylic acid methyl ester | —N(C(O)N(H)—CH$_2$—CF$_3$— |
| Ic-c586 | N-ethyl pyrrolidine-2-carboxylic acid methyl ester | —N(C(O)N(H)—(CH$_2$)$_3$—OH— |
| Ic-c587 | 2-ethyl-1,2,3,4-tetrahydroisoquinoline | —CH(OH)— |
| Ic-c588 | 2-ethyl-1,2,3,4-tetrahydroisoquinoline | —N(C(O)N(H)—CH$_2$—CH$_2$—OH)— |
| Ic-c589 | 2-ethyl-1,2,3,4-tetrahydroisoquinoline | —N(C(O)N(H)—CH$_2$—CH$_2$—F)— |
| Ic-c590 | 2-ethyl-1,2,3,4-tetrahydroisoquinoline | —N(C(O)N(H)—CH$_2$—CH$_2$—OCH$_3$)— |
| Ic-c591 | 2-ethyl-1,2,3,4-tetrahydroisoquinoline | —N(C(O)N(H)—CH$_2$—CH$_2$—CF$_3$)— |
| Ic-c592 | 2-ethyl-1,2,3,4-tetrahydroisoquinoline | —N(C(O)N(H)—CH$_2$—CH$_2$—CF$_3$)— |
| Ic-c593 | 2-ethyl-1,2,3,4-tetrahydroisoquinoline | —N(C(O)N(H)—CH$_2$—CF$_3$)— |
| Ic-c594 | 2-ethyl-1,2,3,4-tetrahydroisoquinoline | —N(C(O)N(H)—(CH$_2$)$_3$—OH)— |
| Ic-c595 | 1-ethyl-2-(pyrrolidin-1-ylmethyl)pyrrolidine | —CH(OH)— |
| Ic-c596 | 1-ethyl-2-(pyrrolidin-1-ylmethyl)pyrrolidine | —N(C(O)N(H)—CH$_2$—CH$_2$—OH)— |

-continued
| | | |
|---|---|---|
| Ic-c597 | 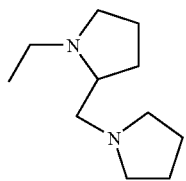 | —N(C(O)N(H)—CH₂—CH₂—F)— |
| Ic-c598 | 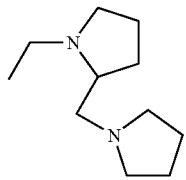 | —N(C(O)N(H)—CH₂—CH₂—OCH₃)— |
| Ic-c599 | 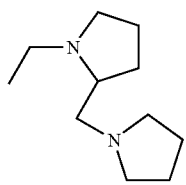 | —N(C(O)N(H)—CH₂—CH₂—CF₃)— |
| Ic-c600 | 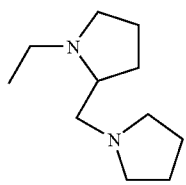 | —N(C(O)N(H)—CH₂—CH₂—CF₃)— |
| Ic-c601 | 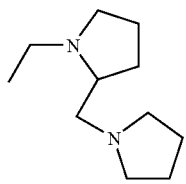 | —N(C(O)N(H)—CH₂—CF₃)— |
| Ic-c602 | 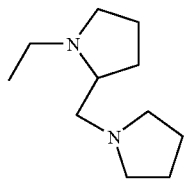 | —N(C(O)N(H)—(CH₂)₃—OH)— |
| Ic-c603 | 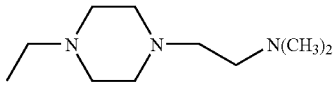 | —CH(OH)— |
| Ic-c604 | 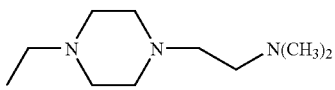 | —N(C(O)N(H)—CH₂—CH₂—OH)— |
| Ic-c605 | 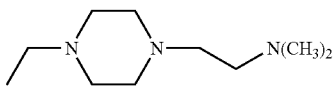 | —N(C(O)N(H)—CH₂—CH₂—F)— |
| Ic-c606 | 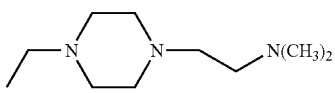 | —N(C(O)N(H)—CH₂—CH₂—OCH₃)— |
| Ic-c607 | 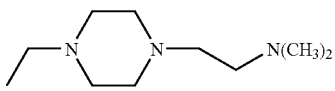 | —N(C(O)N(H)—CH₂—CH₂—CF₃)— |

-continued

| | | |
|---|---|---|
| Ic-c608 | [ethyl-piperazine-CH2CH2-N(CH3)2] | —N(C(O)N(H)—CH2—CH2—CF3— |
| Ic-c609 | [ethyl-piperazine-CH2CH2-N(CH3)2] | —N(C(O)N(H)—CH2—CF3— |
| Ic-c610 | [ethyl-piperazine-CH2CH2-N(CH3)2] | —N(C(O)N(H)—(CH2)3—OH)— |
| Ic-c611 | —CH2—NH—CH2—CH2—CH2—N(CH3)2 | —CH(OH)— |
| Ic-c612 | —CH2—NH—CH2—CH2—CH2—N(CH3)2 | —N(C(O)N(H)—CH2—CH2—OH)— |
| Ic-c613 | —CH2—NH—CH2—CH2—CH2—N(CH3)2 | —N(C(O)N(H)—CH2—CH2—F)— |
| Ic-c614 | —CH2—NH—CH2—CH2—CH2—N(CH3)2 | —N(C(O)N(H)—CH2—CH2—OCH3)— |
| Ic-c615 | —CH2—NH—CH2—CH2—CH2—N(CH3)2 | —N(C(O)N(H)—CH2—CH2—CF3)— |
| Ic-c616 | —CH2—NH—CH2—CH2—CH2—N(CH3)2 | —N(C(O)N(H)—CH2—CH2—CF3)— |
| Ic-c617 | —CH2—NH—CH2—CH2—CH2—N(CH3)2 | —N(C(O)N(H)—CH2—CF3)— |
| Ic-c618 | —CH2—NH—CH2—CH2—CH2—N(CH3)2 | —N(C(O)N(H)—(CH2)3—OH)— |
| Ic-c619 | [N-ethyl-N-methyl-furfurylamine] | —CH(OH)— |
| Ic-c620 | [N-ethyl-N-methyl-furfurylamine] | —N(C(O)N(H)—CH2—CH2—OH)— |
| Ic-c621 | [N-ethyl-N-methyl-furfurylamine] | —N(C(O)N(H)—CH2—CH2—F)— |
| Ic-c622 | [N-ethyl-N-methyl-furfurylamine] | —N(C(O)N(H)—CH2—CH2—OCH3)— |
| Ic-c623 | [N-ethyl-N-methyl-furfurylamine] | —N(C(O)N(H)—CH2—CH2—CF3)— |
| Ic-c624 | [N-ethyl-N-methyl-furfurylamine] | —N(C(O)N(H)—CH2—CH2—CF3)— |
| Ic-c625 | [N-ethyl-N-methyl-furfurylamine] | —N(C(O)N(H)—CH2—CF3)— |
| Ic-c626 | [N-ethyl-N-methyl-furfurylamine] | —N(C(O)N(H)—(CH2)3—OH)— |
| Ic-c627 | [N-ethyl-3-hydroxypyrrolidine] | —CH(OH)— |
| Ic-c628 | [N-ethyl-3-hydroxypyrrolidine] | —N(C(O)N(H)—CH2—CH2—OH)— |

-continued
| | | |
|---|---|---|
| Ic-c629 | 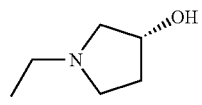 | —N(C(O)N(H)—CH₂—CH₂—F)— |
| Ic-c630 | 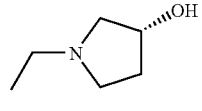 | —N(C(O)N(H)—CH₂—CH₂—OCH₃)— |
| Ic-c631 | 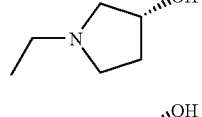 | —N(C(O)N(H)—CH₂—CH₂—CF₃)— |
| Ic-c632 | 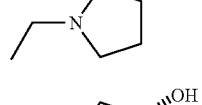 | —N(C(O)N(H)—CH₂—CH₂—CF₃)— |
| Ic-c633 | 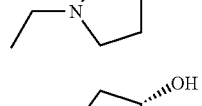 | —N(C(O)N(H)—CH₂—CF₃)— |
| Ic-c634 | 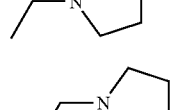 | —N(C(O)N(H)—(CH₂)₃—OH)— |
| Ic-c635 | 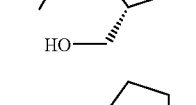 | —CH(OH)— |
| Ic-c636 | 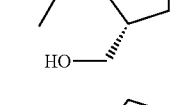 | —N(C(O)N(H)—CH₂—CH₂—OH)— |
| Ic-c637 | 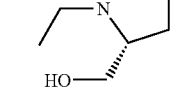 | —N(C(O)N(H)—CH₂—CH₂—F)— |
| Ic-c638 | 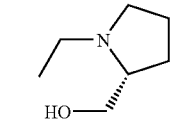 | —N(C(O)N(H)—CH₂—CH₂—OCH₃)— |
| Ic-c639 | 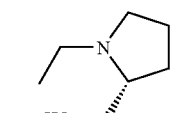 | —N(C(O)N(H)—CH₂—CH₂—CF₃)— |
| Ic-c640 | 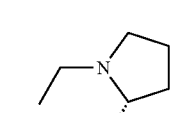 | —N(C(O)N(H)—CH₂—CH₂—CF₃)— |
| Ic-c641 | 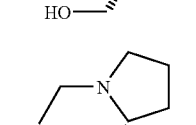 | —N(C(O)N(H)—CH₂—CF₃)— |

-continued
| | | |
|---|---|---|
| Ic-c642 | 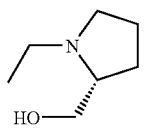 | —N(C(O)N(H)—(CH$_2$)$_3$—OH)— |
| Ic-c643 | 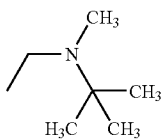 | —CH(OH)— |
| Ic-c644 | 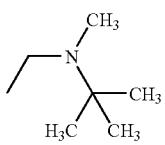 | —N(C(O)N(H)—CH$_2$—CH$_2$—OH)— |
| Ic-c645 | 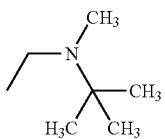 | —N(C(O)N(H)—CH$_2$—CH$_2$—F)— |
| Ic-c646 | 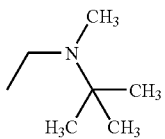 | —N(C(O)N(H)—CH$_2$—CH$_2$—OCH$_3$)— |
| Ic-c647 | 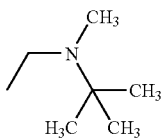 | —N(C(O)N(H)—CH$_2$—CH$_2$—CF$_3$)— |
| Ic-c648 | 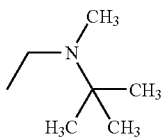 | —N(C(O)N(H)—CH$_2$—CH$_2$—CF$_3$)— |
| Ic-c649 | 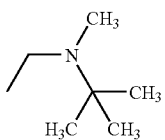 | —N(C(O)N(H)—CH$_2$—CF$_3$)— |
| Ic-c650 | 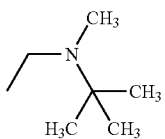 | —N(C(O)N(H)—(CH$_2$)$_3$—OH)— |
| Ic-c651 | 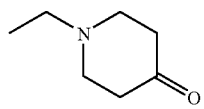 | —CH(OH)— |
| Ic-c652 | 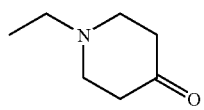 | —N(C(O)N(H)—CH$_2$—CH$_2$—OH)— |

-continued

| | | |
|---|---|---|
| Ic-c653 | 1-ethylpiperidin-4-one | —N(C(O)N(H)—CH₂—CH₂—F)— |
| Ic-c654 | 1-ethylpiperidin-4-one | —N(C(O)N(H)—CH₂—CH₂—OCH₃)— |
| Ic-c655 | 1-ethylpiperidin-4-one | —N(C(O)N(H)—CH₂—CH₂—CF₃)— |
| Ic-c656 | 1-ethylpiperidin-4-one | —N(C(O)N(H)—CH₂—CH₂—CF₃)— |
| Ic-c657 | 1-ethylpiperidin-4-one | —N(C(O)N(H)—CH₂—CF₃)— |
| Ic-c658 | 1-ethylpiperidin-4-one | —N(C(O)N(H)—(CH₂)₃—OH)— |
| Ic-c659 | 1-ethyl-4-hydroxypiperidine | —CH(OH)— |
| Ic-c660 | 1-ethyl-4-hydroxypiperidine | —N(C(O)N(H)—CH₂—CH₂—OH)— |
| Ic-c661 | 1-ethyl-4-hydroxypiperidine | —N(C(O)N(H)—CH₂—CH₂—F)— |
| Ic-c662 | 1-ethyl-4-hydroxypiperidine | —N(C(O)N(H)—CH₂—CH₂—OCH₃)— |
| Ic-c663 | 1-ethyl-4-hydroxypiperidine | —N(C(O)N(H)—CH₂—CH₂—CF₃)— |
| Ic-c664 | 1-ethyl-4-hydroxypiperidine | —N(C(O)N(H)—CH₂—CH₂—CF₃)— |
| Ic-c665 | 1-ethyl-4-hydroxypiperidine | —N(C(O)N(H)—CH₂—CF₃)— |
| Ic-c666 | 1-ethyl-4-hydroxypiperidine | —N(C(O)N(H)—(CH₂)₃—OH)— |
| Ic-c667 | 1-ethyl-3-hydroxypiperidine | —CH(OH)— |

-continued
| | | |
|---|---|---|
| Ic-c668 | 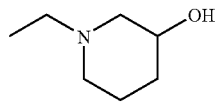 | —N(C(O)N(H)—CH₂—CH₂—OH)— |
| Ic-c669 | 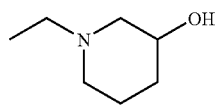 | —N(C(O)N(H)—CH₂—CH₂—F)— |
| Ic-c670 | 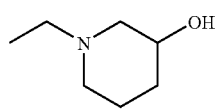 | —N(C(O)N(H)—CH₂—CH₂—OCH₃)— |
| Ic-c671 | 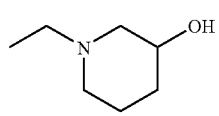 | —N(C(O)N(H)—CH₂—CH₂—CF₃)— |
| Ic-c672 | 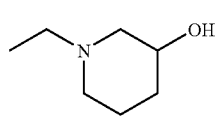 | —N(C(O)N(H)—CH₂—CH₂—CF₃)— |
| Ic-c673 | 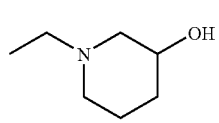 | —N(C(O)N(H)—CH₂—CF₃)— |
| Ic-c674 | 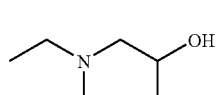 | —N(C(O)N(H)—(CH₂)₃—OH)— |
| Ic-c675 | 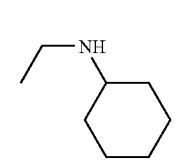 | —CH(OH)— |
| Ic-c676 | 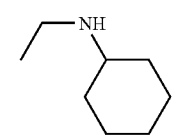 | —N(C(O)N(H)—CH₂—CH₂—OH)— |
| Ic-c677 | 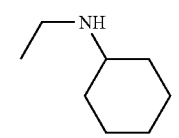 | —N(C(O)N(H)—CH₂—CH₂—F)— |
| Ic-c678 | 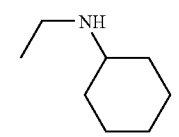 | —N(C(O)N(H)—CH₂—CH₂—OCH₃)— |
| Ic-c679 | 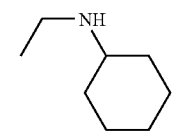 | —N(C(O)N(H)—CH₂—CH₂—CF₃)— |

-continued

| | | |
|---|---|---|
| Ic-c680 | ethyl-NH-cyclohexyl | —N(C(O)N(H)—CH₂—CH₂—CF₃)— |
| Ic-c681 | ethyl-NH-cyclohexyl | —N(C(O)N(H)—CH₂—CF₃)— |
| Ic-c682 | ethyl-NH-cyclohexyl | —N(C(O)N(H)—(CH₂)₃—OH)— |
| Ic-c683 | ethyl-NH-cyclopentyl | —CH(OH)— |
| Ic-c684 | ethyl-NH-cyclopentyl | —N(C(O)N(H)—CH₂—CH₂—OH)— |
| Ic-c685 | ethyl-NH-cyclopentyl | —N(C(O)N(H)—CH₂—CH₂—F)— |
| Ic-c686 | ethyl-NH-cyclopentyl | —N(C(O)N(H)—CH₂—CH₂—OCH₃)— |
| Ic-c687 | ethyl-NH-cyclopentyl | —N(C(O)N(H)—CH₂—CH₂—CF₃)— |
| Ic-c688 | ethyl-NH-cyclopentyl | —N(C(O)N(H)—CH₂—CH₂—CF₃)— |
| Ic-c689 | ethyl-NH-cyclopentyl | —N(C(O)N(H)—CH₂—CF₃)— |
| Ic-c690 | ethyl-NH-cyclopentyl | —N(C(O)N(H)—(CH₂)₃—OH)— |
| Ic-c691 | ethyl-NH-CH₂-cyclohexyl | —CH(OH)— |

| | | |
|---|---|---|
| Ic-c692 | 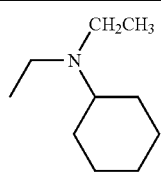 | —N(C(O)N(H)—CH₂—CH₂—OH)— |
| Ic-c693 | 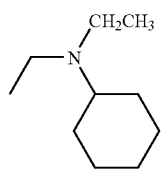 | —N(C(O)N(H)—CH₂—CH₂—F)— |
| Ic-c694 | 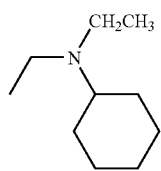 | —N(C(O)N(H)—CH₂—CH₂—OCH₃)— |
| Ic-c695 | 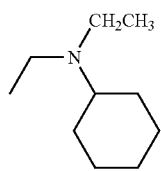 | —N(C(O)N(H)—CH₂—CH₂—CF₃)— |
| Ic-c696 | 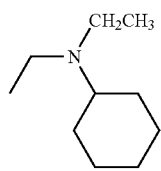 | —N(C(O)N(H)—CH₂—CH₂—CF₃)— |
| Ic-c697 | 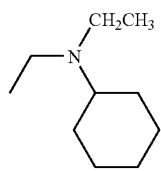 | —N(C(O)N(H)—CH₂—CF₃)— |
| Ic-c698 | 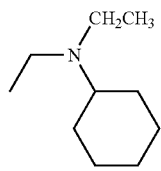 | —N(C(O)N(H)—(CH₂)₃—OH)— |
| Ic-c699 | 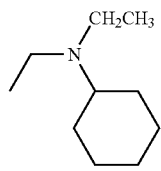 | —CH(OH)— |
| Ic-c700 | 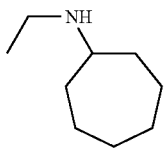 | —N(C(O)N(H)—CH₂—CH₂—OH)— |

-continued
| | | |
|---|---|---|
| Ic-c701 | 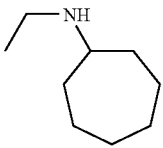 | —N(C(O)N(H)—CH₂—CH₂—F)— |
| Ic-c702 | 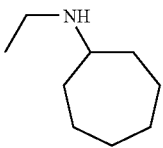 | —N(C(O)N(H)—CH₂—CH₂—OCH₃)— |
| Ic-c703 | 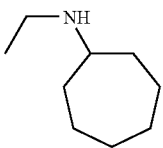 | —N(C(O)N(H)—CH₂—CH₂—CF₃)— |
| Ic-c704 | 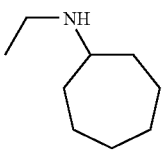 | —N(C(O)N(H)—CH₂—CH₂—CF₃)— |
| Ic-c705 | 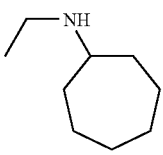 | —N(C(O)N(H)—CH₂—CF₃)— |
| Ic-c706 | 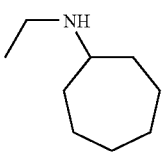 | —N(C(O)N(H)—(CH₂)₃—OH)— |
| Ic-c707 | 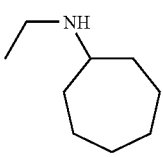 | —CH(OH)— |
| Ic-c708 | 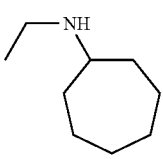 | —N(C(O)N(H)—CH₂—CH₂—OH)— |
| Ic-c709 | 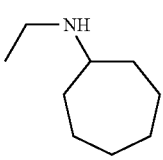 | —N(C(O)N(H)—CH₂—CH₂—F)— |
| Ic-c710 | 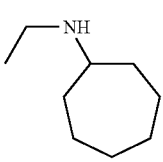 | —N(C(O)N(H)—CH₂—CH₂—OCH₃)— |

-continued

| ID | R | Linker |
|---|---|---|
| Ic-c711 | ethyl-NH-cycloheptyl | —N(C(O)N(H)—CH₂—CH₂—CF₃)— |
| Ic-c712 | ethyl-NH-cycloheptyl | —N(C(O)N(H)—CH₂—CH₂—CF₃)— |
| Ic-c713 | ethyl-NH-cycloheptyl | —N(C(O)N(H)—CH₂—CF₃)— |
| Ic-c714 | ethyl-NH-cycloheptyl | —N(C(O)N(H)—(CH₂)₃—OH)— |
| Ic-c715 | N-ethyl-thiomorpholine | —CH(OH)— |
| Ic-c716 | N-ethyl-thiomorpholine | —N(C(O)N(H)—CH₂—CH₂—OH)— |
| Ic-c717 | N-ethyl-thiomorpholine | —N(C(O)N(H)—CH₂—CH₂—F)— |
| Ic-c718 | N-ethyl-thiomorpholine | —N(C(O)N(H)—CH₂—CH₂—OCH₃)— |
| Ic-c719 | N-ethyl-thiomorpholine | —N(C(O)N(H)—CH₂—CH₂—CF₃)— |
| Ic-c720 | N-ethyl-thiomorpholine | —N(C(O)N(H)—CH₂—CH₂—CF₃)— |
| Ic-c721 | N-ethyl-thiomorpholine | —N(C(O)N(H)—CH₂—CF₃)— |
| Ic-c722 | N-ethyl-thiomorpholine | —N(C(O)N(H)—(CH₂)₃—OH)— |
| Ic-c723 | N-ethyl-4-(hydroxymethyl)piperidine | —CH(OH)— |
| Ic-c724 | N-ethyl-4-(hydroxymethyl)piperidine | —N(C(O)N(H)—CH₂—CH₂—OH)— |

-continued
| | | |
|---|---|---|
| Ic-c725 | 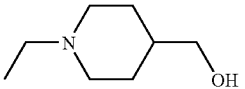 | —N(C(O)N(H)—CH₂—CH₂—F)— |
| Ic-c726 | 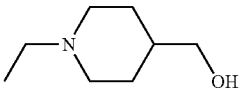 | —N(C(O)N(H)—CH₂—CH₂—OCH₃)— |
| Ic-c727 | 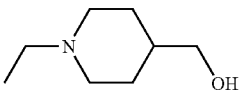 | —N(C(O)N(H)—CH₂—CH₂—CF₃)— |
| Ic-c728 | 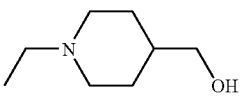 | —N(C(O)N(H)—CH₂—CH₂—CF₃)— |
| Ic-c729 | 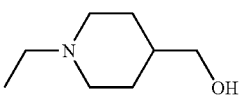 | —N(C(O)N(H)—CH₂—CF₃)— |
| Ic-c730 | 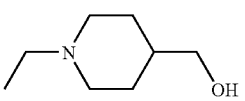 | —N(C(O)N(H)—(CH₂)₃—OH)— |
| Ic-c731 | 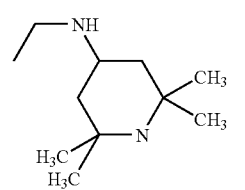 | —CH(OH)— |
| Ic-c732 | 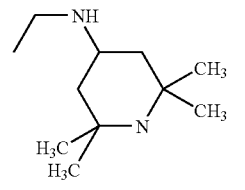 | —N(C(O)N(H)—CH₂—CH₂—OH)— |
| Ic-c733 | 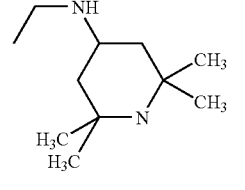 | —N(C(O)N(H)—CH₂—CH₂—F)— |
| Ic-c734 | 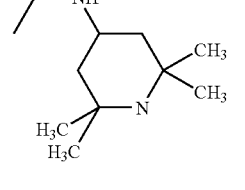 | —N(C(O)N(H)—CH₂—CH₂—OCH₃)— |
| Ic-c735 | 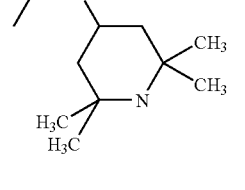 | —N(C(O)N(H)—CH₂—CH₂—CF₃)— |

| | | |
|---|---|---|
| Ic-c736 | 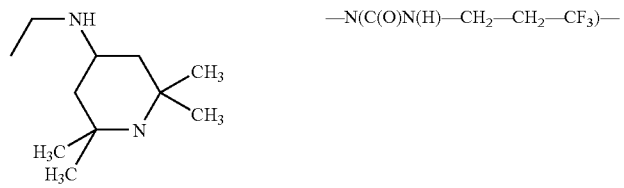 | —N(C(O)N(H)—CH$_2$—CH$_2$—CF$_3$)— |
| Ic-c737 | 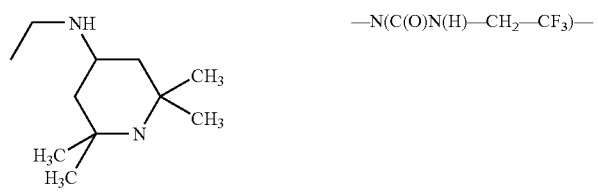 | —N(C(O)N(H)—CH$_2$—CF$_3$)— |
| Ic-c738 | 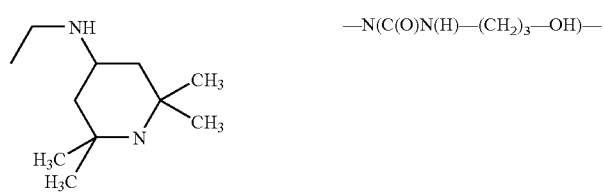 | —N(C(O)N(H)—(CH$_2$)$_3$—OH)— |
| Ic-c739 | 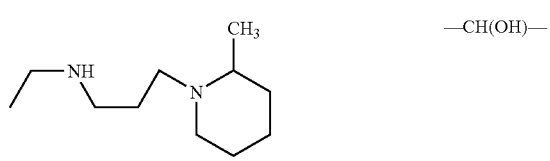 | —CH(OH)— |
| Ic-c740 | 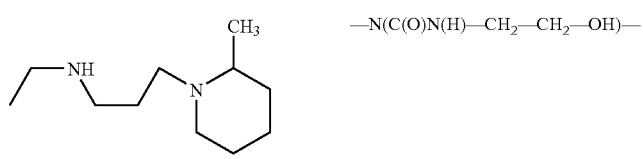 | —N(C(O)N(H)—CH$_2$—CH$_2$—OH)— |
| Ic-c741 | 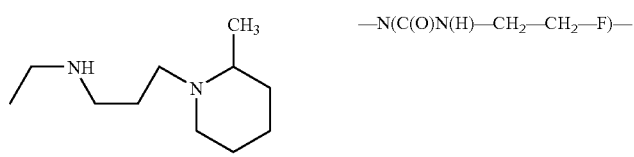 | —N(C(O)N(H)—CH$_2$—CH$_2$—F)— |
| Ic-c742 | 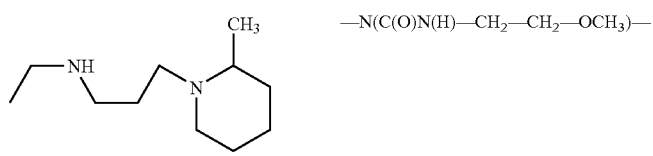 | —N(C(O)N(H)—CH$_2$—CH$_2$—OCH$_3$)— |
| Ic-c743 | 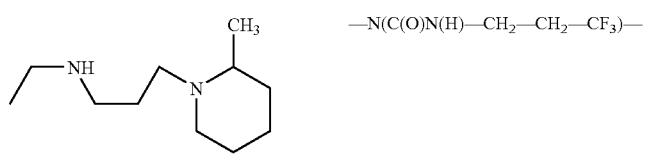 | —N(C(O)N(H)—CH$_2$—CH$_2$—CF$_3$)— |
| Ic-c744 | 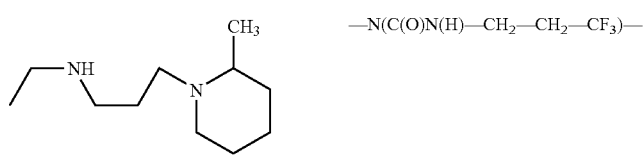 | —N(C(O)N(H)—CH$_2$—CH$_2$—CF$_3$)— |

-continued
| | | |
|---|---|---|
| Ic-c745 | 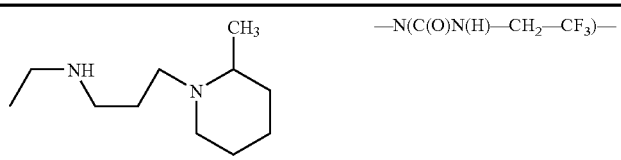 | —N(C(O)N(H)—CH₂—CF₃)— |
| Ic-c746 | 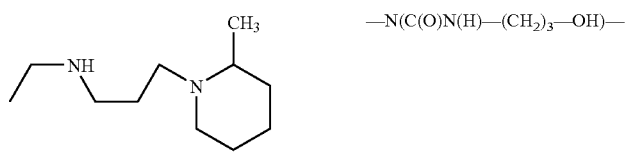 | —N(C(O)N(H)—(CH₂)₃—OH)— |
| Ic-c747 | 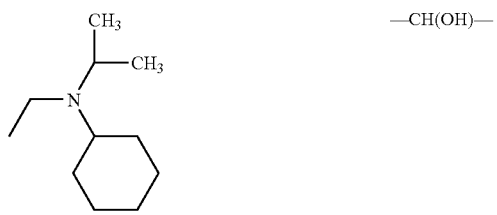 | —CH(OH)— |
| Ic-c748 | 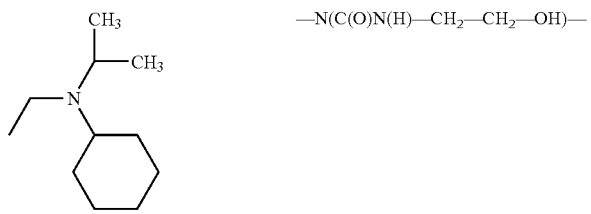 | —N(C(O)N(H)—CH₂—CH₂—OH)— |
| Ic-c749 | 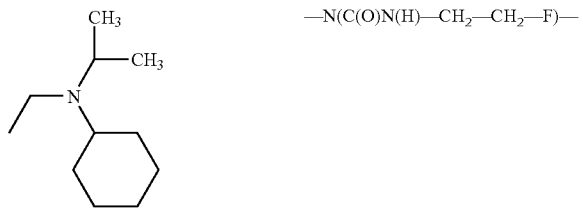 | —N(C(O)N(H)—CH₂—CH₂—F)— |
| Ic-c750 | 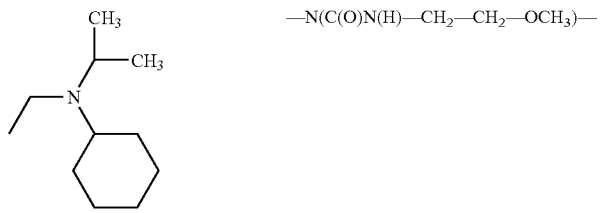 | —N(C(O)N(H)—CH₂—CH₂—OCH₃)— |
| Ic-c751 |  | —N(C(O)N(H)—CH₂—CH₂—CF₃)— |
| Ic-c752 |  | —N(C(O)N(H)—CH₂—CH₂—CF₃)— |

-continued
| | | |
|---|---|---|
| Ic-c753 | 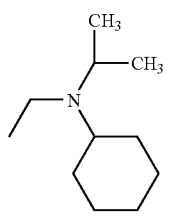 | —N(C(O)N(H)—CH₂—CF₃)— |
| Ic-c754 | 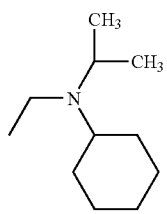 | —N(C(O)N(H)—(CH₂)₃—OH)— |
| Ic-c755 | 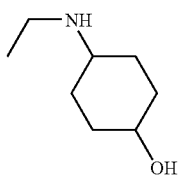 | —CH(OH)— |
| Ic-c756 | 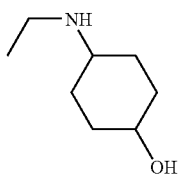 | —N(C(O)N(H)—CH₂—CH₂—OH)— |
| Ic-c757 | 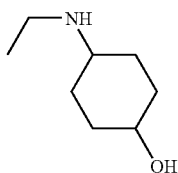 | —N(C(O)N(H)—CH₂—CH₂—F)— |
| Ic-c758 | 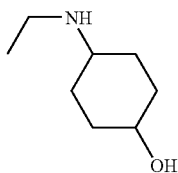 | —N(C(O)N(H)—CH₂—CH₂—OCH₃)— |
| Ic-c759 | 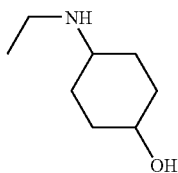 | —N(C(O)N(H)—CH₂—CH₂—CF₃)— |
| Ic-c760 | 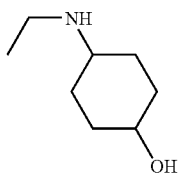 | —N(C(O)N(H)—CH₂—CH₂—CF₃)— |
Note: For Ic-c753 and Ic-c754, the linker should read $-N(C(O)N(H)-CH_2-CF_3)-$ and $-N(C(O)N(H)-(CH_2)_3-OH)-$ respectively, with subscripts rendered in the table as shown.

-continued
| | | |
|---|---|---|
| Ic-c761 | 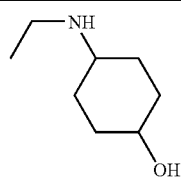 | —N(C(O)N(H)—CH₂—CF₃)— |
| Ic-c762 | 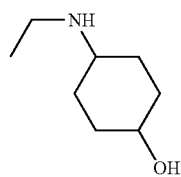 | —N(C(O)N(H)—(CH₂)₃—OH)— |
| Ic-c763 | 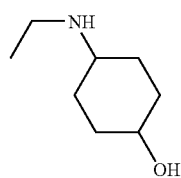 | —CH(OH)— |
| Ic-c764 | 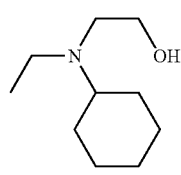 | —N(C(O)N(H)—CH₂—CH₂—OH)— |
| Ic-c765 | 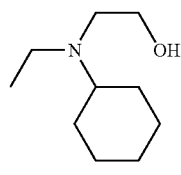 | —N(C(O)N(H)—CH₂—CH₂—F)— |
| Ic-c766 | 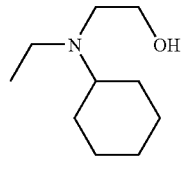 | —N(C(O)N(H)—CH₂—CH₂—OCH₃)— |
| Ic-c767 | 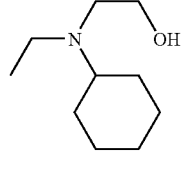 | —N(C(O)N(H)—CH₂—CH₂—CF₃)— |
| Ic-c768 | 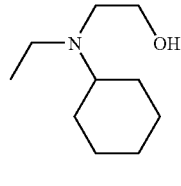 | —N(C(O)N(H)—CH₂—CH₂—CF₃)— |
| Ic-c769 | 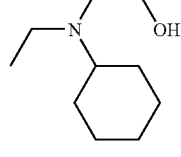 | —N(C(O)N(H)—CH₂—CF₃)— |

-continued

| | | |
|---|---|---|
| Ic-c770 | 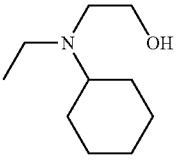 | —N(C(O)N(H)—(CH₂)₃—OH)— |
| Ic-c771 | 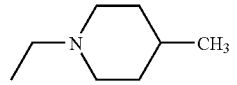 | —CH(OH)— |
| Ic-c772 |  | —N(C(O)N(H)—CH₂—CH₂—OH)— |
| Ic-c773 |  | —N(C(O)N(H)—CH₂—CH₂—F)— |
| Ic-c774 |  | —N(C(O)N(H)—CH₂—CH₂—OCH₃)— |
| Ic-c775 | 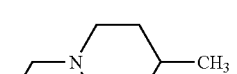 | —N(C(O)N(H)—CH₂—CH₂—CF₃)— |
| Ic-c776 | 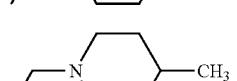 | —N(C(O)N(H)—CH₂—CH₂—CF₃)— |
| Ic-c777 | 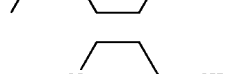 | —N(C(O)N(H)—CH₂—CF₃)— |
| Ic-c778 | 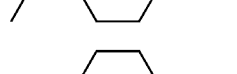 | —N(C(O)N(H)—(CH₂)₃—OH)— |
| Ic-c779 | —CH₂—NH—CH₃ | —CH(OH)— |
| Ic-c780 | —CH₂—NH—CH₃ | —N(C(O)N(H)—CH₂—CH₂—OH)— |
| Ic-c781 | —CH₂—NH—CH₃ | —N(C(O)N(H)—CH₂—CH₂—F)— |
| Ic-c782 | —CH₂—NH—CH₃ | —N(C(O)N(H)—CH₂—CH₂—OCH₃)— |
| Ic-c783 | —CH₂—NH—CH₃ | —N(C(O)N(H)—CH₂—CH₂—CF₃)— |
| Ic-c784 | —CH₂—NH—CH₃ | —N(C(O)N(H)—CH₂—CH₂—CF₃)— |
| Ic-c785 | —CH₂—NH—CH₃ | —N(C(O)N(H)—CH₂—CF₃)— |
| Ic-c786 | —CH₂—NH—CH₃ | —N(C(O)N(H)—(CH₂)₃—OH)— |
| Ic-c787 | —CH₂—NH—CH₂—CH₃ | —CH(OH)— |
| Ic-c788 | —CH₂—NH—CH₂—CH₃ | —N(C(O)N(H)—CH₂—CH₂—OH)— |
| Ic-c789 | —CH₂—NH—CH₂—CH₃ | —N(C(O)N(H)—CH₂—CH₂—F)— |
| Ic-c790 | —CH₂—NH—CH₂—CH₃ | —N(C(O)N(H)—CH₂—CH₂—OCH₃)— |
| Ic-c791 | —CH₂—NH—CH₂—CH₃ | —N(C(O)N(H)—CH₂—CH₂—CF₃)— |
| Ic-c792 | —CH₂—NH—CH₂—CH₃ | —N(C(O)N(H)—CH₂—CH₂—CF₃)— |
| Ic-c793 | —CH₂—NH—CH₂—CH₃ | —N(C(O)N(H)—CH₂—CF₃)— |
| Ic-c794 | —CH₂—NH—CH₂—CH₃ | —N(C(O)N(H)—(CH₂)₃—OH)— |
| Ic-c795 | —CH₂—NH—CH₂—CH₂—CH₃ | —CH(OH)— |
| Ic-c796 | —CH₂—NH—CH₂—CH₂—CH₃ | —N(C(O)N(H)—CH₂—CH₂—OH)— |
| Ic-c797 | —CH₂—NH—CH₂—CH₂—CH₃ | —N(C(O)N(H)—CH₂—CH₂—F)— |
| Ic-c798 | —CH₂—NH—CH₂—CH₂—CH₃ | —N(C(O)N(H)—CH₂—CH₂—OCH₃)— |
| Ic-c799 | —CH₂—NH—CH₂—CH₂—CH₃ | —N(C(O)N(H)—CH₂—CH₂—CF₃)— |
| Ic-c800 | —CH₂—NH—CH₂—CH₂—CH₃ | —N(C(O)N(H)—CH₂—CH₂—CF₃)— |
| Ic-c801 | —CH₂—NH—CH₂—CH₂—CH₃ | —N(C(O)N(H)—CH₂—CF₃)— |
| Ic-c802 | —CH₂—NH—CH₂—CH₂—CH₃ | —N(C(O)N(H)—(CH₂)₃—OH)— |
| Ic-c803 | 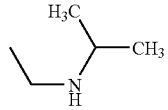 | —CH(OH)— |

-continued

| | | |
|---|---|---|
| Ic-c804 | H₃C-CH(CH₃)-NH-CH₂CH₃ | —N(C(O)N(H)—CH₂—CH₂—OH)— |
| Ic-c805 | H₃C-CH(CH₃)-NH-CH₂CH₃ | —N(C(O)N(H)—CH₂—CH₂—F)— |
| Ic-c806 | H₃C-CH(CH₃)-NH-CH₂CH₃ | —N(C(O)N(H)—CH₂—CH₂—OCH₃)— |
| Ic-c807 | H₃C-CH(CH₃)-NH-CH₂CH₃ | —N(C(O)N(H)—CH₂—CH₂—CF₃)— |
| Ic-c808 | H₃C-CH(CH₃)-NH-CH₂CH₃ | —N(C(O)N(H)—CH₂—CH₂—CF₃)— |
| Ic-c809 | H₃C-CH(CH₃)-NH-CH₂CH₃ | —N(C(O)N(H)—CH₂—CF₃)— |
| Ic-c810 | H₃C-CH(CH₃)-NH-CH₂CH₃ | —N(C(O)N(H)—(CH₂)₃—OH)— |
| Ic-c811 | H₃C-CH(CH₃)-CH(NHEt)-C(O)OMe | —CH(OH)— |
| Ic-c812 | H₃C-CH(CH₃)-CH(NHEt)-C(O)OMe | —N(C(O)N(H)—CH₂—CH₂—OH)— |
| Ic-c813 | H₃C-CH(CH₃)-CH(NHEt)-C(O)OMe | —N(C(O)N(H)—CH₂—CH₂—F)— |
| Ic-c814 | H₃C-CH(CH₃)-CH(NHEt)-C(O)OMe | —N(C(O)N(H)—CH₂—CH₂—OCH₃)— |

-continued
| | | |
|---|---|---|
| Ic-c815 | 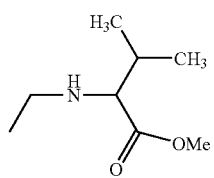 | —N(C(O)N(H)—CH$_2$—CH$_2$—CF$_3$)— |
| Ic-c816 | 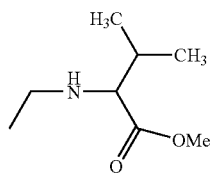 | —N(C(O)N(H)—CH$_2$—CH$_2$—CF$_3$)— |
| Ic-c817 | 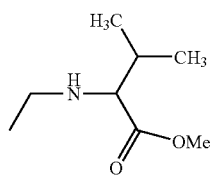 | N(C(O)N(H)—CH$_2$—CF$_3$)— |
| Ic-c818 | 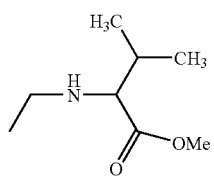 | N(C(O)N(H)—(CH$_2$)$_3$—OH)— |
| Ic-c819 | 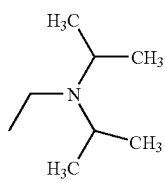 | —CH(OH)— |
| Ic-c820 | 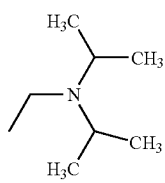 | —N(C(O)N(H)—CH$_2$—CH$_2$—OH)— |
| Ic-c821 | 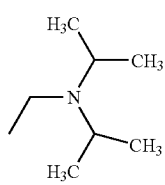 | —N(C(O)N(H)—CH$_2$—CH$_2$—F)— |
| Ic-c822 | 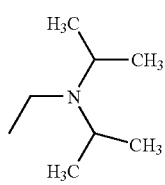 | —N(C(O)N(H)—CH$_2$—CH$_2$—OCH$_3$)— |

-continued

| | | |
|---|---|---|
| Ic-c823 | H₃C-CH(CH₃)-N(Et)-CH(CH₃)-CH₃ (diisopropylethylamine group) | —N(C(O)N(H)—CH₂—CH₂—CF₃)— |
| Ic-c824 | diisopropylethylamine group | —N(C(O)N(H)—CH₂—CH₂—CF₃)— |
| Ic-c825 | diisopropylethylamine group | —N(C(O)N(H)—CH₂—CF₃)— |
| Ic-c826 | diisopropylethylamine group | —N(C(O)N(H)—(CH₂)₃—OH)— |
| Ic-c827 | N-ethyl-N-methyl-2-(pyridin-2-yl)ethylamine group | —CH(OH)— |
| Ic-c828 | N-ethyl-N-methyl-2-(pyridin-2-yl)ethylamine group | —N(C(O)N(H)—CH₂—CH₂—OH)— |
| Ic-c829 | N-ethyl-N-methyl-2-(pyridin-2-yl)ethylamine group | —N(C(O)N(H)—CH₂—CH₂—F)— |
| Ic-c830 | N-ethyl-N-methyl-2-(pyridin-2-yl)ethylamine group | —N(C(O)N(H)—CH₂—CH₂—OCH₃)— |
| Ic-c831 | N-ethyl-N-methyl-2-(pyridin-2-yl)ethylamine group | —N(C(O)N(H)—CH₂—CH₂—CF₃)— |
| Ic-c832 | N-ethyl-N-methyl-2-(pyridin-2-yl)ethylamine group | —N(C(O)N(H)—CH₂—CH₂—CF₃)— |
| Ic-c833 | N-ethyl-N-methyl-2-(pyridin-2-yl)ethylamine group | —N(C(O)N(H)—CH₂—CF₃)— |

-continued

| | | |
|---|---|---|
| Ic-c834 | [structure: ethyl(methyl)amino-CH2-CH2-pyridin-2-yl] | —N(C(O)N(H)—(CH₂)₃—OH)— |
| Ic-c835 | [structure: diethylamino-CH2-pyridin-4-yl] | —CH(OH)— |
| Ic-c836 | [structure: diethylamino-CH2-pyridin-4-yl] | —N(C(O)N(H)—CH₂—CH₂—OH)— |
| Ic-c837 | [structure: diethylamino-CH2-pyridin-4-yl] | —N(C(O)N(H)—CH₂—CH₂—F)— |
| Ic-c838 | [structure: diethylamino-CH2-pyridin-4-yl] | —N(C(O)N(H)—CH₂—CH₂—OCH₃)— |
| Ic-c839 | [structure: diethylamino-CH2-pyridin-4-yl] | —N(C(O)N(H)—CH₂—CH₂—CF₃)— |
| Ic-c840 | [structure: diethylamino-CH2-pyridin-4-yl] | —N(C(O)N(H)—CH₂—CH₂—CF₃)— |
| Ic-c841 | [structure: diethylamino-CH2-pyridin-4-yl] | —N(C(O)N(H)—CH₂—CF₃)— |
| Ic-c842 | [structure: diethylamino-CH2-pyridin-3-yl] | —N(C(O)N(H)—(CH₂)₃—OH)— |
| Ic-c843 | [structure: ethyl(methyl)(2-hydroxyethyl)amino] | —CH(OH)— |
| Ic-c844 | [structure: ethyl(methyl)(2-hydroxyethyl)amino] | —N(C(O)N(H)—CH₂—CH₂—OH)— |
| Ic-c845 | [structure: ethyl(methyl)(2-hydroxyethyl)amino] | —N(C(O)N(H)—CH₂—CH₂—F)— |
| Ic-c846 | [structure: ethyl(methyl)(2-hydroxyethyl)amino] | —N(C(O)N(H)—CH₂—CH₂—OCH₃)— |
| Ic-c847 | [structure: ethyl(methyl)(2-hydroxyethyl)amino] | —N(C(O)N(H)—CH₂—CH₂—CF₃)— |

-continued

| | | |
|---|---|---|
| Ic-c848 | CH₃, Et-N-CH₂CH₂OH | —N(C(O)N(H)—CH₂—CH₂—CF₃)— |
| Ic-c849 | CH₃, Et-N-CH₂CH₂OH | —N(C(O)N(H)—CH₂—CF₃)— |
| Ic-c850 | CH₃, Et-N-CH₂CH₂OH | —N(C(O)N(H)—(CH₂)₃—OH)— |
| Ic-c851 | Et-piperidine-piperidine | —CH(OH)— |
| Ic-c852 | Et-piperidine-piperidine | —N(C(O)N(H)—CH₂—CH₂—OH)— |
| Ic-c853 | Et-piperidine-piperidine | —N(C(O)N(H)—CH₂—CH₂—F)— |
| Ic-c854 | Et-piperidine-piperidine | —N(C(O)N(H)—CH₂—CH₂—OCH₃)— |
| Ic-c855 | Et-piperidine-piperidine | —N(C(O)N(H)—CH₂—CH₂—CF₃)— |
| Ic-c856 | Et-piperidine-piperidine | —N(C(O)N(H)—CH₂—CH₂—CF₃)— |
| Ic-c857 | Et-piperidine-piperidine | —N(C(O)N(H)—CH₂—CF₃)— |
| Ic-c858 | Et-piperidine-piperidine | —N(C(O)N(H)—(CH₂)₃—OH)— |
| Ic-c859 | Et-NH-CH₂-piperidine | —CH(OH)— |
| Ic-c860 | Et-NH-CH₂-piperidine | —N(C(O)N(H)—CH₂—CH₂—OH)— |
| Ic-c861 | Et-NH-CH₂-piperidine | —N(C(O)N(H)—CH₂—CH₂—F)— |
| Ic-c862 | Et-NH-CH₂-piperidine | —N(C(O)N(H)—CH₂—CH₂—OCH₃)— |
| Ic-c863 | Et-NH-CH₂-piperidine | —N(C(O)N(H)—CH₂—CH₂—CF₃)— |

| | | |
|---|---|---|
| Ic-c864 | ethyl-NH-CH2CH2-N(piperidine) | —N(C(O)N(H)—CH2—CH2—CF3)— |
| Ic-c865 | ethyl-NH-CH2CH2-N(piperidine) | —N(C(O)N(H)—CH2—CF3)— |
| Ic-c866 | ethyl-NH-CH2CH2-N(piperidine) | —N(C(O)N(H)—(CH2)3—OH)— |
| Ic-c867 | ethyl-N(CH3)-CH2-furan | —CH(OH)— |
| Ic-c868 | ethyl-N(CH3)-CH2-furan | —N(C(O)N(H)—CH2—CH2—OH)— |
| Ic-c869 | ethyl-N(CH3)-CH2-furan | —N(C(O)N(H)—CH2—CH2—F)— |
| Ic-c870 | ethyl-N(CH3)-CH2-furan | —N(C(O)N(H)—CH2—CH2—OCH3)— |
| Ic-c871 | ethyl-N(CH3)-CH2-furan | —N(C(O)N(H)—CH2—CH2—CF3)— |
| Ic-c872 | ethyl-N(CH3)-CH2-furan | —N(C(O)N(H)—CH2—CH2—CF3)— |
| Ic-c873 | ethyl-N(CH3)-CH2-furan | —N(C(O)N(H)—CH2—CF3)— |
| Ic-c874 | ethyl-N(CH3)-CH2-furan | —N(C(O)N(H)—(CH2)3—OH)— |
| Ic-c875 | ethyl-NH-CH2CH2CH2-(2-pyridyl) | —CH(OH)— |
| Ic-c876 | ethyl-NH-CH2CH2CH2-(2-pyridyl) | —N(C(O)N(H)—CH2—CH2—OH)— |
| Ic-c877 | ethyl-NH-CH2CH2CH2-(2-pyridyl) | —N(C(O)N(H)—CH2—CH2—F)— |

| | | -continued |
|---|---|---|
| Ic-c878 | 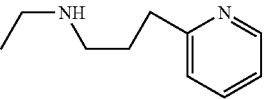 | —N(C(O)N(H)—CH₂—CH₂—OCH₃)— |
| Ic-c879 | 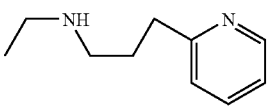 | —N(C(O)N(H)—CH₂—CH₂—CF₃)— |
| Ic-c880 | 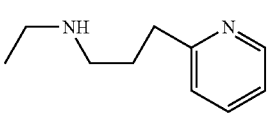 | —N(C(O)N(H)—CH₂—CH₂—CF₃)— |
| Ic-c881 | 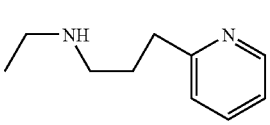 | —N(C(O)N(H)—CH₂—CF₃)— |
| Ic-c882 | 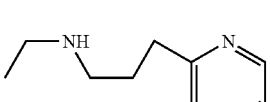 | —N(C(O)N(H)—(CH₂)₃—OH)— |
| Ic-c883 | 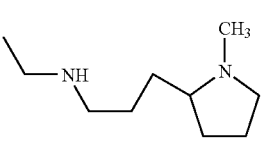 | —CH(OH)— |
| Ic-c884 | 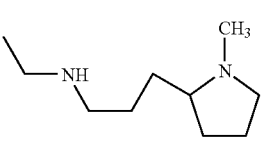 | —N(C(O)N(H)—CH₂—CH₂—OH)— |
| Ic-c885 | 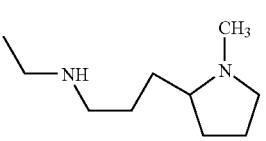 | —N(C(O)N(H)—CH₂—CH₂—F)— |
| Ic-c886 | 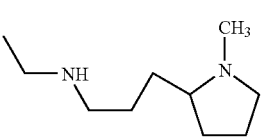 | —N(C(O)N(H)—CH₂—CH₂—OCH₃)— |
| Ic-c887 | 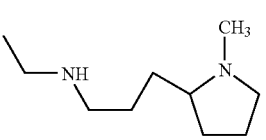 | —N(C(O)N(H)—CH₂—CH₂—CF₃)— |
| Ic-c888 | 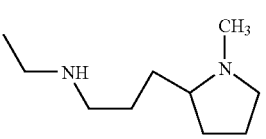 | —N(C(O)N(H)—CH₂—CH₂—CF₃)— |
| Ic-c889 | 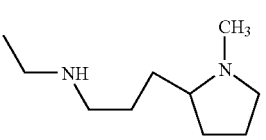 | —N(C(O)N(H)—CH₂—CF₃)— |

| | | |
|---|---|---|
| Ic-c890 | ethyl-NH-CH2CH2CH2-(N-methylpyrrolidin-2-yl) | —N(C(O)N(H)—(CH₂)₃—OH)— |
| Ic-c891 | 1-ethylpiperazine (NH) | —CH(OH)— |
| Ic-c892 | 1-ethylpiperazine (NH) | —N(C(O)N(H)—CH₂—CH₂—OH)— |
| Ic-c893 | 1-ethylpiperazine (NH) | —N(C(O)N(H)—CH₂—CH₂—F)— |
| Ic-c894 | 1-ethylpiperazine (NH) | —N(C(O)N(H)—CH₂—CH₂—OCH₃)— |
| Ic-c895 | 1-ethylpiperazine (NH) | —N(C(O)N(H)—CH₂—CH₂—CF₃)— |
| Ic-c896 | 1-ethylpiperazine (NH) | —N(C(O)N(H)—CH₂—CH₂—CF₃)— |
| Ic-c897 | 1-ethylpiperazine (NH) | —N(C(O)N(H)—CH₂—CF₃)— |
| Ic-c898 | 1-ethylpiperazine (NH) | —N(C(O)N(H)—(CH₂)₃—OH)— |
| Ic-c899 | 1-ethyl-4-ethylpiperazine (with CH₃) | —CH(OH)— |
| Ic-c900 | 1-ethyl-4-ethylpiperazine (with CH₃) | —N(C(O)N(H)—CH₂—CH₂—OH)— |
| Ic-c901 | 1-ethyl-4-ethylpiperazine (with CH₃) | —N(C(O)N(H)—CH₂—CH₂—F)— |
| Ic-c902 | 1-ethyl-4-ethylpiperazine (with CH₃) | —N(C(O)N(H)—CH₂—CH₂—OCH₃)— |
| Ic-c903 | 1-ethyl-4-ethylpiperazine (with CH₃) | —N(C(O)N(H)—CH₂—CH₂—CF₃)— |
| Ic-c904 | 1-ethyl-4-ethylpiperazine (with CH₃) | —N(C(O)N(H)—CH₂—CH₂—CF₃)— |

-continued

| | | |
|---|---|---|
| Ic-c905 | 1,4-diethylpiperazine (N-CH₃ shown) | —N(C(O)N(H)—CH₂—CF₃— |
| Ic-c906 | 1,4-diethylpiperazine (N-CH₃ shown) | —N(C(O)N(H)—(CH₂)₃—OH— |
| Ic-c907 | cyclopropyl-CH₂-NH— | —CH(OH)— |
| Ic-c908 | cyclopropyl-CH₂-NH— | —N(C(O)N(H)—CH₂—CH₂—OH— |
| Ic-c909 | cyclopropyl-CH₂-NH— | —N(C(O)N(H)—CH₂—CH₂—F— |
| Ic-c910 | cyclopropyl-CH₂-NH— | —N(C(O)N(H)—CH₂—CH₂—OCH₃— |
| Ic-c911 | cyclopropyl-CH₂-NH— | —N(C(O)N(H)—CH₂—CH₂—CF₃— |
| Ic-c912 | cyclopropyl-CH₂-NH— | —N(C(O)N(H)—CH₂—CH₂—CF₃— |
| Ic-c913 | cyclopropyl-CH₂-NH— | —N(C(O)N(H)—CH₂—CF₃— |
| Ic-c914 | cyclopropyl-CH₂-NH— | —N(C(O)N(H)—(CH₂)₃—OH— |
| Ic-c915 | 1-ethyl-4-(2-hydroxyethyl)piperazine | —CH(OH)— |
| Ic-c916 | 1-ethyl-4-(2-hydroxyethyl)piperazine | —N(C(O)N(H)—CH₂—CH₂—OH— |
| Ic-c917 | 1-ethyl-4-(2-hydroxyethyl)piperazine | —N(C(O)N(H)—CH₂—CH₂—F— |
| Ic-c918 | 1-ethyl-4-(2-hydroxyethyl)piperazine | —N(C(O)N(H)—CH₂—CH₂—OCH₃— |
| Ic-c919 | 1-ethyl-4-(2-hydroxyethyl)piperazine | —N(C(O)N(H)—CH₂—CH₂—CF₃— |

| | | |
|---|---|---|
| Ic-c920 | 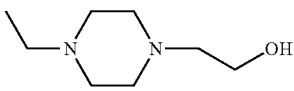 | —N(C(O)N(H)—CH₂—CH₂—CF₃)— |
| Ic-c921 | 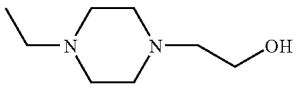 | —N(C(O)N(H)—CH₂—CF₃)— |
| Ic-c922 | 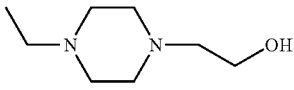 | —N(C(O)N(H)—(CH₂)₃—OH)— |
| Ic-c923 | 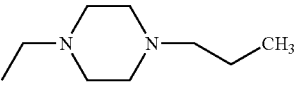 | —CH(OH)— |
| Ic-c924 | 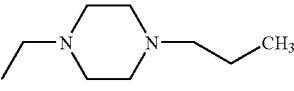 | —N(C(O)N(H)—CH₂—CH₂—OH)— |
| Ic-c925 | 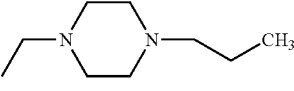 | —N(C(O)N(H)—CH₂—CH₂—F)— |
| Ic-c926 | 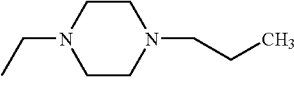 | —N(C(O)N(H)—CH₂—CH₂—OCH₃)— |
| Ic-c927 | 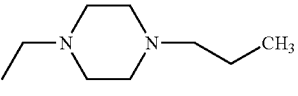 | —N(C(O)N(H)—CH₂—CH₂—CF₃)— |
| Ic-c928 | 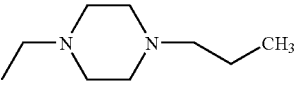 | —N(C(O)N(H)—CH₂—CH₂—CF₃)— |
| Ic-c929 | 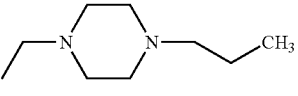 | —N(C(O)N(H)—CH₂—CF₃)— |
| Ic-c930 | 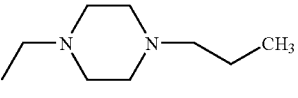 | —N(C(O)N(H)—(CH₂)₃—OH)— |
| Ic-c931 | 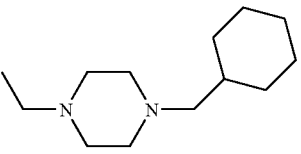 | —CH(OH)— |
| Ic-c932 | 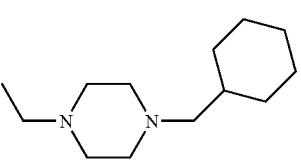 | —N(C(O)N(H)—CH₂—CH₂—OH)— |
| Ic-c933 | 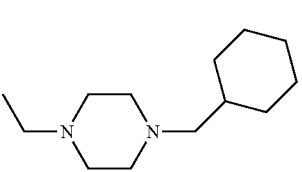 | —N(C(O)N(H)—CH₂—CH₂—F)— |

- Ic-c920: $-N(C(O)N(H)-CH_2-CH_2-CF_3)-$
- Ic-c921: $-N(C(O)N(H)-CH_2-CF_3)-$
- Ic-c922: $-N(C(O)N(H)-(CH_2)_3-OH)-$
- Ic-c923: $-CH(OH)-$
- Ic-c924: $-N(C(O)N(H)-CH_2-CH_2-OH)-$
- Ic-c925: $-N(C(O)N(H)-CH_2-CH_2-F)-$
- Ic-c926: $-N(C(O)N(H)-CH_2-CH_2-OCH_3)-$
- Ic-c927: $-N(C(O)N(H)-CH_2-CH_2-CF_3)-$
- Ic-c928: $-N(C(O)N(H)-CH_2-CH_2-CF_3)-$
- Ic-c929: $-N(C(O)N(H)-CH_2-CF_3)-$
- Ic-c930: $-N(C(O)N(H)-(CH_2)_3-OH)-$
- Ic-c931: $-CH(OH)-$
- Ic-c932: $-N(C(O)N(H)-CH_2-CH_2-OH)-$
- Ic-c933: $-N(C(O)N(H)-CH_2-CH_2-F)-$

-continued

| | | |
|---|---|---|
| Ic-c934 | 1-ethyl-4-(cyclohexylmethyl)piperazine | —N(C(O)N(H)—CH₂—CH₂—OCH₃— |
| Ic-c935 | 1-ethyl-4-(cyclohexylmethyl)piperazine | —N(C(O)N(H)—CH₂—CH₂—CF₃— |
| Ic-c936 | 1-ethyl-4-(cyclohexylmethyl)piperazine | —N(C(O)N(H)—CH₂—CH₂—CF₃— |
| Ic-c937 | 1-ethyl-4-(cyclohexylmethyl)piperazine | —N(C(O)N(H)—CH₂—CF₃— |
| Ic-c938 | 1-ethyl-4-(cyclohexylmethyl)piperazine | —N(C(O)N(H)—(CH₂)₃—OH)— |
| Ic-c939 | 1-ethyl-4-ethoxypiperidine | —CH(OH)— |
| Ic-c940 | 1-ethyl-4-ethoxypiperidine | —N(C(O)N(H)—CH₂—CH₂—OH)— |
| Ic-c941 | 1-ethyl-4-ethoxypiperidine | —N(C(O)N(H)—CH₂—CH₂—F)— |
| Ic-c942 | 1-ethyl-4-ethoxypiperidine | —N(C(O)N(H)—CH₂—CH₂—OCH₃)— |
| Ic-c943 | 1-ethyl-4-ethoxypiperidine | —N(C(O)N(H)—CH₂—CH₂—CF₃)— |
| Ic-c944 | 1-ethyl-4-ethoxypiperidine | —N(C(O)N(H)—CH₂—CH₂—CF₃)— |
| Ic-c945 | 1-ethyl-4-ethoxypiperidine | —N(C(O)N(H)—CH₂—CF₃)— |
| Ic-c946 | 1-ethyl-4-ethoxypiperidine | —N(C(O)N(H)—(CH₂)₃—OH)— |

-continued
| | | |
|---|---|---|
| Ic-c947 | 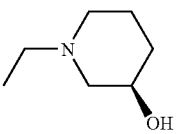 | —CH(OH)— |
| Ic-c948 | 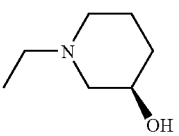 | —N(C(O)N(H)—CH$_2$—CH$_2$—OH)— |
| Ic-c949 | 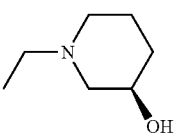 | —N(C(O)N(H)—CH$_2$—CH$_2$—F)— |
| Ic-c950 | 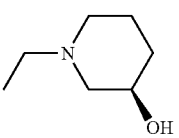 | —N(C(O)N(H)—CH$_2$—CH$_2$—OCH$_3$)— |
| Ic-c951 | 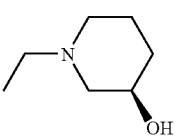 | —N(C(O)N(H)—CH$_2$—CH$_2$—CF$_3$)— |
| Ic-c952 | 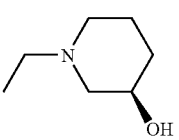 | —N(C(O)N(H)—CH$_2$—CH$_2$—CF$_3$)— |
| Ic-c953 | 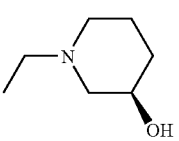 | —N(C(O)N(H)—CH$_2$—CF$_3$)— |
| Ic-c954 | 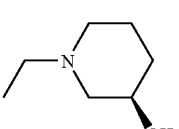 | —N(C(O)N(H)—(CH$_2$)$_3$—OH)— |
| Ic-c955 | 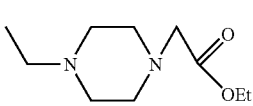 | —CH(OH)— |
| Ic-c956 | 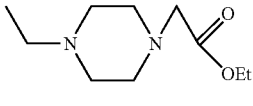 | —N(C(O)N(H)—CH$_2$—CH$_2$—OH)— |
| Ic-c957 | 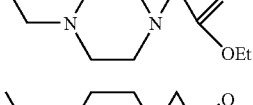 | —N(C(O)N(H)—CH$_2$—CH$_2$—F)— |
| Ic-c958 | 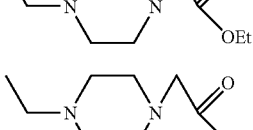 | —N(C(O)N(H)—CH$_2$—CH$_2$—OCH$_3$)— |
| Ic-c959 |  | —N(C(O)N(H)—CH$_2$—CH$_2$—CF$_3$)— |

-continued

| | | |
|---|---|---|
| Ic-c960 | 4-ethylpiperazin-1-yl-CH₂-C(O)-OEt | —N(C(O)N(H)—CH₂—CH₂—CF₃)— |
| Ic-c961 | 4-ethylpiperazin-1-yl-CH₂-C(O)-OEt | —N(C(O)N(H)—CH₂—CF₃)— |
| Ic-c962 | 4-ethylpiperazin-1-yl-CH₂-C(O)-OEt | —N(C(O)N(H)—(CH₂)₃—OH)— |
| Ic-c963 | —CH₂—N(CH₂CH₃)(CH₃) | —CH(OH)— |
| Ic-c964 | —CH₂—N(CH₂CH₃)(CH₃) | —N(C(O)N(H)—CH₂—CH₂—OH)— |
| Ic-c965 | —CH₂—N(CH₂CH₃)(CH₃) | —N(C(O)N(H)—CH₂—CH₂—F)— |
| Ic-c966 | —CH₂—N(CH₂CH₃)(CH₃) | —N(C(O)N(H)—CH₂—CH₂—OCH₃)— |
| Ic-c967 | —CH₂—N(CH₂CH₃)(CH₃) | —N(C(O)N(H)—CH₂—CH₂—CF₃)— |
| Ic-c968 | —CH₂—N(CH₂CH₃)(CH₃) | —N(C(O)N(H)—CH₂—CH₂—CF₃)— |
| Ic-c969 | —CH₂—N(CH₂CH₃)(CH₃) | —N(C(O)N(H)—CH₂—CF₃)— |
| Ic-c970 | —CH₂—N(CH₂CH₃)(CH₃) | —N(C(O)N(H)—(CH₂)₃—OH)— |
| Ic-c971 | —CH₂—N(CH₂CH₂CH₃)(CH₃) | —CH(OH)— |
| Ic-c972 | —CH₂—N(CH₂CH₂CH₃)(CH₃) | —N(C(O)N(H)—CH₂—CH₂—OH)— |
| Ic-c973 | —CH₂—N(CH₂CH₂CH₃)(CH₃) | —N(C(O)N(H)—CH₂—CH₂—F)— |
| Ic-c974 | —CH₂—N(CH₂CH₂CH₃)(CH₃) | —N(C(O)N(H)—CH₂—CH₂—OCH₃)— |
| Ic-c975 | —CH₂—N(CH₂CH₂CH₃)(CH₃) | —N(C(O)N(H)—CH₂—CH₂—CF₃)— |
| Ic-c976 | —CH₂—N(CH₂CH₂CH₃)(CH₃) | —N(C(O)N(H)—CH₂—CH₂—CF₃)— |
| Ic-c977 | —CH₂—N(CH₂CH₂CH₃)(CH₃) | —N(C(O)N(H)—CH₂—CF₃)— |
| Ic-c978 | —CH₂—N(CH₂CH₂CH₃)(CH₃) | —N(C(O)N(H)—(CH₂)₃—OH)— |
| Ic-c979 | —CH₂—N(CH₂CH₂CH₂CH₃)(CH₃) | —CH(OH)— |
| Ic-c980 | —CH₂—N(CH₂CH₂CH₂CH₃)(CH₃) | —N(C(O)N(H)—CH₂—CH₂—OH)— |
| Ic-c981 | —CH₂—N(CH₂CH₂CH₂CH₃)(CH₃) | —N(C(O)N(H)—CH₂—CH₂—F)— |
| Ic-c982 | —CH₂—N(CH₂CH₂CH₂CH₃)(CH₃) | —N(C(O)N(H)—CH₂—CH₂—OCH₃)— |
| Ic-c983 | —CH₂—N(CH₂CH₂CH₂CH₃)(CH₃) | —N(C(O)N(H)—CH₂—CH₂—CF₃)— |
| Ic-c984 | —CH₂—N(CH₂CH₂CH₂CH₃)(CH₃) | —N(C(O)N(H)—CH₂—CH₂—CF₃)— |
| Ic-c985 | —CH₂—N(CH₂CH₂CH₂CH₃)(CH₃) | —N(C(O)N(H)—CH₂—CF₃)— |
| Ic-c986 | —CH₂—N(CH₂CH₂CH₂CH₃)(CH₃) | —N(C(O)N(H)—(CH₂)₃—OH)— |
| Ic-c987 | —CH₂—NH—CH₂CH₂CH₂CH₃ | —CH(OH)— |
| Ic-c988 | —CH₂—NH—CH₂CH₂CH₂CH₃ | —N(C(O)N(H)—CH₂—CH₂—OH)— |
| Ic-c989 | —CH₂—NH—CH₂CH₂CH₂CH₃ | —N(C(O)N(H)—CH₂—CH₂—F)— |
| Ic-c990 | —CH₂—NH—CH₂CH₂CH₂CH₃ | —N(C(O)N(H)—CH₂—CH₂—OCH₃)— |
| Ic-c991 | —CH₂—NH—CH₂CH₂CH₂CH₃ | —N(C(O)N(H)—CH₂—CH₂—CF₃)— |
| Ic-c992 | —CH₂—NH—CH₂CH₂CH₂CH₃ | —N(C(O)N(H)—CH₂—CH₂—CF₃)— |
| Ic-c993 | —CH₂—NH—CH₂CH₂CH₂CH₃ | —N(C(O)N(H)—CH₂—CF₃)— |
| Ic-c994 | —CH₂—NH—CH₂CH₂CH₂CH₃ | —N(C(O)N(H)—(CH₂)₃—OH)— |
| Ic-c995 | —CH₂—NH—CH₂CH₂—O—CH₃ | —CH(OH)— |
| Ic-c996 | —CH₂—NH—CH₂CH₂—O—CH₃ | —N(C(O)N(H)—CH₂—CH₂—OH)— |
| Ic-c997 | —CH₂—NH—CH₂CH₂—O—CH₃ | —N(C(O)N(H)—CH₂—CH₂—F)— |
| Ic-c998 | —CH₂—NH—CH₂CH₂—O—CH₃ | —N(C(O)N(H)—CH₂—CH₂—OCH₃)— |
| Ic-c999 | —CH₂—NH—CH₂CH₂—O—CH₃ | —N(C(O)N(H)—CH₂—CH₂—CF₃)— |
| Ic-c1000 | —CH₂—NH—CH₂CH₂—O—CH₃ | —N(C(O)N(H)—CH₂—CH₂—CF₃)— |
| Ic-c1001 | —CH₂—NH—CH₂CH₂—O—CH₃ | —N(C(O)N(H)—CH₂—CF₃)— |
| Ic-c1002 | —CH₂—NH—CH₂CH₂—O—CH₃ | —N(C(O)N(H)—(CH₂)₃—OH)— |
| Ic-c1003 | 4-ethylpiperazin-1-yl-CH₂CH₂-OMe | —CH(OH)— |
| Ic-c1004 | 4-ethylpiperazin-1-yl-CH₂CH₂-OMe | —N(C(O)N(H)—CH₂—CH₂—OH)— |
| Ic-c1005 | 4-ethylpiperazin-1-yl-CH₂CH₂-OMe | —N(C(O)N(H)—CH₂—CH₂—F)— |
| Ic-c1006 | 4-ethylpiperazin-1-yl-CH₂CH₂-OMe | —N(C(O)N(H)—CH₂—CH₂—OCH₃)— |
| Ic-c1007 | 4-ethylpiperazin-1-yl-CH₂CH₂-OMe | —N(C(O)N(H)—CH₂—CH₂—CF₃)— |

-continued

| | | |
|---|---|---|
| Ic-c1008 | [1-ethyl-4-(2-methoxyethyl)piperazine] | —N(C(O)N(H)—CH$_2$—CH$_2$—CF$_3$)— |
| Ic-c1009 | [1-ethyl-4-(2-methoxyethyl)piperazine] | —N(C(O)N(H)—CH$_2$—CF$_3$)— |
| Ic-c1010 | [1-ethyl-4-(2-methoxyethyl)piperazine] | —N(C(O)N(H)—(CH$_2$)$_3$—OH)— |
| Ic-c1011 | [1-ethyl-4-(OPO(OH)$_2$)piperidine] | —CH(OH)— |
| Ic-c1012 | [1-ethyl-4-(OPO(OH)$_2$)piperidine] | —N(C(O)N(H)—CH$_2$—CH$_2$—OH)— |
| Ic-c1013 | [1-ethyl-4-(OPO(OH)$_2$)piperidine] | —N(C(O)N(H)—CH$_2$—CH$_2$—F)— |
| Ic-c1014 | [1-ethyl-4-(OPO(OH)$_2$)piperidine] | —N(C(O)N(H)—CH$_2$—CH$_2$—OCH$_3$)— |
| Ic-c1015 | [1-ethyl-4-(OPO(OH)$_2$)piperidine] | —N(C(O)N(H)—CH$_2$—CH$_2$—CF$_3$)— |
| Ic-c1016 | [1-ethyl-4-(OPO(OH)$_2$)piperidine] | —N(C(O)N(H)—CH$_2$—CH$_2$—CF$_3$)— |
| Ic-c1017 | [1-ethyl-4-(OPO(OH)$_2$)piperidine] | —N(C(O)N(H)—CH$_2$—CF$_3$)— |
| Ic-c1018 | [1-ethyl-4-(OPO(OH)$_2$)piperidine] | —N(C(O)N(H)—(CH$_2$)$_3$—OH)— |
| Ic-c1019 | [1-ethyl-4-(CH$_2$OPO(OH)$_2$)piperidine] | —CH(OH)— |
| Ic-c1020 | [1-ethyl-4-(CH$_2$OPO(OH)$_2$)piperidine] | —N(C(O)N(H)—CH$_2$—CH$_2$—OH)— |
| Ic-c1021 | [1-ethyl-4-(CH$_2$OPO(OH)$_2$)piperidine] | —N(C(O)N(H)—CH$_2$—CH$_2$—F)— |

-continued
| | | |
|---|---|---|
| Ic-c1022 | 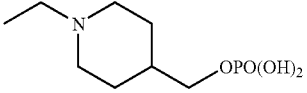 | —N(C(O)N(H)—CH₂—CH₂—OCH₃)— |
| Ic-c1023 | 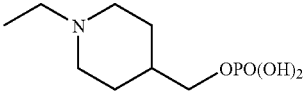 | —N(C(O)N(H)—CH₂—CH₂—CF₃)— |
| Ic-c1024 | 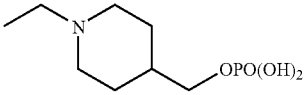 | —N(C(O)N(H)—CH₂—CH₂—CF₃)— |
| Ic-c1025 | 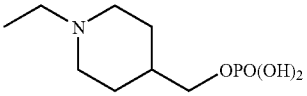 | —N(C(O)N(H)—CH₂—CF₃)— |
| Ic-c1026 | 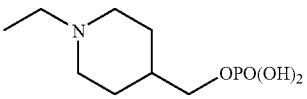 | —N(C(O)N(H)—(CH₂)₃—OH)— |
| Ic-c1027 | 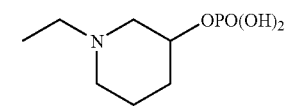 | —CH(OH)— |
| Ic-c1028 | 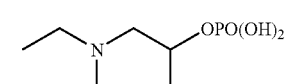 | —N(C(O)N(H)—CH₂—CH₂—OH)— |
| Ic-c1029 | 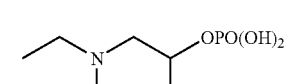 | —N(C(O)N(H)—CH₂—CH₂—F)— |
| Ic-c1030 | 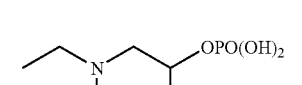 | —N(C(O)N(H)—CH₂—CH₂—OCH₃)— |
| Ic-c1031 | 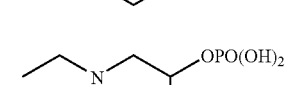 | —N(C(O)N(H)—CH₂—CH₂—CF₃)— |
| Ic-c1032 | 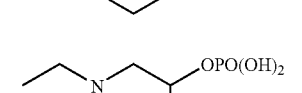 | —N(C(O)N(H)—CH₂—CH₂—CF₃)— |
| Ic-c1033 | 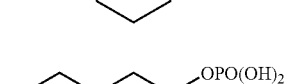 | —N(C(O)N(H)—CH₂—CF₃)— |
| Ic-c1034 | 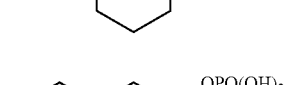 | —N(C(O)N(H)—(CH₂)₃—OH)— |

-continued
| | | |
|---|---|---|
| Ic-c1035 | 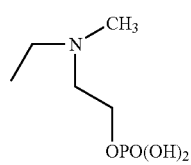 | —CH(OH)— |
| Ic-c1036 | 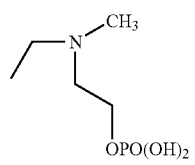 | —N(C(O)N(H)—CH$_2$—CH$_2$—OH)— |
| Ic-c1037 | 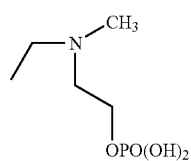 | —N(C(O)N(H)—CH$_2$—CH$_2$—F)— |
| Ic-c1038 | 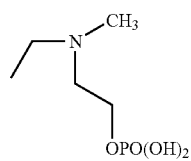 | —N(C(O)N(H)—CH$_2$—CH$_2$—OCH$_3$)— |
| Ic-c1039 | 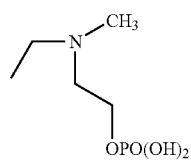 | —N(C(O)N(H)—CH$_2$—CH$_2$—CF$_3$)— |
| Ic-c1040 | 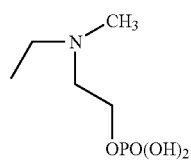 | —N(C(O)N(H)—CH$_2$—CH$_2$—CF$_3$)— |
| Ic-c1041 | 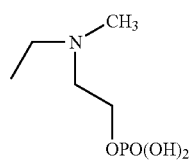 | —N(C(O)N(H)—CH$_2$—CF$_3$)— |
| Ic-c1042 | 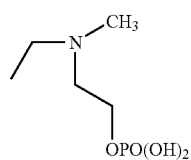 | —N(C(O)N(H)—(CH$_2$)$_3$—OH)— |
| Ic-c1043 | 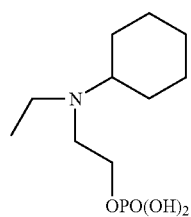 | —CH(OH)— |

-continued
| | | |
|---|---|---|
| Ic-c1044 | 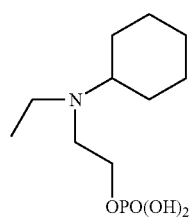 | —N(C(O)N(H)—CH$_2$—CH$_2$—OH)— |
| Ic-c1045 | 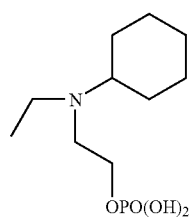 | —N(C(O)N(H)—CH$_2$—CH$_2$—F)— |
| Ic-c1046 | 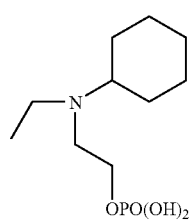 | —N(C(O)N(H)—CH$_2$—CH$_2$—OCH$_3$)— |
| Ic-c1047 | 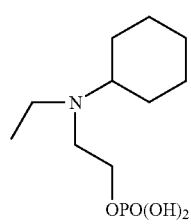 | —N(C(O)N(H)—CH$_2$—CH$_2$—CF$_3$)— |
| Ic-c1048 | 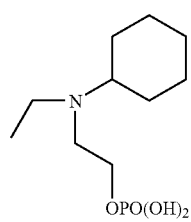 | —N(C(O)N(H)—CH$_2$—CH$_2$—CF$_3$)— |
| Ic-c1049 | 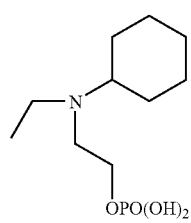 | —N(C(O)N(H)—CH$_2$—CF$_3$)— |
| Ic-c1050 | 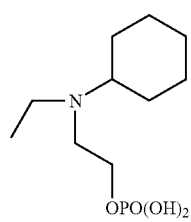 | —N(C(O)N(H)—(CH$_2$)$_3$—OH)— |

-continued
| | | |
|---|---|---|
| Ic-c1051 | 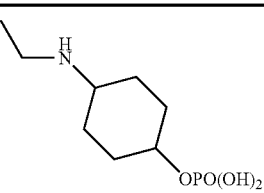 | —CH(OH)— |
| Ic-c1052 | 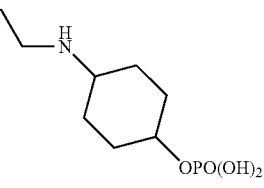 | —N(C(O)N(H)—CH₂—CH₂—OH)— |
| Ic-c1053 | 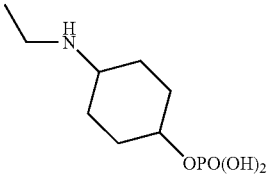 | —N(C(O)N(H)—CH₂—CH₂—F)— |
| Ic-c1054 | 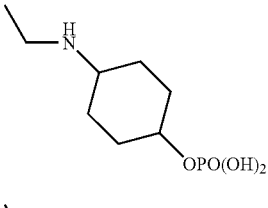 | —N(C(O)N(H)—CH₂—CH₂—OCH₃)— |
| Ic-c1055 | 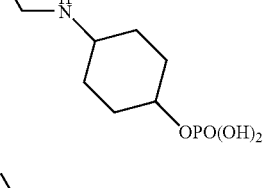 | —N(C(O)N(H)—CH₂—CH₂—CF₃)— |
| Ic-c1056 | 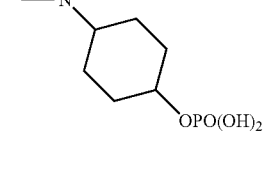 | —N(C(O)N(H)—CH₂—CH₂—CF₃)— |
| Ic-c1057 | 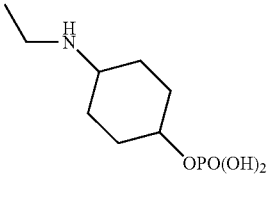 | —N(C(O)N(H)—CH₂—CF₃)— |
| Ic-c1058 | 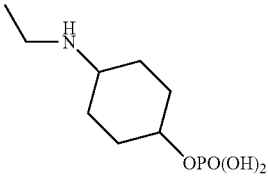 | —N(C(O)N(H)—(CH₂)₃—OH)— |
and pharmaceutically acceptable salts thereof.

5.5 The Indenoisoquinolinone Analogs of Formula (IIa)

The present invention provides Indenoisoquinolinone Analogs according to Formula (IIa), below:

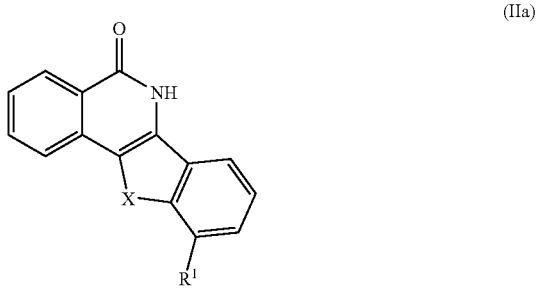

(IIa)

and pharmaceutically acceptable salts thereof,
wherein:

X and $R^1$ are as defined above for the compounds of Formula (Ia).

In one embodiment, X is —$CH_2$—. In another embodiment, X is —O—. In another embodiment, X is —C(O)—. In another embodiment, X is —NH—. In another embodiment, X is —N($C_1$-$C_4$ alkyl)-. In another embodiment, X is —S—. In another embodiment, X is —CH(OH)—.

In one embodiment, n is 1. In another embodiment, n is 2.
In one embodiment, X is —$CH_2$— and n is 1.
In one embodiment, X is —$CH_2$— and n is 2.
In one embodiment, X is —CH(OH)— and n is 1.
In one embodiment, X is —CH(OH)— and n is 2.

In one embodiment, $R^2$ is —$C_1$-$C_6$ alkyl and $R^3$ is —C(O)—($C_1$-$C_6$ alkylene)-(3- to 7-membered monocyclic heterocycle).

In one embodiment, $R^2$ is —H and $R^3$ is —C(O)—($C_1$-$C_6$ alkylene)-(3- to 7-membered monocyclic heterocycle).

In one embodiment, n is 1 and $R^3$ is a nitrogen-containing 3- to 7-membered monocyclic heterocycle which is substituted with one —C(O)O—$C_1$-$C_6$ alkyl.

In another embodiment, n is 1 and $R^3$ is $C_3$-$C_8$ monocyclic cycloalkyl substituted with one hydroxy-substituted $C_1$-$C_5$ alkyl.

In one embodiment, n is 2 and $R^3$ is a nitrogen-containing 3- to 7-membered monocyclic heterocycle which is substituted with one —C(O)O—$C_1$-$C_6$ alkyl.

In another embodiment, n is 2 and $R^3$ is $C_3$-$C_8$ monocyclic cycloalkyl substituted with one hydroxy-substituted $C_1$-$C_5$ alkyl.

In one embodiment, N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —$CH_2$—, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —$CH_2$—, n is 1, and $R^2$ is $C_3$-$C_8$ monocyclic cycloalkyl.

In one embodiment, X is —$CH_2$—, n is 1, and $R^3$ is a nitrogen-containing 3- to 7-membered monocyclic heterocycle which is substituted with one —C(O)O—$C_1$-$C_6$ alkyl.

In one embodiment, X is —$CH_2$—, n is 1, and $R^3$ is $C_3$-$C_8$ monocyclic cycloalkyl which is substituted with one hydroxy-substituted $C_1$-$C_5$ alkyl.

In one embodiment, X is —$CH_2$—, n is 1, $R^2$ is —H, and $R^3$ is a nitrogen-containing 3- to 7-membered monocyclic heterocycle which is substituted with one —C(O)O—$C_1$-$C_6$ alkyl.

In one embodiment, X is —$CH_2$—, n is 1, $R^2$ is —H, and $R^3$ is $C_3$-$C_8$ monocyclic cycloalkyl which is substituted with one hydroxy-substituted $C_1$-$C_5$ alkyl.

In another embodiment, X is —$CH_2$—, n is 1 and $R^3$ is —C(O)—$C_1$-$C_6$ alkylene-(3- to 7-membered monocyclic heterocycle).

In one embodiment, X is —CH(OH)—, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —CH(OH)—, n is 1, and $R^2$ is $C_3$-$C_8$ monocyclic cycloalkyl.

In one embodiment, X is —CH(OH)—, n is 1, and $R^3$ is a nitrogen-containing 3- to 7-membered monocyclic heterocycle which is substituted with one —C(O)O—$C_1$-$C_6$ alkyl.

In one embodiment, X is —CH(OH)—, n is 1, and $R^3$ is $C_3$-$C_8$ monocyclic cycloalkyl which is substituted with one hydroxy-substituted $C_1$-$C_5$ alkyl.

In one embodiment, X is —CH(OH)—, n is 1, $R^2$ is —H, and $R^3$ is a nitrogen-containing 3- to 7-membered monocyclic heterocycle which is substituted with one —C(O)O—$C_1$-$C_6$ alkyl.

In one embodiment, X is —CH(OH)—, n is 1, $R^2$ is —H, and $R^3$ is $C_3$-$C_8$ monocyclic cycloalkyl which is substituted with one hydroxy-substituted $C_1$-$C_5$ alkyl.

In another embodiment, X is —CH(OH)—, n is 1 and $R^3$ is —C(O)—$C_1$-$C_6$ alkylene-(3- to 7-membered monocyclic heterocycle).

In various embodiments, —R[1] is:
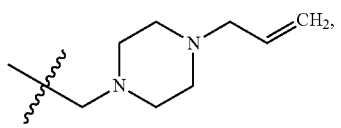
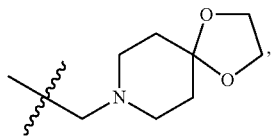
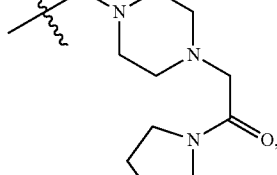
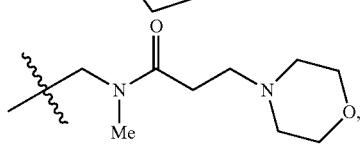
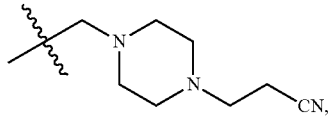
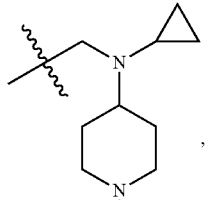
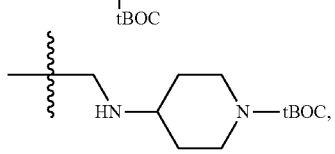
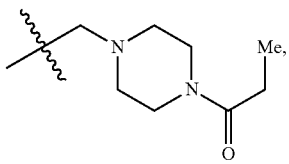
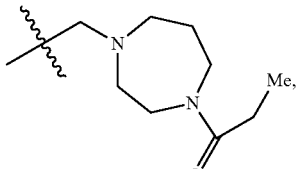
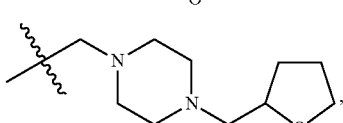
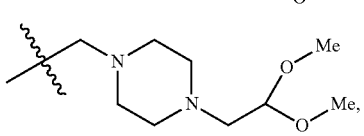
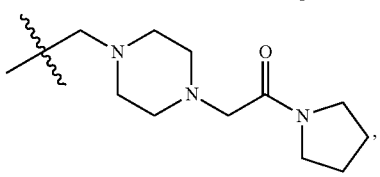
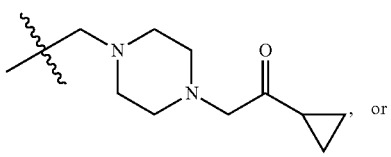
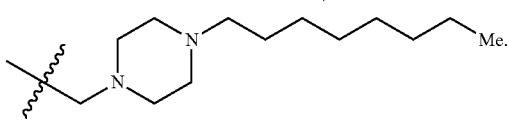
Illustrative examples of the Indenoisoquinolinone Analogs include the compounds of Formula (IIa) in which n is 1 as set forth below:
(IIa)
| Compound | —R[1] | X |
|---|---|---|
| IIa-1 | 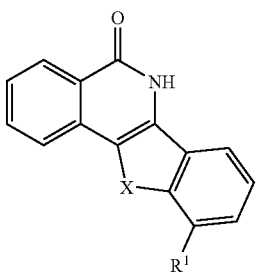 | —CH₂— |

-continued

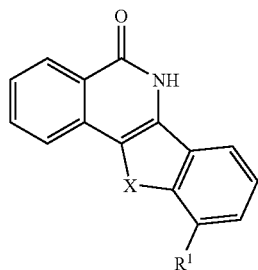
(IIa)

| Compound | —R¹ | X |
|---|---|---|
| IIa-a1 | ![piperazine-N-ethyl, N-allyl] | —CH(OH)— |
| IIa-2 | ![piperazine-N-ethyl, N-allyl] | —O— |
| IIa-3 | ![piperazine-N-ethyl, N-allyl] | —C(O)— |
| IIa-4 | ![piperazine-N-ethyl, N-allyl] | —NH— |
| IIa-5 | ![piperazine-N-ethyl, N-allyl] | —S— |
| IIa-6 | ![piperazine-N-ethyl, N-allyl] | —N(CH₃)— |
| IIa-7 | ![piperazine-N-ethyl, N-allyl] | —N(CH₂CH₃)— |
| IIa-8 | ![piperazine-N-ethyl, N-allyl] | —N(CH₂CH₂CH₃)— |
| IIa-9 | ![piperazine-N-ethyl, N-allyl] | —N(CH₂CH₂CH₂CH₃)— |
| IIa-10 | ![piperazine-N-ethyl, N-allyl] | —N(C(H)(CH₃)(CH₂CH₃))— |

-continued
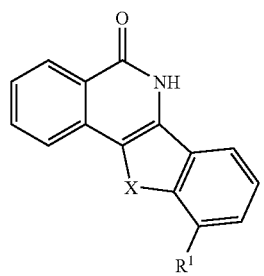
(IIa)
| Compound | —R¹ | X |
|---|---|---|
| IIa-11 | (4-ethylpiperazin-1-yl)allyl | —N(C(H)(CH₃)₂)— |
| IIa-12 | (4-ethylpiperazin-1-yl)allyl | —N(CH₂C(H)(CH₃)₂)— |
| IIa-13 | (4-ethylpiperazin-1-yl)allyl | —N(C(CH₃)₃)— |
| IIa-14 | 8-ethyl-1,4-dioxa-8-azaspiro[4.5]decane | —CH₂— |
| IIa-a14 | 8-ethyl-1,4-dioxa-8-azaspiro[4.5]decane | —CH(OH)— |
| IIa-15 | 8-ethyl-1,4-dioxa-8-azaspiro[4.5]decane | —O— |
| IIa-16 | 8-ethyl-1,4-dioxa-8-azaspiro[4.5]decane | —C(O)— |
| IIa-17 | 8-ethyl-1,4-dioxa-8-azaspiro[4.5]decane | —NH— |
| IIa-18 | 8-ethyl-1,4-dioxa-8-azaspiro[4.5]decane | —S— |

-continued

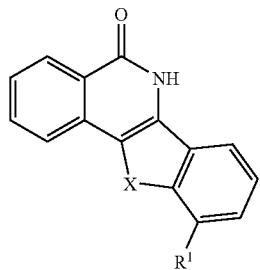

(IIa)

| Compound | —R¹ | X |
|---|---|---|
| IIa-19 | ![N-ethyl piperidine dioxolane spiro] | —N(CH₃)— |
| IIa-20 | ![N-ethyl piperidine dioxolane spiro] | —N(CH₂CH₃)— |
| IIa-21 | ![N-ethyl piperidine dioxolane spiro] | —N(CH₂CH₂CH₃)— |
| IIa-22 | ![N-ethyl piperidine dioxolane spiro] | —N(CH₂CH₂CH₂CH₃)— |
| IIa-23 | ![N-ethyl piperidine dioxolane spiro] | —N(C(H)(CH₃)(CH₂CH₃))— |
| IIa-24 | ![N-ethyl piperidine dioxolane spiro] | —N(C(H)(CH₃)₂)— |
| IIa-25 | ![N-ethyl piperidine dioxolane spiro] | —N(CH₂C(H)(CH₃)₂)— |
| IIa-26 | ![N-ethyl piperidine dioxolane spiro] | —N(C(CH₃)₃)— |
| IIa-27 | ![ethylamino cyclopentyl methanol] | —CH₂— |

-continued
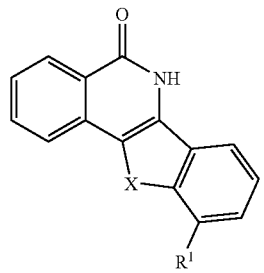
(IIa)
| Compound | —R¹ | X |
|---|---|---|
| IIa-a27 | 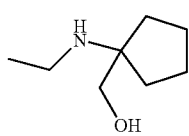 | —CH(OH)— |
| IIa-28 | 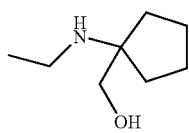 | —O— |
| IIa-29 | 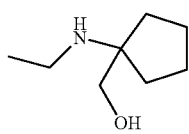 | —C(O)— |
| IIa-30 | 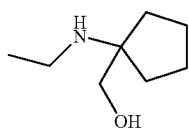 | —NH— |
| IIa-31 | 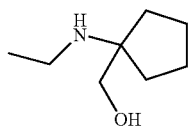 | —S— |
| IIa-32 | 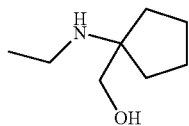 | —N(CH$_3$)— |
| IIa-33 | 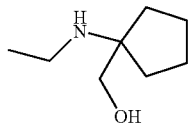 | —N(CH$_2$CH$_3$)— |
| IIa-34 | 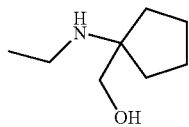 | —N(CH$_2$CH$_2$CH$_3$)— |
| IIa-35 | 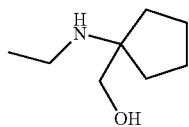 | —N(CH$_2$CH$_2$CH$_2$CH$_3$)— |

-continued

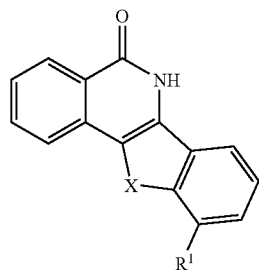
(IIa)

| Compound | —R¹ | X |
|---|---|---|
| IIa-36 | ethylamino-1-(hydroxymethyl)cyclopentyl | —N(C(H)(CH₃)(CH₂CH₃))— |
| IIa-37 | ethylamino-1-(hydroxymethyl)cyclopentyl | —N(C(H)(CH₃)₂)— |
| IIa-38 | ethylamino-1-(hydroxymethyl)cyclopentyl | —N(CH₂C(H)(CH₃)₂)— |
| IIa-39 | ethylamino-1-(hydroxymethyl)cyclopentyl | —N(C(CH₃)₃)— |
| IIa-40 | 4-ethylpiperazinyl-acetyl-pyrrolidine | —CH₂— |
| IIa-a40 | 4-ethylpiperazinyl-acetyl-pyrrolidine | —CH(OH)— |
| IIa-41 | 4-ethylpiperazinyl-acetyl-pyrrolidine | —O— |

-continued
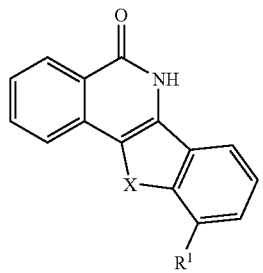
(IIa)
| Compound | —R¹ | X |
|---|---|---|
| IIa-42 | 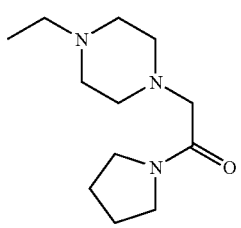 | —C(O)— |
| IIa-43 | 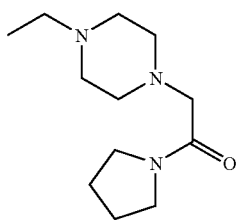 | —NH— |
| IIa-44 | 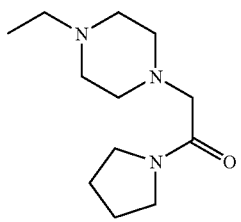 | —S— |
| IIa-45 | 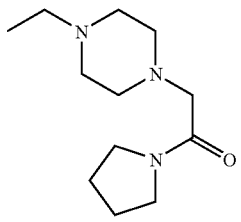 | —N(CH₃)— |
| IIa-46 | 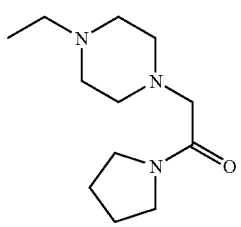 | —N(CH₂CH₃)— |

-continued
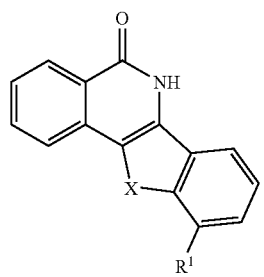
(IIa)
| Compound | —R¹ | X |
|---|---|---|
| IIa-47 | 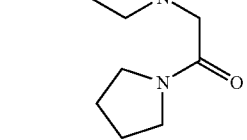 | —N(CH₂CH₂CH₃)— |
| IIa-48 | 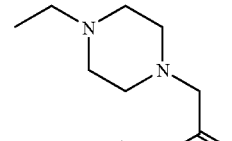 | —N(CH₂CH₂CH₃)— |
| IIa-49 | 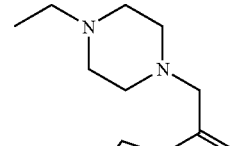 | —N(C(H)(CH₃)(CH₂CH₃))— |
| IIa-50 | 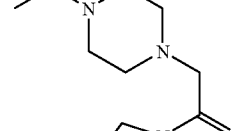 | —N(C(H)(CH₃)₂)— |
| IIa-51 | 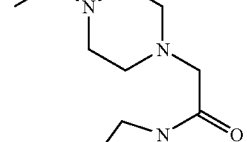 | —N(CH₂C(H)(CH₃)₂)— |

-continued

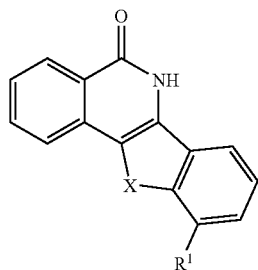
(IIa)

| Compound | —R¹ | X |
|---|---|---|
| IIa-52 | ![structure] ethyl-piperazine-CH2-C(O)-pyrrolidine | —N(C(CH₃)₃)— |
| IIa-53 | ![structure] N-ethyl-N-methyl propanamide morpholine | —CH₂— |
| IIa-a53 | ![structure] N-ethyl-N-methyl propanamide morpholine | —CH(OH)— |
| IIa-54 | ![structure] N-ethyl-N-methyl propanamide morpholine | —O— |
| IIa-55 | ![structure] N-ethyl-N-methyl propanamide morpholine | —C(O)— |
| IIa-56 | ![structure] N-ethyl-N-methyl propanamide morpholine | —NH— |
| IIa-57 | ![structure] N-ethyl-N-methyl propanamide morpholine | —S— |
| IIa-58 | ![structure] N-ethyl-N-methyl propanamide morpholine | —N(CH₃)— |

-continued

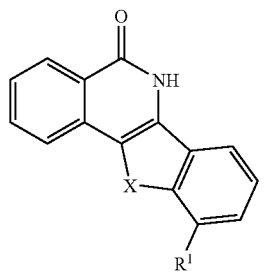
(IIa)

| Compound | —R¹ | X |
|---|---|---|
| IIa-59 | N(Me)(Et)C(O)CH₂CH₂-morpholine | —N(CH₂CH₃)— |
| IIa-60 | N(Me)(Et)C(O)CH₂CH₂-morpholine | —N(CH₂CH₂CH₃)— |
| IIa-61 | N(Me)(Et)C(O)CH₂CH₂-morpholine | —N(CH₂CH₂CH₃)— |
| IIa-62 | N(Me)(Et)C(O)CH₂CH₂-morpholine | —N(C(H)(CH₃)(CH₂CH₃))— |
| IIa-63 | N(Me)(Et)C(O)CH₂CH₂-morpholine | —N(C(H)(CH₃)₂)— |
| IIa-64 | N(Me)(Et)C(O)CH₂CH₂-morpholine | —N(CH₂C(H)(CH₃)₂)— |
| IIa-65 | N(Me)(Et)C(O)CH₂CH₂-morpholine | —N(C(CH₃)₃)— |
| IIa-66 | 4-ethylpiperazinyl-CH₂CH₂CN | —CH₂— |
| IIa-a66 | 4-ethylpiperazinyl-CH₂CH₂CN | —CH(OH)— |

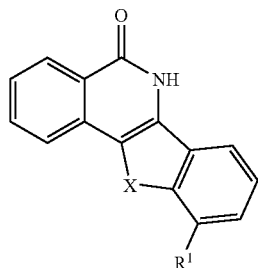

(IIa)

| Compound | —R¹ | X |
|---|---|---|
| IIa-67 | (4-ethylpiperazin-1-yl)CH₂CH₂CN | —O— |
| IIa-68 | (4-ethylpiperazin-1-yl)CH₂CH₂CN | —C(O)— |
| IIa-69 | (4-ethylpiperazin-1-yl)CH₂CH₂CN | —NH— |
| IIa-70 | (4-ethylpiperazin-1-yl)CH₂CH₂CN | —S— |
| IIa-71 | (4-ethylpiperazin-1-yl)CH₂CH₂CN | —N(CH₃)— |
| IIa-72 | (4-ethylpiperazin-1-yl)CH₂CH₂CN | —N(CH₂CH₃)— |
| IIa-73 | (4-ethylpiperazin-1-yl)CH₂CH₂CN | —N(CH₂CH₂CH₃)— |
| IIa-74 | (4-ethylpiperazin-1-yl)CH₂CH₂CN | —N(CH₂CH₂CH₂CH₃)— |
| IIa-75 | (4-ethylpiperazin-1-yl)CH₂CH₂CN | —N(C(H)(CH₃)(CH₂CH₃))— |
| IIa-76 | (4-ethylpiperazin-1-yl)CH₂CH₂CN | —N(C(H)(CH₃)₂)— |

-continued
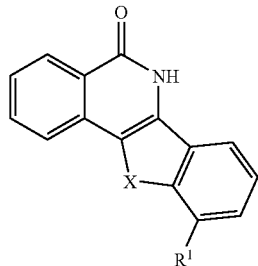
(IIa)
| Compound | —R¹ | X |
|---|---|---|
| IIa-77 | 4-ethylpiperazine with CH₂CH₂CN | —N(CH₂C(H)(CH₃)₂)— |
| IIa-78 | 4-ethylpiperazine with CH₂CH₂CN | —N(C(CH₃)₃)— |
| IIa-79 | N-ethyl-N-cyclopropyl-4-aminopiperidine-N-tBOC | —CH₂— |
| IIa-a79 | N-ethyl-N-cyclopropyl-4-aminopiperidine-N-tBOC | —CH(OH)— |
| IIa-80 | N-ethyl-N-cyclopropyl-4-aminopiperidine-N-tBOC | —O— |
| IIa-81 | N-ethyl-N-cyclopropyl-4-aminopiperidine-N-tBOC | —C(O)— |

-continued
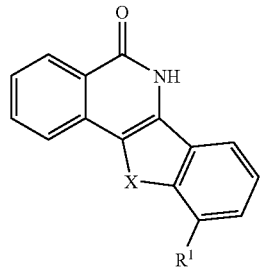
(IIa)
| Compound | —R¹ | X |
|---|---|---|
| IIa-82 | 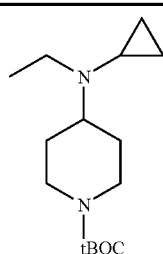 | —NH— |
| IIa-83 | 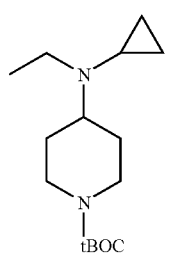 | —S— |
| IIa-84 | 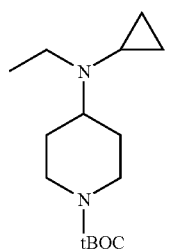 | —N(CH₃)— |
| IIa-85 | 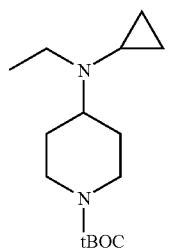 | —N(CH₂CH₃)— |
| IIa-86 | 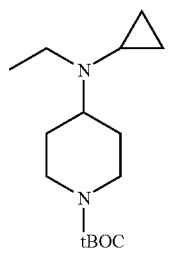 | —N(CH₂CH₂CH₃)— |

-continued
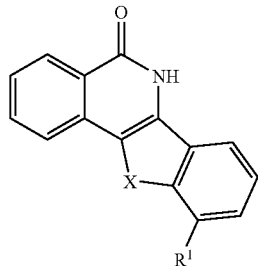
(IIa)
| Compound | —R¹ | X |
|---|---|---|
| IIa-87 | 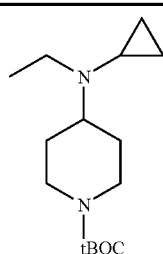 | —N(CH₂CH₂CH₂CH₃)— |
| IIa-88 | 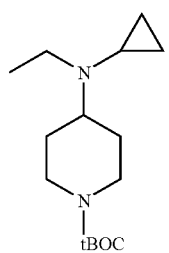 | —N(C(H)(CH₃)(CH₂CH₃))— |
| IIa-89 | 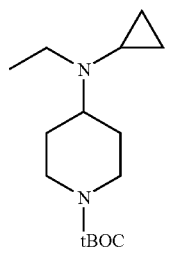 | —N(C(H)(CH₃)₂)— |
| IIa-90 | 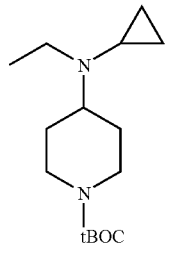 | —N(CH₂C(H)(CH₃)₂)— |
| IIa-91 | 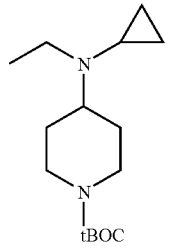 | —N(C(CH₃)₃)— |

-continued (IIa)

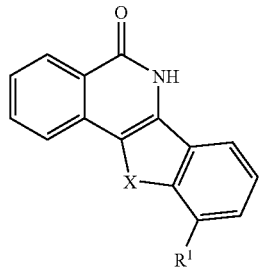

| Compound | —R¹ | X |
|---|---|---|
| IIa-92 | HN—[piperidine]—N—tBOC | —CH$_2$— |
| IIa-a92 | HN—[piperidine]—N—tBOC | —CH(OH)— |
| IIa-93 | HN—[piperidine]—N—tBOC | —O— |
| IIa-94 | HN—[piperidine]—N—tBOC | —C(O)— |
| IIa-95 | HN—[piperidine]—N—tBOC | —NH— |
| IIa-96 | HN—[piperidine]—N—tBOC | —S— |
| IIa-97 | HN—[piperidine]—N—tBOC | —N(CH$_3$)— |
| IIa-98 | HN—[piperidine]—N—tBOC | —N(CH$_2$CH$_3$)— |
| IIa-99 | HN—[piperidine]—N—tBOC | —N(CH$_2$CH$_2$CH$_3$)— |
| IIa-100 | HN—[piperidine]—N—tBOC | —N(CH$_2$CH$_2$CH$_2$CH$_3$)— |
| IIa-101 | HN—[piperidine]—N—tBOC | —N(C(H)(CH$_3$)(CH$_2$CH$_3$))— |
| IIa-102 | HN—[piperidine]—N—tBOC | —N(C(H)(CH$_3$)$_2$)— |
| IIa-103 | HN—[piperidine]—N—tBOC | —N(CH$_2$C(H)(CH$_3$)$_2$)— |

-continued
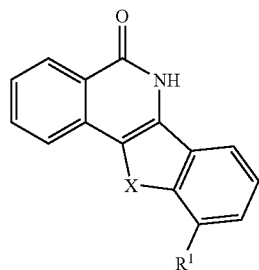
(IIa)
| Compound | —R¹ | X |
|---|---|---|
| IIa-104 | HN—⟨piperidine⟩—tBOC (ethyl linker) | —N(C(CH₃)₃)— |
| IIa-105 | ethyl-piperazine-C(O)-Me | —CH₂— |
| IIa-a105 | ethyl-piperazine-C(O)-Me | —CH(OH)— |
| IIa-106 | ethyl-piperazine-C(O)-Me | —O— |
| IIa-107 | ethyl-piperazine-C(O)-Me | —C(O)— |
| IIa-108 | ethyl-piperazine-C(O)-Me | —NH— |
| IIa-109 | ethyl-piperazine-C(O)-Me | —S— |
| IIa-110 | ethyl-piperazine-C(O)-Me | —N(CH₃)— |

-continued

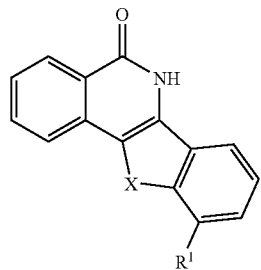

(IIa)

| Compound | —R¹ | X |
|---|---|---|
| IIa-111 | 4-ethylpiperazine-1-yl with propanoyl, Me | —N(CH₂CH₃)— |
| IIa-112 | 4-ethylpiperazine-1-yl with propanoyl, Me | —N(CH₂CH₂CH₃)— |
| IIa-113 | 4-ethylpiperazine-1-yl with propanoyl, Me | —N(CH₂CH₂CH₃)— |
| IIa-114 | 4-ethylpiperazine-1-yl with propanoyl, Me | —N(C(H)(CH₃)(CH₂CH₃))— |
| IIa-115 | 4-ethylpiperazine-1-yl with propanoyl, Me | —N(C(H)(CH₃)₂)— |
| IIa-116 | 4-ethylpiperazine-1-yl with propanoyl, Me | —N(CH₂C(H)(CH₃)₂)— |
| IIa-117 | 4-ethylpiperazine-1-yl with propanoyl, Me | —N(C(CH₃)₃)— |
| IIa-118 | 4-ethyl-1,4-diazepane with propanoyl, Me | —CH₂— |

-continued
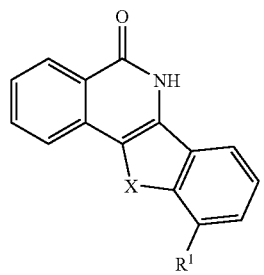
(IIa)
| Compound | —R¹ | X |
|---|---|---|
| IIa-a118 | (4-ethyl-1,4-diazepan-1-yl with N-propanoyl-Me) | —CH(OH)— |
| IIa-119 | (4-ethyl-1,4-diazepan-1-yl with N-propanoyl-Me) | —O— |
| IIa-120 | (4-ethyl-1,4-diazepan-1-yl with N-propanoyl-Me) | —C(O)— |
| IIa-121 | (4-ethyl-1,4-diazepan-1-yl with N-propanoyl-Me) | —NH— |
| IIa-122 | (4-ethyl-1,4-diazepan-1-yl with N-propanoyl-Me) | —S— |
| IIa-123 | (4-ethyl-1,4-diazepan-1-yl with N-propanoyl-Me) | —N(CH₃)— |

-continued
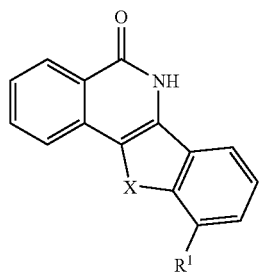
(IIa)
| Compound | —R¹ | X |
|---|---|---|
| IIa-124 | 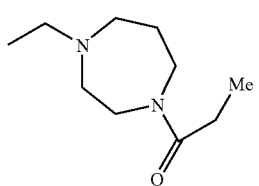 | —N(CH₂CH₃)— |
| IIa-125 | 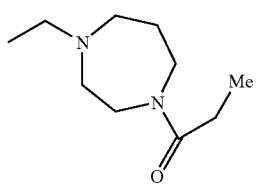 | —N(CH₂CH₃)— |
| IIa-126 | 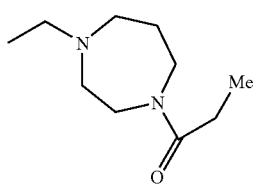 | —N(CH₂CH₂CH₃)— |
| IIa-127 | 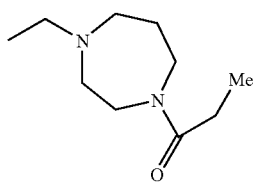 | —N(C(H)(CH₃)(CH₂CH₃))— |
| IIa-128 | 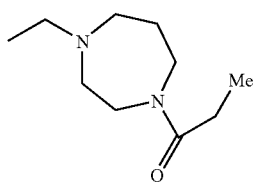 | —N(C(H)(CH₃)₂)— |
| IIa-129 | 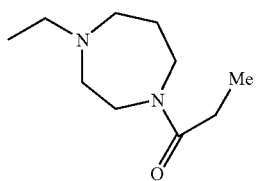 | —N(CH₂C(H)(CH₃)₂)— |

-continued
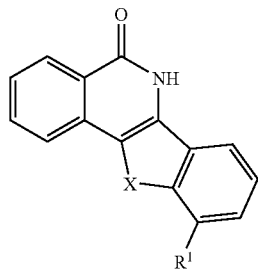
(IIa)
| Compound | —R¹ | X |
|---|---|---|
| IIa-130 | 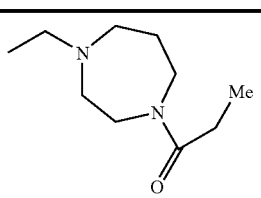 | —N(C(CH₃)₃)— |
| IIa-131 | 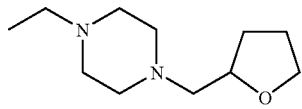 | —CH₂— |
| IIa-a131 | 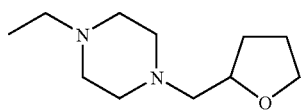 | —CH(OH)— |
| IIa-132 | 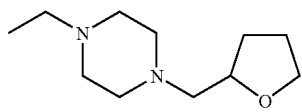 | —O— |
| IIa-133 | 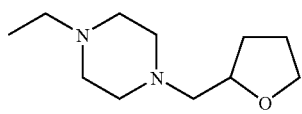 | —C(O)— |
| IIa-134 | 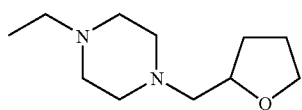 | —NH— |
| IIa-135 | 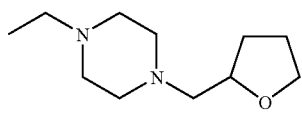 | —S— |
| IIa-136 | 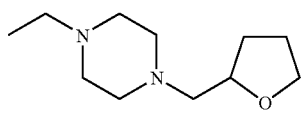 | —N(CH₃)— |
| IIa-137 | 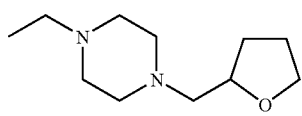 | —N(CH₂CH₃)— |
| IIa-138 | 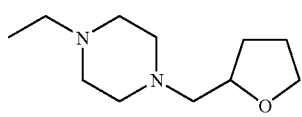 | —N(CH₂CH₂CH₃)— |

-continued

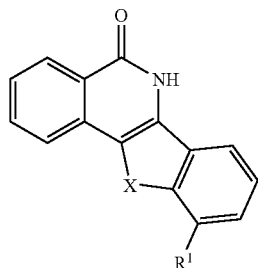
(IIa)

| Compound | —R¹ | X |
|---|---|---|
| IIa-139 | [piperazine-CH2-tetrahydrofuran] | —N(CH₂CH₂CH₂CH₃)— |
| IIa-140 | [piperazine-CH2-tetrahydrofuran] | —N(C(H)(CH₃)(CH₂CH₃))— |
| IIa-141 | [piperazine-CH2-tetrahydrofuran] | —N(C(H)(CH₃)₂)— |
| IIa-142 | [piperazine-CH2-tetrahydrofuran] | —N(CH₂C(H)(CH₃)₂)— |
| IIa-143 | [piperazine-CH2-tetrahydrofuran] | —N(C(CH₃)₃)— |
| IIa-144 | [piperazine-CH2-CH(OMe)₂] | —CH₂— |
| IIa-a144 | [piperazine-CH2-CH(OMe)₂] | —CH(OH)— |
| IIa-145 | [piperazine-CH2-CH(OMe)₂] | —O— |
| IIa-146 | [piperazine-CH2-CH(OMe)₂] | —C(O)— |
| IIa-147 | [piperazine-CH2-CH(OMe)₂] | —NH— |

-continued

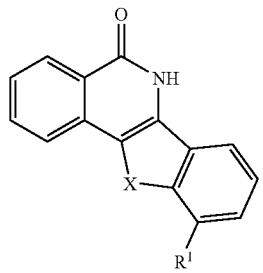
(IIa)

| Compound | —R¹ | X |
|---|---|---|
| IIa-148 | ethyl-piperazine-CH₂-CH(OMe)₂ | —S— |
| IIa-149 | ethyl-piperazine-CH₂-CH(OMe)₂ | —N(CH₃)— |
| IIa-150 | ethyl-piperazine-CH₂-CH(OMe)₂ | —N(CH₂CH₃)— |
| IIa-151 | ethyl-piperazine-CH₂-CH(OMe)₂ | —N(CH₂CH₂CH₃)— |
| IIa-152 | ethyl-piperazine-CH₂-CH(OMe)₂ | —N(CH₂CH₂CH₂CH₃)— |
| IIa-153 | ethyl-piperazine-CH₂-CH(OMe)₂ | —N(C(H)(CH₃)(CH₂CH₃))— |
| IIa-154 | ethyl-piperazine-CH₂-CH(OMe)₂ | —N(C(H)(CH₃)₂)— |
| IIa-155 | ethyl-piperazine-CH₂-CH(OMe)₂ | —N(CH₂C(H)(CH₃)₂)— |
| IIa-156 | ethyl-piperazine-CH₂-CH(OMe)₂ | —N(C(CH₃)₃)— |
| IIa-157 | ethyl-piperazine-CH₂-C(O)-pyrrolidine | —CH₂— |

-continued
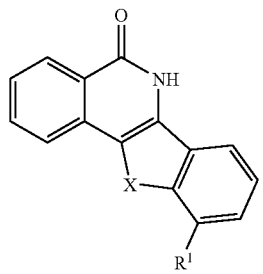
(IIa)
| Compound | —R¹ | X |
|---|---|---|
| IIa-a157 | ![piperazine-ethyl-pyrrolidine] | —CH(OH)— |
| IIa-158 | ![piperazine-ethyl-pyrrolidine] | —O— |
| IIa-159 | ![piperazine-ethyl-pyrrolidine] | —C(O)— |
| IIa-160 | ![piperazine-ethyl-pyrrolidine] | —NH— |
| IIa-161 | ![piperazine-ethyl-pyrrolidine] | —S— |
| IIa-162 | ![piperazine-ethyl-pyrrolidine] | —N(CH₃)— |
| IIa-163 | ![piperazine-ethyl-pyrrolidine] | —N(CH₂CH₃)— |

-continued

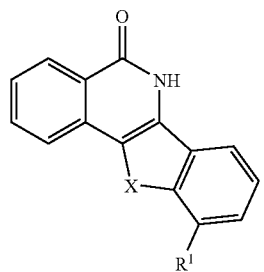

(IIa)

| Compound | —R¹ | X |
|---|---|---|
| IIa-164 | ![R1 structure] | —N(CH₂CH₂CH₃)— |
| IIa-165 | ![R1 structure] | —N(CH₂CH₂CH₂CH₃)— |
| IIa-166 | ![R1 structure] | —N(C(H)(CH₃)(CH₂CH₃))— |
| IIa-167 | ![R1 structure] | —N(C(H)(CH₃)₂)— |
| IIa-168 | ![R1 structure] | —N(CH₂C(H)(CH₃)₂)— |
| IIa-169 | ![R1 structure] | —N(C(CH₃)₃)— |
| IIa-170 | ![R1 structure] | —CH₂— |
| IIa-a170 | ![R1 structure] | —CH(OH)— |

(Note: R¹ for IIa-164 through IIa-169 is 4-ethylpiperazin-1-yl-CH₂-C(O)-pyrrolidin-1-yl; R¹ for IIa-170 and IIa-a170 is 4-ethylpiperazin-1-yl-CH₂-C(O)-cyclopropyl)

-continued

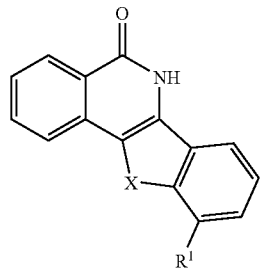
(IIa)

| Compound | —R¹ | X |
|---|---|---|
| IIa-171 | (4-ethylpiperazin-1-yl)-CH₂-C(O)-cyclopropyl | —O— |
| IIa-172 | (4-ethylpiperazin-1-yl)-CH₂-C(O)-cyclopropyl | —C(O)— |
| IIa-173 | (4-ethylpiperazin-1-yl)-CH₂-C(O)-cyclopropyl | —NH— |
| IIa-174 | (4-ethylpiperazin-1-yl)-CH₂-C(O)-cyclopropyl | —S— |
| IIa-175 | (4-ethylpiperazin-1-yl)-CH₂-C(O)-cyclopropyl | —N(CH₃)— |
| IIa-176 | (4-ethylpiperazin-1-yl)-CH₂-C(O)-cyclopropyl | —N(CH₂CH₃)— |
| IIa-177 | (4-ethylpiperazin-1-yl)-CH₂-C(O)-cyclopropyl | —N(CH₂CH₂CH₃)— |
| IIa-178 | (4-ethylpiperazin-1-yl)-CH₂-C(O)-cyclopropyl | —N(CH₂CH₂CH₂CH₃)— |

-continued

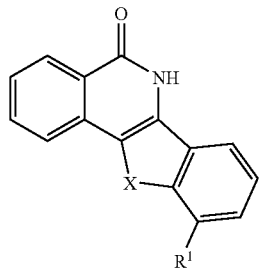

(IIa)

| Compound | —R¹ | X |
|---|---|---|
| IIa-179 | [4-ethylpiperazin-1-yl-CH2-C(O)-cyclopropyl] | —N(C(H)(CH₃)(CH₂CH₃))— |
| IIa-180 | [4-ethylpiperazin-1-yl-CH2-C(O)-cyclopropyl] | —N(C(H)(CH₃)₂)— |
| IIa-181 | [4-ethylpiperazin-1-yl-CH2-C(O)-cyclopropyl] | —N(CH₂C(H)(CH₃)₂)— |
| IIa-182 | [4-ethylpiperazin-1-yl-CH2-C(O)-cyclopropyl] | —N(C(CH₃)₃)— |
| IIa-183 | [4-ethylpiperazin-1-yl-heptyl-Me] | —CH₂— |
| IIa-a183 | [4-ethylpiperazin-1-yl-heptyl-Me] | —CH(OH)— |
| IIa-184 | [4-ethylpiperazin-1-yl-heptyl-Me] | —O— |
| IIa-185 | [4-ethylpiperazin-1-yl-heptyl-Me] | —C(O)— |
| IIa-186 | [4-ethylpiperazin-1-yl-heptyl-Me] | —NH— |
| IIa-187 | [4-ethylpiperazin-1-yl-heptyl-Me] | —S— |

-continued

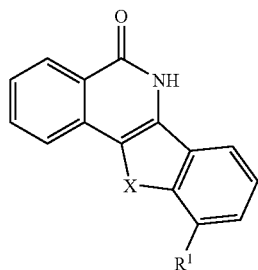

(IIa)

| Compound | —R¹ | X |
|---|---|---|
| IIa-188 | 4-ethylpiperazinyl-(CH₂)₇-Me | —N(CH₃)— |
| IIa-189 | 4-ethylpiperazinyl-(CH₂)₇-Me | —N(CH₂CH₃)— |
| IIa-190 | 4-ethylpiperazinyl-(CH₂)₇-Me | —N(CH₂CH₂CH₃)— |
| IIa-191 | 4-ethylpiperazinyl-(CH₂)₇-Me | —N(CH₂CH₂CH₂CH₃)— |
| IIa-192 | 4-ethylpiperazinyl-(CH₂)₇-Me | —N(C(H)(CH₃)(CH₂CH₃))— |
| IIa-193 | 4-ethylpiperazinyl-(CH₂)₇-Me | —N(C(H)(CH₃)₂)— |
| IIa-194 | 4-ethylpiperazinyl-(CH₂)₇-Me | —N(CH₂C(H)(CH₃)₂)— |
| IIa-195 | 4-ethylpiperazinyl-(CH₂)₇-Me | —N(C(CH₃)₃)— |
| IIa-196 | 4-ethylpiperazinyl-CH₂-CH(OEt)₂ | —CH₂— |
| IIa-197 | 4-ethylpiperazinyl-CH₂-CH(OEt)₂ | —CH(OH)— |
| IIa-198 | 4-ethylpiperazinyl-CH₂-CH(OEt)₂ | —O— |

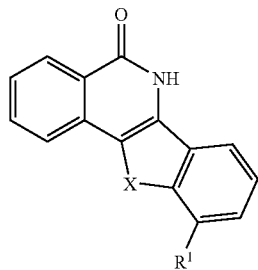

(IIa)

| Compound | —R¹ | X |
|---|---|---|
| IIa-199 | [piperazine-CH2-CH(OEt)2 with N-ethyl] | —C(O)— |
| IIa-200 | [piperazine-CH2-CH(OEt)2 with N-ethyl] | —NH— |
| IIa-201 | [piperazine-CH2-CH(OEt)2 with N-ethyl] | —S— |
| IIa-202 | [piperazine-CH2-CH(OEt)2 with N-ethyl] | —N(CH₃)— |
| IIa-203 | [piperazine-CH2-CH(OEt)2 with N-ethyl] | —N(CH₂CH₃)— |
| IIa-204 | [piperazine-CH2-CH(OEt)2 with N-ethyl] | —N(CH₂CH₂CH₃)— |
| IIa-205 | [piperazine-CH2-CH(OEt)2 with N-ethyl] | —N(CH₂CH₂CH₂CH₃)— |
| IIa-206 | [piperazine-CH2-CH(OEt)2 with N-ethyl] | —N(C(H)(CH₃)(CH₂CH₃))— |
| IIa-207 | [piperazine-CH2-CH(OEt)2 with N-ethyl] | —N(C(H)(CH₃)₂)— |
| IIa-208 | [piperazine-CH2-CH(OEt)2 with N-ethyl] | —N(CH₂C(H)(CH₃)₂)— |
| IIa-209 | [piperazine-CH2-CH(OEt)2 with N-ethyl] | —N(C(CH₃)₃)— | and pharmaceutically acceptable salts thereof.

5.6 The Indenoisoquinolinone Analogs of Formula (IIb)

The present invention provides Indenoisoquinolinone Analogs according to Formula (IIb) below:

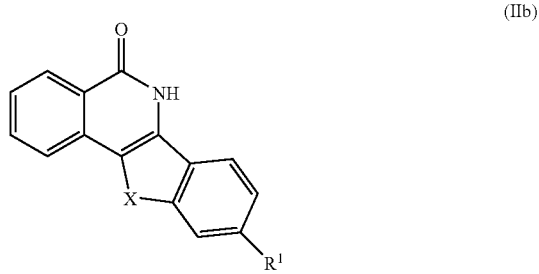

(IIb)

and pharmaceutically acceptable salts thereof,
wherein:

$X$ and $R^1$ are as defined above for the compounds of Formula (IIb).

In one embodiment, X is —$CH_2$—. In another embodiment, X is —O—. In another embodiment, X is —C(O)—. In another embodiment, X is —NH—. In another embodiment, X is —N($C_1$-$C_4$ alkyl)-. In another embodiment, X is —S—. In another embodiment, X is —CH(OH)—.

In one embodiment, n is 1. In another embodiment, n is 2.
In one embodiment, X is —$CH_2$— and n is 1.
In one embodiment, X is —$CH_2$— and n is 2.
In one embodiment, X is —CH(OH)— and n is 1.
In one embodiment, X is —CH(OH)— and n is 2.

In one embodiment, $R^2$ is —$C_1$-$C_6$ alkyl and $R^3$ is —C(O)—($C_1$-$C_6$ alkylene)-(3- to 7-membered monocyclic heterocycle).

In one embodiment, $R^2$ is —H and $R^3$ is —C(O)—($C_1$-$C_6$ alkylene)-(3- to 7-membered monocyclic heterocycle).

In one embodiment, n is 1 and $R^3$ is a nitrogen-containing 3- to 7-membered monocyclic heterocycle which is substituted with one —C(O)O—$C_1$-$C_6$ alkyl.

In another embodiment, n is 1 and $R^3$ is $C_3$-$C_8$ monocyclic cycloalkyl substituted with one hydroxy-substituted $C_1$-$C_5$ alkyl.

In one embodiment, n is 2 and $R^3$ is a nitrogen-containing 3- to 7-membered monocyclic heterocycle which is substituted with one —C(O)O—$C_1$-$C_6$ alkyl.

In another embodiment, n is 2 and $R^3$ is $C_3$-$C_8$ monocyclic cycloalkyl substituted with one hydroxy-substituted $C_1$-$C_5$ alkyl.

In one embodiment, N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —$CH_2$—, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —$CH_2$—, n is 1, and $R^2$ is $C_3$-$C_8$ monocyclic cycloalkyl.

In one embodiment, X is —$CH_2$—, n is 1, and $R^3$ is a nitrogen-containing 3- to 7-membered monocyclic heterocycle which is substituted with one —C(O)O—$C_1$-$C_6$ alkyl.

In one embodiment, X is —$CH_2$—, n is 1, and $R^3$ is $C_3$-$C_8$ monocyclic cycloalkyl which is substituted with one hydroxy-substituted $C_1$-$C_5$ alkyl.

In one embodiment, X is —$CH_2$—, n is 1, $R^2$ is —H, and $R^3$ is a nitrogen-containing 3- to 7-membered monocyclic heterocycle which is substituted with one —C(O)O—$C_1$-$C_6$ alkyl.

In one embodiment, X is —$CH_2$—, n is 1, $R^2$ is —H, and $R^3$ is $C_3$-$C_8$ monocyclic cycloalkyl which is substituted with one hydroxy-substituted $C_1$-$C_5$ alkyl.

In another embodiment, X is —$CH_2$—, n is 1 and $R^3$ is —C(O)—$C_1$-$C_6$ alkylene-(3- to 7-membered monocyclic heterocycle).

In one embodiment, X is —CH(OH)—, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —CH(OH)—, n is 1, and $R^2$ is $C_3$-$C_8$ monocyclic cycloalkyl.

In one embodiment, X is —CH(OH)—, n is 1, and $R^3$ is a nitrogen-containing 3- to 7-membered monocyclic heterocycle which is substituted with one —C(O)O—$C_1$-$C_6$ alkyl.

In one embodiment, X is —CH(OH)—, n is 1, and $R^3$ is $C_3$-$C_8$ monocyclic cycloalkyl which is substituted with one hydroxy-substituted $C_1$-$C_5$ alkyl.

In one embodiment, X is —CH(OH)—, n is 1, $R^2$ is —H, and $R^3$ is a nitrogen-containing 3- to 7-membered monocyclic heterocycle which is substituted with one —C(O)O—$C_1$-$C_6$ alkyl.

In one embodiment, X is —CH(OH)—, n is 1, $R^2$ is —H, and $R^3$ is $C_3$-$C_8$ monocyclic cycloalkyl which is substituted with one hydroxy-substituted $C_1$-$C_5$ alkyl.

In another embodiment, X is —CH(OH)—, n is 1 and $R^3$ is —C(O)—$C_1$-$C_6$ alkylene-(3- to 7-membered monocyclic heterocycle).

In various embodiments, —R¹ is:
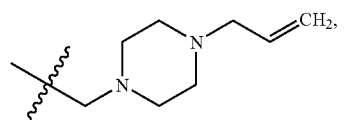
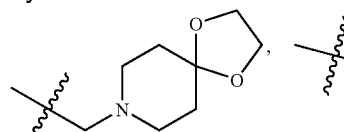
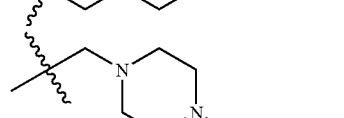
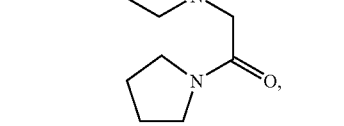
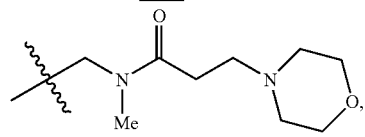
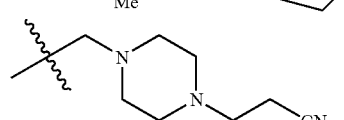
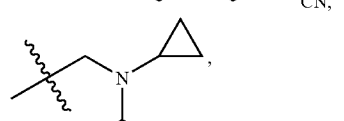
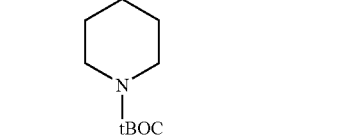
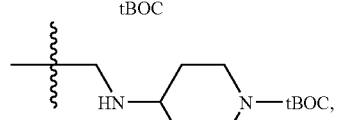
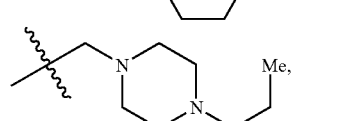
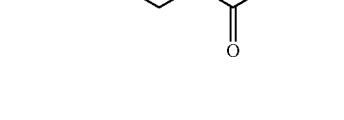
-continued
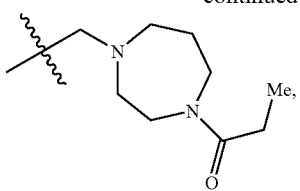
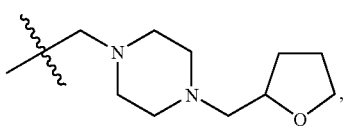
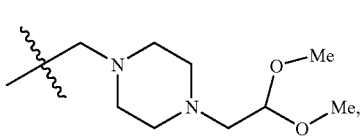
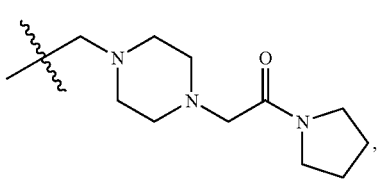
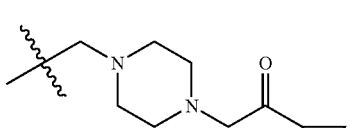
or
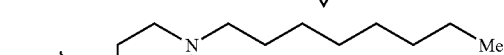
Illustrative examples of the Indenoisoquinolinone Analogs include the compounds of Formula (IIb) in which n is 1 as set forth below:
| Compound | —R¹ | X |
|---|---|---|
| IIb-1 |  | —CH₂— |
| IIb-b1 | | —CH(OH)— |

-continued
| Compound | —R¹ | X |
|---|---|---|
| IIb-2 | 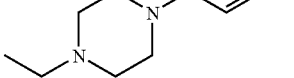 | —O— |
| IIb-3 | 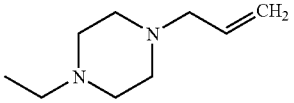 | —C(O)— |
| IIb-4 | 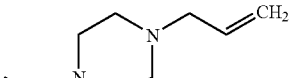 | —NH— |
| IIb-5 | 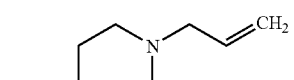 | —S— |
| IIb-6 | 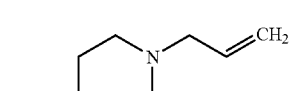 | —N(CH$_3$)— |
| IIb-7 | 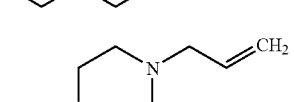 | —N(CH$_2$CH$_3$)— |
| IIb-8 | 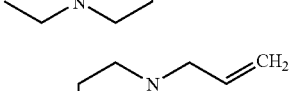 | —N(CH$_2$CH$_2$CH$_3$)— |
| IIb-9 | 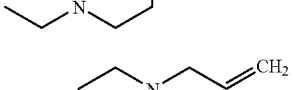 | —N(CH$_2$CH$_2$CH$_2$CH$_3$)— |
| IIb-10 | 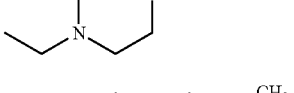 | —N(C(H)(CH$_3$)(CH$_2$CH$_3$))— |
| IIb-11 | 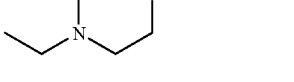 | —N(C(H)(CH$_3$)$_2$)— |
| IIb-12 | 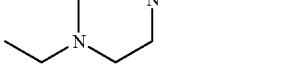 | —N(CH$_2$C(H)(CH$_3$)$_2$)— |
| IIb-13 | 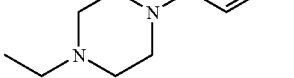 | —N(C(CH$_3$)$_3$)— |
| IIb-14 | 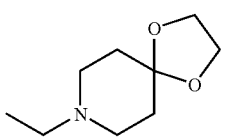 | —CH$_2$— |

| Compound | —R¹ | X |
|---|---|---|
| IIb-b14 | 1-ethyl-1,4-dioxa-8-azaspiro[4.5]decane | —CH(OH)— |
| IIb-15 | 1-ethyl-1,4-dioxa-8-azaspiro[4.5]decane | —O— |
| IIb-16 | 1-ethyl-1,4-dioxa-8-azaspiro[4.5]decane | —C(O)— |
| IIb-17 | 1-ethyl-1,4-dioxa-8-azaspiro[4.5]decane | —NH— |
| IIb-18 | 1-ethyl-1,4-dioxa-8-azaspiro[4.5]decane | —S— |
| IIb-19 | 1-ethyl-1,4-dioxa-8-azaspiro[4.5]decane | —N(CH$_3$)— |
| IIb-20 | 1-ethyl-1,4-dioxa-8-azaspiro[4.5]decane | —N(CH$_2$CH$_3$)— |
| IIb-21 | 1-ethyl-1,4-dioxa-8-azaspiro[4.5]decane | —N(CH$_2$CH$_2$CH$_3$)— |
| IIb-22 | 1-ethyl-1,4-dioxa-8-azaspiro[4.5]decane | —N(CH$_2$CH$_2$CH$_2$CH$_3$)— |
| IIb-23 | 1-ethyl-1,4-dioxa-8-azaspiro[4.5]decane | —N(C(H)(CH$_3$)(CH$_2$CH$_3$))— |
| IIb-24 | 1-ethyl-1,4-dioxa-8-azaspiro[4.5]decane | —N(C(H)(CH$_3$)$_2$)— |

-continued

| Compound | —R¹ | X |
|---|---|---|
| IIb-25 | N-ethyl-1,4-dioxa-8-azaspiro[4.5]decane | —N(CH₂C(H)(CH₃)₂)— |
| IIb-26 | N-ethyl-1,4-dioxa-8-azaspiro[4.5]decane | —N(C(CH₃)₃)— |
| IIb-27 | ethylamino-1-(hydroxymethyl)cyclopentane | —CH₂— |
| IIb-b27 | ethylamino-1-(hydroxymethyl)cyclopentane | —CH(OH)— |
| IIb-28 | ethylamino-1-(hydroxymethyl)cyclopentane | —O— |
| IIb-29 | ethylamino-1-(hydroxymethyl)cyclopentane | —C(O)— |
| IIb-30 | ethylamino-1-(hydroxymethyl)cyclopentane | —NH— |
| IIb-31 | ethylamino-1-(hydroxymethyl)cyclopentane | —S— |
| IIb-32 | ethylamino-1-(hydroxymethyl)cyclopentane | —N(CH₃)— |
| IIb-33 | ethylamino-1-(hydroxymethyl)cyclopentane | —N(CH₂CH₃)— |
| IIb-34 | ethylamino-1-(hydroxymethyl)cyclopentane | —N(CH₂CH₂CH₃)— |

-continued

| Compound | —R¹ | X |
|---|---|---|
| IIb-35 | ethylamino-1-(hydroxymethyl)cyclopentyl | —N(CH₂CH₂CH₂CH₃)— |
| IIb-36 | ethylamino-1-(hydroxymethyl)cyclopentyl | —N(C(H)(CH₃)(CH₂CH₃))— |
| IIb-37 | ethylamino-1-(hydroxymethyl)cyclopentyl | —N(C(H)(CH₃)₂)— |
| IIb-38 | ethylamino-1-(hydroxymethyl)cyclopentyl | —N(CH₂C(H)(CH₃)₂)— |
| IIb-39 | ethylamino-1-(hydroxymethyl)cyclopentyl | —N(C(CH₃)₃)— |
| IIb-40 | 4-ethylpiperazin-1-yl-acetyl-pyrrolidine | —CH₂— |
| IIb-b40 | 4-ethylpiperazin-1-yl-acetyl-pyrrolidine | —CH(OH)— |
| IIb-41 | 4-ethylpiperazin-1-yl-acetyl-pyrrolidine | —O— |
| IIb-42 | 4-ethylpiperazin-1-yl-acetyl-pyrrolidine | —C(O)— |

| Compound | —R¹ | X |
|---|---|---|
| IIb-43 | 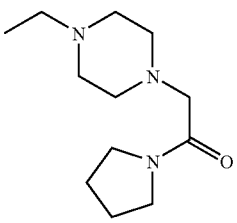 | —NH— |
| IIb-44 | 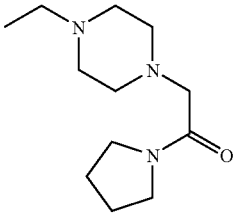 | —S— |
| IIb-45 | 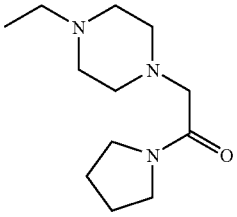 | —N(CH₃)— |
| IIb-46 | 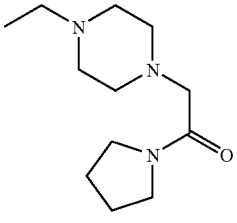 | —N(CH₂CH₃)— |
| IIb-47 | 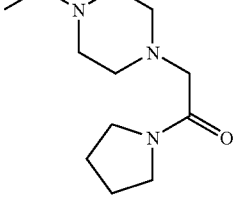 | —N(CH₂CH₂CH₃)— |
| IIb-48 | 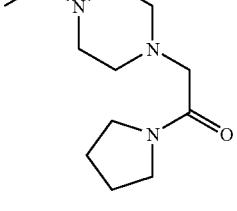 | —N(CH₂CH₂CH₂CH₃)— |
| IIb-49 | 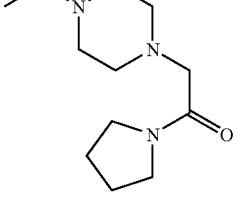 | —N(C(H)(CH₃)(CH₂CH₃))— |

-continued
| Compound | —R¹ | X |
|---|---|---|
| IIb-50 | 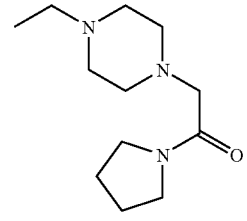 | —N(C(H)(CH₃)₂)— |
| IIb-51 | 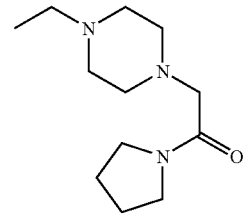 | —N(CH₂C(H)(CH₃)₂)— |
| IIb-52 | 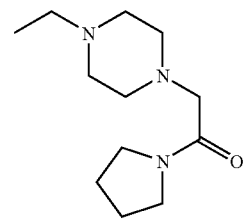 | —N(C(CH₃)₃)— |
| IIb-53 | 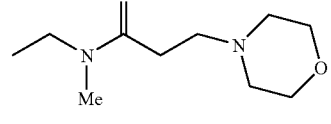 | —CH₂— |
| IIb-b53 | 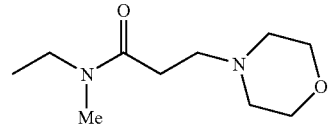 | —CH(OH)— |
| IIb-54 | 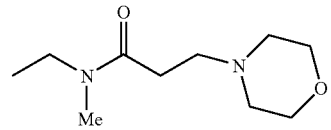 | —O— |
| IIb-55 | 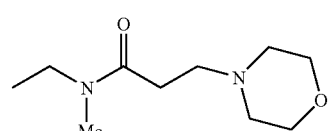 | —C(O)— |
| IIb-56 | 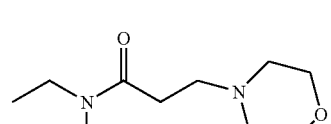 | —NH— |
| IIb-57 | 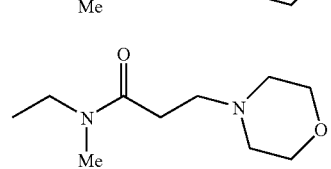 | —S— |

-continued

| Compound | —R¹ | X |
|---|---|---|
| IIb-58 | *N-ethyl-N-methyl-3-morpholinopropanamide* | —N(CH₃)— |
| IIb-59 | *N-ethyl-N-methyl-3-morpholinopropanamide* | —N(CH₂CH₃)— |
| IIb-60 | *N-ethyl-N-methyl-3-morpholinopropanamide* | —N(CH₂CH₂CH₃)— |
| IIb-61 | *N-ethyl-N-methyl-3-morpholinopropanamide* | —N(CH₂CH₂CH₃)— |
| IIb-62 | *N-ethyl-N-methyl-3-morpholinopropanamide* | —N(C(H)(CH₃)(CH₂CH₃))— |
| IIb-63 | *N-ethyl-N-methyl-3-morpholinopropanamide* | —N(C(H)(CH₃)₂)— |
| IIb-64 | *N-ethyl-N-methyl-3-morpholinopropanamide* | —N(CH₂C(H)(CH₃)₂)— |
| IIb-65 | *N-ethyl-N-methyl-3-morpholinopropanamide* | —N(C(CH₃)₃)— |
| IIb-66 | *3-(4-ethylpiperazin-1-yl)propanenitrile* | —CH₂— |
| IIb-b66 | *3-(4-ethylpiperazin-1-yl)propanenitrile* | —CH(OH)— |
| IIb-67 | *3-(4-ethylpiperazin-1-yl)propanenitrile* | —O— |

-continued
| Compound | —R¹ | X |
|---|---|---|
| IIb-68 | 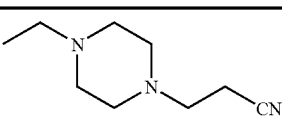 | —C(O)— |
| IIb-69 | 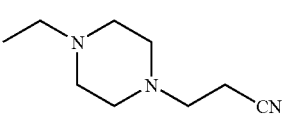 | —NH— |
| IIb-70 | 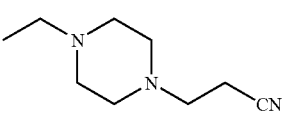 | —S— |
| IIb-71 | 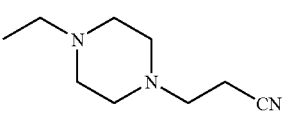 | —N(CH₃)— |
| IIb-72 | 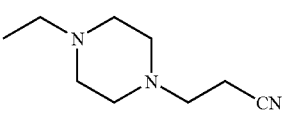 | —N(CH₂CH₃)— |
| IIb-73 | 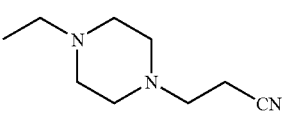 | —N(CH₂CH₂CH₃)— |
| IIb-74 | 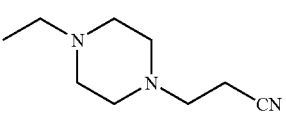 | —N(CH₂CH₂CH₂CH₃)— |
| IIb-75 | 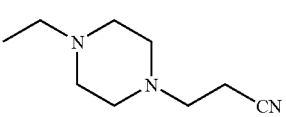 | —N(C(H)(CH₃)(CH₂CH₃))— |
| IIb-76 | 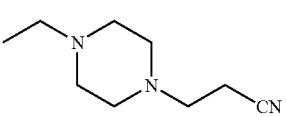 | —N(C(H)(CH₃)₂)— |
| IIb-77 | 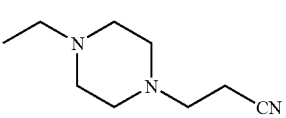 | —N(CH₂C(H)(CH₃)₂)— |
| IIb-78 | 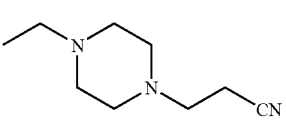 | —N(C(CH₃)₃)— |
| IIb-79 | 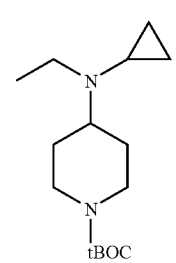 | —CH₂— |

-continued

| Compound | —R¹ | X |
|---|---|---|
| IIb-b79 | [structure: N-ethyl-N-cyclopropyl-4-aminopiperidine-N-tBOC] | —CH(OH)— |
| IIb-80 | [structure: N-ethyl-N-cyclopropyl-4-aminopiperidine-N-tBOC] | —O— |
| IIb-81 | [structure: N-ethyl-N-cyclopropyl-4-aminopiperidine-N-tBOC] | —C(O)— |
| IIb-82 | [structure: N-ethyl-N-cyclopropyl-4-aminopiperidine-N-tBOC] | —NH— |
| IIb-83 | [structure: N-ethyl-N-cyclopropyl-4-aminopiperidine-N-tBOC] | —S— |
| IIb-84 | [structure: N-ethyl-N-cyclopropyl-4-aminopiperidine-N-tBOC] | —N(CH₃)— |

-continued
| Compound | —R¹ | X |
|---|---|---|
| IIb-85 | 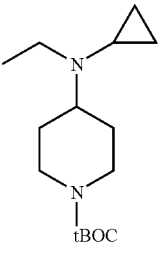 | —N(CH$_2$CH$_3$)— |
| IIb-86 | 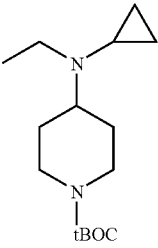 | —N(CH$_2$CH$_2$CH$_3$)— |
| IIb-87 | 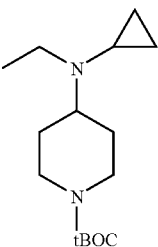 | —N(CH$_2$CH$_2$CH$_2$CH$_3$)— |
| IIb-88 | 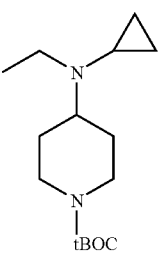 | —N(C(H)(CH$_3$)(CH$_2$CH$_3$))— |
| IIb-89 | 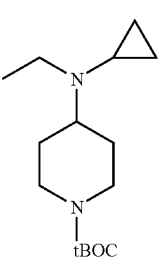 | —N(C(H)(CH$_3$)$_2$)— |
| IIb-90 | 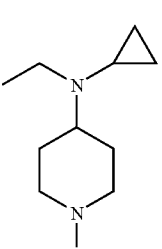 | —N(CH$_2$C(H)(CH$_3$)$_2$)— |

-continued
| Compound | —R¹ | X |
|---|---|---|
| IIb-91 | 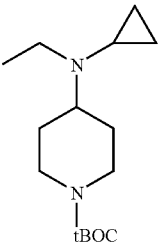 | —N(C(CH₃)₃)— |
| IIb-92 | 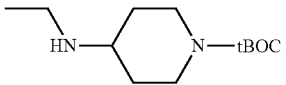 | —CH₂— |
| IIb-b92 | 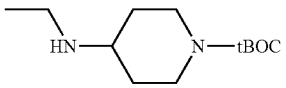 | —CH(OH)— |
| IIb-93 | 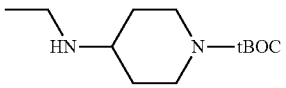 | —O— |
| IIb-94 | 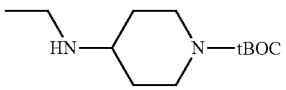 | —C(O)— |
| IIb-95 | 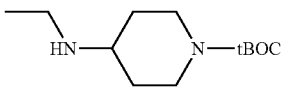 | —NH— |
| IIb-96 | 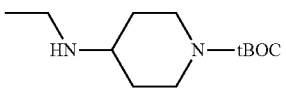 | —S— |
| IIb-97 | 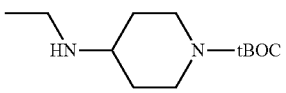 | —N(CH₃)— |
| IIb-98 | 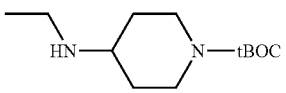 | —N(CH₂CH₃)— |
| IIb-99 | 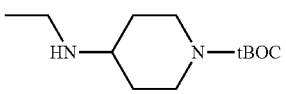 | —N(CH₂CH₂CH₃)— |
| IIb-100 | 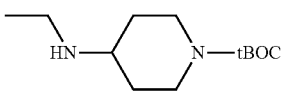 | —N(CH₂CH₂CH₂CH₃)— |
| IIb-101 |  | —N(C(H)(CH₃)(CH₂CH₃))— |
| IIb-102 | 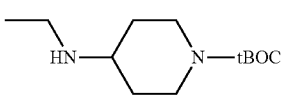 | —N(C(H)(CH₃)₂)— |
| IIb-103 | 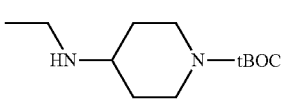 | —N(CH₂C(H)(CH₃)₂)— |

-continued

| Compound | —R¹ | X |
|---|---|---|
| IIb-104 | 4-(ethylamino)-piperidine-1-tBOC | —N(C(CH₃)₃)— |
| IIb-105 | 1-ethyl-4-(propanoyl)piperazine | —CH₂— |
| IIb-b105 | 1-ethyl-4-(propanoyl)piperazine | —CH(OH)— |
| IIb-106 | 1-ethyl-4-(propanoyl)piperazine | —O— |
| IIb-107 | 1-ethyl-4-(propanoyl)piperazine | —C(O)— |
| IIb-108 | 1-ethyl-4-(propanoyl)piperazine | —NH— |
| IIb-109 | 1-ethyl-4-(propanoyl)piperazine | —S— |
| IIb-110 | 1-ethyl-4-(propanoyl)piperazine | —N(CH₃)— |
| IIb-111 | 1-ethyl-4-(propanoyl)piperazine | —N(CH₂CH₃)— |
| IIb-112 | 1-ethyl-4-(propanoyl)piperazine | —N(CH₂CH₂CH₃)— |

-continued

| Compound | —R¹ | X |
|---|---|---|
| IIb-113 | (4-ethylpiperazin-1-yl with propanoyl, Me) | —N(CH₂CH₂CH₂CH₃)— |
| IIb-114 | (4-ethylpiperazin-1-yl with propanoyl, Me) | —N(C(H)(CH₃)(CH₂CH₃))— |
| IIb-115 | (4-ethylpiperazin-1-yl with propanoyl, Me) | —N(C(H)(CH₃)₂)— |
| IIb-116 | (4-ethylpiperazin-1-yl with propanoyl, Me) | —N(CH₂C(H)(CH₃)₂)— |
| IIb-117 | (4-ethylpiperazin-1-yl with propanoyl, Me) | —N(C(CH₃)₃)— |
| IIb-118 | (4-ethyl-1,4-diazepan-1-yl with propanoyl, Me) | —CH₂— |
| IIb-b118 | (4-ethyl-1,4-diazepan-1-yl with propanoyl, Me) | —CH(OH)— |
| IIb-119 | (4-ethyl-1,4-diazepan-1-yl with propanoyl, Me) | —O— |
| IIb-120 | (4-ethyl-1,4-diazepan-1-yl with propanoyl, Me) | —C(O)— |

-continued
| Compound | —R¹ | X |
|---|---|---|
| IIb-121 | 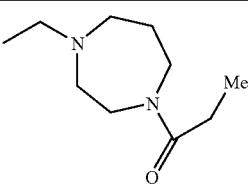 | —NH— |
| IIb-122 | 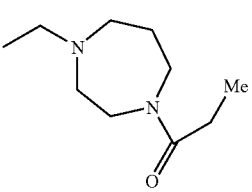 | —S— |
| IIb-123 | 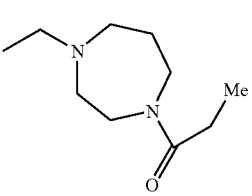 | —N(CH₃)— |
| IIb-124 | 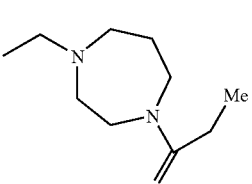 | —N(CH₂CH₃)— |
| IIb-125 | 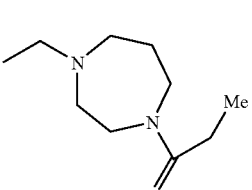 | —N(CH₂CH₃)— |
| IIb-126 | 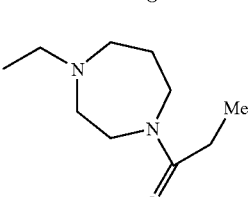 | —N(CH₂CH₂CH₂CH₃)— |
| IIb-127 | 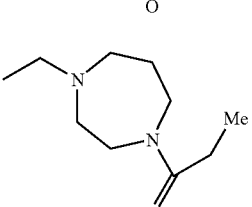 | —N(C(H)(CH₃)(CH₂CH₃))— |
| IIb-128 | 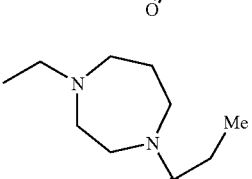 | —N(C(H)(CH₃)₂)— |

-continued
| Compound | —R¹ | X |
|---|---|---|
| IIb-129 | 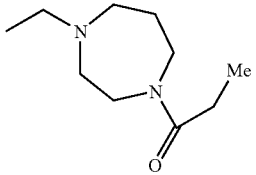 | —N(CH₂C(H)(CH₃)₂)— |
| IIb-130 | 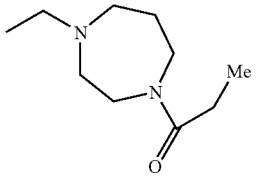 | —N(C(CH₃)₃)— |
| IIb-131 | 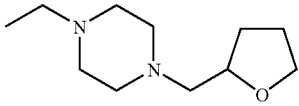 | —CH₂— |
| IIb-b131 | 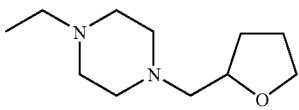 | —CH(OH)— |
| IIb-132 | 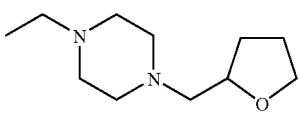 | —O— |
| IIb-133 | 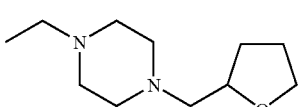 | —C(O)— |
| IIb-134 | 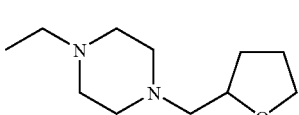 | —NH— |
| IIb-135 | 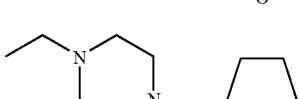 | —S— |
| IIb-136 | 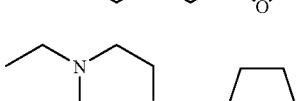 | —N(CH₃)— |
| IIb-137 | 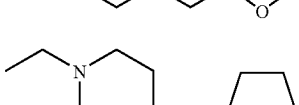 | —N(CH₂CH₃)— |
| IIb-138 | 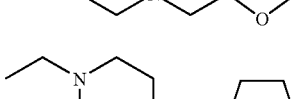 | —N(CH₂CH₂CH₃)— |
| IIb-139 | 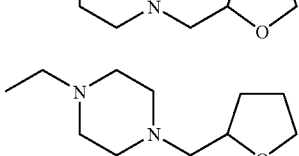 | —N(CH₂CH₂CH₂CH₃)— |

-continued
| Compound | —R¹ | X |
|---|---|---|
| IIb-140 | 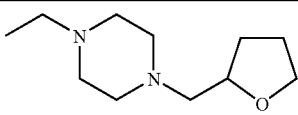 | —N(C(H)(CH₃)(CH₂CH₃))— |
| IIb-141 | 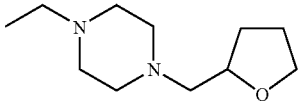 | —N(C(H)(CH₃)₂)— |
| IIb-142 | 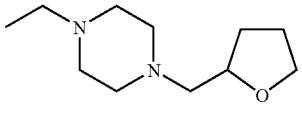 | —N(CH₂C(H)(CH₃)₂)— |
| IIb-143 | 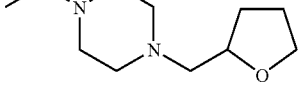 | —N(C(CH₃)₃)— |
| IIb-144 | 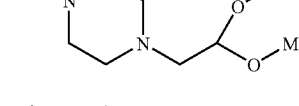 | —CH₂— |
| IIb-b144 | 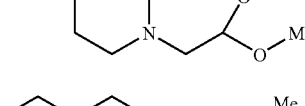 | —CH(OH)— |
| IIb-145 | 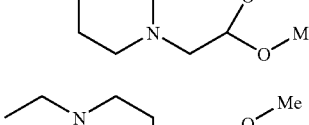 | —O— |
| IIb-146 | 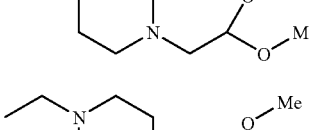 | —C(O)— |
| IIb-147 | 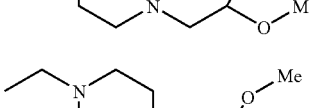 | —NH— |
| IIb-148 | 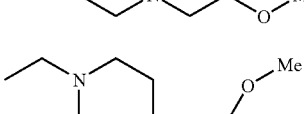 | —S— |
| IIb-149 | 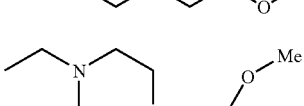 | —N(CH₃)— |
| IIb-150 | 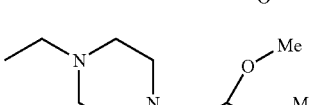 | —N(CH₂CH₃)— |
| IIb-151 |  | —N(CH₂CH₂CH₃)— |

-continued

| Compound | —R¹ | X |
|---|---|---|
| IIb-152 | 4-ethylpiperazin-1-yl-CH₂-CH(OMe)₂ | —N(CH₂CH₂CH₂CH₃)— |
| IIb-153 | 4-ethylpiperazin-1-yl-CH₂-CH(OMe)₂ | —N(C(H)(CH₃)(CH₂CH₃))— |
| IIb-154 | 4-ethylpiperazin-1-yl-CH₂-CH(OMe)₂ | —N(C(H)(CH₃)₂)— |
| IIb-155 | 4-ethylpiperazin-1-yl-CH₂-CH(OMe)₂ | —N(CH₂C(H)(CH₃)₂)— |
| IIb-156 | 4-ethylpiperazin-1-yl-CH₂-CH(OMe)₂ | —N(C(CH₃)₃)— |
| IIb-157 | 4-ethylpiperazin-1-yl-CH₂-C(O)-pyrrolidin-1-yl | —CH₂— |
| IIb-b157 | 4-ethylpiperazin-1-yl-CH₂-C(O)-pyrrolidin-1-yl | —CH(OH)— |
| IIb-158 | 4-ethylpiperazin-1-yl-CH₂-C(O)-pyrrolidin-1-yl | —O— |
| IIb-159 | 4-ethylpiperazin-1-yl-CH₂-C(O)-pyrrolidin-1-yl | —C(O)— |
| IIb-160 | 4-ethylpiperazin-1-yl-CH₂-C(O)-pyrrolidin-1-yl | —NH— |
| IIb-161 | 4-ethylpiperazin-1-yl-CH₂-C(O)-pyrrolidin-1-yl | —S— |

-continued

| Compound | —R¹ | X |
|---|---|---|
| IIb-162 | (ethylpiperazinyl-CH2-C(O)-pyrrolidinyl) | —N(CH_3)— |
| IIb-163 | (ethylpiperazinyl-CH2-C(O)-pyrrolidinyl) | —N(CH_2CH_3)— |
| IIb-164 | (ethylpiperazinyl-CH2-C(O)-pyrrolidinyl) | —N(CH_2CH_2CH_3)— |
| IIb-165 | (ethylpiperazinyl-CH2-C(O)-pyrrolidinyl) | —N(CH_2CH_2CH_2CH_3)— |
| IIb-166 | (ethylpiperazinyl-CH2-C(O)-pyrrolidinyl) | —N(C(H)(CH_3)(CH_2CH_3))— |
| IIb-167 | (ethylpiperazinyl-CH2-C(O)-pyrrolidinyl) | —N(C(H)(CH_3)_2)— |
| IIb-168 | (ethylpiperazinyl-CH2-C(O)-pyrrolidinyl) | —N(CH_2C(H)(CH_3)_2)— |
| IIb-169 | (ethylpiperazinyl-CH2-C(O)-pyrrolidinyl) | —N(C(CH_3)_3)— |
| IIb-170 | (ethylpiperazinyl-CH2-C(O)-cyclopropyl) | —CH_2— |

-continued
| Compound | —R¹ | X |
|---|---|---|
| IIb-b170 | 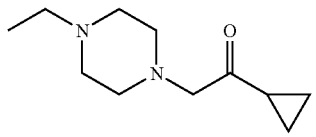 | —CH(OH)— |
| IIb-171 | 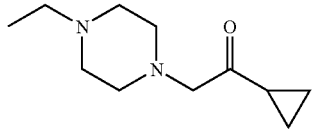 | —O— |
| IIb-172 | 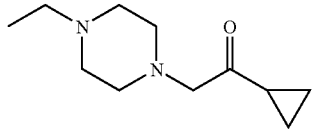 | —C(O)— |
| IIb-173 | 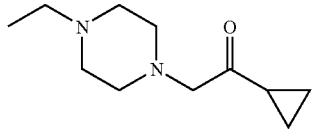 | —NH— |
| IIb-174 | 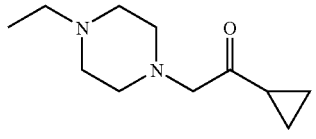 | —S— |
| IIb-175 | 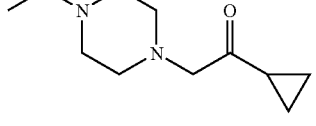 | —N(CH$_3$)— |
| IIb-176 | 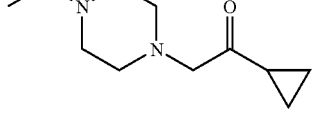 | —N(CH$_2$CH$_3$)— |
| IIb-177 | 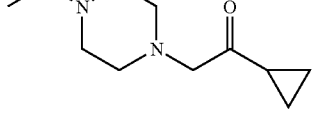 | —N(CH$_2$CH$_2$CH$_3$)— |
| IIb-178 | 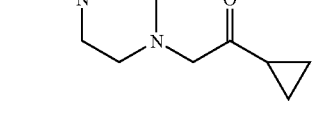 | —N(CH$_2$CH$_2$CH$_2$CH$_3$)— |
| IIb-179 | 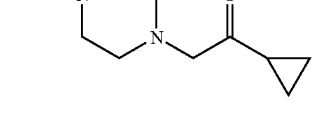 | —N(C(H)(CH$_3$)(CH$_2$CH$_3$))— |

-continued

| Compound | —R¹ | X |
|---|---|---|
| IIb-180 | 4-ethylpiperazin-1-yl-CH₂-C(O)-cyclopropyl | —N(C(H)(CH₃)₂)— |
| IIb-181 | 4-ethylpiperazin-1-yl-CH₂-C(O)-cyclopropyl | —N(CH₂C(H)(CH₃)₂)— |
| IIb-182 | 4-ethylpiperazin-1-yl-CH₂-C(O)-cyclopropyl | —N(C(CH₃)₃)— |
| IIb-183 | 4-ethylpiperazin-1-yl-(CH₂)₇-Me | —CH₂— |
| IIb-b183 | 4-ethylpiperazin-1-yl-(CH₂)₇-Me | —CH(OH)— |
| IIb-184 | 4-ethylpiperazin-1-yl-(CH₂)₇-Me | —O— |
| IIb-185 | 4-ethylpiperazin-1-yl-(CH₂)₇-Me | —C(O)— |
| IIb-186 | 4-ethylpiperazin-1-yl-(CH₂)₇-Me | —NH— |
| IIb-187 | 4-ethylpiperazin-1-yl-(CH₂)₇-Me | —S— |
| IIb-188 | 4-ethylpiperazin-1-yl-(CH₂)₇-Me | —N(CH₃)— |
| IIb-189 | 4-ethylpiperazin-1-yl-(CH₂)₇-Me | —N(CH₂CH₃)— |
| IIb-190 | 4-ethylpiperazin-1-yl-(CH₂)₇-Me | —N(CH₂CH₂CH₃)— |
| IIb-191 | 4-ethylpiperazin-1-yl-(CH₂)₇-Me | —N(CH₂CH₂CH₂CH₃)— |

-continued
| Compound | —R¹ | X |
|---|---|---|
| IIb-192 | 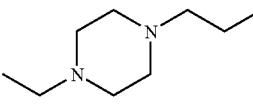 | —N(C(H)(CH₃)(CH₂CH₃))— |
| IIb-193 | 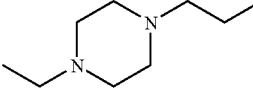 | —N(C(H)(CH₃)₂)— |
| IIb-194 | 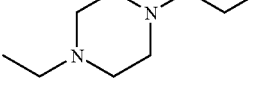 | —N(CH₂C(H)(CH₃)₂)— |
| IIb-195 | 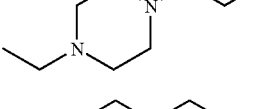 | —N(C(CH₃)₃)— |
| IIb-196 | 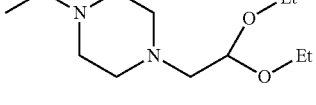 | —CH₂— |
| IIb-197 | 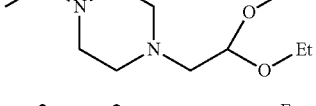 | —CH(OH)— |
| IIb-198 | 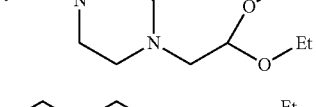 | —O— |
| IIb-199 | 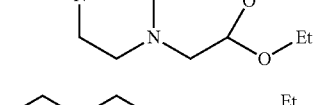 | —C(O)— |
| IIb-200 | 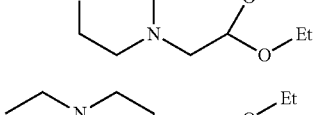 | —NH— |
| IIb-201 | 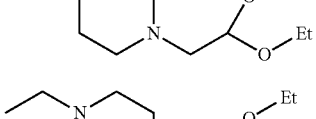 | —S— |
| IIb-202 | 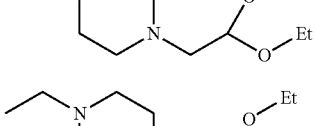 | —N(CH₃)— |
| IIb-203 | 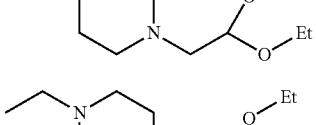 | —N(CH₂CH₃)— |
| IIb-204 | 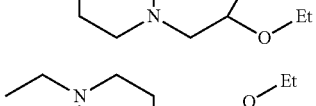 | —N(CH₂CH₂CH₃)— |
| IIb-205 | 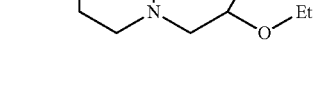 | —N(CH₂CH₂CH₂CH₃)— |

-continued

| Compound | —R¹ | X |
|---|---|---|
| IIb-206 | 1-ethylpiperazine-CH₂-CH(OEt)₂ | —N(C(H)(CH₃)(CH₂CH₃))— |
| IIb-207 | 1-ethylpiperazine-CH₂-CH(OEt)₂ | —N(C(H)(CH₃)₂)— |
| IIb-208 | 1-ethylpiperazine-CH₂-CH(OEt)₂ | —N(CH₂C(H)(CH₃)₂)— |
| IIb-209 | 1-ethylpiperazine-CH₂-CH(OEt)₂ | —N(C(CH₃)₃)— |
| IIb-210 | 1-ethyl-4-(2-(pyrrolidin-1-yl)ethyl)piperidine | —CH₂— |
| IIb-211 | 1-ethyl-4-(2-(pyrrolidin-1-yl)ethyl)piperidine | —CH(OH)— |
| IIb-212 | 1-ethyl-4-(2-(pyrrolidin-1-yl)ethyl)piperidine | —O— |
| IIb-213 | 1-ethyl-4-(2-(pyrrolidin-1-yl)ethyl)piperidine | —C(O)— |
| IIb-214 | 1-ethyl-4-(2-(pyrrolidin-1-yl)ethyl)piperidine | —NH— |
| IIb-215 | 1-ethyl-4-(2-(pyrrolidin-1-yl)ethyl)piperidine | —S— |
| IIb-216 | 1-ethyl-4-(2-(pyrrolidin-1-yl)ethyl)piperidine | —N(CH₃)— |

-continued

| Compound | —R¹ | X |
|---|---|---|
| IIb-217 | (ethyl-piperidinyl-ethyl-pyrrolidinyl) | —N(CH₂CH₃)— |
| IIb-218 | (ethyl-piperidinyl-ethyl-pyrrolidinyl) | —N(CH₂CH₂CH₃)— |
| IIb-219 | (ethyl-piperidinyl-ethyl-pyrrolidinyl) | —N(CH₂CH₂CH₂CH₃)— |
| IIb-220 | (ethyl-piperidinyl-ethyl-pyrrolidinyl) | —N(C(H)(CH₃)(CH₂CH₃))— |
| IIb-221 | (ethyl-piperidinyl-ethyl-pyrrolidinyl) | —N(C(H)(CH₃)₂)— |
| IIb-222 | (ethyl-piperidinyl-ethyl-pyrrolidinyl) | —N(CH₂C(H)(CH₃)₂)— |
| IIb-223 | (ethyl-piperidinyl-ethyl-pyrrolidinyl) | —N(C(CH₃)₃)— | and pharmaceutically acceptable salts thereof.

5.7 The Indenoisoquinolinone Analogs of Formula (IIc)

The present invention provides Indenoisoquinolinone Analogs according to Formula (IIc) below:

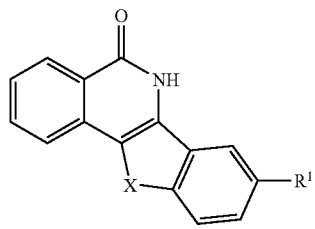

(IIc)

and pharmaceutically acceptable salts thereof, wherein:

X and R¹ are as defined above for the compounds of Formula (IIc).

In one embodiment, X is —CH₂—. In another embodiment, X is —O—. In another embodiment, X is —C(O)—. In another embodiment, X is —NH—. In another embodiment, X is —N(C₁-C₄ alkyl)-. In another embodiment, X is —S—. In another embodiment, X is —CH(OH)—.

In one embodiment, n is 1. In another embodiment, n is 2.
In one embodiment, X is —CH₂— and n is 1.
In one embodiment, X is —CH₂— and n is 2.
In one embodiment, X is —CH(OH)— and n is 1.
In one embodiment, X is —CH(OH)— and n is 2.

In one embodiment, R² is —C₁-C₆ alkyl and R³ is —C(O)—(C₁-C₆ alkylene)-(3- to 7-membered monocyclic heterocycle).

In one embodiment, R² is —H and R³ is —C(O)—(C₁-C₆ alkylene)-(3- to 7-membered monocyclic heterocycle).

In one embodiment, n is 1 and R³ is a nitrogen-containing 3- to 7-membered monocyclic heterocycle which is substituted with one —C(O)O—C₁-C₆ alkyl.

In another embodiment, n is 1 and $R^3$ is $C_3$-$C_8$ monocyclic cycloalkyl substituted with one hydroxy-substituted $C_1$-$C_5$ alkyl.

In one embodiment, n is 2 and $R^3$ is a nitrogen-containing 3- to 7-membered monocyclic heterocycle which is substituted with one —C(O)O—$C_1$-$C_6$ alkyl.

In another embodiment, n is 2 and $R^3$ is $C_3$-$C_8$ monocyclic cycloalkyl substituted with one hydroxy-substituted $C_1$-$C_5$ alkyl.

In one embodiment, N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —$CH_2$—, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —$CH_2$—, n is 1, and $R^2$ is $C_3$-$C_8$ monocyclic cycloalkyl.

In one embodiment, X is —$CH_2$—, n is 1, and $R^3$ is a nitrogen-containing 3- to 7-membered monocyclic heterocycle which is substituted with one —C(O)O—$C_1$-$C_6$ alkyl.

In one embodiment, X is —$CH_2$—, n is 21, and $R^3$ is $C_3$-$C_8$ monocyclic cycloalkyl which is substituted with one hydroxy-substituted $C_1$-$C_5$ alkyl.

In one embodiment, X is —$CH_2$—, n is 1, $R^2$ is —H, and $R^3$ is a nitrogen-containing 3- to 7-membered monocyclic heterocycle which is substituted with one —C(O)O—$C_1$-$C_6$ alkyl.

In one embodiment, X is —$CH_2$—, n is 1, $R^2$ is —H, and $R^3$ is $C_3$-$C_8$ monocyclic cycloalkyl which is substituted with one hydroxy-substituted $C_1$-$C_5$ alkyl.

In another embodiment, X is —$CH_2$—, n is 1 and $R^3$ is —C(O)—$C_1$-$C_6$ alkylene-(3- to 7-membered monocyclic heterocycle).

In one embodiment, X is —CH(OH)—, n is 1 and N, $R^2$ and $R^3$ are taken together to form a nitrogen-containing 3- to 7-membered monocyclic heterocycle, which substituted with one of —$C_2$-$C_6$ alkenyl, —C(O)—$C_1$-$C_6$ alkyl, —($C_1$-$C_4$ alkylene)-C(O)—($C_3$-$C_8$ monocyclic cycloalkyl), —$C_7$-$C_{10}$ alkyl, —($C_1$-$C_5$ alkylene)-C(H)(—O—$C_1$-$C_4$ alkyl)$_2$, -(cyano-substituted) $C_1$-$C_5$ alkyl, —($C_1$-$C_5$ alkylene)-C(O)-(nitrogen-containing 3- to 7-membered monocyclic heterocycle), or —($C_1$-$C_5$ alkylene)-(3- to 7-membered monocyclic heterocycle).

In one embodiment, X is —CH(OH)—, n is 1, and $R^2$ is $C_3$-$C_8$ monocyclic cycloalkyl.

In one embodiment, X is —CH(OH)—, n is 1, and $R^3$ is a nitrogen-containing 3- to 7-membered monocyclic heterocycle which is substituted with one —C(O)O—$C_1$-$C_6$ alkyl.

In one embodiment, X is —CH(OH)—, n is 1, and $R^3$ is $C_3$-$C_8$ monocyclic cycloalkyl which is substituted with one hydroxy-substituted $C_1$-$C_5$ alkyl.

In one embodiment, X is —CH(OH)—, n is 1, $R^2$ is —H, and $R^3$ is a nitrogen-containing 3- to 7-membered monocyclic heterocycle which is substituted with one —C(O)O—$C_1$-$C_6$ alkyl.

In one embodiment, X is —CH(OH)—, n is 1, $R^2$ is —H, and $R^3$ is $C_3$-$C_8$ monocyclic cycloalkyl which is substituted with one hydroxy-substituted $C_1$-$C_5$ alkyl.

In another embodiment, X is —CH(OH)—, n is 1 and $R^3$ is —C(O)—$C_1$-$C_6$ alkylene-(3- to 7-membered monocyclic heterocycle).

In various embodiments, —$R^1$ is:

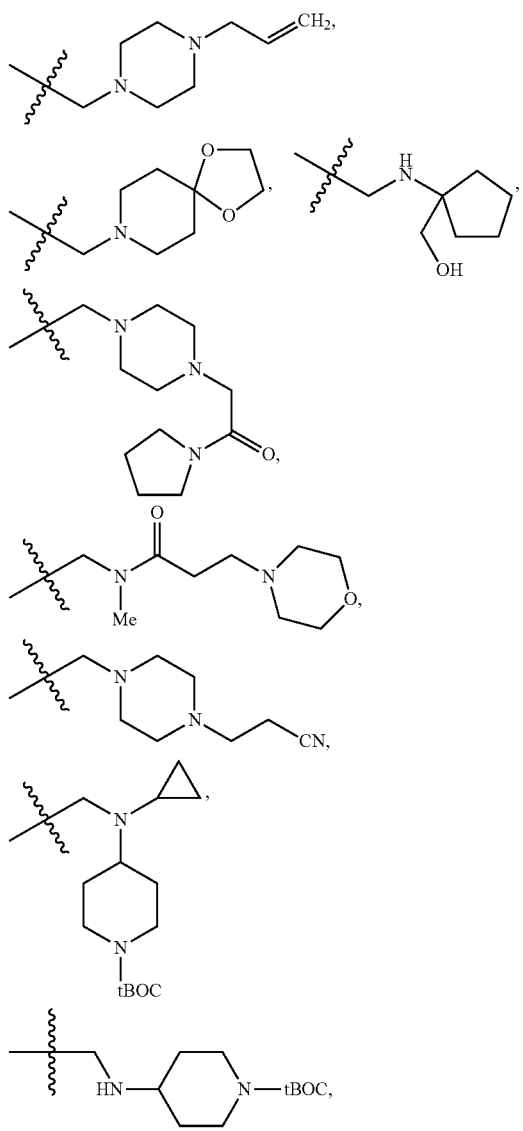

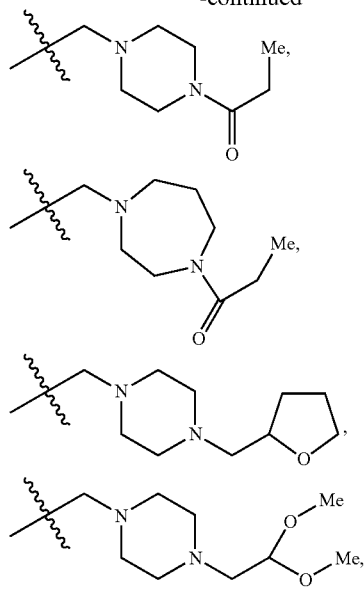

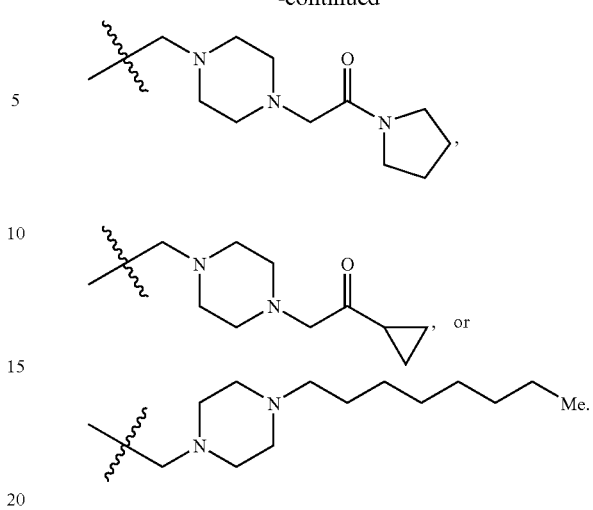

Illustrative examples of the Indenoisoquinolinone Analogs include the compounds of Formula (IIc) in which n is 1 as set forth below:

| Compound | —R¹ | X |
|---|---|---|
| IIc-1 | ethyl-piperazinyl-CH₂-CH= | —CH₂— |
| IIc-c1 | ethyl-piperazinyl-CH₂-CH= | —CH(OH)— |
| IIc-2 | ethyl-piperazinyl-CH₂-CH= | —O— |
| IIc-3 | ethyl-piperazinyl-CH₂-CH= | —C(O)— |
| IIc-4 | ethyl-piperazinyl-CH₂-CH= | —NH— |
| IIc-5 | ethyl-piperazinyl-CH₂-CH= | —S— |
| IIc-6 | ethyl-piperazinyl-CH₂-CH= | —N(CH₃)— |
| IIc-7 | ethyl-piperazinyl-CH₂-CH= | —N(CH₂CH₃)— |

-continued
| Compound | —R¹ | X |
|---|---|---|
| IIc-8 | 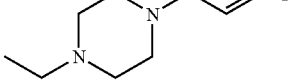 | —N(CH₂CH₂CH₃)— |
| IIc-9 | 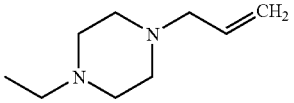 | —N(CH₂CH₂CH₃)— |
| IIc-10 | 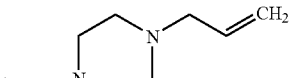 | —N(C(H)(CH₃)(CH₂CH₃))— |
| IIc-11 | 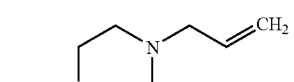 | —N(C(H)(CH₃)₂)— |
| IIc-12 | 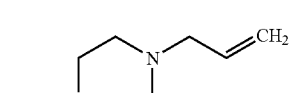 | —N(CH₂C(H)(CH₃)₂)— |
| IIc-13 | 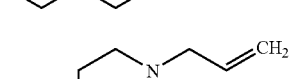 | —N(C(CH₃)₃)— |
| IIc-14 | 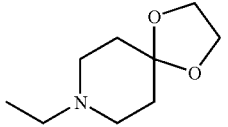 | —CH₂— |
| IIc-c14 | 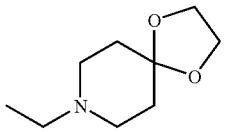 | —CH(OH)— |
| IIc-15 | 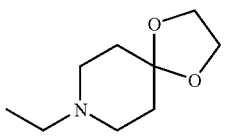 | —O— |
| IIc-16 | 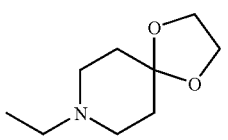 | —C(O)— |
| IIc-17 | 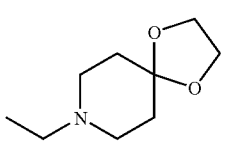 | —NH— |
| IIc-18 | 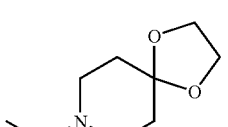 | —S— |

-continued

| Compound | —R¹ | X |
|---|---|---|
| IIc-19 | 8-ethyl-1,4-dioxa-8-azaspiro[4.5]decane | —N(CH₃)— |
| IIc-20 | 8-ethyl-1,4-dioxa-8-azaspiro[4.5]decane | —N(CH₂CH₃)— |
| IIc-21 | 8-ethyl-1,4-dioxa-8-azaspiro[4.5]decane | —N(CH₂CH₂CH₃)— |
| IIc-22 | 8-ethyl-1,4-dioxa-8-azaspiro[4.5]decane | —N(CH₂CH₂CH₂CH₃)— |
| IIc-23 | 8-ethyl-1,4-dioxa-8-azaspiro[4.5]decane | —N(C(H)(CH₃)(CH₂CH₃))— |
| IIc-24 | 8-ethyl-1,4-dioxa-8-azaspiro[4.5]decane | —N(C(H)(CH₃)₂)— |
| IIc-25 | 8-ethyl-1,4-dioxa-8-azaspiro[4.5]decane | —N(CH₂C(H)(CH₃)₂)— |
| IIc-26 | 8-ethyl-1,4-dioxa-8-azaspiro[4.5]decane | —N(C(CH₃)₃)— |
| IIc-27 | 1-(ethylamino)-1-(hydroxymethyl)cyclopentane | —CH₂— |
| IIc-c27 | 1-(ethylamino)-1-(hydroxymethyl)cyclopentane | —CH(OH)— |
| IIc-28 | 1-(ethylamino)-1-(hydroxymethyl)cyclopentane | —O— |

-continued

| Compound | —R¹ | X |
|---|---|---|
| IIc-29 | ethylamino-1-(hydroxymethyl)cyclopentyl | —C(O)— |
| IIc-30 | ethylamino-1-(hydroxymethyl)cyclopentyl | —NH— |
| IIc-31 | ethylamino-1-(hydroxymethyl)cyclopentyl | —S— |
| IIc-32 | ethylamino-1-(hydroxymethyl)cyclopentyl | —N(CH$_3$)— |
| IIc-33 | ethylamino-1-(hydroxymethyl)cyclopentyl | —N(CH$_2$CH$_3$)— |
| IIc-34 | ethylamino-1-(hydroxymethyl)cyclopentyl | —N(CH$_2$CH$_2$CH$_3$)— |
| IIc-35 | ethylamino-1-(hydroxymethyl)cyclopentyl | —N(CH$_2$CH$_2$CH$_2$CH$_3$)— |
| IIc-36 | ethylamino-1-(hydroxymethyl)cyclopentyl | —N(C(H)(CH$_3$)(CH$_2$CH$_3$))— |
| IIc-37 | ethylamino-1-(hydroxymethyl)cyclopentyl | —N(C(H)(CH$_3$)$_2$)— |
| IIc-38 | ethylamino-1-(hydroxymethyl)cyclopentyl | —N(CH$_2$C(H)(CH$_3$)$_2$)— |
| IIc-39 | ethylamino-1-(hydroxymethyl)cyclopentyl | —N(C(CH$_3$)$_3$)— |

-continued
| Compound | —R¹ | X |
|---|---|---|
| IIc-40 | 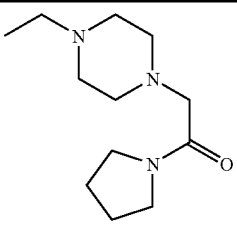 | —CH₂— |
| IIc-c40 | 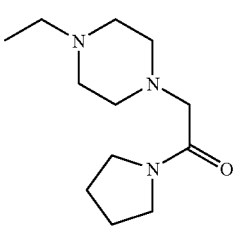 | —CH(OH)— |
| IIc-41 | 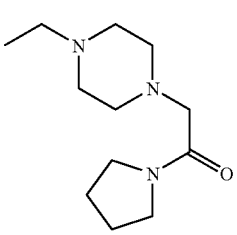 | —O— |
| IIc-42 | 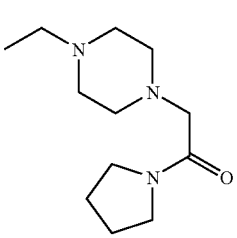 | —C(O)— |
| IIc-43 | 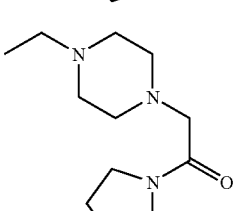 | —NH— |
| IIc-44 | 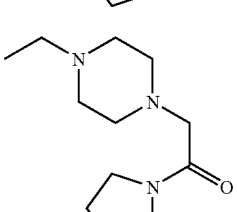 | —S— |
| IIc-45 | 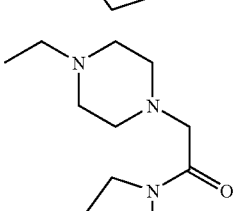 | —N(CH₃)— |

-continued
| Compound | —R¹ | X |
|---|---|---|
| IIc-46 | 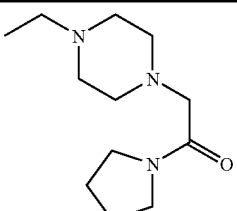 | —N(CH₂CH₃)— |
| IIc-47 | 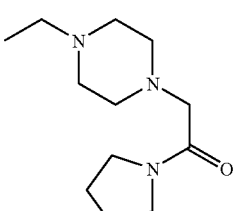 | —N(CH₂CH₂CH₃)— |
| IIc-48 | 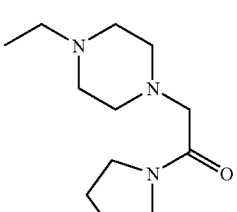 | —N(CH₂CH₂CH₂CH₃)— |
| IIc-49 | 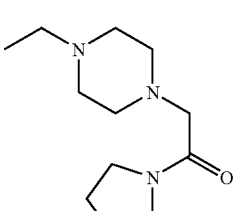 | —N(C(H)(CH₃)(CH₂CH₃))— |
| IIc-50 | 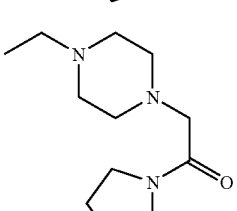 | —N(C(H)(CH₃)₂)— |
| IIc-51 | 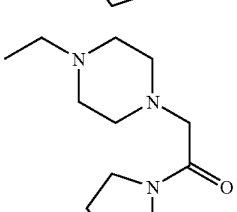 | —N(CH₂C(H)(CH₃)₂)— |
| IIc-52 | 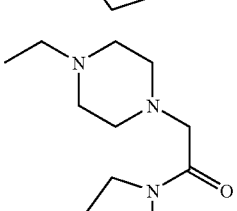 | —N(C(CH₃)₃)— |

-continued

| Compound | —R¹ | X |
|---|---|---|
| IIc-53 | N-ethyl-N-methyl-3-morpholinopropanamide | —CH₂— |
| IIc-c53 | N-ethyl-N-methyl-3-morpholinopropanamide | —CH(OH)— |
| IIc-54 | N-ethyl-N-methyl-3-morpholinopropanamide | —O— |
| IIc-55 | N-ethyl-N-methyl-3-morpholinopropanamide | —C(O)— |
| IIc-56 | N-ethyl-N-methyl-3-morpholinopropanamide | —NH— |
| IIc-57 | N-ethyl-N-methyl-3-morpholinopropanamide | —S— |
| IIc-58 | N-ethyl-N-methyl-3-morpholinopropanamide | —N(CH₃)— |
| IIc-59 | N-ethyl-N-methyl-3-morpholinopropanamide | —N(CH₂CH₃)— |
| IIc-60 | N-ethyl-N-methyl-3-morpholinopropanamide | —N(CH₂CH₂CH₃)— |
| IIc-61 | N-ethyl-N-methyl-3-morpholinopropanamide | —N(CH₂CH₂CH₂CH₃)— |
| IIc-62 | N-ethyl-N-methyl-3-morpholinopropanamide | —N(C(H)(CH₃)(CH₂CH₃))— |

-continued

| Compound | —R¹ | X |
|---|---|---|
| IIc-63 | *N-ethyl-N-methyl-3-morpholinopropanamide* | —N(C(H)(CH₃)₂)— |
| IIc-64 | *N-ethyl-N-methyl-3-morpholinopropanamide* | —N(CH₂C(H)(CH₃)₂)— |
| IIc-65 | *N-ethyl-N-methyl-3-morpholinopropanamide* | —N(C(CH₃)₃)— |
| IIc-66 | *3-(4-ethylpiperazin-1-yl)propanenitrile* | —CH₂— |
| IIc-c66 | *3-(4-ethylpiperazin-1-yl)propanenitrile* | —CH(OH)— |
| IIc-67 | *3-(4-ethylpiperazin-1-yl)propanenitrile* | —O— |
| IIc-68 | *3-(4-ethylpiperazin-1-yl)propanenitrile* | —C(O)— |
| IIc-69 | *3-(4-ethylpiperazin-1-yl)propanenitrile* | —NH— |
| IIc-70 | *3-(4-ethylpiperazin-1-yl)propanenitrile* | —S— |
| IIc-71 | *3-(4-ethylpiperazin-1-yl)propanenitrile* | —N(CH₃)— |
| IIc-72 | *3-(4-ethylpiperazin-1-yl)propanenitrile* | —N(CH₂CH₃)— |
| IIc-73 | *3-(4-ethylpiperazin-1-yl)propanenitrile* | —N(CH₂CH₂CH₃)— |

-continued

| Compound | —R¹ | X |
|---|---|---|
| IIc-74 | 4-ethylpiperazinyl with N-CH2CH2CN | —N(CH₂CH₂CH₂CH₃)— |
| IIc-75 | 4-ethylpiperazinyl with N-CH2CH2CN | —N(C(H)(CH₃)(CH₂CH₃))— |
| IIc-76 | 4-ethylpiperazinyl with N-CH2CH2CN | —N(C(H)(CH₃)₂)— |
| IIc-77 | 4-ethylpiperazinyl with N-CH2CH2CN | —N(CH₂C(H)(CH₃)₂)— |
| IIc-78 | 4-ethylpiperazinyl with N-CH2CH2CN | —N(C(CH₃)₃)— |
| IIc-79 | N-ethyl-N-cyclopropyl-1-tBOC-piperidin-4-yl amine | —CH₂— |
| IIc-c79 | N-ethyl-N-cyclopropyl-1-tBOC-piperidin-4-yl amine | —CH(OH)— |
| IIc-80 | N-ethyl-N-cyclopropyl-1-tBOC-piperidin-4-yl amine | —O— |
| IIc-81 | N-ethyl-N-cyclopropyl-1-tBOC-piperidin-4-yl amine | —C(O)— |

-continued

| Compound | —R¹ | X |
|---|---|---|
| IIc-82 | N-ethyl-N-cyclopropyl-piperidine-4-yl (N-tBOC) | —NH— |
| IIc-83 | N-ethyl-N-cyclopropyl-piperidine-4-yl (N-tBOC) | —S— |
| IIc-84 | N-ethyl-N-cyclopropyl-piperidine-4-yl (N-tBOC) | —N(CH₃)— |
| IIc-85 | N-ethyl-N-cyclopropyl-piperidine-4-yl (N-tBOC) | —N(CH₂CH₃)— |
| IIc-86 | N-ethyl-N-cyclopropyl-piperidine-4-yl (N-tBOC) | —N(CH₂CH₂CH₃)— |
| IIc-87 | N-ethyl-N-cyclopropyl-piperidine-4-yl (N-tBOC) | —N(CH₂CH₂CH₂CH₃)— |

-continued
| Compound | —R¹ | X |
|---|---|---|
| IIc-88 | 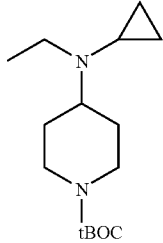 | —N(C(H)(CH₃)(CH₂CH₃))— |
| IIc-89 | 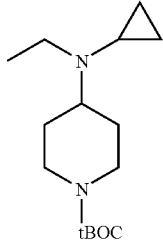 | —N(C(H)(CH₃)₂)— |
| IIc-90 | 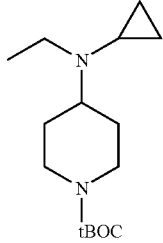 | —N(CH₂C(H)(CH₃)₂)— |
| IIc-91 | 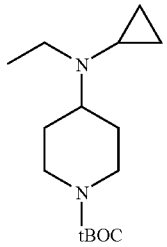 | —N(C(CH₃)₃)— |
| IIc-92 | 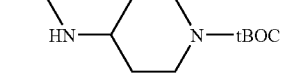 | —CH₂— |
| IIc-c92 | 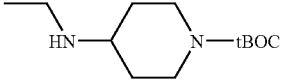 | —CH(OH)— |
| IIc-93 | 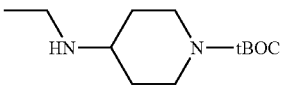 | —O— |
| IIc-94 | 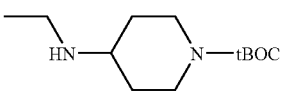 | —C(O)— |
| IIc-95 | 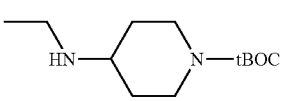 | —NH— |

-continued

| Compound | —R¹ | X |
|---|---|---|
| IIc-96 | HN-(ethyl)-piperidine-N-tBOC | —S— |
| IIc-97 | HN-(ethyl)-piperidine-N-tBOC | —N(CH$_3$)— |
| IIc-98 | HN-(ethyl)-piperidine-N-tBOC | —N(CH$_2$CH$_3$)— |
| IIc-99 | HN-(ethyl)-piperidine-N-tBOC | —N(CH$_2$CH$_2$CH$_3$)— |
| IIc-100 | HN-(ethyl)-piperidine-N-tBOC | —N(CH$_2$CH$_2$CH$_2$CH$_3$)— |
| IIc-101 | HN-(ethyl)-piperidine-N-tBOC | —N(C(H)(CH$_3$)(CH$_2$CH$_3$))— |
| IIc-102 | HN-(ethyl)-piperidine-N-tBOC | —N(C(H)(CH$_3$)$_2$)— |
| IIc-103 | HN-(ethyl)-piperidine-N-tBOC | —N(CH$_2$C(H)(CH$_3$)$_2$)— |
| IIc-104 | HN-(ethyl)-piperidine-N-tBOC | —N(C(CH$_3$)$_3$)— |
| IIc-105 | 4-ethyl-piperazine-1-propanoyl | —CH$_2$— |
| IIc-c105 | 4-ethyl-piperazine-1-propanoyl | —CH(OH)— |
| IIc-106 | 4-ethyl-piperazine-1-propanoyl | —O— |
| IIc-107 | 4-ethyl-piperazine-1-propanoyl | —C(O)— |

-continued
| Compound | —R¹ | X |
|---|---|---|
| IIc-108 | 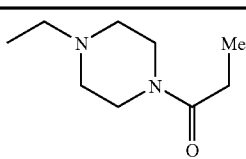 | —NH— |
| IIc-109 | 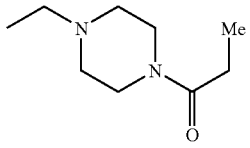 | —S— |
| IIc-110 | 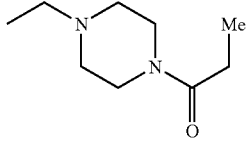 | —N(CH₃)— |
| IIc-111 | 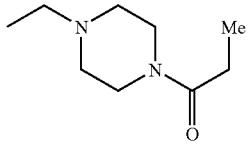 | —N(CH₂CH₃)— |
| IIc-112 | 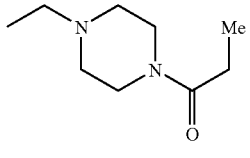 | —N(CH₂CH₂CH₃)— |
| IIc-113 | 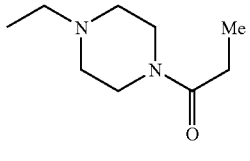 | —N(CH₂CH₂CH₂CH₃)— |
| IIc-114 | 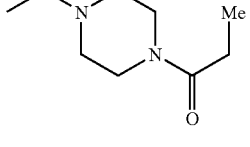 | —N(C(H)(CH₃)(CH₂CH₃))— |
| IIc-115 | 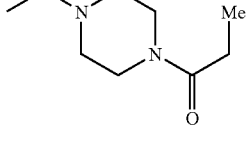 | —N(C(H)(CH₃)₂)— |
| IIc-116 | 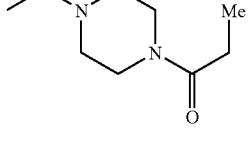 | —N(CH₂C(H)(CH₃)₂)— |
| IIc-117 | 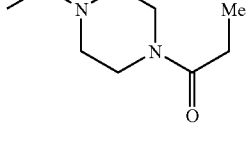 | —N(C(CH₃)₃)— |

| Compound | —R¹ | X |
|---|---|---|
| IIc-118 | 4-ethyl-1,4-diazepane with N-C(O)-Et acyl group | —CH₂— |
| IIc-c118 | 4-ethyl-1,4-diazepane with N-C(O)-Et acyl group | —CH(OH)— |
| IIc-119 | 4-ethyl-1,4-diazepane with N-C(O)-Et acyl group | —O— |
| IIc-120 | 4-ethyl-1,4-diazepane with N-C(O)-Et acyl group | —C(O)— |
| IIc-121 | 4-ethyl-1,4-diazepane with N-C(O)-Et acyl group | —NH— |
| IIc-122 | 4-ethyl-1,4-diazepane with N-C(O)-Et acyl group | —S— |
| IIc-123 | 4-ethyl-1,4-diazepane with N-C(O)-Et acyl group | —N(CH₃)— |
| IIc-124 | 4-ethyl-1,4-diazepane with N-C(O)-Et acyl group | —N(CH₂CH₃)— |

| Compound | —R¹ | X |
|---|---|---|
| IIc-125 | (4-ethyl-1,4-diazepan-1-yl with propionyl on N) | —N(CH₂CH₂CH₃)— |
| IIc-126 | (4-ethyl-1,4-diazepan-1-yl with propionyl on N) | —N(CH₂CH₂CH₂CH₃)— |
| IIc-127 | (4-ethyl-1,4-diazepan-1-yl with propionyl on N) | —N(C(H)(CH₃)(CH₂CH₃))— |
| IIc-128 | (4-ethyl-1,4-diazepan-1-yl with propionyl on N) | —N(C(H)(CH₃)₂)— |
| IIc-129 | (4-ethyl-1,4-diazepan-1-yl with propionyl on N) | —N(CH₂C(H)(CH₃)₂)— |
| IIc-130 | (4-ethyl-1,4-diazepan-1-yl with propionyl on N) | —N(C(CH₃)₃)— |
| IIc-131 | (4-ethyl-piperazinyl-CH₂-tetrahydrofuran-2-yl) | —CH₂— |
| IIc-c131 | (4-ethyl-piperazinyl-CH₂-tetrahydrofuran-2-yl) | —CH(OH)— |
| IIc-132 | (4-ethyl-piperazinyl-CH₂-tetrahydrofuran-2-yl) | —O— |
| IIc-133 | (4-ethyl-piperazinyl-CH₂-tetrahydrofuran-2-yl) | —C(O)— |

-continued

| Compound | —R¹ | X |
|---|---|---|
| IIc-134 | ethyl-piperazine-CH₂-tetrahydrofuran | —NH— |
| IIc-135 | ethyl-piperazine-CH₂-tetrahydrofuran | —S— |
| IIc-136 | ethyl-piperazine-CH₂-tetrahydrofuran | —N(CH$_3$)— |
| IIc-137 | ethyl-piperazine-CH₂-tetrahydrofuran | —N(CH$_2$CH$_3$)— |
| IIc-138 | ethyl-piperazine-CH₂-tetrahydrofuran | —N(CH$_2$CH$_2$CH$_3$)— |
| IIc-139 | ethyl-piperazine-CH₂-tetrahydrofuran | —N(CH$_2$CH$_2$CH$_2$CH$_3$)— |
| IIc-140 | ethyl-piperazine-CH₂-tetrahydrofuran | —N(C(H)(CH$_3$)(CH$_2$CH$_3$))— |
| IIc-141 | ethyl-piperazine-CH₂-tetrahydrofuran | —N(C(H)(CH$_3$)$_2$)— |
| IIc-142 | ethyl-piperazine-CH₂-tetrahydrofuran | —N(CH$_2$C(H)(CH$_3$)$_2$)— |
| IIc-143 | ethyl-piperazine-CH₂-tetrahydrofuran | —N(C(CH$_3$)$_3$)— |
| IIc-144 | ethyl-piperazine-CH₂-CH(OMe)$_2$ | —CH$_2$— |
| IIc-c144 | ethyl-piperazine-CH₂-CH(OMe)$_2$ | —CH(OH)— |
| IIc-145 | ethyl-piperazine-CH₂-CH(OMe)$_2$ | —O— |
| IIc-146 | ethyl-piperazine-CH₂-CH(OMe)$_2$ | —C(O)— |

-continued

| Compound | —R¹ | X |
|---|---|---|
| IIc-147 | ethylpiperazine-CH₂-CH(OMe)₂ | —NH— |
| IIc-148 | ethylpiperazine-CH₂-CH(OMe)₂ | —S— |
| IIc-149 | ethylpiperazine-CH₂-CH(OMe)₂ | —N(CH₃)— |
| IIc-150 | ethylpiperazine-CH₂-CH(OMe)₂ | —N(CH₂CH₃)— |
| IIc-151 | ethylpiperazine-CH₂-CH(OMe)₂ | —N(CH₂CH₂CH₃)— |
| IIc-152 | ethylpiperazine-CH₂-CH(OMe)₂ | —N(CH₂CH₂CH₂CH₃)— |
| IIc-153 | ethylpiperazine-CH₂-CH(OMe)₂ | —N(C(H)(CH₃)(CH₂CH₃))— |
| IIc-154 | ethylpiperazine-CH₂-CH(OMe)₂ | —N(C(H)(CH₃)₂)— |
| IIc-155 | ethylpiperazine-CH₂-CH(OMe)₂ | —N(CH₂C(H)(CH₃)₂)— |
| IIc-156 | ethylpiperazine-CH₂-CH(OMe)₂ | —N(C(CH₃)₃)— |
| IIc-157 | ethylpiperazine-CH₂-C(O)-pyrrolidine | —CH₂— |
| IIc-c157 | ethylpiperazine-CH₂-C(O)-pyrrolidine | —CH(OH)— |

-continued

| Compound | —R¹ | X |
|---|---|---|
| IIc-158 | ethyl-piperazine-CH₂-C(O)-pyrrolidine | —O— |
| IIc-159 | ethyl-piperazine-CH₂-C(O)-pyrrolidine | —C(O)— |
| IIc-160 | ethyl-piperazine-CH₂-C(O)-pyrrolidine | —NH— |
| IIc-161 | ethyl-piperazine-CH₂-C(O)-pyrrolidine | —S— |
| IIc-162 | ethyl-piperazine-CH₂-C(O)-pyrrolidine | —N(CH$_3$)— |
| IIc-163 | ethyl-piperazine-CH₂-C(O)-pyrrolidine | —N(CH$_2$CH$_3$)— |
| IIc-164 | ethyl-piperazine-CH₂-C(O)-pyrrolidine | —N(CH$_2$CH$_2$CH$_3$)— |
| IIc-165 | ethyl-piperazine-CH₂-C(O)-pyrrolidine | —N(CH$_2$CH$_2$CH$_2$CH$_3$)— |
| IIc-166 | ethyl-piperazine-CH₂-C(O)-pyrrolidine | —N(C(H)(CH$_3$)(CH$_2$CH$_3$))— |

| Compound | —R¹ | X |
|---|---|---|
| IIc-167 | (4-ethylpiperazinyl)-CH₂-C(O)-pyrrolidinyl | —N(C(H)(CH₃)₂)— |
| IIc-168 | (4-ethylpiperazinyl)-CH₂-C(O)-pyrrolidinyl | —N(CH₂C(H)(CH₃)₂)— |
| IIc-169 | (4-ethylpiperazinyl)-CH₂-C(O)-pyrrolidinyl | —N(C(CH₃)₃)— |
| IIc-170 | (4-ethylpiperazinyl)-CH₂-C(O)-cyclopropyl | —CH₂— |
| IIc-c170 | (4-ethylpiperazinyl)-CH₂-C(O)-cyclopropyl | —CH(OH)— |
| IIc-171 | (4-ethylpiperazinyl)-CH₂-C(O)-cyclopropyl | —O— |
| IIc-172 | (4-ethylpiperazinyl)-CH₂-C(O)-cyclopropyl | —C(O)— |
| IIc-173 | (4-ethylpiperazinyl)-CH₂-C(O)-cyclopropyl | —NH— |
| IIc-174 | (4-ethylpiperazinyl)-CH₂-C(O)-cyclopropyl | —S— |
| IIc-175 | (4-ethylpiperazinyl)-CH₂-C(O)-cyclopropyl | —N(CH₃)— |

-continued

| Compound | —R¹ | X |
|---|---|---|
| IIc-176 | 4-ethylpiperazin-1-yl-CH₂-C(O)-cyclopropyl | —N(CH₂CH₃)— |
| IIc-177 | 4-ethylpiperazin-1-yl-CH₂-C(O)-cyclopropyl | —N(CH₂CH₂CH₃)— |
| IIc-178 | 4-ethylpiperazin-1-yl-CH₂-C(O)-cyclopropyl | —N(CH₂CH₂CH₂CH₃)— |
| IIc-179 | 4-ethylpiperazin-1-yl-CH₂-C(O)-cyclopropyl | —N(C(H)(CH₃)(CH₂CH₃))— |
| IIc-180 | 4-ethylpiperazin-1-yl-CH₂-C(O)-cyclopropyl | —N(C(H)(CH₃)₂)— |
| IIc-181 | 4-ethylpiperazin-1-yl-CH₂-C(O)-cyclopropyl | —N(CH₂C(H)(CH₃)₂)— |
| IIc-182 | 4-ethylpiperazin-1-yl-CH₂-C(O)-cyclopropyl | —N(C(CH₃)₃)— |
| IIc-183 | 4-ethyl-1-(octyl)piperazine | —CH₂— |
| IIc-c183 | 4-ethyl-1-(octyl)piperazine | —CH(OH)— |
| IIc-184 | 4-ethyl-1-(octyl)piperazine | —O— |
| IIc-185 | 4-ethyl-1-(octyl)piperazine | —C(O)— |
| IIc-186 | 4-ethyl-1-(octyl)piperazine | —NH— |

-continued
| Compound | —R¹ | X |
|---|---|---|
| IIc-187 | 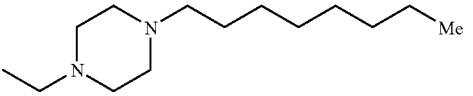 | —S— |
| IIc-188 | 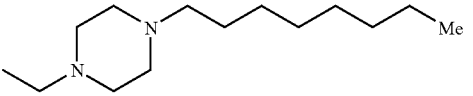 | —N(CH₃)— |
| IIc-189 | 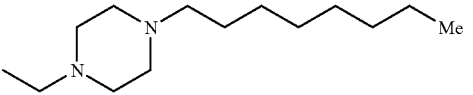 | —N(CH₂CH₃)— |
| IIc-190 | 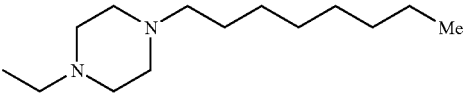 | —N(CH₂CH₂CH₃)— |
| IIc-191 | 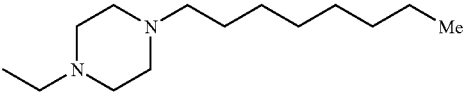 | —N(CH₂CH₂CH₂CH₃)— |
| IIc-192 | 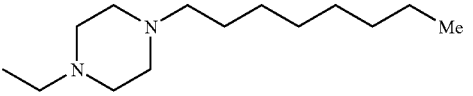 | —N(C(H)(CH₃)(CH₂CH₃))— |
| IIc-193 | 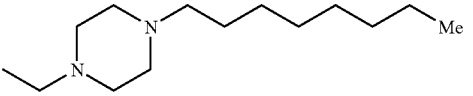 | —N(C(H)(CH₃)₂)— |
| IIc-194 | 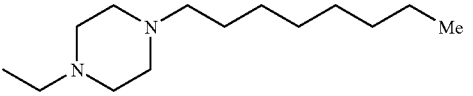 | —N(CH₂C(H)(CH₃)₂)— |
| IIc-195 | 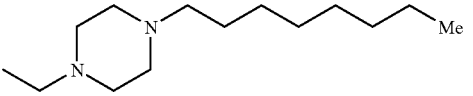 | —N(C(CH₃)₃)— |
| IIc-196 | 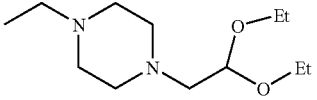 | —CH₂— |
| IIc-197 | 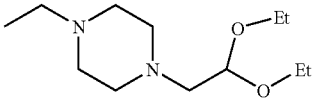 | —CH(OH)— |
| IIc-198 | 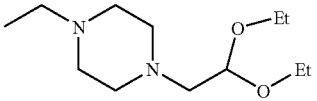 | —O— |
| IIc-199 | 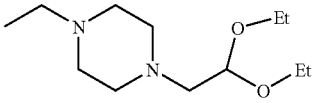 | —C(O)— |
| IIc-200 | 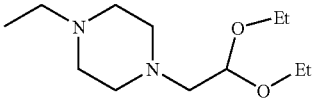 | —NH— |

-continued

| Compound | —R¹ | X |
|---|---|---|
| IIc-201 | 4-ethylpiperazin-1-yl-CH₂-CH(OEt)₂ | —S— |
| IIc-202 | 4-ethylpiperazin-1-yl-CH₂-CH(OEt)₂ | —N(CH₃)— |
| IIc-203 | 4-ethylpiperazin-1-yl-CH₂-CH(OEt)₂ | —N(CH₂CH₃)— |
| IIc-204 | 4-ethylpiperazin-1-yl-CH₂-CH(OEt)₂ | —N(CH₂CH₂CH₃)— |
| IIc-205 | 4-ethylpiperazin-1-yl-CH₂-CH(OEt)₂ | —N(CH₂CH₂CH₂CH₃)— |
| IIc-206 | 4-ethylpiperazin-1-yl-CH₂-CH(OEt)₂ | —N(C(H)(CH₃)(CH₂CH₃))— |
| IIc-207 | 4-ethylpiperazin-1-yl-CH₂-CH(OEt)₂ | —N(C(H)(CH₃)₂)— |
| IIc-208 | 4-ethylpiperazin-1-yl-CH₂-CH(OEt)₂ | —N(CH₂C(H)(CH₃)₂)— |
| IIc-209 | 4-ethylpiperazin-1-yl-CH₂-CH(OEt)₂ | —N(C(CH₃)₃)— | and pharmaceutically acceptable salts thereof.

5.8 The Indenoisoquinolinone Analogs of Formula (IIIa)
The present invention provides the following Indenoisoquinolinone Analogs according to Formula (IIIa) as set forth below:
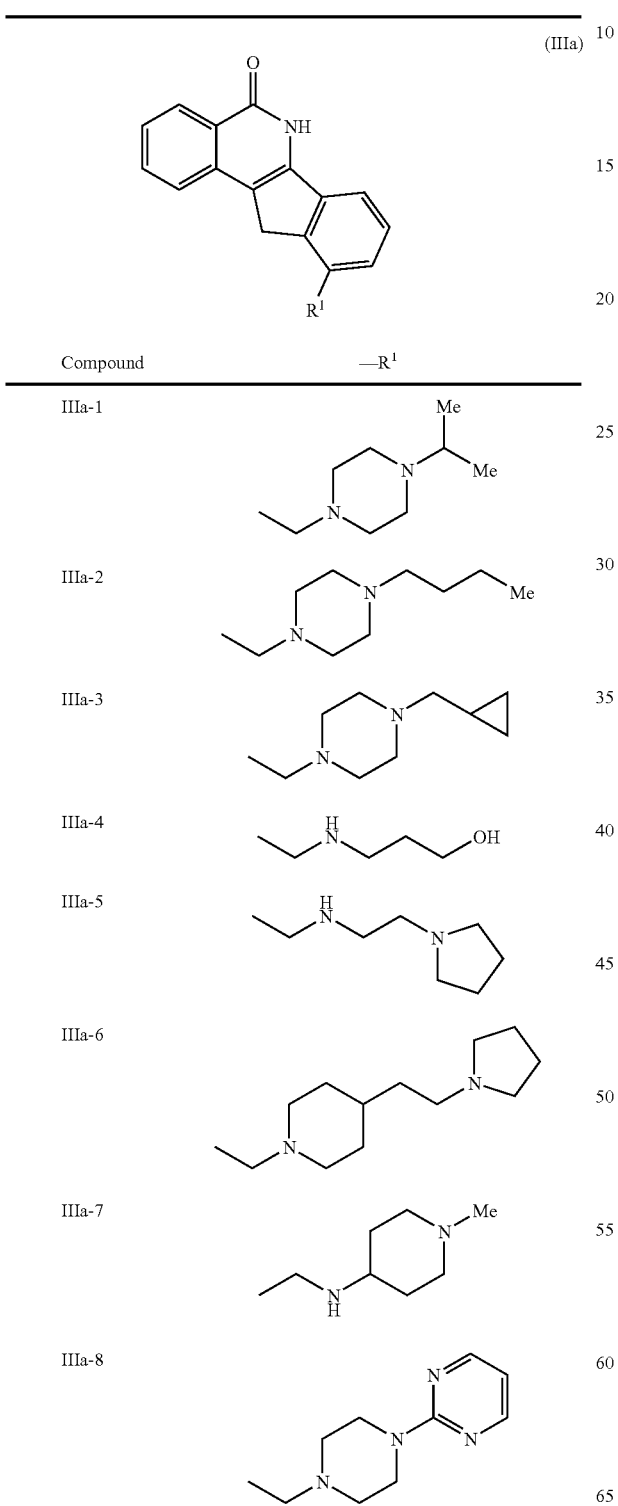
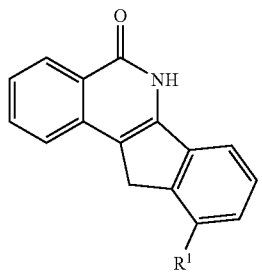
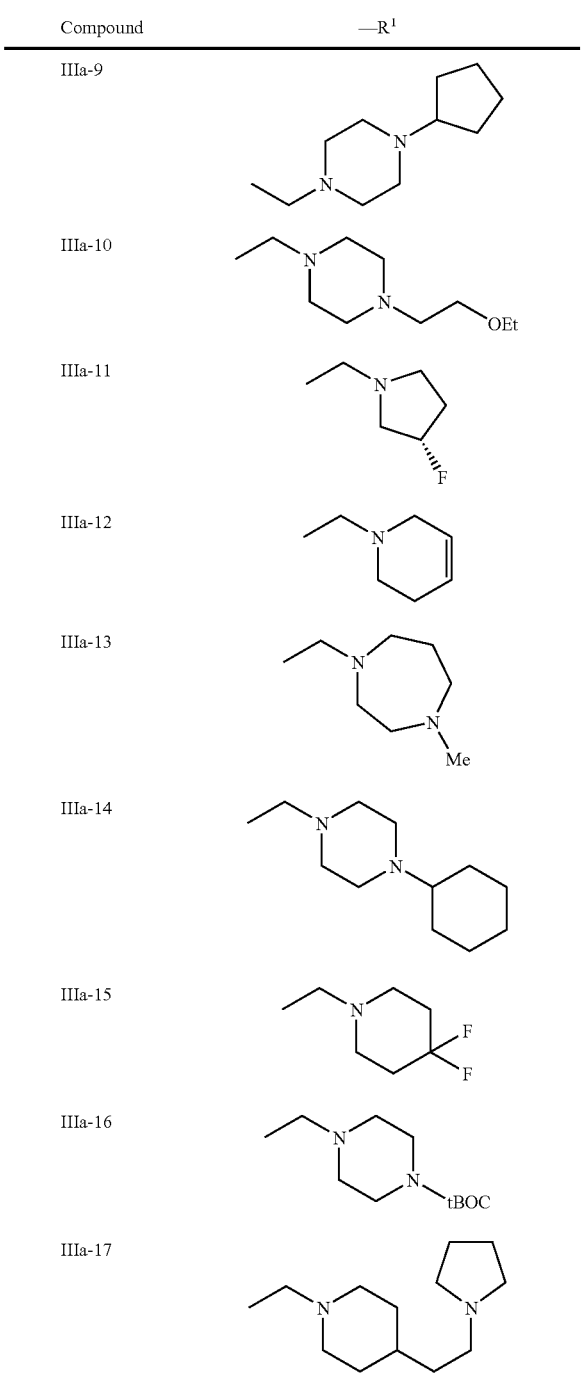

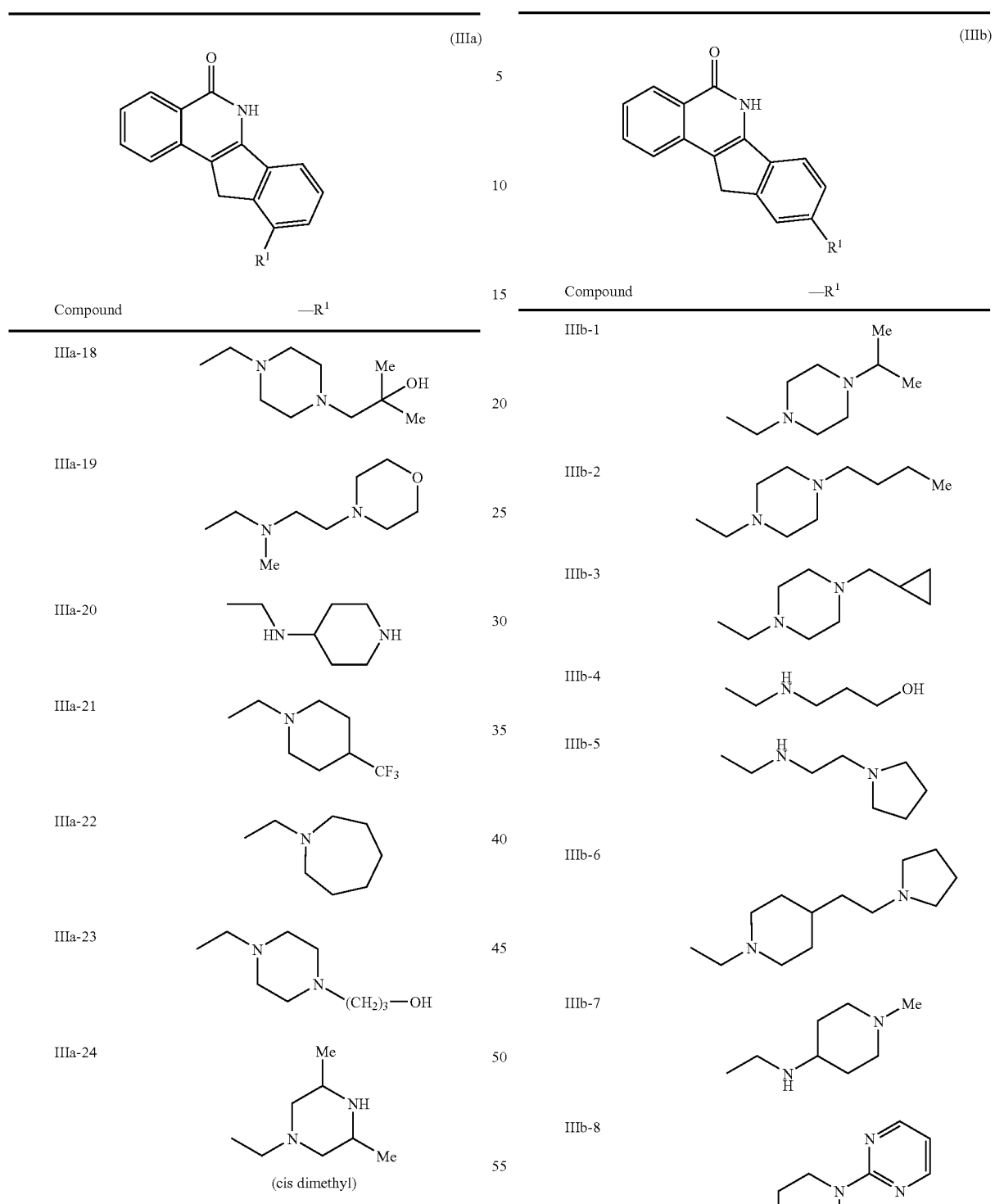
and pharmaceutically acceptable salts thereof.
5.9 The Indenoisoquinolinone Analogs of Formula (IIIb)
The present invention provides the following Indenoisoquinolinone Analogs according to Formula (IIIb) as set forth below:

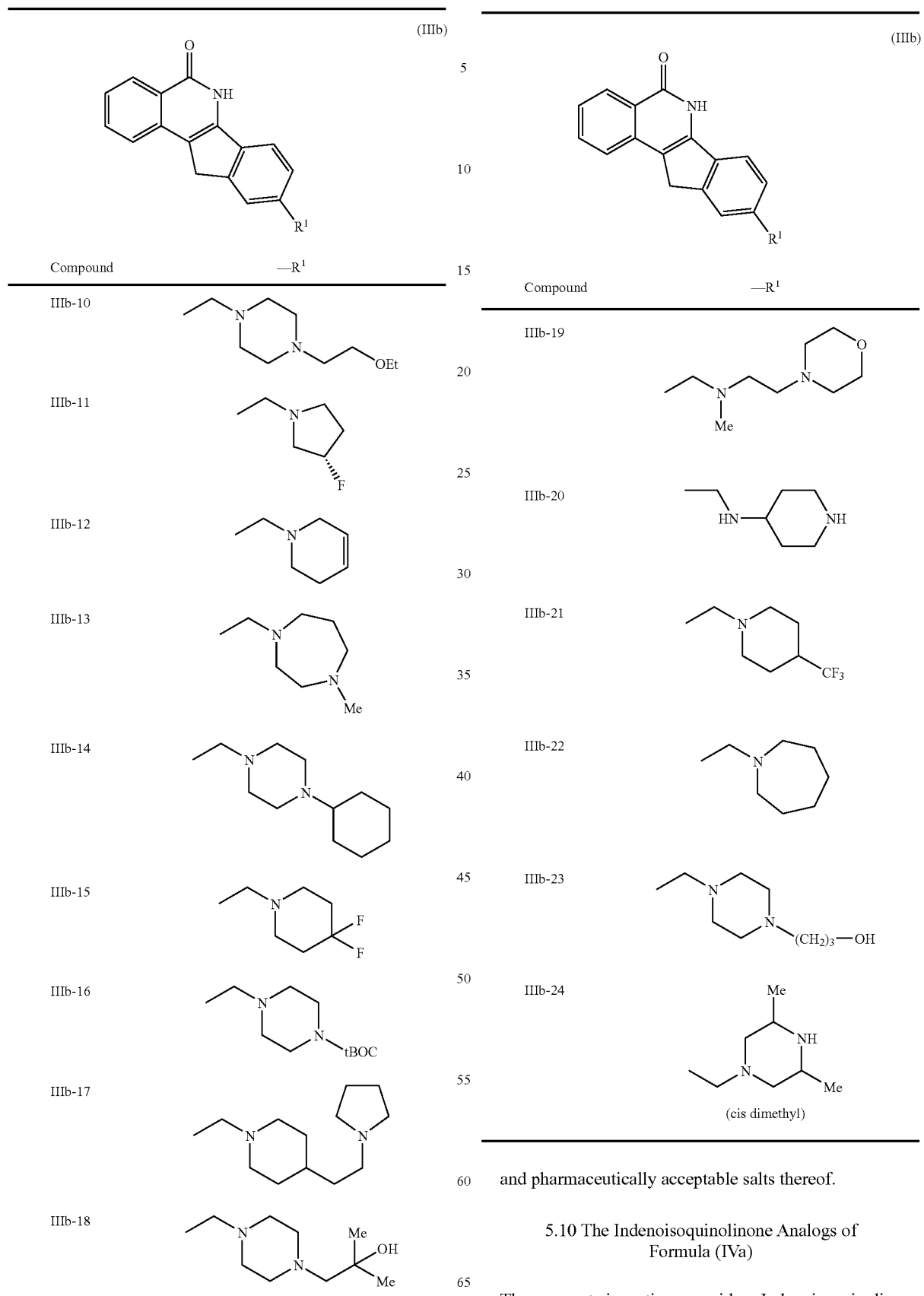
and pharmaceutically acceptable salts thereof.
5.10 The Indenoisoquinolinone Analogs of Formula (IVa)
The present invention provides Indenoisoquinolinone Analogs according to Formula (IVa), below:

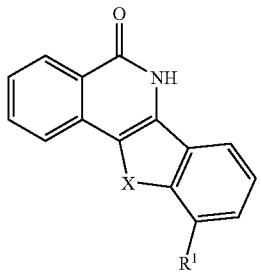
(IVa)

and pharmaceutically acceptable salts thereof,
wherein X and $R^1$ are as defined above for the Indenoisoquinolinone Analogs of Formula (IVa).

In one embodiment, X is —N($CH_3$)—. In another embodiment, X is —N($CH_2CH_3$)—. In another embodiment, X is —N($CH_2CH_2CH_3$)—. In another embodiment, X is —N($CH_2CH_2CH_2CH_3$)—. In another embodiment, X is —N(C(H)($CH_3$)($CH_2CH_3$))—. In another embodiment, X is —N(C(H)($CH_3$)$_2$)—. In another embodiment, X is —N($CH_2$C(H)($CH_3$)$_2$)—. In another embodiment, X is —N(C($CH_3$)$_3$)—.

In one embodiment, X is —O—. In one embodiment, X is —$CH_2$—. In one embodiment, X is —C(O)—. In one embodiment, X is —NH—. In one embodiment, X is —S—. In one embodiment, X is —CH(OH)—.

In one embodiment, each $C_1$-$C_3$ alkyl is independent of the other $C_1$-$C_3$ alkyl.

In one embodiment, each $C_1$-$C_3$ alkyl is methyl.

In one embodiment, each $C_1$-$C_3$ alkyl is methyl and X is —$CH_2$—.

In one embodiment, each $C_1$-$C_3$ alkyl is methyl and X is —CH(OH)—.

In one embodiment, each $C_1$-$C_3$ alkyl is methyl, X is —$CH_2$— and n is 1.

In one embodiment, each $C_1$-$C_3$ alkyl is methyl, X is —CH(OH)— and n is 1.

In another embodiment, X is —CH(OH)— and n is 1.
In another embodiment, X is —N(C(O)N(H)—($CH_2$)$_p$—Z)—.
In another embodiment, X is —N(C(O)N(H)—($CH_2$)—Z)—.
In another embodiment, X is —N(C(O)N(H)—($CH_2$)$_2$—Z)—.
In another embodiment, X is —N(C(O)N(H)—($CH_2$)$_p$—Z)— and n is 1.
In yet another embodiment, X is —N(C(O)N(H)—($CH_2$)$_2$—Z)— and n is 2.
In still another embodiment, X is —N(C(O)N(H)—($CH_2$)—Z)— and n is 1.
In one embodiment, X is —N(($CH_2$)$_q$—Z)—.
In another embodiment, X is —N(($CH_2$)—Z)—.
In another embodiment, X is —N(($CH_2$)$_2$—Z)—.
In another embodiment, X is —N(($CH_2$)$_q$—Z)— and n is 1.
In yet another embodiment, X is —N(($CH_2$)$_q$—Z)— and n is 2.
In still another embodiment, X is —N(($CH_2$)—Z)— and n is 1.
In still another embodiment, X is —N(($CH_2$)—Z)— and n is 2.
In one embodiment, Z is —$CF_3$.
In another embodiment, Z is —F.
In yet another embodiment, Z is —OH.
In still another embodiment, Z is —O—$CH_3$.
In another embodiment, X is —N(C(O)N(H)—($CH_2$)$_p$—OH)—.
In another embodiment, X is —N(C(O)N(H)—($CH_2$)$_2$—OH)—.
In another embodiment, X is —N(C(O)N(H)—($CH_2$)$_p$—OH)— and n is 1.
In yet another embodiment, X is —N(C(O)N(H)—($CH_2$)$_p$—OH)— and n is 2.
In still another embodiment, X is —N(C(O)N(H)—($CH_2$)$_2$—OH)— and n is 1.
In still another embodiment, X is —N(C(O)N(H)—($CH_2$)$_2$—OH)— and n is 2.
In one embodiment, X is —N(($CH_2$)$_q$—OH)—.
In another embodiment, X is —N(($CH_2$)$_2$—OH)—.
In another embodiment, X is —N(($CH_2$)$_q$—OH)— and n is 1.
In yet another embodiment, X is —N(($CH_2$)$_q$—OH)— and n is 2.
In still another embodiment, X is —N(($CH_2$)$_2$—OH)— and n is 1.
In another embodiment, X is —N(C(O)N(H)—($CH_2$)$_p$—F)—.
In another embodiment, X is —N(C(O)N(H)—($CH_2$)—F)—.
In another embodiment, X is —N(C(O)N(H)—($CH_2$)$_p$—F)— and n is 1.
In yet another embodiment, X is —N(C(O)N(H)—($CH_2$)$_p$—F)— n is 2.
In still another embodiment, X is —N(C(O)N(H)—($CH_2$)—F)— and n is 1.
In one embodiment, X is —N(($CH_2$)$_q$—F)—.
In another embodiment, X is —N(($CH_2$)—F)—.
In another embodiment, X is —N(($CH_2$)$_q$—F)— and n is 1.
In yet another embodiment, X is —N(($CH_2$)$_q$—F)— and n is 2.
In still another embodiment, X is —N(($CH_2$)—F)— and n is 1.
In another embodiment, X is —N(C(O)N(H)—($CH_2$)$_p$—OMe)-.
In another embodiment, X is —N(C(O)N(H)—($CH_2$)$_2$—OMe)-.
In another embodiment, X is —N(C(O)N(H)—($CH_2$)$_p$—OMe)- and n is 1.
In yet another embodiment, X is —N(C(O)N(H)—($CH_2$)$_p$—OMe)- and n is 2.
In still another embodiment, X is —N(C(O)N(H)—($CH_2$)$_2$—OMe)- and n is 1.
In one embodiment, X is —N(($CH_2$)$_q$—OMe)-.
In another embodiment, X is —N(($CH_2$)$_2$—OMe)-.
In another embodiment, X is —N(($CH_2$)$_q$—OMe)- and n is 1.
In yet another embodiment, X is —N(($CH_2$)$_q$—OMe)- and n is 2.
In still another embodiment, X is —N(($CH_2$)$_2$—OMe)- and n is 1.
In another embodiment, X is —N(C(O)N(H)—($CH_2$)$_p$—$CF_3$)—.
In another embodiment, X is —N(C(O)N(H)—($CH_2$)—$CF_3$)—.
In another embodiment, X is —N(C(O)N(H)—($CH_2$)$_p$—$CF_3$)— and n is 1.
In yet another embodiment, X is —N(C(O)N(H)—($CH_2$)$_p$—$CF_3$)— and n is 2.
In still another embodiment, X is —N(C(O)N(H)—($CH_2$)—$CF_3$)— and n is 1.
In one embodiment, X is —N(($CH_2$)$_q$—$CF_3$)—.

In another embodiment, X is —N((CH$_2$)—CF$_3$)—.
In another embodiment, X is —N((CH$_2$)$_q$—CF$_3$)— and n is 1.
In yet another embodiment, X is —N((CH$_2$)$_q$—CF$_3$)— and n is 2.
In still another embodiment, X is —N((CH$_2$)—CF$_3$)— and n is 1.
In another embodiment, X is —N(C(O)N(H)—(CH$_2$)$_p$—CF$_3$)—.
In another embodiment, X is —N(C(O)N(H)—(CH$_2$)—CF$_3$)—.
In another embodiment, X is —N(C(O)N(H)—(CH$_2$)$_p$—CF$_3$)— and n is 1.
In yet another embodiment, X is —N(C(O)N(H)—(CH$_2$)$_p$—CF$_3$)— and n is 2.
In still another embodiment, X is —N(C(O)N(H)—(CH$_2$)—CF$_3$)— and n is 1.
In one embodiment, X is —N((CH$_2$)$_q$—CF$_3$)—.
In another embodiment, X is —N((CH$_2$)—CF$_3$)—.
In another embodiment, X is —N((CH$_2$)$_q$—CF$_3$)— and n is 1.
In yet another embodiment, X is —N((CH$_2$)$_q$—CF$_3$)— and n is 2.
In still another embodiment, X is —N((CH$_2$)—CF$_3$)— and n is 1.
In one embodiment, n is 1.
In another embodiment, n is 2.
In yet another embodiment, n is 3.
In a further embodiment, n is 4, 5, or 6.
In yet a further embodiment, n is 7, 8, or 9.
In still a further embodiment, n is 10.
In one embodiment, p is 1.
In another embodiment, p is 2.
In yet another embodiment, p is an integer ranging from 2 to 5.
In one embodiment, q is 1.
In another embodiment, q is 2.
In yet another embodiment, q is an integer ranging from 2 to 5.
In one embodiment, n is 1 and X is —N(CH$_3$)—.
In another embodiment, n is 1 and X is —N(CH$_2$CH$_3$).
In another embodiment, n is 1 and X is —N(CH$_2$CH$_2$CH$_3$)—.
In another embodiment, n is 1 and X is —N(CH$_2$CH$_2$CH$_2$CH$_3$)—.
In another embodiment, n is 1 and X is —N(C(H)(CH$_3$)(CH$_2$CH$_3$))—.
In another embodiment, n is 1 and X is —N(C(H)(CH$_3$)$_2$)—.
In another embodiment, n is 1 and X is —N(CH$_2$C(H)(CH$_3$)$_2$)—.
In another embodiment, n is 1 and X is —N(C(CH$_3$)$_3$)—.
In one embodiment, one R$^2$ is —H, and the other R$^2$ is —C$_1$-C$_6$ alkyl.
In another embodiment, each R$^2$ is —C$_1$-C$_6$ alkyl.
In another embodiment, each R$^2$ is -methyl.
In various embodiments, —N(R$^2$)(R$^2$) is:

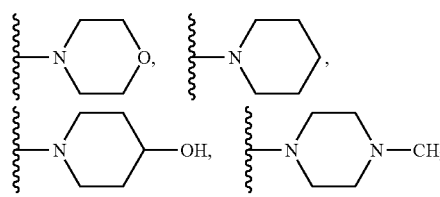

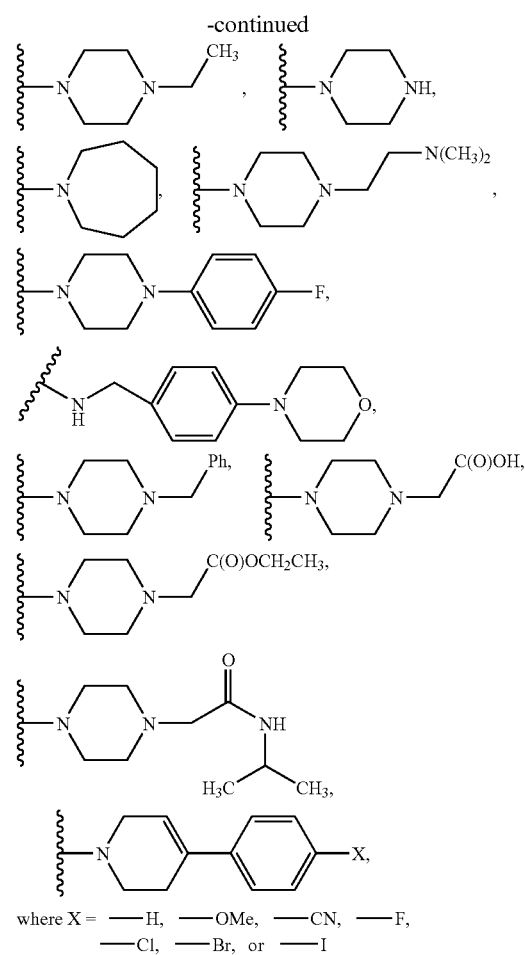

where X = —H, —OMe, —CN, —F, —Cl, —Br, or —I

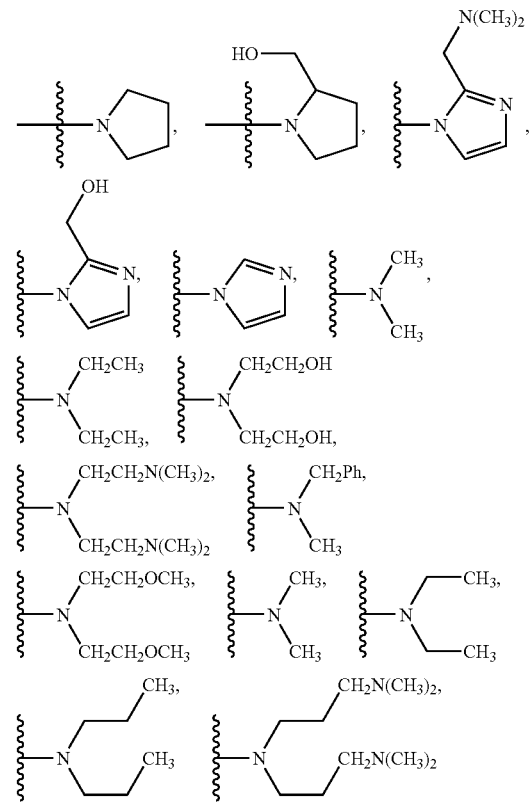

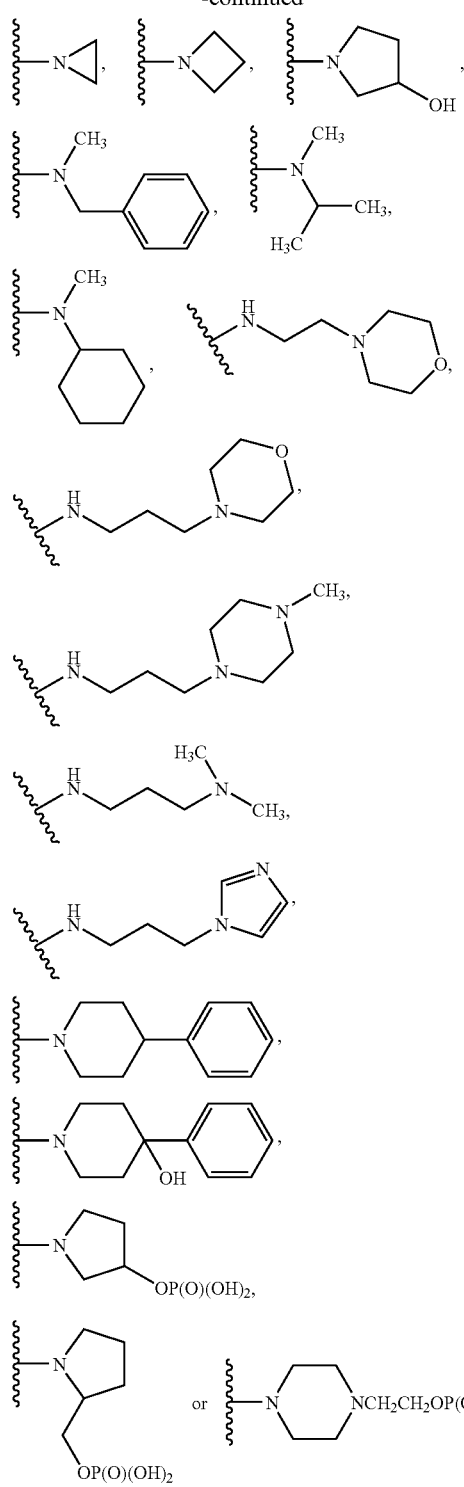
In other embodiments, —N(R²)(R²) is:
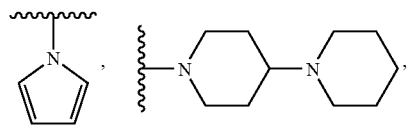
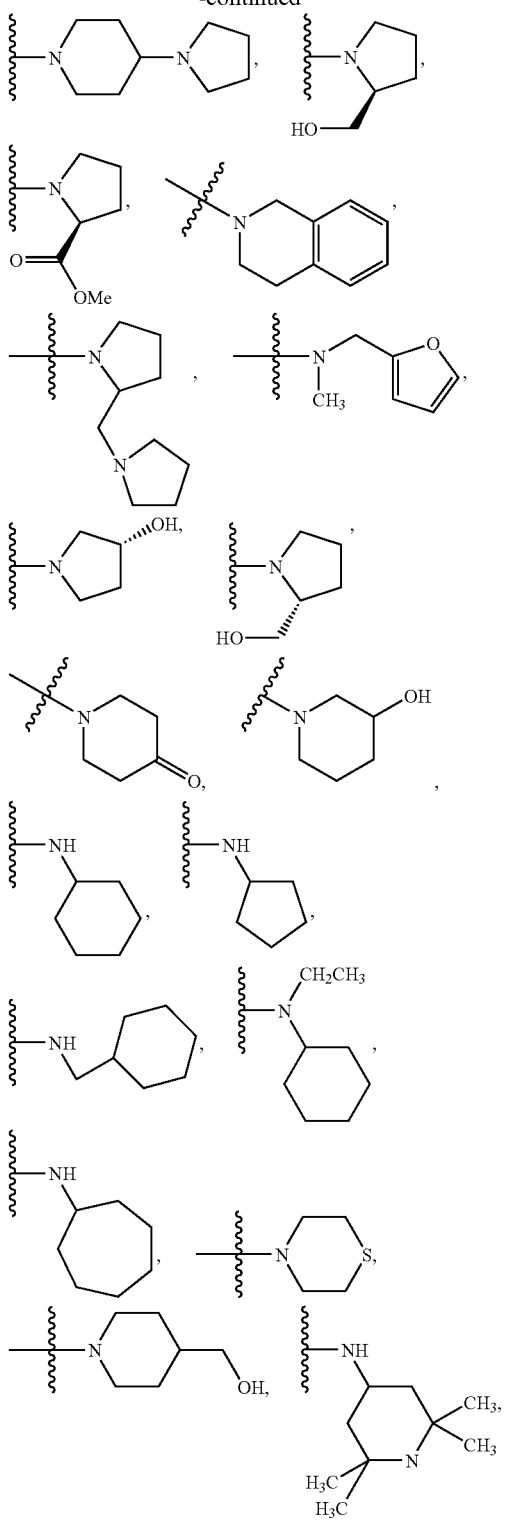

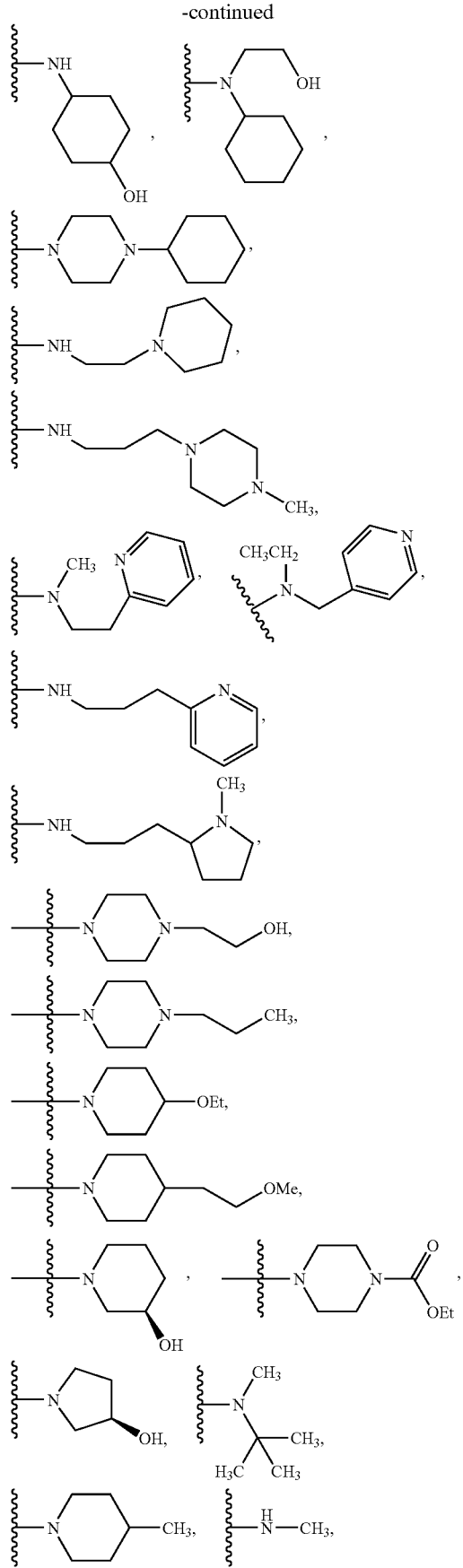
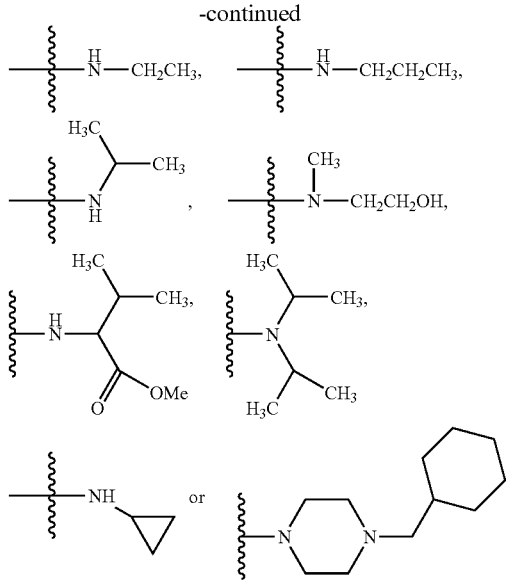
In some embodiments, —N(R²)(R²) is
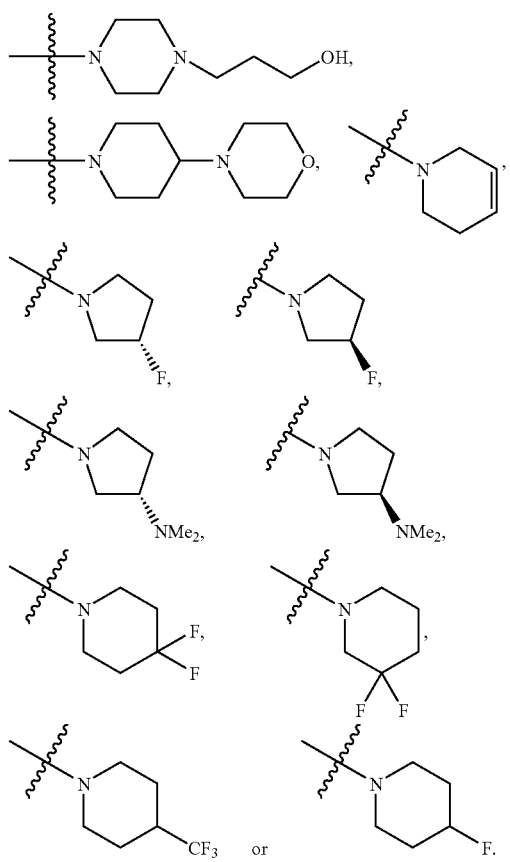
In still other embodiments, —N(R²)(R²) is
—N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.

In some embodiments, —N(R²)(R²) is
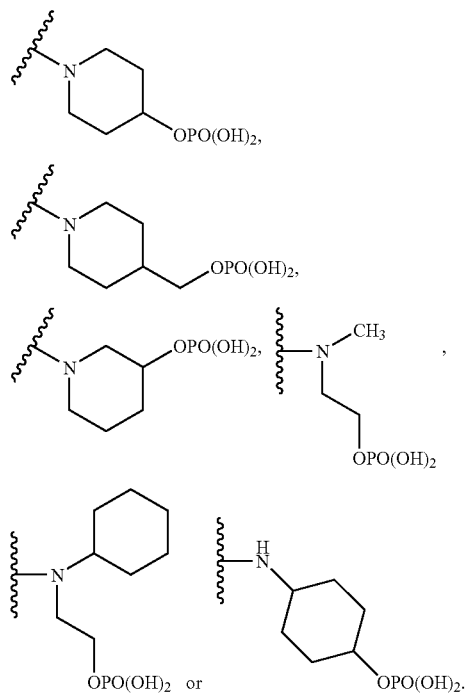
In various embodiments, —N(Z₃)(Z₄) is:
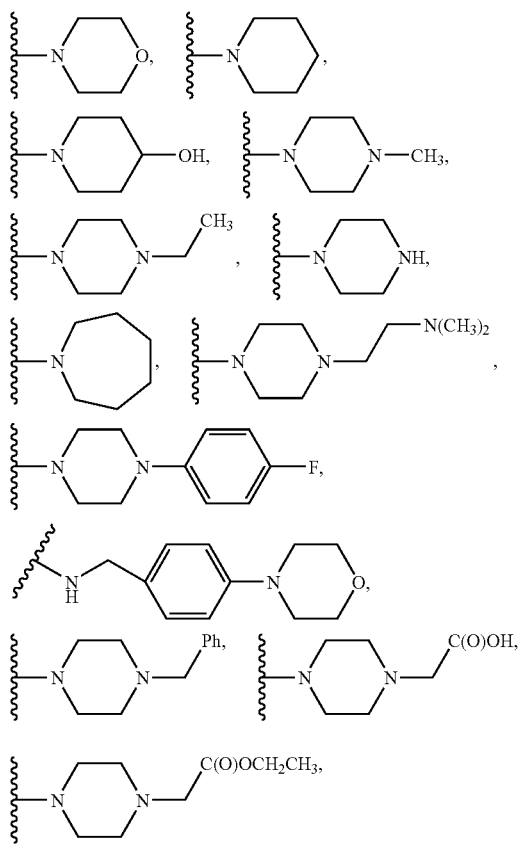
-continued
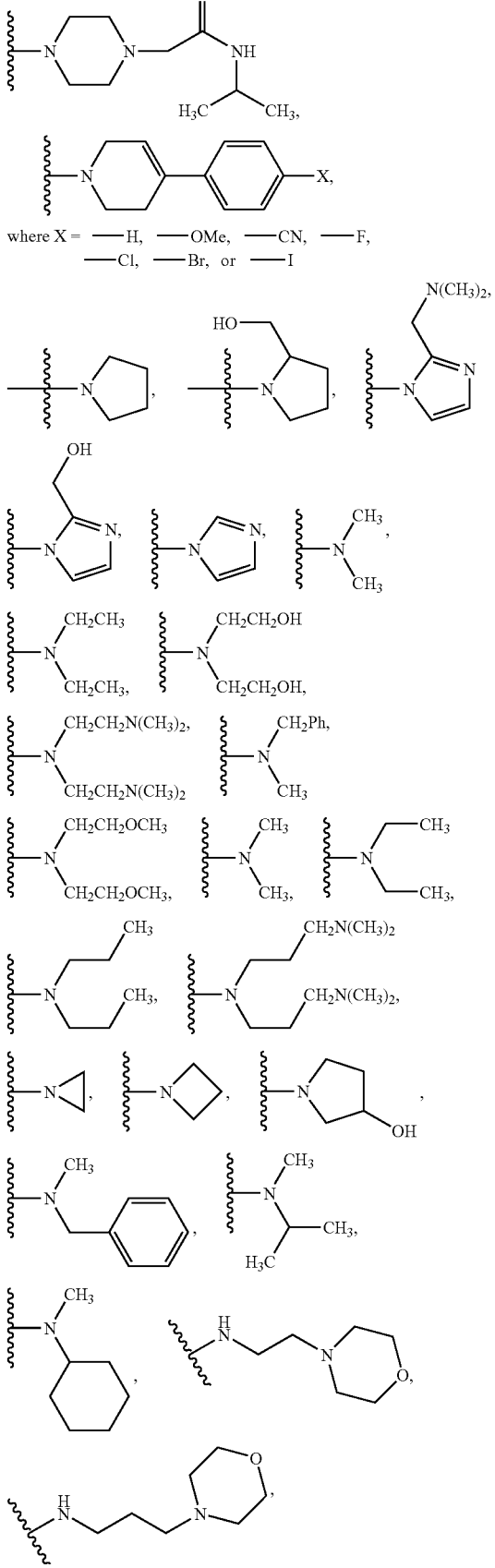

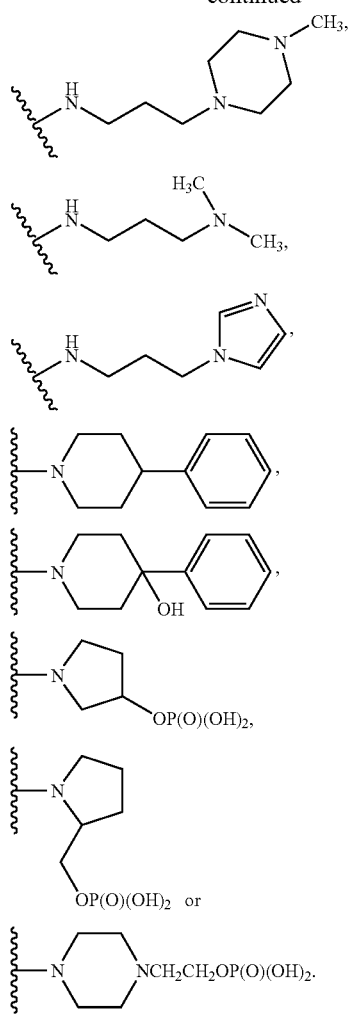
In other embodiments, —N(Z₃)(Z₄) is:

-continued

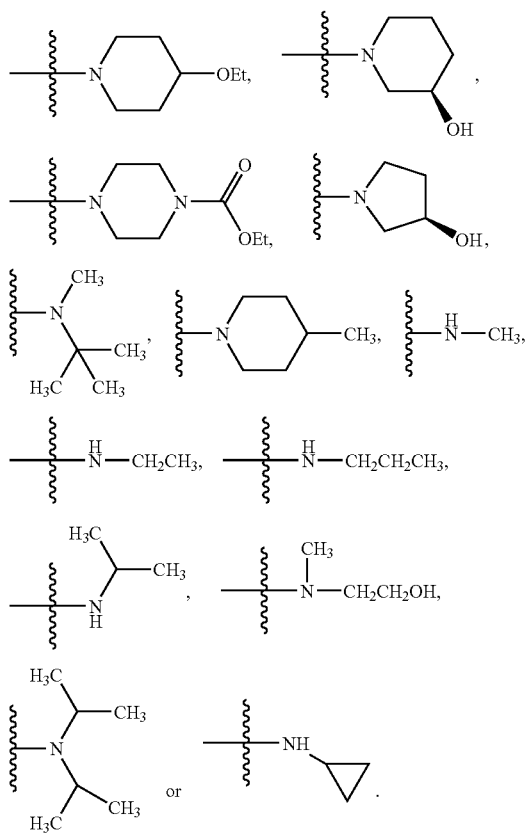

In some embodiments, —N(Z$_3$)(Z$_4$) is

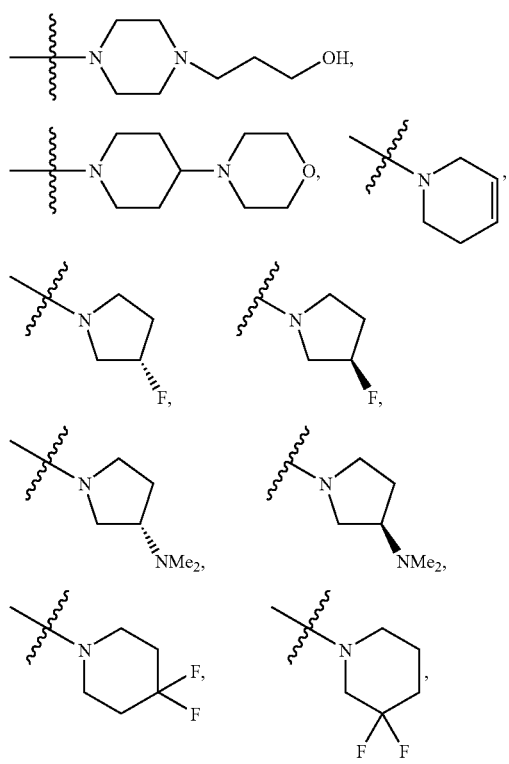

-continued

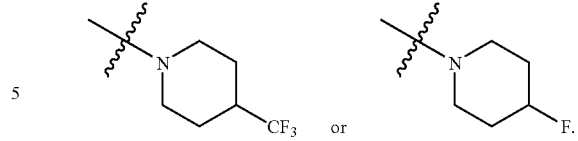

In still other embodiments, —N(Z$_3$)(Z$_4$) is
—N(CH$_2$CH$_3$)(CH$_3$),
—N(CH$_2$CH$_2$CH$_3$)(CH$_3$),
—N(CH$_2$CH$_2$CH$_2$CH$_3$)(CH$_3$),
—NH—CH$_2$CH$_2$CH$_2$CH$_3$, or
—NH—CH$_2$CH$_2$—O—CH$_3$.
In some embodiments, —N(Z$_3$)(Z$_4$) is

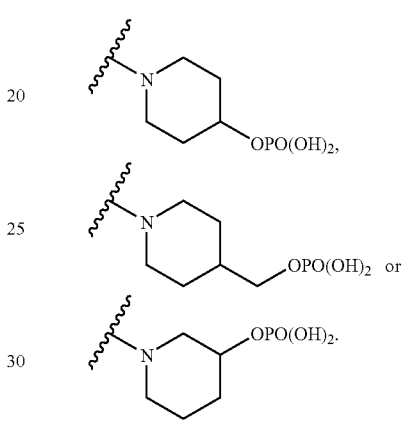

In one embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—;

n is an integer ranging from 1 to 3;

each R$^2$ is independently —H, —C$_1$-C$_6$ alkyl, cyclopropyl, cyclobutyl, cyclopentyl, cyclohexyl, —(C$_1$-C$_6$ alkylene)-phenyl or -phenyl, each of which other than hydrogen is unsubstituted or substituted with one or more of -halo, —OH, —OP(O)(OH)$_2$, —OS(O)$_2$OH or —N(Z$_3$)(Z$_4$), where Z$_3$ and Z$_4$ are independently —H, —C$_1$-C$_5$ alkyl, or —(C$_1$-C$_5$ alkylene)-O—C$_1$-C$_5$ alkyl, each of which other than hydrogen is unsubstituted or substituted with one or more of -halo, —OH or —NH$_2$;

or N, Z$_3$ and Z$_4$ are taken together to form a nitrogen-containing 3- to 7-membered monocyclic heterocycle which is unsubstituted or substituted with one to three of —C$_1$-C$_5$ alkyl, -phenyl, —(C$_1$-C$_5$ alkylene)-phenyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —C$_1$-C$_5$ alkylene-C(O)O—(C$_1$-C$_5$ alkylene)-N(R$^a$)$_2$, —COOH, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, -benzyl, or —C$_1$-C$_{10}$ alkyl;

or N and both R$^2$ groups are taken together to form a nitrogen-containing 3- to 7-membered monocyclic heterocycle which is unsubstituted or substituted with one to three of —C$_1$-C$_5$ alkyl, -phenyl, —(C$_1$-C$_5$ alkylene)-phenyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —($C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, or —$C_1$-$C_{10}$ alkyl.

In one embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—;

n is an integer ranging from 1 to 3; and at least one $C_1$-$C_3$ alkyl is methyl.

In another embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—; at least one $C_1$-$C_3$ alkyl is methyl; and at least one $R^2$ is ethyl.

In yet another embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—; at least one $C_1$-$C_3$ alkyl is methyl; and at least one $R^2$ is propyl.

In one embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—; at least one $C_1$-$C_3$ alkyl is methyl; and at least one $R^2$ is —$C_3$-$C_8$ monocyclic cycloalkyl.

In another embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—; at least one $C_1$-$C_3$ alkyl is methyl; and at least one $R^2$ is cyclohexyl.

In yet another embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—; and at least one $C_1$-$C_3$ alkyl is methyl, wherein N and both $R^2$ groups are taken together to form a nitrogen-containing 3- to 7-membered monocyclic heterocycle.

In one embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—; and at least one $C_1$-$C_3$ alkyl is methyl, wherein N and both $R^2$ groups are taken together to form a nitrogen-containing 3- to 7-membered monocyclic heterocycle, which is substituted with a hydroxyl.

In another embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—; and at least one $C_1$-$C_3$ alkyl is methyl, wherein N and both $R^2$ groups are taken together to form a nitrogen-containing 3- to 7-membered monocyclic heterocycle, which is substituted with a nitrogen-containing 3- to 7-membered monocyclic heterocycle.

Illustrative examples of the Indenoisoquinolinone Analogs include the compounds of Formula (IVa) as set forth below:

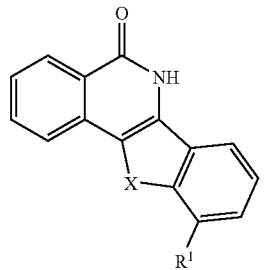

(IVa)

| Compound | —$R^1$ | X |
|---|---|---|
| IVa-1 | —OC(Me)(Me)—CH$_2$—N(Et)(Et) | —O— |
| IVa-2 | —OC(Me)(Me)—CH$_2$—N(Et)(Et) | —CH$_2$— |
| IVa-3 | —OC(Me)(Me)—CH$_2$—N(Et)(Et) | —C(O)— |
| IVa-4 | —OC(Me)(Me)—CH$_2$—N(Et)(Et) | —NH— |
| IVa-5 | —OC(Me)(Me)—CH$_2$—N(Et)(Et) | —S— |
| IVa-6 | —OC(Me)(Me)—CH$_2$—N(Et)(Et) | —N(CH$_3$)— |
| IVa-7 | —OC(Me)(Me)—CH$_2$—N(Et)(Et) | —N(CH$_2$CH$_3$)— |
| IVa-8 | —OC(Me)(Me)—CH$_2$—N(Et)(Et) | —N(CH$_2$CH$_2$CH$_3$)— |
| IVa-9 | —OC(Me)(Me)—CH$_2$—N(Et)(Et) | —N(CH$_2$CH$_2$CH$_2$CH$_3$)— |
| IVa-10 | —OC(Me)(Me)—CH$_2$—N(Et)(Et) | —N(C(H)(CH$_3$)(CH$_2$CH$_3$))— |
| IVa-11 | —OC(Me)(Me)—CH$_2$—N(Et)(Et) | —N(C(H)(CH$_3$)$_2$)— |
| IVa-12 | —OC(Me)(Me)—CH$_2$—N(Et)(Et) | —N(CH$_2$C(H)(CH$_3$)$_2$)— |
| IVa-13 | —OC(Me)(Me)—CH$_2$—N(Et)(Et) | —N(C(CH$_3$)$_3$)— |
| IVa-14 | —OC(Me)(Me)—CH$_2$—N(Et)(Et) | —CH(OH)— |
| IVa-15 | —OC(Me)(Me)—CH$_2$—N(Et)(Et) | —N(C(O)N(H)—CH$_2$—CH$_2$—OH)— |
| IVa-16 | —OC(Me)(Me)—CH$_2$—N(Et)(Et) | —N(C(O)N(H)—CH$_2$—CH$_2$—F)— |
| IVa-17 | —OC(Me)(Me)—CH$_2$—N(Et)(Et) | —N(CH$_2$—CH$_2$—OH)— |
| IVa-18 | —OC(Me)(Me)—CH$_2$—N(Et)(Et) | —N(CH$_2$—CH$_2$—F)— |
| IVa-19 | —OC(Me)(Me)—CH$_2$—N(Et)(Et) | —N(CH$_2$—CH$_2$—OCH$_3$)— |
| IVa-20 | —OC(Me)(Me)—CH$_2$—N(Et)(Et) | —N(CH$_2$—CH$_2$—CF$_3$)— |

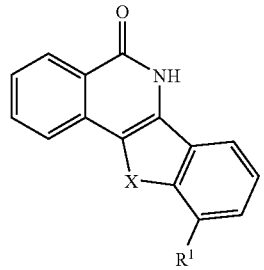

(IVa)

| Compound | —R¹ | X |
|---|---|---|
| IVa-21 | —OC(Me)(Me)—CH₂—N(Et)(Et) | —N(C(O)N(H)—CH₂—CH₂—OCH₃)— |
| IVa-22 | —OC(Me)(Me)—CH₂—N(Et)(Et) | —N(C(O)N(H)—CH₂—CH₂—CF₃)— |
| IVa-23 | —OC(Me)(Et)—CH₂—N(Et)(Et) | —O— |
| IVa-24 | —OC(Me)(Et)—CH₂—N(Et)(Et) | —CH₂— |
| IVa-25 | —OC(Me)(Et)—CH₂—N(Et)(Et) | —C(O)— |
| IVa-26 | —OC(Me)(Et)—CH₂—N(Et)(Et) | —NH— |
| IVa-27 | —OC(Me)(Et)—CH₂—N(Et)(Et) | —S— |
| IVa-28 | —OC(Me)(Et)—CH₂—N(Et)(Et) | —N(CH₃)— |
| IVa-29 | —OC(Me)(Et)—CH₂—N(Et)(Et) | —N(CH₂CH₃)— |
| IVa-30 | —OC(Me)(Et)—CH₂—N(Et)(Et) | —N(CH₂CH₂CH₃)— |
| IVa-31 | —OC(Me)(Et)—CH₂—N(Et)(Et) | —N(CH₂CH₂CH₂CH₃)— |
| IVa-32 | —OC(Me)(Et)—CH₂—N(Et)(Et) | —N(C(H)(CH₃)(CH₂CH₃))— |
| IVa-33 | —OC(Me)(Et)—CH₂—N(Et)(Et) | —N(C(H)(CH₃)₂)— |
| IVa-34 | —OC(Me)(Et)—CH₂—N(Et)(Et) | —N(CH₂C(H)(CH₃)₂)— |
| IVa-35 | —OC(Me)(Et)—CH₂—N(Et)(Et) | —N(C(CH₃)₃)— |
| IVa-36 | —OC(Me)(Et)—CH₂—N(Et)(Et) | —CH(OH)— |
| IVa-37 | —OC(Me)(Et)—CH₂—N(Et)(Et) | —N(C(O)N(H)—CH₂—CH₂—OH)— |
| IVa-38 | —OC(Me)(Et)—CH₂—N(Et)(Et) | —N(C(O)N(H)—CH₂—CH₂—F)— |
| IVa-39 | —OC(Me)(Et)—CH₂—N(Et)(Et) | —N(CH₂—CH₂—OH)— |
| IVa-40 | —OC(Me)(Et)—CH₂—N(Et)(Et) | —N(CH₂—CH₂—F)— |
| IVa-41 | —OC(Me)(Et)—CH₂—N(Et)(Et) | —N(CH₂—CH₂—OCH₃)— |
| IVa-42 | —OC(Me)(Et)—CH₂—N(Et)(Et) | —N(CH₂—CH₂—CF₃)— |
| IVa-43 | —OC(Me)(Et)—CH₂—N(Et)(Et) | —N(C(O)N(H)—CH₂—CH₂—OCH₃)— |
| IVa-44 | —OC(Me)(Et)—CH₂—N(Et)(Et) | —N(C(O)N(H)—CH₂—CH₂—CF₃)— |
| IVa-45 | —OC(Me)(Pr)—CH₂—N(Et)(Et) | —O— |
| IVa-46 | —OC(Me)(Pr)—CH₂—N(Et)(Et) | —CH₂— |
| IVa-47 | —OC(Me)(Pr)—CH₂—N(Et)(Et) | —C(O)— |
| IVa-48 | —OC(Me)(Pr)—CH₂—N(Et)(Et) | —NH— |
| IVa-49 | —OC(Me)(Pr)—CH₂—N(Et)(Et) | —S— |
| IVa-50 | —OC(Me)(Pr)—CH₂—N(Et)(Et) | —N(CH₃)— |
| IVa-51 | —OC(Me)(Pr)—CH₂—N(Et)(Et) | —N(CH₂CH₃)— |
| IVa-52 | —OC(Me)(Pr)—CH₂—N(Et)(Et) | —N(CH₂CH₃)— |
| IVa-53 | —OC(Me)(Pr)—CH₂—N(Et)(Et) | —N(CH₂CH₂CH₂CH₃)— |
| IVa-54 | —OC(Me)(Pr)—CH₂—N(Et)(Et) | —N(C(H)(CH₃)(CH₂CH₃))— |
| IVa-55 | —OC(Me)(Pr)—CH₂—N(Et)(Et) | —N(C(H)(CH₃)₂)— |
| IVa-56 | —OC(Me)(Pr)—CH₂—N(Et)(Et) | —N(CH₂C(H)(CH₃)₂)— |
| IVa-57 | —OC(Me)(Pr)—CH₂—N(Et)(Et) | —N(C(CH₃)₃)— |
| IVa-58 | —OC(Me)(Pr)—CH₂—N(Et)(Et) | —CH(OH)— |
| IVa-59 | —OC(Me)(Pr)—CH₂—N(Et)(Et) | —N(C(O)N(H)—CH₂—CH₂—OH)— |
| IVa-60 | —OC(Me)(Pr)—CH₂—N(Et)(Et) | —N(C(O)N(H)—CH₂—CH₂—F)— |
| IVa-61 | —OC(Me)(Pr)—CH₂—N(Et)(Et) | —N(CH₂—CH₂—OH)— |
| IVa-62 | —OC(Me)(Pr)—CH₂—N(Et)(Et) | —N(CH₂—CH₂—F)— |
| IVa-63 | —OC(Me)(Pr)—CH₂—N(Et)(Et) | —N(CH₂—CH₂—OCH₃)— |
| IVa-64 | —OC(Me)(Pr)—CH₂—N(Et)(Et) | —N(CH₂—CH₂—CF₃)— |
| IVa-65 | —OC(Me)(Pr)—CH₂—N(Et)(Et) | —N(C(O)N(H)—CH₂—CH₂—OCH₃)— |
| IVa-66 | —OC(Me)(Pr)—CH₂—N(Et)(Et) | —N(C(O)N(H)—CH₂—CH₂—CF₃)— |
| IVa-67 | —OC(Me)(i-Pr)—CH₂—N(H)(cyclopropyl) | —O— |
| IVa-68 | —OC(Me)(i-Pr)—CH₂—N(H)(cyclopropyl) | —CH₂— |
| IVa-69 | —OC(Me)(i-Pr)—CH₂—N(H)(cyclopropyl) | —C(O)— |
| IVa-70 | —OC(Me)(i-Pr)—CH₂—N(H)(cyclopropyl) | —NH— |
| IVa-71 | —OC(Me)(i-Pr)—CH₂—N(H)(cyclopropyl) | —S— |
| IVa-72 | —OC(Me)(i-Pr)—CH₂—N(H)(cyclopropyl) | —N(CH₃)— |
| IVa-73 | —OC(Me)(i-Pr)—CH₂—N(H)(cyclopropyl) | —N(CH₂CH₃)— |
| IVa-74 | —OC(Me)(i-Pr)—CH₂—N(H)(cyclopropyl) | —N(CH₂CH₂CH₃)— |
| IVa-75 | —OC(Me)(i-Pr)—CH₂— | —N(CH₂CH₂CH₂CH₃)— |

-continued

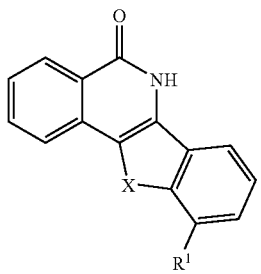
(IVa)

| Compound | —R¹ | X |
|---|---|---|
| IVa-76 | —OC(Me)(i-Pr)—CH₂—N(H)(cyclopropyl) | —N(C(H)(CH₃)(CH₂CH₃))— |
| IVa-77 | —OC(Me)(i-Pr)—CH₂—N(H)(cyclopropyl) | —N(C(H)(CH₃)₂)— |
| IVa-78 | —OC(Me)(i-Pr)—CH₂—N(H)(cyclopropyl) | —N(CH₂C(H)(CH₃)₂)— |
| IVa-79 | —OC(Me)(i-Pr)—CH₂—N(H)(cyclopropyl) | —N(C(CH₃)₃)— |
| IVa-80 | —OC(Me)(i-Pr)—CH₂—N(H)(cyclopropyl) | —CH(OH)— |
| IVa-81 | —OC(Me)(i-Pr)—CH₂—N(H)(cyclopropyl) | —N(C(O)N(H)—CH₂—CH₂—OH)— |
| IVa-82 | —OC(Me)(i-Pr)—CH₂—N(H)(cyclopropyl) | —N(C(O)N(H)—CH₂—CH₂—F)— |
| IVa-83 | —OC(Me)(i-Pr)—CH₂—N(H)(cyclopropyl) | —N(CH₂—CH₂—OH)— |
| IVa-84 | —OC(Me)(i-Pr)—CH₂—N(H)(cyclopropyl) | —N(CH₂—CH₂—F)— |
| IVa-85 | —OC(Me)(i-Pr)—CH₂—N(H)(cyclopropyl) | —N(CH₂—CH₂—OCH₃)— |
| IVa-86 | —OC(Me)(i-Pr)—CH₂—N(H)(cyclopropyl) | —N(CH₂—CH₂—CF₃)— |
| IVa-87 | —OC(Me)(i-Pr)—CH₂—N(H)(cyclopropyl) | —N(C(O)N(H)—CH₂—CH₂—OCH₃)— |
| IVa-88 | —OC(Me)(i-Pr)—CH₂—N(H)(cyclopropyl) | —N(C(O)N(H)—CH₂—CH₂—CF₃)— | and pharmaceutically acceptable salts thereof.

5.11 The Indenoisoquinolinone Analogs of Formula (IVb)

The present invention provides Indenoisoquinolinone Analogs according to Formula (IVb), below:

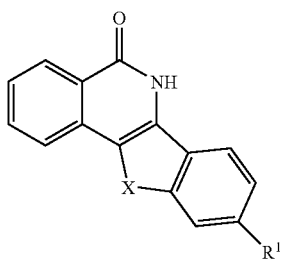
(IVb)

and pharmaceutically acceptable salts thereof,
wherein X and R¹ are as defined above for the Indenoisoquinolinone Analogs of Formula (IVb).

In one embodiment, X is —N(CH₃)—. In another embodiment, X is —N(CH₂CH₃)—. In another embodiment, X is —N(CH₂CH₂CH₃)—. In another embodiment, X is —N(CH₂CH₂CH₂CH₃)—. In another embodiment, X is —N(C(H)(CH₃)(CH₂CH₃))—. In another embodiment, X is —N(C(H)(CH₃)₂)—. In another embodiment, X is —N(CH₂C(H)(CH₃)₂)—. In another embodiment, X is —N(C(CH₃)₃)—.

In one embodiment, X is —O—. In one embodiment, X is —CH₂—. In one embodiment, X is —C(O)—. In one embodiment, X is —NH—. In one embodiment, X is —S—. In one embodiment, X is —CH(OH)—.

In one embodiment, each $C_1$-$C_3$ alkyl is independent of the other $C_1$-$C_3$ alkyl.

In one embodiment, each $C_1$-$C_3$ alkyl is methyl.

In one embodiment, each $C_1$-$C_3$ alkyl is methyl and X is —CH₂—.

In one embodiment, each $C_1$-$C_3$ alkyl is methyl and X is —CH(OH)—.

In one embodiment, each $C_1$-$C_3$ alkyl is methyl, X is —CH₂— and n is 1.

In one embodiment, each $C_1$-$C_3$ alkyl is methyl, X is —CH(OH)— and n is 1.

In another embodiment, X is —CH(OH)— and n is 1.

In another embodiment, X is —N(C(O)N(H)—(CH₂)$_p$—Z)—.

In another embodiment, X is —N(C(O)N(H)—(CH₂)—Z)—.

In another embodiment, X is —N(C(O)N(H)—(CH₂)₂—Z)—.

In another embodiment, X is —N(C(O)N(H)—(CH₂)$_p$—Z)— and n is 1.

In yet another embodiment, X is —N(C(O)N(H)—(CH$_2$)$_2$—Z)— and n is 2.

In still another embodiment, X is —N(C(O)N(H)—(CH$_2$)—Z)— and n is 1.

In one embodiment, X is —N((CH$_2$)$_q$—Z)—.

In another embodiment, X is —N((CH$_2$)—Z)—.

In another embodiment, X is —N((CH$_2$)$_2$—Z)—.

In another embodiment, X is —N((CH$_2$)$_q$—Z)— and n is 1.

In yet another embodiment, X is —N((CH$_2$)$_q$—Z)— and n is 2.

In still another embodiment, X is —N((CH$_2$)—Z)— and n is 1.

In still another embodiment, X is —N((CH$_2$)—Z)— and n is 2.

In one embodiment, Z is —CF$_3$.

In another embodiment, Z is —F.

In yet another embodiment, Z is —OH.

In still another embodiment, Z is —O—CH$_3$.

In another embodiment, X is —N(C(O)N(H)—(CH$_2$)$_p$—OH)—.

In another embodiment, X is —N(C(O)N(H)—(CH$_2$)$_2$—OH)—.

In another embodiment, X is —N(C(O)N(H)—(CH$_2$)$_p$—OH)— and n is 1.

In yet another embodiment, X is —N(C(O)N(H)—(CH$_2$)$_p$—OH)— and n is 2.

In still another embodiment, X is —N(C(O)N(H)—(CH$_2$)$_2$—OH)— and n is 1.

In still another embodiment, X is —N(C(O)N(H)—(CH$_2$)$_2$—OH)— and n is 2.

In one embodiment, X is —N((CH$_2$)$_q$—OH)—.

In another embodiment, X is —N((CH$_2$)$_2$—OH)—.

In another embodiment, X is —N((CH$_2$)$_q$—OH)— and n is 1.

In yet another embodiment, X is —N((CH$_2$)$_q$—OH)— and n is 2.

In still another embodiment, X is —N((CH$_2$)$_2$—OH)— and n is 1.

In another embodiment, X is —N(C(O)N(H)—(CH$_2$)$_p$—F)—.

In another embodiment, X is —N(C(O)N(H)—(CH$_2$)—F)—.

In another embodiment, X is —N(C(O)N(H)—(CH$_2$)$_p$—F)— and n is 1.

In yet another embodiment, X is —N(C(O)N(H)—(CH$_2$)$_p$—F)— n is 2.

In still another embodiment, X is —N(C(O)N(H)—(CH$_2$)—F)— and n is 1.

In one embodiment, X is —N((CH$_2$)$_q$—F)—.

In another embodiment, X is —N((CH$_2$)—F)—.

In another embodiment, X is —N((CH$_2$)$_q$—F)— and n is 1.

In yet another embodiment, X is —N((CH$_2$)$_q$—F)— and n is 2.

In still another embodiment, X is —N((CH$_2$)—F)— and n is 1.

In another embodiment, X is —N(C(O)N(H)—(CH$_2$)$_p$—OMe)-.

In another embodiment, X is —N(C(O)N(H)—(CH$_2$)$_2$—OMe)-.

In another embodiment, X is —N(C(O)N(H)—(CH$_2$)$_p$—OMe)- and n is 1.

In yet another embodiment, X is —N(C(O)N(H)—(CH$_2$)$_p$—OMe)- and n is 2.

In still another embodiment, X is —N(C(O)N(H)—(CH$_2$)$_2$—OMe)- and n is 1.

In one embodiment, X is —N((CH$_2$)$_q$—OMe)-.

In another embodiment, X is —N((CH$_2$)$_2$—OMe)-.

In another embodiment, X is —N((CH$_2$)$_q$—OMe)- and n is 1.

In yet another embodiment, X is —N((CH$_2$)$_q$—OMe)- and n is 2.

In still another embodiment, X is —N((CH$_2$)$_2$—OMe)- and n is 1.

In another embodiment, X is —N(C(O)N(H)—(CH$_2$)$_p$—CF$_3$)—.

In another embodiment, X is —N(C(O)N(H)—(CH$_2$)—CF$_3$)—.

In another embodiment, X is —N(C(O)N(H)—(CH$_2$)$_p$—CF$_3$)— and n is 1.

In yet another embodiment, X is —N(C(O)N(H)—(CH$_2$)$_p$—CF$_3$)— and n is 2.

In still another embodiment, X is —N(C(O)N(H)—(CH$_2$)—CF$_3$)— and n is 1.

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and n is 1.

In yet another embodiment, X is —N((CH$_2$)$_q$—CF$_3$)— and n is 2.

In still another embodiment, X is —N((CH$_2$)—CF$_3$)— and n is 1.

In another embodiment, X is —N(C(O)N(H)—(CH$_2$)$_p$—CF$_3$)—.

In another embodiment, X is —N(C(O)N(H)—(CH$_2$)—CF$_3$)—.

In another embodiment, X is —N(C(O)N(H)—(CH$_2$)$_p$—CF$_3$)— and n is 1.

In yet another embodiment, X is —N(C(O)N(H)—(CH$_2$)$_p$—CF$_3$)— and n is 2.

In still another embodiment, X is —N(C(O)N(H)—(CH$_2$)—CF$_3$)— and n is 1.

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and n is 1.

In yet another embodiment, X is —N((CH$_2$)$_q$—CF$_3$)— and n is 2.

In still another embodiment, X is —N((CH$_2$)—CF$_3$)— and n is 1.

In one embodiment, n is 1.

In another embodiment, n is 2.

In yet another embodiment, n is 3.

In a further embodiment, n is 4, 5, or 6.

In yet a further embodiment, n is 7, 8, or 9.

In still a further embodiment, n is 10.

In one embodiment, p is 1.

In another embodiment, p is 2.

In yet another embodiment, p is an integer ranging from 2 to 5.

In one embodiment, q is 1.

In another embodiment, q is 2.

In yet another embodiment, q is an integer ranging from 2 to 5.

In one embodiment, n is 1 and X is —N(CH$_3$)—.

In another embodiment, n is 1 and X is —N(CH$_2$CH$_3$).

In another embodiment, n is 1 and X is —N(CH$_2$CH$_2$CH$_3$)—.

In another embodiment, n is 1 and X is —N(CH$_2$CH$_2$CH$_2$CH$_3$)—.

In another embodiment, n is 1 and X is —N(C(H)(CH$_3$)(CH$_2$CH$_3$))—.

In another embodiment, n is 1 and X is —N(C(H)(CH$_3$)$_2$)—.

In another embodiment, n is 1 and X is —N(CH$_2$C(H)(CH$_3$)$_2$)—.
In another embodiment, n is 1 and X is —N(C(CH$_3$)$_3$)—.
In one embodiment, one R$^2$ is —H, and the other R$^2$ is —C$_1$-C$_6$ alkyl.
In another embodiment, each R$^2$ is —C$_1$-C$_6$ alkyl.
In another embodiment, each R$^2$ is -methyl.
In various embodiments, —N(R$^2$)(R$^2$) is:
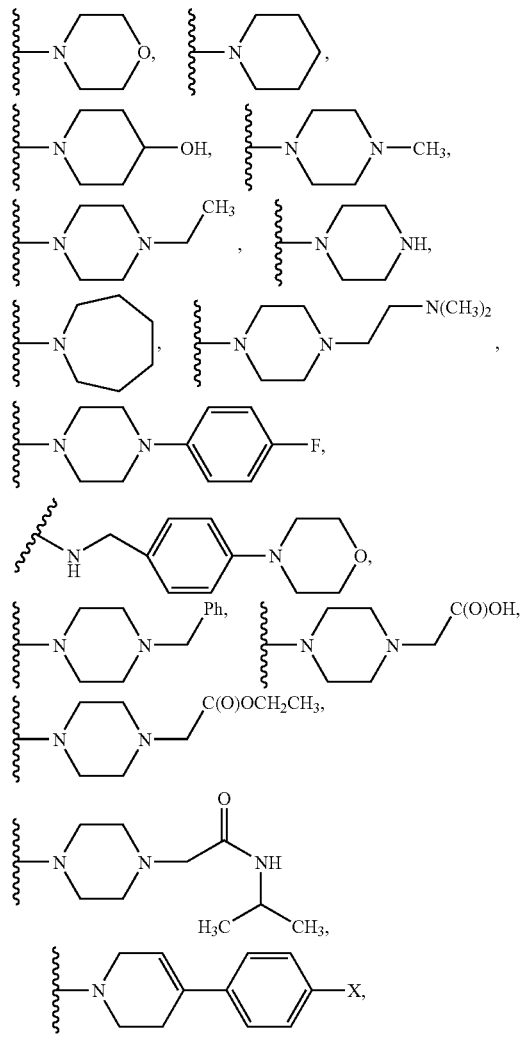
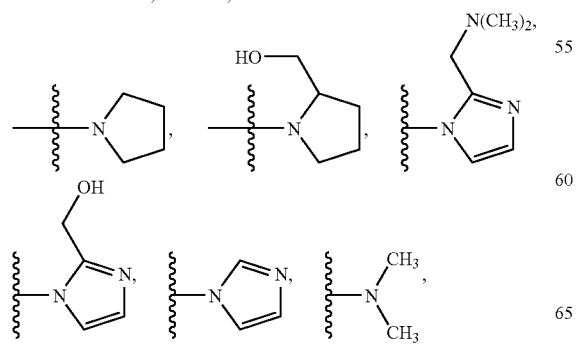
where X = —H, —OMe, —CN, —F, —Cl, —Br, or —I
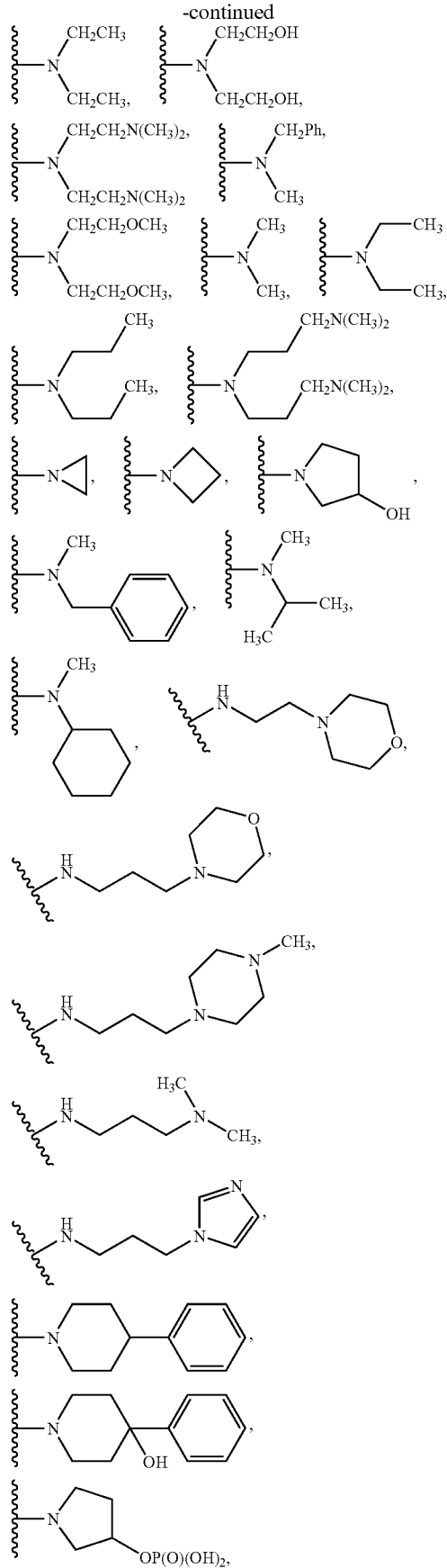

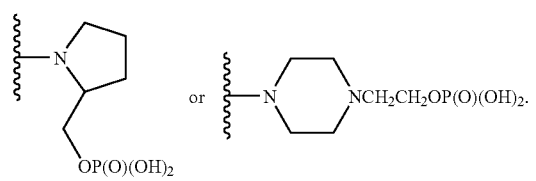
In other embodiments, —N(R²)(R²) is:
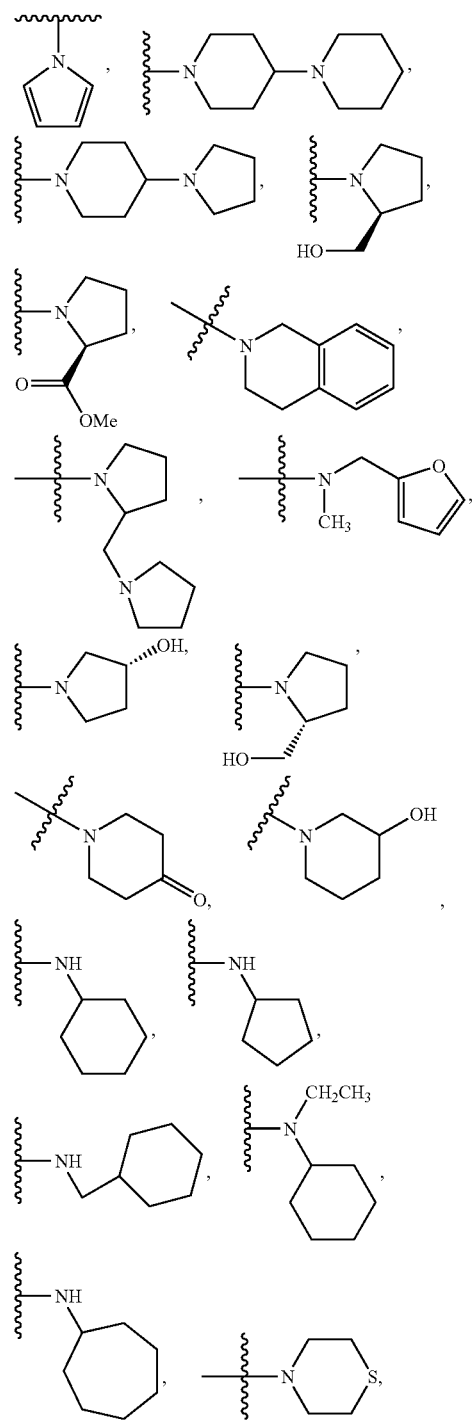
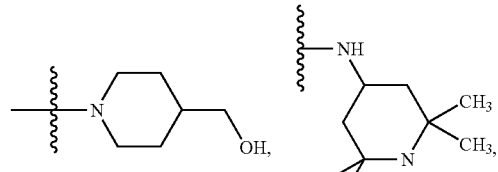
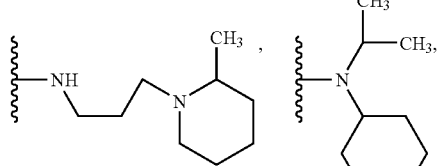
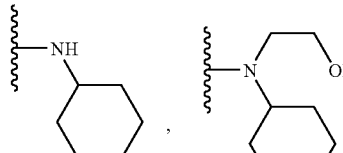
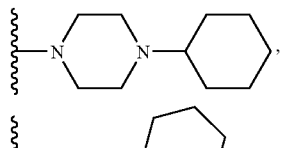
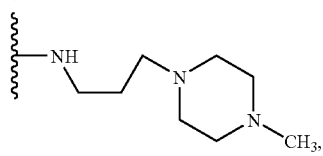
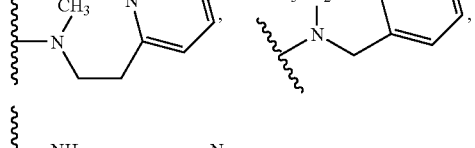
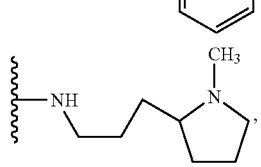
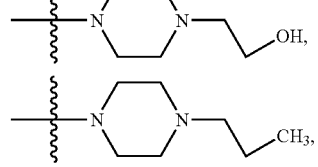
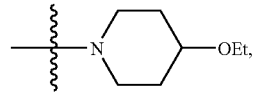

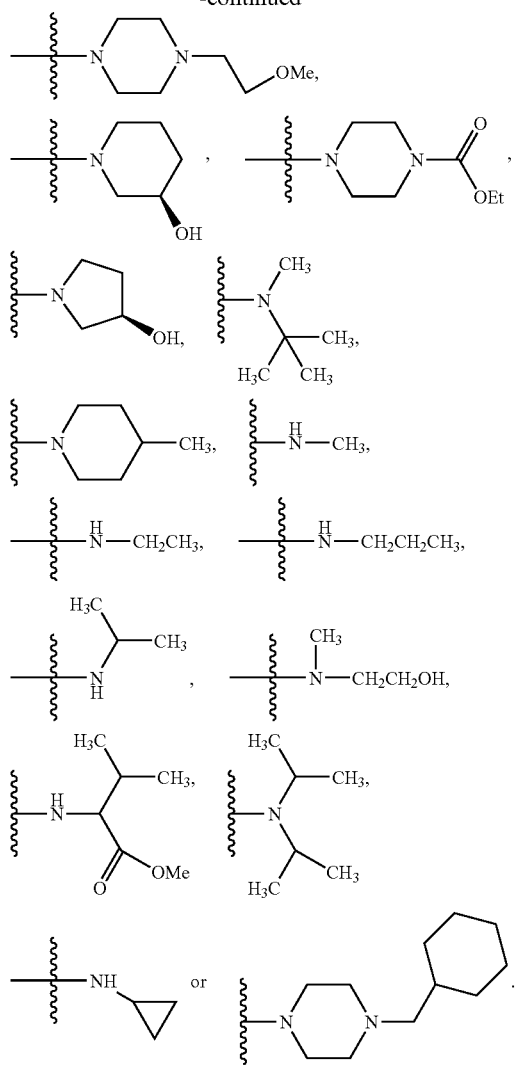
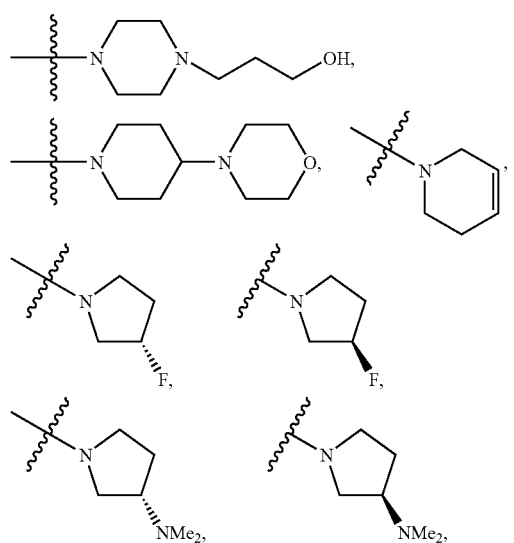
In some embodiments, —N(R²)(R²) is
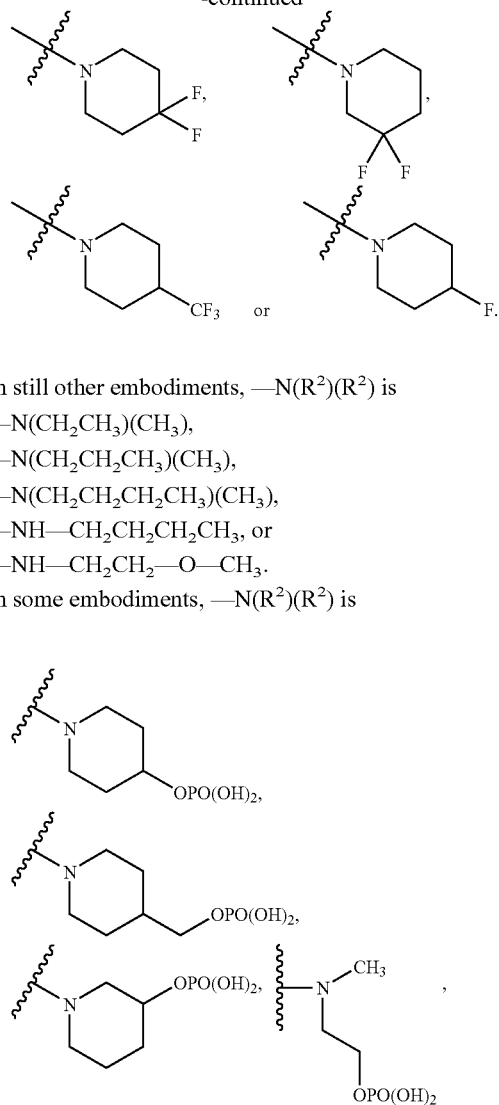
In still other embodiments, —N(R²)(R²) is
—N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.
In some embodiments, —N(R²)(R²) is
In various embodiments, —N(Z₃)(Z₄) is:
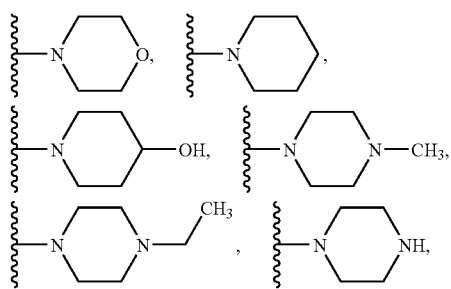

1003
-continued
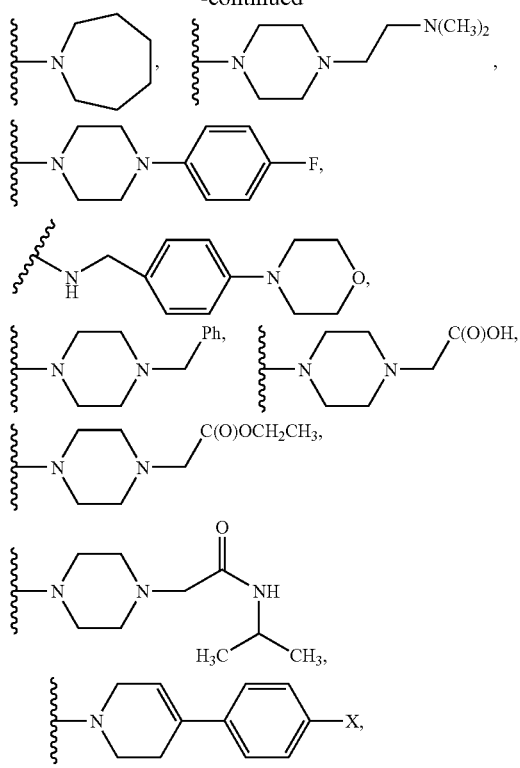
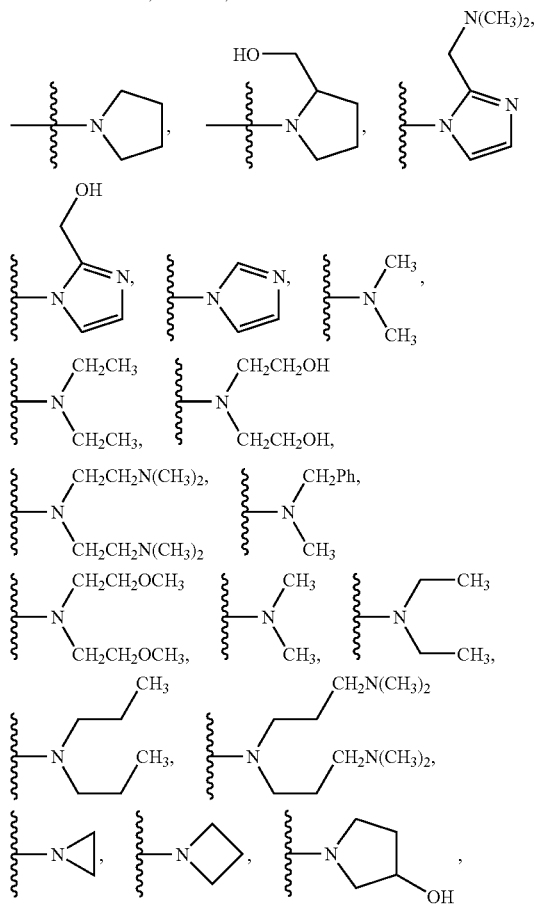
1004
-continued
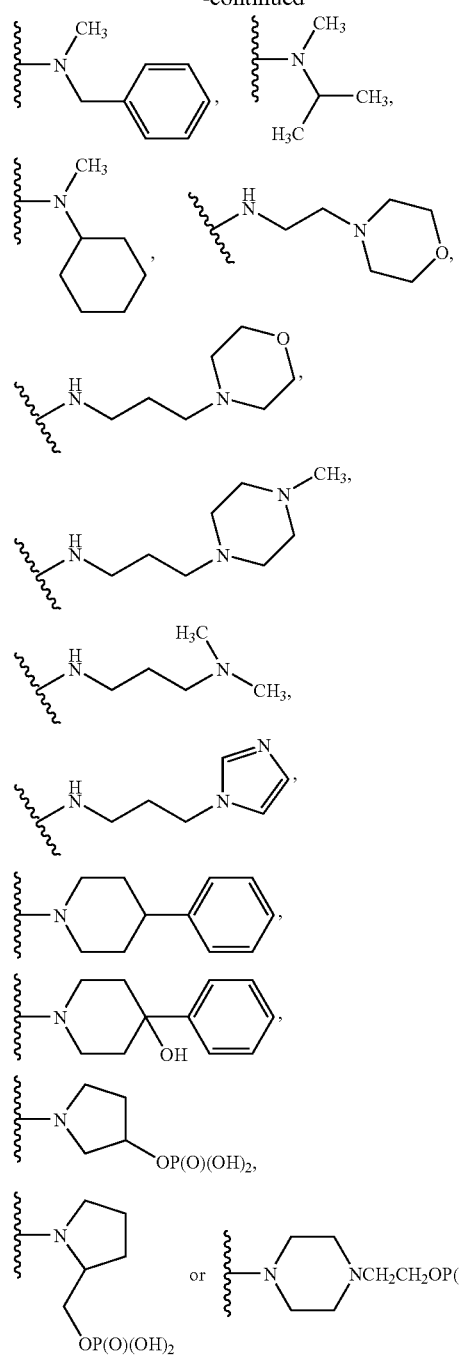
In other embodiments, —N($Z_3$)($Z_4$) is:
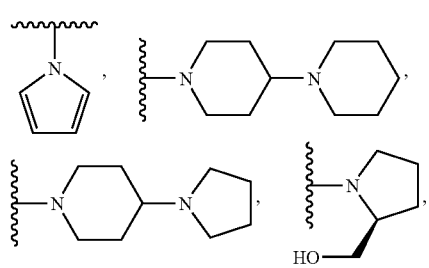

1005
-continued
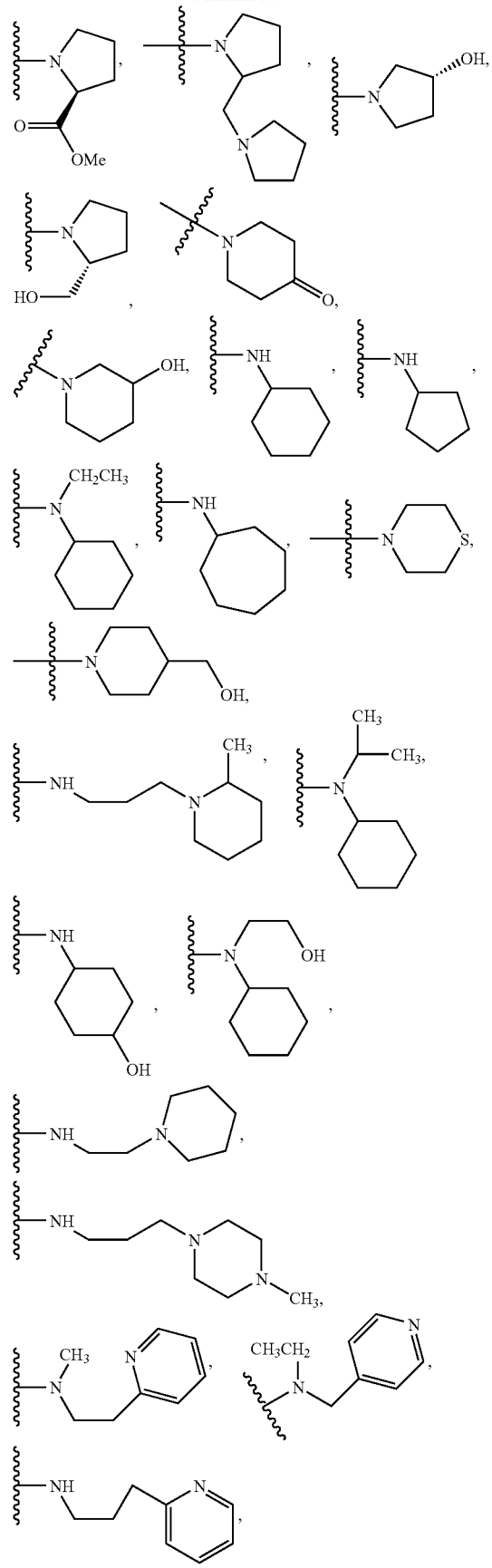
1006
-continued
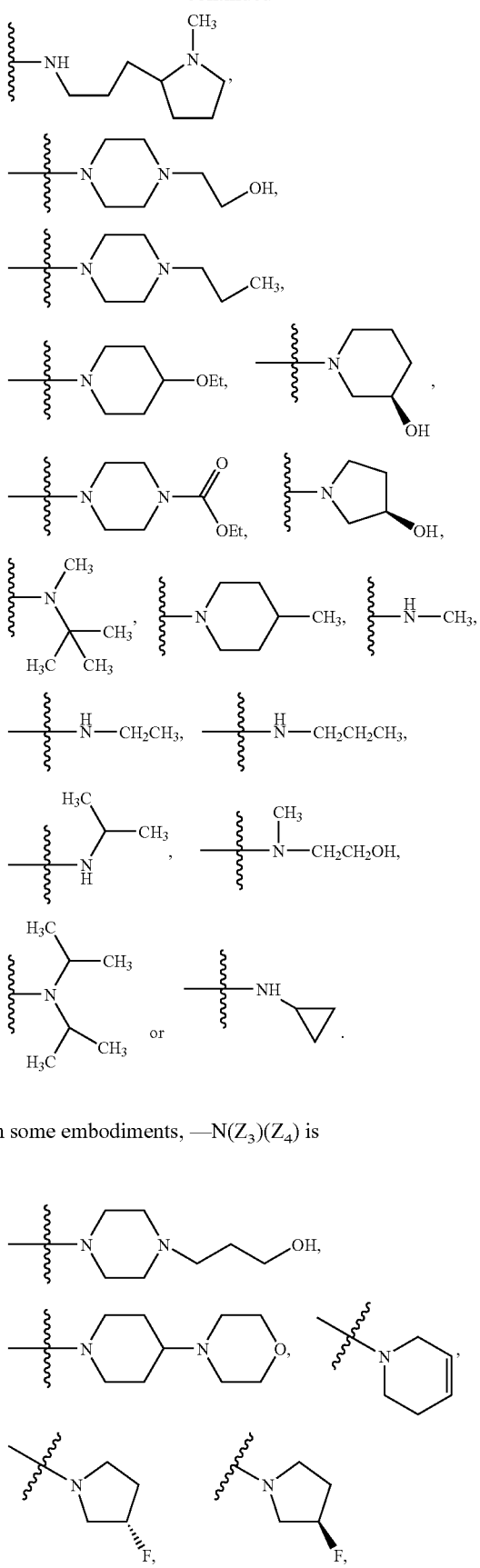
In some embodiments, —N(Z₃)(Z₄) is
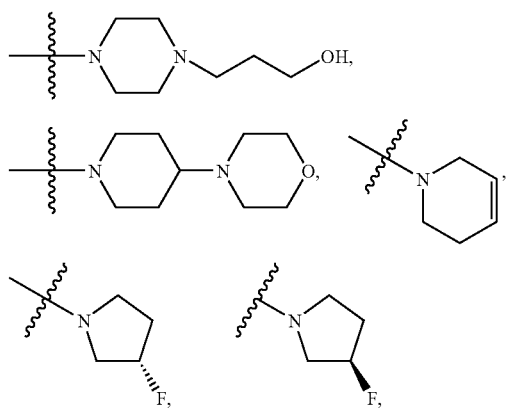

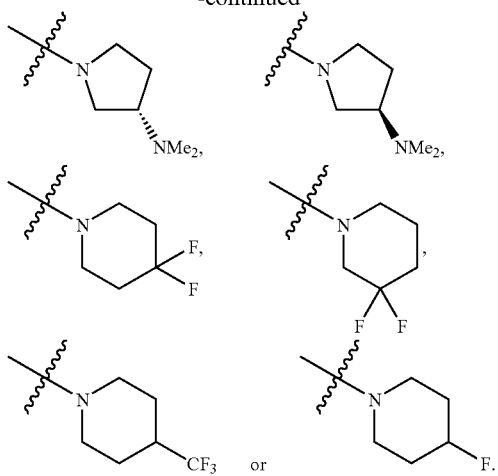

In still other embodiments, —N(Z₃)(Z₄) is
—N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.

In some embodiments, —N(Z₃)(Z₄) is

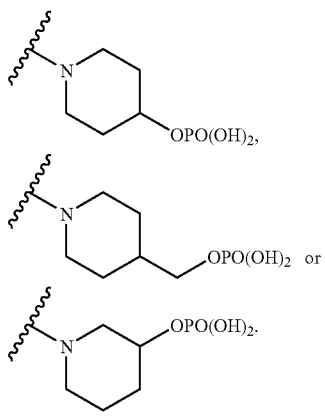

In one embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—;

n is an integer ranging from 1 to 3;

each R² is independently —H, —C₁-C₆ alkyl, cyclopropyl, cyclobutyl, cyclopentyl, cyclohexyl, —(C₁-C₆ alkylene)-phenyl or -phenyl, each of which other than hydrogen is unsubstituted or substituted with one or more of -halo, —OH, —OP(O)(OH)₂, —OS(O)₂OH or —N(Z₃)(Z₄), where Z₃ and Z₄ are independently —H, —C₁-C₅ alkyl, or —(C₁-C₅ alkylene)-O—C₁-C₅ alkyl, each of which other than hydrogen is unsubstituted or substituted with one or more of -halo, —OH or —NH₂;

or N, Z₃ and Z₄ are taken together to form a nitrogen-containing 3- to 7-membered monocyclic heterocycle which is unsubstituted or substituted with one to three of —C₁-C₅ alkyl, -phenyl, —(C₁-C₅ alkylene)-phenyl, -(hydroxy-substituted) C₁-C₅ alkyl, -halo, -(halo-substituted) C₁-C₅ alkyl, -(halo-substituted) phenyl, -phenylene-O—C₁-C₅ alkyl, -(cyano-substituted) phenyl, —OH, —O—C₁-C₅ alkyl, —N(Rᵃ)₂, —(C₁-C₅ alkylene)-N(Rᵃ)₂, —C₁-C₅ alkylene-C(O)O—(C₁-C₅ alkylene)-N(Rᵃ)₂, —COOH, —(C₁-C₅ alkylene)-COOH, —OP(O)(OH)₂, —OS(O)₂OH, —(C₁-C₅ alkylene)-OP(O)(OH)₂, —(C₁-C₅ alkylene)-OS(O)₂OH, —C(O)O—C₁-C₅ alkyl, —OC(O)—C₁-C₅ alkyl, —(C₁-C₅ alkylene)-C(O)O—C₁-C₅ alkyl, —(C₁-C₅ alkylene)-C(O)NH—C₁-C₅ alkyl, —C(O)NH₂, or —NO₂, wherein each occurrence of Rᵃ is independently —H, -benzyl, or —C₁-C₁₀ alkyl;

or N and both R² groups are taken together to form a nitrogen-containing 3- to 7-membered monocyclic heterocycle which is unsubstituted or substituted with one to three of —C₁-C₅ alkyl, -phenyl, —(C₁-C₅ alkylene)-phenyl, -(hydroxy-substituted) C₁-C₅ alkyl, -halo, -(halo-substituted) C₁-C₅ alkyl, -(halo-substituted) phenyl, -phenylene-O—C₁-C₅ alkyl, -(cyano-substituted) phenyl, —OH, —O—C₁-C₅ alkyl, —N(Rᵃ)₂, —(C₁-C₅ alkylene)-N(Rᵃ)₂, —(C₁-C₅ alkylene)-C(O)O—(C₁-C₅ alkylene)-N(Rᵃ)₂, —COOH, —(C₁-C₅ alkylene)-COOH, —OP(O)(OH)₂, —OS(O)₂OH, —(C₁-C₅ alkylene)-OP(O)(OH)₂, —(C₁-C₅ alkylene)-OS(O)₂OH, —C(O)O—C₁-C₅ alkyl, —OC(O)—C₁-C₅ alkyl, —(C₁-C₅ alkylene)-C(O)O—C₁-C₅ alkyl, —(C₁-C₅ alkylene)-C(O)NH—C₁-C₅ alkyl, —C(O)NH₂, or —NO₂, wherein each occurrence of Rᵃ is independently —H, -benzyl, or —C₁-C₁₀ alkyl.

In one embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—;

n is an integer ranging from 1 to 3; and at least one C₁-C₃ alkyl is methyl.

In another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; at least one C₁-C₃ alkyl is methyl; and at least one R² is ethyl.

In yet another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; at least one C₁-C₃ alkyl is methyl; and at least one R² is propyl.

In one embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; at least one C₁-C₃ alkyl is methyl; and at least one R² is —C₃-C₈ monocyclic cycloalkyl.

In another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; at least one C₁-C₃ alkyl is methyl; and at least one R² is cyclohexyl.

In yet another embodiment, X is —N(CH₃)—, —N(CH₂CH₃)—, —N(CH₂CH₂CH₃)—, —N(CH₂CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; and at least one C₁-C₃ alkyl is methyl, wherein N and both R² groups are taken together to form a nitrogen-containing 3- to 7-membered monocyclic heterocycle.

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—; and at least one C₁-C₃ alkyl is methyl, wherein N and both R² groups are taken together to form a nitrogen-containing 3- to 7-membered monocyclic heterocycle, which is substituted with a hydroxyl.

In another embodiment, X is —N(CH$_3$)—, —N(CH$_2$CH$_3$)—, —N(CH$_2$CH$_2$CH$_3$)—, —N(CH$_2$CH$_2$CH$_2$CH$_3$)—, —N(C(H)(CH$_3$)(CH$_2$CH$_3$))—, —N(C(H)(CH$_3$)$_2$)—, —N(CH$_2$C(H)(CH$_3$)$_2$)— or —N(C(CH$_3$)$_3$)—;

and at least one C$_1$-C$_3$ alkyl is methyl, wherein N and both R$^2$ groups are taken together to form a nitrogen-containing 3- to 7-membered monocyclic heterocycle, which is substituted with a nitrogen-containing 3- to 7-membered monocyclic heterocycle.

Illustrative examples of the Indenoisoquinolinone Analogs include the compounds of Formula (IVb) as set forth below:

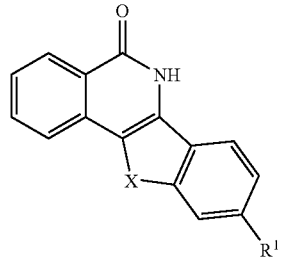

(IVb)

| Compound | —R$^1$ | X |
|---|---|---|
| IVb-1 | —OC(Me)(Me)—CH$_2$—N(Et)(Et) | —O— |
| IVb-2 | —OC(Me)(Me)—CH$_2$—N(Et)(Et) | —CH$_2$— |
| IVb-3 | —OC(Me)(Me)—CH$_2$—N(Et)(Et) | —C(O)— |
| IVb-4 | —OC(Me)(Me)—CH$_2$—N(Et)(Et) | —NH— |
| IVb-5 | —OC(Me)(Me)—CH$_2$—N(Et)(Et) | —S— |
| IVb-6 | —OC(Me)(Me)—CH$_2$—N(Et)(Et) | —N(CH$_3$)— |
| IVb-7 | —OC(Me)(Me)—CH$_2$—N(Et)(Et) | —N(CH$_2$CH$_3$)— |
| IVb-8 | —OC(Me)(Me)—CH$_2$—N(Et)(Et) | —N(CH$_2$CH$_2$CH$_3$)— |
| IVb-9 | —OC(Me)(Me)—CH$_2$—N(Et)(Et) | —N(CH$_2$CH$_2$CH$_2$CH$_3$)— |
| IVb-10 | —OC(Me)(Me)—CH$_2$—N(Et)(Et) | —N(C(H)(CH$_3$)(CH$_2$CH$_3$))— |
| IVb-11 | —OC(Me)(Me)—CH$_2$—N(Et)(Et) | —N(C(H)(CH$_3$)$_2$)— |
| IVb-12 | —OC(Me)(Me)—CH$_2$—N(Et)(Et) | —N(CH$_2$C(H)(CH$_3$)$_2$)— |
| IVb-13 | —OC(Me)(Me)—CH$_2$—N(Et)(Et) | —N(C(CH$_3$)$_3$)— |
| IVb-14 | —OC(Me)(Me)—CH$_2$—N(Et)(Et) | —CH(OH)— |
| IVb-15 | —OC(Me)(Me)—CH$_2$—N(Et)(Et) | —N(C(O)N(H)—CH$_2$—CH$_2$—OH)— |
| IVb-16 | —OC(Me)(Me)—CH$_2$—N(Et)(Et) | —N(C(O)N(H)—CH$_2$—CH$_2$—F)— |
| IVb-17 | —OC(Me)(Me)—CH$_2$—N(Et)(Et) | —N(CH$_2$—CH$_2$—OH)— |
| IVb-18 | —OC(Me)(Me)—CH$_2$—N(Et)(Et) | —N(CH$_2$—CH$_2$—F)— |
| IVb-19 | —OC(Me)(Me)—CH$_2$—N(Et)(Et) | —N(CH$_2$—CH$_2$—OCH$_3$)— |
| IVb-20 | —OC(Me)(Me)—CH$_2$—N(Et)(Et) | —N(CH$_2$—CH$_2$—CF$_3$)— |
| IVb-21 | —OC(Me)(Me)—CH$_2$—N(Et)(Et) | —N(C(O)N(H)—CH$_2$—CH$_2$—OCH$_3$)— |
| IVb-22 | —OC(Me)(Me)—CH$_2$—N(Et)(Et) | —N(C(O)N(H)—CH$_2$—CH$_2$—CF$_3$)— |
| IVb-23 | —OC(Me)(Et)—CH$_2$—N(Et)(Et) | —O— |
| IVb-24 | —OC(Me)(Et)—CH$_2$—N(Et)(Et) | —CH$_2$— |
| IVb-25 | —OC(Me)(Et)—CH$_2$—N(Et)(Et) | —C(O)— |
| IVb-26 | —OC(Me)(Et)—CH$_2$—N(Et)(Et) | —NH— |
| IVb-27 | —OC(Me)(Et)—CH$_2$—N(Et)(Et) | —S— |
| IVb-28 | —OC(Me)(Et)—CH$_2$—N(Et)(Et) | —N(CH$_3$)— |
| IVb-29 | —OC(Me)(Et)—CH$_2$—N(Et)(Et) | —N(CH$_2$CH$_3$)— |
| IVb-30 | —OC(Me)(Et)—CH$_2$—N(Et)(Et) | —N(CH$_2$CH$_2$CH$_3$)— |
| IVb-31 | —OC(Me)(Et)—CH$_2$—N(Et)(Et) | —N(CH$_2$CH$_2$CH$_2$CH$_3$)— |
| IVb-32 | —OC(Me)(Et)—CH$_2$—N(Et)(Et) | —N(C(H)(CH$_3$)(CH$_2$CH$_3$))— |
| IVb-33 | —OC(Me)(Et)—CH$_2$—N(Et)(Et) | —N(C(H)(CH$_3$)$_2$)— |
| IVb-34 | —OC(Me)(Et)—CH$_2$—N(Et)(Et) | —N(CH$_2$C(H)(CH$_3$)$_2$)— |
| IVb-35 | —OC(Me)(Et)—CH$_2$—N(Et)(Et) | —N(C(CH$_3$)$_3$)— |
| IVb-36 | —OC(Me)(Et)—CH$_2$—N(Et)(Et) | —CH(OH)— |
| IVb-37 | —OC(Me)(Et)—CH$_2$—N(Et)(Et) | —N(C(O)N(H)—CH$_2$—CH$_2$—OH)— |
| IVb-38 | —OC(Me)(Et)—CH$_2$—N(Et)(Et) | —N(C(O)N(H)—CH$_2$—CH$_2$—F)— |
| IVb-39 | —OC(Me)(Et)—CH$_2$—N(Et)(Et) | —N(CH$_2$—CH$_2$—OH)— |
| IVb-40 | —OC(Me)(Et)—CH$_2$—N(Et)(Et) | —N(CH$_2$—CH$_2$—F)— |
| IVb-41 | —OC(Me)(Et)—CH$_2$—N(Et)(Et) | —N(CH$_2$—CH$_2$—OCH$_3$)— |
| IVb-42 | —OC(Me)(Et)—CH$_2$—N(Et)(Et) | —N(CH$_2$—CH$_2$—CF$_3$)— |
| IVb-43 | —OC(Me)(Et)—CH$_2$—N(Et)(Et) | —N(C(O)N(H)—CH$_2$—CH$_2$—OCH$_3$)— |
| IVb-44 | —OC(Me)(Et)—CH$_2$—N(Et)(Et) | —N(C(O)N(H)—CH$_2$—CH$_2$—CF$_3$)— |
| IVb-45 | —OC(Me)(Pr)—CH$_2$—N(Et)(Et) | —O— |
| IVb-46 | —OC(Me)(Pr)—CH$_2$—N(Et)(Et) | —CH$_2$— |
| IVb-47 | —OC(Me)(Pr)—CH$_2$—N(Et)(Et) | —C(O)— |
| IVb-48 | —OC(Me)(Pr)—CH$_2$—N(Et)(Et) | —NH— |
| IVb-49 | —OC(Me)(Pr)—CH$_2$—N(Et)(Et) | —S— |
| IVb-50 | —OC(Me)(Pr)—CH$_2$—N(Et)(Et) | —N(CH$_3$)— |
| IVb-51 | —OC(Me)(Pr)—CH$_2$—N(Et)(Et) | —N(CH$_2$CH$_3$)— |
| IVb-52 | —OC(Me)(Pr)—CH$_2$—N(Et)(Et) | —N(CH$_2$CH$_2$CH$_3$)— |
| IVb-53 | —OC(Me)(Pr)—CH$_2$—N(Et)(Et) | —N(CH$_2$CH$_2$CH$_2$CH$_3$)— |
| IVb-54 | —OC(Me)(Pr)—CH$_2$—N(Et)(Et) | —N(C(H)(CH$_3$)(CH$_2$CH$_3$))— |

-continued

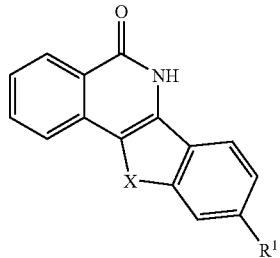
(IVb)

| Compound | —R¹ | X |
|---|---|---|
| IVb-55 | —OC(Me)(Pr)—CH₂—N(Et)(Et) | —N(C(H)(CH₃)₂)— |
| IVb-56 | —OC(Me)(Pr)—CH₂—N(Et)(Et) | —N(CH₂C(H)(CH₃)₂)— |
| IVb-57 | —OC(Me)(Pr)—CH₂—N(Et)(Et) | —N(C(CH₃)₃)— |
| IVb-58 | —OC(Me)(Pr)—CH₂—N(Et)(Et) | —CH(OH)— |
| IVb-59 | —OC(Me)(Pr)—CH₂—N(Et)(Et) | —N(C(O)N(H)—CH₂—CH₂—OH)— |
| IVb-60 | —OC(Me)(Pr)—CH₂—N(Et)(Et) | —N(C(O)N(H)—CH₂—CH₂—F)— |
| IVb-61 | —OC(Me)(Pr)—CH₂—N(Et)(Et) | —N(CH₂—CH₂—OH)— |
| IVb-62 | —OC(Me)(Pr)—CH₂—N(Et)(Et) | —N(CH₂—CH₂—F)— |
| IVb-63 | —OC(Me)(Pr)—CH₂—N(Et)(Et) | —N(CH₂—CH₂—OCH₃)— |
| IVb-64 | —OC(Me)(Pr)—CH₂—N(Et)(Et) | —N(CH₂—CH₂—CF₃)— |
| IVb-65 | —OC(Me)(Pr)—CH₂—N(Et)(Et) | —N(C(O)N(H)—CH₂—CH₂—OCH₃)— |
| IVb-66 | —OC(Me)(Pr)—CH₂—N(Et)(Et) | —N(C(O)N(H)—CH₂—CH₂—CF₃)— |
| IVb-67 | —OC(Me)(i-Pr)—CH₂—N(H)(cyclopropyl) | —O— |
| IVb-68 | —OC(Me)(i-Pr)—CH₂—N(H)(cyclopropyl) | —CH₂— |
| IVb-69 | —OC(Me)(i-Pr)—CH₂—N(H)(cyclopropyl) | —C(O)— |
| IVb-70 | —OC(Me)(i-Pr)—CH₂—N(H)(cyclopropyl) | —NH— |
| IVb-71 | —OC(Me)(i-Pr)—CH₂—N(H)(cyclopropyl) | —S— |
| IVb-72 | —OC(Me)(i-Pr)—CH₂—N(H)(cyclopropyl) | —N(CH₃)— |
| IVb-73 | —OC(Me)(i-Pr)—CH₂—N(H)(cyclopropyl) | —N(CH₂CH₃)— |
| IVb-74 | —OC(Me)(i-Pr)—CH₂—N(H)(cyclopropyl) | —N(CH₂CH₂CH₃)— |
| IVb-75 | —OC(Me)(i-Pr)—CH₂—N(H)(cyclopropyl) | —N(CH₂CH₂CH₂CH₃)— |
| IVb-76 | —OC(Me)(i-Pr)—CH₂—N(H)(cyclopropyl) | —N(C(H)(CH₃)(CH₂CH₃))— |
| IVb-77 | —OC(Me)(i-Pr)—CH₂—N(H)(cyclopropyl) | —N(C(H)(CH₃)₂)— |
| IVb-78 | —OC(Me)(i-Pr)—CH₂—N(H)(cyclopropyl) | —N(CH₂C(H)(CH₃)₂)— |
| IVb-79 | —OC(Me)(i-Pr)—CH₂—N(H)(cyclopropyl) | —N(C(CH₃)₃)— |
| IVb-80 | —OC(Me)(i-Pr)—CH₂—N(H)(cyclopropyl) | —CH(OH)— |
| IVb-81 | —OC(Me)(i-Pr)—CH₂—N(H)(cyclopropyl) | —N(C(O)N(H)—CH₂—CH₂—OH)— |
| IVb-82 | —OC(Me)(i-Pr)—CH₂—N(H)(cyclopropyl) | —N(C(O)N(H)—CH₂—CH₂—F)— |
| IVb-83 | —OC(Me)(i-Pr)—CH₂—N(H)(cyclopropyl) | —N(CH₂—CH₂—OH)— |
| IVb-84 | —OC(Me)(i-Pr)—CH₂—N(H)(cyclopropyl) | —N(CH₂—CH₂—F)— |
| IVb-85 | —OC(Me)(i-Pr)—CH₂—N(H)(cyclopropyl) | —N(CH₂—CH₂—OCH₃)— |
| IVb-86 | —OC(Me)(i-Pr)—CH₂—N(H)(cyclopropyl) | —N(CH₂—CH₂—CF₃)— |
| IVb-87 | —OC(Me)(i-Pr)—CH₂—N(H)(cyclopropyl) | —N(C(O)N(H)—CH₂—CH₂—OCH₃)— |
| IVb-88 | —OC(Me)(i-Pr)—CH₂—N(H)(cyclopropyl) | —N(C(O)N(H)—CH₂—CH₂—CF₃)— | and pharmaceutically acceptable salts thereof.

5.12 The Indenoisoquinolinone Analogs of Formula (IVc)

The present invention provides Indenoisoquinolinone Analogs according to Formula (IVc), below:

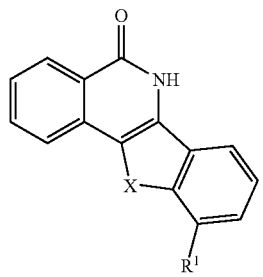

(IVc)

and pharmaceutically acceptable salts thereof,
wherein X and R$^1$ are as defined above for the Indenoisoquinolinone Analogs of Formula (IVc).

In one embodiment, X is —N(CH$_3$)—. In another embodiment, X is —N(CH$_2$CH$_3$)—. In another embodiment, X is —N(CH$_2$CH$_2$CH$_3$)—. In another embodiment, X is —N(CH$_2$CH$_2$CH$_2$CH$_3$)—. In another embodiment, X is —N(C(H)(CH$_3$)(CH$_2$CH$_3$))—. In another embodiment, X is —N(C(H)(CH$_3$)$_2$)—. In another embodiment, X is —N(CH$_2$C(H)(CH$_3$)$_2$)—. In another embodiment, X is —N(C(CH$_3$)$_3$)—.

In one embodiment, X is —O—. In one embodiment, X is —CH$_2$—. In one embodiment, X is —C(O)—. In one embodiment, X is —NH—. In one embodiment, X is —S—. In one embodiment, X is —CH(OH)—.

In one embodiment, each C$_1$-C$_3$ alkyl is independent of the other C$_1$-C$_3$ alkyl.

In one embodiment, each C$_1$-C$_3$ alkyl is methyl.

In one embodiment, each C$_1$-C$_3$ alkyl is methyl and X is —CH$_2$—.

In one embodiment, each C$_1$-C$_3$ alkyl is methyl and X is —CH(OH)—.

In one embodiment, each C$_1$-C$_3$ alkyl is methyl, X is —CH$_2$— and n is 1.

In one embodiment, each C$_1$-C$_3$ alkyl is methyl, X is —CH(OH)— and n is 1.

In another embodiment, X is —CH(OH)— and n is 1.

In another embodiment, X is —N(C(O)N(H)—(CH$_2$)$_p$—Z)—.

In another embodiment, X is —N(C(O)N(H)—(CH$_2$)—Z)—.

In another embodiment, X is —N(C(O)N(H)—(CH$_2$)$_2$—Z)—.

In another embodiment, X is —N(C(O)N(H)—(CH$_2$)$_p$—Z)— and n is 1.

In yet another embodiment, X is —N(C(O)N(H)—(CH$_2$)$_2$—Z)— and n is 2.

In still another embodiment, X is —N(C(O)N(H)—(CH$_2$)—Z)— and n is 1.

In one embodiment, X is —N((CH$_2$)$_q$—Z)—.
In another embodiment, X is —N((CH$_2$)—Z)—.
In another embodiment, X is —N((CH$_2$)$_2$—Z)—.
In another embodiment, X is —N((CH$_2$)$_q$—Z)— and n is 1.
In yet another embodiment, X is —N((CH$_2$)$_q$—Z)— and n is 2.
In still another embodiment, X is —N((CH$_2$)—Z)— and n is 1.
In still another embodiment, X is —N((CH$_2$)—Z)— and n is 2.

In one embodiment, Z is —CF$_3$.
In another embodiment, Z is —F.
In yet another embodiment, Z is —OH.
In still another embodiment, Z is —O—CH$_3$.

In another embodiment, X is —N(C(O)N(H)—(CH$_2$)$_p$—OH)—.
In another embodiment, X is —N(C(O)N(H)—(CH$_2$)$_2$—OH)—.
In another embodiment, X is —N(C(O)N(H)—(CH$_2$)$_p$—OH)— and n is 1.
In yet another embodiment, X is —N(C(O)N(H)—(CH$_2$)$_p$—OH)— and n is 2.
In still another embodiment, X is —N(C(O)N(H)—(CH$_2$)$_2$—OH)— and n is 1.
In still another embodiment, X is —N(C(O)N(H)—(CH$_2$)$_2$—OH)— and n is 2.

In one embodiment, X is —N((CH$_2$)$_q$—OH)—.
In another embodiment, X is —N((CH$_2$)$_2$—OH)—.
In another embodiment, X is —N((CH$_2$)$_q$—OH)— and n is 1.
In yet another embodiment, X is —N((CH$_2$)$_q$—OH)— and n is 2.
In still another embodiment, X is —N((CH$_2$)$_2$—OH)— and n is 1.

In another embodiment, X is —N(C(O)N(H)—(CH$_2$)$_p$—F)—.
In another embodiment, X is —N(C(O)N(H)—(CH$_2$)—F)—.
In another embodiment, X is —N(C(O)N(H)—(CH$_2$)$_p$—F)— and n is 1.
In yet another embodiment, X is —N(C(O)N(H)—(CH$_2$)$_p$—F)— n is 2.
In still another embodiment, X is —N(C(O)N(H)—(CH$_2$)—F)— and n is 1.

In one embodiment, X is —N((CH$_2$)$_q$—F)—.
In another embodiment, X is —N((CH$_2$)—F)—.
In another embodiment, X is —N((CH$_2$)$_q$—F)— and n is 1.
In yet another embodiment, X is —N((CH$_2$)$_q$—F)— and n is 2.
In still another embodiment, X is —N((CH$_2$)—F)— and n is 1.

In another embodiment, X is —N(C(O)N(H)—(CH$_2$)$_p$—OMe)-.
In another embodiment, X is —N(C(O)N(H)—(CH$_2$)$_2$—OMe)-.
In another embodiment, X is —N(C(O)N(H)—(CH$_2$)$_p$—OMe)- and n is 1.
In yet another embodiment, X is —N(C(O)N(H)—(CH$_2$)$_p$—OMe)- and n is 2.
In still another embodiment, X is —N(C(O)N(H)—(CH$_2$)$_2$—OMe)- and n is 1.

In one embodiment, X is —N((CH$_2$)$_q$—OMe)-.
In another embodiment, X is —N((CH$_2$)$_2$—OMe)-.
In another embodiment, X is —N((CH$_2$)$_q$—OMe)- and n is 1.
In yet another embodiment, X is —N((CH$_2$)$_q$—OMe)- and n is 2.
In still another embodiment, X is —N((CH$_2$)$_2$—OMe)- and n is 1.

In another embodiment, X is —N(C(O)N(H)—(CH$_2$)$_p$—CF$_3$)—.
In another embodiment, X is —N(C(O)N(H)—(CH$_2$)—CF$_3$)—.

In another embodiment, X is —N(C(O)N(H)—(CH$_2$)$_p$—CF$_3$)— and n is 1.

In yet another embodiment, X is —N(C(O)N(H)—(CH$_2$)$_p$—CF$_3$)— and n is 2.

In still another embodiment, X is —N(C(O)N(H)—(CH$_2$)—CF$_3$)— and n is 1.

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and n is 1.

In yet another embodiment, X is —N((CH$_2$)$_q$—CF$_3$)— and n is 2.

In still another embodiment, X is —N((CH$_2$)—CF$_3$)— and n is 1.

In another embodiment, X is —N(C(O)N(H)—(CH$_2$)$_p$—CF$_3$)—.

In another embodiment, X is —N(C(O)N(H)—(CH$_2$)—CF$_3$)—.

In another embodiment, X is —N(C(O)N(H)—(CH$_2$)$_p$—CF$_3$)— and n is 1.

In yet another embodiment, X is —N(C(O)N(H)—(CH$_2$)$_p$—CF$_3$)— and n is 2.

In still another embodiment, X is —N(C(O)N(H)—(CH$_2$)—CF$_3$)— and n is 1.

In one embodiment, X is —N((CH$_2$)$_q$—CF$_3$)—.

In another embodiment, X is —N((CH$_2$)—CF$_3$)—.

In another embodiment, X is —N((CH$_2$)$_q$—CF$_3$)— and n is 1.

In yet another embodiment, X is —N((CH$_2$)$_q$—CF$_3$)— and n is 2.

In still another embodiment, X is —N((CH$_2$)—CF$_3$)— and n is 1.

In one embodiment, n is 1.

In another embodiment, n is 2.

In yet another embodiment, n is 3.

In a further embodiment, n is 4, 5, or 6.

In yet a further embodiment, n is 7, 8, or 9.

In still a further embodiment, n is 10.

In one embodiment, p is 1.

In another embodiment, p is 2.

In yet another embodiment, p is an integer ranging from 2 to 5.

In one embodiment, q is 1.

In another embodiment, q is 2.

In yet another embodiment, q is an integer ranging from 2 to 5.

In one embodiment, n is 1 and X is —N(CH$_3$)—.

In another embodiment, n is 1 and X is —N(CH$_2$CH$_3$).

In another embodiment, n is 1 and X is —N(CH$_2$CH$_2$CH$_3$)—.

In another embodiment, n is 1 and X is —N(CH$_2$CH$_2$CH$_2$CH$_3$)—.

In another embodiment, n is 1 and X is —N(C(H)(CH$_3$)(CH$_2$CH$_3$))—.

In another embodiment, n is 1 and X is —N(C(H)(CH$_3$)$_2$)—.

In another embodiment, n is 1 and X is —N(CH$_2$C(H)(CH$_3$)$_2$)—.

In another embodiment, n is 1 and X is —N(C(CH$_3$)$_3$)—.

In one embodiment, one R$^2$ is —H, and the other R$^2$ is —C$_1$-C$_6$ alkyl.

In another embodiment, each R$^2$ is —C$_1$-C$_6$ alkyl.

In another embodiment, each R$^2$ is -methyl.

In various embodiments, —N(R$^2$)(R$^2$) is:

[Chemical structures shown including: morpholine, piperidine, 4-hydroxypiperidine, 4-methylpiperazine, 4-ethylpiperazine, piperazine, azepane, 4-(2-(dimethylamino)ethyl)piperazine, 4-(4-fluorophenyl)piperazine, N-(4-morpholinobenzyl)amine, 4-benzylpiperazine, 4-(carboxymethyl)piperazine, 4-(ethoxycarbonylmethyl)piperazine, 4-(N-isopropylcarbamoylmethyl)piperazine, 4-(4-X-phenyl)-1,2,3,6-tetrahydropyridine]

where X = —H, —OMe, —CN, —F, —Cl, —Br, or —I

[Additional structures: pyrrolidine, 2-(hydroxymethyl)pyrrolidine, 2-((dimethylamino)methyl)imidazole, 2-(hydroxymethyl)imidazole, imidazole, N,N-dimethylamine, N,N-diethylamine, N,N-bis(2-hydroxyethyl)amine, N,N-bis(2-(dimethylamino)ethyl)amine, N-benzyl-N-methylamine]

-continued
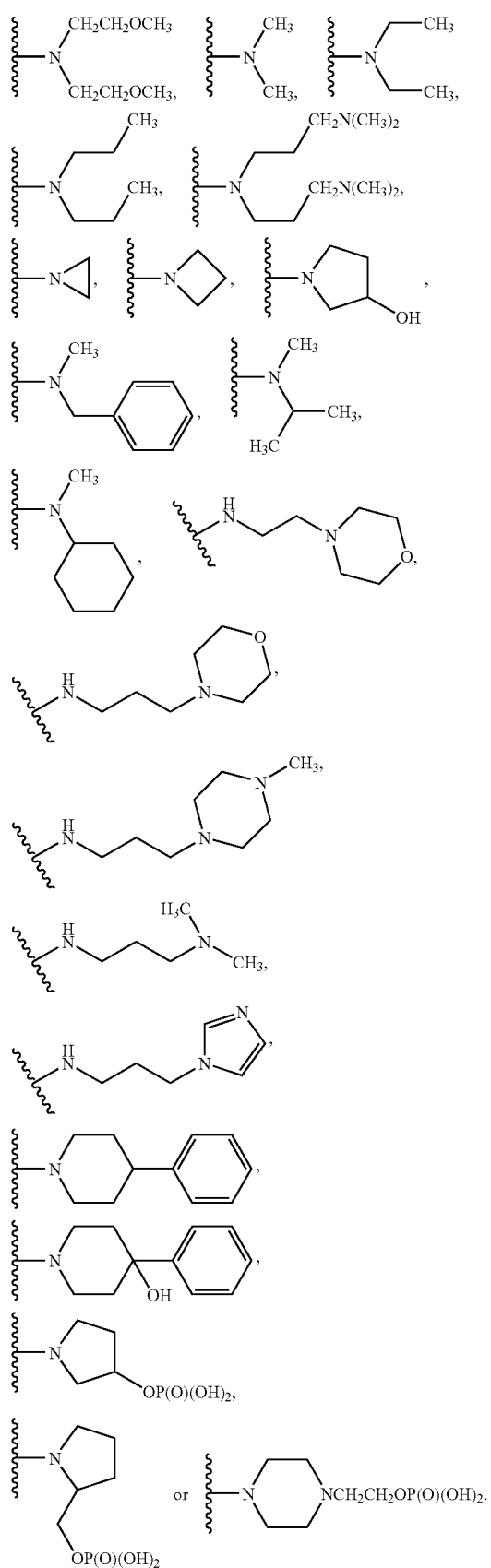
In other embodiments, —N(R²)(R²) is:
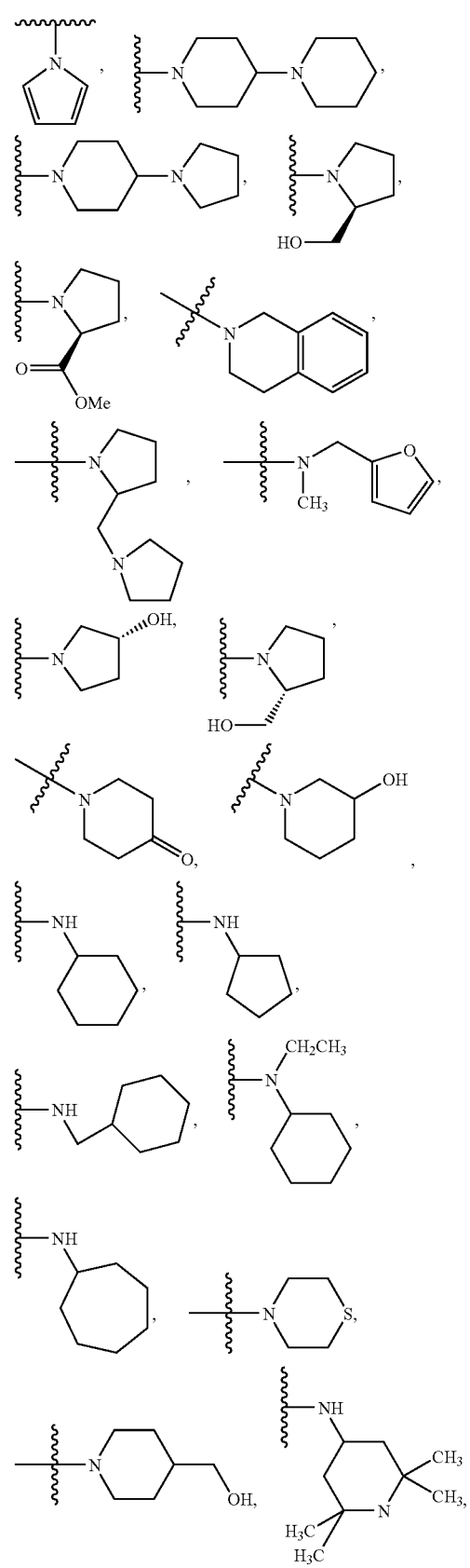

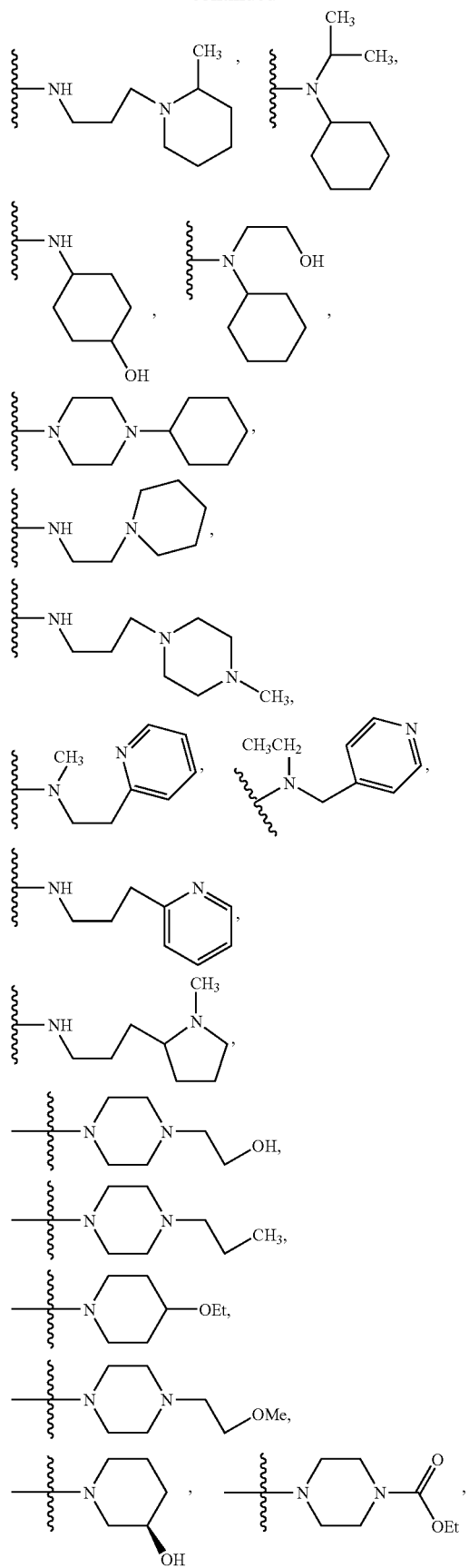
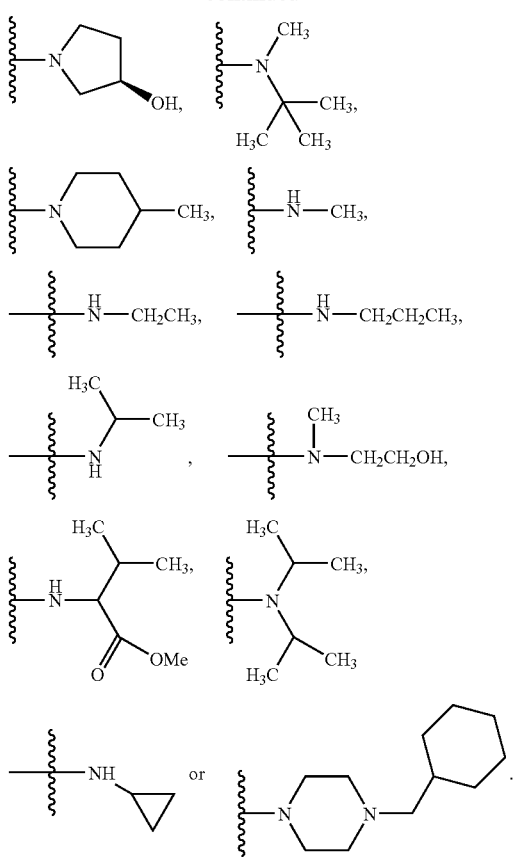
In some embodiments, —N(R²)(R²) is

-continued
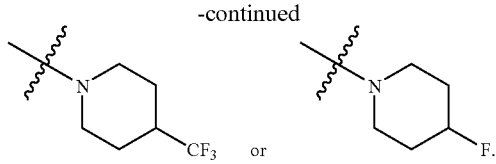
In still other embodiments, —N(R²)(R²) is
—N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.
In some embodiments, —N(R²)(R²) is
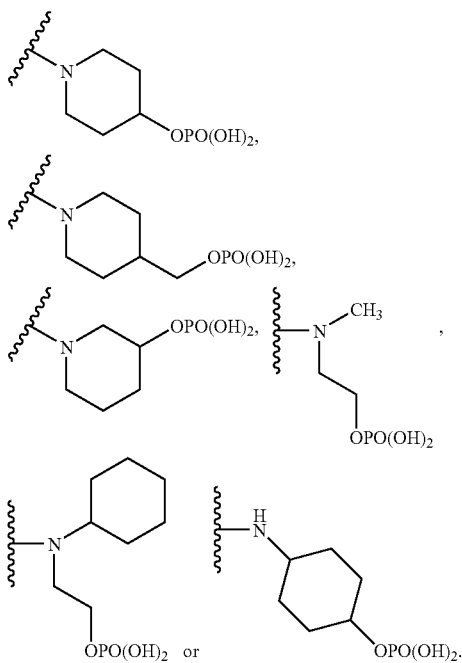
In various embodiments, —N(Z₃)(Z₄) is:
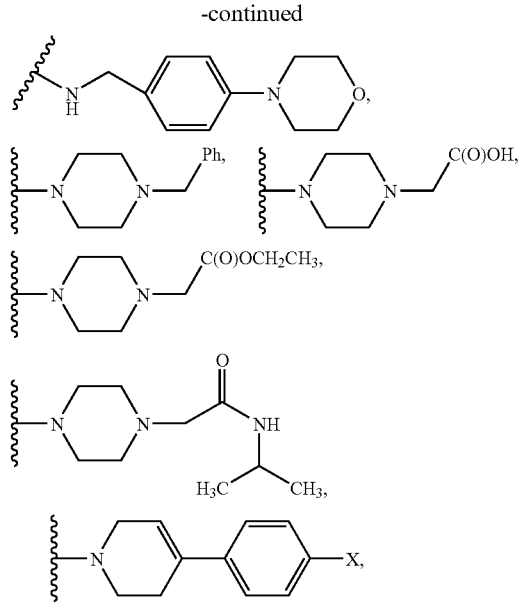
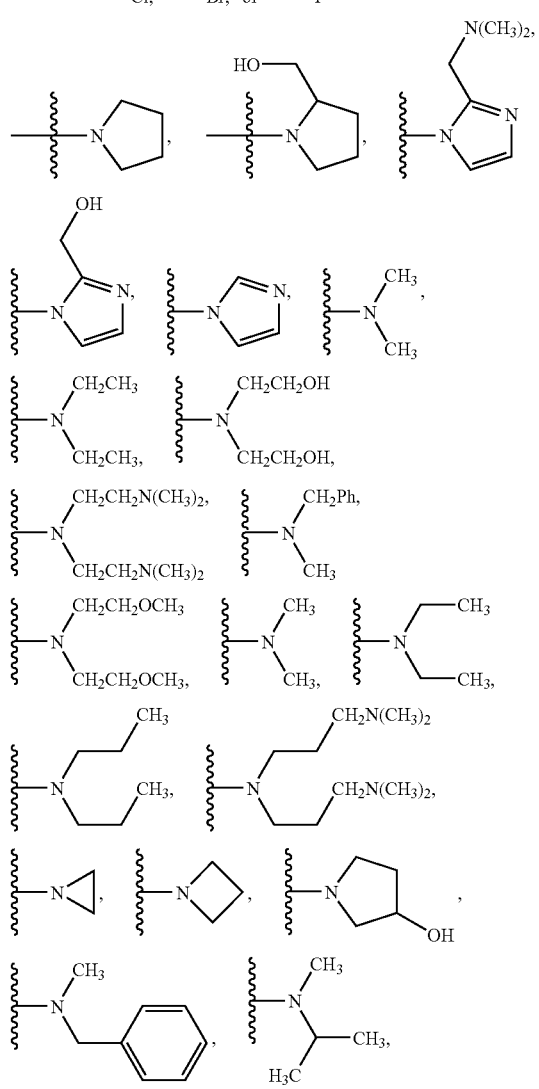
where X = —H, —OMe, —CN, —F, —Cl, —Br, or —I

1023
-continued
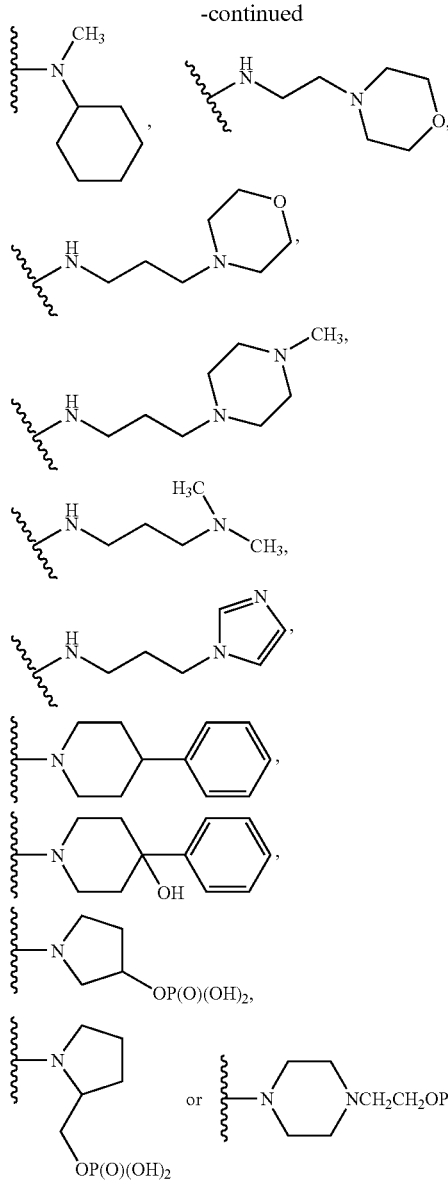
In other embodiments, —N(Z₃)(Z₄) is:
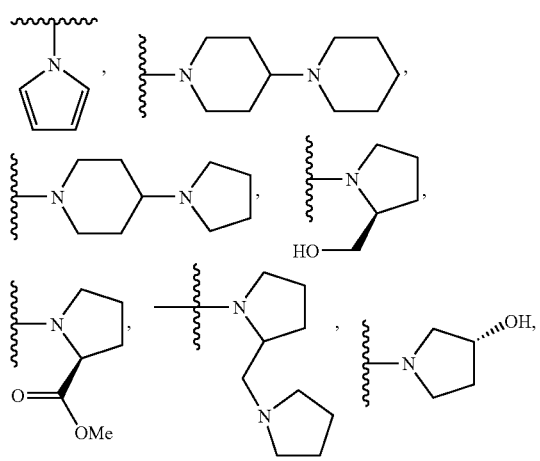
1024
-continued
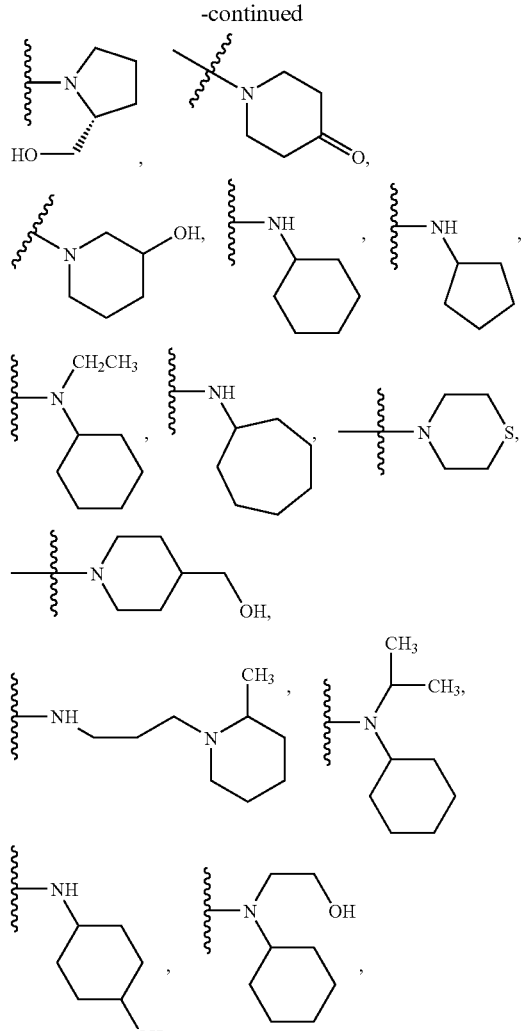
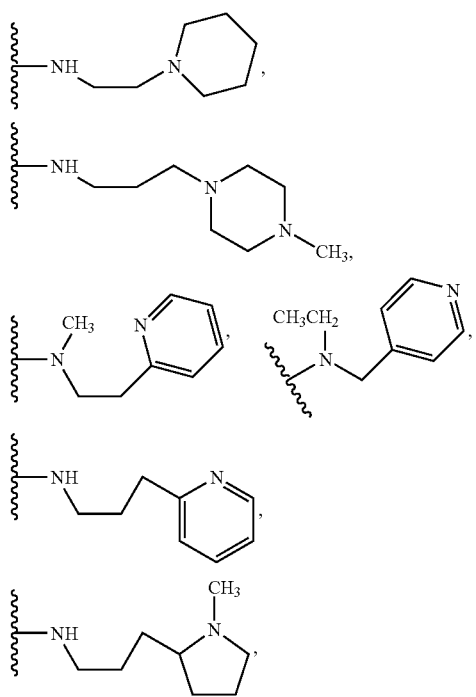

-continued

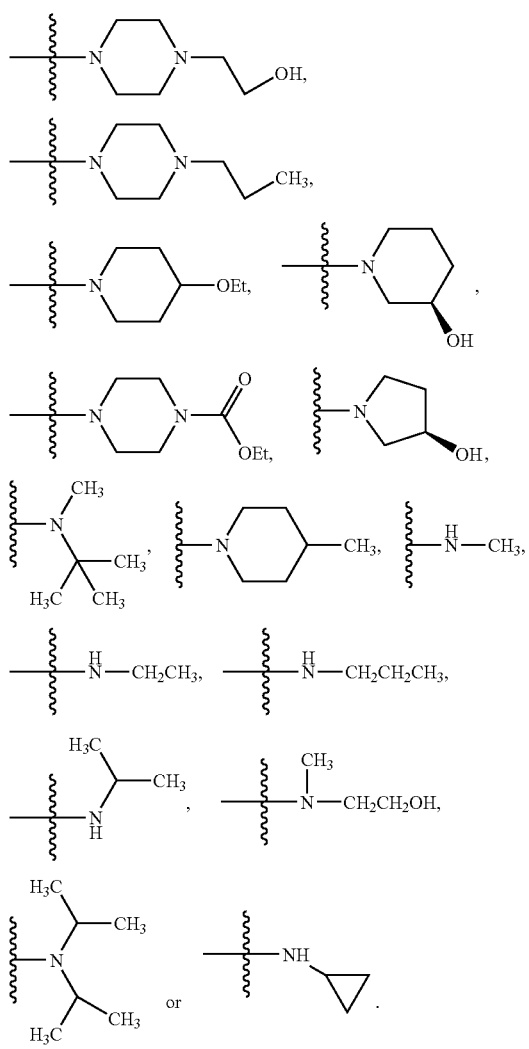

In some embodiments, —N(Z₃)(Z₄) is

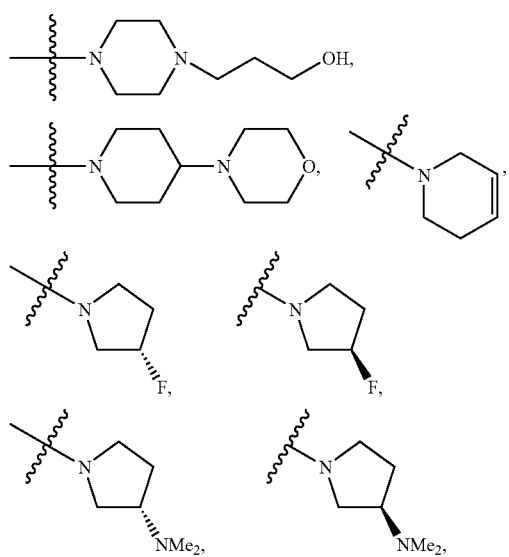

-continued

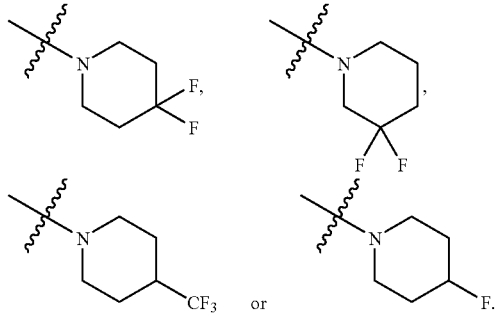

In still other embodiments, —N(Z₃)(Z₄) is
—N(CH₂CH₃)(CH₃),
—N(CH₂CH₂CH₃)(CH₃),
—N(CH₂CH₂CH₂CH₃)(CH₃),
—NH—CH₂CH₂CH₂CH₃, or
—NH—CH₂CH₂—O—CH₃.
In some embodiments, —N(Z₃)(Z₄) is

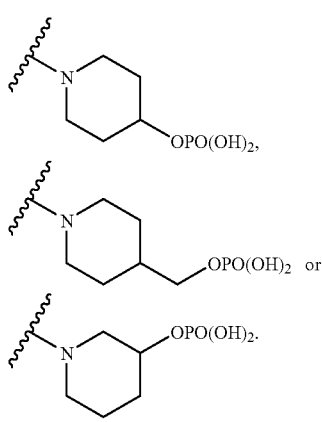

In one embodiment, X is —N(CH₃)—, —N(CH₂CH₃)—, —N(CH₂CH₂CH₃)—, —N(CH₂ CH₂CH₂CH₃)—, —N(C(H)(CH₃)(CH₂CH₃))—, —N(C(H)(CH₃)₂)—, —N(CH₂C(H)(CH₃)₂— or —N(C(CH₃)₃)—;

n is an integer ranging from 1 to 3;

each $R^2$ is independently —H, —$C_1$-$C_6$ alkyl, cyclopropyl, cyclobutyl, cyclopentyl, cyclohexyl, —($C_1$-$C_6$ alkylene)-phenyl or -phenyl, each of which other than hydrogen is unsubstituted or substituted with one or more of -halo, —OH, —OP(O)(OH)₂, —OS(O)₂OH or —N(Z₃)(Z₄), where $Z_3$ and $Z_4$ are independently —H, —$C_1$-$C_5$ alkyl, or —($C_1$-$C_5$ alkylene)-O—$C_1$-$C_5$ alkyl, each of which other than hydrogen is unsubstituted or substituted with one or more of -halo, —OH or —NH₂;

or N, $Z_3$ and $Z_4$ are taken together to form a nitrogen-containing 3- to 7-membered monocyclic heterocycle which is unsubstituted or substituted with one to three of —$C_1$-$C_5$ alkyl, -phenyl, —($C_1$-$C_5$ alkylene)-phenyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)₂, —($C_1$-$C_5$ alkylene)-N($R^a$)₂, —$C_1$-$C_5$ alkylene-C(O)O—($C_1$-$C_5$ alkylene)-N($R^a$)₂, —COOH, —($C_1$-$C_5$ alkylene)-COOH, —OP(O)(OH)₂, —OS(O)₂OH, —($C_1$-$C_5$ alkylene)-OP(O)(OH)₂, —($C_1$-$C_5$ alkylene)-OS(O)₂OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)$NH_2$, or —$NO_2$, wherein each occurrence of $R^a$ is independently —H, -benzyl, or —$C_1$-$C_{10}$ alkyl;

or N and both $R^2$ groups are taken together to form a nitrogen-containing 3- to 7-membered monocyclic heterocycle which is unsubstituted or substituted with one to three of —$C_1$-$C_5$ alkyl, -phenyl, —($C_1$-$C_5$ alkylene)-phenyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —($C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)$NH_2$, or —$NO_2$, wherein each occurrence of $R^a$ is independently —H, -benzyl, or —$C_1$-$C_{10}$ alkyl.

In one embodiment, X is —N($CH_3$)—, —N($CH_2CH_3$)—, —N($CH_2CH_2CH_3$)—, —N($CH_2$ $CH_2CH_2CH_3$)—, —N(C(H)($CH_3$)($CH_2CH_3$))—, —N(C(H)($CH_3$)$_2$)—, —N($CH_2$C(H)($CH_3$)$_2$— or —N(C($CH_3$)$_3$)—;

n is an integer ranging from 1 to 3; and at least one $C_1$-$C_3$ alkyl is methyl.

In another embodiment, X is —N($CH_3$)—, —N($CH_2CH_3$)—, —N($CH_2CH_2CH_3$)—, —N($CH_2CH_2CH_2CH_3$)—, —N(C(H)($CH_3$)($CH_2CH_3$))—, —N(C(H)($CH_3$)$_2$)—, —N($CH_2$C(H)($CH_3$)$_2$— or —N(C($CH_3$)$_3$)—; at least one $C_1$-$C_3$ alkyl is methyl; and at least one $R^2$ is ethyl.

In yet another embodiment, X is —N($CH_3$)—, —N($CH_2CH_3$)—, —N($CH_2CH_2CH_3$)—, —N($CH_2CH_2CH_2CH_3$)—, —N(C(H)($CH_3$)($CH_2CH_3$))—, —N(C(H)($CH_3$)$_2$)—, —N($CH_2$C(H)($CH_3$)$_2$— or —N(C($CH_3$)$_3$)—; at least one $C_1$-$C_3$ alkyl is methyl; and at least one $R^2$ is propyl.

In one embodiment, X is —N($CH_3$)—, —N($CH_2CH_3$)—, —N($CH_2CH_2CH_3$)—, —N($CH_2$ $CH_2CH_2CH_3$)—, —N(C(H)($CH_3$)($CH_2CH_3$))—, —N(C(H)($CH_3$)$_2$)—, —N($CH_2$C(H)($CH_3$)$_2$— or —N(C($CH_3$)$_3$)—; at least one $C_1$-$C_3$ alkyl is methyl; and at least one $R^2$ is —$C_3$-$C_8$ monocyclic cycloalkyl.

In another embodiment, X is —N($CH_3$)—, —N($CH_2CH_3$)—, —N($CH_2CH_2CH_3$)—, —N($CH_2$ $CH_2CH_2CH_3$)—, —N(C(H)($CH_3$)($CH_2CH_3$))—, —N(C(H)($CH_3$)$_2$)—, —N($CH_2$C(H)($CH_3$)$_2$— or —N(C($CH_3$)$_3$)—; at least one $C_1$-$C_3$ alkyl is methyl; and at least one $R^2$ is cyclohexyl.

In yet another embodiment, X is —N($CH_3$)—, —N($CH_2CH_3$)—, —N($CH_2CH_2CH_3$)—, —N($CH_2CH_2CH_2CH_3$)—, —N(C(H)($CH_3$)($CH_2CH_3$))—, —N(C(H)($CH_3$)$_2$)—, —N($CH_2$C(H)($CH_3$)$_2$— or —N(C($CH_3$)$_3$)—; and at least one $C_1$-$C_3$ alkyl is methyl, wherein N and both $R^2$ groups are taken together to form a nitrogen-containing 3- to 7-membered monocyclic heterocycle.

In one embodiment, X is —N($CH_3$)—, —N($CH_2CH_3$)—, —N($CH_2CH_2CH_3$)—, —N($CH_2$ $CH_2CH_2CH_3$)—, —N(C(H)($CH_3$)($CH_2CH_3$))—, —N(C(H)($CH_3$)$_2$)—, —N($CH_2$C(H)($CH_3$)$_2$— or —N(C($CH_3$)$_3$)—; and at least one $C_1$-$C_3$ alkyl is methyl, wherein N and both $R^2$ groups are taken together to form a nitrogen-containing 3- to 7-membered monocyclic heterocycle, which is substituted with a hydroxyl.

In another embodiment, X is —N($CH_3$)—, —N($CH_2CH_3$)—, —N($CH_2CH_2CH_3$)—, —N($CH_2$ $CH_2CH_2CH_3$)—, —N(C(H)($CH_3$)($CH_2CH_3$))—, —N(C(H)($CH_3$)$_2$)—, —N($CH_2$C(H)($CH_3$)$_2$— or —N(C($CH_3$)$_3$)—; and at least one $C_1$-$C_3$ alkyl is methyl, wherein N and both $R^2$ groups are taken together to form a nitrogen-containing 3- to 7-membered monocyclic heterocycle, which is substituted with a nitrogen-containing 3- to 7-membered monocyclic heterocycle.

Illustrative examples of the Indenoisoquinolinone Analogs include the compounds of Formula (IVc) as set forth below:

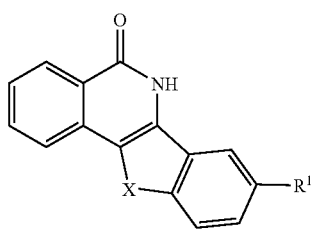

(IVc)

| Compound | —$R^1$ | X |
|---|---|---|
| IVb-1 | —OC(Me)(Me)—$CH_2$—N(Et)(Et) | —O— |
| IVc-2 | —OC(Me)(Me)—$CH_2$—N(Et)(Et) | —$CH_2$— |
| IVc-3 | —OC(Me)(Me)—$CH_2$—N(Et)(Et) | —C(O)— |
| IVc-4 | —OC(Me)(Me)—$CH_2$—N(Et)(Et) | —NH— |
| IVc-5 | —OC(Me)(Me)—$CH_2$—N(Et)(Et) | —S— |
| IVc-6 | —OC(Me)(Me)—$CH_2$—N(Et)(Et) | —N($CH_3$)— |
| IVc-7 | —OC(Me)(Me)—$CH_2$—N(Et)(Et) | —N($CH_2CH_3$)— |
| IVc-8 | —OC(Me)(Me)—$CH_2$—N(Et)(Et) | —N($CH_2CH_2CH_3$)— |
| IVc-9 | —OC(Me)(Me)—$CH_2$—N(Et)(Et) | —N($CH_2CH_2CH_2CH_3$)— |
| IVc-10 | —OC(Me)(Me)—$CH_2$—N(Et)(Et) | —N(C(H)($CH_3$)($CH_2CH_3$))— |
| IVc-11 | —OC(Me)(Me)—$CH_2$—N(Et)(Et) | —N(C(H)($CH_3$)$_2$)— |
| IVc-12 | —OC(Me)(Me)—$CH_2$—N(Et)(Et) | —N($CH_2$C(H)($CH_3$)$_2$)— |
| IVc-13 | —OC(Me)(Me)—$CH_2$—N(Et)(Et) | —N(C($CH_3$)$_3$)— |
| IVc-14 | —OC(Me)(Me)—$CH_2$—N(Et)(Et) | —CH(OH)— |
| IVc-15 | —OC(Me)(Me)—$CH_2$—N(Et)(Et) | —N(C(O)N(H)—$CH_2$—$CH_2$—OH)— |
| IVc-16 | —OC(Me)(Me)—$CH_2$—N(Et)(Et) | —N(C(O)N(H)—$CH_2$—$CH_2$—F)— |
| IVc-17 | —OC(Me)(Me)—$CH_2$—N(Et)(Et) | —N($CH_2$—$CH_2$—OH)— |
| IVc-18 | —OC(Me)(Me)—$CH_2$—N(Et)(Et) | —N($CH_2$—$CH_2$—F)— |

-continued

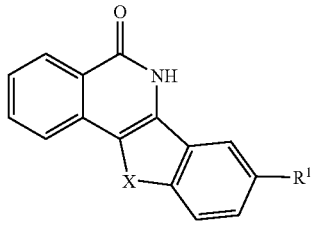
(IVc)

| Compound | —R¹ | X |
|---|---|---|
| IVc-19 | —OC(Me)(Me)—CH₂—N(Et)(Et) | —N(CH₂—CH₂—OCH₃)— |
| IVc-20 | —OC(Me)(Me)—CH₂—N(Et)(Et) | —N(CH₂—CH₂—CF₃)— |
| IVc-21 | —OC(Me)(Me)—CH₂—N(Et)(Et) | —N(C(O)N(H)—CH₂—CH₂—OCH₃)— |
| IVc-22 | —OC(Me)(Me)—CH₂—N(Et)(Et) | —N(C(O)N(H)—CH₂—CH₂—CF₃)— |
| IVc-23 | —OC(Me)(Et)—CH₂—N(Et)(Et) | —O— |
| IVc-24 | —OC(Me)(Et)—CH₂—N(Et)(Et) | —CH₂— |
| IVc-25 | —OC(Me)(Et)—CH₂—N(Et)(Et) | —C(O)— |
| IVc-26 | —OC(Me)(Et)—CH₂—N(Et)(Et) | —NH— |
| IVc-27 | —OC(Me)(Et)—CH₂—N(Et)(Et) | —S— |
| IVc-28 | —OC(Me)(Et)—CH₂—N(Et)(Et) | —N(CH₃)— |
| IVc-29 | —OC(Me)(Et)—CH₂—N(Et)(Et) | —N(CH₂CH₃)— |
| IVc-30 | —OC(Me)(Et)—CH₂—N(Et)(Et) | —N(CH₂CH₂CH₃)— |
| IVc-31 | —OC(Me)(Et)—CH₂—N(Et)(Et) | —N(CH₂CH₂CH₂CH₃)— |
| IVc-32 | —OC(Me)(Et)—CH₂—N(Et)(Et) | —N(C(H)(CH₃)(CH₂CH₃))— |
| IVc-33 | —OC(Me)(Et)—CH₂—N(Et)(Et) | —N(C(H)(CH₃)₂)— |
| IVc-34 | —OC(Me)(Et)—CH₂—N(Et)(Et) | —N(CH₂C(H)(CH₃)₂)— |
| IVc-35 | —OC(Me)(Et)—CH₂—N(Et)(Et) | —N(C(CH₃)₃)— |
| IVc-36 | —OC(Me)(Et)—CH₂—N(Et)(Et) | —CH(OH)— |
| IVc-37 | —OC(Me)(Et)—CH₂—N(Et)(Et) | —N(C(O)N(H)—CH₂—CH₂—OH)— |
| IVc-38 | —OC(Me)(Et)—CH₂—N(Et)(Et) | —N(C(O)N(H)—CH₂—CH₂—F)— |
| IVc-39 | —OC(Me)(Et)—CH₂—N(Et)(Et) | —N(CH₂—CH₂—OH)— |
| IVc-40 | —OC(Me)(Et)—CH₂—N(Et)(Et) | —N(CH₂—CH₂—F)— |
| IVc-41 | —OC(Me)(Et)—CH₂—N(Et)(Et) | —N(CH₂—CH₂—OCH₃)— |
| IVc-42 | —OC(Me)(Et)—CH₂—N(Et)(Et) | —N(CH₂—CH₂—CF₃)— |
| IVc-43 | —OC(Me)(Et)—CH₂—N(Et)(Et) | —N(C(O)N(H)—CH₂—CH₂—OCH₃)— |
| IVc-44 | —OC(Me)(Et)—CH₂—N(Et)(Et) | —N(C(O)N(H)—CH₂—CH₂—CF₃)— |
| IVc-45 | —OC(Me)(Pr)—CH₂—N(Et)(Et) | —O— |
| IVc-46 | —OC(Me)(Pr)—CH₂—N(Et)(Et) | —CH₂— |
| IVc-47 | —OC(Me)(Pr)—CH₂—N(Et)(Et) | —C(O)— |
| IVc-48 | —OC(Me)(Pr)—CH₂—N(Et)(Et) | —NH— |
| IVc-49 | —OC(Me)(Pr)—CH₂—N(Et)(Et) | —S— |
| IVc-50 | —OC(Me)(Pr)—CH₂—N(Et)(Et) | —N(CH₃)— |
| IVc-51 | —OC(Me)(Pr)—CH₂—N(Et)(Et) | —N(CH₂CH₃)— |
| IVc-52 | —OC(Me)(Pr)—CH₂—N(Et)(Et) | —N(CH₂CH₂CH₃)— |
| IVc-53 | —OC(Me)(Pr)—CH₂—N(Et)(Et) | —N(CH₂CH₂CH₂CH₃)— |
| IVc-54 | —OC(Me)(Pr)—CH₂—N(Et)(Et) | —N(C(H)(CH₃)(CH₂CH₃))— |
| IVc-55 | —OC(Me)(Pr)—CH₂—N(Et)(Et) | —N(C(H)(CH₃)₂)— |
| IVc-56 | —OC(Me)(Pr)—CH₂—N(Et)(Et) | —N(CH₂C(H)(CH₃)₂)— |
| IVc-57 | —OC(Me)(Pr)—CH₂—N(Et)(Et) | —N(C(CH₃)₃)— |
| IVc-58 | —OC(Me)(Pr)—CH₂—N(Et)(Et) | —CH(OH)— |
| IVc-59 | —OC(Me)(Pr)—CH₂—N(Et)(Et) | —N(C(O)N(H)—CH₂—CH₂—OH)— |
| IVc-60 | —OC(Me)(Pr)—CH₂—N(Et)(Et) | —N(C(O)N(H)—CH₂—CH₂—F)— |
| IVc-61 | —OC(Me)(Pr)—CH₂—N(Et)(Et) | —N(CH₂—CH₂—OH)— |
| IVc-62 | —OC(Me)(Pr)—CH₂—N(Et)(Et) | —N(CH₂—CH₂—F)— |
| IVc-63 | —OC(Me)(Pr)—CH₂—N(Et)(Et) | —N(CH₂—CH₂—OCH₃)— |
| IVc-64 | —OC(Me)(Pr)—CH₂—N(Et)(Et) | —N(CH₂—CH₂—CF₃)— |
| IVc-65 | —OC(Me)(Pr)—CH₂—N(Et)(Et) | —N(C(O)N(H)—CH₂—CH₂—OCH₃)— |
| IVc-66 | —OC(Me)(Pr)—CH₂—N(Et)(Et) | —N(C(O)N(H)—CH₂—CH₂—CF₃)— |
| IVc-67 | —OC(Me)(i-Pr)—CH₂—N(H)(cyclopropyl) | —O— |
| IVc-68 | —OC(Me)(i-Pr)—CH₂—N(H)(cyclopropyl) | —CH₂— |
| IVc-69 | —OC(Me)(i-Pr)—CH₂—N(H)(cyclopropyl) | —C(O)— |
| IVc-70 | —OC(Me)(i-Pr)—CH₂—N(H)(cyclopropyl) | —NH— |
| IVc-71 | —OC(Me)(i-Pr)—CH₂—N(H)(cyclopropyl) | —S— |
| IVc-72 | —OC(Me)(i-Pr)—CH₂—N(H)(cyclopropyl) | —N(CH₃)— |
| IVc-73 | —OC(Me)(i-Pr)—CH₂—N(H)(cyclopropyl) | —N(CH₂CH₃)— |
| IVc-74 | —OC(Me)(i-Pr)—CH₂—N(H)(cyclopropyl) | —N(CH₂CH₂CH₃)— |
| IVc-75 | —OC(Me)(i-Pr)—CH₂— | —N(CH₂CH₂CH₂CH₃)— |

-continued (IVc)

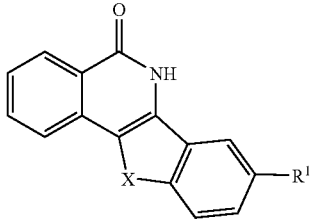

| Compound | —R[1] | X |
|---|---|---|
| IVc-76 | —OC(Me)(i-Pr)—CH$_2$—N(H)(cyclopropyl) | —N(C(H)(CH$_3$)(CH$_2$CH$_3$))— |
| IVc-77 | —OC(Me)(i-Pr)—CH$_2$—N(H)(cyclopropyl) | —N(C(H)(CH$_3$)$_2$)— |
| IVc-78 | —OC(Me)(i-Pr)—CH$_2$—N(H)(cyclopropyl) | —N(CH$_2$C(H)(CH$_3$)$_2$)— |
| IVc-79 | —OC(Me)(i-Pr)—CH$_2$—N(H)(cyclopropyl) | —N(C(CH$_3$)$_3$)— |
| IVc-80 | —OC(Me)(i-Pr)—CH$_2$—N(H)(cyclopropyl) | —CH(OH)— |
| IVc-81 | —OC(Me)(i-Pr)—CH$_2$—N(H)(cyclopropyl) | —N(C(O)N(H)—CH$_2$—CH$_2$—OH)— |
| IVc-82 | —OC(Me)(i-Pr)—CH$_2$—N(H)(cyclopropyl) | —N(C(O)N(H)—CH$_2$—CH$_2$—F)— |
| IVc-83 | —OC(Me)(i-Pr)—CH$_2$—N(H)(cyclopropyl) | —N(CH$_2$—CH$_2$—OH)— |
| IVc-84 | —OC(Me)(i-Pr)—CH$_2$—N(H)(cyclopropyl) | —N(CH$_2$—CH$_2$—F)— |
| IVc-85 | —OC(Me)(i-Pr)—CH$_2$—N(H)(cyclopropyl) | —N(CH$_2$—CH$_2$—OCH$_3$)— |
| IVc-86 | —OC(Me)(i-Pr)—CH$_2$—N(H)(cyclopropyl) | —N(CH$_2$—CH$_2$—CF$_3$)— |
| IVc-87 | —OC(Me)(i-Pr)—CH$_2$—N(H)(cyclopropyl) | —N(C(O)N(H)—CH$_2$—CH$_2$—OCH$_3$)— |
| IVc-88 | —OC(Me)(i-Pr)—CH$_2$—N(H)(cyclopropyl) | —N(C(O)N(H)—CH$_2$—CH$_2$—CF$_3$)— | and pharmaceutically acceptable salts thereof.

5.13 The Indenoisoquinolinone Analogs of Formula (Va)

The present invention provides Indenoisoquinolinone Analogs according to Formula (Va), below:

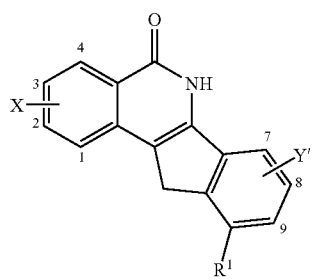

(Va)

and pharmaceutically acceptable salts thereof,
wherein R[1], X and Y' are as defined above for the Indenoisoquinolinone Analogs of Formula (Va).

In one embodiment, R[1] is —(CH$_2$)$_n$—NHR$^2$ and R$^2$ is a —C$_3$-C$_8$ monocyclic cycloalkyl.

In another embodiment, R[1] is —(CH$_2$)$_n$—NHR$^2$ and R$^2$ is a —C$_3$-C$_8$ monocyclic cycloalkyl substituted with one or more of -(hydroxy-substituted) C$_1$-C$_5$ alkyl.

In one embodiment, R[1] is —(CH$_2$)$_n$—NHR$^2$, R$^2$ is a —C$_3$-C$_8$ monocyclic cycloalkyl, and X is fluoro.

In one embodiment, R[1] is —(CH$_2$)$_n$—NHR$^2$, R$^2$ is a —C$_3$-C$_8$ monocyclic cycloalkyl, and X is chloro.

In one embodiment, R[1] is —(CH$_2$)$_n$—NHR$^2$ and R$^2$ is cyclopentyl.

In another embodiment, R[1] is —(CH$_2$)$_n$—NHR$^2$, R$^2$ is a —C$_3$-C$_8$ monocyclic cycloalkyl substituted with one or more of -(hydroxy-substituted) C$_1$-C$_5$ alkyl, and X is fluoro.

In another embodiment, R[1] is —(CH$_2$)$_n$—NHR$^2$, R$^2$ is cyclopentyl substituted with one or more of -(hydroxy-substituted C$_1$-C$_5$ alkyl), and X is fluoro.

In one embodiment, R[1] is —(CH$_2$)$_n$—NHR$^2$, R$^2$ is a —C$_3$-C$_8$ monocyclic cycloalkyl, and Y' is fluoro.

In another embodiment, R[1] is —(CH$_2$)$_n$—NHR$^2$, R$^2$ is a —C$_3$-C$_8$ monocyclic cycloalkyl substituted with one or more of -(hydroxy-substituted C$_1$-C$_5$ alkyl), and Y' is fluoro.

In another embodiment, R[1] is —(CH$_2$)$_n$—NHR$^2$, R$^2$ is a —C$_3$-C$_8$ monocyclic cycloalkyl substituted with one or more of -(hydroxy-substituted) C$_1$-C$_5$ alkyl, and X and Y' are fluoro.

In another embodiment, $R^1$ is —$(CH_2)_n$—$NHR^2$, $R^2$ is a 3- to 7-membered monocyclic heterocycle, and X is fluoro.

In another embodiment, $R^1$ is —$(CH_2)_n$—$NHR^2$, $R^2$ is a 3- to 7-membered monocyclic heterocycle, and Y' is fluoro.

In another embodiment, $R^1$ is —$(CH_2)_n$—$NHR^2$ and $R^2$ is tetrahydropyranyl.

In one embodiment, $R^2$ is tetrahydropyranyl, or cyclopentyl which is unsubstituted or substituted with one or more of -(hydroxy-substituted $C_1$-$C_5$ alkyl).

In another embodiment, one of X and Y' is fluoro.

Illustrative examples of the Indenoisoquinolinone Analogs include the compounds of Formula (Va) as set forth below:

(Va)

[Structure of Formula (Va): indenoisoquinolinone core with X on the isoquinolinone ring (positions 1-4), Y' on the indene aromatic ring (positions 7-9), and $R^1$ substituent]

| Compound | —$R^1$ | X | Y' |
|---|---|---|---|
| Va-1 | —CH₂CH₂—NH—cyclopentyl | —Cl, at position 4 | —H |
| Va-2 | —CH₂CH₂—NH—cyclopentyl | —F, at position 2 | —H |
| Va-3 | —CH₂CH₂—NH—cyclopentyl | —F, at position 3 | —H |
| Va-4 | —CH₂CH₂—NH—cyclopentyl | —F, at position 4 | —H |
| Va-5 | —CH₂CH₂—NH—tetrahydropyranyl | —F, at position 3 | —H |
| Va-6 | —CH₂CH₂—NH—tetrahydropyranyl | —F, at position 1 | —H |
| Va-7 | —CH₂CH₂—NH—cyclopentyl | —F, at position 1 | —H |
| Va-8 | —CH₂CH₂—NH—tetrahydropyranyl | —F, at position 2 | —H |

(Va)
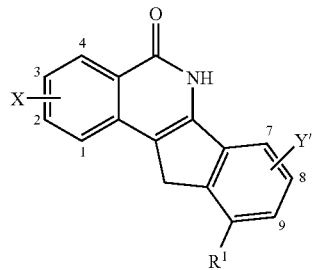
| Compound | —R¹ | X | Y' |
|---|---|---|---|
| Va-9 | ethyl-NH-C(cyclopentyl)(CH₂OH) | —H | —F, at position 8 |
| Va-10 | ethyl-NH-C(cyclopentyl)(CH₂OH) | —F, at position 3 | —F, at position 8 |
5.14 Methods for Making Indenoisoquinolinone Analogs
Methods useful for making the Indenoisoquinolinone Analogs are set forth in the Examples below and generalized in Schemes 1-7.
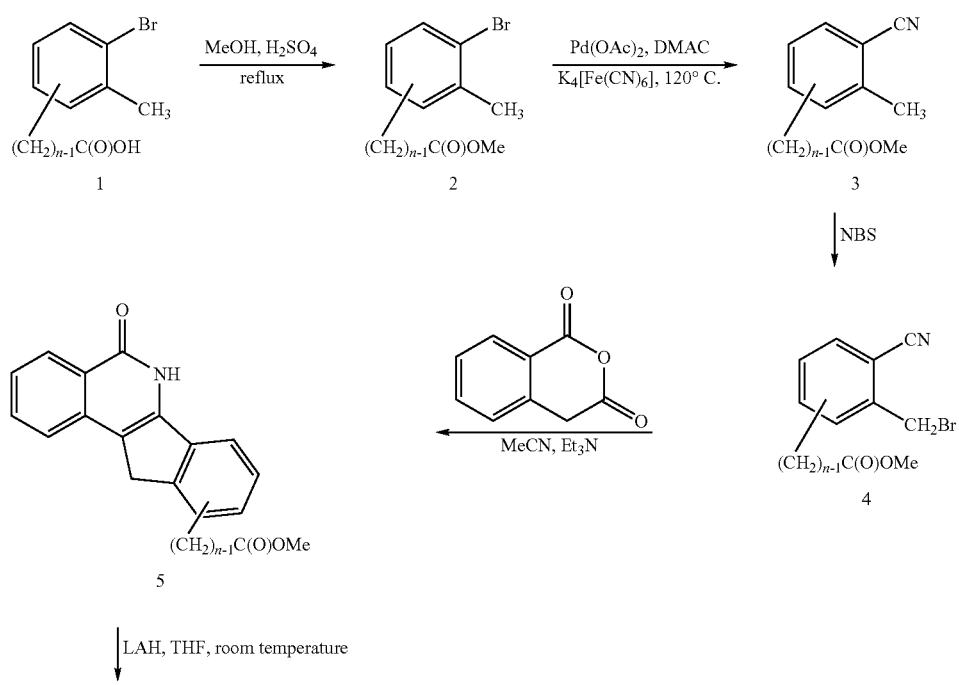
Scheme 1

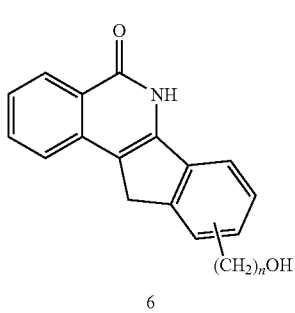

6

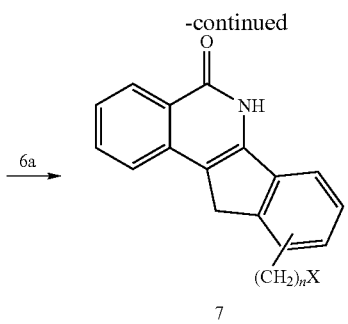

7

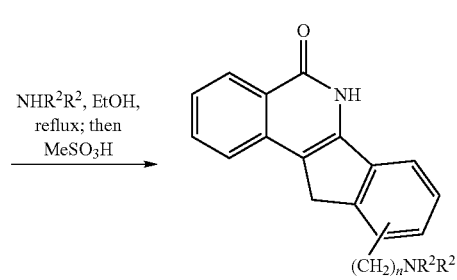

wherein n and each R² is defined above for the Indenoisoquinolinone Analogs of Formula (IIa), (IIb), (IIc), (IIIa), (IIIb), (IVa), (IVb) or (IVc), and X is —Br, —I, —Cl, —O-Ts, —O-Ms, —O-Triflate, or —O-Acetate.

As shown in Scheme 1, a compound of formula 1 can be reacted with methanol in the presence of an acid, for example, sulphuric acid, to provide a compound of formula 2. The compound of formula 2 can then be reacted with cyanide to provide a compound of formula 3. The compound of formula 3 can be brominated using, for example, N-bromosuccinimide, to provide a compound of formula 4. The compound of formula 4 can then be reacted with homophthalic anhydride to provide a compound of formula 5. The compound of formula 5 can then be reduced, for example with lithium aluminum hydride (LAH), to provide a compound of formula 6.

Scheme 2

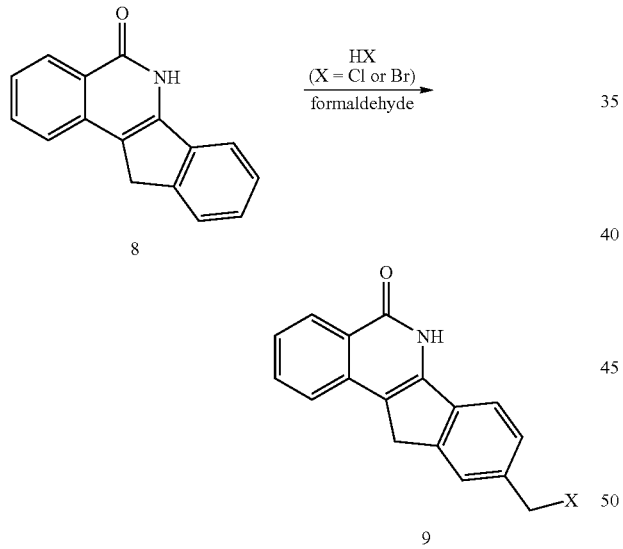

As shown in Scheme 2, an indenoisoquinolinone compound of formula 8 can be reacted with hydrochloric acid or hydrobromic acid in the presence of formaldehyde to provide a halomethyl compound of formula 9. The compound of formula 9 can then be reacted with an amine of formula NH(R²)(R³) to provide an Indenoisoquinolinone Analog of Formula (IIb), wherein R¹=—(CH₂)—N(R²)(R³), wherein each R² and R³ are as defined above. Alternatively, the compound of formula 9 can be reacted with an appropriate amine to provide an Indenoisoquinolinone Analog of Formula (IIIb) or (IVb).

A compound of formula 6 can be reacted with a reagent 6a to provide a compound of formula 7 (see, e.g., Scheme 1). Suitable reagents 6a include, but are not limited to, PBr₃, HBr, HI, SOCl₂, Ts-Cl, pyrene, MsCl, CF₃SO₂Cl, acetic anhydride, acetyl chloride or NEt₃. The compound of formula 7 can then be reacted with an amine of formula NH(R²)(R³) to provide an Indenoisoquinolinone Analog of Formula (IIa), (IIb) or (IIc) wherein R¹=—(CH₂)$_n$—N(R²)(R³), wherein n, R² and R³ are as defined above. Alternatively, the compound of formula 7 can be reacted with an appropriate amine to provide an Indenoisoquinolinone Analog of Formula (IIIa) or (IIIb). Using similar methods, Indenoisoquinolinone Analogs of Formula (IVa), (IVb) or (IVc) can also be obtained using an appropriate analog of the compound of formula 1, as would be apparent to one of ordinary skill in the art.

Scheme 3

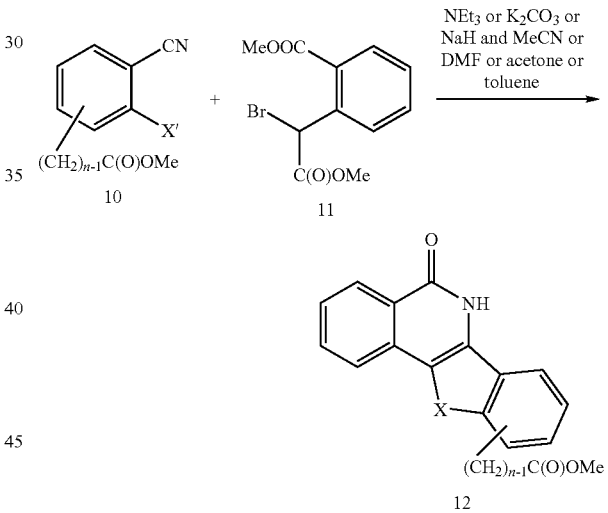

wherein n is defined above for the Indenoisoquinolinone Analogs of Formula (Ia), (Ib), (Ic), (IIa), (IIIb) or (IIc) and X' is —OH, —SH, —NHC(O)OMe, or —N(C₁-C₄ alkyl). As set forth in Scheme 3, a compound of formula 10 is reacted with a compound of formula 11 in the presence of triethylamine to provide a compound of formula 12, wherein X is —O—, —S—, —N(C(O)OMe)-, or —N(C₁-C₄ alkyl)-. The compound of formula 12 can then be converted to provide an Indenoisoquinolinone Analog of Formula (Ia), (Ib), (Ic), (Ia), (IIb) or (IIc), e.g., using procedures outlined in Scheme 1 and/or 2. The compound of formula 12, wherein X is —N(C(O)OMe)-, can be deprotected, for example using hydrazine, to provide a compound, wherein X is —N(H)—. Using similar methods, Indenoisoquinolinone Analogs of Formula (IVa), (IVb) or (IVc) can also be obtained using an appropriate analog of the compound of formula 1, as would be apparent to one of ordinary skill in the art.

Scheme 4

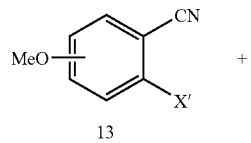

13 wherein X' is —OH, —SH, or NHC(O)OMe or —N($C_1$-$C_4$ alkyl).

As set forth in Scheme 4, a compound of formula 13 is reacted with a compound of formula 11, to provide a compound of formula 14, wherein X is —O—, —S—, —N(C(O)OMe)-, or —N($C_1$-$C_4$ alkyl)-. The compound of formula 14 is then converted to provide an Indenoisoquinolinone Analog of Formula (Ia), (Ib), (Ic), wherein $R^1$=–O—$(CH_2)_m$—N($R^2$)($R^2$) or an Indenoisoquinolinone Analog of Formula (IVa), (IVb) or (IVc), for example using methods described in Schemes 1 and/or 5.

Scheme 5

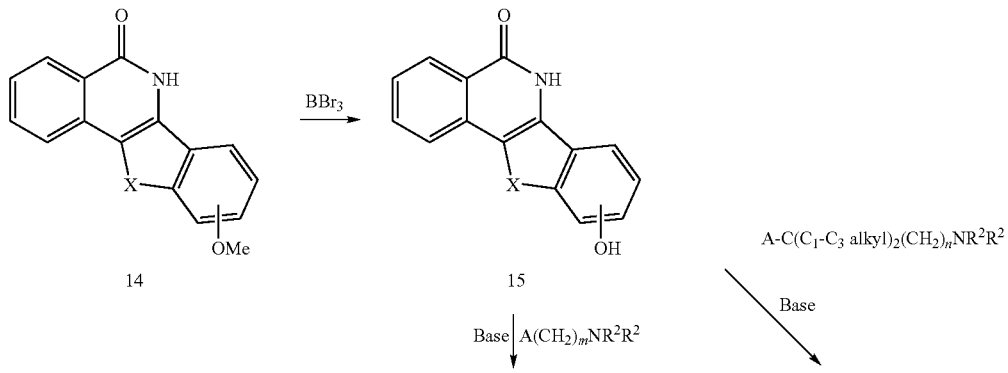

wherein X, m, n, each $R^2$ and each $C_1$-$C_3$ alkyl is defined above for the Indenoisoquinolinone Analogs of Formula (Ia), (Ib), (Ic), (IVa), (IVb) or (IVc) and A is a halogen.

As set forth in Scheme 5, a compound of formula 14 is demethylated, for example using boron tribromide, to provide a compound of formula 15. A compound of formula 15 is then reacted in the presence of base with A$(CH_2)_m$NR$^2$R$^2$ to provide the compound of the general formula 15a, an Indenoisoquinolinone Analog of Formula (Ia), (Ib), or (Ic), wherein $R^1$=—O—$(CH_2)_m$—N($R^2$)($R^2$). Alternatively, a compound of formula 15 is reacted in the presence of base with A-C($C_1$-$C_3$ alkyl)$_2$$(CH_2)_n$NR$^2$R$^2$ to provide the compound of the general formula 15b, an Indenoisoquinolinone Analog of Formula (IVa), (IVb), or (IVc).

-continued

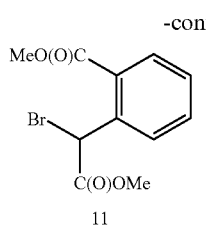

11

NEt$_3$ or K$_2$CO$_3$ or NaH and MeCN or DMF or acetone or toluene

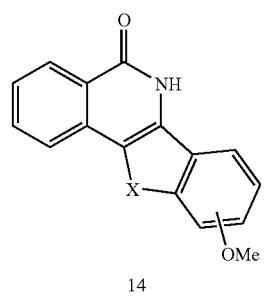

14

Scheme 6

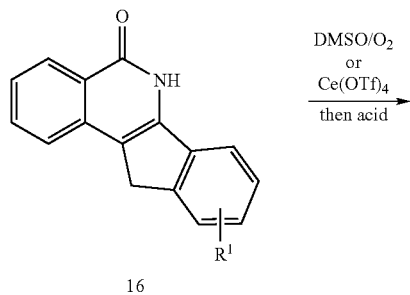

16

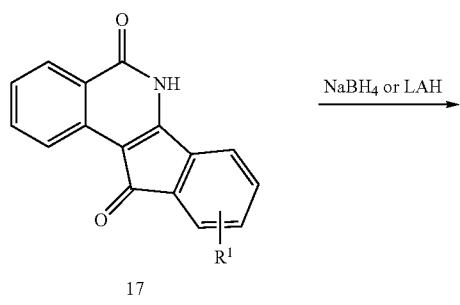

17

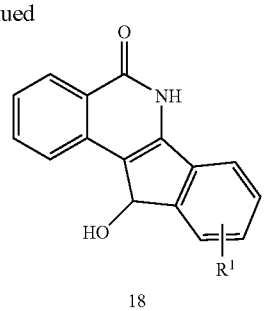

18 wherein $R^1$ is as defined above for the Indenoisoquinolinone Analogs of Formula (IIa), (IIb), (IIc), (IVa), (IVb) or (IVc).

As set forth in Scheme 6, compounds of the general formula 16, which can be prepared, for example, according to Schemes 1 or 2, can be oxidized to provide a compound of the general formula 17, which is an Indenoisoquinolinone Analog of Formula (IIa), (IIb), (IIc), (IVa), (IVb) or (IVc), wherein X is —C(O)—. In one embodiment, the oxidation is achieved using $O_2$ and dimethylsulfoxide. In one aspect, the $O_2$ is that which is present in air. In another embodiment, the oxidation is achieved using Cerium(IV) triflate (Ce(OTf)$_4$). Optional protecting groups can be used (Greene et al., *Protective Groups in Organic Synthesis* (3$^{rd}$ ed. 1999)). For example, where $R^1$ is —(CH$_2$)$_n$—OH, protecting groups such as —SiEt$_3$, can be used to protect the $R^1$ hydroxyl group during the oxidation and can then be removed, for example with an acid. The compound of the general formula 17, can be reduced, for example with sodium borohydride or lithium aluminum hydride, to provide the compound of the general formula 18, which is an Indenoisoquinolinone Analog of Formula (IIa), (IIb), (IIc), (IVa), (IVb) or (IVc), wherein X is —CH(OH)—.

Scheme 7

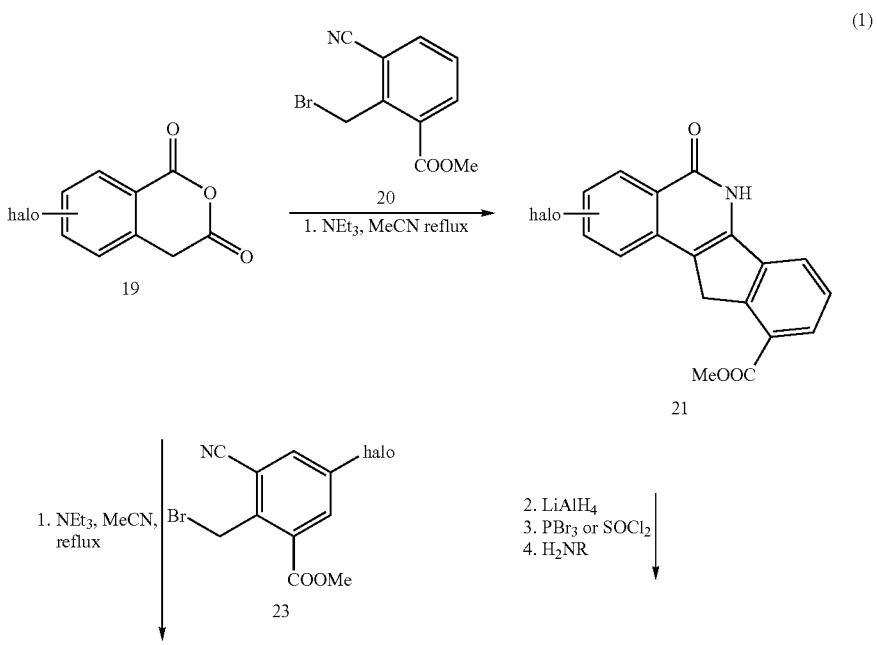

(1)

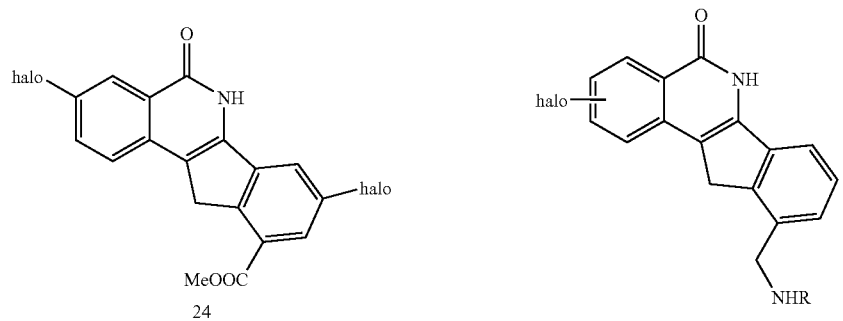

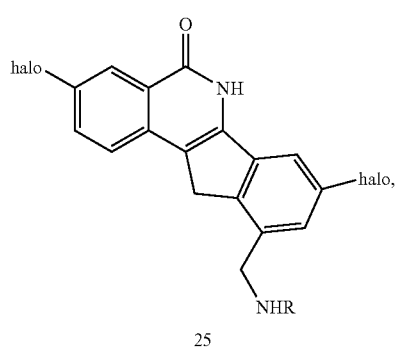

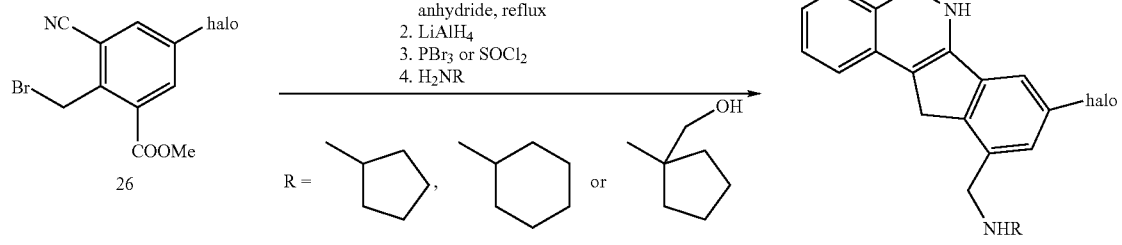

As set forth in Scheme 7, Indenoisoquinolinone Analogs of Formula (Va) can be prepared, for example, as illustrated in part (1) of the scheme by reacting compound 19 with either compounds 20 or 23 to yield compounds 21 and 24, respectively. Compounds 21 and 24 can then be reacted with the selected amine to form compounds 22 and 25 respectively. Compounds 22 and 25 are representative of an Indenoisoquinolinone Analog of Formula (Va). In part (2) of the scheme, reaction of compound 26 under suitable conditions and in the presence of homophthalic anhydride and the desired amine yields compound 27, which is an Indenoisoquinolinone Analog of Formula of Formula (Va).

5.15 Treatment or Prevention of a Condition

In accordance with the invention, an Indenoisoquinolinone Analog is useful for treatment or prevention of a Condition as set forth below.

5.8.1 Treatment or Prevention of an Inflammatory Disease

The Indenoisoquinolinone Analogs are useful for treating or preventing an inflammatory disease. An inflammatory disease can arise where there is an inflammation of the body tissue. These include local inflammatory responses and systemic inflammation. Examples of inflammatory diseases include, but are not limited to, lupus; pancreatitis; macular degeneration; chronic obstructive pulmonary disease; organ transplant rejection; a chronic inflammatory disease of a joint, including arthritis, rheumatoid arthritis, osteoarthritis and a bone disease associated with increased bone resorption; an inflammatory bowel disease such as ileitis, ulcerative colitis, Barrett's syndrome, and Crohn's disease; an inflammatory lung disease such as asthma, adult respiratory distress syndrome, and chronic obstructive airway disease; an inflammatory disease of the eye including corneal dystrophy, trachoma, onchocerciasis, uveitis, sympathetic ophthalmitis and endophthalmitis; a chronic inflammatory disease of the gum, including gingivitis and periodontitis; tuberculosis; leprosy; an inflammatory disease of the kidney including a uremic complication, glomerulonephritis and nephrosis; an inflammatory disease of the skin including sclerodermatitis, psoriasis and eczema; an inflammatory disease of the central nervous system, including a chronic demyelinating disease of the nervous system, multiple sclerosis, AIDS-related neurodegeneration and Alzheimer's disease, infectious meningitis, encephalomyelitis, Huntington's disease, amyotrophic lateral sclerosis and viral or autoimmune encephalitis; as well as any other disease that can have a significant inflammatory component, including preeclampsia, chronic liver failure, and brain and spinal cord trauma. The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

In one embodiment, the inflammatory disease is an inflammatory disease of a joint, a chronic inflammatory disease of the gum, an inflammatory bowel disease, an inflammatory lung disease, an inflammatory disease of the central nervous system, an inflammatory disease of the eye, gram-positive shock, gram negative shock, Rickettsial shock, fungal shock, hemorrhagic shock, anaphylactic shock, traumatic shock or chemotherapeutic shock.

5.8.2 Treatment or Prevention of a Reperfusion Injury

The Indenoisoquinolinone Analogs are useful for treating or preventing a reperfusion injury. Reperfusion refers to the process whereby blood-flow in the blood vessels is resumed following ischemia, such as occurs following constriction or obstruction of the vessel. Reperfusion injury can result following a naturally occurring episode, such as a myocardial infarction, stroke, or during a surgical procedure where blood flow in vessels is intentionally or unintentionally blocked. Examples of reperfusion injuries include, but are not limited to, intestinal reperfusion injury, myocardial reperfusion injury, and reperfusion injury resulting from cardiopulmonary bypass surgery, aortic aneurysm repair surgery, carotid endarterectomy surgery, and hemorrhagic shock.

In one embodiment, the reperfusion injury results from cardiopulmonary bypass surgery, aortic aneurysm repair surgery, carotid endarterectomy surgery or hemorrhagic shock.

In another embodiment, the reperfusion injury is stroke or myocardial infarction.

5.8.3 Treatment or Prevention of Reoxygenation Injury Resulting from Organ Transplantation The Indenoisoquinolinone Analogs are useful for treating or preventing reoxygenation injury resulting from organ transplantation. Examples of reoxygenation injuries include, but are not limited to, transplantation of one or more of the following: heart, lung, liver, kidney, pancreas, intestine and cornea.

In one embodiment, reoxygenation injury resulting from organ transplantation occurs during the organ transplantation.

The Indenoisoquinolinone Analogs are also useful for treating or preventing allograph rejection. Accordingly, the invention provides methods for treating or preventing allograph rejection, comprising administering an effective amount of an Indenoisoquinolinone Analog to a subject in need thereof. In one embodiment, the methods further comprise administering an effective amount of another agent useful for treating or preventing allograph rejection. The other agent includes, but is not limited to, SK-506 and cyclosporine.

5.8.4 Treatment or Prevention of an Ischemic Condition

The Indenoisoquinolinone Analogs are useful for treating or preventing an ischemic condition. Examples of ischemic conditions include, but are not limited to, stable angina, unstable angina, myocardial ischemia, hepatic ischemia, mesenteric artery ischemia, ischemic heart disease, intestinal ischemia, critical limb ischemia, chronic critical limb ischemia, cerebral ischemia, acute cardiac ischemia, and an ischemic disease of the central nervous system, such as stroke or cerebral ischemia.

In one embodiment, the ischemic condition is myocardial ischemia, stable angina, unstable angina, stroke, ischemic heart disease or cerebral ischemia.

5.8.5 Treatment or Prevention of Renal Failure

The Indenoisoquinolinone Analogs are useful for treating or preventing renal failure.

In one embodiment, the renal failure is chronic renal failure.

In another embodiment, the renal failure is acute renal failure.

5.8.6 Treatment or Prevention of a Vascular Disease

The Indenoisoquinolinone Analogs are useful for treating or preventing a vascular disease other than a cardiovascular disease. Examples of vascular diseases include, but are not limited to, hemorrahgic stroke, peripheral arterial occlusion, thromboangitis obliterans, Reynaud's disease and phenomenon, acrocyanosis, erythromelalgia, venous thrombosis, varicose veins, arteriovenous fistula, lymphedema, and lipedema.

In embodiment, the vascular disease is peripheral arterial occlusion, thromboangitis obliterans, Reynaud's disease and phenomenon, acrocyanosis, erythromelalgia, venous thrombosis, varicose veins, arteriovenous fistula, lymphedema or lipedema.

5.8.7 Treatment or Prevention of a Cardiovascular Disease

The Indenoisoquinolinone Analogs are useful for treating or preventing a cardiovascular disease. Examples of cardiovascular diseases include, but are not limited to, congestive heart failure (such as chronic or acute heart failure), atherosclerosis, hypercholesterolemia, circulatory shock, cardiomyopathy, cardiac transplant, myocardial infarction, and a cardiac arrhythmia, such as atrial fibrillation, supraventricular tachycardia, atrial flutter, and paroxysmal atrial tachycardia.

In one embodiment, the cardiovascular disease is chronic heart failure.

In another embodiment, the cardiovascular disease is acute heart failure.

In yet another embodiment, the cardiovascular disease is cardiac arrhythmia.

In still another embodiment, the cardiac arrhythmia is atrial fibrillation, supraventricular tachycardia, atrial flutter or paroxysmal atrial tachycardia.

In one embodiment, the cardiovascular disease is chronic heart failure, atrial fibrillation, supraventricular tachycardia, atrial flutter or paroxysmal atrial tachycardia.

5.8.8 Treatment or Prevention of Diabetes Mellitus or a Diabetic Complication The Indenoisoquinolinone Analogs are useful for treating or preventing diabetes mellitus or one or more of its complications. Examples of diabetes mellitus include, but are not limited to, Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by β-cell toxins.

The Indenoisoquinolinone Analogs are useful for treating or preventing a complication of diabetes mellitus. Examples of complications of diabetes mellitus include, but are not limited to, diabetic cataract, glaucoma, retinopathy, nephropathy (such as microalbuminuria or progressive diabetic nephropathy), polyneuropathy, gangrene of the feet, immune-complex vasculitis, systemic lupus erythematosus (SLE), atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication (such as an infection, a shin spot, a candidal infection or necrobiosis lipoidica diabeticorumobesity), hyperlipidemia, hypertension, syndrome of insulin resistance, coronary artery disease, retinopathy, neuropathy (such as diabetic neuropathy, polyneuropathy or mononeuropathy), autonomic neuropathy, a foot ulcer, a joint problem, a fungal infection, cardiomyopathy, and a bacterial infection.

In one embodiment diabetes mellitus is Type I diabetes mellitus or Type II diabetes mellitus.

5.8.9 Treatment or Prevention of a Neurodegenerative Disease

The Indenoisoquinolinone Analogs are useful for treating or preventing a neurodegenerative disease. Examples of neurodegenerative diseases include, but are not limited to, Alzheimer's disease, Parkinson's disease and amyotrophic lateral sclerosis.

5.8.10 Treatment or Prevention of Cancer

The Indenoisoquinolinone Analogs are useful for treating or preventing cancer.

Accordingly, the invention provides methods for treating or preventing cancer, comprising administering an effective amount of an Indenoisoquinolinone Analog to a subject in need thereof. In one embodiment, the methods further comprise administering an effective amount of another anticancer agent.

Examples of cancers include, but are not limited to, the cancers disclosed below in Table 1 and metastases thereof.

TABLE 1

| Solid tumors, including but not limited to: |
| --- |
| fibrosarcoma |
| myxosarcoma |
| liposarcoma |
| chondrosarcoma |
| osteogenic sarcoma |
| chordoma |
| angiosarcoma |
| endotheliosarcoma |
| lymphangiosarcoma |
| lymphangioendotheliosarcoma |
| synovioma |
| mesothelioma |
| Ewing's tumor |
| leiomyosarcoma |
| rhabdomyosarcoma |
| colon cancer |
| colorectal cancer |
| kidney cancer |
| pancreatic cancer |
| bone cancer |
| breast cancer |
| ovarian cancer |
| prostate cancer |
| esophageal cancer |
| stomach cancer |
| oral cancer |
| nasal cancer |
| throat cancer |
| squamous cell carcinoma |
| basal cell carcinoma |
| adenocarcinoma |
| sweat gland carcinoma |
| sebaceous gland carcinoma |
| papillary carcinoma |
| papillary adenocarcinomas |
| cystadenocarcinoma |
| medullary carcinoma |
| bronchogenic carcinoma |
| renal cell carcinoma |
| hepatoma |
| bile duct carcinoma |
| choriocarcinoma |
| seminoma |
| embryonal carcinoma |
| Wilms' tumor |
| cervical cancer |
| uterine cancer |
| testicular cancer |
| small cell lung carcinoma |
| bladder carcinoma |
| lung cancer |
| epithelial carcinoma |
| skin cancer |
| melanoma |
| metastatic melanoma |
| neuroblastoma |
| retinoblastoma |
| blood-borne cancers, including but not limited to: |
| acute lymphoblastic leukemia ("ALL") |
| acute lymphoblastic B-cell leukemia |
| acute lymphoblastic T-cell leukemia |
| acute myeloblastic leukemia ("AML") |
| acute promyelocytic leukemia ("APL") |
| acute monoblastic leukemia |
| acute erythroleukemic leukemia |
| acute megakaryoblastic leukemia |
| acute myelomonocytic leukemia |
| acute nonlymphocytic leukemia |

TABLE 1-continued acute undifferentiated leukemia
chronic myelocytic leukemia ("CML")
chronic lymphocytic leukemia ("CLL")
hairy cell leukemia
multiple myeloma
acute and chronic leukemias:

lymphoblastic
myelogenous
lymphocytic
myelocytic leukemias
Lymphomas:

Hodgkin's disease
non-Hodgkin's Lymphoma
Multiple myeloma
Waldenström's macroglobulinemia
Heavy chain disease
Polycythemia vera
Central nervous system lymphomas
CNS and Brain cancers:

glioma
pilocytic astrocytoma
astrocytoma
anaplastic astrocytoma
glioblastoma multiforme
medulloblastoma
craniopharyngioma
ependymoma
pinealoma
hemangioblastoma
acoustic neuroma
oligodendroglioma
meningioma
vestibular schwannoma
adenoma
metastatic brain tumor
meningioma
spinal tumor
medulloblastoma In one embodiment, the cancer is lung cancer, breast cancer, colorectal cancer, prostate cancer, a leukemia, a lymphoma, non-Hodgkin's lymphoma, skin cancer, a brain cancer, a cancer of the central nervous system, ovarian cancer, uterine cancer, stomach cancer, pancreatic cancer, esophageal cancer, kidney cancer, liver cancer, or a head and neck cancer.

In another embodiment, the cancer is metastatic cancer.

In yet another embodiment, the cancer is brain cancer or melanoma.

In one embodiment, the brain cancer is metastatic brain cancer or a glioma.

In one embodiment, the glioma is pilocytic astrocytoma, astrocytoma, anaplastic astrocytoma or glioblastoma multiforme.

In one embodiment, the cancer is homologous-recombination deficient, such as BRCA-1 or BRCA-2 deficient, or is deficient in one or more proteins of the Fanconi family. In one embodiment, the deficiency is caused by a genetic mutation. In another embodiment, the phenotype resulting from the deficiency is caused by abnormally low expression of BRCA-1 or BRCA-2 protein. In another embodiment, the phenotype resulting from the deficiency is caused by abnormally low expression of one or more proteins of the Fanconi family.

In still another embodiment, the subject in need of treatment has previously undergone or is presently undergoing treatment for cancer. The treatment includes, but is not limited to, chemotherapy, radiation therapy, surgery or immunotherapy, such as administration of a cancer vaccine.

The Indenoisoquinolinone Analogs are also useful for treating or preventing a cancer caused by a virus. Such viruses include human papilloma virus, which can lead to cervical cancer (see, e.g., Hernandez-Avila et al., Archives of Medical Research (1997) 28:265-271); Epstein-Barr virus (EBV), which can lead to lymphoma (see, e.g., Herrmann et al., J Pathol (2003) 199(2):140-5); hepatitis B or C virus, which can lead to liver carcinoma (see, e.g., El-Serag, J Clin Gastroenterol (2002) 35(5 Suppl 2):S72-8); human T cell leukemia virus (HTLV)-I, which can lead to T-cell leukemia (see e.g., Mortreux et al., Leukemia (2003) 17(1):26-38); human herpesvirus-8 infection, which can lead to Kaposi's sarcoma (see, e.g., Kadow et al., Curr Opin Investig Drugs (2002) 3(11):1574-9); and Human Immune deficiency Virus (HIV) infection, which can lead to cancer as a consequence of immunodeficiency (see, e.g., Dal Maso et al., Lancet Oncol (2003) 4(2):110-9).

5.8.10.1 Prophylactic Methods for Cancer

The Indenoisoquinolinone Analogs are also useful for preventing cancer, or preventing progression of a cancer, including but not limited to the cancers listed in Table 1. Such prophylactic use includes that in which non-neoplastic cell growth such as hyperplasia, metaplasia, or most specifically, dysplasia has occurred.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic or therapeutic administration of an Indenoisoquinolinone Analog. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, is treatable or preventable according to the present methods.

In another embodiment, fibrocystic disease (cystic hyperplasia, mammary dysplasia, specifically adenosis (benign epithelial hyperplasia)) is treatable or preventable according to the present methods.

In other embodiments, a subject that has one or more of the following predisposing factors for malignancy can be treated by administration of an effective amount of an Indenoisoquinolinone Analog: a chromosomal translocation associated with a malignancy (e.g., the Philadelphia chromosome for chronic myelogenous leukemia; t(14; 18) for follicular lymphoma); familial polyposis or Gardner's syndrome; benign monoclonal gammopathy; a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's

5.8.10.2 Combination Chemotherapy for the Treatment of Cancer

In one aspect, the present methods for treating or preventing cancer can further comprise the administration of another anticancer agent.

In one embodiment, the present invention provides methods for treating or preventing cancer, comprising the administration of an effective amount of an Indenoisoquinolinone Analog and another anticancer agent to a subject in need thereof.

The Indenoisoquinolinone Analog and another anticancer agent can be administered concurrently. In this embodiment, the Indenoisoquinolinone Analog and another anticancer agent can be administered within the same composition, or can be administered from different compositions, via the same or different routes of administration.

In another embodiment, the Indenoisoquinolinone Analog is administered during a time when the other anticancer agent exerts its prophylactic or therapeutic effect, or vice versa.

In another embodiment, the Indenoisoquinolinone Analog or other anticancer agent are administered in doses commonly employed when such agents are used as monotherapy for the treatment of cancer.

In one embodiment, the Indenoisoquinolinone Analog or other anticancer agent are administered in doses that are lower than the doses commonly employed when such agents are used as monotherapy for the treatment of cancer.

In another embodiment, the Indenoisoquinolinone Analog and other anticancer agent act synergistically and are administered in doses that are lower than the doses commonly employed when such agents are used as monotherapy for the treatment of cancer.

The dosage of the Indenoisoquinolinone Analog or other anticancer agent administered as well as the dosing schedule can depend on various parameters, including, but not limited to, the cancer being treated, the subject's general health, and the administering physician's discretion.

An Indenoisoquinolinone Analog can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent, to a subject in need thereof. In various embodiments an Indenoisoquinolinone Analog and the other anticancer agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, an Indenoisoquinolinone Analog and the other anticancer agent are administered within 3 hours. In another embodiment, an Indenoisoquinolinone Analog and the other anticancer agent are administered at 1 minute to 24 hours apart.

In one embodiment, an effective amount of an Indenoisoquinolinone Analog and an effective amount of other anticancer agent are present in the same composition. In one embodiment, this composition is useful for oral administration. In another embodiment, this composition is useful for intravenous administration.

In one embodiment, the compositions comprise an amount of an Indenoisoquinolinone Analog and the other anticancer agent which together are effective to treat or prevent cancer.

In another embodiment, the compositions comprise an effective amount of temozolomide, procarbazine, dacarbazine, interleukin-2, irinotecan, or doxorubicin, a physiologically acceptable carrier or vehicle, and an effective amount of an Indenoisoquinolinone Analog.

In one embodiment, the amount of an Indenoisoquinolinone Analog and the other anticancer agent is at least about 0.01% of the combined combination chemotherapy agents by weight of the composition. When intended for oral administration, this amount can be varied from about 0.1% to about 80% by weight of the composition. Some oral compositions can comprise from about 4% to about 50% of combined amount of an Indenoisoquinolinone Analog and the other anticancer agent by weight of the composition. Other compositions of the present invention are prepared so that a parenteral dosage unit contains from about 0.01% to about 2% by weight of the composition.

Cancers that can be treated or prevented by administering an Indenoisoquinolinone Analog and the other anticancer agent include, but are not limited to, the list of cancers set forth above in Table 1.

In one embodiment, the cancer is brain cancer.

In specific embodiments, the brain cancer is pilocytic astrocytoma, astrocytoma, anaplastic astrocytoma, glioblastoma multiforme or a metastatic brain tumor.

In one embodiment, the cancer is melanoma.

In a specific embodiment, the melanoma is metastatic melanoma.

The Indenoisoquinolinone Analog and other anticancer agent can act additively or synergistically. A synergistic combination of an Indenoisoquinolinone Analog and the other anticancer agent, might allow the use of lower dosages of one or both of these agents and/or less frequent administration of the agents to a subject with cancer. The ability to utilize lower dosages of one or both of the Indenoisoquinolinone Analog and other anticancer agent and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

In one embodiment, the administration of an effective amount of an Indenoisoquinolinone Analog and an effective amount of another anticancer agent inhibits the resistance of a cancer to the other anticancer agent. In one embodiment, the cancer is a tumor.

Suitable other anticancer agents useful in the methods and compositions of the present invention include, but are not limited to temozolomide, a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, taxanes such as docetaxel and paclitaxel, leucovorin, levamisole, irinotecan, estramustine, etoposide, nitrogen mustards, BCNU, nitrosoureas such as carmustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins herbimycin A, genistein, erbstatin, and lavendustin A.

In one embodiment, the other anticancer agent is, but is not limited to, a drug listed in Table 2.

TABLE 2

| Alkylating agents | |
|---|---|
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| | Procarbazine |
| | Temozolomide |
| Platinum containing complexes: | Cisplatin |
| | Carboplatin |
| | Aroplatin |
| | Oxaliplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxel |
| DNA Topoisomerase Inhibitors | |
| Epipodophyllins: | Etoposide |
| | Teniposide |
| | Topotecan |
| | 9-aminocamptothecin |
| | Camptothecin |
| | Crisnatol |
| Mitomycins: | Mitomycin C |
| | Anti-metabolites |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonuclotide reductase Inhibitors: | Hydroxyurea |
| | Deferoxamine |
| Pyrimidine Analogs: | |
| Uracil Analogs: | 5-Fluorouracil |
| | Fluoxuridine |
| | Doxifluridine |
| | Ralitrexed |
| Cytosine Analogs: | Cytarabine (ara C) |
| | Cytosine arabinoside |
| | Fludarabine |
| | Gemcitabine |
| | Capecitabine |
| Purine Analogs: | Mercaptopurine |
| | Thioguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |

TABLE 2-continued

| | beta-TGDR |
|---|---|
| | cyclocytidine |
| | guanazole |
| | inosine glycodialdehyde |
| | macebecin II |
| | Pyrazoloimidazole |
| Hormonal therapies: | |
| Receptor antagonists: | |
| Anti-estrogen: | Tamoxifen |
| | Raloxifene |
| | Megestrol |
| LHRH agonists: | Goscrelin |
| | Leuprolide acetate |
| Anti-androgens: | Flutamide |
| | Bicalutamide |
| Retinoids/Deltoids | |
| Vitamin A derivative: | Cis-retinoic acid |
| | All-trans retinoic acid (ATRA-IV) |
| Vitamin D3 Analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A (2BA-2-DMHA) |
| Cytokines: | Interferon-α |
| | Interferon-β |
| | Interferon-γ |
| | Tumor necrosis factor |
| | Interleukin-2 |
| Angiogenesis Inhibitors: | Angiostatin (plasminogen fragment) |
| | antiangiogenic antithrombin III |
| | Angiozyme |
| | ABT-627 |
| | Bay 12-9566 |
| | Benefin |
| | Bevacizumab |
| | BMS-275291 |
| | cartilage-derived inhibitor (CDI) |
| | CAI |
| | CD59 complement fragment |
| | CEP-7055 |
| | Col 3 |
| | Combretastatin A-4 |
| | Endostatin (collagen XVIII fragment) |
| | Fibronectin fragment |
| | Gro-beta |
| | Halofuginone |
| | Heparinases |
| | Heparin hexasaccharide fragment |
| | HMV833 |
| | Human chorionic gonadotropin (hCG) |
| | IM-862 |
| | Interferon alpha/beta/gamma |
| | Interferon inducible protein (IP-10) |
| | Interleukin-12 |
| | Kringle 5 (plasminogen fragment) |
| | Marimastat |
| | Metalloproteinase inhibitors (TIMPs) |
| | 2-Methoxyestradiol |
| | MMI 270 (CGS 27023A) |
| | MoAb IMC-1C11 |
| | Neovastat |
| | NM-3 |
| | Panzem |
| | PI-88 |
| | Placental ribonuclease inhibitor |
| | Plasminogen activator inhibitor |
| | Platelet factor-4 (PF4) |
| | Prinomastat |
| | Prolactin 16 kD fragment |
| | Proliferin-related protein (PRP) |

TABLE 2-continued

| | |
|---|---|
| | PTK 787/ZK 222594 |
| | Retinoids |
| | Solimastat |
| | Squalamine |
| | SS 3304 |
| | SU 5416 |
| | SU6668 |
| | SU11248 |
| | Tetrahydrocortisol-S |
| | Tetrathiomolybdate |
| | Thalidomide |
| | Thrombospondin-1 (TSP-1) |
| | TNP-470 |
| | Transforming growth factor-beta (TGF-β) |
| | Vasculostatin |
| | Vasostatin (calreticulin fragment) |
| | ZD6126 |
| | ZD 6474 |
| | farnesyl transferase inhibitors (FTI) |
| | Bisphosphonates |
| Antimitotic agents: | Allocolchicine |
| | Halichondrin B |
| | Colchicine |
| | colchicine derivative |
| | dolstatin 10 |
| | Maytansine |
| | Rhizoxin |
| | Thiocolchicine |
| | trityl cysteine |
| Others: | |
| Isoprenylation inhibitors: | |
| Dopaminergic neurotoxins: | 1-methyl-4-phenylpyridinium ion |
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | Verapamil |
| $Ca^{2+}$ ATPase inhibitors: | Thapsigargin |

Other additional anticancer agents that are useful in the compositions and methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; interleukin-2 (including recombinant interleukin-2, or rIL2), interferon alfa-2a; interferon alfa-2β; interferon alfa-n1; interferon alfa-n3; interferon beta-Iα; interferon gamma-Iβ; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Further anticancer drugs that are useful in the methods and compositions of the invention include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta Lactam Derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene Analogues; clotrimazole; collismycin A; collismycin B; combretastatin A4; combretastatin Analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B;

deslorelin; dexamethasone; dexifosfamide; dexrazoxane; dexverapamil; diaziquone; didemnin B; didox; diethylnorspermine; dihydro-5-acytidine; dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine Analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine Analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin Analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agents; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel Analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In one another embodiment, the other anticancer agent is interferon-α.

In another embodiment, the other anticancer agent is interleukin-2.

In one embodiment, the other anticancer agent is an alkylating agent, such as a nitrogen mustard, a nitrosourea, an alkylsulfonate, a triazene, or a platinum-containing agent.

In one embodiment, the other anticancer agent is a triazene alkylating agent.

In another embodiment, the other anticancer agent is temozolomide, procarbazine, dacarbazine, interleukin-2, irinotecan, doxorubicin, or a combination thereof.

In a specific embodiment, the other anticancer agent is temozolomide.

Temozolomide can be administered to a subject at dosages ranging from about 60 mg/m$^2$ (of a subject's body surface area) to about 250 mg/m$^2$ and from about 100 mg/m$^2$ to about 200 mg/m$^2$. In specific embodiments, the dosages of temozolomide are about 10 mg/m$^2$, about 1 mg/m$^2$, about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, or about 250 mg/m$^2$.

In a specific embodiment, temozolomide is administered orally.

In one embodiment, temozolomide is administered orally to a subject at a dose ranging from about 150 mg/m$^2$ to about 200 mg/m$^2$.

In another embodiment, temozolomide is administered orally to a subject once per day for five consecutive days at a dose ranging from about 150 mg/m$^2$ to about 200 mg/m$^2$.

In a specific embodiment, temozolomide is administered orally to a subject once per day for five consecutive days at a dose ranging from about 150 mg/m² to about 200 mg/m² on days 1-5, then again orally once per day for five consecutive days on days 28-32 at a dose ranging from about 150 mg/m² to about 200 mg/m², then again orally once per day for five consecutive days on days 55-59 at a dose ranging from about 150 mg/m² to about 200 mg/m².

In another embodiment, temozolomide is administered orally to a subject once per day for a week, two weeks, three weeks, a month or longer at the foregoing daily dosage.

In a specific embodiment, the other anticancer agent is procarbazine.

Procarbazine can be administered to a subject at dosages ranging from about 50 mg/m² (of a subject's body surface area) to about 100 mg/m² and from about 60 mg/m² to about 100 mg/m². In specific embodiments, the dosages of procarbazine are about 10 mg/m², about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m², about 490 mg/m², or about 500 mg/m².

In a specific embodiment, procarbazine is administered intravenously.

In one embodiment, procarbazine is administered intravenously to a subject at a dose ranging from about 50 mg/m² to about 100 mg/m².

In another embodiment, procarbazine is administered intravenously to a subject once per day for five consecutive days at a dose ranging from about 50 mg/m² to about 100 mg/m².

In a specific embodiment, procarbazine is administered intravenously to a subject once per day for five consecutive days at a dose ranging from about 50 mg/m² to about 100 mg/m² on days 1-5, then again intravenously once per day for five consecutive days on days 28-32 at a dose ranging from about 50 mg/m² to about 100 mg/m², then again intravenously once per day for five consecutive days on days 55-59 at a dose ranging from about 50 mg/m to about 100 mg/m².

In another embodiment, procarbazine is administered once intravenously to a subject at a dose ranging from about 50 mg/m² to about 100 mg/m².

In another embodiment, procarbazine is administered intravenously to a subject once per day for a week, two weeks, three weeks, a month or longer at the foregoing daily dosage.

In a specific embodiment, the other anticancer agent is dacarbazine.

Dacarbazine can be administered to a subject at dosages ranging from about 60 mg/m² (of a subject's body surface area) to about 250 mg/m² and from about 150 mg/m² to about 250 mg/m². In specific embodiments, the dosages of dacarbazine are about 10 mg/m, about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m², about 490 mg/m², or about 500 mg/m².

In a specific embodiment, dacarbazine is administered intravenously.

In one embodiment, dacarbazine is administered intravenously to a subject at a dose ranging from about 150 mg/m² to about 250 mg/m².

In another embodiment, dacarbazine is administered intravenously to a subject once per day for five consecutive days at a dose ranging from about 150 mg/m² to about 250 mg/m².

In a specific embodiment, dacarbazine is administered intravenously to a subject once per day for five consecutive days at a dose ranging from about 150 mg/m² to about 250 mg/m² on days 1-5, then again intravenously once per day for five consecutive days on days 28-32 at a dose ranging from about 150 mg/m² to about 250 mg/m², then again intravenously once per day for five consecutive days on days 55-59 at a dose ranging from about 150 mg/m² to about 250 mg/m².

In one embodiment, dacarbazine is administered once intravenously to a subject at a dose ranging from about 150 mg/m² to about 250 mg/m².

In another embodiment, dacarbazine is administered intravenously to a subject once per day for a week, two weeks, three weeks, a month or longer at the foregoing daily dosage.

In a specific embodiment, the other anticancer agent is doxorubicin.

Doxorubicin can be administered to a subject at dosages ranging from about 50 mg/m² (of a subject's body surface area) to about 100 mg/m² and from about 60 mg/m² to about 100 mg/m². In specific embodiments, the dosages of doxorubicin are about 10 mg/m², about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m², about 490 mg/m², or about 500 mg/m².

In a specific embodiment, doxorubicin is administered intravenously.

In one embodiment, doxorubicin is administered intravenously to a subject at a dose ranging from about 50 mg/m² to about 100 mg/m².

In another embodiment, doxorubicin is administered intravenously to a subject once per day for five consecutive days at a dose ranging from about 50 mg/m² to about 100 mg/m².

In a specific embodiment, doxorubicin is administered intravenously to a subject once per day for five consecutive days at a dose ranging from about 50 mg/m² to about 100 mg/m² on days 1-5, then again intravenously once per day for five consecutive days on days 28-32 at a dose ranging from about 50 mg/m² to about 100 mg/m², then again intravenously once per day for five consecutive days on days 55-59 at a dose ranging from about 50 mg/m² to about 100 mg/m².

In another embodiment, doxorubicin is administered once intravenously to a subject at a dose ranging from about 50 mg/m² to about 100 mg/m².

In another embodiment, doxorubicin is administered intravenously to a subject once per day for a week, two weeks, three weeks, a month or longer at the foregoing daily dosage.

In one embodiment, the other anticancer agent is a Topoisomerase I inhibitor, such as etoposide, teniposide, topotecan, irinotecan, 9-aminocamptothecin, camptothecin, or crisnatol.

In a specific embodiment, the other anticancer agent is irinotecan.

Irinotecan can be administered to a subject at dosages ranging from about 50 mg/m² (of a subject's body surface area) to about 150 mg/m² and from about 75 mg/m² to about 150 mg/m². In specific embodiments, the dosages of irinotecan are about 10 mg/m², about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m², about 490 mg/m², or about 500 mg/m².

In a specific embodiment, irinotecan is administered intravenously.

In one embodiment, irinotecan is administered intravenously to a subject at a dose ranging from about 50 mg/m² to about 150 mg/m².

In another embodiment, irinotecan is administered intravenously to a subject once per day for five consecutive days at a dose ranging from about 50 mg/m² to about 150 mg/m².

In a specific embodiment, irinotecan is administered intravenously to a subject once per day for five consecutive days at a dose ranging from about 50 mg/m² to about 150 mg/m² on days 1-5, then again intravenously once per day for five consecutive days on days 28-32 at a dose ranging from about 50 mg/m² to about 150 mg/m², then again intravenously once per day for five consecutive days on days 55-59 at a dose ranging from about 50 mg/m² to about 150 mg/m².

In another embodiment, irinotecan is administered intravenously to a subject once per day for a week, two weeks, three weeks, a month or longer at the foregoing daily dosage.

In one embodiment, the other anticancer agent is O-6-benzylguanine.

In another embodiment, the other anticancer agent is O-6-benzylguanine and temozolomide.

In another embodiment, the other anticancer agent is O-6-benzylguanine and procarbazine.

In still another embodiment, the other anticancer agent is O-6-benzylguanine and dacarbazine.

5.8.10.3 Multi-Therapy for Cancer

The Indenoisoquinolinone Analogs can be administered to a subject that has undergone or is currently undergoing one or more additional anticancer therapies including, but not limited to, surgery, radiation therapy, or immunotherapy, such as cancer vaccines.

In one embodiment, the invention provides methods for treating or preventing cancer comprising administering to a subject in need thereof an effective amount of an Indenoisoquinolinone Analog to treat or prevent cancer and another anticancer therapy including, but not limited to, surgery, radiation therapy, or immunotherapy, such as a cancer vaccine.

In one embodiment, the other anticancer therapy is radiation therapy.

In another embodiment, the other anticancer therapy is surgery.

In still another embodiment, the other anticancer therapy is immunotherapy.

In a specific embodiment, the present methods for treating or preventing cancer comprise administering an effective amount of an Indenoisoquinolinone Analog and radiation therapy. The radiation therapy can be administered concurrently with, prior to, or subsequent to the Indenoisoquinolinone Analog, in one embodiment at least an hour, five hours, 12 hours, a day, a week, a month, in another embodiment several months (e.g., up to three months), prior or subsequent to administration of the Indenoisoquinolinone Analog.

Where the other anticancer therapy is radiation therapy, any radiation therapy protocol can be administered depending upon the type of cancer to be treated. For example, but not by way of limitation, X-ray radiation can be administered; specifically, high-energy megavoltage (radiation of greater that 1 MeV energy) can be administered for deep tumors, and electron beam and orthovoltage X-ray radiation can be administered for skin cancers. Gamma-ray emitting radioisotopes, such as radioactive isotopes of radium, cobalt and other elements, can also be administered.

Additionally, the invention provides methods of treatment of cancer comprising administering an Indenoisoquinolinone Analog as an alternative to chemotherapy or radiation therapy where the chemotherapy or the radiation therapy results in a negative side effect in the subject being treated. The subject being treated can, optionally, be treated with another anticancer therapy such as surgery, radiation therapy, or immunotherapy.

The Indenoisoquinolinone Analogs can also be administered in vitro or ex vivo, such as for the treatment of certain cancers, including, but not limited to leukemias and lymphomas, such treatment involving autologous stem cell transplants. This can involve a process in which the subject's autologous hematopoietic stem cells are harvested and purged of all cancer cells, the subject's remaining bone-marrow cell population is then eradicated via the administration of an Indenoisoquinolinone Analog and/or radiation, and the resultant stem cells are infused back into the subject. Sup-

5.8.11 Treatment or Prevention of Erectile Dysfunction

The Indenoisoquinolinone Analogs are useful for treating or preventing erectile dysfunction. Erectile dysfunction includes an inability to achieve or maintain a full erection, specifically that which is sufficient to achieve or maintain sexual intercourse. The inability can be a total inability, an inconsistent ability, or a tendency to maintain only a brief erection. Erectile dysfunction includes idiopathic erectile dysfunction, as well as that which can result, for example, from trauma, including mechanical trauma, specifically that resulting from surgery, to the nerves (such as during prostatectomy); diabetes mellitus; a cardiovascular disease, including atherosclerosis; radiation; or certain drugs. The erectile dysfunction can also be age-related.

In one embodiment, the erectile dysfunction results from prostate surgery.

In a further embodiment, the erectile dysfunction results from prostate nerve injury.

5.8.12 Treatment or Prevention of Urinary Incontinence

The Indenoisoquinolinone Analogs are also useful for treating or preventing urinary incontinence. Urinary incontinence can result, for example, from trauma, including mechanical trauma, specifically during childbirth or that resulting from surgery, to the nerves (such as during prostatectomy or gynecological surgery); diabetes mellitus; a cardiovascular disease, including atherosclerosis; radiation; or certain drugs. The urinary incontinence can also be age-related.

In one embodiment, the subject in need of urinary incontinence treatment or prevention is male.

In one embodiment, the subject in need of urinary incontinence treatment or prevention is female.

5.8.13 Treatment or Prevention of a Complication of Prematurity

The Indenoisoquinolinone Analogs are also useful for treating or preventing a complication of prematurity. Examples of complications of prematurity include, but are not limited to, retinopathy, hyaline-membrane disease and necrotizing enterocolitis.

5.8.14 Treatment or Prevention of Cardiomyopathy

The Indenoisoquinolinone Analogs are also useful for treating or preventing cardiomyopathy.

5.8.15 Treatment or Prevention of Retinopathy

The Indenoisoquinolinone Analogs are also useful for treating or preventing retinopathy.

5.8.16 Treatment or Prevention of Nephropathy

The Indenoisoquinolinone Analogs are also useful for treating or preventing nephropathy.

5.8.17 Treatment or Prevention of Neuropathy

The Indenoisoquinolinone Analogs are also useful for treating or preventing neuropathy.

5.9 Therapeutic/Prophylactic Administration and Compositions of the Invention Due to their activity, the Indenoisoquinolinone Analogs are advantageously useful in veterinary and human medicine. As described above, the Indenoisoquinolinone Analogs are useful for treating or preventing a Condition in a subject in need thereof.

The Indenoisoquinolinone Analogs can be administered in amounts that are effective to treat or prevent a Condition in a subject in need thereof.

When administered to a subject, the Indenoisoquinolinone Analogs can be administered as a component of a composition that comprises a physiologically acceptable carrier or vehicle. The present compositions, which comprise an Indenoisoquinolinone Analog, can be administered orally. The Indenoisoquinolinone Analogs can also be administered by any other convenient route, for example, by infusion or bolus injection, by absorption through epithelial or mucocutaneous linings (e.g., oral, rectal, or intestinal mucosa) and can be administered together with another biologically active agent. Administration can be systemic or local. Various delivery systems are known, e.g., encapsulation in liposomes, microparticles, microcapsules and capsules.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, specifically to the ears, nose, eyes, or skin. In some instances, administration will result in the release of an Indenoisoquinolinone Analog into the bloodstream.

In one embodiment, the Indenoisoquinolinone Analogs are administered orally.

In other embodiments, it can be desirable to administer the Indenoisoquinolinone Analogs locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Indenoisoquinolinone Analogs into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon oar, synthetic pulmonary surfactant. In certain embodiments, the Indenoisoquinolinone Analogs can be formulated as a suppository, with traditional binders and excipients such as triglycerides.

In another embodiment Indenoisoquinolinone Analogs can be delivered in a vesicle, specifically a liposome (see Langer, *Science* 249:1527-1533 (1990) and Treat or prevent et al., *Liposomes in Therapy of Infectious Disease and Cancer* 317-327 and 353-365 (1989)).

In yet another embodiment, the Indenoisoquinolinone Analogs can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment a controlled- or sustained-release system can be placed in proximity of a target of the Indenoisoquinolinone Analogs, e.g., the spinal column, brain, skin, lung, or gastrointestinal tract, thus requiring only a fraction of the systemic dose.

The present compositions can optionally comprise a suitable amount of a pharmaceutically acceptable excipient so as to provide the form for proper administration to the subject.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when the Indenoisoquinolinone Analog is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions. aerosols, sprays, suspensions, or any other form suitable for use. In one embodiment, the composition is in the form of a capsule (see e.g. U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

In one embodiment, the Indenoisoquinolinone Analog is formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving an Indenoisoquinolinone Analog are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Indenoisoquinolinone Analogs can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized-powder or water-free concentrate in a hermetically sealed container such as an ampule or sachette indicating the quantity of active agent. Where the Indenoisoquinolinone Analogs are to be administered by infusion, they can be dispensed, for example, with an infusion bottle containing sterile pharmaceutical grade water or saline. Where the Indenoisoquinolinone Analogs are administered by injection, an ampule of sterile water for injection or saline can be provided so that the ingredients can be mixed prior to administration.

Indenoisoquinolinone Analogs can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of an Indenoisoquinolinone Analog to treat or prevent the Condition over a period of time. Advantages of controlled- or sustained-release compositions include extended activity of the drug, reduced dosage frequency, and increased subject compliance. In addition, controlled- or sustained-release compositions can favorably affect the time of onset of action or other characteristics, such as blood levels of the Indenoisoquinolinone Analog, and can thus reduce the occurrence of adverse side effects.

Controlled- or sustained-release compositions can initially release an amount of an Indenoisoquinolinone Analog that promptly produces the desired therapeutic or prophylactic effect, and gradually and continually release other amounts of the Indenoisoquinolinone Analog to maintain this level of therapeutic or prophylactic effect over an extended period of time. To maintain a constant level of the Indenoisoquinolinone Analog in the body, the Indenoisoquinolinone Analog can be released from the dosage form at a rate that will replace the amount of Indenoisoquinolinone Analog being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Indenoisoquinolinone Analog that is effective in the treatment or prevention of a Condition can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies. Suitable effective dosage amounts, however, range from about 10 micrograms to about 5 grams about every 4 hours, although they are typically about 500 mg or less per every 4 hours. In one embodiment, the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one Indenoisoquinolinone Analog is administered, the effective dosage amounts correspond to the total amount administered.

Compositions can be prepared according to conventional mixing, granulating or coating methods, respectively, and the present compositions can contain, in one embodiment, from about 0.1% to about 99%; and in another embodiment from about 1% to about 70% of the Indenoisoquinolinone Analog by weight or volume.

The dosage regimen utilizing the Indenoisoquinolinone Analog can be selected in accordance with a variety of factors including type, species, age, weight, sex and medical condition of the subject; the severity of the condition to be treated; the route of administration; the renal or hepatic function of the subject; and the specific Indenoisoquinolinone Analog employed. A person skilled in the art can readily determine the effective amount of the drug useful for treating or preventing the Condition.

An Indenoisoquinolinone Analog can be administered in a single daily dose, or the total daily dosage can be administered in divided doses of two, three or four times daily. Furthermore, an Indenoisoquinolinone Analog can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of Indenoisoquinolinone Analog ranges from about 0.1% to about 15%, w/w or w/v.

The Indenoisoquinolinone Analogs can be assayed in vitro or in vivo for the desired therapeutic or prophylactic activity prior to use in humans. Animal model systems can be used to demonstrate safety and efficacy.

The present methods for treating or preventing a Condition in a subject in need thereof can further comprise administering another prophylactic or therapeutic agent to the subject being administered an Indenoisoquinolinone Analog. In one embodiment, the other prophylactic or therapeutic agent is administered in an effective amount. The other prophylactic or therapeutic agent includes, but is not limited to, an anti-inflammatory agent, an anti-renal failure agent, an anti-diabetic agent, and anti-cardiovasculare disease agent, an anti-emetic agent, a hematopoietic colony stimulating factor, an anxiolytic agent, and an analgesic agent.

In one embodiment, the other prophylactic or therapeutic agent is an agent useful for reducing any potential side effect of an Indenoisoquinolinone Analog. Such potential side effects include, but are not limited to, nausea, vomiting, headache, low white blood cell count, low red blood cell count, low platelet count, headache, fever, lethargy, a muscle ache, general pain, bone pain, pain at an injection site, diarrhea, neuropathy, pruritis, a mouth sore, alopecia, anxiety or depression.

In one embodiment, the Indenoisoquinolinone Analog can be administered prior to, concurrently with, or after an anti-inflammatory agent, or on the same day, or within 1 hour, 2 hours, 12 hours, 24 hours, 48 hours or 72 hours of each other.

In another embodiment, the Indenoisoquinolinone Analog can be administered prior to, concurrently with, or after an anti-renal failure agent, or on the same day, or within 1 hour, 2 hours, 12 hours, 24 hours, 48 hours or 72 hours of each other.

In still another embodiment, the Indenoisoquinolinone Analog can be administered prior to, concurrently with, or after an anti-diabetic agent, or on the same day, or within 1 hour, 2 hours, 12 hours, 24 hours, 48 hours or 72 hours of each other.

In yet another embodiment, the Indenoisoquinolinone Analog can be administered prior to, concurrently with, or after an anti-cardiovascular disease agent, or on the same day, or within 1 hour, 2 hours, 12 hours, 24 hours, 48 hours or 72 hours of each other.

In a further embodiment, the Indenoisoquinolinone Analog can be administered prior to, concurrently with, or after an antiemetic agent, or on the same day, or within 1 hour, 2 hours, 12 hours, 24 hours, 48 hours or 72 hours of each other.

In another embodiment, the Indenoisoquinolinone Analog can be administered prior to, concurrently with, or after a hematopoietic colony stimulating factor, or on the same day, or within 1 hour, 2 hours, 12 hours, 24 hours, 48 hours, 72 hours, 1 week, 2 weeks, 3 weeks or 4 weeks of each other.

In still embodiment, the Indenoisoquinolinone Analog can be administered prior to, concurrently with, or after an opioid or non-opioid analgesic agent, or on the same day, or within 1 hour, 2 hours, 12 hours, 24 hours, 48 hours or 72 hours of each other.

In yet another embodiment, the Indenoisoquinolinone Analog can be administered prior to, concurrently with, or after an anxiolytic agent, or on the same day, or within 1 hour, 2 hours, 12 hours, 24 hours, 48 hours or 72 hours of each other.

Effective amounts of the other prophylactic or therapeutic agents are well known to those skilled in the art. However, it is well within the skilled artisan's purview to determine the other prophylactic or therapeutic agent's optimal effective amount range. In one embodiment of the invention, where another prophylactic or therapeutic agent is administered to a subject, the effective amount of the Indenoisoquinolinone Analog is less than its effective amount would be where the other prophylactic or therapeutic agent is not administered. In this case, without being bound by theory, it is believed that Indenoisoquinolinone Analogs and the other prophylactic or therapeutic agent act synergistically to treat or prevent a Condition.

In one embodiment, the other therapeutic or prophylactic agent is an anti-inflammatory agent. Anti-inflammatory agents useful in the methods of the present invention include but are not limited to adrenocorticosteroids, such as cortisol, cortisone, fludrocortisone, prednisone, prednisolone, 6α-methylprednisolone, triamcinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

In one embodiment, the other therapeutic or prophylactic agent is an anti-renal failure agent. Anti-renal failure agents useful in the methods of the present invention include include but are not limited to ACE (angiotensin-converting enzyme) inhibitors, such as captopril, enalaprilat, lisinopril, benazepril, fosinopril, trandolapril, quinapril, and ramipril; diuretics, such as mannitol, glycerin, furosemide, toresemide, tripamide, chlorothiazide, methyclothiazide, indapamide, amiloride, and spironolactone; and fibric acid agents, such as clofibrate, gemfibrozil, fenofibrate, ciprofibrate, and bezafibrate.

In one embodiment, the other therapeutic or prophylactic agent is an anti-diabetic agent. Anti-diabetic agents useful in the methods of the present invention include include but are not limited to glucagons; somatostatin; diazoxide; sulfonylureas, such as tolbutamide, acetohexamide, tolazamide, chloropropamide, glybenclamide, glipizide, gliclazide, and glimepiride; insulin secretagogues, such as repaglinide, and nateglinide; biguanides, such as metformin and phenformin; thiazolidinediones, such as pioglitazone, rosiglitazone, and troglitazone; and α-glucosidase inhibitors, such as acarbose and miglitol.

In one embodiment, the other therapeutic or prophylactic agent is an anti-cardiovascular agent. Anti-cardiovascular disease agents useful in the methods of the present invention include include but are not limited to carnitine; thiamine; and muscarinic receptor antagonists, such as atropine, scopolamine, homatropine, tropicamide, pirenzipine, ipratropium, tiotropium, and tolterodine.

In one embodiment, the other therapeutic or prophylactic agent is an antiemetic agent. Antiemetic agents useful in the methods of the present invention include include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

In one embodiment, the other therapeutic or prophylactic agent is a hematopoietic colony stimulating factor. Hematopoietic colony stimulating factors useful in the methods of the present invention include, but are not limited to, filgrastim, sargramostim, molgramostim and epoietin alfa.

In one embodiment, the other therapeutic or prophylactic agent is an opioid analgesic agent. Opioid analgesic agents useful in the methods of the present invention include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene.

In one embodiment, the other therapeutic or prophylactic agent is a non-opioid analgesic agent. Non-opioid analgesic agents useful in the methods of the present invention include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In one embodiment, the other therapeutic or prophylactic agent is an anxiolytic agent. Anxiolytic agents useful in the methods of the present invention include, but are not limited to, buspirone, and benzodiazepines such as diazepam, lorazepam, oxazapam, chlorazepate, clonazepam, chlordiazepoxide and alprazolam.

5.10 Kits

The invention encompasses kits that can simplify the administration of an Indenoisoquinolinone Analog to a subject.

A typical kit of the invention comprises a unit dosage form of an Indenoisoquinolinone Analog. In one embodiment, the unit dosage form is a container, which can be sterile, containing an effective amount of an Indenoisoquinolinone Analog and a physiologically acceptable carrier or vehicle. The kit can further comprise a label or printed instructions instructing the use of the Indenoisoquinolinone Analog to treat or prevent a Condition. The kit can also further comprise a unit dosage form of another prophylactic or therapeutic agent, for example, a container containing an effective amount of the other prophylactic or therapeutic agent. In one embodiment, the kit comprises a container containing an effective amount of an Indenoisoquinolinone Analog and an effective amount of another prophylactic or therapeutic agent. Examples of other prophylactic or therapeutic agents include, but are not limited to, those listed above.

The invention is further described in the following examples, which do not limit the scope of the invention described in the claims.

6. EXAMPLES

Example 1

Illustrative Indenoisoquinolinone Analogs

General Methods:
$^1$H-NMR spectra were obtained using Varian 300 MHz spectrophotometer and chemical shifts (δ) are reported in parts per million (ppm). $^1$H-NMR spectra were obtained using DMSO-$d_6$ or CDCl$_3$ as solvents. Analytical thin layer chromatography (TLC) was performed using TLC plates pre-coated with silica gel 60 F-254. Compounds were visualized with short wavelength UV light. All final compounds were characterized on the basis of $^1$H-NMR or mass-spectrometry (MS) data. Homophthalic anhydride, 2-methyl-3-bromobenzoic acid, benzonitrile, and 3-methyl-4-bromobenzoic acid were obtained commercially (Sigma-Aldrich Corp., St. Louis, Mo.).

A. Synthesis of Indenoisocquinolinone Analogs of Formula Ia and IIIa

Methyl 3-bromo-2-methylbenzoate 2 mL of concentrated sulfuric acid were added to a solution of 3-bromo-2-methylbenzoic acid (20 g, 93 mmol) in methanol (150 mL). The resultant mixture was refluxed for 6 hours. Methanol was removed under reduced pressure, and the residue was dissolved in a mixture of chloroform (100 mL) and saturated solution of Na$_2$CO$_3$ (100 mL). The organic layer was separated and washed with brine, dried over Na$_2$SO$_4$ and concentrated to provide methyl 3-bromo-2-methylbenzoate (21.1 g). $^1$H NMR spectrum (in DMSO-$d_6$): δ 7.79 (d, J=8.0 Hz, 1H); 7.69 (d, J=7.9 Hz, 1H); 7.23 (t, 1H); 3.82 (s, 3H).

Methyl 3-cyano-2-methylbenzoate

To a flask was added methyl 3-bromo-2-methylbenzoate (21 g, 91.7 mmol), potassium hexacyanoferrate (II) trihydrate (9.7 g, 22.9 mmol), Na$_2$CO$_3$ (9.7 g, 91.7 mmol) and Pd(OAc)$_2$ (102 mg) in N,N-dimethylacetamide (100 mL). The flask's atmosphere was evacuated and replaced with nitrogen, and the reaction mixture heated at 120° C. for 10 hours. The reaction mixture was cooled to room temperature and diluted with ethyl acetate (150 mL). The resultant slurry was filtered and washed thoroughly with ethyl acetate (2×50 mL). The combined filtrate was washed with brine and water, dried over Na$_2$SO$_4$ and evaporated under reduced pressure. The residue obtained after the concentration was purified using flash chromatography (ethyl acetate-hexanes (1:9) as the eluent) to provide methyl 3-cyano-2-methylbenzoate (11.2 g, 70% yield). $^1$H NMR spectrum (in DMSO-$d_6$): δ 8.03 (d, J=8.1 Hz, 1H); 7.98 (d, J=7.9 Hz, 1H); 7.49 (t, 1H); 3.84 (s, 3H); 2.65 (s, 3H).

Methyl 2-bromomethyl-3-cyanobenzoate

A suspension of methyl 3-cyano-2-methylbenzoate (10.6 g, 60.5 mmol), NBS (16.2 g, 90.7 mmol) and azobisisobutyronitrile (AIBN) (100 mg) in tetrachloromethane (200 mL) was refluxed under nitrogen atmosphere for 6 hours. TLC analysis indicated the complete consumption of methyl 3-cyano-2-methylbenzoate (TLC solvent: 10% ethyl acetate in hexane). The reaction mixture was filtered and washed with chloroform (3×20 mL). The combined filtrate and washings were concentrated under reduced pressure. The residue was washed through a short column of silica gel using 10% ethyl acetate in hexanes as an eluent. The eluent was concentrated and the resultant product dried under vacuum overnight to provide 15.1 g of methyl 2-bromomethyl-3-cyanobenzoate (98% yield). $^1$H NMR spectrum (in DMSO-$d_6$): δ 8.15 (d, J=8.0 Hz, 1H); 8.12 (d, J=7.9 Hz, 1H); 7.67 (t, 1H); 5.04 (s, 2H); 3.89 (s, 3H).

Methyl 5,6-dihydro-5-oxo-11-H-indeno[1,2-c]isoquinoline-10-carboxylate

A mixture of methyl 2-bromomethyl-3-cyanobenzoate (14.1 g, 55.5 mmol) and homophthalic anhydride (22.5 g, 138.8 mmol) in acetonitrile (150 mL) was stirred at room temperature. A solution of triethylamine (23.2 mL) in acetonitrile (100 mL) was added dropwise over the period of 1 hour. After the completion of addition, the resultant suspension was refluxed for 4 hours. The reaction mixture was then cooled to room temperature and filtered. The resultant solid was washed thoroughly with acetonitrile (100 mL) and ethanol (2×100 mL) and dried in vacuum oven at 50° C. to provide methyl 5,6-dihydro-5-oxo-11-H-indeno[1,2-c]isoquinoline-10-carboxylate was obtained in 81% yield (13.1 g). $^1$H NMR spectrum (in DMSO-$d_6$): δ 12.21 (s, 1H); 8.20 (m, 2H); 7.83 (d, J=7.5 Hz, 1H); 7.71 (m, 2H); 7.47 (m, 2H); 4.07 (s, 2H); 3.89 (s, 3H).

10-Hydroxymethyl-5,6-dihydro-5-oxo-11-H-indeno[1,2-c]isoquinoline

Fine powder of methyl 5,6-dihydro-5-oxo-11-H-indeno[1,2-c]isoquinoline-10-carboxylate (11.3 g, 28.8 mmol) was suspended in THF (150 mL) and stirred at room temperature. A 2M solution of Lithium aluminium hydride (LAH) in THF (39 mL) was added slowly to the stirred suspension. After the complete addition, the mixture was stirred at room temperature for 6 hours, then cooled to 0° C. The reaction mixture was quenched with dropwise addition of ethyl acetate (50 mL). During the quenching the reaction temperature was kept below 50° C. The reaction mixture was poured into 1N HCl solution (200 mL) and stirred for 1 hour. The resultant solid was collected by filtration, washed with 1N HCl solution (20 mL) and ethyl acetate, and dried in a vacuum oven overnight to provide 10-hydroxymethyl-5,6-dihydro-5-oxo-11-H-indeno[1,2-c]isoquinoline in 93% yield (9.5 g). $^1$H NMR spectrum (in DMSO-$d_6$): δ 12.28 (s, 1H); 8.23 (d, J=8.1 Hz, 1H); 7.89 (m, 1H); 7.73 (m, 2H); 7.45 (m, 1H); 7.36 (m, 2H); 5.22 (d, J=5.1 Hz, 1H), 4.68 (d, 2H); 3.85 (s, 2H).

10-Bromomethyl-5,6-dihydro-5-oxo-11-H-indeno[1,2-c]isoquinoline

Fine powder of 10-hydroxymethyl-5,6-dihydro-5-oxo-11-H-indeno[1,2-c]isoquinoline (7.3 g, 27.7 mmol) was suspended in THF (150 mL). A solution of PBr$_3$ (83 mL, 1M in dichloromethane) was added dropwise at room temperature. After the complete addition, the resultant mixture was stirred overnight and quenched by addition of water (150 mL). The suspension was stirred for 1 hour and filtered. The resultant solid was washed with water (2×100 mL) and ethyl acetate (2×100 mL) and dried in a vacuum oven to provide 110-Bromomethyl-5,6-dihydro-5-oxo-11-H-indeno[1,2-c]isoquinoline in 81% yield. $^1$H NMR spectrum (in DMSO-$d_6$): δ 12.31 (s, 1H); 8.23 d, J=7.5 Hz, 1H); 7.95 (m, 1H); 7.75 (m, 2H); 7.45 (m, 2H); 4.87 (s, 2H); 3.97 (s, 2H).

General Procedure for the Amination Reaction:

A suspension of 10-bromomethyl-5,6-dihydro-5-oxo-11-H-indeno[1,2-c]isoquinoline (0.425 g, 1.3 mmol) or a higher alkylene chain bromo-derivative, an appropriate amine in ethanol or DMF and ethanol and in the presence of base is refluxed for 2 hrs to overnight. The reaction mixture is stirred at room temperature for about 30 minutes and filtered. The resultant solid is washed with ethanol (2×20 mL) and dried in a vacuum oven to provide an Indenoisoquinolinone Analog of Formula IIa or IIIa.

Methanesulfonate or Hydrochloride Salt Formation:

Free base of an Indenoisoquinolinone Analog of Formula IIb or IIIb is suspended in ethanol. To the stirred suspension, methanesulfonic acid or hydrochloric acid is added (2 to 10 equivalents). After some time, the resultant salt starts to precipitate from the solution. The mixture is stirred at room temperature for about 2 hours, filtered and washed with ethanol (2×20 mL). The filtered solid is dissolved in water (10 mL) and filtered. The filtrate is lyophilized to provide the corresponding salt of the free base of the Indenoisoquinolinone Analog of Formula Ia or IIIa.

B. Synthesis of Indenoisoquinolinone Analogs of Formula IIb and IIIb

Methyl 4-cyano-3-methylbenzoate

Methyl 4-cyano-3-methylbenzoate was obtained in 86% yield according to the procedure used to prepare methyl 3-cyano-2-methylbenzoate, except that methyl 4-bromo-3-methylbenzoate was used in place of methyl 3-bromo-2-methylbenzoate. $^1$H NMR spectrum (in DMSO-$d_6$): δ 7.96 (s, 1H); 7.85 (m, 2H); 3.85 (s, 3H); 2.46 (s, 3H).

Methyl 3-bromomethyl-4-cyanobenzoate

Methyl 3-bromomethyl-4-cyanobenzoate was obtained in 60% yield according to the procedure used to prepare methyl 2-bromomethyl-3-cyanobenzoate (supra), except that methyl 4-cyano-3-methylbenzoate was used in place of methyl 3-cyano-2-methylbenzoate. $^1$H NMR spectrum (in DMSO-$d_6$): δ 8.26 (s, 1H); 8.02 (s, 2H); 4.89 (s, 2H); 3.88 (s, 3H).

Methyl 5,6-dihydro-5-oxo-11-H-indeno[1,2-c]isoquinoline-9-carboxylate

Methyl 5,6-dihydro-5-oxo-11-H-indeno[1,2-c]isoquinoline-9-carboxylate was obtained in 65% yield according to the procedure used to prepare methyl 5,6-dihydro-5-oxo-11-H-indeno[1,2-c]isoquinoline-10-carboxylate, except that methyl 3-bromomethyl-4-cyanobenzoate was used in place of methyl 2-bromomethyl-3-cyanobenzoate. $^1$H NMR spectrum (in DMSO-$d_6$): δ 12.35 (s, 1H); 8.25 (d, J=8.1 Hz, 1H); 8.11 (s, 1H); 8.06 (d, J=7.8 Hz, 1H); 7.98 (d, J=8.1 Hz, 1H); 7.75 (m, 2H); 7.49 (m, 1H); 3.95 (s, 2H); 3.85 (s, 3H).

9-Hydroxymethyl-5,6-dihydro-5-oxo-11-H-indeno[1,2-c]isoquinoline

9-Hydroxymethyl-5,6-dihydro-5-oxo-11-H-indeno[1,2-c]isoquinoline was obtained in 96% yield according to the procedure used to prepare 10-hydroxymethyl-5,6-dihydro-5-oxo-11-H-indeno[1,2-c]isoquinoline, except that methyl 5,6-dihydro-5-oxo-11-H-indeno[1,2-c]isoquinoline-9-carboxylate was used in place of methyl 5,6-dihydro-5-oxo-11-H-indeno[1,2-c]isoquinoline-10-carboxylate. $^1$H NMR spectrum (in DMSO-$d_6$): δ 12.26 (s, 1H); 8.22 (d, J=8.1 Hz, 1H); 7.91 (s, J=8.1 Hz, 1H); 7.70 (m, 2H); 7.54 (s, 1H); 7.42 (m, 1H); 7.30 (d, J=8.1 Hz, 1H); 5.21 (d, 1H); 4.55 (d, J=5.4 Hz, 2H); 3.89 (s, 2H).

9-Bromomethyl-5,6-dihydro-5-oxo-11-H-indeno[1,2-c]isoquinoline

9-Bromomethyl-5,6-dihydro-5-oxo-11-H-indeno[1,2-c]isoquinoline was obtained in 65% yield according to the procedure used to prepare 10-bromomethyl-5,6-dihydro-5-oxo-11-H-indeno[1,2-c]isoquinoline, except that 9-hydroxymethyl-5,6-dihydro-5-oxo-11-H-indeno[1,2-c]isoquinoline was used in place of 10-hydroxymethyl-5,6-dihydro-5-oxo-11-H-indeno[1,2-c]isoquinoline. $^1$H NMR spectrum (in DMSO-$d_6$): δ 12.24 (s, 1H); 8.23 (d, J=7.5 Hz, 1H); 7.94 (d, J=7.8 Hz, 1H); 7.72 (m, 2H); 7.65 (s, 1H); 7.45 (m, 2H); 4.79 (s, 2H); 3.89 (s, 2H).

General Procedure for the Amination Reaction:

A suspension of 9-bromomethyl-5,6-dihydro-5-oxo-11-H-indeno[1,2-c]isoquinoline (0.425 g, 1.3 mmol) or a higher alkylene chain bromo-derivative, an appropriate amine in ethanol or DMF and ethanol and in the presence of base is refluxed for 2 hrs to overnight. The reaction mixture is stirred at room temperature for about 30 minutes and filtered. The resultant solid is washed with ethanol (2×20 mL) and dried in a vacuum oven to provide an Indenoisoquinolinone Analog of Formula IIb or IIIb.

Methanesulfonate or Hydrochloride Salt Formation:

Free base of an Indenoisoquinolinone Analog of Formula IIb or IIIb is suspended in ethanol. To the stirred suspension, methanesulfonic acid or hydrochloric acid is added (2 to 10 equivalents). After some time, the resultant salt starts to precipitate from the solution. The mixture is stirred at room temperature for about 2 hours, filtered and washed with ethanol (2×20 mL). The filtered solid is dissolved in water (10 mL) and filtered. The filtrate is lyophilized to provide the corresponding salt of the free base of the Indenoisoquinolinone Analog of Formula IIb or IIIb.

$^1$H NMR data for illustrative Indenoisoquinolinone Analogs are presented below in Table 3.

TABLE 3

| Compound | $^1$H NMR (DMSO-$d_6$ or DMSO-$d_6$ and $D_2O$) |
|---|---|
| IIa-1 | 10-[1-(4-Allylpiperazino)methyl]-5,6-dihydro-5-oxo-11-H-indeno[1,2-c]isoquinoline: $^1$H NMR (DMSO) δ 12.28 (s, 1H); 8.23 (d, J = 8.1 Hz, 1H); 7.89 (d, J = 7.2 Hz, 1H); 7.75 (m, 2H); 7.45 (m, 1H); 7.37 (t, J = 7.5 Hz, 1H); 7.28 (d, J = 7.5 Hz, 1H); 5.77 (m, 1H); 5.14 (d, J = 18.6 Hz, 1H); 5.08 (d, J = 10.8 Hz, 1H); 3.89 (s, 2H); 3.61 (s, 2H); 2.89 (d, J = 6.0 Hz, 2H); 2.40 (m, 8H). MS: m/z = 372 (M$^+$ – H) |
| IIIa-2 | 10-[1-(4-Butylpiperazino)methyl]-5,6-dihydro-5-oxo-11-H-indeno[1,2-c]isoquinoline: $^1$H NMR (DMSO) δ 12.28 (s, 1H); 8.24 (d, J = 7.8 Hz, 1H); 7.90 (d, J = 7.2 Hz, 1H); 7.74 (m, 2H); 7.45 (m, 1H); 7.36 (t, J = 7.5 Hz, 1H); 7.27 (d, J = 7.2 Hz, 1H); 3.90 (s, 2H); 3.64 (s, 2H); 2.38 (m, 10H); 1.41 (m, 2H); 1.24 (m, 2H); 0.85 (t, J = 7.2 Hz, 3H). MS: m/z = 388 (M$^+$ – H). |
| Dihydrochloride salt of IIa-1 | 10-[1-(4-Allylpiperazino)methyl]-5,6-dihydro-5-oxo-11-H-indeno[1,2-c]isoquinoline dihydrochloride: $^1$H NMR (DMSO & $D_2O$) δ 12.35 (s, 1H); 8.25 (d, J = 8.1 Hz, 1H); 8.04 (d, J = 7.5 Hz, 1H); 7.78 (t, J = 7.5 Hz, 1H); 7.72 (d, J = 7.5 Hz, 1H); 7.58 (s, 1H); 7.48 (m, 2H); 5.94 (m, 1H); 5.56 (d, J = 19.2 Hz, 1H); 5.48 (d, J = 10.5 Hz, 1H); 4.15 (s, 2H); 3.73 (s, 2H); 3.51 (m, 10H). |
| Dihydrochloride salt of IIIa-2 | 10-[1-(4-Butylpiperazino)methyl]-5,6-dihydro-5-oxo-11-H-indeno[1,2-c]isoquinoline dihydrochloride: $^1$H NMR (DMSO & $D_2O$) δ 12.35 (s, 1H); 8.25 (d, J = 8.1 Hz, 1H); 8.04 (d, J = 7.2 Hz, 1H); 7.78 (t, J = 7.2 Hz, 1H); 7.71 (d, J = 7.2 Hz, 1H); 7.58 (s, 1H); 7.48 (m, 2H); 4.15 (s, 2H); 3.53 (m, 10H); 3.04 (s, 2H); 1.62 (m, 2H); 1.30 (m, 2H); 0.88 (t, J = 7.2 Hz, 3H). MS: m/z = 388 (M$^+$ – H). |
| IIIa-3 | 10-[1-(4-Cyclopropylmethylpiperazino)methyl]-5,6-dihydro-5-oxo-11-H-indeno[1,2-c]isoquinoline: $^1$H NMR (DMSO) δ 12.23 (s, 1H); 8.24 (d, J = 7.8 Hz, 1H); 7.90 (d, J = 7.2 Hz, 1H); 7.74 (m, 2H); 7.44 (m, 1H); 7.35 (t, J = 7.5 Hz, 1H); 7.27 (d, J = 7.2 Hz, 1H); 3.88 (s, 2H); 3.61 (s, 2H); 2.42 (m, 8H); 2.13 (d, J = 5.7 Hz, 2H); 0.78 (m, 2H); 0.40 (d, J = 6.6 Hz, 2H); 0.02 (m, 2H). MS: m/z = 386 (M$^+$ – H). |
| IIa-14 | 10-[(4,4-Ethylenedioxy-piperidino)methyl]-5,6-dihydro-5-oxo-11-H-indeno[1,2-c]isoquinoline: $^1$H NMR (DMSO): δ 12.28 (s, 1H); 8.24 (d, J = 7.8 Hz, 1H); 7.90 (d, J = 7.2 Hz, 1H); 7.76 (m, 2H); 7.45 (m, 1H); 7.36 (t, J = 7.5 Hz, 1H); 7.29 (d, J = 7.2 Hz, 1H); 3.90 (s, 2H); 3.84 (s, 4H); 3.64 (s, 2H); 2.45 (m, 4H); 1.61 (m, 4H). MS: m/z 389 (M$^+$ – H). |
| IIIa-5 | 10-[N-(2-Pyrollidinoethyl)aminomethyl}-5,6-dihydro-5-oxo-11-H-indeno[1,2-c]isoquinoline: $^1$H NMR (DMSO) δ 12.23 (s, 1H); 8.23 (d, J = 8.1 Hz, 1H); 7.88 (dd, J = 2.1 Hz, 6.3 Hz, 1H); 7.74 (d, J = 3.6 Hz, 2H); 7.44 (m, 1H); 7.34 (m, 2H); 3.89 (s, |

TABLE 3-continued

| Compound | ¹H NMR (DMSO-d₆ or DMSO-d₆ and D₂O) |
|---|---|
|  | 2H); 3.87 (s, 2H); 2.62 (t, J = 6.3, 2H); 2.52 (m, 2H); 2.37 (m, 4H); 1.61 (m, 4H). MS: m/z 360 (M⁺ − H). |
| IIa-27 | 10-{N-[1-(Hydroxymethyl)cyclopentyl]aminomethyl}-5,6-dihydro-5-oxo-11-H-indeno[1,2-c]isoquinoline: ¹H NMR (DMSO) δ 12.28 (s, 1H); 8.23 (d, J = 7.8 Hz, 1H); 7.86 (d, J = 6.9 Hz, 1H); 7.73 (m, 1H); 7.45 (m, 1H); 7.36 (m, 2H); 4.56 (s, 1H); 3.90 (s, 2H); 3.79 (s, 2H); 3.41 (s, 2H); 1.69 (m, 2H); 1.53 (m, 4H). MS: m/z = 361 (M⁺ − H). |
| IIIa-6 | 10-{1-[4-(2-Pyrollidinoethyl)piperidino]methyl}-5,6-dihydro-5-oxo-11-H-indeno[1,2-c]isoquinoline: ¹H NMR (DMSO) δ 12.24 (s, 1H); 8.24 (d, J = 7.8 Hz, 1H); 7.89 (d, J = 7.2 Hz, 1H); 7.75 (m, 2H); 7.45 (m, 1H); 7.35 (t, J = 7.2 Hz, 1H); 7.28 (d, J = 7.2 Hz, 1H); 3.89 (s, 2H); 3.58 (s, 2H); 2.79 (d, J = 9.9 Hz, 2H); 2.35 (m, 6H); 1.95 (t, J = 10.6 Hz, 2H); 1.62 (m, 6H); 1.33 (m, 3H); 1.12 (m, 2H). MS: m/z = 428 (M⁺ − H). |
| IIIa-7 | 10-{N-[4-(1-Methylpiperidyl)]aminomethyl}-5,6-dihydro-5-oxo-11-H-indeno[1,2-c]isoquinoline: ¹H NMR (DMSO) δ 12.23 (s, 1H); 8.23 (d, J = 7.8 Hz, 1H); 7.87 (m, 1H); 7.75 (m, 2H); 7.46 (m, 1H); 7.36 (m, 2H); 3.90 (s, 2H); 3.88 (s, 2H); 2.68 (d, J = 11.7 Hz, 2H); 2.40 (m, 1H); 2.11 (s, 3H); 1.82 (m, 4H); 1.30 (m, 2H). |
| IIIa-9 | 10-[1-(4-Cyclopentylpiperazino)methyl]-5,6-dihydro-5-oxo-11-H-indeno[1,2-c]isoquinoline: ¹H NMR (DMSO) δ 12.23 (s, 1H); 8.24 (d, J = 7.8 Hz, 1H); 7.90 (d, J = 7.2 Hz, 1H); 7.74 (m, 2H); 7.44 (m, 1H); 7.35 (t, J = 7.5 Hz, 1H); 7.28 (d, J = 7.2 Hz, 1H); 3.89 (s, 2H); 3.60 (s, 2H); 2.41 (m, 9H); 1.71 (m, 2H); 1.56 (m, 2H); 1.45 (m, 2H); 1.28 (m, 2H). MS: m/z = 400 (M⁺ − H). |
| IIIa-8 | 10-{1-[4-(2-Pyrimidyl)piperazino]methyl}-5,6-dihydro-5-oxo-11-H-indeno[1,2-c]isoquinoline: ¹H NMR (DMSO) δ 12.28 (s, 1H); 8.32 (d, J = 4.8, 2H); 8.24 (d, J = 7.8 Hz, 1H); 7.92 (d, J = 6.8 Hz, 1H); 7.74 (m, 2H); 7.44 (m, 1H); 7.35 (m, 2H); 6.59 (t, J = 4.8 Hz, 1H); 3.94 (s, 2H); 3.73 (m, 4H); 3.68 (s, 2H); 2.46 (m, 4H). MS: m/z = 410 (M⁺ − H). |
| IIIa-10 | 10-{1-[4-(2-Ethoxyethyl)piperazino]methyl}-5,6-dihydro-5-oxo-11-H-indeno[1,2-c]isoquinoline: ¹H NMR (DMSO) δ 12.28 (s, 1H); 8.23 (d, J = 7.8 Hz, 1H); 7.90 (d, J = 7.2 Hz, 1H); 7.76 (m, 2H); 7.45 (m, 1H); 7.35 (t, J = 7.5 Hz, 1H); 7.27 (d, J = 7.2 Hz, 1H); 3.89 (s, 2H); 3.60 (s, 2H); 3.38 (m, 4H); 2.40 (m, 10H); 1.06 (t, J = 6.9 Hz, 3H). MS: m/z = 404 (M⁺ − H). |
| IIb-1 | 9-[1-(4-Allylpiperazino)methyl]-5,6-dihydro-5-oxo-11-H-indeno[1,2-c]isoquinoline: ¹H NMR (DMSO) δ 12.23 (s, 1H); 8.22 (d, J = 7.8 Hz, 1H); 7.91 (d, J = 7.8 Hz, 1H); 7.71 (m, 2H); 7.51 (s, 1H); 7.44 (m, 1H); 7.28 (d, J = 7.5 Hz, 1H); 5.76 (m, 1H); 5.13 (d, J = 18.9 Hz, 1H); 5.08 (d, J = 11.2 Hz, 1H); 3.86 (s, 2H); 3.51 (s, 2H); 2.90 (d, J = 6.0 Hz, 2H); 2.37 (m, 8H). MS: m/z = 372 (M⁺ − H). |
| IIIb-1 | 9-[1-(4-iso-Propylpiperazino)methyl]-5,6-dihydro-5-oxo-11-H-indeno[1,2-c]isoquinoline: ¹H NMR (DMSO) δ 12.22 (s, 1H); 8.23 (d, J = 7.8 Hz, 1H); 7.92 (d, J = 7.8 Hz, 1H); 7.71 (m, 2H); 7.50 (s, 1H); 7.43 (m, 1H); 7.28 (d, J = 7.8 Hz, 1H); 3.86 (s, 2H); 3.50 (s, 2H); 2.60 (m, 1H); 2.46-2.35 (m, 8H); 0.94 (d, J = 6.3 Hz, 6H). MS: m/z = 374 (M⁺ − H). |
| IIIb-13 | 9-[1-(4-Methylhomopiperazino)methyl]-5,6-dihydro-5-oxo-11-H-indeno[1,2-c]isoquinoline: ¹H NMR (DMSO) δ 12.24 (s, 1H); 8.23 (d, J = 8.1 Hz, 1H); 7.91 (d, J = 7.8 Hz, 1H); 7.71 (m, 2H); 7.53 (s, 1H); 7.43 (m, 1H); 7.31 (d, J = 7.8 Hz, 1H); 3.86 (s, 2H); 3.65 (s, 2H); 2.66-2.50 (m, 8H); 2.25 (s, 3H); 1.71 (m, 2H). m/z = 360 (M⁺ − H). |
| Dihydrochloride salt of IIIb-3 | 9-[1-(4-Cyclopropylmethylpiperazino)methyl]-5,6-dihydro-5-oxo-11-H-indeno[1,2-c]isoquinoline dihydrochloride: ¹H NMR (DMSO & D₂O) δ 8.22 (d, J = 7.8 Hz, 1H); 7.98 (t, J = 7.5 Hz, 1H); 7.74 (m, 3H); 7.50 (m, 2H); 4.35 (s, 2H); 3.87 (s, 2H); 3.38 (m, 8H); 3.04 (d, J = 6.3 Hz, 2H); 1.02 (m, 1H); 0.62 (d, J = 6.3 Hz, 2H); 0.34 (m, 2H). MS: m/z = 386 (M⁺ − H). |
| Dihydrochloride salt of IIIb-1 | 9-[1-(4-iso-Propylpiperazino)methyl]-5,6-dihydro-5-oxo-11-H-indeno[1,2-c]isoquinoline dihydrochloride: ¹H NMR (DMSO) δ 12.22 (s, 1H); 8.22 (d, J = 8.1 Hz, 1H); 7.99 (d, J = 7.8 Hz, 1H); 7.75 (m, 3H); 7.56 (d, J = 7.8 Hz, 1H); 7.47 (m, 1H); 4.39 (s, 2H); 3.90 (s, 2H); 3.54 (m, 9H); 1.23 (d, J = 6.0 Hz, 6H). MS: m/z = 374 (M⁺ − H). |
| IIIb-2 | 9-[1-(4-Butylpiperazino)methyl]-5,6-dihydro-5-oxo-11-H-indeno[1,2-c]isoquinoline: ¹H NMR (DMSO) δ 12.23 (s, 1H); 8.22 (d, J = 8.1 Hz, 1H); 7.91 (d, J = 7.8 Hz, 1H); 7.71 (m, 2H); 7.50 (s, 1H); 7.43 (m, 1H); 7.27 (d, J = 7.8 Hz, 1H); 3.86 (s, 2H); 3.50 (s, 2H); 2.35 (m, 8H); 2.22 (t, J = 6.9 Hz, 2H); 1.37-1.20 (m, 4H); 0.84 (t, J = 6.9 Hz, 3H). MS: m/z = 388 (M⁺ − H). |
| Dihydrochloride salt of IIIb-2 | 9-[1-(4-Butylpiperazino)methyl]-5,6-dihydro-5-oxo-11-H-indeno[1,2-c]isoquinoline dihydrochloride: ¹H NMR (DMSO) δ 12.23 (s, 1H); 8.23 (d, J = 7.8 Hz, 1H); 8.00 (d, J = 8.1 Hz, 1H); 7.76 (m, 3H); 7.55 (d, J = 7.5 Hz, 1H); 7.48 (m, 1H); 4.36 (s, 2H); 3.91 (s, 2H); 3.40 (m, 8H); 3.09 (t, J = 7.5 Hz, 2H); 1.58 (m, 2H); 1.28 (m, 1H); 0.86 (t, J = 7.2 Hz, 3H). MS: m/z = 388 (M⁺ − H). |
| Dihydrochloride salt of IIb-1 | 9-[1-(4-Allylpiperazino)methyl]-5,6-dihydro-5-oxo-11-H-indeno[1,2-c]isoquinoline dihydrochloride: ¹H NMR (DMSO & D₂O) δ 8.22 (d, J = 8.1 Hz, 1H); 7.97 (d, J = 7.8 Hz, 1H); 7.75 (m, 3H); 7.49 (m, 2H); 5.83 (m, 1H); 5.53 (d, J = 19.5 Hz, 1H); 5.08 (d, J = 9.6 Hz, 1H); 4.29 (s, 2H); 3.91 (s, 2H); 3.71 (d, J = 6.9 Hz, 2H); 3.32 (m, 8H). |
| Dihydrochloride salt of IIIb-14 | 9-[1-(4-Cyclohexylpiperazino)methyl]-5,6-dihydro-5-oxo-11-H-indeno[1,2-c]isoquinoline dihydrochloride: ¹H NMR (DMSO & D₂O) δ 8.21 (d, J = 8.1 Hz, 1H); 7.94 (d, J = 7.8 Hz, 1H); 7.75 (m, 3.9 Hz, 2H); 7.70 (s, 1H); 7.48 (m, 2H); 3.92 (s, 2H); 3.57 (s, 3H); 3.27 (m, 8H); 2.05 (s, 2H); 1.79 (d, J = 10.8 Hz, 2H); 1.57 (d, J = 11.1 Hz, 1H); 1.43-1.05 (m, 5H). |
| IIIb-24 | 9-[1-(3,5-Dimethylpiperazino)methyl]-5,6-dihydro-5-oxo-11-H-indeno[1,2-c]isoquinoline: ¹H NMR (DMSO) δ 12.22 (s, 1H); 8.22 (d, J = 7.8 Hz, 1H); 7.91 (d, J = 7.8 Hz, 1H); 7.71 (m, 2H); 7.49 (s, 1H); 7.44 (m, 1H); 7.28 (d, J = 7.8 Hz, 1H); 3.87 (s, 2H); 3.46 (s, 2H); 2.72 (m, 2H); 2.65 (d, J = 9.3 Hz, 2H); 1.49 (t, J = 10.1 Hz, 3H); 0.87 (d, J = 6.0 Hz, 6H). MS: m/z = 360 (M⁺ − H). |
| IIIb-17 | 9-{1-[4-(2-Pyrrolidinoethyl)piperidino]methyl}-5,6-dihydro-5-oxo-11-H-indeno[1,2-c]isoquinoline: ¹H NMR (DMSO) δ 12.23 (s, 1H); 8.22 (d, J = 8.1 Hz, 1H); 7.91 (d, J = 7.5 Hz, 1H); 7.73 (m, 2H); 7.50 (s, 1H); 7.44 (m, 1H); 7.28 (d, J = 7.8 Hz, 1H); 3.87 (s, 2H); 3.48 (s, 2H); 2.79 (d, J = 11.1 Hz, 2H); 2.35 (m, 6H); 1.90 (t, J = 10.6 Hz, 2H); 1.62 (m, 6H); 1.33 (m, 3H); 1.15 (m, 2H). MS: m/z = 428 (M⁺ − H). |
| IIb-92 | 9-{N-[4-(1-Boc-piperidyl)]aminomethyl}-5,6-dihydro-5-oxo-11-H-indeno[1,2-c]isoquinoline: ¹H NMR (DMSO) δ 12.23 (s, 1H); 8.23 (d, J = 7.8 Hz, 1H); 7.90 (d, J = 7.5 Hz, 1H); 7.71 (m, 2H); 7.57 (s, 1H); 7.43 (m, 1H); 7.34 (d, J = 7.5 Hz, 1H); 3.86 (s, 2H); 3.79 (m, 4H); 2.78 (m, 2H); 2.56 (m, 1H); 1.79 (d, J = 12.0 Hz, 2H); 1.37 (s, 9H); 1.15 (m, 2H). MS: m/z = 446 (M⁺ − H). |
| IIIb-9 | 9-[1-(4-Cyclopentylpiperazino)methyl]-5,6-dihydro-5-oxo-11-H-indeno[1,2-c]isoquinoline dihydrochloride: ¹H NMR (DMSO) δ 12.22 (s, 1H); 8.22 (d, J = 8.1 Hz, 1H); 7.91 (d, J = 8.1 Hz, 1H); 7.71 (m, 2H); 7.51 (s, 1H); 7.44 (m, 1H); 7.28 (d, J = 7.5 Hz, 1H); 3.87 (s, 2H); 3.50 (s, 2H); 2.83 (m, 1H); 2.38 (m, 8H); 1.71 (m, 2H); 1.51 (m, 4H); 1.27 (m, 2H). MS: m/z = 400 (M⁺ − H). |
| IIIb-10 | 9-{1-[4-(2-Ethoxyethyl)piperazino]methyl}-5,6-dihydro-5-oxo-11-H-indeno[1,2-c]isoquinoline: ¹H NMR (DMSO) δ 12.28 (s, 1H); 8.23 (d, J = 7.8 Hz, 1H); 7.91 (d, J = 7.8 Hz, 1H); 7.71 (m, 2H); 7.51 (s, 1H); 7.43 (m, 1H); 7.29 (d, J = 7.8 Hz, 1H); 3.87 (s, 2H); 3.50 (s, 2H); 3.38 (m, 4H); 2.38 (m, 10H); 1.06 (t, J = 6.9 Hz, 3H). MS: m/z = 404 (M⁺ − H). |
| IIb-196 | 9-{1-[4-(2,2-Diethoxyethyl)piperazino]methyl}-5,6-dihydro-5-oxo-11-H-indeno[1,2-c]isoquinoline: ¹H NMR (DMSO) δ 12.29 (s, 1H); 8.22 (d, J = 7.8 Hz, 1H); 7.91 (d, J = 7.8 Hz, 1H); 7.71 (m, 2H); 7.50 (s, 1H); 7.43 (m, 1H); 7.28 (d, J = 7.8 Hz, 1H); 4.54 (t, J = 4.8 Hz, 1H); 3.87 (s, 2H); 3.50 (m, 6H); 3.38 (m, 8H); 1.07 (t, J = 7.2 Hz, 3H). MS: m/z = 448 (M⁺ − H). |
| IIb-53 | 9-[(1-N-Methyl-3-morpholinopropynyl)methyl]-5,6-dihydro-5-oxo-11-H-indeno[1,2-c]isoquinoline: ¹H NMR (DMSO) δ 12.28 (bs, 1H); 8.25 (d, J = 7.5 Hz, 1H); 7.98 (m, 1H); 7.76 (m, 2H); 7.51 (s, 1H); 7.47 (m, 1H); 7.26 (m, 1H); 4.67 (s, 1H); 4.59 (s, 1H); 3.83 (m, 2H); 3.58-3.49 (m, 4H); 2.96 (s, 2H); 2.84 (m, 1H); 2.73-2.32 (m, 8H). |
| IIb-16 | 9-[(4-tert-Butoxycarbonyl-piperazino)methyl]-5,6-dihydro-5-oxo-11-H-indeno[1,2-c]isoquinoline: ¹H NMR (DMSO) δ 12.29 (s, 1H); 8.25 (d, J = 7.5 Hz, 1H); 7.95 (d, J = 7.8 Hz, 1H); 7.74 (m, 1H); 7.48 (m, 1H); 7.32 (d, J = 7.8, 1H); 3.89 (s, 2H); 3.56 (s, 2H); 3.32 (m, 2H); 2.50 (m, 2H); 2.33 (m, 4H); 1.39 (s, 9H). |
| IIb-105 | 9-[(4-Propionyl-piperazino)methyl]-5,6-dihydro-5-oxo-11-H-indeno[1,2-c]isoquinoline: ¹H NMR (DMSO) δ 12.32 (s, 1H); 8.25 (d, J = 7.5 Hz, 1H); 7.95 (d, J = 7.8 Hz, 1H); 7.75 (m, 2H); |

TABLE 3-continued

| Compound | $^1$H NMR (DMSO-d$_6$ or DMSO-d$_6$ and D$_2$O) |
|---|---|
| | 7.55 (s, 1H); 7.47 (m, 1H); 7.33 (d, J = 8.1); 3.90 (s, 2H); 3.57 (s, 2H); 3.44 (m, 4H); 2.33 (m, 6H); 0.97 (t, J = 7.5, 3H). MS: m/z = 388 (M$^+$ − H). |
| IIIb-18 | 9-[4-(2-Hydroxy-2-methyl-propyl-piperazino)methyl]-5,6-dihydro-5-oxo-11-H-indeno[1,2-c]isoquinoline dihydrochloride: $^1$H NMR (DMSO) δ 12.37 (s, 1H); 8.27 (d, J = 7.8 Hz, 1H); 8.05 (m, 1H); 7.78 (m, 3H); 7.50 (m, 2H); 3.96 (s, 2H); 3.72-2.73 (m, 12H); 1.20 (s, 6H). MS: m/z = 404 (M$^+$ − H). |
| IIb-118 | 9-[(4-Propionyl-homopiperazino)methyl]-5,6-dihydro-5-oxo-11-H-indeno[1,2-c]isoquinoline hydrochloride: $^1$H NMR (DMSO) δ 12.39 (s, 1H); 10.71 (bs, 1H); 8.27 (d, J = 8.1, 1H); 8.06 (d, J = 7.5 Hz, 1H); 7.81 (m, 3H); 7.64 (m, 1H); 7.51 (m, 1H); 4.42 (s, 2H); 4.15-2.99 (m, 14H); 0.99 (t, J = 7.2 Hz, 1H). MS: m/z = 402 (M$^+$ − H). |
| Dihydrochloride salt of IIIb-19 | 9-[(1-N-Methyl-2-morpholino-aminoethyl)methyl]-5,6-dihydro-5-oxo-11-H-indeno[1,2-c]isoquinoline dihydrochloride: $^1$H NMR (DMSO) δ 12.41 (s, 1H); 11.64 (bs, 1H); 11.35 (bs, 1H); 8.27 (d, J = 6.9, 1H); 8.07 (d, J = 6.9, 1H); 7.90 (s, 1H); 7.74 (m, 3H); 7.51 (m, 1H); 4.62 (m, 1H); 4.39 (m, 1H); 3.96 (s, 2H); 3.83-3.17 (m, 12H); 2.73 (s, 3H). MS: m/z = 390 (M$^+$ − H). |
| IIIa-11 | 10-[S-(3-Fluoropyrrolidino)methyl]-5,6-dihydro-5-oxo-11-H-indeno[1,2-c]isoquinoline: $^1$H NMR (DMSO) δ 12.30 (s, 1H); 8.24 (d, J = 8.1 Hz, 1H); 7.91 (d, J = 7.5); 7.75 (m, 2H); 7.48-7.30 (m, 3H); 5.30 (m, 0.5H); 5.11 (m, 0.5H); 3.89 (s, 2H); 3.78 (s, 2H); 2.87-1.86 (m, 6H). MS: m/z = 335 (M$^+$ − H). |
| IIIa-12 | 10-[(3,4-Dehydropiperidino)methyl]-5,6-dihydro-5-oxo-11-H-indeno[1,2-c]isoquinoline: $^1$H NMR (DMSO) δ 12.29 (s, 1H); 8.26 (d, J = 7.2 Hz, 1H); 7.93 (d, J = 6.6); 7.77 (m, 2H); 7.46-7.33 (m, 3H); 5.67 (m, 2H); 3.91 (s, 2H); 3.71 (s, 2H); 2.92 (m, 2H); 2.56 (m, 2H); 2.09 (m, 2H). MS: m/z = 329 (M$^+$ − H). |
| IIIa-4 | 10-[N-1-(3-Hydroxypropyl)aminomethyl]-5,6-dihydro-5-oxo-11-H-indeno[1,2-c]isoquinoline: $^1$H NMR (DMSO) δ 12.25 (s, 1H); 8.23 (d, J = 8.1 Hz, 1H); 7.87 (dd, J = 2.9 Hz, 5.9 Hz, 1H); 7.75 (m, 2H); 7.44 (m, 1H); 7.34 (m, 1H); 3.89 (s, 2H); 3.85 (s, 2H); 3.46 (t, J = 6.3 Hz, 2H); 2.60 (t, J = 6.9 Hz, 2H); 1.60 (m, J = 6.3 Hz, 2H). MS: m/z = 321 (M$^+$ − H). |
| IIIa-1 | 10-[1-(4-iso-Propylpiperazino)methyl]-5,6-dihydro-5-oxo-11-H-indeno[1,2-c]isoquinoline: $^1$H NMR (DMSO) δ 12.28 (s, 1H); 8.23 (d, J = 8.1 Hz, 1H); 7.90 (d, J = 7.5 Hz, 1H); 7.75 (m, 2H); 7.44 (m, 1H); 7.35 (m, 1H); 7.27 (d, J = 7.2 Hz, 1H); 3.89 (s, 2H); 3.59 (s, 2H); 2.58 (m, 1H); 2.46-2.35 (m, 8H); 0.92 (d, J = 6.3 Hz, 6H). MS: m/z = 374 (M$^+$ − H). |
| IIa-40 | 10-{1-[4-(1-pyrrolidinocarbonylmethyl)piperazino]methyl}-5,6-dihydro-5-oxo-11-H-indeno[1,2-c]isoquinoline: $^1$H NMR (DMSO) δ 12.25 (s, 1H); 8.24 (d, J = 8.1 Hz, 1H); 7.90 (d, J = 7.2 Hz, 1H); 7.76 (m, 2H); 7.45 (m, 1H); 7.36 (t, J = 7.8 Hz, 1H); 7.28 (d, J = 7.8 Hz, 1H); 3.90 (s, 2H); 3.62 (s, 2H); 3.44 (t, J = 6.6 Hz, 2H); 3.24 (m, J = 6.9 Hz, 2H); 3.04 (s, 2H); 2.43 (m, 8H); 1.81 (m, 2H); 1.72 (m, 2H). MS: m/z = 443 (M$^+$ − H). |
| Dihydrochloride salt of IIIb-13 | 9-[1-(4-Methylhomopiperazino)methyl]-5,6-dihydro-5-oxo-11-H-indeno[1,2-c]isoquinoline dihydrochloride: $^1$H NMR (DMSO) δ 12.35 (s, 1H); 8.23 (d, J = 7.8 Hz, 1H); 8.02 (d, J = 7.8 Hz, 1H); 7.84 (s, 1H); 7.76 (m, J = 3.3 Hz, 1H); 7.65 (d, J = 7.2 Hz, 1H); 7.47 (m, 1H); 4.42 (s, 2H); 3.92 (s, 2H); 3.32 (m, 8H); 2.76 (s, 3H); 2.19 (m, 2H). MS: m/z = 360 (M$^+$ − H). |
| IIb-66 | 9-{1-[4-(2-Cyanoethyl)piperazino]methyl}-5,6-dihydro-5-oxo-11-H-indeno[1,2-c]isoquinoline: $^1$H NMR (DMSO) δ 12.25 (s, 1H); 8.22 (d, J = 8.1 Hz, 1H); 7.92 (d, J = 7.5 Hz, 1H); 7.71 (m, 2H); 7.51 (s, 1H); 7.44 (m, 1H); 7.29 (d, J = 7.5 Hz, 1H); 3.87 (s, 2H); 3.52 (s, 2H); 2.62 (m, J = 6.1 Hz, 2H); 2.54 (d, J = 6.1 Hz, 2H); 2.41 (m, 8H). MS: m/z = 385 (M$^+$ − H). |
| Methylsulfonate salt of IIIb-15 | 9-[1-(4,4-Difluoropiperidino)methyl]-5,6-dihydro-5-oxo-11-H-indeno[1,2-c]isoquinoline methylsulfonate: $^1$H NMR (DMSO) δ 12.36 (s, 1H); 9.75 (m, 1H); 8.25 (d, J = 8.1 Hz, 1H); 8.06 (d, J = 8.1 Hz, 1H); 7.77 (m, 3H); 7.51 (m, 2H); 4.47 (s, 2H); 3.96 (s, 2H); 3.42 (m, 2H); 3.19 (m, 2H); 2.32 (s, 3H); 2.29 (m, 4H). MS: m/z = 367 (M$^+$ − H). |
| IIb-79 | 9-{N-[4-(1-Boc-piperidyl)]-N-cyclopropylaminomethyl}-5,6-dihydro-5-oxo-11-H-indeno[1,2-c]isoquinoline: $^1$H NMR (DMSO) δ 12.28 (s, 1H); 8.22 (d, J = 8.1 Hz, 1H); 7.88 (d, J = 8.1 Hz, 1H); 7.71 (m, 2H); 7.48 (m, 1H); 7.43 (m, 1H); 7.27 (d, J = 7.8 Hz, 1H); 3.94 (m, 2H); 3.85 (m, 2H); 3.81 (s, 2H); 2.61 (m, 3H); 2.01 (m, 1H); 1.74 (m, 2H); 1.36 (m, 11H); 0.42 (m, 2H); 0.25 (m, 2H). MS: m/z = 486 (M$^+$ − H). |
| IIb-131 | 9-{1-[4-(2-Furyl)piperazino]methyl}-5,6-dihydro-5-oxo-11-H-indeno[1,2-c]isoquinoline: $^1$H NMR (DMSO) δ 12.28 (s, 1H); 8.23 (d, J = 8.1 Hz, 1H); 7.92 (d, J = 7.8 Hz, 1H); 7.72 (m, 2H); 7.51 (s, 1H); 7.44 (m, 1H); 7.29 (d, J = 8.1 Hz, 1H); 3.88 (s, 3H); 3.68 (dt, J = 6.9 Hz, 7.5 Hz, 1H); 3.55 (dt, J = 6.9 Hz, 7.5 Hz, 1H); 3.51 (s, 2H); 2.37 (m, 10H); 1.86 (m, 1H); 1.73 (m, 2H); 1.45 (m, 2H). MS: m/z = 416 (M$^+$ − H). |
| IIb-157 | 9-{1-[4-(1-Pyrrolidinocarbonylmethyl)piperazino]methyl}-5,6-dihydro-5-oxo-11-H-indeno[1,2-c] isoquinoline: $^1$H NMR (DMSO) δ 12.27 (s, 1H); 8.23 (d, J = 7.8 Hz, 1H); 7.92 (d, J = 8.1 Hz, 1H); 7.72 (m, 2H); 7.51 (s, 1H); 7.44 (m, 1H); 7.29 (d, J = 7.8 Hz, 1H); 3.88 (s, 2H); 3.51 (m, 2H); 3.43 (t, J = 6.5 Hz, 2H); 3.24 (t, J = 6.6 Hz, 2H); 3.04 (s, 2H); 2.38 (m, 8H); 1.77 (m, 4H). MS: m/z = 443 (M$^+$ − H). |
| IIIb-20 | 9-(N-4-Piperidylaminomethyl)-5,6-dihydro-5-oxo-11-H-indeno[1,2-c]isoquinoline: $^1$H NMR (DMSO) δ 12.35 (s, 1H); 9.67 (s, 2H); 9.04 (s, 1H); 8.90 (s, 1H); 8.25 (d, J = 7.8 Hz, 1H); 8.01 (d, J = 7.8 Hz, 1H); 7.83 (m, 1H); 7.77 (m, 1H); 7.63 (d, J = 7.5 Hz, 1H); 7.48 (m, 1H); 4.23 (s, 2H); 3.94 (s, 2H); 3.32 (m, 3H); 2.90 (m, 2H); 2.27 (m, 2H); 1.92 (m, 2H). MS: m/z = 346 (M$^+$ − H). |
| IIIb-8 | 9-{1-[4-(2-Pyrimidyl)piperazino]methyl}-5,6-dihydro-5-oxo-11-H-indeno[1,2-c]isoquinoline: $^1$H NMR (DMSO) δ 12.29 (s, 1H); 8.32 (d, J = 5.1 Hz, 2H); 8.23 (d, J = 8.1 Hz, 1H); 7.94 (d, J = 7.5 Hz, 1H); 7.72 (m, 2H); 7.57 (s, 1H); 7.45 (m, 1H); 7.34 (d, J = 7.5 Hz, 1H); 6.59 (t, J = 4.8 Hz, 1H); 3.89 (s, 2H); 3.72 (m, 4H); 3.58 (s, 2H); 2.44 (m, 4H). MS: m/z = 410 (M$^+$ − H). |
| IIb-170 | 9-{1-[4-(Cyclopropylcarbonyl)piperazino]methyl}-5,6-dihydro-5-oxo-11-H-indeno[1,2-c]isoquinoline: $^1$H NMR (DMSO) δ 12.23 (s, 1H); 8.24 (d, J = 8.1 Hz, 1H); 7.94 (d, J = 7.8 Hz, 1H); 7.72 (m, 2H); 7.55 (s, 1H); 7.45 (m, 1H); 7.33 (d, J = 7.2 Hz, 1H); 3.89 (s, 2H); 3.66 (m, 2H); 3.57 (s, 2H); 3.46 (m, 2H); 2.40 (m, 4H); 1.93 (m, 1H); 0.68 (m, 4H). MS: m/z = 400 (M$^+$ − H). |
| IIIb-21 | 9-{1-[4-(Trifluoromethyl)piperidino]methyl}-5,6-dihydro-5-oxo-11-H-indeno[1,2-c]isoquinoline: $^1$H NMR (DMSO) δ 12.23 (s, 1H); 8.23 (d, J = 7.8 Hz, 1H); 7.93 (d, J = 8.1 Hz, 1H); 7.72 (m, 2H); 7.52 (s, 1H); 7.44 (m, 1H); 7.30 (d, J = 7.8 Hz, 1H); 3.87 (s, 2H); 3.54 (s, 2H); 2.89 (d, J = 11.3 Hz, 2H); 2.21 (m, 1H); 1.97 (t, J = 11.5 Hz, 2H); 1.76 (d, J = 11.6 Hz, 2H); 1.45 (m, 2H). MS: m/z = 399 (M$^+$ − H). |
| IIIb-22 | 9-(1-Homopiperidinomethyl)-5,6-dihydro-5-oxo-11-H-indeno[1,2-c]isoquinoline: $^1$H NMR (DMSO) δ 12.18 (s, 1H); 8.23 (d, J = 7.8 Hz, 1H); 7.90 (d, J = 7.8 Hz, 1H); 7.71 (m, 2H); 7.54 (s, 1H); 7.43 (m, 1H); 7.31 (d, J = 7.8 Hz, 1H); 3.86 (s, 2H); 3.65 (2, 1H); 2.57 (m, 4H); 1.57 (m, 8H). MS: m/z = 345 (M$^+$ − H). |
| IIb-183 | 9-[1-(4-Octylpiperazino)methyl]-5,6-dihydro-5-oxo-11-H-indeno[1,2-c]isoquinoline: $^1$H NMR (DMSO) δ 12.28 (s, 1H); 8.23 (d, J = 8.1 Hz, 1H); 7.93 (d, J = 7.8 Hz, 1H); 7.72 (m, 2H); 7.53 (s, 1H); 7.44 (m, 1H); 7.31 (d, J = 7.2 Hz, 1H); 3.88 (s, 2H); 3.58 (s, 2H); 2.87 (m, 4H); 2.41 (m, 6H); 1.55 (m, 2H); 1.23 (m, 10H); 0.84 (t, J = 6.9 Hz, 3H). MS: m/z = 444 (M$^+$ − H). |
| IIIb-23 | 9-{1-[4-(3-Hydroxypropyl)piperazino]methyl}-5,6-dihydro-5-oxo-11-H-indeno[1,2-c]isoquinoline: $^1$H NMR (DMSO) δ 12.27 (s, 1H); 8.22 (d, J = 7.5 Hz, 1H); 7.92 (d, J = 7.8 Hz, 1H); 7.71 (m, 2H); 7.51 (s, 1H); 7.44 (m, 1H); 7.27 (d, J = 7.8 Hz, 1H); 3.87 (s, 2H); 3.51 (s, 2H); 3.40 (t, J = 6.3 Hz, 2H); 2.37 (m, 10H); 1.53 (t, J = 6.3 Hz, 3H). MS: m/z = 390 (M$^+$ − H). |
| IIb-40 | 9-((4-(2-oxo-2-(pyrrolidin-1-yl)ethyl)piperazin-1-yl)methyl)-6,11-dihydro-5H-indeno[1,2-c]isoquinolin-5-one: $^1$H NMR (DMSO-d$_6$): δ 12.27 (s, 1H); 8.23 (d, J = 7.8 Hz, 1H); 7.92 (d, J = 8.1 Hz, 1H); 7.72 (m, 2H); 7.51 (s, 1H); 7.43 (t, J = 7.8 Hz, 1H); 7.29 (d, J = 7.8 Hz, 1H); 3.87 (s, 2H); 3.51 (s, 2H); 3.43 (t, J = 6.6 Hz, 2H); 3.24 (t, J = 6.6 Hz, 2H); 3.04 (s, 2H); 2.38 (m, 8H); 1.80 (m, 2H); 1.72 (m, 2H). |
| IIb-27 | 9-((1-(hydroxymethyl)cyclopentylamino)methyl)-6,11-dihydro-5H-indeno[1,2-c]isoquinolin-5-one: $^1$H NMR (DMSO-d$_6$): δ 12.35 (s, 1H); 8.86 (s, 2H); 8.26 (d, J = 8.1 Hz, 1H); 8.03 (d, J = 7.2 Hz, 1H); 7.78 (m, 3H); 7.55 (m, 2H); 5.74 (s, 1H); 4.19 (s, 2H); 3.97 (s, 2H); 3.58 (s, 2H); 1.76 (m, 6H); 1.58 (m, 2H). MS: m/z 361 (M − H$^+$). |

TABLE 3-continued

| Compound | $^1$H NMR (DMSO-$d_6$ or DMSO-$d_6$ and $D_2O$) |
|---|---|
| IIb-210 | 9-((4-(2-(pyrrolidin-1-yl)ethyl)piperidin-1-yl)methyl)-6,11-dihydro-5H-indeno[1,2-c]isoquinolin-5-one: $^1$H NMR (DMSO-$d_6$): δ 12.24 (s, 1H); 8.22 (d, J = 8.1 Hz, 1H); 7.91 (d, J = 7.5 Hz, 1H); 7.70 (m, 2H); 7.50 (s, 1H); 7.43 (t, J = 7.8 Hz, 1H); 7.27 (d, J = 7.8 Hz, 1H); 3.86 (s, 2H); 3.48 (s, 2H); 2.78 (d, J = 11.1 Hz, 2H); 2.35 (m, 6H); 1.89 (t, J = 10.6 Hz, 2H); 1.62 (m, 6H); 1.35 (m, 3H); 1.15 (m, 2H). MS: m/z 428 (M − H$^+$). |
| IIa-28 | 10-((1-hydroxymethyl)cyclopentylamino)methyl)benzofuro[3,2-c]isoquinolin-5(6H)-one: $^1$H NMR (DMSO-$d_6$): δ 12.52 (s, 1H); 9.16 (s, 2H); 8.35 (d, J = 8.1 Hz, 1H); 8.08 (m, 2H); 7.94 (t, J = 7.5 Hz, 1H); 7.69 (t, J = 7.2 Hz, 1H); 7.63 (d, J = 7.8 Hz, 1H); 7.46 (t, J = 7.5 Hz, 1H); 5.85 (s, 1H); 4.51 (s, 2H); 3.68 (s, 2H); 1.91 (m, 5H); 1.79 (m, 2H); 1.63 (m, 2H). |
| Va-1 | 4-chloro-10-((cyclopentylamino)methyl)-6,11-dihydro-5H-indeno[1,2-c]isoquinolin-5-one $^1$H NMR (DMSO-$d_6$).: δ 8.94 (bs, 2H), 8.13 (m, 1H), 7.85 (m, 2H), 7.51 (m, 3H), 4.39 (m, 2H), 4.10 (s, 2H), 3.67 (m, 1H), 2.07 (m, 2H), 1.65 (m, 4H), 1.54 (m, 2H). MS: m/z 365.2 (M − H$^+$). |
| Va-2 | 10-((cyclopentylamino)methyl)-2-fluoro-6,11-dihydro-5H-indeno[1,2-c]isoquinolin-5-one $^1$H NMR (DMSO-$d_6$).: δ 12.46 (bs, 1H), 8.95 (bs, 2H), 8.32 (dd, J = 6.0, 6.0 Hz, 1H), 8.07 (dd, J = 2.0, 5.0 Hz, 1H), 7.54 (m, 3H), 7.33 (dd, J = 6.0, 6.0 Hz, 1H), 4.29 (m, 2H), 4.06 (s, 2H), 3.65 (m, 1H), 2.06 (m, 2H), 1.72 (m, 4H), 1.58 (m, 2H). MS: m/z 349.0 (M − H$^+$). |
| Va-3 | 10-((cyclopentylamino)methyl)-3-fluoro-6,11-dihydro-5H-indeno[1,2-c]isoquinolin-5-one $^1$H NMR (DMSO-$d_6$).: δ 12.53 (bs, 1H); 8.95 (bs, 2H), 8.04 (dd, J = 6.0, 7.2 Hz, 1H), 7.98 (m, 1H), 7.73 (m, 1H), 7.51 (m, 2H), 4.31 (dd, J = 5.2, 5.2 Hz, 2H), 4.06 (s, 2H), 3.65 (m, 1H), 2.07 (m, 2H), 1.72 (m, 4H), 1.57 (m, 2H). MS: m/z 348.9 (M − H$^+$). |
| Va-4 | 10-((cyclopentylamino)methyl)-4-fluoro-6,11-dihydro-5H-indeno[1,2-c]isoquinolin-5-one $^1$H NMR (DMSO-$d_6$).: δ 12.37 (bs,1H), 8.86 (bs, 2H), 8.05 (dd, J = 2.0, 6.8 Hz, 1H), 7.77 (m, 1H), 7.54 (m, 3H); 7.23 (m, 1H), 4.30 (dd, J = 6.0, 6.0 Hz, 2H); 4.04 (s, 2H); 3.65 (m, 1H); 2.31 (m, 2H); 1.71 (m, 4H); 1.57 (m, 2H). MS: m/z 348.9 (M − H$^+$) |
| Va-5 | 3-fluoro-10-((tetrahydro-2H-pyran-4-ylamino)methyl)-6,11-dihydro-5H-indeno[1,2-c]isoquinolin-5-one $^1$H NMR (DMSO-$d_6$).: δ 12.47 (bs, 1H), 8.85 (bs, 2H), 7.98 (d, J = 6.5 Hz, 2H), 7.67 (m, 1H), 7.44 (m, 3H), 4.38 (m, 2H), 4.27 (m, 2H), 3.99 (dd, J = 3.6, 11.6 Hz, 2H), 3.53 (m, 2H), 3.42 (m, 1H), 2.01 (m, 2H), 1.58 (m, 2H) MS: m/z 365.30 (M − H+). |
| Va-6 | 1-fluoro-10-((tetrahydro-2H-pyran-4-ylamino)methyl)-6,11-dihydro-5H-indeno[1,2-c]isoquinolin-5-one $^1$H NMR (DMSO-$d_6$).: δ 12.49 (bs, 1H), 8.93 (bs, 2H). 8.65 (m, 1H), 7.95 (dd, J = 2.0, 8.9 Hz, 1H), 7.89 (dd, J = 2.5, 8.9, 1H), 7.75 (m, 2H), 7.42 (dd, J = 4.0, 8.0 Hz, 1H), 5.81 (bs, 1H), 4.28 (m, 2H), 4.07 (s, 2H), 3.65 (m, 2H), 3.49 (m, 1H), 1.84 (m, 8H). MS: m/z 379.2 (M − H$^+$) |
| Va-7 | 10-((cyclopentylamino)methyl)-1-fluoro-6,11-dihydro-5H-indeno[1,2-c]isoquinolin-5-one $^1$H NMR (DMSO-$d_6$).: δ 12.58 (bs, 1H), 8.94 (bs, 2H), 8.13 (d, J = 2.8, 7,6 Hz, 2H), 7.65 (m, 1H), 7.51 (m, 3H), 4.34 (dd, J = 6.0, 6.0 Hz, 2H), 4.20 (s, 2H), 3.67 (m, 1H), 2.07 (m, 2H), 1.69 (m, 4H), 1.57 (m, 2H). MS: m/z 348.9 (M − H$^+$). |
| Va-8 | 2-fluoro-10-((tetrahydro-2H-pyran-4-ylamino)methyl)-6,11-dihydro-5H-indeno[1,2-c]isoquinolin-5-one $^1$H NMR (DMSO-$d_6$).: δ 12.70 (bs, 1H), 9.16 (bs, 2H), 8.57 (m, 1H), 8.33 (m, 1H), 7.77 (m, 3H), 7.55 (m, 1H), 4.60 (m, 2H), 4.27 (m, 2H), 4.21 (m, 2H), 3.65 (m, 2H), 3.55 (m, 1H), 2.31 (m, 2H), 1.92 (m, 2H). MS: m/z 365.3 (M − H$^+$). |
| Va-9 | 8-fluoro-10-((1-(hydroxymethyl)cyclopentylamino)methyl)-6,11-dihydro-5H-indeno[1,2-c]isoquinolin-5-one $^1$H NMR (DMSO-$d_6$).: δ 12.59 (bs, 1H), 8.90 (bs, 2H); 8.12 (d, J = 8.0 Hz, 2H), 7.65 (m, 1H), 7.52 (m, 3H), 4.38 (m, 2H), 4.20 (s, 2H), 3.97 (dd J = 2.0, 10 Hz, 2H), 3.55 (m, 2H), 3.42 (m, 1H), 2.13 (m, 2H); 1.65 (m, 2H). MS: m/z 365.3 (M − H$^+$). |
| Va-10 | 3,8-difluoro-10-((1-(hydroxymethyl)cyclopentylamino)methyl)-6,11-dihydro-5H-indeno[1,2-c]isoquinolin-5-one $^1$H NMR (DMSO-$d_6$).: δ 12.49 (bs, 1H); 9.12 (bs, 2H), 8.66 (m, 1H), 7.96 (m, 2H), 7.89 (m, 1H); 7.75 (m, 1H), 5.84 (bs, 1H), 4.28 (m, 2H), 4.07 (s, 2H), 3.65 (m, 2H); 3.45 (m, 1H), 1.84 (m, 4H), 1.64 (m, 4H). MS: m/z 397.2 (M − H$^+$). |

Example 2

Determination of the Effect of Indenoisoquinolinone Analogs on in vitro PARP Activity The ability of an illustrative Indenoisoquinolinone Analog to inhibit PARP and prevent peroxynitrite induced cytotoxicity can be demonstrated using methods described in Virag et al., Br. J. Pharmacol. 1999, 126(3):769-77; and Immunology 1998, 94(3):345-55.

The potency of inhibition of purified PARP enzyme can be subsequently determined for selected Indenoisoquinolinone Analogs, and the potency is compared with that of 3-aminobenzamide, a prototypical benchmark PARP inhibitor. The assay is performed in 96 well ELISA plates according to instructions provided with a commercially available PARP inhibition assay kit (for example, from Trevigen, Gaithersburg, Md.).

Example 3

Determination of the Effect of Indenoisoquinolinone Analogs in an In Vitro Model of Cell Death Using an in vitro, oxidant-stimulated thymocyte assay (described, in detail, in Virag et al., Immunology 94(3):345-55, 1998), an illustrative Indenoisoquinolinone Analog can be tested for its ability to prevent the oxidant-induced suppression of the viability of the cells and as such, this assay represents an in vitro model of reperfusion related cell death in ischemic organs.

Example 4

Determination of the Effect of Indenoisoquinolinone Analogs on in vivo Models of Inflammatory Diseases The effect of an illustrative Indenoisoquinolinone Analog can be determined using a systemic inflammatory model induced by bacterial lipopolysaccharide (LPS), which is reported to be responsible for causing reperfusion injurys and inflammatory diseases such as septic shock and systemic inflammatory response syndrome in animals (see Parrillo, N. Engl. J. Med., 328:1471-1478 (1993) and Lamping, J. Clin. Invest. 101:2065-2071 (1998).

Example 5

Determination of the Effect of Indenoisoquinolinone Analogs on In Vivo Models of Reperfusion injury The efficacy of an illustrative Indenoisoquinolinone Analog in a mouse model of ischemic and reperfused gut can be determined according to the method described in Liaudet et al., Shock 2000, 14(2):134-41.

In another set of experiments, the effect of an illustrative Indenoisoquinolinone Analog in a rat model of middle cerebral artery occlusion/reperfusion can be assayed as described in Abdelkarim et al, *Int. J. Mol. Med.* 2001, 7(3):255-60.

Example 6

Determination of the Effect of Indenoisoquinolinone Analogs in an In Vivo Model of Diabetes Mellitus PARP inhibitors and PARP deficiency are known to reduce the development of diabetes mellitus and the incidence of diabetic complications. The anti-diabetic effect of an illustrative Indenoisoquinolinone Analog can be determined using a single high-dose streptozotocin model of diabetes mellitus, which can be used as conducted as described in Mabley et al., *Br. J. Pharmacol.* 2001, 133(6):909-9; and Soriano et al., *Nat. Med.* 2001, 7(1): 108-13. Briefly, 160 mg/kg streptozotocin is injected to mice treated with vehicle (control) or with an illustrative Indenoisoquinolinone Analog intraperitoneally (3 mg/kg) and 3 days later blood sugar levels are determined using a blood glucose meter.

Example 7

Determination of the Effect of Indenoisoquinolinone Analogs in an In Vivo Model of Erectile Dysfunction Experiments are conducted in male Sprague-Dawley rats according to previously published methods for forceps-induced nerve crush injury and erectile function measurements (Rehman, J., et al., *Urology* 51:640-644, 1998; Sezen, S. F., et al., *Int. J. Impot. Res.* 14:506-12, 2002). Subjects are anesthetized with Phenobarbital. The prostate of the subjects is exposed and the cavernosal nerve is clipped on either side with a forceps to induce mechanical injury (crush). This rat model mimics the nerve injury that develops during human male prostatectomy, leading to nerve injury and subsequent erectile dysfunction. Subjects are studied 2 weeks after the injury. Two groups of subjects are used, one group treated with vehicle and one group treated with an illustrative Indenoisoquinolinone Analog. The illustrative Indenoisoquinolinone Analog is injected at 30 mg/kg i.v. immediately before the crush injury, and on the following day at the same dose. Thereafter, for 12 days, subjects are treated with 60 mg/kg of the illustrative Indenoisoquinolinone Analog intraperitoneally. At 2 weeks, subjects are re-anesthetized and measured for mean arterial blood pressure (MAP) and intracavernosal pressure (ICP). Cavernosal nerve stimulation is conducted at 5 and 7.5 V using a square pulse stimulator for 30 msec. ICP is determined as the area under curve (mmHg×sec). In addition, IPC/MAP ratios are determined.

Example 8

Effect of Indenoisoquinolinone Analogs on PARP Activity in Cultured Macrophages, Using a Whole-Cell Based Assay Demonstration of Indenoisoquinolinone Analogs' ability to inhibit PARP and prevent peroxynitrite induced cytotoxicity was shown using methods described in Virag et al., *Br. J. Pharmacol.* 1999, 126(3):769-77; and *Immunology* 1998, 94(3):345-55. The murine RAW macrophages (ATCC, American Type Culture Collection, Manassas, Va.) were grown in RPMI 1650 (Invitrogen Life Technologies; Carlsbad, Calif.) medium supplemented with 10% heat-inactivated FBS, 2 mM L-glutamine, and 100 U/ml of penicillin and streptomycin. Cells, between passages 5 and 15, were seeded at a density of 250,000 cells/well in 12 well plates and allowed to grow 48 hours before use. Growth medium was changed on the day of use. Cells were treated with an Indenoisoquinolinone Analog diluted in a growth medium supplemented with 10% fetal bovine serum (FBS) for 1 hour prior to the addition of hydrogen peroxide (0.5 mM) for a further 25 minutes. For the measurement of PARP activity, media was removed and replaced with 0.5 ml of the assay buffer (56 mM HEPES-pH 7.5, 28 mM KCl, 28 mM NaCl, 2 mM $MgCl_2$, 0.01% digitonin, and 0.5 μCi/ml of $3H-NAD^+$) for 20 minutes. After aspirating the assay buffer, cells were lysed and transferred to eppendorf tubes containing 250 μl of 50% ice-cold trichloroacetic acid (TCA), which were then placed at 4° C. for 4 hours. Samples were centrifuged at 10,000 g for 10 minutes and supernatant removed. The pellets were washed twice with 500 μl of ice-cold 5% w/v TCA. The pellets were then solubilized in 250 μl of NaOH (0.1 M) containing 2% SDS overnight at 37° C. and the PARP activity was then determined by measuring the radioactivity incorporated using a Wallac scintillation counter. The solubilized protein (250 μl) was mixed with 5 ml of scintillation fluid (ScintiSafe Plus, Fisher Scientific) before being counted for 3 minutes. $EC_{50}$ values were determined from a dose-response curve.

TABLE 4

| Compound | $EC_{50}$ value [nM] |
| --- | --- |
| IIa-1 | 20 |
| IIa-14 | 30 |
| IIa-27 | <10 |
| IIIa-2 | 25 |
| IIIa-3 | 20 |
| IIIa-4 | 15 |
| IIIa-5 | 40 |
| IIIa-6 | 50 |
| IIIa-7 | 60 |
| IIIa-8 | 75 |
| IIIa-9 | 60 |
| IIIa-10 | 60 |
| IIIa-11 | 12 |
| IIIa-12 | 7 |
| IIb-1 | 45 |
| IIb-53 | >50 |
| IIb-66 | 45 |
| IIb-79 | >60 |
| IIb-92 | >60 |
| IIb-105 | 100 |
| IIb-118 | 60 |
| IIb-170 | 75 |
| IIb-131 | 75 |
| IIb-196 | 75 |
| IIb-183 | 100 |
| IIb-157 | 75 |
| IIIb-1 | 20 |
| IIIb-2 | 25 |
| Dihydrochloride salt of IIIb-3 | 10 |
| IIIb-8 | 75 |
| IIIb-9 | 20 |
| IIIb-10 | 75 |
| IIIb-13 | 25 |
| Dihydrochloride salt of IIIb-14 | 20 |
| Methylsulfonate salt of IIIb-15 | 55 |
| IIIb-16 | >100 |
| IIIb-17 | 100 |
| IIIb-18 | 75 |
| IIIb-19 | 30 |
| Dihydrochloride salt of IIIb-20 | 100 |
| IIIb-21 | 100 |
| IIIb-22 | >100 |
| IIIb-24 | >60 |

TABLE 4-continued

| Compound | EC$_{50}$ value [nM] |
|---|---|
| IIIa-1 | 45 |
| IIb-23 | 80 |
| Va-1 | >100 |
| Va-3 | 9 |
| Va-4 | 4 |
| Va-5 | 5 |
| Va-7 | 5 |
| Va-9 | 3 |
| Va-10 | 3 |

The present invention is not to be limited in scope by the specific embodiments disclosed in the examples, which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which have been incorporated herein in their entirety.

What is claimed is:

1. A compound having the formula:

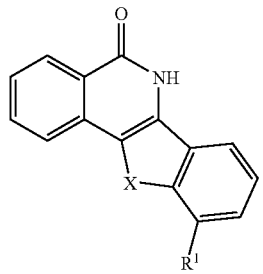

(Ia)

or a pharmaceutically acceptable salt thereof,
wherein
X is —CH(OH)—;
R$^1$ is —(CH$_2$)$_n$—N(R$^2$)(R$^2$) or —O—(CH$_2$)$_m$—N(R$^2$)(R$^2$);
each R$^2$ is independently —H, —C$_1$-C$_6$ alkyl, —C$_3$-C$_8$ monocyclic cycloalkyl, —C$_1$-C$_6$ alkylene phenyl, phenyl, an N-terminal alpha amino acid residue, an N-terminal alpha amino hydroxymethyl residue, a —C$_1$-C$_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —C$_1$-C$_6$ alkyl, —O—C$_1$-C$_6$ alkyl, —C$_3$-C$_8$ monocyclic cycloalkyl, a 3- to 7-membered monocyclic heterocycle, —(C$_1$-C$_6$ alkyl-substituted) 3- to 7-membered monocyclic heterocycle, or —N(Z$_3$)(Z$_4$), where Z$_3$ and Z$_4$ are independently —H, —C$_1$-C$_5$ alkyl, —(C$_1$-C$_5$ alkylene)-O—C$_1$-C$_5$ alkyl, benzyl, or —C$_3$-C$_8$ monocyclic cycloalkyl, each of which other than hydrogen is independently unsubstituted or substituted with one or more of -halo, —OH, —N(R$^a$)$_2$, —(C$_1$-C$_5$ alkylene)-O—C$_1$-C$_5$ alkyl, —NH$_2$, a nitrogen-containing 3- to 7-membered monocyclic heterocycle, or a —(C$_1$-C$_6$ alkyl-substituted) nitrogen-containing 3- to 7-membered monocyclic heterocycle, wherein each occurrence of R$^a$ is independently —H, benzyl, or —C$_1$-C$_{10}$ alkyl; or N, Z$_3$ and Z$_4$ are taken together to form a nitrogen-containing 3- to 7-membered monocyclic heterocycle which is unsubstituted or substituted with one or more of —C$_1$-C$_5$ alkyl, phenyl, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —(C$_1$-C$_5$ alkylene)-C(O)O—(C$_1$-C$_5$ alkylene)-N(R$^a$)$_2$, —COOH, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, benzyl, or —C$_1$-C$_{10}$ alkyl; or N and both R$^a$ groups are taken together to form a nitrogen-containing 3- to 7-membered monocyclic heterocycle;
or N and both R$^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —C$_1$-C$_5$ alkyl, —C$_3$-C$_8$ monocyclic cycloalkyl, phenyl, a nitrogen-containing 3- to 7-membered monocyclic heterocycle, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —C$_1$-C$_5$ alkylene-C(O)O—(C$_1$-C$_5$ alkylene)-N(R$^a$)$_2$, —COOH, —(C$_1$-C$_5$ alkylene)-O—C$_1$-C$_5$ alkyl, —(C$_1$-C$_5$ alkylene)-C$_3$-C$_8$ monocyclic cycloalkyl, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, -benzyl, —C$_1$-C$_{10}$ alkyl; or N and both R$^a$ groups are taken together to form a nitrogen-containing 3- to 7-membered monocyclic heterocycle;
n is an integer ranging from 1 to 10; and
m is an integer ranging from 2 to 10.

2. The compound or a pharmaceutically acceptable salt of the compound of claim 1, wherein at least one R$^2$ is —C$_1$-C$_6$ alkyl or —C$_3$-C$_8$ monocyclic cycloalkyl.

3. The compound or a pharmaceutically acceptable salt of the compound of claim 1, wherein n is 1.

4. The compound or a pharmaceutically acceptable salt of the compound of claim 1, wherein each R$^2$ is independently —C$_1$-C$_6$ alkyl.

5. The compound or a pharmaceutically acceptable salt of the compound of claim 1, wherein one R$^2$ is —H.

6. A compound having the formula:

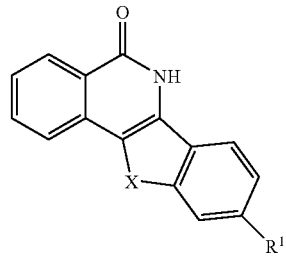

(Ib)

or a pharmaceutically acceptable salt thereof wherein
X is —CH(OH)—;
R$^1$ is —(CH$_2$)$_n$—N(R$^2$)(R$^2$) or —O—(CH$_2$)$_m$—N(R$^2$)(R$^2$);
each R$^2$ is independently —H, —C$_1$-C$_6$ alkyl, —C$_3$-C$_8$ monocyclic cycloalkyl, —C$_1$-C$_6$ alkylene phenyl, phenyl, an N-terminal alpha amino acid residue, an N-terminal alpha amino hydroxymethyl residue, a C$_1$-C$_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —C$_1$-C$_6$ alkyl, —O—C$_1$-C$_6$ alkyl, —C$_3$-C$_8$ monocyclic cycloalkyl, a 3- to 7-membered monocyclic heterocycle, —(C$_1$-C$_6$ alkyl-substituted) 3- to 7-membered monocyclic heterocycle, or —N(Z$_3$)(Z$_4$), where Z$_3$ and Z$_4$ are independently —H, —C$_1$-C$_5$ alkyl, —(C$_1$-C$_5$ alkylene)-O—C$_1$-C$_5$ alkyl, benzyl, or —C$_3$-C$_8$ monocyclic cycloalkyl, each of which other than hydrogen is independently unsubstituted or substituted with one or more of -halo, —OH, —N(R$^a$)$_2$, —(C$_1$-C$_5$ alkylene)-O—C$_1$-C$_5$ alkyl, —NH$_2$, a nitrogen-containing 3- to 7-membered monocyclic heterocycle, or a —(C$_1$-C$_6$ alkyl-substituted) nitrogen-containing 3- to 7-membered monocyclic heterocycle, wherein each occurrence of R$^a$ is independently —H, benzyl, or —C$_1$-C$_{10}$ alkyl; or N, Z$_3$ and Z$_4$ are taken together to form a nitrogen-containing 3- to 7-membered monocyclic heterocycle which is unsubstituted or substituted with one or more of —C$_1$-C$_5$ alkyl, phenyl, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —(C$_1$-C$_5$ alkylene)-C(O)O—(C$_1$-C$_5$ alkylene)-N(R$^a$)$_2$, —COOH, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, benzyl, or —C$_1$-C$_{10}$ alkyl; or N and both R$^a$ groups are taken together to form a nitrogen-containing 3- to 7-membered monocyclic heterocycle;
or N and both R$^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —C$_1$-C$_5$ alkyl, —C$_3$-C$_8$ monocyclic cycloalkyl, phenyl, a nitrogen-containing 3- to 7-membered monocyclic heterocycle, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —C$_1$-C$_5$ alkylene-C(O)O—(C$_1$-C$_5$ alkylene)-N(R$^a$)$_2$, —COOH, —(C$_1$-C$_5$ alkylene)-O—C$_1$-C$_5$ alkyl, —(C$_1$-C$_5$ alkylene)-C$_3$-C$_8$ monocyclic cycloalkyl, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, -benzyl, —C$_1$-C$_{10}$ alkyl; or N and both R$^a$ groups are taken together to form a nitrogen-containing 3- to 7-membered monocyclic heterocycle;
n is an integer ranging from 1 to 10; and
m is an integer ranging from 2 to 10.

7. The compound or a pharmaceutically acceptable salt of the compound of claim 6, wherein at least one R$^2$ is —C$_1$-C$_6$ alkyl or —C$_3$-C$_8$ monocyclic cycloalkyl.

8. The compound or a pharmaceutically acceptable salt of the compound of claim 6, wherein n is 1.

9. The compound or a pharmaceutically acceptable salt of the compound of claim 6, wherein each R$^2$ is independently —C$_1$-C$_6$ alkyl.

10. The compound or a pharmaceutically acceptable salt of the compound of claim 6, wherein one R$^2$ is —H.

11. A compound having the formula:

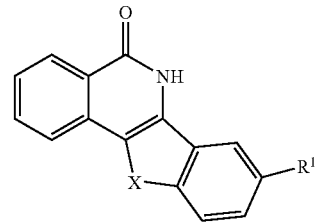

(Ic)

or a pharmaceutically acceptable salt thereof
wherein
X is —CH(OH)—;
R$^1$ is —(CH$_2$)$_n$—N(R$^2$)(R$^2$) or —O—(CH$_2$)$_m$—N(R$^2$)(R$^2$);
each R$^2$ is independently —H, —C$_1$-C$_6$ alkyl, —C$_3$-C$_8$ monocyclic cycloalkyl, —C$_1$-C$_6$ alkylene phenyl, phenyl, an N-terminal alpha amino acid residue, an N-terminal alpha amino hydroxymethyl residue, a C$_1$-C$_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —C$_1$-C$_6$ alkyl, —O—C$_1$-C$_6$ alkyl, —C$_3$-C$_8$ monocyclic cycloalkyl, a 3- to 7-membered monocyclic heterocycle, —(C$_1$-C$_6$ alkyl-substituted) 3- to 7-membered monocyclic heterocycle, or —N(Z$_3$)(Z$_4$), where Z$_3$ and Z$_4$ are independently —H, —C$_1$-C$_5$ alkyl, —(C$_1$-C$_5$ alkylene)-O—C$_1$-C$_5$ alkyl, benzyl, or —C$_3$-C$_8$ monocyclic cycloalkyl, each of which other than hydrogen is independently unsubstituted or substituted with one or more of -halo, —OH, —N(R$^a$)$_2$, —(C$_1$-C$_5$ alkylene)-O—C$_1$-C$_5$ alkyl, —NH$_2$, a nitrogen-containing 3- to 7-membered monocyclic heterocycle, or a —(C$_1$-C$_6$ alkyl-substituted) nitrogen-containing 3- to 7-membered monocyclic heterocycle, wherein each occurrence of R$^a$ is independently —H, benzyl, or —C$_1$-C$_{10}$ alkyl; or N, Z$_3$ and Z$_4$ are taken together to form a nitrogen-containing 3- to 7-membered monocyclic heterocycle which is unsubstituted or substituted with one or more of —C$_1$-C$_5$ alkyl, phenyl, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —(C$_1$-C$_5$ alkylene)-C(O)O—(C$_1$-C$_5$ alkylene)-N(R$^a$)$_2$, —COOH, —(C$_1$-C$_5$ alkylene)-

COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, benzyl, or —C$_1$-C$_{10}$ alkyl; or N and both R$^a$ groups are taken together to form a nitrogen-containing 3- to 7-membered monocyclic heterocycle;

or N and both R$^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —C$_1$-C$_5$ alkyl, —C$_3$-C$_8$ monocyclic cycloalkyl, phenyl, a nitrogen-containing 3- to 7-membered monocyclic heterocycle, -(phenyl-substituted) C$_1$-C$_5$ alkyl, -(hydroxy-substituted) C$_1$-C$_5$ alkyl, -halo, -(halo-substituted) C$_1$-C$_5$ alkyl, -(halo-substituted) phenyl, -phenylene-O—C$_1$-C$_5$ alkyl, -(cyano-substituted) phenyl, —OH, —O—C$_1$-C$_5$ alkyl, —N(R$^a$)$_2$, —(C$_1$-C$_5$ alkylene)-N(R$^a$)$_2$, —C$_1$-C$_5$ alkylene-C(O)O—(C$_1$-C$_5$ alkylene)-N(R$^a$)$_2$, —COOH, —(C$_1$-C$_5$ alkylene)-O—C$_1$-C$_5$ alkyl, —(C$_1$-C$_5$ alkylene)-C$_3$-C$_8$ monocyclic cycloalkyl, —(C$_1$-C$_5$ alkylene)-COOH, —OP(O)(OH)$_2$, —OS(O)$_2$OH, —(C$_1$-C$_5$ alkylene)-OP(O)(OH)$_2$, —(C$_1$-C$_5$ alkylene)-OS(O)$_2$OH, —C(O)O—C$_1$-C$_5$ alkyl, —OC(O)—C$_1$-C$_5$ alkyl, —(C$_1$-C$_5$ alkylene)-C(O)O—C$_1$-C$_5$ alkyl, —(C$_1$-C$_5$ alkylene)-C(O)NH—C$_1$-C$_5$ alkyl, —C(O)NH$_2$, or —NO$_2$, wherein each occurrence of R$^a$ is independently —H, -benzyl, —C$_1$-C$_{10}$ alkyl; or N and both R$^a$ groups are taken together to form a nitrogen-containing 3- to 7-membered monocyclic heterocycle;

n is an integer ranging from 1 to 10; and m is an integer ranging from 2 to 10.

12. The compound or a pharmaceutically acceptable salt of the compound of claim 11, wherein at least one R$^2$ is —C$_1$-C$_6$ alkyl or —C$_3$-C$_8$ monocyclic cycloalkyl.

13. The compound or a pharmaceutically acceptable salt of the compound of claim 11, wherein n is 1.

14. The compound or a pharmaceutically acceptable salt of the compound of claim 11, wherein each R$^2$ is independently —C$_1$-C$_6$ alkyl.

15. The compound or a pharmaceutically acceptable salt of the compound of claim 11, wherein one R$^2$ is —H.

16. A compound having the formula:

(IIa)

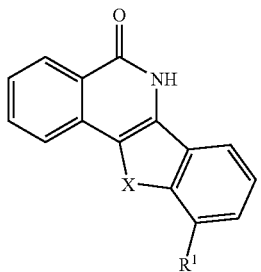

or a pharmaceutically acceptable salt thereof, wherein

X is —CH(OH)—;

R$^1$ is —(CH$_2$)$_n$—N(R$^2$)(R$^3$) or

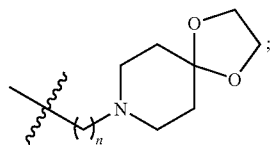

R$^2$ is —H, —C$_1$-C$_6$ alkyl, or —C$_3$-C$_8$ monocyclic cycloalkyl;

R$^3$ is —C(O)—(C$_1$-C$_6$ alkylene)-(3- to 7-membered monocyclic heterocycle), a nitrogen-containing 3- to 7-membered monocyclic heterocycle which is substituted with one or more of —C(O)O—C$_1$-C$_6$ alkyl, or —C$_3$-C$_8$ monocyclic cycloalkyl which is substituted with one or more of (hydroxy-substituted) C$_1$-C$_5$ alkyl groups;

or N, R$^2$ and R$^3$ are taken together to form a nitrogen-containing 3- to 7-membered monocyclic heterocycle, which is substituted with one or more of —C$_2$-C$_6$ alkenyl, —C(O)—C$_1$-C$_6$ alkyl, —(C$_1$-C$_4$ alkylene)-C(O)—(C$_3$-C$_8$ monocyclic cycloalkyl), —C$_7$-C$_{10}$ alkyl, —(C$_1$-C$_5$ alkylene)-C(H)(—O—C$_1$-C$_4$ alkyl)$_2$, -(cyano-substituted) C$_1$-C$_5$ alkyl, —(C$_1$-C$_5$ alkylene)-C(O)-(nitrogen-containing 3- to 7-membered monocyclic heterocycle) or —(C$_1$-C$_5$ alkylene)-(3- to 7-membered monocyclic heterocycle) groups; and an n is an integer ranging from 1 to 10.

17. The compound or a pharmaceutically acceptable salt of the compound of claim 16, wherein R$^2$ is —H, and R$^3$ is a nitrogen-containing 3- to 7-membered monocyclic heterocycle which is substituted with one or more of —C(O)O—C$_1$-C$_6$ alkyl groups.

18. The compound or a pharmaceutically acceptable salt of the compound of claim 16, wherein R$^3$ is —C$_3$-C$_8$ monocyclic cycloalkyl which is substituted with one or more of hydroxy-substituted C$_1$-C$_5$ alkyl groups.

19. The compound or a pharmaceutically acceptable salt of the compound of claim 16, wherein R$^3$ is —C(O)—C$_1$-C$_6$ alkylene-3- to 7-membered monocyclic heterocycle.

20. A compound having the formula:

(IIb)

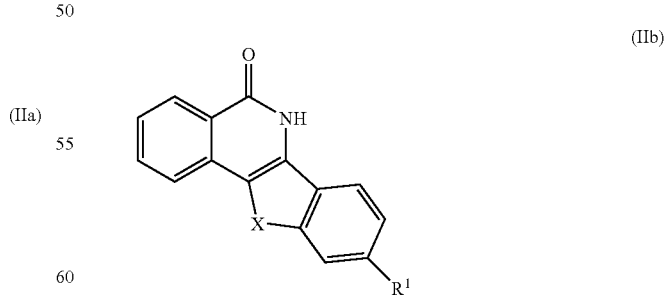

or a pharmaceutically acceptable salt thereof, wherein

X is —CH(OH)—;

R$^1$ is —(CH$_2$)$_n$—N(R$^2$)(R$^3$) or

1089

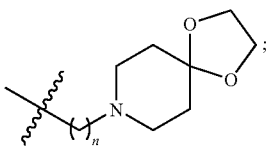

R² is —H, —C₁-C₆ alkyl, or —C₃-C₈ monocyclic cycloalkyl;

R³ is —C(O)—(C₁-C₆ alkylene)-(3- to 7-membered monocyclic heterocycle), a nitrogen-containing 3- to 7-membered monocyclic heterocycle which is substituted with one or more of —C(O)O—C₁-C₆ alkyl, or —C₃-C₈ monocyclic cycloalkyl which is substituted with one or more of (hydroxy-substituted) C₁-C₅ alkyl groups;

or N, R² and R³ are taken together to form a nitrogen-containing 3- to 7-membered monocyclic heterocycle, which is substituted with one or more of —C₂-C₆ alkenyl, —C(O)—C₁-C₆ alkyl, —(C₁-C₄ alkylene)-C(O)—(C₃-C₈ monocyclic cycloalkyl), —C₇-C₁₀ alkyl, —(C₁-C₅ alkylene)-C(H)(—O—C₁-C₄ alkyl)₂, -(cyano-substituted) C₁-C₅ alkyl, —(C₁-C₅ alkylene)-C(O)-(nitrogen-containing 3- to 7-membered monocyclic heterocycle) or —(C₁-C₅ alkylene)-(3- to 7-membered monocyclic heterocycle) groups; and an n is an integer ranging from 1 to 10.

21. The compound or a pharmaceutically acceptable salt of the compound of claim 20, wherein R² is —H, and R³ is a nitrogen-containing 3- to 7-membered monocyclic heterocycle which is substituted with one or more of —C(O)O—C₁-C₆ alkyl groups.

22. The compound or a pharmaceutically acceptable salt of the compound of claim 20, wherein R³ is —C₃-C₈ monocyclic cycloalkyl which is substituted with one or more of hydroxy-substituted C₁-C₅ alkyl groups.

23. The compound or a pharmaceutically acceptable salt of the compound of claim 20, wherein R³ is —C(O)—C₁-C₆ alkylene-3- to 7-membered monocyclic heterocycle.

24. A compound having the formula:

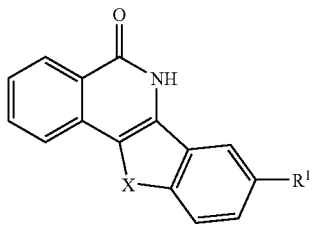

(IIc)

or a pharmaceutically acceptable salt thereof, wherein

X is —CH(OH)—;

R¹ is —(CH₂)ₙ—N(R²)(R³) or

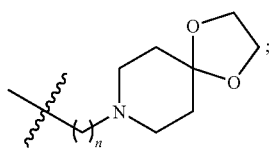

1090

R² is —H, —C₁-C₆ alkyl, or —C₃-C₈ monocyclic cycloalkyl;

R³ is —C(O)—(C₁-C₆ alkylene)-(3- to 7-membered monocyclic heterocycle), a nitrogen-containing 3- to 7-membered monocyclic heterocycle which is substituted with one or more of —C(O)O—C₁-C₆ alkyl, or —C₃-C₈ monocyclic cycloalkyl which is substituted with one or more of (hydroxy-substituted) C₁-C₅ alkyl groups;

or N, R² and R³ are taken together to form a nitrogen-containing 3- to 7-membered monocyclic heterocycle, which is substituted with one or more of —C₂-C₆ alkenyl, —C(O)—C₁-C₆ alkyl, —(C₁-C₄ alkylene)-C(O)—(C₃-C₈ monocyclic cycloalkyl), —C₇-C₁₀ alkyl, —(C₁-C₅ alkylene)-C(H)(—O—C₁-C₄ alkyl)₂, -(cyano-substituted) C₁-C₅ alkyl, —(C₁-C₅ alkylene)-C(O)-(nitrogen-containing 3- to 7-membered monocyclic heterocycle) or —(C₁-C₅ alkylene)-(3- to 7-membered monocyclic heterocycle) groups; and an n is an integer ranging from 1 to 10.

25. The compound or a pharmaceutically acceptable salt of the compound of claim 24, wherein R² is —H, and R³ is a nitrogen-containing 3- to 7-membered monocyclic heterocycle which is substituted with one or more of —C(O)O—C₁-C₆ alkyl groups.

26. The compound or a pharmaceutically acceptable salt of the compound of claim 24, wherein R³ is —C₃-C₈ monocyclic cycloalkyl which is substituted with one or more of hydroxy-substituted C₁-C₅ alkyl groups.

27. The compound or a pharmaceutically acceptable salt of the compound of claim 24, wherein R³ is —C(O)—C₁-C₆ alkylene-3- to 7-membered monocyclic heterocycle.

28. A composition comprising a physiologically acceptable carrier or vehicle and an effective amount of a compound or a pharmaceutically acceptable salt of a compound of claim 1.

29. A composition comprising a physiologically acceptable carrier or vehicle and an effective amount of a compound or a pharmaceutically acceptable salt of a compound of claim 6.

30. A composition comprising a physiologically acceptable carrier or vehicle and an effective amount of a compound or a pharmaceutically acceptable salt of a compound of claim 11.

31. A composition comprising a physiologically acceptable carrier or vehicle and an effective amount of a compound or a pharmaceutically acceptable salt of a compound of claim 16.

32. A composition comprising a physiologically acceptable carrier or vehicle and an effective amount of a compound or a pharmaceutically acceptable salt of a compound of claim 20.

33. A composition comprising a physiologically acceptable carrier or vehicle and an effective amount of a compound or a pharmaceutically acceptable salt of a compound of claim 24.

34. A compound having the formula:

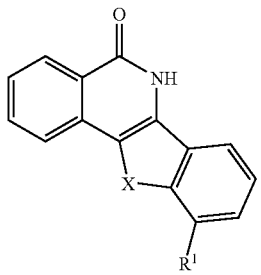

(IVa)

or a pharmaceutically acceptable salt thereof,
wherein
X is —CH(OH)—;
$R^1$ is —OC($C_1$-$C_3$alkyl)$_2$-(CH$_2$)$_n$—N($R^2$)($R^2$);
each $R^2$ is independently —H, —$C_1$-$C_6$ alkyl, —$C_3$-$C_8$ monocyclic cycloalkyl, —$C_1$-$C_6$ alkylene phenyl, phenyl, an N-terminal alpha amino acid residue, an N-terminal alpha amino hydroxymethyl residue, a $C_1$-$C_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$), where $Z_3$ and $Z_4$ are independently —H, —$C_1$-$C_5$ alkyl, —($C_1$-$C_5$ alkylene)-O—$C_1$-$C_5$ alkyl, benzyl, or —$C_3$-$C_8$ monocyclic cycloalkyl, each of which other than hydrogen is independently unsubstituted or substituted with one or more of -halo, —OH, —N($R^a$)$_2$, —($C_1$-$C_5$ alkylene)-O—$C_1$-$C_5$ alkyl, —NH$_2$, a nitrogen-containing 3- to 7-membered monocyclic heterocycle, or a —($C_1$-$C_6$ alkyl-substituted) nitrogen-containing 3- to 7-membered monocyclic heterocycle, wherein each occurrence of $R^a$ is independently —H, benzyl, or —$C_1$-$C_{10}$ alkyl; or N, $Z_3$ and $Z_4$ are taken together to form a nitrogen-containing 3- to 7-membered monocyclic heterocycle which is unsubstituted or substituted with one or more of —$C_1$-$C_5$ alkyl, phenyl, -(phenyl-substituted) $C_1$-$C_5$ alkyl, -(hydroxy-substituted)$C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —($C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, benzyl, or —$C_1$-$C_{10}$ alkyl; or N and both $R^a$ groups are taken together to form a nitrogen-containing 3- to 7-membered monocyclic heterocycle;
or N and both $R^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —$C_1$-$C_5$ alkyl, —$C_3$-$C_8$ monocyclic cycloalkyl, phenyl, a nitrogen-containing 3- to 7-membered monocyclic heterocycle, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene-C(O)O—($C_1$-$C_5$ alkylene)-N($R^a$)$_2$, —COOH, —($C_1$-$C_5$ alkylene)-O—$C_1$-$C_5$ alkyl, —($C_1$-$C_5$ alkylene)-$C_3$-$C_8$ monocyclic cycloalkyl, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, —$C_1$-$C_{10}$ alkyl; or N and both $R^a$ groups are taken together to form a nitrogen-containing 3- to 7-membered monocyclic heterocycle;
n is an integer ranging from 1 to 10.

35. A compound having the formula:

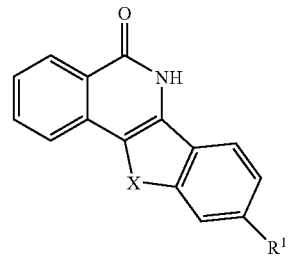

(IVb)

or a pharmaceutically acceptable salt thereof,
wherein
X is —CH(OH)—;
$R^1$ is —O—C($C_1$-$C_3$ alkyl)$_2$-(CH$_2$)$_n$—N($R^2$)($R^2$);
each $R^2$ is independently —H, —$C_1$-$C_6$ alkyl, —$C_3$-$C_8$ monocyclic cycloalkyl, —$C_1$-$C_6$ alkylene phenyl, phenyl, an N-terminal alpha amino acid residue, an N-terminal alpha amino hydroxymethyl residue, a $C_1$-$C_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$), where $Z_3$ and $Z_4$ are independently —H, —$C_1$-$C_5$ alkyl, —($C_1$-$C_5$ alkylene)-O—$C_1$-$C_5$ alkyl, benzyl, or —$C_3$-$C_8$ monocyclic cycloalkyl, each of which other than hydrogen is independently unsubstituted or substituted with one or more of -halo, —OH, —N($R^a$)$_2$, —($C_1$-$C_5$ alkylene)-O—$C_1$-$C_5$ alkyl, —NH$_2$, a nitrogen-containing 3- to 7-membered monocyclic heterocycle, or a —($C_1$-$C_6$ alkyl-substituted) nitrogen-containing 3- to 7-membered monocyclic heterocycle, wherein each occurrence of $R^a$ is independently —H, benzyl, or —$C_1$-$C_{10}$ alkyl; or N, $Z_3$ and $Z_4$ are taken together to form a nitrogen-containing 3- to 7-membered monocyclic heterocycle which is unsubstituted or substituted with one or more of —$C_1$-$C_5$ alkyl, phenyl, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —($C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, benzyl, or —$C_1$-$C_{10}$ alkyl; or N and both $R^a$ groups are taken together to form a nitrogen-containing 3- to 7-membered monocyclic heterocycle;

or N and both $R^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —$C_1$-$C_5$ alkyl, —$C_3$-$C_8$ monocyclic cycloalkyl, phenyl, a nitrogen-containing 3- to 7-membered monocyclic heterocycle, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene-C(O)O—($C_1$-$C_5$ alkylene)-N($R^a$)$_2$, —COOH, —($C_1$-$C_5$ alkylene)-O—$C_1$-$C_5$ alkyl, —($C_1$-$C_5$ alkylene)-$C_3$-$C_8$ monocyclic cycloalkyl, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, —$C_1$-$C_{10}$ alkyl; or N and both $R^a$ groups are taken together to form a nitrogen-containing 3- to 7-membered monocyclic heterocycle;

n is an integer ranging from 1 to 10.

36. A compound having the formula:

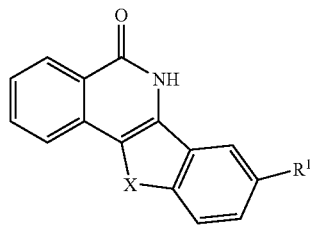

(IVc)

or a pharmaceutically acceptable salt thereof,
wherein
X is —CH(OH)—;
$R^1$ is —O—C($C_1$-$C_3$ alkyl)$_2$-(CH$_2$)$_n$—N($R^2$)($R^2$);
each $R^2$ is independently —H, —$C_1$-$C_6$ alkyl, —$C_3$-$C_8$ monocyclic cycloalkyl, —$C_1$-$C_6$ alkylene phenyl, phenyl, an N-terminal alpha amino acid residue, an N-terminal alpha amino hydroxymethyl residue, a $C_1$-$C_6$ alkyl ester of an N-terminal alpha amino acid residue, or a nitrogen-containing 3- to 7-membered monocyclic heterocycle, each of which other than hydrogen is independently unsubstituted or substituted with one or more of -halo, —OH, —OP(O)(OH)$_2$, —OS(O)$_2$OH, —$C_1$-$C_6$ alkyl, —O—$C_1$-$C_6$ alkyl, —$C_3$-$C_8$ monocyclic cycloalkyl, a 3- to 7-membered monocyclic heterocycle, —($C_1$-$C_6$ alkyl-substituted) 3- to 7-membered monocyclic heterocycle, or —N($Z_3$)($Z_4$), where $Z_3$ and $Z_4$ are independently —H, —$C_1$-$C_5$ alkyl, —($C_1$-$C_5$ alkylene)-O—$C_1$-$C_5$ alkyl, benzyl, or —$C_3$-$C_8$ monocyclic cycloalkyl, each of which other than hydrogen is independently unsubstituted or substituted with one or more of -halo, —OH, —N($R^a$)$_2$, —($C_1$-$C_5$ alkylene)-O—$C_1$-$C_5$ alkyl, —NH$_2$, a nitrogen-containing 3- to 7-membered monocyclic heterocycle, or a —($C_1$-$C_6$ alkyl-substituted) nitrogen-containing 3- to 7-membered monocyclic heterocycle, wherein each occurrence of $R^a$ is independently —H, benzyl, or —$C_1$-$C_{10}$ alkyl; or N, $Z_3$ and $Z_4$ are taken together to form a nitrogen-containing 3- to 7-membered monocyclic heterocycle which is unsubstituted or substituted with one or more of —$C_1$-$C_5$ alkyl, phenyl, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —($C_1$-$C_5$ alkylene)-C(O)O—($C_1$-$C_5$ alkylene)-N($R^a$)$_2$, —COOH, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, benzyl, or —$C_1$-$C_{10}$ alkyl; or N and both $R^a$ groups are taken together to form a nitrogen-containing 3- to 7-membered monocyclic heterocycle;

or N and both $R^2$ groups are taken together to form a nitrogen-containing 3- to 7-membered monocyclic heterocycle or a nitrogen-containing 7- to 10-membered bicyclic heterocycle, each of which is unsubstituted or substituted with one or more of —$C_1$-$C_5$ alkyl, —$C_3$-$C_8$ monocyclic cycloalkyl, phenyl, a nitrogen-containing 3- to 7-membered monocyclic heterocycle, -(phenyl-substituted) $C_1$-$C_5$ alkyl, -(hydroxy-substituted) $C_1$-$C_5$ alkyl, -halo, -(halo-substituted) $C_1$-$C_5$ alkyl, -(halo-substituted) phenyl, -phenylene-O—$C_1$-$C_5$ alkyl, -(cyano-substituted) phenyl, —OH, —O—$C_1$-$C_5$ alkyl, —N($R^a$)$_2$, —($C_1$-$C_5$ alkylene)-N($R^a$)$_2$, —$C_1$-$C_5$ alkylene-C(O)O—($C_1$-$C_5$ alkylene)-N($R^a$)$_2$, —COOH, —($C_1$-$C_5$ alkylene)-O—$C_1$-$C_5$ alkyl, —($C_1$-$C_5$ alkylene)-$C_3$-$C_8$ monocyclic cycloalkyl, —($C_1$-$C_5$ alkylene)-COOH, —OP(O)(OH)$_2$, —OS(O)$_2$OH, —($C_1$-$C_5$ alkylene)-OP(O)(OH)$_2$, —($C_1$-$C_5$ alkylene)-OS(O)$_2$OH, —C(O)O—$C_1$-$C_5$ alkyl, —OC(O)—$C_1$-$C_5$ alkyl, —($C_1$-$C_5$ alkylene)-C(O)O—$C_1$-$C_5$ alkyl, —($C_1$-$C_5$ alkylene)-C(O)NH—$C_1$-$C_5$ alkyl, —C(O)NH$_2$, or —NO$_2$, wherein each occurrence of $R^a$ is independently —H, -benzyl, —$C_1$-$C_{10}$ alkyl; or N and both $R^a$ groups are taken together to form a nitrogen-containing 3- to 7-membered monocyclic heterocycle;

n is an integer ranging from 1 to 10.

37. A composition comprising a physiologically acceptable carrier or vehicle and an effective amount of a compound or a pharmaceutically acceptable salt of a compound of claim 36.

38. A composition comprising a physiologically acceptable carrier or vehicle and an effective amount of a compound or a pharmaceutically acceptable salt of a compound of claim 34.

39. A composition comprising a physiologically acceptable carrier or vehicle and an effective amount of a compound or a pharmaceutically acceptable salt of a compound of claim 35.

40. A compound having the formula:

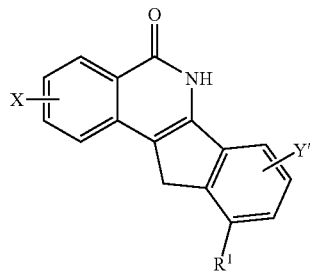

(Va)

or pharmaceutically acceptable salt thereof, wherein $R^1$ is $CH_2NH-R^2$, $R^2$ is a $-C_3-C_8$ monocyclic cycloalkyl which is unsubstituted or substituted with one or more of (hydroxyl-substituted) $C_1-C_5$ alkyl; or a 3- to 7-membered monocyclic heterocycle;

X is halo or —H; and

Y' is halo or —H, wherein at least one of X and Y' is halo.

41. The compound or a pharmaceutically acceptable salt of the compound of claim 40 wherein $R^2$ is tetrahydropyranyl; or cyclopentyl which is unsubstituted or substituted with one or more of -(hydroxyl-substituted) $C_1-C_5$ alkyl.

42. The compound or a pharmaceutically acceptable salt of the compound of claim 40 wherein one of X and Y' is fluoro.

43. A composition comprising a physiologically acceptable carrier or vehicle and an effective amount of a compound or a pharmaceutically acceptable salt of a compound of claim 40.

* * * * *